US011396508B2

(12) United States Patent
Greenwood et al.

(10) Patent No.: US 11,396,508 B2
(45) Date of Patent: Jul. 26, 2022

(54) TYK2 INHIBITORS AND USES THEREOF

(71) Applicant: Nimbus Lakshmi, Inc., Cambridge, MA (US)

(72) Inventors: Jeremy Robert Greenwood, Brooklyn, NY (US); Silvana Marcel Leit de Moradei, Burlington, MA (US); Craig E. Masse, Cambridge, MA (US); Thomas H. McLean, Cambridge, MA (US); Sayan Mondal, New York, NY (US)

(73) Assignee: Nimbus Lakshmi, Inc., Cambridge, MA (US)

( * ) Notice: Subject to any disclaimer, the term of this patent is extended or adjusted under 35 U.S.C. 154(b) by 0 days.

(21) Appl. No.: 16/804,951

(22) Filed: Feb. 28, 2020

(65) Prior Publication Data

US 2021/0094948 A1     Apr. 1, 2021

Related U.S. Application Data

(62) Division of application No. 15/789,588, filed on Oct. 20, 2017, now Pat. No. 10,647,713.

(60) Provisional application No. 62/560,610, filed on Sep. 19, 2017, provisional application No. 62/560,607, filed on Sep. 19, 2017, provisional application No. 62/546,422, filed on Aug. 16, 2017, provisional application No. 62/468,789, filed on Mar. 8, 2017, provisional application No. 62/468,728, filed on Mar. 8, 2017, provisional application No. 62/411,194, filed on Oct. 21, 2016.

(51) Int. Cl.
| | |
|---|---|
| *C07D 471/04* | (2006.01) |
| *C07D 473/36* | (2006.01) |
| *C07D 473/32* | (2006.01) |
| *C07D 473/28* | (2006.01) |
| *A61P 25/28* | (2006.01) |
| *A61P 35/02* | (2006.01) |
| *A61P 5/26* | (2006.01) |
| *A61P 3/10* | (2006.01) |
| *A61P 37/00* | (2006.01) |

(52) U.S. Cl.
CPC ............ *C07D 471/04* (2013.01); *A61P 3/10* (2018.01); *A61P 5/26* (2018.01); *A61P 25/28* (2018.01); *A61P 35/02* (2018.01); *A61P 37/00* (2018.01); *C07D 473/28* (2013.01); *C07D 473/32* (2013.01); *C07D 473/36* (2013.01)

(58) Field of Classification Search
CPC .. C07D 471/04; C07D 473/28; C07D 473/32; C07D 473/36; A61P 37/00; A61P 25/28; A61P 5/26; A61P 35/02; A61P 3/10
See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 5,360,819 A | 11/1994 | Giese |
| 5,516,931 A | 5/1996 | Giese et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 5,753,635 A | 5/1998 | Buckman et al. |
| 6,552,065 B2 | 4/2003 | Remiszewski et al. |
| 7,390,799 B2 | 6/2008 | Bruncko et al. |
| 8,138,347 B2 | 3/2012 | Knight et al. |
| 9,340,540 B2 | 5/2016 | Masse et al. |
| 9,630,970 B2 | 4/2017 | Masse et al. |
| 10,023,571 B2 | 7/2018 | Masse et al. |
| 10,196,390 B2 | 2/2019 | Masse et al. |
| 10,253,046 B2 | 4/2019 | Dahlgren et al. |
| 10,323,036 B2 | 6/2019 | Greenwood et al. |
| 10,336,752 B2 | 7/2019 | Greenwood et al. |
| 10,508,120 B2 | 12/2019 | Masse et al. |
| 10,562,906 B2 | 2/2020 | Masse et al. |
| 10,562,907 B2 | 2/2020 | Masse et al. |
| 10,570,145 B2 | 2/2020 | Masse et al. |
| 10,577,373 B2 | 3/2020 | Masse et al. |
| 10,647,713 B2 * | 5/2020 | Greenwood ............ A61P 35/02 |
| 10,781,204 B2 | 9/2020 | Masse et al. |
| 10,793,574 B2 | 10/2020 | Greenwood et al. |
| 10,968,236 B2 | 4/2021 | Masse et al. |
| 11,040,967 B2 | 6/2021 | Greenwood et al. |
| 11,046,698 B2 | 6/2021 | Masse et al. |
| 11,053,241 B2 | 7/2021 | Greenwood et al. |
| 11,174,264 B2 | 11/2021 | Masse |
| 11,220,508 B2 | 1/2022 | Greenwood et al. |
| 2003/0225278 A1 | 12/2003 | Ciszewski et al. |

(Continued)

FOREIGN PATENT DOCUMENTS

| | | |
|---|---|---|
| GB | 878646 A | 10/1961 |
| JP | H02273692 A | 11/1990 |

(Continued)

OTHER PUBLICATIONS

Kontzias; CurrOpin Pharmacol. 2012, 12, 464-470. doi: 10.1016/j.coph.2012.06.008 (Year: 2012).*

(Continued)

*Primary Examiner* — Daniel R Carcanague

(74) *Attorney, Agent, or Firm* — Andrea L. C. Reid; Joseph W. Arico; Dechert LLP

(57) ABSTRACT

The present invention provides compounds, compositions thereof, and methods of using the same for the inhibition of TYK2, and the treatment of TYK2-mediated disorders.

20 Claims, No Drawings

(56) References Cited

U.S. PATENT DOCUMENTS

| | | | |
|---|---|---|---|
| 2004/0110775 A1 | 6/2004 | Griffin et al. | |
| 2005/0043328 A1 | 2/2005 | Dolezal et al. | |
| 2007/0249639 A1* | 10/2007 | Baenteli | A61K 31/52 544/264 |
| 2008/0085898 A1* | 4/2008 | Lu | C07D 473/32 514/263.21 |
| 2008/0214580 A1* | 9/2008 | Neagu | C07D 473/18 514/263.2 |
| 2008/0261973 A1* | 10/2008 | Capraro | A61P 29/00 514/234.2 |
| 2010/0120797 A1 | 5/2010 | Eriksen et al. | |
| 2010/0311721 A1* | 12/2010 | Stadtmueller | A61P 35/00 514/263.22 |
| 2011/0224217 A1 | 9/2011 | Mortensen et al. | |
| 2011/0251172 A1 | 10/2011 | Rivkin et al. | |
| 2012/0122840 A1* | 5/2012 | Kumar | C07D 519/00 514/210.21 |
| 2012/0171199 A1 | 7/2012 | Dotson et al. | |
| 2013/0072506 A1 | 3/2013 | Zahajska et al. | |
| 2013/0096104 A1* | 4/2013 | Lai | A61P 29/00 514/210.21 |
| 2013/0143915 A1* | 6/2013 | Ellard | A61K 31/4196 546/119 |
| 2014/0228367 A1 | 8/2014 | Flynn | |
| 2015/0218155 A1 | 8/2015 | Heinrich et al. | |
| 2015/0266875 A1 | 9/2015 | Masse et al. | |
| 2016/0251376 A1 | 9/2016 | Dahlgren et al. | |
| 2017/0305933 A1 | 10/2017 | Dahlgren et al. | |
| 2018/0155349 A1 | 6/2018 | Greenwood et al. | |
| 2019/0031664 A1 | 1/2019 | Masse et al. | |
| 2019/0241575 A1 | 8/2019 | Masse et al. | |
| 2019/0241576 A1 | 8/2019 | Masse et al. | |
| 2019/0241577 A1 | 8/2019 | Masse et al. | |
| 2019/0248797 A1 | 8/2019 | Masse et al. | |
| 2019/0248810 A1 | 8/2019 | Dahlgren et al. | |
| 2019/0256519 A1 | 8/2019 | Masse et al. | |
| 2019/0284194 A1 | 9/2019 | Greenwood et al. | |
| 2020/0131201 A1* | 4/2020 | Masse | C07D 487/04 |
| 2020/0172540 A1* | 6/2020 | Greenwood | C07D 519/00 |
| 2020/0231594 A1* | 7/2020 | Masse | C07D 519/00 |
| 2021/0047319 A1 | 2/2021 | Masse et al. | |
| 2021/0238198 A1 | 8/2021 | Dahlgren et al. | |

FOREIGN PATENT DOCUMENTS

| | | | |
|---|---|---|---|
| WO | 199807725 A1 | 2/1998 | |
| WO | 2001009134 A1 | 2/2001 | |
| WO | WO-2001042246 | 6/2001 | |
| WO | WO-2002088112 | 11/2002 | |
| WO | 2003040144 A2 | 5/2003 | |
| WO | WO-2003063794 | 8/2003 | |
| WO | WO-2004019973 | 3/2004 | |
| WO | WO-2004089925 | 10/2004 | |
| WO | WO2004106328 | 12/2004 | |
| WO | WO-2005007623 | 1/2005 | |
| WO | 2005016528 A2 | 2/2005 | |
| WO | 2005028479 A2 | 3/2005 | |
| WO | 2005047524 A2 | 5/2005 | |
| WO | 2005113556 A1 | 12/2005 | |
| WO | WO-2005113554 | 12/2005 | |
| WO | WO-2006078846 | 7/2006 | |
| WO | WO-2006122806 | 11/2006 | |
| WO | WO-2007016176 | 2/2007 | |
| WO | WO-2007044729 | 4/2007 | |
| WO | WO-2007053452 | 5/2007 | |
| WO | WO-2007070514 | 6/2007 | |
| WO | WO-2007084786 | 7/2007 | |
| WO | WO-2007129161 | 11/2007 | |
| WO | WO-2008039218 | 4/2008 | |
| WO | 2008073687 A2 | 6/2008 | |
| WO | WO-2008109943 | 9/2008 | |
| WO | 2008116909 A1 | 10/2008 | |
| WO | WO-2008118802 | 10/2008 | |
| WO | 2009003428 A2 | 1/2009 | |
| WO | WO-2009114512 | 9/2009 | |
| WO | 2009143389 A1 | 11/2009 | |
| WO | WO-2011090760 | 7/2011 | |
| WO | 2011113802 A2 | 9/2011 | |
| WO | 2011149827 A1 | 12/2011 | |
| WO | 2012082997 A1 | 6/2012 | |
| WO | 2013037333 A1 | 3/2013 | |
| WO | WO-2014074660 A1 | 5/2014 | |
| WO | WO-2014074661 A1 | 5/2014 | |
| WO | WO-2014075393 A1 | 5/2014 | |
| WO | WO-2015089143 A1 | 6/2015 | |
| WO | WO-2015131080 A1 | 9/2015 | |
| WO | WO-2015144773 A1 * | 10/2015 | A61P 11/00 |
| WO | WO-2016022645 A1 | 2/2016 | |
| WO | 2016115434 A1 | 7/2016 | |
| WO | 2016130920 A2 | 8/2016 | |
| WO | 2016138352 A1 | 9/2016 | |
| WO | 2017040757 A1 | 3/2017 | |
| WO | WO-2018075937 A1 | 10/2017 | |
| WO | 2018071794 A1 | 4/2018 | |
| WO | WO-2018081488 A1 | 5/2018 | |
| WO | 2018165240 A1 | 9/2018 | |
| WO | 2019023468 A1 | 1/2019 | |
| WO | 2020081508 A1 | 4/2020 | |
| WO | 2020112937 A1 | 6/2020 | |
| WO | 2020154474 A1 | 7/2020 | |

OTHER PUBLICATIONS

Sanda; Cancer Discov. 2013, 3, 564-577. doi: 10.1158/2159-8290. CD-12-0504 (Year: 2013).*

Jang; Bioorg Med Chem Lett. 2015, 25, 3947-3952. doi: 10.1016/j.bmcl.2015.07.037. (Year: 2015).*

Ghoreschi; Immunol Rev. 2009, 228, 273-287. doi:10.1111/j.1600-065X.2008.00754.x (Year: 2009).*

Loza-Mejia; Journal of Molecular Graphics and Modelling 2009, 27, 900-907. DOI: 10.1016/j.jmgm.2009.02.001 (Year: 2009).*

Anastassiadis; Nature Biotechnology, 2011, 29, 1039-1046, and supplementary data tables, 86 pages, doi:10.1038/nbt.2017 (Year: 2011).*

Gehringer; ChemMedChem 2014, 9, 2516-2527. DOI: 10.1002/cmdc.201402252 (Year: 2014).*

Haim; Journal of Neuroscience, 2015, 35, 2817-2829. DOI: 10.1523/JNEUROSCI.3516-14.2015 (Year: 2015).*

Degryse; Journal of Hematology & Oncology 2015, 8, 91. doi: 10.1186/s13045-015-0192-7 (Year: 2015).*

Miao; Potent and Selective Tyk2 Inhibitors Block Th1- and Th17-Mediated Immune Responses and Reduce Disease Progression in Rodent Models of Delayed-Type Hypersensitivity and Psoriasis [abstract]. Arthritis Rheumatol. 2015; 67 (suppl 10). First published Sep. 29, 2015. (Year: 2015).*

Bajusz; J. Chem. Inf. Model. 2016, 56, 234-247. DOI: 10.1021/acs.jcim.5b00634 (Year: 2016).*

Roskoski; Pharmacological Research 2016, 111, 784-803.doi: 10.1016/j.phrs.2016.07.038 (Year: 2016).*

Chae; J Med Chem 1995, 38, 359-365. doi: 10.1021/jm00002a018 (Year: 1995).*

Ciszewski et al., "A Practical Synthesis of 2-Arylamino-6-alkylaminopurines from 2,6-Dichloropurine," Org. Process Res. Dev. 2006; 10(4): 799-802.

Kato et al., "Gene expression signatures and small-molecule compounds link a protein kinase to Plasmodium falciparum motility," Nat Chem Biol. 2008; 4(6): 347-356.

Liu et al., "Synthesis and Inhibitory Activity Evaluation of 2,6-Disubstituted Purine Derivatives," Journal of Heterocyclic Chemistry. 2015; 52: 473-477.

Lu et al., "Microwave assisted synthesis of 2,6-substituted aromatic-aminopurine derivatives," Journal of Heterocyclic Chemistry. 2011; 48(5): 1140-1144.

Supplementary European Search Report in EP17862825, dated Mar. 9, 2020 (11 pages).

Bacon et al., "Interleukin 12 (IL-12) induces tyrosine phosphorylation of Jak2 and Tyk2: differential use of Janus family kinases by IL-2 and IL-12," The Journal of Experimental Medicine, vol. 181, Jan. 1995 (pp. 399-404).

(56) References Cited

OTHER PUBLICATIONS

Ban et al., "Replication analysis identifies TYK2 as a multiple sclerosis susceptibility factor," European Journal of Human Genetics, vol. 17, Mar. 2009 (pp. 1309-1313).
Berge et al., "Pharmaceutical Salts," Journal of Pharmaceutical Sciences, vol. 66, No. 1, Jan. 1977 (pp. 1-19).
Cherkasov, "Synthesis of 8-trifluoromethylpurines," Chemistry of Heterocyclic Compounds, CAS Abstract, vol. 6, 1970, (pp. 1476-1477).
Cho et al., "Genomics and the multifactorial nature of human auto-immune disease," The New England Journal of Medicine, vol. 365, No. 17, Oct. 2011 (pp. 1612-1623).
Cortes et al., "Identification of multiple risk variants for ankylosing spondylitis through high-density genotyping of immune-related loci," Nature Genetics, vol. 14, No. 7, Jul. 2013 (pp. 730-738).
Duerr et al., "A Genome-Wide Association Study Identifies IL23R as an Inflammatory Bowel Disease Gene," Science, vol. 314, Dec. 2006 (pp. 1461-1463).
Finbloom et al., "IL-10 induces the tyrosine phosphorylation of Tyk2 and Jak1 and the differential assembly of Stat1 and Stat3 complexes in human T cells and monocytes," The Journal of Immunology, vol. 155, No. 3, Aug. 1995 (p. 1079-1090).
Fontan et al. "Discovering What Makes STAT Signaling TYK in T-ALL," Cancer Discovery, vol. 3, May 2013 (pp. 494-496).
Graham et al., "Association of NCF2, IKZF1, IRF8, IFIH1, and TYK2 with Systemic Lupus Erythematosus," PLoS Genetics, vol. 7, No. 10, Oct. 2011 (9 pages).
Harel et al., "Pharmacologic inhibition of JAK-STAT signaling promotes hair growth," Science Advances, vol. 1, No. 9, Oct. 2015 (12 pages).
Heinrich et al., "Fragment-Based Discovery of New Highly Substituted 1H-Pyrrolo[2,3-b]- and 3H-Imidazolo[4,5-b]-Pyridines as Focal Adhesion Kinase Inhibitors," J. Med. Chem., vol. 56, 2013 (pp. 1160-1170).
International Search Report and Written Opinion issued by the United States Patent and Trademark Office as Searching Authority for International Patent Application No. PCT/US2017/057676 dated Jan. 3, 2018 (9 pages).
Ishizaki et al., "Tyk2 deficiency protects joints against destruction in anti-type II collagen antibody-induced arthritis in mice," International Immunology, vol. 23, No. 9, Jul. 2011 (pp. 575-582).
Ishizaki et al., "Tyk2 is a therapeutic target for psoriasis-like skin inflammation," International Immunology, Dec. 2013 (11 pages).
Levenberg, "A method for the solution of certain non-linear problems in least squares," Quarterly of Applied Mathematics, vol. 2, 1944 (pp. 164-168).
National Center for Biotechnology Information. PubChem Database. SID 181849788, Source=ChemBridge, https://pubchenn.ncbi.nInn.nih.gov/substance/181849788 (accessed on Jun. 10, 2019) Available Jun. 9, 2014.
Norman, "Selective JAK1 inhibitor and selective Tyk2 inhibitor patents," Expert Opinion on Therapeutic Patents, vol. 22, 2012 (pp. 1233-1249).
Oyamada et al., "Tyrosine Kinase 2 Plays Critical Roles in the Pathogenic CD4 T Cell Responses for the Development of Experimental Autoimmune Encephalomyelitis," The Journal of Immunology, vol. 183, 2009, (pp. 7539-7546).
Parham et al., "A receptor for the heterodimeric cytokine IL-23 is composed of IL-12Rβ1 and a novel cytokine receptor subunit, IL-23R," The Journal of Immunology, vol. 168, 2002 (pp. 5699-5708).
PubChem, Compound Summary for CID 52000, Adenine, N-(o-methoxyphenyl)-, Mar. 27, 2005 (14 pages).
Ramirez et al., "Defining causative factors contributing in the activation of hedgehog signaling in diffuse large B-cell lymphoma," Leukemia Research, vol. 36, No. 10, Oct. 2012 (pp. 1267-1273).
Remmers et al., "Genome-wide association study identifies variants in the MHC class I, IL10, and IL23R-IL12RB2 regions associated with Behçet's disease," Nature Genetics, vol. 42, No. 8, Aug. 2010 (pp. 698-702).
Rostovtsev et al., "A Stepwise Huisgen Cycloaddition Process: Copper(I)-Catalyzed Regioselective "Ligation" of Azides and Terminal Alkynes," Angewandte Chemie International Edition, vol. 114, No. 14, 2002 (pp. 2708-2711).
Sanda et al. "TYK2-STAT1-BCL2 Pathway Dependence in T-Cell Acute Lymphoblastic Leukemia," Cancer Discovery, vol. 3, No. 5 May 2013 (pp. 564-577).
Sigurdsson et al., "Polymorphisms in the Tyrosine Kinase 2 and Interferon Regulatory Factor 5 Genes Are Associated with Systemic Lupus Erythematosus," The American Journal of Human Genetics, vol. 76, Jan. 2005 (pp. 528-537).
Simma et al. "Identification of an Indispensable Role for Tyrosine Kinase 2 in CTL-Mediated Tumor Surveillance," Cancer Research, vol. 69, No. 1, Jan. 2009 (pp. 203-211).
Stahl et al., "Association and activation of Jak-Tyk kinases by CNTF-LIF-OSM-IL-6β receptor components," Science, vo. 263, Jan. 1994 (pp. 92-95).
Strange et al., "A genome-wide association study identifies new psoriasis susceptibility loci and an interaction between HLA-C and ERAP1," Nature Genetics, vol. 42, No. 11, Nov. 2010 (pp. 985-992).
Sun et al., "Carbohydrate and Protein Immobilization onto Solid Surfaces by Sequential Diels—Alder and Azide—Alkyne Cycloadditions," Bioconjugate Chemistry, vol. 17, 2006 (pp. 52-57).
Supniewski, Dissertationes Pharmaceuticae, Abstract from CAS CAPLUS Database vol. 13, 1961 (pp. 127-130).
Susvilo et al., "A Novel and Efficient Synthesis of 6-Dialkylamino-9-benzyl-8- methoxypurines and 6-Dialkylamino-9-benzylpurin-8-ones by Reaction of Methyl N-Benzyl-N-(6-dialkylamino-5-nitropyrimidin-4-yl)glycinates with Sodium Alkoxides," Synlett, vol. 9, 2006 (pp. 1422-1424).
Temple et al., "Synthesis of potential anticancer agents: imidazo[4,5-c]pyridines and imidazo[4,5-b]pyridines," J. Med. Chem., vol. 30, 1987 (pp. 1746-1751).
Velasquez et al., "A protein kinase in the interferon α/β signaling pathway," Cell, vol. 70, Jul. 1992 (pp. 313-322).
Wan et al. "Tyk/STAT3 Signaling Mediates β-Amyloid-Induced Neuronal Cell Death: Implications in Alzheimer's Disease," The Journal of Neuroscience, vol. 30, No. 20, May 2010 (pp. 6873-6881).
Welham et al., "Interleukin-13 signal transduction in lymphohemopoietic cells: similarities and differences in signal transduction with interleukin-4 and insulin," The Journal of Biological Chemistry, vol. 270, No. 20, May 1995 (pp. 12286-12296).
Xing et al., "Alopecia areata is driven by cytotoxic T lymphocytes and is reversed by JAK inhibition," Nature Medicine, vol. 20, No. 9, Sep. 2014 (pp. 1043-1049).
Zhang et al., "Docking protein Gab2 regulates mucin expression and goblet cell hyperplasia through TYK2/STAT6 pathway," The FASEB Journal, vol. 26, 2012 (pp. 1-11).
De Roos et al., "Deazapurine derivatives.VII. Synthesis of substituted imidazo-and triazolo-pyridines," Recueil. 1971; 1166-1180.
PubChem, Pub Chern SID: 181849788, 2014.
Schelling et al., "Deazapurine derivatives XIII 5,7-Disubstituted imidazo[4,5-b]pyridines. A new synthesis of 1-deazaguanine," Recueil des Travaux Chimiques des Pays-Bas. 1974; 160-162.
Tedder et al., "Structure-based design, synthesis, and antimicrobial activity of purine derived SAH/MTA nucleosidase inhibitors," Bioorganic & Medicinal Chemistry Letters. 2004; 14(12): 3165-3168.
Itoh et al., "Synthetic studies of Potential Antimetabolites," 1972; 465-470.

\* cited by examiner

TYK2 INHIBITORS AND USES THEREOF

CROSS-REFERENCE TO RELATED APPLICATIONS

The present application is a divisional application of U.S. Ser. No. 15/789,588 filed on Oct. 20, 2017, now issued as U.S. Pat. No. 10,647,713, which claims the benefit of U.S. Provisional Application No. 62/560,607, filed Sep. 19, 2017, U.S. Provisional Application No. 62/560,610, filed Sep. 19, 2017, U.S. Provisional Application No. 62/546,422, filed Aug. 16, 2017, U.S. Provisional Application No. 62/468,728, filed Mar. 8, 2017, U.S. Provisional Application No. 62/468,789, filed Mar. 8, 2017, U.S. Provisional Application No. 62/411,194, filed Oct. 21, 2016, the entirety of each of which is incorporated herein by reference.

TECHNICAL FIELD OF THE INVENTION

The present invention relates to compounds and methods useful for inhibiting non-receptor tyrosine-protein kinase 2 ("TYK2"), also known as Tyrosine kinase 2. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is the protein kinase family.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxins, and $H_2O_2$), cytokines (e.g., interleukin-1 (IL-1), interleukin-8 (IL-8), and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by kinase-mediated events. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of TYK2 kinase.

Compounds of the present invention, and pharmaceutically acceptable compositions thereof, are useful for treating a variety of diseases, disorders or conditions, associated with regulation of signaling pathways implicating TYK2 kinases. Such diseases, disorders, or conditions include those described herein.

Compounds provided by this invention are also useful for the study of TYK2 enzymes in biological and pathological phenomena; the study of intracellular signal transduction pathways occurring in bodily tissues; and the comparative evaluation of new TYK2 inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention

Compounds of the present invention, and compositions thereof, are useful as inhibitors of TYK2 protein kinase.

The pseudokinase binding pocket of TYK2 contains a plurality of hydration sites, each of which is occupied by a single molecule of water. Each of these water molecules has a stability rating associated with it. As used herein, the term "stability rating" refers to a numerical calculation which incorporates the enthalpy, entropy, and free energy values associated with each water molecule. This stability rating allows for a measurable determination of the relative stability of water molecules that occupy hydration sites in the binding pocket of TYK2.

Water molecules occupying hydration sites in the binding pocket of TYK2 having a stability rating of >2.5 kcal/mol are referred to as "unstable waters."

Without wishing to be bound by any particular theory, it is believed that displacement or disruption of an unstable water molecule (i.e., a water molecule having a stability rating of >2.5 kcal/mol), or replacement of a stable water (i.e., a water molecule having a stability rating of <1 kcal/mol), by an inhibitor results in tighter binding of that inhibitor. Accordingly, inhibitors designed to displace one or more unstable water molecules (i.e., those unstable water molecules not displaced by any known inhibitor) will be a tighter binder and, therefore, more potent inhibitor as compared to an inhibitor that does not displace unstable water molecules.

It was surprisingly found that provided compounds displace or disrupt one or more unstable water molecules. In some embodiments, a provided compound displaces or disrupts at least two unstable water molecules.

In certain embodiments, the present invention provides a compound of formula I:

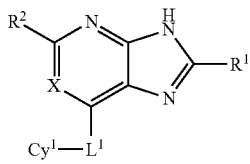

I or a pharmaceutically acceptable salt thereof, wherein each of X, $L^1$, $R^1$, $R^2$, and $Cy^1$ is as defined below and described in embodiments herein, both singly and in combination.

In certain embodiments, the present invention provides a compound of formula I':

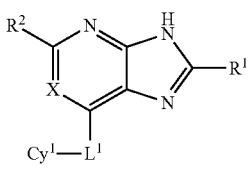

I' or a pharmaceutically acceptable salt thereof, wherein each of X, $L^1$, $R^1$, $R^2$, and $Cy^1$ is as defined below and described in embodiments herein, both singly and in combination.

In certain embodiments, the present invention provides a compound of formula X:

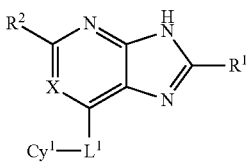

X or a pharmaceutically acceptable salt thereof, wherein each of X, $L^1$, $R^1$, $R^2$, and $Cy^1$ is as defined below and described in embodiments herein, both singly and in combination.

In some embodiments, the present invention provides a pharmaceutical composition comprising a compound of formula I, I', or X, and a pharmaceutically acceptable carrier, adjuvant, or diluent.

In some embodiments, the present invention provides a method of treating a TYK2-mediated disease, disorder, or condition comprising administering to a patient in need thereof, a compound of formula I, I', or X or a pharmaceutically acceptable salt thereof.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

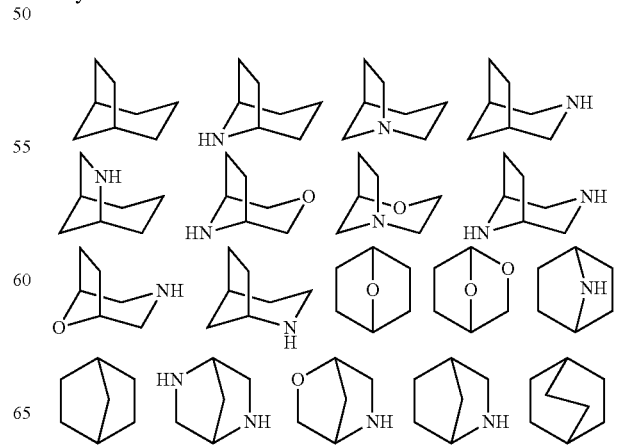

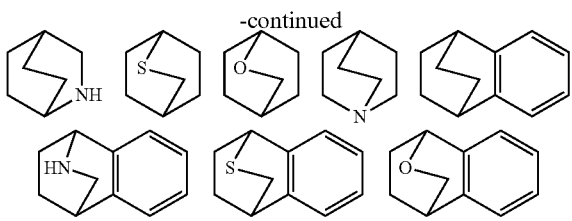

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR$; $-SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R$; $-N(R^\circ)S(O)_2NR^\circ_2$; $-N(R^\circ)S(O)_2R$; $-N(OR)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $-SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_1$-aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+$ ($C_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms. In certain embodiments, Ring B of a provided compound may be substituted with one or more deuterium atoms.

As used herein, the term "inhibitor" is defined as a compound that binds to and/or inhibits TYK2 with measurable affinity. In certain embodiments, an inhibitor has an IC$_{50}$ and/or binding constant of less than about 50 µM, less than about 1 µM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethyl-rhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a TYK2 protein kinase activity between a sample comprising a compound of the present invention, or composition thereof, and a TYK2 protein kinase, and an equivalent sample comprising an TYK2 protein kinase, in the absence of said compound, or composition thereof.

3. Description of Exemplary Embodiments

As described above, in certain embodiments, the present invention provides a compound of formula I:

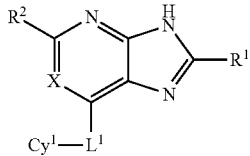

I or a pharmaceutically acceptable salt thereof, wherein:
X is N or C($R^3$);
$R^1$ is D, R, $R^D$, —$NR_2$, —$NRR^D$, —$N(R^D)_2$, —OR, or —$OR^D$;
$R^2$ is H, $R^C$, —N(R)C(O)$Cy^2$, —N(R)S(O)$_2Cy^2$, —N(R)$Cy^2$, —$OCy^2$, —$SCy^2$, or $Cy^2$;
$R^3$ is H, halogen, or $C_{1-6}$ aliphatic; or
$R^2$ and $R^3$ are taken together with their intervening atoms to form a 4-7 membered partially unsaturated or aromatic ring having 0-3 heteroatoms independently selected from nitrogen, oxygen, and sulfur; wherein said ring is substituted with m instances of $R^4$;
each of $Cy^1$ and $Cy^2$ is independently phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein $Cy^1$ is substituted with n instances of $R^5$; and; wherein $Cy^2$ is substituted with p instances of $R^6$;
$L^1$ is a covalent bond or a $C_{1-4}$ bivalent saturated or unsaturated, straight or branched hydrocarbon chain wherein one or two methylene units of the chain are optionally and independently replaced by —C($R^7$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;
each instance of $R^4$, $R^5$, $R^6$, and $R^7$ is independently $R^A$ or $R^B$, and is substituted by q instances of $R^C$;
each instance of $R^A$ is independently oxo, halogen, —CN, —$NO_2$, —OR, —$OR^D$, —SR, —$NR_2$, —S(O)$_2$R, —S(O)$_2NR_2$, —S(O)R, —S(O)$NR_2$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)C(NR)$NR_2$, —N(R)S(O)$_2NR_2$, or —N(R)S(O)$_2$R;
each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;
each instance of $R^C$ is independently oxo, halogen, —CN, —$NO_2$, —OR, —SR, —$NR_2$, —S(O)$_2$R, —S(O)$_2NR_2$, —S(O)R, —S(O)$NR_2$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)C(NR)$NR_2$, —N(R)S(O)$_2NR_2$, or —N(R)S(O)$_2$R or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
$R^D$ is a $C_{1-4}$ aliphatic group wherein one or more hydrogens are replaced by deuterium;
each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and
each of m, n, p, and q is independently 0, 1, 2, 3, or 4.

As described above, in certain embodiments, the present invention provides a compound of formula I':

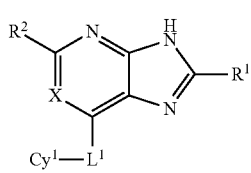

I' or a pharmaceutically acceptable salt thereof, wherein:

X is N or C(R$^3$);

R$^1$ is D, R, R$^D$, —NR$_2$, —NRR$^D$, —N(R$^D$)$_2$, —OR, or —OR$^D$;

R$^2$ is H, R$^C$, —N(R)C(O)Cy$^2$, —N(R)S(O)$_2$Cy$^2$, —N(R)Cy$^2$, —OCy$^2$, —SCy$^2$, or Cy$^2$;

R$^3$ is H, halogen, or C$_{1-6}$ aliphatic; or

R$^2$ and R$^3$ are taken together with their intervening atoms to form a 4-7 membered partially unsaturated or aromatic ring having 0-3 heteroatoms independently selected from nitrogen, oxygen, and sulfur; wherein said ring is substituted with m instances of R$^4$;

each of Cy$^1$ and Cy$^2$ is independently phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein Cy$^1$ is substituted with n instances of R$^5$; and; wherein Cy$^2$ is substituted with p instances of R$^6$;

L$^1$ is a covalent bond or a C$_{1-4}$ bivalent saturated or unsaturated, straight or branched hydrocarbon chain wherein one or two methylene units of the chain are optionally and independently replaced by —C(R$^7$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

each instance of R$^4$, R$^5$, R$^6$, and R$^7$ is independently R$^A$ or R$^B$, and is substituted by q instances of R$^C$;

each instance of R$^A$ is independently oxo, halogen, —CN, —NO$_2$, —OR, —OR$^D$, —SR, —NR$_2$, —S(O)$_2$R, —S(O)(NR)R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —N(R$^D$)S(O)$_2$R, —N(R)S(O)$_2$R$^D$, —N(R$^D$)S(O)$_2$R$^D$, or —P(O)R$_2$;

each instance of R$^B$ is independently C$_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of R$^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

R$^D$ is a C$_{1-4}$ aliphatic group wherein one or more hydrogens are replaced by deuterium;

each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and each of m, n, p, and q is independently 0, 1, 2, 3, or 4.

As defined generally above, X is N or C(R$^3$). In some embodiments, X is N. In some embodiments, X is C(R$^3$). In some embodiments, X is C(H). In some embodiments, X is C(R$^3$), where R$^3$ is halogen. In some embodiments, X is C(R$^3$), where R$^3$ is fluoro.

As defined generally above, R$^1$ is D, R, R$^D$, —NR$_2$, —NRR$^D$, —N(R$^D$)$_2$, —OR, or —OR$^D$. In some embodiments, R$^1$ is D. In some embodiments, R$^1$ is R. In some embodiments, R$^1$ is R$^D$. In some embodiments, R$^1$ is —NR$_2$. In some embodiments, R$^1$ is —NRR$^D$. In some embodiments, R$^1$ is —N(R$^D$)$_2$. In some embodiments, R$^1$ is —OR. In some embodiments, R$^1$ is —OR$^D$. In some embodiments, R$^1$ is an optionally substituted C$_{1-6}$ aliphatic group. In some embodiments, R$^1$ is an optionally substituted ethyl group. In some embodiments, R$^1$ is hydrogen, methyl or —CD$_3$. In some embodiments, R$^1$ is hydrogen. In some embodiments, R$^1$ is methyl or —CD$_3$. In some embodiments, R$^1$ is methyl. In some embodiments, R$^1$ is —CD$_3$. In some embodiments, R$^1$ is —OCH$_3$. In some embodiments, R$^1$ is D, R, R$^D$, —NR$_2$, —NRR$^D$, —N(R$^D$)$_2$, —OR, or —OR$^D$, wherein R$^1$ is not hydrogen. In some embodiments, R$^1$ is —CH$_2$F, —CHF$_2$, or —CF$_3$. In some embodiments, R$^1$ is —CHF$_2$.

As defined generally above, R$^2$ is H, R$^C$, —N(R)C(O)Cy$^2$, —N(R)Cy$^2$, —OCy$^2$, —SCy$^2$, or Cy$^2$. In some embodiments, R$^2$ is H. In some embodiments, R$^2$ is R$^C$, —N(R)C(O)Cy$^2$, —N(R)Cy$^2$, —OCy$^2$, —SCy$^2$, or Cy$^2$. In some embodiments, R$^2$ is R$^C$. In some embodiments, R$^2$ is —N(R)C(O)R. In some embodiments, R$^2$ is —N(R)C(O)Cy$^2$, —N(R)Cy$^2$, or Cy$^2$. In some embodiments, R$^2$ is —N(R)C(O)R, —N(R)C(O)Cy$^2$, —N(R)Cy$^2$, or Cy$^2$. In some embodiments, R$^2$ is —N(H)C(O)R, —N(H)C(O)Cy$^2$, —N(H)Cy$^2$, or Cy$^2$. In some embodiments, R$^2$ is —N(H)C(O)R, —N(H)C(O)Cy$^2$, or —N(H)Cy$^2$. In some embodiments, R$^2$ is —N(H)C(O)R. In some embodiments, R$^2$ is —N(H)C(O)R wherein R in this instance is optionally substituted C$_{1-6}$ aliphatic. In some embodiments, R$^2$ is —N(H)C(O)Cy$^2$. In some embodiments, R$^2$ is —N(H)Cy$^2$. In some embodiments, R$^2$ is —N(H)C(O)Cy$^2$ where Cy$^2$ is cyclopropyl. In some embodiments, R$^2$ is

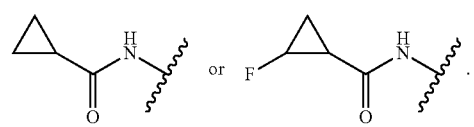 [SMILES: *NC(=O)C1CC1 ; *NC(=O)C1CC1F]

As defined generally above, R$^3$ is H, halogen, or C$_{1-6}$ aliphatic. In some embodiments, R$^3$ is H. In some embodiments, $R^3$ is halogen, or $C_{1-6}$ aliphatic. In some embodiments, $R^3$ is halogen. In some embodiments, $R^3$ is fluoro. In some embodiments, $R^3$ is $C_{1-6}$ aliphatic.

In some embodiments, $R^2$ and $R^3$ are taken together with their intervening atoms to form a 4-7 membered partially unsaturated or aromatic ring having 0-3 heteroatoms independently selected from nitrogen, oxygen, and sulfur; wherein said ring is substituted with m instances of $R^4$. In some embodiments, $R^2$ and $R^3$ are taken together with their intervening atoms to form a 5-membered partially unsaturated or aromatic ring having 1-3 heteroatoms independently selected from nitrogen, oxygen, and sulfur; wherein said ring is substituted with m instances of $R^4$.

As defined generally above, $Cy^1$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein $Cy^1$ is substituted with n instances of $R^5$.

In some embodiments, $Cy^1$ is phenyl. In some embodiments, $Cy^1$ is a 5-6 membered heteroaryl having 1-4 heteroatoms independently selected from nitrogen, oxygen, and sulfur. In some embodiments, $Cy^1$ is a 5-membered heteroaryl having 1-4 heteroatoms independently selected from nitrogen, oxygen, and sulfur. In some embodiments, $Cy^1$ is a 6-membered heteroaryl having 1-4 nitrogens. In some embodiments, $Cy^1$ is pyridyl. In some embodiments, $Cy^1$ is pyrazinyl. In some embodiments, $Cy^1$ is pyrimidinyl. In some embodiments, $Cy^1$ is triazinyl. In some embodiments, $Cy^1$ is pyrrolyl, pyrazolyl, imidazolyl, triazolyl, or tetrazolyl. In some embodiments, $Cy^1$ is furanyl, oxazolyl, isoxazolyl, or oxadiazolyl, In some embodiments, $Cy^1$ is thiophenyl, thiazolyl, isothiazolyl, or thiadiazolyl. In some embodiments, $Cy^1$ is an 8-10 membered bicyclic heteroaryl ring having 1-4 heteroatoms independently selected from nitrogen, oxygen, and sulfur. In some embodiments, $Cy^1$ is a 3-7 membered saturated or partially unsaturated heterocyclic ring having 1-2 heteroatoms independently selected from nitrogen, oxygen, and sulfur. In some embodiments, $Cy^1$ is a 3-7 membered saturated or partially unsaturated monocyclic carbocyclic ring. In some embodiments, $Cy^1$ is a 7-12 membered saturated or partially unsaturated bicyclic heterocyclic ring having 1-4 heteroatoms independently selected from nitrogen, oxygen, and sulfur.

In some embodiments, $Cy^1(R^5)_n$ taken together is selected from the following:

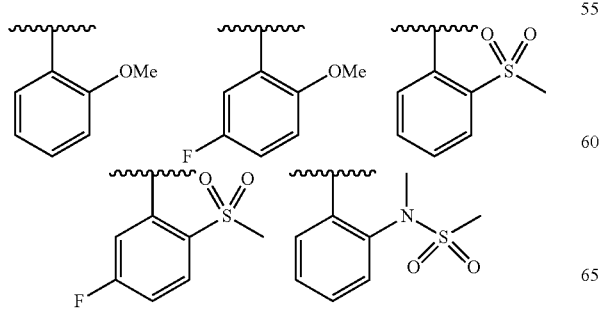

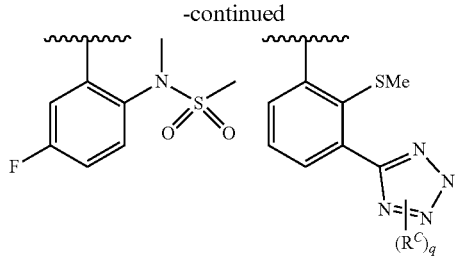

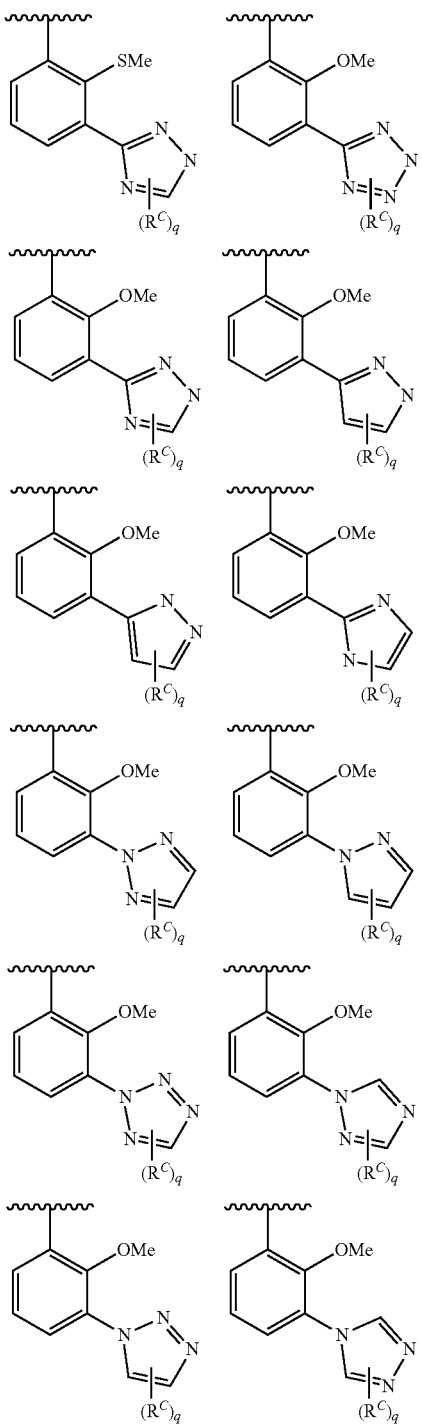

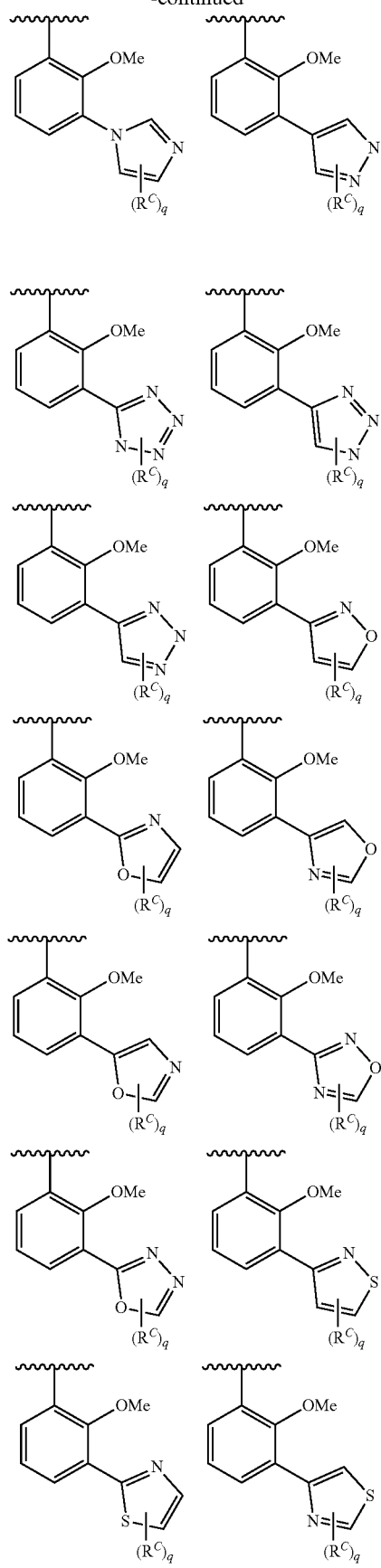
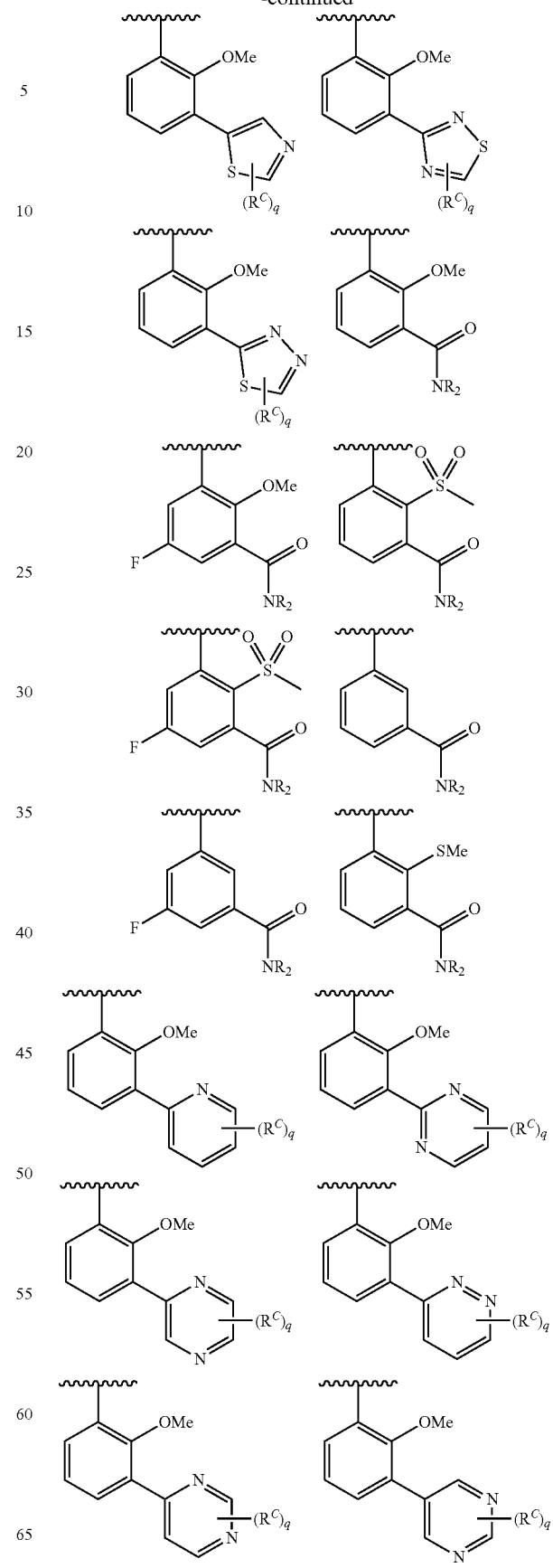

-continued
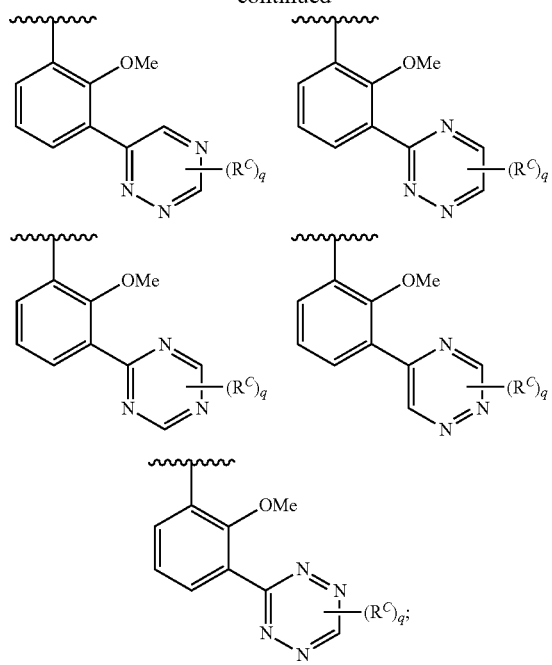
wherein each of R, $R^C$, and q is as defined above and described in embodiments herein, both singly and in combination.
In some embodiments, $Cy^1(R^5)_n$ taken together is selected from the groups in the preceding paragraph and the following groups:
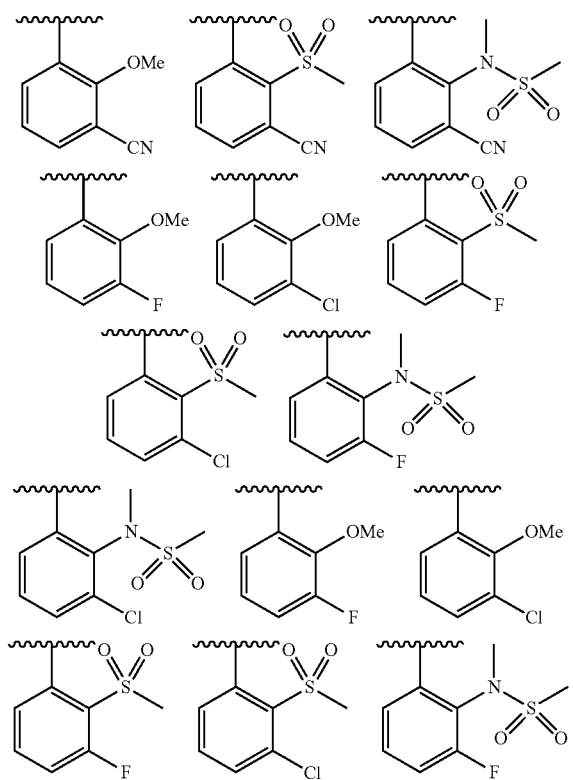
-continued
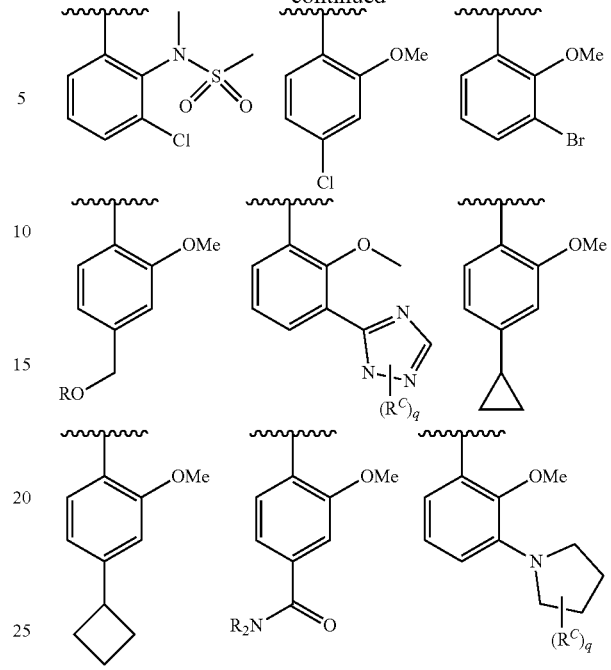
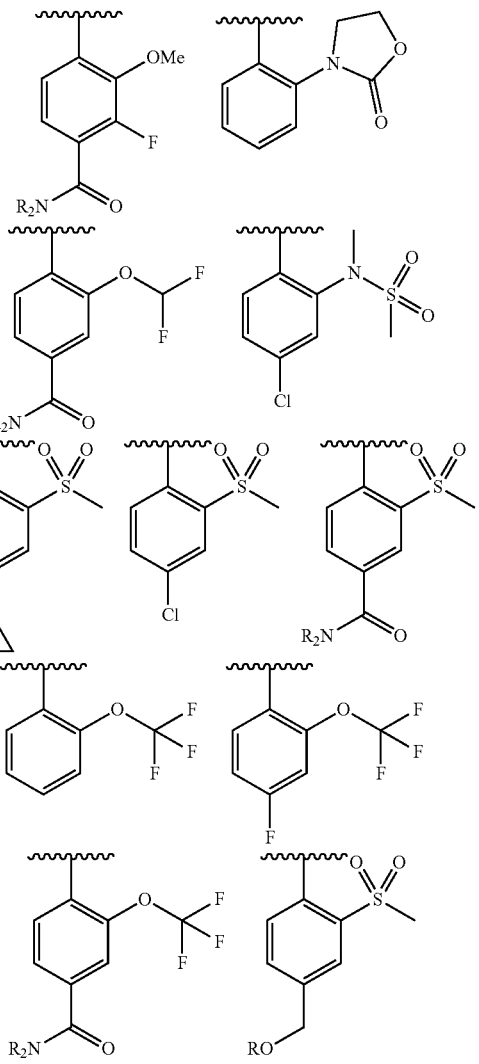

-continued

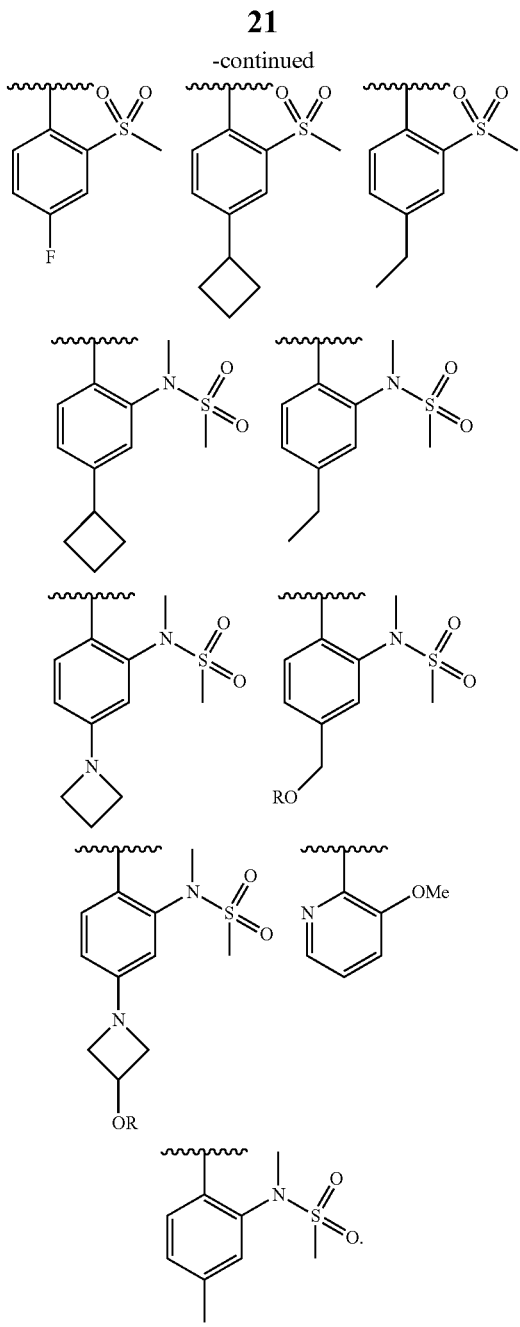

In some embodiments, Cy$^1$(R$^5$)$_n$ taken together is selected from the groups in the preceding paragraphs and the following groups:

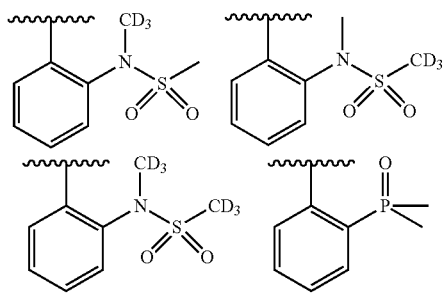

-continued

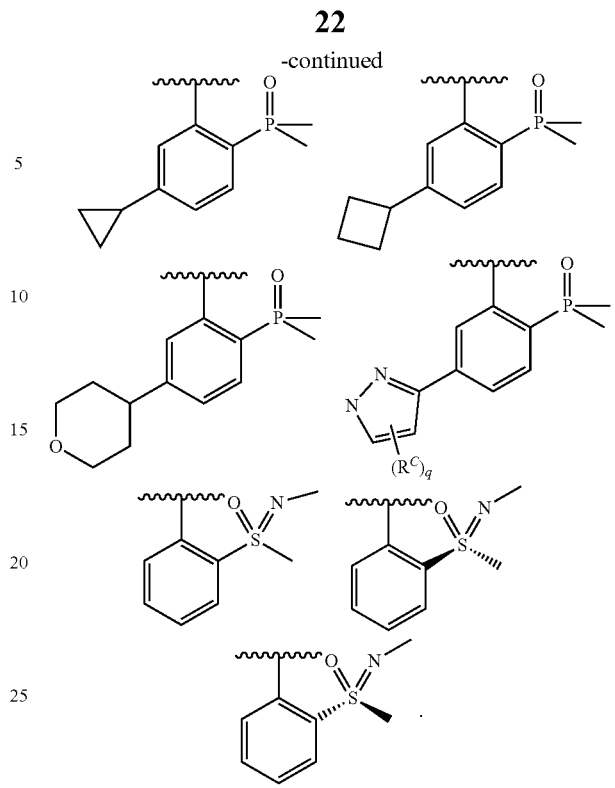

As defined generally above, Cy$^2$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein Cy$^2$ is substituted with p instances of R$^6$.

In some embodiments, Cy$^2$ is phenyl. In some embodiments, Cy$^2$ is a 5-6 membered heteroaryl having 1-4 heteroatoms independently selected from nitrogen, oxygen, and sulfur. In some embodiments, Cy$^2$ is a 5-membered heteroaryl having 1-4 heteroatoms independently selected from nitrogen, oxygen, and sulfur. In some embodiments, Cy$^2$ is a 6-membered heteroaryl having 1-4 nitrogens. In some embodiments, Cy$^2$ is pyridyl. In some embodiments, Cy$^2$ is pyrazinyl. In some embodiments, Cy$^2$ is pyrimidinyl. In some embodiments, Cy$^2$ is triazinyl. In some embodiments, Cy$^2$ is pyrrolyl, pyrazolyl, imidazolyl, triazolyl, or tetrazolyl. In some embodiments, Cy$^2$ is furanyl, oxazolyl, isoxazolyl, or oxadiazolyl. In some embodiments, Cy$^2$ is thiophenyl, thiazolyl, isothiazolyl, or thiadiazolyl. In some embodiments, Cy$^2$ is an 8-10 membered bicyclic heteroaryl ring having 1-4 heteroatoms independently selected from nitrogen, oxygen, and sulfur. In some embodiments, Cy$^2$ is a 3-7 membered saturated or partially unsaturated heterocyclic ring having 1-2 heteroatoms independently selected from nitrogen, oxygen, and sulfur. In some embodiments, Cy$^2$ is a 3-7 membered saturated or partially unsaturated monocyclic carbocyclic ring. In some embodiments, Cy$^2$ is C$_{3-7}$ cycloalkyl. In some embodiments, Cy$^2$ is cyclopropyl. In some embodiments, Cy$^2$ is a 7-12 membered saturated or partially unsaturated bicyclic heterocyclic ring having 1-4 heteroatoms independently selected from nitrogen, oxygen, and sulfur.

In some embodiments, Cy² is selected from the following, each of which is substituted by p instances of R⁶:

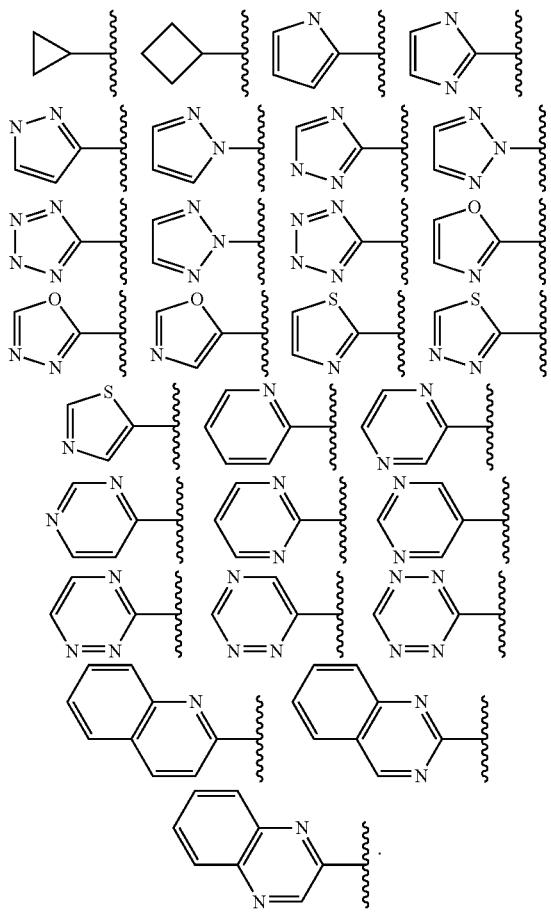

In some embodiments, Cy² is selected from the groups in the preceding paragraph or from the following, each of which is substituted by p instances of R⁶:

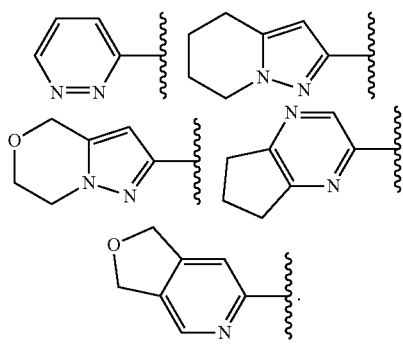

As defined generally above, $L^1$ is a covalent bond or a $C_{1-4}$ bivalent saturated or unsaturated, straight or branched hydrocarbon chain wherein one or two methylene units of the chain are optionally and independently replaced by —C(R⁷)₂—, —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—. In some embodiments, $L^1$ is a covalent bond. In some embodiments, $L^1$ is a $C_{1-4}$ bivalent saturated or unsaturated, straight or branched hydrocarbon chain wherein one or two methylene units of the chain are optionally and independently replaced by —C(R⁷)₂—, —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—. In some embodiments, $L^1$ is —N(R)—. In some embodiments, $L^1$ is —N(H)—.

As defined generally above, m is 0, 1, 2, 3, or 4. In some embodiments, m is 0. In some embodiments, m is 1, 2, 3, or 4. In some embodiments, m is 1. In some embodiments, m is 2. In some embodiments, m is 3. In some embodiments, m is 4.

As defined generally above, n is 0, 1, 2, 3, or 4. In some embodiments, n is 0. In some embodiments, n is 1, 2, 3, or 4. In some embodiments, n is 1. In some embodiments, n is 2. In some embodiments, n is 3. In some embodiments, n is 4.

As defined generally above, p is 0, 1, 2, 3, or 4. In some embodiments, p is 0. In some embodiments, p is 1, 2, 3, or 4. In some embodiments, p is 1. In some embodiments, p is 2. In some embodiments, p is 3. In some embodiments, p is 4.

In some embodiments, the present invention provides a compound of formula I or I', wherein $L^1$ is —N(H)—, thereby forming a compound of formula I-a:

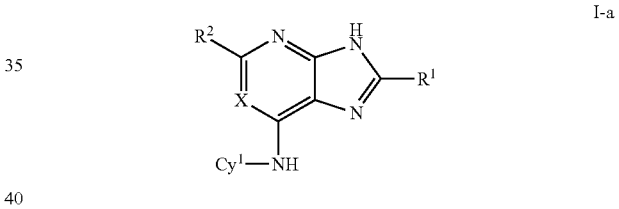

or a pharmaceutically acceptable salt thereof, wherein each of X, Cy¹, R¹, and R² is as defined above and described in embodiments herein, both singly and in combination.

In some embodiments, the present invention provides a compound of formula I or I', wherein X is N or C(R³), thereby forming a compound of formulas I-b or I-c respectively:

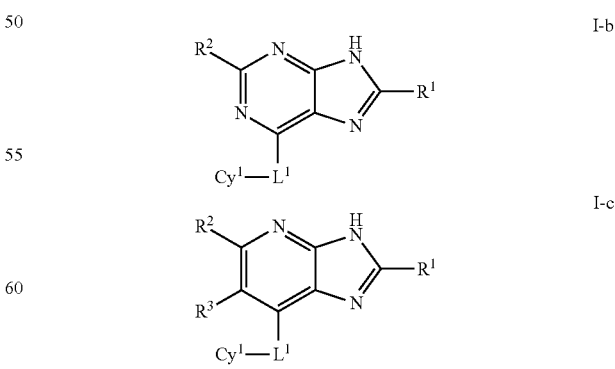

or a pharmaceutically acceptable salt thereof, wherein each of Cy¹, L¹, R¹, R², and R³ is as defined above and described in embodiments herein, both singly and in combination.

In some embodiments, the present invention provides a compound of formula I-a, wherein $L^1$ is N or $C(R^3)$, thereby forming a compound of formulas II-a or II-b respectively:

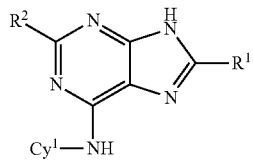

II-a

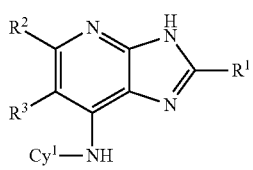

II-b or a pharmaceutically acceptable salt thereof, wherein each of $Cy^1$, $R^1$, $R^2$, and $R^3$ is as defined above and described in embodiments herein, both singly and in combination.

In some embodiments, the present invention provides a compound of formula II-a or II-b wherein $Cy^1$ is phenyl, thereby forming a compound of formulas III-a or III-b respectively:

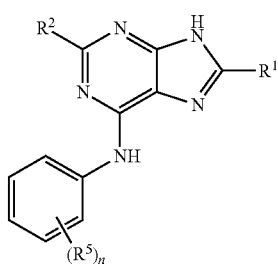

III-a

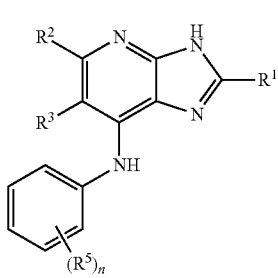

III-b or a pharmaceutically acceptable salt thereof, wherein each of $R^1$, $R^2$, $R^3$, $R^5$, and n is as defined above and described in embodiments herein, both singly and in combination.

In some embodiments, the present invention provides a compound of formula III-a or III-b, wherein n is 1, 2 or 3, and at least one instance of $R^5$ is ortho to the NH point of attachment, thereby forming a compound of formulas IV-a or IV-b respectively:

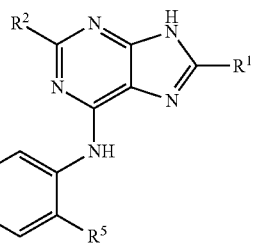

IV-a

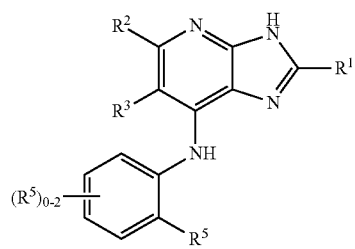

IV-b or a pharmaceutically acceptable salt thereof, wherein each of $R^1$, $R^2$, $R^3$, and $R^5$ is as defined above and described in embodiments herein, both singly and in combination.

In some embodiments, the present invention provides a compound of formula IV-a or IV-b, wherein the ortho $R^5$ group is —OR, —S(O)$_2$R, —C(O)NR$_2$, or —N(R)S(O)$_2$R, thereby forming a compound of formulas V-a, V-b, V-c, V-d, V-e, V-f, V-g, or V-h respectively:

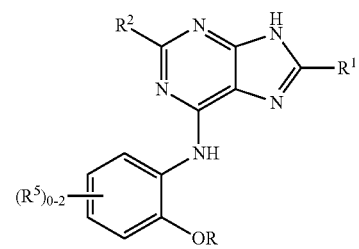

V-a

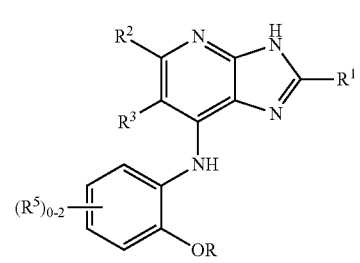

V-b

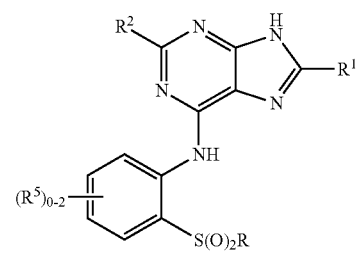

V-c

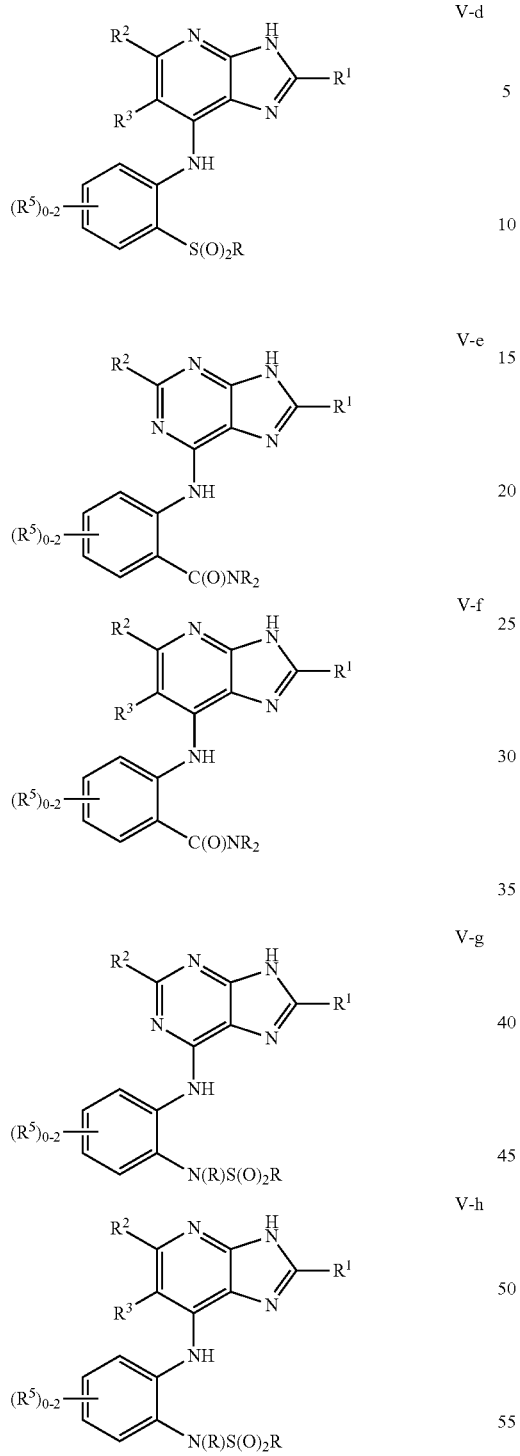

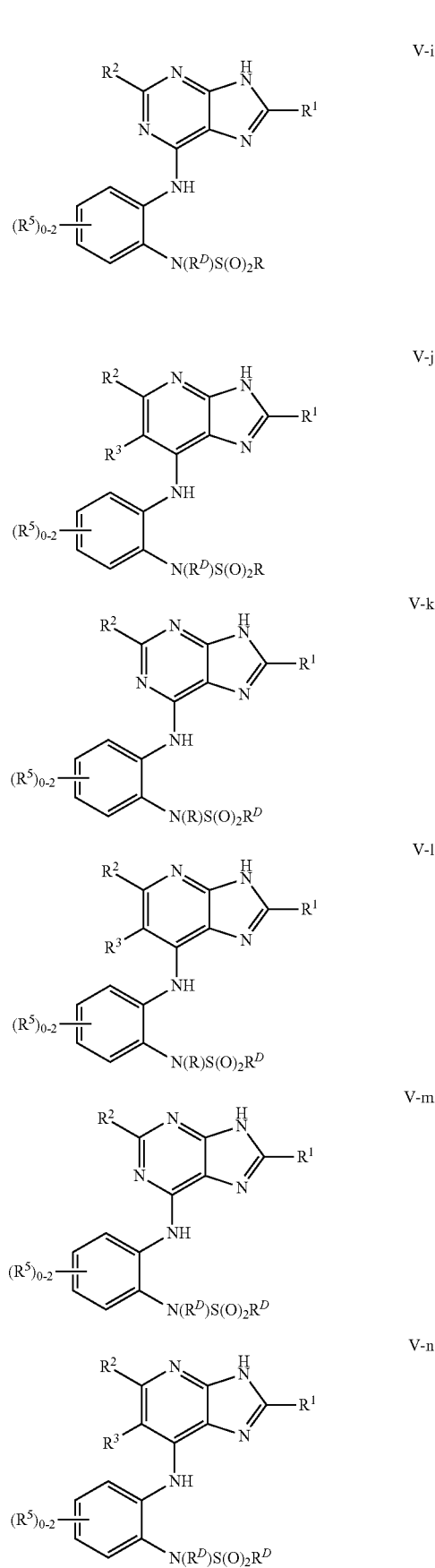

or a pharmaceutically acceptable salt thereof, wherein each of R, $R^1$, $R^2$, $R^3$, and $R^5$ is as defined above and described in embodiments herein, both singly and in combination.

In some embodiments, the present invention provides a compound of formula IV-a or IV-b, wherein the ortho $R^5$ group is —N($R^D$)S(O)$_2$R, —N(R)S(O)$_2R^D$, —N($R^D$)S(O)$_2$ $R^D$, —S(O)(NR)R, or —P(O)R$_2$, thereby forming a compound of formulas V-i, V-j, V-k, V-l, V-m, V-n, V-o, V-p, V-q or V-r respectively:

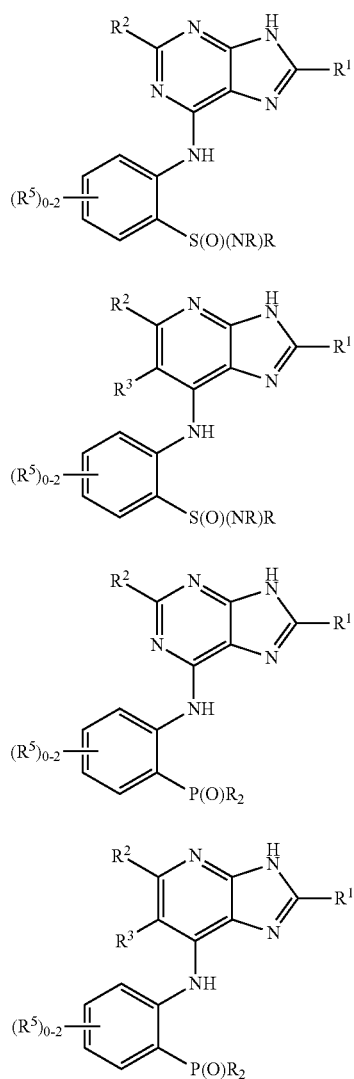

V-o

V-p

V-q

V-r or a pharmaceutically acceptable salt thereof, wherein each of R, $R^1$, $R^2$, $R^3$, and $R^5$ is as defined above and described in embodiments herein, both singly and in combination.

In some embodiments, the present invention provides a compound of formula V-a or V-b, wherein a second $R^5$ group ($R^{5b}$) is meta to the NH point of attachment, thereby forming a compound of formula VI-a, or VI-b respectively:

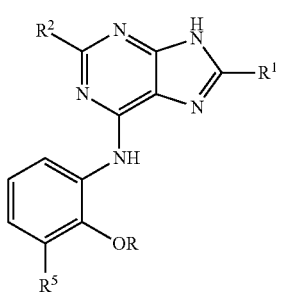

VI-a

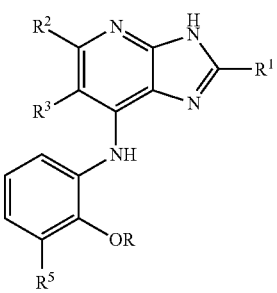

VI-b or a pharmaceutically acceptable salt thereof, wherein each of R, $R^1$, $R^2$, $R^3$, and $R^5$ is as defined above and described in embodiments herein, both singly and in combination.

In some embodiments, the present invention provides a compound of formula VI-a or VI-b, wherein $R^5$ is $R^B$. In some embodiments, the present invention provides a compound of formula VI-a or VI-b, wherein $R^5$ is —C(O)NR$_2$ or a 5-6 membered monocyclic heteroaryl ring having 1-4 heteroatoms independently selected from nitrogen, oxygen, and sulfur, said ring being substituted by q instances of $R^C$.

In some embodiments, the present invention provides a compound of formula VI-a or VI-b, wherein —OR is methoxy, fluoromethoxy, or difluoromethoxy.

In some embodiments, the present invention provides a compound of formula II-a or II-b wherein $Cy^1$ is pyridyl, n is 2, and one instance of $R^5$ is oxo, thereby forming a pyridone compound of formulas VII-a or VII-b respectively:

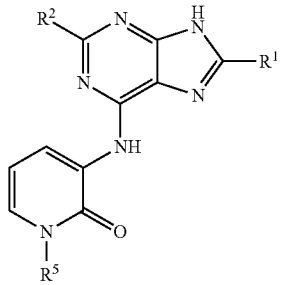

VII-a

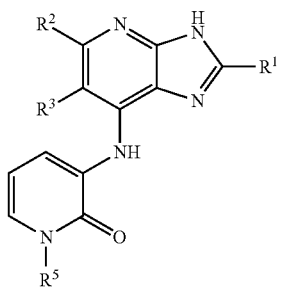

VII-b or a pharmaceutically acceptable salt thereof, wherein each of $R^1$, $R^2$, $R^3$, and $R^5$, is as defined above and described in embodiments herein, both singly and in combination.

In some embodiments, the present invention provides a compound of formula I or I' wherein $R^1$ is —CHF$_2$, thereby forming a compound of formula VIII:

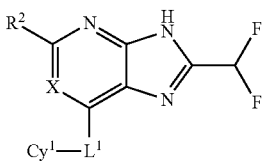

VIII or a pharmaceutically acceptable salt thereof, wherein each of X, $L^1$, $R^2$, and $Cy^1$ is as defined above and described in embodiments herein, both singly and in combination.

In some embodiments, the present invention provides a compound of formula VIII wherein $L^1$ is —NH—, thereby forming a compound of formula IX:

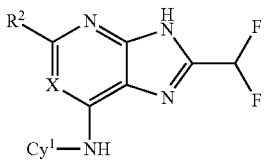

IX or a pharmaceutically acceptable salt thereof, wherein each of X, $R^2$, and $Cy^1$ is as defined above and described in embodiments herein, both singly and in combination.

As described above, in certain embodiments, the present invention provides a compound of formula X:

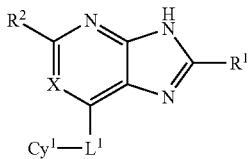

X or a pharmaceutically acceptable salt thereof, wherein:
X is N or $C(R^3)$;
$R^1$ is —$CH_2F$, —$CHF_2$, or —$CF_3$;
$R^2$ is H, $R^C$, —N(R)C(O)$Cy^2$, —N(R)S(O)$_2$$Cy^2$, —N(R)$Cy^2$, —O$Cy^2$, —S$Cy^2$, or $Cy^2$;
$R^3$ is H, halogen, or $C_{1-6}$ aliphatic; or
$R^2$ and $R^3$ are taken together with their intervening atoms to form a 4-7 membered partially unsaturated or aromatic ring having 0-3 heteroatoms independently selected from nitrogen, oxygen, and sulfur; wherein said ring is substituted with m instances of $R^4$;
each of $Cy^1$ and $Cy^2$ is independently phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein $Cy^1$ is substituted with n instances of $R^5$; and; wherein $Cy^2$ is substituted with p instances of $R^6$;

$L^1$ is a covalent bond or a $C_{1-4}$ bivalent saturated or unsaturated, straight or branched hydrocarbon chain wherein one or two methylene units of the chain are optionally and independently replaced by —$C(R^7)_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

each instance of $R^4$, $R^5$, $R^6$, and $R^7$ is independently $R^A$ or $R^B$, and is substituted by q instances of $R^C$;

each instance of $R^A$ is independently oxo, halogen, —CN, —$NO_2$, —OR, —$OR^D$, —SR, —$NR_2$, —S(O)$_2$R, —S(O)$_2$$NR_2$, —S(O)R, —S(O)$NR_2$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)C(NR)$NR_2$, —N(R)S(O)$_2$$NR_2$, or —N(R)S(O)$_2$R;

each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of $R^C$ is independently oxo, halogen, —CN, —$NO_2$, —OR, —SR, —$NR_2$, —S(O)$_2$R, —S(O)$_2$$NR_2$, —S(O)R, —S(O)$NR_2$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)C(NR)$NR_2$, —N(R)S(O)$_2$$NR_2$, or —N(R)S(O)$_2$R or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^D$ is a $C_{1-4}$ aliphatic group wherein one or more hydrogens are replaced by deuterium;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and each of m, n, p, and q is independently 0, 1, 2, 3, or 4.

As defined generally above, X is N or $C(R^3)$. In some embodiments, X is N. In some embodiments, X is $C(R^3)$. In some embodiments, X is C(H). In some embodiments, X is $C(R^3)$, where $R^3$ is halogen. In some embodiments, X is $C(R^3)$, where $R^3$ is fluoro.

As defined generally above, $R^1$ is —$CH_2F$, —$CHF_2$, or —$CF_3$. In some embodiments, $R^1$ is —$CHF_2$.

As defined generally above, $R^2$ is H, $R^C$, —N(R)C(O)$Cy^2$, —N(R)$Cy^2$, —O$Cy^2$, —S$Cy^2$, or $Cy^2$. In some embodiments, $R^2$ is H. In some embodiments, $R^2$ is $R^C$, —N(R)C(O)$Cy^2$, —N(R)$Cy^2$, —O$Cy^2$, —S$Cy^2$, or $Cy^2$. In some embodiments, R² is R^C. In some embodiments, R² is —N(R)C(O)R. In some embodiments, R² is —N(R)C(O)Cy², —N(R)Cy², or Cy². In some embodiments, R² is —N(R)C(O)R, —N(R)C(O)Cy², —N(R)Cy², or Cy². In some embodiments, R² is —N(H)C(O)R, —N(H)C(O)Cy², —N(H)Cy², or Cy². In some embodiments, R² is —N(H)C(O)R, —N(H)C(O)Cy², or —N(H)Cy². In some embodiments, R² is —N(H)C(O)R. In some embodiments, R² is —N(H)C(O)R wherein R in this instance is optionally substituted C$_{1-6}$ aliphatic. In some embodiments, R² is —N(H)C(O)Cy². In some embodiments, R² is —N(H)Cy². In some embodiments, R² is —N(H)C(O)Cy² where Cy² is cyclopropyl. In some embodiments, R² is

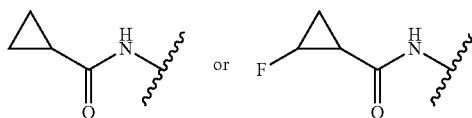

As defined generally above, R³ is H, halogen, or C$_{1-6}$ aliphatic. In some embodiments, R³ is H. In some embodiments, R³ is halogen, or C$_{1-6}$ aliphatic. In some embodiments, R³ is halogen. In some embodiments, R³ is fluoro. In some embodiments, R³ is C$_{1-6}$ aliphatic.

In some embodiments, R² and R³ are taken together with their intervening atoms to form a 4-7 membered partially unsaturated or aromatic ring having 0-3 heteroatoms independently selected from nitrogen, oxygen, and sulfur; wherein said ring is substituted with m instances of R⁴. In some embodiments, R² and R³ are taken together with their intervening atoms to form a 5-membered partially unsaturated or aromatic ring having 1-3 heteroatoms independently selected from nitrogen, oxygen, and sulfur; wherein said ring is substituted with m instances of R⁴.

As defined generally above, Cy¹ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein Cy¹ is substituted with n instances of R⁵.

In some embodiments, Cy¹ is phenyl. In some embodiments, Cy¹ is a 5-6 membered heteroaryl having 1-4 heteroatoms independently selected from nitrogen, oxygen, and sulfur. In some embodiments, Cy¹ is a 5-membered heteroaryl having 1-4 heteroatoms independently selected from nitrogen, oxygen, and sulfur. In some embodiments, Cy¹ is a 6-membered heteroaryl having 1-4 nitrogens. In some embodiments, Cy¹ is pyridyl. In some embodiments, Cy¹ is pyrazinyl. In some embodiments, Cy¹ is pyrimidinyl. In some embodiments, Cy¹ is triazinyl. In some embodiments, Cy¹ is pyrrolyl, pyrazolyl, imidazolyl, triazolyl, or tetrazolyl. In some embodiments, Cy¹ is furanyl, oxazolyl, isoxazolyl, or oxadiazolyl, In some embodiments, Cy¹ is thiophenyl, thiazolyl, isothiazolyl, or thiadiazolyl. In some embodiments, Cy¹ is an 8-10 membered bicyclic heteroaryl ring having 1-4 heteroatoms independently selected from nitrogen, oxygen, and sulfur. In some embodiments, Cy¹ is a 3-7 membered saturated or partially unsaturated heterocyclic ring having 1-2 heteroatoms independently selected from nitrogen, oxygen, and sulfur. In some embodiments, Cy¹ is a 3-7 membered saturated or partially unsaturated monocyclic carbocyclic ring. In some embodiments, Cy¹ is a 7-12 membered saturated or partially unsaturated bicyclic heterocyclic ring having 1-4 heteroatoms independently selected from nitrogen, oxygen, and sulfur.

In some embodiments, Cy¹(R⁵)$_n$ taken together is selected from the following:

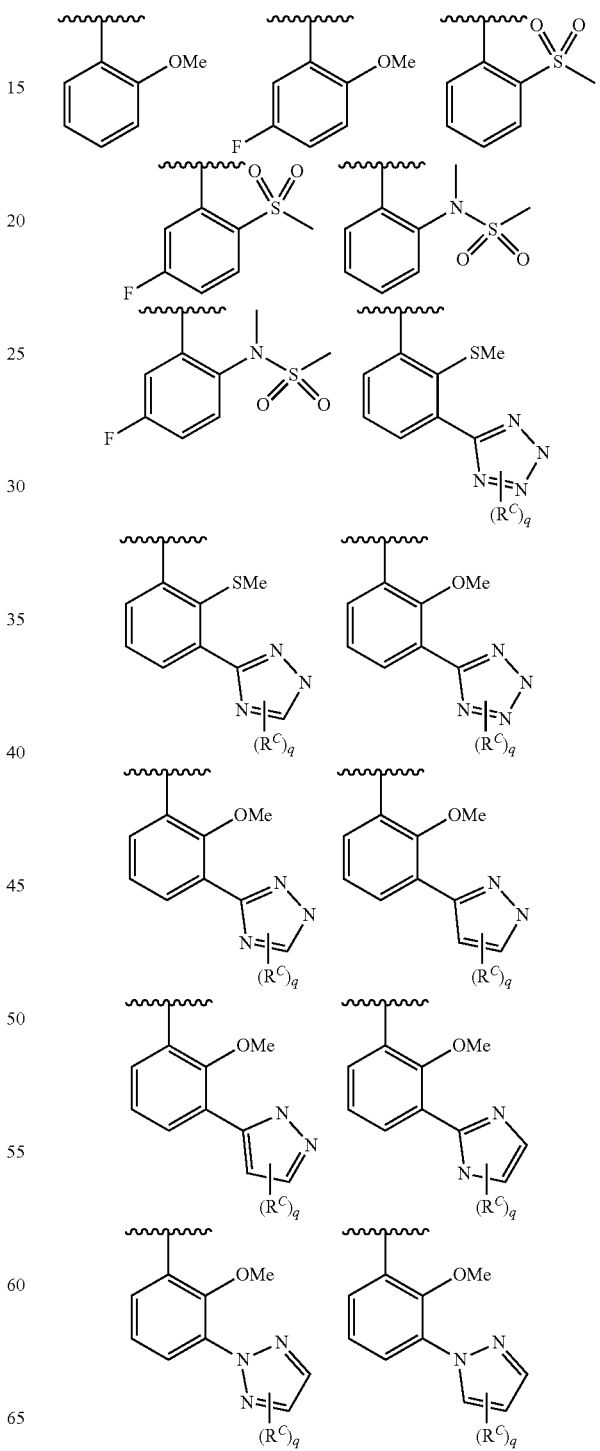

-continued
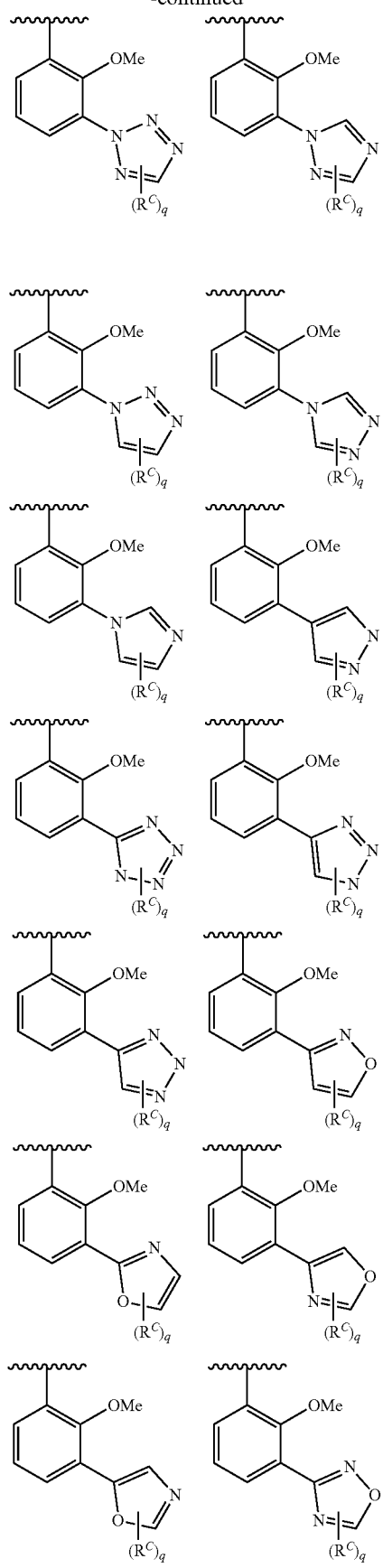
-continued
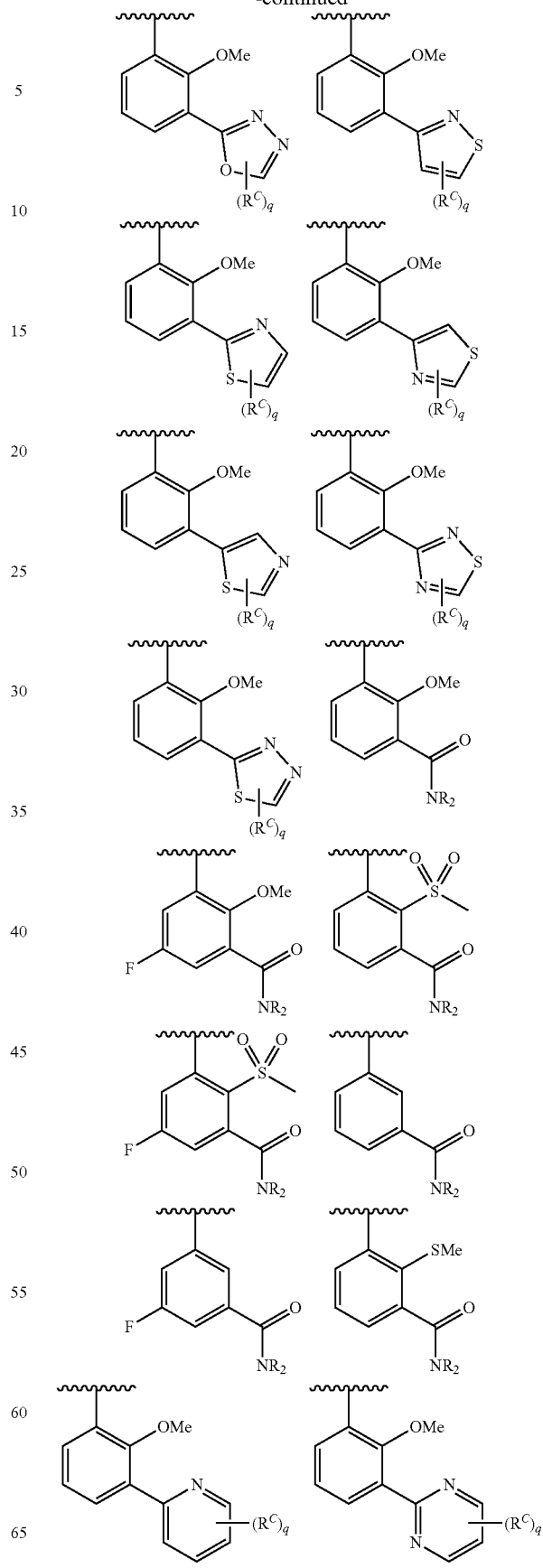

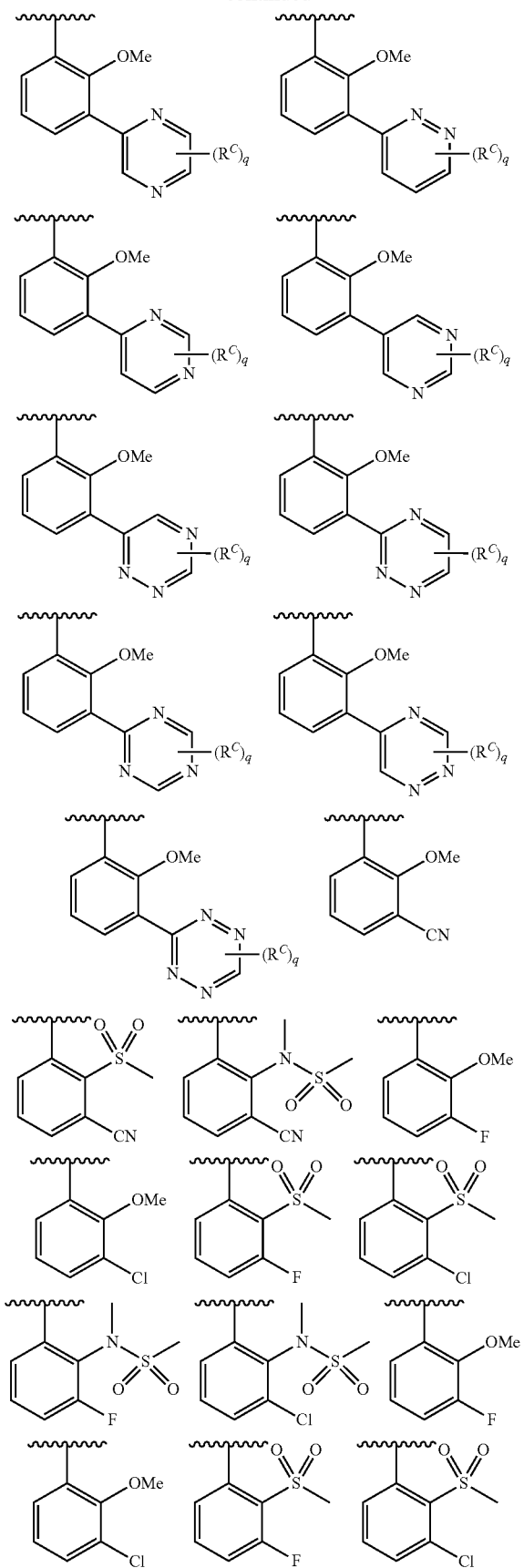
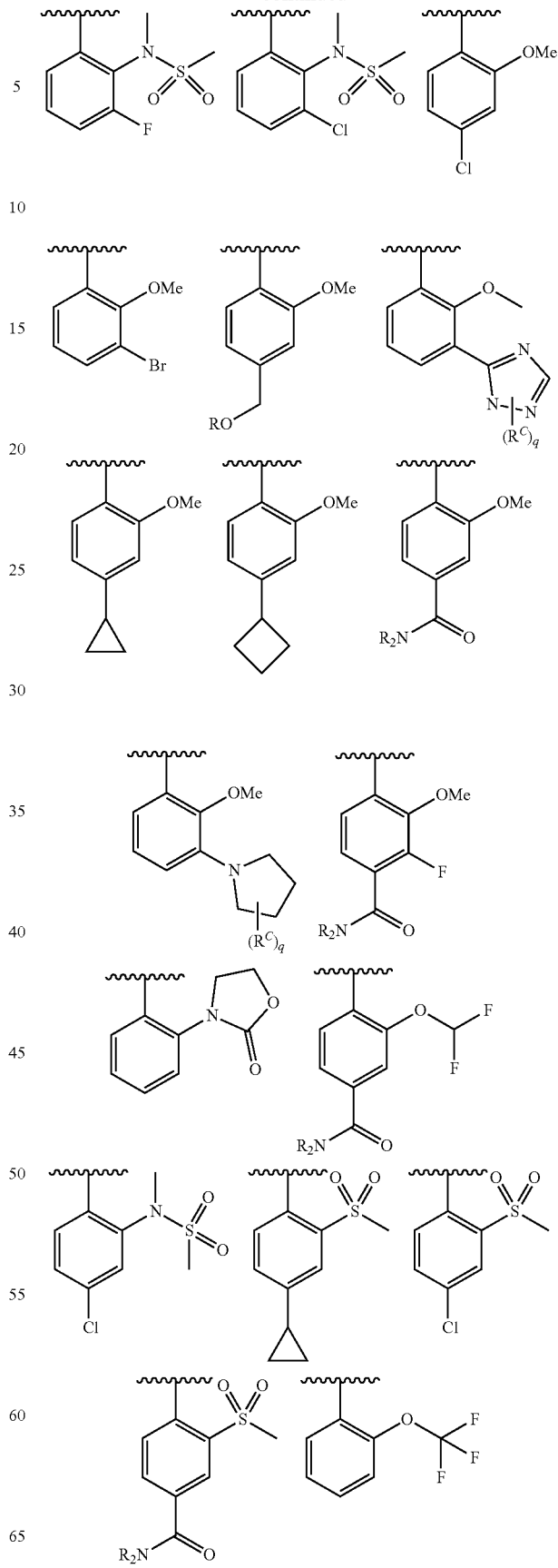

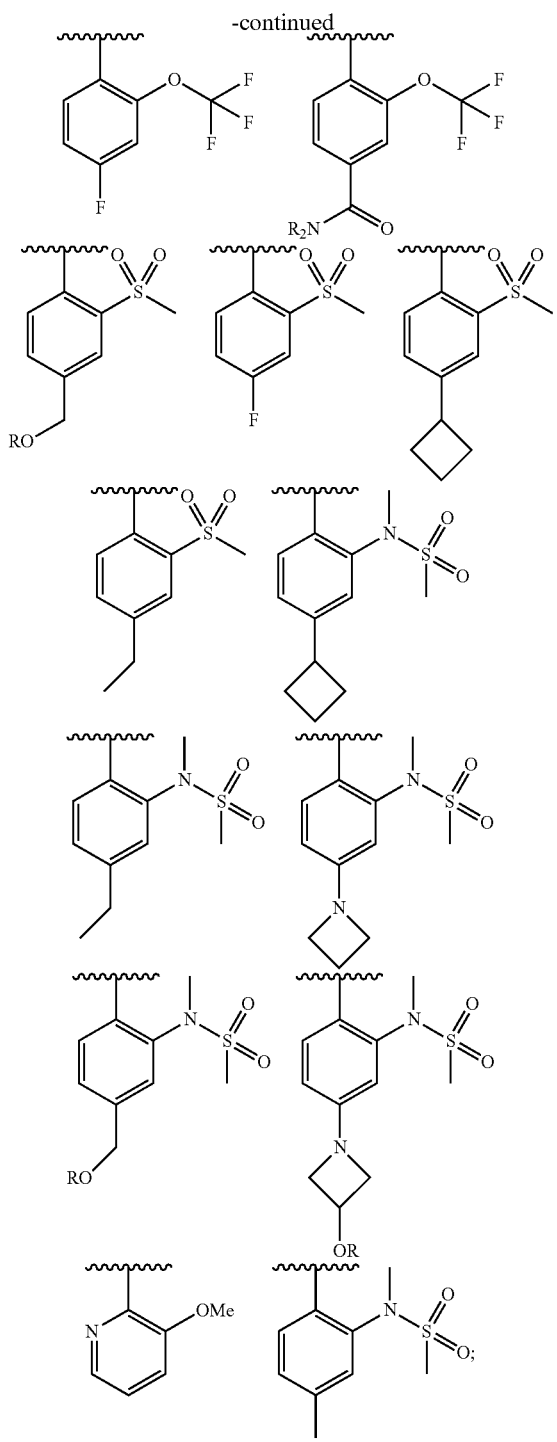

wherein
each of R, $R^C$, and q is as defined above and described in embodiments herein, both singly and in combination.

As defined generally above, $Cy^2$ is phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein $Cy^2$ is substituted with p instances of $R^6$.

In some embodiments, $Cy^2$ is phenyl. In some embodiments, $Cy^2$ is a 5-6 membered heteroaryl having 1-4 heteroatoms independently selected from nitrogen, oxygen, and sulfur. In some embodiments, $Cy^2$ is a 5-membered heteroaryl having 1-4 heteroatoms independently selected from nitrogen, oxygen, and sulfur. In some embodiments, $Cy^2$ is a 6-membered heteroaryl having 1-4 nitrogens. In some embodiments, $Cy^2$ is pyridyl. In some embodiments, $Cy^2$ is pyrazinyl. In some embodiments, $Cy^2$ is pyrimidinyl. In some embodiments, $Cy^2$ is triazinyl. In some embodiments, $Cy^2$ is pyrrolyl, pyrazolyl, imidazolyl, triazolyl, or tetrazolyl. In some embodiments, $Cy^2$ is furanyl, oxazolyl, isoxazolyl, or oxadiazolyl, In some embodiments, $Cy^2$ is thiophenyl, thiazolyl, isothiazolyl, or thiadiazolyl. In some embodiments, $Cy^2$ is an 8-10 membered bicyclic heteroaryl ring having 1-4 heteroatoms independently selected from nitrogen, oxygen, and sulfur. In some embodiments, $Cy^2$ is a 3-7 membered saturated or partially unsaturated heterocyclic ring having 1-2 heteroatoms independently selected from nitrogen, oxygen, and sulfur. In some embodiments, $Cy^2$ is a 3-7 membered saturated or partially unsaturated monocyclic carbocyclic ring. In some embodiments, $Cy^2$ is $C_{3-7}$ cycloalkyl. In some embodiments, $Cy^2$ is cyclopropyl. In some embodiments, $Cy^2$ is a 7-12 membered saturated or partially unsaturated bicyclic heterocyclic ring having 1-4 heteroatoms independently selected from nitrogen, oxygen, and sulfur.

In some embodiments, $Cy^2$ is selected from the following, each of which is substituted by p instances of $R^6$:

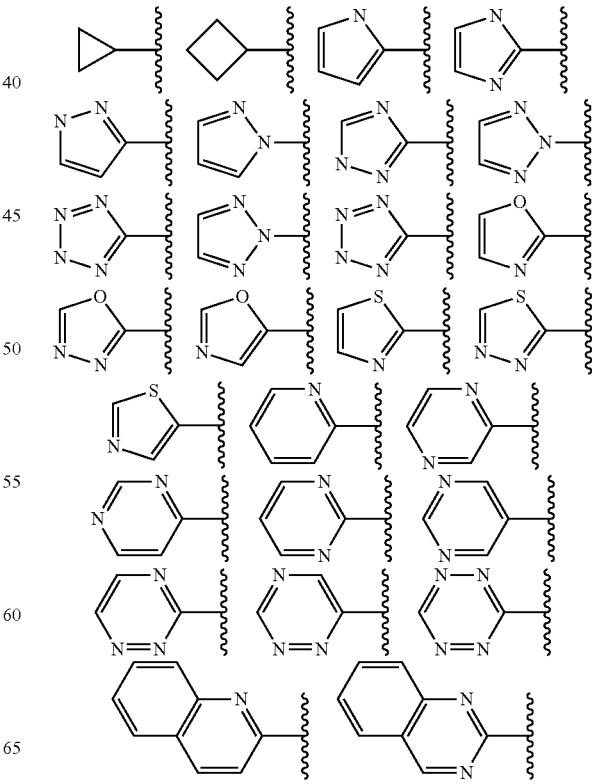

-continued

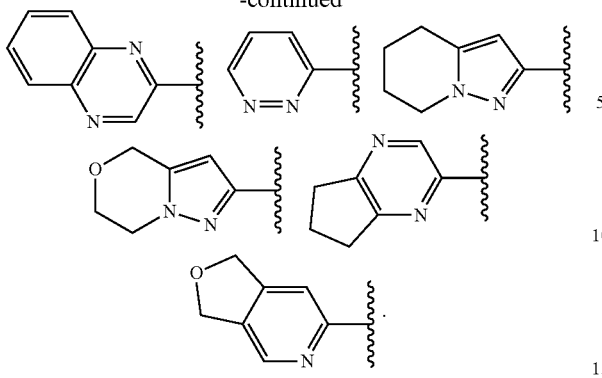

As defined generally above, $L^1$ is a covalent bond or a $C_{1-4}$ bivalent saturated or unsaturated, straight or branched hydrocarbon chain wherein one or two methylene units of the chain are optionally and independently replaced by —C(R$^7$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—. In some embodiments, $L^1$ is a covalent bond. In some embodiments, $L^1$ is a $C_{1-4}$ bivalent saturated or unsaturated, straight or branched hydrocarbon chain wherein one or two methylene units of the chain are optionally and independently replaced by —C(R$^7$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—. In some embodiments, $L^1$ is —N(R)—. In some embodiments, $L^1$ is —N(H)—.

As defined generally above, m is 0, 1, 2, 3, or 4. In some embodiments, m is 0. In some embodiments, m is 1, 2, 3, or 4. In some embodiments, m is 1. In some embodiments, m is 2. In some embodiments, m is 3. In some embodiments, m is 4.

As defined generally above, n is 0, 1, 2, 3, or 4. In some embodiments, n is 0. In some embodiments, n is 1, 2, 3, or 4. In some embodiments, n is 1. In some embodiments, n is 2. In some embodiments, n is 3. In some embodiments, n is 4.

As defined generally above, p is 0, 1, 2, 3, or 4. In some embodiments, p is 0. In some embodiments, p is 1, 2, 3, or 4. In some embodiments, p is 1. In some embodiments, p is 2. In some embodiments, p is 3. In some embodiments, p is 4.

In some embodiments, the present invention provides a compound of formula X, wherein $L^1$ is —N(H)—, thereby forming a compound of formula X-a:

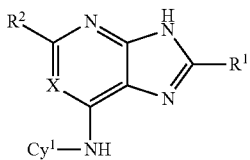

X-a or a pharmaceutically acceptable salt thereof, wherein each of X, Cy$^1$, R$^1$, and R$^2$ is as defined above and described in embodiments herein, both singly and in combination.

In some embodiments, the present invention provides a compound of formula X, wherein X is N or C(R$^3$), thereby forming a compound of formulas X-b or X-c respectively:

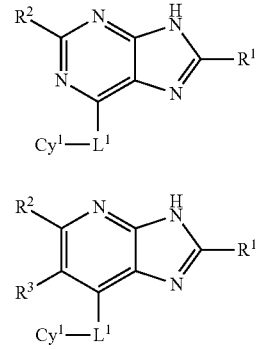

or a pharmaceutically acceptable salt thereof, wherein each of Cy$^1$, L$^1$, R$^1$, R$^2$, and R$^3$ is as defined above and described in embodiments herein, both singly and in combination.

In some embodiments, the present invention provides a compound of formula X-a, wherein X is N or C(R$^3$), thereby forming a compound of formulas XI-a or XI-b respectively:

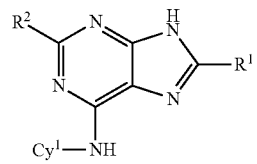

XI-a

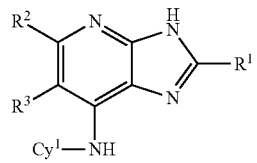

XI-b or a pharmaceutically acceptable salt thereof, wherein each of Cy$^1$, R$^1$, R$^2$, and R$^3$ is as defined above and described in embodiments herein, both singly and in combination.

In some embodiments, the present invention provides a compound of formula XI-a or XI-b wherein Cy$^1$ is phenyl, thereby forming a compound of formulas XII-a or XII-b respectively:

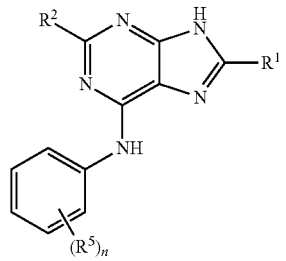

XII-a

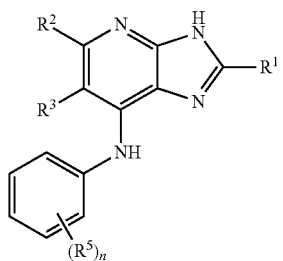

XII-b or a pharmaceutically acceptable salt thereof, wherein each of $R^1$, $R^2$, $R^3$, $R^5$, and n is as defined above and described in embodiments herein, both singly and in combination.

In some embodiments, the present invention provides a compound of formula XII-a or XII-b, wherein n is 1, 2 or 3, and at least one instance of $R^5$ is ortho to the NH point of attachment, thereby forming a compound of formulas XIII-a or XIII-b respectively:

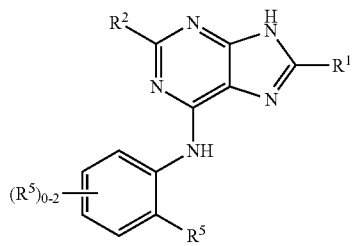

XIII-a

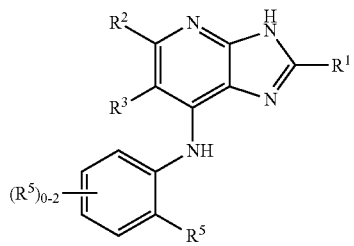

XIII-b or a pharmaceutically acceptable salt thereof, wherein each of $R^1$, $R^2$, $R^3$, and $R^5$ is as defined above and described in embodiments herein, both singly and in combination.

In some embodiments, the present invention provides a compound of formula XIII-a or XIII-b, wherein the ortho $R^5$ group is —OR, —S(O)$_2$R, —C(O)NR$_2$, or —N(R)S(O)$_2$R, thereby forming a compound of formulas XIV-a, XIV-b, XIV-c, XIV-d, XIV-e, XIV-f, XIV-g, or XIV-h respectively:

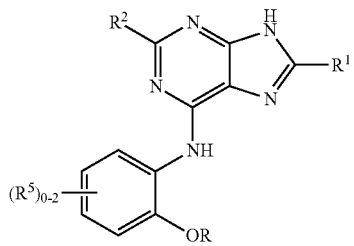

XIV-a

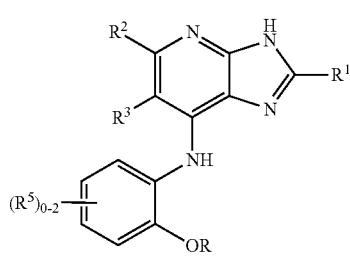

XIV-b

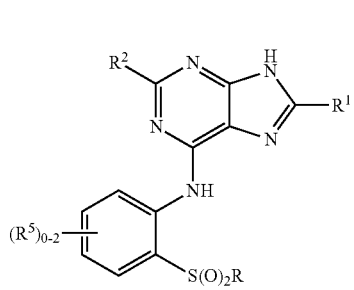

XIV-c

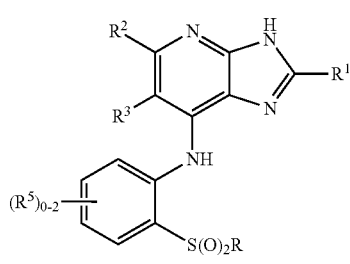

XIV-d

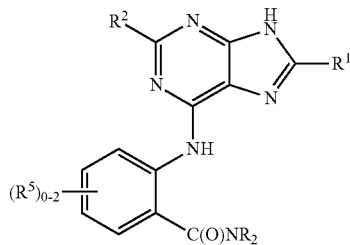

XIV-e

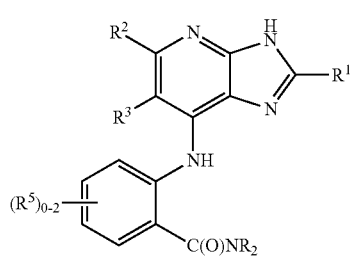

XIV-f

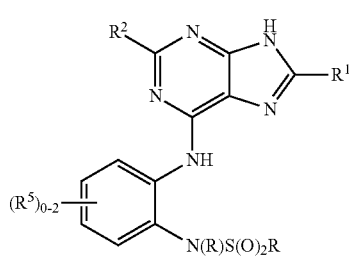

XIV-g

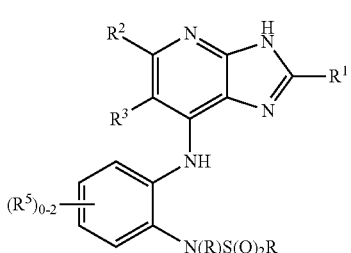
XIV-h or a pharmaceutically acceptable salt thereof, wherein each of R, $R^1$, $R^2$, $R^3$, and $R^5$ is as defined above and described in embodiments herein, both singly and in combination.

In some embodiments, the present invention provides a compound of formula XIV-a or XIV-b, wherein a second $R^5$ group ($R^{5b}$) is meta to the NH point of attachment, thereby forming a compound of formulas XV-a, or XV-b respectively:

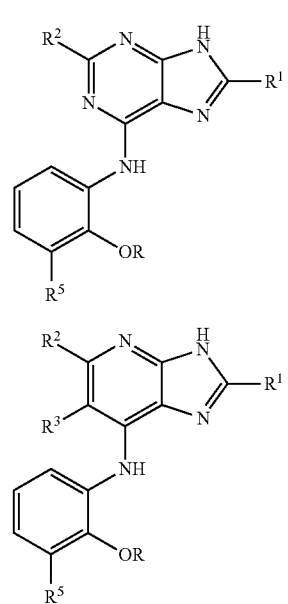
XV-a

XV-b or a pharmaceutically acceptable salt thereof, wherein each of R, $R^1$, $R^2$, $R^3$, and $R^5$ is as defined above and described in embodiments herein, both singly and in combination.

In some embodiments, the present invention provides a compound of formula XV-a or XV-b, wherein $R^5$ is $R^B$. In some embodiments, the present invention provides a compound of formula XV-a or XV-b, wherein $R^5$ is —C(O)NR$_2$ or a 5-6 membered monocyclic heteroaryl ring having 1-4 heteroatoms independently selected from nitrogen, oxygen, and sulfur, said ring being substituted by q instances of $R^C$.

In some embodiments, the present invention provides a compound of formula XV-a or XV-b, wherein —OR is methoxy, fluoromethoxy, or difluoromethoxy.

In some embodiments, the present invention provides a compound of formula XI-a or XI-b wherein $Cy^1$ is pyridyl, n is 2, and one instance of $R^5$ is oxo, thereby forming a pyridone compound of formulas XVI-a or XVI-b respectively:

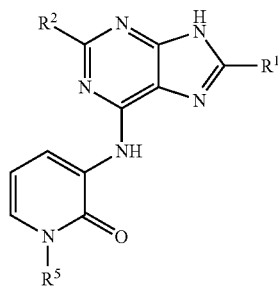
XVI-a

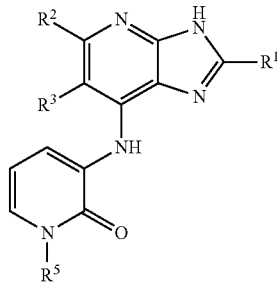
XVI-b or a pharmaceutically acceptable salt thereof, wherein each of $R^1$, $R^2$, $R^3$, and $R^5$, is as defined above and described in embodiments herein, both singly and in combination.

In some embodiments, the present invention provides a compound of formula X wherein $R^1$ is —CHF$_2$, thereby forming a compound of formula XVII:

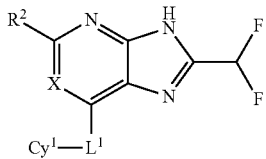
XVII or a pharmaceutically acceptable salt thereof, wherein each of X, $L^1$, $R^2$, and $Cy^1$ is as defined above and described in embodiments herein, both singly and in combination.

In some embodiments, the present invention provides a compound of formula XVII wherein $L^1$ is —NH—, thereby forming a compound of formula XVIII:

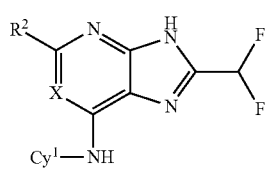
XVIII or a pharmaceutically acceptable salt thereof, wherein each of X, $R^2$, and $Cy^1$ is as defined above and described in embodiments herein, both singly and in combination.

Exemplary compounds of the invention are set forth in Table 1, below.

TABLE
| Exemplary Compounds | |
|---|---|
| Compound | Structure |
| I-1 | 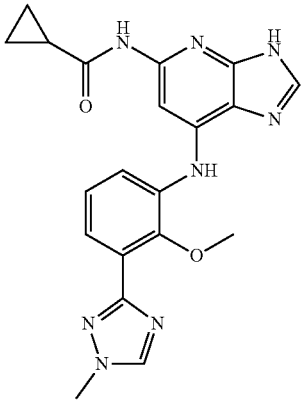 [SMILES: COc1c(Nc2cc(NC(=O)C3CC3)nc3[nH]cnc23)cccc1-c1ncn(C)n1] |
| I-2 | 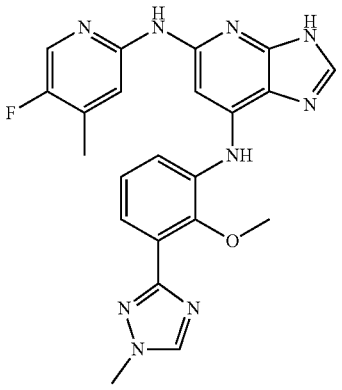 [SMILES: COc1c(Nc2cc(Nc3cc(C)c(F)cn3)nc3[nH]cnc23)cccc1-c1ncn(C)n1] |
| I-3 | 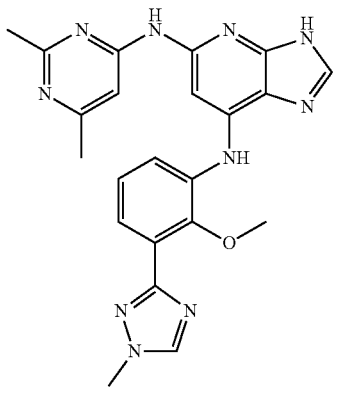 [SMILES: COc1c(Nc2cc(Nc3cc(C)nc(C)n3)nc3[nH]cnc23)cccc1-c1ncn(C)n1] |

TABLE-continued
Exemplary Compounds
| Compound | Structure |
|---|---|
| I-4 | 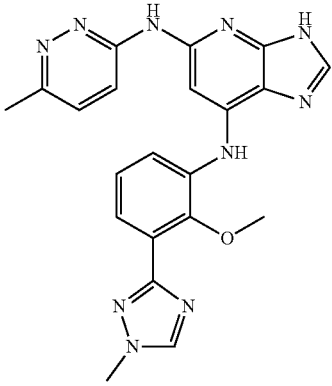 [SMILES: COc1c(Nc2cc(Nc3ccc(C)nn3)nc3[nH]cnc23)cccc1-c1ncn(C)n1] |
| I-5 | 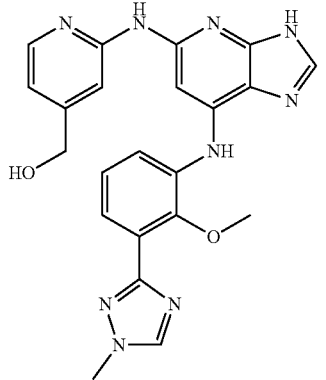 [SMILES: COc1c(Nc2cc(Nc3cc(CO)ccn3)nc3[nH]cnc23)cccc1-c1ncn(C)n1] |
| I-6 | 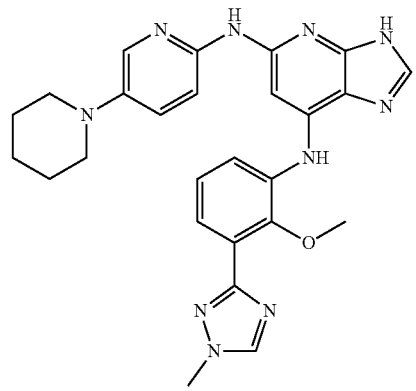 [SMILES: COc1c(Nc2cc(Nc3ccc(N4CCCCC4)cn3)nc3[nH]cnc23)cccc1-c1ncn(C)n1] |

TABLE-continued
Exemplary Compounds
| Compound | Structure |
|---|---|
| I-7 | 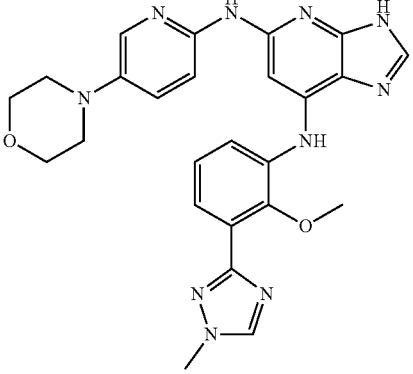 |
| I-8 | 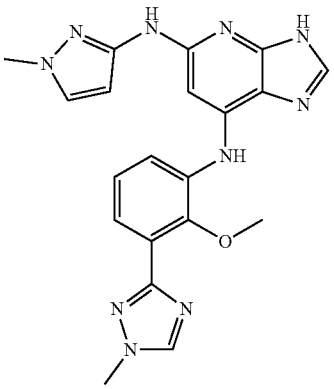 [SMILES: COc1c(Nc2cc(Nc3ccn(C)n3)nc3[nH]cnc23)cccc1-c1ncn(C)n1] |
| I-9 | 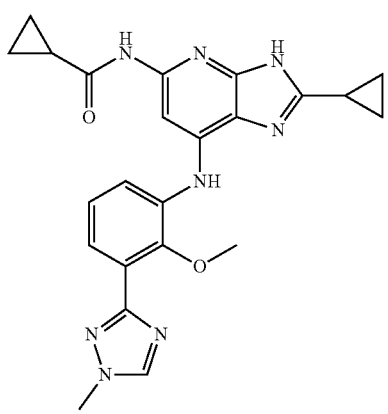 [SMILES: COc1c(Nc2cc(NC(=O)C3CC3)nc3[nH]c(C4CC4)nc23)cccc1-c1ncn(C)n1] |

TABLE-continued
Exemplary Compounds
| Compound | Structure |
|---|---|
| I-10 | 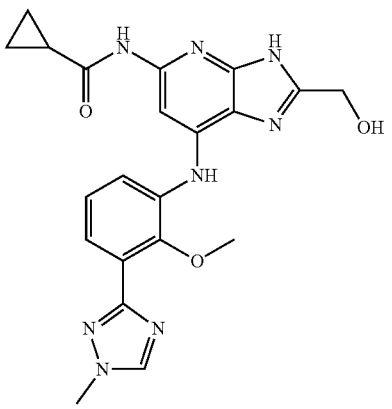 [SMILES: COc1c(Nc2cc(NC(=O)C3CC3)nc3[nH]c(CO)nc23)cccc1-c1ncn(C)n1] |
| I-11 | 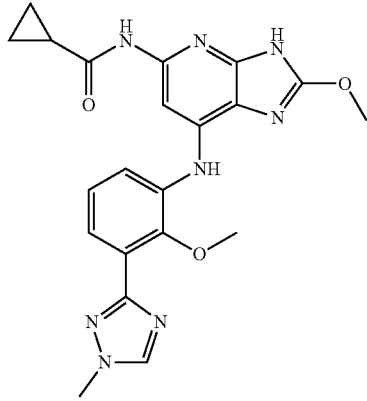 [SMILES: COc1nc2c(Nc3cccc(-c4ncn(C)n4)c3OC)cc(NC(=O)C3CC3)nc2[nH]1] |
| I-12 | 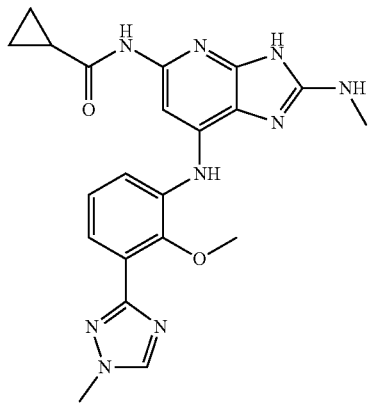 [SMILES: CNc1nc2c(Nc3cccc(-c4ncn(C)n4)c3OC)cc(NC(=O)C3CC3)nc2[nH]1] |

TABLE-continued
Exemplary Compounds
| Compound | Structure |
|---|---|
| I-13 | 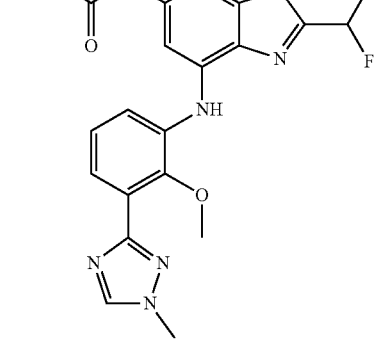 |
| I-14 | 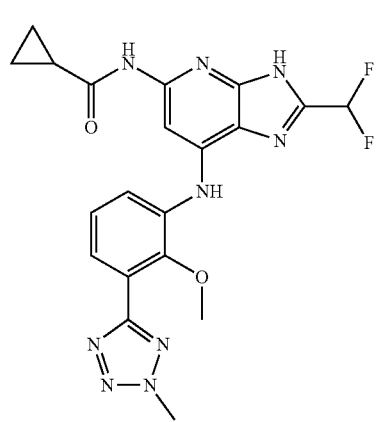 [SMILES: COc1c(Nc2cc(NC(=O)C3CC3)nc3[nH]c(C(F)F)nc23)cccc1-c1nnn(C)n1] |
| I-15 | 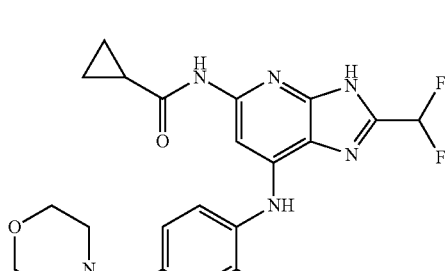 |
| I-16 | 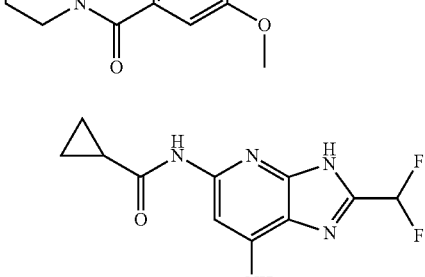 |

TABLE-continued

Exemplary Compounds

| Compound | Structure |
|---|---|
| I-17 | *(structure)* |
| I-18 | *(structure)* |
| I-19 | *(structure)* |
| I-20 | *(structure)* |

TABLE-continued
Exemplary Compounds
| Compound | Structure |
|---|---|
| I-21 | 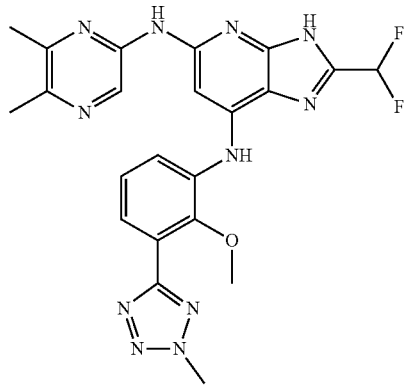 |
| I-22 | 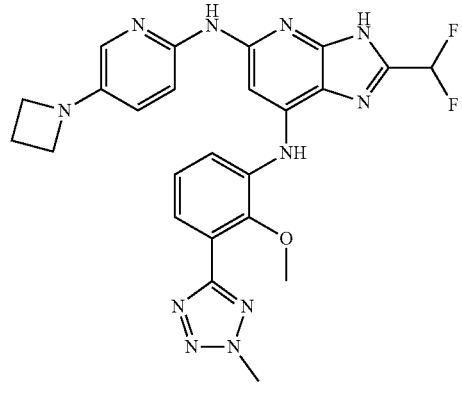 [SMILES: COc1c(Nc2cc(Nc3ccc(N4CCC4)cn3)nc3[nH]c(C(F)F)nc23)cccc1-c1nnn(C)n1] |
| I-23 | 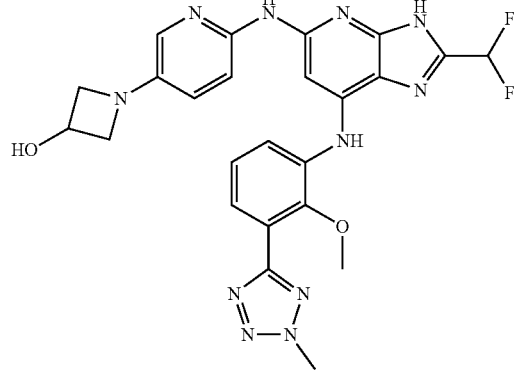 |

TABLE-continued
Exemplary Compounds
| Compound | Structure |
|---|---|
| I-24 | 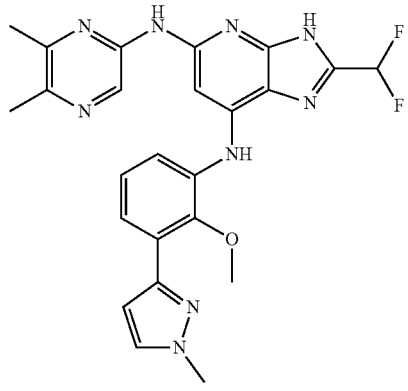 [SMILES: COc1c(Nc2cc(Nc3cnc(C)c(C)n3)nc3[nH]c(C(F)F)nc23)cccc1-c1ccn(C)n1] |
| I-25 | 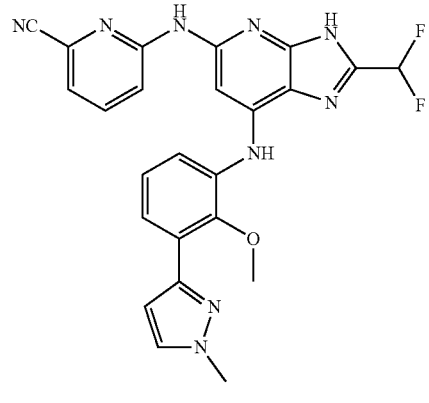 |
| I-26 | 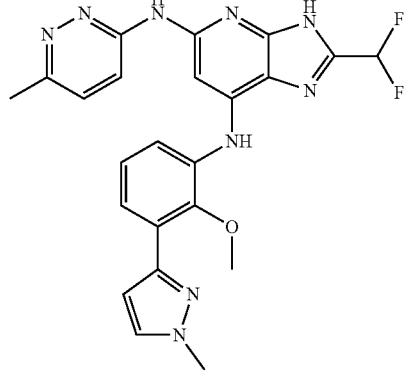 |

TABLE-continued

Exemplary Compounds

| Compound | Structure |
|---|---|
| I-27 | 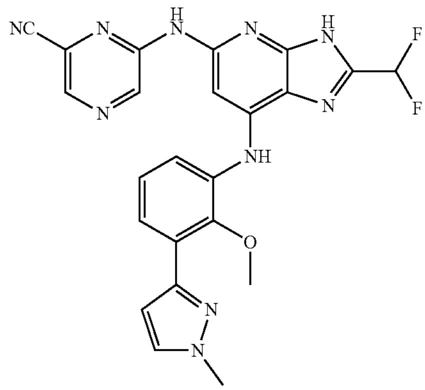 [SMILES: COc1c(Nc2cc(Nc3cncc(C#N)n3)nc3[nH]c(C(F)F)nc23)cccc1-c1ccn(C)n1] |
| I-28 | 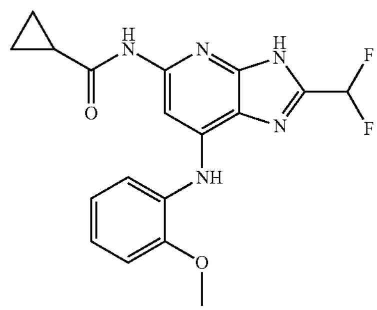 [SMILES: COc1ccccc1Nc1cc(NC(=O)C2CC2)nc2[nH]c(C(F)F)nc12] |
| I-29 | 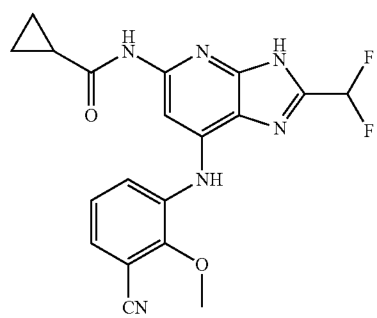 [SMILES: COc1c(C#N)cccc1Nc1cc(NC(=O)C2CC2)nc2[nH]c(C(F)F)nc12] |
| I-30 | 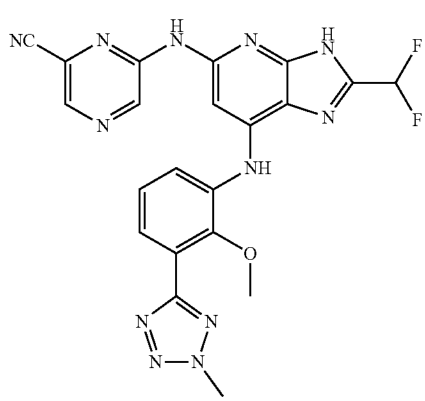 [SMILES: COc1c(Nc2cc(Nc3cncc(C#N)n3)nc3[nH]c(C(F)F)nc23)cccc1-c1nnn(C)n1] |

| TABLE-continued |
| --- |
| Exemplary Compounds |

| Compound | Structure |
| --- | --- |
| I-31 | 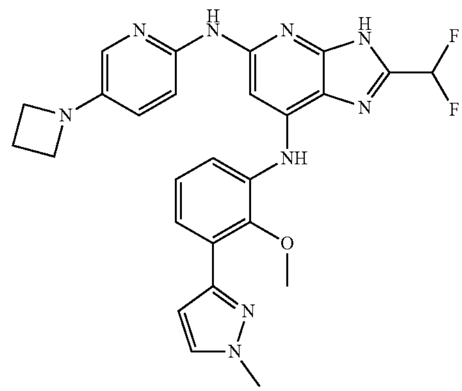 [SMILES: COc1c(Nc2cc(Nc3ccc(N4CCC4)cn3)nc3[nH]c(C(F)F)nc23)cccc1-c1ccn(C)n1] |
| I-32 | 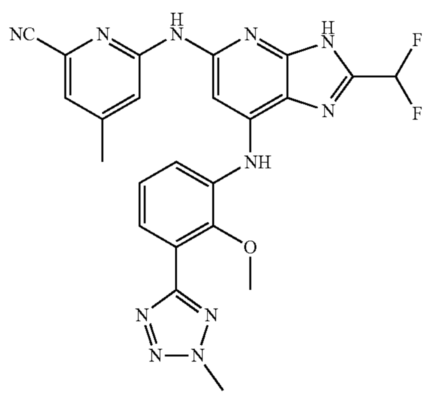 [SMILES: COc1c(Nc2cc(Nc3cc(C)cc(C#N)n3)nc3[nH]c(C(F)F)nc23)cccc1-c1nnn(C)n1] |
| I-33 | 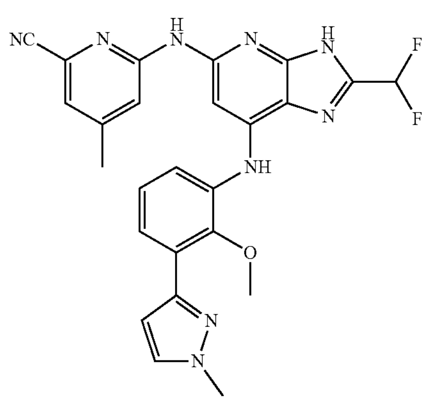 [SMILES: COc1c(Nc2cc(Nc3cc(C)cc(C#N)n3)nc3[nH]c(C(F)F)nc23)cccc1-c1ccn(C)n1] |

TABLE-continued
Exemplary Compounds
| Compound | Structure |
|---|---|
| I-34 | 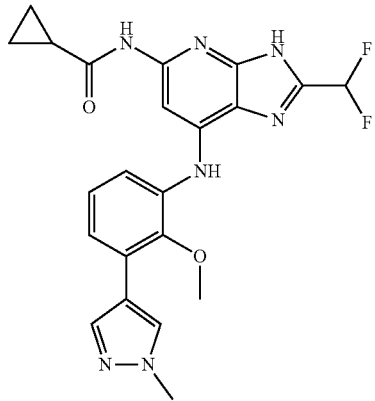 |
| I-35 | 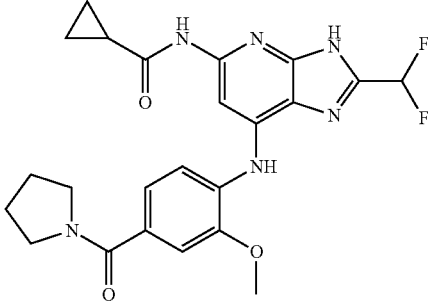 [SMILES: COc1cc(C(=O)N2CCCC2)ccc1Nc1cc(NC(=O)C2CC2)nc2[nH]c(C(F)F)nc12] |
| I-36 | 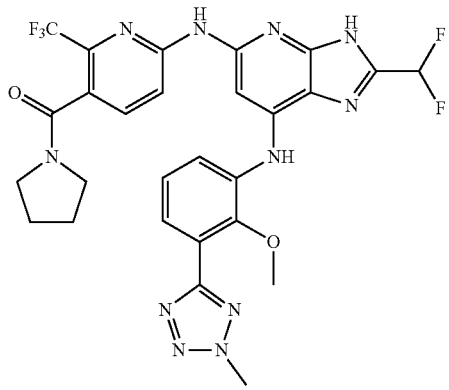 [SMILES: COc1c(Nc2cc(Nc3ccc(C(=O)N4CCCC4)c(C(F)(F)F)n3)nc3[nH]c(C(F)F)nc23)cccc1-c1nnn(C)n1] |
| I-37 | 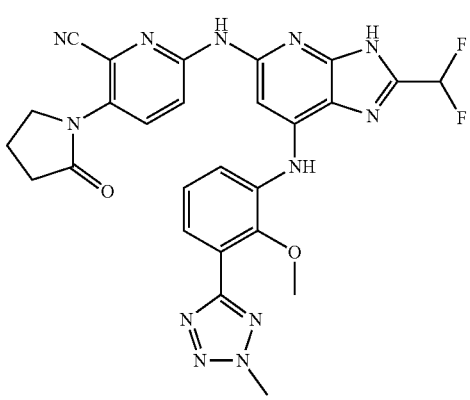 [SMILES: COc1c(Nc2cc(Nc3ccc(N4CCCC4=O)c(C#N)n3)nc3[nH]c(C(F)F)nc23)cccc1-c1nnn(C)n1] |

TABLE-continued
Exemplary Compounds
| Compound | Structure |
|---|---|
| I-38 | 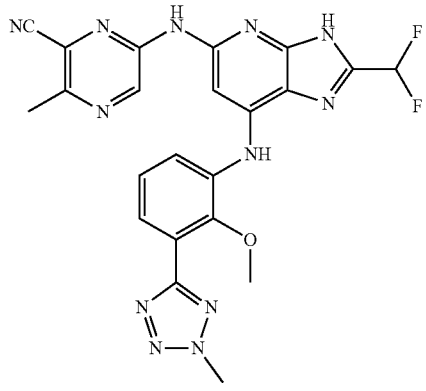 [SMILES: COc1c(Nc2cc(Nc3cnc(C)c(C#N)n3)nc3[nH]c(C(F)F)nc23)cccc1-c1nnn(C)n1] |
| I-39 | 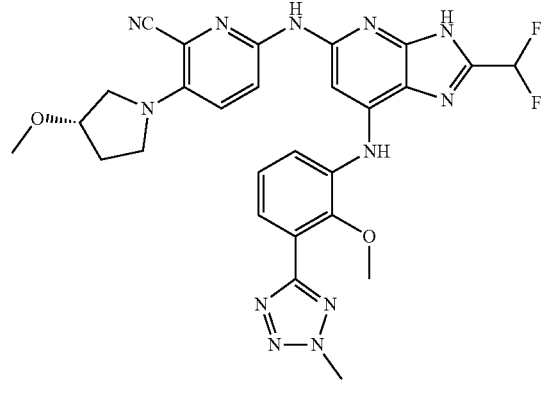 [SMILES: COc1c(Nc2cc(Nc3ccc(N4CC[C@H](OC)C4)c(C#N)n3)nc3[nH]c(C(F)F)nc23)cccc1-c1nnn(C)n1] |
| I-40 | 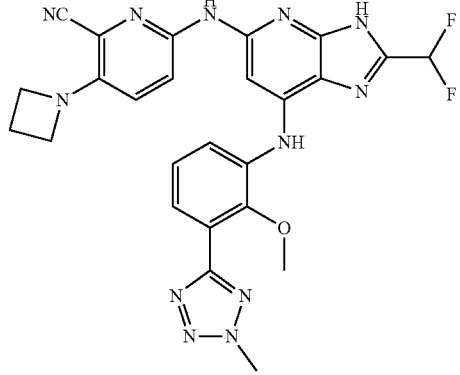 |

TABLE-continued
Exemplary Compounds
| Compound | Structure |
|---|---|
| I-41 | 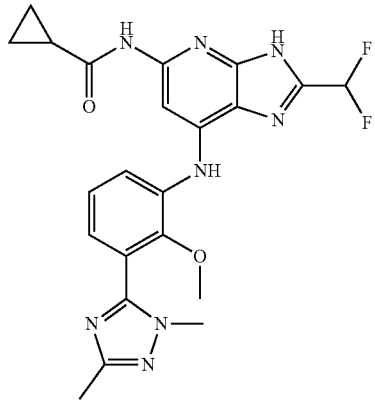 [SMILES: COc1c(Nc2cc(NC(=O)C3CC3)nc3[nH]c(C(F)F)nc23)cccc1-c1nc(C)nn1C] |
| I-42 | 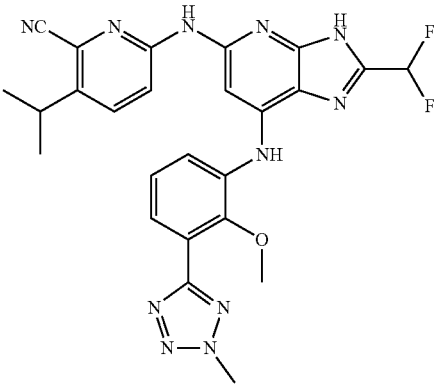 [SMILES: COc1c(Nc2cc(Nc3ccc(C(C)C)c(C#N)n3)nc3[nH]c(C(F)F)nc23)cccc1-c1nnn(C)n1] |
| I-43 | 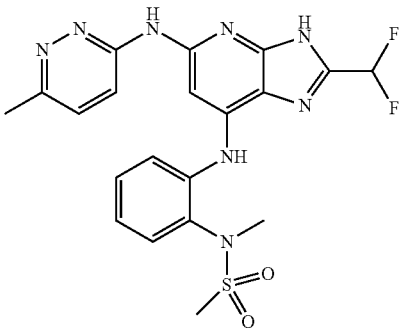 [SMILES: Cc1ccc(Nc2cc(Nc3ccccc3N(C)S(C)(=O)=O)c3nc(C(F)F)[nH]c3n2)nn1] |
| I-44 | 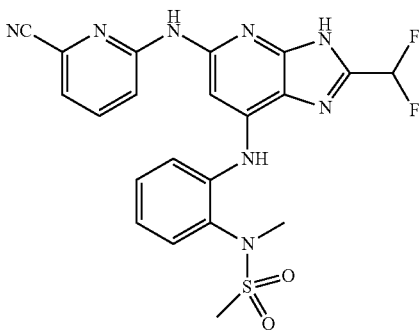 [SMILES: CN(c1ccccc1Nc1cc(Nc2cccc(C#N)n2)nc2[nH]c(C(F)F)nc12)S(C)(=O)=O] |

TABLE-continued

Exemplary Compounds

| Compound | Structure |
|---|---|
| I-45 | 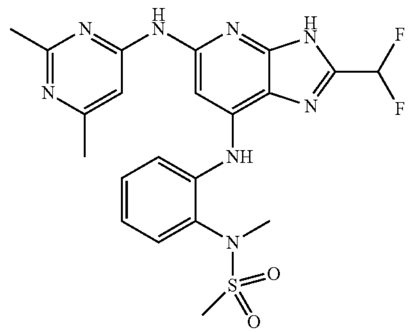 [SMILES: Cc1cc(Nc2cc(Nc3ccccc3N(C)S(C)(=O)=O)c3nc(C(F)F)[nH]c3n2)nc(C)n1] |
| I-46 | 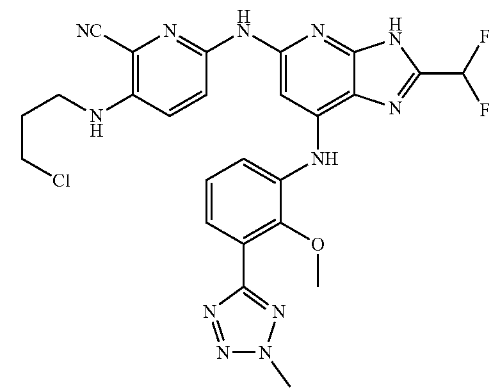 [SMILES: COc1c(Nc2cc(Nc3ccc(NCCCCl)c(C#N)n3)nc3[nH]c(C(F)F)nc23)cccc1-c1nnn(C)n1] |
| I-47 | 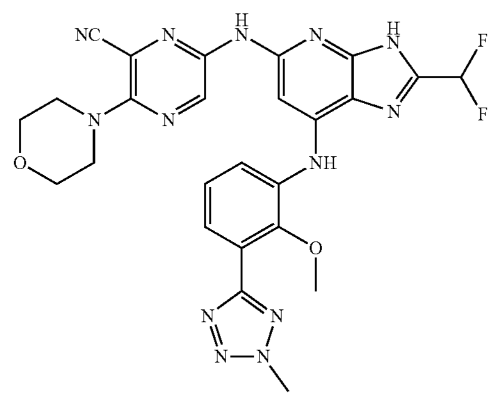 [SMILES: COc1c(Nc2cc(Nc3cnc(N4CCOCC4)c(C#N)n3)nc3[nH]c(C(F)F)nc23)cccc1-c1nnn(C)n1] |
| I-48 | 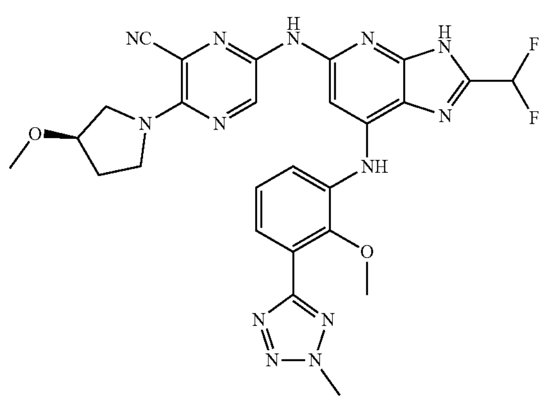 [SMILES: COc1c(Nc2cc(Nc3cnc(N4CC[C@@H](OC)C4)c(C#N)n3)nc3[nH]c(C(F)F)nc23)cccc1-c1nnn(C)n1] |

TABLE-continued
Exemplary Compounds
| Compound | Structure |
|---|---|
| I-49 | 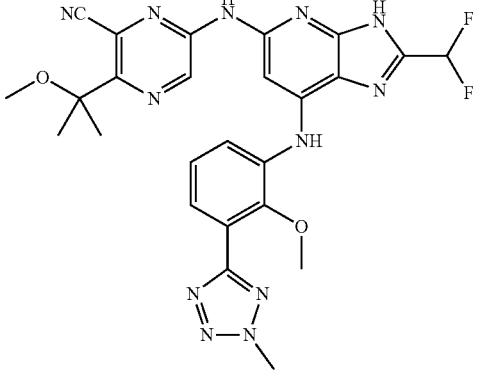 |
| I-50 | 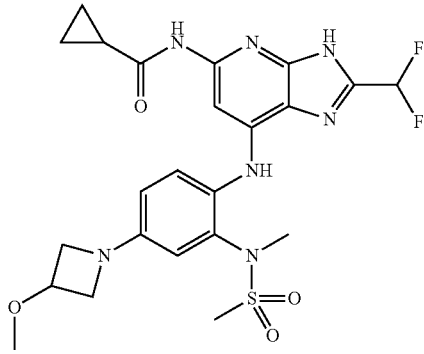 [SMILES: COC1CN(c2ccc(Nc3cc(NC(=O)C4CC4)nc4[nH]c(C(F)F)nc34)c(N(C)S(C)(=O)=O)c2)C1] |
| I-51 | 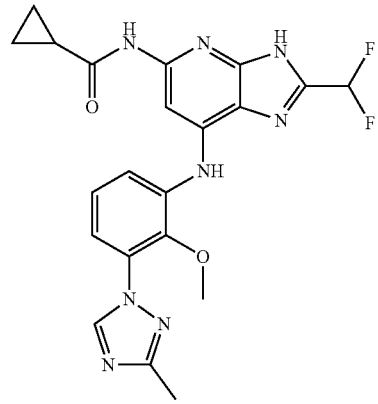 [SMILES: COc1c(Nc2cc(NC(=O)C3CC3)nc3[nH]c(C(F)F)nc23)cccc1-n1cnc(C)n1] |
| I-52 | 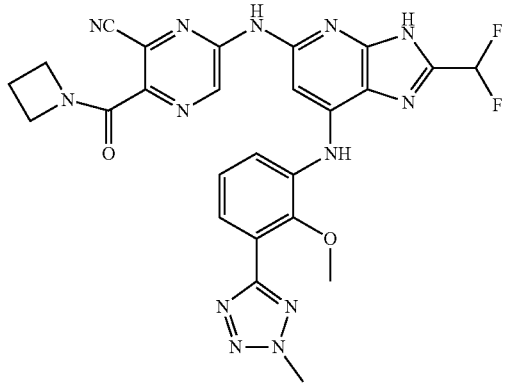 [SMILES: COc1c(Nc2cc(Nc3cnc(C(=O)N4CCC4)c(C#N)n3)nc3[nH]c(C(F)F)nc23)cccc1-c1nnn(C)n1] |

TABLE-continued
Exemplary Compounds
| Compound | Structure |
|---|---|
| I-53 | 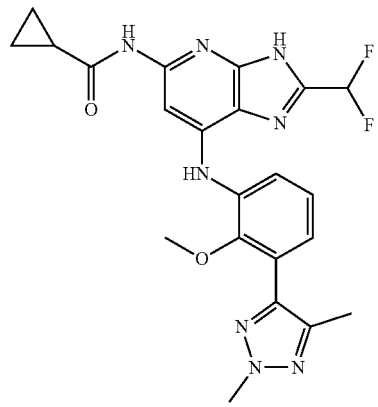 [SMILES: COc1c(Nc2cc(NC(=O)C3CC3)nc3[nH]c(C(F)F)nc23)cccc1-c1nn(C)nc1C] |
| I-54 | 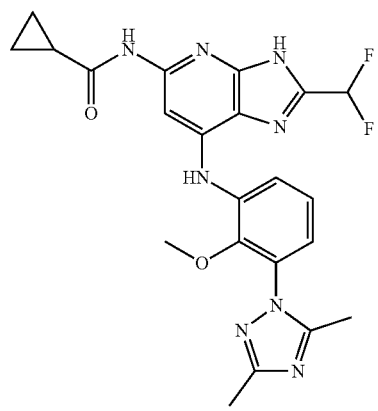 [SMILES: COc1c(Nc2cc(NC(=O)C3CC3)nc3[nH]c(C(F)F)nc23)cccc1-n1nc(C)nc1C] |
| I-55 | 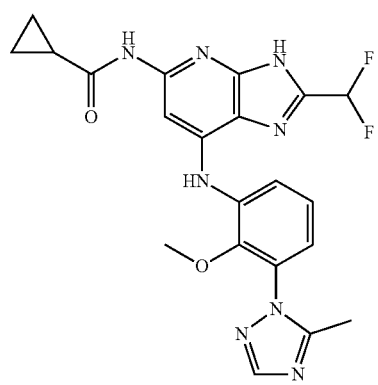 [SMILES: COc1c(Nc2cc(NC(=O)C3CC3)nc3[nH]c(C(F)F)nc23)cccc1-n1ncnc1C] |

TABLE-continued

Exemplary Compounds

| Compound | Structure |
|---|---|
| I-56 | 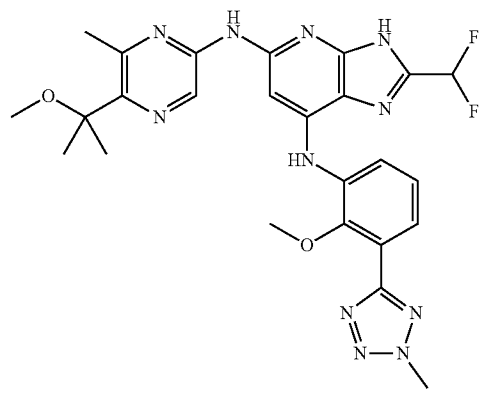 [SMILES: COc1c(Nc2cc(Nc3cnc(C(C)(C)OC)c(C)n3)nc3[nH]c(C(F)F)nc23)cccc1-c1nnn(C)n1] |
| I-57 | 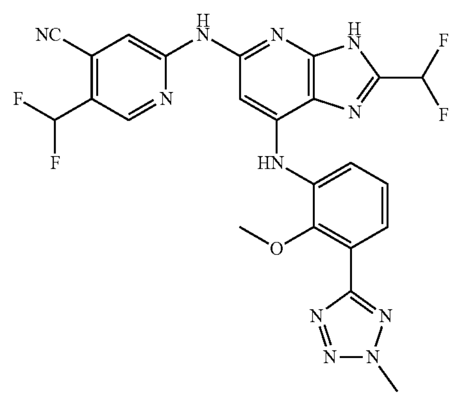 [SMILES: COc1c(Nc2cc(Nc3cc(C#N)c(C(F)F)cn3)nc3[nH]c(C(F)F)nc23)cccc1-c1nnn(C)n1] |
| I-58 | 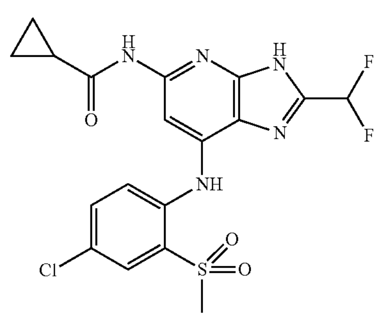 [SMILES: CS(=O)(=O)c1cc(Cl)ccc1Nc1cc(NC(=O)C2CC2)nc2[nH]c(C(F)F)nc12] |
| I-59 | 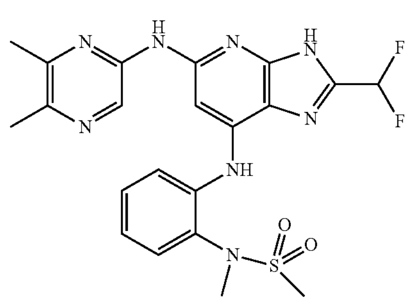 [SMILES: Cc1ncc(Nc2cc(Nc3ccccc3N(C)S(C)(=O)=O)c3nc(C(F)F)[nH]c3n2)nc1C] |

TABLE-continued
Exemplary Compounds
| Compound | Structure |
|---|---|
| I-60 | 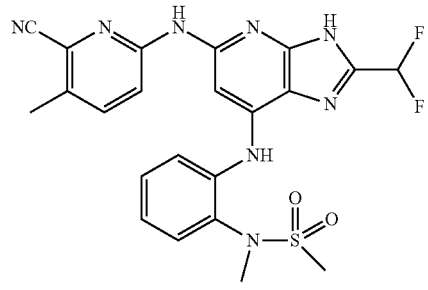 [SMILES: Cc1ccc(Nc2cc(Nc3ccccc3N(C)S(C)(=O)=O)c3nc(C(F)F)[nH]c3n2)nc1C#N] |
| I-61 | 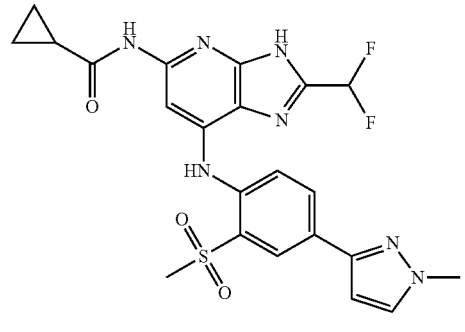 [SMILES: Cn1ccc(-c2ccc(Nc3cc(NC(=O)C4CC4)nc4[nH]c(C(F)F)nc34)c(S(C)(=O)=O)c2)n1] |
| I-62 | 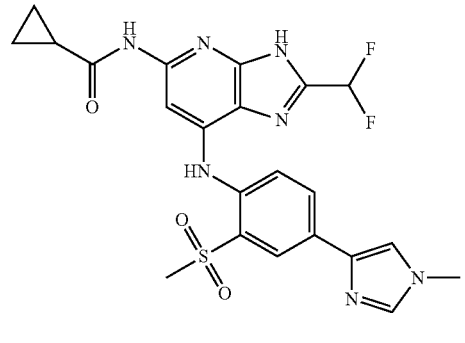 [SMILES: Cn1cnc(-c2ccc(Nc3cc(NC(=O)C4CC4)nc4[nH]c(C(F)F)nc34)c(S(C)(=O)=O)c2)c1] |
| I-63 | 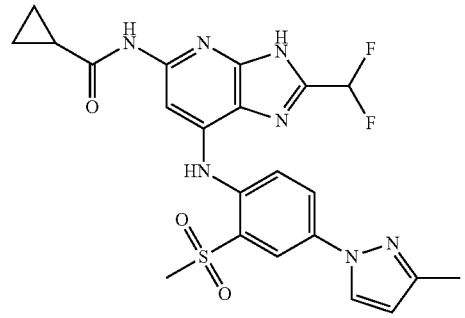 [SMILES: Cc1ccn(-c2ccc(Nc3cc(NC(=O)C4CC4)nc4[nH]c(C(F)F)nc34)c(S(C)(=O)=O)c2)n1] |

TABLE-continued

Exemplary Compounds

| Compound | Structure |
|---|---|
| I-64 | 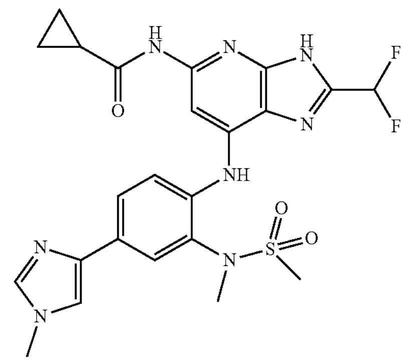 [SMILES: CN(c1cc(-c2cn(C)cn2)ccc1Nc1cc(NC(=O)C2CC2)nc2[nH]c(C(F)F)nc12)S(C)(=O)=O] |
| I-65 | 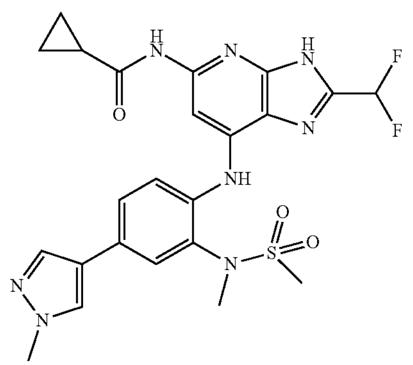 [SMILES: CN(c1cc(-c2cnn(C)c2)ccc1Nc1cc(NC(=O)C2CC2)nc2[nH]c(C(F)F)nc12)S(C)(=O)=O] |
| I-70 | 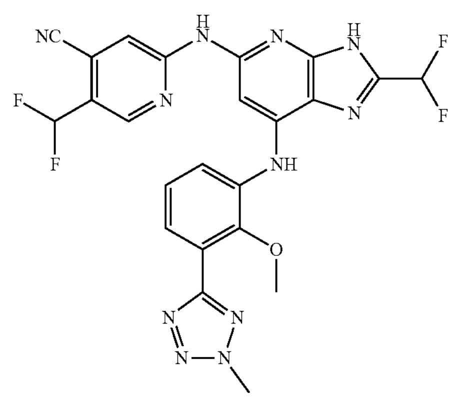 [SMILES: COc1c(Nc2cc(Nc3cc(C#N)c(C(F)F)cn3)nc3[nH]c(C(F)F)nc23)cccc1-c1nnn(C)n1] |
| I-72 | 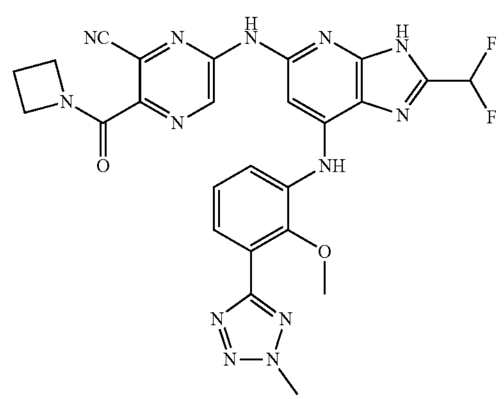 [SMILES: COc1c(Nc2cc(Nc3cnc(C(=O)N4CCC4)c(C#N)n3)nc3[nH]c(C(F)F)nc23)cccc1-c1nnn(C)n1] |

TABLE-continued

Exemplary Compounds

| Compound | Structure |
|---|---|
| I-78 | 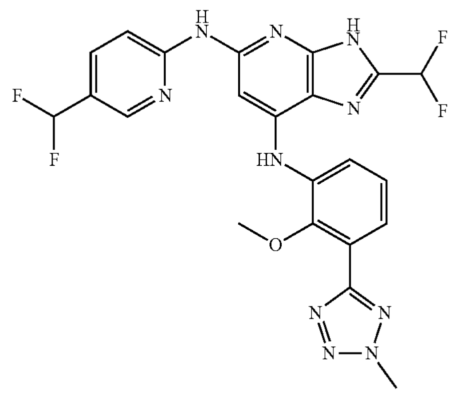 [SMILES: COc1c(Nc2cc(Nc3ccc(C(F)F)cn3)nc3[nH]c(C(F)F)nc23)cccc1-c1nnn(C)n1] |
| I-79 | 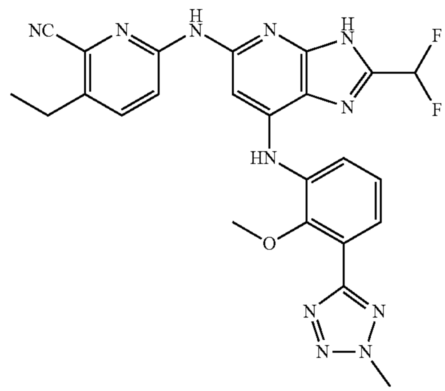 [SMILES: CCc1ccc(Nc2cc(Nc3cccc(-c4nnn(C)n4)c3OC)c3nc(C(F)F)[nH]c3n2)nc1C#N] |
| I-80 | 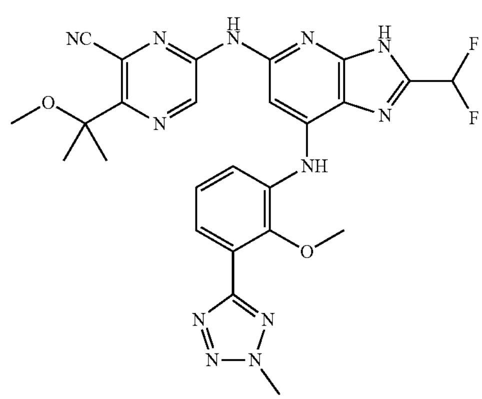 [SMILES: COc1c(Nc2cc(Nc3cnc(C(C)(C)OC)c(C#N)n3)nc3[nH]c(C(F)F)nc23)cccc1-c1nnn(C)n1] |

TABLE-continued

Exemplary Compounds

| Compound | Structure |
|---|---|
| I-81 | 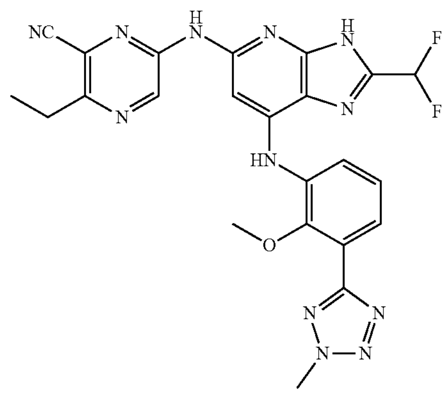 [SMILES: CCc1ncc(Nc2cc(Nc3cccc(-c4nnn(C)n4)c3OC)c3nc(C(F)F)[nH]c3n2)nc1C#N] |
| I-82 | 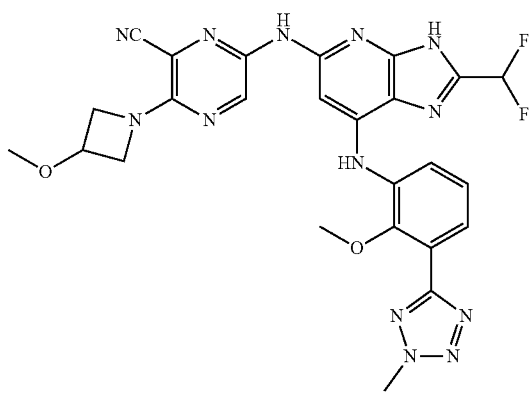 [SMILES: COc1c(Nc2cc(Nc3cnc(N4CC(OC)C4)c(C#N)n3)nc3[nH]c(C(F)F)nc23)cccc1-c1nnn(C)n1] |
| I-83 | 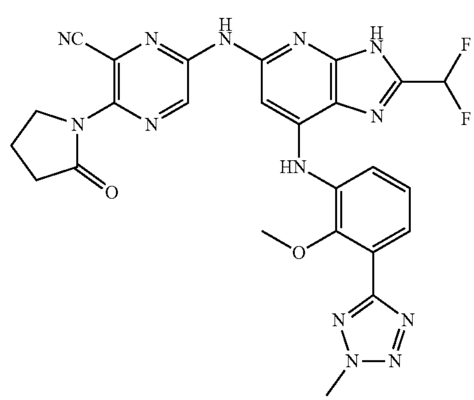 [SMILES: COc1c(Nc2cc(Nc3cnc(N4CCCC4=O)c(C#N)n3)nc3[nH]c(C(F)F)nc23)cccc1-c1nnn(C)n1] |

TABLE-continued
Exemplary Compounds
| Compound | Structure |
|---|---|
| I-84 | 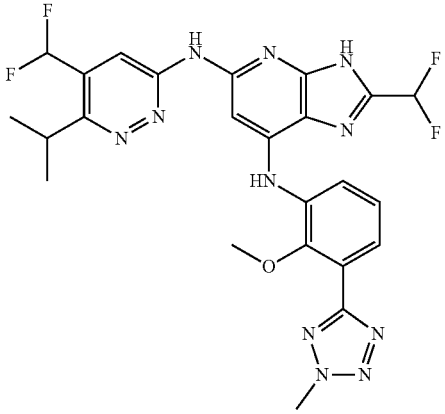 [SMILES: COc1c(Nc2cc(Nc3cc(C(F)F)c(C(C)C)nn3)nc3[nH]c(C(F)F)nc23)cccc1-c1nnn(C)n1] |
| I-85 | 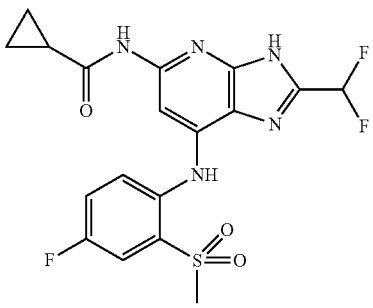 [SMILES: CS(=O)(=O)c1cc(F)ccc1Nc1cc(NC(=O)C2CC2)nc2[nH]c(C(F)F)nc12] |
| I-86 | 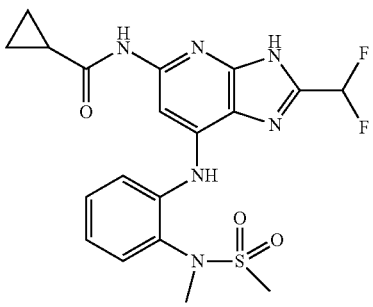 [SMILES: CN(c1ccccc1Nc1cc(NC(=O)C2CC2)nc2[nH]c(C(F)F)nc12)S(C)(=O)=O] |
| I-87 | 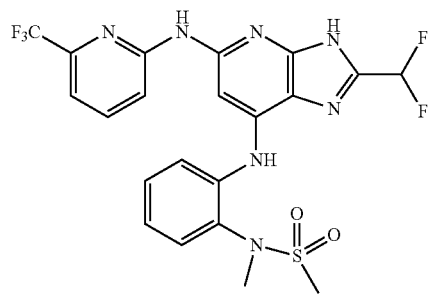 [SMILES: CN(c1ccccc1Nc1cc(Nc2cccc(C(F)(F)F)n2)nc2[nH]c(C(F)F)nc12)S(C)(=O)=O] |

TABLE-continued

Exemplary Compounds

| Compound | Structure |
|---|---|
| I-88 | 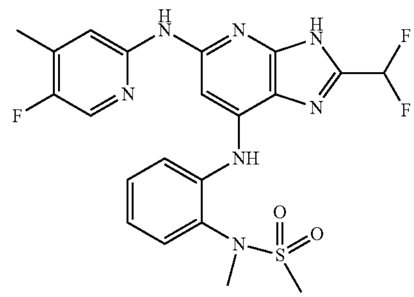 [SMILES: Cc1cc(Nc2cc(Nc3ccccc3N(C)S(C)(=O)=O)c3nc(C(F)F)[nH]c3n2)ncc1F] |
| I-89 | 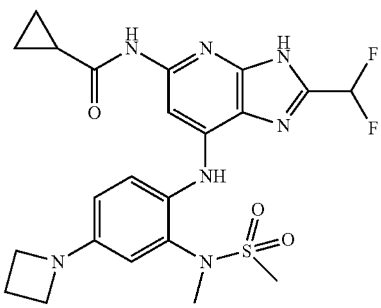 [SMILES: CN(c1cc(N2CCC2)ccc1Nc1cc(NC(=O)C2CC2)nc2[nH]c(C(F)F)nc12)S(C)(=O)=O] |
| I-90 | 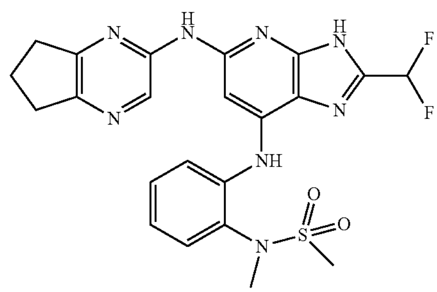 [SMILES: CN(c1ccccc1Nc1cc(Nc2cnc3c(n2)CCC3)nc2[nH]c(C(F)F)nc12)S(C)(=O)=O] |
| I-91 | 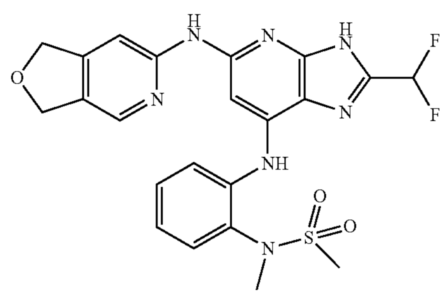 [SMILES: CN(c1ccccc1Nc1cc(Nc2cc3c(cn2)COC3)nc2[nH]c(C(F)F)nc12)S(C)(=O)=O] |
| I-92 | 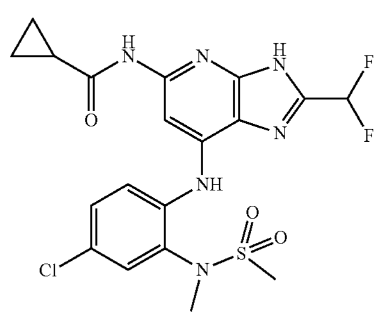 [SMILES: CN(c1cc(Cl)ccc1Nc1cc(NC(=O)C2CC2)nc2[nH]c(C(F)F)nc12)S(C)(=O)=O] |

TABLE-continued

Exemplary Compounds

| Compound | Structure |
|---|---|
| I-93 | 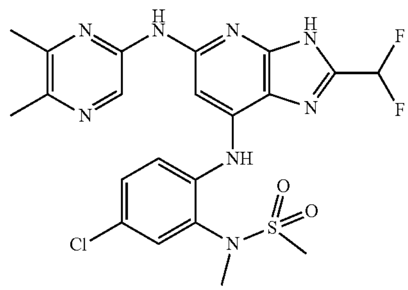 [SMILES: Cc1ncc(Nc2cc(Nc3ccc(Cl)cc3N(C)S(C)(=O)=O)c3nc(C(F)F)[nH]c3n2)nc1C] |
| I-94 | 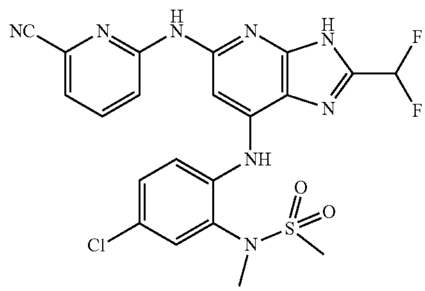 [SMILES: CN(c1cc(Cl)ccc1Nc1cc(Nc2cccc(C#N)n2)nc2[nH]c(C(F)F)nc12)S(C)(=O)=O] |
| I-95 | 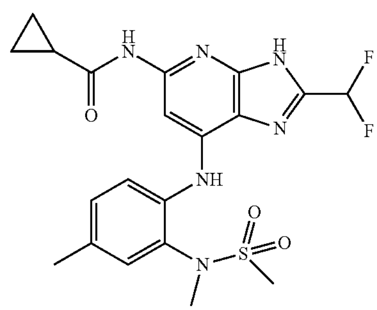 [SMILES: Cc1ccc(Nc2cc(NC(=O)C3CC3)nc3[nH]c(C(F)F)nc23)c(N(C)S(C)(=O)=O)c1] |
| I-96 | 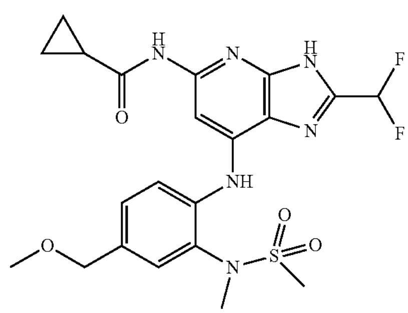 [SMILES: COCc1ccc(Nc2cc(NC(=O)C3CC3)nc3[nH]c(C(F)F)nc23)c(N(C)S(C)(=O)=O)c1] |
| I-97 | 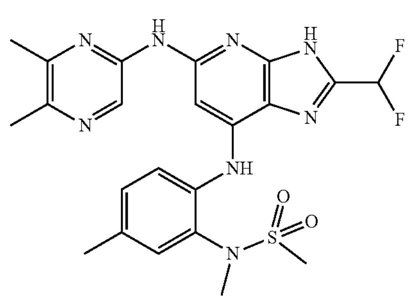 [SMILES: Cc1ccc(Nc2cc(Nc3cnc(C)c(C)n3)nc3[nH]c(C(F)F)nc23)c(N(C)S(C)(=O)=O)c1] |

TABLE-continued
Exemplary Compounds
| Compound | Structure |
|---|---|
| I-98 | 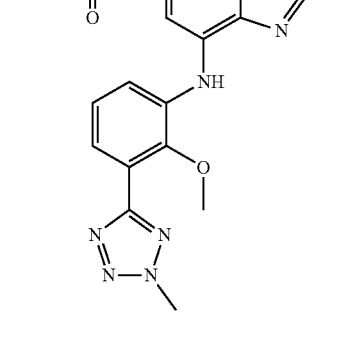 |
| I-100 | 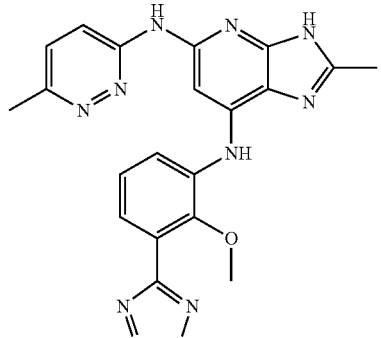 |
| I-101 | 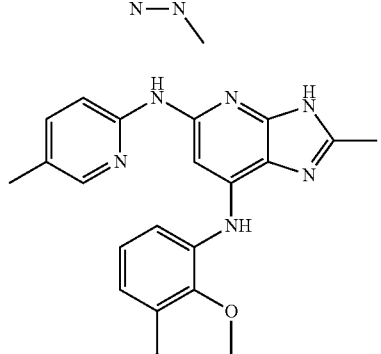 |
| I-103 | 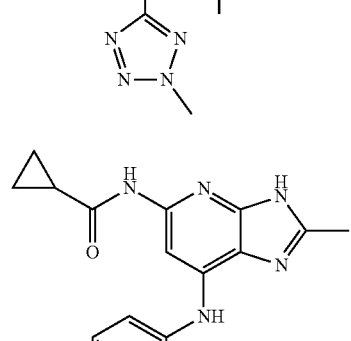 |

TABLE-continued
Exemplary Compounds
| Compound | Structure |
|---|---|
| I-104 | 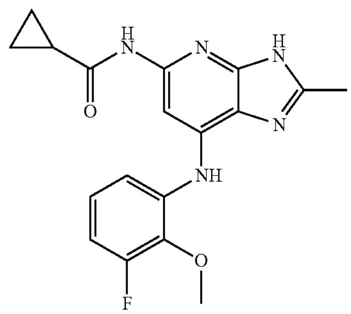 [SMILES: COc1c(F)cccc1Nc1cc(NC(=O)C2CC2)nc2[nH]c(C)nc12] |
| I-105 | 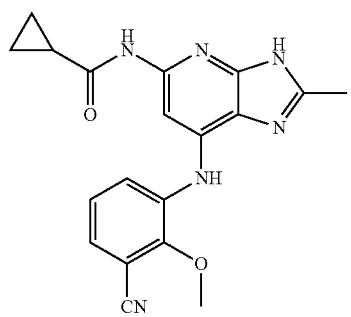 [SMILES: COc1c(C#N)cccc1Nc1cc(NC(=O)C2CC2)nc2[nH]c(C)nc12] |
| I-106 | 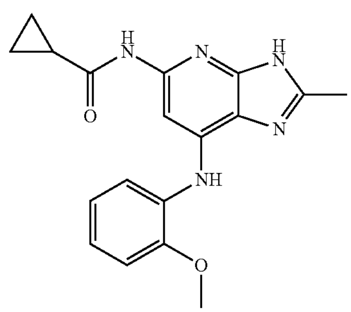 [SMILES: COc1ccccc1Nc1cc(NC(=O)C2CC2)nc2[nH]c(C)nc12] |
| I-107 | 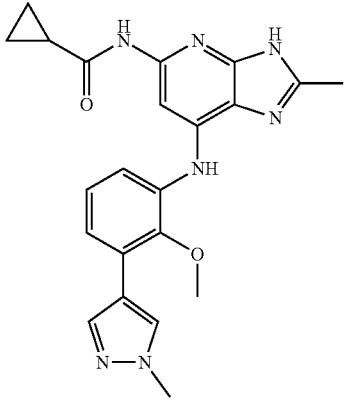 [SMILES: COc1c(Nc2cc(NC(=O)C3CC3)nc3[nH]c(C)nc23)cccc1-c1cnn(C)c1] |

TABLE-continued
Exemplary Compounds
| Compound | Structure |
|---|---|
| I-108 | 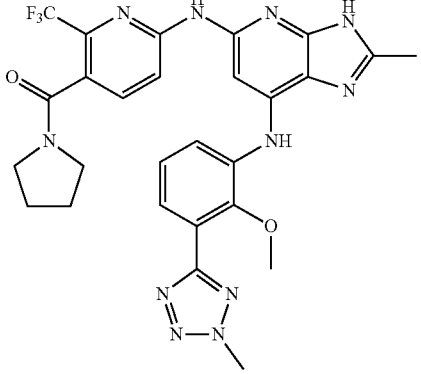 |
| I-109 | 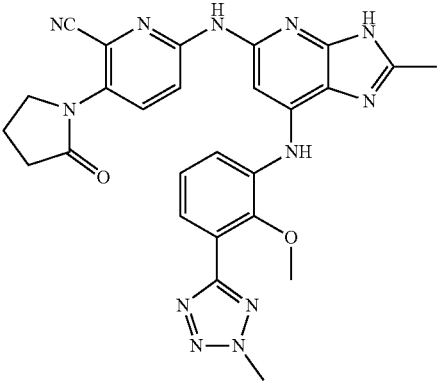 [SMILES: COc1c(Nc2cc(Nc3ccc(N4CCCC4=O)c(C#N)n3)nc3[nH]c(C)nc23)cccc1-c1nnn(C)n1] |
| I-110 | 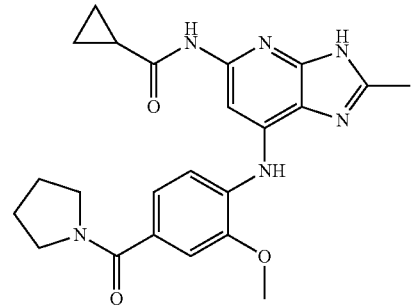 [SMILES: COc1cc(C(=O)N2CCCC2)ccc1Nc1cc(NC(=O)C2CC2)nc2[nH]c(C)nc12] |
| I-111 | 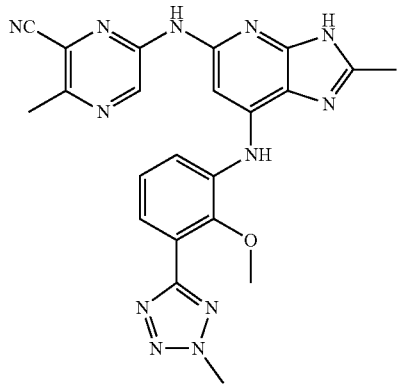 |

TABLE-continued
Exemplary Compounds
| Compound | Structure |
|---|---|
| I-112 | 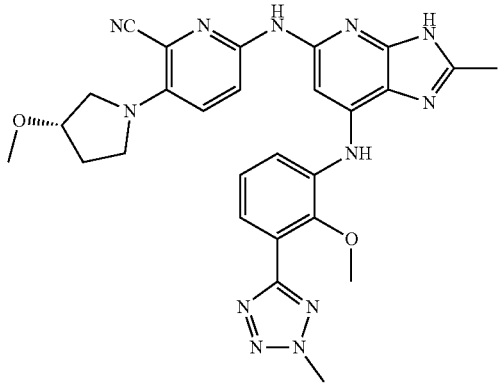 |
| I-113 | 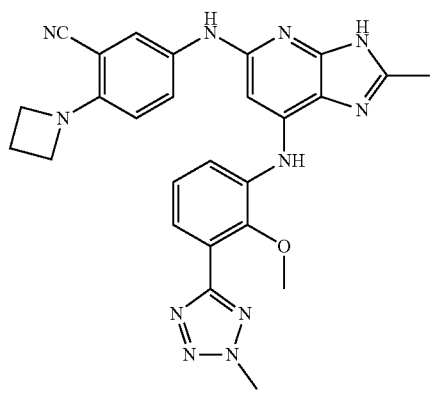 [SMILES: COc1c(Nc2cc(Nc3ccc(N4CCC4)c(C#N)c3)nc3[nH]c(C)nc23)cccc1-c1nnn(C)n1] |
| I-114 | 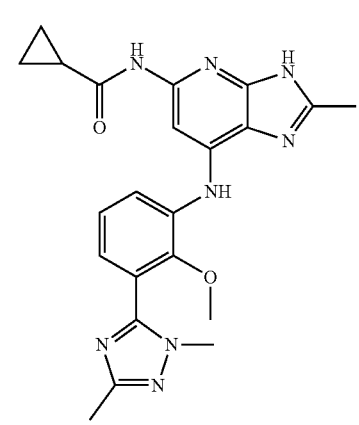 [SMILES: COc1c(Nc2cc(NC(=O)C3CC3)nc3[nH]c(C)nc23)cccc1-c1nc(C)nn1C] |

TABLE-continued

Exemplary Compounds

| Compound | Structure |
| --- | --- |
| I-115 | 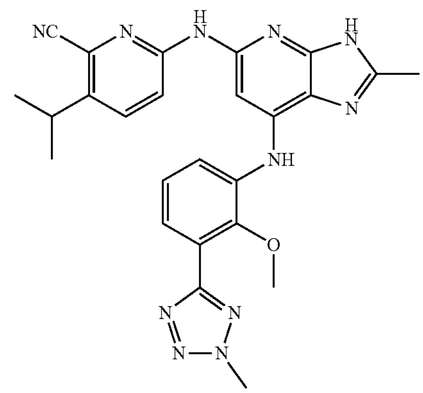 [SMILES: COc1c(Nc2cc(Nc3ccc(C(C)C)c(C#N)n3)nc3[nH]c(C)nc23)cccc1-c1nnn(C)n1] |
| I-116 | 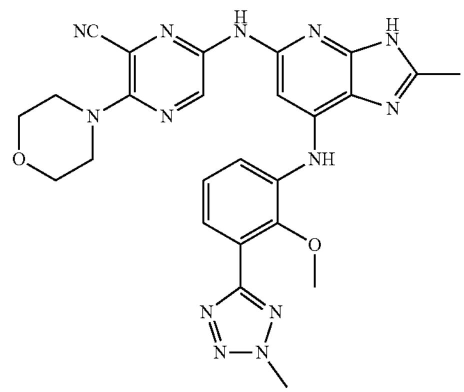 [SMILES: COc1c(Nc2cc(Nc3cnc(N4CCOCC4)c(C#N)n3)nc3[nH]c(C)nc23)cccc1-c1nnn(C)n1] |
| I-117 | 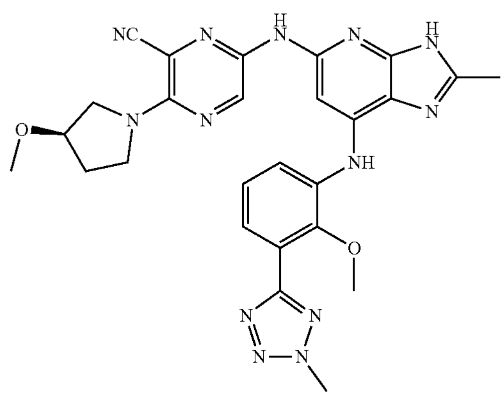 |
| I-118 | 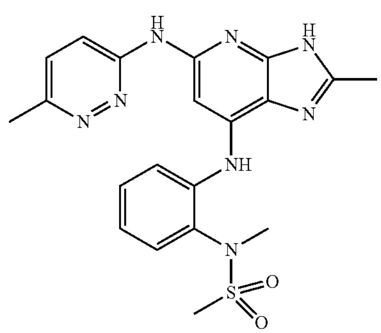 |

TABLE-continued

Exemplary Compounds

| Compound | Structure |
|---|---|
| I-120 | 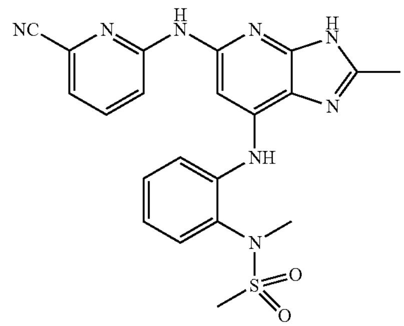 [SMILES: Cc1nc2c(Nc3ccccc3N(C)S(C)(=O)=O)cc(Nc3cccc(C#N)n3)nc2[nH]1] |
| I-121 | 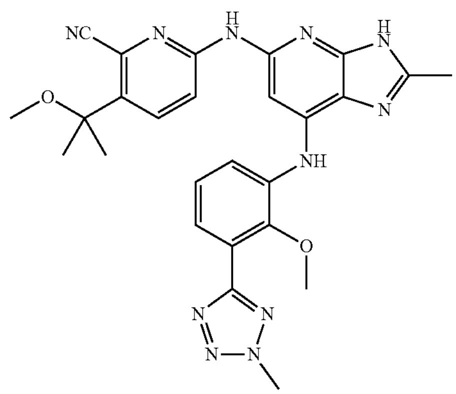 |
| I-122 | 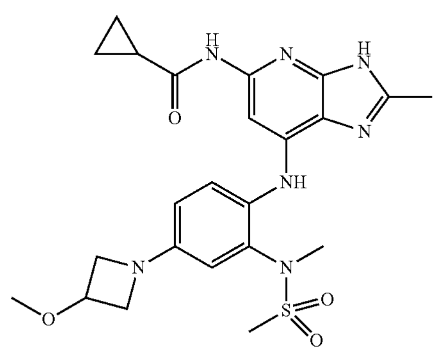 |
| I-123 | 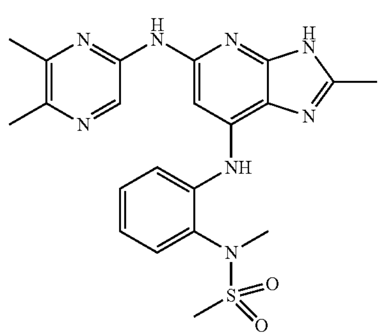 |

TABLE-continued
Exemplary Compounds
| Compound | Structure |
|---|---|
| I-124 | 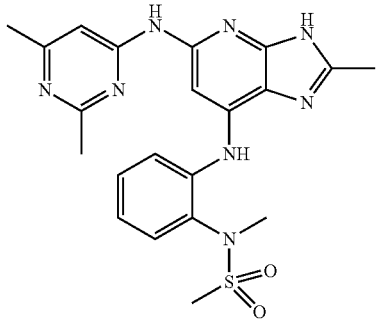 |
| I-125 | 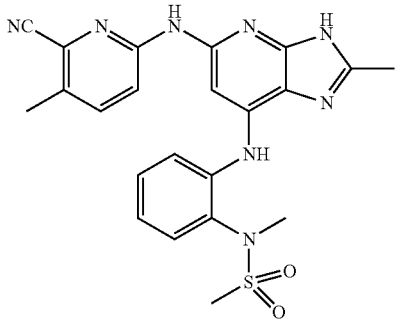 |
| I-126 | 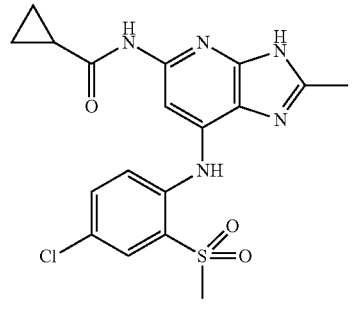 [SMILES: Cc1nc2c(Nc3ccc(Cl)cc3S(C)(=O)=O)cc(NC(=O)C3CC3)nc2[nH]1] |
| I-127 | 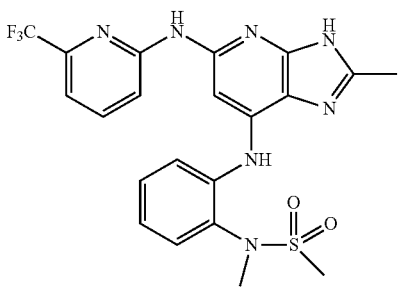 [SMILES: Cc1nc2c(Nc3ccccc3N(C)S(C)(=O)=O)cc(Nc3cccc(C(F)(F)F)n3)nc2[nH]1] |

TABLE-continued
Exemplary Compounds
| Compound | Structure |
|---|---|
| I-128 | 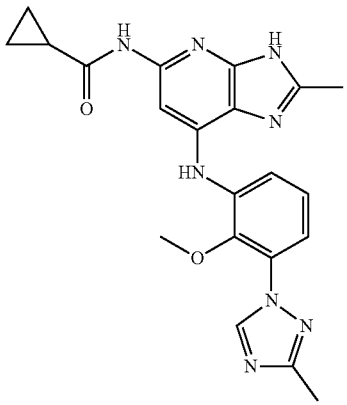 [SMILES: COc1c(Nc2cc(NC(=O)C3CC3)nc3[nH]c(C)nc23)cccc1-n1cnc(C)n1] |
| I-129 | 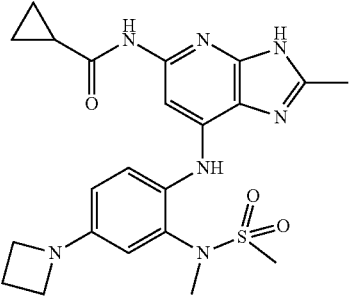 [SMILES: Cc1nc2c(Nc3ccc(N4CCC4)cc3N(C)S(C)(=O)=O)cc(NC(=O)C3CC3)nc2[nH]1] |
| I-130 | 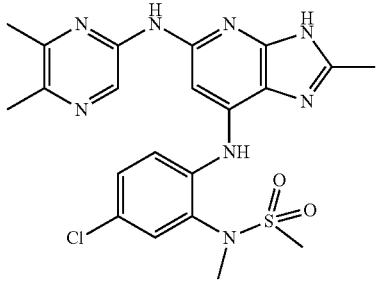 |
| I-131 | 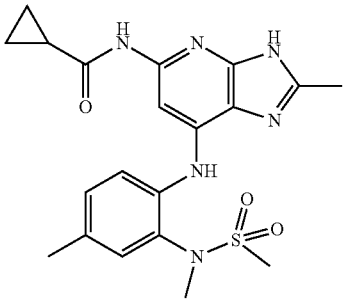 [SMILES: Cc1ccc(Nc2cc(NC(=O)C3CC3)nc3[nH]c(C)nc23)c(N(C)S(C)(=O)=O)c1] |

TABLE-continued

Exemplary Compounds

| Compound | Structure |
|---|---|
| I-132 | 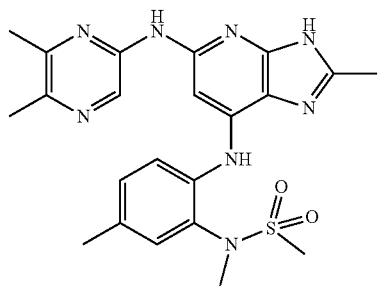 |
| I-133 | 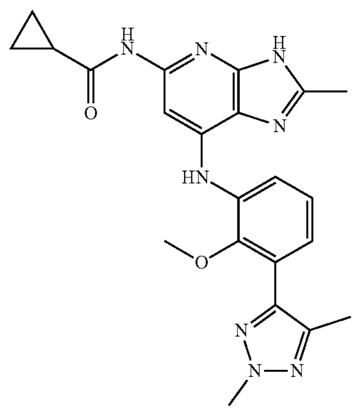 [SMILES: COc1c(Nc2cc(NC(=O)C3CC3)nc3[nH]c(C)nc23)cccc1-c1nn(C)nc1C] |
| I-134 | 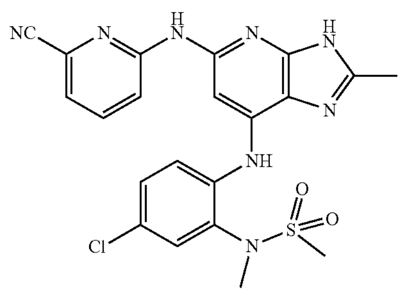 [SMILES: Cc1nc2c(Nc3ccc(Cl)cc3N(C)S(C)(=O)=O)cc(Nc3cccc(C#N)n3)nc2[nH]1] |
| I-135 | 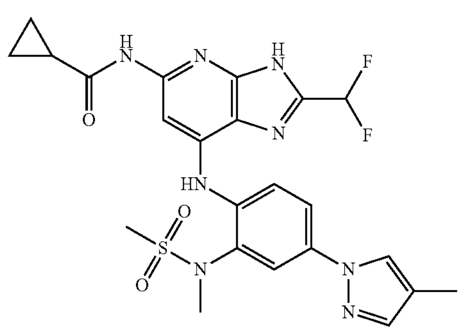 [SMILES: Cc1cnn(-c2ccc(Nc3cc(NC(=O)C4CC4)nc4[nH]c(C(F)F)nc34)c(N(C)S(C)(=O)=O)c2)c1] |

TABLE-continued
Exemplary Compounds
| Compound | Structure |
|---|---|
| I-136 | 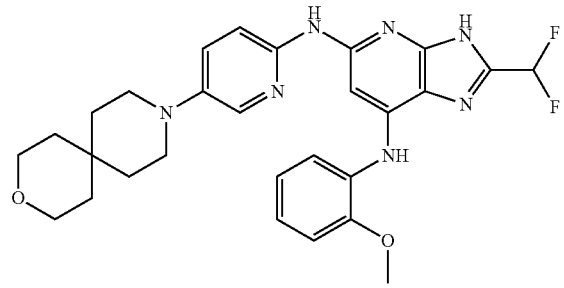 [SMILES: COc1ccccc1Nc1cc(Nc2ccc(N3CCC4(CCOCC4)CC3)cn2)nc2[nH]c(C(F)F)nc12] |
| I-137 | 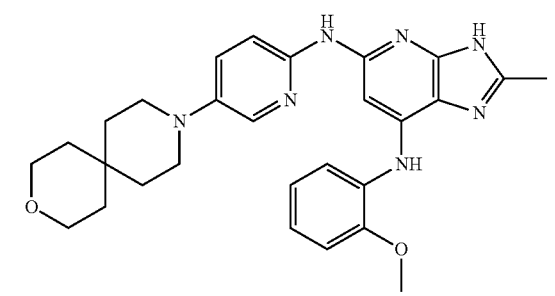 [SMILES: COc1ccccc1Nc1cc(Nc2ccc(N3CCC4(CCOCC4)CC3)cn2)nc2[nH]c(C)nc12] |
| I-138 | 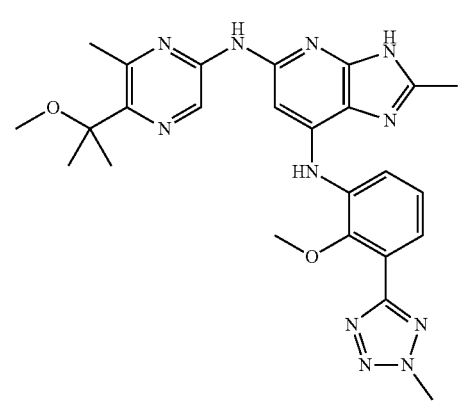 |
| I-139 | 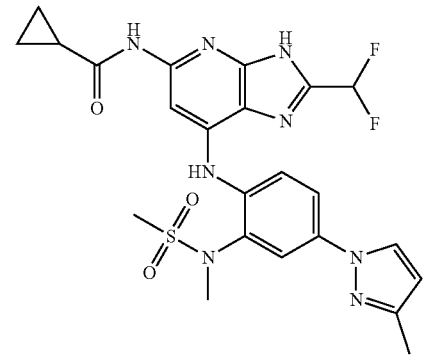 [SMILES: Cc1ccn(-c2ccc(Nc3cc(NC(=O)C4CC4)nc4[nH]c(C(F)F)nc34)c(N(C)S(C)(=O)=O)c2)n1] |

TABLE-continued
Exemplary Compounds
| Compound | Structure |
|---|---|
| I-140 | 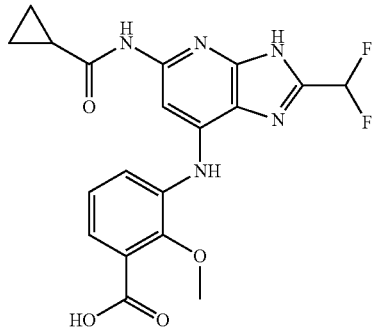 [SMILES: COc1c(Nc2cc(NC(=O)C3CC3)nc3[nH]c(C(F)F)nc23)cccc1C(=O)O] |
| I-141 | 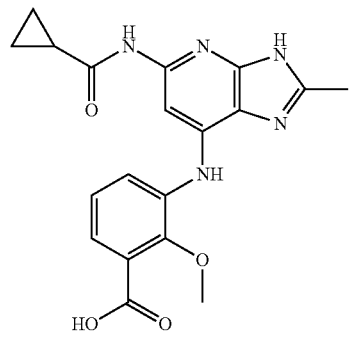 [SMILES: COc1c(Nc2cc(NC(=O)C3CC3)nc3[nH]c(C)nc23)cccc1C(=O)O] |
| I-142 | 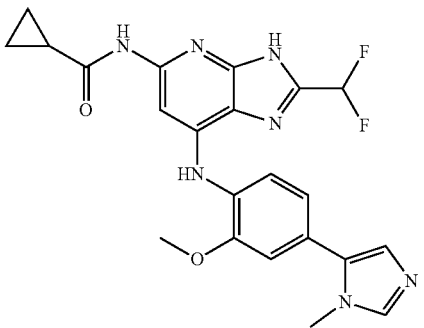 [SMILES: COc1cc(-c2cncn2C)ccc1Nc1cc(NC(=O)C2CC2)nc2[nH]c(C(F)F)nc12] |
| I-143 | 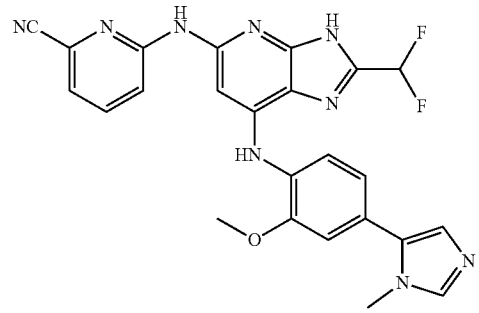 [SMILES: COc1cc(-c2cncn2C)ccc1Nc1cc(Nc2cccc(C#N)n2)nc2[nH]c(C(F)F)nc12] |

| Compound | Structure |
|---|---|
| I-144 | 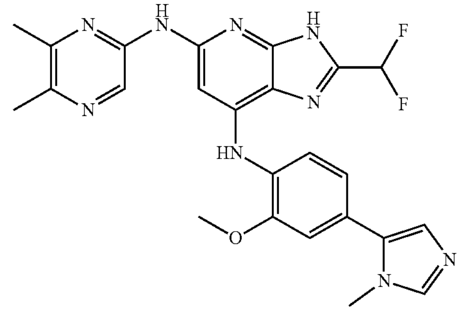 [SMILES: COc1cc(-c2cncn2C)ccc1Nc1cc(Nc2cnc(C)c(C)n2)nc2[nH]c(C(F)F)nc12] |
| I-145 | 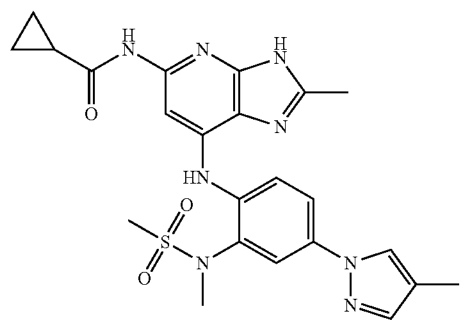 [SMILES: Cc1cnn(-c2ccc(Nc3cc(NC(=O)C4CC4)nc4[nH]c(C)nc34)c(N(C)S(C)(=O)=O)c2)c1] |
| I-146 | 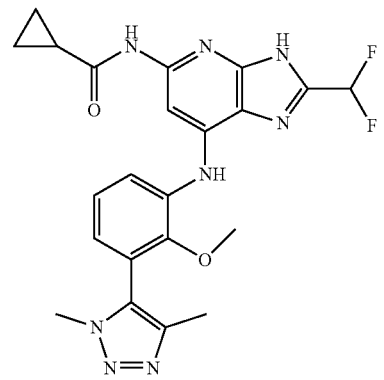 [SMILES: COc1c(Nc2cc(NC(=O)C3CC3)nc3[nH]c(C(F)F)nc23)cccc1-c1c(C)nnn1C] |
| I-147 | 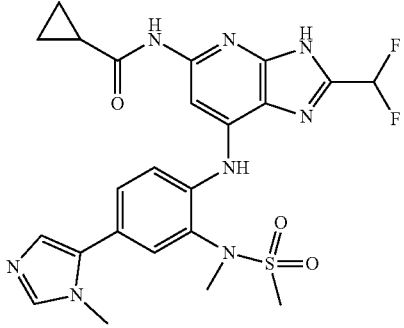 [SMILES: CN(c1cc(-c2cncn2C)ccc1Nc1cc(NC(=O)C2CC2)nc2[nH]c(C(F)F)nc12)S(C)(=O)=O] |

| Compound | Structure |
|---|---|
| I-148 | *(structure)* |
| I-149 | *(structure)* |
| I-150 | *(structure)* |
| I-151 | *(structure)* |

TABLE-continued

Exemplary Compounds

| Compound | Structure |
|---|---|
| I-152 | 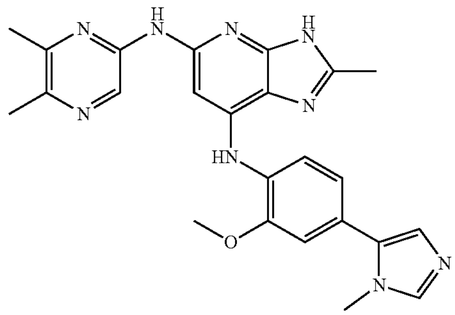 [SMILES: COc1cc(-c2cncn2C)ccc1Nc1cc(Nc2cnc(C)c(C)n2)nc2[nH]c(C)nc12] |
| I-153 | 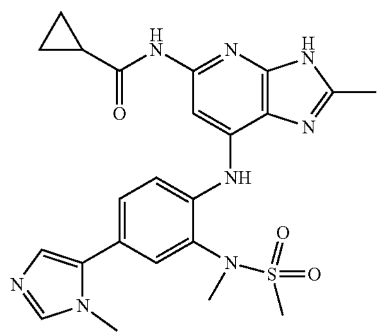 [SMILES: Cc1nc2c(Nc3ccc(-c4cncn4C)cc3N(C)S(C)(=O)=O)cc(NC(=O)C3CC3)nc2[nH]1] |
| I-154 | 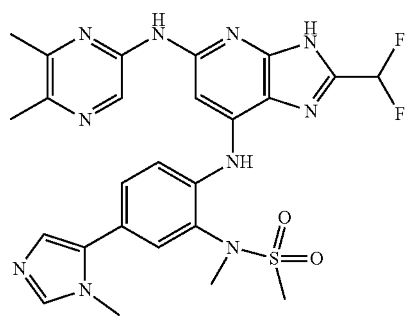 [SMILES: Cc1ncc(Nc2cc(Nc3ccc(-c4cncn4C)cc3N(C)S(C)(=O)=O)c3nc(C(F)F)[nH]c3n2)nc1C] |
| I-155 | 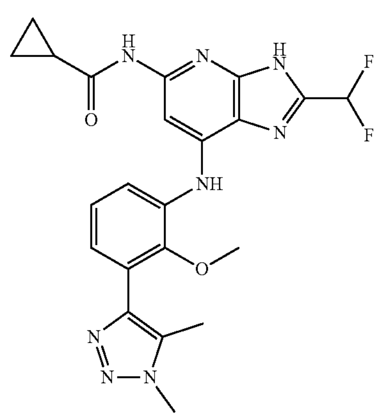 [SMILES: COc1c(Nc2cc(NC(=O)C3CC3)nc3[nH]c(C(F)F)nc23)cccc1-c1nnn(C)c1C] |

TABLE-continued
Exemplary Compounds
| Compound | Structure |
|---|---|
| I-156 | 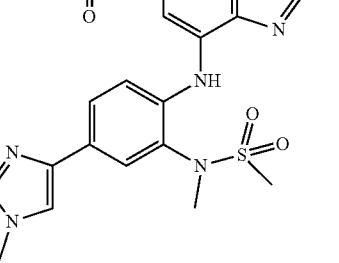 |
| I-157 | 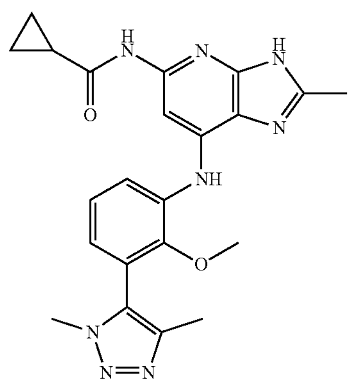 [SMILES: COc1c(Nc2cc(NC(=O)C3CC3)nc3[nH]c(C)nc23)cccc1-c1c(C)nnn1C] |
| I-158 | 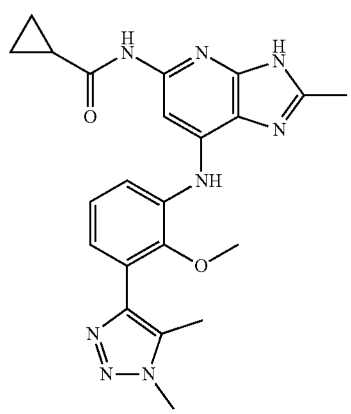 [SMILES: COc1c(Nc2cc(NC(=O)C3CC3)nc3[nH]c(C)nc23)cccc1-c1nnn(C)c1C] |
| I-159 | 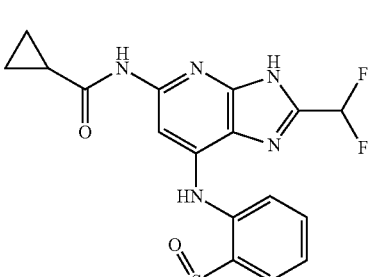 |

| Compound | Structure |
|---|---|
| I-160 | 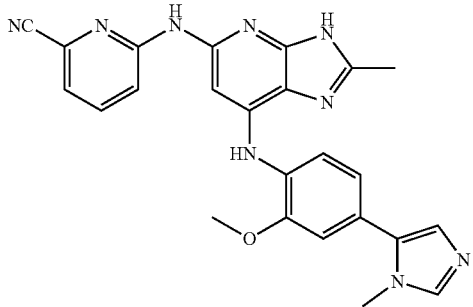 [SMILES: COc1cc(-c2cncn2C)ccc1Nc1cc(Nc2cccc(C#N)n2)nc2[nH]c(C)nc12] |
| I-161 | 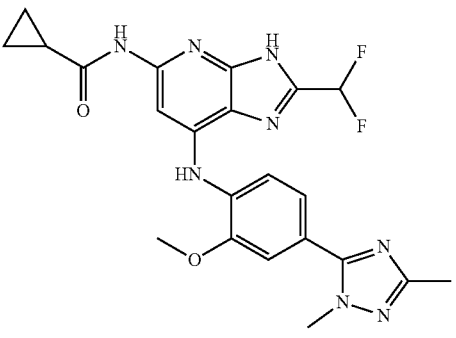 [SMILES: COc1cc(-c2nc(C)nn2C)ccc1Nc1cc(NC(=O)C2CC2)nc2[nH]c(C(F)F)nc12] |
| I-162 | 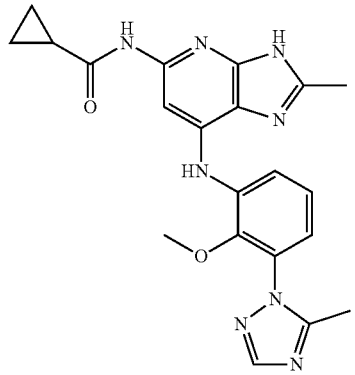 [SMILES: COc1c(Nc2cc(NC(=O)C3CC3)nc3[nH]c(C)nc23)cccc1-n1ncnc1C] |
| I-163 | 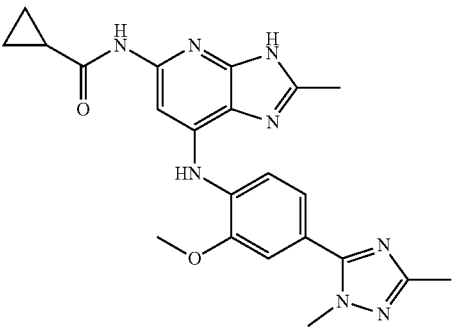 [SMILES: COc1cc(-c2nc(C)nn2C)ccc1Nc1cc(NC(=O)C2CC2)nc2[nH]c(C)nc12] |

TABLE-continued
Exemplary Compounds
| Compound | Structure |
|---|---|
| I-164 | 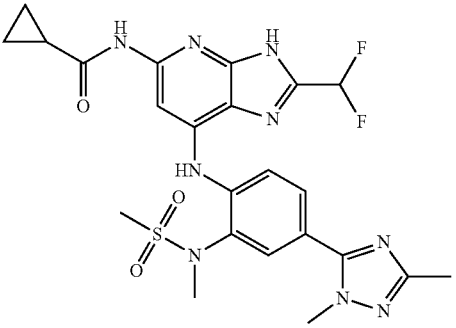 [SMILES: Cc1nc(-c2ccc(Nc3cc(NC(=O)C4CC4)nc4[nH]c(C(F)F)nc34)c(N(C)S(C)(=O)=O)c2)n(C)n1] |
| I-165 | 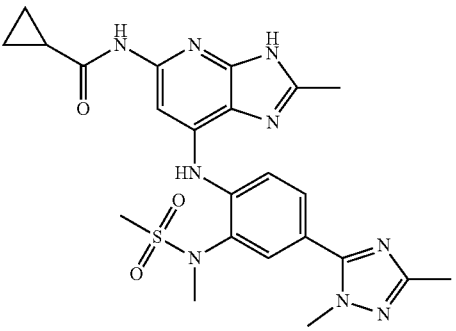 [SMILES: Cc1nc(-c2ccc(Nc3cc(NC(=O)C4CC4)nc4[nH]c(C)nc34)c(N(C)S(C)(=O)=O)c2)n(C)n1] |
| I-166 | 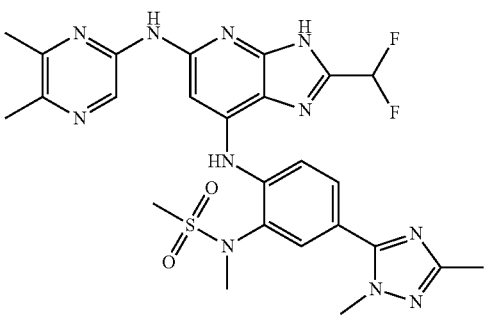 |
| I-167 | 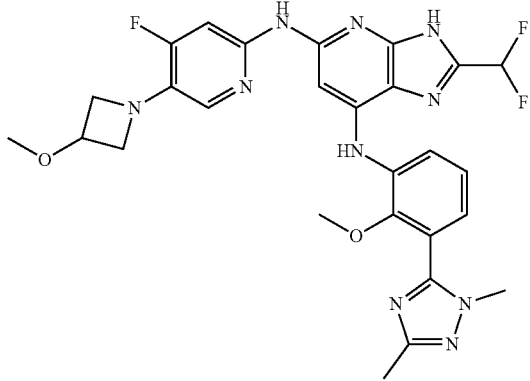 [SMILES: COc1c(Nc2cc(Nc3cc(F)c(N4CC(OC)C4)cn3)nc3[nH]c(C(F)F)nc23)cccc1-c1nc(C)nn1C] |

TABLE-continued
Exemplary Compounds
| Compound | Structure |
|---|---|
| I-168 | 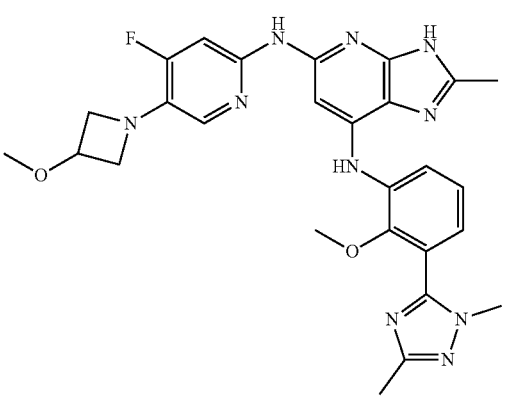 |
| I-169 | 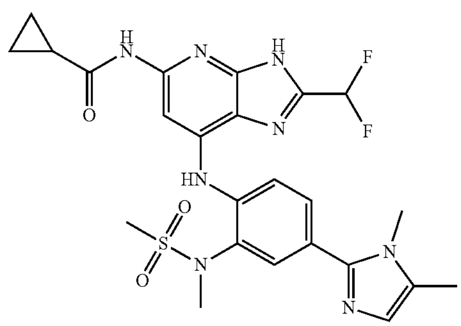 [SMILES: Cc1cnc(-c2ccc(Nc3cc(NC(=O)C4CC4)nc4[nH]c(C(F)F)nc34)c(N(C)S(C)(=O)=O)c2)n1C] |
| I-170 | 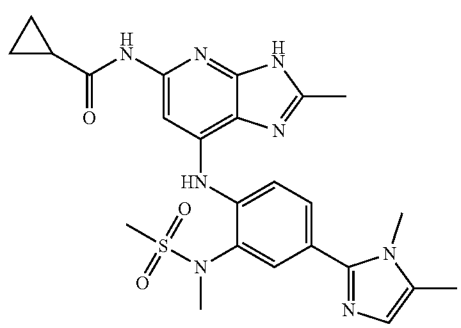 [SMILES: Cc1nc2c(Nc3ccc(-c4ncc(C)n4C)cc3N(C)S(C)(=O)=O)cc(NC(=O)C3CC3)nc2[nH]1] |
| I-171 | 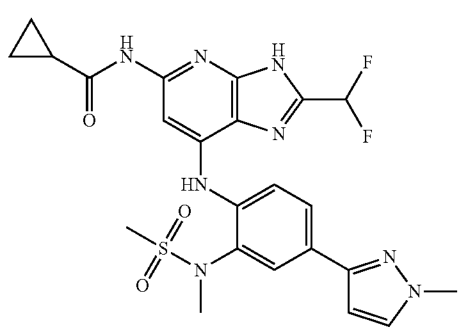 [SMILES: CN(c1cc(-c2ccn(C)n2)ccc1Nc1cc(NC(=O)C2CC2)nc2[nH]c(C(F)F)nc12)S(C)(=O)=O] |

TABLE-continued

Exemplary Compounds

| Compound | Structure |
|---|---|
| I-172 | 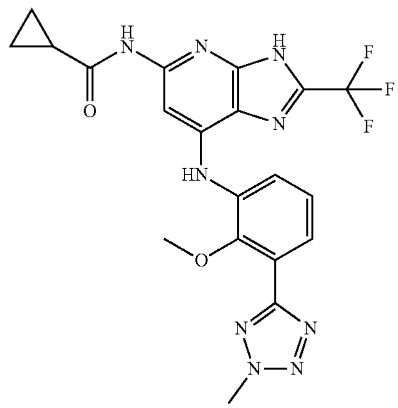 [SMILES: COc1c(Nc2cc(NC(=O)C3CC3)nc3[nH]c(C(F)(F)F)nc23)cccc1-c1nnn(C)n1] |
| I-173 | 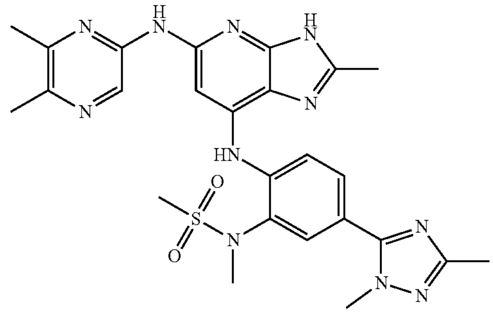 |
| I-174 | 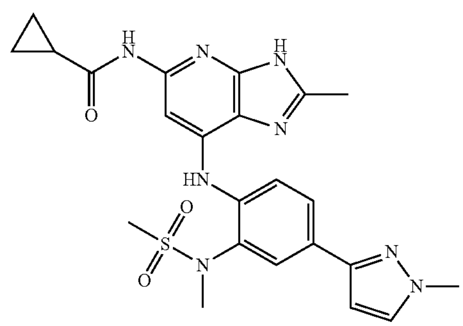 [SMILES: Cc1nc2c(Nc3ccc(-c4ccn(C)n4)cc3N(C)S(C)(=O)=O)cc(NC(=O)C3CC3)nc2[nH]1] |
| I-175 | 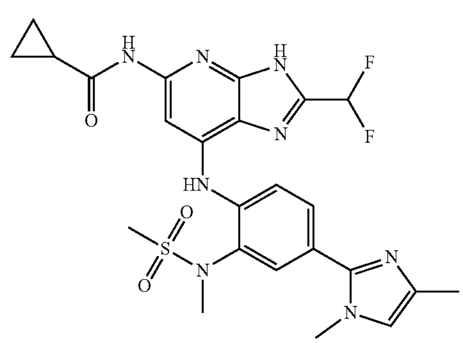 [SMILES: Cc1cn(C)c(-c2ccc(Nc3cc(NC(=O)C4CC4)nc4[nH]c(C(F)F)nc34)c(N(C)S(C)(=O)=O)c2)n1] |

TABLE-continued

Exemplary Compounds

| Compound | Structure |
|---|---|
| I-176 | 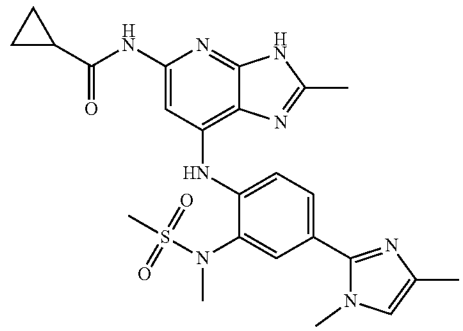 [SMILES: Cc1cn(C)c(-c2ccc(Nc3cc(NC(=O)C4CC4)nc4[nH]c(C)nc34)c(N(C)S(C)(=O)=O)c2)n1] |
| I-177 | 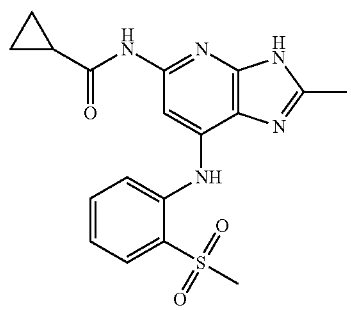 [SMILES: Cc1nc2c(Nc3ccccc3S(C)(=O)=O)cc(NC(=O)C3CC3)nc2[nH]1] |
| I-178 | 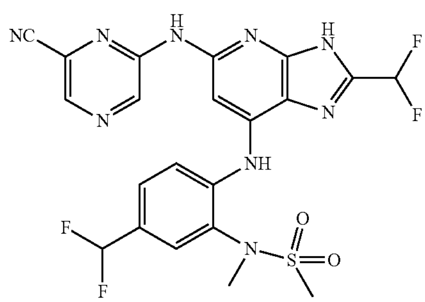 [SMILES: CN(c1cc(C(F)F)ccc1Nc1cc(Nc2cncc(C#N)n2)nc2[nH]c(C(F)F)nc12)S(C)(=O)=O] |
| I-179 | 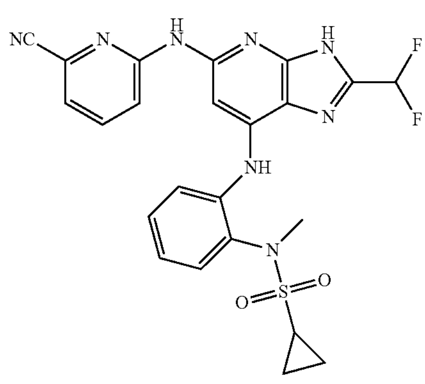 [SMILES: CN(c1ccccc1Nc1cc(Nc2cccc(C#N)n2)nc2[nH]c(C(F)F)nc12)S(=O)(=O)C1CC1] |

TABLE-continued
Exemplary Compounds
| Compound | Structure |
|---|---|
| I-180 | 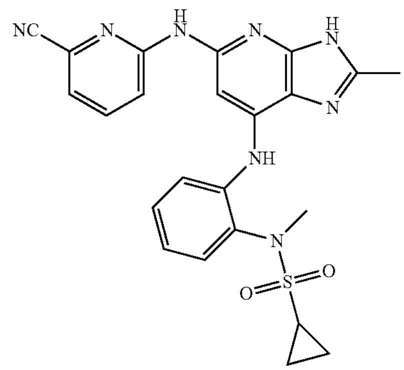 [SMILES: Cc1nc2c(Nc3ccccc3N(C)S(=O)(=O)C3CC3)cc(Nc3cccc(C#N)n3)nc2[nH]1] |
| I-181 | 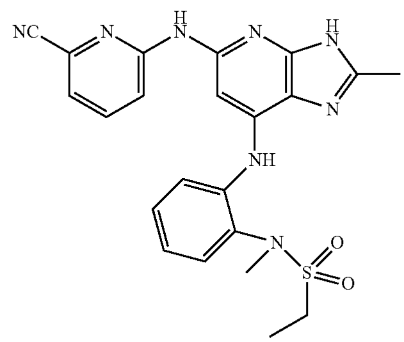 [SMILES: CCS(=O)(=O)N(C)c1ccccc1Nc1cc(Nc2cccc(C#N)n2)nc2[nH]c(C)nc12] |
| I-182 | 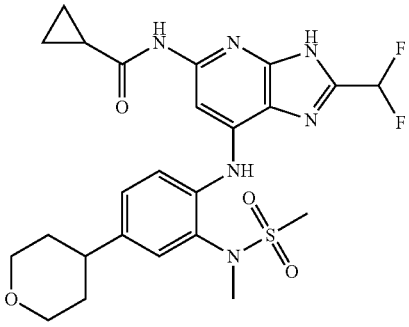 [SMILES: CN(c1cc(C2CCOCC2)ccc1Nc1cc(NC(=O)C2CC2)nc2[nH]c(C(F)F)nc12)S(C)(=O)=O] |
| I-183 | 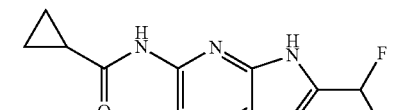 |

TABLE-continued

Exemplary Compounds

| Compound | Structure |
|---|---|
| I-184 | 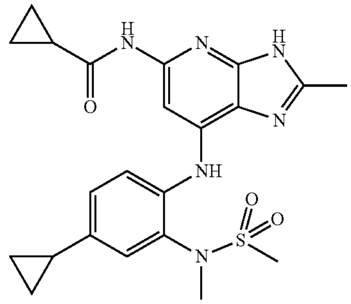 [SMILES: Cc1nc2c(Nc3ccc(C4CC4)cc3N(C)S(C)(=O)=O)cc(NC(=O)C3CC3)nc2[nH]1] |
| I-185 | 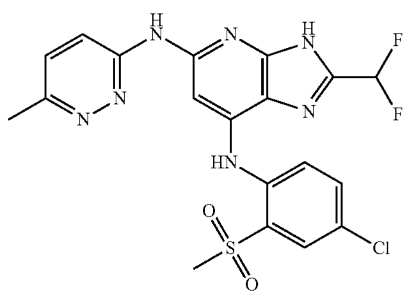 [SMILES: Cc1ccc(Nc2cc(Nc3ccc(Cl)cc3S(C)(=O)=O)c3nc(C(F)F)[nH]c3n2)nn1] |
| I-186 | 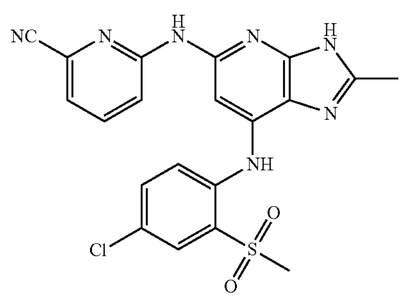 [SMILES: Cc1nc2c(Nc3ccc(Cl)cc3S(C)(=O)=O)cc(Nc3cccc(C#N)n3)nc2[nH]1] |
| I-187 | 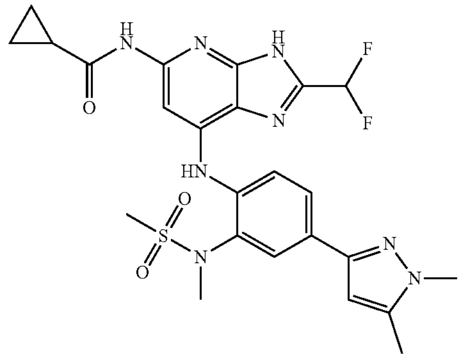 [SMILES: Cc1cc(-c2ccc(Nc3cc(NC(=O)C4CC4)nc4[nH]c(C(F)F)nc34)c(N(C)S(C)(=O)=O)c2)nn1C] |

TABLE-continued

Exemplary Compounds

| Compound | Structure |
|---|---|
| I-188 | 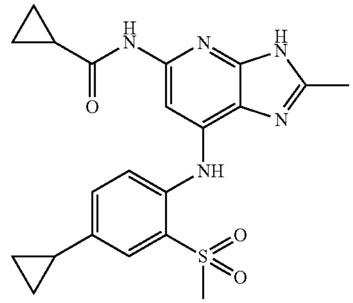 [SMILES: Cc1nc2c(Nc3ccc(C4CC4)cc3S(C)(=O)=O)cc(NC(=O)C3CC3)nc2[nH]1] |
| I-189 | 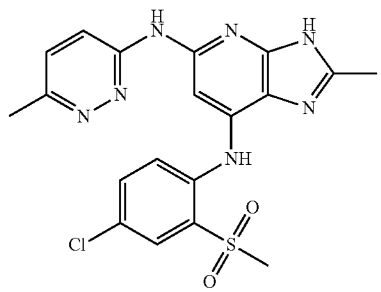 |
| I-190 | 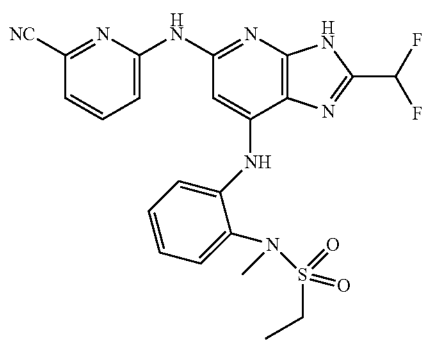 [SMILES: CCS(=O)(=O)N(C)c1ccccc1Nc1cc(Nc2cccc(C#N)n2)nc2[nH]c(C(F)F)nc12] |
| I-191 | 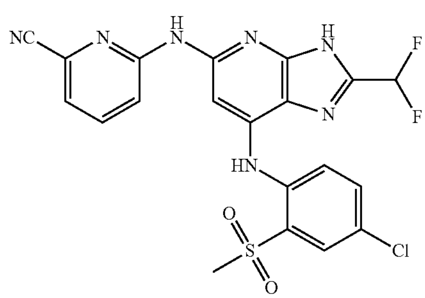 [SMILES: CS(=O)(=O)c1cc(Cl)ccc1Nc1cc(Nc2cccc(C#N)n2)nc2[nH]c(C(F)F)nc12] |
| I-192 | 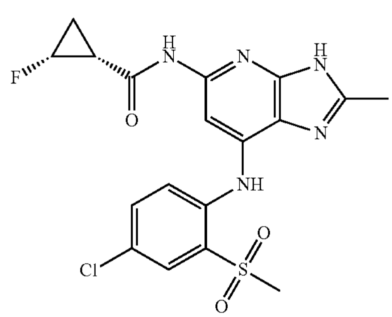 [SMILES: Cc1nc2c(Nc3ccc(Cl)cc3S(C)(=O)=O)cc(NC(=O)[C@H]3C[C@H]3F)nc2[nH]1] |

TABLE-continued

Exemplary Compounds

| Compound | Structure |
|---|---|
| I-193 | 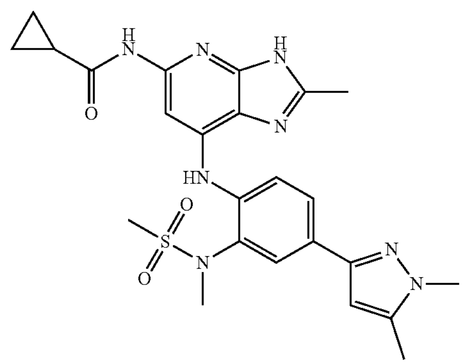 [SMILES: Cc1nc2c(Nc3ccc(-c4cc(C)n(C)n4)cc3N(C)S(C)(=O)=O)cc(NC(=O)C3CC3)nc2[nH]1] |
| I-194 | 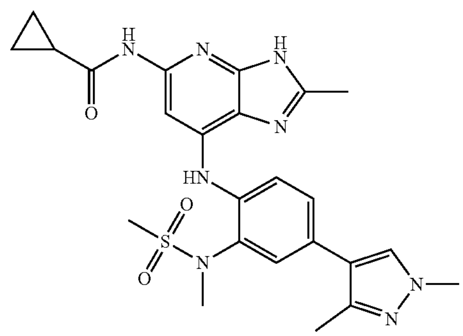 [SMILES: Cc1nc2c(Nc3ccc(-c4cn(C)nc4C)cc3N(C)S(C)(=O)=O)cc(NC(=O)C3CC3)nc2[nH]1] |
| I-195 | 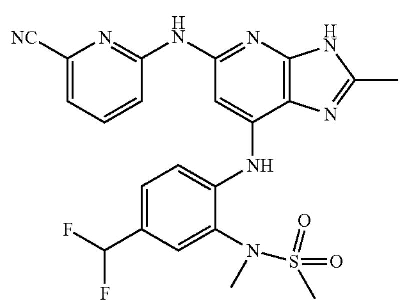 [SMILES: Cc1nc2c(Nc3ccc(C(F)F)cc3N(C)S(C)(=O)=O)cc(Nc3cccc(C#N)n3)nc2[nH]1] |
| I-196 | 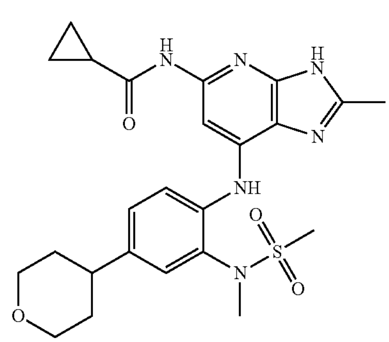 [SMILES: Cc1nc2c(Nc3ccc(C4CCOCC4)cc3N(C)S(C)(=O)=O)cc(NC(=O)C3CC3)nc2[nH]1] |

TABLE-continued
Exemplary Compounds
| Compound | Structure |
|---|---|
| I-197 | 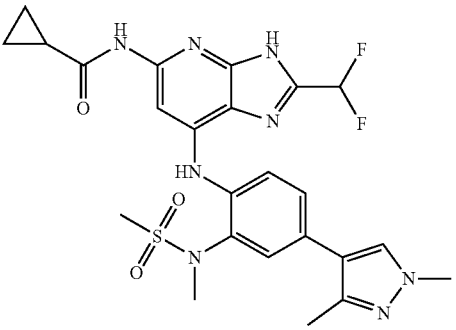 [SMILES: Cc1nn(C)cc1-c1ccc(Nc2cc(NC(=O)C3CC3)nc3[nH]c(C(F)F)nc23)c(N(C)S(C)(=O)=O)c1] |
| I-198 | 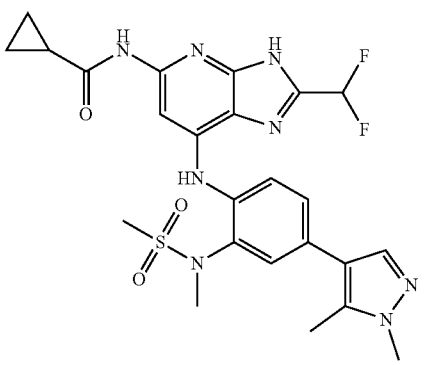 [SMILES: Cc1c(-c2ccc(Nc3cc(NC(=O)C4CC4)nc4[nH]c(C(F)F)nc34)c(N(C)S(C)(=O)=O)c2)cnn1C] |
| I-199 | 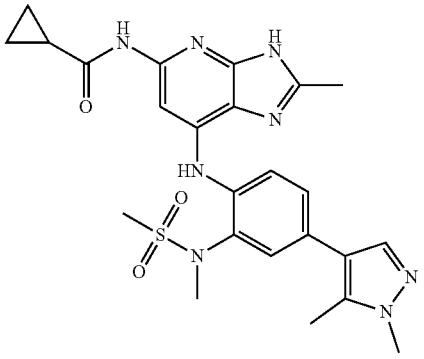 [SMILES: Cc1nc2c(Nc3ccc(-c4cnn(C)c4C)cc3N(C)S(C)(=O)=O)cc(NC(=O)C3CC3)nc2[nH]1] |
| I-200 | 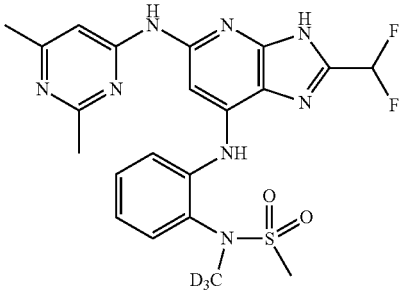 [SMILES: [2H]C([2H])([2H])N(c1ccccc1Nc1cc(Nc2cc(C)nc(C)n2)nc2[nH]c(C(F)F)nc12)S(C)(=O)=O] |

TABLE-continued

Exemplary Compounds

| Compound | Structure |
|---|---|
| I-201 | 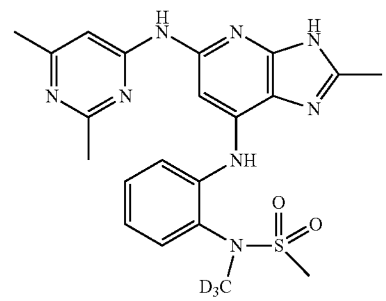 |
| I-202 | 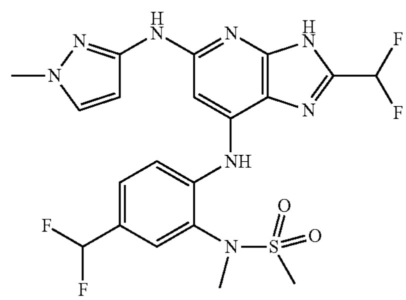 [SMILES: CN(c1cc(C(F)F)ccc1Nc1cc(Nc2ccn(C)n2)nc2[nH]c(C(F)F)nc12)S(C)(=O)=O] |
| I-203 | 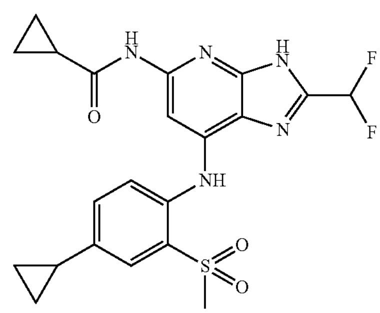 [SMILES: CS(=O)(=O)c1cc(C2CC2)ccc1Nc1cc(NC(=O)C2CC2)nc2[nH]c(C(F)F)nc12] |
| I-204 | 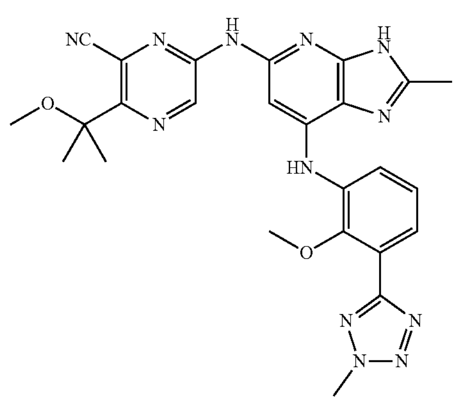 |

| Compound | Structure |
|---|---|
| I-205 | 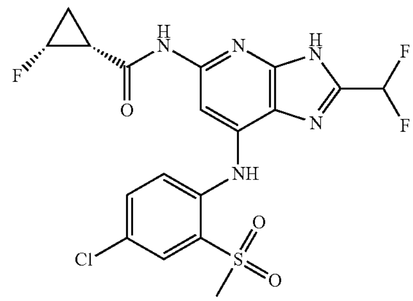 [SMILES: CS(=O)(=O)c1cc(Cl)ccc1Nc1cc(NC(=O)[C@H]2C[C@H]2F)nc2[nH]c(C(F)F)nc12] |
| I-206 | 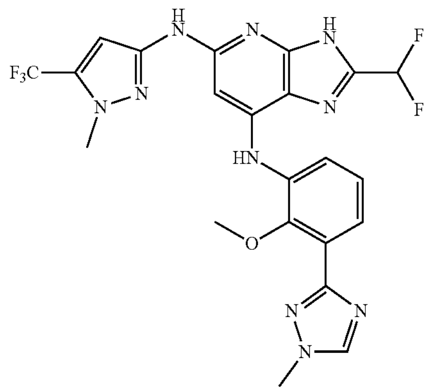 [SMILES: COc1c(Nc2cc(Nc3cc(C(F)(F)F)n(C)n3)nc3[nH]c(C(F)F)nc23)cccc1-c1ncn(C)n1] |
| I-207 | 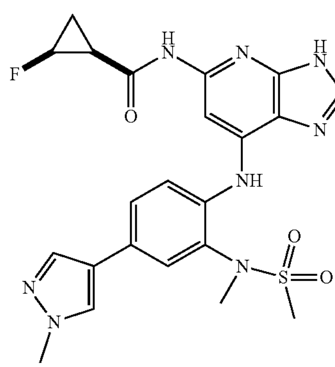 |
| I-208 | 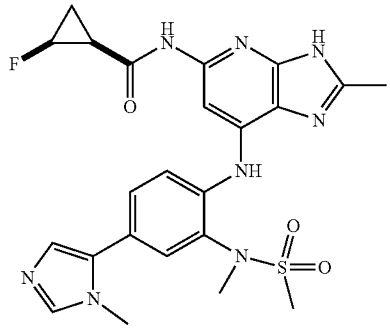 [SMILES: Cc1nc2c(Nc3ccc(-c4cncn4C)cc3N(C)S(C)(=O)=O)cc(NC(=O)[C@@H]3C[C@@H]3F)nc2[nH]1] |

TABLE-continued
Exemplary Compounds
| Compound | Structure |
|---|---|
| I-209 | 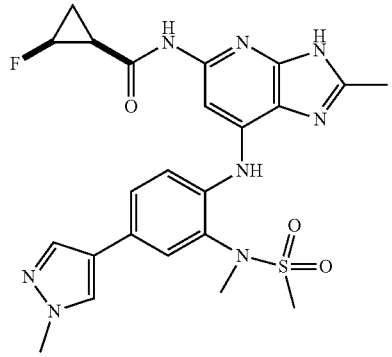 [SMILES: Cc1nc2c(Nc3ccc(-c4cnn(C)c4)cc3N(C)S(C)(=O)=O)cc(NC(=O)[C@@H]3C[C@@H]3F)nc2[nH]1] |
| I-210 | 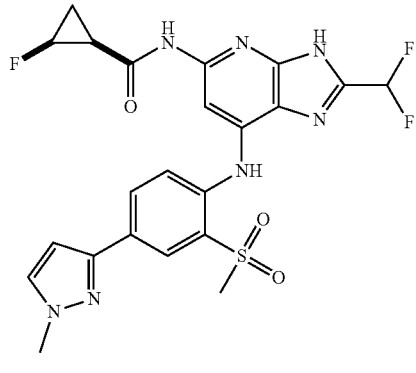 [SMILES: Cn1ccc(-c2ccc(Nc3cc(NC(=O)[C@@H]4C[C@@H]4F)nc4[nH]c(C(F)F)nc34)c(S(C)(=O)=O)c2)n1] |
| I-211 | 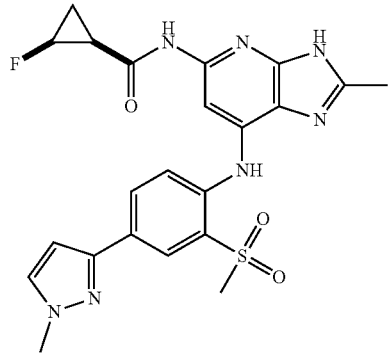 [SMILES: Cc1nc2c(Nc3ccc(-c4ccn(C)n4)cc3S(C)(=O)=O)cc(NC(=O)[C@@H]3C[C@@H]3F)nc2[nH]1] |
| I-212 | 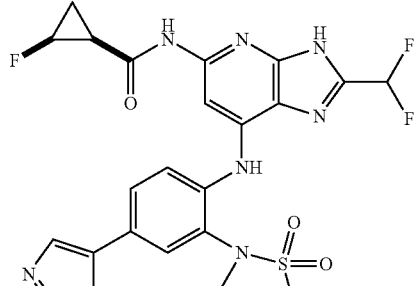 |

TABLE-continued
Exemplary Compounds
| Compound | Structure |
|---|---|
| I-213 | 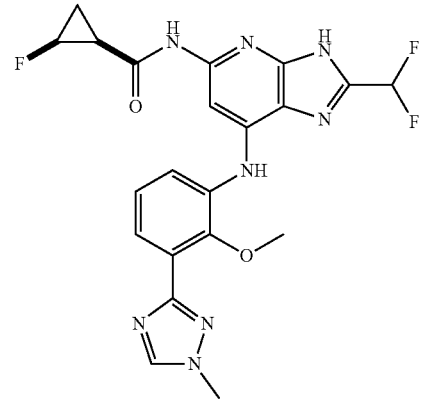 [SMILES: COc1c(Nc2cc(NC(=O)[C@@H]3C[C@@H]3F)nc3[nH]c(C(F)F)nc23)cccc1-c1ncn(C)n1] |
| I-214 | 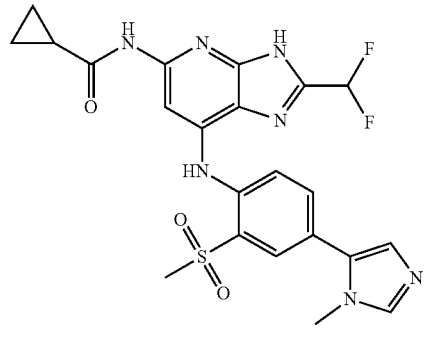 [SMILES: Cn1cncc1-c1ccc(Nc2cc(NC(=O)C3CC3)nc3[nH]c(C(F)F)nc23)c(S(C)(=O)=O)c1] |
| I-215 | 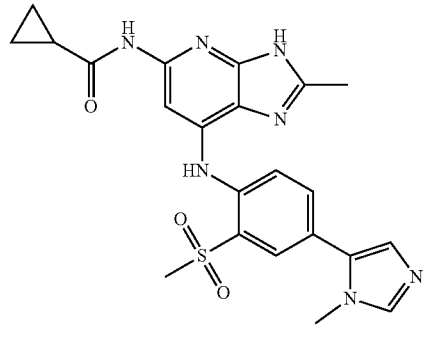 [SMILES: Cc1nc2c(Nc3ccc(-c4cncn4C)cc3S(C)(=O)=O)cc(NC(=O)C3CC3)nc2[nH]1] |
| I-216 | 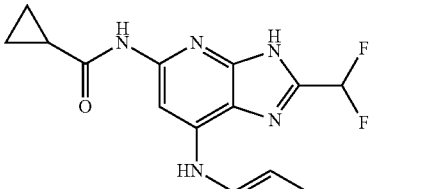 |

TABLE-continued
Exemplary Compounds
| Compound | Structure |
|---|---|
| I-217 | 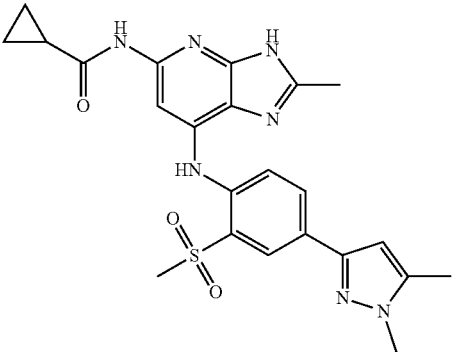 [SMILES: Cc1nc2c(Nc3ccc(-c4cc(C)n(C)n4)cc3S(C)(=O)=O)cc(NC(=O)C3CC3)nc2[nH]1] |
| I-218 | 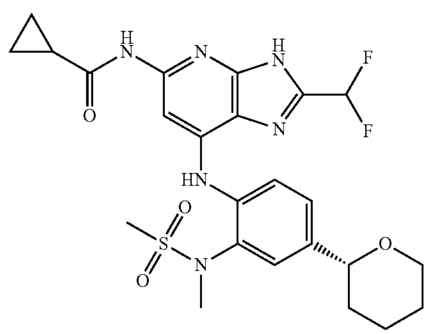 [SMILES: CN(c1cc([C@H]2CCCCO2)ccc1Nc1cc(NC(=O)C2CC2)nc2[nH]c(C(F)F)nc12)S(C)(=O)=O] |
| I-219 | 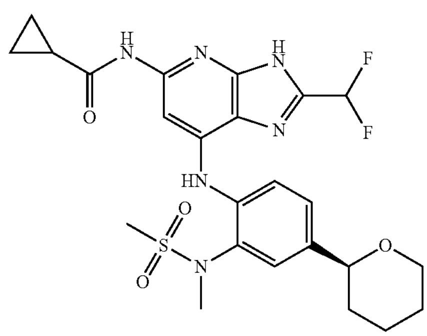 [SMILES: CN(c1cc([C@@H]2CCCCO2)ccc1Nc1cc(NC(=O)C2CC2)nc2[nH]c(C(F)F)nc12)S(C)(=O)=O] |
| I-220 | 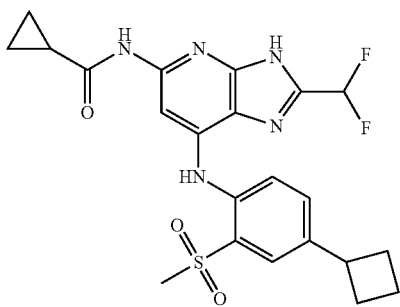 [SMILES: CS(=O)(=O)c1cc(C2CCC2)ccc1Nc1cc(NC(=O)C2CC2)nc2[nH]c(C(F)F)nc12] |

TABLE-continued
Exemplary Compounds
| Compound | Structure |
|---|---|
| I-221 | 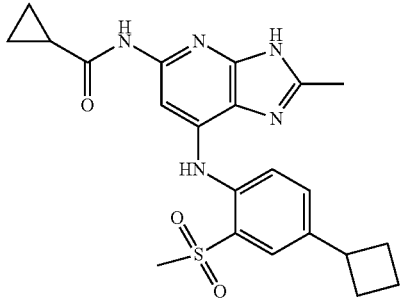 [SMILES: Cc1nc2c(Nc3ccc(C4CCC4)cc3S(C)(=O)=O)cc(NC(=O)C3CC3)nc2[nH]1] |
| I-222 | 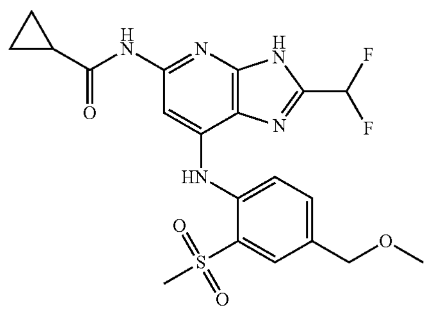 [SMILES: COCc1ccc(Nc2cc(NC(=O)C3CC3)nc3[nH]c(C(F)F)nc23)c(S(C)(=O)=O)c1] |
| I-223 | 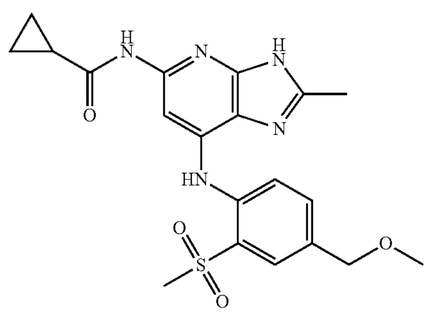 [SMILES: COCc1ccc(Nc2cc(NC(=O)C3CC3)nc3[nH]c(C)nc23)c(S(C)(=O)=O)c1] |
| I-224 | 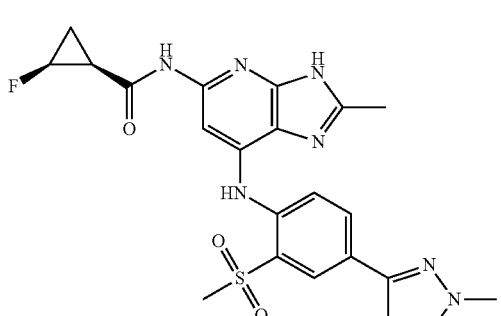 |

| Compound | Structure |
|---|---|
| I-225 | 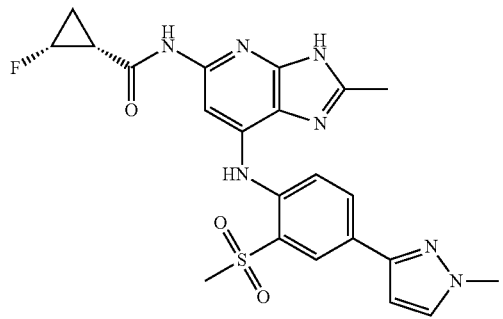 [SMILES: Cc1nc2c(Nc3ccc(-c4ccn(C)n4)cc3S(C)(=O)=O)cc(NC(=O)[C@H]3C[C@H]3F)nc2[nH]1] |
| I-226 | 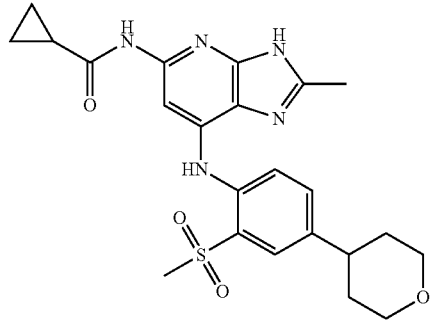 [SMILES: Cc1nc2c(Nc3ccc(C4CCOCC4)cc3S(C)(=O)=O)cc(NC(=O)C3CC3)nc2[nH]1] |
| I-227 | 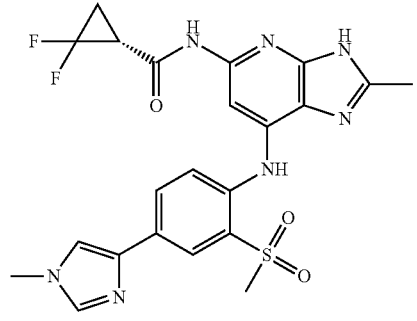 |
| I-228 | 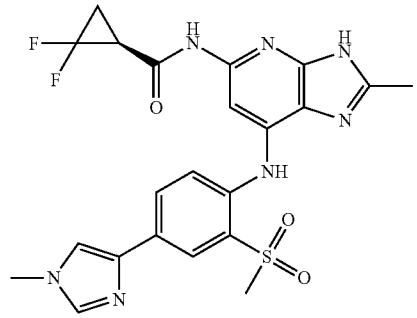 |

TABLE-continued
Exemplary Compounds
| Compound | Structure |
|---|---|
| I-229 | 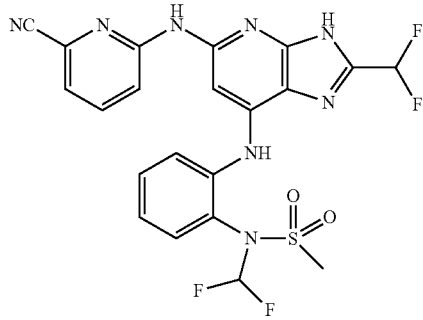 [SMILES: CS(=O)(=O)N(c1ccccc1Nc1cc(Nc2cccc(C#N)n2)nc2[nH]c(C(F)F)nc12)C(F)F] |
| I-230 | 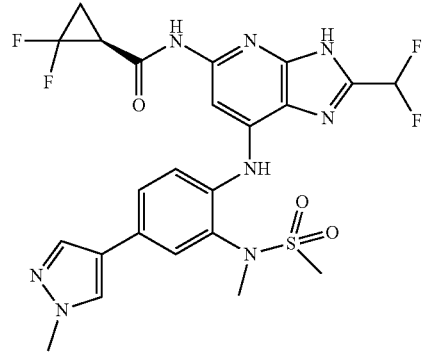 [SMILES: CN(c1cc(-c2cnn(C)c2)ccc1Nc1cc(NC(=O)[C@@H]2CC2(F)F)nc2[nH]c(C(F)F)nc12)S(C)(=O)=O] |
| I-231 | 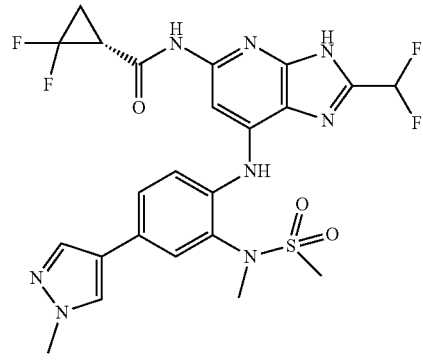 [SMILES: CN(c1cc(-c2cnn(C)c2)ccc1Nc1cc(NC(=O)[C@H]2CC2(F)F)nc2[nH]c(C(F)F)nc12)S(C)(=O)=O] |
| I-232 | 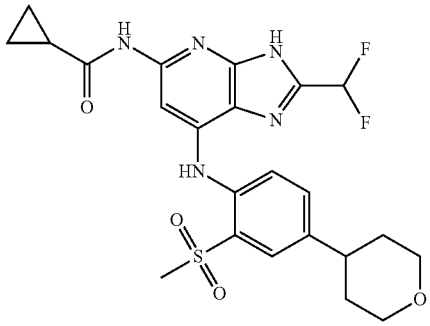 [SMILES: CS(=O)(=O)c1cc(C2CCOCC2)ccc1Nc1cc(NC(=O)C2CC2)nc2[nH]c(C(F)F)nc12] |

TABLE-continued
Exemplary Compounds
| Compound | Structure |
|---|---|
| I-233 | 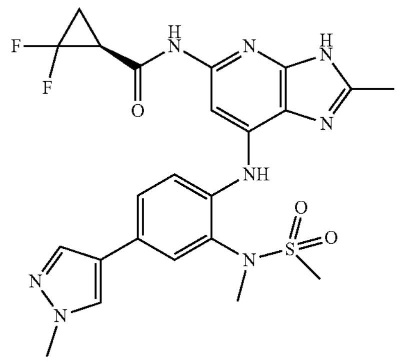 [SMILES: Cc1nc2c(Nc3ccc(-c4cnn(C)c4)cc3N(C)S(C)(=O)=O)cc(NC(=O)[C@@H]3CC3(F)F)nc2[nH]1] |
| I-234 | 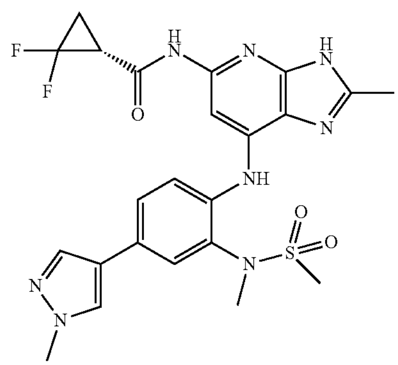 [SMILES: Cc1nc2c(Nc3ccc(-c4cnn(C)c4)cc3N(C)S(C)(=O)=O)cc(NC(=O)[C@H]3CC3(F)F)nc2[nH]1] |
| I-235 | 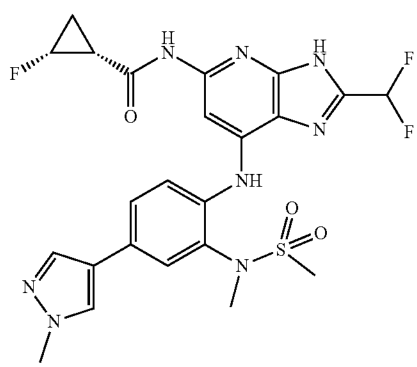 [SMILES: CN(c1cc(-c2cnn(C)c2)ccc1Nc1cc(NC(=O)[C@H]2C[C@H]2F)nc2[nH]c(C(F)F)nc12)S(C)(=O)=O] |
| I-236 | 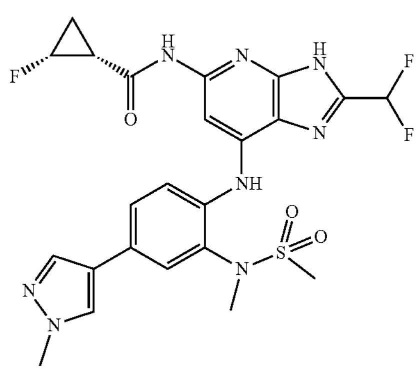 [SMILES: CN(c1cc(-c2cnn(C)c2)ccc1Nc1cc(NC(=O)[C@H]2C[C@H]2F)nc2[nH]c(C(F)F)nc12)S(C)(=O)=O] |

TABLE-continued
Exemplary Compounds
| Compound | Structure |
|---|---|
| I-237 | 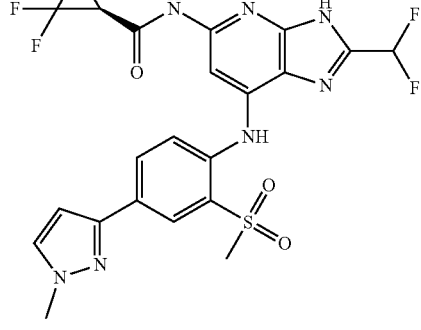 |
| I-238 | 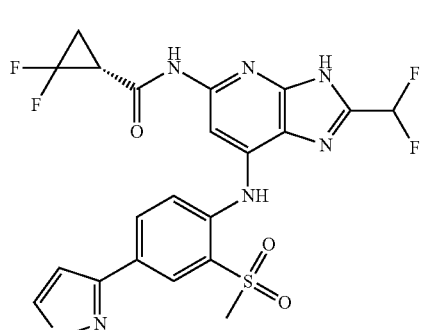 |
| I-239 | 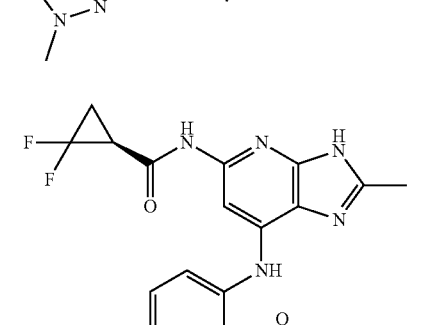 |
| I-240 | 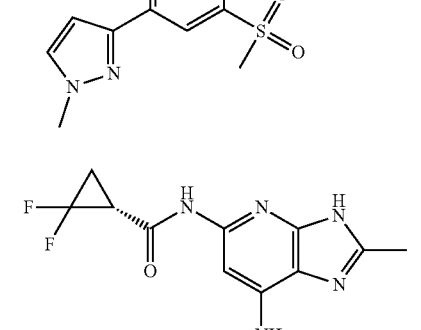 |

TABLE-continued
Exemplary Compounds
| Compound | Structure |
|---|---|
| I-241 | 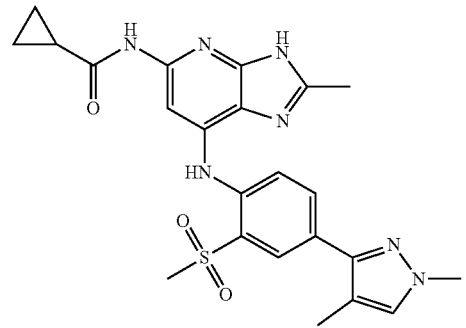 [SMILES: Cc1nc2c(Nc3ccc(-c4nn(C)cc4C)cc3S(C)(=O)=O)cc(NC(=O)C3CC3)nc2[nH]1] |
| I-242 | 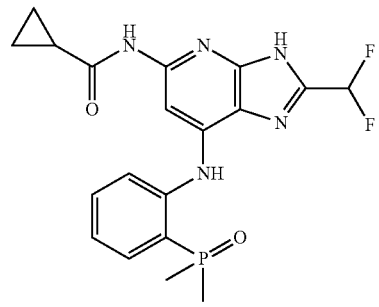 [SMILES: CP(C)(=O)c1ccccc1Nc1cc(NC(=O)C2CC2)nc2[nH]c(C(F)F)nc12] |
| I-243 | 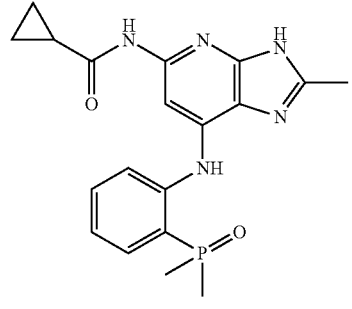 [SMILES: Cc1nc2c(Nc3ccccc3P(C)(C)=O)cc(NC(=O)C3CC3)nc2[nH]1] |
| I-244 | 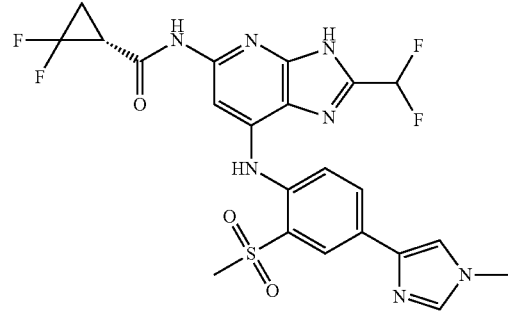 |

| Compound | Structure |
|---|---|
| I-245 | 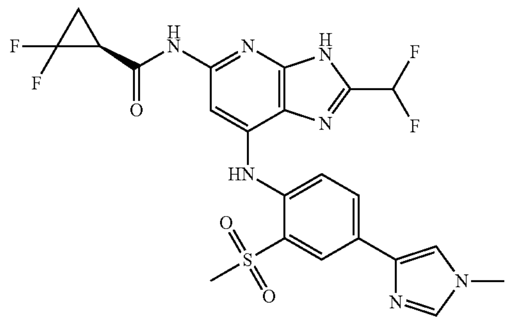 [SMILES: Cn1cnc(-c2ccc(Nc3cc(NC(=O)[C@@H]4CC4(F)F)nc4[nH]c(C(F)F)nc34)c(S(C)(=O)=O)c2)c1] |
| I-246 | 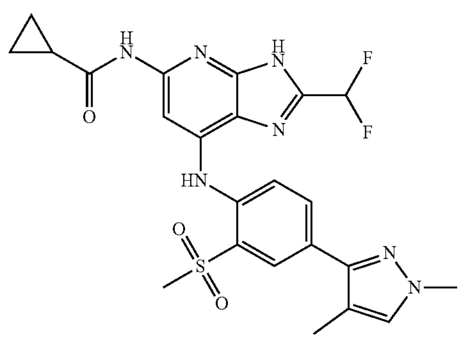 [SMILES: Cc1cn(C)nc1-c1ccc(Nc2cc(NC(=O)C3CC3)nc3[nH]c(C(F)F)nc23)c(S(C)(=O)=O)c1] |
| I-247 | 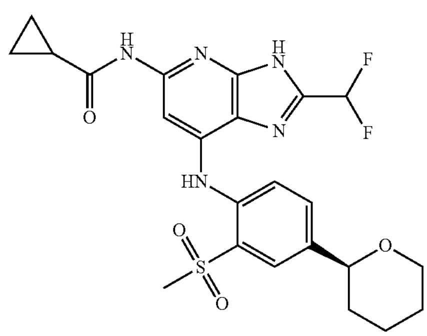 [SMILES: CS(=O)(=O)c1cc([C@@H]2CCCCO2)ccc1Nc1cc(NC(=O)C2CC2)nc2[nH]c(C(F)F)nc12] |
| I-248 | 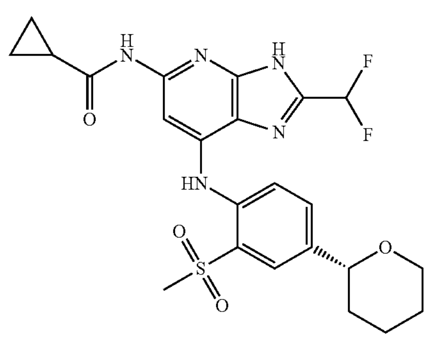 |

| TABLE-continued |
|---|
| Exemplary Compounds |

| Compound | Structure |
|---|---|
| I-249 | 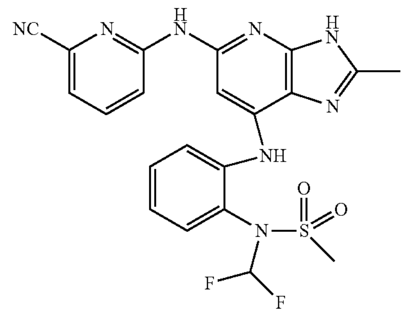 [SMILES: Cc1nc2c(Nc3ccccc3N(C(F)F)S(C)(=O)=O)cc(Nc3cccc(C#N)n3)nc2[nH]1] |
| I-250 | 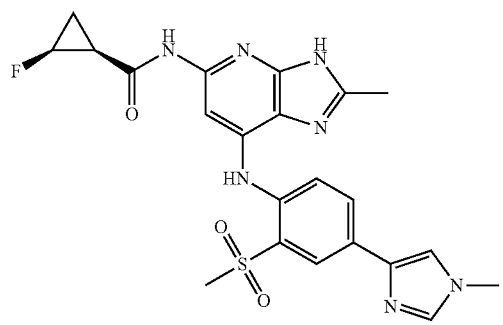 [SMILES: Cc1nc2c(Nc3ccc(-c4cn(C)cn4)cc3S(C)(=O)=O)cc(NC(=O)[C@@H]3C[C@@H]3F)nc2[nH]1] |
| I-251 | 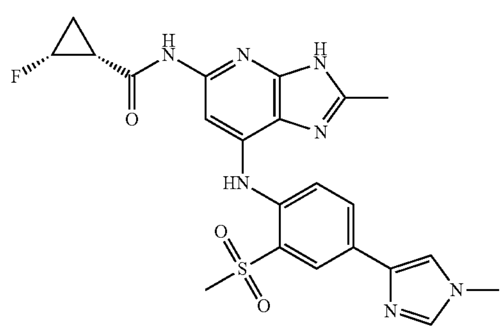 [SMILES: Cc1nc2c(Nc3ccc(-c4cn(C)cn4)cc3S(C)(=O)=O)cc(NC(=O)[C@H]3C[C@H]3F)nc2[nH]1] |
| I-252 | 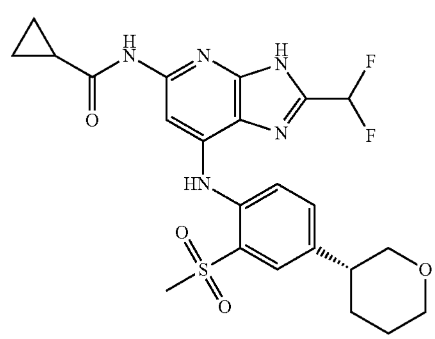 [SMILES: CS(=O)(=O)c1cc([C@H]2CCCOC2)ccc1Nc1cc(NC(=O)C2CC2)nc2[nH]c(C(F)F)nc12] |

TABLE-continued
Exemplary Compounds
| Compound | Structure |
|---|---|
| I-253 | 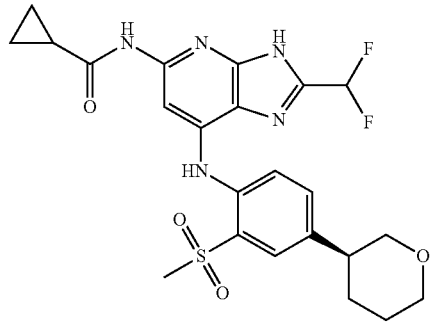 [SMILES: CS(=O)(=O)c1cc([C@@H]2CCCOC2)ccc1Nc1cc(NC(=O)C2CC2)nc2[nH]c(C(F)F)nc12] |
| I-254 | 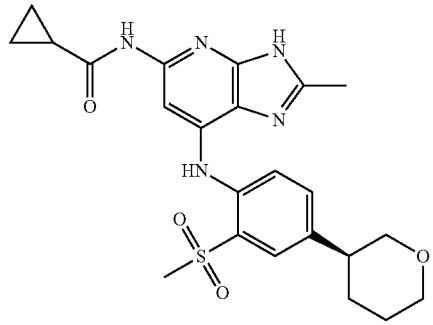 [SMILES: Cc1nc2c(Nc3ccc([C@@H]4CCCOC4)cc3S(C)(=O)=O)cc(NC(=O)C3CC3)nc2[nH]1] |
| I-255 | 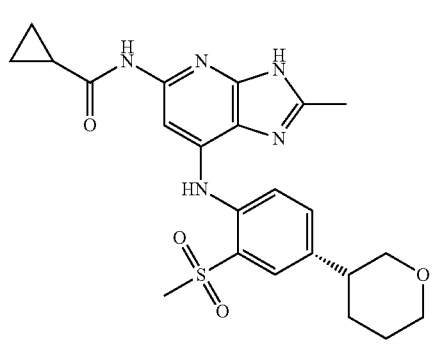 |
| I-256 | 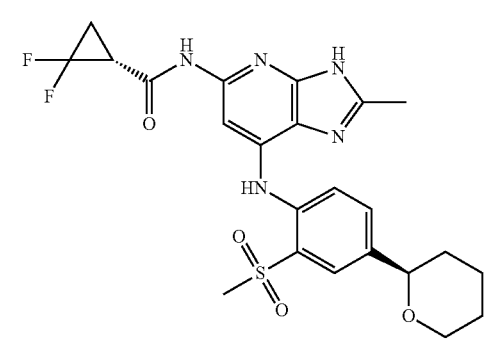 [SMILES: Cc1nc2c(Nc3ccc([C@H]4CCCCO4)cc3S(C)(=O)=O)cc(NC(=O)[C@H]3CC3(F)F)nc2[nH]1] |

TABLE-continued
Exemplary Compounds
| Compound | Structure |
|---|---|
| I-257 | 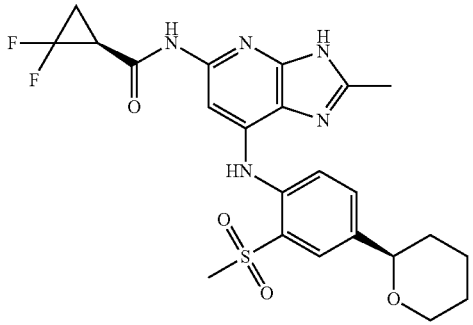 [SMILES: Cc1nc2c(Nc3ccc([C@H]4CCCCO4)cc3S(C)(=O)=O)cc(NC(=O)[C@@H]3CC3(F)F)nc2[nH]1] |
| I-258 | 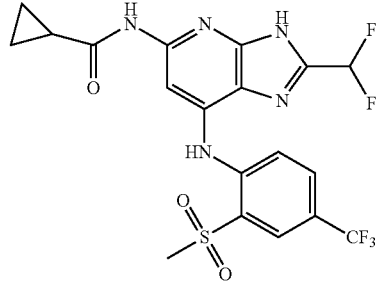 [SMILES: CS(=O)(=O)c1cc(C(F)(F)F)ccc1Nc1cc(NC(=O)C2CC2)nc2[nH]c(C(F)F)nc12] |
| I-259 | 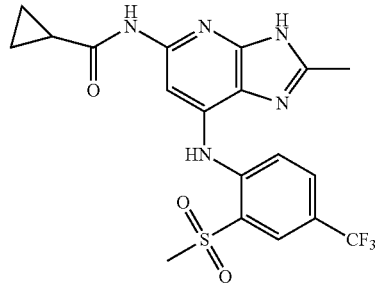 [SMILES: Cc1nc2c(Nc3ccc(C(F)(F)F)cc3S(C)(=O)=O)cc(NC(=O)C3CC3)nc2[nH]1] |
| I-260 | 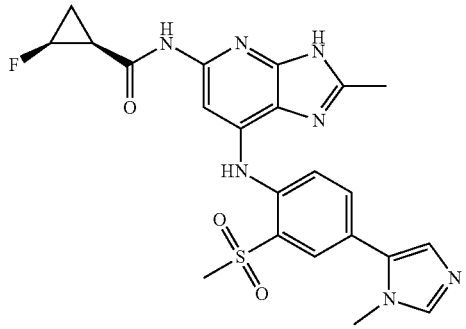 [SMILES: Cc1nc2c(Nc3ccc(-c4cncn4C)cc3S(C)(=O)=O)cc(NC(=O)[C@@H]3C[C@@H]3F)nc2[nH]1] |

TABLE-continued
Exemplary Compounds
| Compound | Structure |
|---|---|
| I-261 | 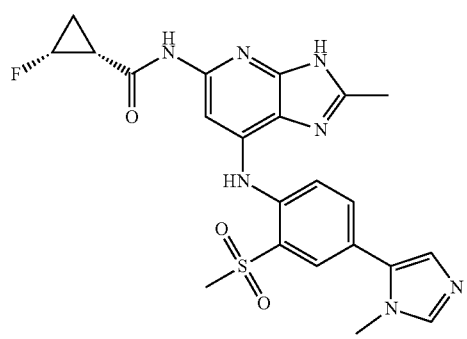 [SMILES: Cc1nc2c(Nc3ccc(-c4cncn4C)cc3S(C)(=O)=O)cc(NC(=O)[C@H]3C[C@H]3F)nc2[nH]1] |
| I-262 | 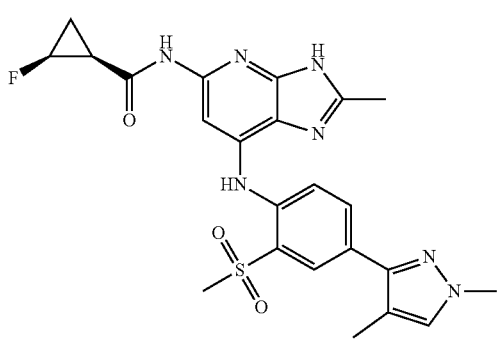 [SMILES: Cc1nc2c(Nc3ccc(-c4nn(C)cc4C)cc3S(C)(=O)=O)cc(NC(=O)[C@@H]3C[C@@H]3F)nc2[nH]1] |
| I-263 | 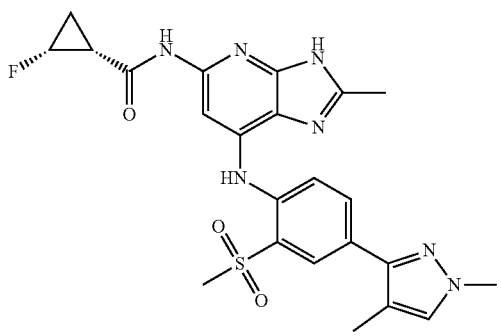 [SMILES: Cc1nc2c(Nc3ccc(-c4nn(C)cc4C)cc3S(C)(=O)=O)cc(NC(=O)[C@H]3C[C@H]3F)nc2[nH]1] |
| I-264 | 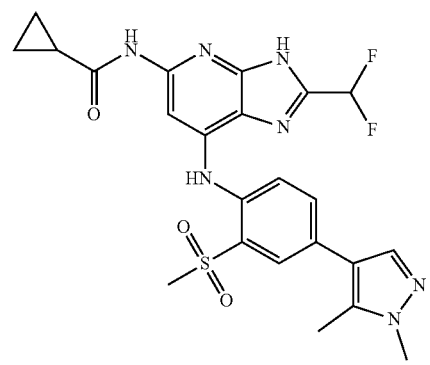 [SMILES: Cc1c(-c2ccc(Nc3cc(NC(=O)C4CC4)nc4[nH]c(C(F)F)nc34)c(S(C)(=O)=O)c2)cnn1C] |

TABLE-continued

Exemplary Compounds

| Compound | Structure |
|---|---|
| I-265 | 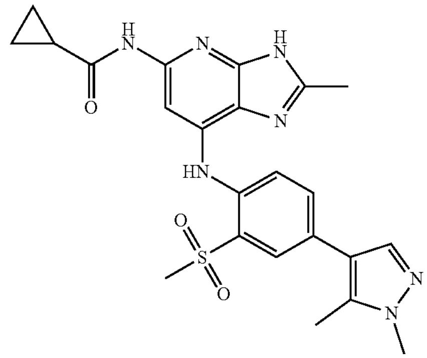 [SMILES: Cc1nc2c(Nc3ccc(-c4cnn(C)c4C)cc3S(C)(=O)=O)cc(NC(=O)C3CC3)nc2[nH]1] |
| I-266 | 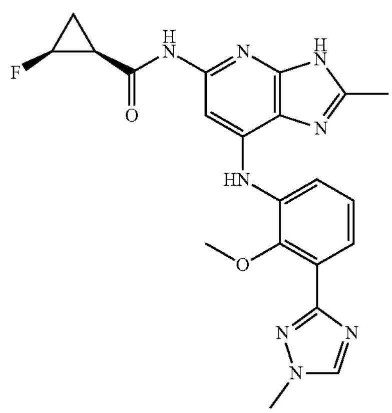 [SMILES: COc1c(Nc2cc(NC(=O)[C@@H]3C[C@@H]3F)nc3[nH]c(C)nc23)cccc1-c1ncn(C)n1] |
| I-267 | 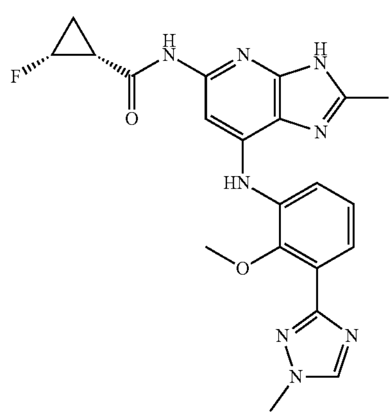 [SMILES: COc1c(Nc2cc(NC(=O)[C@H]3C[C@H]3F)nc3[nH]c(C)nc23)cccc1-c1ncn(C)n1] |
| I-268 | 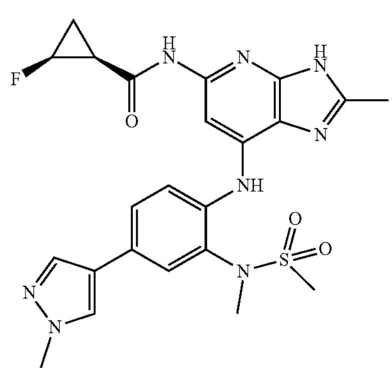 [SMILES: Cc1nc2c(Nc3ccc(-c4cnn(C)c4)cc3N(C)S(C)(=O)=O)cc(NC(=O)[C@@H]3C[C@@H]3F)nc2[nH]1] |

TABLE-continued
Exemplary Compounds
| Compound | Structure |
|---|---|
| I-269 | 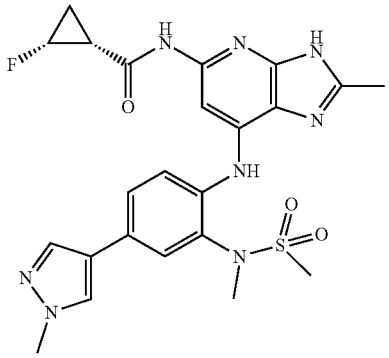 [SMILES: Cc1nc2c(Nc3ccc(-c4cnn(C)c4)cc3N(C)S(C)(=O)=O)cc(NC(=O)[C@H]3C[C@H]3F)nc2[nH]1] |
| I-270 | 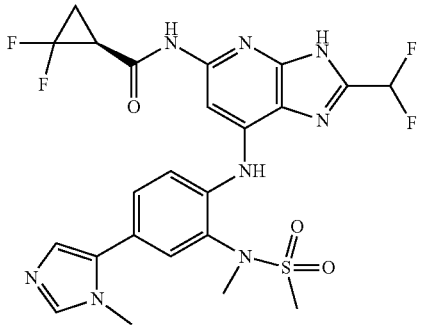 [SMILES: CN(c1cc(-c2cncn2C)ccc1Nc1cc(NC(=O)[C@@H]2CC2(F)F)nc2[nH]c(C(F)F)nc12)S(C)(=O)=O] |
| I-271 | 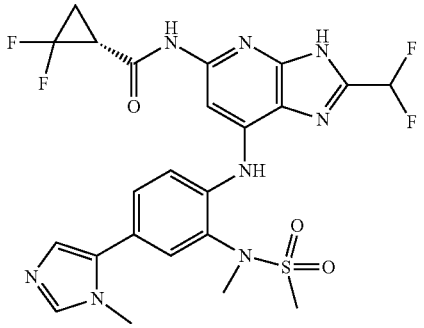 [SMILES: CN(c1cc(-c2cncn2C)ccc1Nc1cc(NC(=O)[C@H]2CC2(F)F)nc2[nH]c(C(F)F)nc12)S(C)(=O)=O] |
| I-272 | 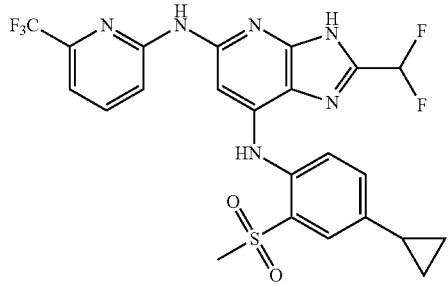 [SMILES: CS(=O)(=O)c1cc(C2CC2)ccc1Nc1cc(Nc2cccc(C(F)(F)F)n2)nc2[nH]c(C(F)F)nc12] |

TABLE-continued
Exemplary Compounds
| Compound | Structure |
|---|---|
| I-273 | 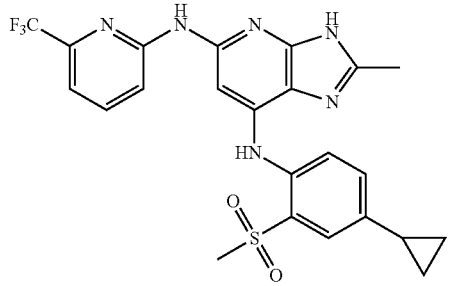 [SMILES: Cc1nc2c(Nc3ccc(C4CC4)cc3S(C)(=O)=O)cc(Nc3cccc(C(F)(F)F)n3)nc2[nH]1] |
| I-274 | 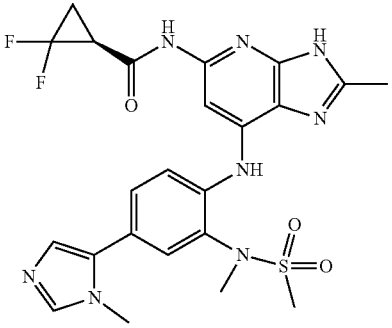 [SMILES: Cc1nc2c(Nc3ccc(-c4cncn4C)cc3N(C)S(C)(=O)=O)cc(NC(=O)[C@@H]3CC3(F)F)nc2[nH]1] |
| I-275 | 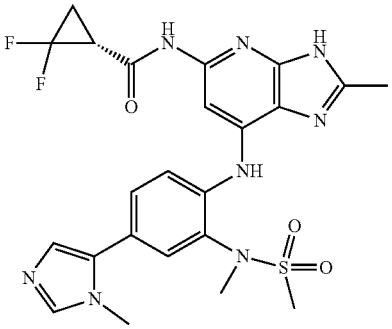 [SMILES: Cc1nc2c(Nc3ccc(-c4cncn4C)cc3N(C)S(C)(=O)=O)cc(NC(=O)[C@H]3CC3(F)F)nc2[nH]1] |
| I-276 | 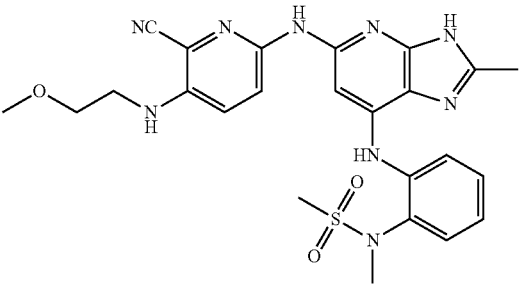 |

TABLE-continued
Exemplary Compounds
| Compound | Structure |
|---|---|
| I-277 | 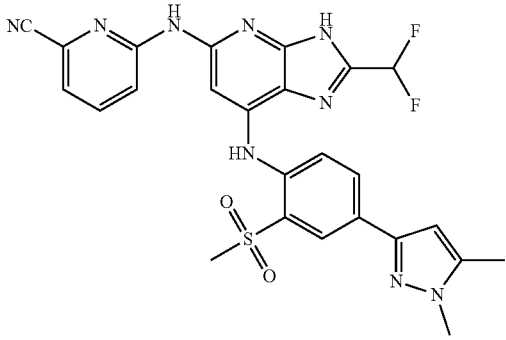 [SMILES: Cc1cc(-c2ccc(Nc3cc(Nc4cccc(C#N)n4)nc4[nH]c(C(F)F)nc34)c(S(C)(=O)=O)c2)nn1C] |
| I-278 | 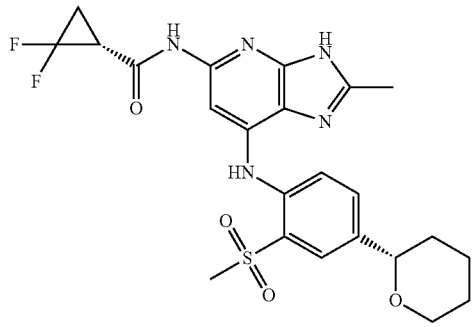 [SMILES: Cc1nc2c(Nc3ccc([C@@H]4CCCCO4)cc3S(C)(=O)=O)cc(NC(=O)[C@H]3CC3(F)F)nc2[nH]1] |
| I-279 | 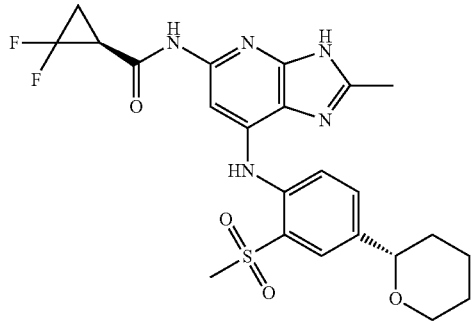 [SMILES: Cc1nc2c(Nc3ccc([C@@H]4CCCCO4)cc3S(C)(=O)=O)cc(NC(=O)[C@@H]3CC3(F)F)nc2[nH]1] |
| I-280 | 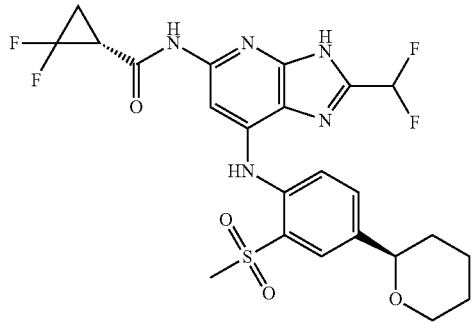 [SMILES: CS(=O)(=O)c1cc([C@H]2CCCCO2)ccc1Nc1cc(NC(=O)[C@H]2CC2(F)F)nc2[nH]c(C(F)F)nc12] |

TABLE-continued

Exemplary Compounds

| Compound | Structure |
|---|---|
| I-281 | 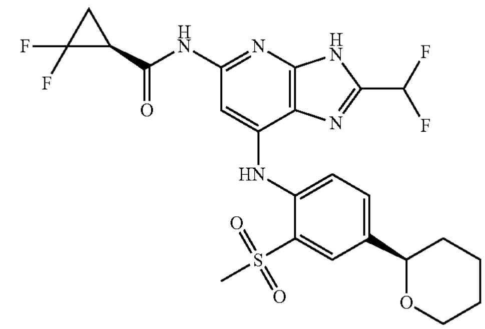 [SMILES: CS(=O)(=O)c1cc([C@H]2CCCCO2)ccc1Nc1cc(NC(=O)[C@@H]2CC2(F)F)nc2[nH]c(C(F)F)nc12] |
| I-282 | 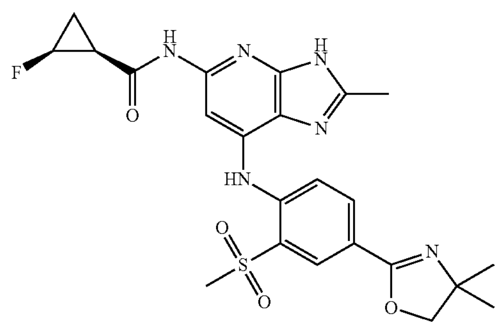 [SMILES: Cc1nc2c(Nc3ccc(C4=NC(C)(C)CO4)cc3S(C)(=O)=O)cc(NC(=O)[C@@H]3C[C@@H]3F)nc2[nH]1] |
| I-283 | 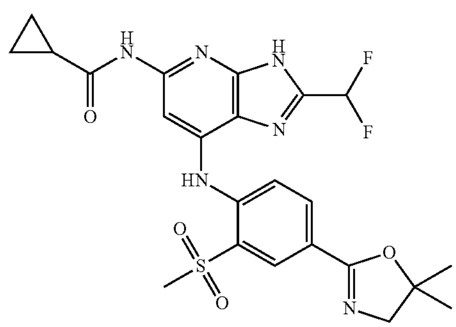 [SMILES: CC1(C)CN=C(c2ccc(Nc3cc(NC(=O)C4CC4)nc4[nH]c(C(F)F)nc34)c(S(C)(=O)=O)c2)O1] |
| I-284 | 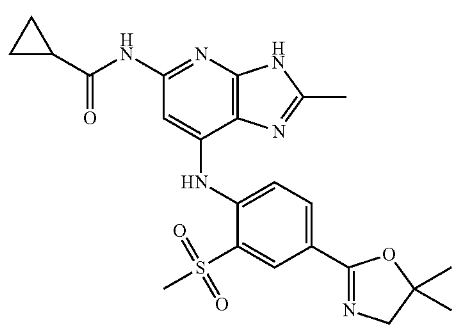 [SMILES: Cc1nc2c(Nc3ccc(C4=NCC(C)(C)O4)cc3S(C)(=O)=O)cc(NC(=O)C3CC3)nc2[nH]1] |

TABLE-continued

Exemplary Compounds

| Compound | Structure |
|---|---|
| I-285 | 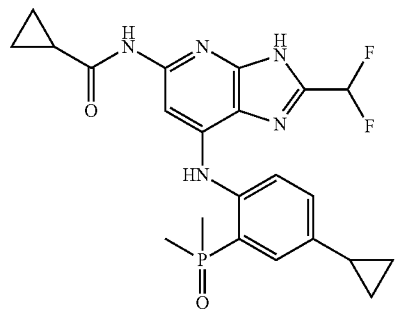 [SMILES: CP(C)(=O)c1cc(C2CC2)ccc1Nc1cc(NC(=O)C2CC2)nc2[nH]c(C(F)F)nc12] |
| I-286 | 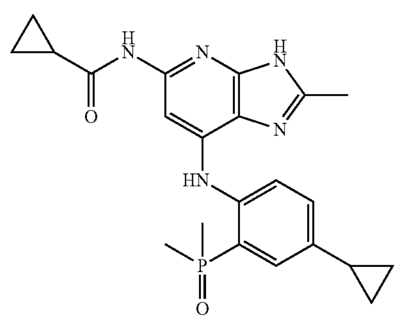 [SMILES: Cc1nc2c(Nc3ccc(C4CC4)cc3P(C)(C)=O)cc(NC(=O)C3CC3)nc2[nH]1] |
| I-287 | 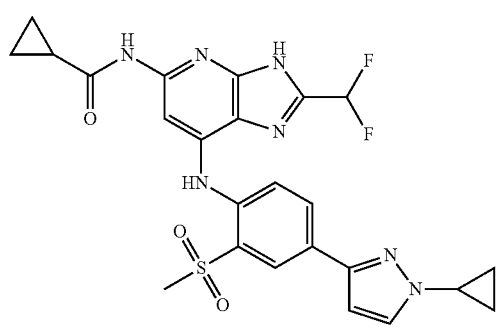 [SMILES: CS(=O)(=O)c1cc(-c2ccn(C3CC3)n2)ccc1Nc1cc(NC(=O)C2CC2)nc2[nH]c(C(F)F)nc12] |
| I-288 | 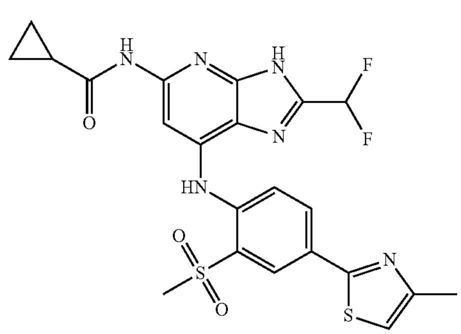 [SMILES: Cc1csc(-c2ccc(Nc3cc(NC(=O)C4CC4)nc4[nH]c(C(F)F)nc34)c(S(C)(=O)=O)c2)n1] |

TABLE-continued
Exemplary Compounds
| Compound | Structure |
|---|---|
| I-289 | 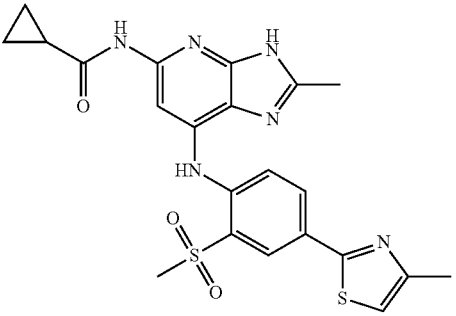 [SMILES: Cc1csc(-c2ccc(Nc3cc(NC(=O)C4CC4)nc4[nH]c(C)nc34)c(S(C)(=O)=O)c2)n1] |
| I-290 | 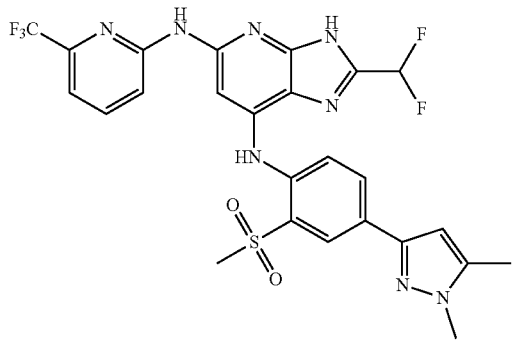 [SMILES: Cc1cc(-c2ccc(Nc3cc(Nc4cccc(C(F)(F)F)n4)nc4[nH]c(C(F)F)nc34)c(S(C)(=O)=O)c2)nn1C] |
| I-291 | 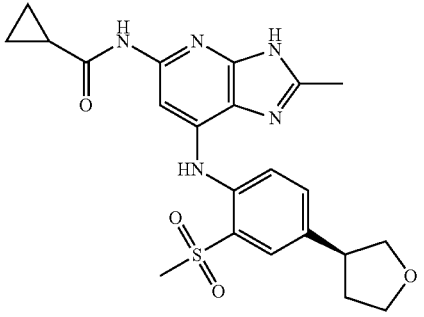 [SMILES: Cc1nc2c(Nc3ccc([C@@H]4CCOC4)cc3S(C)(=O)=O)cc(NC(=O)C3CC3)nc2[nH]1] |
| I-292 | 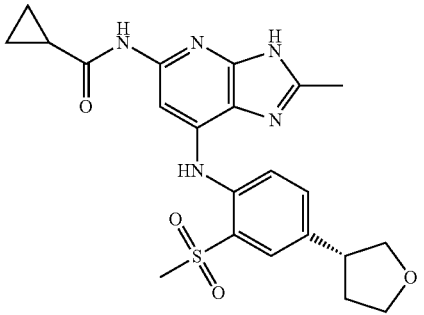 [SMILES: Cc1nc2c(Nc3ccc([C@H]4CCOC4)cc3S(C)(=O)=O)cc(NC(=O)C3CC3)nc2[nH]1] |

TABLE-continued
Exemplary Compounds
| Compound | Structure |
|---|---|
| I-293 | 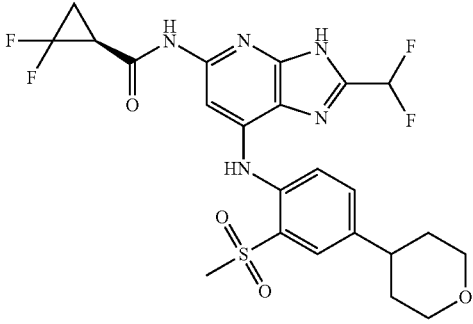 [SMILES: CS(=O)(=O)c1cc(C2CCOCC2)ccc1Nc1cc(NC(=O)[C@@H]2CC2(F)F)nc2[nH]c(C(F)F)nc12] |
| I-294 | 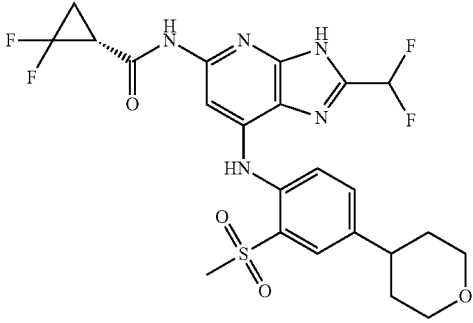 [SMILES: CS(=O)(=O)c1cc(C2CCOCC2)ccc1Nc1cc(NC(=O)[C@H]2CC2(F)F)nc2[nH]c(C(F)F)nc12] |
| I-295 | 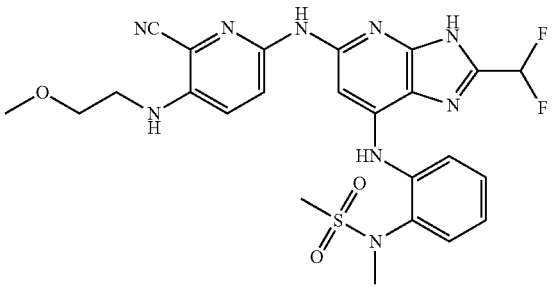 [SMILES: COCCNc1ccc(Nc2cc(Nc3ccccc3N(C)S(C)(=O)=O)c3nc(C(F)F)[nH]c3n2)nc1C#N] |
| I-296 | 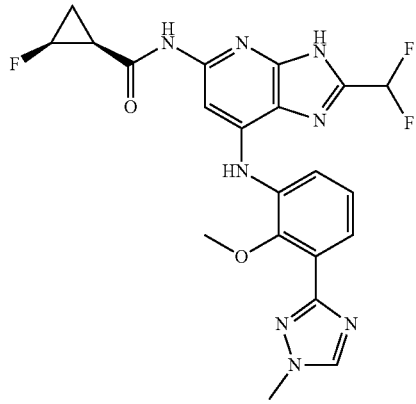 [SMILES: COc1c(Nc2cc(NC(=O)[C@@H]3C[C@@H]3F)nc3[nH]c(C(F)F)nc23)cccc1-c1ncn(C)n1] |

| Compound | Structure |
|---|---|
| I-297 | 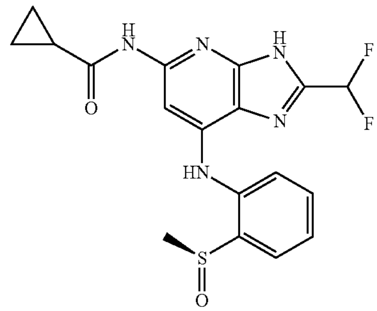 [SMILES: C[S@](=O)c1ccccc1Nc1cc(NC(=O)C2CC2)nc2[nH]c(C(F)F)nc12] |
| I-298 | 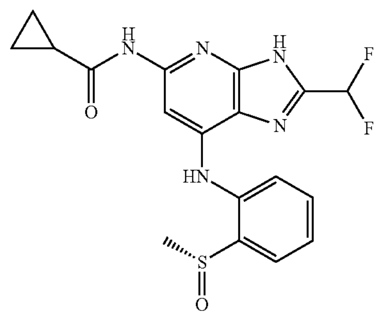 [SMILES: C[S@@](=O)c1ccccc1Nc1cc(NC(=O)C2CC2)nc2[nH]c(C(F)F)nc12] |
| I-299 | 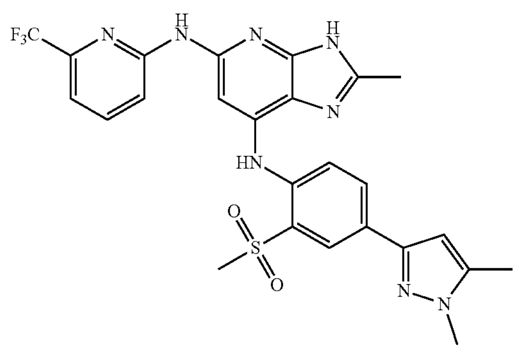 [SMILES: Cc1nc2c(Nc3ccc(-c4cc(C)n(C)n4)cc3S(C)(=O)=O)cc(Nc3cccc(C(F)(F)F)n3)nc2[nH]1] |
| I-300 | 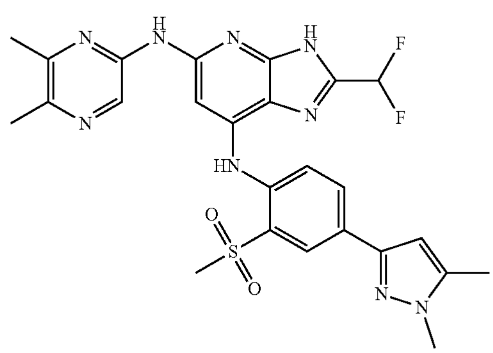 |

TABLE-continued
Exemplary Compounds
| Compound | Structure |
|---|---|
| I-301 | 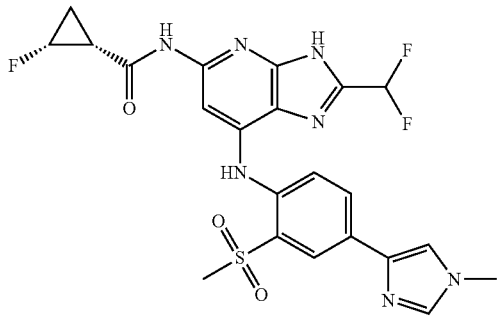 [SMILES: Cn1cnc(-c2ccc(Nc3cc(NC(=O)[C@H]4C[C@H]4F)nc4[nH]c(C(F)F)nc34)c(S(C)(=O)=O)c2)c1] |
| I-302 | 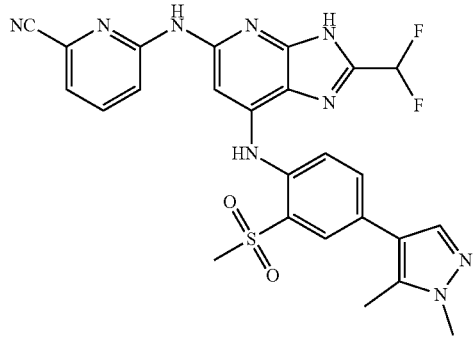 [SMILES: Cc1c(-c2ccc(Nc3cc(Nc4cccc(C#N)n4)nc4[nH]c(C(F)F)nc34)c(S(C)(=O)=O)c2)cnn1C] |
| I-303 | 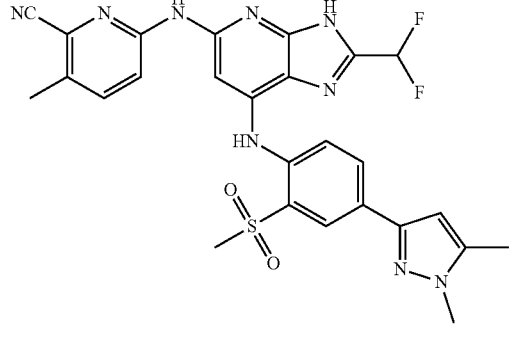 |
| I-304 | 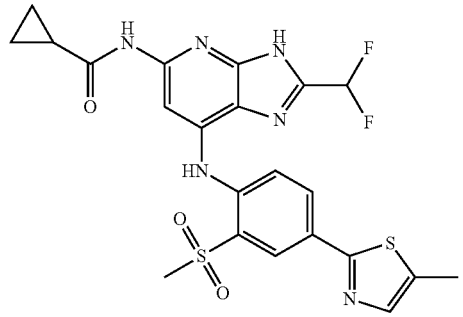 [SMILES: Cc1cnc(-c2ccc(Nc3cc(NC(=O)C4CC4)nc4[nH]c(C(F)F)nc34)c(S(C)(=O)=O)c2)s1] |

TABLE-continued
Exemplary Compounds
| Compound | Structure |
|---|---|
| I-305 | 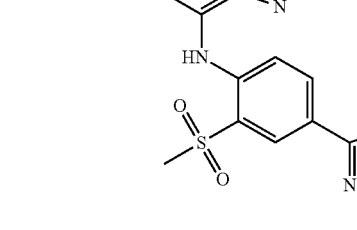 |
| I-306 | 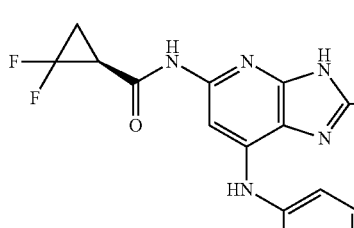 |
| I-307 | 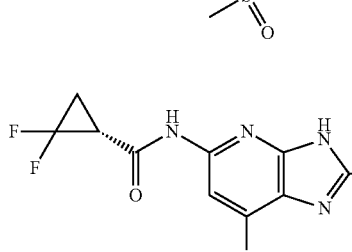 |
| I-308 | 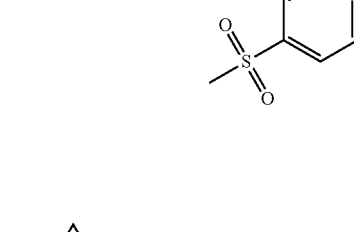 |

TABLE-continued

Exemplary Compounds

| Compound | Structure |
|---|---|
| I-309 | 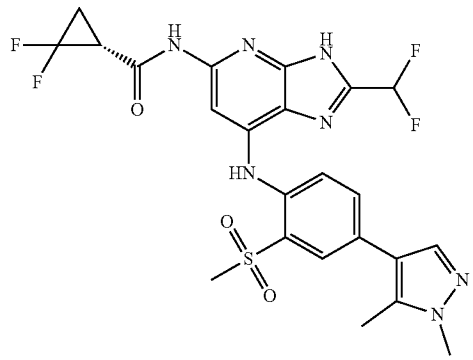 [SMILES: Cc1c(-c2ccc(Nc3cc(NC(=O)[C@H]4CC4(F)F)nc4[nH]c(C(F)F)nc34)c(S(C)(=O)=O)c2)cnn1C] |
| I-310 | 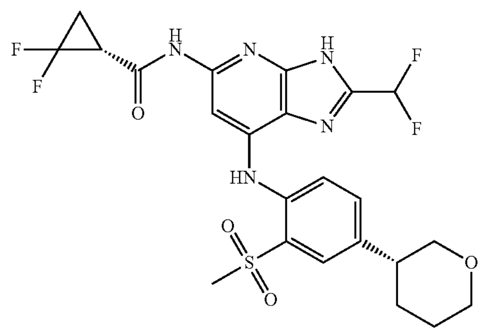 |
| I-311 | 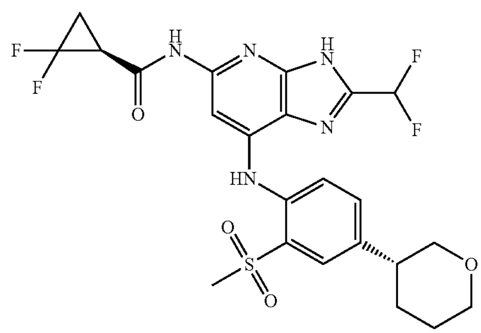 [SMILES: CS(=O)(=O)c1cc([C@H]2CCCOC2)ccc1Nc1cc(NC(=O)[C@@H]2CC2(F)F)nc2[nH]c(C(F)F)nc12] |
| I-312 | 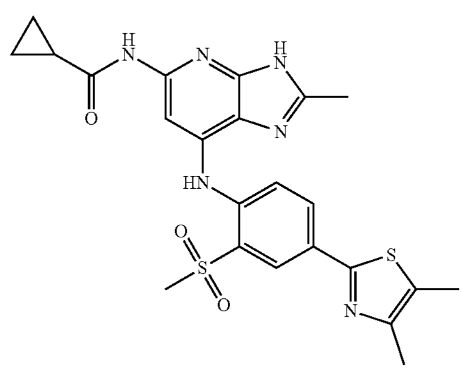 [SMILES: Cc1nc2c(Nc3ccc(-c4nc(C)c(C)s4)cc3S(C)(=O)=O)cc(NC(=O)C3CC3)nc2[nH]1] |

TABLE-continued
Exemplary Compounds
| Compound | Structure |
|---|---|
| I-313 | 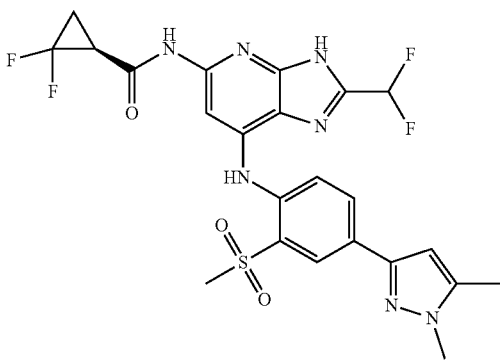 [SMILES: Cc1cc(-c2ccc(Nc3cc(NC(=O)[C@@H]4CC4(F)F)nc4[nH]c(C(F)F)nc34)c(S(C)(=O)=O)c2)nn1C] |
| I-314 | 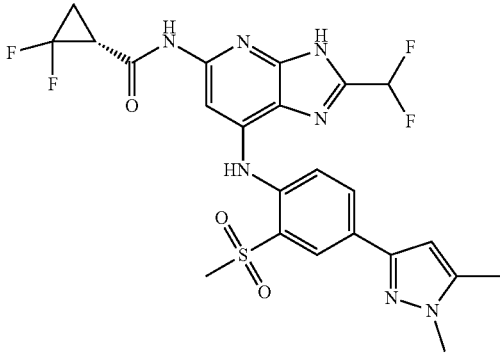 [SMILES: Cc1cc(-c2ccc(Nc3cc(NC(=O)[C@H]4CC4(F)F)nc4[nH]c(C(F)F)nc34)c(S(C)(=O)=O)c2)nn1C] |
| I-315 | 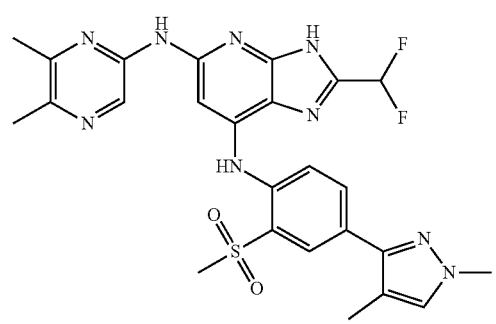 |
| I-316 | 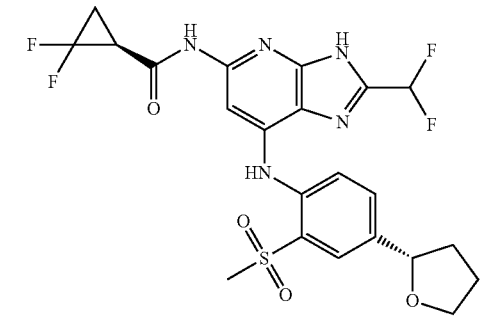 [SMILES: CS(=O)(=O)c1cc([C@@H]2CCCO2)ccc1Nc1cc(NC(=O)[C@@H]2CC2(F)F)nc2[nH]c(C(F)F)nc12] |

TABLE-continued
Exemplary Compounds
| Compound | Structure |
|---|---|
| I-317 | 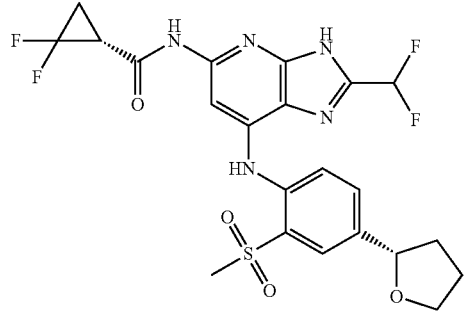 [SMILES: CS(=O)(=O)c1cc([C@@H]2CCCO2)ccc1Nc1cc(NC(=O)[C@H]2CC2(F)F)nc2[nH]c(C(F)F)nc12] |
| I-318 | 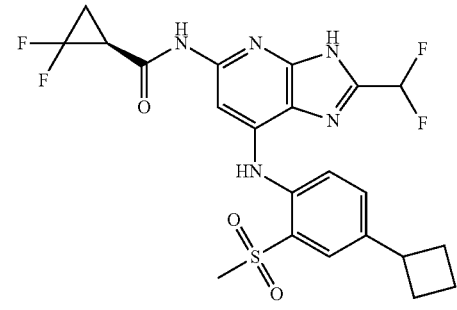 [SMILES: CS(=O)(=O)c1cc(C2CCC2)ccc1Nc1cc(NC(=O)[C@@H]2CC2(F)F)nc2[nH]c(C(F)F)nc12] |
| I-319 | 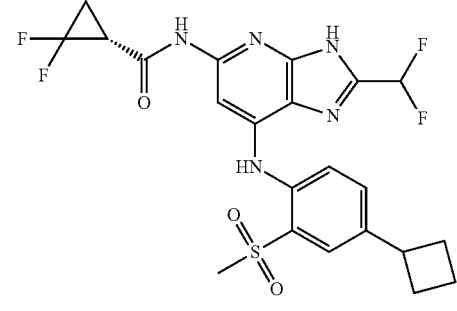 [SMILES: CS(=O)(=O)c1cc(C2CCC2)ccc1Nc1cc(NC(=O)[C@H]2CC2(F)F)nc2[nH]c(C(F)F)nc12] |
| I-320 | 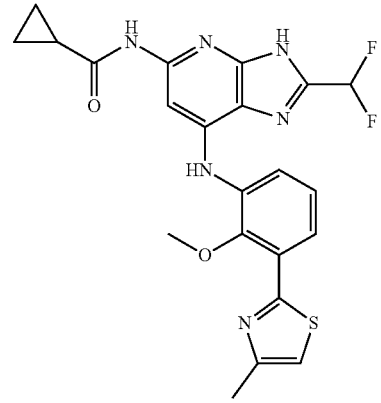 [SMILES: COc1c(Nc2cc(NC(=O)C3CC3)nc3[nH]c(C(F)F)nc23)cccc1-c1nc(C)cs1] |

TABLE-continued

Exemplary Compounds

| Compound | Structure |
|---|---|
| I-321 | 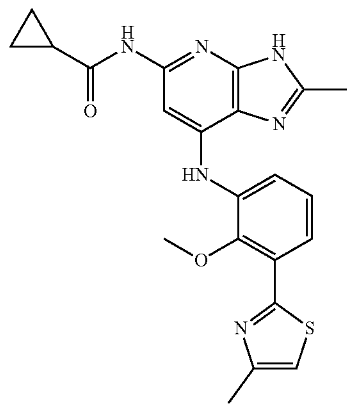 [SMILES: COc1c(Nc2cc(NC(=O)C3CC3)nc3[nH]c(C)nc23)cccc1-c1nc(C)cs1] |
| I-322 | 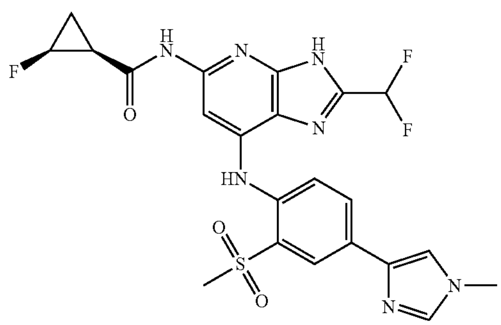 [SMILES: Cn1cnc(-c2ccc(Nc3cc(NC(=O)[C@@H]4C[C@@H]4F)nc4[nH]c(C(F)F)nc34)c(S(C)(=O)=O)c2)c1] |
| I-323 | 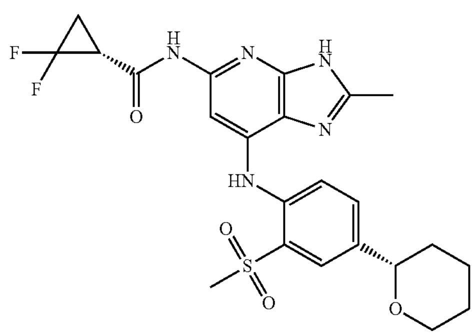 [SMILES: Cc1nc2c(Nc3ccc([C@@H]4CCCCO4)cc3S(C)(=O)=O)cc(NC(=O)[C@H]3CC3(F)F)nc2[nH]1] |
| I-324 | 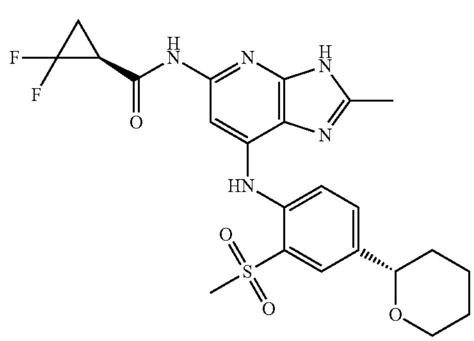 [SMILES: Cc1nc2c(Nc3ccc([C@@H]4CCCCO4)cc3S(C)(=O)=O)cc(NC(=O)[C@@H]3CC3(F)F)nc2[nH]1] |

TABLE-continued
Exemplary Compounds
| Compound | Structure |
|---|---|
| I-325 | 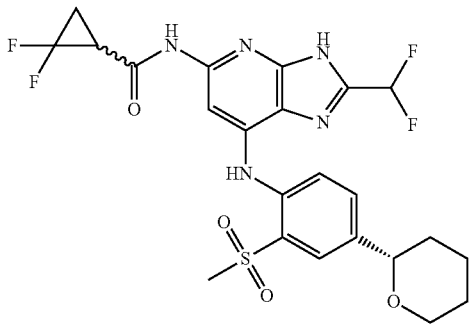 [SMILES: CS(=O)(=O)c1cc([C@@H]2CCCCO2)ccc1Nc1cc(NC(=O)C2CC2(F)F)nc2[nH]c(C(F)F)nc12] |
| I-326 | 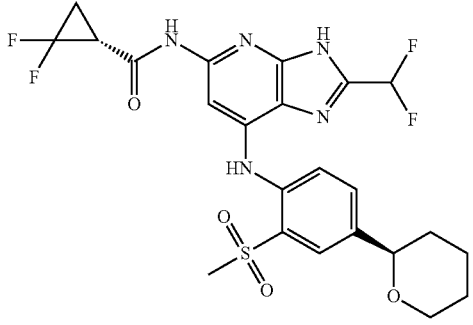 [SMILES: CS(=O)(=O)c1cc([C@H]2CCCCO2)ccc1Nc1cc(NC(=O)[C@H]2CC2(F)F)nc2[nH]c(C(F)F)nc12] |
| I-327 | 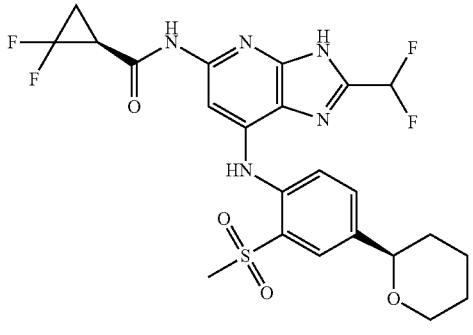 [SMILES: CS(=O)(=O)c1cc([C@H]2CCCCO2)ccc1Nc1cc(NC(=O)[C@@H]2CC2(F)F)nc2[nH]c(C(F)F)nc12] |
| I-328 | 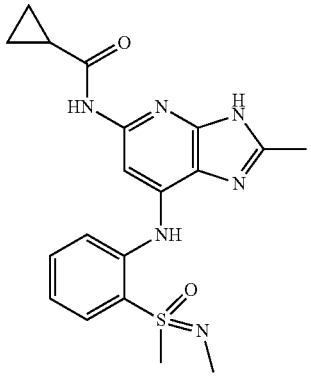 [SMILES: CN=S(C)(=O)c1ccccc1Nc1cc(NC(=O)C2CC2)nc2[nH]c(C)nc12] |

TABLE-continued
Exemplary Compounds
| Compound | Structure |
|---|---|
| I-329 | 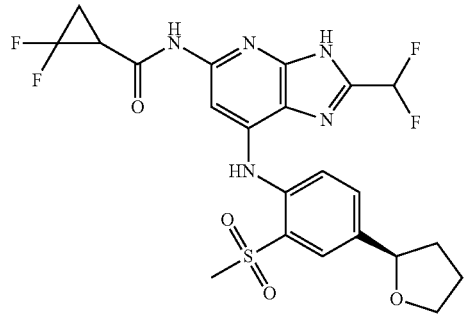 [SMILES: CS(=O)(=O)c1cc([C@H]2CCCO2)ccc1Nc1cc(NC(=O)C2CC2(F)F)nc2[nH]c(C(F)F)nc12] |
| I-330 | 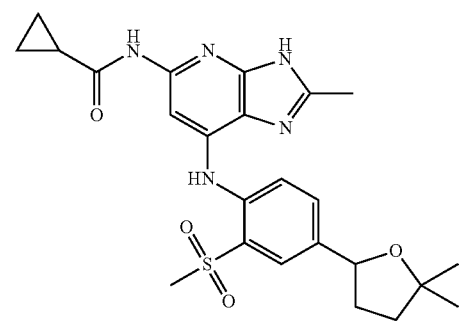 [SMILES: Cc1nc2c(Nc3ccc(C4CCC(C)(C)O4)cc3S(C)(=O)=O)cc(NC(=O)C3CC3)nc2[nH]1] |
| I-331 | 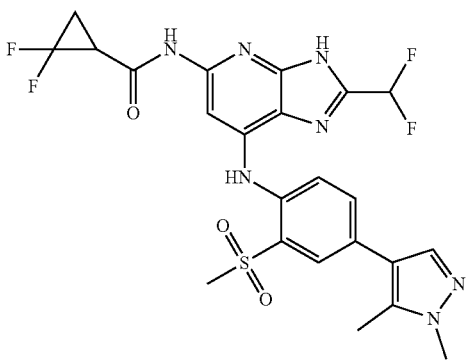 [SMILES: Cc1c(-c2ccc(Nc3cc(NC(=O)C4CC4(F)F)nc4[nH]c(C(F)F)nc34)c(S(C)(=O)=O)c2)cnn1C] |
| I-332 | 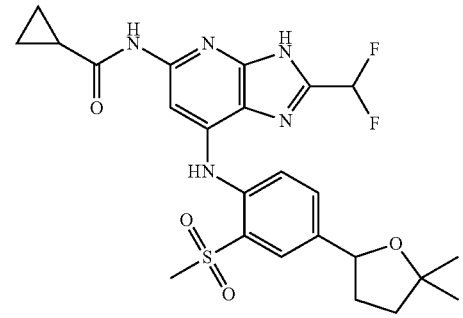 [SMILES: CC1(C)CCC(c2ccc(Nc3cc(NC(=O)C4CC4)nc4[nH]c(C(F)F)nc34)c(S(C)(=O)=O)c2)O1] |

TABLE-continued
Exemplary Compounds
| Compound | Structure |
|---|---|
| I-333 | 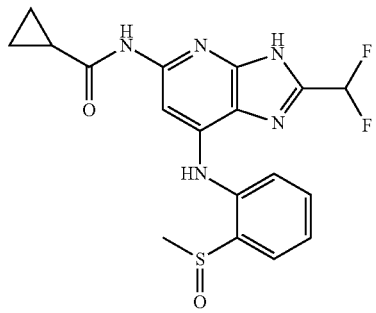 [SMILES: CS(=O)c1ccccc1Nc1cc(NC(=O)C2CC2)nc2[nH]c(C(F)F)nc12] |
| I-334 | 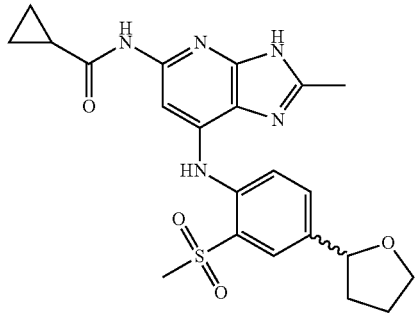 [SMILES: Cc1nc2c(Nc3ccc(C4CCCO4)cc3S(C)(=O)=O)cc(NC(=O)C3CC3)nc2[nH]1] |
| I-335 | 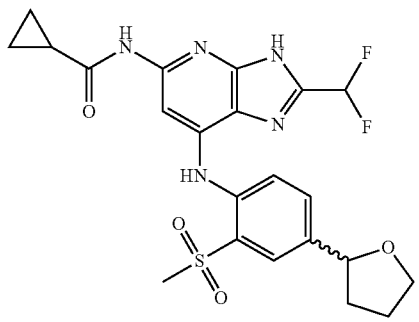 [SMILES: CS(=O)(=O)c1cc(C2CCCO2)ccc1Nc1cc(NC(=O)C2CC2)nc2[nH]c(C(F)F)nc12] |
| I-336 | 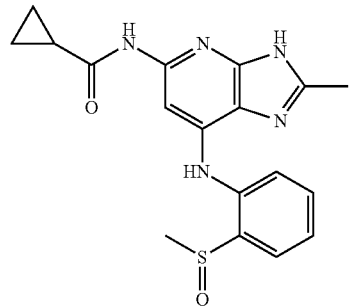 [SMILES: Cc1nc2c(Nc3ccccc3S(C)=O)cc(NC(=O)C3CC3)nc2[nH]1] |

TABLE-continued
Exemplary Compounds
| Compound | Structure |
|---|---|
| I-337 | 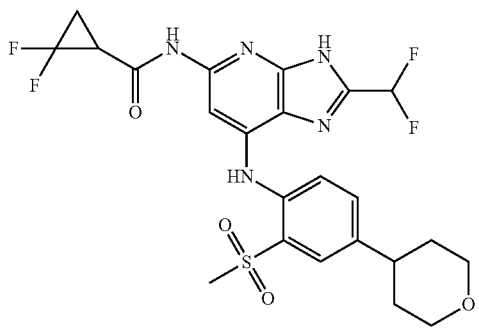 [SMILES: CS(=O)(=O)c1cc(C2CCOCC2)ccc1Nc1cc(NC(=O)C2CC2(F)F)nc2[nH]c(C(F)F)nc12] |
| I-338 | 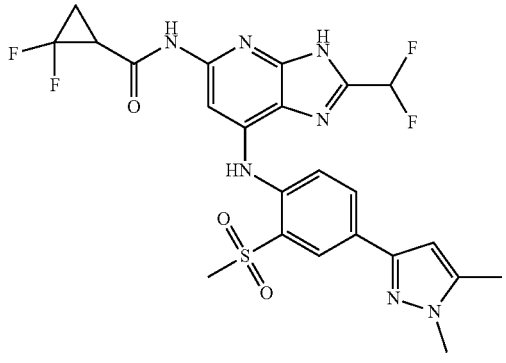 |
| I-339 | 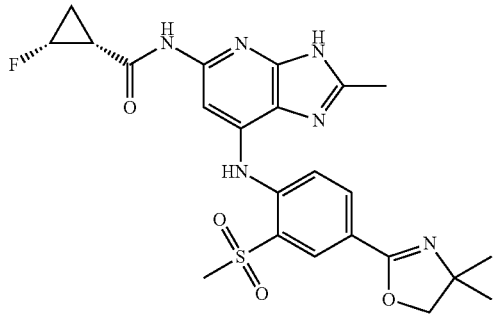 [SMILES: Cc1nc2c(Nc3ccc(C4=NC(C)(C)CO4)cc3S(C)(=O)=O)cc(NC(=O)[C@H]3C[C@H]3F)nc2[nH]1] |
| I-340 | 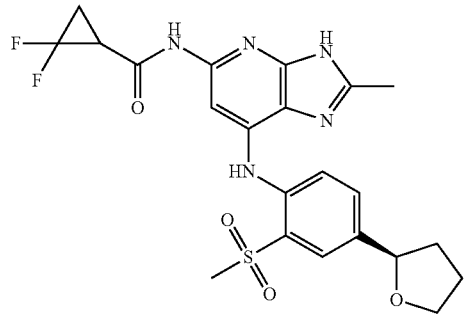 [SMILES: Cc1nc2c(Nc3ccc([C@H]4CCCO4)cc3S(C)(=O)=O)cc(NC(=O)C3CC3(F)F)nc2[nH]1] |

TABLE-continued

Exemplary Compounds

| Compound | Structure |
|---|---|
| I-341 | 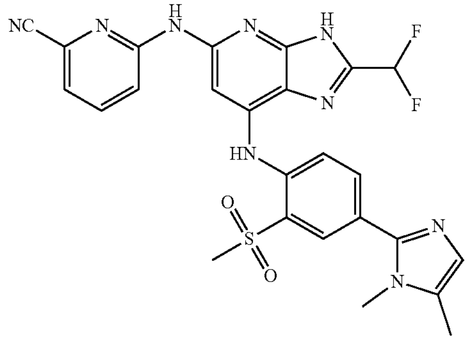 [SMILES: Cc1cnc(-c2ccc(Nc3cc(Nc4cccc(C#N)n4)nc4[nH]c(C(F)F)nc34)c(S(C)(=O)=O)c2)n1C] |
| I-342 | 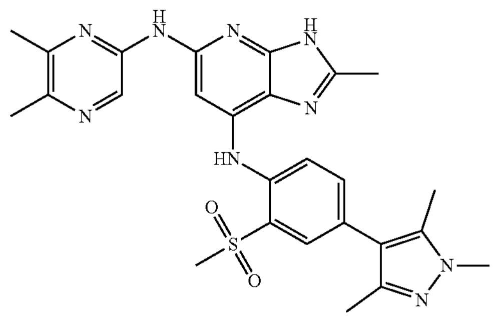 |
| I-343 | 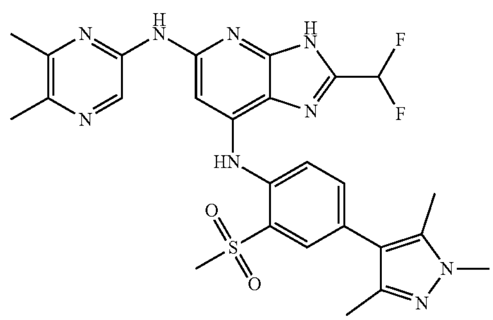 |
| I-344 | 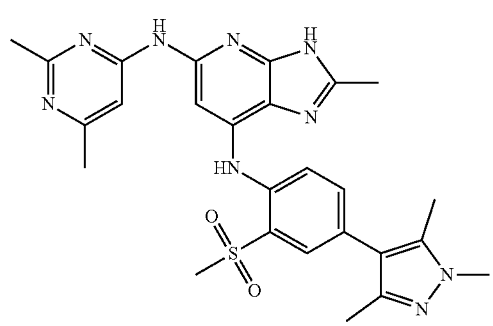 |

| Compound | Structure |
|---|---|
| I-345 | 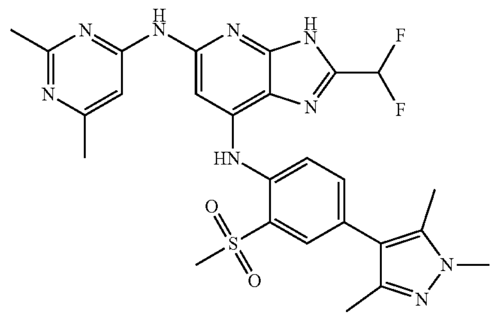 |
| I-346 | 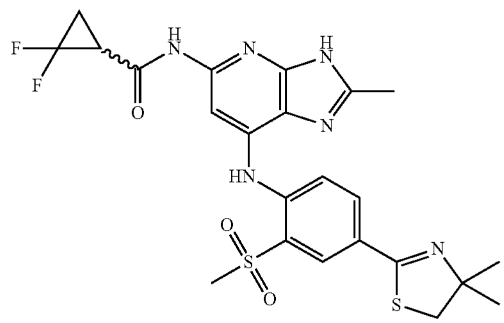 [SMILES: Cc1nc2c(Nc3ccc(C4=NC(C)(C)CS4)cc3S(C)(=O)=O)cc(NC(=O)C3CC3(F)F)nc2[nH]1] |
| I-347 | 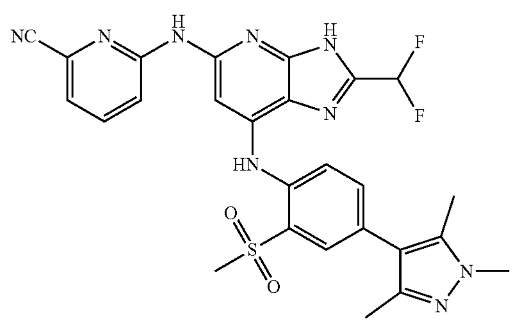 [SMILES: Cc1nn(C)c(C)c1-c1ccc(Nc2cc(Nc3cccc(C#N)n3)nc3[nH]c(C(F)F)nc23)c(S(C)(=O)=O)c1] |
| I-348 | 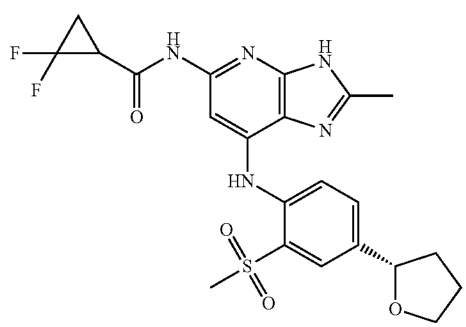 [SMILES: Cc1nc2c(Nc3ccc([C@@H]4CCCO4)cc3S(C)(=O)=O)cc(NC(=O)C3CC3(F)F)nc2[nH]1] |

TABLE-continued

Exemplary Compounds

| Compound | Structure |
|---|---|
| I-349 | 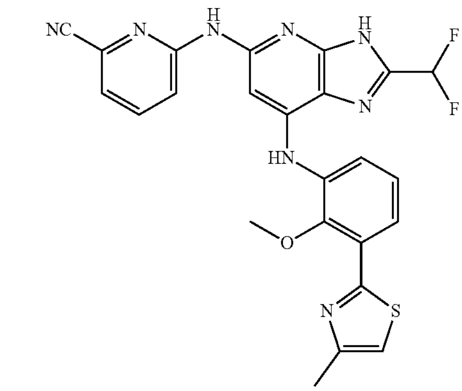 [SMILES: COc1c(Nc2cc(Nc3cccc(C#N)n3)nc3[nH]c(C(F)F)nc23)cccc1-c1nc(C)cs1] |
| I-350 | 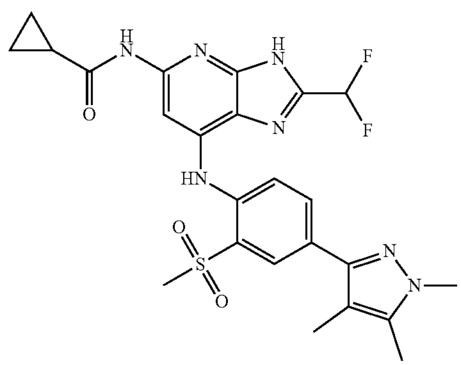 [SMILES: Cc1c(-c2ccc(Nc3cc(NC(=O)C4CC4)nc4[nH]c(C(F)F)nc34)c(S(C)(=O)=O)c2)nn(C)c1C] |
| I-351 | 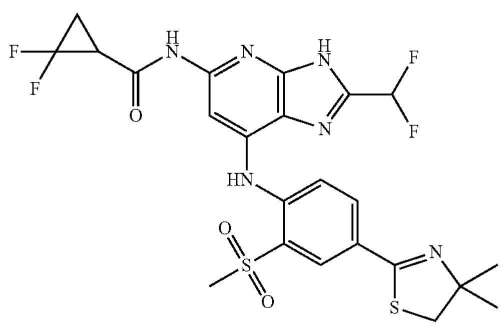 |
| I-352 | 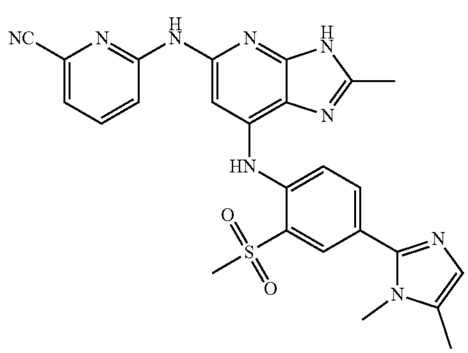 [SMILES: Cc1nc2c(Nc3ccc(-c4ncc(C)n4C)cc3S(C)(=O)=O)cc(Nc3cccc(C#N)n3)nc2[nH]1] |

TABLE-continued

Exemplary Compounds

| Compound | Structure |
|---|---|
| I-353 | 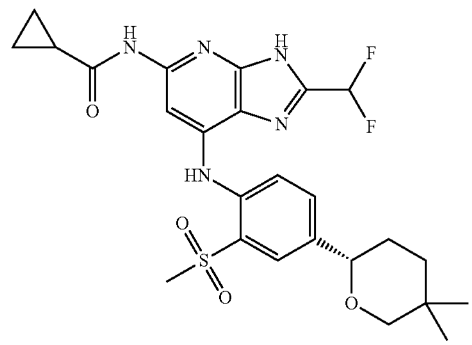 [SMILES: CC1(C)CC[C@@H](c2ccc(Nc3cc(NC(=O)C4CC4)nc4[nH]c(C(F)F)nc34)c(S(C)(=O)=O)c2)OC1] |
| I-354 | 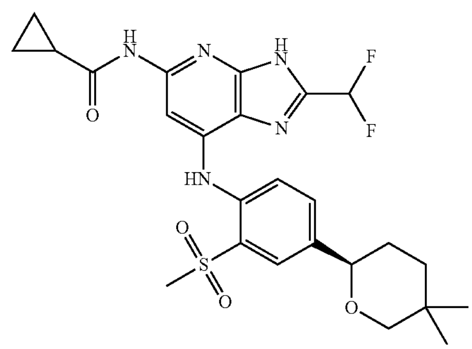 [SMILES: CC1(C)CC[C@H](c2ccc(Nc3cc(NC(=O)C4CC4)nc4[nH]c(C(F)F)nc34)c(S(C)(=O)=O)c2)OC1] |
| I-355 | 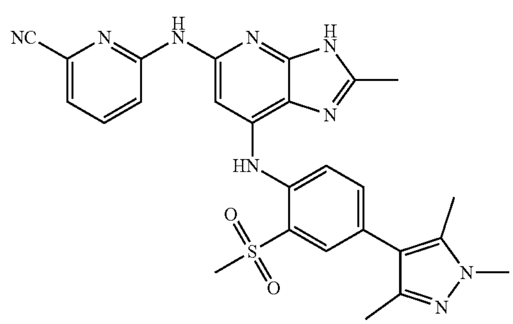 [SMILES: Cc1nc2c(Nc3ccc(-c4c(C)nn(C)c4C)cc3S(C)(=O)=O)cc(Nc3cccc(C#N)n3)nc2[nH]1] |
| I-356 | 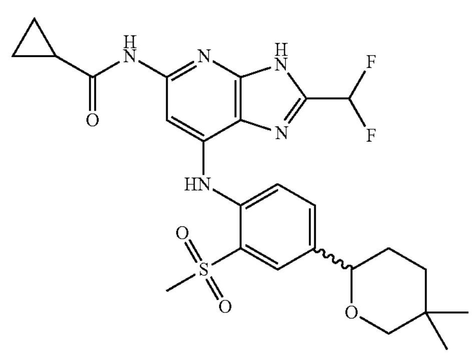 |

TABLE-continued
Exemplary Compounds
| Compound | Structure |
|---|---|
| I-357 | 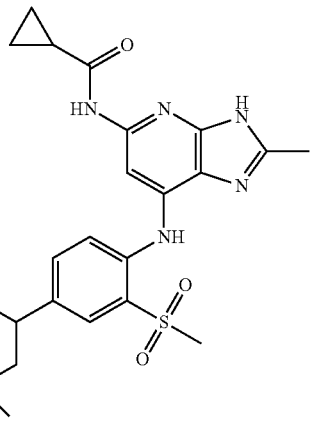 |
| I-358 | 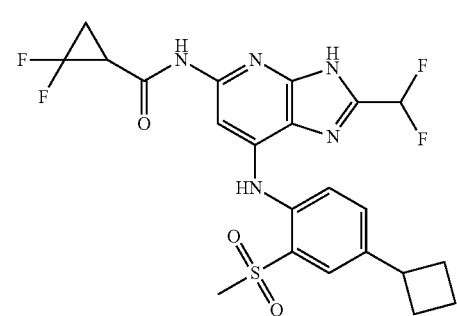 |
| I-359 | 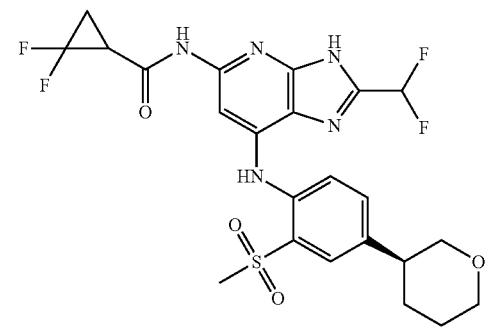 [SMILES: CS(=O)(=O)c1cc([C@@H]2CCCOC2)ccc1Nc1cc(NC(=O)C2CC2(F)F)nc2[nH]c(C(F)F)nc12] |
| I-360 | 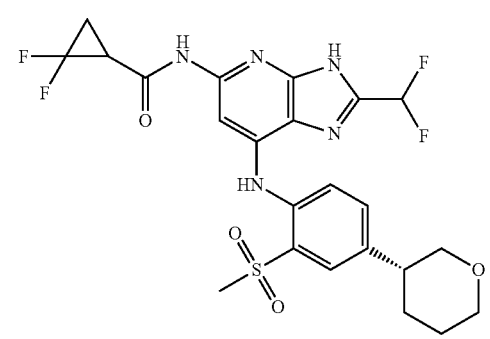 [SMILES: CS(=O)(=O)c1cc([C@H]2CCCOC2)ccc1Nc1cc(NC(=O)C2CC2(F)F)nc2[nH]c(C(F)F)nc12] |

TABLE-continued
Exemplary Compounds
| Compound | Structure |
|---|---|
| I-361 | 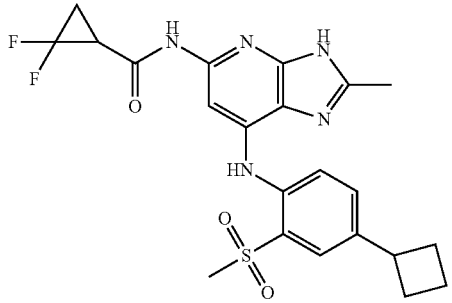 [SMILES: Cc1nc2c(Nc3ccc(C4CCC4)cc3S(C)(=O)=O)cc(NC(=O)C3CC3(F)F)nc2[nH]1] |
| I-362 | 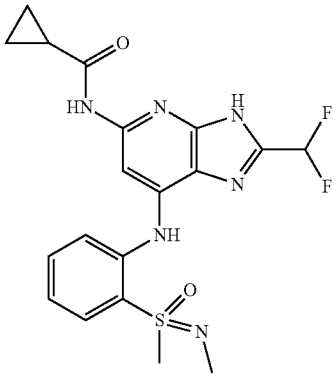 [SMILES: CN=S(C)(=O)c1ccccc1Nc1cc(NC(=O)C2CC2)nc2[nH]c(C(F)F)nc12] |
| I-363 | 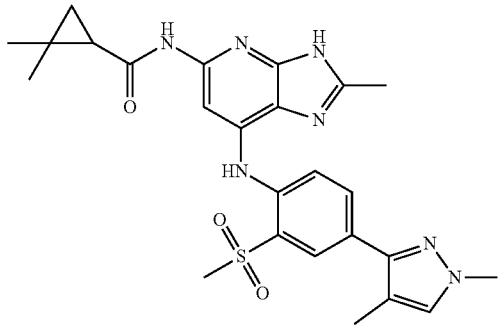 |
| I-364 | 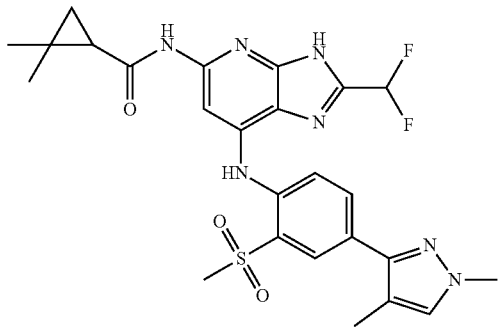 |

| Compound | Structure |
|---|---|
| I-365 | 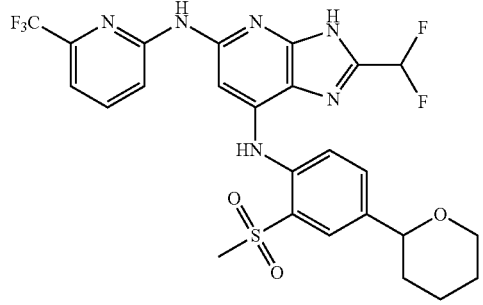 [SMILES: CS(=O)(=O)c1cc(C2CCCCO2)ccc1Nc1cc(Nc2cccc(C(F)(F)F)n2)nc2[nH]c(C(F)F)nc12] |
| I-366 | 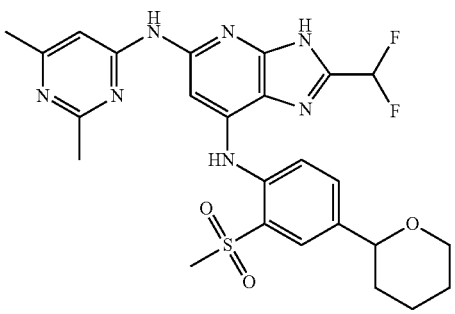 [SMILES: Cc1cc(Nc2cc(Nc3ccc(C4CCCCO4)cc3S(C)(=O)=O)c3nc(C(F)F)[nH]c3n2)nc(C)n1] |
| I-367 | 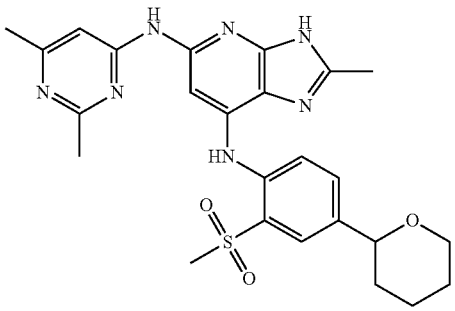 [SMILES: Cc1cc(Nc2cc(Nc3ccc(C4CCCCO4)cc3S(C)(=O)=O)c3nc(C)[nH]c3n2)nc(C)n1] |
| I-368 | 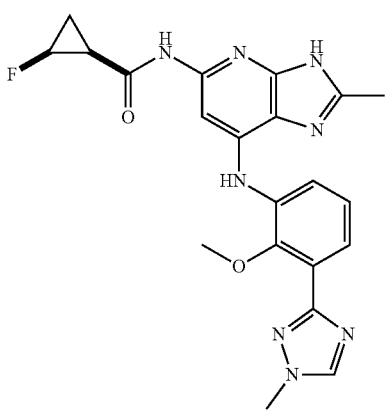 |

TABLE-continued

Exemplary Compounds

| Compound | Structure |
|---|---|
| I-369 | 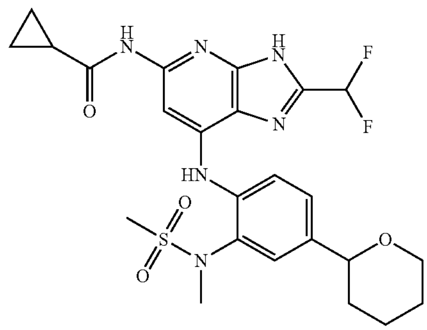 [SMILES: CN(c1cc(C2CCCCO2)ccc1Nc1cc(NC(=O)C2CC2)nc2[nH]c(C(F)F)nc12)S(C)(=O)=O] |
| I-370 | 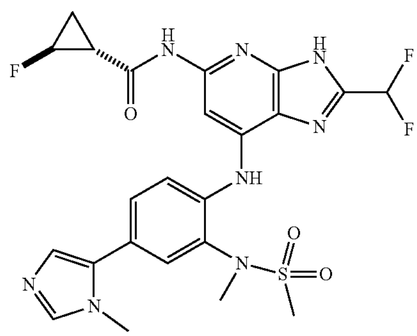 |
| I-371 | 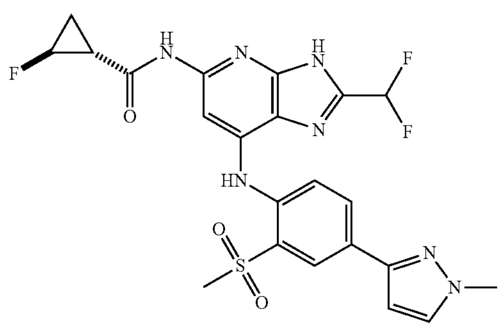 |
| I-372 | 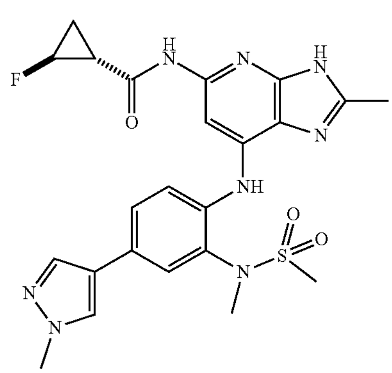 |

| Compound | Structure |
|---|---|
| I-373 | 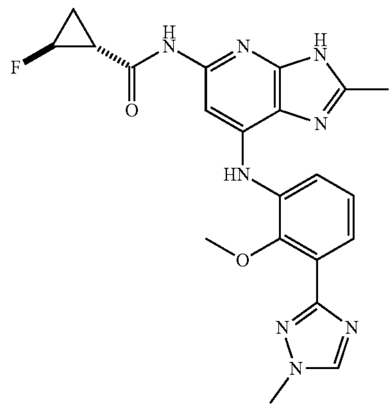 |
| I-374 | 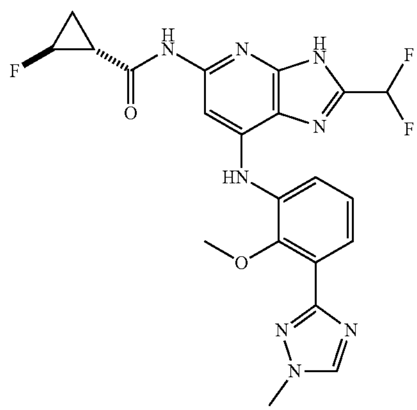 |
| I-375 | 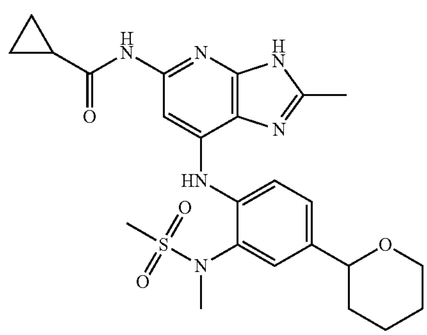 [SMILES: Cc1nc2c(Nc3ccc(C4CCCCO4)cc3N(C)S(C)(=O)=O)cc(NC(=O)C3CC3)nc2[nH]1] |
| I-376 | 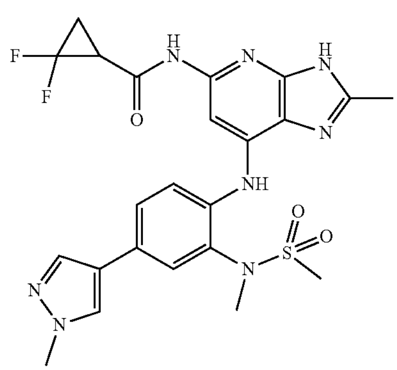 [SMILES: Cc1nc2c(Nc3ccc(-c4cnn(C)c4)cc3N(C)S(C)(=O)=O)cc(NC(=O)C3CC3(F)F)nc2[nH]1] |

TABLE-continued

Exemplary Compounds

| Compound | Structure |
|---|---|
| I-377 | 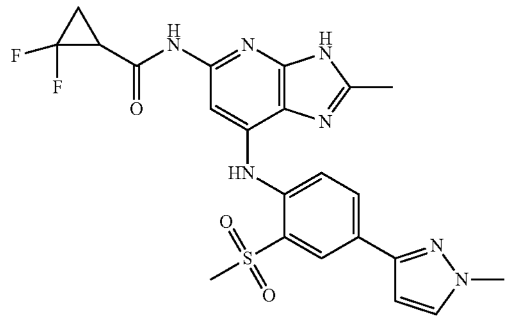 [SMILES: Cc1nc2c(Nc3ccc(-c4ccn(C)n4)cc3S(C)(=O)=O)cc(NC(=O)C3CC3(F)F)nc2[nH]1] |
| I-378 | 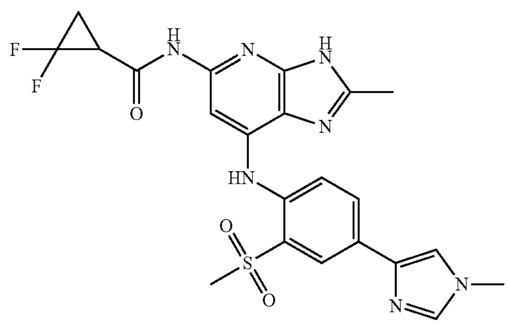 [SMILES: Cc1nc2c(Nc3ccc(-c4cn(C)cn4)cc3S(C)(=O)=O)cc(NC(=O)C3CC3(F)F)nc2[nH]1] |
| I-379 | 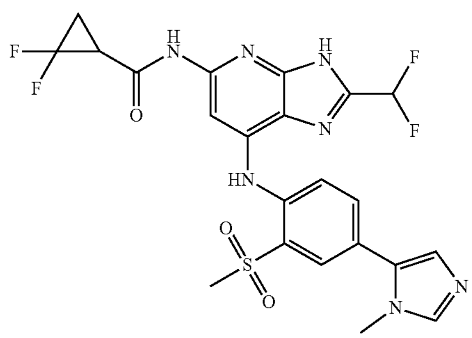 [SMILES: Cn1cncc1-c1ccc(Nc2cc(NC(=O)C3CC3(F)F)nc3[nH]c(C(F)F)nc23)c(S(C)(=O)=O)c1] |
| I-380 | 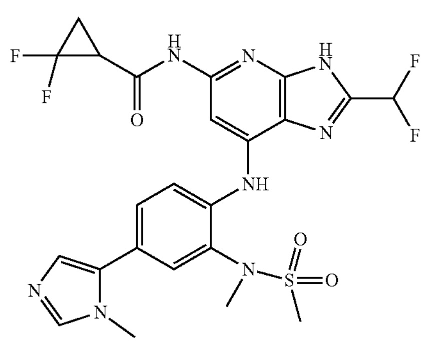 |

TABLE-continued

Exemplary Compounds

| Compound | Structure |
|---|---|
| I-381 | 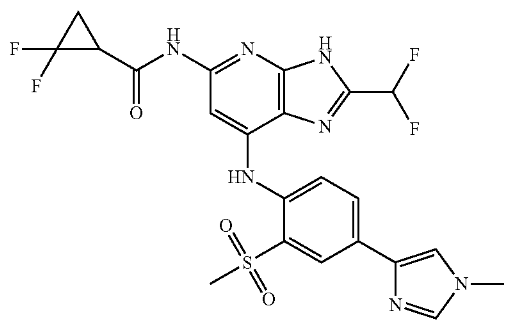 |
| I-382 | 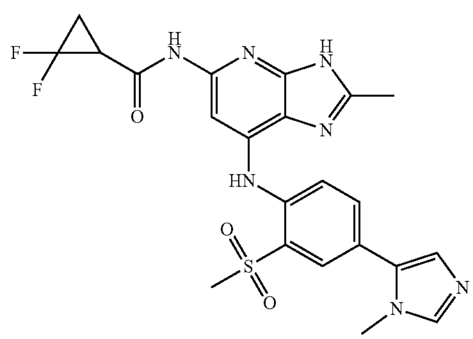 [SMILES: Cc1nc2c(Nc3ccc(-c4cncn4C)cc3S(C)(=O)=O)cc(NC(=O)C3CC3(F)F)nc2[nH]1] |
| I-383 | 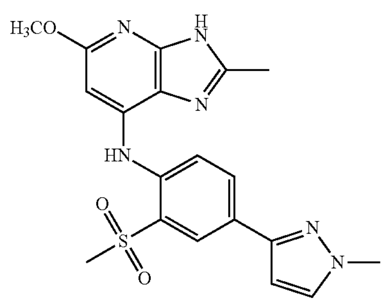 [SMILES: COc1cc(Nc2ccc(-c3ccn(C)n3)cc2S(C)(=O)=O)c2nc(C)[nH]c2n1] |
| I-384 | 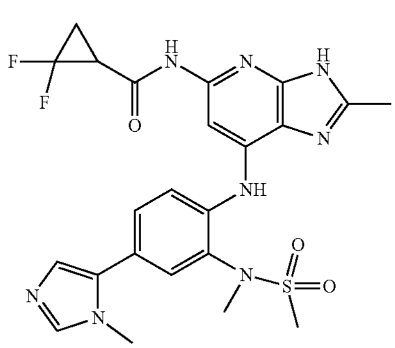 |

TABLE-continued
Exemplary Compounds
| Compound | Structure |
|---|---|
| I-385 | 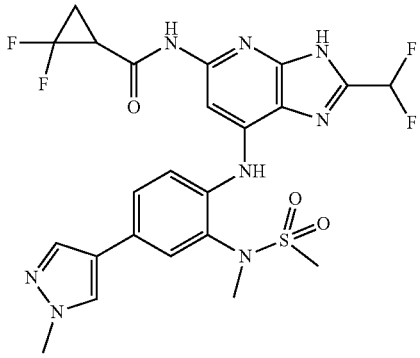 [SMILES: CN(c1cc(-c2cnn(C)c2)ccc1Nc1cc(NC(=O)C2CC2(F)F)nc2[nH]c(C(F)F)nc12)S(C)(=O)=O] |
| I-386 | 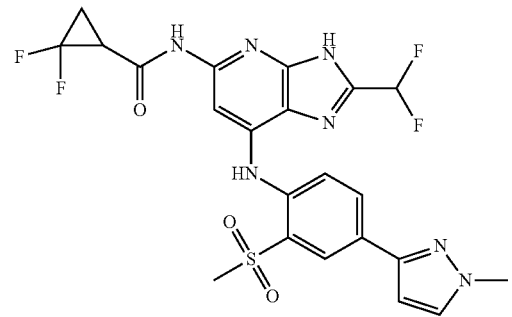 [SMILES: Cn1ccc(-c2ccc(Nc3cc(NC(=O)C4CC4(F)F)nc4[nH]c(C(F)F)nc34)c(S(C)(=O)=O)c2)n1] |
| I-387 | 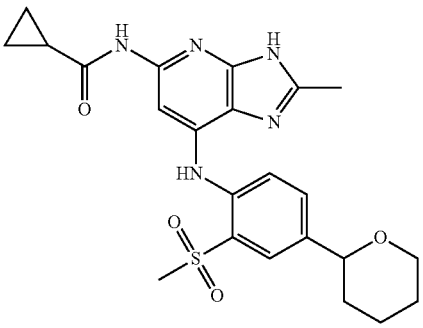 [SMILES: Cc1nc2c(Nc3ccc(C4CCCCO4)cc3S(C)(=O)=O)cc(NC(=O)C3CC3)nc2[nH]1] |
| I-388 | 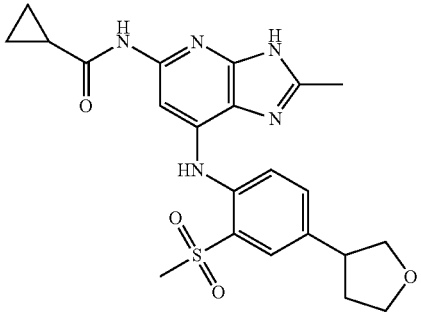 [SMILES: Cc1nc2c(Nc3ccc(C4CCOC4)cc3S(C)(=O)=O)cc(NC(=O)C3CC3)nc2[nH]1] |

TABLE-continued
Exemplary Compounds
| Compound | Structure |
|---|---|
| I-389 | 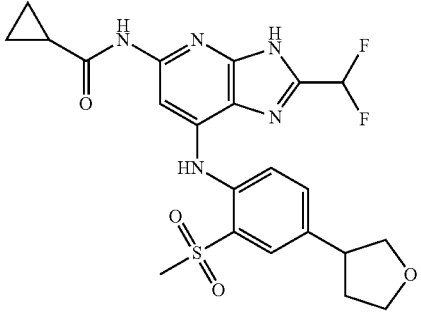 [SMILES: CS(=O)(=O)c1cc(C2CCOC2)ccc1Nc1cc(NC(=O)C2CC2)nc2[nH]c(C(F)F)nc12] |
| I-390 | 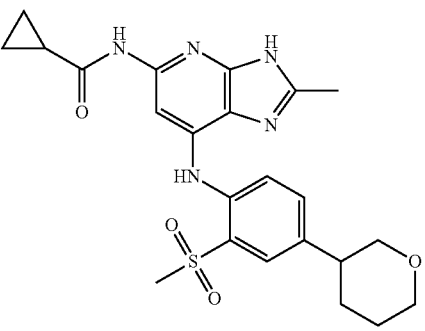 |
| I-391 | 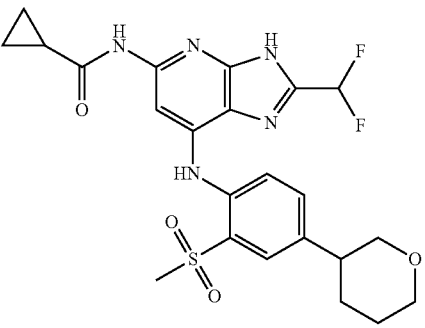 [SMILES: CS(=O)(=O)c1cc(C2CCCOC2)ccc1Nc1cc(NC(=O)C2CC2)nc2[nH]c(C(F)F)nc12] |
| I-392 | 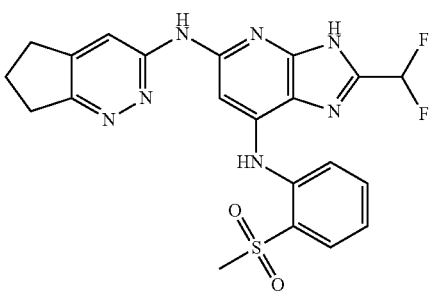 [SMILES: CS(=O)(=O)c1ccccc1Nc1cc(Nc2cc3c(nn2)CCC3)nc2[nH]c(C(F)F)nc12] |

TABLE-continued

Exemplary Compounds

| Compound | Structure |
|---|---|
| I-393 | 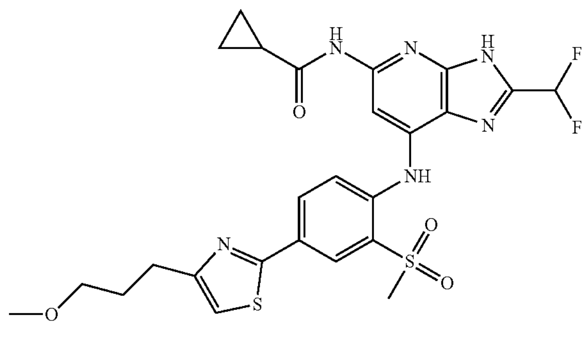 [SMILES: COCCCc1csc(-c2ccc(Nc3cc(NC(=O)C4CC4)nc4[nH]c(C(F)F)nc34)c(S(C)(=O)=O)c2)n1] |
| I-394 | 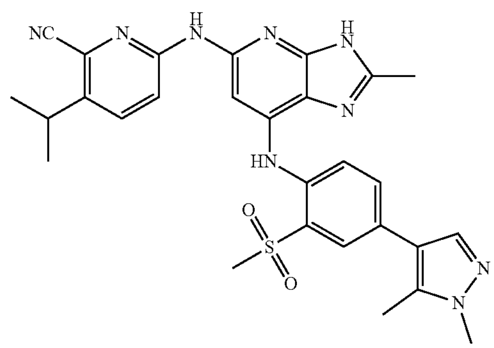 [SMILES: Cc1nc2c(Nc3ccc(-c4cnn(C)c4C)cc3S(C)(=O)=O)cc(Nc3ccc(C(C)C)c(C#N)n3)nc2[nH]1] |
| I-395 | 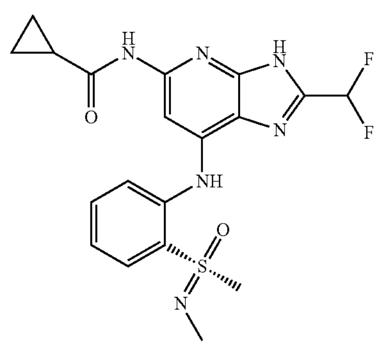 [SMILES: CN=[S@](C)(=O)c1ccccc1Nc1cc(NC(=O)C2CC2)nc2[nH]c(C(F)F)nc12] |
| I-396 | 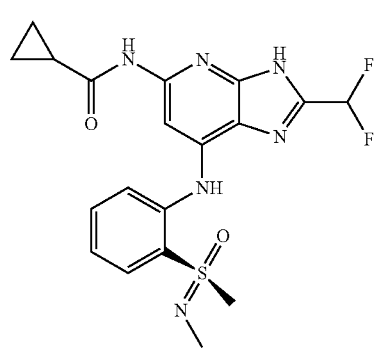 [SMILES: CN=[S@@](C)(=O)c1ccccc1Nc1cc(NC(=O)C2CC2)nc2[nH]c(C(F)F)nc12] |

US 11,396,508 B2
243                                                                          244
TABLE-continued
Exemplary Compounds
| Compound | Structure |
|---|---|
| I-397 | 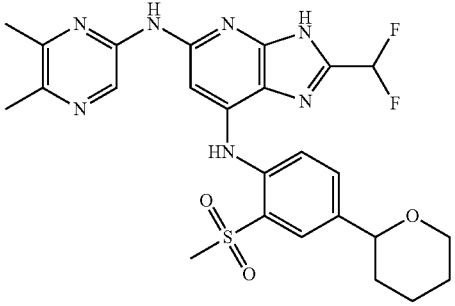 |
| I-398 | 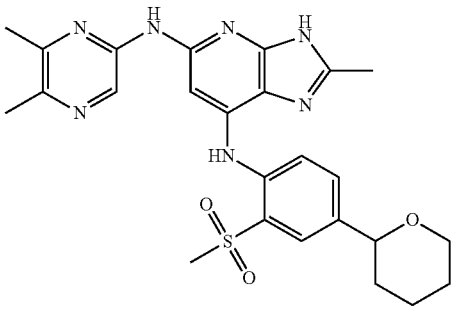 [SMILES: Cc1nc2c(Nc3ccc(C4CCCCO4)cc3S(C)(=O)=O)cc(Nc3cnc(C)c(C)n3)nc2[nH]1] |
| I-399 | 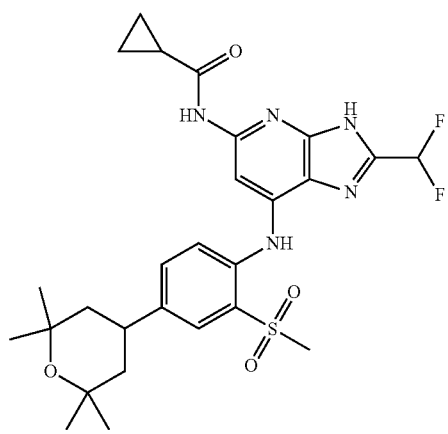 [SMILES: CC1(C)CC(c2ccc(Nc3cc(NC(=O)C4CC4)nc4[nH]c(C(F)F)nc34)c(S(C)(=O)=O)c2)CC(C)(C)O1] |
| I-400 | 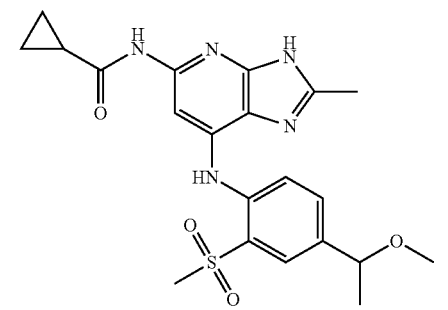 [SMILES: COC(C)c1ccc(Nc2cc(NC(=O)C3CC3)nc3[nH]c(C)nc23)c(S(C)(=O)=O)c1] |

TABLE-continued
Exemplary Compounds
| Compound | Structure |
|---|---|
| I-401 | 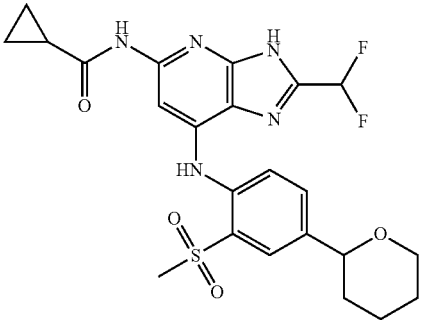 [SMILES: CS(=O)(=O)c1cc(C2CCCCO2)ccc1Nc1cc(NC(=O)C2CC2)nc2[nH]c(C(F)F)nc12] |
| I-402 | 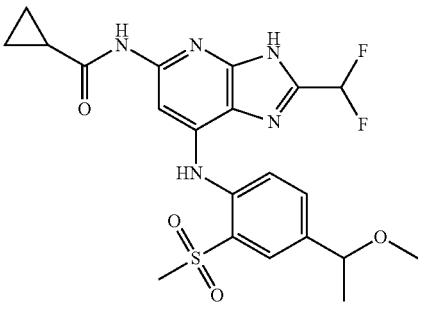 |
| I-403 | 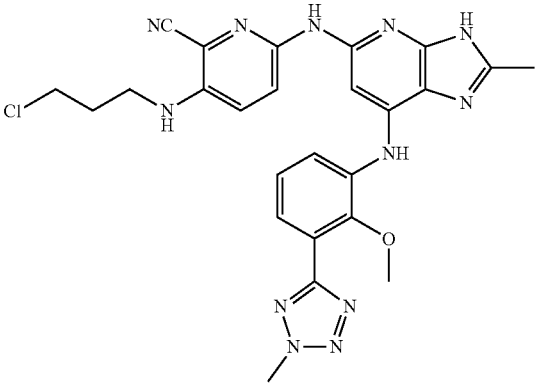 [SMILES: COc1c(Nc2cc(Nc3ccc(NCCCCl)c(C#N)n3)nc3[nH]c(C)nc23)cccc1-c1nnn(C)n1] |
| I-404 | 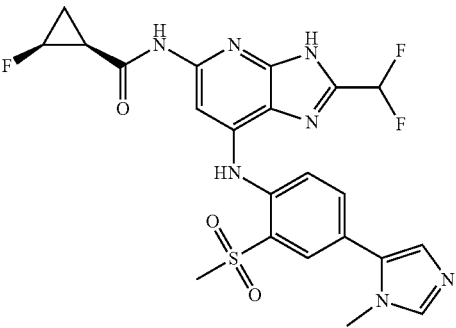 [SMILES: Cn1cncc1-c1ccc(Nc2cc(NC(=O)[C@@H]3C[C@@H]3F)nc3[nH]c(C(F)F)nc23)c(S(C)(=O)=O)c1] |

TABLE-continued
Exemplary Compounds
| Compound | Structure |
|---|---|
| I-405 | 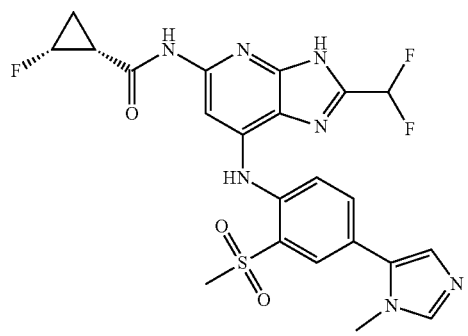 [SMILES: Cn1cncc1-c1ccc(Nc2cc(NC(=O)[C@H]3C[C@H]3F)nc3[nH]c(C(F)F)nc23)c(S(C)(=O)=O)c1] |
| I-406 | 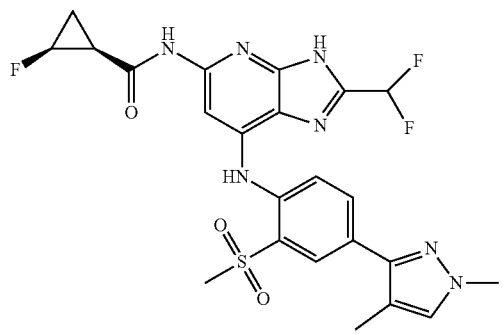 [SMILES: Cc1cn(C)nc1-c1ccc(Nc2cc(NC(=O)[C@@H]3C[C@@H]3F)nc3[nH]c(C(F)F)nc23)c(S(C)(=O)=O)c1] |
| I-407 | 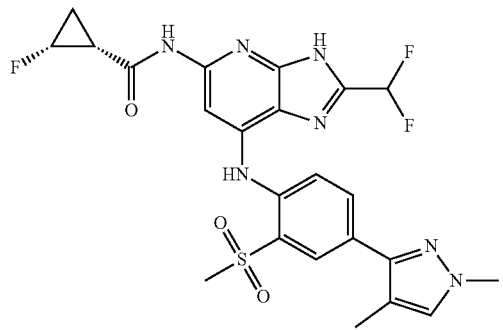 [SMILES: Cc1cn(C)nc1-c1ccc(Nc2cc(NC(=O)[C@H]3C[C@H]3F)nc3[nH]c(C(F)F)nc23)c(S(C)(=O)=O)c1] |
| I-408 | 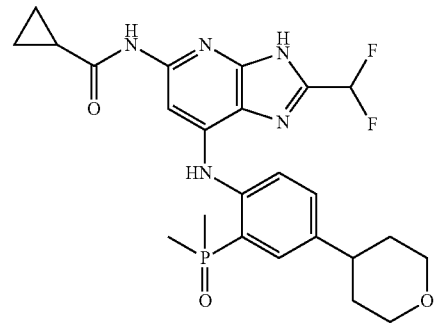 [SMILES: CP(C)(=O)c1cc(C2CCOCC2)ccc1Nc1cc(NC(=O)C2CC2)nc2[nH]c(C(F)F)nc12] |

TABLE-continued

Exemplary Compounds

| Compound | Structure |
|---|---|
| I-409 | 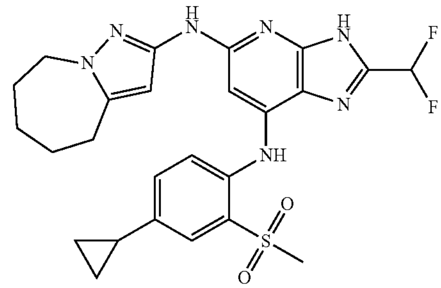 [SMILES: CS(=O)(=O)c1cc(C2CC2)ccc1Nc1cc(Nc2cc3n(n2)CCCCC3)nc2[nH]c(C(F)F)nc12] |
| I-410 | 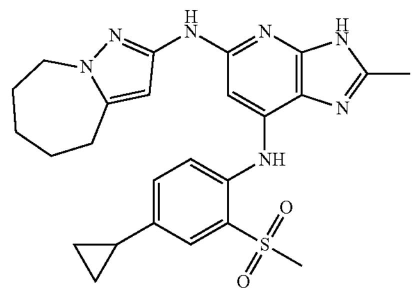 [SMILES: Cc1nc2c(Nc3ccc(C4CC4)cc3S(C)(=O)=O)cc(Nc3cc4n(n3)CCCCC4)nc2[nH]1] |
| I-411 | 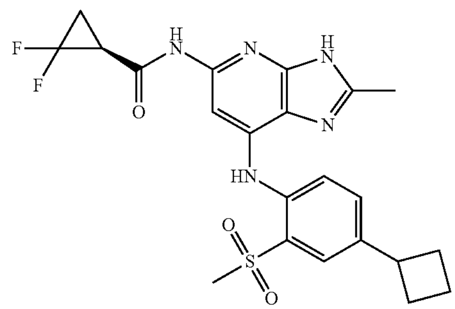 [SMILES: Cc1nc2c(Nc3ccc(C4CCC4)cc3S(C)(=O)=O)cc(NC(=O)[C@@H]3CC3(F)F)nc2[nH]1] |
| I-412 | 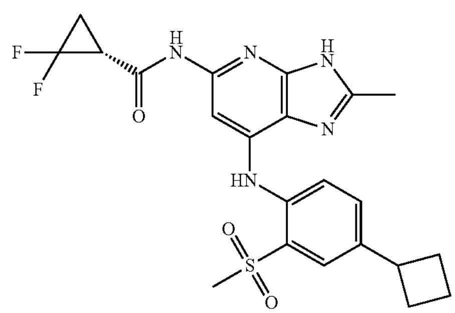 [SMILES: Cc1nc2c(Nc3ccc(C4CCC4)cc3S(C)(=O)=O)cc(NC(=O)[C@H]3CC3(F)F)nc2[nH]1] |
| I-413 | 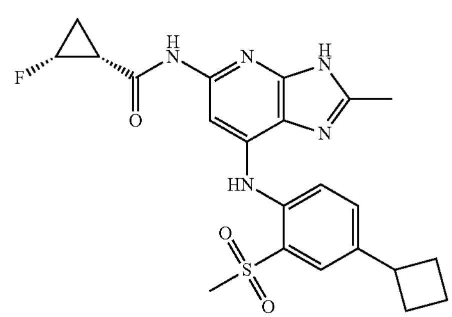 [SMILES: Cc1nc2c(Nc3ccc(C4CCC4)cc3S(C)(=O)=O)cc(NC(=O)[C@H]3C[C@H]3F)nc2[nH]1] |

TABLE-continued
Exemplary Compounds
| Compound | Structure |
|---|---|
| I-414 | 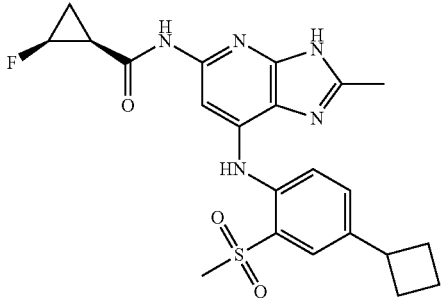 [SMILES: Cc1nc2c(Nc3ccc(C4CCC4)cc3S(C)(=O)=O)cc(NC(=O)[C@@H]3C[C@@H]3F)nc2[nH]1] |
| I-415 | 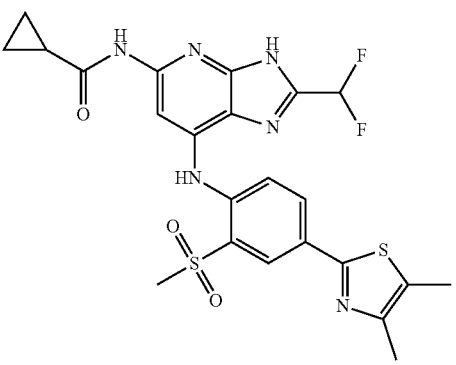 [SMILES: Cc1nc(-c2ccc(Nc3cc(NC(=O)C4CC4)nc4[nH]c(C(F)F)nc34)c(S(C)(=O)=O)c2)sc1C] |
| I-416 | 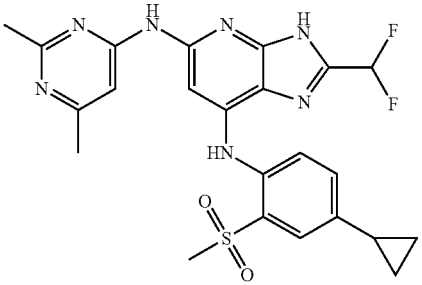 [SMILES: Cc1cc(Nc2cc(Nc3ccc(C4CC4)cc3S(C)(=O)=O)c3nc(C(F)F)[nH]c3n2)nc(C)n1] |
| I-417 | 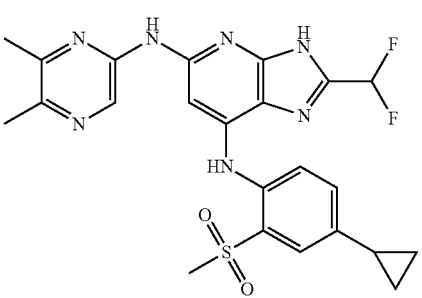 [SMILES: Cc1ncc(Nc2cc(Nc3ccc(C4CC4)cc3S(C)(=O)=O)c3nc(C(F)F)[nH]c3n2)nc1C] |

TABLE-continued
Exemplary Compounds
| Compound | Structure |
|---|---|
| I-418 | 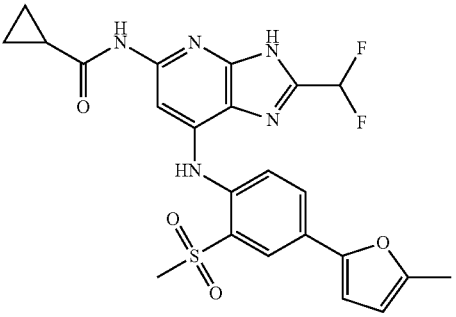 [SMILES: Cc1ccc(-c2ccc(Nc3cc(NC(=O)C4CC4)nc4[nH]c(C(F)F)nc34)c(S(C)(=O)=O)c2)o1] |
| I-419 | 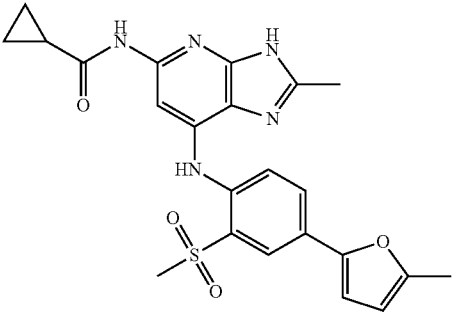 [SMILES: Cc1nc2c(Nc3ccc(-c4ccc(C)o4)cc3S(C)(=O)=O)cc(NC(=O)C3CC3)nc2[nH]1] |
| I-420 | 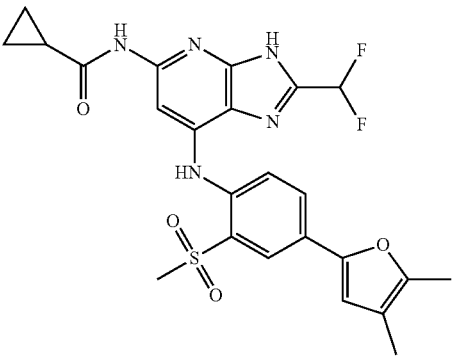 [SMILES: Cc1cc(-c2ccc(Nc3cc(NC(=O)C4CC4)nc4[nH]c(C(F)F)nc34)c(S(C)(=O)=O)c2)oc1C] |
| I-421 | 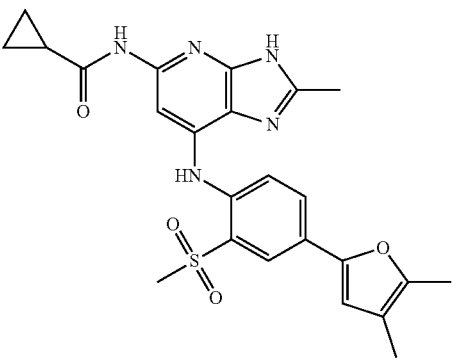 [SMILES: Cc1nc2c(Nc3ccc(-c4cc(C)c(C)o4)cc3S(C)(=O)=O)cc(NC(=O)C3CC3)nc2[nH]1] |

TABLE-continued

Exemplary Compounds

| Compound | Structure |
|---|---|
| I-422 | 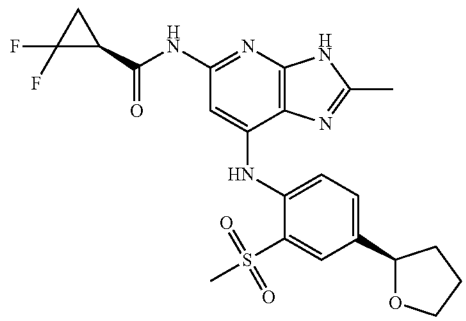 [SMILES: Cc1nc2c(Nc3ccc([C@H]4CCCO4)cc3S(C)(=O)=O)cc(NC(=O)[C@@H]3CC3(F)F)nc2[nH]1] |
| I-423 | 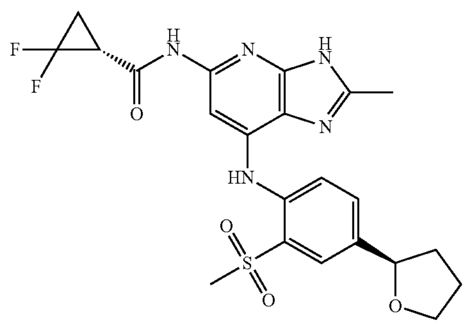 [SMILES: Cc1nc2c(Nc3ccc([C@H]4CCCO4)cc3S(C)(=O)=O)cc(NC(=O)[C@H]3CC3(F)F)nc2[nH]1] |
| I-424 | 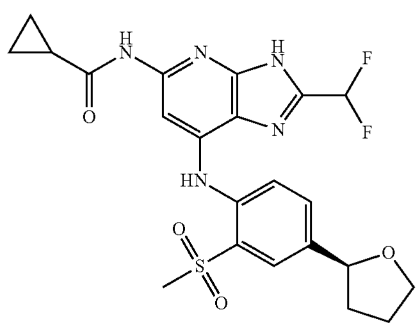 [SMILES: CS(=O)(=O)c1cc([C@@H]2CCCO2)ccc1Nc1cc(NC(=O)C2CC2)nc2[nH]c(C(F)F)nc12] |
| I-425 | 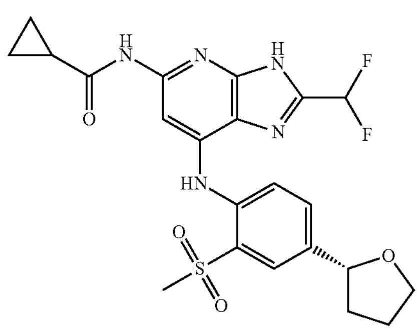 [SMILES: CS(=O)(=O)c1cc([C@H]2CCCO2)ccc1Nc1cc(NC(=O)C2CC2)nc2[nH]c(C(F)F)nc12] |

TABLE-continued
Exemplary Compounds
| Compound | Structure |
|---|---|
| I-426 | 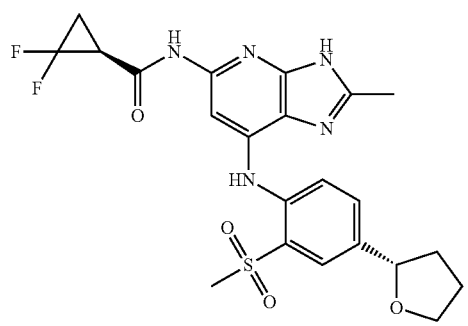 [SMILES: Cc1nc2c(Nc3ccc([C@@H]4CCCO4)cc3S(C)(=O)=O)cc(NC(=O)[C@@H]3CC3(F)F)nc2[nH]1] |
| I-427 | 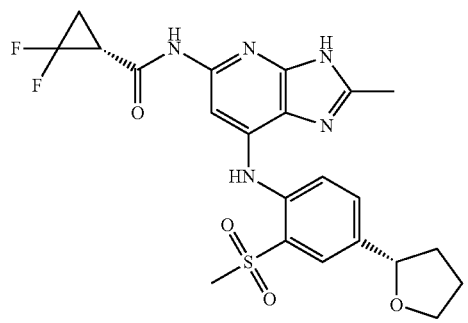 [SMILES: Cc1nc2c(Nc3ccc([C@@H]4CCCO4)cc3S(C)(=O)=O)cc(NC(=O)[C@H]3CC3(F)F)nc2[nH]1] |
| I-428 | 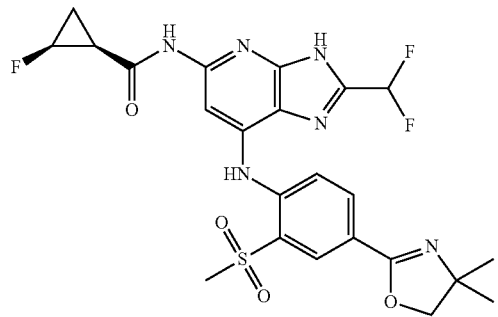 [SMILES: CC1(C)COC(c2ccc(Nc3cc(NC(=O)[C@@H]4C[C@@H]4F)nc4[nH]c(C(F)F)nc34)c(S(C)(=O)=O)c2)=N1] |
| I-429 | 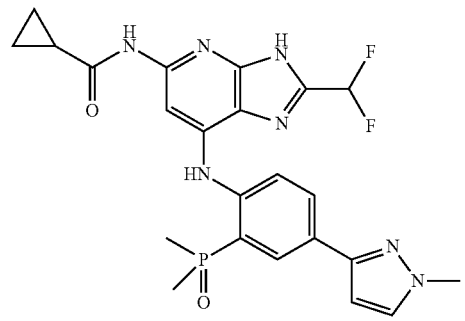 [SMILES: Cn1ccc(-c2ccc(Nc3cc(NC(=O)C4CC4)nc4[nH]c(C(F)F)nc34)c(P(C)(C)=O)c2)n1] |

TABLE-continued
Exemplary Compounds
| Compound | Structure |
|---|---|
| I-430 | 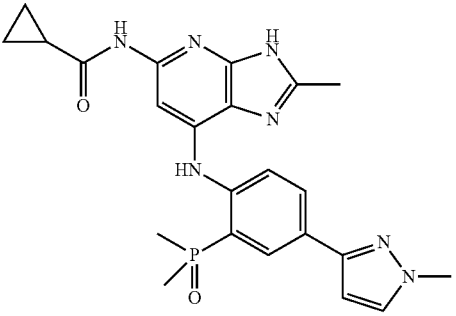 [SMILES: Cc1nc2c(Nc3ccc(-c4ccn(C)n4)cc3P(C)(C)=O)cc(NC(=O)C3CC3)nc2[nH]1] |
| I-431 | 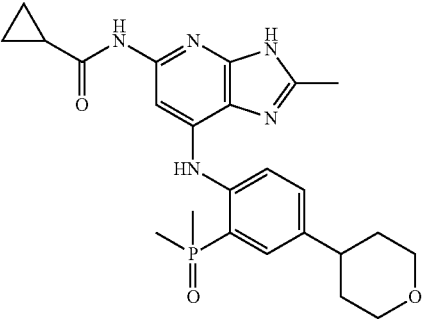 [SMILES: Cc1nc2c(Nc3ccc(C4CCOCC4)cc3P(C)(C)=O)cc(NC(=O)C3CC3)nc2[nH]1] |
| I-432 | 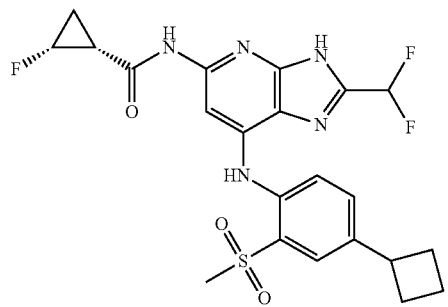 [SMILES: CS(=O)(=O)c1cc(C2CCC2)ccc1Nc1cc(NC(=O)[C@H]2C[C@H]2F)nc2[nH]c(C(F)F)nc12] |
| I-433 | 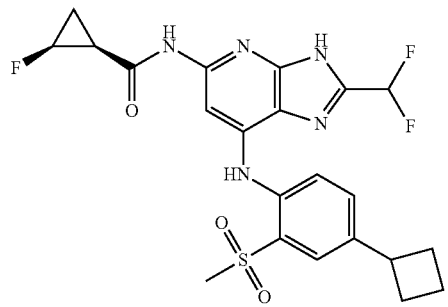 [SMILES: CS(=O)(=O)c1cc(C2CCC2)ccc1Nc1cc(NC(=O)[C@@H]2C[C@@H]2F)nc2[nH]c(C(F)F)nc12] |

TABLE-continued

Exemplary Compounds

| Compound | Structure |
|---|---|
| I-434 | 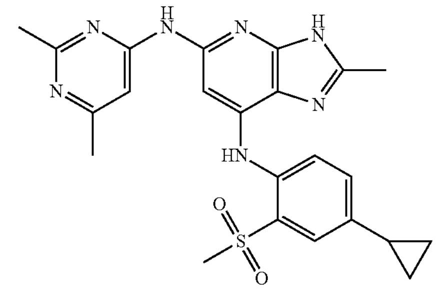 [SMILES: Cc1cc(Nc2cc(Nc3ccc(C4CC4)cc3S(C)(=O)=O)c3nc(C)[nH]c3n2)nc(C)n1] |
| I-435 | 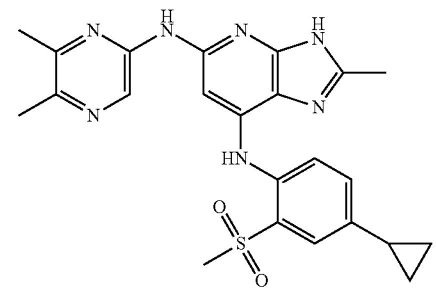 [SMILES: Cc1nc2c(Nc3ccc(C4CC4)cc3S(C)(=O)=O)cc(Nc3cnc(C)c(C)n3)nc2[nH]1] |
| I-436 | 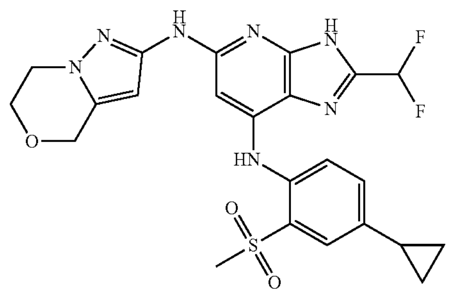 [SMILES: CS(=O)(=O)c1cc(C2CC2)ccc1Nc1cc(Nc2cc3n(n2)CCOC3)nc2[nH]c(C(F)F)nc12] |
| I-437 | 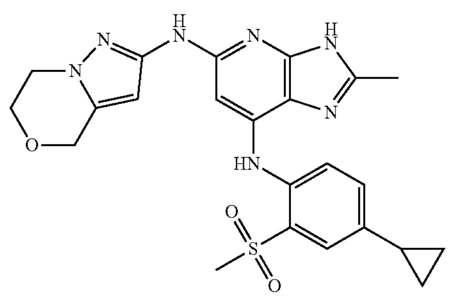 [SMILES: Cc1nc2c(Nc3ccc(C4CC4)cc3S(C)(=O)=O)cc(Nc3cc4n(n3)CCOC4)nc2[nH]1] |
| I-438 | 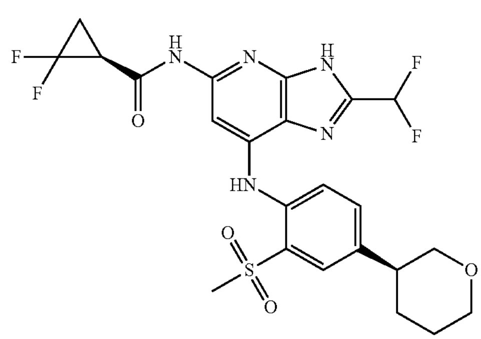 [SMILES: CS(=O)(=O)c1cc([C@@H]2CCCOC2)ccc1Nc1cc(NC(=O)[C@@H]2CC2(F)F)nc2[nH]c(C(F)F)nc12] |

TABLE-continued

Exemplary Compounds

| Compound | Structure |
|---|---|
| I-439 | 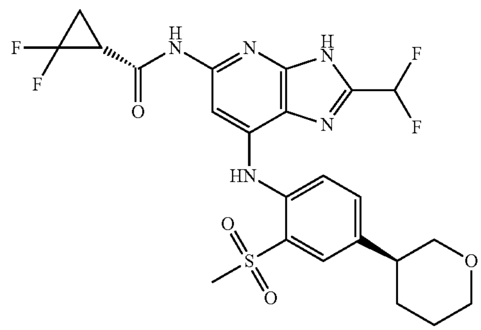 |
| I-440 | 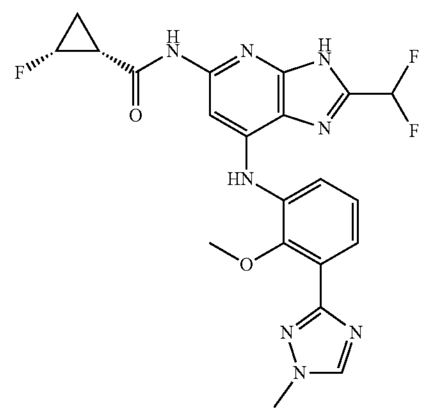 [SMILES: COc1c(Nc2cc(NC(=O)[C@H]3C[C@H]3F)nc3[nH]c(C(F)F)nc23)cccc1-c1ncn(C)n1] |
| I-441 | 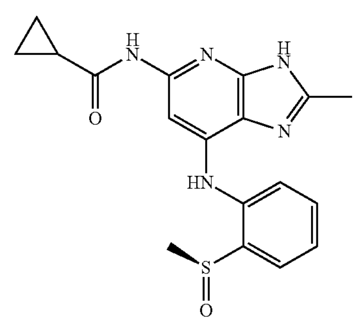 [SMILES: Cc1nc2c(Nc3ccccc3[S@](C)=O)cc(NC(=O)C3CC3)nc2[nH]1] |
| I-442 | 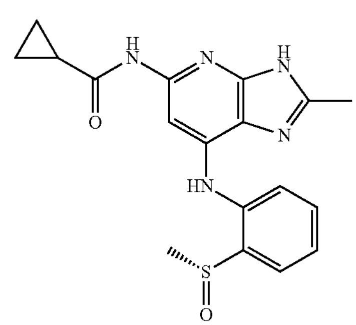 [SMILES: Cc1nc2c(Nc3ccccc3[S@@](C)=O)cc(NC(=O)C3CC3)nc2[nH]1] |

TABLE-continued

Exemplary Compounds

| Compound | Structure |
|---|---|
| I-443 | 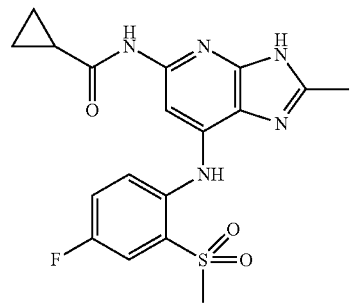 [SMILES: Cc1nc2c(Nc3ccc(F)cc3S(C)(=O)=O)cc(NC(=O)C3CC3)nc2[nH]1] |
| I-444 | 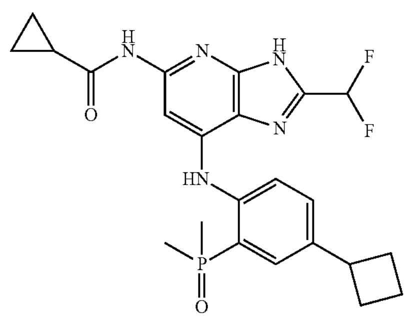 [SMILES: CP(C)(=O)c1cc(C2CCC2)ccc1Nc1cc(NC(=O)C2CC2)nc2[nH]c(C(F)F)nc12] |
| I-445 | 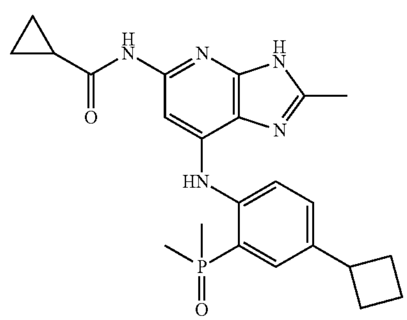 [SMILES: Cc1nc2c(Nc3ccc(C4CCC4)cc3P(C)(C)=O)cc(NC(=O)C3CC3)nc2[nH]1] |
| I-446 | 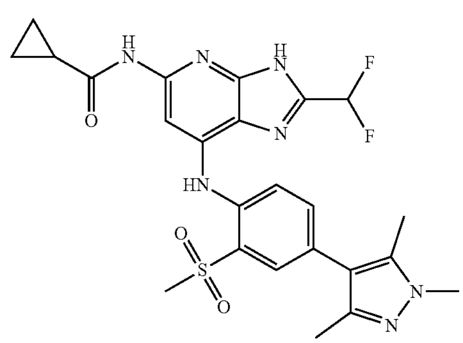 [SMILES: Cc1nn(C)c(C)c1-c1ccc(Nc2cc(NC(=O)C3CC3)nc3[nH]c(C(F)F)nc23)c(S(C)(=O)=O)c1] |

TABLE-continued
Exemplary Compounds
| Compound | Structure |
|---|---|
| I-447 | 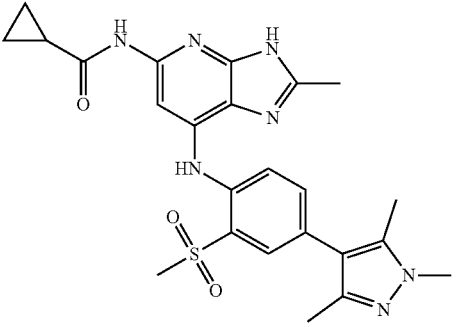 [SMILES: Cc1nc2c(Nc3ccc(-c4c(C)nn(C)c4C)cc3S(C)(=O)=O)cc(NC(=O)C3CC3)nc2[nH]1] |
| I-448 | 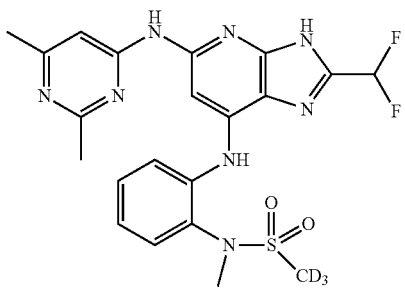 [SMILES: [2H]C([2H])([2H])S(=O)(=O)N(C)c1ccccc1Nc1cc(Nc2cc(C)nc(C)n2)nc2[nH]c(C(F)F)nc12] |
| I-449 | 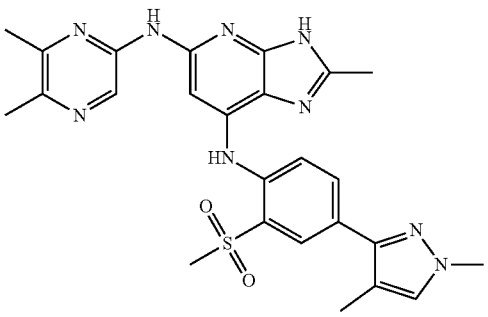 |
| I-450 | 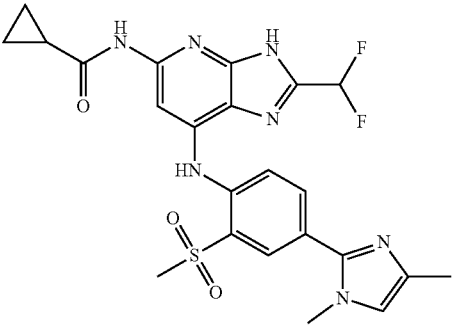 [SMILES: Cc1cn(C)c(-c2ccc(Nc3cc(NC(=O)C4CC4)nc4[nH]c(C(F)F)nc34)c(S(C)(=O)=O)c2)n1] |

TABLE-continued

Exemplary Compounds

| Compound | Structure |
|---|---|
| I-451 | 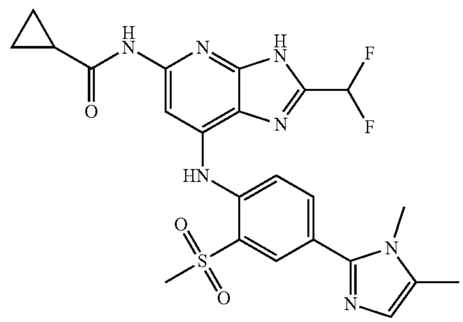 [SMILES: Cc1cnc(-c2ccc(Nc3cc(NC(=O)C4CC4)nc4[nH]c(C(F)F)nc34)c(S(C)(=O)=O)c2)n1C] |
| I-452 | 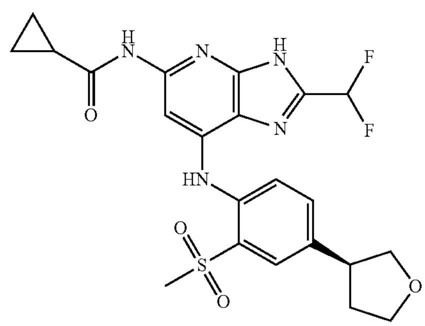 [SMILES: CS(=O)(=O)c1cc([C@@H]2CCOC2)ccc1Nc1cc(NC(=O)C2CC2)nc2[nH]c(C(F)F)nc12] |
| I-453 | 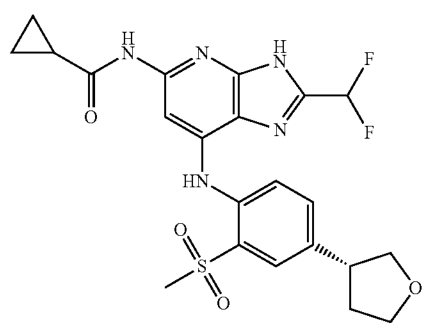 [SMILES: CS(=O)(=O)c1cc([C@H]2CCOC2)ccc1Nc1cc(NC(=O)C2CC2)nc2[nH]c(C(F)F)nc12] |
| I-454 | 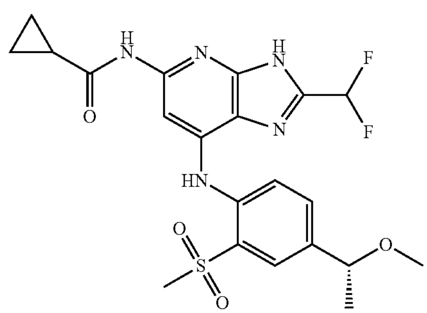 |

TABLE-continued
Exemplary Compounds
| Compound | Structure |
|---|---|
| I-455 | 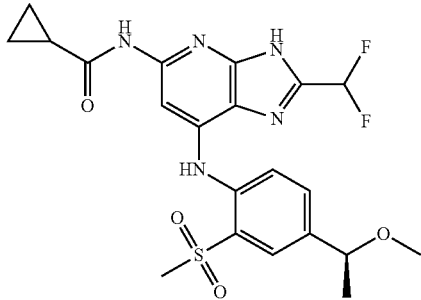 [SMILES: CO[C@@H](C)c1ccc(Nc2cc(NC(=O)C3CC3)nc3[nH]c(C(F)F)nc23)c(S(C)(=O)=O)c1] |
| I-456 | 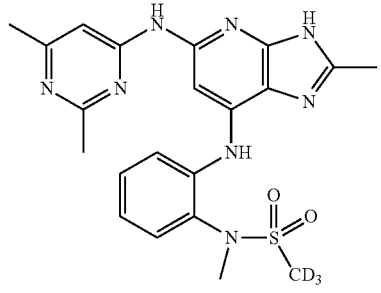 |
| I-457 | 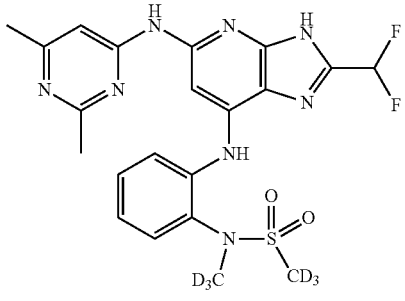 [SMILES: [2H]C([2H])([2H])N(c1ccccc1Nc1cc(Nc2cc(C)nc(C)n2)nc2[nH]c(C(F)F)nc12)S(=O)(=O)C([2H])([2H])[2H]] |
| I-458 | 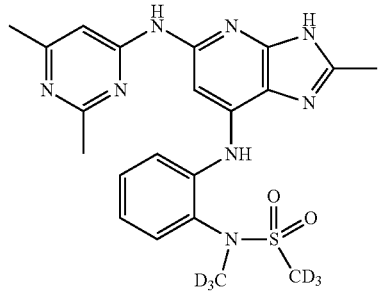 |
| I-459 | 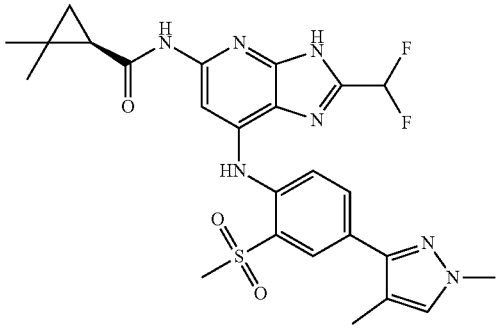 |

TABLE-continued
Exemplary Compounds
| Compound | Structure |
|---|---|
| I-460 | 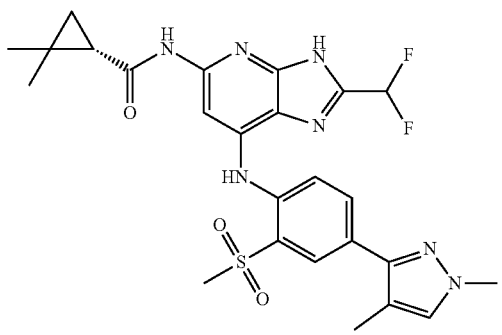 |
| I-461 | 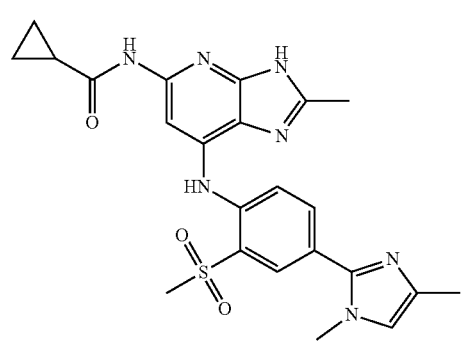 [SMILES: Cc1cn(C)c(-c2ccc(Nc3cc(NC(=O)C4CC4)nc4[nH]c(C)nc34)c(S(C)(=O)=O)c2)n1] |
| I-462 | 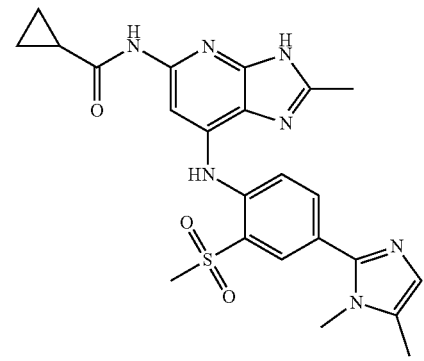 [SMILES: Cc1nc2c(Nc3ccc(-c4ncc(C)n4C)cc3S(C)(=O)=O)cc(NC(=O)C3CC3)nc2[nH]1] |
| I-463 | 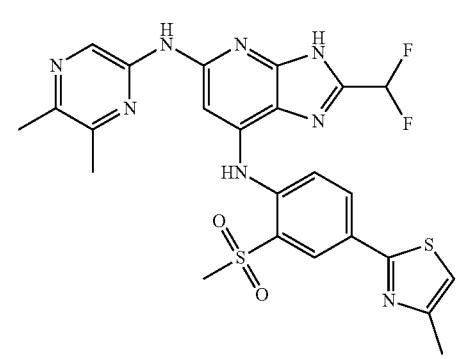 [SMILES: Cc1csc(-c2ccc(Nc3cc(Nc4cnc(C)c(C)n4)nc4[nH]c(C(F)F)nc34)c(S(C)(=O)=O)c2)n1] |

TABLE-continued
Exemplary Compounds
| Compound | Structure |
|---|---|
| I-464 | 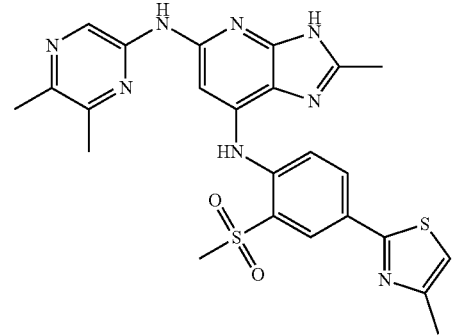 [SMILES: Cc1csc(-c2ccc(Nc3cc(Nc4cnc(C)c(C)n4)nc4[nH]c(C)nc34)c(S(C)(=O)=O)c2)n1] |
| I-465 | 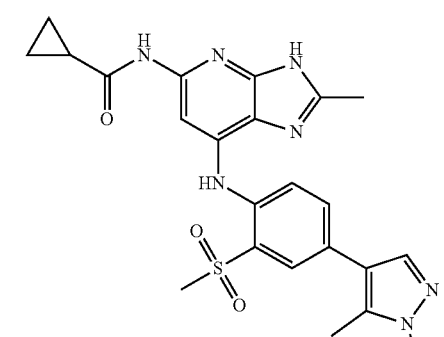 |
| I-466 | 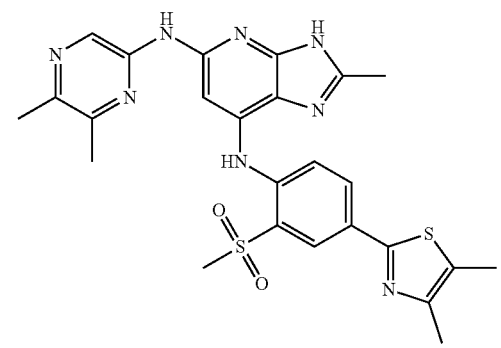 |
| I-467 | 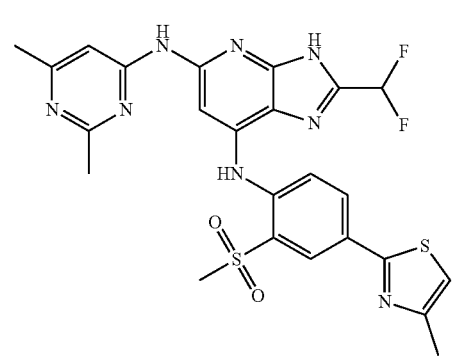 [SMILES: Cc1cc(Nc2cc(Nc3ccc(-c4nc(C)cs4)cc3S(C)(=O)=O)c3nc(C(F)F)[nH]c3n2)nc(C)n1] |

TABLE-continued
Exemplary Compounds
| Compound | Structure |
|---|---|
| I-468 | 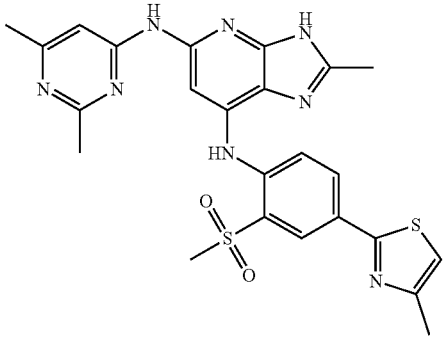 [SMILES: Cc1cc(Nc2cc(Nc3ccc(-c4nc(C)cs4)cc3S(C)(=O)=O)c3nc(C)[nH]c3n2)nc(C)n1] |
| I-469 | 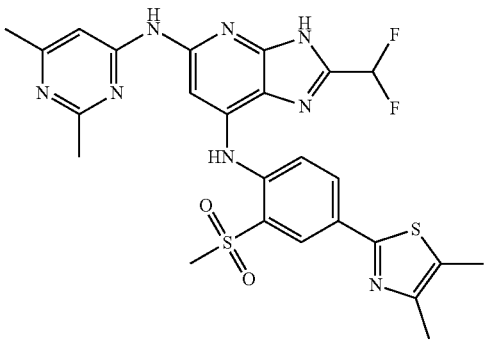 |
| I-470 | 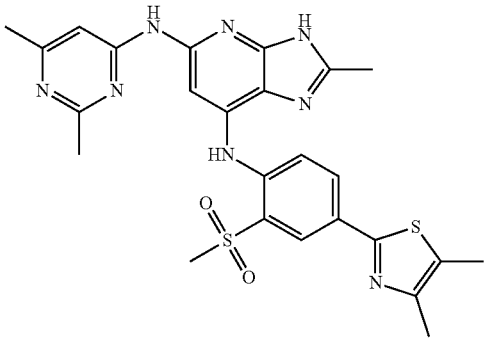 |
| I-471 | 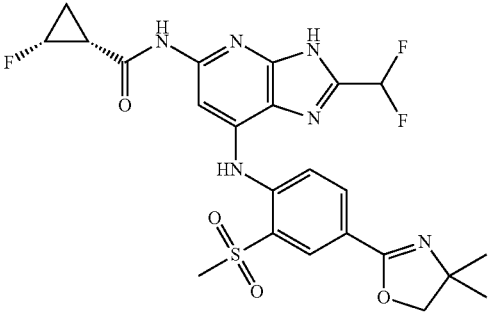 [SMILES: CC1(C)COC(c2ccc(Nc3cc(NC(=O)[C@H]4C[C@H]4F)nc4[nH]c(C(F)F)nc34)c(S(C)(=O)=O)c2)=N1] |

TABLE-continued

Exemplary Compounds

| Compound | Structure |
|---|---|
| I-472 | 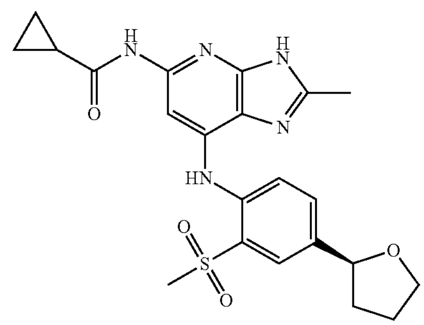 [SMILES: Cc1nc2c(Nc3ccc([C@@H]4CCCO4)cc3S(C)(=O)=O)cc(NC(=O)C3CC3)nc2[nH]1] |
| I-473 | 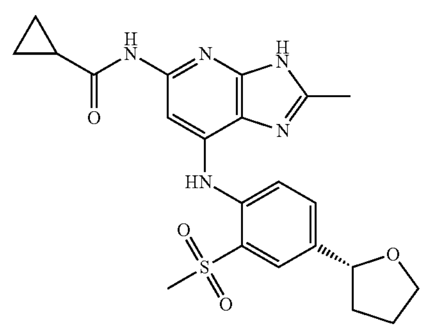 |
| I-474 | 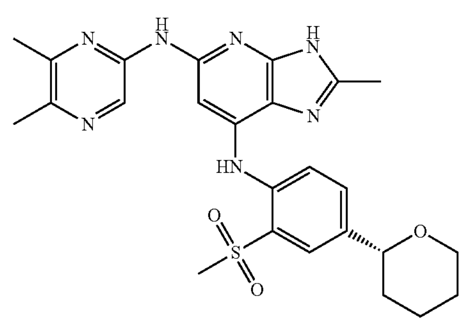 |
| I-475 | 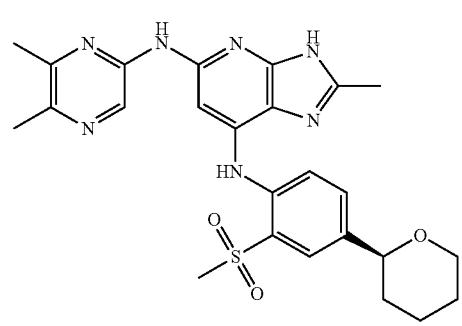 [SMILES: Cc1nc2c(Nc3ccc([C@@H]4CCCCO4)cc3S(C)(=O)=O)cc(Nc3cnc(C)c(C)n3)nc2[nH]1] |

| Compound | Structure |
|---|---|
| I-476 | 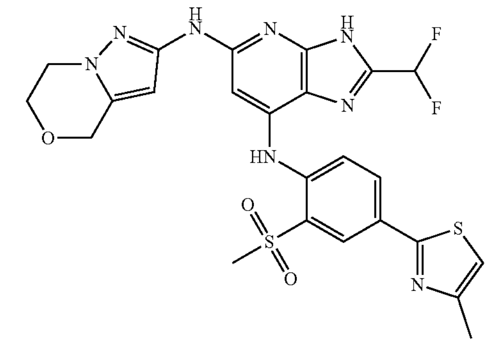 [SMILES: Cc1csc(-c2ccc(Nc3cc(Nc4cc5n(n4)CCOC5)nc4[nH]c(C(F)F)nc34)c(S(C)(=O)=O)c2)n1] |
| I-477 | 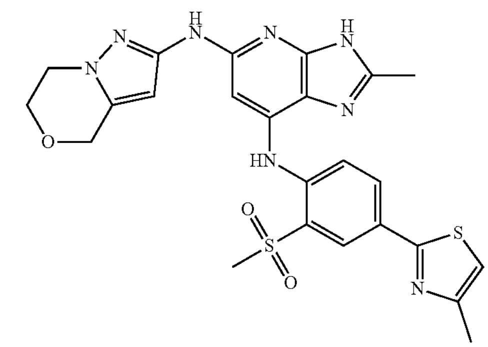 [SMILES: Cc1csc(-c2ccc(Nc3cc(Nc4cc5n(n4)CCOC5)nc4[nH]c(C)nc34)c(S(C)(=O)=O)c2)n1] |
| I-478 | 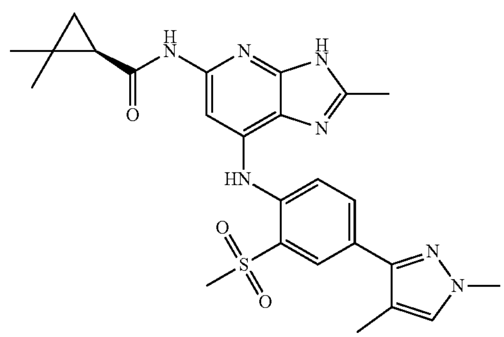 |
| I-479 | 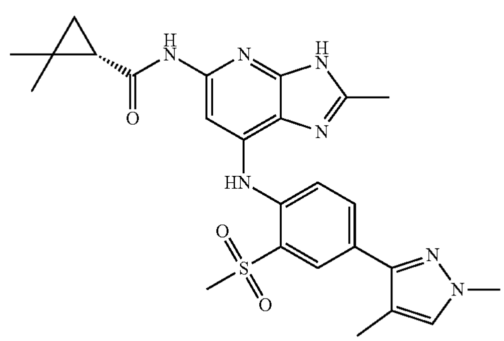 |

TABLE-continued
Exemplary Compounds
| Compound | Structure |
|---|---|
| I-480 | 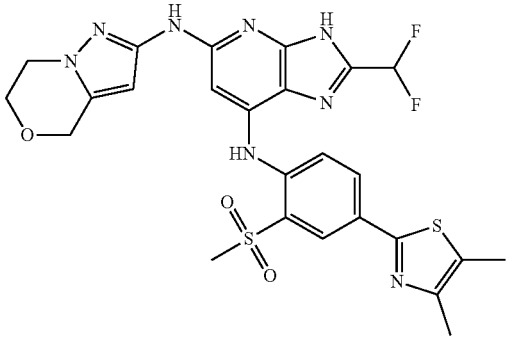 [SMILES: Cc1nc(-c2ccc(Nc3cc(Nc4cc5n(n4)CCOC5)nc4[nH]c(C(F)F)nc34)c(S(C)(=O)=O)c2)sc1C] |
| I-481 | 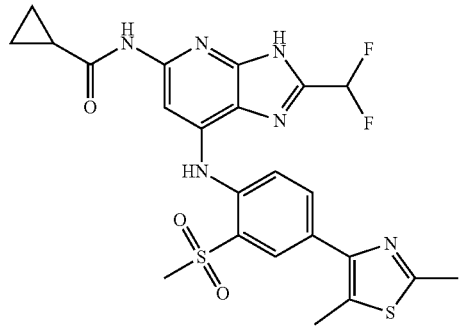 [SMILES: Cc1nc(-c2ccc(Nc3cc(NC(=O)C4CC4)nc4[nH]c(C(F)F)nc34)c(S(C)(=O)=O)c2)c(C)s1] |
| I-482 | 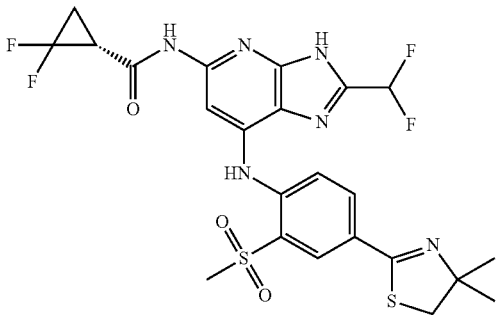 [SMILES: CC1(C)CSC(c2ccc(Nc3cc(NC(=O)[C@H]4CC4(F)F)nc4[nH]c(C(F)F)nc34)c(S(C)(=O)=O)c2)=N1] |
| I-483 | 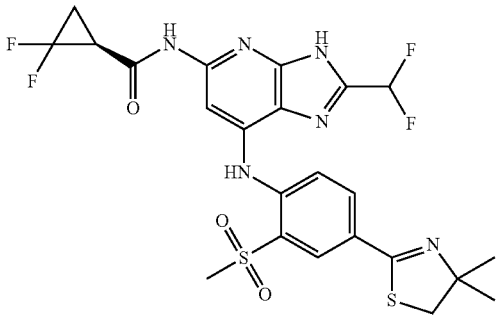 [SMILES: CC1(C)CSC(c2ccc(Nc3cc(NC(=O)[C@@H]4CC4(F)F)nc4[nH]c(C(F)F)nc34)c(S(C)(=O)=O)c2)=N1] |

TABLE-continued

Exemplary Compounds

| Compound | Structure |
|---|---|
| I-484 | 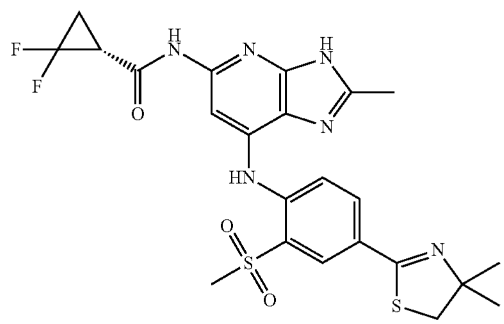 |
| I-485 | 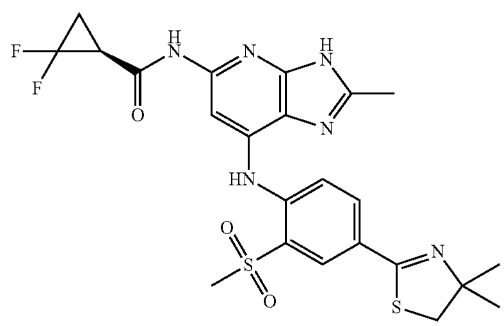 [SMILES: Cc1nc2c(Nc3ccc(C4=NC(C)(C)CS4)cc3S(C)(=O)=O)cc(NC(=O)[C@@H]3CC3(F)F)nc2[nH]1] |
| I-486 | 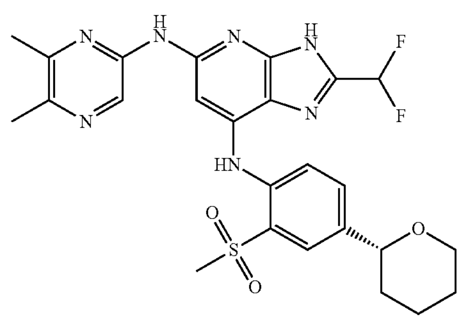 [SMILES: Cc1ncc(Nc2cc(Nc3ccc([C@H]4CCCCO4)cc3S(C)(=O)=O)c3nc(C(F)F)[nH]c3n2)nc1C] |
| I-487 | 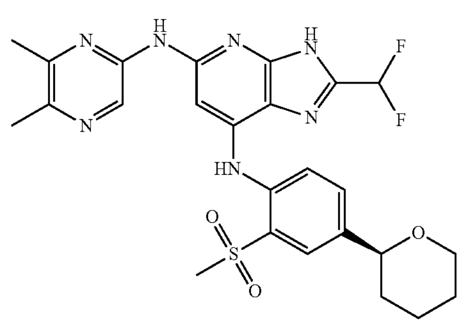 [SMILES: Cc1ncc(Nc2cc(Nc3ccc([C@@H]4CCCCO4)cc3S(C)(=O)=O)c3nc(C(F)F)[nH]c3n2)nc1C] |

TABLE-continued
Exemplary Compounds
| Compound | Structure |
|---|---|
| I-488 | 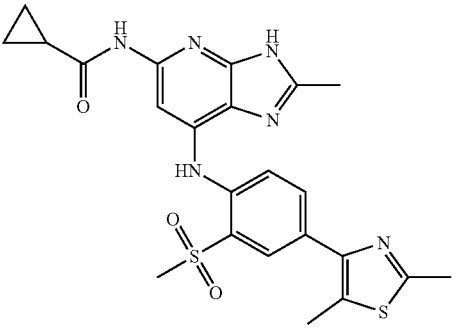 [SMILES: Cc1nc2c(Nc3ccc(-c4nc(C)sc4C)cc3S(C)(=O)=O)cc(NC(=O)C3CC3)nc2[nH]1] |
| I-489 | 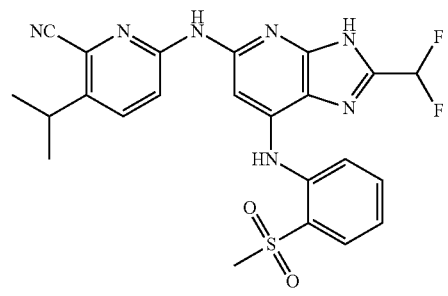 [SMILES: CC(C)c1ccc(Nc2cc(Nc3ccccc3S(C)(=O)=O)c3nc(C(F)F)[nH]c3n2)nc1C#N] |
| I-490 | 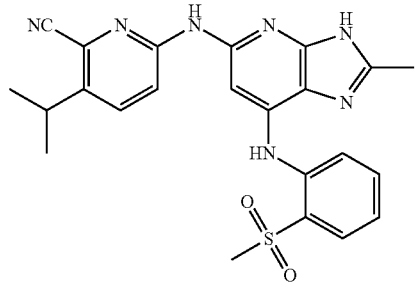 [SMILES: Cc1nc2c(Nc3ccccc3S(C)(=O)=O)cc(Nc3ccc(C(C)C)c(C#N)n3)nc2[nH]1] |
| I-491 | 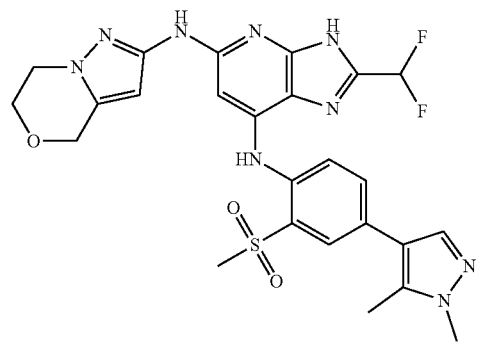 [SMILES: Cc1c(-c2ccc(Nc3cc(Nc4cc5n(n4)CCOC5)nc4[nH]c(C(F)F)nc34)c(S(C)(=O)=O)c2)cnn1C] |

TABLE-continued

Exemplary Compounds

| Compound | Structure |
|---|---|
| I-492 | 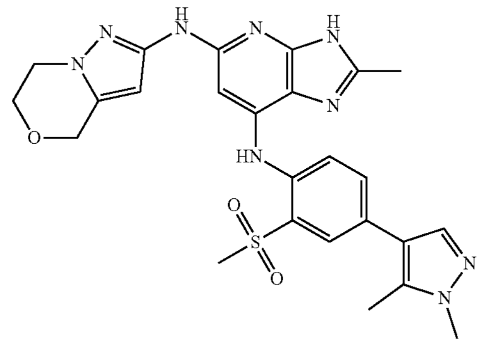 [SMILES: Cc1nc2c(Nc3ccc(-c4cnn(C)c4C)cc3S(C)(=O)=O)cc(Nc3cc4n(n3)CCOC4)nc2[nH]1] |
| I-493 | 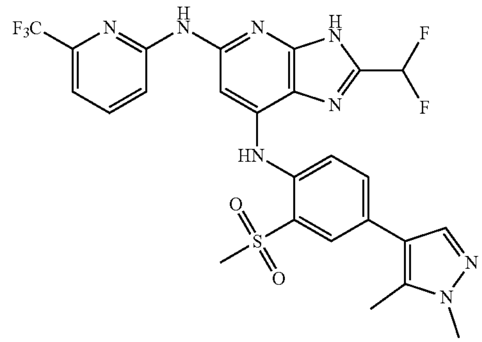 [SMILES: Cc1c(-c2ccc(Nc3cc(Nc4cccc(C(F)(F)F)n4)nc4[nH]c(C(F)F)nc34)c(S(C)(=O)=O)c2)cnn1C] |
| I-494 | 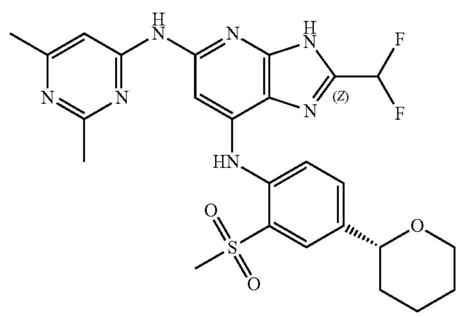 [SMILES: Cc1cc(Nc2cc(Nc3ccc([C@H]4CCCCO4)cc3S(C)(=O)=O)c3nc(C(F)F)[nH]c3n2)nc(C)n1] |
| I-495 | 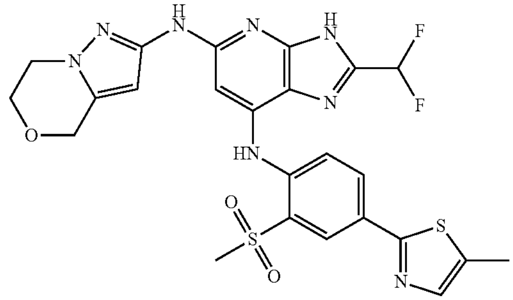 [SMILES: Cc1cnc(-c2ccc(Nc3cc(Nc4cc5n(n4)CCOC5)nc4[nH]c(C(F)F)nc34)c(S(C)(=O)=O)c2)s1] |

TABLE-continued
Exemplary Compounds
| Compound | Structure |
|---|---|
| I-496 | 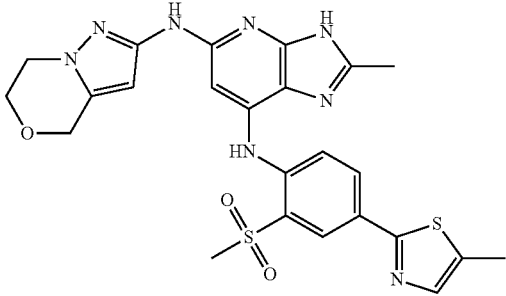 [SMILES: Cc1nc2c(Nc3ccc(-c4ncc(C)s4)cc3S(C)(=O)=O)cc(Nc3cc4n(n3)CCOC4)nc2[nH]1] |
| I-497 | 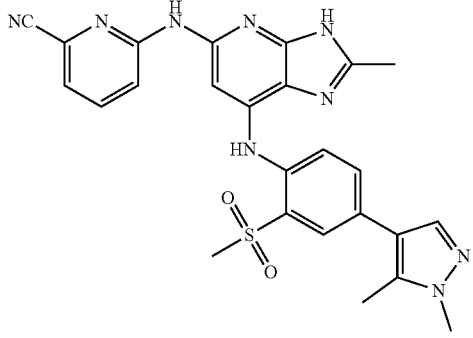 [SMILES: Cc1nc2c(Nc3ccc(-c4cnn(C)c4C)cc3S(C)(=O)=O)cc(Nc3cccc(C#N)n3)nc2[nH]1] |
| I-498 | 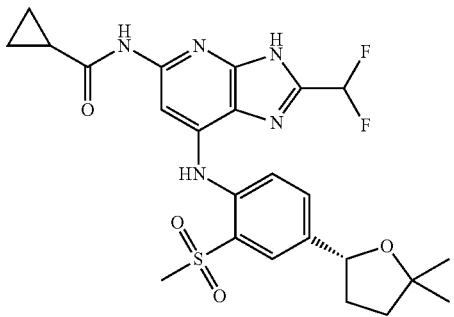 |
| I-499 | 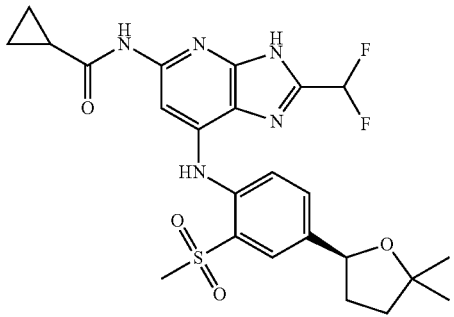 [SMILES: CC1(C)CC[C@@H](c2ccc(Nc3cc(NC(=O)C4CC4)nc4[nH]c(C(F)F)nc34)c(S(C)(=O)=O)c2)O1] |

TABLE-continued
Exemplary Compounds
| Compound | Structure |
|---|---|
| I-500 | 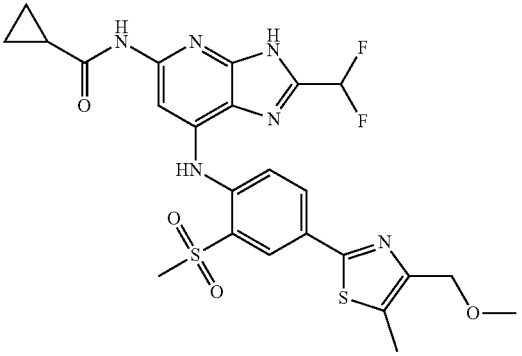 [SMILES: COCc1nc(-c2ccc(Nc3cc(NC(=O)C4CC4)nc4[nH]c(C(F)F)nc34)c(S(C)(=O)=O)c2)sc1C] |
| I-501 | 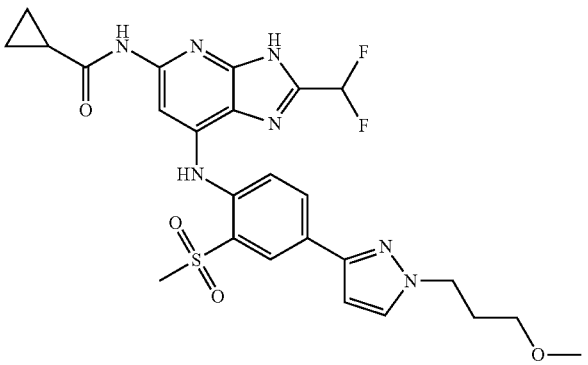 [SMILES: COCCCn1ccc(-c2ccc(Nc3cc(NC(=O)C4CC4)nc4[nH]c(C(F)F)nc34)c(S(C)(=O)=O)c2)n1] |
| I-502 | 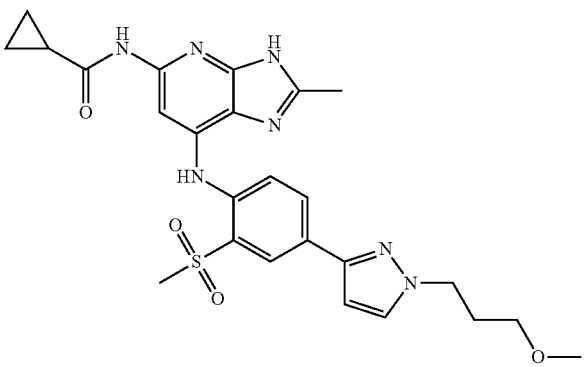 [SMILES: COCCCn1ccc(-c2ccc(Nc3cc(NC(=O)C4CC4)nc4[nH]c(C)nc34)c(S(C)(=O)=O)c2)n1] |
| I-503 | 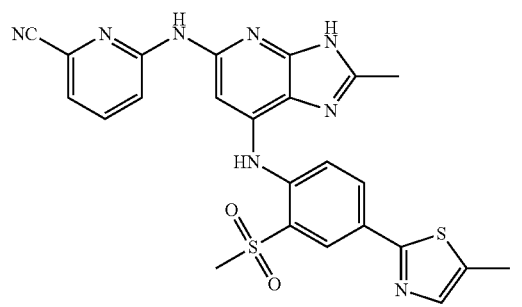 [SMILES: Cc1nc2c(Nc3ccc(-c4ncc(C)s4)cc3S(C)(=O)=O)cc(Nc3cccc(C#N)n3)nc2[nH]1] |

TABLE-continued

Exemplary Compounds

| Compound | Structure |
|---|---|
| I-504 | 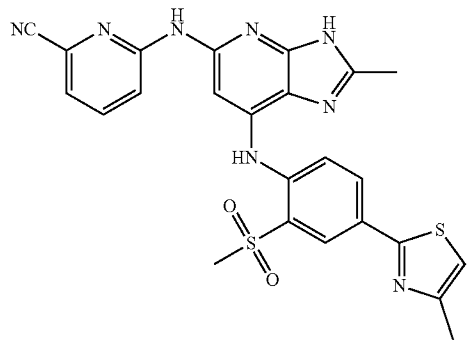 [SMILES: Cc1csc(-c2ccc(Nc3cc(Nc4cccc(C#N)n4)nc4[nH]c(C)nc34)c(S(C)(=O)=O)c2)n1] |
| I-505 | 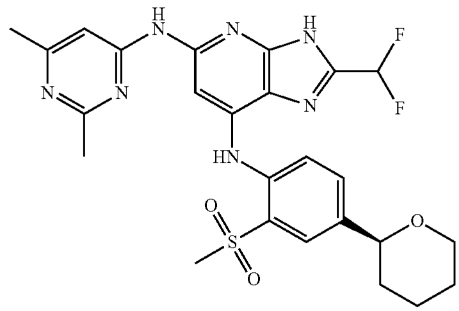 [SMILES: Cc1cc(Nc2cc(Nc3ccc([C@@H]4CCCCO4)cc3S(C)(=O)=O)c3nc(C(F)F)[nH]c3n2)nc(C)n1] |
| I-506 | 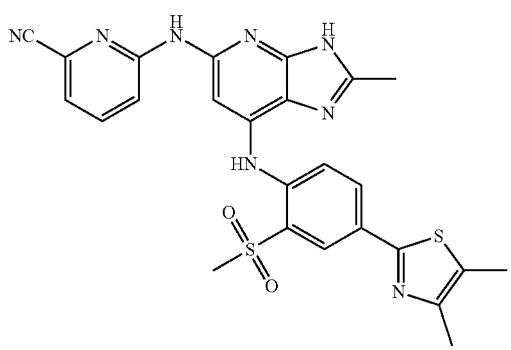 [SMILES: Cc1nc2c(Nc3ccc(-c4nc(C)c(C)s4)cc3S(C)(=O)=O)cc(Nc3cccc(C#N)n3)nc2[nH]1] |
| I-507 | 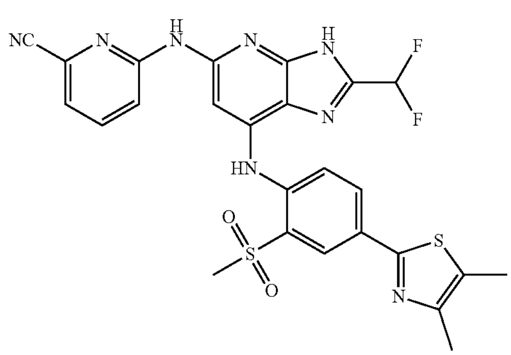 [SMILES: Cc1nc(-c2ccc(Nc3cc(Nc4cccc(C#N)n4)nc4[nH]c(C(F)F)nc34)c(S(C)(=O)=O)c2)sc1C] |

TABLE-continued
Exemplary Compounds
| Compound | Structure |
|---|---|
| I-508 | 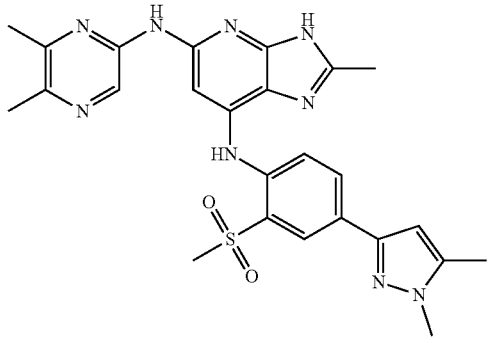 |
| I-509 | 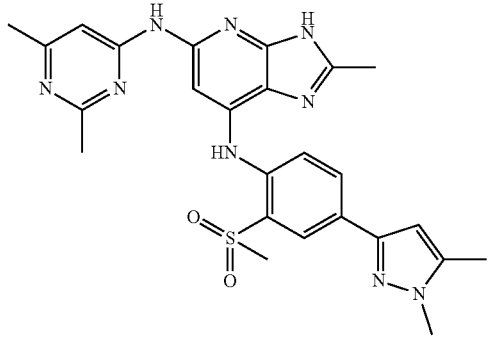 |
| I-510 | 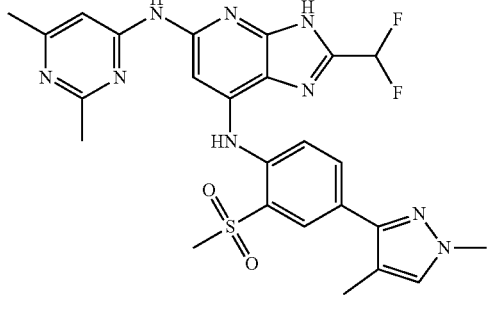 |
| I-511 | 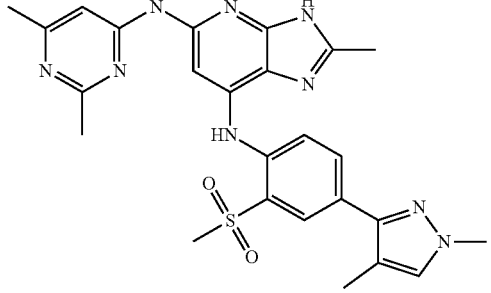 |

| Compound | Structure |
|---|---|
| I-512 | 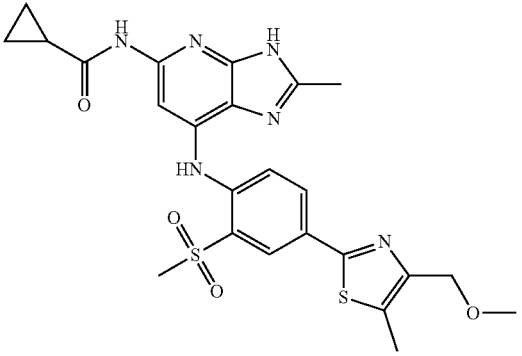 [SMILES: COCc1nc(-c2ccc(Nc3cc(NC(=O)C4CC4)nc4[nH]c(C)nc34)c(S(C)(=O)=O)c2)sc1C] |
| I-513 | 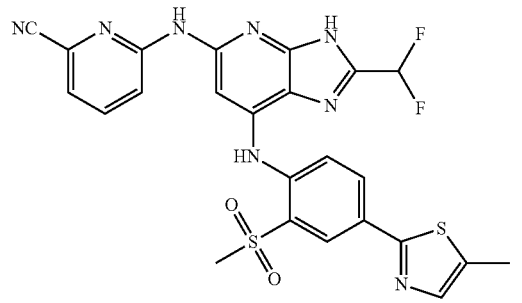 [SMILES: Cc1cnc(-c2ccc(Nc3cc(Nc4cccc(C#N)n4)nc4[nH]c(C(F)F)nc34)c(S(C)(=O)=O)c2)s1] |
| I-514 | 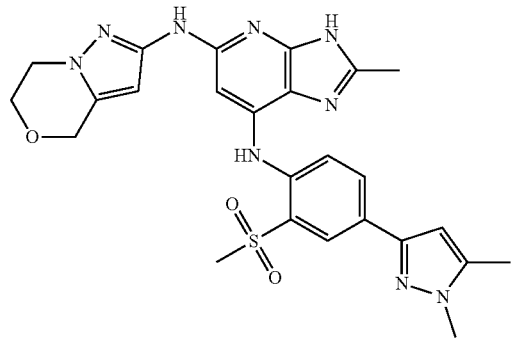 [SMILES: Cc1nc2c(Nc3ccc(-c4cc(C)n(C)n4)cc3S(C)(=O)=O)cc(Nc3cc4n(n3)CCOC4)nc2[nH]1] |
| I-515 | 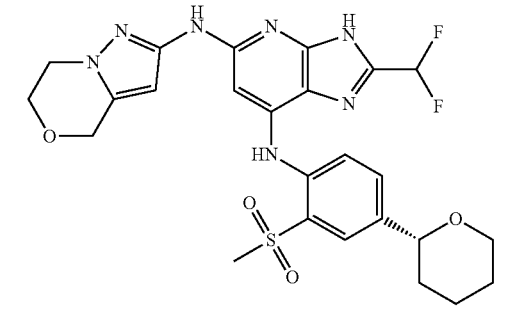 [SMILES: CS(=O)(=O)c1cc([C@H]2CCCCO2)ccc1Nc1cc(Nc2cc3n(n2)CCOC3)nc2[nH]c(C(F)F)nc12] |

TABLE-continued
Exemplary Compounds
| Compound | Structure |
|---|---|
| I-516 | 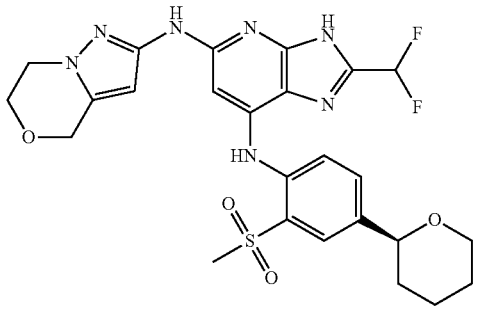 [SMILES: CS(=O)(=O)c1cc([C@@H]2CCCCO2)ccc1Nc1cc(Nc2cc3n(n2)CCOC3)nc2[nH]c(C(F)F)nc12] |
| I-517 | 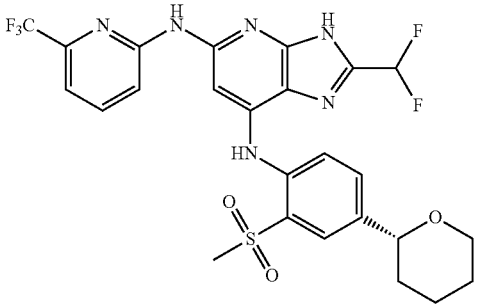 |
| I-518 | 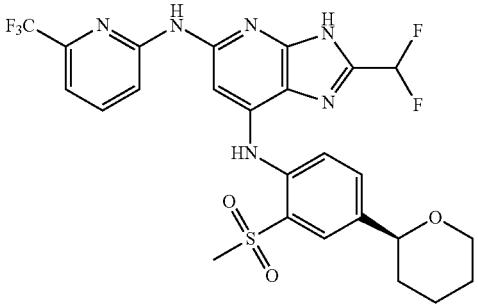 [SMILES: CS(=O)(=O)c1cc([C@@H]2CCCCO2)ccc1Nc1cc(Nc2cccc(C(F)(F)F)n2)nc2[nH]c(C(F)F)nc12] |
| I-519 | 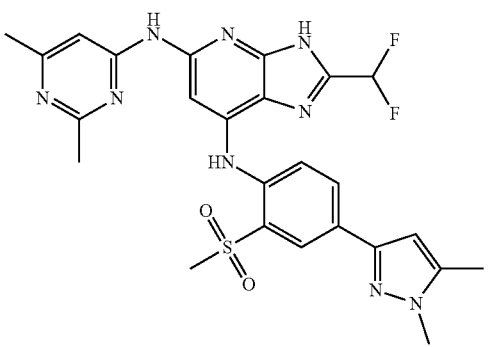 |

TABLE-continued

Exemplary Compounds

| Compound | Structure |
|---|---|
| I-520 | 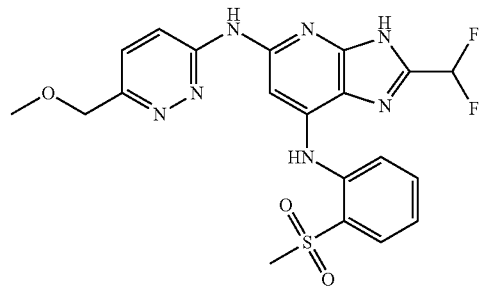 [SMILES: COCc1ccc(Nc2cc(Nc3ccccc3S(C)(=O)=O)c3nc(C(F)F)[nH]c3n2)nn1] |
| I-521 | 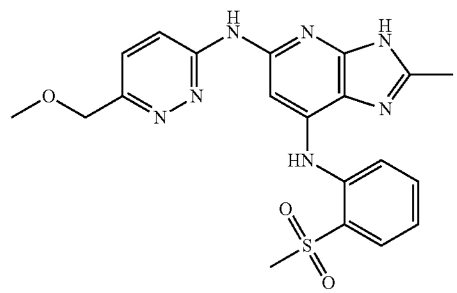 |
| I-522 | 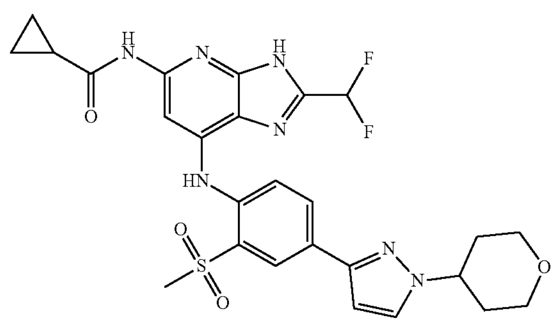 [SMILES: CS(=O)(=O)c1cc(-c2ccn(C3CCOCC3)n2)ccc1Nc1cc(NC(=O)C2CC2)nc2[nH]c(C(F)F)nc12] |
| I-523 | 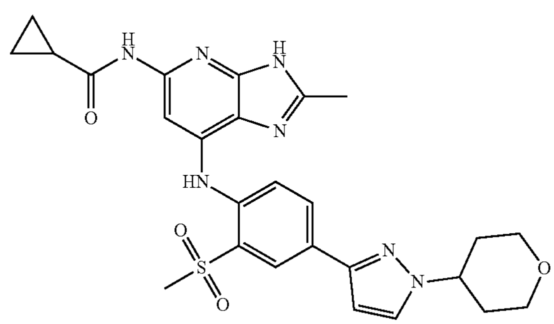 [SMILES: Cc1nc2c(Nc3ccc(-c4ccn(C5CCOCC5)n4)cc3S(C)(=O)=O)cc(NC(=O)C3CC3)nc2[nH]1] |
| I-524 | 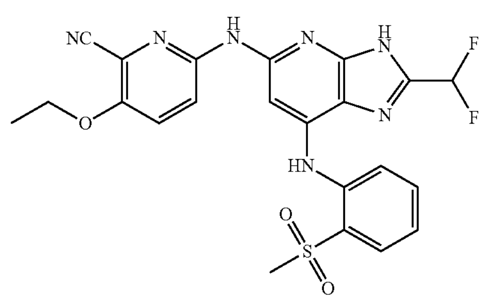 [SMILES: CCOc1ccc(Nc2cc(Nc3ccccc3S(C)(=O)=O)c3nc(C(F)F)[nH]c3n2)nc1C#N] |

TABLE-continued

Exemplary Compounds

| Compound | Structure |
|---|---|
| I-525 | 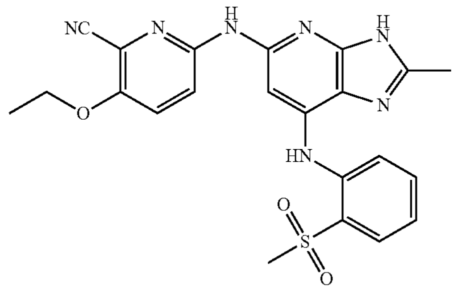 [SMILES: CCOc1ccc(Nc2cc(Nc3ccccc3S(C)(=O)=O)c3nc(C)[nH]c3n2)nc1C#N] |
| I-526 | 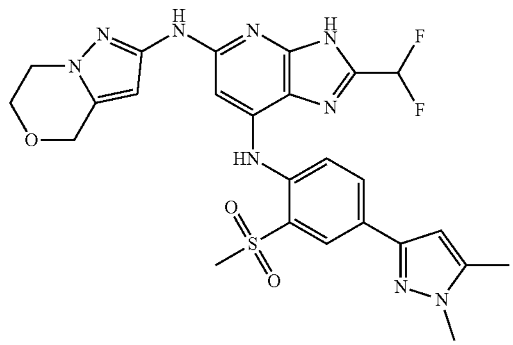 [SMILES: Cc1cc(-c2ccc(Nc3cc(Nc4cc5n(n4)CCOC5)nc4[nH]c(C(F)F)nc34)c(S(C)(=O)=O)c2)nn1C] |
| I-527 | 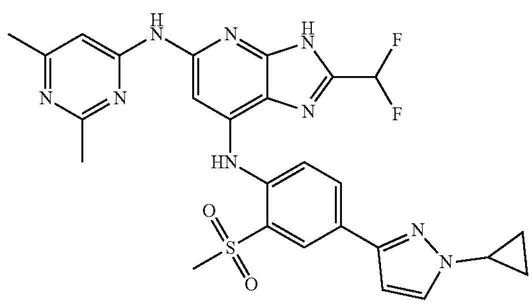 [SMILES: Cc1cc(Nc2cc(Nc3ccc(-c4ccn(C5CC5)n4)cc3S(C)(=O)=O)c3nc(C(F)F)[nH]c3n2)nc(C)n1] |
| I-528 | 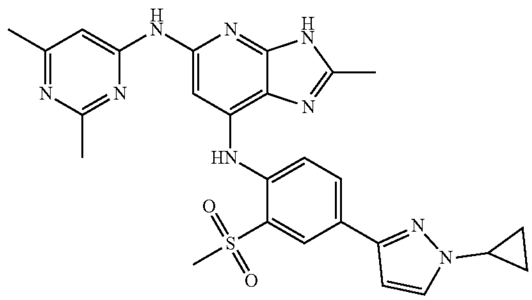 [SMILES: Cc1cc(Nc2cc(Nc3ccc(-c4ccn(C5CC5)n4)cc3S(C)(=O)=O)c3nc(C)[nH]c3n2)nc(C)n1] |
| I-529 | 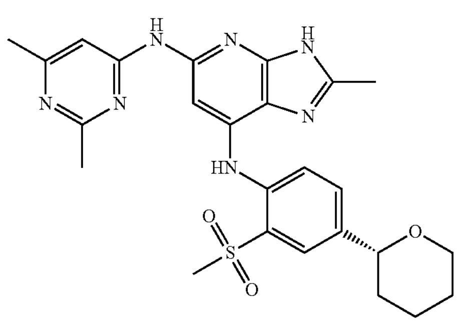 |

TABLE-continued
Exemplary Compounds
| Compound | Structure |
|---|---|
| I-530 | 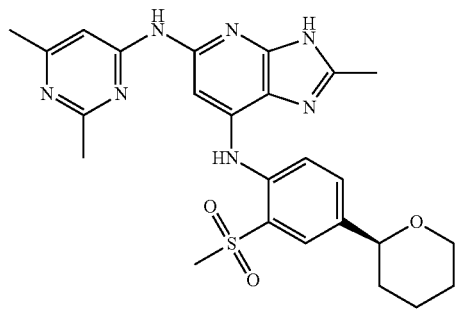 [SMILES: Cc1cc(Nc2cc(Nc3ccc([C@@H]4CCCCO4)cc3S(C)(=O)=O)c3nc(C)[nH]c3n2)nc(C)n1] |
| I-531 | 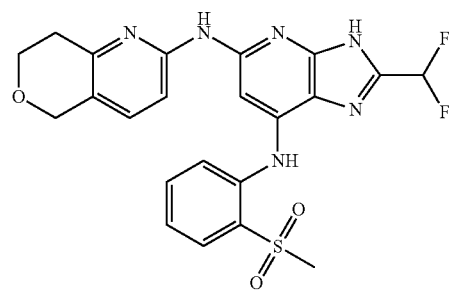 [SMILES: CS(=O)(=O)c1ccccc1Nc1cc(Nc2ccc3c(n2)CCOC3)nc2[nH]c(C(F)F)nc12] |
| I-532 | 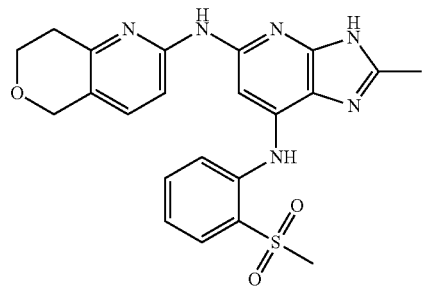 [SMILES: Cc1nc2c(Nc3ccccc3S(C)(=O)=O)cc(Nc3ccc4c(n3)CCOC4)nc2[nH]1] |
| I-533 | 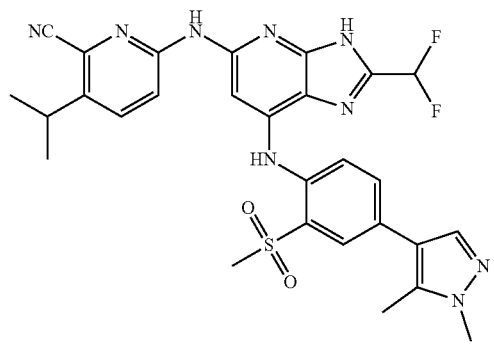 [SMILES: Cc1c(-c2ccc(Nc3cc(Nc4ccc(C(C)C)c(C#N)n4)nc4[nH]c(C(F)F)nc34)c(S(C)(=O)=O)c2)cnn1C] |

TABLE-continued
Exemplary Compounds
| Compound | Structure |
|---|---|
| I-534 | 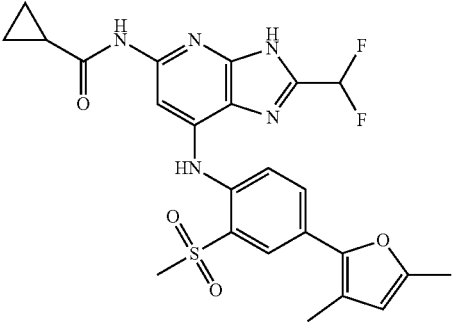 [SMILES: Cc1cc(C)c(-c2ccc(Nc3cc(NC(=O)C4CC4)nc4[nH]c(C(F)F)nc34)c(S(C)(=O)=O)c2)o1] |
| I-536 | 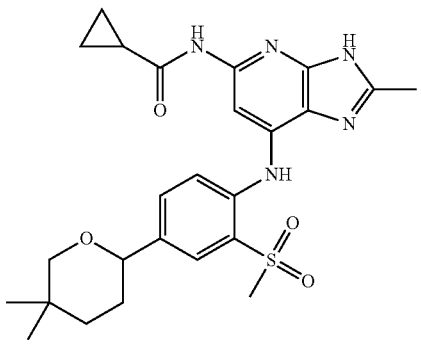 |
| I-537 | 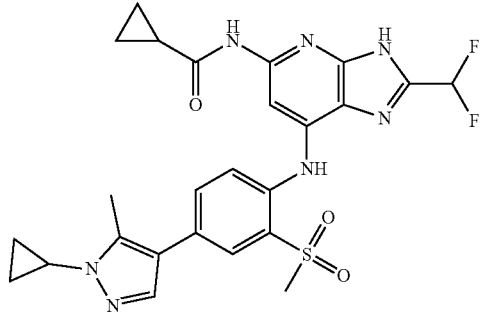 [SMILES: Cc1c(-c2ccc(Nc3cc(NC(=O)C4CC4)nc4[nH]c(C(F)F)nc34)c(S(C)(=O)=O)c2)cnn1C1CC1] |
| I-538 | 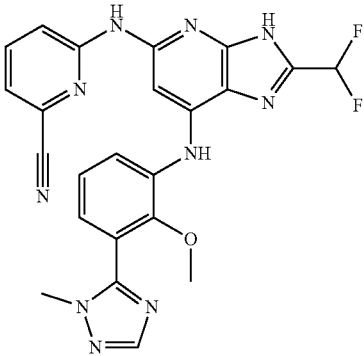 [SMILES: COc1c(Nc2cc(Nc3cccc(C#N)n3)nc3[nH]c(C(F)F)nc23)cccc1-c1ncnn1C] |

TABLE-continued

Exemplary Compounds

| Compound | Structure |
|---|---|
| I-539 | 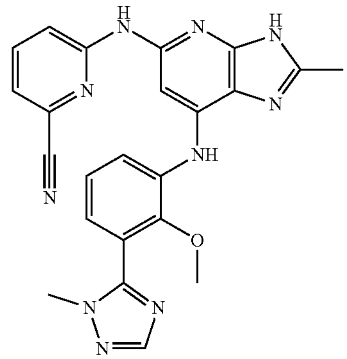 [SMILES: COc1c(Nc2cc(Nc3cccc(C#N)n3)nc3[nH]c(C)nc23)cccc1-c1ncnn1C] |
| I-540 | 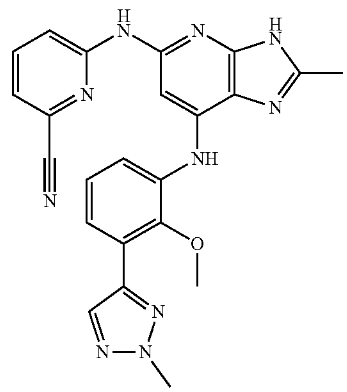 [SMILES: COc1c(Nc2cc(Nc3cccc(C#N)n3)nc3[nH]c(C)nc23)cccc1-c1cnn(C)n1] |
| I-541 | 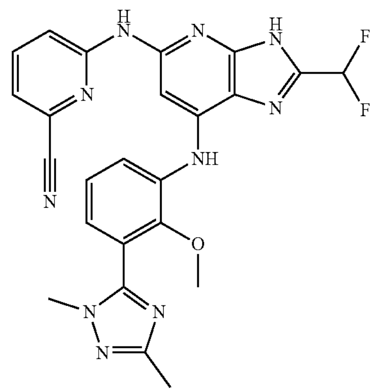 [SMILES: COc1c(Nc2cc(Nc3cccc(C#N)n3)nc3[nH]c(C(F)F)nc23)cccc1-c1nc(C)nn1C] |
| I-542 | 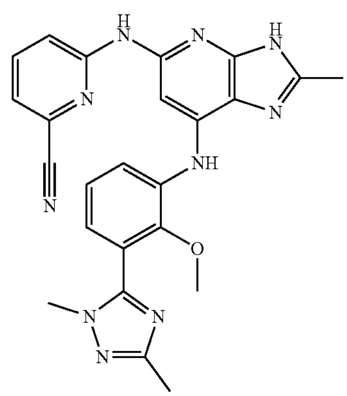 [SMILES: COc1c(Nc2cc(Nc3cccc(C#N)n3)nc3[nH]c(C)nc23)cccc1-c1nc(C)nn1C] |

TABLE-continued

Exemplary Compounds

| Compound | Structure |
|---|---|
| I-543 | 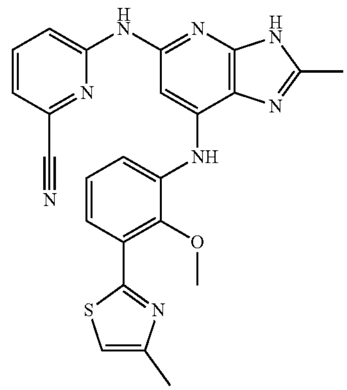 [SMILES: COc1c(Nc2cc(Nc3cccc(C#N)n3)nc3[nH]c(C)nc23)cccc1-c1nc(C)cs1] |
| I-544 | 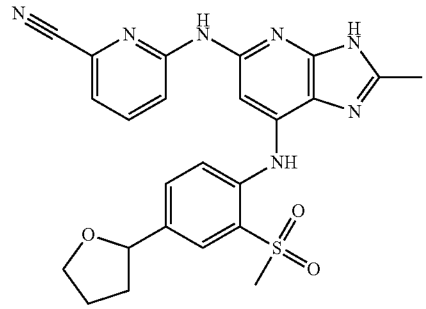 [SMILES: Cc1nc2c(Nc3ccc(C4CCCO4)cc3S(C)(=O)=O)cc(Nc3cccc(C#N)n3)nc2[nH]1] |
| I-545 | 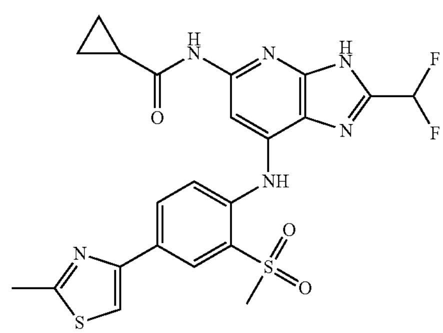 [SMILES: Cc1nc(-c2ccc(Nc3cc(NC(=O)C4CC4)nc4[nH]c(C(F)F)nc34)c(S(C)(=O)=O)c2)cs1] |
| I-546 | 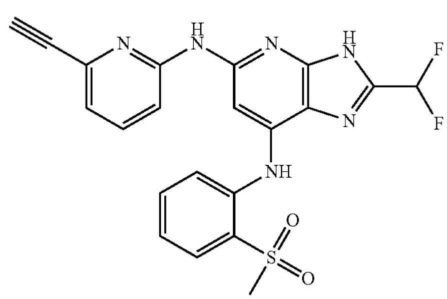 [SMILES: C#Cc1cccc(Nc2cc(Nc3ccccc3S(C)(=O)=O)c3nc(C(F)F)[nH]c3n2)n1] |

US 11,396,508 B2
TABLE-continued
Exemplary Compounds
| Compound | Structure |
|---|---|
| I-547 | 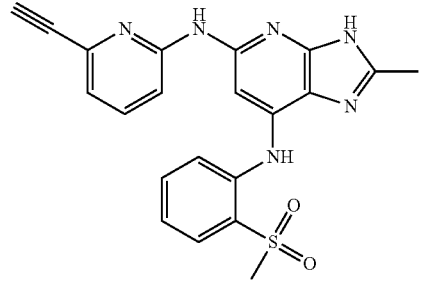 [SMILES: C#Cc1cccc(Nc2cc(Nc3ccccc3S(C)(=O)=O)c3nc(C)[nH]c3n2)n1] |
| I-548 | 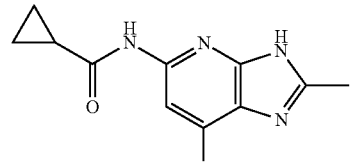 |
| I-549 | 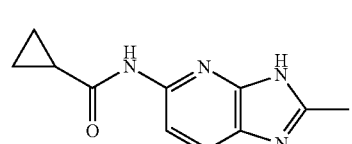 |
| I-550 | 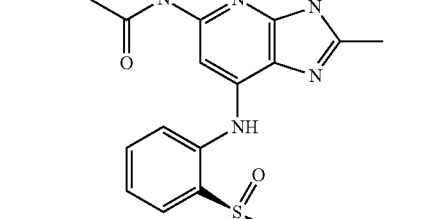 |

TABLE-continued
Exemplary Compounds
| Compound | Structure |
|---|---|
| I-551 | 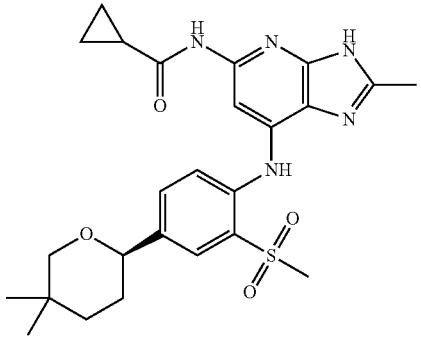 |
| I-552 | 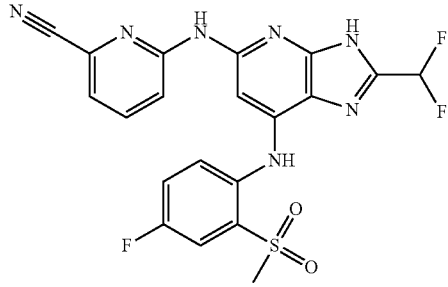 [SMILES: CS(=O)(=O)c1cc(F)ccc1Nc1cc(Nc2cccc(C#N)n2)nc2[nH]c(C(F)F)nc12] |
| I-553 | 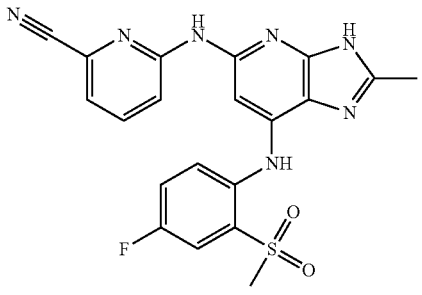 [SMILES: Cc1nc2c(Nc3ccc(F)cc3S(C)(=O)=O)cc(Nc3cccc(C#N)n3)nc2[nH]1] |
| I-554 | 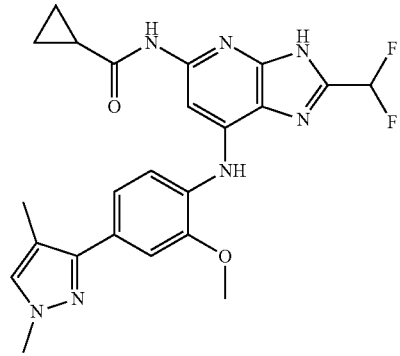 [SMILES: COc1cc(-c2nn(C)cc2C)ccc1Nc1cc(NC(=O)C2CC2)nc2[nH]c(C(F)F)nc12] |

TABLE-continued
Exemplary Compounds
| Compound | Structure |
|---|---|
| I-555 | 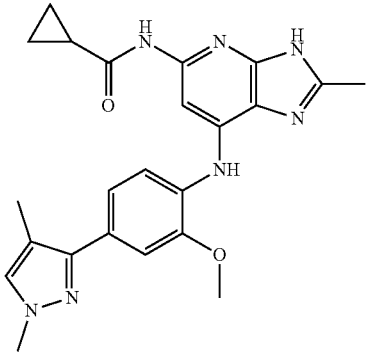 [SMILES: COc1cc(-c2nn(C)cc2C)ccc1Nc1cc(NC(=O)C2CC2)nc2[nH]c(C)nc12] |
| I-556 | 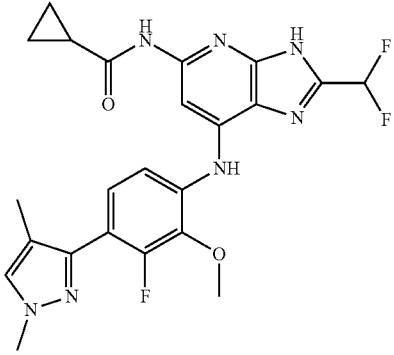 [SMILES: COc1c(Nc2cc(NC(=O)C3CC3)nc3[nH]c(C(F)F)nc23)ccc(-c2nn(C)cc2C)c1F] |
| I-557 | 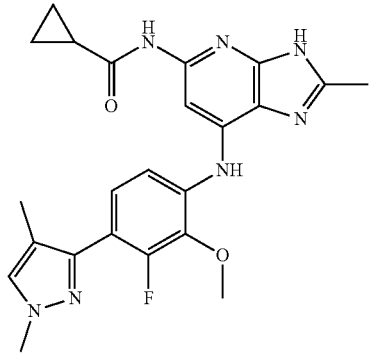 [SMILES: COc1c(Nc2cc(NC(=O)C3CC3)nc3[nH]c(C)nc23)ccc(-c2nn(C)cc2C)c1F] |
| I-558 | 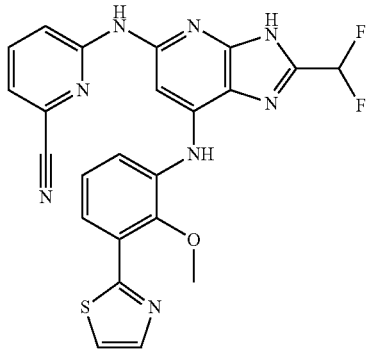 [SMILES: COc1c(Nc2cc(Nc3cccc(C#N)n3)nc3[nH]c(C(F)F)nc23)cccc1-c1nccs1] |

TABLE-continued

Exemplary Compounds

| Compound | Structure |
|---|---|
| I-559 | 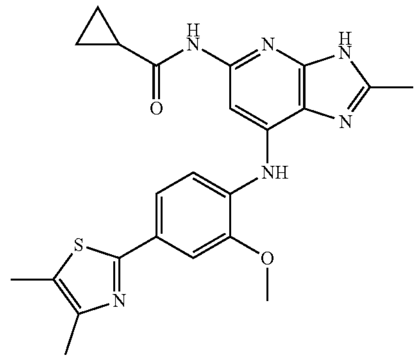 |
| I-560 | 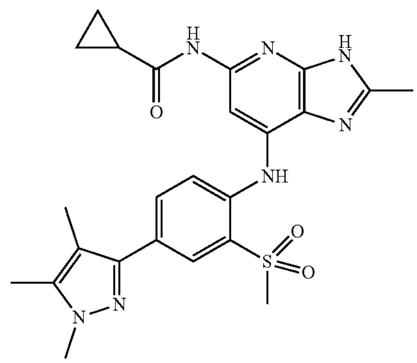 |
| I-561 | 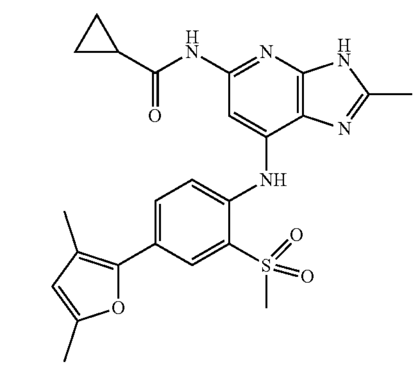 [SMILES: Cc1nc2c(Nc3ccc(-c4oc(C)cc4C)cc3S(C)(=O)=O)cc(NC(=O)C3CC3)nc2[nH]1] |
| I-562 | 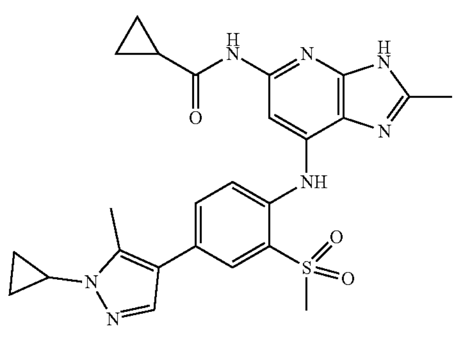 [SMILES: Cc1nc2c(Nc3ccc(-c4cnn(C5CC5)c4C)cc3S(C)(=O)=O)cc(NC(=O)C3CC3)nc2[nH]1] |

TABLE-continued
Exemplary Compounds
| Compound | Structure |
|---|---|
| I-563 | 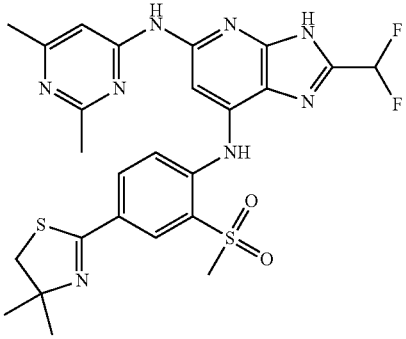 [SMILES: Cc1cc(Nc2cc(Nc3ccc(C4=NC(C)(C)CS4)cc3S(C)(=O)=O)c3nc(C(F)F)[nH]c3n2)nc(C)n1] |
| I-564 | 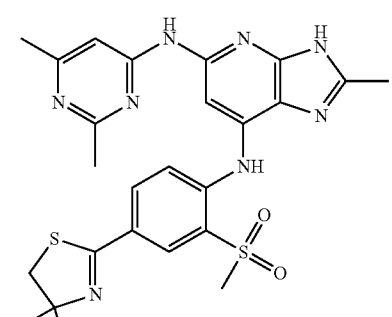 |
| I-565 | 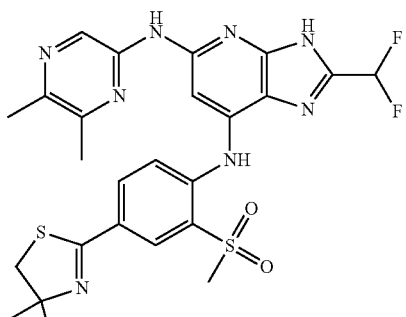 |
| I-566 | 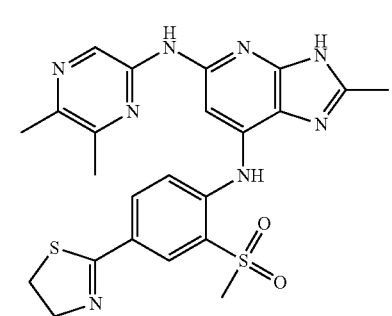 |

TABLE-continued
Exemplary Compounds
| Compound | Structure |
|---|---|
| I-567 | 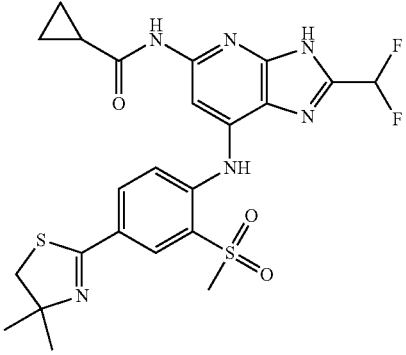 [SMILES: CC1(C)CSC(c2ccc(Nc3cc(NC(=O)C4CC4)nc4[nH]c(C(F)F)nc34)c(S(C)(=O)=O)c2)=N1] |
| I-568 | 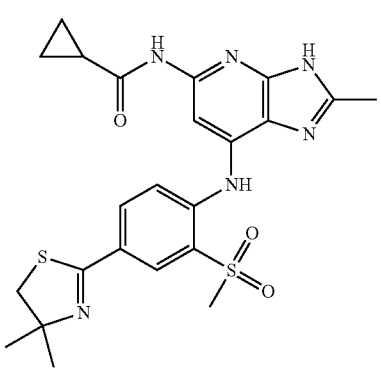 |
| I-569 | 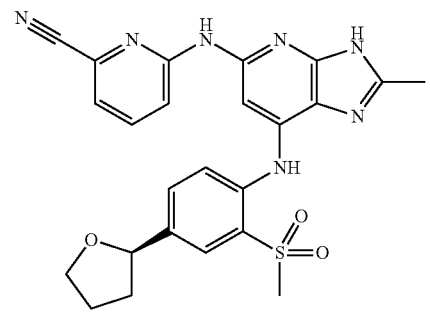 [SMILES: Cc1nc2c(Nc3ccc([C@H]4CCCO4)cc3S(C)(=O)=O)cc(Nc3cccc(C#N)n3)nc2[nH]1] |
| I-570 | 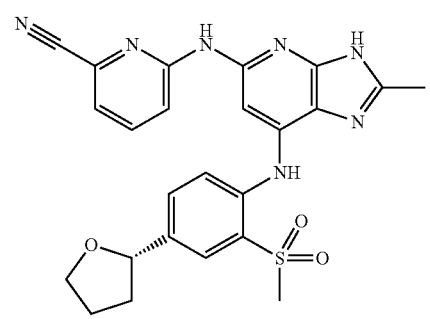 [SMILES: Cc1nc2c(Nc3ccc([C@@H]4CCCO4)cc3S(C)(=O)=O)cc(Nc3cccc(C#N)n3)nc2[nH]1] |

TABLE-continued

Exemplary Compounds

| Compound | Structure |
|---|---|
| I-571 | 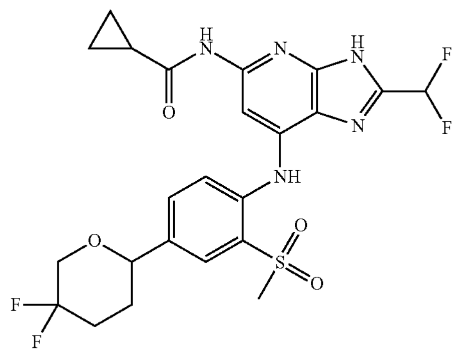 [SMILES: CS(=O)(=O)c1cc(C2CCC(F)(F)CO2)ccc1Nc1cc(NC(=O)C2CC2)nc2[nH]c(C(F)F)nc12] |
| I-572 | 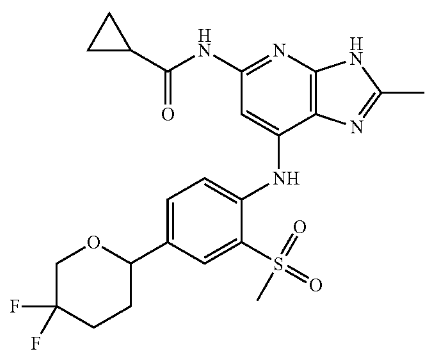 [SMILES: Cc1nc2c(Nc3ccc(C4CCC(F)(F)CO4)cc3S(C)(=O)=O)cc(NC(=O)C3CC3)nc2[nH]1] |
| I-573 | 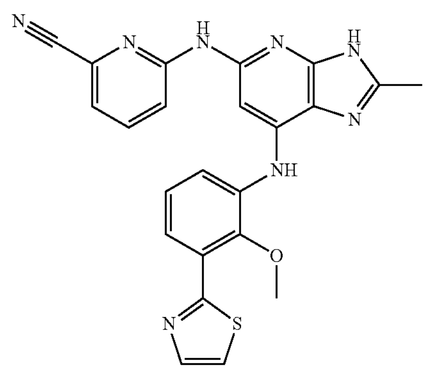 [SMILES: COc1c(Nc2cc(Nc3cccc(C#N)n3)nc3[nH]c(C)nc23)cccc1-c1nccs1] |
| I-574 | 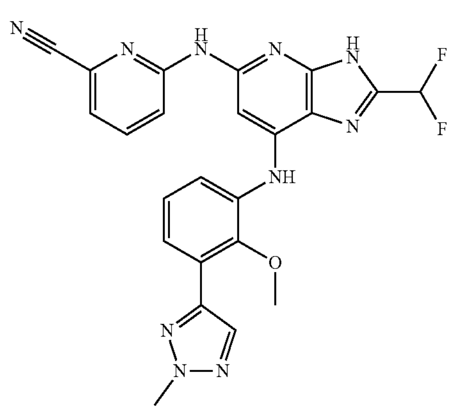 [SMILES: COc1c(Nc2cc(Nc3cccc(C#N)n3)nc3[nH]c(C(F)F)nc23)cccc1-c1cnn(C)n1] |

TABLE-continued
Exemplary Compounds
| Compound | Structure |
|---|---|
| I-575 | 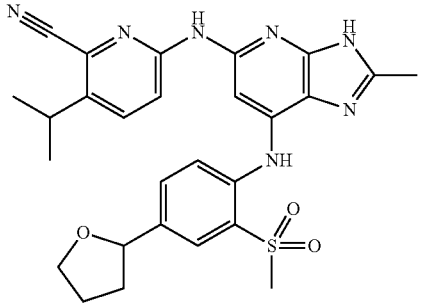 [SMILES: Cc1nc2c(Nc3ccc(C4CCCO4)cc3S(C)(=O)=O)cc(Nc3ccc(C(C)C)c(C#N)n3)nc2[nH]1] |
| I-576 | 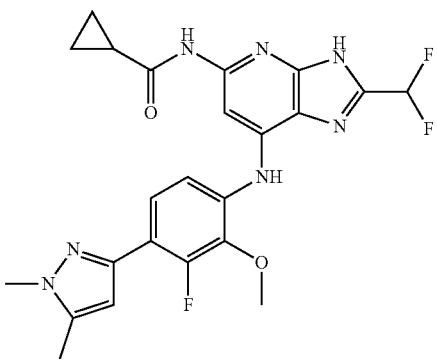 [SMILES: COc1c(Nc2cc(NC(=O)C3CC3)nc3[nH]c(C(F)F)nc23)ccc(-c2cc(C)n(C)n2)c1F] |
| I-577 | 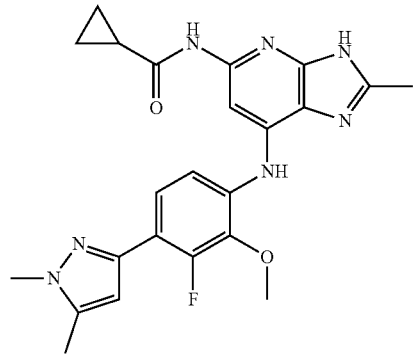 |
| I-578 | 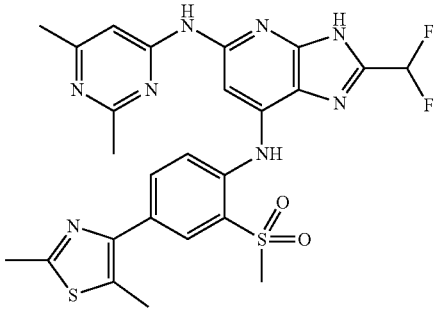 [SMILES: Cc1cc(Nc2cc(Nc3ccc(-c4nc(C)sc4C)cc3S(C)(=O)=O)c3nc(C(F)F)[nH]c3n2)nc(C)n1] |

TABLE-continued
Exemplary Compounds
| Compound | Structure |
|---|---|
| I-579 | 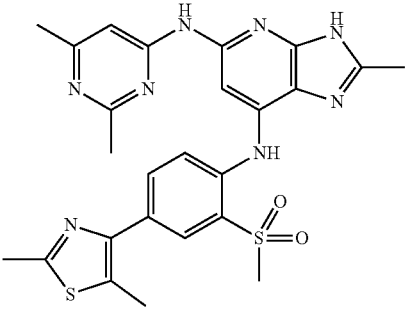 |
| I-580 | 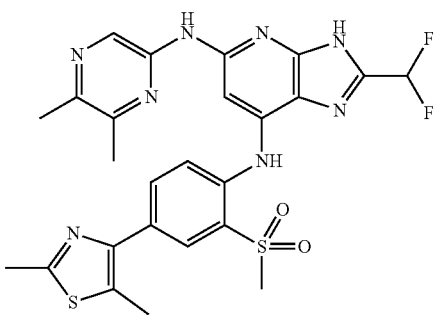 [SMILES: Cc1nc(-c2ccc(Nc3cc(Nc4cnc(C)c(C)n4)nc4[nH]c(C(F)F)nc34)c(S(C)(=O)=O)c2)c(C)s1] |
| I-581 | 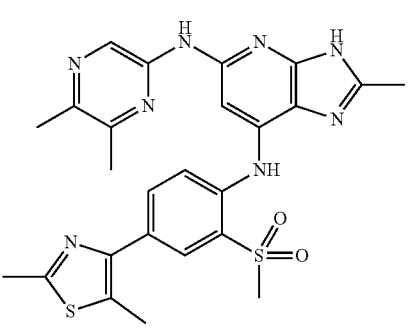 |
| I-582 | 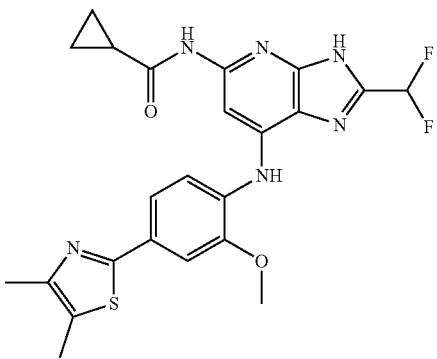 [SMILES: COc1cc(-c2nc(C)c(C)s2)ccc1Nc1cc(NC(=O)C2CC2)nc2[nH]c(C(F)F)nc12] |

TABLE-continued
Exemplary Compounds
| Compound | Structure |
|---|---|
| I-583 | 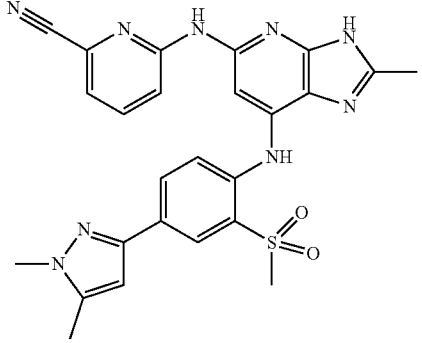 [SMILES: Cc1nc2c(Nc3ccc(-c4cc(C)n(C)n4)cc3S(C)(=O)=O)cc(Nc3cccc(C#N)n3)nc2[nH]1] |
| I-584 | 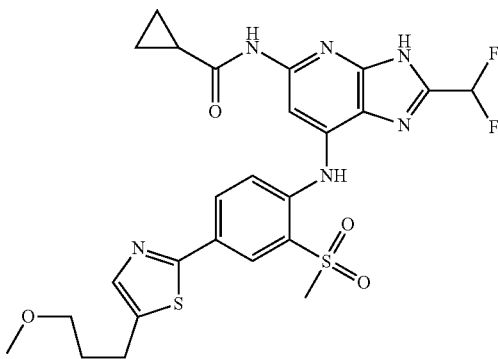 [SMILES: COCCCc1cnc(-c2ccc(Nc3cc(NC(=O)C4CC4)nc4[nH]c(C(F)F)nc34)c(S(C)(=O)=O)c2)s1] |
| I-585 | 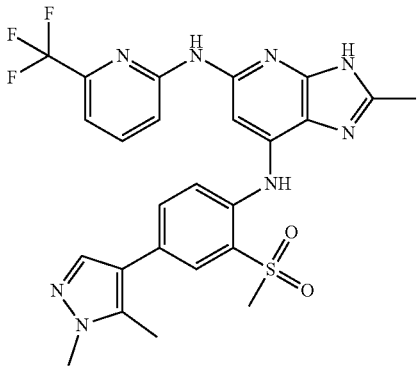 [SMILES: Cc1nc2c(Nc3ccc(-c4cnn(C)c4C)cc3S(C)(=O)=O)cc(Nc3cccc(C(F)(F)F)n3)nc2[nH]1] |
| I-586 | 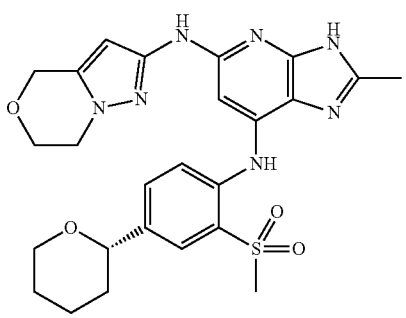 [SMILES: Cc1nc2c(Nc3ccc([C@@H]4CCCCO4)cc3S(C)(=O)=O)cc(Nc3cc4n(n3)CCOC4)nc2[nH]1] |

TABLE-continued
Exemplary Compounds
| Compound | Structure |
|---|---|
| I-587 | 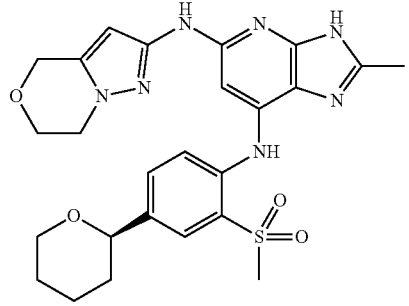 [SMILES: Cc1nc2c(Nc3ccc([C@H]4CCCCO4)cc3S(C)(=O)=O)cc(Nc3cc4n(n3)CCOC4)nc2[nH]1] |
| I-588 | 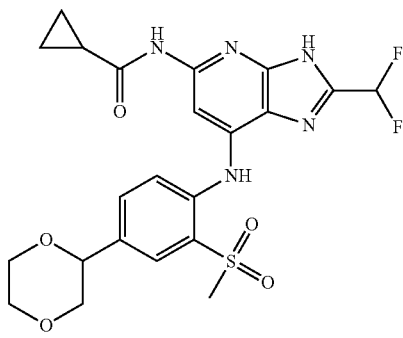 [SMILES: CS(=O)(=O)c1cc(C2COCCO2)ccc1Nc1cc(NC(=O)C2CC2)nc2[nH]c(C(F)F)nc12] |
| I-589 | 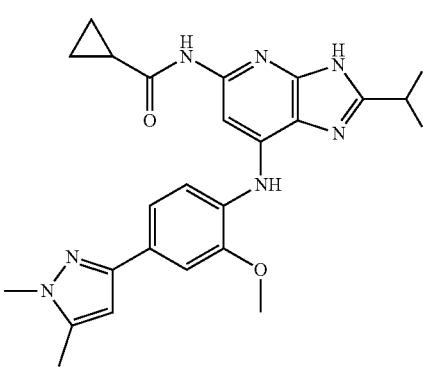 |
| I-590 | 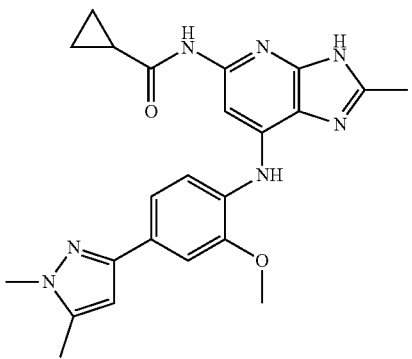 |

TABLE-continued
Exemplary Compounds
| Compound | Structure |
|---|---|
| I-591 | 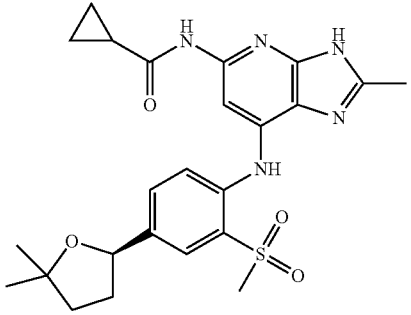 |
| I-592 | 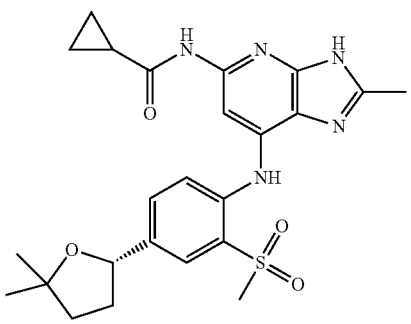 |
| I-593 | 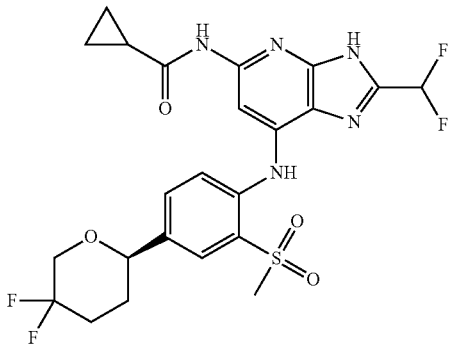 [SMILES: CS(=O)(=O)c1cc([C@H]2CCC(F)(F)CO2)ccc1Nc1cc(NC(=O)C2CC2)nc2[nH]c(C(F)F)nc12] |
| I-594 | 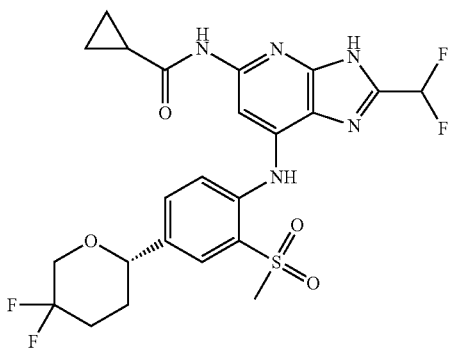 [SMILES: CS(=O)(=O)c1cc([C@@H]2CCC(F)(F)CO2)ccc1Nc1cc(NC(=O)C2CC2)nc2[nH]c(C(F)F)nc12] |

TABLE-continued

Exemplary Compounds

| Compound | Structure |
|---|---|
| I-595 | 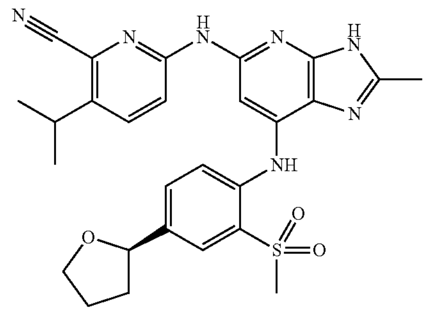 [SMILES: Cc1nc2c(Nc3ccc([C@H]4CCCO4)cc3S(C)(=O)=O)cc(Nc3ccc(C(C)C)c(C#N)n3)nc2[nH]1] |
| I-596 | 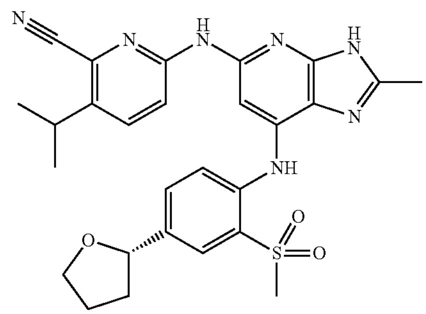 [SMILES: Cc1nc2c(Nc3ccc([C@@H]4CCCO4)cc3S(C)(=O)=O)cc(Nc3ccc(C(C)C)c(C#N)n3)nc2[nH]1] |
| I-597 | 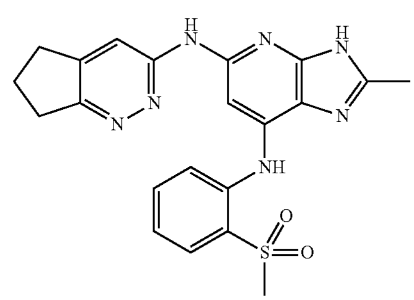 [SMILES: Cc1nc2c(Nc3ccccc3S(C)(=O)=O)cc(Nc3cc4c(nn3)CCC4)nc2[nH]1] |
| I-598 | 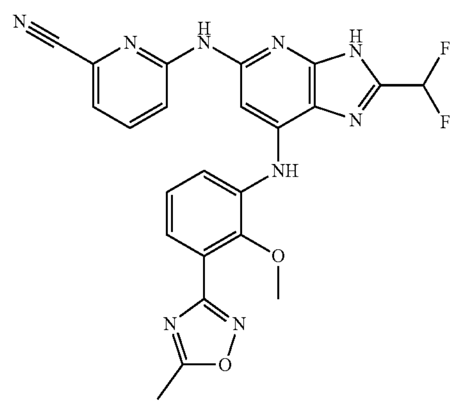 [SMILES: COc1c(Nc2cc(Nc3cccc(C#N)n3)nc3[nH]c(C(F)F)nc23)cccc1-c1noc(C)n1] |

TABLE-continued
Exemplary Compounds
| Compound | Structure |
|---|---|
| I-599 | 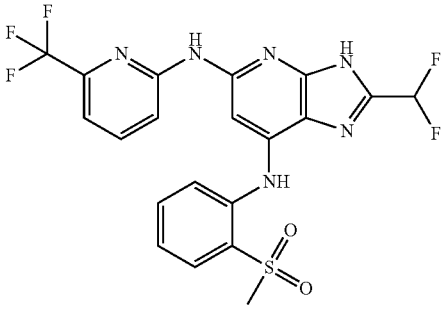 [SMILES: CS(=O)(=O)c1ccccc1Nc1cc(Nc2cccc(C(F)(F)F)n2)nc2[nH]c(C(F)F)nc12] |
| I-600 | 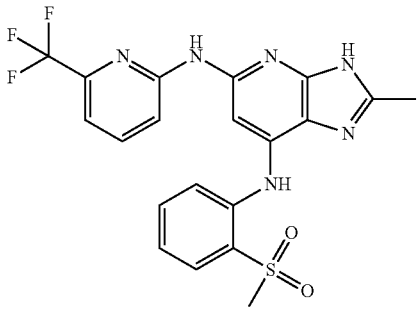 [SMILES: Cc1nc2c(Nc3ccccc3S(C)(=O)=O)cc(Nc3cccc(C(F)(F)F)n3)nc2[nH]1] |
| I-601 | 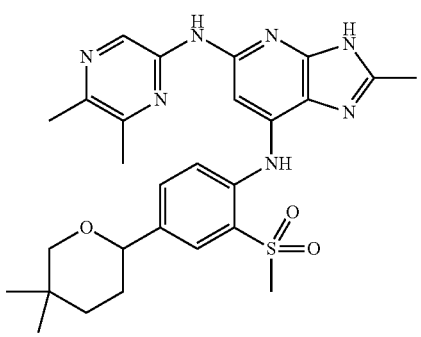 |
| I-602 | 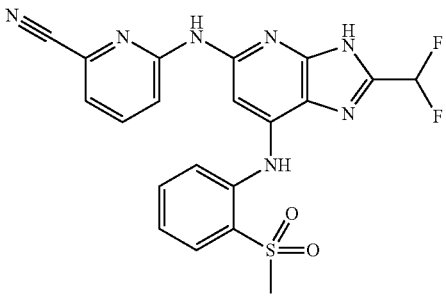 [SMILES: CS(=O)(=O)c1ccccc1Nc1cc(Nc2cccc(C#N)n2)nc2[nH]c(C(F)F)nc12] |

TABLE-continued

Exemplary Compounds

| Compound | Structure |
|---|---|
| I-603 | 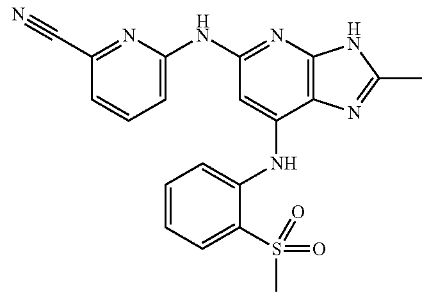 [SMILES: Cc1nc2c(Nc3ccccc3S(C)(=O)=O)cc(Nc3cccc(C#N)n3)nc2[nH]1] |
| I-604 | 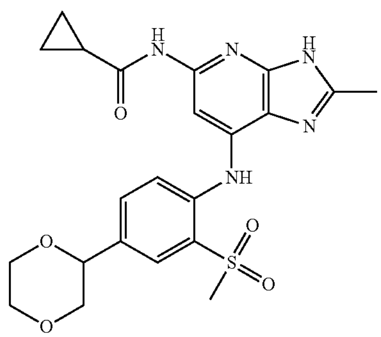 [SMILES: Cc1nc2c(Nc3ccc(C4COCCO4)cc3S(C)(=O)=O)cc(NC(=O)C3CC3)nc2[nH]1] |
| I-605 | 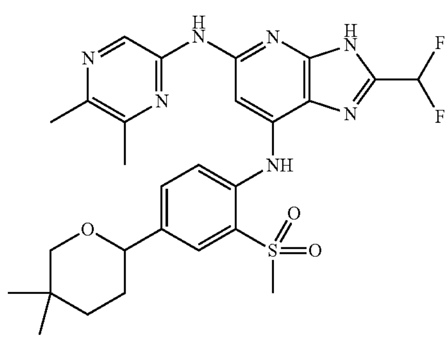 [SMILES: Cc1ncc(Nc2cc(Nc3ccc(C4CCC(C)(C)CO4)cc3S(C)(=O)=O)c3nc(C(F)F)[nH]c3n2)nc1C] |
| I-606 | 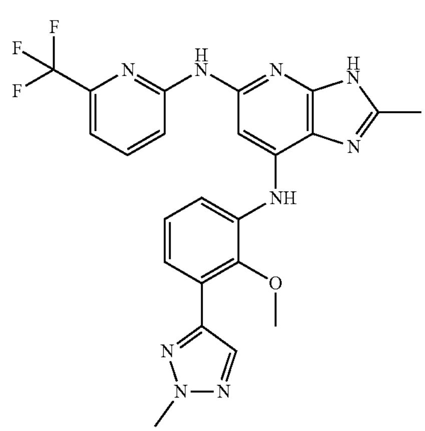 [SMILES: COc1c(Nc2cc(Nc3cccc(C(F)(F)F)n3)nc3[nH]c(C)nc23)cccc1-c1cnn(C)n1] |

TABLE-continued
Exemplary Compounds
| Compound | Structure |
|---|---|
| I-607 | 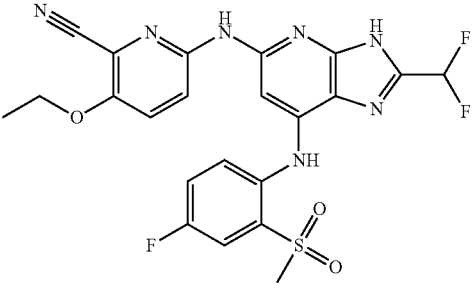 [SMILES: CCOc1ccc(Nc2cc(Nc3ccc(F)cc3S(C)(=O)=O)c3nc(C(F)F)[nH]c3n2)nc1C#N] |
| I-608 | 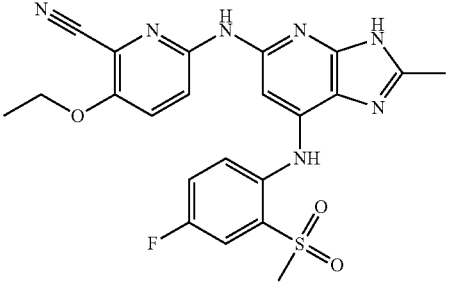 [SMILES: CCOc1ccc(Nc2cc(Nc3ccc(F)cc3S(C)(=O)=O)c3nc(C)[nH]c3n2)nc1C#N] |
| I-609 | 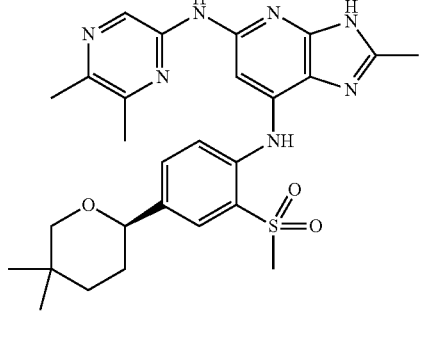 |
| I-610 | 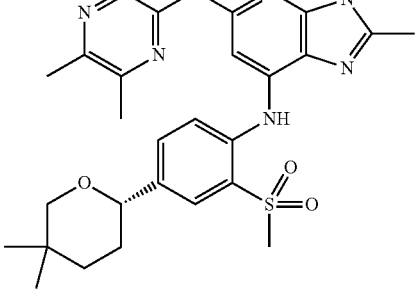 |

TABLE-continued

Exemplary Compounds

| Compound | Structure |
|---|---|
| I-611 | 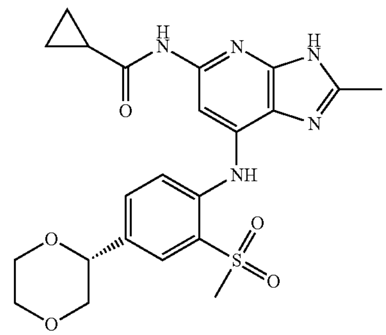 [SMILES: Cc1nc2c(Nc3ccc([C@@H]4COCCO4)cc3S(C)(=O)=O)cc(NC(=O)C3CC3)nc2[nH]1] |
| I-612 | 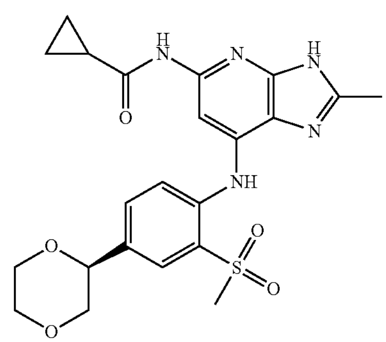 [SMILES: Cc1nc2c(Nc3ccc([C@H]4COCCO4)cc3S(C)(=O)=O)cc(NC(=O)C3CC3)nc2[nH]1] |
| I-613 | 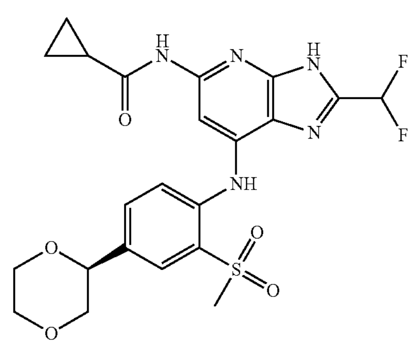 [SMILES: CS(=O)(=O)c1cc([C@H]2COCCO2)ccc1Nc1cc(NC(=O)C2CC2)nc2[nH]c(C(F)F)nc12] |
| I-614 | 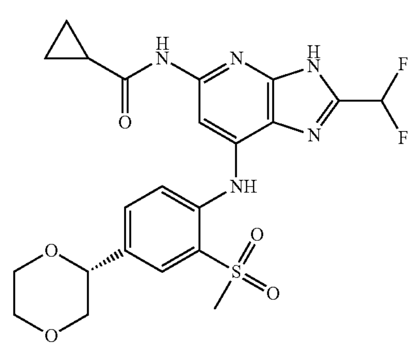 [SMILES: CS(=O)(=O)c1cc([C@@H]2COCCO2)ccc1Nc1cc(NC(=O)C2CC2)nc2[nH]c(C(F)F)nc12] |

TABLE-continued

Exemplary Compounds

| Compound | Structure |
|---|---|
| I-615 | 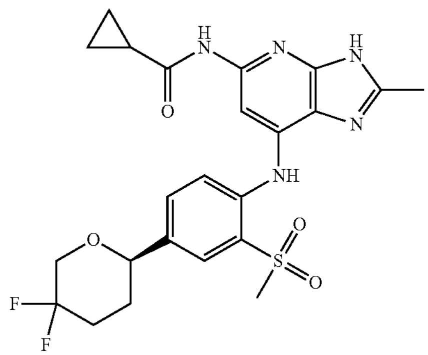 [SMILES: Cc1nc2c(Nc3ccc([C@H]4CCC(F)(F)CO4)cc3S(C)(=O)=O)cc(NC(=O)C3CC3)nc2[nH]1] |
| I-616 | 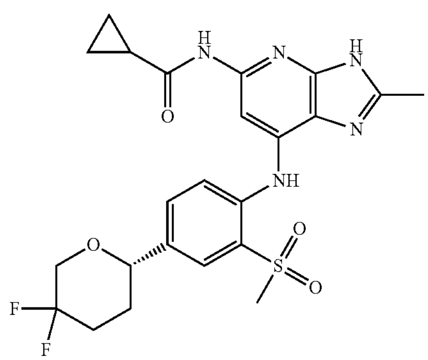 [SMILES: Cc1nc2c(Nc3ccc([C@@H]4CCC(F)(F)CO4)cc3S(C)(=O)=O)cc(NC(=O)C3CC3)nc2[nH]1] |
| I-617 | 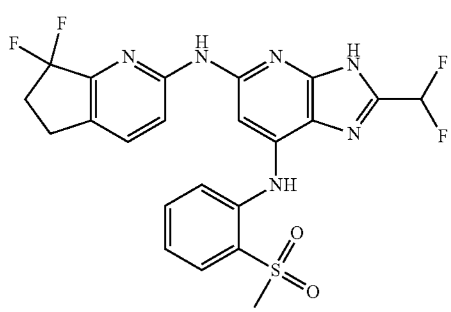 [SMILES: CS(=O)(=O)c1ccccc1Nc1cc(Nc2ccc3c(n2)C(F)(F)CC3)nc2[nH]c(C(F)F)nc12] |
| I-618 | 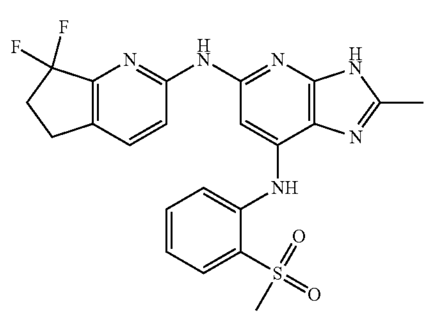 [SMILES: Cc1nc2c(Nc3ccccc3S(C)(=O)=O)cc(Nc3ccc4c(n3)C(F)(F)CC4)nc2[nH]1] |

| Compound | Structure |
|---|---|
| I-619 | 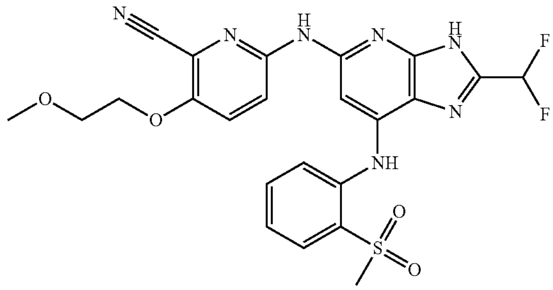 [SMILES: COCCOc1ccc(Nc2cc(Nc3ccccc3S(C)(=O)=O)c3nc(C(F)F)[nH]c3n2)nc1C#N] |
| I-620 | 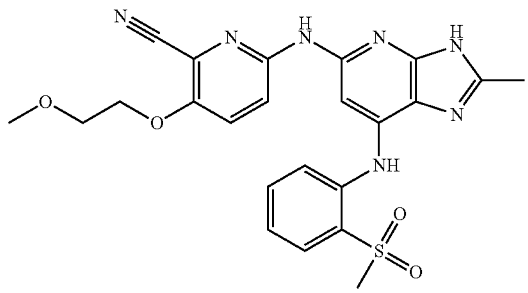 |
| I-621 | 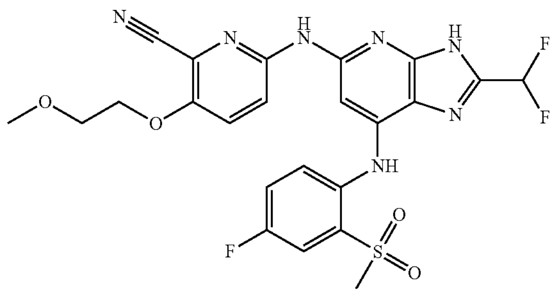 [SMILES: COCCOc1ccc(Nc2cc(Nc3ccc(F)cc3S(C)(=O)=O)c3nc(C(F)F)[nH]c3n2)nc1C#N] |
| I-622 | 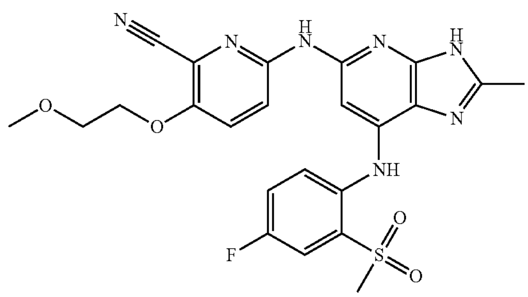 |
| I-623 | 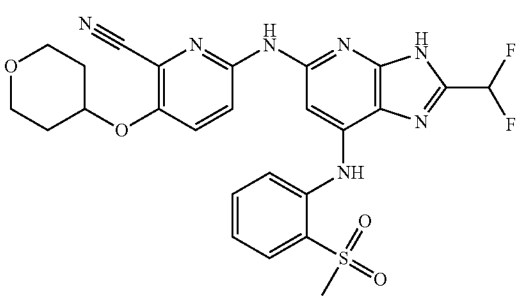 [SMILES: CS(=O)(=O)c1ccccc1Nc1cc(Nc2ccc(OC3CCOCC3)c(C#N)n2)nc2[nH]c(C(F)F)nc12] |

TABLE-continued
Exemplary Compounds
| Compound | Structure |
|---|---|
| I-624 | 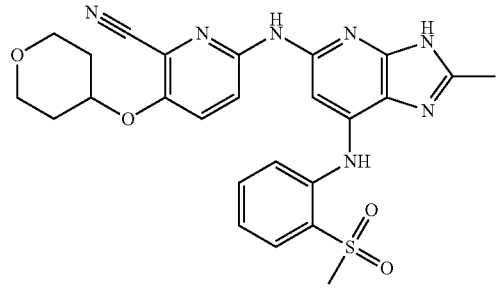 [SMILES: Cc1nc2c(Nc3ccccc3S(C)(=O)=O)cc(Nc3ccc(OC4CCOCC4)c(C#N)n3)nc2[nH]1] |
| I-625 | 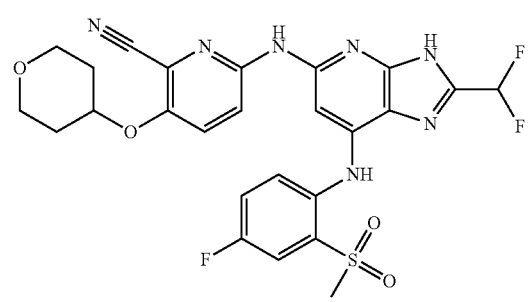 [SMILES: CS(=O)(=O)c1cc(F)ccc1Nc1cc(Nc2ccc(OC3CCOCC3)c(C#N)n2)nc2[nH]c(C(F)F)nc12] |
| I-626 | 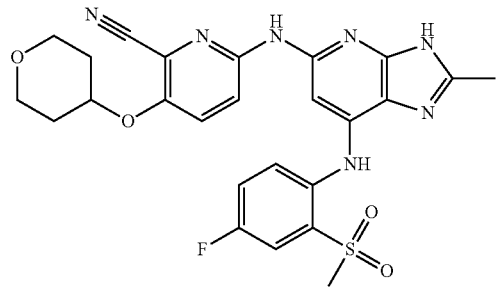 [SMILES: Cc1nc2c(Nc3ccc(F)cc3S(C)(=O)=O)cc(Nc3ccc(OC4CCOCC4)c(C#N)n3)nc2[nH]1] |
| I-627 | 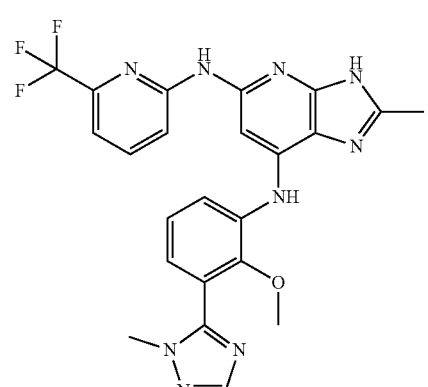 |

TABLE-continued
Exemplary Compounds
| Compound | Structure |
|---|---|
| I-628 | 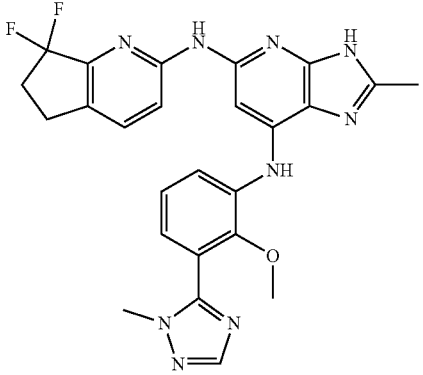 [SMILES: COc1c(Nc2cc(Nc3ccc4c(n3)C(F)(F)CC4)nc3[nH]c(C)nc23)cccc1-c1ncnn1C] |
| I-629 | 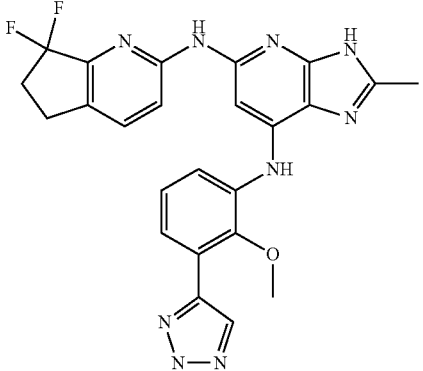 |
| I-630 | 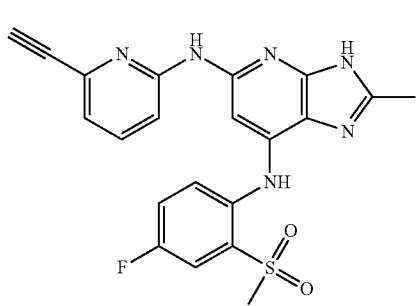 [SMILES: C#Cc1cccc(Nc2cc(Nc3ccc(F)cc3S(C)(=O)=O)c3nc(C)[nH]c3n2)n1] |
| I-631 | 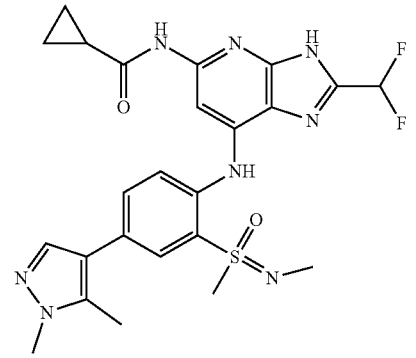 [SMILES: CN=S(C)(=O)c1cc(-c2cnn(C)c2C)ccc1Nc1cc(NC(=O)C2CC2)nc2[nH]c(C(F)F)nc12] |

TABLE-continued
Exemplary Compounds
| Compound | Structure |
|---|---|
| I-632 | 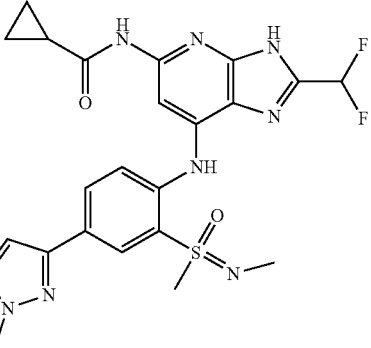 |
| I-633 | 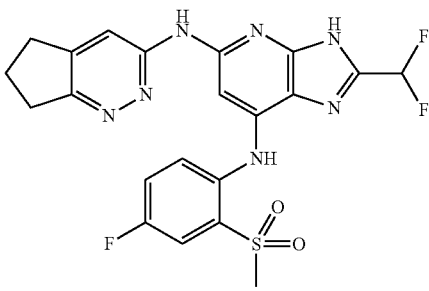 [SMILES: CS(=O)(=O)c1cc(F)ccc1Nc1cc(Nc2cc3c(nn2)CCC3)nc2[nH]c(C(F)F)nc12] |
| I-634 | 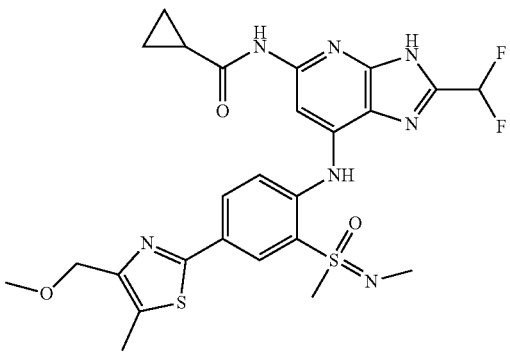 [SMILES: CN=S(C)(=O)c1cc(-c2nc(COC)c(C)s2)ccc1Nc1cc(NC(=O)C2CC2)nc2[nH]c(C(F)F)nc12] |
| I-635 | 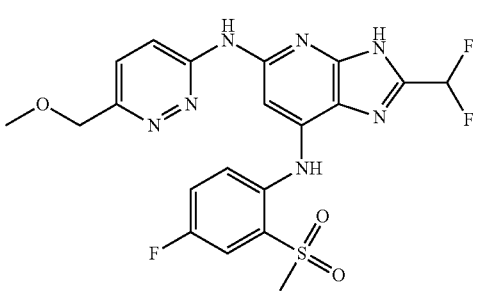 [SMILES: COCc1ccc(Nc2cc(Nc3ccc(F)cc3S(C)(=O)=O)c3nc(C(F)F)[nH]c3n2)nn1] |

TABLE-continued
Exemplary Compounds
| Compound | Structure |
|---|---|
| I-636 | 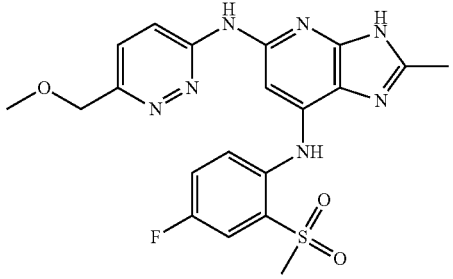 |
| I-637 | 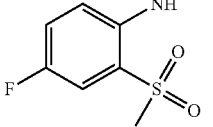 |
| I-638 | 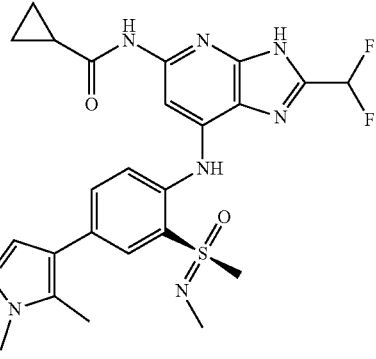 |
| I-639 | 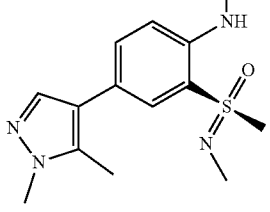 |

TABLE-continued
Exemplary Compounds
| Compound | Structure |
|---|---|
| I-640 | 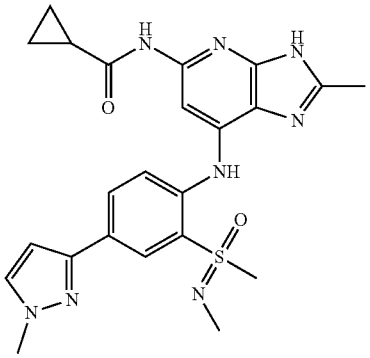 [SMILES: CN=S(C)(=O)c1cc(-c2ccn(C)n2)ccc1Nc1cc(NC(=O)C2CC2)nc2[nH]c(C)nc12] |
| I-641 | 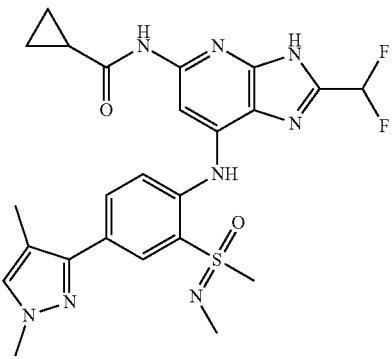 [SMILES: CN=S(C)(=O)c1cc(-c2nn(C)cc2C)ccc1Nc1cc(NC(=O)C2CC2)nc2[nH]c(C(F)F)nc12] |
| I-642 | 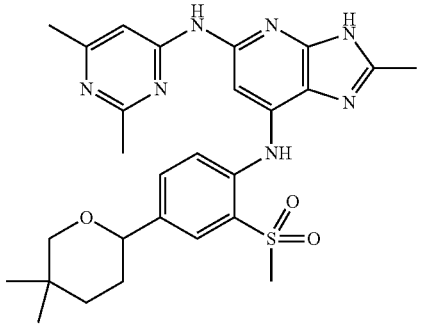 |
| I-643 | 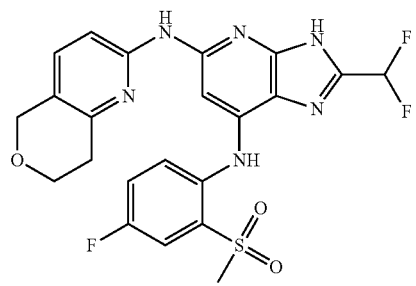 [SMILES: CS(=O)(=O)c1cc(F)ccc1Nc1cc(Nc2ccc3c(n2)CCOC3)nc2[nH]c(C(F)F)nc12] |

TABLE-continued

Exemplary Compounds

| Compound | Structure |
|---|---|
| I-644 | 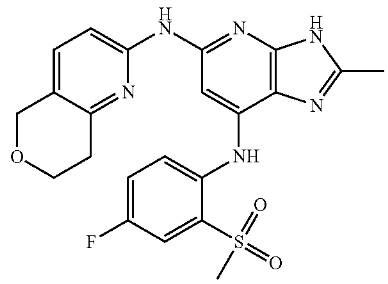 [SMILES: Cc1nc2c(Nc3ccc(F)cc3S(C)(=O)=O)cc(Nc3ccc4c(n3)CCOC4)nc2[nH]1] |
| I-645 | 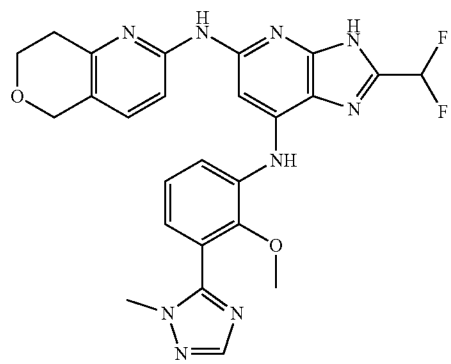 [SMILES: COc1c(Nc2cc(Nc3ccc4c(n3)CCOC4)nc3[nH]c(C(F)F)nc23)cccc1-c1ncnn1C] |
| I-646 | 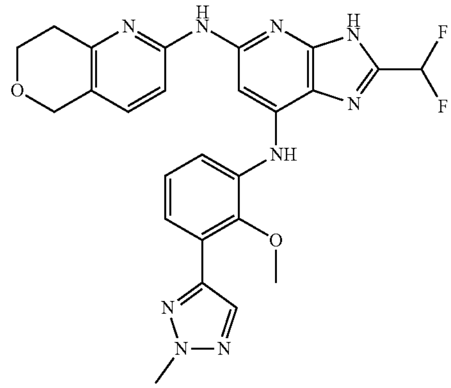 [SMILES: COc1c(Nc2cc(Nc3ccc4c(n3)CCOC4)nc3[nH]c(C(F)F)nc23)cccc1-c1cnn(C)n1] |
| I-647 | 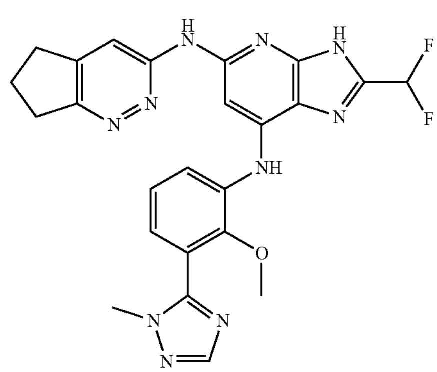 [SMILES: COc1c(Nc2cc(Nc3cc4c(nn3)CCC4)nc3[nH]c(C(F)F)nc23)cccc1-c1ncnn1C] |

TABLE-continued

Exemplary Compounds

| Compound | Structure |
|---|---|
| I-648 | 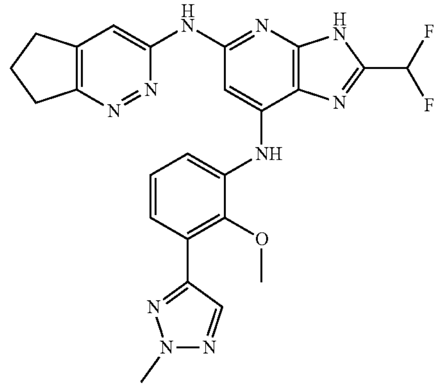 [SMILES: COc1c(Nc2cc(Nc3cc4c(nn3)CCC4)nc3[nH]c(C(F)F)nc23)cccc1-c1cnn(C)n1] |
| I-649 | 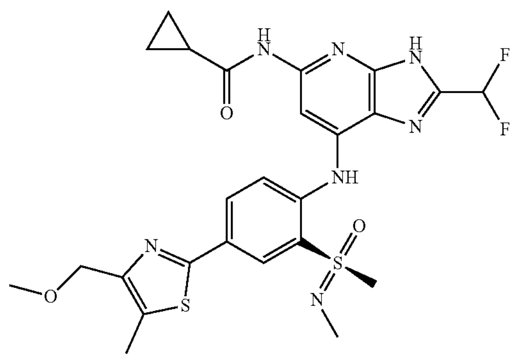 [SMILES: CN=[S@@](C)(=O)c1cc(-c2nc(COC)c(C)s2)ccc1Nc1cc(NC(=O)C2CC2)nc2[nH]c(C(F)F)nc12] |
| I-650 | 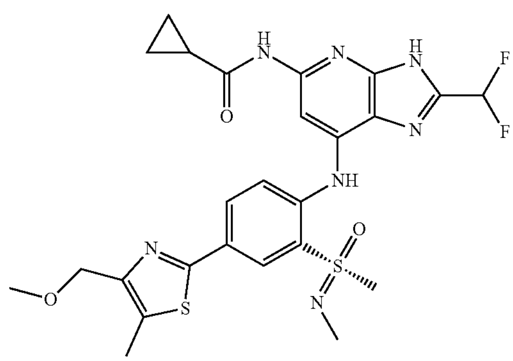 [SMILES: CN=[S@](C)(=O)c1cc(-c2nc(COC)c(C)s2)ccc1Nc1cc(NC(=O)C2CC2)nc2[nH]c(C(F)F)nc12] |

In some embodiments, the present invention provides a compound set forth in Table 1, above, or a pharmaceutically acceptable salt thereof. In some embodiments, the present invention provides a pharmaceutical composition comprising a compound set forth in Table 1 above, or a pharmaceutically acceptable salt thereof, together with a pharmaceutically acceptable carrier, excipient, or diluent.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In some embodiments, compounds of formula I or I' are prepared according to the following general procedure, depicted in Scheme 1.

Scheme 1. Synthesis of compounds of formula I or I'.

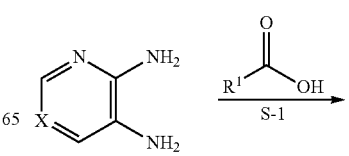

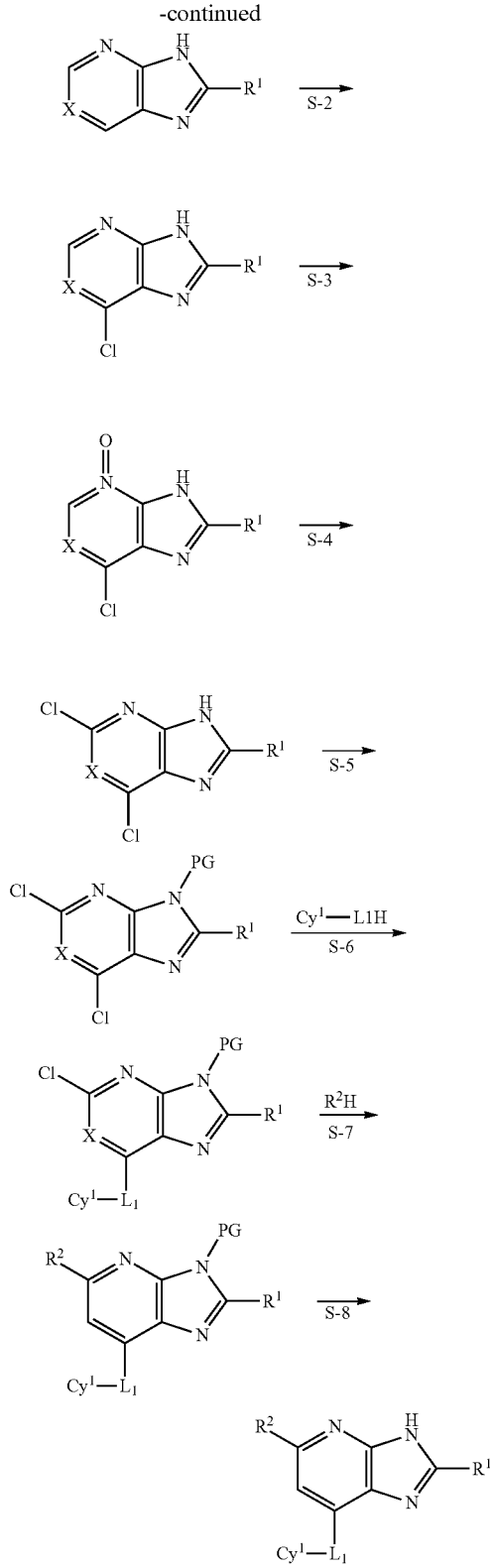

wherein PG is a suitable nitrogen protecting group, and X is as defined above and in embodiments herein.

In some embodiments, compounds of formula X are prepared according to the following general procedure, depicted in Scheme 1-a.

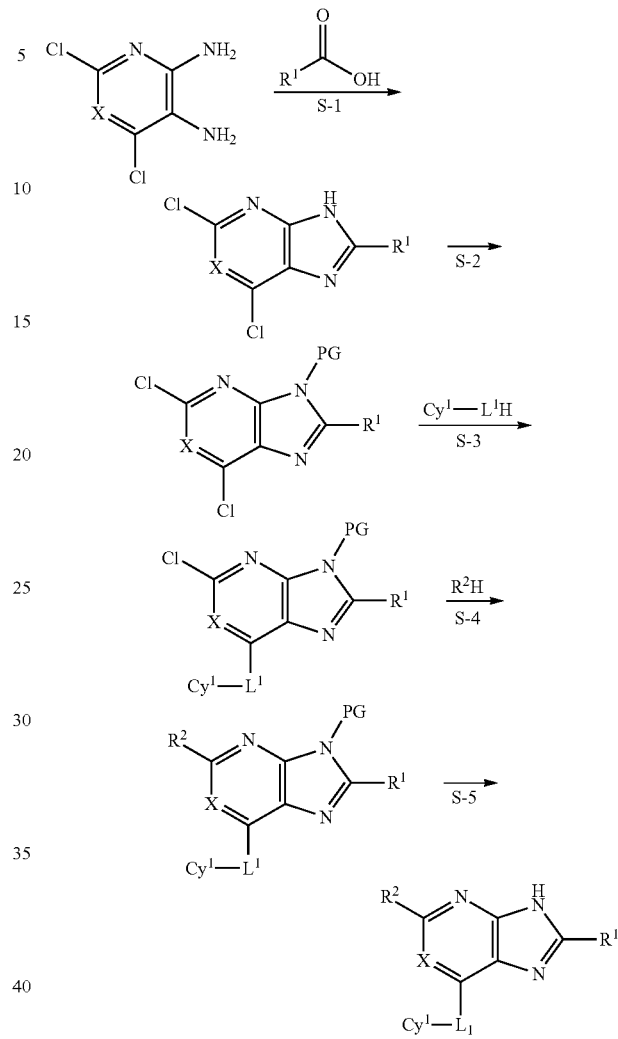

wherein PG is a suitable nitrogen protecting group, and each of X, $R^1$, $R^2$, $L^1$, and $Cy^1$ is as defined above and in embodiments herein, both singly and in combination.

In some embodiments, where $L^1$ is NH, intermediates of formula $Cy^1$-$NH_2$ are prepared according to the methods described in WO2014074660A1, WO2014074661A1, and WO2015089143A1, the entirety of each of which is incorporated herein by reference.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a TYK2 protein kinase, or a mutant thereof, in a biological sample or in a patient. In certain embodiments, the amount of compound in compositions of this invention is such that is effective to measurably inhibit a TYK2 protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of a TYK2 protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration.

Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes. In some embodiments the kinase inhibited by the compounds and methods of the invention is TYK2

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons (e.g. IFN-α, IFN-β, IFN-κ, IFN-δ, IFN-ε, IFN-τ, IFN-ω, and IFN-ζ (also known as limitin), and interleukins (e.g. IL-4, IL-6, IL-10, IL-11, IL-12, IL-13, L-22, IL-23, IL-27, IL-31, oncostatin M, ciliary neurotrophic factor, cardiotrophin 1, cardiotrophin-like cytokine, and LIF). Velasquez et al., "A protein kinase in the interferon α/β signaling pathway," Cell (1992) 70:313; Stahl et al., "Association and activation of Jak-Tyk kinases by CNTF-LIF-OSM-IL-6β receptor components," Science (1994) 263:92; Finbloom et al., "IL-10 induces the tyrosine phosphorylation of Tyk2 and Jak1 and the differential assembly of Stat1 and Stat3 complexes in human T cells and monocytes," J. Immunol. (1995) 155:1079; Bacon et al., "Interleukin 12 (L-12) induces tyrosine phosphorylation of Jak2 and Tyk2: differential use of Janus family kinases by IL-2 and IL-12," J. Exp. Med. (1995) 181:399; Welham et al., "Interleukin-13 signal transduction in lymphohemopoietic cells: similarities and differences in signal transduction with interleukin-4 and insulin," J. Biol. Chem. (1995) 270:12286; Parham et al., "A receptor for the heterodimeric cytokine IL-23 is composed of IL-12R31 and a novel cytokine receptor subunit, IL-23R," J. Immunol. (2002) 168:5699. The activated TYK2 then goes on to phosphorylate further signaling proteins such as members of the STAT family, including STAT1, STAT2, STAT4, and STAT6.

TYK2 activation by IL-23, has been linked to inflammatory bowel disease (IBD), Crohn's disease, and ulcerative colitis. Duerr et al., "A Genome-Wide Association Study Identifies IL23R as an Inflammatory Bowel Disease Gene," Science (2006) 314:1461-1463. As the downstream effector of IL-23, TYK2 also plays a role in psoriasis, ankylosing spondylitis, and Behçet's disease. Cho et al., "Genomics and the multifactorial nature of human auto-immune disease," N. Engl. J. Med (2011) 365:1612-1623; Cortes et al., "Identification of multiple risk variants for ankylosing spondylitis through high-density genotyping of immune-related loci," Nat. Genet. (2013) 45(7):730-738; Remmers et al., "Genome-wide association study identifies variants in the MHC class I, IL10, and L23R-IL12RB2 regions associated with Behçet's disease," Nat. Genet. (2010) 42:698-702. A genome-wide association study of 2,622 individuals with psoriasis identified associations between disease susceptibility and TYK2. Strange et al., "A genome-wide association study identifies new psoriasis susceptibility loci and an interaction between HLA-C and ERAP1," Nat. Genet. (2010) 42:985-992. Knockout or tyrphostin inhibition of TYK2 significantly reduces both IL-23 and IL-22-induced dermatitis. Ishizaki et al., "Tyk2 is a therapeutic target for psoriasis-like skin inflammation," Intl. Immunol. (2013), doi: 10.1093/intimm/dxt062.

TYK2 also plays a role in respiratory diseases such as asthma, chronic obstructive pulmonary disease (COPD), lung cancer, and cystic fibrosis. Goblet cell hyperplasia (GCH) and mucous hypersecretion is mediated by IL-13-induced activation of TYK2, which in turn activates STAT6. Zhang et al., "Docking protein Gab2 regulates mucin expression and goblet cell hyperplasia through TYK2/STAT6 pathway," FASEB J. (2012) 26:1-11. Decreased TYK2 activity leads to protection of joints from collagen antibody-induced arthritis, a model of human rheumatoid arthritis. Mechanistically, decreased Tyk2 activity reduced the production of $T_h1/T_h17$-related cytokines and matrix metalloproteases, and other key markers of inflammation. Ishizaki et al., "Tyk2 deficiency protects joints against destruction in anti-type II collagen antibody-induced arthritis in mice," Intl. Immunol. (2011) 23(9):575-582.

TYK2 knockout mice showed complete resistance in experimental autoimmune encephalomyelitis (EAE, an animal model of multiple sclerosis (MS)), with no infiltration of CD4 T cells in the spinal cord, as compared to controls, suggesting that TYK2 is essential to pathogenic CD4-mediated disease development in MS. Oyamada et al., "Tyrosine Kinase 2 Plays Critical Roles in the Pathogenic CD4 T Cell Responses for the Development of Experimental Autoimmune Encephalomyelitis," J. Immunol. (2009) 183: 7539-7546. This corroborates earlier studies linking increased TYK2 expression with MS susceptibility. Ban et al., "Replication analysis identifies TYK2 as a multiple sclerosis susceptibility factor," Eur J. Hum. Genet. (2009) 17:1309-1313. Loss of function mutation in TYK2, leads to decreased demyelination and increased remyelination of neurons, further suggesting a role for TYK2 inhibitors in the treatment of MS and other CNS demyelination disorders.

TYK2 is the sole signaling messenger common to both IL-12 and IL-23. TYK2 knockout reduced methylated BSA injection-induced footpad thickness, imiquimod-induced psoriasis-like skin inflammation, and dextran sulfate sodium or 2,4,6-trinitrobenzene sulfonic acid-induced colitis in mice.

Joint linkage and association studies of various type I IFN signaling genes with systemic lupus erythematosus (SLE, an autoimmune disorder), showed a strong, and significant correlation between loss of function mutations to TYK2 and decreased prevalence of SLE in families with affected members. Sigurdsson et al., "Polymorphisms in the Tyrosine Kinase 2 and Interferon Regulatory Factor 5 Genes Are Associated with Systemic Lupus Erythematosus," Am. J. Hum. Genet. (2005) 76:528-537. Genome-wide association studies of individuals with SLE versus an unaffected cohort showed highly significant correlation between the TYK2 locus and SLE. Graham et al., "Association of NCF2, IKZF1, IRF8, IFIH1, and TYK2 with Systemic Lupus Erythematosus," PLoS Genetics (2011) 7(10):e1002341.

TYK2 has been shown to play an important role in maintaining tumor surveillance and TYK2 knockout mice showed compromised cytotoxic T cell response, and accelerated tumor development. However, these effects were linked to the efficient suppression of natural killer (NK) and cytotoxic T lymphocytes, suggesting that TYK2 inhibitors would be highly suitable for the treatment of autoimmune disorders or transplant rejection. Although other JAK family members such as JAK3 have similar roles in the immune system, TYK2 has been suggested as a superior target because of its involvement in fewer and more closely related signaling pathways, leading to fewer off-target effects. Simma et al. "Identification of an Indispensable Role for Tyrosine Kinase 2 in CTL-Mediated Tumor Surveillance," Cancer Res. (2009) 69:203-211.

However, paradoxically to the decreased tumor surveillance observed by Simma et al., studies in T-cell acute lymphoblastic leukemia (T-ALL) indicate that T-ALL is highly dependent on IL-10 via TYK2 via STAT1-mediated signal transduction to maintain cancer cell survival through upregulation of anti-apoptotic protein BCL2. Knockdown of TYK2, but not other JAK family members, reduced cell growth. Specific activating mutations to TYK2 that promote cancer cell survival include those to the FERM domain (G36D, S47N, and R425H), the JH2 domain (V731I), and the kinase domain (E957D and R1027H). However, it was also identified that the kinase function of TYK2 is required for increased cancer cell survival, as TYK2 enzymes featuring kinase-dead mutations (M978Y or M978F) in addition to an activating mutation (E957D) resulted in failure to transform. Sanda et al. "TYK2-STAT1-BCL2 Pathway Dependence in T-Cell Acute Lymphoblastic Leukemia," Cancer Disc. (2013) 3(5):564-577.

Thus, selective inhibition of TYK2 has been suggested as a suitable target for patients with IL-10 and/or BCL2-addicted tumors, such as 70% of adult T-cell leukemia cases. Fontan et al. "Discovering What Makes STAT Signaling TYK in T-ALL," Cancer Disc. (2013) 3:494-496.

TYK2 mediated STAT3 signaling has also been shown to mediate neuronal cell death caused by amyloid-β (Aβ) peptide. Decreased TYK2 phosphorylation of STAT3 following Aβ administration lead to decreased neuronal cell death, and increased phosphorylation of STAT3 has been observed in postmortem brains of Alzheimer's patients. Wan et al. "Tyk/STAT3 Signaling Mediates β-Amyloid-Induced Neuronal Cell Death: Implications in Alzheimer's Disease," J. Neurosci. (2010) 30(20):6873-6881.

Inhibition of JAK-STAT signaling pathways is also implicated in hair growth, and the reversal of the hair loss associated with alopecia areata. Xing et al., "Alopecia areata is driven by cytotoxic T lymphocytes and is reversed by JAK inhibition," Nat. Med. (2014) 20: 1043-1049; Harel et al., "Pharmacologic inhibition of JAK-STAT signaling promotes hair growth," Sci. Adv. (2015) 1(9):e1500973.

Accordingly, compounds that inhibit the activity of TYK2 are beneficial, especially those with selectivity over JAK2. Such compounds should deliver a pharmacological response that favorably treats one or more of the conditions described herein without the side-effects associated with the inhibition of JAK2.

Even though TYK2 inhibitors are known in the art, there is a continuing need to provide novel inhibitors having more effective or advantageous pharmaceutically relevant properties. For example, compounds with increased activity, selectivity over other JAK kinases (especially JAK2), and ADMET (absorption, distribution, metabolism, excretion, and/or toxicity) properties. Thus, in some embodiments, the present invention provides inhibitors of TYK2 which show selectivity over JAK2.

The activity of a compound utilized in this invention as an inhibitor of TYK2, or a mutant thereof, may be assayed in vitro, in vivo or in a cell line. In vitro assays include assays that determine inhibition of either the phosphorylation activity and/or the subsequent functional consequences, or ATPase activity of activated TYK2, or a mutant thereof. Alternate in vitro assays quantitate the ability of the inhibitor to bind to TYK2. Inhibitor binding may be measured by radiolabeling the inhibitor prior to binding, isolating the inhibitor/TYK2 complex and determining the amount of radiolabel bound. Alternatively, inhibitor binding may be determined by running a competition experiment where new inhibitors are incubated with TYK2 bound to known radioligands. Representative in vitro and in vivo assays useful in assaying a TYK2 inhibitor include those described and disclosed in, e.g., each of which is herein incorporated by reference in its entirety. Detailed conditions for assaying a compound utilized in this invention as an inhibitor of TYK2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of TYK2 and are therefore useful for treating one or more disorders associated with activity of TYK2 or mutants thereof. Thus, in certain embodiments, the present invention provides a method for treating a TYK2-mediated disorder comprising the step of administering to a patient in need thereof a compound of the present invention, or pharmaceutically acceptable composition thereof.

As used herein, the term "TYK2-mediated" disorders, diseases, and/or conditions as used herein means any disease or other deleterious condition in which TYK2 or a mutant thereof is known to play a role. Accordingly, another embodiment of the present invention relates to treating or lessening the severity of one or more diseases in which TYK2, or a mutant thereof, is known to play a role. Such TYK2-mediated disorders include but are not limited to autoimmune disorders, inflammatory disorders, proliferative disorders, endocrine disorders, neurological disorders and disorders associated with transplantation.

In some embodiments, the present invention provides a method for treating one or more disorders, wherein the disorders are selected from autoimmune disorders, inflammatory disorders, proliferative disorders, endocrine disorders, neurological disorders, and disorders associated with transplantation, said method comprising administering to a patient in need thereof, a pharmaceutical composition comprising an effective amount of a compound of the present invention, or a pharmaceutically acceptable salt thereof.

In some embodiments, the disorder is an autoimmune disorder. In some embodiments the disorder is selected from type 1 diabetes, systemic lupus erythematosus, multiple sclerosis, psoriasis, Behçet's disease, POEMS syndrome, Crohn's disease, ulcerative colitis, and inflammatory bowel disease.

In some embodiments, the disorder is an inflammatory disorder. In some embodiments, the inflammatory disorder is rheumatoid arthritis, asthma, chronic obstructive pulmonary disease, psoriasis, hepatomegaly, Crohn's disease, ulcerative colitis, inflammatory bowel disease.

In some embodiments, the disorder is a proliferative disorder. In some embodiments, the proliferative disorder is a hematological cancer. In some embodiments the proliferative disorder is a leukemia. In some embodiments, the leukemia is a T-cell leukemia. In some embodiments the T-cell leukemia is T-cell acute lymphoblastic leukemia (T-ALL). In some embodiments the proliferative disorder is polycythemia vera, myelofibrosis, essential or thrombocytosis.

In some embodiments, the disorder is an endocrine disorder. In some embodiments, the endocrine disorder is polycystic ovary syndrome, Crouzon's syndrome, or type 1 diabetes.

In some embodiments, the disorder is a neurological disorder. In some embodiments, the neurological disorder is Alzheimer's disease.

In some embodiments the proliferative disorder is associated with one or more activating mutations in TYK2. In some embodiments, the activating mutation in TYK2 is a mutation to the FERM domain, the JH2 domain, or the kinase domain. In some embodiments the activating mutation in TYK2 is selected from G36D, S47N, R425H, V731I, E957D, and R1027H.

In some embodiments, the disorder is associated with transplantation. In some embodiments the disorder associated with transplantation is transplant rejection, or graft versus host disease.

In some embodiments the disorder is associated with type I interferon, IL-10, IL-12, or IL-23 signaling. In some embodiments the disorder is associated with type I interferon signaling. In some embodiments the disorder is associated with IL-10 signaling. In some embodiments the disorder is associated with IL-12 signaling. In some embodiments the disorder is associated with IL-23 signaling.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), and osteoarthritis.

In some embodiments the inflammatory disease which can be treated according to the methods of this invention is a $T_h1$ or $T_h17$ mediated disease. In some embodiments the $T_h17$ mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Furthermore, the invention provides the use of a compound according to the definitions herein, or a pharmaceutically acceptable salt, or a hydrate or solvate thereof for the preparation of a medicament for the treatment of an autoimmune disorder, an inflammatory disorder, or a proliferative disorder, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporine, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I, I', or X and one or more additional therapeutic agents. The therapeutic agent may be administered together with a compound of formula I, I', or X, or may be administered prior to or following administration of a compound of formula I, I', or X. Suitable therapeutic agents are described in further detail below. In certain embodiments, a compound of formula I, I', or X may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I, I', or X may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I, I', or X and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmicort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevirapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I, I', or X and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I, I', or X and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating systemic lupus erythematosus comprising administering to a patient in need thereof a compound of formula I, I', or X and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I, I', or X and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I, I', or X and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmicort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I, I', or X and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmicort®), flunisolide (Aerobid®), Afviar®, Symbicort®, and Dulera®, In another embodiment, the present invention provides a method of treating a hematological malignancy comprising administering to a patient in need thereof a compound of formula I, I', or X and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I, I', or X and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I, I', or X and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I, I', or X and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I, I', or X and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I, I', or X and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleroderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I, I', or X and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I, I', or X and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I, I', or X and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the present invention provides a method of treating or lessening the severity of a disease, comprising administering to a patient in need thereof a TYK2 pseudokinase (JH2) domain binding compound and a TYK2 kinase (JH1) domain binding compound. In some embodiments, the disease is an autoimmune disorder, an inflammatory disorder, a proliferative disorder, an endocrine disorder, a neurological disorder, or a disorder associated with transplantation. In some embodiments the JH2 binding compound is a compound of formula I, I', or X. Other suitable JH2 domain binding compounds include those described in WO2014074660A1, WO2014074661A1, WO2015089143A1, the entirety of each of which is incorporated herein by reference. Suitable JH1 domain binding compounds include those described in WO2015131080A1, the entirety of which is incorporated herein by reference.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting TYK2, or a mutant thereof, activity in a biological sample comprising the step of contacting said biological sample with a compound of this invention, or a composition comprising said compound. In certain embodiments, the invention relates to a method of irreversibly inhibiting TYK2, or a mutant thereof, activity in a biological sample comprising the step of contacting said biological sample with a compound of this invention, or a composition comprising said compound.

In another embodiment, the invention provides a method of selectively inhibiting TYK2 over one or more of JAK1, JAK2, and JAK3. In some embodiments, a compound of the present invention is more than 2-fold selective over JAK1/2/3. In some embodiments, a compound of the present invention is more than 5-fold selective over JAK1/2/3. In some embodiments, a compound of the present invention is more than 10-fold selective over JAK1/2/3. In some embodiments, a compound of the present invention is more than 50-fold selective over JAK1/2/3. In some embodiments, a compound of the present invention is more than 100-fold selective over JAK1/2/3.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of TYK2 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of TYK2, or a mutant thereof, in a patient comprising the step of administering to said patient a compound of the present invention, or a composition comprising said compound. According to certain embodiments, the invention relates to a method of reversibly or irreversibly inhibiting one or more of TYK2, or a mutant thereof, activity in a patient comprising the step of administering to said patient a compound of the present invention, or a composition comprising said compound. In other embodiments, the present invention provides a method for treating a disorder mediated by TYK2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtubulin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; colchicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; ilmofosine; RO318220 and RO320432; GO 6976; Isis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C1-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PR°64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclomethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (ParkeDavis), AWD-12-281 (Asta Medica), CDC-801 (Celgene), SeICID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and terfenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. General Procedure A (1$^{st}$ Buchwald Amination):

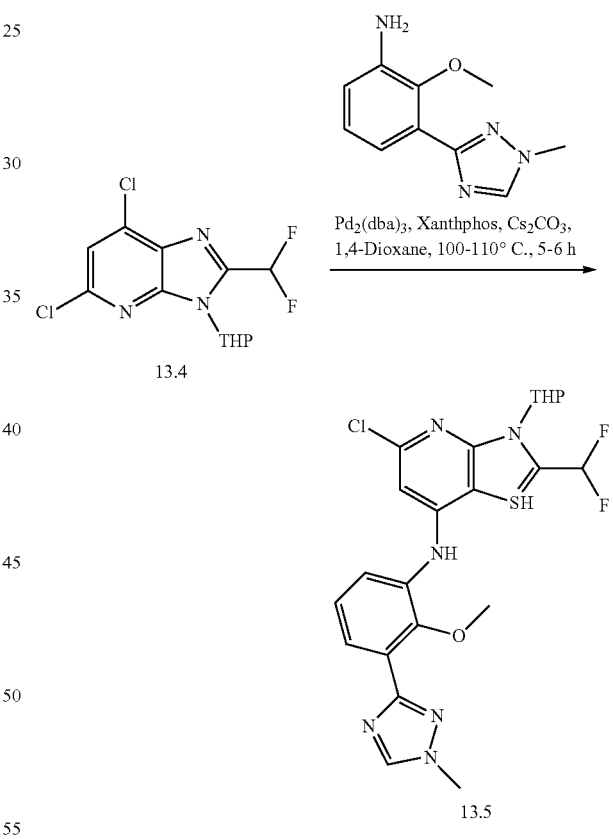

Synthesis of Compound 13.5.

To compound 13.4 (0.500 g, 1.55 mmol, 1.0 eq) in 1,4-dioxane (10 mL) was added 2-methoxy-3-(1-methyl-1H-1,2,4-triazol-3-yl)aniline (0.253 g, 1.24 mmol, 0.8 eq), Cs$_2$CO$_3$ (1.52 g, 4.65 mmol, 3.0 eq). The reaction mixture was degassed for 10 min. under argon atmosphere, then Pd$_2$(dba)$_3$ (0.142 g, 0.155 mmol, 0.1 eq) and Xantphos (0.180 g, 0.3 mmol, 0.2 eq) were added, again degassed for 5 min. The reaction was stirred at 110° C. for 5-6 h. Upon completion, reaction mixture was cooled to r.t., transferred in water and product was extracted with ethyl acetate.

Organic layers were combined, washed with brine, dried over Na$_2$SO$_4$ and concentrated in vacuo to obtain crude product. This was purified by combi flash using 2% MeOH in CH$_2$Cl$_2$ as eluant to obtain pure 1.2 (0.160 g, 45.74%). MS(ES): m/z 490.9 [M]+.

General Procedure B (2$^{nd}$ Buchwald Amination):

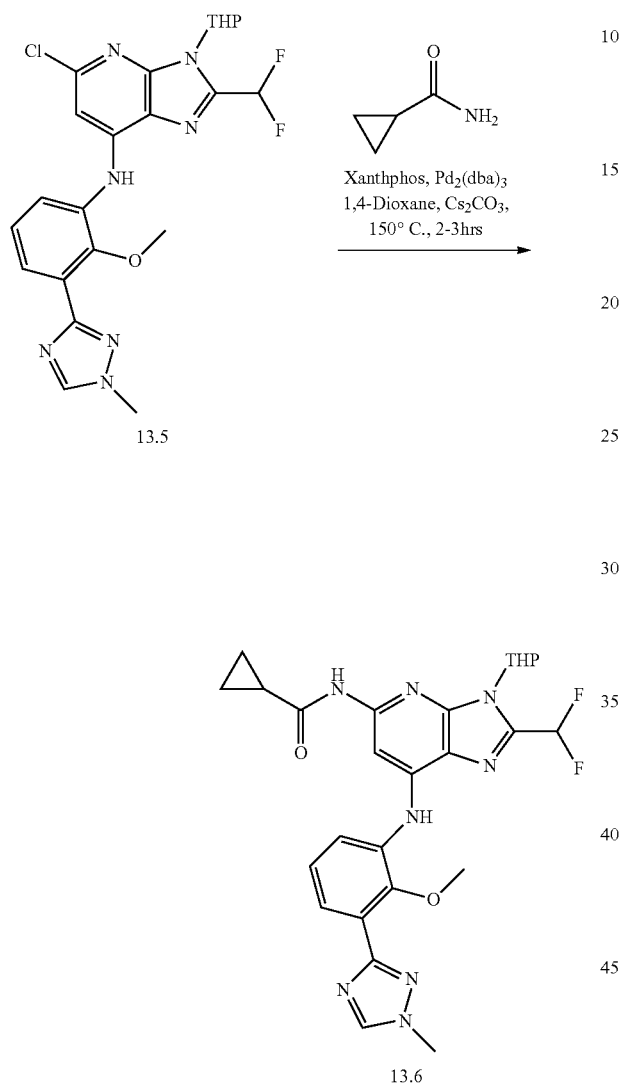

Synthesis of Compound 13.6.

To 13.5 (0.170 g, 0.347 mmol, 1.0 eq) in 1,4-dioxane (3.5 mL) was added cyclopropanecarboxamide (0.089 g, 1.041 mmol, 3.0 eq), Cs$_2$CO$_3$ (0.452 g, 1.388 mmol, 4.0 eq). The reaction mixture was degassed for 10 min. under argon atmosphere, then Pd$_2$(dba)$_3$ (0.031 g, 0.034 mmol, 0.1 eq) and Xantphos (0.040 g, 0.070 mmol, 0.2 eq) were added, again degassed for 5 min. The reaction was stirred at 150° C. for 2-3 h. Upon completion, reaction mixture was cooled to r.t., transferred in water and product was extracted with ethyl acetate. Organic layers were combined, washed with brine, dried over Na$_2$SO$_4$ and concentrated in vacuo to obtain crude product. This was purified by combi flash using 3% MeOH in CH$_2$Cl$_2$ as eluant to obtain pure 11.6 (0.090 g, 48.16%). MS(ES): m/z 539.5 [M+H]$^+$.

General Procedure C (THP-Deprotection):

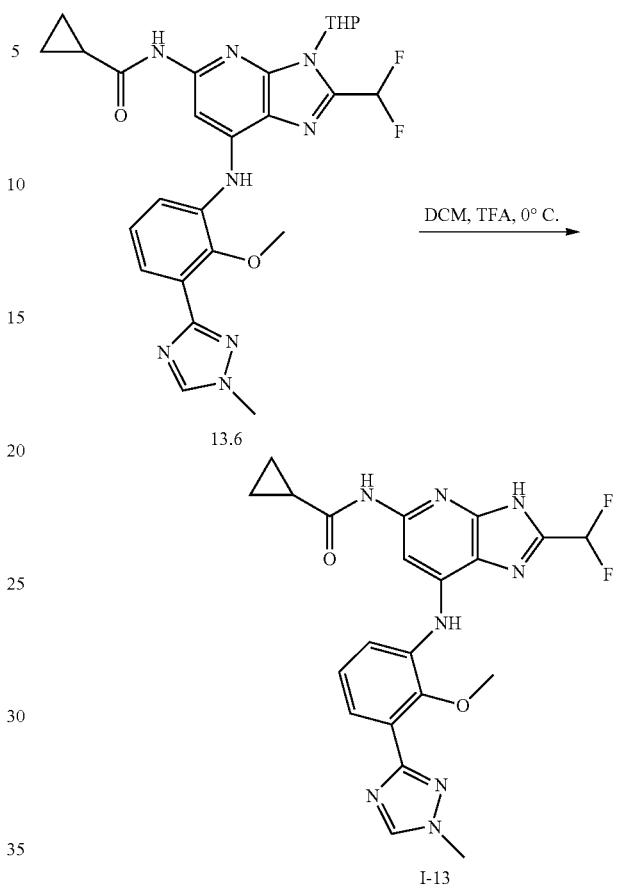

Synthesis of I-13.

To a solution of 13.6 (0.090 g, 0.167 mmol, 1.0 eq) in CH$_2$Cl$_2$ (3 mL) was added trifluoroacetic acid (0.5 mL) at 0° C. The reaction mixture was stirred at r.t. for 1 h. Upon completion, reaction mixture transferred in saturated NaHCO$_3$ solution and product was extracted with CH$_2$Cl$_2$. Organic layers were combined, washed with brine, dried over Na$_2$SO$_4$ and concentrated in vacuo to obtain crude product. This was purified by trituration with diethyl ether/n-pentane mixture to obtain pure 1-13 (0.050 g, 65.84%). MS(ES): m/z 455.54 [M+H]$^+$, LCMS purity: 100.00%, HPLC purity: 98.91%, 1H NMR (MeOD, 400 MHz): 8.51 (s, 1H), 7.88 (s, 1H), 7.72-7.70 (d, J=7.6 Hz, 1H), 7.64-7.62 (d, J=8 Hz, 1H), 7.33-7.29 (t, J=7.6 Hz, 1H), 7.00 (t, 1H), 4.04 (s, 3H), 3.73-3.68 (s, 3H), 1.88 (s, 1H), 0.99-0.97 (m, 2H), 0.91-0.88 (m, 2H).

Example 1: Synthesis of N-(7-((2-methoxy-3-(1-methyl-1H-1,2,4-triazol-3-yl)phenyl)amino)-3H-imidazo[4,5-b]pyridin-5-yl)cyclopropanecarboxamide, I-1

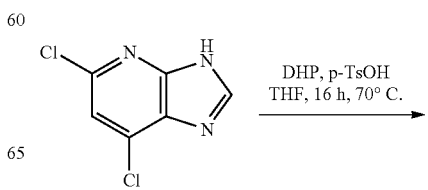

-continued

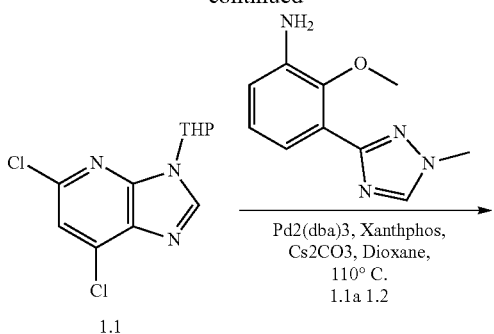

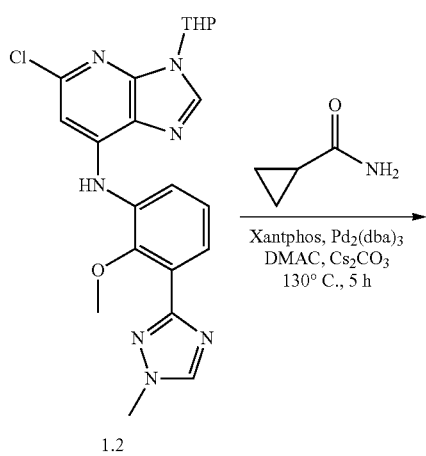

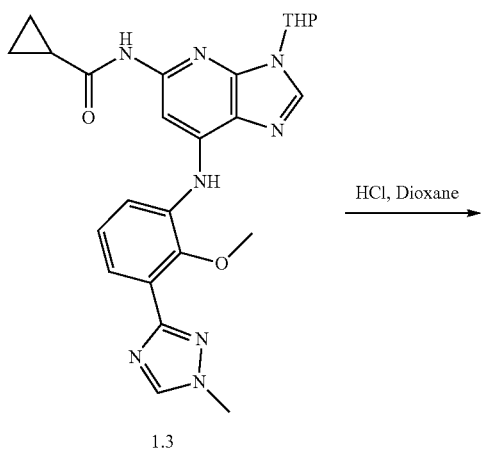

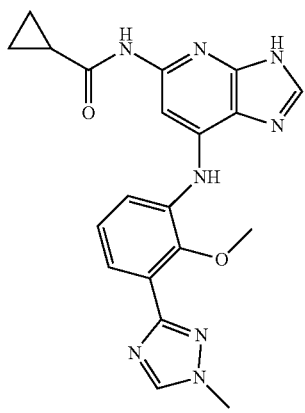

Synthesis of Compound 1.1.

To 5,7-dichloro-3Himidazo[4,5-b]pyridine (3.5 g, 18.62 mmol, 1.0 eq) in tetrahydrofuran (35 mL) was added 3,4-dihydro-2H-pyran (4.69 g, 55.85 mmol, 3.0 eq) followed by addition of p-Toluenesulfonic acid (0.708 g, 3.72 mmol, 0.2 eq). Reaction mixture was heated at 70° C. for 16 h. Upon completion, reaction mixture was concentrated in vacuo to obtain crude product. This was purified by column chromatography and the product was eluted in 15% ethyl acetate in hexane to obtain 1.1 (1.8 g, 35.53%). MS(ES): m/z 273.2 [M]+.

Synthesis of Compound 1.2.

To 1.1 (0.5 g, 1.84 mmol, 1.0 eq) in 1,4-dioxane (5 mL) was added 2-methoxy-3-(1-methyl-1H-1,2,4-triazol-3-yl)aniline (1.1a, 0.338 g, 1.66 mmol, 0.9 eq), $Cs_2CO_3$ (1.8 g, 5.53 mmol, 3.0 eq). The reaction mixture was degassed for 10 min. under argon atmosphere, then $Pd_2(dba)_3$ (0.169 g, 0.184 mmol, 0.1 eq) and Xantphos (0.214 g, 0.369 mmol, 0.2 eq) were added, again degassed for 5 min. The reaction was then heated at 110° C. for 6 h. Upon completion, reaction mixture was cooled to r.t., transferred in water and product was extracted with ethyl acetate. Organic layers were combined, washed with brine, dried over $Na_2SO_4$ and concentrated in vacuo to obtain crude product. [Three batches were taken with same quantity]. Combined crude material was purified by combi flash using 2% MeOH in $CH_2Cl_2$ as eluant to get material which was purified by reverse phase HPLC to obtain pure 1.2 (0.7 g, 28.87%). MS(ES): m/z 440.9 [M]+.

Synthesis of Compound 1.3.

To 1.2 (0.090 g, 0.204 mmol, 1.0 eq) in DMAc (2 mL) was added cyclopropanecarboxamide (0.052 g, 0.613 mmol, 3.0 eq), $Cs_2CO_3$ (0.267 g, 0.818 mmol, 4.0 eq). The reaction mixture was degassed for 10 min. under argon atmosphere, then $Pd_2(dba)_3$ (0.019 g, 0.020 mmol, 0.1 eq) and Xantphos (0.024 g, 0.040 mmol, 0.2 eq) were added, again degassed for 5 min. The reaction was stirred at 130° C. for 5 h. Upon completion, reaction mixture was cooled to r.t., transferred in water and product was extracted with ethyl acetate. Organic layers were combined, washed with brine, dried over $Na_2SO_4$ and concentrated in vacuo to obtain crude product. This was purified by combi flash using 3% MeOH in $CH_2Cl_2$ as eluant to obtain pure 1.3 (0.050 g, 50%). MS(ES): m/z 489.6 [M]+.

Synthesis of I-1.

To a solution of 1.3 (0.050 g, 0.102 mmol, 1.0 eq) in $CH_2Cl_2$ (2 mL) was added HCl, 4M in 1,4-dioxane (1 mL) at 0° C. The reaction mixture was stirred at r.t. for 2 h. Upon completion, reaction mixture transferred in saturated $NaHCO_3$ solution and product was extracted with $CH_2Cl_2$. Organic layers were combined, washed with brine, dried over $Na_2SO_4$ and concentrated in vacuo to obtain crude product. This was purified by combi flash using 5% MeOH in $CH_2Cl_2$ as eluant to obtain pure I-1 (0.017 g, 41%). MS(ES): m/z 405.48 [M+H]$^+$, LCMS purity: 100%, HPLC purity: 99.42%, 1H NMR (DMSO, 400 MHz): 12.61 (s, 1H), 10.51 (s, 1H), 8.53 (s, 1H), 8.34-8.32 (d, J=8 Hz, 1H), 8.18 (s, 1H), 8.02 (s, 1H), 7.82 (s, 1H), 7.37-7.35 (m, 1H), 7.16-7.09 (m, 1H), 3.94 (s, 3H), 3.71 (s, 3H), 2.35-2.34 (m, 1H), 0.84-0.83 (m, 4H).

Example 2: Synthesis of N5-(5-fluoro-4-methylpyridin-2-yl)-N7-(2-methoxy-3-(1-methyl-1H-1,2,4-triazol-3-yl)phenyl)-3H-imidazo[4,5-b]pyridine-5,7-diamine, I-2

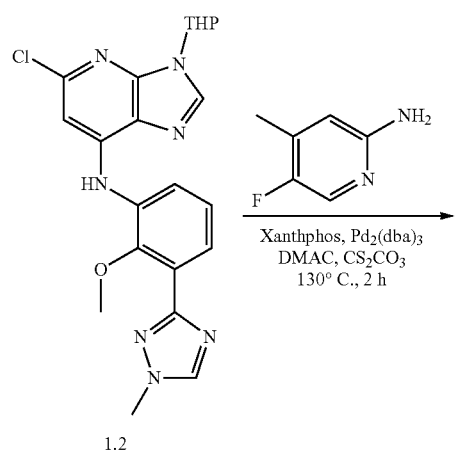

Synthesis of Compound 2.1.

To compound 1.2 (0.100 g, 0.227 mmol, 1.0 eq) in DMAc (2 mL) was added 5-fluoro-4-methylpyridin-2-amine (0.034 g, 0.273 mmol, 1.2 eq), $Cs_2CO_3$ (0.297 g, 0.911 mmol, 4.0 eq). The reaction mixture was degassed for 10 min. under argon atmosphere, then $Pd_2(dba)_3$ (0.021 g, 0.022 mmol, 0.1 eq) and Xantphos (0.026 g, 0.045 mmol, 0.2 eq) were added, again degassed for 5 min. The reaction was stirred at 130° C. for 2 h. Upon completion, reaction mixture was cooled to r.t., transferred in water and product was extracted with ethyl acetate. Organic layers were combined, washed with brine, dried over $Na_2SO_4$ and concentrated in vacuo to obtain crude product. This was purified by combi flash using 3% MeOH in $CH_2Cl_2$ as eluant to obtain pure 2.1 (0.080 g, 66.45%). MS(ES): m/z 530.6 [M]+.

Synthesis of I-2.

To a solution of 2.1 (0.080 g, 0.151 mmol, 1.0 eq) in $CH_2Cl_2$ (2 mL) was added HCl, 4M in 1,4-dioxane (1 mL) at 0° C. The reaction mixture was stirred at r.t. for 2 h. Upon completion, reaction mixture transferred in saturated $NaHCO_3$ solution and product was extracted with $CH_2Cl_2$. Organic layers were combined, washed with brine, dried over $Na_2SO_4$ and concentrated in vacuo to obtain crude product. This was purified by combi flash using 5% MeOH in $CH_2Cl_2$ as eluant to obtain pure 1-2. (0.045 g, 66.8%). MS(ES): m/z 446.53 [M+H]+, LCMS purity: 99.41%, HPLC purity: 99.31%, 1H NMR (DMSO, 400 MHz): 11.12 (s, 1H), 10.27 (s, 1H), 8.68 (s, 1H), 8.62 (s, 1H), 8.33 (s, 1H), 7.87-7.85 (d, J=6.8 Hz, 1H), 7.55-7.54 (d, J=6.8 Hz, 1H), 7.40-7.36 (m, 1H), 7.09-7.08 (d, J=4.8 Hz, 1H), 6.23 (s, 1H), 3.97 (s, 3H), 3.73 (s, 3H), 2.31 (s, 3H).

Example 3: Synthesis of N5-(2,6-dimethylpyrimidin-4-yl)-N7-(2-methoxy-3-(1-methyl-1H-1,2,4-triazol-3-yl)phenyl)-3H-imidazo[4,5-b]pyridine-5,7-diamine, I-3

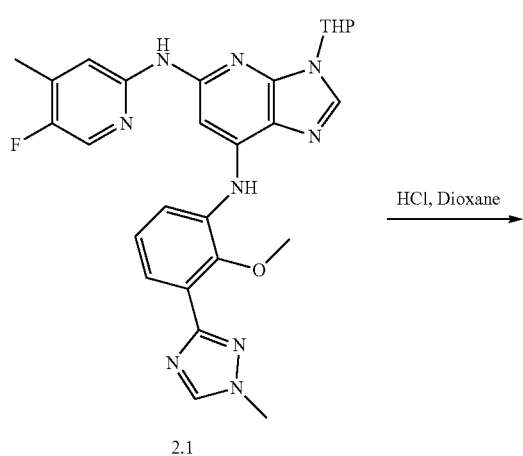

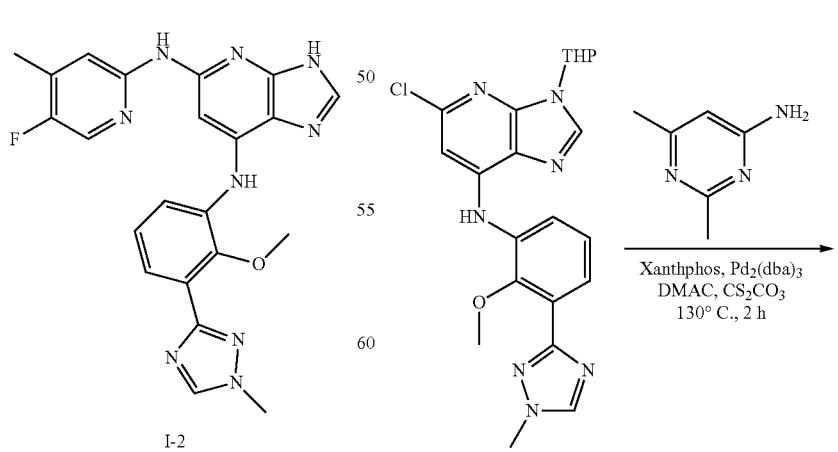

-continued

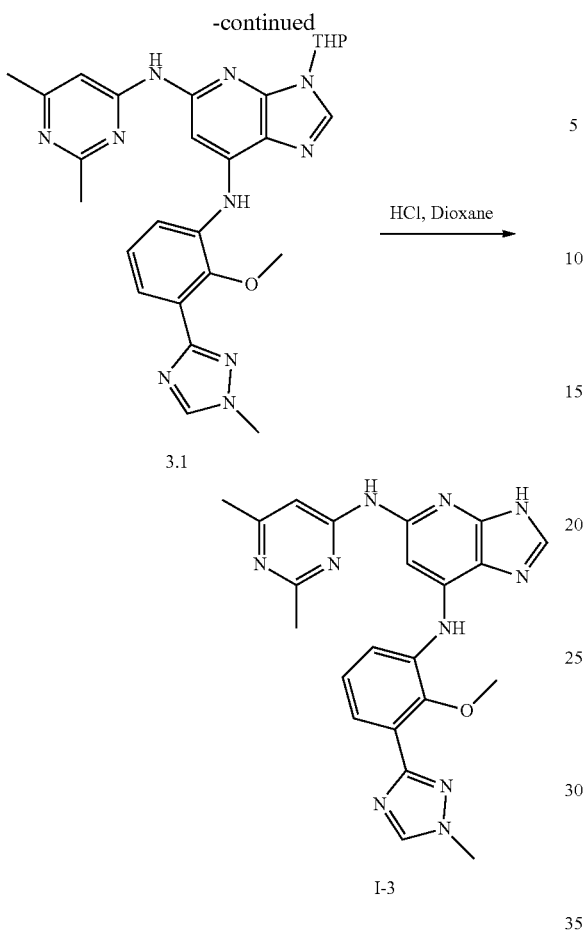

3.1

I-3

Synthesis of Compound 3.1.

To compound 1.2 (0.100 g, 0.227 mmol, 1.0 eq) in DMAc (2 mL) was added 2,6-dimethylpyrimidin-4-amine (0.034 g, 0.273 mmol, 1.2 eq), $Cs_2CO_3$ (0.297 g, 0.911 mmol, 4.0 eq). The reaction mixture was degassed for 10 min. under argon atmosphere, then $Pd_2(dba)_3$ (0.021 g, 0.022 mmol, 0.1 eq) and Xantphos (0.026 g, 0.045 mmol, 0.2 eq) were added, again degassed for 5 min. The reaction was stirred at 130° C. for 2 h. Upon completion, reaction mixture was cooled to r.t., transferred in water and product was extracted with ethyl acetate. Organic layers were combined, washed with brine, dried over $Na_2SO_4$ and concentrated in vacuo to obtain crude product. This was purified by combi flash using 5% MeOH in $CH_2Cl_2$ as eluant to obtain pure 3.1 (0.080 g, 66.83%). MS(ES): m/z 527.6 [M]+.

Synthesis of I-3.

To a solution of 3.1 (0.080 g, 0.151 mmol, 1.0 eq) in $CH_2Cl_2$ (2 mL) was added HCl, 4M in 1,4-dioxane (1 mL) at 0° C. The reaction mixture was stirred at r.t. for 2 h. Upon completion, reaction mixture transferred in saturated $NaHCO_3$ solution and product was extracted with $CH_2Cl_2$. Organic layers were combined, washed with brine, dried over $Na_2SO_4$ and concentrated in vacuo to obtain crude product. This was purified by combi flash using 7% MeOH in $CH_2Cl_2$ as eluant to obtain pure 1-3. (0.050 g, 74.38%). MS(ES): m/z 443.5 [M+H]+, LCMS purity: 100%, HPLC purity: 98.6%, 1H NMR (DMSO, 400 MHz): 11.51 (s, 1H), 9.68 (s, 1H), 9.47 (s, 1H), 8.64 (s, 1H), 7.80-7.78 (d, J=6.4 Hz, 1H), 7.54-7.53 (d, J=7.6 Hz, 2H), 7.40-7.32 (m, 2H), 3.96 (s, 3H), 3.71 (s, 3H), 2.50 (s, 6H).

Example 4: Synthesis of N7-(2-methoxy-3-(1-methyl-1H-1,2,4-triazol-3-yl)phenyl)-N5-(6-methylpyridazin-3-yl)-3H-imidazo[4,5-b]pyridine-5,7-diamine, I-4

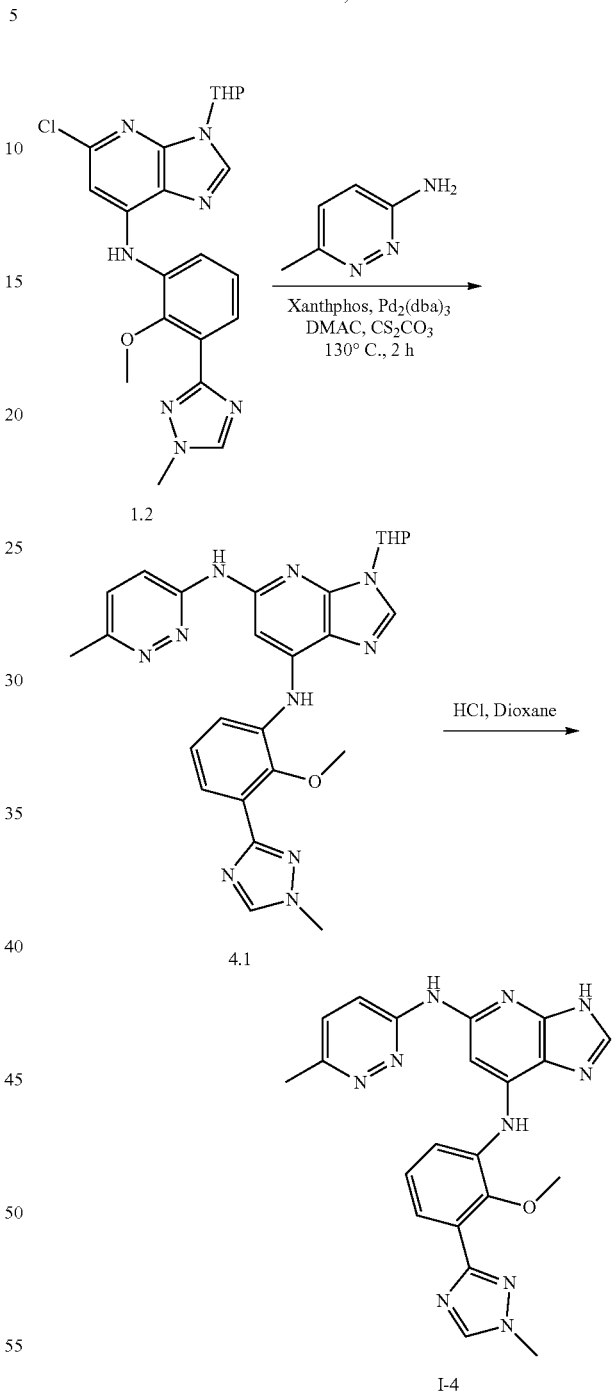

Synthesis of Compound 4.1.

To compound 1.2 (0.100 g, 0.227 mmol, 1.0 eq) in DMAc (2 mL) was added 6-methylpyridazin-3-amine (0.030 g, 0.273 mmol, 1.2 eq), $Cs_2CO_3$ (0.297 g, 0.91 mmol, 4.0 eq). The reaction mixture was degassed for 10 min. under argon atmosphere, then $Pd_2(dba)_3$ (0.021 g, 0.022 mmol, 0.1 eq) and Xantphos (0.026 g, 0.045 mmol, 0.2 eq) were added, again degassed for 5 min. The reaction was stirred at 130° C. for 2 h. Upon completion, reaction mixture was cooled to r.t., transferred in water and product was extracted with ethyl acetate. Organic layers were combined, washed with brine, dried over Na$_2$SO$_4$ and concentrated in vacuo to obtain crude product. This was purified by combi flash using 5% MeOH in CH$_2$Cl$_2$ as eluant to obtain pure 4.1 (0.070 g, 60%). MS(ES): m/z 513.5 [M]+.

Synthesis of I-4.

To a solution of 4.1 (0.070 g, 0.136 mmol, 1.0 eq) in CH$_2$Cl$_2$ (2 mL) was added HCl, 4M in 1,4-dioxane (1 mL) at 0° C. The reaction mixture was stirred at r.t. for 2 h. Upon completion, reaction mixture transferred in saturated NaHCO$_3$ solution and product was extracted with CH$_2$Cl$_2$. Organic layers were combined, washed with brine, dried over Na$_2$SO$_4$ and concentrated in vacuo to obtain crude product. This was purified by combi flash using 8% MeOH in CH$_2$Cl$_2$ as eluant to obtain pure I-4. (0.035 g, 59.82%). MS(ES): m/z 429.43 [M+H]+, LCMS purity: 95.39%, HPLC purity: 95.73%, 1H NMR (DMSO, 400 MHz): 11.79 (s, 1H), 9.79 (s, 1H), 9.15 (s, 1H), 8.64 (s, 1H), 8.11 (s, 1H), 8.02-7.99 (d, J=9.2 Hz, 1H), 7.82-7.80 (d, J=7.6 Hz, 1H), 7.54-7.52 (d, J=7.2 Hz, 2H), 7.38-7.34 (t, 1H), 6.58 (s, 1H), 3.96 (s, 3H), 3.77 (s, 3H), 3.72 (s, 3H)

Example 5: (2-((7-((2-methoxy-3-(1-methyl-1H-1,2,4-triazol-3-yl)phenyl)amino)-3H-imidazo[4,5-b]pyridin-5-yl)amino)pyridin-4-yl)MeOH, I-5

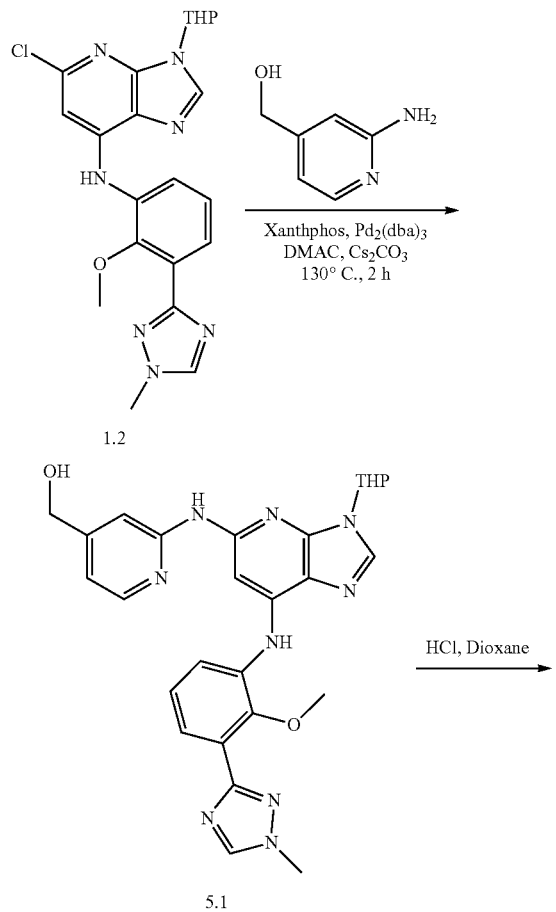

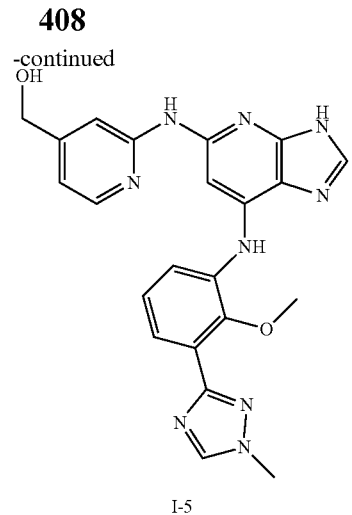

I-5

Synthesis of Compound 5.1.

To compound 1.2 (0.100 g, 0.227 mmol, 1.0 eq) in DMAc (2 mL) was added (2-aminopyridin-4-yl)MeOH (0.034 g, 0.273 mmol, 1.2 eq), Cs$_2$CO$_3$ (0.297 g, 0.911 mmol, 4.0 eq). The reaction mixture was degassed for 10 min. under argon atmosphere, then Pd$_2$(dba)$_3$ (0.021 g, 0.022 mmol, 0.1 eq) and Xantphos (0.026 g, 0.045 mmol, 0.2 eq) were added, again degassed for 5 min. The reaction was stirred at 130° C. for 2 h. Upon completion, reaction mixture was cooled to r.t., transferred in water and product was extracted with ethyl acetate. Organic layers were combined, washed with brine, dried over Na$_2$SO$_4$ and concentrated in vacuo to obtain crude product. This was purified by combi flash using 7% MeOH in CH$_2$Cl$_2$ as eluant to obtain pure 5.1 (0.075 g, 62.5%). MS(ES): m/z 528.5 [M]+.

Synthesis of I-5.

To a solution of 5.1 (0.075 g, 0.136 mmol, 1.0 eq) in CH$_2$Cl$_2$ (2 mL) was added HCl, 4M in 1,4-dioxane (1 mL) at 0° C. The reaction mixture was stirred at r.t. for 2 h. Upon completion, reaction mixture transferred in sat. NaHCO$_3$ solution and product was extracted with CH$_2$Cl2. Organic layers were combined, washed with brine, dried over Na$_2$SO$_4$ and concentrated in vacuo to obtain crude product. This was purified by combi flash using 10% MeOH in CH$_2$Cl$_2$ as eluant to obtain pure I-5. (0.030 g, 47.6%). MS(ES): m/z 444.53[M+H]$^+$, LCMS purity: 95%, HPLC purity: 98.42%, 1H NMR (DMSO, 400 MHz): 11.72 (s, 1H), 9.87 (s, 1H), 9.03 (s, 1H), 8.64 (s, 1H), 8.31-8.30 (d, J=6.4 Hz, 1H), 7.84-7.82 (d, J=7.6 Hz, 1H), 7.55-7.53 (d, J=7.6 Hz, 1H), 7.38-7.34 (t, 1H), 7.29 (s, 1H), 7.16-7.15 (d, J=6 Hz, 1H), 6.33 (s, 1H), 4.63 (s, 2H), 3.96 (s, 3H), 3.72 (s, 3H).

Example 6: N7-(2-methoxy-3-(1-methyl-1H-1,2,4-triazol-3-yl)phenyl)-N5-(5-piperidin-1-yl)pyridin-2-yl)-3H-imidazo[4,5-b]pyridine-5,7-diamine, I-6

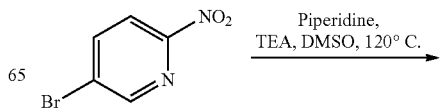

-continued

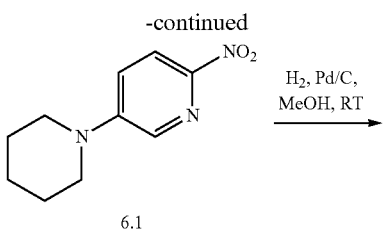

6.1

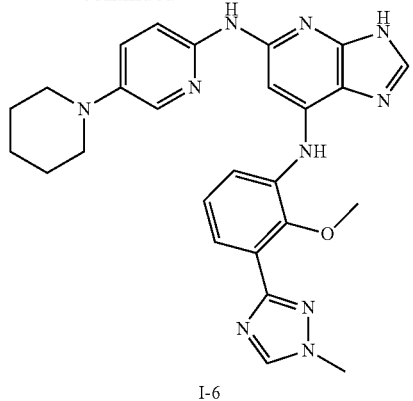

I-6

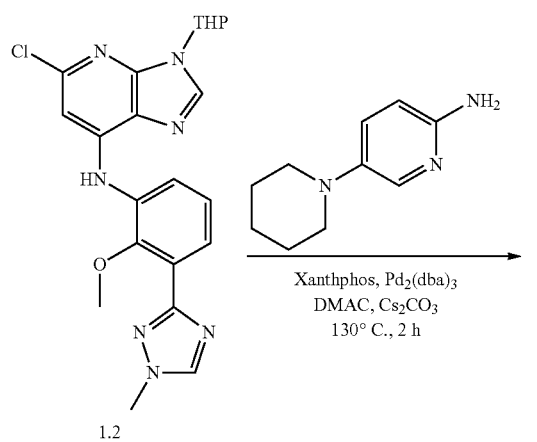

1.2

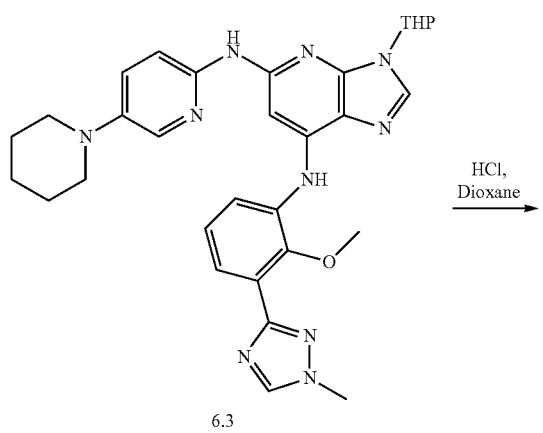

6.3

Synthesis of Compound 6.1.

To a solution of 5-bromo-2-nitropyridine (2.0 g, 9.85 mmol, 1.0 eq), piperidine (1.674 g, 19.7 mmol, 2.0 eq) and triethyl amine (1.09 g, 10.83 mmol, 1.1 eq) in dimethyl sulfoxide (20 mL) was added. Reaction mixture was stirred at 120° C. for 16 h. Upon completion, reaction mixture was transferred into water and extracted with ethyl acetate. Organic layers were combined, dried over $Na_2SO_4$ and concentrated in vacuo to obtain crude product. This was purified by column chromatography and compound was eluted in 20% ethyl acetate in hexane as eluant to obtain pure 6.1 (1.1 g, 53.88%). MS(ES): m/z 208.23 $[M+H]^+$.

Synthesis of Compound 6.2.

To a solution of 6.1 (1.1 g, 5.31 mmol, 1.0 eq) in MeOH (10 mL), 10% Pd/C (0.2 g) was added. Hydrogen was purged through reaction mixture for 4 h. Upon completion, reaction mixture was filtered through celite-bed and washed with MeOH. Filtrate was concentrated in vacuo to obtain 6.2. (0.7 g, 74.40%). MS(ES): m/z 178.25 $[M+H]^+$.

Synthesis of Compound 6.3.

To compound 1.2 (0.100 g, 0.227 mmol, 1.0 eq) in DMAc (2 mL) was added 6.1 (0.048 g, 0.273 mmol, 1.2 eq), $Cs_2CO_3$ (0.297 g, 0.911 mmol, 4.0 eq). The reaction mixture was degassed for 10 min. under argon atmosphere, then $Pd_2(dba)_3$ (0.021 g, 0.022 mmol, 0.1 eq) and Xantphos (0.026 g, 0.045 mmol, 0.2 eq) were added, again degassed for 5 min. The reaction was stirred at 130° C. for 2 h. Upon completion, reaction mixture was cooled to r.t., transferred in water and product was extracted with ethyl acetate. Organic layers were combined, washed with brine, dried over $Na_2SO_4$ and concentrated in vacuo to obtain crude product. This was purified by combi flash using 6% MeOH in $CH_2Cl_2$ as eluant to obtain pure 6.3. (0.060 g, 45.5%). MS(ES): m/z 581.7 [M]+.

Synthesis of I-6.

To a solution of 6.3 (0.060 g, 0.103 mmol, 1.0 eq) in $CH_2Cl_2$ (2 mL) was added HCl, 4M in 1,4-dioxane (1 mL) at 0° C. The reaction mixture was stirred at r.t. for 2 h. Upon completion, reaction mixture transferred in saturated $NaHCO_3$ solution and product was extracted with $CH_2Cl_2$. Organic layers were combined, washed with brine, dried over $Na_2SO_4$ and concentrated in vacuo to obtain crude product. This was purified by combi flash using 8% MeOH in $CH_2Cl_2$ as eluant to obtain pure I-6. (0.030 g, 58.5%). MS(ES): m/z 497.65 $[M+H]^+$, LCMS purity: 98.2%, HPLC purity: 98%, 1H NMR (DMSO, 400 MHz): 11.28 (s, 1H), 9.99 (s, 1H), 8.91 (s, 1H), 8.65 (s, 1H), 8.26 (s, 1H), 8.10-8.08 (d, J=7.2 Hz, 1H), 7.84-7.83 (d, J=6.8 Hz, 1H), 7.55-7.53 (d, J=6.8 Hz, 1H), 7.38-7.34 (t, J=6.8 Hz, 1H), 6.33 (s, 1H), 4.63 (s, 2H), 3.96 (s, 3H), 3.73 (s, 3H), 3.30 (bs, 4H), 1.96 (bs, 4H), 1.60 (bs, 2H).

Example 7: Synthesis of N7-(2-methoxy-3-(1-methyl-1H-1,2,4-triazol-3-yl)phenyl)-N5-(5-morpholinopyridin-2-yl)-3H-imidazo[4,5-b]pyridine-5,7-diamine, I-7

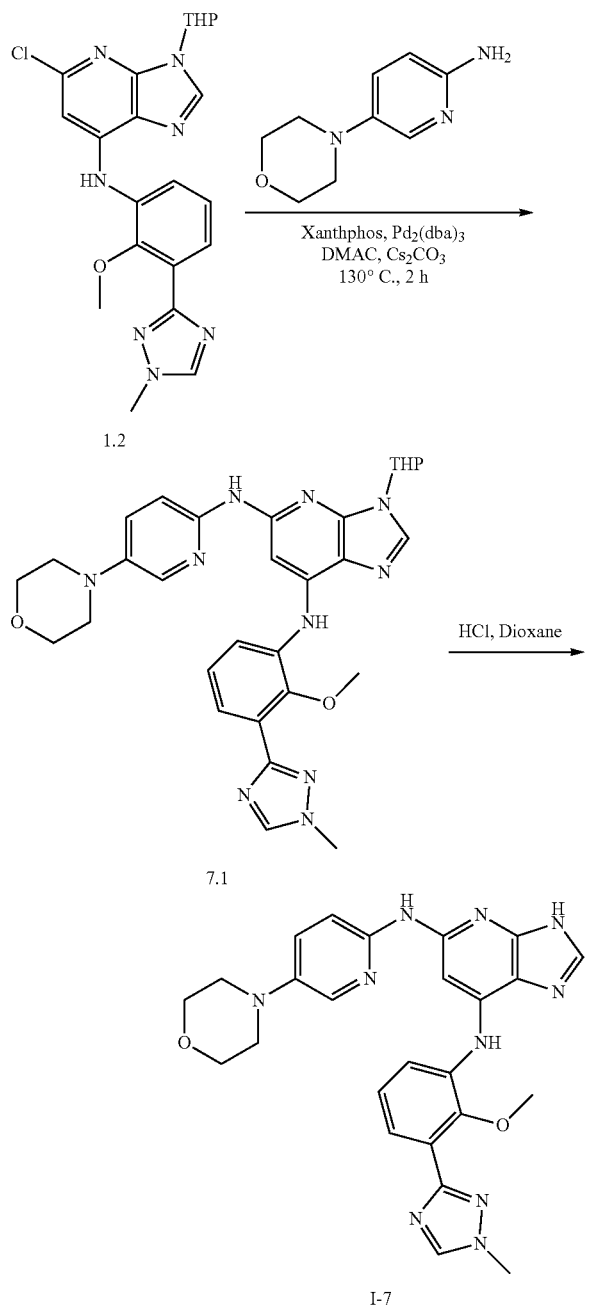

Synthesis of Compound 7.1.

To compound 1.2 (0.100 g, 0.227 mmol, 1.0 eq) in DMAc (2 mL) was added 5-morpholinopyridin-2-amine (0.049 g, 0.273 mmol, 1.2 eq), $Cs_2CO_3$ (0.297 g, 0.91 mmol, 4.0 eq). The reaction mixture was degassed for 10 min. under argon atmosphere, then $Pd_2(dba)_3$ (0.021 g, 0.022 mmol, 0.1 eq) and Xantphos (0.026 g, 0.045 mmol, 0.2 eq) were added, again degassed for 5 min. The reaction was stirred at 130° C. for 2 h. Upon completion, reaction mixture was cooled to r.t., transferred in water and product was extracted with ethyl acetate. Organic layers were combined, washed with brine, dried over $Na_2SO_4$ and concentrated in vacuo to obtain crude product. This was purified by combi flash using 6% MeOH in $CH_2Cl_2$ as eluant to obtain pure 7.1 (0.058, 43.79%). MS(ES): m/z 583.7 [M]+.

Synthesis of I-7.

To a solution of 7.1 (0.058 g, 0.099 mmol, 1.0 eq) in $CH_2Cl_2$ (2 mL) was added HCl, 4M in 1,4-dioxane (1 mL) at 0° C. The reaction mixture was stirred at r.t. for 2 h. Upon completion, reaction mixture transferred in saturated $NaHCO_3$ solution and product was extracted with $CH_2Cl_2$. Organic layers were combined, washed with brine, dried over $Na_2SO_4$ and concentrated in vacuo to obtain crude product. This was purified by combi flash using 8% MeOH in $CH_2Cl_2$ as eluant to obtain pure 1-7. (0.020 g, 40.3%). MS(ES): m/z 499.68 [M+H]+, LCMS purity: 100%, HPLC purity: 98.3%, 1H NMR (DMSO, 400 MHz): 10.98 (s, 1H), 9.91 (s, 1H), 8.59 (s, 1H), 8.39 (s, 1H), 8.09-8.02 (m, 1H), 7.76 (bs, 1H), 7.63-7.56 (m, 2H), 7.34 (bs, 1H), 7.04 (s, 1H), 6.13 (s, 1H), 3.96 (s, 3H), 3.76 (bs, 4H), 3.73 (s, 3H), 3.11 (bs, 4H).

Example 8: Synthesis of N7-(2-methoxy-3-(1-methyl-1H-1,2,4-triazol-3-yl)phenyl)-N5-(1-methyl-1H-pyrazol-3-yl)-3H-imidazo[4,5-b]pyridine-5,7-diamine, I-8

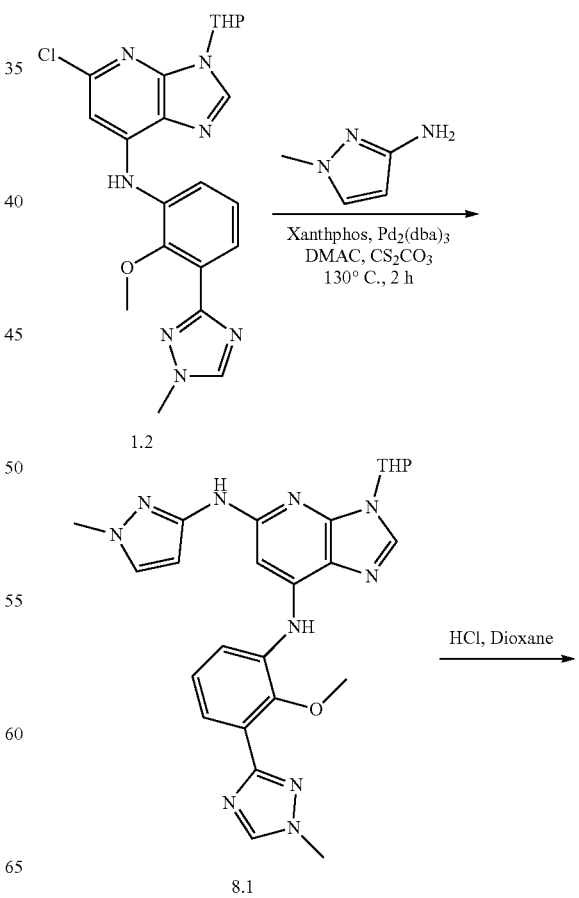

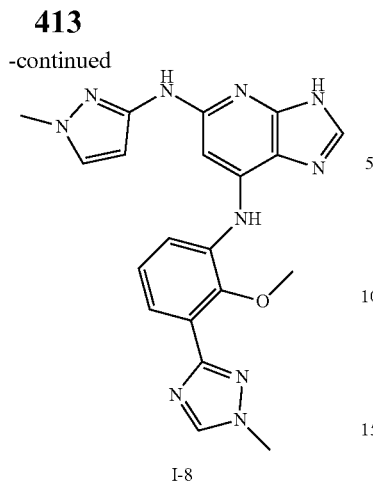

I-8

Synthesis of Compound 8.1.

To compound 1.2 (0.100 g, 0.227 mmol, 1.0 eq) in DMAc (2 mL) was added 1-methyl-1H-pyrazol-3-amine (0.026 g, 0.273 mmol, 1.2 eq), Cs$_2$CO$_3$ (0.297 g, 0.911 mmol, 4.0 eq). The reaction mixture was degassed for 10 min. under argon atmosphere, then Pd$_2$(dba)$_3$ (0.021 g, 0.022 mmol, 0.1 eq) and Xantphos (0.026 g, 0.045 mmol, 0.2 eq) were added, again degassed for 5 min. The reaction was stirred at 130° C. for 2 h. Upon completion, reaction mixture was cooled to r.t., transferred in water and product was extracted with ethyl acetate. Organic layers were combined, washed with brine, dried over Na$_2$SO$_4$ and concentrated in vacuo to obtain crude product. This was purified by combi flash using 5% MeOH in CH$_2$Cl$_2$ as eluant to obtain pure 8.1 (0.055, 48.3%). MS(ES): m/z 501.5 [M]+.

Synthesis of I-8.

To a solution of 8.1 (0.055 g, 0.109 mmol, 1.0 eq) in CH$_2$Cl$_2$ (2 mL) was added HCl, 4M in 1,4-dioxane (1 mL) at 0° C. The reaction mixture was stirred at r.t. for 2 h. Upon completion, reaction mixture transferred in saturated NaHCO$_3$ solution and product was extracted with CH$_2$Cl2. Organic layers were combined, washed with brine, dried over Na$_2$SO$_4$ and concentrated in vacuo to obtain crude product. This was purified by combi flash using 8% MeOH in CH$_2$Cl$_2$ as eluant to obtain pure 1-8. (0.040 g, 87.2%). MS(ES): m/z 417.43 [M+H]$^+$, LCMS purity: 100%, HPLC purity: 96.37%, 1H NMR (DMSO, 400 MHz): 10.55 (s, 1H), 10.12 (s, 1H), 8.66 (s, 1H), 8.55 (s, 1H), 7.84-7.82 (d, J=7.2 Hz, 1H), 7.70 (s, 1H), 7.55-7.53 (d, J=7.6 Hz, 1H), 7.38-7.34 (t, 1H), 6.25 (s, 1H), 5.99 (s, 1H), 3.96 (s, 3H), 3.82 (s, 3H), 3.72 (s, 3H).

Example 9: Synthesis of N-(2-cyclopropyl-7-((2-methoxy-3-(1-methyl-1H-1,2,4-triazol-3-yl)phenyl)amino)-3H-imidazo[4,5-b]pyridin-5-yl)cyclopropanecarboxamide, I-9

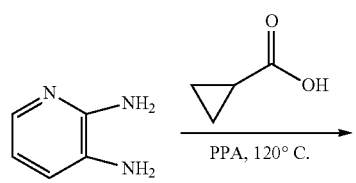

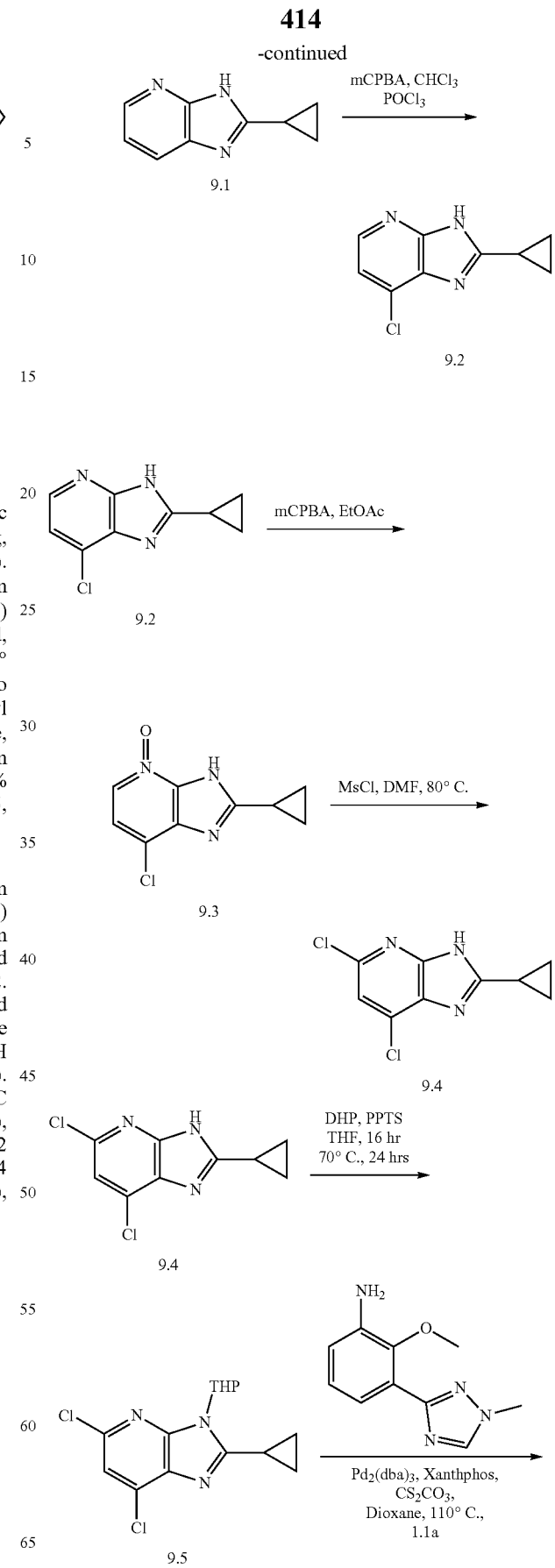

-continued

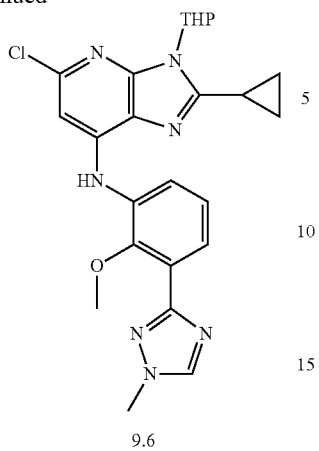

9.6

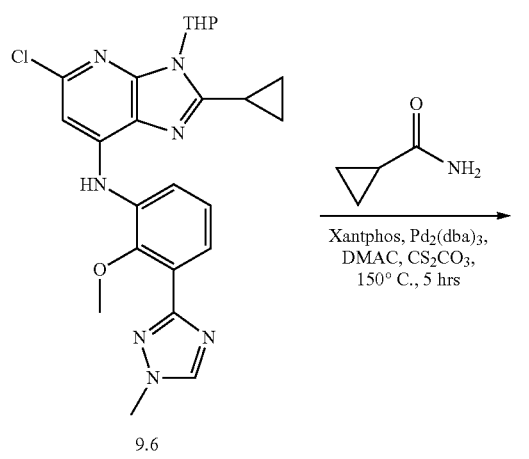

9.6

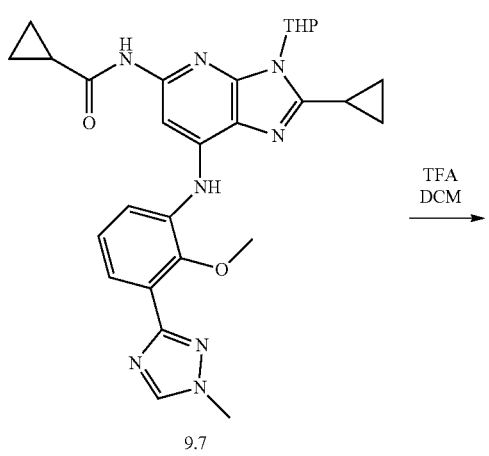

9.7

-continued

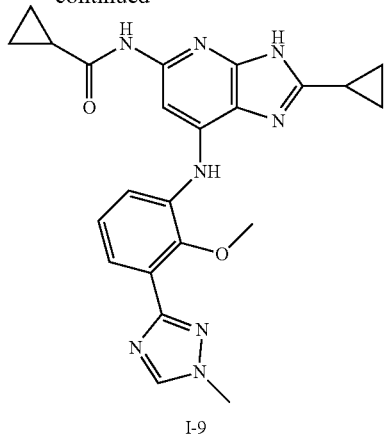

I-9

Synthesis of Compound 9.1.

To a mixture of pyridine-2,3-diamine (5.0 g, 46.0 mmol, 1.0 eq) and cyclopropanecarboxylic acid (3.9 g, 46.0 mmol, 1.0 eq), Polyphosphoric acid (50 mL, 10V) was added. Reaction mixture was stirred at 120° C. for 4 h. Upon completion, reaction mixture was transferred into cold water and the pH of the solution was adjusted to 6-7 by adding 2N sodium hydroxide and then extracted with ethyl acetate. Organic layers were combined, dried over $Na_2SO_4$ and concentrated in vacuo to obtain crude product. This was purified by column chromatography and compound was eluted in 2.5% MeOH in $CH_2Cl_2$ as eluant to obtain pure 9.1 (2.5 g, 34.28%). MS(ES): m/z 160.21 $[M+H]^+$.

Synthesis of Compound 9.2.

To a solution of 9.1 (3.0 g, 18.87 mmol, 1.0 eq) in chloroform (42 mL), meta-chloroperoxybenzoic acid (3.58 g, 20.75 mmol, 1.1 eq) was added. Reaction mixture was stirred at r.t. for 5 h. Reaction mixture was transferred into water and extracted with ethyl acetate. Aqueous layer was concentrated, residue was dissolved in chloroform and phosphorous oxychloride (16 mL) was added. Reaction mixture was stirred at r.t. for 2 h. Reaction mixture was transferred in crushed ice, neutralized with aqueous ammonia and extracted with ethyl acetate. Organic layers were combined, dried over $Na_2SO_4$ and concentrated in vacuo to obtain 9.2 (1.0 g, 82.21%). MS(ES): m/z 194.56 $[M+H]^+$.

Synthesis of Compound 9.3.

To compound 9.2 (0.400 g, 2.066 mmol, 1.0 eq) in ethyl acetate (5 mL), meta-chloroperoxybenzoic acid (0.392 g, 2.273 mmol, 1.1 eq) was added within 15 min at 0° C. The reaction mixture was stirred at r.t. for 24 hrs. The resulting solid formed was collected by filtration and washed with ethyl acetate to obtain pure 9.3 (0.250 g, 57.7%). MS(ES): m/z 210.94 [M]+.

Synthesis of Compound 9.4.

To compound 9.3 (0.250 g, 1.190 mmol, 1.0 eq) in dimethylformamide (1.5 mL), mesyl chloride (0.190 g, 2.273 mmol, 1.4 eq) was added at 50° C. The reaction mixture was stirred at 80° C. for 3 hrs. After completion of the reaction, the reaction mixture was cooled to 0° C., and treated with 10N sodium hydroxide to adjust pH to 7 and then extracted with ethyl acetate. Organic layers were combined, dried over $Na_2SO_4$ and concentrated in vacuo to obtain crude product. This was purified by column chromatography and compound was eluted in 1.5% MeOH in $CH_2Cl_2$ as eluant to obtain pure 9.4 (0.120 g, 44.12%). MS(ES): m/z 229.28 $[M+H]^+$.

Synthesis of Compound 9.5.

To a solution of 9.4 (0.1 g, 43.8 mmol, 1.0 eq) in dry tetrahydrofuran (2 mL) 3,4-Dihydro-2H-pyran (0.075 g, 87.7 mmol, 2.0 eq) was added, followed by Pyridinium p-toluenesulfonate (0.016 g, 6.5 mmol, 0.1 eq) and stirred. Reaction mixture was heated at 70° C. for 16 h. Upon completion, reaction mixture was concentrated in vacuo to obtain crude product. This was purified by column chromatography and the compound was eluted in 15% ethyl acetate in hexane to obtain pure 9.5 (0.130 g, 51.14%). MS(ES): m/z 313.58 [M+H]+.

Synthesis of Compound 9.6.

Compound 9.6 was synthesized from 9.5 and 1.1a using general procedure A. (Yield: 27.10%). MS(ES): m/z 480.23 [M+H]+.

Synthesis of Compound 9.7.

Compound 9.7 was synthesized from 9.6 and cyclopropanecarboxamide using general procedure B. (Yield: 50.85%). MS(ES): m/z 529.84 [M+H]+.

Synthesis of I-9.

Compound I-9 was synthesized using from 9.7 general procedure C. (Yield: 42.47%). MS(ES): m/z 445.63 [M+H]+, LCMS purity: 95.03%, HPLC purity: 95.01%, 1H NMR (MeOD, 400 MHz): 10.55 (s, 1H), 8.51 (s, 1H), 7.82 (s, 1H), 7.69-7.67 (d, J=8 Hz, 1H), 7.57-7.56 (d, J=4 Hz, 1H), 7.29-7.25 (t, 1H), 3.99 (s, 3H), 3.77 (s, 3H), 2.22-2.15 (m, 1H), 1.85 (m, 1H), 1.20-1.16 (m, 4H), 0.97-0.94 (m, 4H).

Example 10: Synthesis of N-(2-(hydroxymethyl)-7-((2-methoxy-3-(1-methyl-1H-1,2,4-triazol-3-yl)phenyl)amino)-3H-imidazo[4,5-b]pyridin-5-yl)cyclopropanecarboxamide, I-10

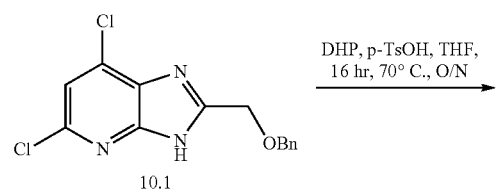

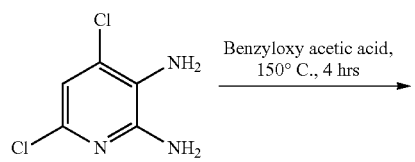

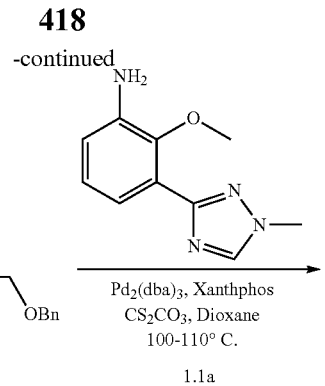

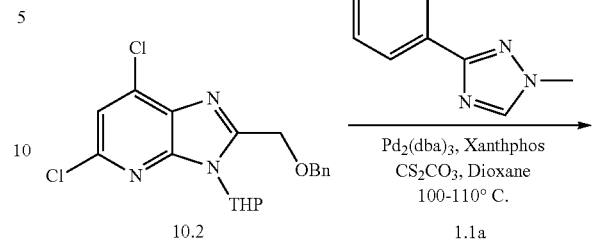

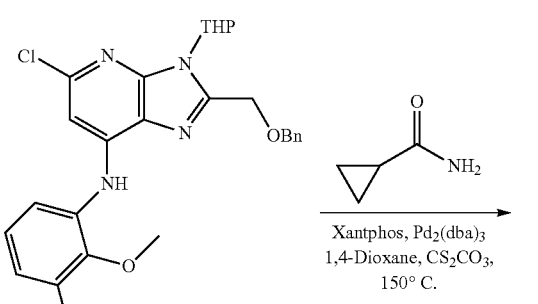

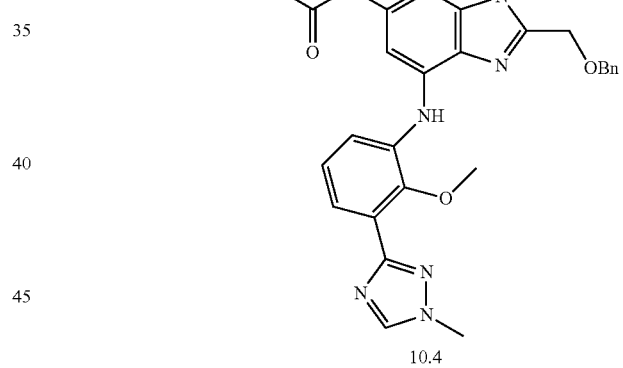

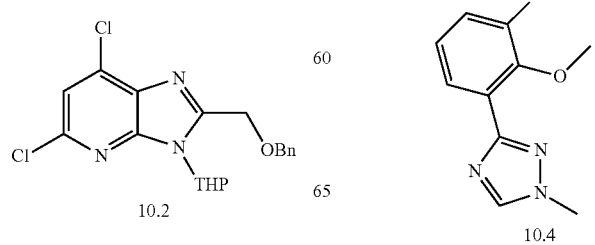

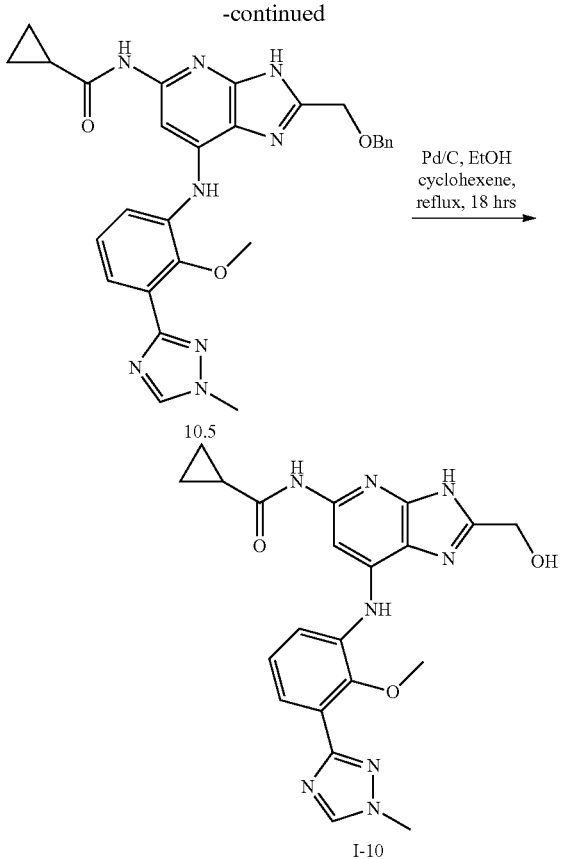

Synthesis of Compound 10.5.

Compound 10.5 was synthesized from 10.4 from using general procedure C. (Yield: 77.36%). MS(ES): m/z 525.56 [M+H]+.

Synthesis of I-10.

To a solution of 10.5 (0.035 g, 6.7 mmol, 1.0 eq) in a mixture of cyclohexene (1 mL) and ethanol (5 mL), 10% Pd/C (0.06 g) was added under nitrogen atmosphere. Reaction mixture was refluxed for 18 hrs. Upon completion, reaction mixture was cooled to r.t., filtered through celite-bed and washed with ethanol. Filtrate was concentrated in vacuo to obtain crude product. The crude product was triturated with 5% $CH_2Cl_2$ in pentane to obtain pure 1-10 (0.012 g, 41.40%). MS(ES): m/z 435.48 [M+H]+, LCMS purity: 100%, HPLC purity: 98.44%, 1H NMR (MeOD, 400 MHz): 8.51 (s, 1H), 7.70-7.69 (d, J=6.4 Hz, 2H), 7.63-7.61 (d, J=8 Hz, 1H), 7.32-7.30 (t, J=8 Hz, 1H), 4.86-4.85 (d, J=4.4 Hz, 2H), 4.04 (s, 3H), 3.72 (s, 3H), 2.17 (s 1H), 1.01-0.98 (m, 2H), 0.93-0.90 (m, 3H).

Example 13: Synthesis of N-(2-(difluoromethyl)-7-((2-methoxy-3-(1-methyl-1H-1,2,4-triazol-3-yl)phenyl)amino)-3H-imidazo[4,5-b]pyridin-5-yl)cyclopropanecarboxamide, I-13

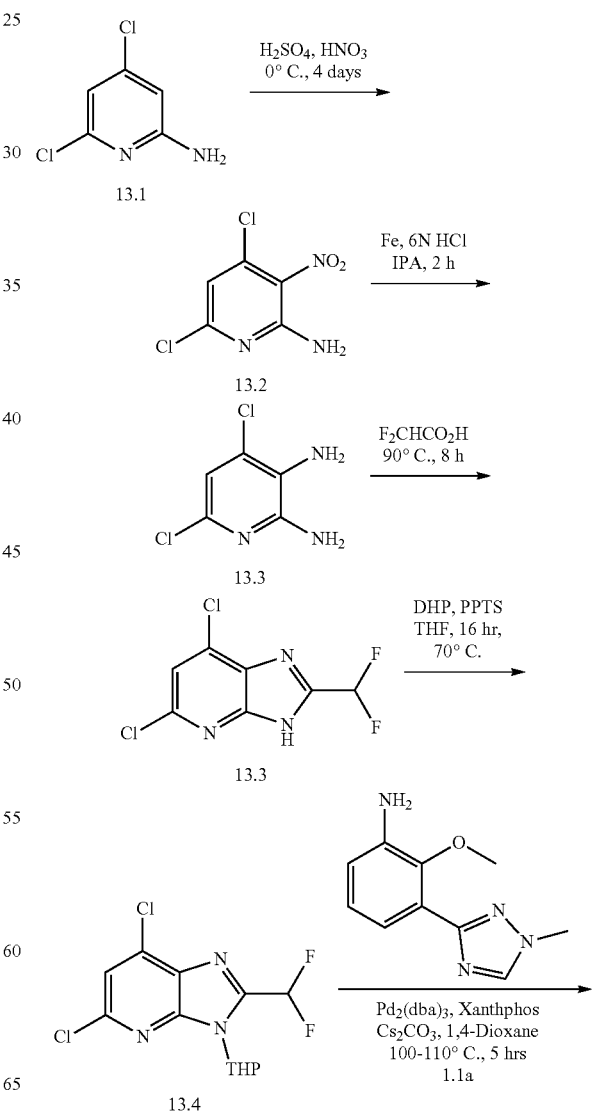

Synthesis of Compound 10.1.

A mixture of compound 4,6-dichloropyridine-2,3-diamine (0.190 g, 1.06 mmol, 1.0 eq) and benzyloxyacetic acid (0.354 g, 2.13 mmol, 2.0 eq) was heated at 150° C. for 4 hrs. After completion of the reaction, reaction mixture was dissolved in ethyl acetate and washed with saturated aqueous $NaHCO_3$. Organic layers were combined, dried over $Na_2SO_4$ and concentrated in vacuo to obtain crude product. This was purified by column chromatography and compound was eluted in 6% ethyl acetate in hexane as eluant to obtain pure 10.1 (0.170 g, 51.69%). MS(ES): m/z 309.51 [M+H]+.

Synthesis of Compound 10.2.

To a solution of 10.1 (0.1 g, 0.325 mmol, 1.0 eq) in dry tetrahydrofuran (2.5 mL) was added 3,4-Dihydro-2H-pyran (0.109 g, 1.298 mmol, 4.0 eq) followed Pyridinium p-toluenesulfonate (0.008 g, 0.032 mmol, 0.1 eq) and stirred. Reaction mixture was heated at 95° C. for 16 h. Upon completion, reaction mixture was concentrated in vacuo to obtain crude product. This was purified by column chromatography and the compound was eluted in 6% ethyl acetate in hexane get pure 10.2 (0.110 g, 86.41%). MS(ES): m/z 393.26 [M+H]+.

Synthesis of Compound 10.3.

Compound was synthesized from 10.2 and 1.1a using general procedure A. (Yield: 35.02%). MS(ES): m/z 561.89 [M+H]+.

Synthesis of Compound 10.4.

Compound 10.4 was synthesized from 10.3 and cyclopropanecarboxamide using general procedure B. (Yield: 22.26%). MS(ES): m/z 609.23 [M+H]+.

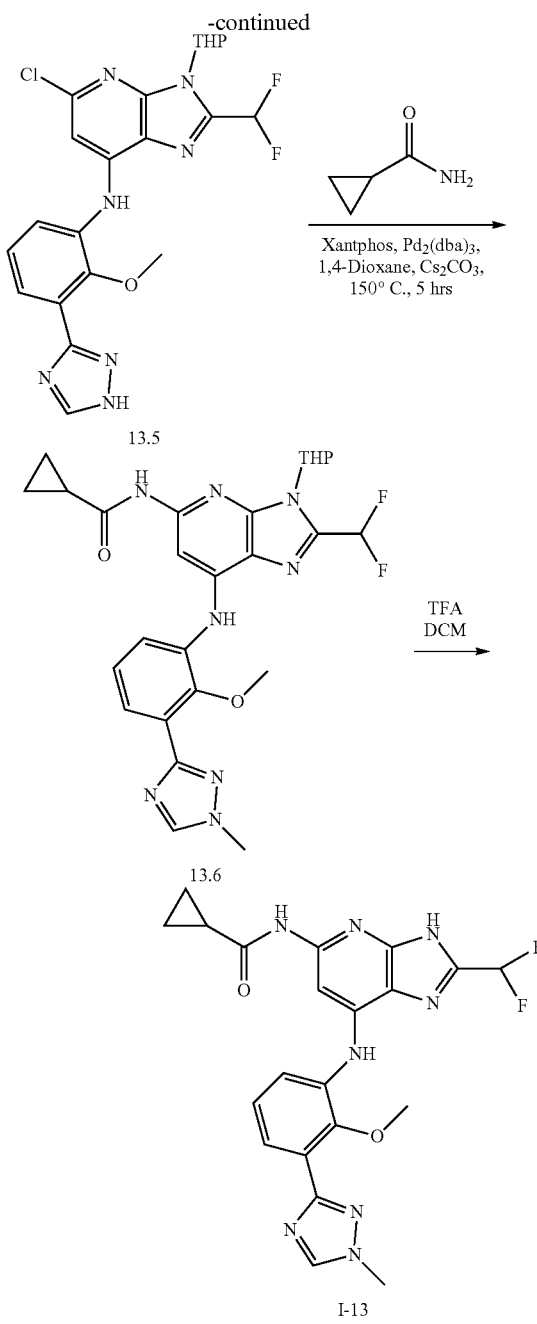

13.5

13.6

I-13

Synthesis of Compound 13.1.

To a concentrated $H_2SO_4$ (265 mL) added 4,6-dichloropyridin-2-amine (50 g, 306 mmol, 1.0 eq) portionwise at −5° C. and stirred for 30 min followed by addition of nitric acid (16.50 mL) dropwise. Reaction mixture was allowed to stand at 0° C. for 4 days. Upon completion, reaction mixture was slowly transferred into crushed ice. Saturated $NaHCO_3$ solution was added to pH 8. Precipitated solid was filtered off to obtain crude compound. This was purified by column chromatography and compound was eluted in 8% ethyl acetate in hexane to get pure 1.1 (30 g, 47%). 1H NMR (CDCl3, 400 MHz): 6.85 (s, 1H), 6.28 (s, 2H).

Synthesis of Compound 13.2.

To a solution of 13.1 (17.5 g, 84.14 mmol, 1.0 eq) in Isopropyl alcohol (525 mL) was added Iron powder (23.6 g, 420 mmol, 5.0 eq) and stirred. To this mixture was added 6N HCl (70 mL) dropwise at 10° C. The reaction mixture was stirred at r.t. for 2 h. After completion of reaction saturated $NaHCO_3$ solution was added to pH 8. Reaction mixture was filtered through celite. Filtrate was extracted with ethyl acetate. Organic layers were combined, washed with brine, dried over $Na_2SO_4$ and concentrated in vacuo to obtain 11.2 (14 g, 93.47%). MS(ES): m/z 178 [M+H]$^+$.

Synthesis of Compound 13.3.

A mixture 13.2 (10 g, 56.10 mmol, 1.0 eq) and difluoroacetic acid (28 mL) was heated in a sealed tube 90° C. for 8 h. Upon completion, reaction mixture was cooled to r.t., neutralised with saturated $NaHCO_3$ solution and product was extracted with ethyl acetate. Organic layers were combined, washed with brine, dried over $Na_2SO_4$ and concentrated in vacuo to obtain crude product. This was purified by column chromatography and the compound was eluted in 20% ethyl acetate in hexane get pure 13.3 (8.0 g, 59.83%). MS(ES): m/z 238.1 [M+H]$^+$.

Synthesis of Compound 13.4.

To a solution of 13.3 (8.0 g, 33.61 mmol, 1.0 eq) in dry tetrahydrofuran (144 mL) was added 3,4-Dihydro-2H-pyran (19.76 g, 235.3 mmol, 7.0 eq) followed Pyridinium p-toluenesulfonate (0.84 g, 3.3 mmol, 0.1 eq) and stirred. Reaction mixture was heated at 70° C. for 16 h. Upon completion, reaction mixture was concentrated in vacuo to obtain crude product. This was purified by column chromatography and the compound was eluted in 2% ethyl acetate in hexane get pure 13.4 (8.0 g, 73.89%). 1H NMR (CDCl3, 400 MHz): 7.41 (s, 1H), 7.30-7.01 (m, 1H), 5.98-5.96 (m, 1H), 4.28-4.25 (m, 1H), 3.81-3.76 (m, 1H), 2.43-2.37 (m, 1H), 2.11-2.02 (m, 2H), 1.82-1.57 (m, 3H).

Synthesis of Compound 13.5.

Compound 13.5 was synthesized from 13.4 and 1.1a using general procedure A. (Yield: 41.90%). MS(ES): m/z 476.91 [M+H]$^+$.

Synthesis of Compound 13.6.

Compound 13.6 was synthesized from 13.5 and cyclopropanecarboxamide using general procedure B. (Yield: 46.78%). MS(ES): m/z 539.51 [M+H]+.

Synthesis of I-13.

Compound I-13 was synthesized from 13.6 using general procedure C. (Yield: 72.42%). MS(ES): m/z 455.54 [M+H]$^+$, LCMS purity: 100%, HPLC purity: 98.91%, 1H NMR (MeOD, 400 MHz): 8.51 (s, 1H), 7.88 (s, 1H), 7.72-7.70 (d, J=7.6 Hz, 1H), 7.64-7.62 (d, J=8 Hz, 1H), 7.33-7.29 (t, J=7.6 Hz, 1H), 7.00 (t, 1H), 4.04 (s, 3H), 3.73-3.68 (s, 3H), 1.88 (s, 1H), 0.99-0.97 (m, 2H), 0.91-0.88 (m, 2H).

Example 14: Synthesis of N-(2-(difluoromethyl)-7-((2-methoxy-3-(2-methyl-2H-tetrazol-5-yl)phenyl)amino)-3H-imidazo[4,5-b]pyridin-5-yl)cyclopropanecarboxamide, I-14

423

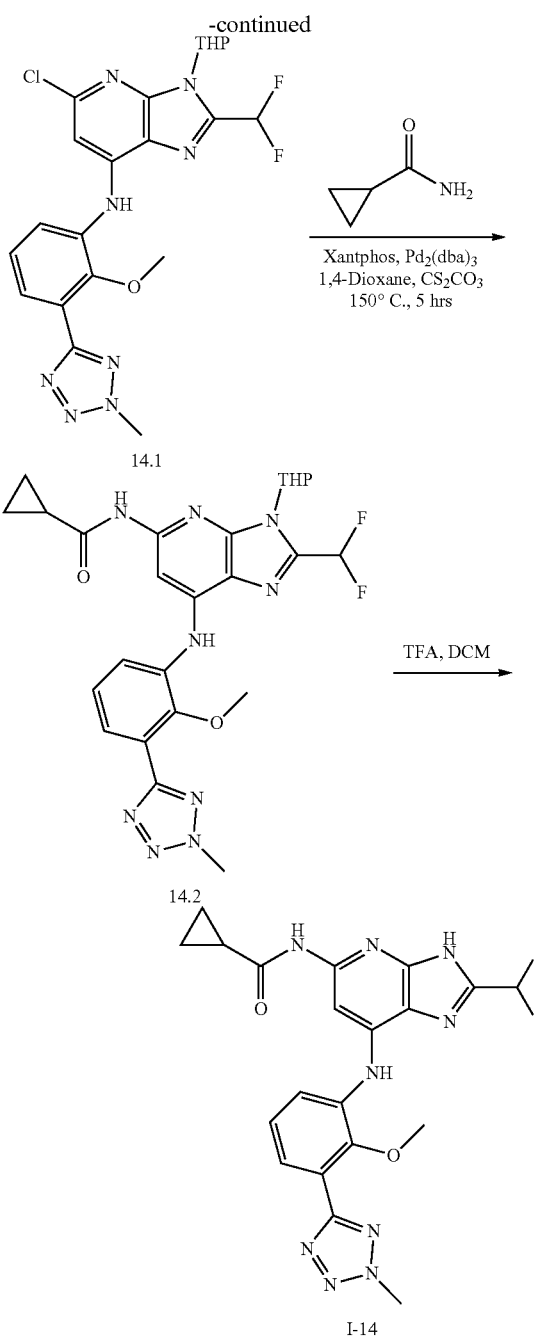

Synthesis of Compound 14.1
Compound 14.1 was synthesized from 13.4 and 14.1a using general procedure A. (Yield: 21.87%). MS(ES): m/z 491.28 [M+H]+.

Synthesis of Compound 14.2.
Compound 14.2 was synthesized from 14.1 using general procedure B. (Yield: 54.59%). MS(ES): m/z 540.89 [M+H]+.

Synthesis of I-14.
Compound I-14 was synthesized from 14.2 using general procedure C (Yield: 59.24%). MS(ES): m/z 456.32 [M+H]+, LCMS purity: 96.13%, HPLC purity 96.29%, 1H NMR (MeOD, 400 MHz): 7.77-7.75 (d, J=8 Hz, 3H), 7.36 (t, 1H), 7.01 (t, 1H), 4.48 (s, 3H), 3.80 (s, 3H), 1.86 (s, 1H), 1.27-1.24 (t, 1H), 0.99-0.88 (m, 4H).

424

Example 15: Synthesis of N-(2-(difluoromethyl)-7-((2-methoxy-4-(morpholine-4-carbonyl)phenyl)amino)-3H-imidazo[4,5-b]pyridin-5-yl)cyclopropanecarboxamide, I-15

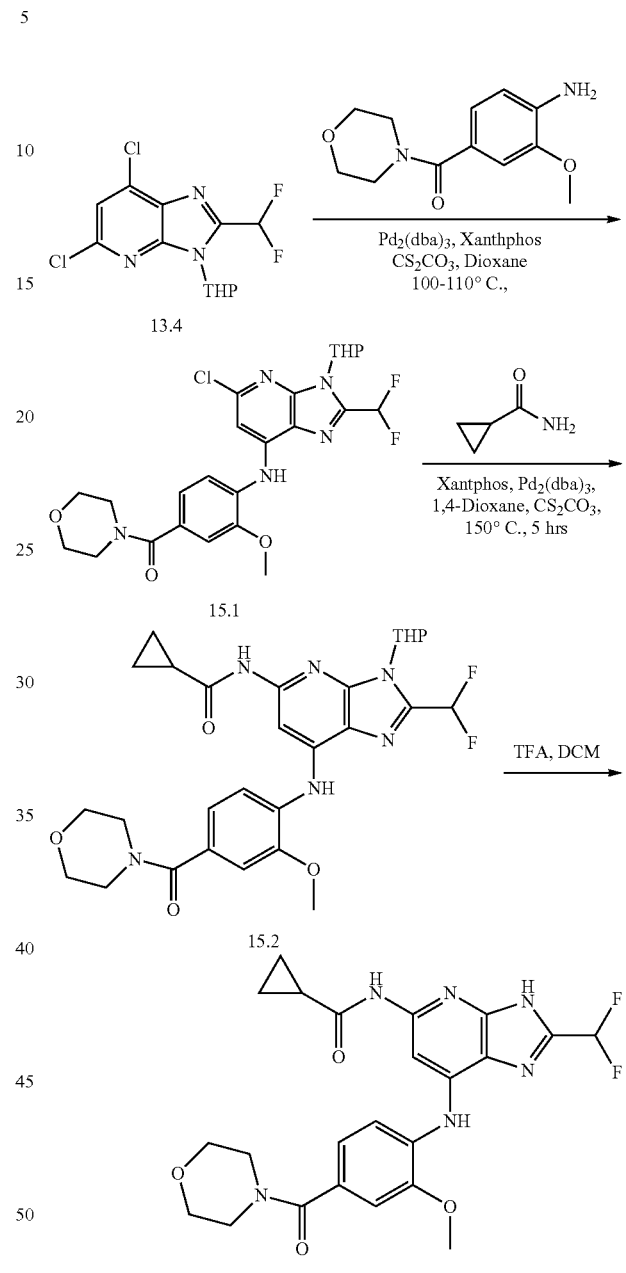

Synthesis of Compound 15.1.
Compound 15.1 was synthesized from 13.4 and (4-amino-3-methoxyphenyl)(morpholino)methanone using general procedure A. (Yield: 20.98%). MS(ES): m/z 522.98 [M+H]+.

Synthesis of Compound 5.2.
Compound 15.2 was synthesized from 15.1 using general procedure B. (Yield: 62.73%). MS(ES): m/z 571.23 [M+H]+.

Synthesis of I-15.
Compound I-15 was synthesized from 15.2 using general procedure C (Yield: 78.19%). MS(ES): m/z 487.48 [M+H]+, LCMS purity: 97.63%, HPLC purity 100.00%, 1H NMR (DMSO, 400 MHz): 13.50 (s, 1H), 10.59 (s, 1H), 8.14 (s, 1H), 7.77 (s, 1H), 7.43-7.41 (d, J=8 Hz, 1H), 7.13 (t, 1H), 7.05-7.03 (d, J=8 Hz, 1H), 3.85 (s, 3H), 3.60 (S, 8H), 1.97 (S, 1H), 0.84 (s, 1H), 0.75 (s, 4H).

Example 16: Synthesis of N-(7-((4-(azetidine-1-carbonyl)-2-methoxyphenyl)amino)-2-(difluoromethyl)-3H-imidazo[4,5-b]pyridin-5-yl)cyclopropanecarboxamide, I-16

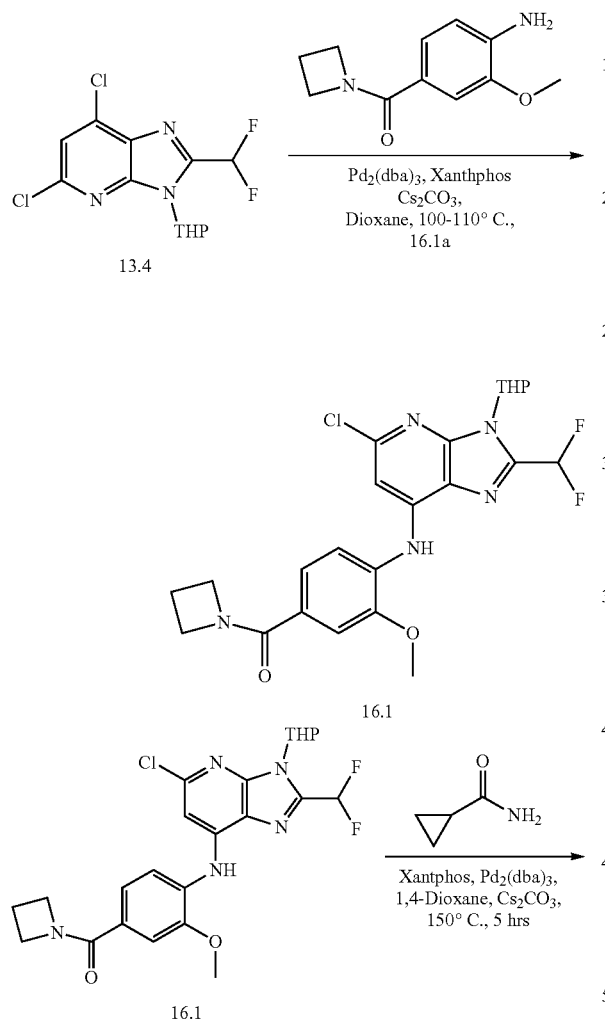

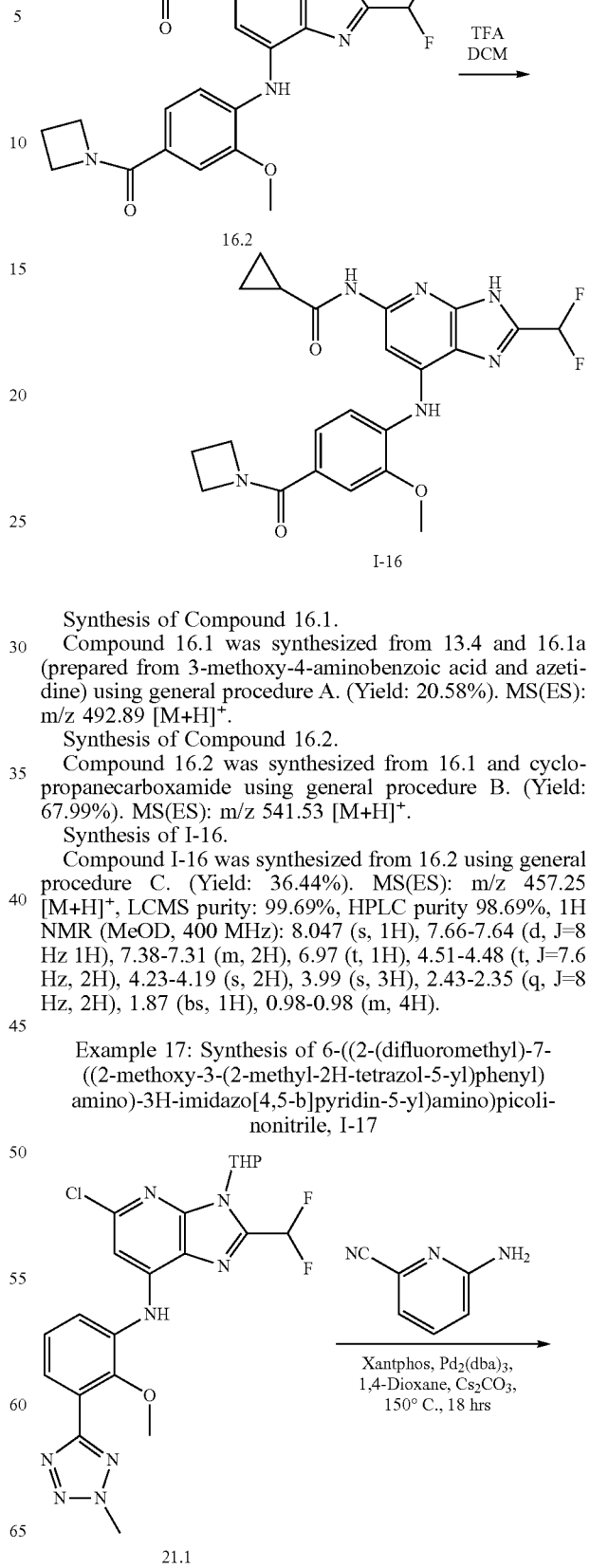

Synthesis of Compound 16.1.

Compound 16.1 was synthesized from 13.4 and 16.1a (prepared from 3-methoxy-4-aminobenzoic acid and azetidine) using general procedure A. (Yield: 20.58%). MS(ES): m/z 492.89 [M+H]+.

Synthesis of Compound 16.2.

Compound 16.2 was synthesized from 16.1 and cyclopropanecarboxamide using general procedure B. (Yield: 67.99%). MS(ES): m/z 541.53 [M+H]+.

Synthesis of I-16.

Compound I-16 was synthesized from 16.2 using general procedure C. (Yield: 36.44%). MS(ES): m/z 457.25 [M+H]+, LCMS purity: 99.69%, HPLC purity 98.69%, 1H NMR (MeOD, 400 MHz): 8.047 (s, 1H), 7.66-7.64 (d, J=8 Hz 1H), 7.38-7.31 (m, 2H), 6.97 (t, 1H), 4.51-4.48 (t, J=7.6 Hz, 2H), 4.23-4.19 (s, 2H), 3.99 (s, 3H), 2.43-2.35 (q, J=8 Hz, 2H), 1.87 (bs, 1H), 0.98-0.98 (m, 4H).

Example 17: Synthesis of 6-((2-(difluoromethyl)-7-((2-methoxy-3-(2-methyl-2H-tetrazol-5-yl)phenyl)amino)-3H-imidazo[4,5-b]pyridin-5-yl)amino)picolinonitrile, I-17

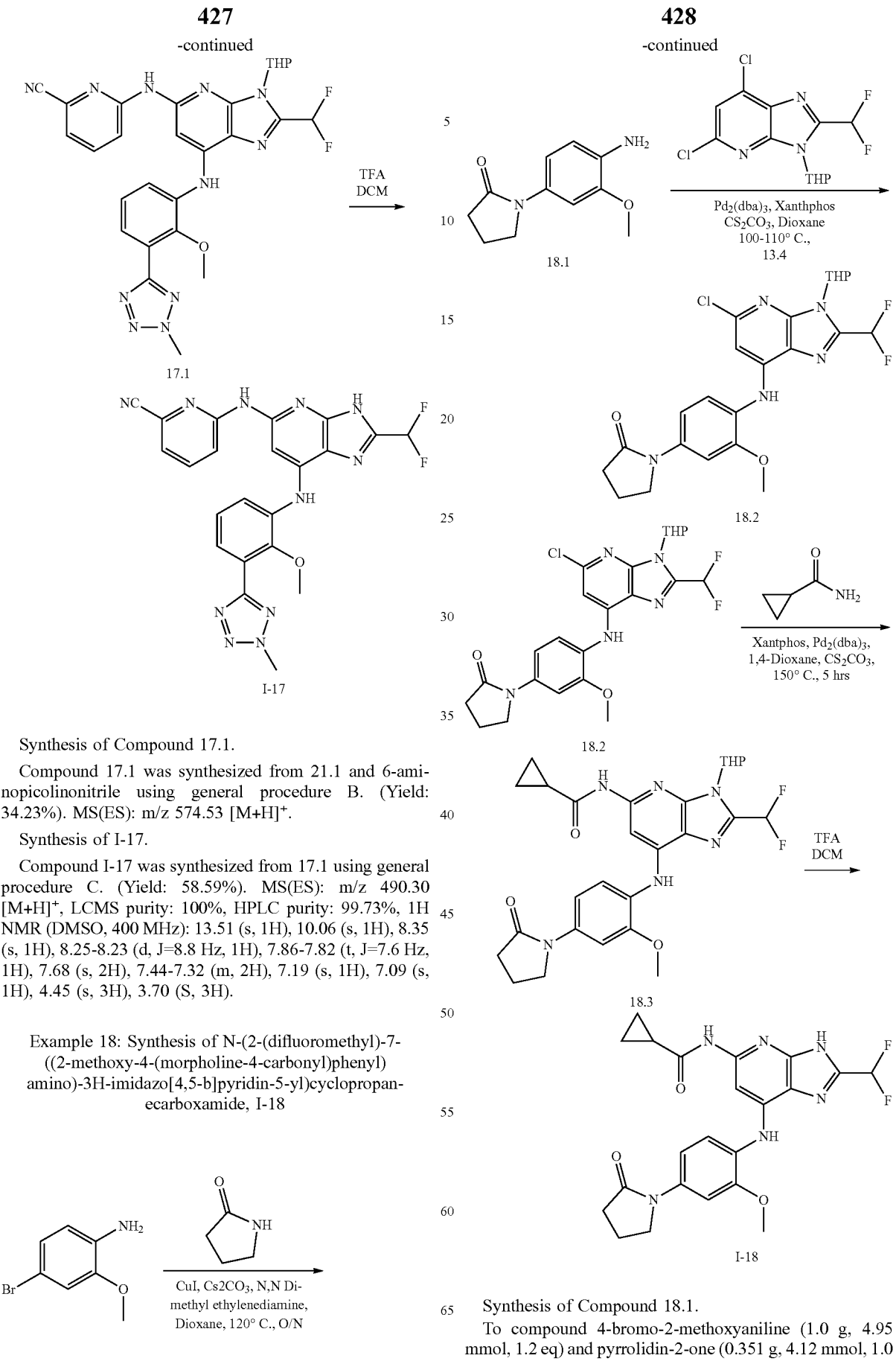

Synthesis of Compound 17.1.

Compound 17.1 was synthesized from 21.1 and 6-aminopicolinonitrile using general procedure B. (Yield: 34.23%). MS(ES): m/z 574.53 [M+H]$^+$.

Synthesis of I-17.

Compound I-17 was synthesized from 17.1 using general procedure C. (Yield: 58.59%). MS(ES): m/z 490.30 [M+H]$^+$, LCMS purity: 100%, HPLC purity: 99.73%, 1H NMR (DMSO, 400 MHz): 13.51 (s, 1H), 10.06 (s, 1H), 8.35 (s, 1H), 8.25-8.23 (d, J=8.8 Hz, 1H), 7.86-7.82 (t, J=7.6 Hz, 1H), 7.68 (s, 2H), 7.44-7.32 (m, 2H), 7.19 (s, 1H), 7.09 (s, 1H), 4.45 (s, 3H), 3.70 (S, 3H).

Example 18: Synthesis of N-(2-(difluoromethyl)-7-((2-methoxy-4-(morpholine-4-carbonyl)phenyl)amino)-3H-imidazo[4,5-b]pyridin-5-yl)cyclopropanecarboxamide, I-18

Synthesis of Compound 18.1.

To compound 4-bromo-2-methoxyaniline (1.0 g, 4.95 mmol, 1.2 eq) and pyrrolidin-2-one (0.351 g, 4.12 mmol, 1.0 eq) in 1,4-dioxane (15 mL), argon was purged for 15 min. Then Cs$_2$CO$_3$ (2.7 g, 8.24 mmol, 2.0 eq) was added, degassed by argon for 5 min. Then N,N-dimethylethylenediamine (0.363 g, 4.12 mmol, 1.0 eq) was added and again degassed for 5 min. Then copper iodide (0.391 g, 2.06 mmol, 0.5 eq) was added followed by argon purging for another 5 min. Then reaction mixture was stirred at 120° C. for 24 hr. After completion of the reaction, the reaction mixture was cooled to r.t. and filtered through celite which was washed with ethyl acetate. The combined filtrate was concentrated in vacuo to obtain crude product. This was purified by column chromatography and compound was eluted in 1.5% MeOH in CH$_2$Cl$_2$ as eluent to obtain the pure 18.1 (0.5 g, 48.98%). MS(ES): m/z 207.49 [M+H]$^+$.

Synthesis of Compound 18.2.

Compound was synthesized from 18.1 and 13.4 using general procedure A. (Yield: 29.47%). MS(ES): m/z 492.57 [M+H]$^+$.

Synthesis of Compound 18.3.

Compound 18.3 was synthesized from 18.2 and cyclopropanecarboxamide using general procedure B. (Yield: 65.72%). MS(ES): m/z 541.54 [M+H]$^+$.

Synthesis of I-18.

Compound I-18 was synthesized from 18.3 using general procedure C. (Yield: 72.88%). MS(ES): m/z 457.25 [M+H]$^+$, LCMS purity: 100%, HPLC purity 100.00%, 1H NMR (DMSO, 400 MHz): 10.48 (s, 1H), 8.07 (s, 1H), 7.60-7.60 (d, J=2 Hz 1H), 7.49 (s, 1H), 7.31-7.29 (d, J=8.8 Hz, 1H), 7.18-7.04 (m, 2H), 3.88-3.85 (t, J=7.2 Hz, 2H), 3.77 (s, 3H), 2.52 (t, 2H), 2.09-2.02 (q, J=7.6 Hz, 3H), 1.97 (m, 1H), 0.73-0.72 (m, 4H).

Example I-19: Synthesis of N-(7-((3-chloro-2-methoxyphenyl)amino)-2-(difluoromethyl)-3H-imidazo[4,5-b]pyridin-5-yl)cyclopropanecarboxamide, I-19

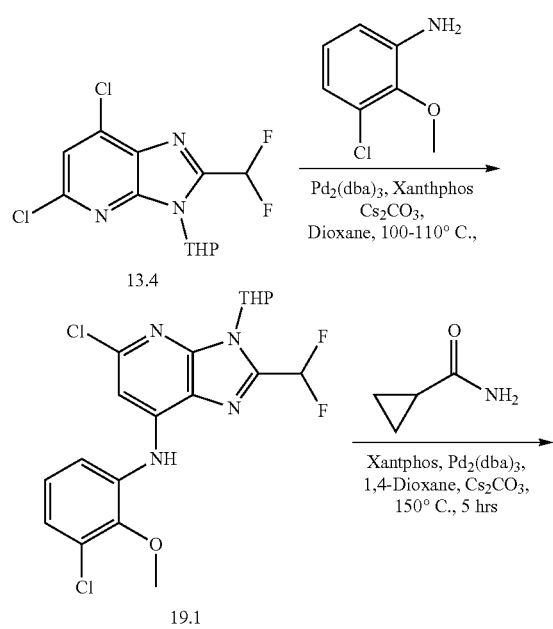

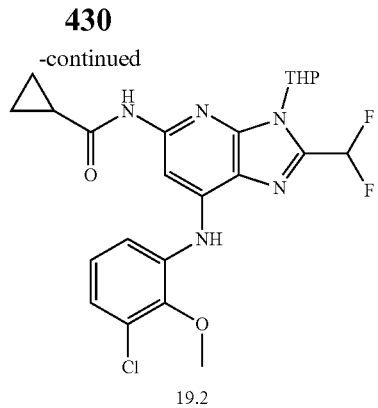

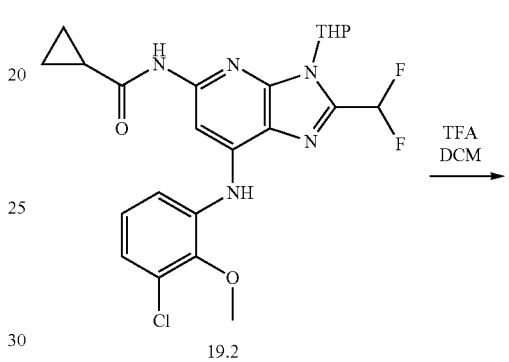

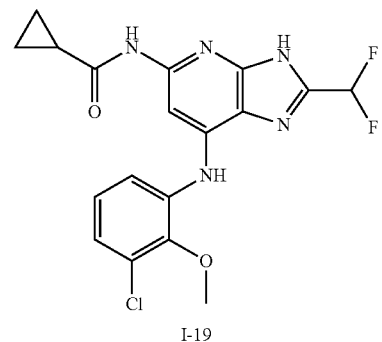

Synthesis of Compound 19.1.

Compound 19.1 was synthesized from 3-chloro-2-methoxyaniline and 13.4 using general procedure A. (Yield: 39.24%). MS(ES): m/z 444.25 [M+H]$^+$.

Synthesis of Compound 19.2.

Compound 19.2 was synthesized from 19.1 and cyclopropanecarboxamide using general procedure B. (Yield: 45.06%). MS(ES): m/z 492.58 [M+H]$^+$.

Synthesis of I-19.

Compound I-19 was synthesized from 19.2 using general procedure C. Yield: 60.31%). MS(ES): m/z 408.27 [M+H]$^+$, LCMS purity: 98.89%, HPLC purity: 99.18%, 1H NMR (DMSO, 400 MHz): 13.46 (s, 1H), 10.57 (s, 1H), 8.44 (s, 1H), 7.56 (s, 1H), 7.35-7.07 (m, 4H), 3.69 (s, 3H), 1.99-1.96 (m, 1H), 0.74-0.72 (m, 4H).

Example 20: Synthesis of N-(2-(difluoromethyl)-7-((3-fluoro-2-methoxyphenyl)amino)-3H-imidazo[4,5-b]pyridin-5-yl)cyclopropanecarboxamide, I-20

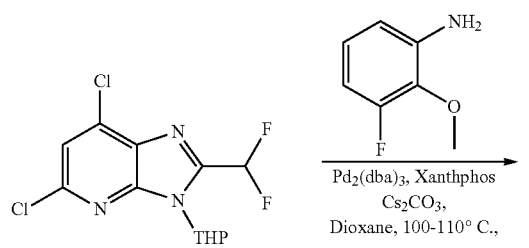

13.4

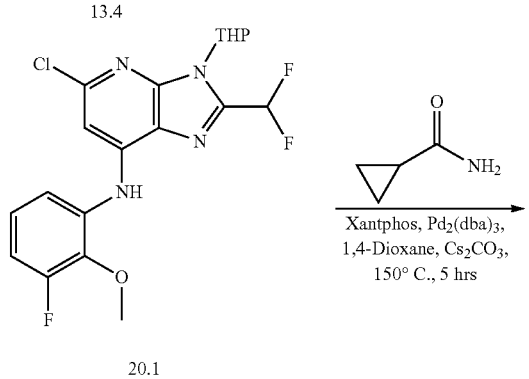

20.1

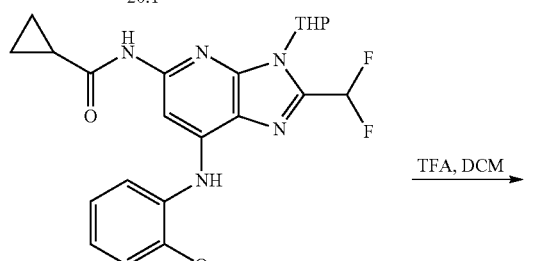

20.2

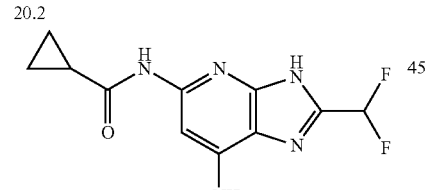

I-20

Synthesis of Compound 20.1.

Compound 20.1 was synthesized from 13.4 and 3-fluoro-2-methoxyaniline using general procedure A. (Yield: 46.96%). MS(ES): m/z 427.85 [M+H]$^+$.

Synthesis of Compound 20.2.

Compound 20.2 was synthesized from 20.1 and cyclopropanecarboxamide using general procedure B. (Yield: 57.71%). MS(ES): m/z 476.54 [M+H]$^+$.

Synthesis of Compound I-20.

Compound I-20 was synthesized from 20.2 using general procedure C. (Yield: 67.50%). MS(ES): m/z 392.23 [M+H]$^+$, LCMS purity: 100%, HPLC purity 99.82%, 1H NMR (DMSO, 400 MHz): 13.47 (s, 1H), 10.55 (s, 1H), 8.42 (s, 1H), 7.59 (s, 1H), 7.19-7.06 (m, 4H), 3.79 (s, 3H), 1.98-1.97 (d, J=3.2 Hz, 1H), 0.74-0.72 (m, 4H).

Example 21: Synthesis of 2-(difluoromethyl)-N5-(5,6-dimethylpyrazin-2-yl)-N7-(2-methoxy-3-(2-methyl-2H-tetrazol-5-yl)phenyl)-3H-imidazo[4,5-b]pyridine-5,7-diamine, I-21

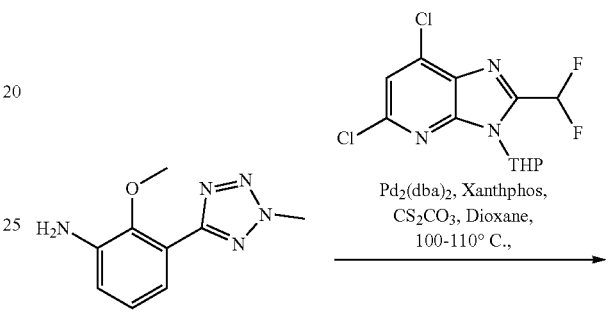

14.1a

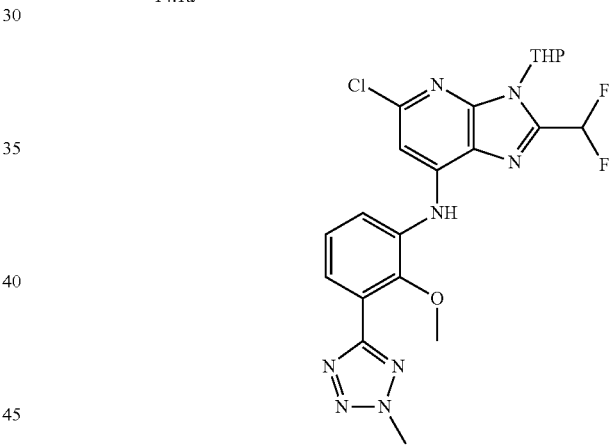

21.1

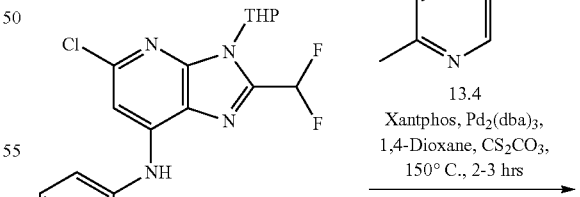

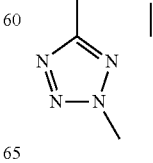

21.1

-continued

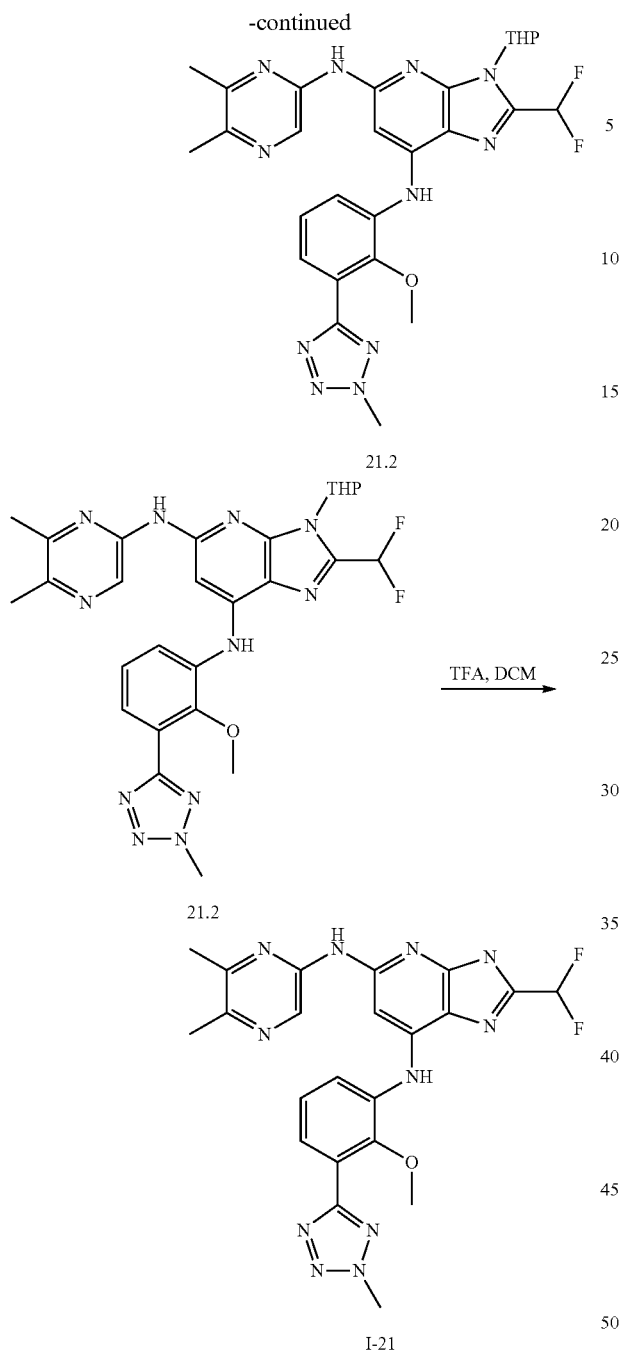

Synthesis of Compound 21.1.

Compound 21.1 was synthesized from 13.4 and 14.1a using general procedure A. (Yield: 30.80%). MS(ES): m/z 491.25 [M+H]⁺.

Synthesis of Compound 21.2.

Compound 21.2 was synthesized from 21.1 and 5,6-dimethylpyrazin-2-amine using general procedure B. (Yield: 50.99%). MS(ES): m/z 577.46 [M+H]⁺.

Synthesis of I-21.

Compound I-21 was synthesized from 21.2 using general procedure C. (Yield: 13.01%). MS(ES): m/z 494.41 [M+H]⁺, LCMS purity: 99.68% HPLC purity 99.61%, 1H NMR (DMSO, 400 MHz): 13.39 (s, 1H), 9.62 (s, 1H), 8.95 (s, 1H), 8.30 (s, 1H), 7.69-7.64 (t, J=8 Hz, 2H), 7.36-7.31 (m, 1H), 7.18-7.04 (m, 1H), 4.44 (s, 3H), 3.69 (s, 3H), 2.33 (s, 3H), 2.26 (s, 3H).

Example 22: Synthesis of N5-(5-(azetidin-1-yl)pyridin-2-yl)-2-(difluoromethyl)-N7-(2-methoxy-3-(2-methyl-2H-tetrazol-5-yl)phenyl)-3H-imidazo[4,5-b]pyridine-5,7-diamine, I-22

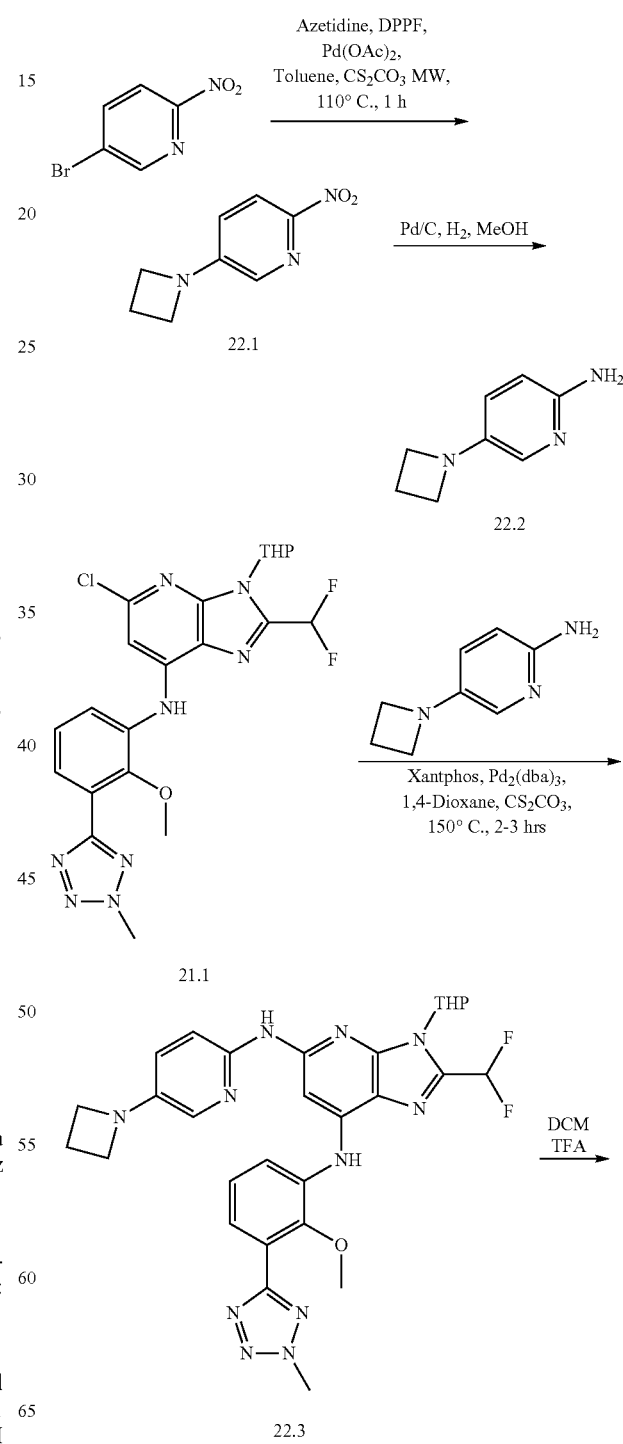

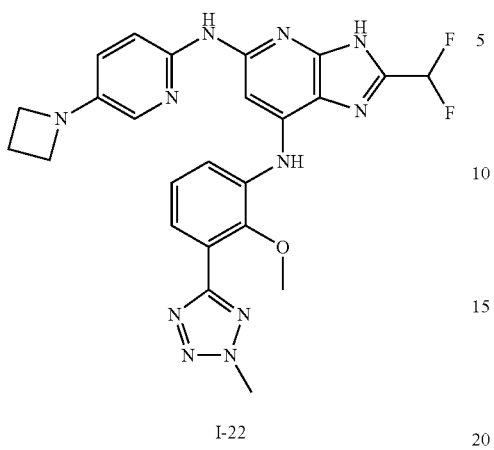

I-22

Synthesis of Compound 22.1.

To compound 5-bromo-2-nitropyridine (2 g, 9.950 mmol, 1.0 eq) in toluene, azetidine (1.9 g, 14.92 mmol, 1.5 eq) and $Cs_2CO_3$ (12.97 g, 39.80 mmol, 4 eq) were added. Reaction mixture was degassed with argon for 15 min. Then palladium acetate (0.225 g, 0.99502 mmol, 0.1 eq) and 1,1'-Bis (diphenylphosphino)ferrocene (1.92 g, 3.4825 mmol, 0.35 eq) were added in the reaction mixture. Reaction mixture was again degassed for 5 min. Reaction mixture was heated in microwave at 110° C. for 1 h. After completion of the reaction, reaction mixture was transferred into cold water and extracted with ethyl acetate. Organic layers were combined, dried over $Na_2SO_4$ and concentrated in vacuo to obtain crude product. This was purified by column chromatography and compound was eluted in 2.5% MeOH in $CH_2Cl_2$ as eluant to obtain pure 22.1 (1.5 g, 84.97%). MS(ES): m/z 180.18 $[M+H]^+$.

Synthesis of Compound 22.2.

To compound 22.1 (1.5 g, 8.379 mmol, 1.0 eq) in MeOH, 10% Pd/C (0.7 g) was added. Hydrogen was purged through reaction mixture for 4 h. Upon completion, reaction mixture was filtered through celite-bed and washed with MeOH. Filtrate was concentrated in vacuo to obtain 22.2 (1.0 g, 80.06%). MS(ES): m/z 150.20 $[M+H]^+$.

Synthesis of Compound 22.3.

Compound 22.3 was synthesized from 21.1 and 22.2 using general procedure B. (Yield: 48.79%). MS(ES): m/z 604.64 $[M+H]^+$.

Synthesis of I-22.

Compound I-22 was synthesized from 22.3 using general procedure C. (Yield: 51.64%). MS(ES): m/z 520.31 $[M+H]^+$, LCMS purity: 97.01% HPLC purity: 95.84%, 1H NMR (DMSO, 400 MHz): 9.28 (s, 1H), 7.82-7.81 (d, J=1.6 Hz, 1H), 7.62-7.59 (d, J=6.8 Hz, 1H), 7.49-7.48 (d, J=2.4 Hz, 1H) 7.43-7.39 (m, 2H), 7.30 (s, 1H), 7.09 (t, 1H), 7.10-7.07 (d, J=9.2 Hz, 1H), 6.06 (s, 1H), 4.44 (s, 3H), 3.88-3.85 (t, J=7.2 Hz, 4H), 3.69 (s, 3H), 2.36-2.31 (m, 2H).

Example 23: Synthesis of 1-(6-((2-(difluoromethyl)-7-((2-methoxy-3-(2-methyl-2H-tetrazol-5-yl)phenyl)amino)-3H-imidazo[4,5-b]pyridin-5-yl)amino)pyridin-3-yl)azetidin-3-ol, I-23

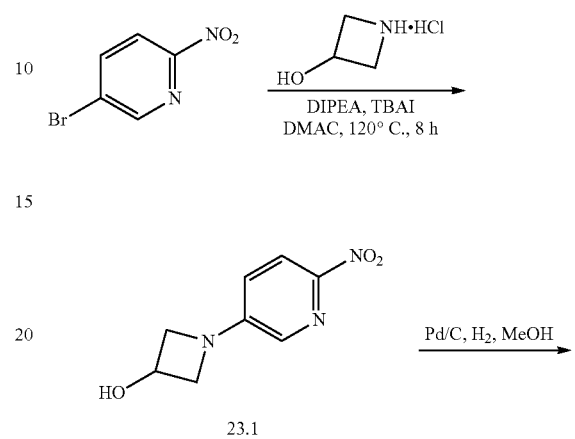

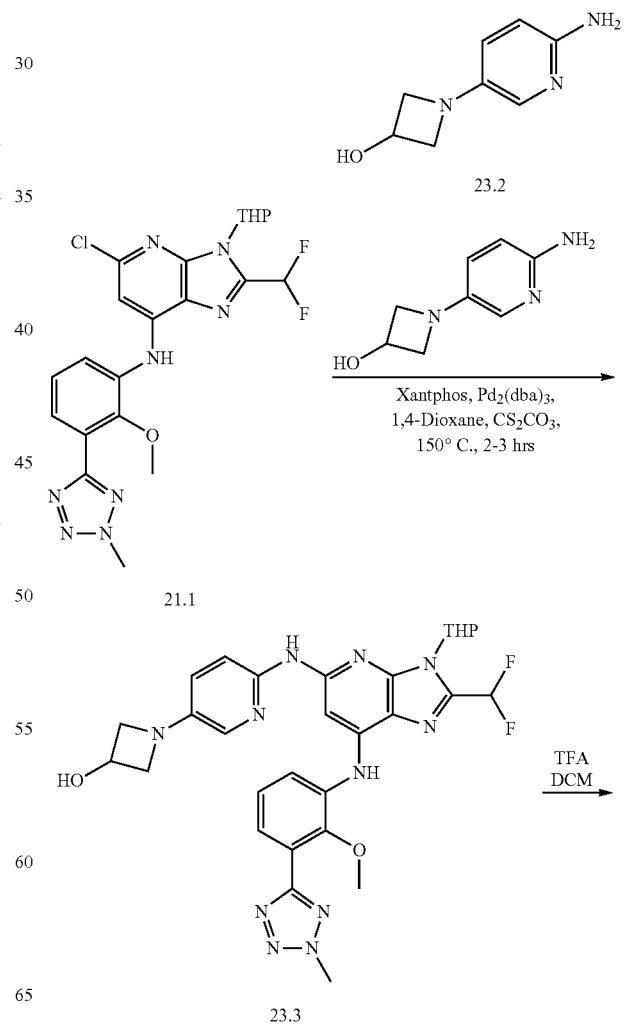

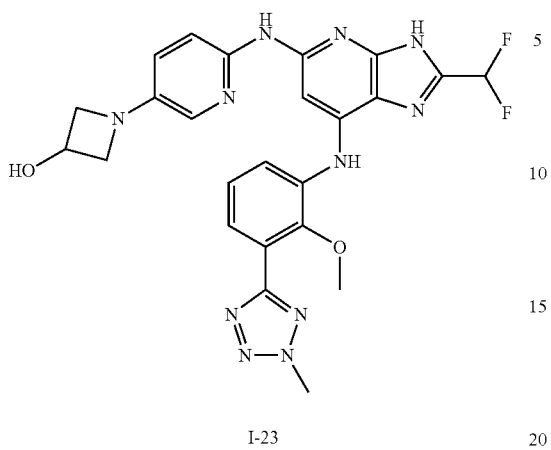

I-23

Synthesis of Compound 23.1.

To a solution of 5-bromo-2-nitropyridine (1.0 g, 4.9 mmol, 1.0 eq) and azetidin-3-ol hydrochloride (0.97 g, 8.8 mmol, 1.8 eq) in DMAc (20 mL), diisopropylethylamine (1.9 g, 14.77 mmol, 3.0 eq) and tetrabutyl ammonium iodide (2.73 g, 7.38 mmol, 1.5 eq) were added. Reaction mixture was heated to 120-140° C. for 8 h. After completion of the reaction, reaction mixture was transferred to water and extracted with ethyl acetate. Organic layers were combined, dried over anhydrous Na$_2$SO$_4$, filtered and concentrated in vacuo to get the crude material. This was purified by column chromatography using 60% ethyl acetate in hexane as eluant to obtain pure 23.1 (0.250 g, 26.00%). MS(ES): m/z 196.52 [M+H]$^+$.

Synthesis of Compound 23.2.

To a solution of 23.1 (0.250 g, 1.77 mmol, 1.0 eq) in ethanol (30 mL), 10% Pd/C (0.100 g) was added. Hydrogen was purged through reaction mixture for 5 h. Upon completion, reaction mixture was filtered through celite-bed and washed with ethanol. Filtrate was concentrated in vacuo to obtain 23.2 (0.2 g, 94.21%). MS(ES): m/z 166.38 [M+H]$^+$.

Synthesis of Compound 23.3.

Compound 23.3 was synthesized from 23.2 and 21.1 using general procedure B. (Yield: 36.98%). MS(ES): m/z 620.49 [M+H]$^+$.

Synthesis of I-23.

Compound I-23 was synthesized from 23.3 using general procedure C. (Yield: 42.98%). MS(ES): m/z 536.31 [M+H]$^+$, LCMS purity: 94.38% HPLC purity: 94.08%, 1H NMR (DMSO, 400 MHz): 11.05 (s, 1H), 9.29 (s, 1H), 7.84-7.82 (d, J=6.1 Hz, 1H), 7.62-7.60 (d, J=7.2 Hz, 1H) 7.60 (s, 1H), 7.44-7.39 (m, 3H), 7.30 (s, 1H), 7.17-7.06 (m, 1H), 6.06 (s, 1H), 4.59 (s, 1H), 4.43 (s, 3H), 4.13-3.99 (m, 2H), 3.69 (s, 3H), 3.58-3.42 (m, 2H).

Example 24: Synthesis of 2-(difluoromethyl)-N5-(5,6-dimethylpyridin-2-yl)-N7-(2-methoxy-3-(1-methyl-1H-pyrazol-3-yl)phenyl)-3H-imidazo[4,5-b]pyridine-5,7-diamine, I-24

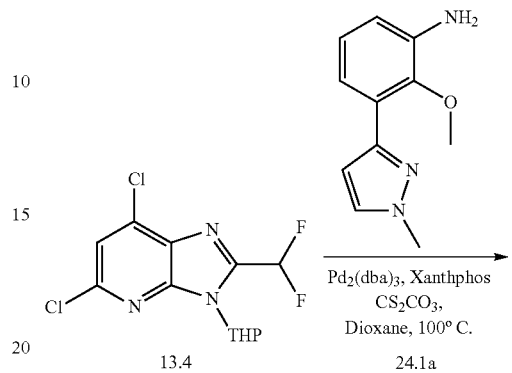

13.4    24.1a

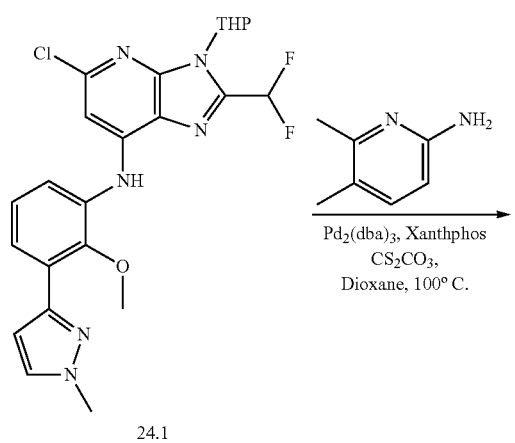

24.1

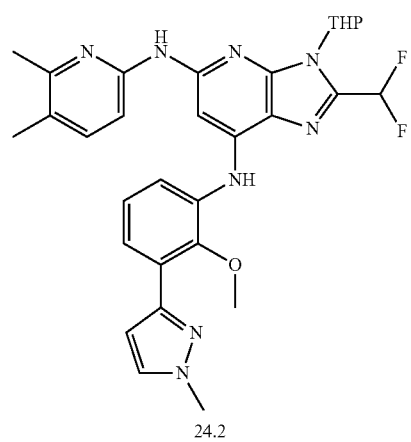

24.2

Example 25: Synthesis of 6-((2-(difluoromethyl)-7-((2-methoxy-3-(1-methyl-1H-pyrazol-3-yl)phenyl)amino)-3H-imidazo[4,5-b]pyridin-5-yl)amino)picolinonitrile, I-25

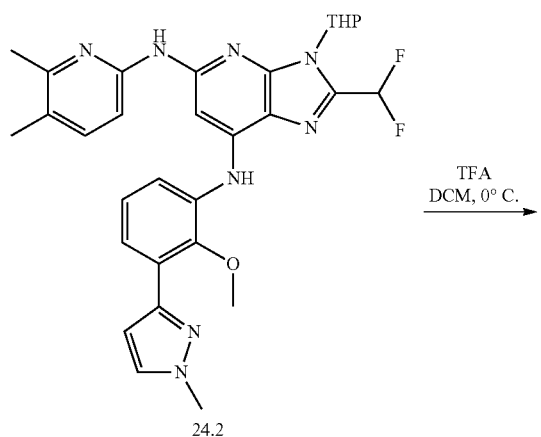

24.2

I-24

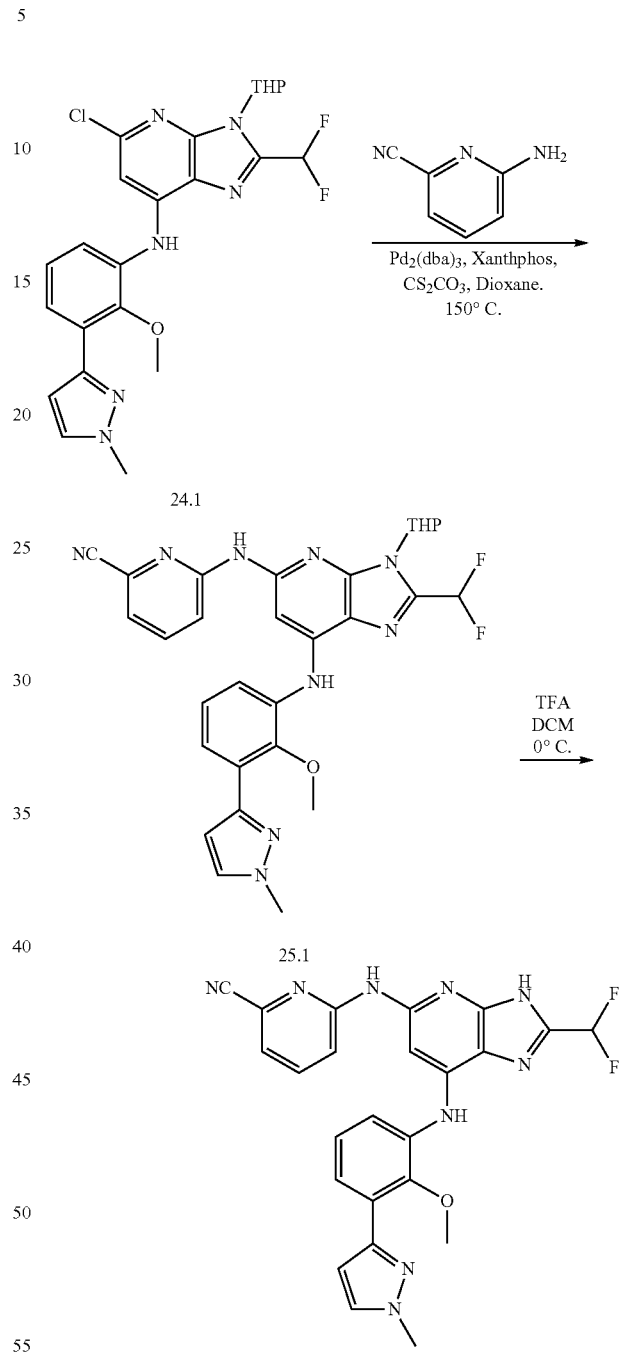

24.1

25.1

I-25

Synthesis of Compound 24.1.

Compound 24.1 was synthesized from 13.4 and 24.1a using general procedure A to obtain 24.1 (Yield: 41.57%). MS (ES): m/z 489.92 [M+H]$^+$.

Synthesis of Compound 24.2.

Compound 24.2 was synthesized from 5,6-dimethylpyridin-2-amine and 24.1 using general procedure B. (Yield: 44.24%). MS (ES): m/z 575.64 [M+H]$^+$.

Synthesis of compound I-24. Compound I-24 was synthesized from 24.2 using general procedure C. (Yield: 72.02%). MS(ES): m/z 492.31 [M+H]$^+$, LCMS purity: 100% HPLC purity 100%, 1H NMR (DMSO, 400 MHz): 13.38 (s, 1H), 9.63 (s, 1H), 8.95 (d, J=8 Hz, 1H), 7.76-7.75 (d, J=2 Hz, 1H), 7.67-7.65 (d, J=7.2 Hz, 1H), 7.45-7.43 (d, J=8 Hz, 3H), 7.21-7.17 (m, 2H), 6.72-6.71 (d, J=2 Hz, 1H), 3.90 (s, 3H), 3.58 (s, 3H), 2.35 (s, 3H), 2.29 (s, 3H).

Synthesis of Compound 25.1.

Compound 25.1 was synthesized from 24.1 and 6-aminopicolinonitrile using general procedure B. (Yield: 41.06%). MS (ES): m/z 572.59 [M+H]$^+$.

Synthesis of Compound I-25.

Compound I-25 was synthesized from 25.1 using general procedure C. (Yield: 68.40%). MS(ES): m/z 488.25 [M+H]$^+$, LCMS purity: 99.41% HPLC purity 100.00%, 1H NMR (DMSO, 400 MHz): 10.08 (s, 1H), 8.26-8.19 (m, 2H), 7.65-7.63 (d, J=7.6 Hz, 1H), 7.49-7.43 (m, 2H), 7.32 (s, 1H), 7.26-7.16 (m, 2H), 7.06 (s, 1H), 6.73-6.72 (d, J=2 Hz, 1H) 3.90 (s, 3H), 3.58 (s, 3H), 2.58 (s, 1H).

Example 26: Synthesis of 2-(difluoromethyl)-N7-(2-methoxy-3-(1-methyl-1H-pyrazol-3-yl)phenyl)-N5-(6-methylpyridazin-3-yl)-3H-imidazo[4,5-b]pyridine-5,7-diamine, I-26

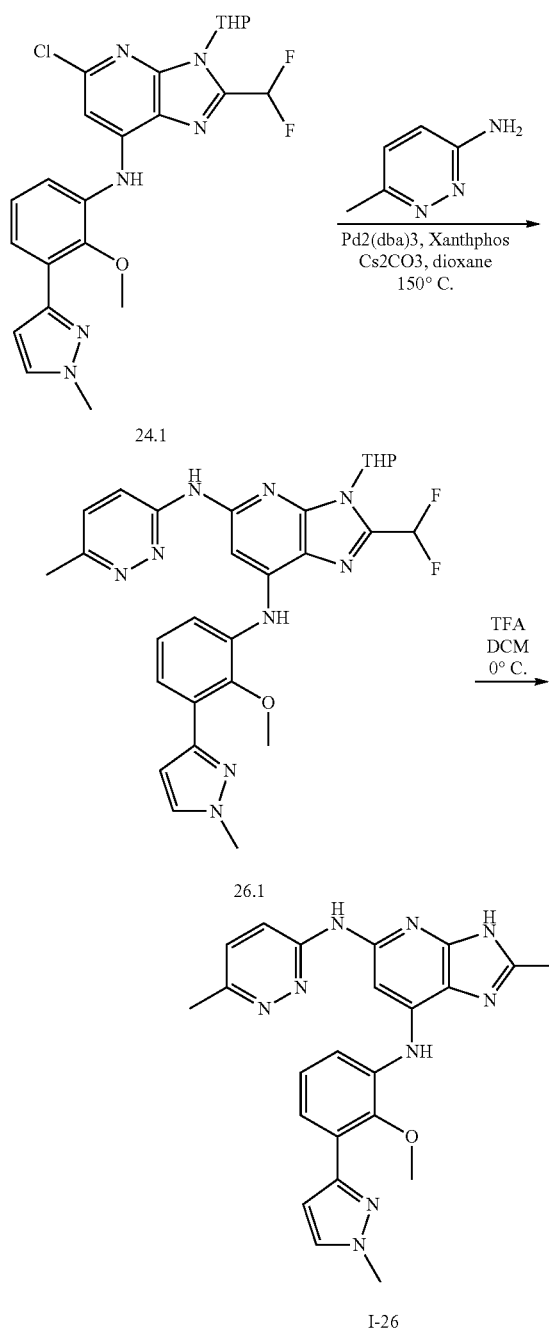

Synthesis of Compound 26.1.

Compound 26.1 was synthesized from 6-methylpyridazin-3-amine and 24.1 using general procedure B. (Yield: 55.72%). MS (ES): m/z 562.60 [M+H]$^+$.

Synthesis of Compound I-26.

Compound I-26 was synthesized from 26.1 using general procedure C (Yield: 51.46%). MS(ES): m/z 478.36 [M+H]$^+$, LCMS purity: 99.18% HPLC purity 98.85%, 1H NMR (DMSO, 400 MHz): 9.94 (s, 1H), 8.40-8.38 (d, J=9.2 Hz, 1H), 8.17 (s, 1H), 7.76-7.76 (d, J=2 Hz, 1H), 7.67-7.65 (d, J=6.8H, 1H), 7.43-7.41 (d, J=8.8H, 2H), 7.21-7.16 (m, 2H), 6.85 (s, 1H), 6.73-6.73 (d, J=2 Hz, 1H), 3.90 (s, 3H), 3.58 (s, 3H), 2.54 (s, 3H).

Example 27: Synthesis of 6-((2-(difluoromethyl)-7-((2-methoxy-3-(1-methyl-1H-pyrazol-3-yl)phenyl)amino)-3H-imidazo[4,5-b]pyridin-5-yl)amino)pyrazine-2-carbonitrile, I-27

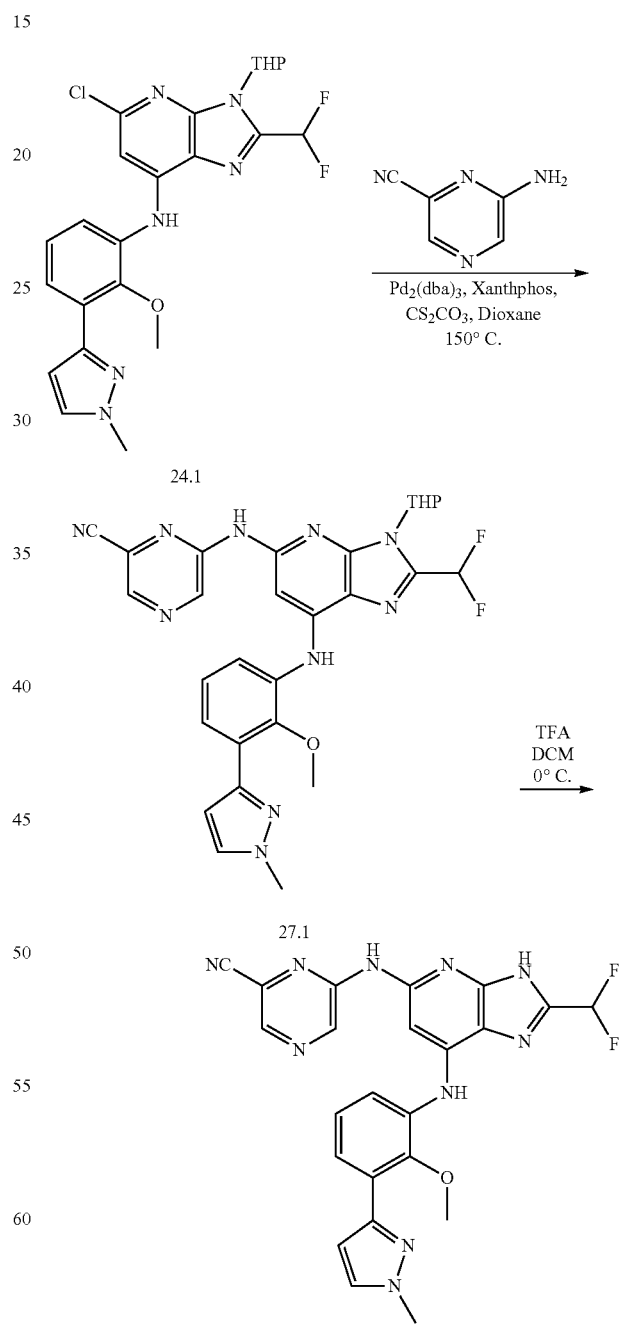

Synthesis of Compound 27.1.

Compound 27.1 was synthesized from 6-aminopyrazine-2-carbonitrile and 24.1 using general procedure B. (Yield: 53.28%). MS (ES): m/z 573.58 [M+H]$^+$.

Synthesis of Compound I-27.

Compound I-27 was synthesized from 27.1 using general procedure C. (Yield: 45.08%). MS(ES): m/z 489.25 [M+H]$^+$, LCMS purity 98.74% HPLC purity 100%, 1H NMR (DMSO, 400 MHz): 13.55 (s, 1H), 10.43 (s, 1H), 9.53 (s, 1H), 8.55 (s, 1H), 8.35 (s, 1H), 7.76-7.67 (dd, J=2 Hz, 2H) 7.45-7.43 (d, J=7.2 Hz, 1H), 7.26-7.21 (t, J=8 Hz, 2H), 6.72-6.72 (d, J=4 Hz, 1H), 3.90 (s, 3H), 3.58 (s, 3H).

Example 28: Synthesis of N-(2-(difluoromethyl)-7-((2-methoxyphenyl)amino)-3H-imidazo[4,5-b]pyridin-5-yl)cyclopropanecarboxamide, I-28

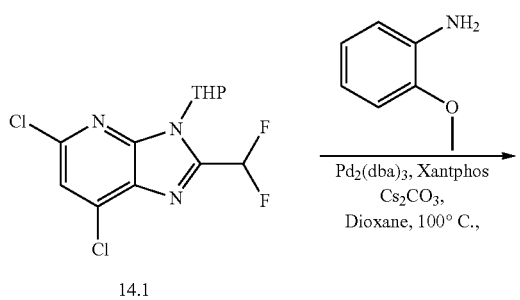

14.1

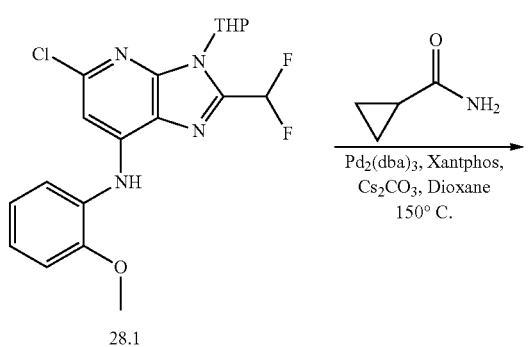

28.1

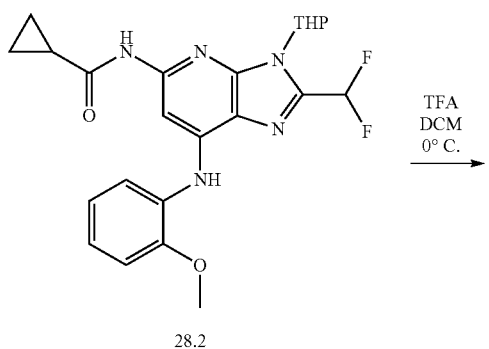

28.2

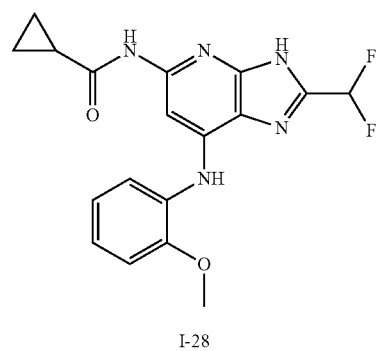

I-28

Synthesis of Compound 28.1.

Compound 28.1 was synthesized from 2-methoxyaniline and 14.1 using general procedure A. (Yield: 31.52%). MS (ES): m/z 409.83 [M+H]$^+$.

Synthesis of Compound 28.2.

Compound 28.2 was synthesized from 28.1 and cyclopropanecarboxamide using general procedure B. (Yield: 44.68%). MS (ES): m/z 458.48 [M+H]$^+$.

Synthesis of Compound I-28.

Compound I-28 was synthesized from 28.2 and cyclopropanecarboxamide using general procedure C. (Yield: 99.56%). MS(ES): m/z 374.30 [M+H]$^+$, LCMS purity 100.00% HPLC purity 99.34%, 1H NMR (DMSO, 400 MHz): 10.51 (s, 1H), 8.02 (s, 1H), 7.65 (s, 1H), 7.37-7.31 (m, 1H), 7.18-6.96 (m, 4H), 3.79 (s, 3H), 1.99-1.95 (m, 1H), 0.74 (s, 4H).

Example 29: Synthesis of N-(7-((3-cyano-2-methoxyphenyl)amino)-2-(difluoromethyl)-3H-imidazo[4,5-b]pyridin-5-yl)cyclopropanecarboxamide, I-29

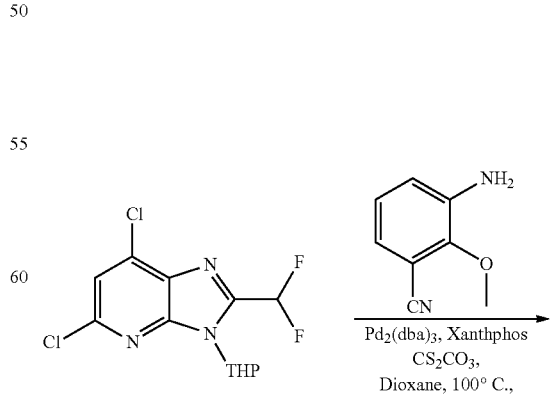

13.4

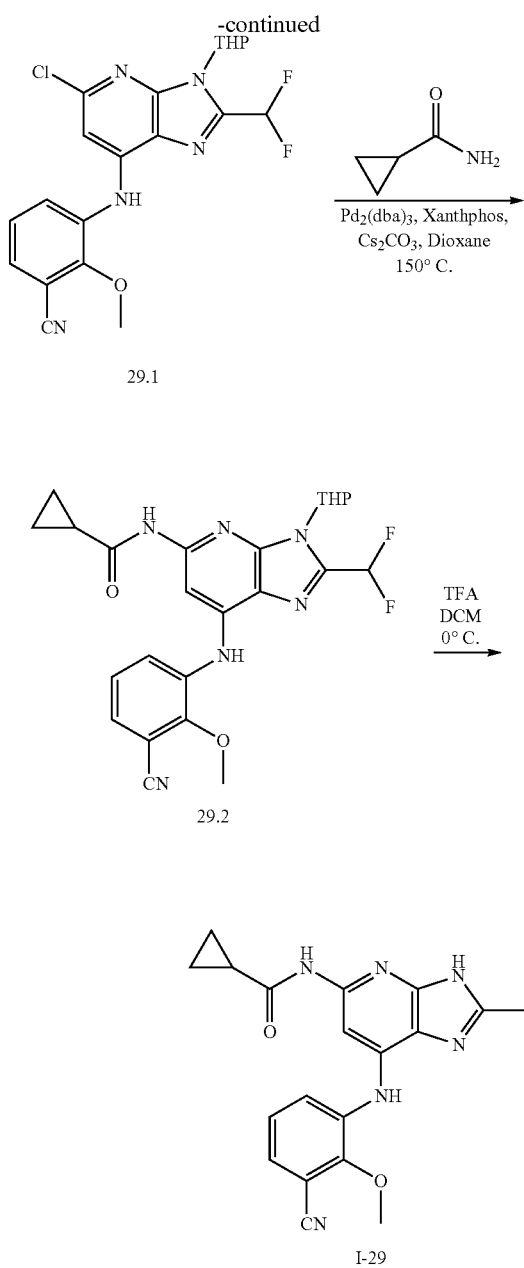

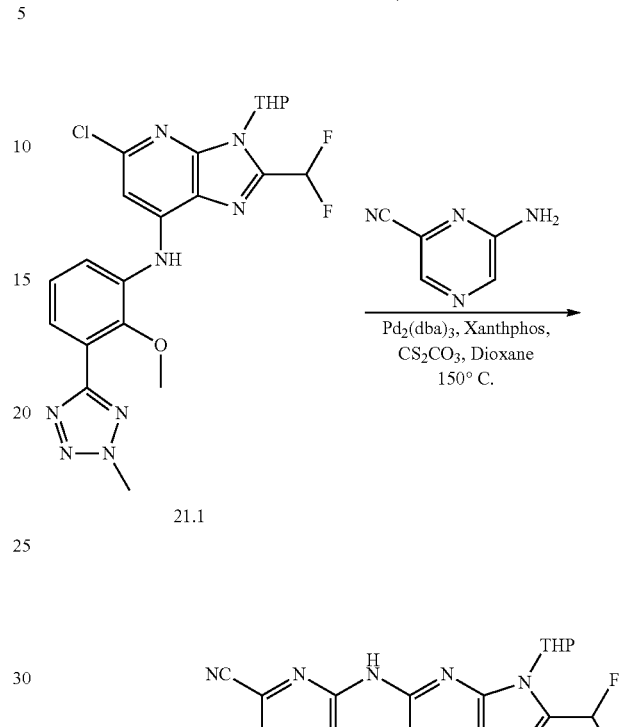

Example 30: Synthesis of 6-((2-(difluoromethyl)-7-((2-methoxy-3-(2-methyl-2H-tetrazol-5-yl)phenyl)amino)-3H-imidazo[4,5-b]pyridin-5-yl)amino)pyrazine-2-carbonitrile, I-30

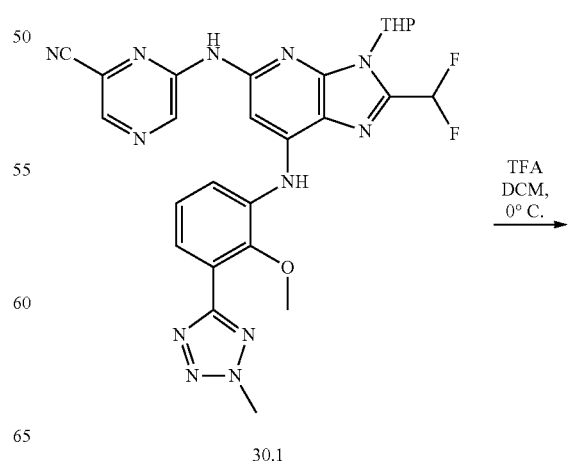

Synthesis of Compound 29.1.

Compound 29.1 was synthesized from 3-amino-2-methoxybenzonitrile and 13.4 using general procedure A. (Yield: 20.79%). MS (ES): m/z 434.84 [M+H]$^+$.

Synthesis of Compound 29.2.

Compound 29.2 was synthesized from 29.1 and cyclopropanecarboxamide using general procedure B. (Yield: 83.49%). MS (ES): m/z 483.49 [M+H]$^+$.

Synthesis of Compound I-29.

Compound I-29 was synthesized from 29.2 using general procedure C. (Yield: 60.85%). MS(ES): m/z 399.23 [M+H]$^+$, LCMS purity 100.00%, HPLC purity 100.00%, 1H NMR (DMSO, 400 MHz): 13.47 (s, 1H), 10.55 (s, 1H), 8.75 (s, 1H), 7.64-7.58 (m, 2H), 7.45 (s, 1H), 7.30-7.26 (t, J=8 Hz, 1H), 7.04 (s, 1H), 3.82 (s, 3H), 1.98-1.96 (m, 1H), 0.73 (m, 4H).

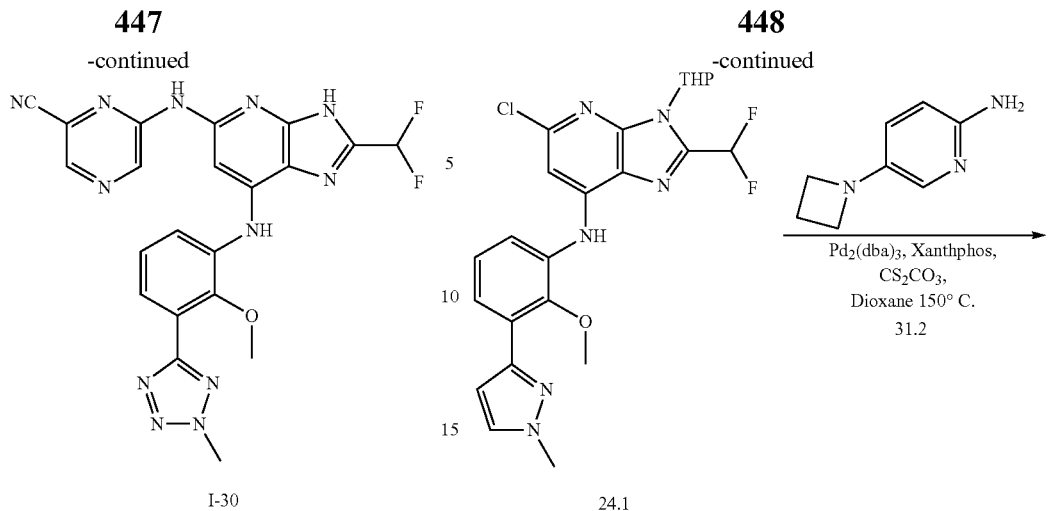

I-30

Synthesis of Compound 30.1.

Compound 30.1 was synthesized from 6-aminopyrazine-2-carbonitrile and 21.1 using general procedure B. (Yield: 81.66%). MS (ES): m/z 575.56 [M+H]$^+$.

Synthesis of Compound I-30.

Compound I-30 was synthesized from 30.1 using general procedure C. (Yield: 50.21%). MS(ES): m/z 491.38 [M+H]$^+$, LCMS purity: 100%, HPLC purity: 98.39%, 1H NMR (DMSO, 400 MHz): 13.53 (s, 1H), 10.41 (s, 1H), 9.49 (s, 1H), 8.54 (s, 2H), 7.71-7.65 (m, 2H), 7.39-7.35 (t, J=8 Hz, 1H), 7.22 (s, 1H), 6.99 (s, 1H), 4.43 (s, 3H), 3.69 (s, 3H).

Example 31: Synthesis of N5-(5-(azetidin-1-yl)pyridin-2-yl)-2-(difluoromethyl)-N7-(2-methoxy-3-(1-methyl-1H-pyrazol-3-yl)phenyl)-3H-imidazo[4,5-b]pyridine-5,7-diamine, I-31

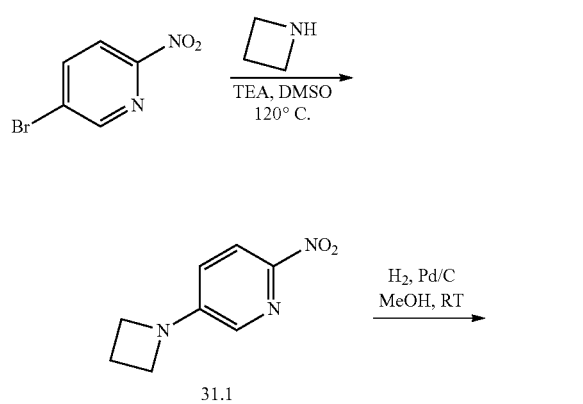

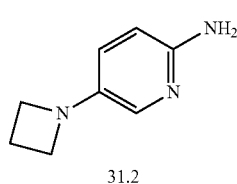

31.2

Synthesis of Compound 31.1.

To a solution of 5-bromo-2-nitropyridine (2.0 g, 9.85 mmol, 1.0 eq) in dimethyl sulfoxide (20 mL) was added Azetidine (1.13 g, 19.70 mmol, 2.0 eq) and triethyl amine (1.09 g, 10.83 mmol, 1.1 eq). Reaction mixture was stirred at 120° C. for 16 h. Upon completion, reaction mixture was transferred into water and extracted with ethyl acetate. Organic layers were combined, dried over Na$_2$SO$_4$ and concentrated in vacuo to obtain crude product. This was purified by column chromatography and compound was eluted in 20% ethyl acetate in hexane as eluant to obtain pure 31.1 (1.2 g, 67.98%). MS(ES): m/z 180.18 [M+H]$^+$.

Synthesis of Compound 31.2.

To a solution of 31.1 (1.2 g, 6.70 mmol, 1.0 eq) in MeOH (10 mL), 10% Pd/C (0.2 g) was added. Hydrogen was purged through reaction mixture for 4 h. Upon completion, reaction mixture was filtered through celite-bed and washed with MeOH. Filtrate was concentrated in vacuo to obtain 31.2. (0.7 g, 75.06%). MS(ES): m/z 150.20 [M+H]+.

Synthesis of Compound 31.3.

Compound 31.3 was synthesized from 31.2 and 24.1 using general procedure B. (Yield: 51.71%). MS (ES): m/z 602.66 [M+H]+.

Synthesis of Compound I-31.

Compound I-31 was synthesized from 31.3 using general procedure C. (Yield: 58.13%). MS(ES): m/z 518.46 [M+H]+, LCMS purity: 99.44%, HPLC purity: 99.04%, 1H NMR (DMSO, 400 MHz): 9.17 (s, 1H), 7.96 (s, 2H), 7.77-7.76 (d, J=2 Hz, 1H), 7.61 (m, 1H), 7.43 (s, 2H), 7.21-7.17 (t, J=3.8 Hz, 2H), 6.89-6.85 (m, 2H), 6.72 (s, 1H), 3.90 (s, 3H), 3.77-3.74 (t, J=6.8 Hz, 4H), 3.59 (s, 3H), 2.29 (s, 2H).

Example 32: Synthesis of 6-((2-(difluoromethyl)-7-((2-methoxy-3-(2-methyl-2H-tetrazol-5-yl)phenyl)amino)-3H-imidazo[4,5-b]pyridin-5-yl)amino)-4-methylpicolinonitrile, I-32

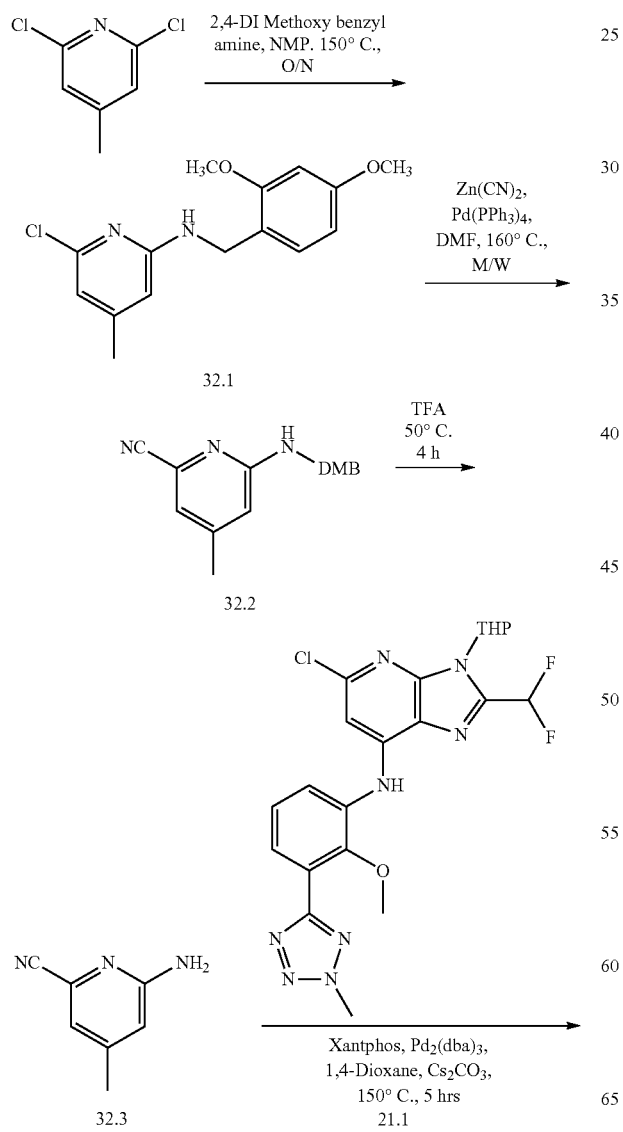

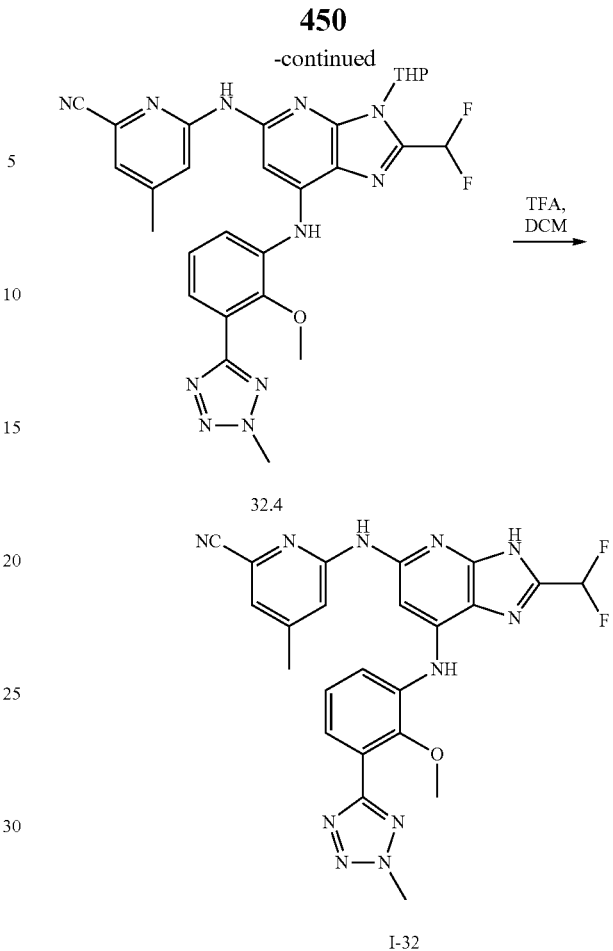

Synthesis of Compound 32.1.

To a solution of 2,6-dichloro-4-methylpyridine (10 g, 18.58 mmol, 1.0 eq) in N-methylpyrrolidine (20 ml), di-isopropyl ethyl amine (6.6 ml, 36.25 mmol, 2.0 eq) and 2,4-di-methoxybenzyl amine (93.2 ml, 18.58 mmol, 1.0 eq) were added. Reaction mixture was heated at 150° C. for 16 h. Upon completion, reaction mixture was transferred in water and extracted with ethyl acetate. Organic layers were combined, dried over $Na_2SO_4$ and concentrated in vacuo to get the crude material. This was purified by column chromatography and compound was eluted in 15% ethylacetate in hexane as eluant to obtain pure 32.1 (7 g, 38.79%). MS(ES): m/z 293.76 [M+H]+.

Synthesis of Compound 32.2.

To compound 32.1 (7 g, 23.89 mmol, 1.0 eq) in dimethylformamide (70 mL), zinc cyanide (5.59 g, 47.78 mmol, 2 eq) was added. Reaction mixture was degassed for 30 min. Then tetrakis(triphenylphosphine)palladium(0) (4.13 g, 3.583 mmol, 0.15 eq) was added to the reaction mixture and further degassed for 5 min. Reaction mixture was stirred at 160° C. for 16 h. After completion of the reaction, the reaction mixture was transferred into cold water and extracted with ethyl acetate. Organic layers were combined, dried over $Na_2SO_4$ and concentrated in vacuo to obtain crude product. This was purified by column chromatography and compound was eluted in 20% ethyl acetate in hexane as eluant to obtain pure 32.2 (3.5 g, 51.66%). MS(ES): m/z 284.83 [M+H]+.

Synthesis of Compound 32.3.

To a compound of 32.2 (0.4 g, 1.413 mmol, 1.0 eq) and trifluoroacetic acid (0.03 mL, 0.14 mmol, 0.1 eq) was added.

Reaction mixture was stirred at 50° C. for 4 h. After completion of reaction, the pH of the solution was adjusted to 7 by using NaHCO$_3$ solution and then extracted with ethyl acetate. Organic layers were combined, dried over Na$_2$SO$_4$ and concentrated in vacuo to obtain crude product. This was purified by column chromatography and compound was eluted in 10% ethyl acetate in hexane as eluant to obtain pure 32.3 (0.2 g, 79.79%). MS(ES): m/z 134.15 [M+H]$^+$.

Synthesis of Compound 32.4.

Compound 32.4 was synthesized from 32.3 and 21.1 using general procedure B. (Yield: 48.79%). MS(ES): m/z 604.64 [M+H]$^+$.

Synthesis of I-32.

Compound I-32 was synthesized from 32.4 using general procedure C. (Yield: 41.50%). MS(ES): m/z 504.43 [M+H]$^+$, LCMS purity: 100% HPLC purity: 100%, 1H NMR (DMSO, 400 MHz): 9.95 (s, 1H), 8.32 (s, 1H), 8.08 (s, 1H), 7.69-7.66 (t, J=6 Hz, 2H) 7.39-7.31 (m, 2H), 7.19 (s, 1H), 7.08 (s, 1H), 4.45 (s, 3H), 3.70 (s, 3H), 2.32 (s, 3H).

Example 33: Synthesis of 6-((2-(difluoromethyl)-7-((2-methoxy-3-(1-methyl-1H-pyrazol-3-yl)phenyl)amino)-3H-imidazo[4,5-b]pyridin-5-yl)amino)-4-methylpicolinonitrile, I-33

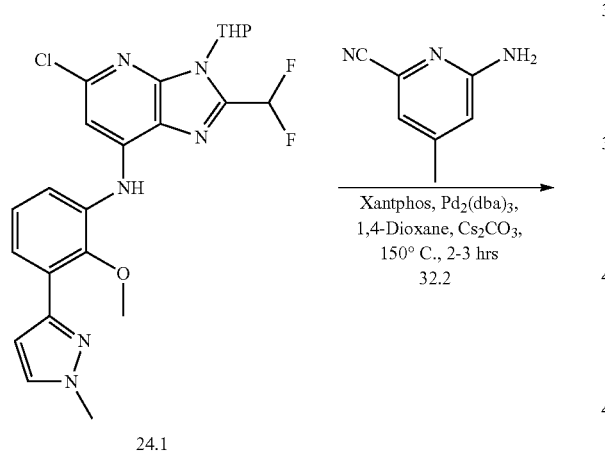

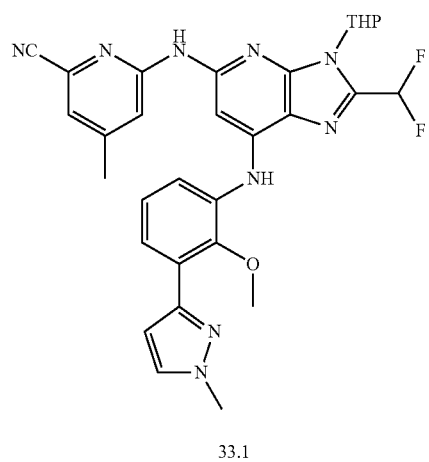

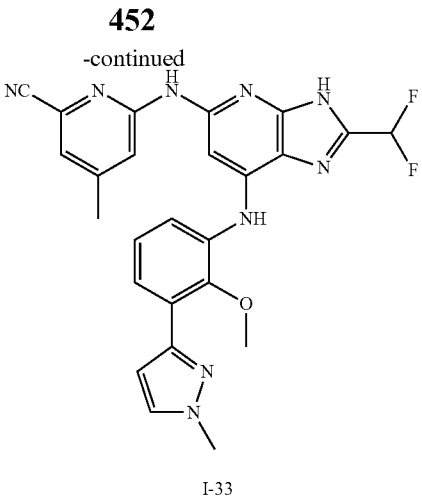

I-33

Synthesis of Compound 33.1.

Compound 33.1 was synthesized from 24.1 and 32.2 using general procedure B. (Yield: 53.43%). MS(ES): m/z 586.62 [M+H]$^+$.

Synthesis of I-33.

Compound I-33 was synthesized from 33.1 using general procedure C. (Yield: 58.39%). MS(ES): m/z 502.43 [M+H]$^+$, LCMS purity: 100% HPLC purity: 96.90%, 1H NMR (DMSO, 400 MHz): 9.85 (s, 1H), 8.13 (s, 1H), 8.02 (s, 1H), 7.77-7.76 (d, J=2.4 Hz, 1H), 7.58-7.52 (m, 2H), 7.27-7.17 (m, 3H), 7.09 (s, 1H), 6.73-6.73 (d, J=2 Hz, 1H), 3.90 (s, 3H), 3.59 (s, 3H), 2.32 (s, 3H).

Example 34: Synthesis of N-(2-(difluoromethyl)-7-((2-methoxy-3-(1-methyl-1H-pyrazol-4-yl)phenyl)amino)-3H-imidazo[4,5-b]pyridin-5-yl)cyclopropanecarboxamide, I-34

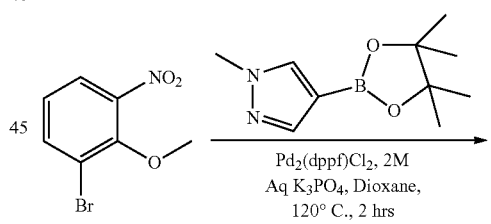

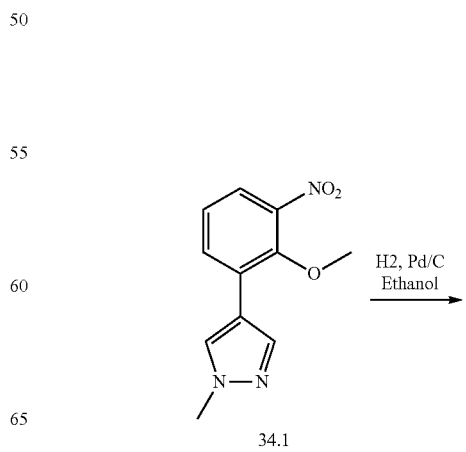

34.1

-continued

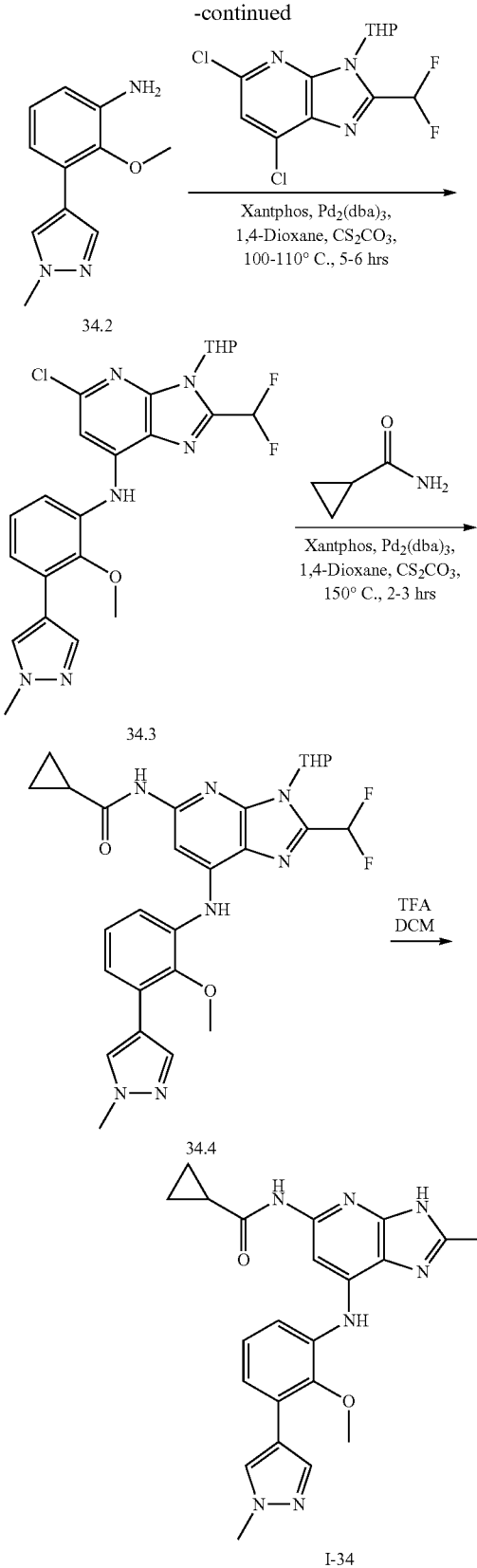

Synthesis of Compound 34.1.
To a solution of 1-bromo-2-methoxy-3-nitrobenzene 1 (2.0 g, 8.62 mmol, 1.0 eq) in 1,4-dioxane (20 mL) was added 1-methyl-4-(4,4,5,5-tetramethyl-1,3,2-dioxaborolan-2-yl)-1H-pyrazole (1.79 g, 8.62 mmol, 1. eq) Reaction mixture was degassed with argon for 10 min. Then [1,1'-Bis(diphenylphosphino)ferrocene]palladium(II) dichloride (0.630 g, 0.862 mmol, 0.1 eq) and 2M aqueous potassium phosphate (5.2 ml) was added into it. Reaction mixture was stirred at 120° C. for 2 hours. Upon completion, reaction mixture was transferred into cold water then extracted with ethyl acetate. Organic layers were combined, dried over $Na_2SO_4$ and concentrated in vacuo to obtain crude product. This was purified by column chromatography and compound was eluted in 3% MeOH in $CH_2Cl_2$ as eluant to obtain pure 34.1 (0.8 g, 39.80%). MS(ES): m/z 234.23 $[M+H]^+$.

Synthesis of Compound 34.2.
To compound 34.1 (0.800 g, 3.43 mmol, 1.0 eq) in MeOH, 10% Pd/C (0.150 g) was added. Hydrogen was purged through reaction mixture for 4 h. Upon completion, reaction mixture was filtered through celite-bed and washed with MeOH. Filtrate was concentrated in vacuo to obtain 34.2 (0.800 g, 96.82%). MS(ES): m/z 204.25 $[M+H]^+$.

Synthesis of Compound 34.3.
Compound 34.3 was synthesized from 13.4 and 34.2 using general procedure A. (Yield: 55.35%). MS(ES): m/z 489.61 $[M+H]^+$.

Synthesis of Compound 34.4.
Compound 34.4 was synthesized from 34.3 and cyclopropanecarboxamide using general procedure B. (Yield: 59.52%). MS(ES): m/z 489.48 $[M+H]^+$.

Synthesis of I-34.
Compound I-34 was synthesized from 34.4 using general procedure C. (Yield: 64.69%). MS(ES): m/z 454.30 $[M+H]^+$, LCMS purity 99.64% HPLC purity 99.44%, 1H NMR (DMSO, 400 MHz): 10.60 (s, 1H), 8.39 (s, 1H), 8.14 (s, 1H), 7.90 (s, 1H), 7.58 (s, 1H), 7.42-7.41 (d, J=6.4 Hz, 1H), 7.24-7.13 (m, 2H), 3.88 (s, 3H), 3.55 (s, 3H), 3.15 (s, 1H), 1.97-1.94 (t, J=11.6 Hz, 1H), 0.74 (bs, 4H).

Example 35: N-(2-(difluoromethyl)-7-((2-methoxy-4-(pyrrolidine-1-carbonyl)phenyl)amino)-3H-imidazo[4,5-b]pyridin-5-yl)cyclopropanecarboxamide, I-35

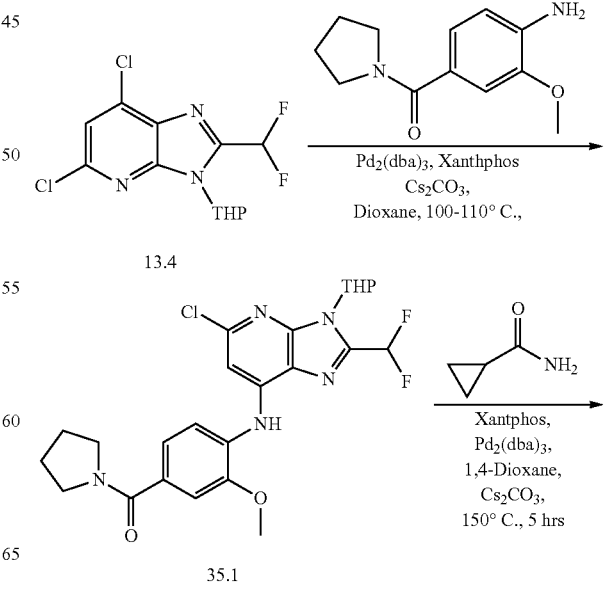

455
-continued

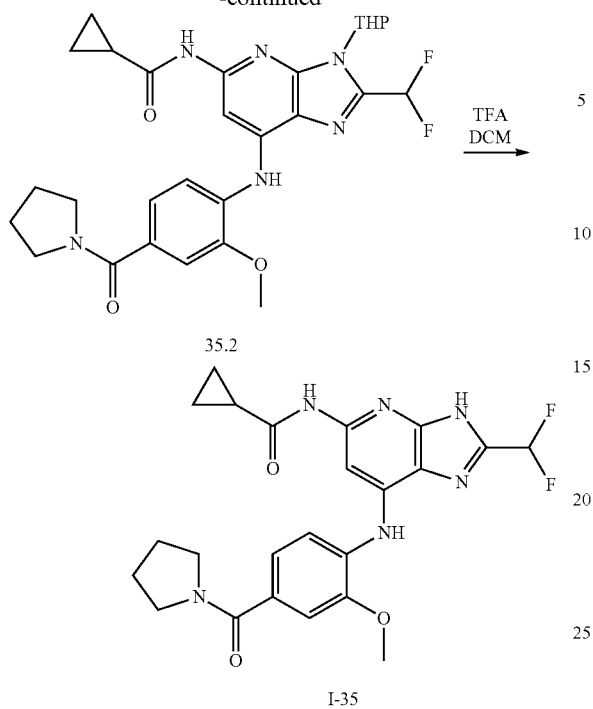

Synthesis of Compound 35.1.

Compound 35.1 was synthesized from the pictured aminobenzamide and 13.4 using general procedure A. (Yield: 28.01%). MS(ES): m/z 506.49 [M+H]$^+$.

Synthesis of Compound 35.2.

Compound 35.2 was synthesized from 35.1 and cyclopropanecarboxamide using general procedure B. (Yield: 66.35%). MS(ES): m/z 555.53 [M+H]$^+$.

Synthesis of I-35 Compound I-35 was synthesized from 35.2 using general procedure C. (Yield: 81.04%). MS(ES): m/z 471.47 [M+H]$^+$, LCMS purity: 100% HPLC purity: 100%, 1H NMR (DMSO, 400 MHz): 13.53 (s, 1H), 10.61 (s, 1H), 8.15 (s, 1H), 7.80 (s, 1H), 7.44-7.42 (d, J=8 Hz, 1H) 7.26-7.17 (m, 2H), 3.87 (s, 3H), 3.49-3.48 (d, J=5.6 Hz, 4H), 2.02-1.99 (m, 1H), 1.88-1.83 (m, 4H), 0.78 (s, 4H).

Example 36: Synthesis of (6-((2-(difluoromethyl)-7-((2-methoxy-3-(2-methyl-2H-tetrazol-5-yl)phenyl) amino)-3H-imidazo[4,5-b]pyridin-5-yl)amino)-2-(trifluoromethyl)pyridin-3-yl)(pyrrolidin-1-yl) methanone, I-36

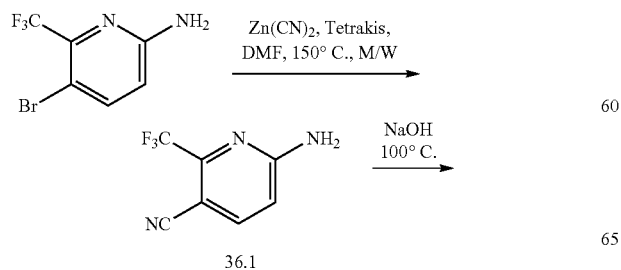

456
-continued

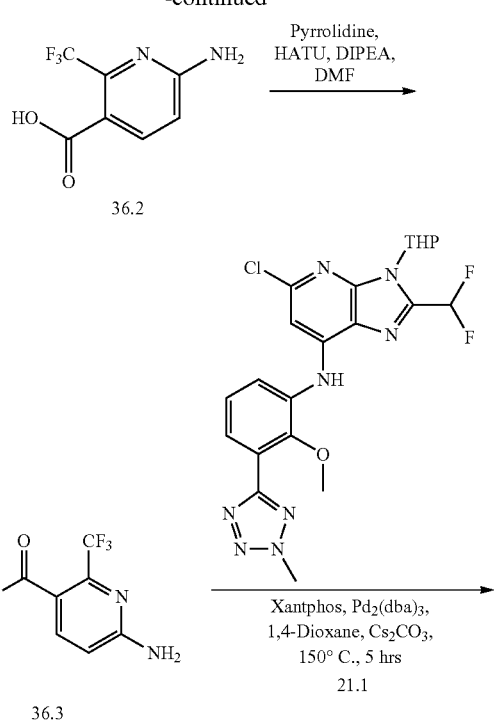

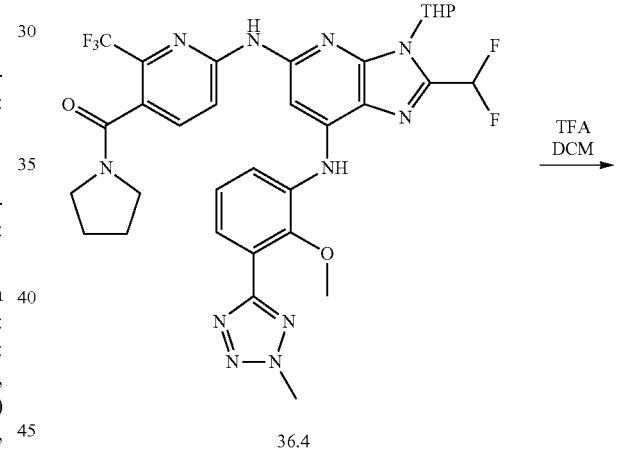

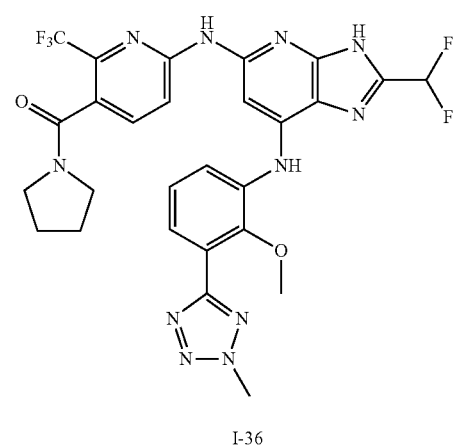

Synthesis of Compound 36.1.

To 5-bromo-6-(trifluoromethyl)pyridin-2-amine (3.0 g, 12.45 mmol, 1.0 eq) in dimethylformamide (1 ml) was added zinc cyanide (1.456 g, 12.45 mmol, 1.0 eq). The reaction mixture was then heated in microwave at 150° C. for 15 min. After completion of reaction, water was added to reaction mixture and extracted with ethyl acetate. Organic layers were combined, dried over Na$_2$SO$_4$ and concentrated in vacuo to obtain crude product. This was purified by column chromatography and compound was eluted in 20% ethyl acetate in hexane to obtain 36.1. (Yield: 68.69%). MS (ES): m/z 188.13 [M+H]$^+$.

Synthesis of Compound 36.2.

To compound 36.1 (1.6 g, 8.55 mmol, 1.0 eq) and sodium hydroxide (1.0 g, 25.65 mmol, 3.0 eq) was added in water (30 mL) The reaction mixture was stirred at 100° C. for 16 h. Upon completion, reaction mixture was extracted with ethyl acetate. Aqueous layer was acidified with HCl and extracted with ethyl acetate. Organic layers were combined, dried over Na$_2$SO$_4$ and concentrated in vacuo to obtain crude product. This was purified by column chromatography and compound was eluted in 5% MeOH in CH$_2$Cl$_2$ to obtain 36.2. (Yield: 62.41%). MS (ES): m/z 207.12 [M+H]$^+$.

Synthesis of Compound 36.3.

To a cooled solution of 36.2 (0.5 g, 2.43 mmol, 1.0 eq) and pyrrolidine (0.19 g, 2.67 mmol, 1.1 eq) in N,N-dimethylformamide (5 mL) at 0° C. was added ((1-[Bis(dimethylamino)methylene]-1H-1,2,3-triazolo[4,5-b]pyridinium3-oxid hexafluoro-phosphate)) (1.846 g, 4.86 mmol, 2.0 eq) followed by N,N-Diisopropylethylamine (0.94 g, 7.29 mmol, 3.0 eq) and the reaction mixture was stirred at r.t. for 16 h. Upon completion, reaction mixture was transferred into water and extracted with ethyl acetate. Organic layers were combined, dried over Na$_2$SO$_4$ and concentrated in vacuo to obtain crude product. This was purified by column chromatography and compound was eluted in 3% MeOH in CH$_2$Cl$_2$ to obtain pure 36.3 (0.39 g, 62.34%). MS(ES): m/z 260.23 [M+H]$^+$.

Synthesis of Compound 36.4.

Compound was synthesized from 36.3 and 21.1 using general procedure B. (Yield: 33.02%). MS(ES): m/z 714.28 [M+H]$^+$.

Synthesis of I-36.

Compound I-36 was synthesized from 36.4 using general procedure C. (Yield: 47.23%). MS(ES): m/z 630.38 [M+H]$^+$, LCMS purity 94.45%, HPLC purity 94.64%, 1H NMR (DMSO, 400 MHz): 10.13 (s, 1H), 8.38 (s, 1H), 8.31-8.29 (d, J=8.8 Hz, 1H), 7.83-7.81 (d, J=8.8 Hz, 1H), 7.70-7.68 (d, J=8 Hz, 1H), 7.64-7.62 (d, J=8 Hz, 1H), 7.38-7.30 (m, 2H), 7.19 (s, 1H), 7.03 (s, 1H), 4.44 (s, 3H), 3.69 (s, 3H), 3.44-3.40 (t, J=6.4 Hz, 2H), 3.10-3.07 (t, J=6.4 Hz, 2H), 1.87-1.78 (m, 4H).

Example 37: Synthesis of 6-((2-(difluoromethyl)-7-((2-methoxy-3-(2-methyl-2H-tetrazol-5-yl)phenyl)amino)-3H-imidazo[4,5-b]pyridin-5-yl)amino)-3-(2-oxopyrrolidin-1-yl)picolinonitrile, I-37

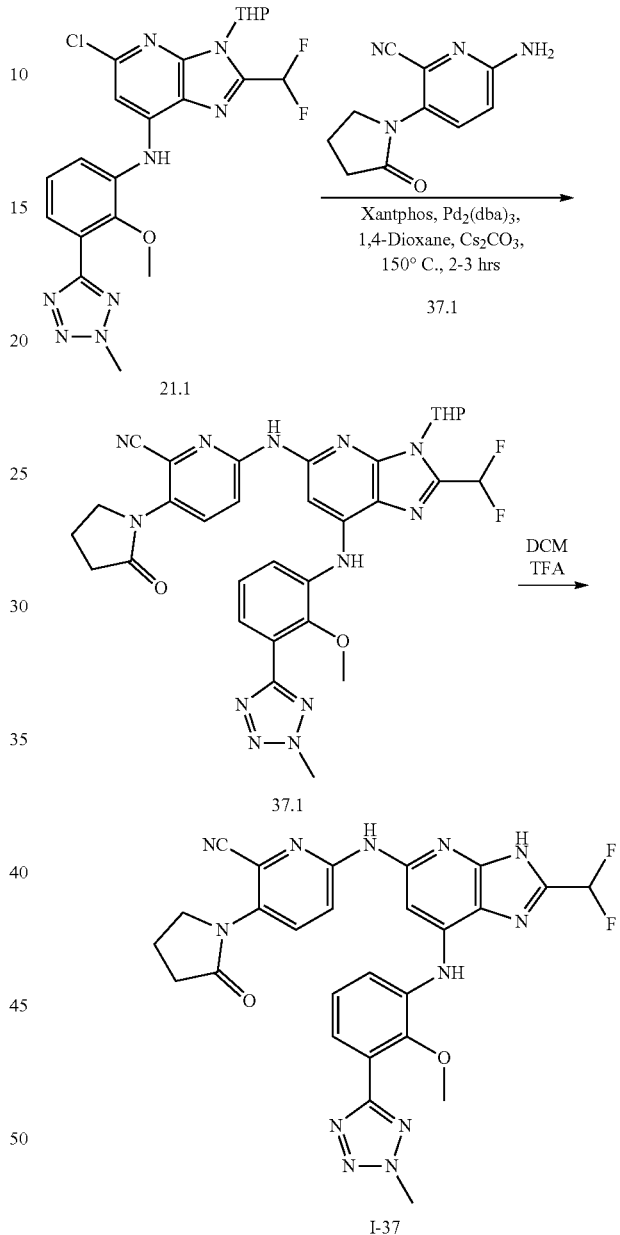

Synthesis of Compound 37.1.

Compound 37.1 was synthesized from 21.1 and 37.1 (prepared from 3-bromo-6-aminopicolinonitrile and pyrrolidinone with copper iodide in dioxane) using general procedure B. (Yield: 54.82%). MS(ES): m/z 657.66 [M+H]$^+$.

Synthesis of I-37.

Compound I-37 was synthesized from 37.1 using general procedure C. (Yield: 52.13%). MS(ES): m/z 573.22 [M+H]$^+$, LCMS purity: 99.71% HPLC purity: 100%, 1H NMR (DMSO, 400 MHz): 10.16 (s, 1H), 8.37-8.33 (m, 1H), 7.89-7.87 (d, J=9.2 Hz, 2H), 7.70-7.68 (d, J=7.6 Hz, 2H), 7.45-7.34 (m, 2H), 7.210 (s, 1H), 7.031 (s, 1H,) 4.46 (s, 3H), 3.84-3.81 (t, J=6.8 Hz, 2H), 3.72 (s, 3H), 2.091 (s, 4H).

Example 38: Synthesis of 6-((2-(difluoromethyl)-7-((2-methoxy-3-(2-methyl-2H-tetrazol-5-yl)phenyl)amino)-3H-imidazo[4,5-b]pyridin-5-yl)amino)-3-methylpyrazine-2-carbonitrile, I-38

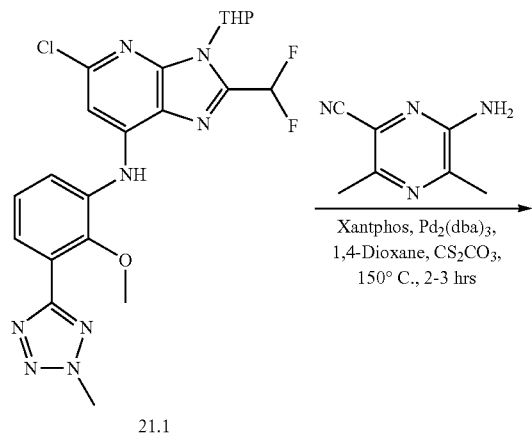

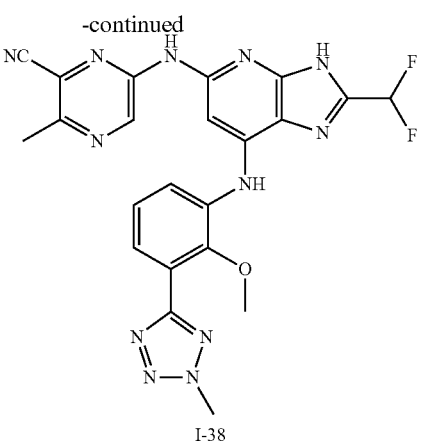

Synthesis of Compound 38.21.

Compound 38.1 was synthesized from 6-amino-3-methylpyrazine-2-carbonitrile and 21.1 using general procedure B. (Yield: 50.04%). MS(ES): m/z 589.58 [M+H]$^+$.

Synthesis of I-38.

Compound I-38 was synthesized from 38.1 using general procedure C. (Yield: 38.89%). MS(ES): m/z 505.43 [M+H]$^+$, LCMS purity: 100% HPLC purity: 94.10%, 1H NMR (DMSO, 400 MHz): 13.55 (s, 1H), 10.26 (s, 1H), 9.44 (s, 1H), 8.47 (s, 1H), 7.72-7.67 (m, 2H), 7.42-7.38 (m, 2H), 6.97 (s, 1H), 4.47 (s, 3H), 3.71 (s, 3H), 2.57 (s, 3H).

Example 39: (S)-6-((2-(difluoromethyl)-7-((2-methoxy-3-(2-methyl-2H-tetrazol-5-yl)phenyl)amino)-3H-imidazo[4,5-b]pyridin-5-yl)amino)-3-(3-methoxypyrrolidin-1-yl)picolinonitrile, I-39

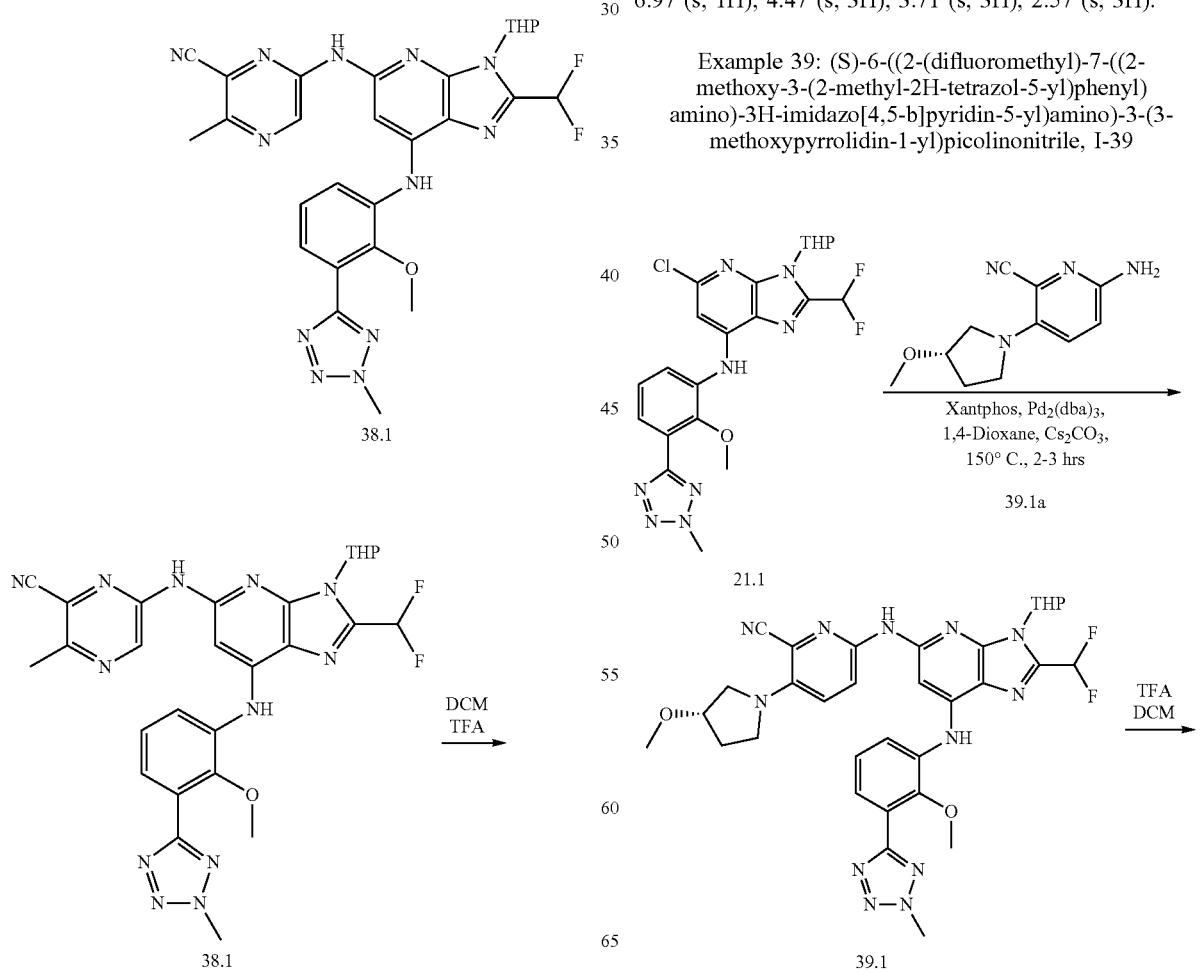

461
-continued

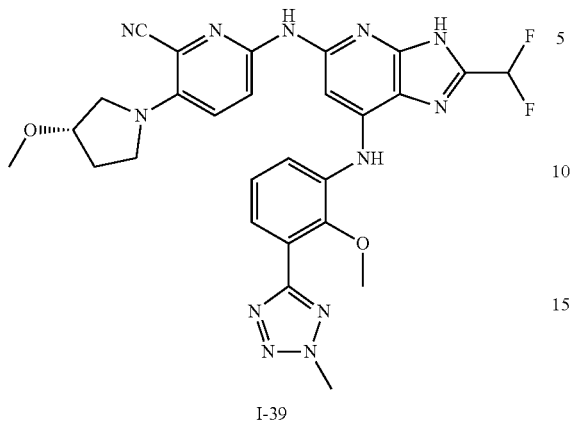

I-39

Synthesis of Compound 39.1.

Compound 39.1 was synthesized from 21.1 and 39.1a (itself prepared from 3-methoxypyrrolidine and 3-bromo-6-aminopicolinonitrile using general procedure B) using general procedure B. (Yield: 39.70%). MS(ES): m/z 673.70 [M+H]$^+$.

Synthesis of I-39.

Compound I-39 was synthesized from 39.1 using general procedure C. (Yield: 58.83%). MS(ES): m/z 589.49 [M+H]$^+$, LCMS purity: 98.08%, HPLC purity: 99.07%, Chiral HPLC purity: 100%, 1H NMR (DMSO, 400 MHz): 13.5 (s, 1H), 9.67 (s, 1H), 8.37 (s, 1H), 7.91 (s, 1H), 7.75-7.70 (m, 2H), 7.46-7.38 (m, 3H), 7.25 (s, 1H), 7.11 (s, 1H), 4.48 (s, 3H), 3.75 (s, 4H), 3.61-3.49 (m, 3H), 3.29 (s, 3H), 2.10-2.00 (m, 2H).

Example 40: Synthesis of 3-(azetidin-1-yl)-6-((2-(difluoromethyl)-7-((2-methoxy-3-(2-methyl-2H-tetrazol-5-yl)phenyl)amino)-3H-imidazo[4,5-b]pyridin-5-yl)amino)picolinonitrile, I-40

462
-continued

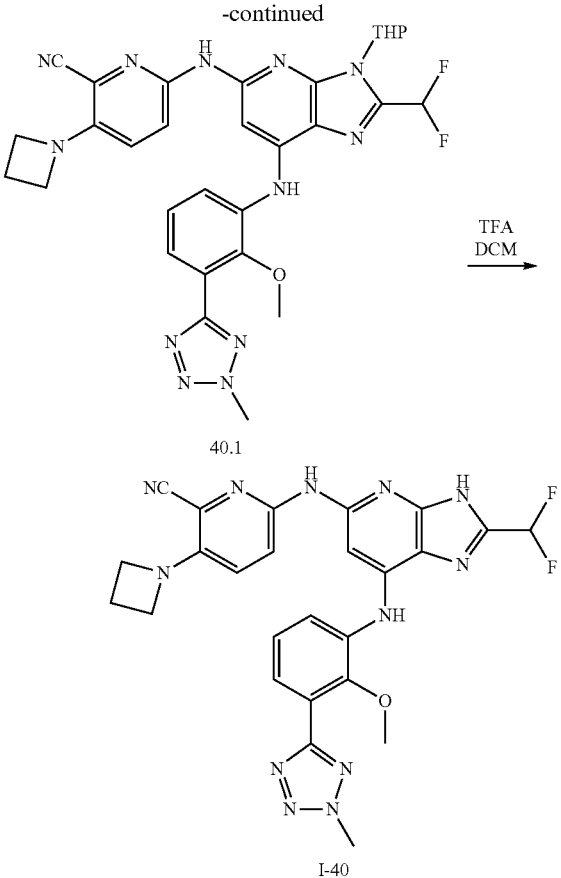

Synthesis of Compound 40.1.

Compound 40.1 was synthesized from 21.1 and 40.2 (prepared from 3-bromo-6-aminopicolinonitrile and azetidine using general procedure B) using general procedure B. (Yield: 62.47%). MS(ES): m/z 629.53 [M+H]$^+$.

Synthesis of I-40.

Compound I-40 was synthesized from 40.1 using general procedure C. (Yield: 68.82%). MS(ES): m/z 545.55 [M+H]$^+$, LCMS purity: 99.57% HPLC purity: 99.07%, 1H NMR (DMSO, 400 MHz): 9.78 (s, 1H), 8.40 (s, 1H), 7.88 (s, 1H), 7.74-7.69 (m, 2H), 7.44-7.36 (m, 1H), 7.23 (s, 1H), 7.16-7.06 (m, 2H), 4.45 (s, 3H), 4.08 (s, 4H) 3.72 (s, 3H) 2.35 (s, 2H).

Example 41: Synthesis of N-(2-(difluoromethyl)-7-((3-(1,3-dimethyl-1H-1,2,4-triazol-5-yl)-2-methoxyphenyl)amino)-3H-imidazo[4,5-b]pyridin-5-yl)cyclopropanecarboxamide, I-41

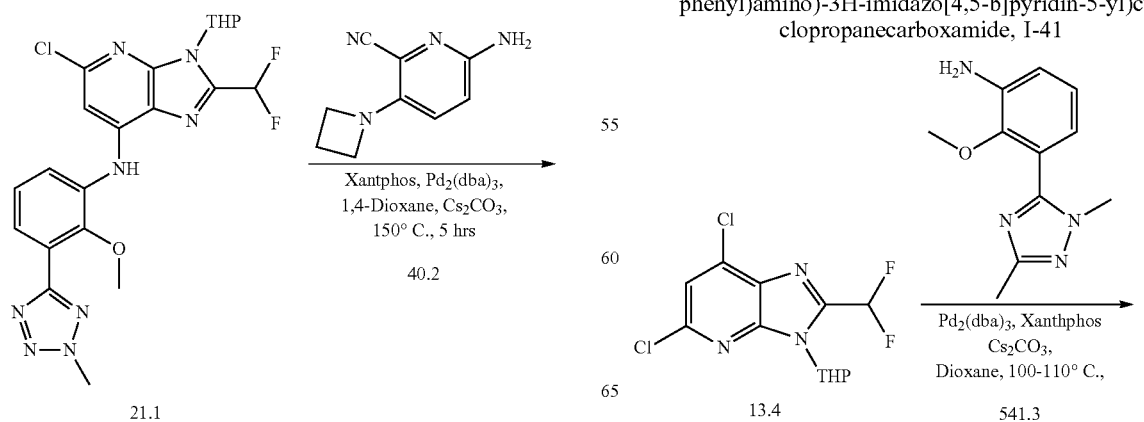

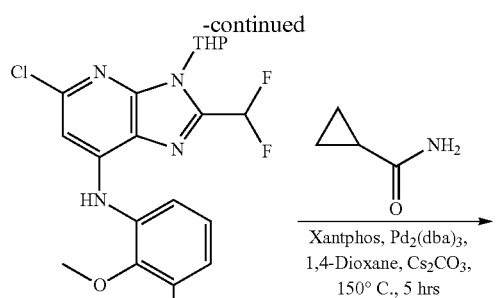

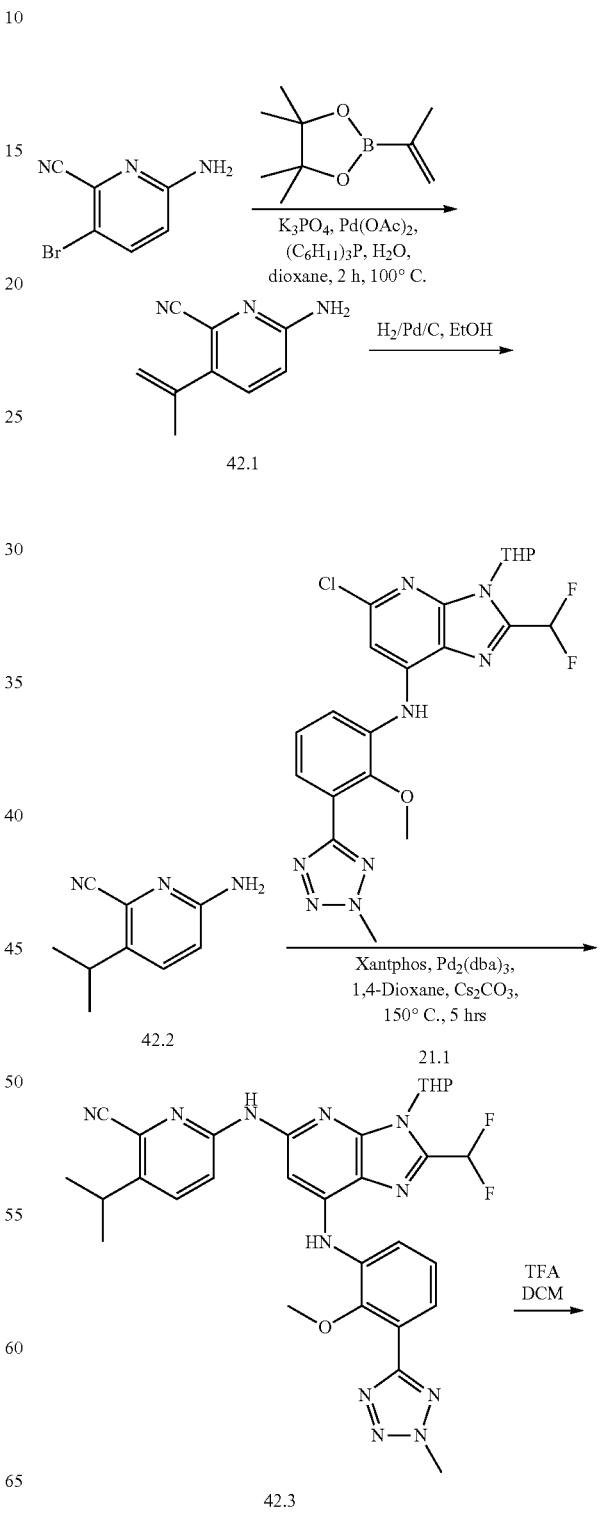

(s, 1H), 7.56-7.55 (d, J=7.5 Hz 2H), 7.39-7.20 (m, 3H) 3.66 (s, 3H) 3.39 (s, 3H), 2.30 (s, 3H), 2.02-1.99 (t, J=6 Hz 1H), 0.74-0.74 (s, 4H).

Example 42: Synthesis of 6-((2-(difluoromethyl)-7-((2-methoxy-3-(2-methyl-2H-tetrazol-5-yl)phenyl)amino)-3H-imidazo[4,5-b]pyridin-5-yl)amino)-3-isopropylpicolinonitrile, I-42

Synthesis of Compound 41.1.

Compound 41.1 was synthesized from 13.4 and 541.3 using general procedure A. (Yield: 39.37%). MS(ES): m/z 504.94 [M+H]$^+$.

Synthesis of Compound 41.2.

Compound 41.2 was synthesized from 41.1 and cyclopropanecarboxamide using general procedure B. (Yield: 59.28%). MS(ES): m/z 553.59 [M+H]$^+$.

Synthesis of I-41.

Compound I-41 was synthesized from 41.2 using general procedure C. (Yield: 45.37%). MS(ES): m/z 469.42 [M+H]$^+$, LCMS purity, 95.30%, HPLC purity: 97.70%, 1H NMR (DMSO, 400 MHz): 13.42 (s, 1H), 10.55 (s, 1H), 8.67

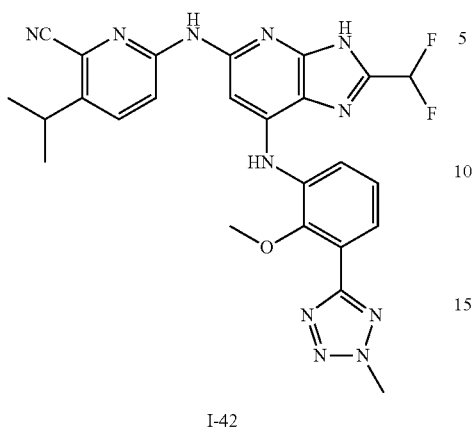

I-42

Synthesis of Compound 42.1.

To a solution of 6-amino-3-bromopicolinonitrile (0.250 g, 1.26 mmol, 1.0 eq) and 4,4,5,5-tetramethyl-2-(prop-1-en-2-yl)-1,3,2-dioxaborolane (0.53 g, 3.172 mmol, 2.5 eq) in a mixture of 1,4-dioxane (6 mL) and water (1 mL), potassium phosphate (0.940 g, 4.44 mmol, 3.5 eq), palladium acetate (0.029 g, 0.126 mmol, 0.1 eq) and triphenylphosphine (0.067 g, 0.253 mmol, 0.2 eq) were added. The reaction mixture was degassed for 15 min and then heated at 100° C. for 2 h. After completion of the reaction, water was added to the reaction mixture and extracted with ethyl acetate. Organic layers were combined, dried over anhydrous $Na_2SO_4$, filtered and concentrated in vacuo to obtain the crude material. This was purified by column chromatography using 2% MeOH in $CH_2Cl_2$ as eluent to obtain pure 42.1 (0.110 g, 54.73%). MS(ES): m/z 160.24 $[M+H]^+$.

Synthesis of Compound 42.2.

To a solution of 42.1 (0.100 g, 6.2 mmol, 1.0 eq) in ethanol (5 mL), 10% Pd/C (0.040 g) was added under nitrogen atmosphere. Hydrogen gas was purged through reaction mixture for 16 hrs. Upon completion, reaction mixture filtered through celite-bed and washed with ethanol. Filtrate was concentrated in vacuo to obtain 42.2 (0.075 g, 74.06%). MS(ES): m/z 162.37 $[M+H]^+$.

Synthesis of Compound 42.3.

Compound 42.3 was synthesized from 6-amino-3-isopropylpicolinonitrile and 21.1 using general procedure B. (Yield: 41.64%). MS(ES): m/z 616.58 $[M+H]^+$.

Synthesis of I-42.

Compound I-42 was synthesized from 42.3 using general procedure C. (Yield: 73.93%). MS(ES): m/z 532.49 $[M+H]^+$, LCMS purity: 96.16%, HPLC purity: 96.88%, 1H NMR (DMSO, 400 MHz): 13.51 (s, 1H), 9.97 (s, 1H), 8.32 (s, 1H), 8.20-8.18 (d, J=8.8 Hz 1H) 7.89-7.87 (d, J=9.2 Hz 1H) 7.74-7.68 (m, 2H), 7.43-7.39 (m, 1H), 7.22 (s, 1H), 7.15 (s, 1H), 4.47 (s, 3H) 3.73 (s, 3H), 3.18-3.15 (t, J=6.8 Hz 1H), 1.27-1.25 (d, J=6.8 Hz 6H).

Example 43: Synthesis of N-(2-((2-(difluoromethyl)-5-((6-methylpyridazin-3-yl)amino)-3H-imidazo[4,5-b]pyridin-7-yl)amino)phenyl)-N-methylmethanesulfonamide, I-43

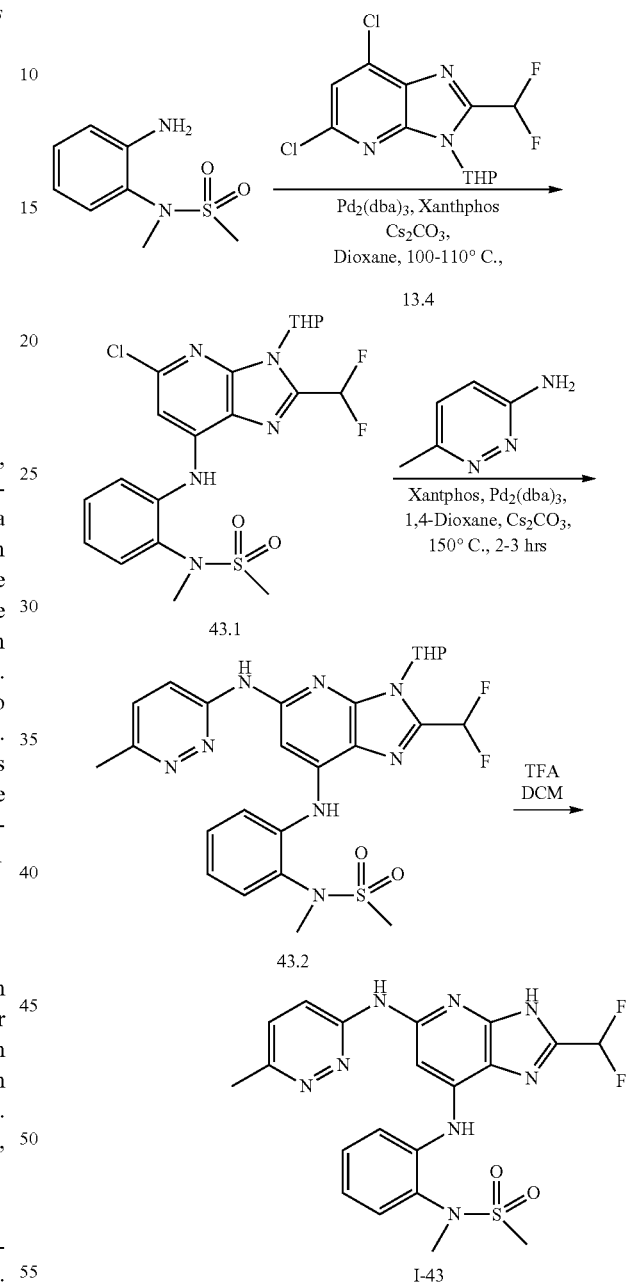

Synthesis of Compound 43.1.

Compound 43.1 was synthesized from 13.4 and N-(2-aminophenyl)-N-methylmethanesulfonamide using general procedure A. (Yield: 24.73%). MS(ES): m/z 486.79 $[M+H]^+$.

Synthesis of Compound 43.2.

Compound 43.2 was synthesized from 6-methylpyridazin-3-amine and 43.1 using general procedure B. (Yield: 39.15%). MS(ES): m/z 559.61 $[M+H]^+$.

Synthesis of I-43.

Compound I-43 was synthesized from 43.2 using general procedure C. (Yield: 78.45%). MS(ES): m/z 475.36 [M+H]+, LCMS purity: 97.00%, HPLC purity: 96.41%, 1H NMR (DMSO, 400 MHz): 13.52 (s, 1H), 10.04 (s, 1H), 8.35-8.33 (d, J=8.8 Hz 1H), 8.09 (s, 1H), 7.71-7.68 (m, 2H), 7.49-7.46 (m, 2H), 7.35-7.22 (m, 2H), 7.11 (s, 1H), 3.35 (s, 3H), 3.20 (s, 3H), 2.52 (s, 3H).

Example 44: N-(2-((5-((6-cyanopyridin-2-yl)amino)-2-(difluoromethyl)-3H-imidazo[4,5-b]pyridin-7-yl)amino)phenyl)-N-methylmethanesulfonamide, I-44

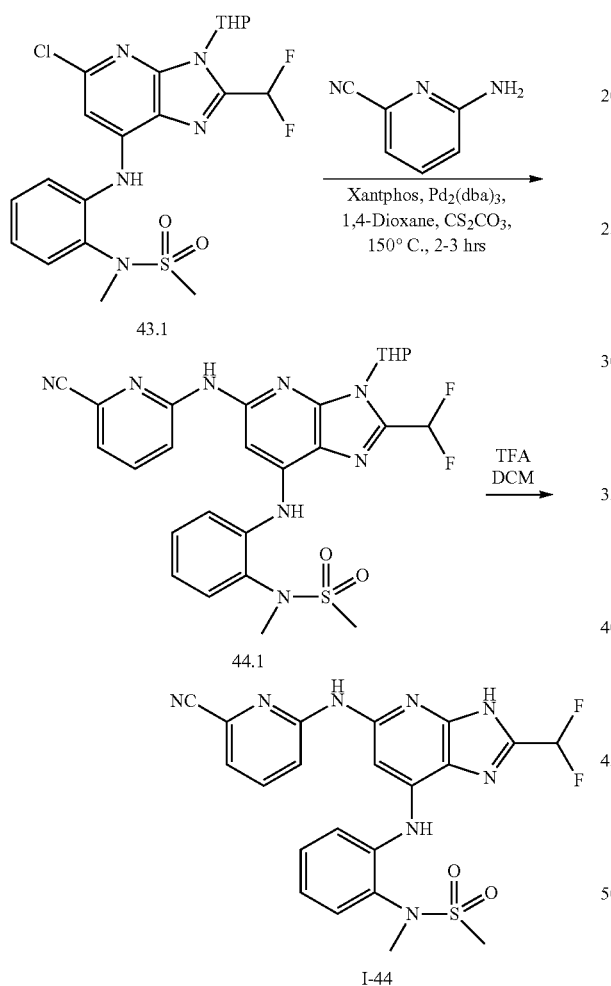

Example 45: Synthesis of N-(2-((2-(difluoromethyl)-5-((2,6-dimethylpyrimidin-4-yl)amino)-3H-imidazo[4,5-b]pyridin-7-yl)amino)phenyl)-N-methylmethanesulfonamide, I-45

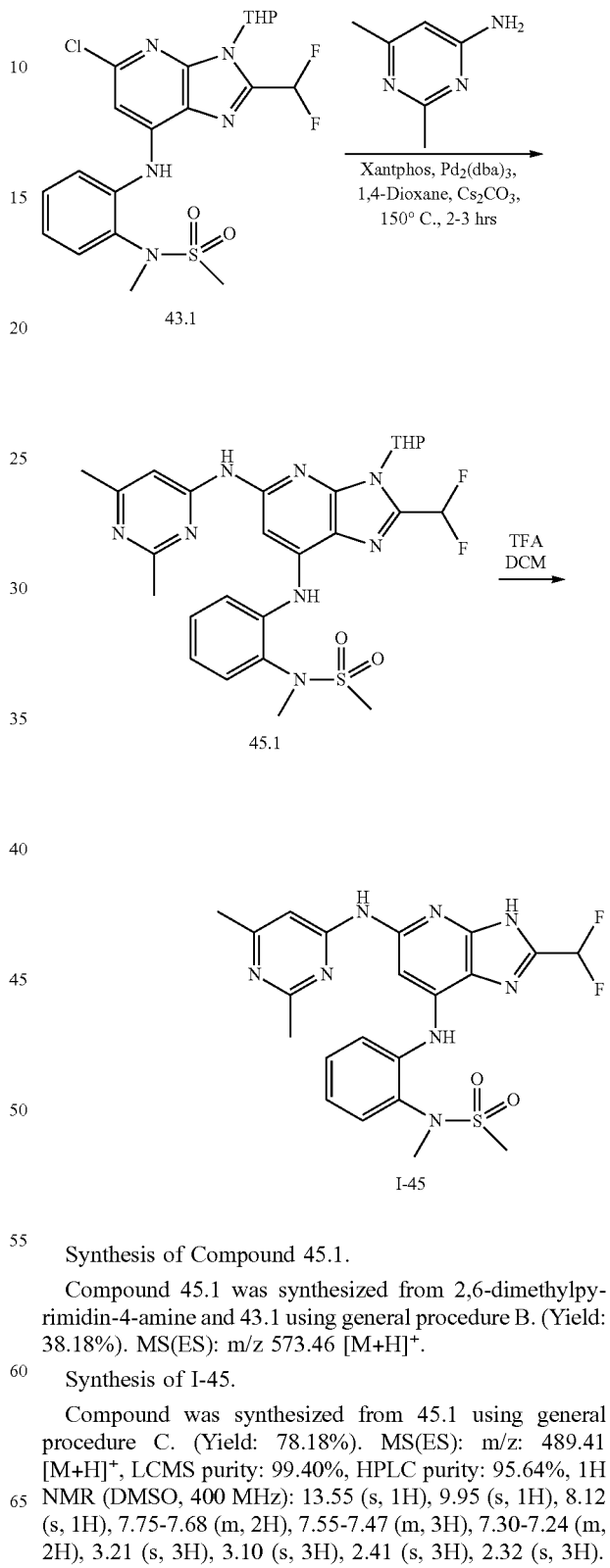

Synthesis of Compound 44.1.

Compound 44.1 was synthesized from 6-aminopicolinonitrile and 43.1 using general procedure B. (Yield: 34.12%). MS(ES): m/z 569.60 [M+H]+.

Synthesis of I-44.

Compound I-44 was synthesized from 44.1 using general procedure C. (Yield: 73.35%). MS(ES): m/z: 485.36 [M+H]+, LCMS purity: 99.02%, HPLC purity: 95.29%, 1H NMR (DMSO, 400 MHz): 10.12 (s, 1H), 8.13 (s, 2H), 7.89-7.85 (t, J=7.6 Hz 1H), 7.78-7.76 (d, J=7.6 Hz 1H), 7.69-7.68 (d, J=7.2 Hz 1H), 7.56-7.52 (t, J=7.2 Hz 1H), 7.48-7.447 (m, 2H), 7.29 (m, 2H), 3.23 (s, 3H), 3.11 (s, 3H).

Synthesis of Compound 45.1.

Compound 45.1 was synthesized from 2,6-dimethylpyrimidin-4-amine and 43.1 using general procedure B. (Yield: 38.18%). MS(ES): m/z 573.46 [M+H]+.

Synthesis of I-45.

Compound was synthesized from 45.1 using general procedure C. (Yield: 78.18%). MS(ES): m/z: 489.41 [M+H]+, LCMS purity: 99.40%, HPLC purity: 95.64%, 1H NMR (DMSO, 400 MHz): 13.55 (s, 1H), 9.95 (s, 1H), 8.12 (s, 1H), 7.75-7.68 (m, 2H), 7.55-7.47 (m, 3H), 7.30-7.24 (m, 2H), 3.21 (s, 3H), 3.10 (s, 3H), 2.41 (s, 3H), 2.32 (s, 3H).

Example 46: Synthesis of 3-((3-chloropropyl)amino)-6-((2-(difluoromethyl)-7-((2-methoxy-3-(2-methyl-2H-tetrazol-5-yl)phenyl)amino)-3H-imidazo[4,5-b]pyridin-5-yl)amino)picolinonitrile, I-46

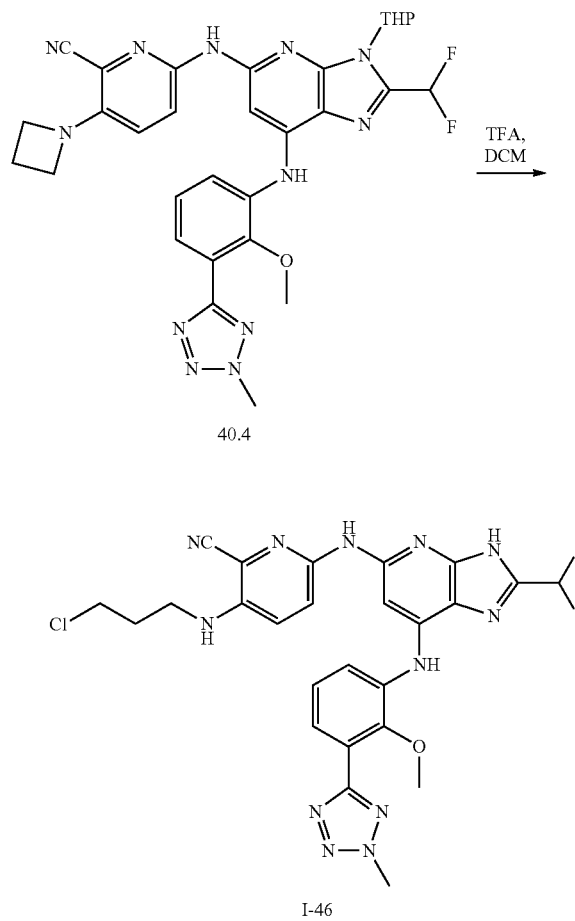

Synthesis of I-46.

Compound I-46 was synthesized from 40.4 using general procedure C. (Yield: 48.61%). MS(ES): m/z: 582.39 [M+H]$^+$, LCMS purity, 100%, HPLC purity: 98.78%, 1H NMR (DMSO, 400 MHz): 13.51 (s, 1H), 9.97 (s, 1H), 8.32 (s, 1H), 8.20-8.18 (d, J=8.8 Hz 1H) 7.89-7.87 (d, J=9.2 Hz 1H) 7.74-7.68 (m, 2H), 7.43-7.39 (m, 1H), 7.22 (s, 1H), 7.15 (s, 1H), 4.475 (s, 3H), 3.730 (s, 3H), 3.714 (s, 2H) 3.334 (s, 2H), 2.016-1.983 (t, J=6.4 Hz 2H).

Example 47: Synthesis of 6-((2-(difluoromethyl)-7-((2-methoxy-3-(2-methyl-2H-tetrazol-5-yl)phenyl)amino)-3H-imidazo[4,5-b]pyridin-5-yl)amino)-3-morpholinopyrazine-2-carbonitrile, I-47

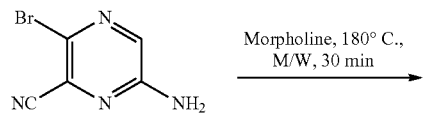

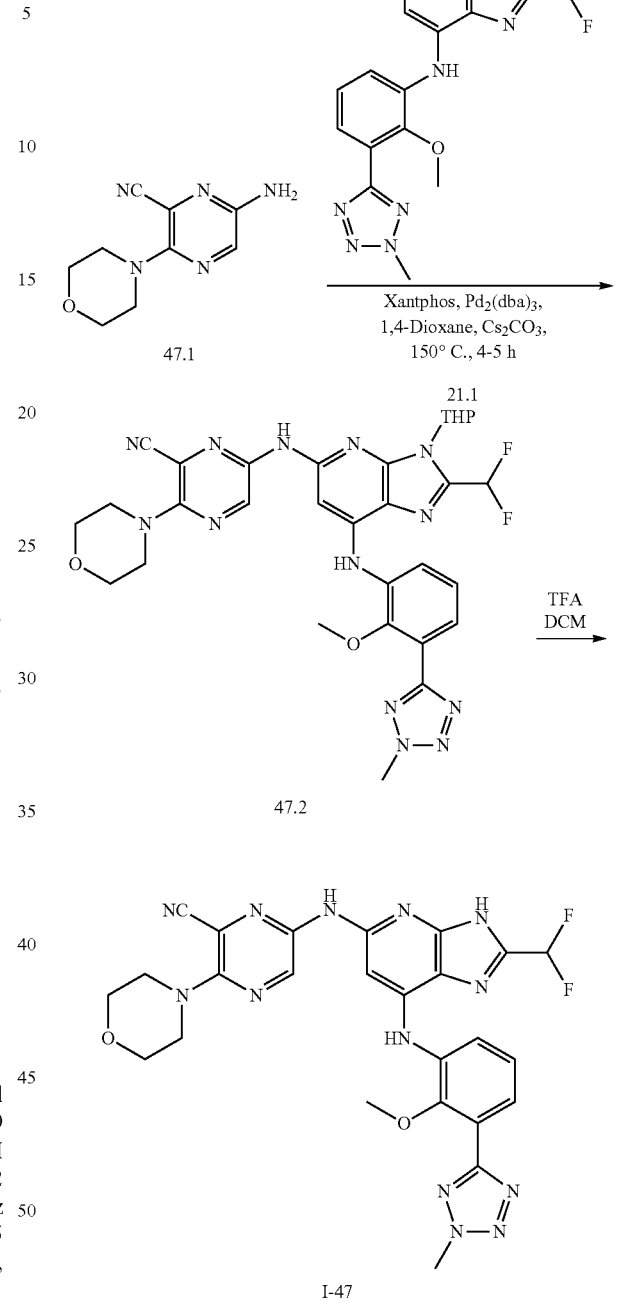

Synthesis of Compound 47.1.

To a mixture of 6-amino-3-bromopyrazine-2-carbonitrile (0.5 g, 2.51 mmol, 1.0 eq) and morpholine (0.262 g, 3.01 mmol, 1.2 eq) was heated at 180° C. under microwave irradiation for 30 min. Upon completion, reaction mixture was concentrated in vacuo to obtain crude product. This was purified by column chromatography using 20% ethyl acetate in hexane to obtain pure 47.1 (0.2 g, Yield: 38.79%). MS(ES): m/z 206.22 [M+H]$^+$.

Synthesis of Compound 47.2.

Compound 47.2 was synthesized from 21.1 and 47.1 using general procedure B. (Yield: 44.65%). MS(ES): m/z 660.66 [M+H]$^+$.

Synthesis of I-47.

Compound I-47 was synthesized from 47.2 using general procedure C. (Yield: 87.33%). MS(ES): m/z: 576.46 [M+H]+, LCMS purity, 99.22%, HPLC purity: 99.47%, 1H NMR (DMSO-d6, 400 MHz): 13.45 (s, 1H), 9.97 (s, 1H), 9.29 (s, 1H), 8.39 (s, 1H), 7.71-7.65 (m, 2H), 7.41-7.33 (m, 1H), 7.20 (t, 1H), 6.78 (s, 1H), 4.47 (s, 3H), 3.77 (s, 4H), 3.46 (s, 3H), 2.48 (s, 4H).

Example 48: Synthesis of (R)-6-((2-(difluoromethyl)-7-((2-methoxy-3-(2-methyl-2H-tetrazol-5-yl)phenyl)amino)-3H-imidazo[4,5-b]pyridin-5-yl)amino)-3-(3-methoxypyrrolidin-1-yl)pyrazine-2-carbonitrile, I-48

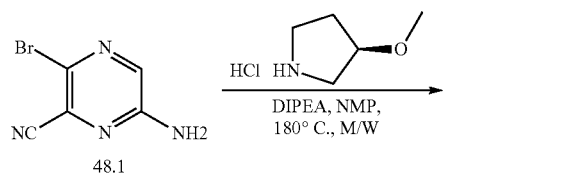

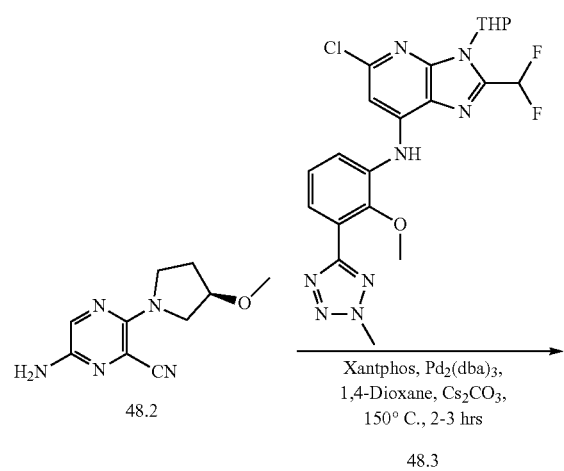

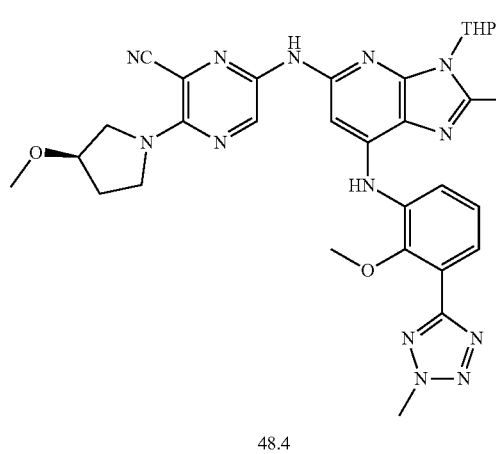

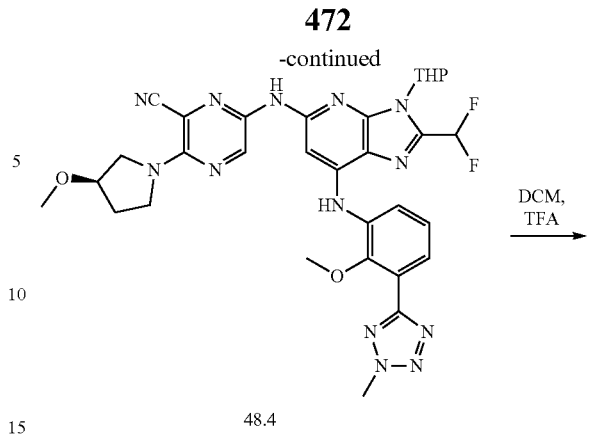

Synthesis of Compound 48.2.

To a mixture of 48.1 (0.5 g, 2.5 mmol, 1.0 eq) in N-methylpyrrolidine (2 mL) and (R)-3-methoxypyrrolidine hydrgochloride (0.41 g, 3.0 mmol, 1.2 eq) was added di-isopropyl ethyl amine (0.8 mL, 6.25 mmol, 2.5 eq) at 0° C. Reaction mixture was stirred at 180° C. 2 h in microwave. Upon completion, reaction mixture was transferred into cold water, extracted with ethyl acetate. Organic layers were combined, dried over Na$_2$SO$_4$ and concentrated in vacuo to obtain crude product. This was purified by column chromatography and compound was eluted in 30% ethyl acetate in hexane as eluant to obtain pure 48.2 (0.140 g, 25.42%). MS(ES): m/z 220.25 [M+H]+.

Synthesis of Compound 48.3.

Compound 48.3 was synthesized as per experimental protocol 1-14.

Synthesis of Compound 48.4.

Compound 48.4 was synthesized from 48.2 and 48.3 using general procedure. B (Yield: 50.28%). MS(ES): m/z 674.69 [M+H]+.

Synthesis of I-48.

Compound I-48 was synthesized from 48.4 using general procedure C. (Yield: 57.96%). MS(ES): m/z: 590.44 [M+H]+, LCMS purity: 98.11%, HPLC purity: 99.08%, 1H NMR (DMSO, 400 MHz): 13.22 (s, 1H), 9.70 (s, 1H), 9.19 (s, 1H), 8.30 (s, 1H), 7.69-7.67 (d, J=7.6 Hz 2H), 7.41-7.37 (t, J=15.6 Hz 1H), 7.19 (t, 1H), 6.7 (bs, 1H), 4.47 (s, 3H), 4.10 (bs, 1H), 3.72 (m, 6H), 3.33 (s, 3H) 3.28 (s, 3H).

Example 49: Synthesis of 6-((2-(difluoromethyl)-7-((2-methoxy-3-(2-methyl-2H-tetrazol-5-yl)phenyl)amino)-3H-imidazo[4,5-b]pyridin-5-yl)amino)-3-(2-methoxypropan-2-yl)picolinonitrile, I-49

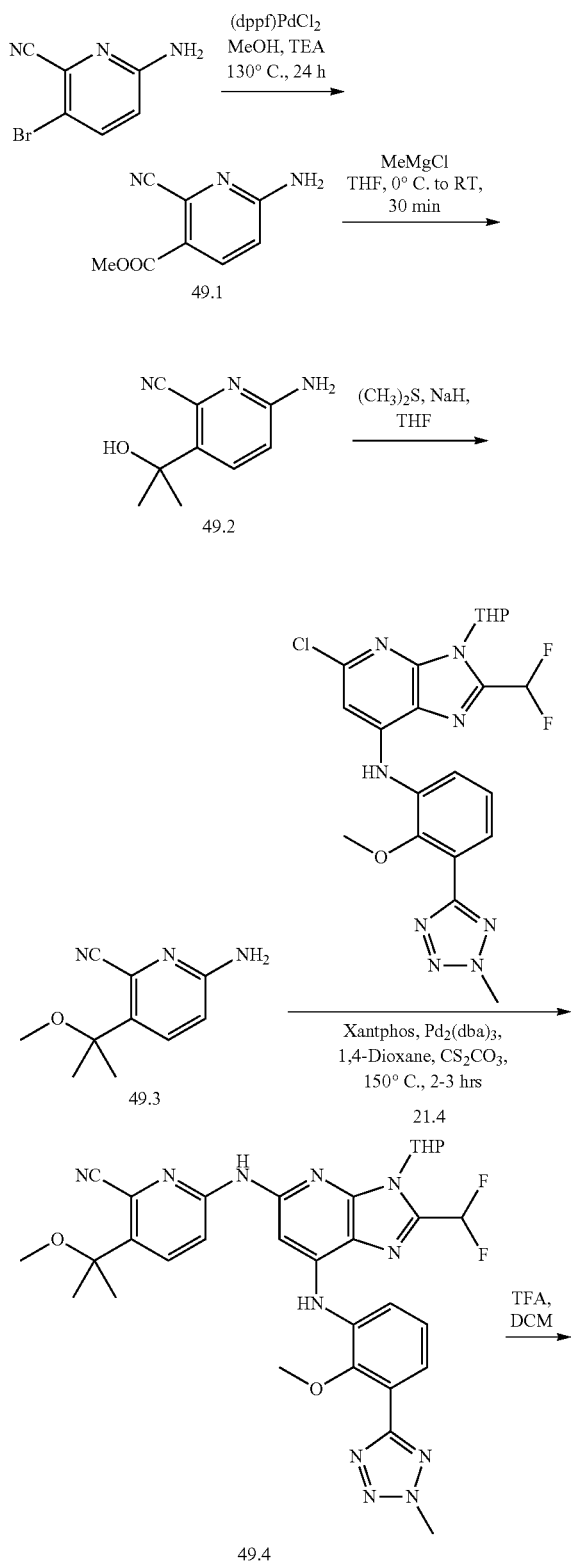

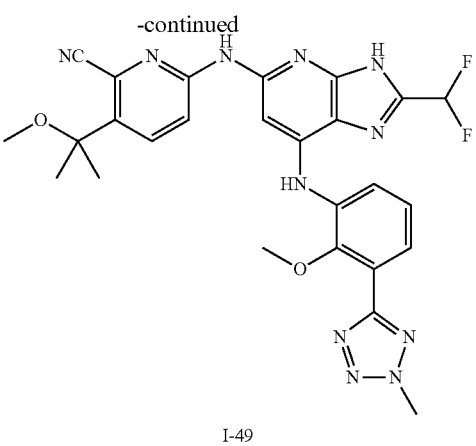

I-49

Synthesis of Compound 49.1.

To a solution of 6-amino-3-bromopicolinonitrile (2.0 g, 1.0 mmol, 1.0 eq) in methanol (40 mL), triethylamine (7.3 mL) was added at 0° C. Carbon dioxide was purged in the reaction mixture for 30 min followed by the addition of 1,1'-bis(diphenylphosphine)ferrocene dichloro palladium (II) (0.82 g, 0.010 mmol, 0.1 eq). Reaction mixture was stirred at 130° C. for 24 h. After completion of the reaction, the reaction mixture was concentrated to obtain 49.1. (1.3 g, 72.65%). MS(ES): m/z 178.43 [M+H]$^+$.

Synthesis of Compound 49.2.

To a solution of compound 49.1 (1.3 g, 7.3 mmol, 1.0 eq) in tetrahydrofuran (52 mL), methyl magnesium chloride (7.3 mL) was added at 0° C. within 15 min. Reaction mixture was stirred at room temperature for 30 min. After completion of the reaction, the reaction mixture gas quenched by water and extracted with 20% methanol in dichloromethane. Organic layer was combined, dried over anhydrous sodium sulfate, filtered and concentrated under reduced pressure to get the crude material. This was further purified by column chromatography using 6% methanol in dichloromethane as eluant to obtain pure 49.2 (1.3 g, 34.61%). MS(ES): m/z 178.42 [M+H]$^+$.

Synthesis of Compound 49.3.

To a solution of sodium hydride in tetrahydrofuran at 0° C., compound 49.2 was added. Reaction mixture was stirred for 5 min at 0° C. Dimethyl sulfide was added and the reaction mixture was stirred at room temperature for 1 h. After completion of the reaction, reaction mixture was quenched by water and extracted with 10% methanol in dichloromethane. Organic layer combined, dried over anhydrous sodium sulfate, filtered and concentrated under reduced pressure to get the crude material. This was further purified by trituration in ether and pentane to obtain pure 49.3 (0.3 g, 92.67%). MS(ES): m/z 192.68 [M+H]$^+$.

Synthesis of Compound 49.4.

Compound was synthesized using from 49.3 and 21.4 general procedure B. (Yield: 45.62%). MS(ES): m/z 646.73 [M+H]$^+$.

Synthesis of I-49.

Compound I-49 was synthesized from 49.1 using general procedure C. (Yield: 63.99%). MS(ES): m/z: 562.40 [M+H]$^+$, LCMS purity, 98.80%, HPLC purity: 98.44%, 1H NMR (DMSO, 400 MHz): 10.05 (s, 1H), 8.49 (s, 1H), 7.83-7.76 (m, 3H), 7.68-7.65 (t, J=13.2 Hz, 2H), 7.50 (s, 1H), 7.39-7.34 (m, 2H), 4.46 (s, 3H), 3.72 (s, 3H), 2.86 (s, 3H), 1.17 (s, 6H).

Example 50: Synthesis of N-(2-(difluoromethyl)-7-((4-(3-methoxyazetidin-1-yl)-2-(N-methylmethyl-sulfonamido)phenyl)amino)-3H-imidazo[4,5-b]pyridin-5-yl)cyclopropanecarboxamide, I-50

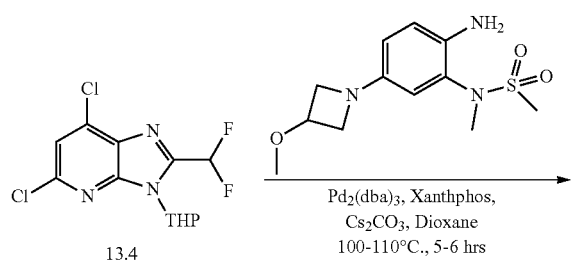

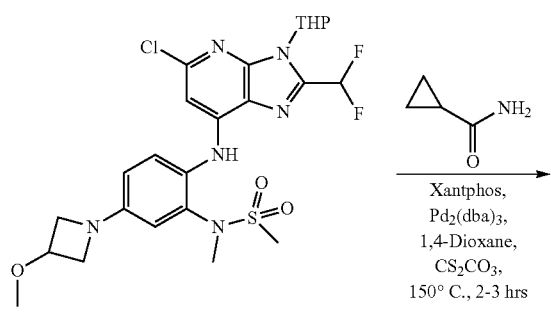

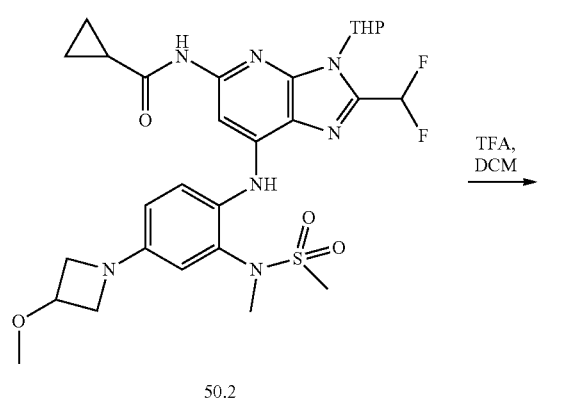

Synthesis of Compound 50.1.

Compound 50.1 was synthesized from 13.4 and 50.1 using general procedure. A (Yield: 36.65%). MS(ES): m/z 572.04 [M+H]⁺.

Synthesis of Compound 50.2.

Compound 50.2 was synthesized from 50.1 and cyclopropanecarboxamide using general procedure. B (Yield: 65.34%). MS(ES): m/z 620.60 [M+H]⁺.

Synthesis of I-50.

Compound I-50 was synthesized from using general procedure. C. (Yield: 58.11%). MS(ES): m/z 536.50 [M+H]⁺, LCMS purity, 98.59%, HPLC purity: 96.72%, 1H NMR (MeOD, 400 MHz): 7.42-7.39 (d, J=8.4 Hz 1H), 7.04 (t, 1H), 6.81 (s, 1H), 6.69 (s, 1H), 6.65-6.62 (m, 1H), 4.43-4.41 (t, J=4.4 Hz 1H), 4.22-4.18 (d, J=7.6 Hz 2H), 3.79-3.75 (m, 2H), 3.39 (s, 3H), 3.25 (s, 3H), 3.02 (s, 3H), 1.81 (s, 1H), 1.03-0.91 (m, 4H).

Example 51: Synthesis of N-(2-(difluoromethyl)-7-((2-methoxy-3-(3-methyl-1H-1,2,4-triazol-1-yl)phenyl)amino)-3H-imidazo[4,5-b]pyridin-5-yl)cyclopropanecarboxamide, I-51

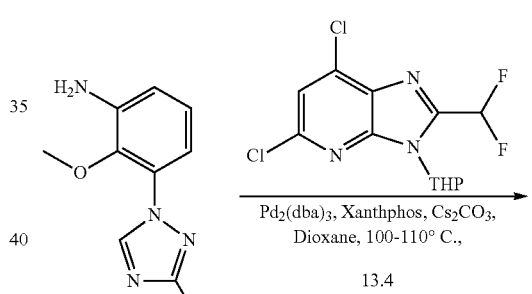

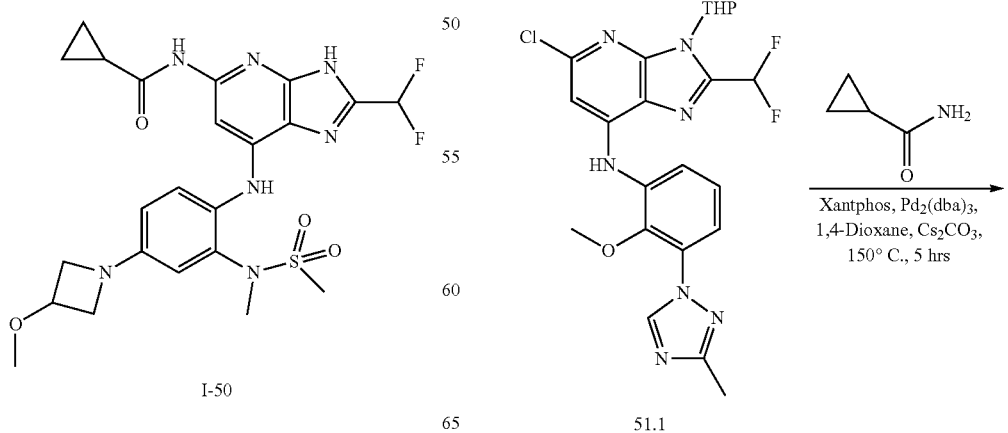

477

-continued

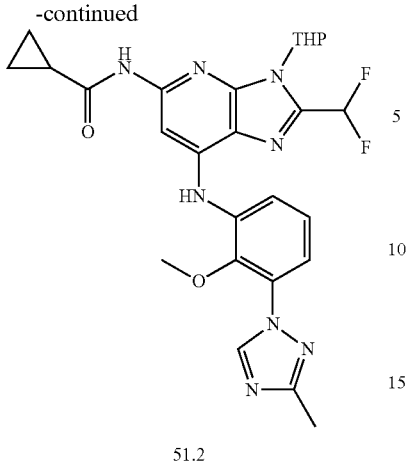

51.2

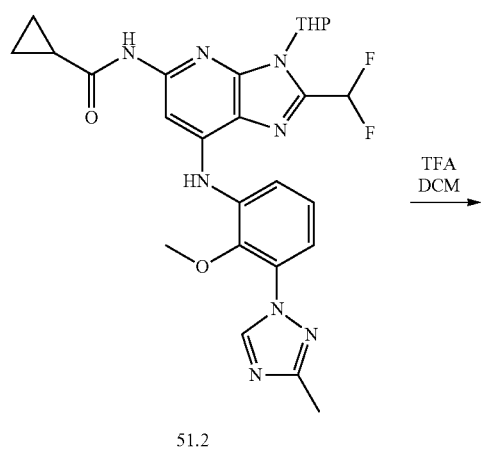

51.2

→ TFA
DCM

478

-continued

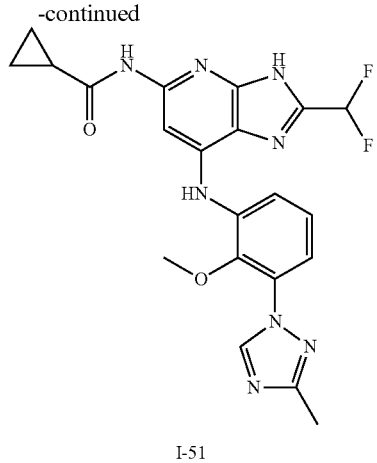

I-51

Synthesis of Compound 51.1.

Compound 51.1 was synthesized from 2-methoxy-3-(3-methyl)-1,2,4-triazol-1-ylaniline and 13.4 using general procedure A. (Yield: 15.63%). MS(ES): m/z 490.91 [M+H]$^+$.

Synthesis of Compound 51.2.

Compound 51.2 was synthesized from 51.1 and cyclopropanecarboxamdie using general procedure B. (Yield: 90.97%). MS(ES): m/z 539.56 [M+H]$^+$.

Synthesis of I-51.

Compound I-51 was synthesized from 51.2 using general procedure C. (Yield: 65.84%). MS(ES): m/z: 455.36 [M+H]$^+$, LCMS purity: 98.15%, HPLC purity: 97.35%, 1H NMR (MeOD, 400 MHz): 8.86 (s, 1H), 7.85 (s, 2H), 7.67-7.65 (d, J=7.2 Hz 1H), 7.49-7.47 (d, J=8.2 Hz, 1H), 6.81 (s, J=8.4 Hz 1H), 7.39-7.35 (t, J=8.4 Hz 1H), 7.00 (m, 2H), 3.59 (s, 3H), 2.49 (s, 3H), 1.65-1.58 (m, 1H), 0.97-0.79 (m, 4H).

Example 53: Synthesis of N-(2-(difluoromethyl)-7-((3-(2,5-dimethyl-2H-1,2,3-triazol-4-yl)-2-methoxyphenyl)amino)-3H-imidazo[4,5-b]pyridin-5-yl)cyclopropanecarboxamide, I-53

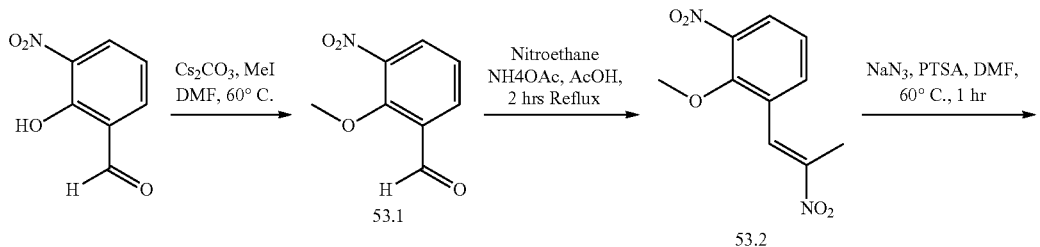

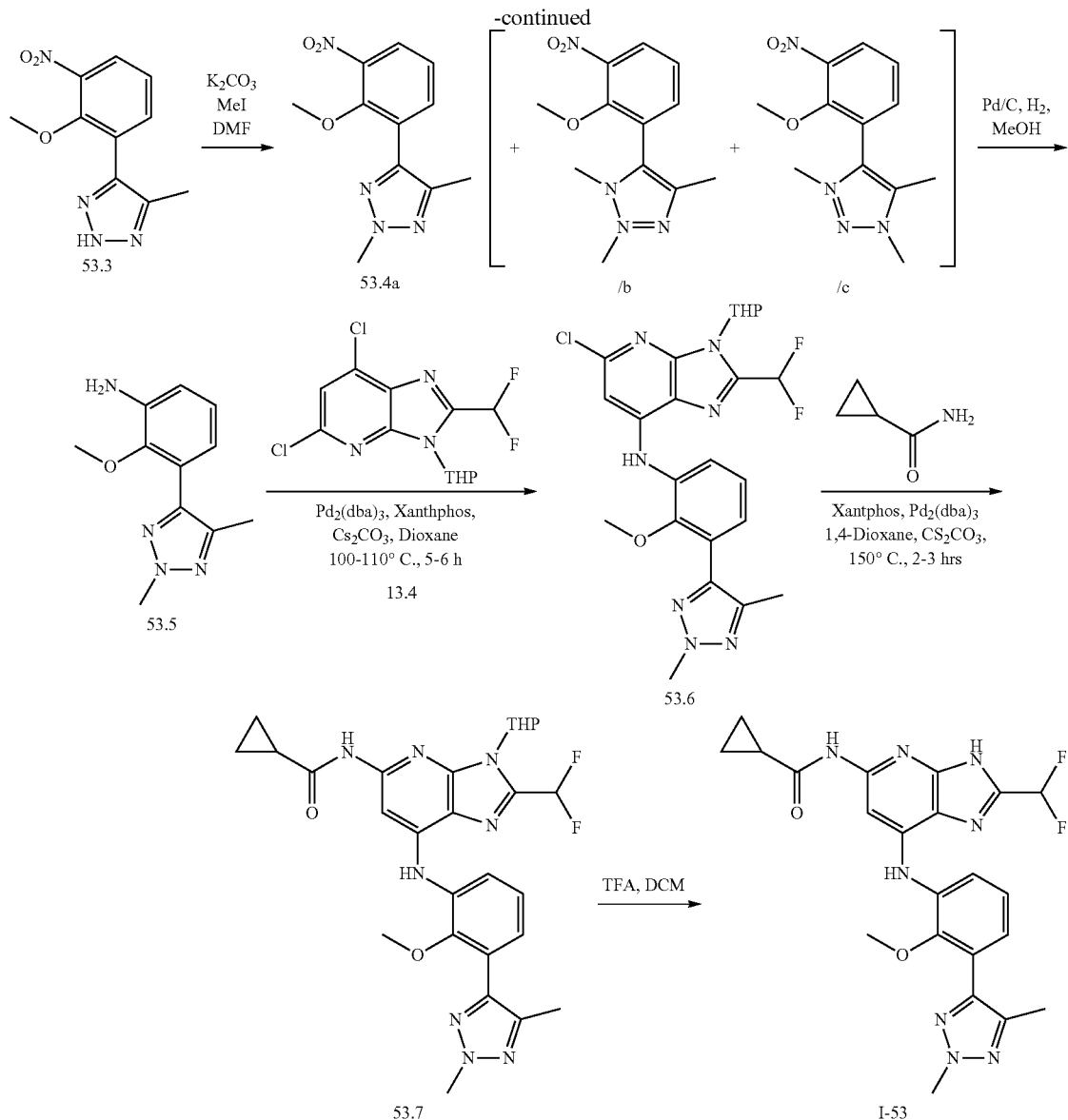

Synthesis of Compound 53.1.

To a solution of 2-hydroxy-3-nitrobenzaldehyde (1 g, 5.9 mmol, 1.0 eq) in dimethylformamide (15 mL) at r.t., $Cs_2CO_3$ (5.8 g, 17.95 mmol, 3.0 eq) was added. After 5 min, methyl iodide (0.45 mL, 7.18 mmol, 1.2 eq) was added. Reaction mixture was stirred at 60° C. for 1 h. After completion of the reaction, the reaction mixture was transferred to water and extracted with ethyl acetate. Organic layers were combined, dried over $Na_2SO_4$, filtered and evaporated under vacuum to get the crude material. This was purified by column chromatography using 15% ethyl acetate in hexane as eluant to obtain pure 53.1 (0.5 g, 46.13%). MS(ES): m/z 182.43 $[M+H]^+$.

Synthesis of Compound 53.2.

To compound 53.1 (0.5 g, 2.7 mmol, 1.0 eq) in acetic acid (10 mL), ammonium acetate (0.12 g, 1.6 mmol, 0.5 eq) and nitroethane (0.24 g, 3.31 mmol, 1.2 eq) were added at r.t. Reaction mixture was stirred at 110° C. for 15 h. After completion of the reaction, the reaction mixture was transferred to water and extracted with ethyl acetate. Organic layers were combined, dried over $Na_2SO_4$, filtered and evaporated under vacuum to get the crude material. This was purified by column chromatography using 17% ethyl acetate in hexane as eluant to obtain pure 53.2 (0.25 g, 38.02%). MS(ES): m/z 239.53 $[M+H]^+$.

Synthesis of Compound 53.3.

To compound 53.2 (0.15 g, 0.42 mmol, 1.0 eq) in dimethylformamide (5 mL) at 0° C., sodium azide (0.06 g, 0.21 mmol, 1.5 eq) and p-toluenesulphonic acid (0.06 g, 0.63 mmol, 0.5 eq) were added. Reaction mixture was stirred at 60° C. for 1 h. After completion of the reaction, the reaction mixture was transferred to water and extracted with ethyl acetate. Organic layers were combined, dried over $Na_2SO_4$, filtered and evaporated under vacuum to get the crude material. This was purified by column chromatography using 1% MeOH in $CH_2Cl_2$ as eluant to obtain pure 53.3 (0.25 g, 38.02%). MS(ES): m/z 239.53 $[M+H]^+$.

Synthesis of Compound 53.4a.

To compound 53.3 (0.1 g, 0.42 mmol, 1.0 eq) in dimethylformamide (5 mL), potassium carbonate (0.101 g, 0.80 mmol, 2 eq) was added at 0° C. Then methyl iodide (0.3 g, 0.55 mmol, 1.3 eq) was added. Reaction mixture was stirred at r.t. for 2 h. After completion of the reaction, the reaction mixture was transferred to cold water and extracted with ethyl acetate. Organic layers were combined, dried over $Na_2SO_4$, filtered and evaporated under vacuum to get the crude material. This was purified by column chromatography using 1% MeOH in $CH_2Cl_2$ as eluent to obtain pure 53.4a (0.010 g, 38.02%). MS(ES): m/z 239.53 $[M+H]^+$.

Synthesis of Compound 53.5.

To compound 53.4a (0.15 g, 0.6 mmol, 1.0 eq) in MeOH (10 mL), 10% palladium on carbon (0.05 g) was added. Hydrogen was purged through the reaction mixture for 2 h. After completion of the reaction, the reaction mixture was filtered through celite bed and washed with MeOH. Filtrate was concentrated in vacuo to obtain 1.5 (0.1 g, 75.82%). MS(ES): m/z 219.63 $[M+H]^+$.

Synthesis of Compound 53.6.

Compound 53.6 was synthesized from 53.5 and 13.4 using general procedure A. (Yield: 21.66%). MS(ES): m/z 504.94 $[M+H]^+$.

Synthesis of Compound 53.7.

Compound 53.7 was synthesized from 53.6 and cyclopropanecarboxamide using general procedure B. (Yield: 45.60%). MS(ES): m/z 554.59 $[M+H]^+$.

Synthesis of I-53.

Compound I-53 was synthesized using general procedure C. (Yield: 58.98%). MS(ES): m/z 469.37 $[M+H]^+$, LCMS purity: 97.97%, HPLC purity: 95.08%, 1H NMR (DMSO, 400 MHz): 8.86 (s, 1H), 7.85 (s, 2H), 7.67-7.65 (d, J=7.2 Hz 1H), 7.49-7.47 (d, J=8.2 Hz 1H), 6.81 (s, J=8.4 Hz 1H), 7.39-7.35 (t, J=8.4 Hz 1H), 7.21 (t, 1H), 3.991 (s, 3H), 2.334 (s, 3H), 3.59 (s, 3H), 1.65-1.58 (m, 1H), 0.97-0.79 (m, 4H).

Example 54: Synthesis of N-(2-(difluoromethyl)-7-((3-(3,5-dimethyl-1H-1,2,4-triazol-1-yl)-2-methoxyphenyl)amino)-3H-imidazo[4,5-b]pyridin-5-yl)cyclopropanecarboxamide, I-54

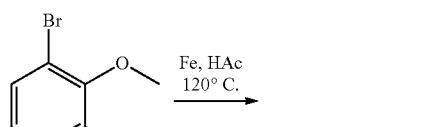

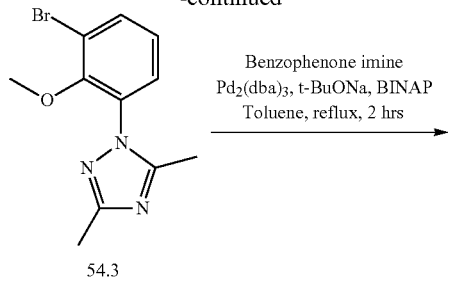

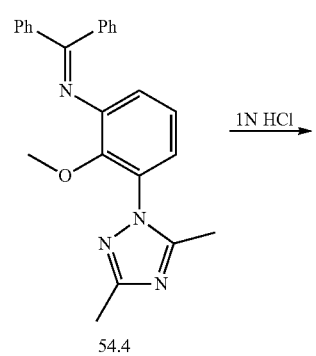

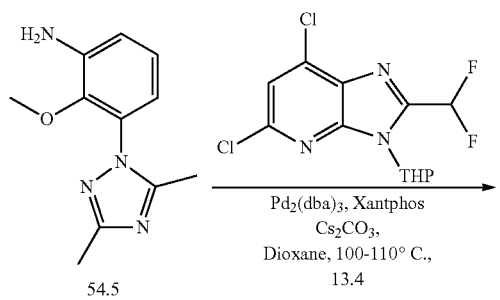

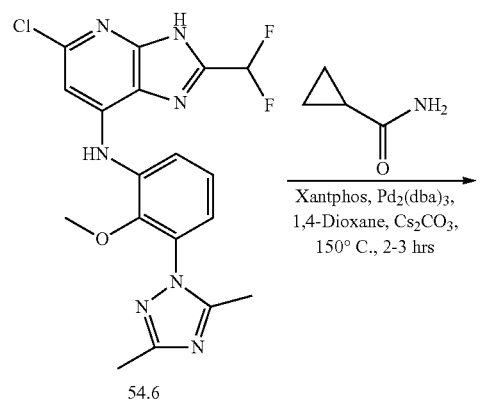

483

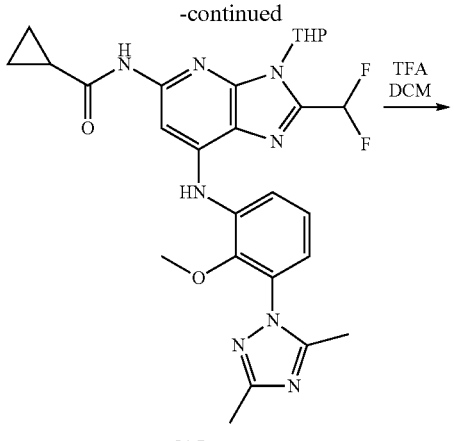

54.7

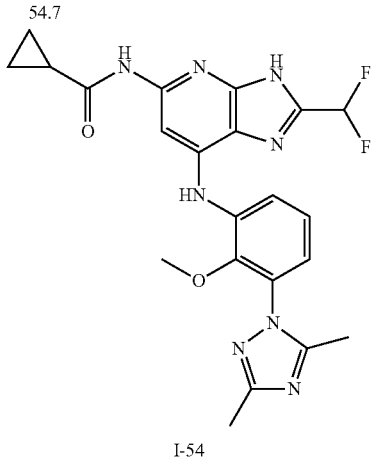

I-54

Synthesis of Compound 54.1.

To a solution of 1-bromo-2-methoxy-3-nitrobenzene (0.482 g, 1.68 mmol, 1.0 eq) in acetic acid (6 mL), iron powder (0.275 g, 5 mmol, 3.0 eq) was added in a single portion. Reaction mixture was stirred at 70° C. for 2 h. After completion of the reaction, the reaction mixture was transferred to water and extracted with ethyl acetate. Organic layers were combined, dried over anhydrous $Na_2SO_4$, filtered and concentrated in vacuo to obtain 54.1 (0.35 g, 83.39%). MS (ES): m/z 204.18 [M+H]$^+$.

Synthesis of Compound 54.2.

To compound 54.1 (6.35 g, 31.7 mmol, 1.0 eq) in 6N HCl (120 mL) at 0° C., sodium nitrite (2.4 g, 34.9 mmol, 1.1 eq) in water was added. Reaction mixture was stirred at 0° C. for 30 min. Then tin chloride (21.45 g, 95 mmol, 3.0 eq) in conc. HCl (31.75 mL) was added to the reaction mixture and stirred at 0° C. for further 2 h. After completion of the reaction, solid obtained in the reaction mixture was filtered, washed with conc. HCl and dried to obtain 54.2 (6.5 g, 95.28%). MS (ES): m/z 252.47 [M+H]$^+$.

Synthesis of Compound 54.3.

To compound 54.2 (1.5 g, 5.8 mmol, 1.0 eq) in pyridine (15 mL), N-acetylacetamide (0.589 g, 5.8 mmol, 1.0 eq) was added. Reaction mixture was heated in microwave at 200° C. for 5 min. After completion of the reaction, the reaction mixture was transferred in water and extracted with ethyl acetate. Organic layers were combined, dried over $Na_2SO_4$, filtered and concentrated in vacuo to get the crude material. This was purified by column chromatography using 15% ethyl acetate in hexane as eluant to obtain pure 54.3 (1.2 g, 61.55%). MS (ES): m/z 283.43 [M+H]$^+$.

484

Synthesis of Compound 54.4.

To compound 54.3 (0.44 g, 1.56 mmol, 1.0 eq) and benzophenone imine (0.37 g, 2.08 mmol, 1.33 eq) in toluene (5 mL), sodium tert-butoxide (0.22 g, 2.34 mmol, 1.5 eq), (2,2'-bis(diphenylphosphino)-1,1'-binaphthyl) (0.14 g, 0.23 mmol, 0.15 eq) and $Pd_2(dba)_3$ (0.1 g, 0.10 mmol, 0.07 eq) were added. After completion of the reaction, the reaction mixture was transferred in water and extracted with ethyl acetate. Organic layers were combined, dried over $Na_2SO_4$, filtered and concentrated in vacuo to get the crude material. This was purified by column chromatography using 15% ethyl acetate in hexane as eluant to obtain pure 54.4 (1.2 g, 83.3%). MS (ES): m/z 383.48 [M+H]$^+$.

Synthesis of Compound 54.5.

To compound 54.4 (0.5 g, 1.44 mmol, 1.0 eq) in tetrahydrofuran (5 mL) at 0° C., 1N HCl (0.5 mL) was added dropwise within 5 min. Reaction mixture was stirred at r.t. for 30 min. After completion of the reaction, the reaction mixture was extracted with ethyl acetate. The aqueous layer was then neutralized with $NaHCO_3$ and then again extracted with ethyl acetate. These Organic layers were combined, fried over $Na_2SO_4$, filtered and concentrated in vacuo to obtain 1.5 (0.250 g, 87.62%). MS (ES): m/z 219.54 [M+H]$^+$.

Synthesis of Compound 54.6.

Compound 54.6 was synthesized from 54.5 and 13.4 using general procedure A. (Yield: 22.64%). MS(ES): m/z 420.58 [M+H]$^+$.

Synthesis of Compound 54.7.

Compound 54.7 was synthesized from 54.6 and cyclopropanecarboxamide using general procedure B. (Yield: 59.69%). MS(ES): m/z 553.46 [M+H]$^+$.

Synthesis of I-54.

Compound I-54 was synthesized from 54.7 using general procedure C. (Yield: 65.53%). MS(ES): m/z: 469.45 [M+H]$^+$, LCMS purity, 94.97%, HPLC purity 95.06%, 1H NMR (DMSO, 400 MHz): 13.49 (s, 1H), 10.60 (s, 1H), 8.76 (s, 1H), 7.60-7.55 (m, 2H), 7.37-7.24 (m, 3H), 3.43 (s, 3H), 2.32 (s, 3H), 2.28 (s, 3H), 2.05 (s, 1H), 0.80-0.78 (t, J=3.2 Hz, 4H).

Example 55: Synthesis of N-(2-(difluoromethyl)-7-((2-methoxy-3-(5-methyl-1H-1,2,4-triazol-1-yl)phenyl)amino)-3H-imidazo[4,5-b]pyridin-5-yl)cyclopropanecarboxamide, I-55

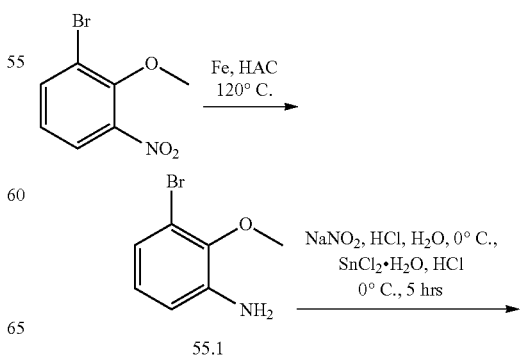

55.1

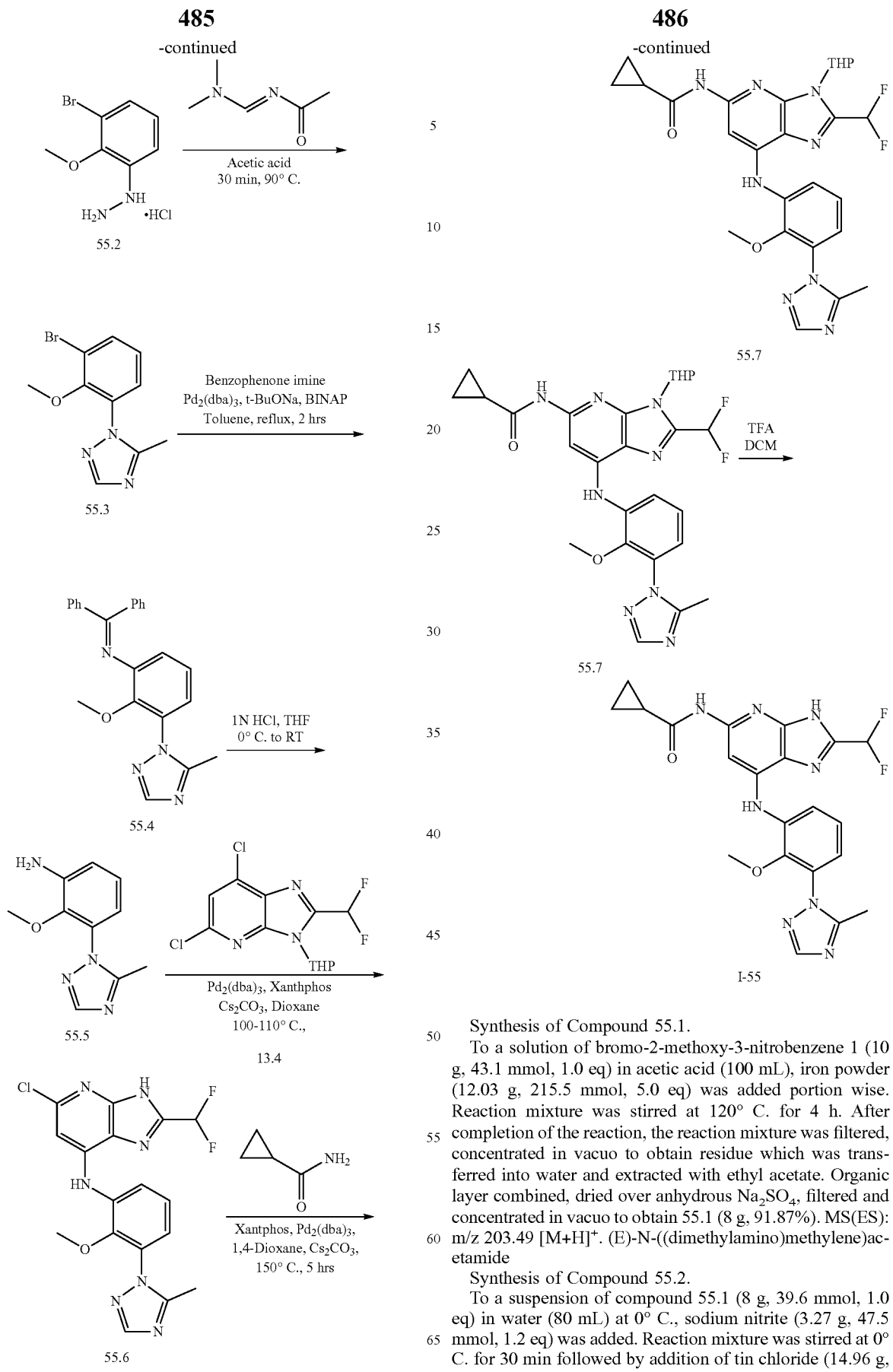

Synthesis of Compound 55.1.

To a solution of bromo-2-methoxy-3-nitrobenzene 1 (10 g, 43.1 mmol, 1.0 eq) in acetic acid (100 mL), iron powder (12.03 g, 215.5 mmol, 5.0 eq) was added portion wise. Reaction mixture was stirred at 120° C. for 4 h. After completion of the reaction, the reaction mixture was filtered, concentrated in vacuo to obtain residue which was transferred into water and extracted with ethyl acetate. Organic layer combined, dried over anhydrous $Na_2SO_4$, filtered and concentrated in vacuo to obtain 55.1 (8 g, 91.87%). MS(ES): m/z 203.49 [M+H]$^+$. (E)-N-((dimethylamino)methylene)acetamide Synthesis of Compound 55.2.

To a suspension of compound 55.1 (8 g, 39.6 mmol, 1.0 eq) in water (80 mL) at 0° C., sodium nitrite (3.27 g, 47.5 mmol, 1.2 eq) was added. Reaction mixture was stirred at 0° C. for 30 min followed by addition of tin chloride (14.96 g, 79.6 mmol, 2.0 eq) at 0° C. and stirred for 3 h. After completion of the reaction, the reaction mixture was extracted with ethyl acetate. Organic layer combined, dried over anhydrous Na$_2$SO$_4$, filtered and concentrated in vacuo to obtain 55.2 (7 g, 81.45%). MS(ES): m/z 218.34 [M+H]$^+$.

Synthesis of compound 55.3

To compound 55.2 (5 g, 23.04 mmol, 1.0 eq) in acetic acid (50 mL), (E)-N-((dimethylamino)methylene)acetamide (2.62 g, 23.04 mmol, 1.0 eq) was added. Reaction mixture was stirred at 90° C. for 30 min. After completion of the reaction, the reaction mixture was transferred to water and neutralised using saturated NaHCO$_3$ solution and extracted with ethyl acetate. Organic layer combined, dried over anhydrous Na$_2$SO$_4$, filtered and concentrated in vacuo to obtain 55.3 (1.9 g, 30.76%). MS(ES): m/z 269.17 [M+H]$^+$.

Synthesis of Compound 55.4.

To compound 55.3 (1.9 g, 7.08 mmol, 1.0 eq) in toluene (20 mL), benzophenone imine (1.53 g, 8.50 mmol, 1.2 eq) and sodium-tert-butoxide (1.35 g, 14.16 mmol, 2.0 eq) were added. Reaction mixture was degassed with argon for 15 min. Pd$_2$(dba)$_3$ (1.2 g, 1.41 mmol, 0.2 eq) and 2,2'-Bis(diphenylphosphino)-1,1'-binaphthyl (2.2 g, 3.54 mmol, 0.5 eq) were added and again degassed for 5 min. Reaction mixture was stirred at 110° C. for 2 h. After completion of the reaction, the reaction mixture was transferred into water and extracted with ethyl acetate. Organic layer combined, dried over anhydrous Na$_2$SO$_4$, filtered and concentrated in vacuo to obtain 55.4 (0.8 g, 30.64%). MS(ES): m/z 369.27 [M+H]$^+$.

Synthesis of Compound 55.5.

To compound 55.4 (0.8 g, 2.17 mmol, 1.0 eq) in tetrahydrofuran (10 mL) at 0° C., 1N HCl (5 mL, 10.08 mmol, 5.0 eq) was added dropwise. Reaction mixture was stirred at r.t. for 3 h. After completion of the reaction the reaction mixture was concentrated in vacuo to obtain residue which was transferred into water and neutralised using saturated NaHCO$_3$ solution, extracted with ethyl acetate. Organic layer combined, dried over anhydrous Na$_2$SO$_4$, filtered and concentrated in vacuo to obtain 55.5 (0.35 g, 78.93%). MS(ES): m/z 205.26 [M+H]$^+$.

Synthesis of Compound 55.6.

Compound 55.6 was synthesized from 13.4 and 55.5 using general procedure A. (Yield: 46.46%). MS(ES): m/z 406.52 [M+H]$^+$.

Synthesis of Compound 55.7.

Compound 55.7 was synthesized from 55.6 and cyclopropanecarboxamide using general procedure B. (Yield: 60.28%). MS(ES): m/z 539.87 [M+H]$^+$.

Synthesis of I-55.

Compound I-55 was synthesized from 55.7 using general procedure C. (Yield: 69.13%). MS(ES): m/z: 455.30 [M+H]$^+$, LCMS purity: 100%, HPLC purity: 100%, 1H NMR (DMSO, 400 MHz): 10.54 (s, 1H), 8.75 (s, 1H), 8.05 (s, 1H), 7.55-7.52 (d, J=10.8 Hz, 2H), 7.34-7.27 (m, 3H), 7.18 (t, 1H), 3.31 (s, 3H), 2.29 (s, 3H), 1.98-1.90 (m, 1H), 0.73 (bs, 4H).

Example 56: Synthesis of 2-(difluoromethyl)-N7-(2-methoxy-3-(2-methyl-2H-tetrazol-5-yl)phenyl)-N5-(5-(2-methoxypropan-2-yl)-6-methylpyrazin-2-yl)-3H-imidazo[4,5-b]pyridine-5,7-diamines, I-56

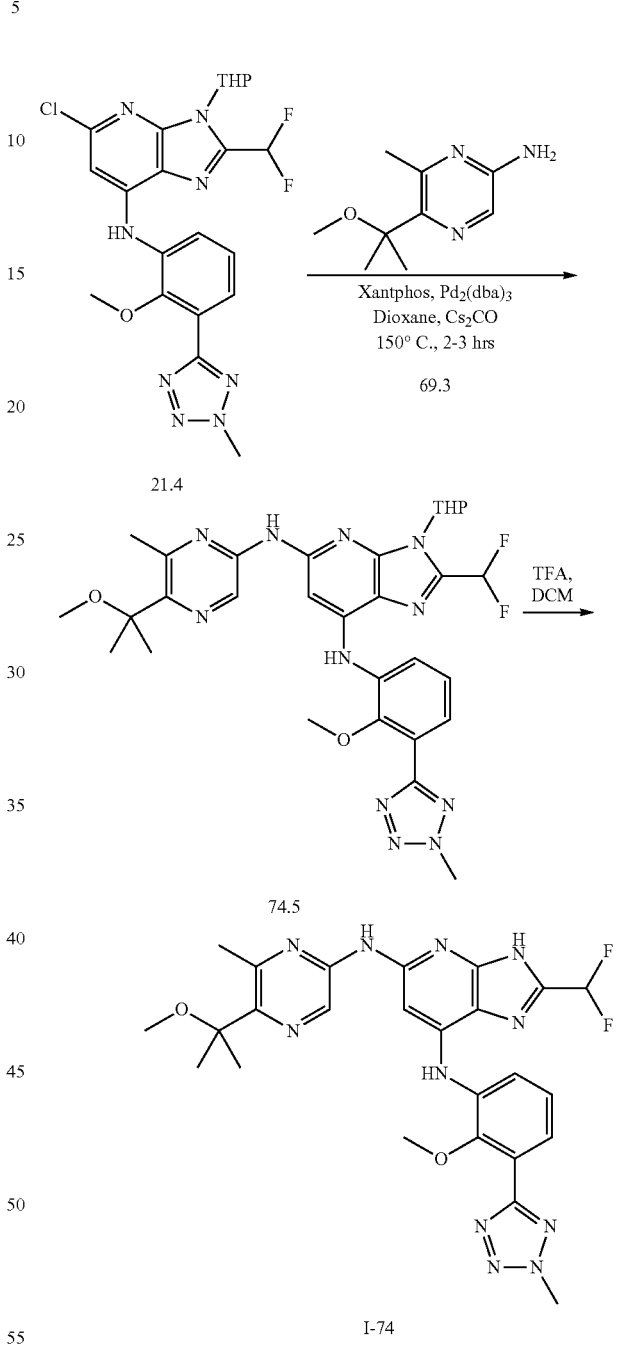

Synthesis of Compound 74.5.

Compound 74.5 was synthesized from 69.3 and 21.4 using general procedure B. (Yield: 43.65%). MS(ES): m/z 636.68 [M+H]$^+$.

Synthesis of I-74.

Compound I-74 was synthesized from 74.5 using general procedure C. (Yield: 70.92%). MS(ES): m/z: 552.55 [M+H]$^+$, LCMS purity 94.96%, HPLC purity 94.40%, 1H NMR (DMSO-d6, 400 MHZ): 9.62 (s, 1H), 8.90 (s, 1H), 7.94 (s, 1H), 7.74-7.72 (d, J=8 Hz, 1H), 7.64-7.62 (d, J=6.8

Hz, 2H), 7.37-7.32 (m, 2H), 4.47 (s, 3H), 3.74 (s, 3H), 3.34 (s, 3H), 2.96 (s, 3H), 2.96-1.49 (d, 6H).

Example 58: Synthesis of N-(7-((4-chloro-2-(methylsulfonyl)phenyl)amino)-2-(difluoromethyl)-3H-imidazo[4,5-b]pyridin-5-yl)cyclopropanecarboxamide, I-58

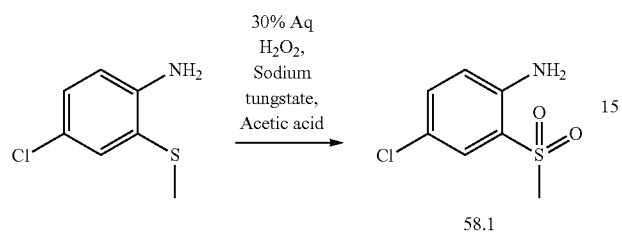

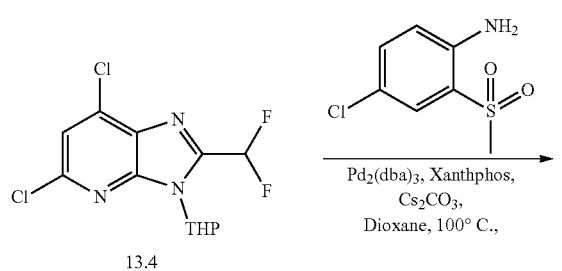

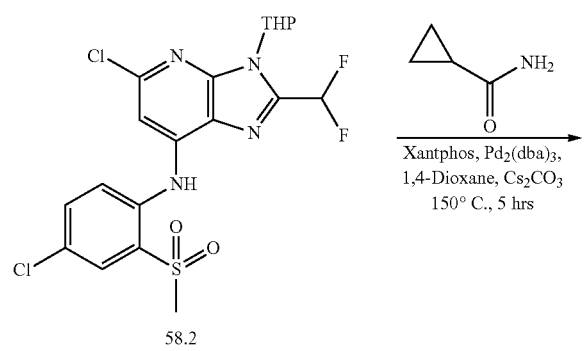

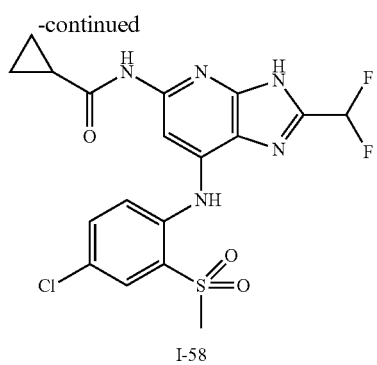

I-58

Synthesis of Compound 58.1.

To a solution of 4-chloro-2-(methylthio)aniline (1 g, 5.78 mmol, 1 eq) in acetic acid (1.2 mL) was added 30% hydrogen peroxide (3.93 g, 0.115 mmol, 20.0 eq) and sodium tungstate dihydrate (1.70 g, 5.78 mmol, 1 eq). Reaction mixture was stirred at r.t. for 2 h. Upon completion, reaction mixture was transferred in ice-water and precipitated product was filtered, washed with 50% ethyl acetate in hexane and dried well to obtain 58.1. (0.500 g, Yield: 42.22%). MS(ES): m/z 206.55 [M+H]$^+$ Synthesis of Compound 58.2.

Compound 58.2 was synthesized from 13.4 and 58.1 using general procedure A. (Yield: 36.28%). MS(ES): m/z 492.33 [M+H]$^+$.

Synthesis of Compound 58.3.

Compound 58.3 was synthesized from 58.2 and cyclopropanecarboxamide using general procedure B. (Yield: 33.36%). MS(ES): m/z 540.98 [M+H]$^+$.

Synthesis of I-58.

Compound I-58 was synthesized from 58.3 using general procedure C. (Yield: 53.84%). MS(ES): m/z: 456.27 [M+H]$^+$, LCMS purity: 97.96%, HPLC purity: 97.97%, 1H NMR (DMSO, 400 MHz): 13.70 (s, 1H), 10.78 (s, 1H), 8.77 (s, 1H), 8.04 (s, 1H), 7.89-7.84 (m, 2H), 7.79 (s, 1H), 7.25 (s, 1H), 3.24 (s, 3H), 1.98 (s, 1H) 0.79 (s, 4H).

Example 59: Synthesis of N-(2-((2-(difluoromethyl)-5-((5,6-dimethylpyrazin-2-yl)amino)-3H-imidazo[4,5-b]pyridin-7-yl)amino)phenyl)-N-methyl-methanesulfonamide, I-59

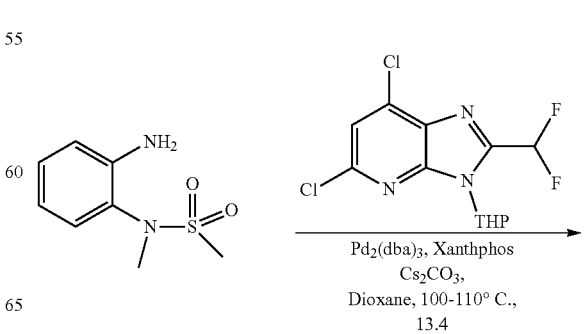

491

-continued

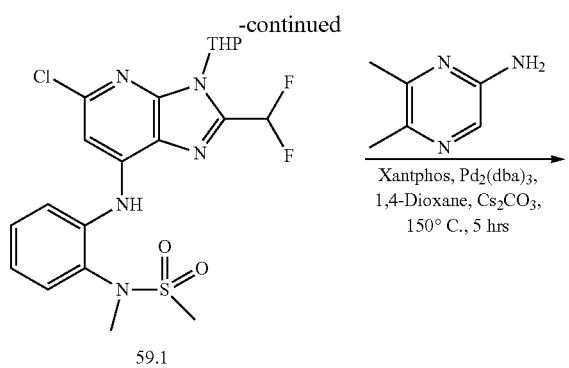

59.1

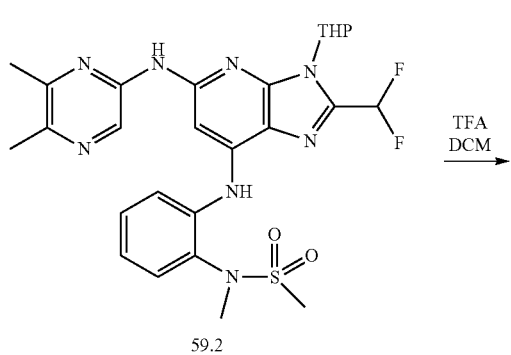

59.2

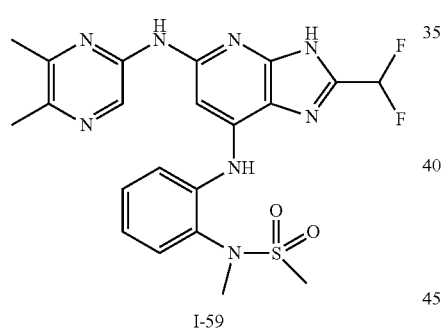

I-59

Synthesis of Compound 59.1.

Compound 59.1 was synthesized from 13.4 and N-(2-aminophenyl)-N-methylmethanesulfonamide using general procedure A. (Yield: 26.37%). MS(ES): m/z 486.52 [M+H]⁺.

Synthesis of Compound 59.2.

Compound 59.2 was synthesized from 5,6-dimethylpyrazin-2-amine and 59.1 using general procedure B. (Yield: 34.47%). MS(ES): m/z 573.64 [M+H]⁺.

Synthesis of I-59.

Compound I-59 was synthesized from 59-2 using general procedure C. (Yield: 27.37%). MS(ES): m/z: 489.36 [M+H]⁺, LCMS purity: 99.20%, HPLC purity: 97.79%, 1H NMR (DMSO, 400 MHz): 13.46 (s, 1H), 9.71 (s, 1H), 8.98 (s, 1H), 8.06 (s, 1H), 7.74-7.67 (m, 2H), 7.50-7.46 (t, J=8 Hz 1H), 7.37 (s, 1H), 7.29-7.25 (m, 1H), 3.22 (s, 3H), 3.11 (s, 3H) 2.39-2.39 (d, J=6.4 Hz 6H).

492

Example 60: Synthesis of N-(2-((5-((6-cyano-5-methylpyridin-2-yl)amino)-2-(difluoromethyl)-3H-imidazo[4,5-b]pyridin-7-yl)amino)phenyl)-N-methylmethanesulfonamides, I-60

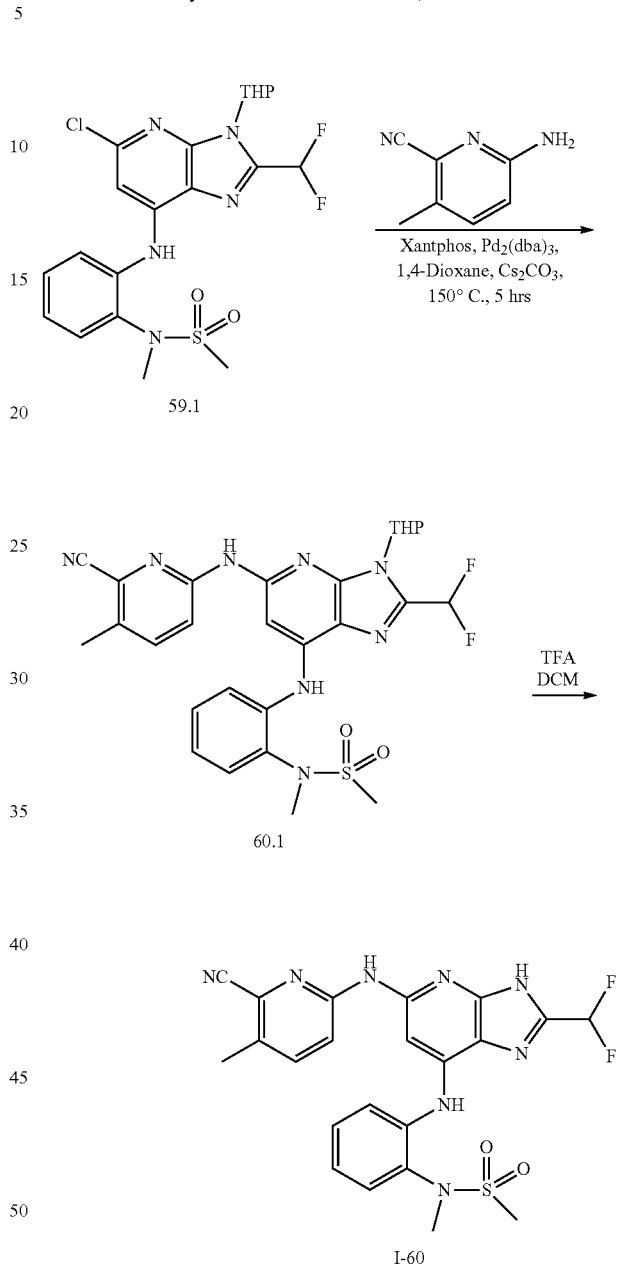

Synthesis of Compound 60.1.

Compound 60.1 was synthesized from 6-amino-3-methylpicolinonitrile and 59.1 using general procedure B. (Yield: 33.36%). MS(ES): m/z 583.24 [M+H]⁺.

Synthesis of I-60.

Compound I-60 was synthesized form 60.1 using general procedure C. (Yield: 81.81%). MS(ES): m/z: 499.38 [M+H]⁺, LCMS purity: 97.00%, HPLC purity: 97.57%, 1H NMR (DMSO, 400 MHz): 13.52 (s, 1H), 9.99 (s, 1H), 8.10 (m, 2H), 7.79-7.75 (m, 2H), 7.69-7.67 (m, 1H), 7.56-7.52 (m, 1H), 7.36 (s, 1H), 7.28-7.23 (m, 2H), 3.23 (s, 3H), 3.11 (s, 3H), 2.41 (s, 3H).

Example 61: Synthesis of N-(2-(difluoromethyl)-7-((4-(1-methyl-1H-pyrazol-3-yl)-2-(methylsulfonyl)phenyl)amino)-3H-imidazo[4,5-b]pyridin-5-yl)cyclopropanecarboxamide, I-61

Example 62: Synthesis of N-(2-(difluoromethyl)-7-((4-(1-methyl-1H-imidazol-4-yl)-2-(methylsulfonyl)phenyl)amino)-3H-imidazo[4,5-b]pyridin-5-yl)cyclopropanecarboxamide, I-62

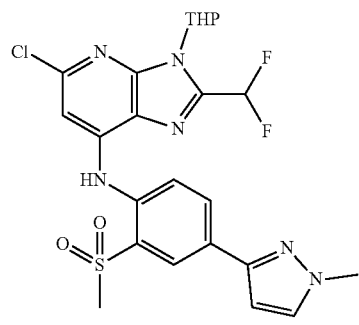

171.2

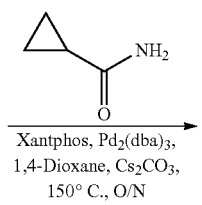

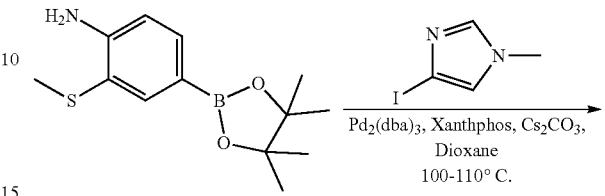

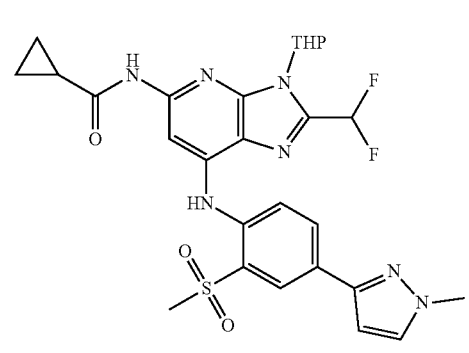

61.1

TFA / DCM

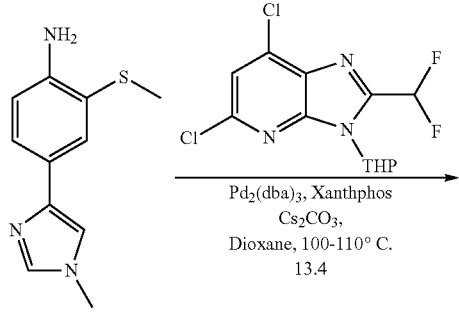

62.1

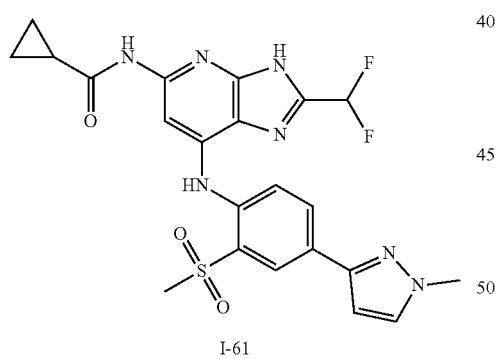

I-61

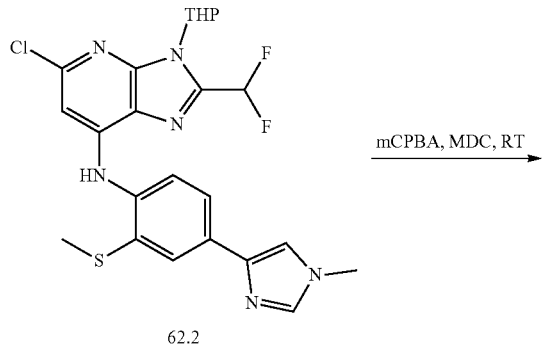

62.2 mCPBA, MDC, RT

Synthesis of Compound 61.1.

Compound 61.1 was synthesized from 171.2 and cyclopropanecarboxamide using general procedure B. (Yield: 42.79%). MS(ES): m/z 589.64 [M+H]$^+$.

Synthesis of I-61.

Compound I-61 was synthesized from 61.1 using general procedure C. (Yield: 91.75%). MS(ES): m/z: 502.36 [M+H]$^+$, LCMS purity, 98.50%, HPLC purity 97.87%, 1H NMR (DMSO, 400 MHz): 8.93 (s, 1H), 8.36-8.35 (d, J=1.6 Hz, 1H), 8.16-8.13 (d, J=8 Hz 1H), 7.96 (s, 1H), 7.81 (s, 1H), 7.78 (s, 1H), 7.41 (s, 1H), 7.27 (t, 1H), 6.83-6.83 (s, 1H), 3.92 (s, 3H), 3.26 (s, 3H), 1.96 (s, 1H) 0.84 (S, 4H).

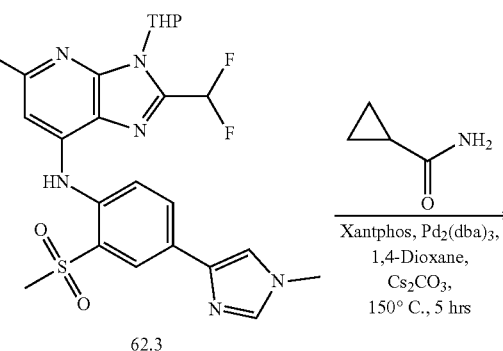

62.3

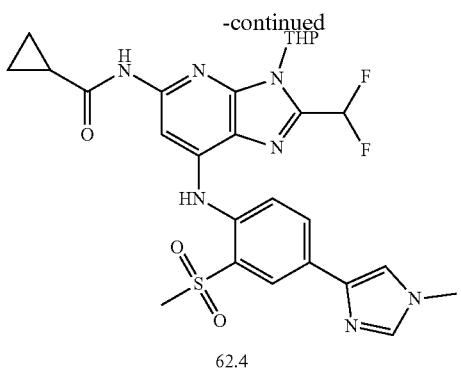

62.4

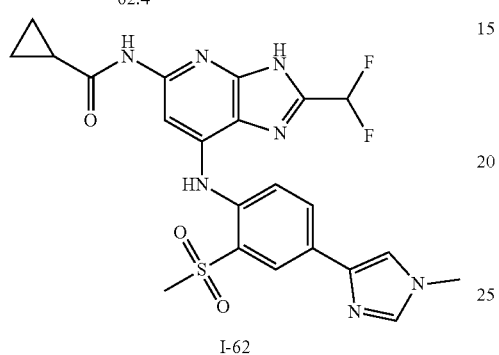

I-62

Synthesis of Compound 62.1.

To compound 62.1a (0.280 g, 0.866 mmol, 1.0 eq) in 1,4-dioxane (5.6 mL) was added 4-iodo-1-methyl-1H-imidazole (0.151 g, 0.693 mmol, 0.8 eq), Cs₂CO₃ (0.566 g, 1.73 mmol, 2.0 eq). The reaction mixture was degassed for 10 min. under argon atmosphere, then Pd₂(dba)₃ (0.079 g, 0.173 mmol, 0.1 eq) and Xantphos (0.100 g, 0.173 mmol, 0.2 eq) were added, again degassed for 5 min. The reaction was stirred at 110° C. for 2 h. Upon completion, reaction mixture was cooled to r.t., transferred in water and product was extracted with ethyl acetate. Organic layers were combined, washed with brine, dried over Na₂SO₄ and concentrated in vacuo to obtain crude product. This was purified by combi flash using 2% MeOH in CH₂Cl₂ as eluent to obtain pure 62.1 (0.110 g, 47.50%). MS(ES): m/z 220.48 [M]⁺.

Synthesis of Compound 62.2.

Compound 62.2 was synthesized from 62.1 and 13.4 using general procedure A. (Yield: 30.16%). MS(ES): m/z 505.43 [M+H]⁺.

Synthesis of Compound 62.3.

To compound 62.2 (0.130 g, 0.257 mmol, 1.0 eq) in CH₂Cl₂ (3 mL), m-chloroperoxybenzoic acid (0.088 g, 0.514 mmol, 2.0 eq) was added dropwise at 10° C. Then the reaction mixture was taken to r.t. and stirred for 30 min. After completion of the reaction, the reaction mixture was dumped was quenched by NaHCO₃ and then extracted with ethyl acetate. The combined filtrate was combined and concentrated in vacuo to get the crude product. This was purified by column chromatography and compound was eluted in 27% ethyl acetate in hexane as eluent to get the pure 62.3 (0.1 g, 72.34%). MS(ES): m/z 537.57 [M+H]⁺.

Synthesis of Compound 62.4.

Compound 62.4 was synthesized from 62.3 and cyclopropanecarboxamide using general procedure B. (Yield: 35.76%). MS(ES): m/z 586.21 [M+H]⁺.

Synthesis of I-62.

Compound I-62 was synthesized from 62.4 using general procedure C. (Yield: 74.85%). MS(ES): m/z: 502.41 [M+H]⁺, LCMS purity, 98.75%, HPLC purity 96.64%, 1H NMR (DMSO, 400 MHz): 13.66 (s, 1H), 10.72 (s, 1H), 8.69 (s, 1H), 8.31-8.3 (d, J=2 Hz, 1H), 8.08-8.03 (m, 2H), 7.78-7.74 (t, J=4.8 Hz, 2H), 7.70 (s, 1H), 3.71 (s, 3H), 3.21 (s, 3H), 1.99 (s, 1H), 0.78 (s, 4H).

Example 63: Synthesis of N-(2-(difluoromethyl)-7-((4-(3-methyl-1H-pyrazol-1-yl)-2-(methylsulfonyl)phenyl)amino)-3H-imidazo[4,5-b]pyridin-5-yl)cyclopropanecarboxamide, I-63

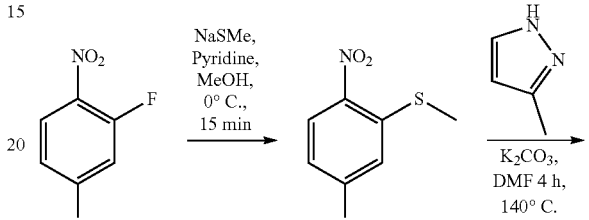

63.1

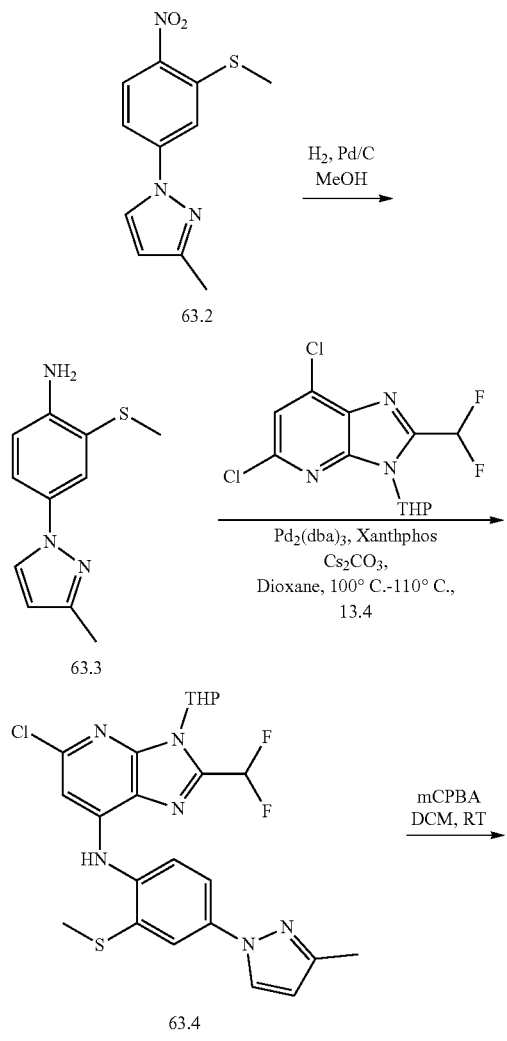

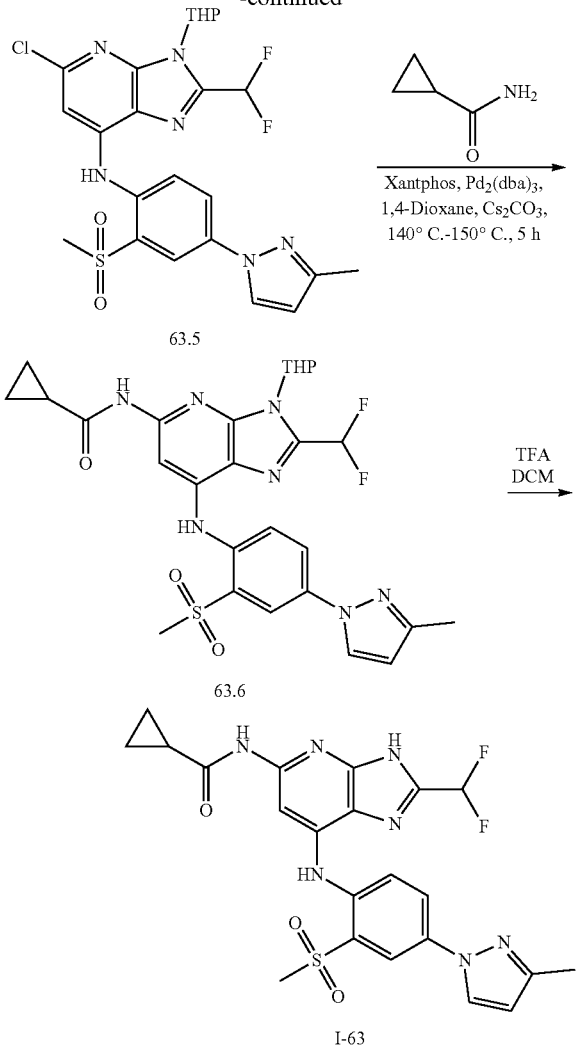

through reaction mixture for 2-3 h. Upon completion, reaction mixture was filtered through celite-bed and washed with ethanol. Filtrate was concentrated in vacuo to obtain 63.3 (1.5 g, 85.25%). MS(ES): m/z 220.31 [M+H]$^+$.

Synthesis of Compound 63.4.

Compound 63.4 was synthesized from 63.3 and 13.4 using general procedure A. (Yield: 34.74%). MS(ES): m/z: 505.98 [M+H]$^+$.

Synthesis of Compound 63.5.

To a solution of 63.4 (0.08 g, 0.158 mmol, 1.0 eq) in CH$_2$Cl$_2$ (2 mL) was added meta-chloro perbenzoic acid (0.054 g, 0.316 mmol, 2.0 eq) at 0° C. and stirred the reaction mixture at r.t. for 2 h. Upon completion, reaction mixture was transferred into aqueous solution of NaHCO$_3$ and extracted with CH$_2$Cl$_2$. Organic layer was concentrated in vacuo to obtain crude product. This was purified by column chromatography using 20% ethyl acetate in hexane to obtain pure 63.5 (0.07 g, Yield: 82.29%). MS(ES): m/z 537.98 [M+H]$^+$.

Synthesis of Compound 63.6.

Compound 63.6 was synthesized from 63.5 and cyclopropanecarboxamide using general procedure A. (Yield: 39.30%). MS(ES): m/z: 586.63 [M+H]$^+$.

Synthesis of I-63.

Compound I-63 was synthesized from 63.6 using general procedure C. (Yield: 38.92%). MS(ES): m/z: 502.36 [M+H]$^+$, LCMS purity, 96.02%, HPLC purity 93.38%, 1H NMR (DMSO-d6, 400 MHz): 13.68 (s, 1H), 10.76 (s, 1H), 8.75 (s, 1H), 8.53 (s, 1H), 8.34 (s, 1H), 8.21-8.20 (d, J=2.8 Hz, 1H), 8.04 (s, 1H), 7.87-7.85 (m, 1H), 6.41 (s, 1H), 3.29 (s, 3H), 2.32 (s, 3H), 1.26 (s, 1H), 0.80 (s, 4H).

Example 64: Synthesis of N-(2-(difluoromethyl)-7-((4-(1-methyl-1H-imidazol-4-yl)-2-(N-methylmethylsulfonamido)phenyl)amino)-3H-imidazo[4,5-b]pyridin-5-yl)cyclopropanecarboxamide, I-64

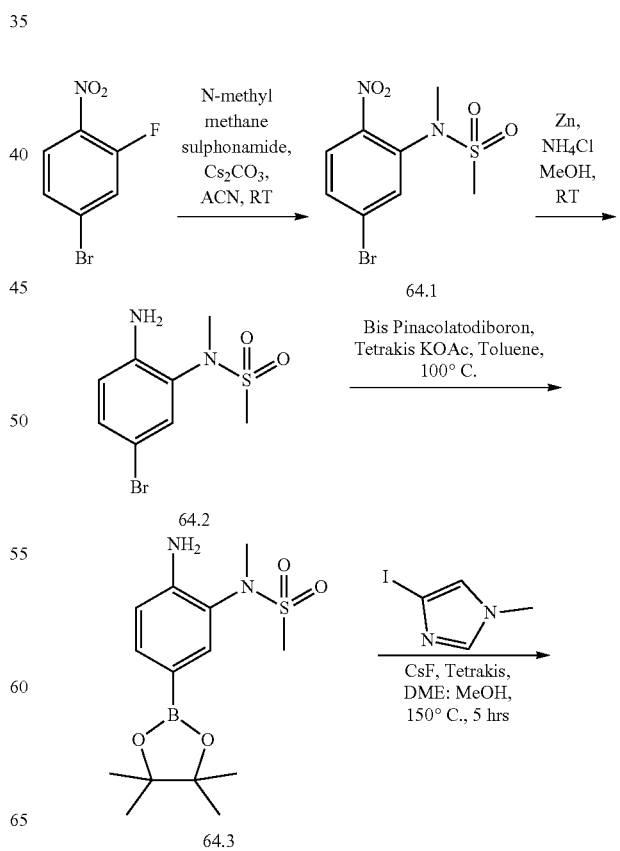

Synthesis of Compound 63.1.

To a solution of 2,4-difluoro-1-nitrobenzene (5.0 g, 31.43 mmol, 1.0 eq) in a mixture of pyridine (5 mL) and MeOH (10 mL) was added sodium thiomethoxide (2.2 g, 31.43 mmol, 1.0 eq) at 0° C. and stirred the reaction mixture for 15 min. Upon completion, reaction mixture was transferred into aqueous solution of HCl and extracted with ethyl acetate. Organic layer was concentrated in vacuo to obtain crude product. This was purified by column chromatography using 10% ethyl acetate in hexane to obtain pure 63.1 (4.0 g, Yield: 67.99%). MS(ES): m/z 188.19 [M+H]$^+$.

Synthesis of Compound 63.2.

To a solution of 63.1 (4.0 g, 21.37 mmol, 1.0 eq) in N,N-dimethylformamide (40 mL) was added potassium carbonate (5.9 g, 42.74 mmol, 2.0 eq) followed by 3-methyl-1H-pyrazole (2.1 g, 25.64 mmol, 1.2 eq). The reaction mixture was stirred at 140° C. for 4 h. Upon completion, reaction mixture was transferred into ice cold water and extracted with ethyl acetate. Organic layer was concentrated in vacuo to obtain crude product. This was purified by column chromatography using 30% ethyl acetate in hexane to obtain pure 63.2 (2.0 g, Yield: 37.54%). MS(ES): m/z 250.29 [M+H]$^+$.

Synthesis of Compound 63.3.

To a solution of 63.2 (2.0 g, 8.02 mmol, 1.0 eq) in MeOH (20 mL), 10% Pd/C (1 g) was added. Hydrogen was purged

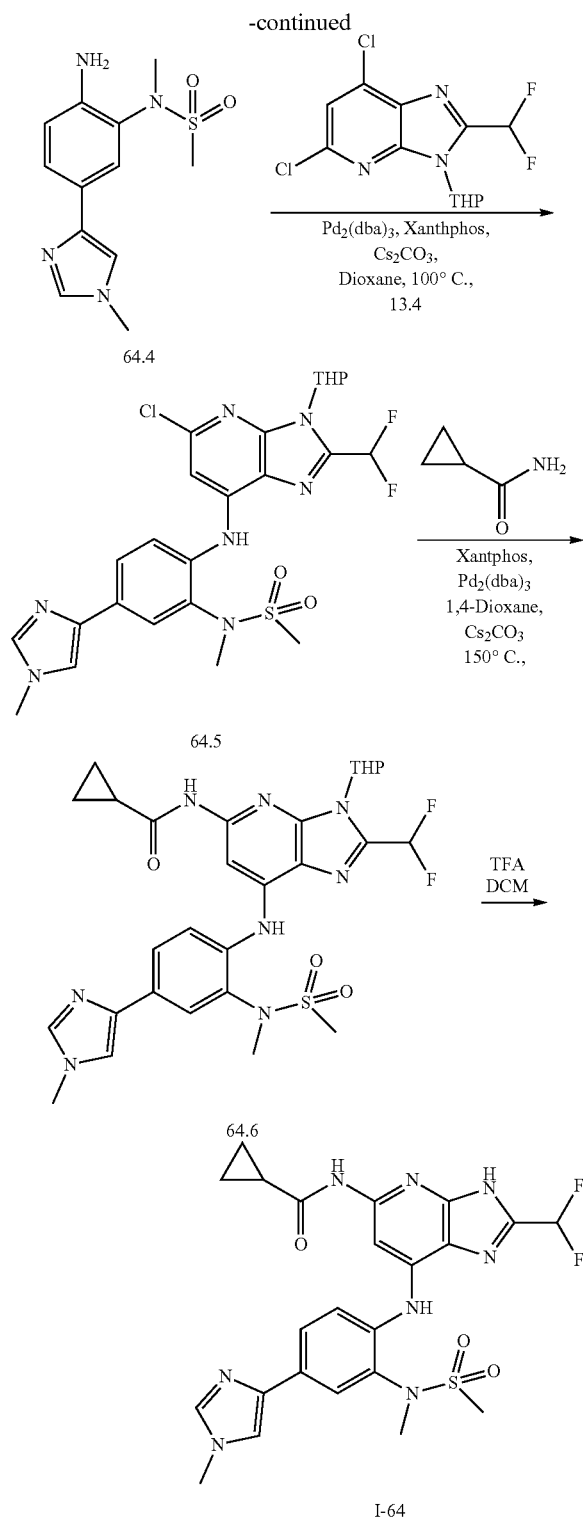

Synthesis of Compound 64.1.

To a suspension of Cs₂CO₃ (70 g, 0.215 mmol, 1.9 eq) in acetonitrile (500 mL), N-methyl methane sulfonamide (13.62 g, 0.125 mmol, 1.1 eq) was added and cooled to 0° C. Then compound 4-bromo-2-fluoro-1-nitrobenzene (25 g, 113.64 mmol, 1 eq) was added dropwise in the reaction mixture within 15 min. Reaction mixture was stirred at r.t. for 12 hours. After completion of the reaction, the reaction mixture was filtered and the filtrate was concentrated in vacuo to obtain 64.1. (27 g, 76.86%). MS(ES): m/z 310.13 [M+H]⁺.

Synthesis of Compound 64.2.

To a solution of 64.1 (27 g, 87.34 mmol, 1 eq), in MeOH (27 mL), was added ammonium chloride (50 mL), and zinc dust (28.39 g, 43.68 mmol, 5 eq).

Reaction mixture was stirred at r.t. for 2 h. After completion of reaction, the reaction mixture was transferred into NaHCO₃ solution and extracted with ethyl acetate. Combined Organic layer dried over Na₂SO₄ and concentrated in vacuo to obtain crude product. This was purified by column chromatography and compound was eluted in 30% ethyl acetate in hexane to obtain pure 64.2. (16 g, 65.62%). MS(ES): m/z 280.15 [M+H]⁺

Synthesis of Compound 64.3.

To a solution of 64.2 (7 g, 25.08 mmol, 1.0 eq), in toluene (60 mL) was added Bis Pinacolatodiboron (9.55 g, 37.63 mmol, 1.5 eq). The reaction mixture was degassed by argon for 30 min. Tetrakis(triphenylphosphine)palladium (2.89 g, 2.50 mmol, 0.1 eq), potassium acetate (8.1 g, 82.79 mmol, 3.3 eq,) was added into reaction mixture and again reaction mixture was degassed by argon for 30 min. Further reaction mixture was stirred at 100° C. for 3 h. After completion of reaction, water was added to reaction mixture and extracted with ethyl acetate. Organic layers were combined, dried over Na₂SO₄ and concentrated in vacuo to obtain crude product. This was purified by column chromatography and compound was eluted in 20% ethyl acetate in hexane to obtain pure 64.3 (3.5 g, 42.79%). MS(ES): m/z 327.22 [M+H]⁺.

Synthesis of Compound 64.4.

To a solution of 64.3 (0.400 g, 1.23 mmol, 1.0 eq) 4-iodo-1-methyl-1H-imidazole (0.306 g, 1.47 mmol, 1.2 eq) in mixture of MeOH (4 mL) and dimethoxymethane (1 mL). The reaction mixture was degassed by argon for 30 min. Tetrakis(triphenylphosphine)palladium (0.141 g, 0.122 mmol, 0.1 eq), Cesium fluoride (0.610 g, 4.04 mmol, 3.3 eq,) was added into reaction mixture and again reaction mixture was degassed by argon for 30 min. Further reaction mixture was stirred at 150° C. for 5 h. After completion of reaction, water was added to reaction mixture and extracted with ethyl acetate. Organic layers were combined, dried over Na₂SO₄ and concentrated in vacuo to obtain crude product. This was purified by column chromatography and compound was eluted in 20% ethyl acetate in hexane to obtain pure 64.4 (0.200 g, 58.18%). MS(ES): m/z 281.35 [M+H]⁺.

Synthesis of Compound 64.5.

Compound 64.5 was synthesized from 64.4 and 13.4 using general procedure A (Yield: 37.94%). MS(ES): m/z 567.02 [M+H]⁺.

Synthesis of Compound 64.6.

Compound 64.6 was synthesized from 64.5 and cyclopropanecarboxamide using general procedure B. (Yield: 48.34%). MS(ES): m/z 615.67 [M+H]⁺.

Synthesis of I-64.

Compound I-64 was synthesized from 64-6 using general procedure C. (Yield: 68.96%). MS(ES): m/z: 531.44 [M+H]⁺, LCMS purity, 99.64%, HPLC purity 99.59%, 1H NMR (DMSO, 400 MHz): 13.54 (s, 1H), 10.61 (s, 1H), 8.15 (s, 1H), 8.10 (s, 1H), 7.98 (s, 1H), 7.84 (s, 1H), 7.79-7.74 (d, 1H), 7.72-7.69 (d, 1H), 7.58-7.56 (d, J=8.4 Hz, 1H), 7.25 (t, 1H), 3.73 (s, 3H), 3.24 (s, 3H), 3.09 (s, 3H), 2.02-2.01 (m, J=4.8 Hz, 1H) 0.77-0.76 (d, J=7.2 Hz, 4H).

Example 65: Synthesis of N-(2-(difluoromethyl)-7-((4-(1-methyl-1H-pyrazol-4-yl)-2-(N-methylmethyl-sulfonamido)phenyl)amino)-3H-imidazo[4,5-b]pyridin-5-yl)cyclopropanecarboxamide, I-65

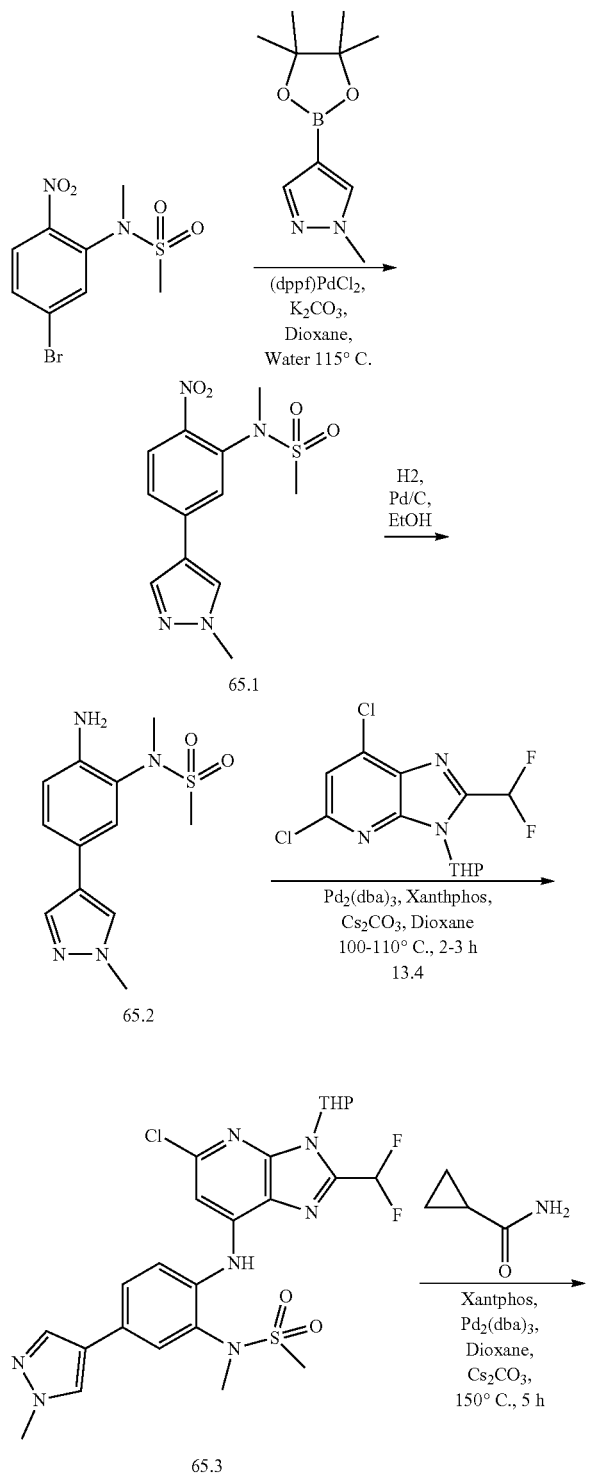

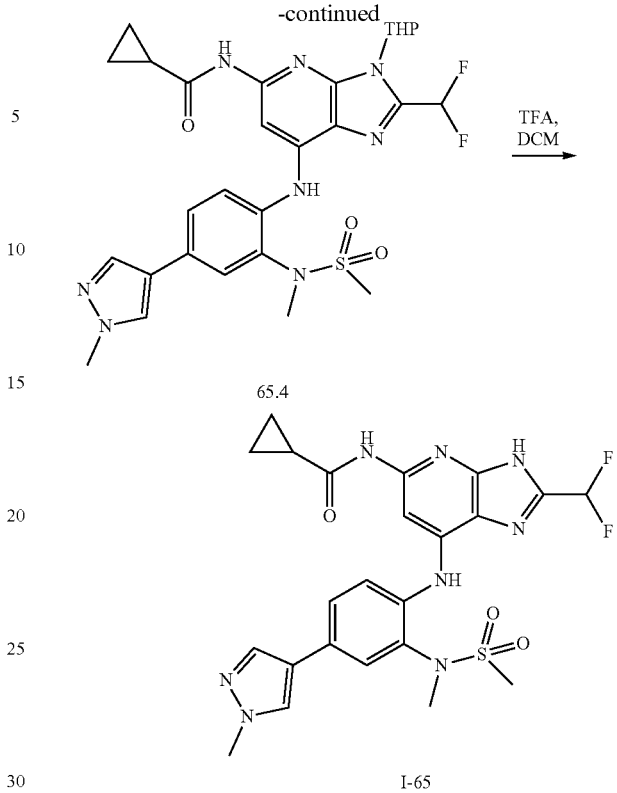

Synthesis of Compound 65.1.

To N-(5-bromo-2-nitrophenyl)-N-methylmethanesulfonamide (1.0 g, 3.23 mmol, 1.0 eq) and 1-methyl-4-(4,4,5,5-tetramethyl-1,3,2-dioxaborolan-2-yl)-1H-pyrazole (1.0 g, 4.85 mmol, 1.5 eq) in a mixture of dioxane (6 mL) and water (4 mL). Reaction mixture was degassed with argon atmosphere for 10 minute. Then [1,1'-Bis(diphenylphosphino)ferrocene]palladium(II) dichloride (0.12 g, 0.16 mmol, 0.05 eq) and potassium carbonate (0.89 g, 6.46 mmol, 2.0 eq) was added into it. Reaction mixture was stirred at 115° C. for 24 h. Upon completion, reaction mixture was transferred into cold water then extracted with ethyl acetate. Organic layers were combined, dried over $Na_2SO_4$ and concentrated in vacuo to obtain crude product. This was purified by column chromatography and compound was eluted in 15% ethyl acetate in $CH_2Cl_2$ as eluant to obtain pure 65.1 (0.8 g, 79.69%). MS(ES): m/z 311.33 [M+H]$^+$.

Synthesis of Compound 65.2.

To compound 65.1 (0.3 g, 9.66 mmol, 1.0 eq) in MeOH, 10% Pd/C (0.056 g) was added. Hydrogen was purged through reaction mixture for 4 h. Upon completion, reaction mixture was filtered through celite-bed and washed with MeOH. Filtrate was concentrated in vacuo to obtain 65.2 (0.22 g, 81.18%). MS(ES): m/z 281.35 [M+H]$^+$.

Synthesis of Compound 65.3.

Compound 65.3 was synthesized from 65.2 and 13.4 using general procedure B to obtain 1.3. (Yield: 34.02%). MS(ES): m/z 567.06 [M+H]$^+$.

Synthesis of Compound 65.4.

Compound 65.4 was synthesized from 65.3 and cyclopropanecarboxamide using general procedure B. (Yield: 60.59%). MS(ES): m/z 603.66 [M+H]$^+$.

Synthesis of I-65.

Compound I-65 was synthesized from 65.4 using general procedure C. (Yield: 75.31%). MS(ES): m/z: 531.49

[M+H]+, LCMS purity: 99.75%, HPLC purity: 99.36%, 1H NMR (DMSO-d6, 400 MHz): 10.61 (s, 1H), 8.23 (s, 1H), 8.08 (s, 1H), 7.97 (s, 1H), 7.84 (s, 2H), 7.65-7.626 (d, J=8 Hz, 1H), 7.56-7.54 (d, J=8.4 Hz, 1H), 3.89 (s, 3H), 3.24 (s, 3H), 3.09 (s, 3H), 2.01-1.99 (m, 1H), 0.76 (s, 4H).

Example 80: Synthesis of 6-((2-(difluoromethyl)-7-((2-methoxy-3-(2-methyl-2H-tetrazol-5-yl)phenyl)amino)-3H-imidazo[4,5-b]pyridin-5-yl)amino)-3-(2-methoxypropan-2-yl)pyrazine-2-carbonitrile, I-80

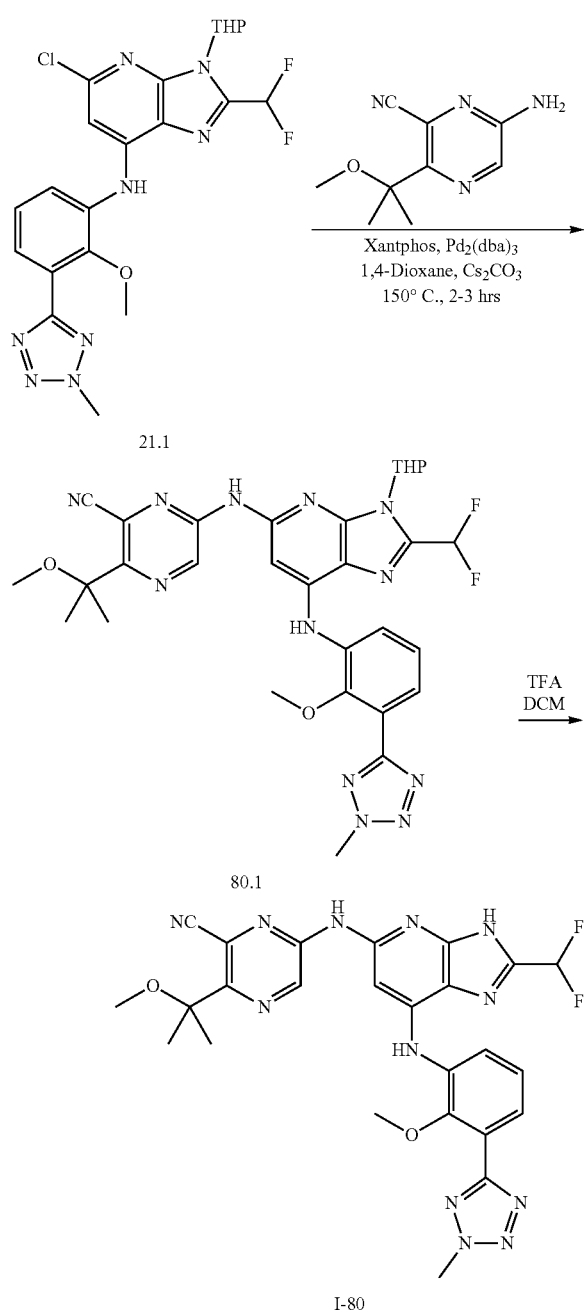

Synthesis of Compound 80.1.

Compound 80.1 was synthesized from 6-amino-3-(2-methoxypropan-2-yl)pyrazine-2-carbonitrile and 21.1 using general procedure B. (Yield: 61.49%). MS(ES): m/z 647.66 [M+H]+.

Synthesis of I-80.

Compound I-80 was synthesized from 80.1 using general procedure C. (Yield: 49.67%). MS(ES): m/z: 563.47 [M+H]+, LCMS purity: 99.59%, HPLC purity 96.08%, 1H NMR (DMSO-d6, 400 MHz): 13.54 (s, 1H), 10.41 (s, 1H), 9.53 (s, 1H), 8.52 (s, 1H), 7.74-7.67 (m, 2H), 7.43-7.37 (m, 1H), 7.24-7.12 (m, 1H), 6.92 (s, 1H), 4.48 (s, 3H), 3.72 (s, 3H), 3.17 (s, 3H), 1.55 (s, 6H).

Example 85: Synthesis of N-(2-(difluoromethyl)-7-((4-fluoro-2-(methylsulfonyl)phenyl)amino)-3H-imidazo[4,5-b]pyridin-5-yl)cyclopropanecarboxamide, I-85

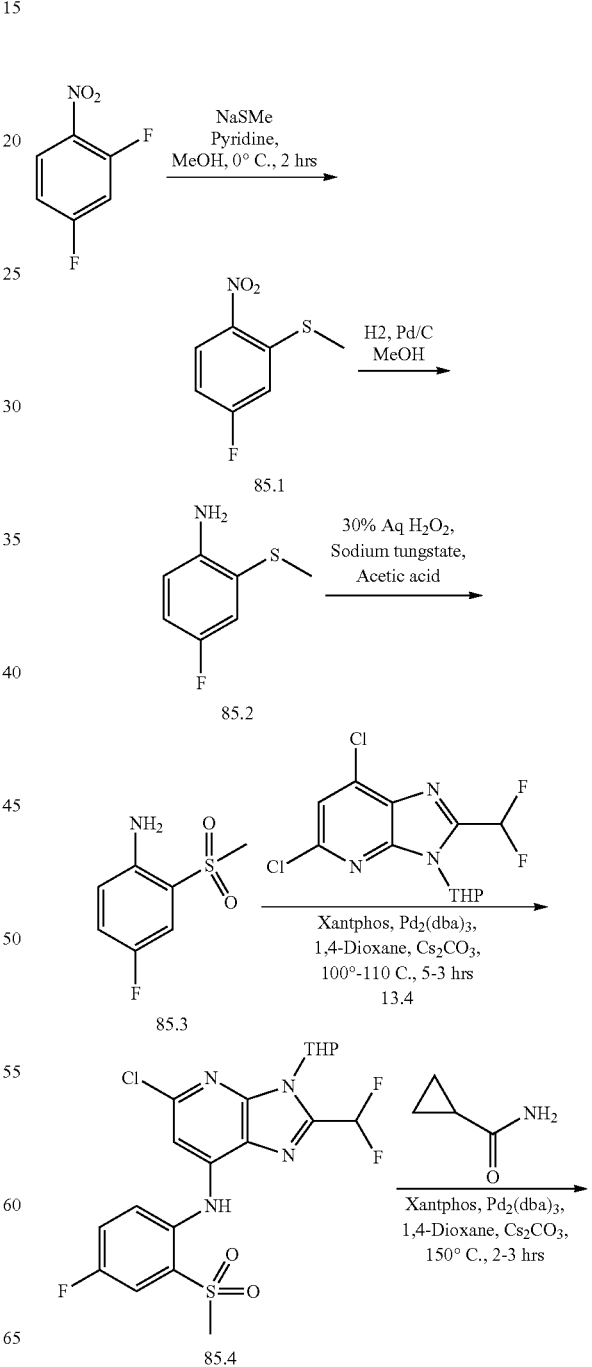

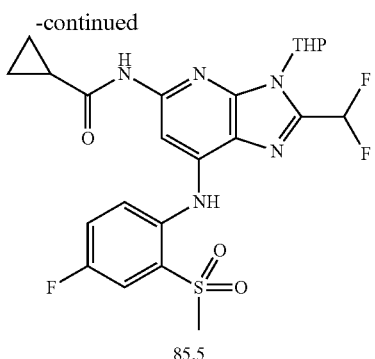

85.5

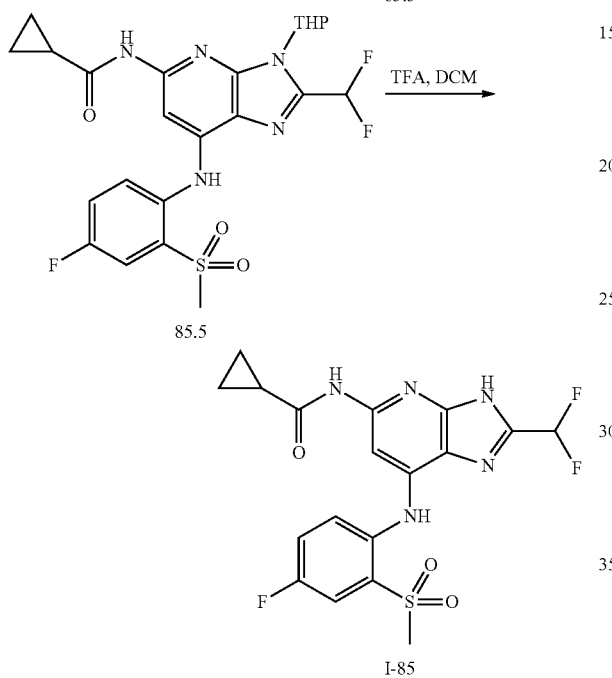

Synthesis of Compound 85.1.

To 2,4-difluoro-1-nitrobenzene (2 g, 12.5 mmol, 1.0 eq) in pyridine (20 mL) was added at 0° C. sodium methyl sulfide (0.779 g, 12.5 mmol, 1 eq) and MeOH (1 ml). Reaction mixture was stirred at 0° C. for 2 h. Upon completion, reaction mixture was transferred into cold water and extracted with CH$_2$Cl$_2$. Organic layers were combined, dried over Na$_2$SO$_4$ and concentrated in vacuo to obtain crude product. This was purified by column chromatography and compound was eluted in 2.5% MeOH in CH$_2$Cl$_2$ as eluant to obtain pure 85.1 (1.5 g, 63.74%). MS(ES): m/z 188.19 [M+H]$^+$.

Synthesis of Compound 85.2.

To compound 85.1 (2 g, 19.5 mmol, 1.0 eq) in MeOH, 10% Pd/C (0.175 g) was added. Hydrogen was purged through reaction mixture for 4 h. Upon completion, reaction mixture was filtered through celite-bed and washed with MeOH. Filtrate was concentrated in vacuo to obtain 85.2 (1.1 g, 87.32%). MS(ES): m/z 158.21 [M+H]$^+$.

Synthesis of Compound 85.3.

To compound 85.2 (1.1 g, 2.83 mmol, 1.0 eq) in acetic acid (10 mL), sodium tungstate (1 g, 1.05 mmol, 1.005 eq) was added in portions. Reaction mixture was allowed to stir at r.t. for 5 min. Then, 30% hydrogen peroxide solution (18 mL) was added dropwise at r.t. Reaction mixture was allowed to stir at r.t. for 10 min. After completion of the reaction, the reaction mixture was transferred into water. The pH of the solution was adjusted to 7 by using saturated NaHCO$_3$ and then extracted with ethyl acetate. Organic layer combined, dried over anhydrous Na$_2$SO$_4$, filtered and concentrated in vacuo to obtain the crude material. This was purified by column chromatography using 10-13% ethyl acetate in hexane as eluant to obtain pure 85.3 (0.410 g, 30.97%). MS(ES): m/z 190.20 [M+H]$^+$.

Synthesis of Compound 85.4.

Compound 85.4 was synthesized from 85.3 and 13.4 using general procedure A. (Yield: 23.91%). MS(ES): m/z 475.88 [M+H]$^+$.

Synthesis of Compound 85.5.

Compound 85.5 was synthesized from 85.4 and cyclopropanecarboxamide using general procedure B. (Yield: 49.13%). MS(ES): m/z 524.53 [M+H]$^+$.

Synthesis of I-85.

Compound I-85 was synthesized from 85.5 using general procedure C. (Yield: 47.66%). MS(ES): m/z 440.55 [M+H]$^+$, LCMS purity: 98.57%, HPLC purity: 98.64%, 1H NMR (DMSO, 400 MHz): 13.56 (s, 1H), 10.66 (s, 1H), 8.54 (s, 1H), 7.84 (s, 1H), 7.80 (s, 1H), 7.79 (s, 2H), 3.23 (s, 3H), 2.03-2.00 (t, J=11.2 Hz, 1H), 1.95-1.92 (m, 1H), 0.77 (bs, 4H).

Example 87: N-(2-((2-(difluoromethyl)-5-((6-(trifluoromethyl)pyridin-2-yl)amino)-3H-imidazo[4,5-b]pyridin-7-yl)amino)phenyl)-N-methylmethanesulfonamide, I-87

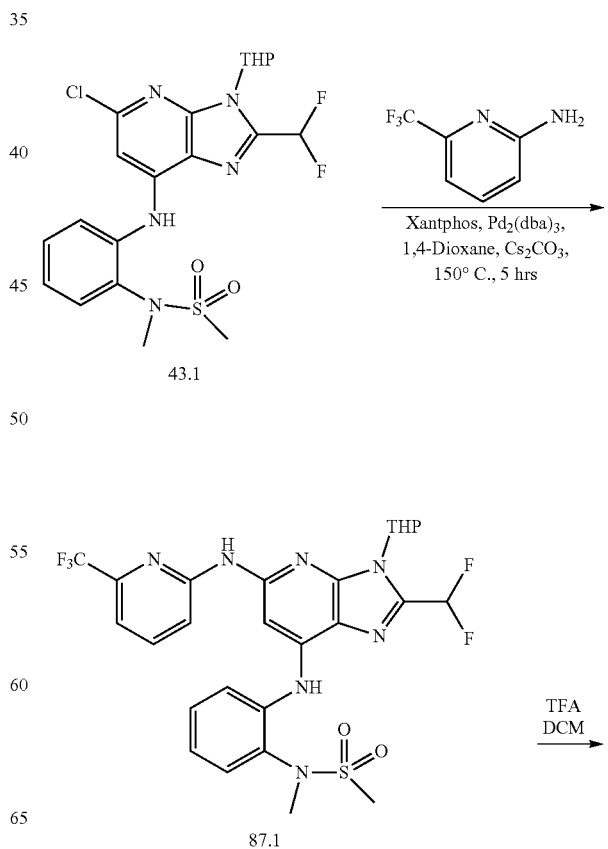

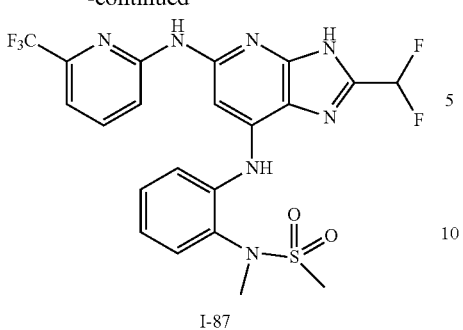

I-87

Synthesis of Compound 87.1.

Compound 87.1 was synthesized from 6-(trifluoromethyl)pyridin-2-amine and 43.1 using general procedure B. (Yield: 47.67%). MS(ES): m/z 612.43 [M+H]$^+$.

Synthesis of I-87.

Compound I-87 was synthesized from 87.1 using general procedure C. (Yield: 86.96%). MS(ES): m/z: 528.31 [M+H]$^+$, LCMS purity: 99.56%, HPLC purity: 99.86%, 1H NMR (DMSO, 400 MHz): 13.53 (s, 1H), 10.07 (s, 1H), 8.23-8.20 (d, J=8.4 Hz, 1H), 8.09 (s, 1H), 7.93-7.89 (t, J=8 Hz, 1H), 7.70-7.66 (t, J=9.2 Hz, 2H), 7.46-7.42 (t, 1H), 7.36-7.34 (d, 1H), 7.31-7.26 (m, 3H), 3.21 (s, 3H), 3.10 (s, 3H).

Example 89: Synthesis of N-(7-((4-(azetidin-1-yl)-2-(N-methylmethylsulfonamido)phenyl)amino)-2-(difluoromethyl)-3H-imidazo[4,5-b]pyridin-5-yl)cyclopropanecarboxamide, I-89

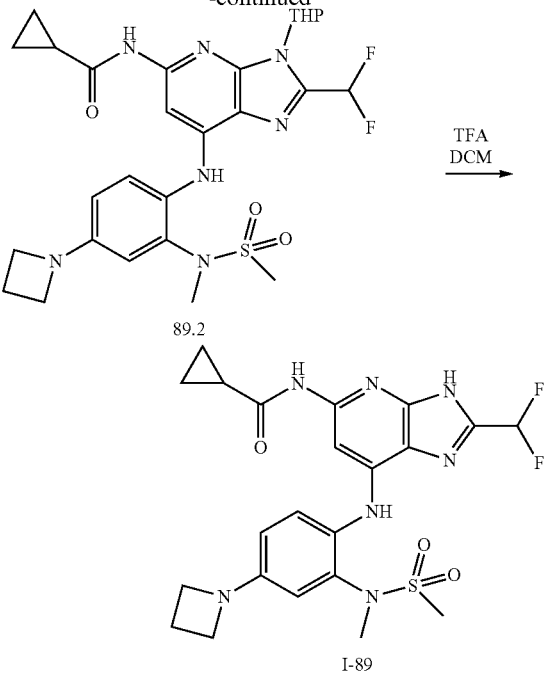

I-89

Synthesis of Compound 89.1.

Compound 89.1 was synthesized from 13.4 and 89.1a (prepared from 129.1 and azetidine) using general procedure A. (Yield: 26.96%). MS(ES): m/z 542.68 [M+H]$^+$.

Synthesis of Compound 89.2.

Compound 89.2 was synthesized from 89.1 and cyclopropanecarboxaamide using general procedure B. (Yield: 65.14%). MS(ES): m/z 590.26 [M+H]$^+$.

Synthesis of I-89.

Compound I-89 was synthesized from 89.2 using general procedure C. (Yield: 65.71%). MS(ES): m/z: 506.43 [M+H]$^+$, LCMS purity: 95.17%, HPLC purity: 95.17%, 1H NMR (DMSO, 400 MHz): 13.41 (s, 1H), 10.49 (s, 1H), 7.79 (s, 1H), 7.45 (s, 1H), 7.34-7.26 (m, 1H), 7.21 (s, 1H), 6.60 (s, 1H), 6.50-6.48 (m, 1H), 3.89-3.85 (t, J=7.2 Hz, 4H), 3.125 (s, 3H), 3.03 (s, 3H), 2.35-2.31 (t, J=3.6 Hz, 2H), 1.99 (s, 1H), 0.75 (s, 4H).

Example 93: Synthesis of N-(5-chloro-2-((2-(difluoromethyl)-5-((5,6-dimethylpyrazin-2-yl)amino)-3H-imidazo[4,5-b]pyridin-7-yl)amino)phenyl)-N-methylmethanesulfonamide, I-93

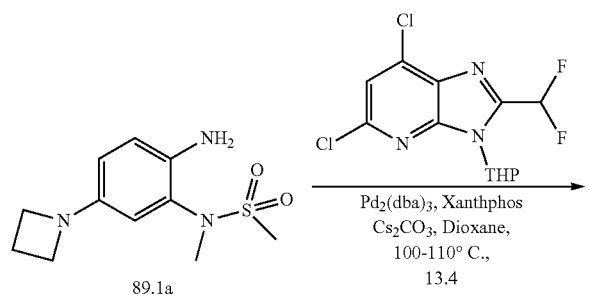

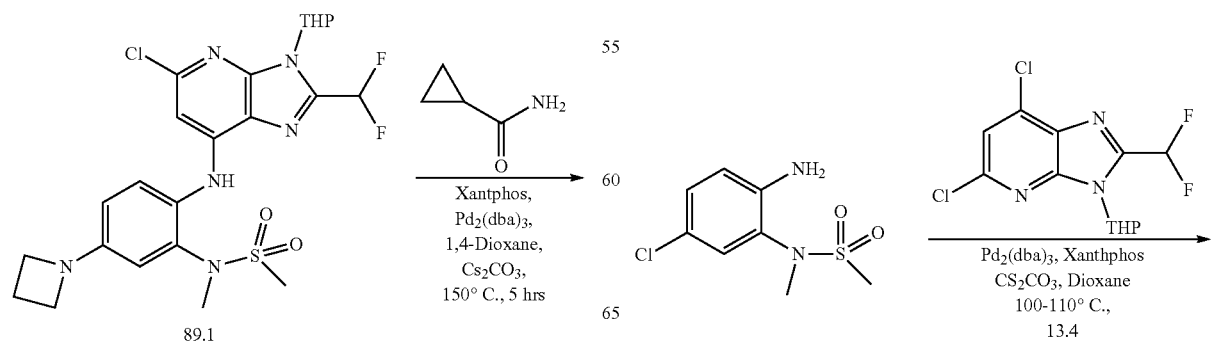

-continued

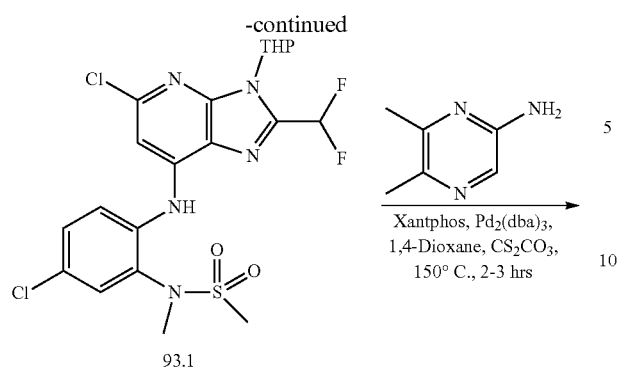

93.1

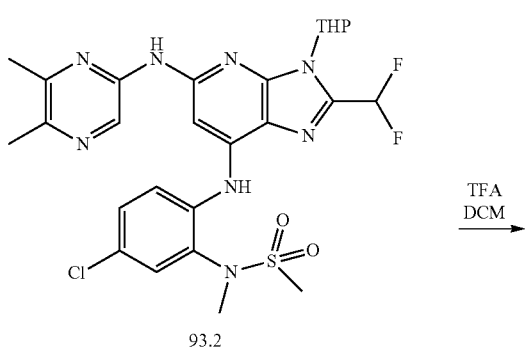

93.2

TFA
DCM

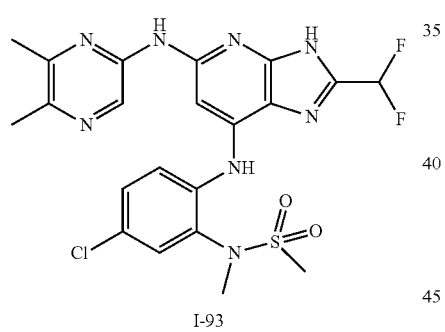

I-93

Synthesis of Compound 93.1.

Compound 93.1 was synthesized from 13.4 and N-(2-amino-5-chlorophenyl)-N-methylmethanesulfonamide using general procedure A. (Yield: 23.20%). MS(ES): m/z 521.46 [M+H]⁺.

Synthesis of Compound 93.2.

Compound 93.2 was synthesized from 5,6-dimethylpyrazin-2-amine and 93.1 using general procedure B. (Yield: 11.18%). MS(ES): m/z 608.45 [M+H]⁺.

Synthesis of I-93.

Compound I-93 was synthesized from 93.2 using general procedure C. (Yield: 64.49%). MS(ES): m/z: 523.21 [M+H]⁺, LCMS purity: 95.68%, HPLC purity: 99.55%, 1H NMR (DMSO, 400 MHz): 13.47 (s, 1H), 9.69 (s, 1H), 8.99 (s, 1H), 8.09 (s, 1H), 7.84-7.83 (d, J=2.8 Hz, 1H), 7.71-7.68 (d, J=8.8 Hz, 1H), 7.54-7.51 (m, 1H), 7.25 (s, 1H), 3.23 (s, 3H), 3.12 (s, 3H), 2.396-2.373 (d, J=9.2 Hz, 6H).

Example 94: Synthesis of N-(5-chloro-2-((5-((6-cyanopyridin-2-yl)amino)-2-(difluoromethyl)-3H-imidazo[4,5-b]pyridin-7-yl)amino)phenyl)-N-methylmethanesulfonamide, I-94

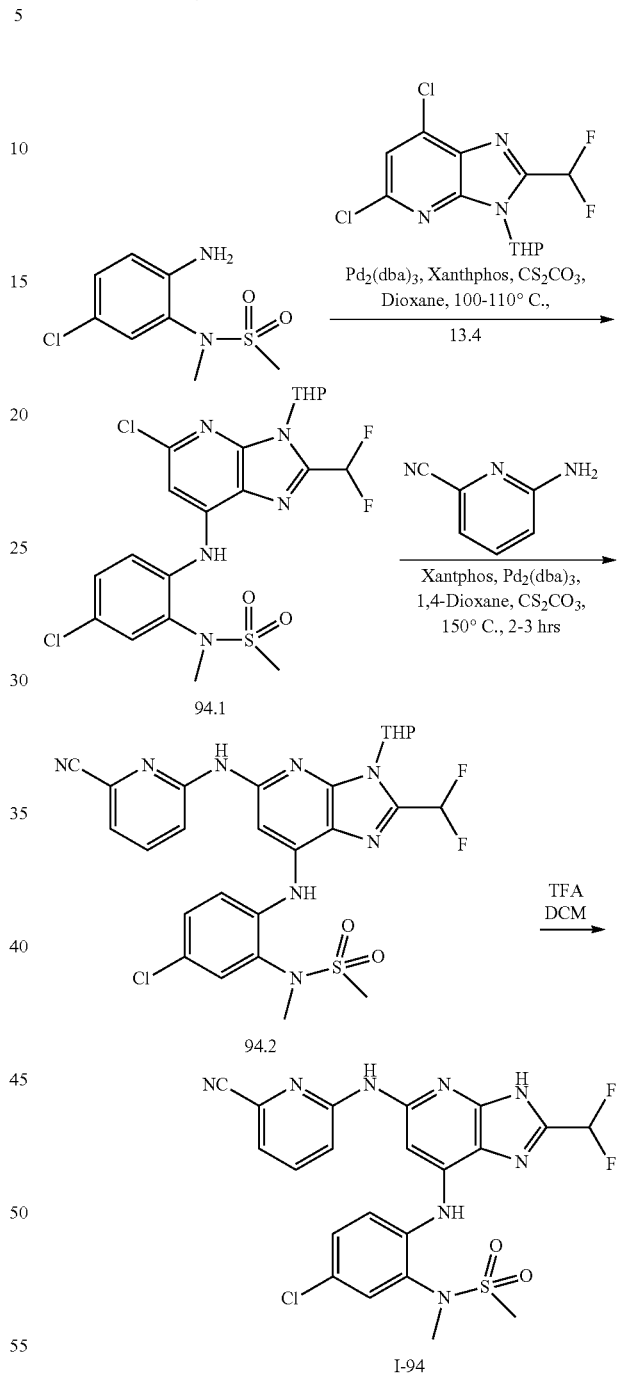

Synthesis of Compound 94.1.

Compound 94.1 was synthesized from 13.4 and N-(2-amino-5-chlorophenyl)-N-methylmethanesulfonamide using general procedure A. (Yield: 48.11%). MS(ES): m/z 521.71 [M+H].

Synthesis of Compound 94.2.

Compound 94.2 was synthesized from 6-aminopicolinonitrile and 94.1 using general procedure B. (Yield: 24.27%). MS(ES): m/z 604.57 [M+H]⁺.

Synthesis of I-94.

Compound I-94 was synthesized from 94.2 using general procedure C. (Yield: 58.10%). MS(ES): m/z: 519.21 [M+H]+, LCMS purity: 96.44%, HPLC purity: 95.53%, 1H NMR (DMSO, 400 MHz): 10.12 (s, 1H), 8.16 (s, 1H), 8.13-8.12 (d, J=8.4 Hz 1H), 7.89-7.84 (m, 2H), 7.76-7.74 (d, J=8.8 Hz, 1H), 7.58-7.56 (m, 1H), 7.49-7.47 (d, J=7.2 Hz, 1H), 7.39 (s, 1H), 7.23 (s, 1H), 3.24 (s, 3H), 3.13 (s, 3H).

Example 95: Synthesis of N-(2-(difluoromethyl)-7-((4-methyl-2-(N-methylmethylsulfonamido)phenyl)amino)-3H-imidazo[4,5-b]pyridin-5-yl)cyclopropanecarboxamide, I-95

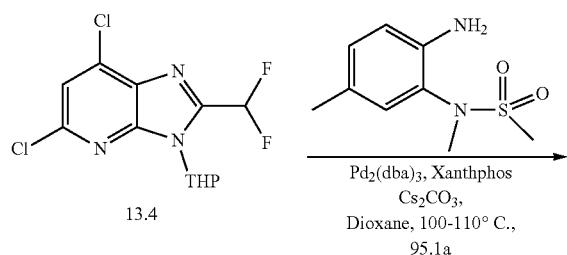

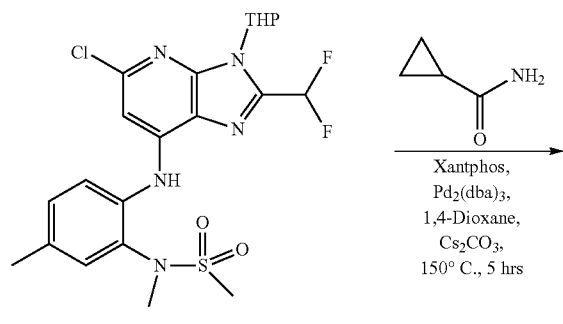

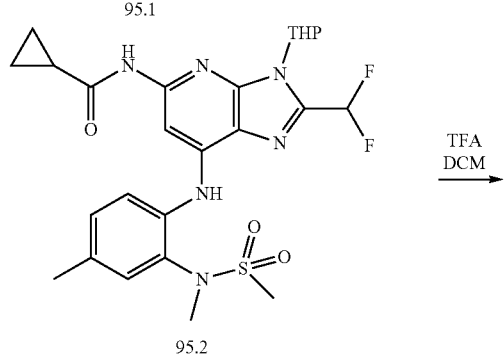

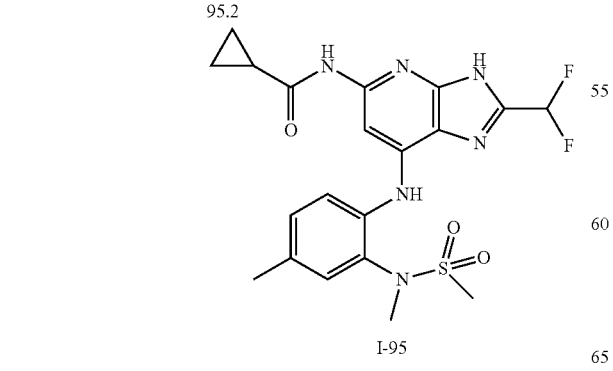

Synthesis of Compound 95.1.

Compound 95.1 was prepared from 13.4 and 95.1a (prepared from Pd coupling of 135.2 and trimethylboroxine) using general procedure A. (Yield: 24.26%). MS(ES): m/z 500.21 [M+H]+.

Synthesis of Compound 95.2.

Compound 95.2 was synthesized from 95.1 and cyclopropanecarboxamide using general procedure B. (Yield: 25.75%). MS(ES): m/z 549.56 [M+H]+.

Synthesis of I-95.

Compound I-95 was synthesized from 95.2 using general procedure C. (Yield: 54.51%). MS(ES): m/z: 465.32 [M+H]+, LCMS purity, 99.07%, HPLC purity 99.11%, 1H NMR (DMSO, 400 MHz): 13.51 (s, 1H), 10.59 (s, 1H), 8.02 (s, 1H), 7.77 (s, 1H), 7.49 (s, 1H), 7.37 (t, 1H), 7.27-7.25 (d, J=9.2 Hz, 1H), 3.18 (s, 3H), 3.07 (s, 3H), 2.37 (s, 3H), 2.02-2.00 (m, 1H), 0.77 (s, 4H).

Example 96: Synthesis of N-(2-(difluoromethyl)-7-((4-(methoxymethyl)-2-(N-methylmethylsulfonamido)phenyl)amino)-3H-imidazo[4,5-b]pyridin-5-yl)cyclopropanecarboxamide, I-96

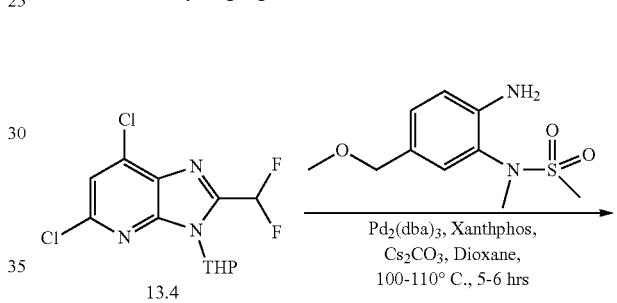

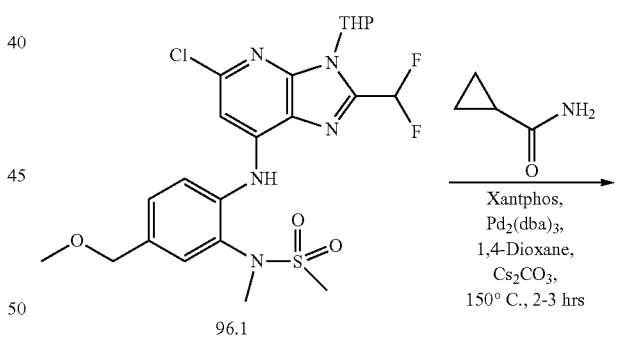

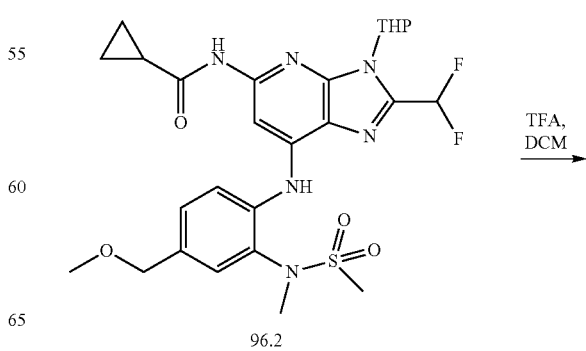

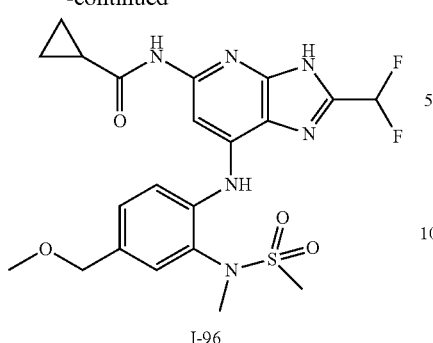

I-96

Synthesis of Compound 96.1.

Compound 96.1 was synthesized from 13.4 and 96.1a (prepared by Stille coupling of 135.2 and $Bu_3SnCH_2OMe$, followed by hydrogenation) using general procedure. A (Yield: 25.35%). MS(ES): m/z 530.99 $[M+H]^+$.

Synthesis of Compound 96.2.

Compound 96.2 was synthesized from 96.1 and cyclopropanecarboxamide using general procedure. B (Yield: 46.63%). MS(ES): m/z 579.64 $[M+H]^+$.

Synthesis of I-96.

Compound I-96 was synthesized from 96.2 using general procedure C. (Yield: 52.24%). MS(ES): m/z: 495.26 $[M+H]^+$, LCMS purity, 99.12%, HPLC purity 99.76%, 1H NMR (DMSO, 400 MHz): 13.53 (s, 1H), 10.64 (s, 1H), 8.14 (s, 1H), 7.81 (s, 1H), 7.60-7.55 (m, 2H), 7.39-7.37 (d, J=7.2 Hz, 1H), 7.11 (t, 1H), 4.45 (s, 2H), 3.40 (s, 3H), 3.20 (s, 3H), 3.07 (s, 3H), 2.01 (m, 1H), 0.86 (bs, 4H).

Example 97: Synthesis of N-(2-((2-(difluoromethyl)-5-((5,6-dimethylpyrazin-2-yl)amino)-3H-imidazo[4,5-b]pyridin-7-yl)amino)-5-methylphenyl)-N-methylmethanesulfonamide, I-97

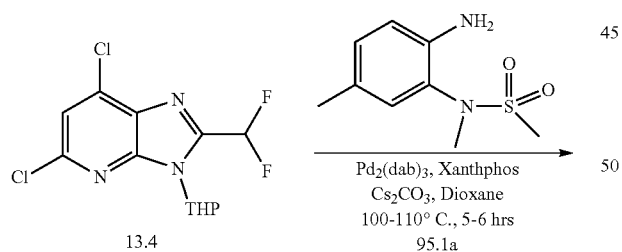

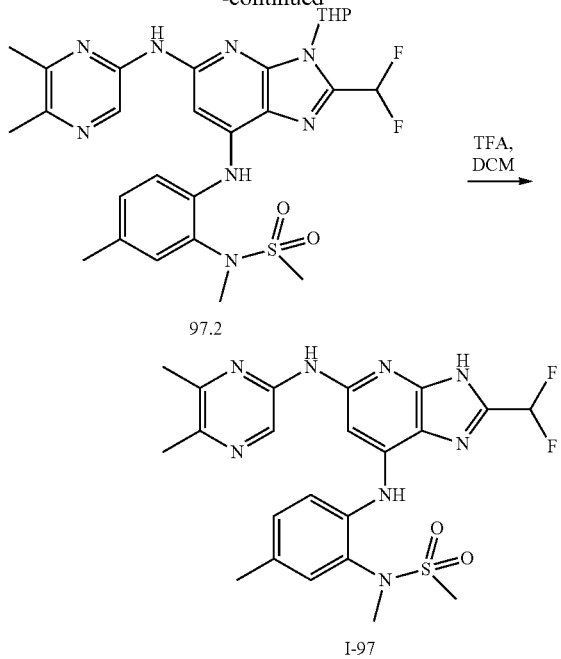

Synthesis of Compound 97.1.

Compound 97.1 was synthesized from 13.4 and 95.1a using general procedure. A (Yield: 30.51%). MS(ES): m/z 500.8 $[M+H]^+$.

Synthesis of Compound 97.2.

Compound 97.2 was synthesized from 97.1 and 5,6-dimethylpyrazin-2-amine using general procedure. B (Yield: 35.51%). MS(ES): m/z 587.6 $[M+H]^+$.

Synthesis of I-97.

Compound I-97 was synthesized from 97.2 using general procedure C. (Yield: 60.70%). MS(ES): m/z: 503.36 $[M+H]^+$, LCMS purity: 99.47%, HPLC purity: 99.55%, 1H NMR (DMSO, 400 MHz): 13.42 (s, 1H), 9.81 (s, 1H), 8.45 (s, 1H), 8.08 (s, 1H), 7.94-7.92 (m, 1H), 7.82 (s, 1H), 7.38 (s, 1H), 7.22-7.19 (d, 1H), 7.16 (t, 1H), 3.17 (s, 3H), 3.10 (s, 3H), 2.42-2.41 (d, J=4 Hz, 6H), 2.34 (s, 3H).

Example 98: Synthesis of N-(7-((2-methoxy-3-(2-methyl-2H-tetrazol-5-yl)phenyl)amino)-2-methyl-3H-imidazo[4,5-b]pyridin-5-yl)cyclopropanecarboxamide, I-98

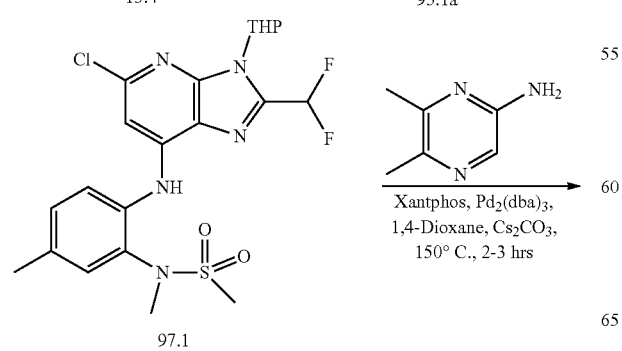

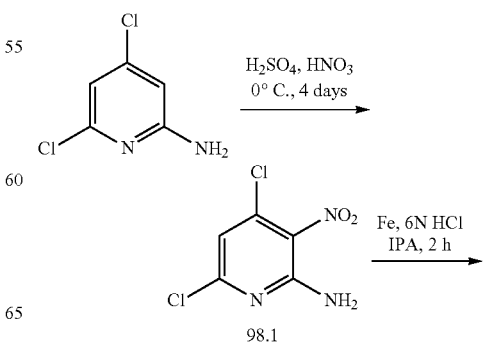

-continued

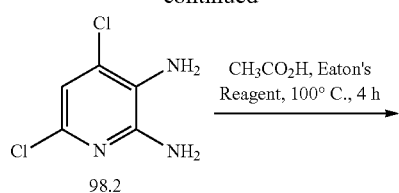
98.2

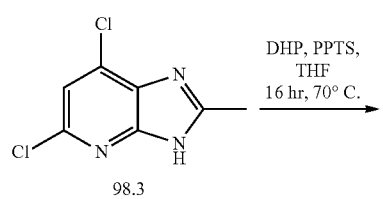
98.3

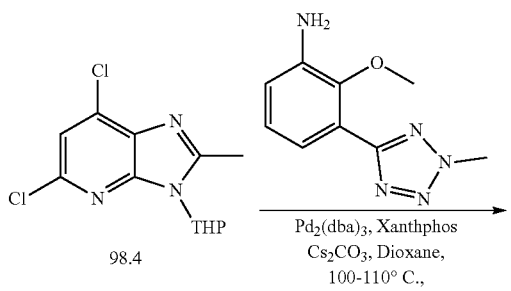
98.4

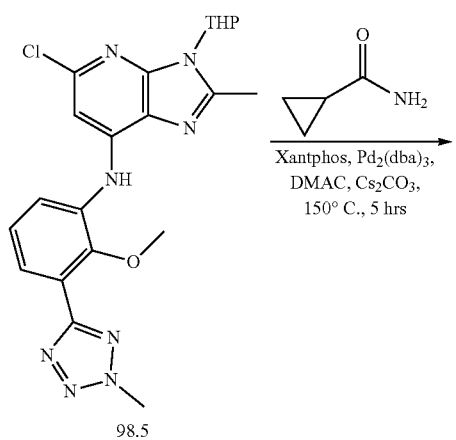
98.5

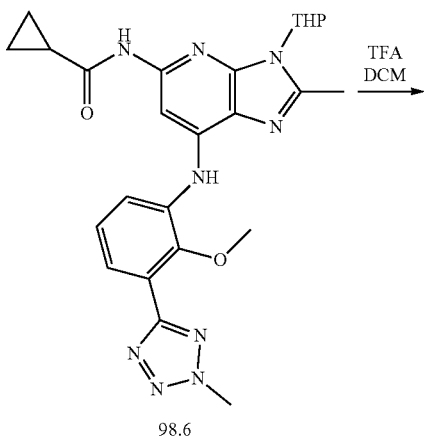
98.6

-continued

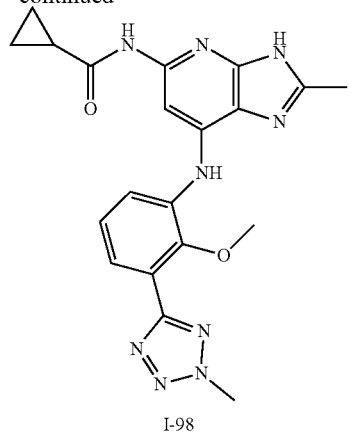
I-98

Synthesis of Compound 98.1.

To a concentrated H₂SO₄ (265 mL) added 4,6-dichloro-pyridin-2-amine (50 g, 306 mmol, 1.0 eq) portionwise at −5° C. and stirred for 30 min followed by addition of nitric acid (16.50 mL) dropwise. Reaction mixture was allowed to stand at 0° C. for 4 days. Upon completion, reaction mixture was slowly transferred into crushed ice. Saturated NaHCO₃ solution was added to pH 8. Precipitated solid was filtered off to obtain crude compound. This was purified by column chromatography and compound was eluted in 8% ethyl acetate in hexane to get pure 98.1 (30 g, 47%). 1H NMR (CDCl3, 400 MHz): 6.85 (s, 1H), 6.28 (s, 2H).

Synthesis of Compound 98.2.

To a solution of 98.1 (17.5 g, 84.14 mmol, 1.0 eq) in Isopropyl alcohol (525 mL) was added Iron powder (23.6 g, 420 mmol, 5.0 eq) and stirred. To this mixture was added 6N HCl (70 mL) dropwise at 10° C. The reaction mixture was stirred at r.t. for 2 h. After completion of reaction saturated NaHCO₃ solution was added to pH 8. Reaction mixture was filtered through celite. Filtrate was extracted with ethyl acetate. Organic layers were combined, washed with brine, dried over Na₂SO₄ and concentrated in vacuo to obtain 98.2 (14 g, 93.47%). MS(ES): m/z 178 [M+H]⁺.

Synthesis of Compound 98.3.

To a mixture of 98.2 (10 g, 56.10 mmol, 1.0 eq) and acetic acid (3.7 g, 61.71 mmol, 1.1 eq) was added Eaton's Reagent (4.5 mL, 4.5 v) and heated at 100° C. for 4 h. Upon completion, reaction mixture was cooled to r.t., neutralised with saturated NaHCO₃ solution and precipitated product was filtered, dried well to obtain 98.3 (8.0 g, 70.49%). MS(ES): m/z 203.2 [M+H]⁺.

Synthesis of Compound 98.4.

To a solution of 1.3 (8.0 g, 39.61 mmol, 1.0 eq) in dry tetrahydrofuran (144 mL) was added 3,4-Dihydro-2H-pyran (23.2 g, 277.3 mmol, 7.0 eq) followed Pyridinium p-toluenesulfonate (0.99 g, 3.96 mmol, 0.1 eq) and stirred. Reaction mixture was heated at 70° C. for 16 h. Upon completion, reaction mixture was concentrated in vacuo to obtain crude product. This was purified by column chromatography and the compound was eluted in 20% ethyl acetate in hexane get pure 98.4 (8.0 g, 70.60%). 1H NMR (CDCl3, 400 MHz): 7.30 (s, 1H), 5.89-5.85 (m, 1H), 4.23-4.19 (m, 1H), 3.81-3.75 (m, 1H), 2.82 (s, 3H), 2.40-2.31 (m, 1H), 2.12-2.10 (m, 1H), 1.95-1.92 (m, 1H), 1.85-1.66 (m, 3H).

Synthesis of Compound 98.5.

Compound 98.5 was synthesized from 98.4 and 2-methoxy-3-(2-methyl-2H-tetrazol-5-yl)aniline using general procedure A. (Yield: 26.96%). MS(ES): m/z 455.23 [M+H]⁺.

517

Synthesis of Compound 98.6.

Compound 98.6 was synthesized from 98.5 and cyclopropanecarboxamide using general procedure B. (Yield: 62.33%). MS(ES): m/z 504.58 [M+H]$^+$.

Synthesis of I-98.

Compound I-98 was synthesized from 98.6 using general procedure C (Yield: 74.04%). MS(ES): m/z 420.48 [M+H]$^+$, LCMS purity: 100%, HPLC purity: 98.15%, 1H NMR (MeOD, 400 MHz): 7.88 (s, 1H), 7.75 (m, 1H), 7.71-7.68 (dd, J=1.2 Hz, 7.6 Hz, 1H), 7.35-7.31 (t, J=8 Hz, 1H), 4.49 (s, 3H), 3.82 (s, 3H), 2.60 (s, 3H), 1.87 (s 1H), 0.98-0.95 (m, 2H), 0.90-0.86 (s, 2H).

Example 100: Synthesis of N-7-(2-methoxy-3-(2-methyl-2H-tetrazol-5-yl)phenyl)-2-methyl-N5-(6-methylpyridazin-3-yl)-3H-imidazo[4,5-b]pyridine-5,7-diamine, I-100

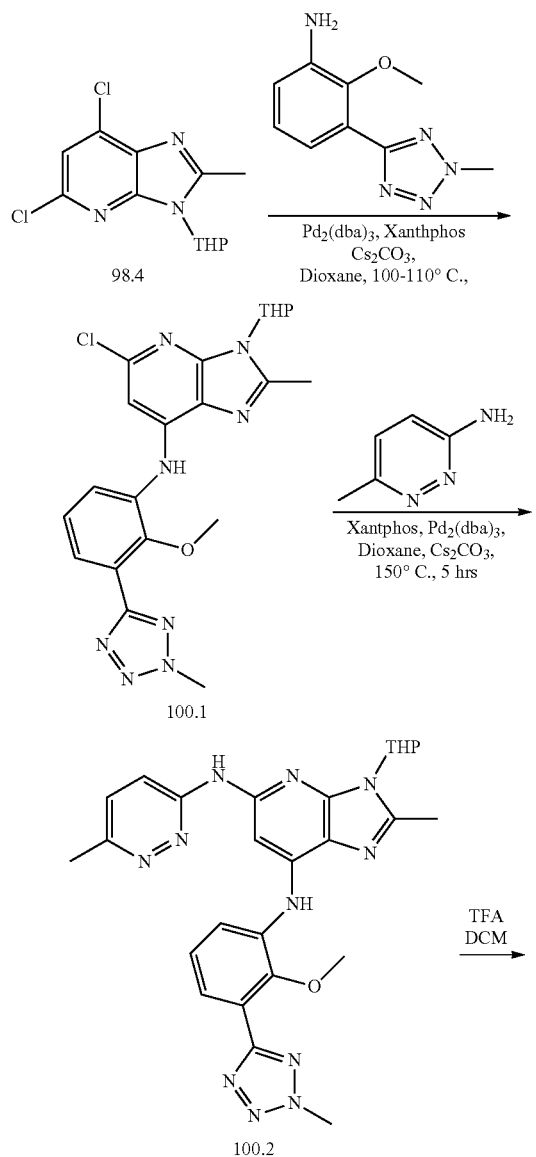

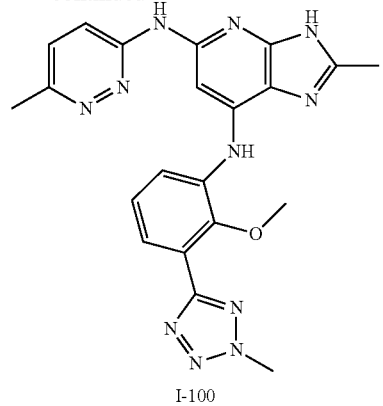

I-100

Synthesis of Compound 100.1.

Compound 100.1 was synthesized from 98.4 and 2-methoxy-3-(2-methyl-2H-tetrazol-5-yl)aniline using general procedure A. (Yield: 26.96%). MS(ES): m/z 455.23 [M+H]$^+$.

Synthesis of Compound 100.2.

Compound 100.2 was synthesized from 6-methylpyridazin-3-amine and 100.1 using general procedure B. (Yield: 60.36%). MS(ES): m/z 527.54 [M+H]$^+$.

Synthesis of I-100.

Compound I-100 was synthesized from 100.2 using general procedure C. (Yield: 49.29%). MS(ES): m/z 444.37 [M+H]$^+$, LCMS purity: 100%, HPLC purity: 97.35%, 1H NMR (MeOD, 400 MHz): 8.20 (s, 1H). 7.75-7.73 (d, J=8 Hz, 2H), 7.55-7.52 (d, 1H), 7.39-7.35 (t, J=8.4 Hz, 1H) 6.92 (s 1H), 4.49 (s 3H), 3.80 (s, 3H), 2.62-2.57 (d, J=8.4 Hz, 6H).

Example 101: Synthesis of N7-(2-methoxy-3-(2-methyl-2H-tetrazol-5-yl)phenyl)-2-methyl-N5-(5-methylpyridin-2-yl)-3H-imidazo[4,5-b]pyridine-5,7-diamine, I-101

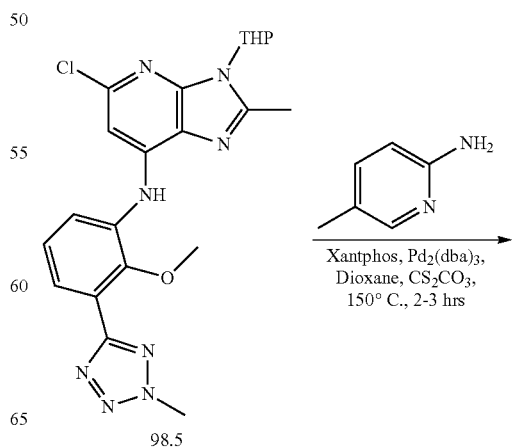

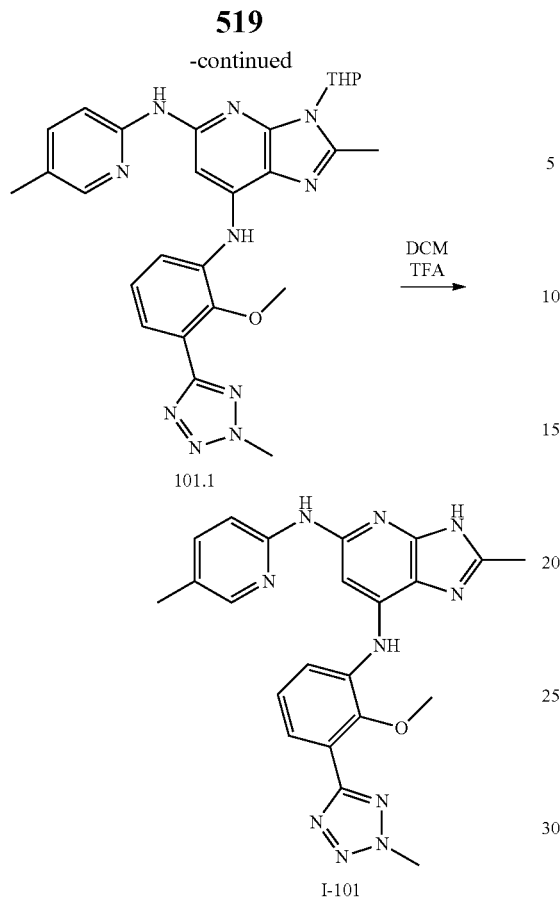

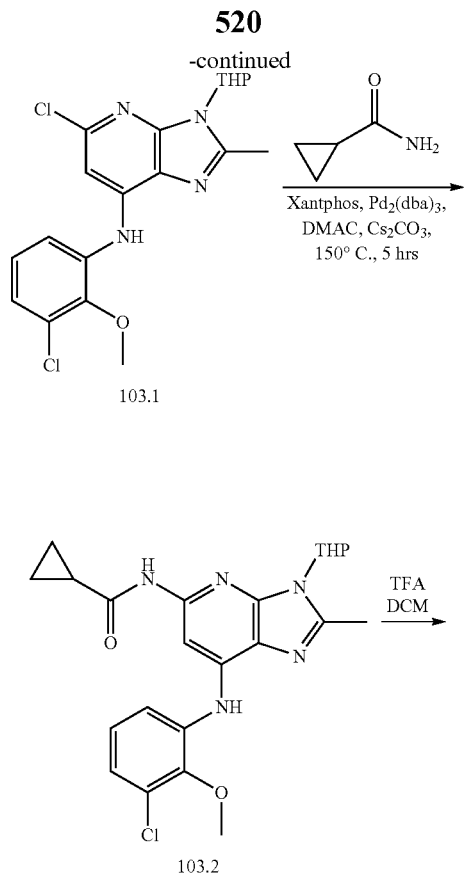

Synthesis of Compound 101.1.

Compound 101.1 was synthesized from 5-methylpyridin-2-amine and 98.5 using general procedure B. (Yield: 60.47%). MS(ES): m/z 527.61 [M+H]⁺.

Synthesis of I-101.

Compound I-101 was synthesized from 101.1 using general procedure C. (Yield: 44.20%). MS(ES): m/z 443.68 [M+H]⁺, LCMS purity: 96.63%, HPLC purity: 100.00%, 1H NMR (DMSO, 400 MHz): 9.65 (s, 1H). 8.18 (s, 1H), 7.95-7.95 (d, J=8 Hz, 1H), 7.88-7.85 (d, J=8.8 Hz, 1H), 7.64-7.63 (d, J=6.8 Hz, 1H), 7.46-7.42 (t, J=8.4 Hz, 1H), 7.24-7.22 (d, J=8.4 Hz, 1H) 7.13-7.11 (m, 1H) 4.47 (s, 3H), 3.74 (s, 3H), 3.57 (s, 1H), 2.69 (s, 3H), 2.334 (s, 3H).

Example 103: Synthesis of N-(7-((3-chloro-2-methoxyphenyl)amino)-2-methyl-3H-imidazo[4,5-b]pyridin-5-yl)cyclopropanecarboxamide, I-103

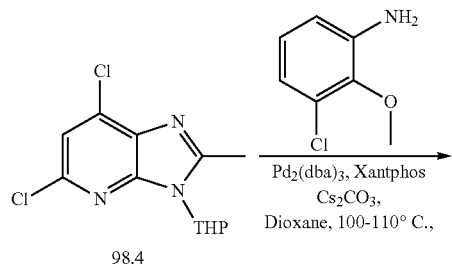

Synthesis of Compound 103.1.

Compound 103.1 was synthesized from 3-chloro-2-methoxyaniline and 98.4 using general procedure A. (Yield: 21.08%). MS(ES): m/z 408.89 [M+H]⁺.

Synthesis of Compound 103.2.

Compound 103.2 was synthesized from 103.1 and cyclopropanecarboxamide using general procedure B. (Yield: 67.49%). MS(ES): m/z 456.25 [M+H]⁺.

Synthesis of I-103.

Compound I-103 was synthesized from 103.2 using general procedure C. (Yield: 46.89%). MS(ES): m/z 372.32 [M+H]⁺, LCMS purity: 100.00%, HPLC purity 98.56%, 1H NMR (DMSO, 400 MHz): 12.36 (s, 1H), 10.45 (s, 1H), 7.99 (s, 1H), 7.67 (s, 1H), 7.37-7.35 (d, J=6.8 Hz, 1H), 7.21-7.13 (m, 2H), 3.74 (s, 3H), 2.47 (s, 3H), 1.99-1.97 (d, J=8.4 Hz, 1H), 0.75-0.73 (d, J=6.4 Hz, 4H).

Example 104: Synthesis of N-(7-((3-fluoro-2-methoxyphenyl)amino)-2-methyl-3H-imidazo[4,5-b]pyridin-5-yl)cyclopropanecarboxamide, I-104

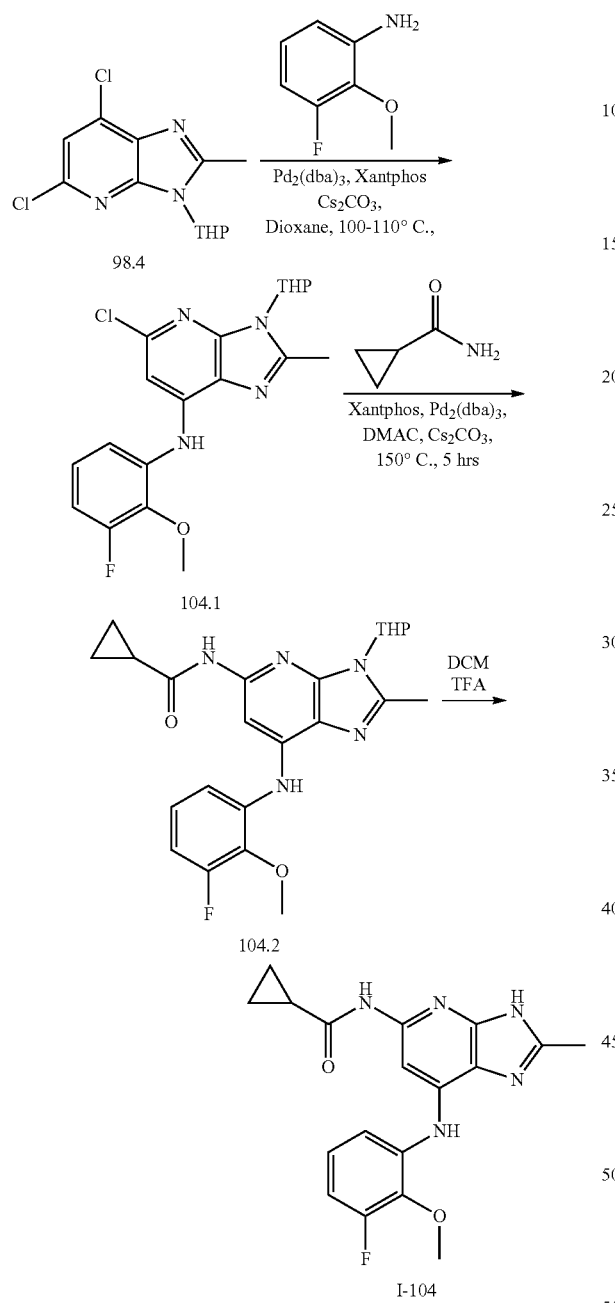

Synthesis of Compound 104.1.
Compound 104.1 was synthesized from 3-fluoro-2-methoxyaniline and 98.4 using general procedure A. (Yield: 23.43%). MS(ES): m/z 391.84 [M+H]⁺.

Synthesis of Compound 104.2.
Compound 104.2 was synthesized from 104.1 and cyclopropanecarboxamide using general procedure B. (Yield: 47.24%). MS(ES): m/z 440.49 [M+H]⁺.

Synthesis of I-104.
Compound I-104 was synthesized from 104.2 using general procedure C. (Yield: 58.20032593 MS(ES): m/z 356.36 [M+H]⁺, LCMS purity: 99.83%, HPLC purity: 98.65%, 1H NMR (DMSO-d6, 400 MHz): 12.34 (s, 1H) 10.53-10.53 (s, 1H), 7.93 (s, 1H), 7.67 (s, 1H), 7.22-7.20 (d, J=8 Hz, 1H), 7.15-7.06 (q, J=8.4 Hz, 1H), 6.99-6.93 (m, 1H), 3.82 (s, 3H), 2.48 (s, 3H), 1.95-1.94 (m, 1H), 0.73-0.71 (m, 4H).

Example 105: Synthesis of N-(7-((3-cyano-2-methoxyphenyl)amino)-2-methyl-3H-imidazo[4,5-b]pyridin-5-yl)cyclopropanecarboxamide, I-105

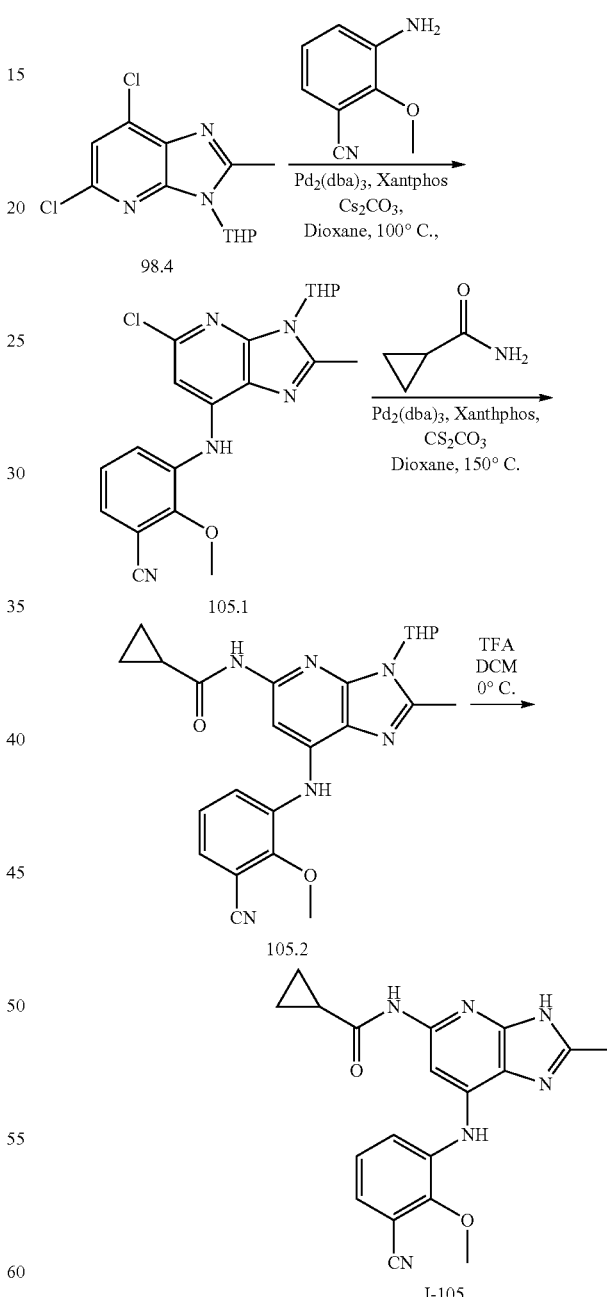

Synthesis of Compound 105.1.
Compound 105.1 was synthesized from 3-amino-2-methoxybenzonitrile and 98.4 using general procedure A. (Yield: 21.58%). MS (ES): m/z 398.86 [M+H]⁺.

523

Synthesis of Compound 105.2.

Compound 105.2 was synthesized from 105.1 and cyclopropanecarboxamide using general procedure B. (Yield: 81.66%). MS (ES): m/z 447.51 [M+H]⁺.

Synthesis of compound I-105. Compound I-105 was synthesized from 105.2 using general procedure C. (Yield: 56.01%). MS(ES): m/z 363.28 [M+H]⁺, LCMS purity: 97.78%, HPLC purity: 97.09%, 1H NMR (DMSO, 400 MHz): 10.40 (s, 1H), 8.27 (s, 1H), 7.62-7.60 (d, J=7.2 Hz, 1H), 7.56-7.41 (m, 2H), 7.27-7.23 (t, J=8 Hz, 1H), 3.88 (s, 3H), 2.44 (s, 3H), 1.97-1.93 (m, 1H), 0.72 (s, 4H).

Example 106: Synthesis of N-(7-((2-methoxyphenyl)amino)-2-methyl-3H-imidazo[4,5-b]pyridin-5-yl)cyclopropanecarboxamide, I-106

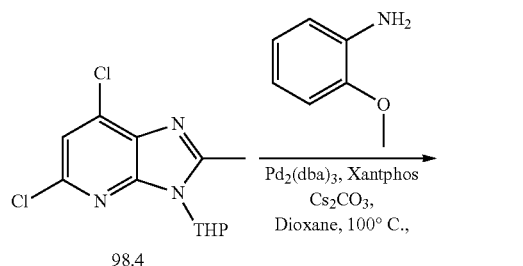

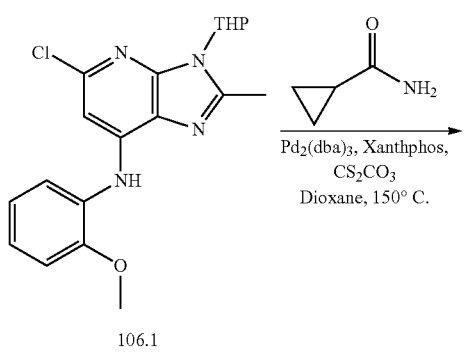

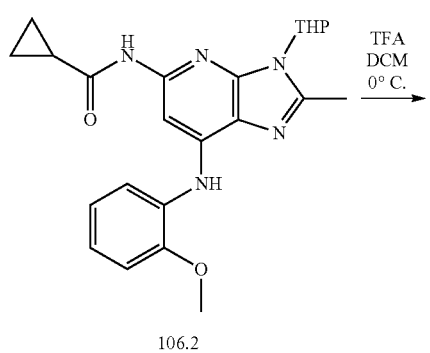

524

-continued

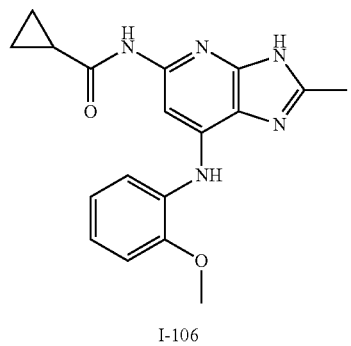

I-106

Synthesis of Compound 106.1.

Compound 106.1 was synthesized from 2-methoxyaniline and 98.4 using general procedure A. (Yield: 22.06%). MS (ES): m/z 373.85 [M+H]⁺.

Synthesis of Compound 106.2.

Compound 106.2 was synthesized from 106.1 and cyclopropanecarboxamide using general procedure B. (Yield: 56.92%). MS (ES): m/z 422.50 [M+H]⁺.

Synthesis of compound I-106. Compound I-106 was synthesized from 106.2 using general procedure C. (Yield: 43.90%). MS(ES): m/z 338.28 [M+H]⁺, LCMS purity: 99.35%, HPLC purity: 99.21%, 1H NMR (DMSO, 400 MHz): 13.25 (s, 1H), 10.53 (s, 1H), 7.96 (s, 1H), 7.66 (s, 1H), 7.38-7.36 (d, J=7.6 Hz, 1H), 7.11-7.12 (d, J=3.2 Hz, 2H), 6.99-6.97 (m, 1H), 3.82 (s, 3H), 2.53 (s, 3H), 1.94 (s, 1H), 0.74 (s, 4H).

Example 107: Synthesis of N-(7-((2-methoxy-3-(1-methyl-1H-pyrazol-4-yl)phenyl)amino)-2-methyl-3H-imidazo[4,5-b]pyridin-5-yl)cyclopropanecarboxamide, I-107

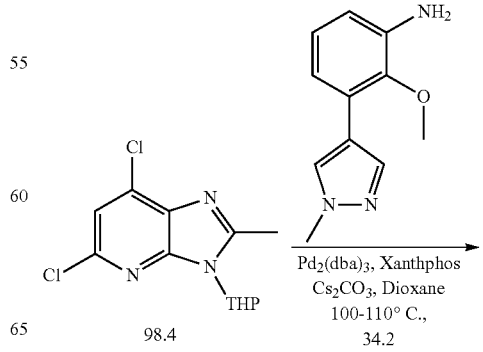

-continued

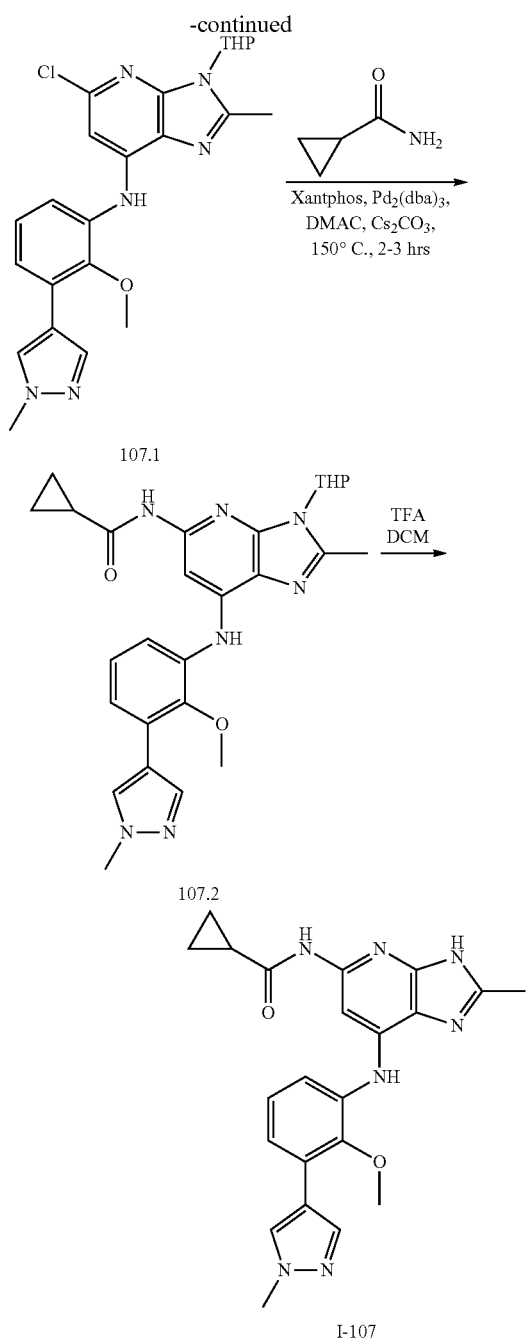

Synthesis of Compound 107.1

Compound 107.1 was synthesized from 98.4 and 34.2 using general procedure A. (Yield: 14.37%). MS(ES): m/z 453.62 [M+H]⁺.

Synthesis of Compound 107.2.

Compound 107.2 was synthesized from 107.1 and cyclopropanecarboxamide using general procedure B. (Yield: 60.20%). MS(ES): m/z 502.72 [M+H]⁺.

Synthesis of I-107.

Compound I-107 was synthesized from 107.2 using general procedure C. (Yield: 64.08%). MS(ES): m/z 418.44 [M+H]⁺, LCMS purity 96.42% HPLC purity 99.75%, 1H NMR (DMSO, 400 MHz): 12.33 (s, 1H), 10.41 (s, 1H), 8.14 (s, 1H), 7.89 (s, 1H), 7.85 (s, 1H), 7.70 (s, 1H), 7.32-7.31 (d, J=7.6 Hz, 1H), 7.26-7.24 (d, J=7.6 Hz, 1H), 7.14-7.10 (t, 1H), 3.88 (s, 3H), 3.56 (s, 3H), 3.32 (s, 3H), 1.97-1.89 (m, 1H), 0.72 (bs, 4H).

Example 108: Synthesis of (6-((7-((2-methoxy-3-(2-methyl-2H-tetrazol-5-yl)phenyl)amino)-2-methyl-3H-imidazo[4,5-b]pyridin-5-yl)amino)-2-(trifluoromethyl)pyridin-3-yl)(pyrrolidin-1-yl)methanone, I-108

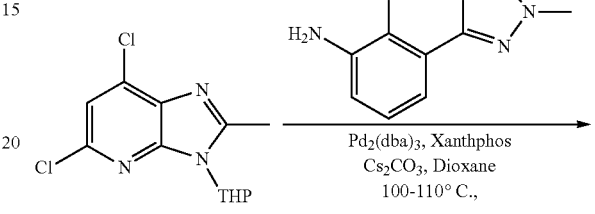

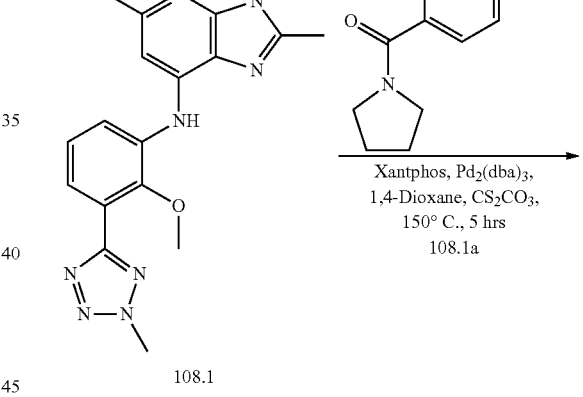

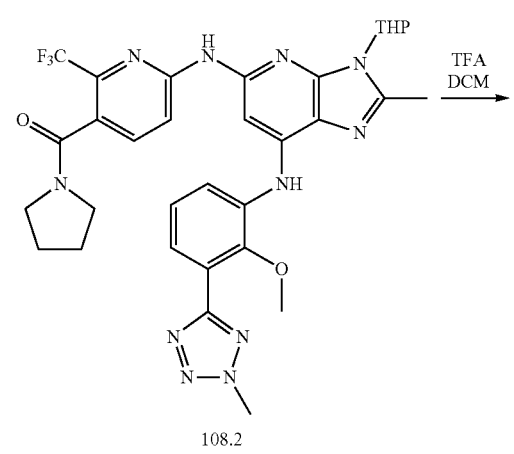

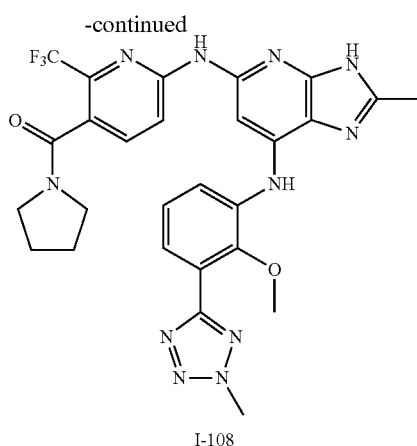

I-108

Synthesis of Compound 108.1.

Compound 108.1 was synthesized from 98.4 and 2-methoxy-3-(2-methyl-2H-tetrazol-5-yl)aniline using general procedure A. (Yield: 37.59%). MS(ES): m/z 455.62 [M+H]⁺.

Synthesis of Compound 108.2.

Compound 108.2 was synthesized from 108.1 and 108.1a (prepared from the corresponding carboxylic acid and pyrrolidine) using general procedure B. (Yield: 32.22%). MS(ES): m/z 678.81 [M+H]⁺.

Synthesis of I-108.

Compound I-108 was synthesized from 108.2 using general procedure C. (Yield: 85.63%). MS(ES): m/z 594.52 [M+H]⁺, LCMS purity 94.54% HPLC purity 94.49%, 1H NMR (DMSO, 400 MHz): 12.45 (s, 1H), 9.99 (s, 1H), 8.20-8.18 (d, J=8.8 Hz, 1H), 7.98 (s, 1H), 7.79-7.77 (d, J=8.8 Hz, 1H), 7.69-7.67 (d, J=7.6 Hz, 1H), 7.61-7.59 (d, J=7.2 Hz, 2H), 7.31-7.20 (m, 2H), 4.45 (s, 3H), 3.72 (s, 3H), 3.44-3.40 (t, J=6 Hz, 2H), 3.32 (s, 3H), 3.11-3.08 (t, J=6.4 Hz, 2H), 1.89-1.78 (m, 4H).

Example 109: Synthesis of 6-((7-((2-methoxy-3-(2-methyl-2H-tetrazol-5-yl)phenyl)amino)-2-methyl-3H-imidazo[4,5-b]pyridin-5-yl)amino)-3-(2-oxopyrrolidin-1-yl)picolinonitrile, I-109

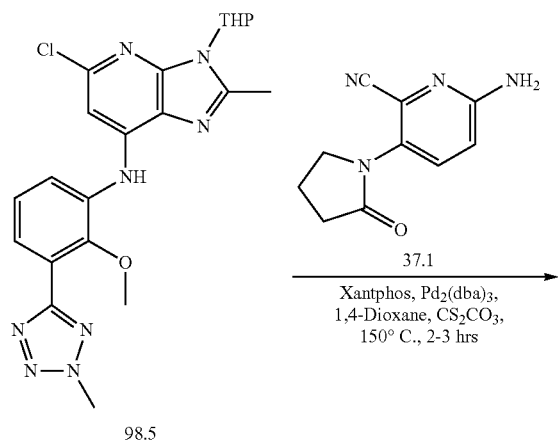

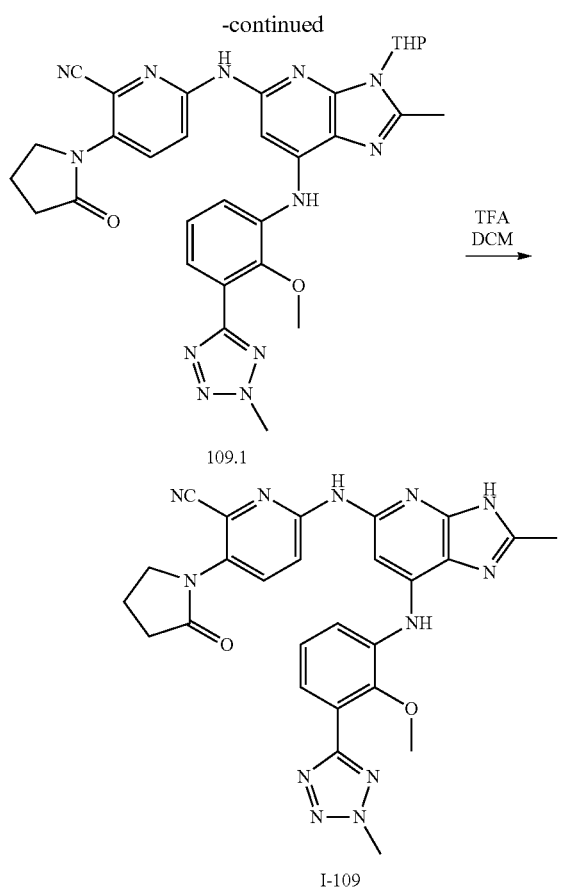

I-109

Synthesis of Compound 109.1.

Compound 109.1 was synthesized from 98.5 and 37.1 using general procedure B. (Yield: 43.98%). MS(ES): m/z 621.57 [M+H]⁺.

Synthesis of I-109.

Compound I-109 was synthesized from 109.1 using general procedure C. (Yield: 89.97%). MS(ES): m/z 537.50 [M+H]⁺, LCMS purity 99.64% HPLC purity: 99.16%, 1H NMR (DMSO, 400 MHz): 12.86 (s, 1H). 10.07 (s, 1H). 8.17-8.11 (m, 2H). 7.85-7.82 (d, J=9.2 Hz. 1H). 7.73-7.71 (d, J=8 Hz, 1H), 7.62-7.60 (d, J=7.6 Hz, 1H), 7.39-7.35 (t, J=8 Hz, 1H), 7.23 (s, 1H), 4.45 (s, 3H), 3.81-3.78 (t, J=6.8 Hz, 2H), 3.39-3.34 (m, 2H), 3.72 (s, 3H), 2.48 (s, 3H), 2.17-2.07 (m, 2H).

Example 110: Synthesis of N-(7-((2-methoxy-4-(pyrrolidine-1-carbonyl)phenyl)amino)-2-methyl-3H-imidazo[4,5-b]pyridin-5-yl)cyclopropanecarboxamide, I-110

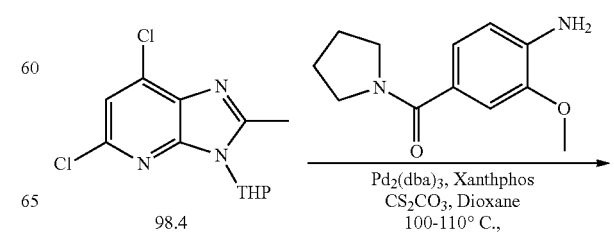

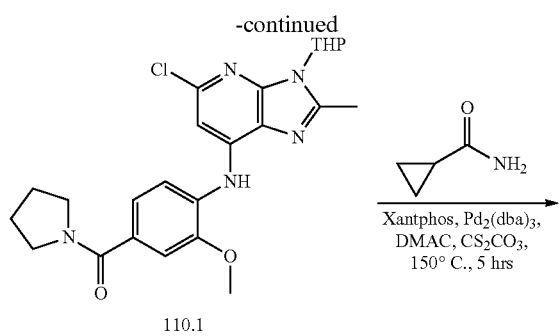

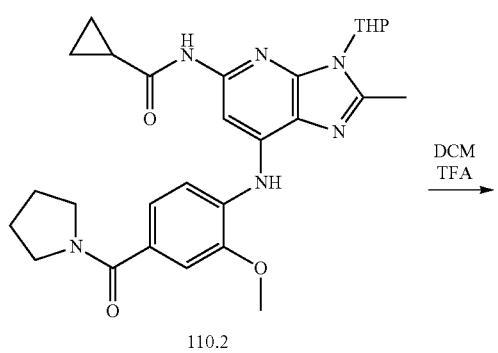

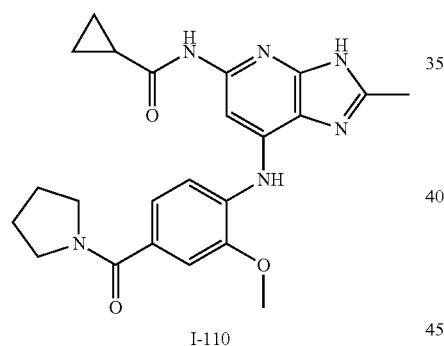

Example 111: Synthesis of 6-((7-((2-methoxy-3-(2-methyl-2H-tetrazol-5-yl)phenyl)amino)-2-methyl-3H-imidazo[4,5-b]pyridin-5-yl)amino)-3-methylpyrazine-2-carbonitrile, I-111

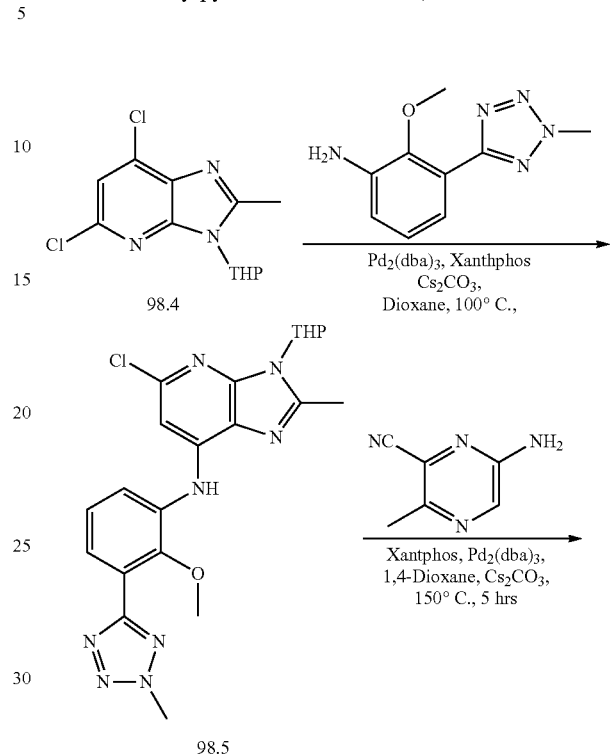

Synthesis of Compound 110.1.

Compound 110.1 was synthesized from 98.4 and (4-amino-3-methoxyphenyl)(pyrrolidin-1-yl)methanone using general procedure A. (Yield: 30.44%). MS(ES): m/z 470.53 [M+H]$^+$.

Synthesis of Compound 110.2.

Compound 110.2 was synthesized from 110.1 and cyclopropanecarboxamide using general procedure B. (Yield: 60.41%). MS(ES): m/z 519.64 [M+H]$^+$.

Synthesis of I-110.

Compound I-110 was synthesized from 110.2 using general procedure C. (Yield: 71.62%). MS(ES): m/z 435.37 [M+H]$^+$, LCMS purity 100% HPLC purity 100%, 1H NMR (DMSO, 400 MHz): 12.38 (s, 1H), 10.48 (s, 1H), 7.88 (s, 1H), 7.76 (s, 1H), 7.45-7.44 (d, J=7.2 Hz, 1H) 7.24 (s, 1H), 7.19-7.17 (d, J=8 Hz, 1H), 3.91 (s, 3H), 3.51-3.48 (t, J=6 Hz, 4H), 2.48 (s, 3H), 1.86-1.85 (d, J=4 Hz, 4H), 1.99 (s, 1H), 0.79-0.75 (m, 4H).

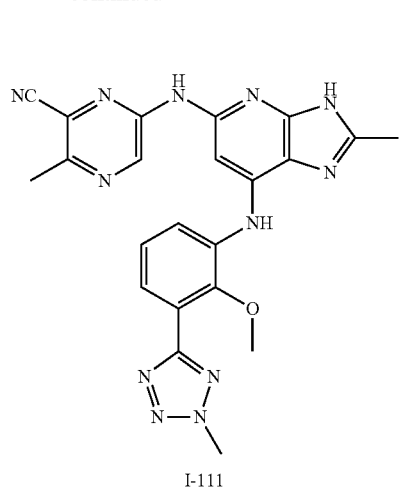

I-111

Synthesis of Compound 111.1.

Compound 111.1 was synthesized from 98.4 and 2-methoxy-3-(2-methyl-2H-tetrazol-5-yl)aniline using general procedure A. (Yield: 32.90%). MS(ES): m/z 455.29 [M+H]+.

Synthesis of Compound 111.2.

Compound 111.2 was synthesized from 6-amino-3-methylpyrazine-2-carbonitrile and 111.1 using general procedure B. (Yield: 41.16%). MS(ES): m/z 553.64 [M+H]+.

Synthesis of I-111. Compound I-111 was synthesized from 111.2 using general procedure C. (Yield: 65.53%). MS(ES): m/z 469.42 [M+H]+, LCMS purity 93.31% HPLC purity 95.22%, 1H NMR (DMSO, 400 MHz): 12.44 (s, 1H), 10.15 (s, 1H), 9.28 (s, 1H), 8.03 (s, 1H), 7.79-7.72 (d, J=7.6 Hz, 1H), 7.65-7.63 (d, J=7.6 Hz, 1H), 7.38 (s, 1H), 7.19 (s, 1H), 4.47 (s, 3H), 3.73 (s, 3H), 2.56 (s, 3H), 2.51 (s, 3H).

Example 112: Synthesis of (S)-6-((7-((2-methoxy-3-(2-methyl-2H-tetrazol-5-yl)phenyl)amino)-2-methyl-3H-imidazo[4,5-b]pyridin-5-yl)amino)-3-(3-methoxypyrrolidin-1-yl)picolinonitrile, I-112

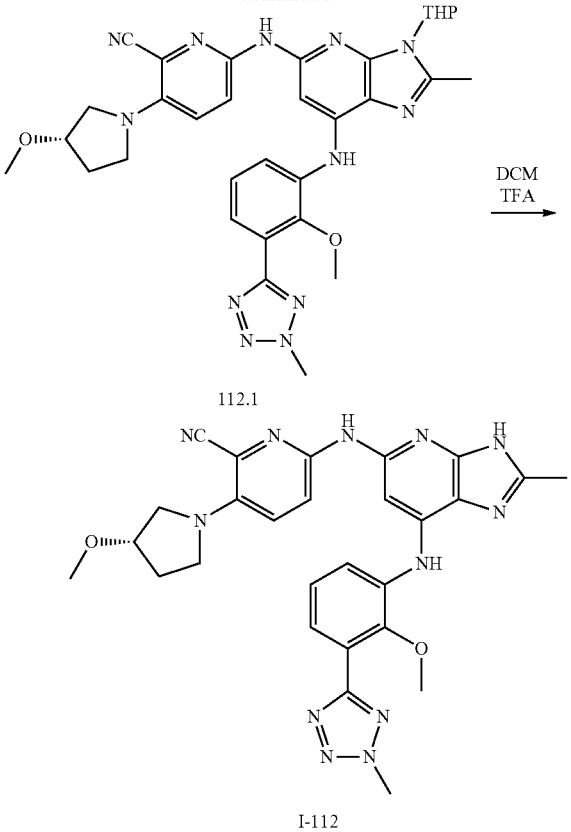

Synthesis of Compound 112.1

Compound 112.1 was Synthesized from 98.5 and 112.1a (prepared from condensation of the corresponding bromopyridine and methoxypyrrolidine) using general procedure. B (Yield: 41.15%). MS(ES): m/z 637.72 [M+H]+.

Synthesis of I-112.

Compound I-112 was synthesized from 112.1 using general procedure C (Yield: 80.02%). MS(ES): m/z 553.55 [M+H]+, LCMS purity: 99.67% HPLC purity: 99.02%, 1H NMR (DMSO, 400 MHz): 12.30 (s, 1H), 9.39 (s, 1H), 7.89-7.79 (m, 3H), 7.58-7.56 (d, J=8 Hz, 1H), 7.42-7.33 (m, 3H), 4.47 (s, 3H), 4.09 (s, 1H), 3.76 (s, 3H), 3.57-3.46 (m, 3H), 3.28 (s, 3H), 2.46 (s, 4H), 2.08-1.99 (s, 2H).

Example 113: Synthesis of 3-(azetidin-1-yl)-6-((7-((2-methoxy-3-(2-methyl-2H-tetrazol-5-yl)phenyl)amino)-2-methyl-3H-imidazo[4,5-b]pyridin-5-yl)amino)picolinonitrile, I-113

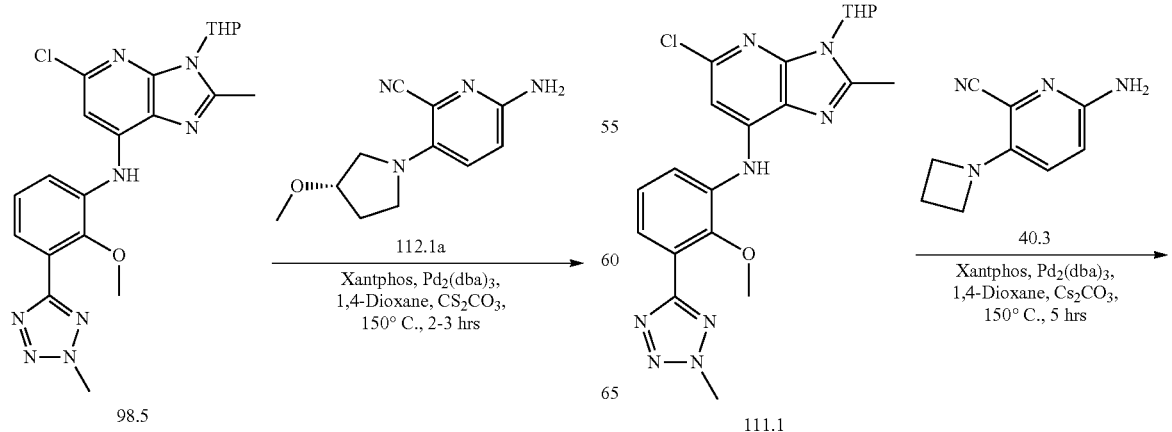

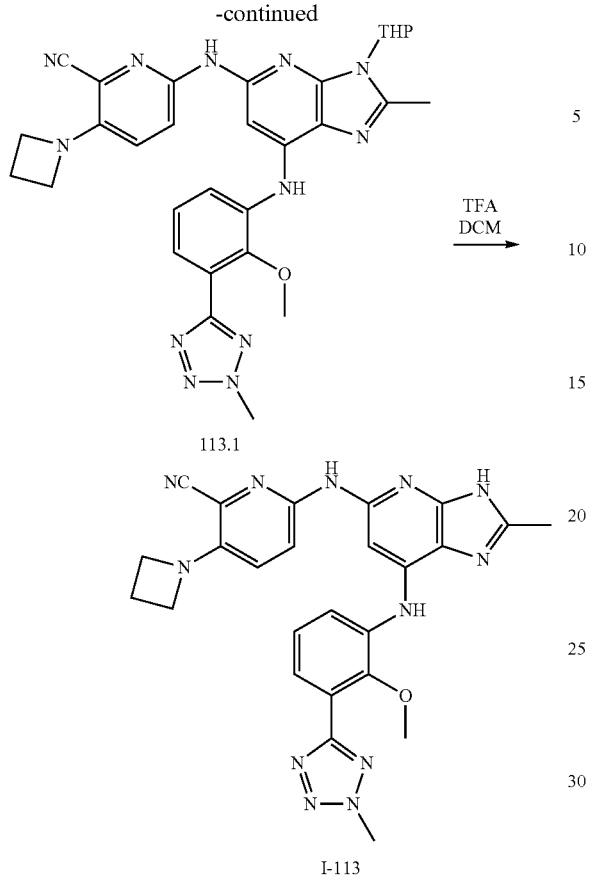

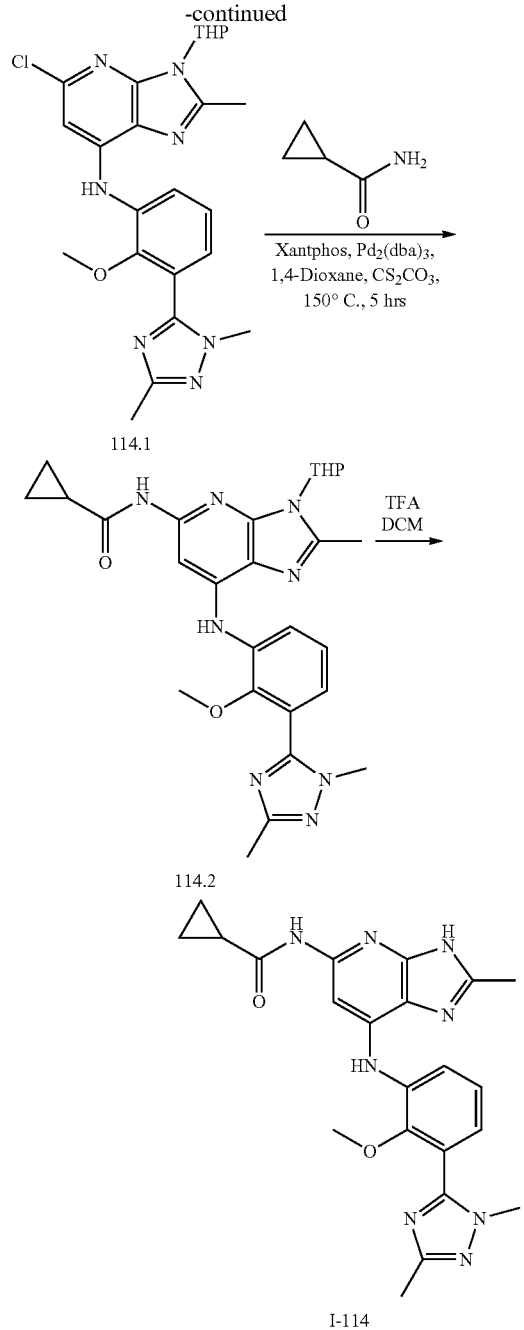

Synthesis of Compound 113.1.

Compound was synthesized from 111.1 and 40.3 using general procedure B. (Yield: 53.93%). MS(ES): m/z 593.42 [M+H]+.

Synthesis of I-113.

Compound I-113 was synthesized from 113.1 using general procedure C. (Yield: 48.22%). MS(ES): m/z 509.48 [M+H]+, LCMS purity, 99.37%, HPLC purity: 97.42%, 1H NMR (DMSO, 400 MHz): 7.76-7.74 (d, J=7.6 Hz 1H), 7.69-7.67 (d, J=7.6 Hz 1H), 7.49 (m, 1H), 7.46-7.42 (t, 1H), 7.18-7.15 (d, J=7.6 Hz 1H), 6.90 (s, 1H), 4.45 (s, 3H), 4.11-4.07 (t, J=7.2 Hz 3H), 3.71 (s, 3H), 2.671 (s, 4H), 2.36-2.32 (t, J=8 Hz 2H).

Example 114: Synthesis of N-(7-((3-(1,3-dimethyl-1H-1,2,4-triazol-5-yl)-2-methoxyphenyl)amino)-2-methyl-3H-imidazo[4,5-b]pyridin-5-yl)cyclopropanecarboxamide, I-114

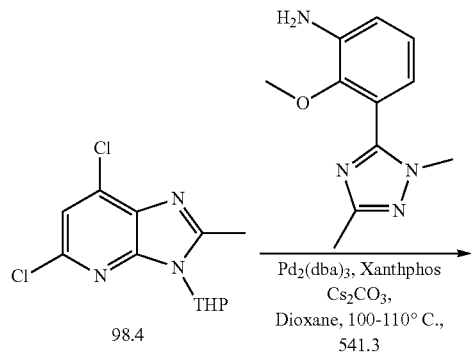

Synthesis of Compound 114.1.

Compound 114.1 was synthesized from 98.4 and 541.3 using general procedure A. (Yield: 37.31%). MS(ES): m/z 468.51 [M+H]+.

Synthesis of Compound 114.2.

Compound 114.1 was synthesized from 114.1 and cyclopropanecaboxamide using general procedure B. (Yield: 86.05%). MS(ES): m/z 517.42 [M+H]+.

Synthesis of I-114.

Compound I-114 was synthesized from 114.2 using general procedure C. (Yield: 88.02%). MS(ES): m/z 433.34 [M+H]+, LCMS purity, 99.18%, HPLC purity: 98.32%, 1H NMR (DMSO, 400 MHz): 10.43 (s, 1H), 8.239 (s, 1H), 7.56-7.54 (d, J=7.6 Hz 3H), 7.30-7.19 (m, 2H), 3.67 (s, 3H), 3.35 (s, 6H), 2.34 (s, 3H), 2.00-1.92 (m, 1H), 0.68-0.64 (m, 4H).

Example 115: Synthesis of 3-isopropyl-6-((7-((2-methoxy-3-(2-methyl-2H-tetrazol-5-yl)phenyl)amino)-2-methyl-3H-imidazo[4,5-b]pyridin-5-yl)amino)picolinonitrile, I-115

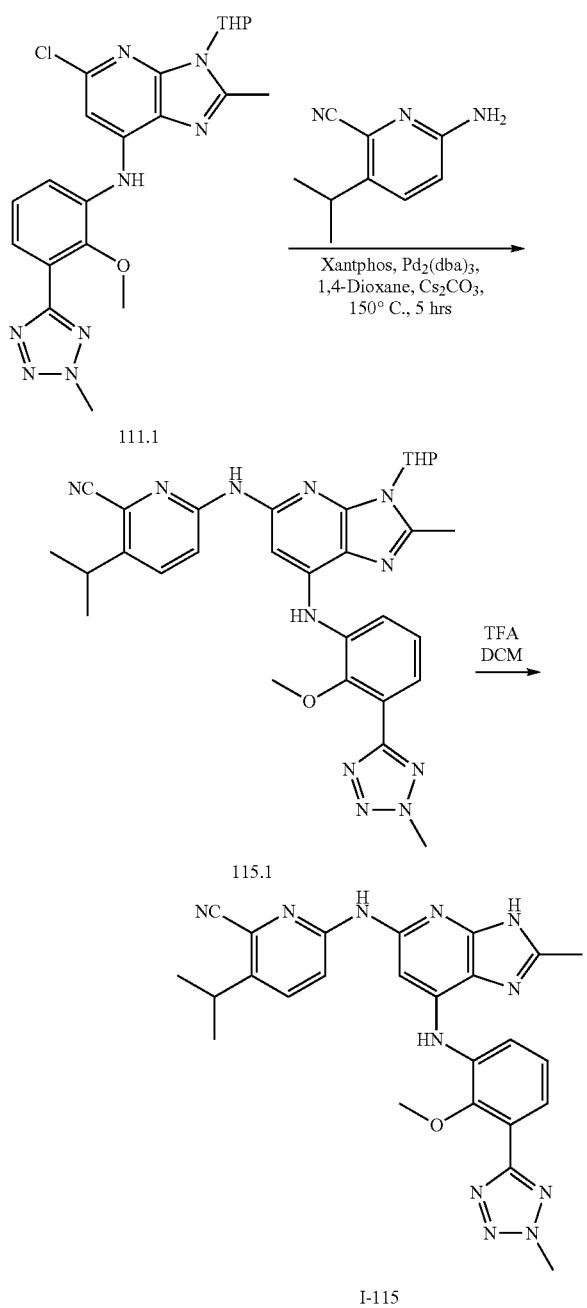

Synthesis of Compound 115.1.

Compound 115.1 was synthesized from 6-amino-3-isopropylpicolinonitrile and 111.1 using general procedure B. (Yield: 43.16%). MS(ES): m/z 580.46 [M+H]$^+$.

Synthesis of I-115.

Compound I-115 was synthesized from 115.1 using general procedure C. (Yield: 74.44%). MS(ES): m/z 496.46 [M+H]$^+$, LCMS purity: 97.94%, HPLC purity: 98.18%, 1H NMR (DMSO, 400 MHz): 12.41 (s, 1H), 9.81 (s, 1H), 8.07-8.04 (s, J=8.8 Hz 1H), 7.95 (s, 1H), 7.85-7.76 (m, 2H), 7.61-7.59 (d, J=7.6 Hz 1H), 7.42-7.34 (m, 2H), 4.47 (s, 3H), 3.34 (m, 1H), 3.75 (s, 3H), 3.18 (s, 3H), 1.25 (s, 6H).

Example 116: Synthesis of 6-((7-((2-methoxy-3-(2-methyl-2H-tetrazol-5-yl)phenyl)amino)-2-methyl-3H-imidazo[4,5-b]pyridin-5-yl)amino)-3-morpholinopyrazine-2-carbonitrile, I-116

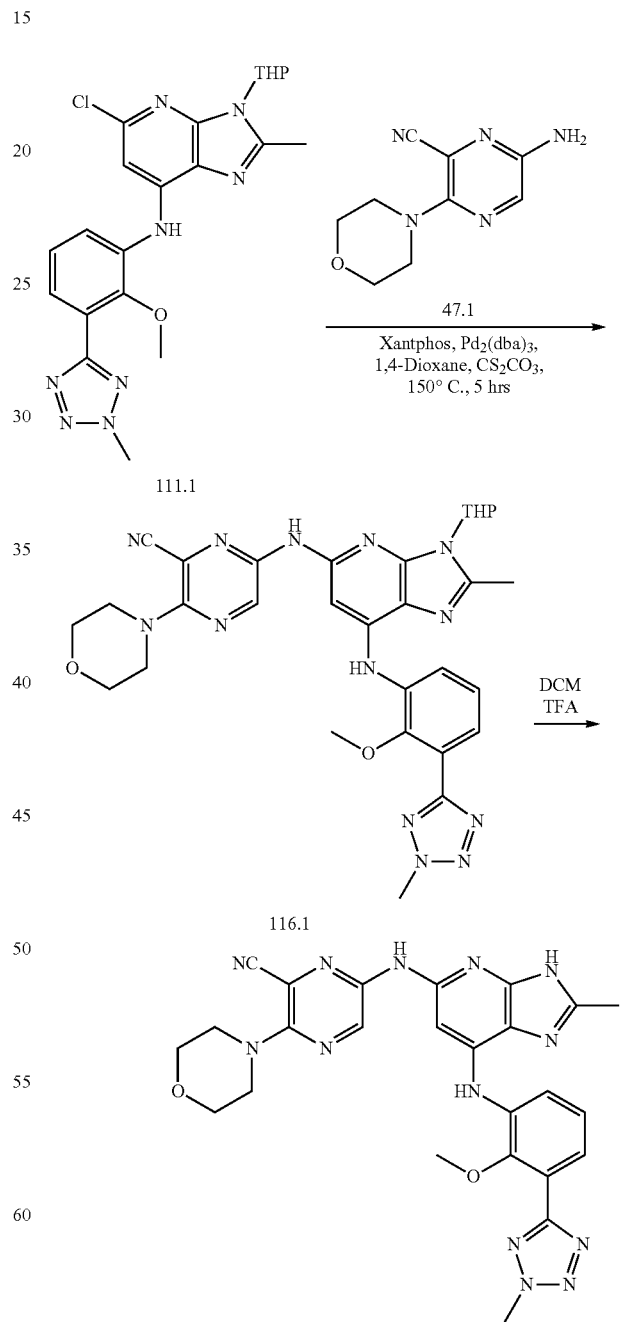

Synthesis of Compound 116.1.

Compound 116.1 was synthesized by 111.1 and 47.1 using general procedure. B (Yield: 47.41%). MS(ES): m/z 624.68 [M+H]⁺.

Synthesis of I-116.

Compound I-116 was synthesized from 116.1 using general procedure C. (Yield: 80.02%). MS(ES): m/z 540.50 [M+H]⁺, LCMS purity: 98.06%, HPLC purity: 97.35%, 1H NMR (DMSO, 400 MHz): 9.86 (s, 1H), 9.17 (s, 1H), 7.98 (s, 1H), 7.73-7.72 (s, J=6.8 Hz, 1H), 7.64-7.62 (d, J=8 Hz, 1H), 7.40-7.36 (t, J=8 Hz, 2H), 7.03 (s, 1H), 4.48 (s, 3H), 3.77 (s, 7H), 3.46 (s, 4H), 2.48 (s, 3H).

Example 117: Synthesis of (R)-6-((7-((2-methoxy-3-(2-methyl-2H-tetrazol-5-yl)phenyl)amino)-2-methyl-3H-imidazo[4,5-b]pyridin-5-yl)amino)-3-(3-methoxypyrrolidin-1-yl)pyrazine-2-carbonitrile, I-117

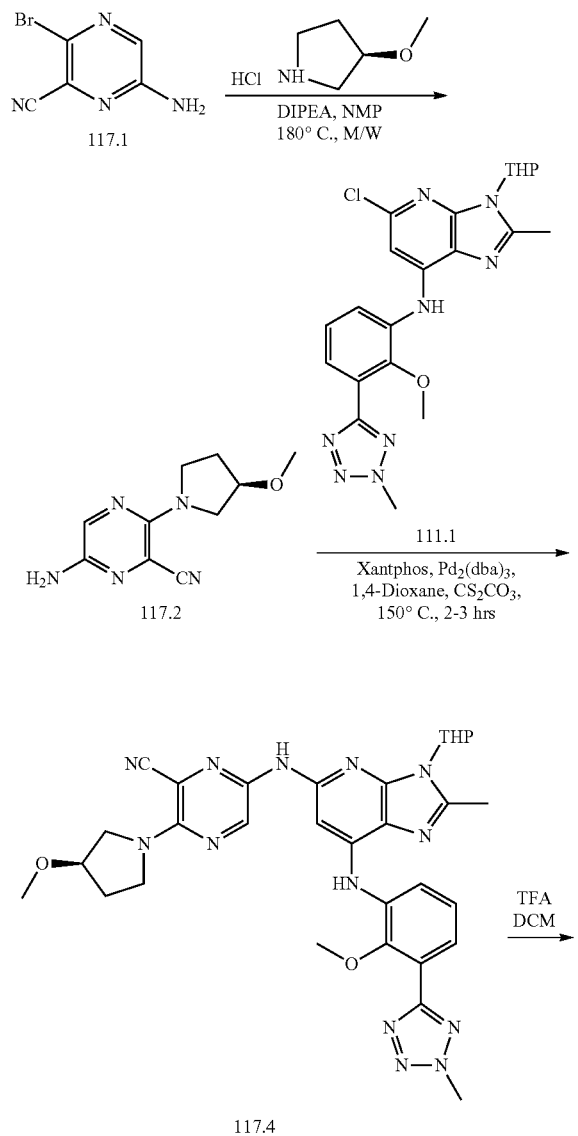

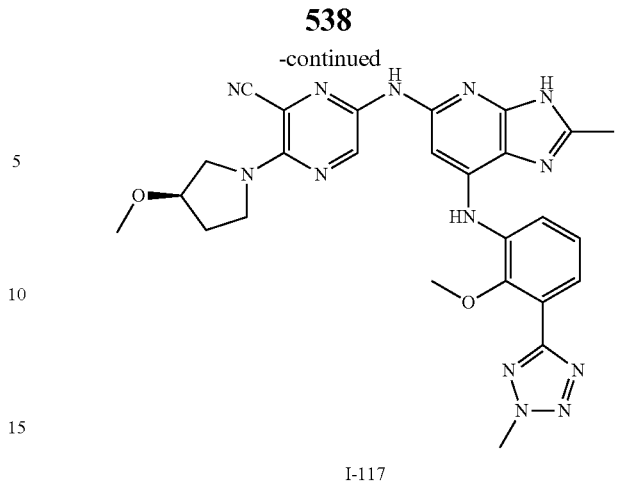

I-117

Synthesis of Compound 117.2.

To compound of 117.1 (0.5 g, 2.5 mmol, 1.0 eq) in N-methyl pyrrolidine (1 mL) compound (R)-3-methoxypyrrolidine hydrochloride 1.1 (0.41 g, 3.0 mmol, 1.2 eq) was added followed by addition of di-isopropylethylamine (1.0 mL, 6.2 mmol, 2.5 eq) dropwise at 0° C. Reaction mixture was stirred at 180° C. 2 h in microwave. Upon completion, reaction mixture was transferred into cold water extracted with ethyl acetate. Organic layer combined, dried over $Na_2SO_4$ and concentrated in vacuo to obtain crude product. This was purified by column chromatography using 30% ethyl acetate in hexane as eluant to obtain pure 117.2 (0.140 g, 25.42%). MS(ES): m/z 220.25 [M+H]⁺.

Synthesis of Compound 117.3.

Compound 117.3 was synthesized as per experimental protocol of I-111.

Synthesis of Compound 117.4.

Compound 117.4 was synthesized from 117.2 and 117.3 using general procedure. B (Yield: 45.37%). MS(ES): m/z 638.71 [M+H]⁺.

Synthesis of I-117.

Compound I-117 was synthesized from 117.4 using general procedure C. (Yield: 70.89%). MS(ES): m/z 554.45 [M+H]⁺, LCMS purity: 97.24%, HPLC purity: 97.40%, 1H NMR (DMSO, 400 MHz): 12.35 (s, 1H), 9.57 (s, 1H), 9.06 (s, 1H), 7.94 (s, 1H), 7.72-7.70 (d, J=8 Hz 1H), 7.61-7.59 (d, J=8 Hz 1H), 7.39-7.35 (t, 1H), 7.00 (s, 1H), 4.47 (s, 3H), 4.09 (bs, 1H), 3.68-3.61 (m, 2H), 3.31 (s, 4H), 3.28 (s, 3H), 2.46 (s, 2H), 2.09-2.02 (m, 2H), 1.29-1.23 (m, 1H), 0.88-0.84 (t, 1H).

Example 118: Synthesis of N-methyl-N-(2-((2-methyl-5-((6-methylpyridazin-3-yl)amino)-3H-imidazo[4,5-b]pyridin-7-yl)amino)phenyl)methanesulfonamide, I-118

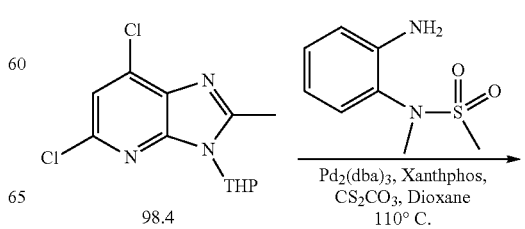

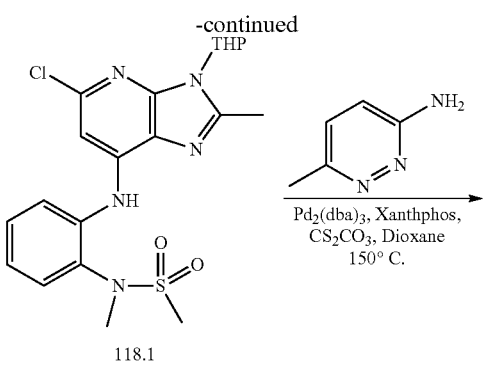

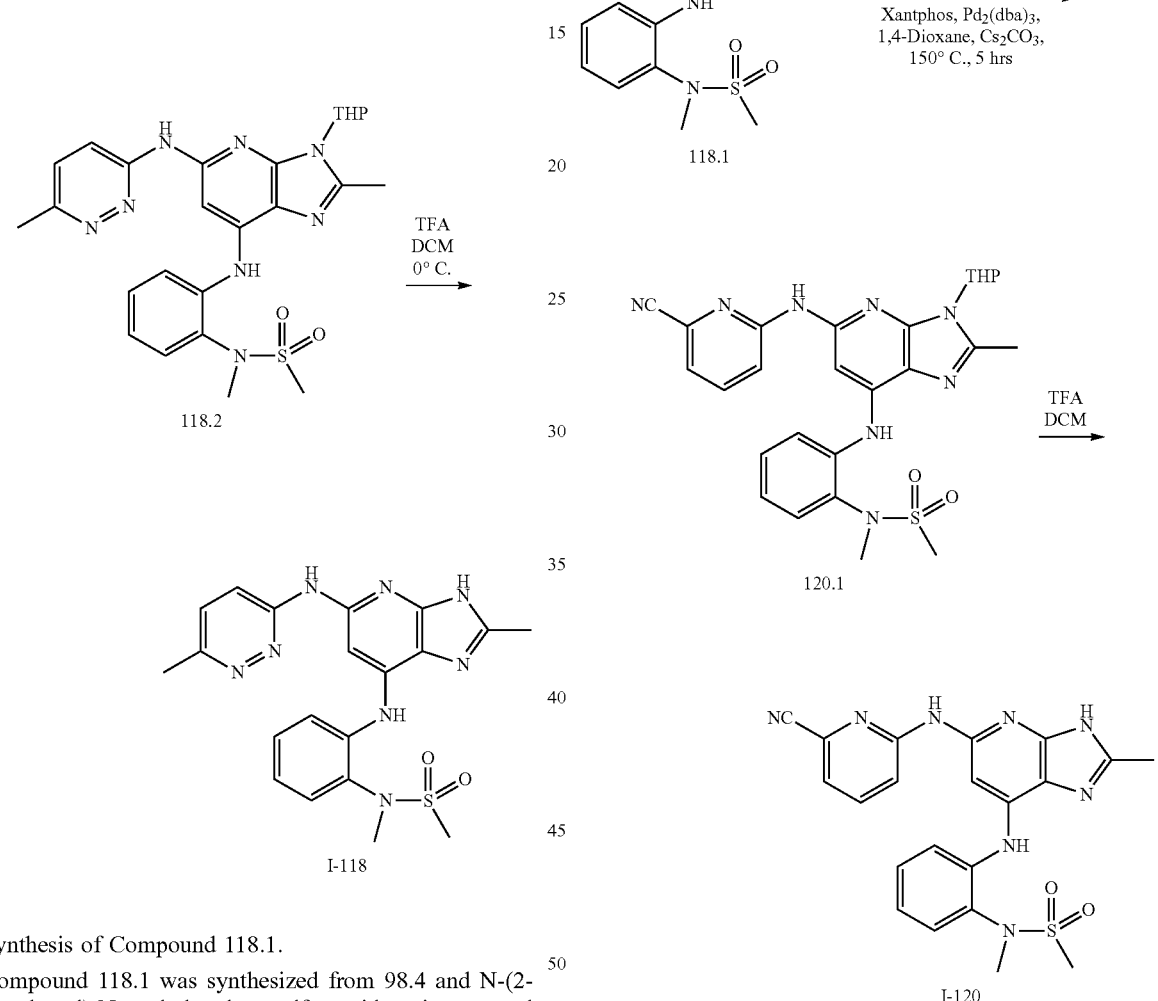

Example 120: Synthesis of N-(2-((5-((6-cyanopyridin-2-yl)amino)-2-methyl-3H-imidazo[4,5-b]pyridin-7-yl)amino)phenyl)-N-methylmethanesulfonamide, I-120

Synthesis of Compound 118.1.

Compound 118.1 was synthesized from 98.4 and N-(2-aminophenyl)-N-methylmethanesulfonamide using general procedure A. (Yield: 50.88%). MS (ES): m/z 450.95 [M+H]$^+$.

Synthesis of Compound 118.2.

Compound 118.2 was synthesized from 6-methylpyridazin-3-amine and 118.1 using general procedure B. (Yield: 11.41%). MS (ES): m/z 523.63 [M+H]$^+$.

Synthesis of Compound I-118.

Compound I-118 was synthesized from 118.2 using general procedure C. (Yield: 78.51%). MS(ES): m/z 439.32 [M+H]$^+$, LCMS purity: 93.91%, HPLC purity: 96.25%, 1H NMR (DMSO, 400 MHz): 9.75 (s, 1H), 8.27-8.25 (d, J=9.2 Hz 1H), 7.86 (s, 1H), 7.71-7.64 (m, 2H), 7.46-7.40 (m, 2H), 7.22-7.18 (t, J=7.2 Hz 1H), 7.14 (s, 1H), 3.30 (s, 3H), 3.22 (s, 3H), 3.13 (s, 3H), 2.45 (s, 3H).

Synthesis of Compound 120.1.

Compound 120.1 was synthesized from 6-aminopicolinonitrile and 118.1 using general procedure B. (Yield: 57.45%). MS(ES): m/z 533.86 [M+H]$^+$.

Synthesis of I-120.

Compound I-120 was synthesized from 120.1 using general procedure C. (Yield: 87.32%). MS(ES): m/z: 449.41 [M+H]$^+$, LCMS purity, 96.00%, HPLC purity: 95.57%, 1H NMR (DMSO, 400 MHz): 9.95 (s, 1H), 8.02-7.99 (d, J=8.8 Hz 1H), 7.93 (s, 1H), 7.85-7.81 (d, J=7.2 Hz 1H), 7.76-7.74 (d, J=8 Hz 1H), 7.67-7.65 (d, J=7.2 Hz 1H), 7.54-7.50 (t, J=7.2 Hz 1H), 7.43-7.42 (d, J=6.8 Hz 2H), 7.23-7.19 (t, J=8 Hz 1H), 3.35 (s, 3H), 3.22 (s, 3H) 3.13 (s, 3H).

Example 121: Synthesis of 6-((7-(2-m ethoxy-3-(2-methyl-2H-tetrazol-5-yl)benzyl)-2-methyl-3H-imidazo[4,5-b]pyridin-5-yl)amino)-3-(2-methoxypropan-2-yl)picolinonitrile, I-121

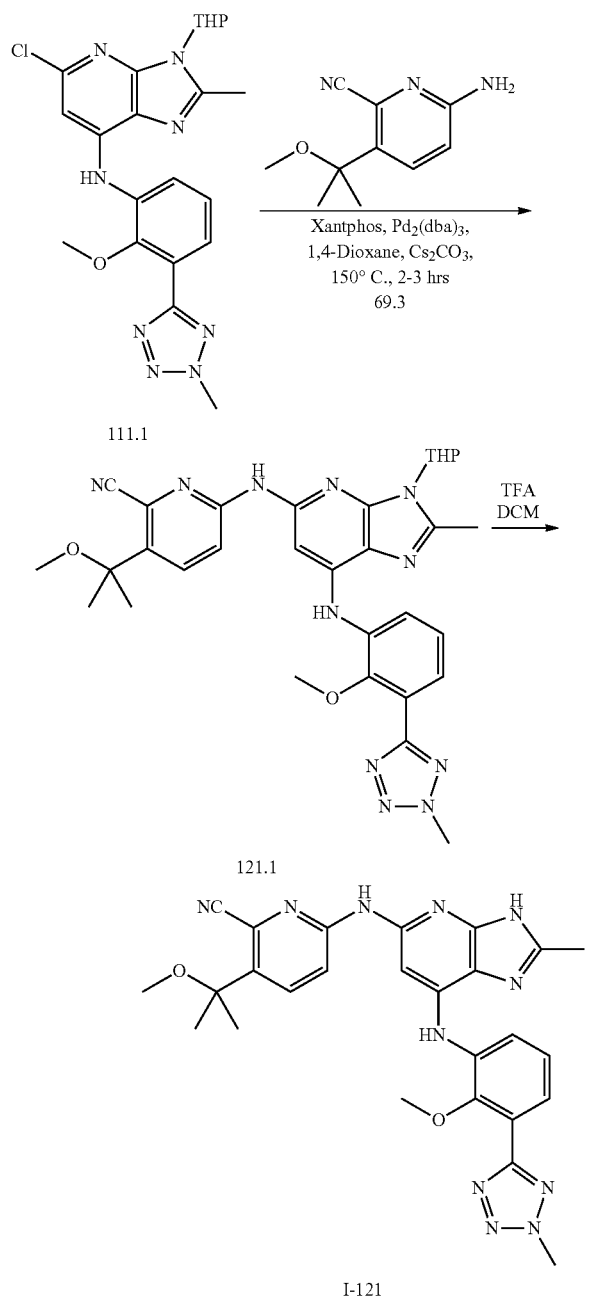

Synthesis of Compound 121.1.

Compound 121.1 was synthesized from 111.1 and 69.3 using general procedure. B (Yield: 26.11%). MS(ES): m/z 610.70 [M+H]⁺.

Synthesis of I-121.

Compound I-121 was synthesized from 121.1 using general procedure C. (yield: 71.08%) MS(ES): m/z: 526.49 [M+H]⁺, LCMS purity: 99.72%, HPLC purity: 97.52%, 1H NMR (DMSO, 400 MHz): 9.93 (s, 1H), 8.04 (s, 1H), 7.81-7.79 (d, J=8.8 Hz 1H), 7.72-7.69 (m, 2H), 7.64-7.62 (d, J=8.8 Hz 1H), 7.58 (s, 1H), 7.37-7.33 (t, J=7.6 Hz 1H), 4.46 (s, 3H), 3.74 (s, 3H), 2.88 (s, 3H), 2.48 (s, 3H) 1.24 (s, 6H).

Example 122: Synthesis of N-(7-((4-(3-methoxyazetidin-1-yl)-2-(N-methylmethylsulfonamido)phenyl)amino)-2-methyl-3H-imidazo[4,5-b]pyridin-5-yl)cyclopropanecarboxamide, I-122

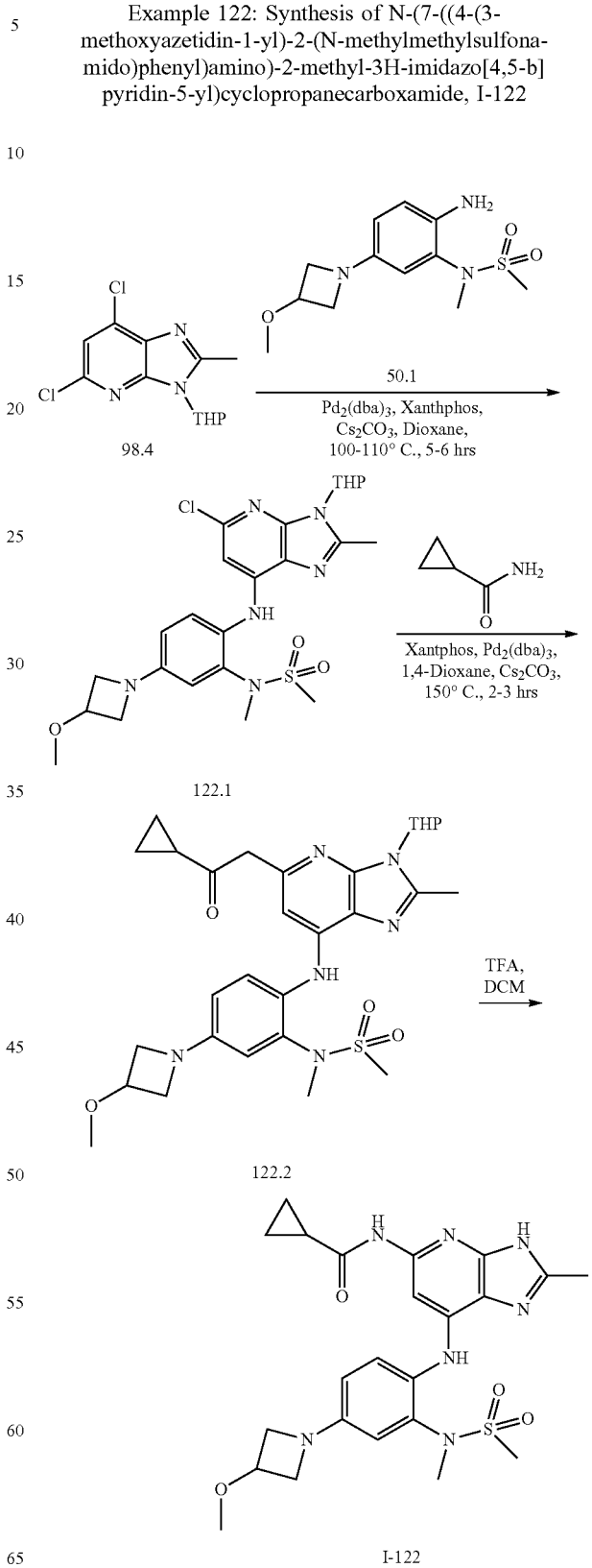

Synthesis of Compound 122.1.

Compound 122.1 was synthesized from 98.4 and 50.1 using general procedure. A (Yield: 35.56%). MS(ES): m/z 536.06 [M+H]+.

Synthesis of compound 122.2 Compound 122.2 was synthesized from 122.1 and cyclopropanecarboxamide using general procedure. B (Yield: 62.44%). MS(ES): m/z 584.71 [M+H]+.

Synthesis of I-122.

Compound I-122 was synthesized from 122.2 using general procedure C. (Yield: 53.17%). MS(ES): m/z: 500.41 [M+H]+, LCMS purity, 97.61%, HPLC purity: 98.53%, 1H NMR (MeOD, 400 MHz): 7.42-7.39 (d, J=8.4 Hz 1H), 7.18 (s, 1H), 7.04 (s, 1H), 6.91 (s, 1H), 6.81 (s, 1H), 6.69 (s, 1H), 6.65-6.62 (m, 1H), 4.41-4.40 (m, 1H), 4.21-4.17 (t, J=7.6 Hz 2H), 3.78-3.75 (m, 2H), 3.39 (s, 3H), 3.23 (s, 3H), 3.01 (s, 3H), 2.64 (s, 3H), 1.81-1.78 (t, J=4.4 Hz 1H), 0.99-0.91 (m, 4H).

Example 123: Synthesis of N-(2-((5-((5,6-dimethylpyrazin-2-yl)amino)-2-methyl-3H-imidazo[4,5-b]pyridin-7-yl)amino)phenyl)-N-methylmethanesulfonamide, I-123

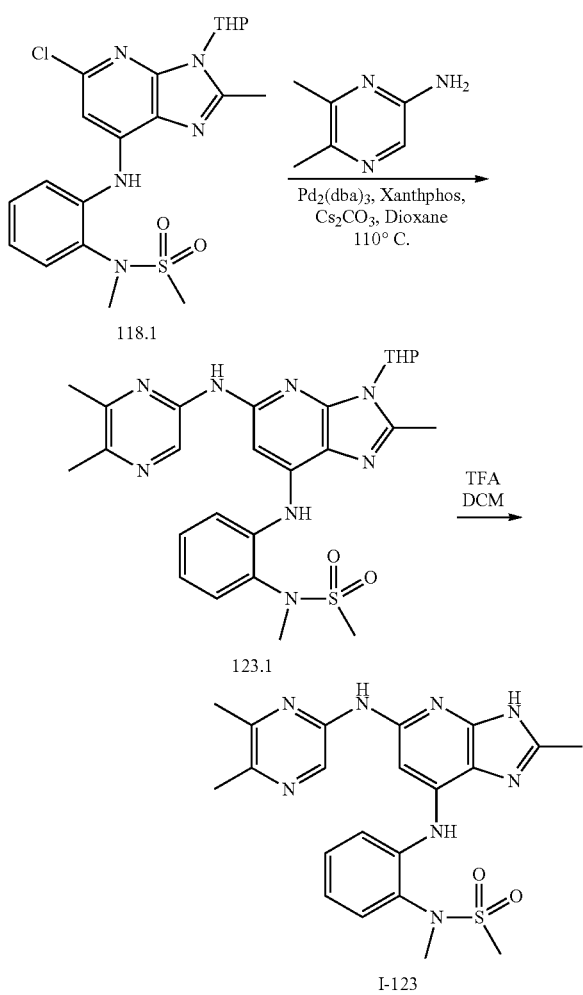

Synthesis of Compound 123.1.

Compound 123.1 was synthesized from 5,6-dimethylpyrazin-2-amine and 123.1 using general procedure B. (Yield: 24.58%). MS (ES): m/z 537.66 [M+H]+.

Synthesis of Compound I-123.

Compound I-123 was synthesized from 123.1 using general procedure C. (Yield: 83.71%), MS(ES): m/z: 453.30 [M+H]+, LCMS purity: 99.46%, HPLC purity: 98.39%, 1H NMR (DMSO, 400 MHz): 9.48 (s, 1H), 8.86 (s, 1H), 7.85 (s, 1H), 7.74-7.72 (d, J=8 Hz, 1H), 7.68-7.65 (d, J=10 Hz, 1H), 7.46-7.42 (t, J=7.6 Hz, 1H), 7.38 (s, 1H), 7.21-7.17 (t, J=7.6 Hz, 1H), 3.21 (s, 3H), 3.12 (s, 3H), 2.45 (s, 3H) 2.37 (s, 6H).

Example 124: Synthesis of N-(2-((5-((2,6-dimethylpyrimidin-4-yl)amino)-2-methyl-3H-imidazo[4,5-b]-pyridin-7-yl)amino)phenyl)-N-methylmethanesulfonamide, I-124

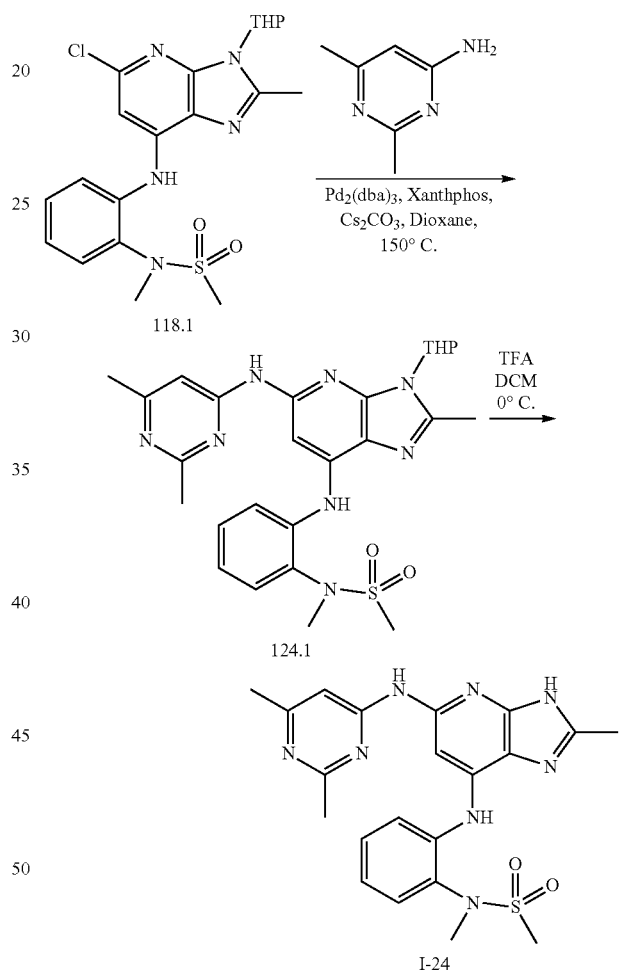

Synthesis of Compound 124.1.

Compound 124.1 was synthesized from 2,6-dimethylpyrimidin-4-amine and 118.1 using general procedure B. (Yield: 66.24%). MS (ES): m/z 537.66 [M+H]+.

Synthesis of Compound I-124.

Compound I-124 was synthesized from 124.1 using general procedure C. (Yield: 60.04), MS(ES). m/z: 453.54[M+H]+, LCMS purity: 100%, HPLC purity: 98.66%, 1H NMR (DMSO, 400 MHz): 12.39 (s, 1H), 9.74 (s, 1H), 7.89 (s, 1H), 7.74-7.72 (d, J=8 Hz, 1H), 7.66-7.65 (d, J=8 Hz, 1H), 7.48-7.42 (m, 2H), 7.22-7.20 (t, J=8 Hz, 1H), 3.21 (s, 3H), 3.11 (s, 3H), 2.46 (s, 3H) 2.40 (s, 3H) 2.29 (s, 3H).

Example 125: Synthesis of N-(2-((5-((6-cyano-5-methylpyridin-2-yl)amino)-2-methyl-3H-imidazo[4,5-b]pyridin-7-yl)amino)phenyl)-N-methylmethanesulfonamide, I-125

Example 126: Synthesis of N-(7-((4-chloro-2-(methylsulfonyl)phenyl)amino)-2-methyl-3H-imidazo[4,5-b]pyridin-5-yl)cyclopropanecarboxamide, I-126

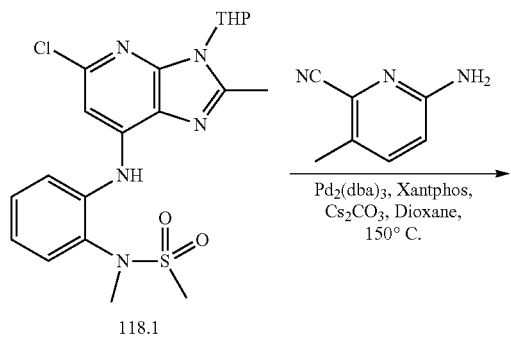

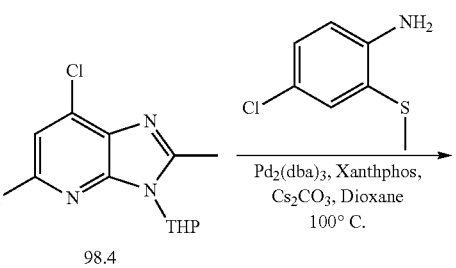

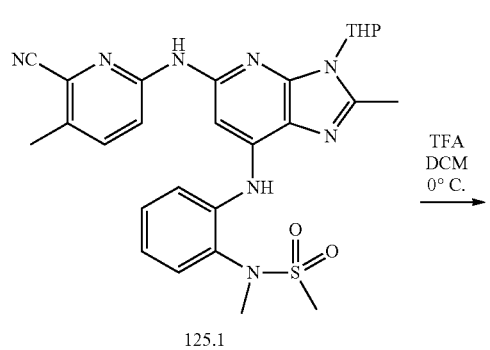

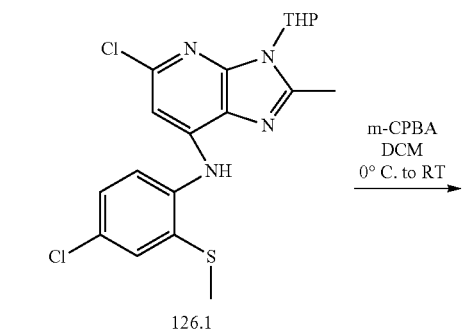

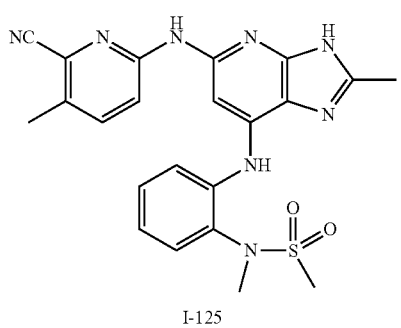

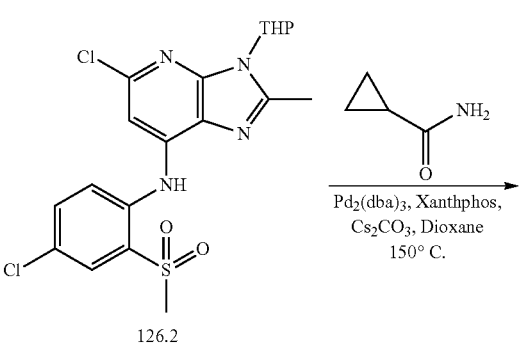

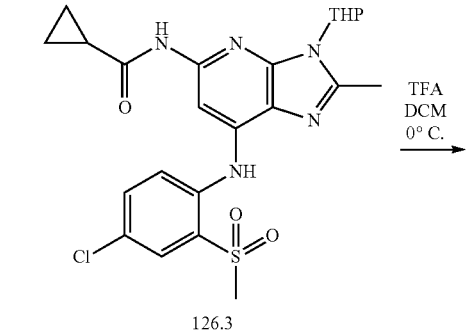

Synthesis of Compound 125.1.

Compound 125.1 was synthesized from 6-amino-3-methylpicolinonitrile and 118.1 using general procedure B to obtain 1.2 (Yield: 61.73%), MS (ES): m/z 547.65 [M+H]⁺.

Synthesis of I-125.

Compound I-125 was synthesized from 125.1 using general procedure C. (Yield: 63.03%), MS(ES): m/z: 463.30 [M+H]⁺, LCMS purity: 95.86%, HPLC purity: 93.98%, 1H NMR (DMSO, 400 MHz): 10.08 (s, 1H), 9.84 (s, 1H), 8.13 (s, 1H), 7.87 (s, 1H), 7.80-7.78 (d, J=8.4 Hz, 1H), 7.70-7.68 (d, J=7.6 Hz, 1H), 7.65-7.65 (d, J=7.6 Hz, 1H), 7.55-7.51 (t, J=7.6 Hz 1H), 7.32 (m, 2H), 3.22 (s, 3H), 3.08 (s, 3H), 2.67 (s, 3H) 2.39 (s, 3H).

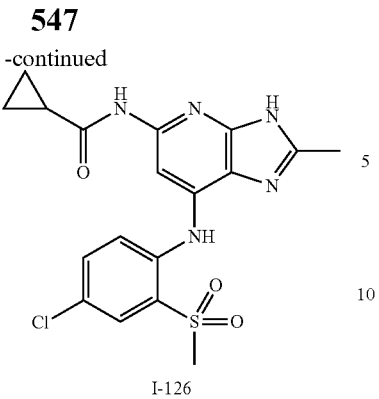

Synthesis of Compound 126.1.

Compound 126.1 was synthesized from 4-chloro-2-(methylthio)aniline using and 98.4 using general procedure A. (Yield: 17.41%). MS (ES): m/z 424.36 [M+H]$^+$ Synthesis of Compound 126.2.

To a cooled solution of 126.1 (0.170 g, 4.01 mmol, 1 eq) in CH$_2$Cl$_2$ (5 mL) at 0° C. was added meta chloroperbenzoic acid(0.076 g, 4.41 mmol, 1.1 eq) portionwise. The reaction mixture was stirred at r.t. for 1 hr. After completion of reaction, the reaction mixture was transferred into saturated NaHCO$_3$ solution and extracted with CH$_2$Cl$_2$. Combined Organic layer dried over Na$_2$SO$_4$ and concentrated in vacuo to obtain crude product. This was purified by column chromatography and compound was eluted in 2% MeOH in CH$_2$Cl$_2$ to obtain pure 126.2 (0.100 g, 54.69%). MS(ES): m/z 456.35 [M+H]$^+$.

Synthesis of Compound 126.3.

Compound was synthesized from 126.2 and cyclopropanecarboxamide using general procedure B. (Yield: 45.17%). MS (ES): m/z 505.00 [M+H]$^+$.

Synthesis of Compound I-126.

Compound I-126 was synthesized from 126.3 using general procedure C. (Yield: 60.02%). MS(ES): m/z: 420.35 [M+H]$^+$, LCMS purity: 98.82%, HPLC purity: 99.01%, 1H NMR (DMSO, 400 MHz): 12.53 (s, 1H), 10.62 (s, 1H), 8.59 (s, 1H), 7.98 (s, 1H), 7.86-7.74 (m, 3H), 3.35 (s, 3H), 2.52 (s, 3H), 2.01-1.99 (m, 1H), 0.79 (s, 4H).

Example 127: Synthesis of N-methyl-N-(2-((2-methyl-5-((6-(trifluoromethyl)pyridin-2-yl)amino)-3H-imidazo[4,5-b]pyridin-7-yl)amino)phenyl)methanesulfonamide, I-127

Synthesis of Compound 127.1.

Compound 127.1 was synthesized from 6-(trifluoromethyl)pyridin-2-amine and 118.1 using general procedure B. (Yield: 54.72%). MS (ES): m/z 576.61 [M+H]$^+$.

Synthesis of Compound I-127.

Compound I-127 was synthesized from 127.1 using general procedure C. (Yield: 41.83%), MS(ES): m/z: 492.43 [M+H]$^+$, LCMS purity: 99.59%, HPLC purity: 99.22%, 1H NMR (DMSO, 400 MHz): 12.41 (s, 1H), 9.89 (s, 1H), 8.11-8.09 (m, 1H), 7.91-7.85 (m, 2H), 7.71-7.64 (m, 2H), 7.43-7.39 (m, 2H), 7.26-7.24 (m, 2H), 3.35 (s, 3H), 3.22 (s, 3H), 2.48 (s, 3H).

Example 128: Synthesis of N-(7-((2-methoxy-3-(3-methyl-1H-1,2,4-triazol-1-yl)phenyl)amino)-2-methyl-3H-imidazo[4,5-b]pyridin-5-yl)cyclopropanecarboxamide, I-128

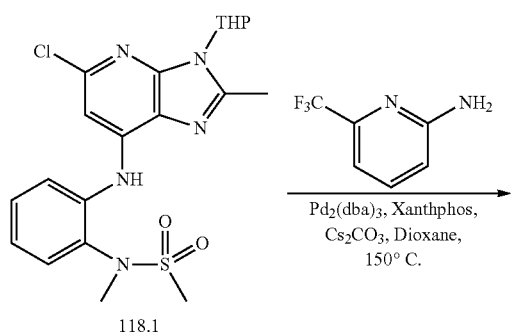

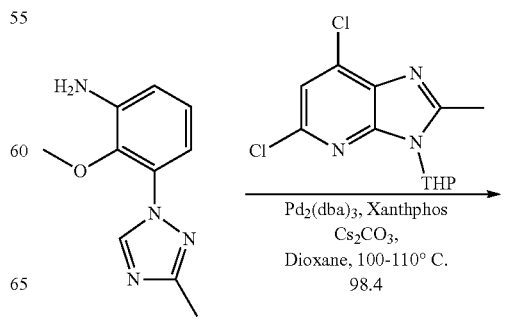

-continued

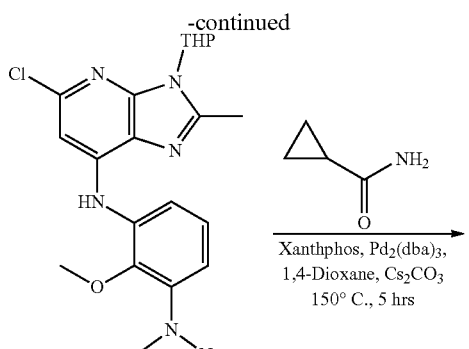

128.1

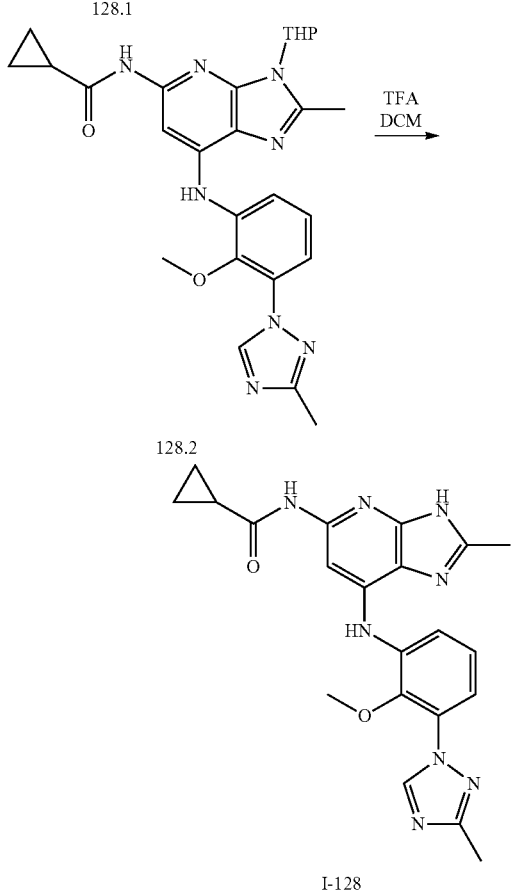

Synthesis of Compound 128.1.

Compound 128.1 was synthesized from 98.4 and 2-methoxy-3-(4-methyl)-1,2,4-triazol-1ylaniline using general procedure A. (Yield: 32.99%). MS(ES): m/z 454.93 [M+H]$^+$.

Synthesis of Compound 128.2.

Compound 128.2 was synthesized from 128.1 and cyclopropanecarboxamide using general procedure B. (Yield: 49027%). MS(ES): m/z 503.58 [M+H]$^+$.

Synthesis of I-128.

Compound I-128 was synthesized from 128.2 using general procedure C. (Yield: 55.05%). MS(ES): m/z: 419.34 [M+H]$^+$, LCMS purity: 94.68%, HPLC purity: 95.18%, 1H NMR (DMSO, 400 MHz): 10.45 (s, 1H), 8.79 (s, 1H), 8.23 (s, 1H), 7.67 (s, 1H), 7.45-7.43 (d, J=7.6 Hz, 1H), 7.36-7.35 (d, J=6.8 Hz, 1H), 7.29-7.26 (t, J=8 Hz, 1H), 3.51 (s, 3H), 2.49 (s, 3H), 2.36 (s, 3H), 1.98 (s, 1H) 0.75 (bs, 4H).

Example 129: Synthesis of N-(7-((4-(azetidin-1-yl)-2-(N-methylmethylsulfonamido)phenyl)amino)-2-methyl-3H-imidazo[4,5-b]pyridin-5-yl)cyclopropanecarboxamide, I-129

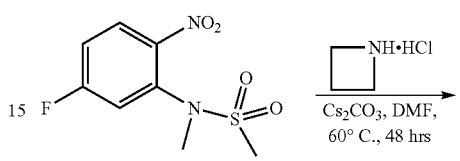

129.2

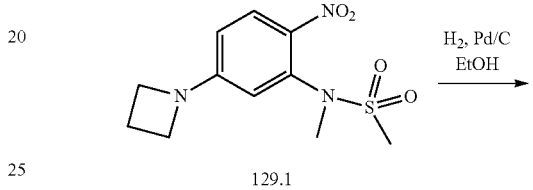

129.1

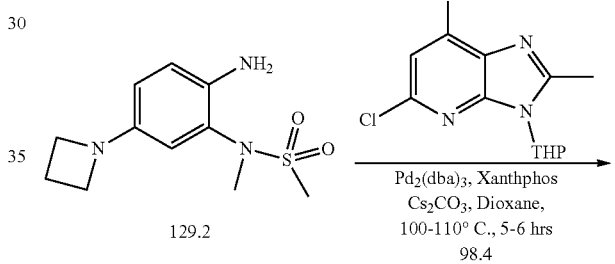

129.2

98.4

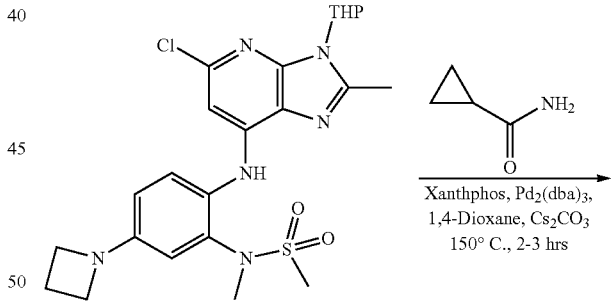

129.3

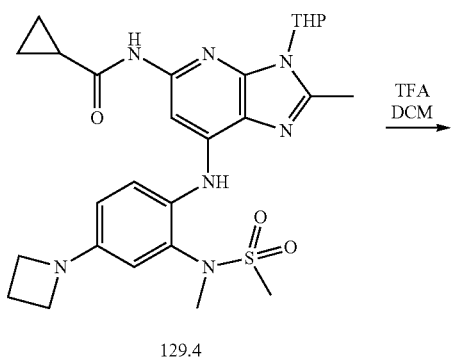

129.4

Example 130: Synthesis of N-(5-chloro-2-((5-((5,6-dimethylpyrazin-2-yl)amino)-2-methyl-3H-imidazo[4,5-b]pyridin-7-yl)amino)phenyl)-N-methylmethanesulfonamide, I-130

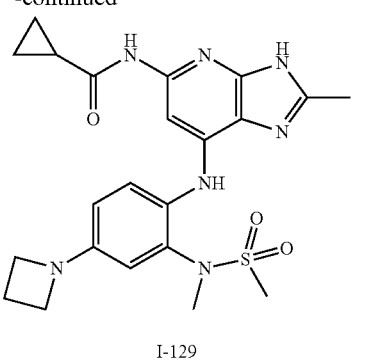

I-129

Synthesis of Compound 129.1.

To a solution of 129.1 (prepared from 3-fluoro-6-nitroaniline and mesyl chloride followed by methyl iodide) (5.0 g, 20.14 mmol, 1.0 eq) in N,N-dimethylformamide (50 mL) was added Cs₂CO₃ (7.98 g, 24.57 mmol, 1.22 eq) followed by addition of azetidine hydrochloride (1.88 g, 24.57 mmol, 1.22 eq). The reaction mixture was stirred at 60° C. for 48 h. Upon completion, reaction mixture was transferred in to 10% solution of sodium phosphate (90 mL) and extracted with ethyl acetate. Organic layers were combined, dried over Na₂SO₄ and concentrated in vacuo to obtain crude product. This was purified by column chromatography and compound was eluted in 35% ethyl acetate in hexane as eluent to obtain 129.1. (3.4 g, 59.16%). MS(ES): m/z 286.32 [M+H]⁺.

Synthesis of Compound 129.2.

To a solution of 129.1 (2.0 g, 7.01 mmol, 1.0 eq) in ethanol (20 mL), 10% Pd/C (0.8 g) was added. Hydrogen was purged through reaction mixture for 4 h. Upon completion, reaction mixture was filtered through celite-bed and washed with ethanol. Filtrate was concentrated in vacuo to obtain 129.2. (1.5 g, 83.84%). MS(ES): m/z 256.34 [M+H]⁺.

Synthesis of Compound 129.3.

Compound 129.3 was synthesized from 98.4 and 129.2 using general procedure A. (Yield: 19.43%). MS(ES): m/z 506.47 [M+H]⁺.

Synthesis of Compound 129.4.

Compound 129.4 was synthesized from 129.3 and cyclopropanecarboxamide using general procedure B. (Yield: 37.25%). MS(ES): m/z 554.28 [M+H]⁺.

Synthesis of I-129.

Compound I-129 was synthesized from 129.4 using general procedure C. (Yield: 60.16%). MS(ES): m/z: 470.47 [M+H]⁺, LCMS purity, 94.35%, HPLC purity 93.66%, 1H NMR (DMSO-d6, 400 MHz): 12.33 (s, 1H), 10.36 (s, 1H), 7.54 (s, 1H), 7.37 (s, 1H), 7.29-7.27 (d, J=8.8 Hz, 1H), 6.59 (s, 1H), 6.49-6.47 (m, 1H), 3.88-3.81 (m, 4H), 3.14 (s, 3H), 3.07 (s, 3H), 2.34-2.29 (m, 3H), 1.92 (m, 2H), 1.24 (s, 1H), 0.73 (bs, 4H).

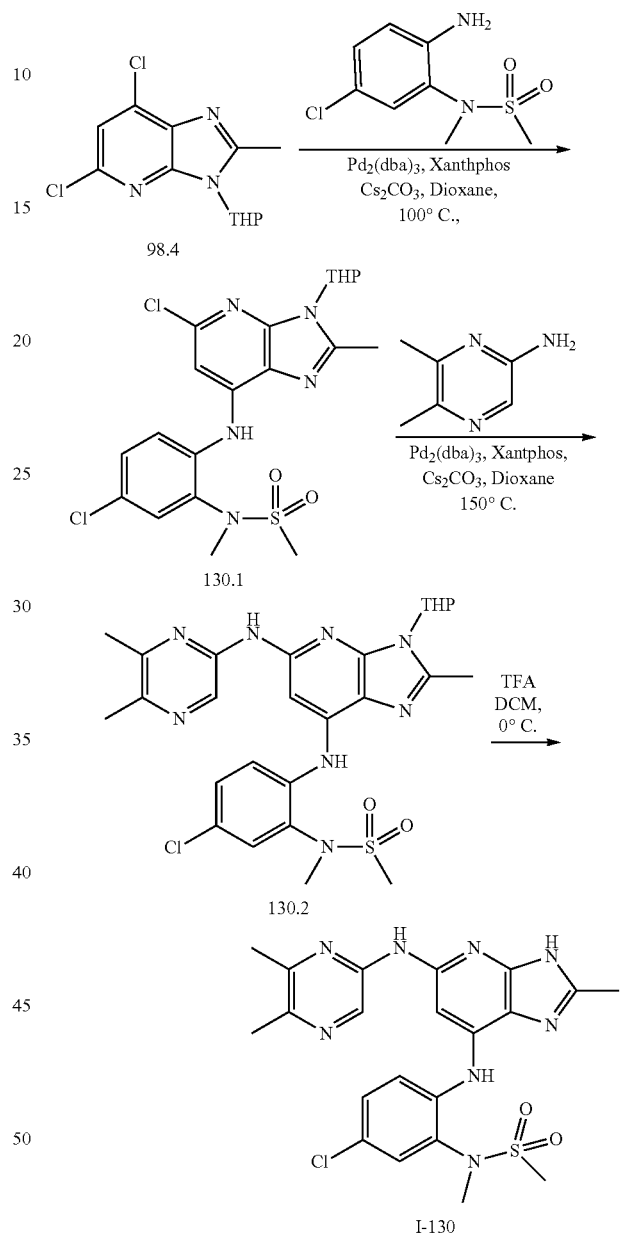

Synthesis of Compound 130.1.

Compound 130.1 was synthesized from 98.4 and N-(2-amino-5-chlorophenyl)-N-methylmethanesulfonamide using general procedure A. (Yield: 33.76%). MS (ES): m/z 485.40 [M+H]⁺.

Synthesis of Compound 130.2.

Compound 130.2 was synthesized from 5,6-dimethylpyrazin-2-amine and 130.1 using general procedure B. (Yield: 16.96%). MS (ES): m/z 572.10 [M+H]⁺.

Synthesis of Compound I-130.

Compound I-130 was synthesized from 130.2 using general procedure C. (Yield: 73.30%). MS(ES): m/z: 487.25

[M+H]+, LCMS purity: 93.34%, HPLC purity: 99.73%, 1H NMR (DMSO, 400 MHz): 9.49 (s, 1H), 8.89 (s, 1H), 7.87 (s, 1H), 7.81-7.80 (d, J=2.4 Hz, 1H), 7.71-7.69 (d, J=8.8 Hz, 1H), 7.51-0.48 (m, 1H), 7.29 (s, 1H), 3.23 (s, 3H), 3.15 (s, 3H), 2.46 (s, 3H), 2.38-2.37 (d, J=3.6 Hz, 6H).

Example 131: Synthesis of N-(2-methyl-7-((4-methyl-2-(N-methylmethylsulfonamido)phenyl)amino)-3H-imidazo[4,5-b]pyridin-5-yl)cyclopropanecarboxamide, I-131

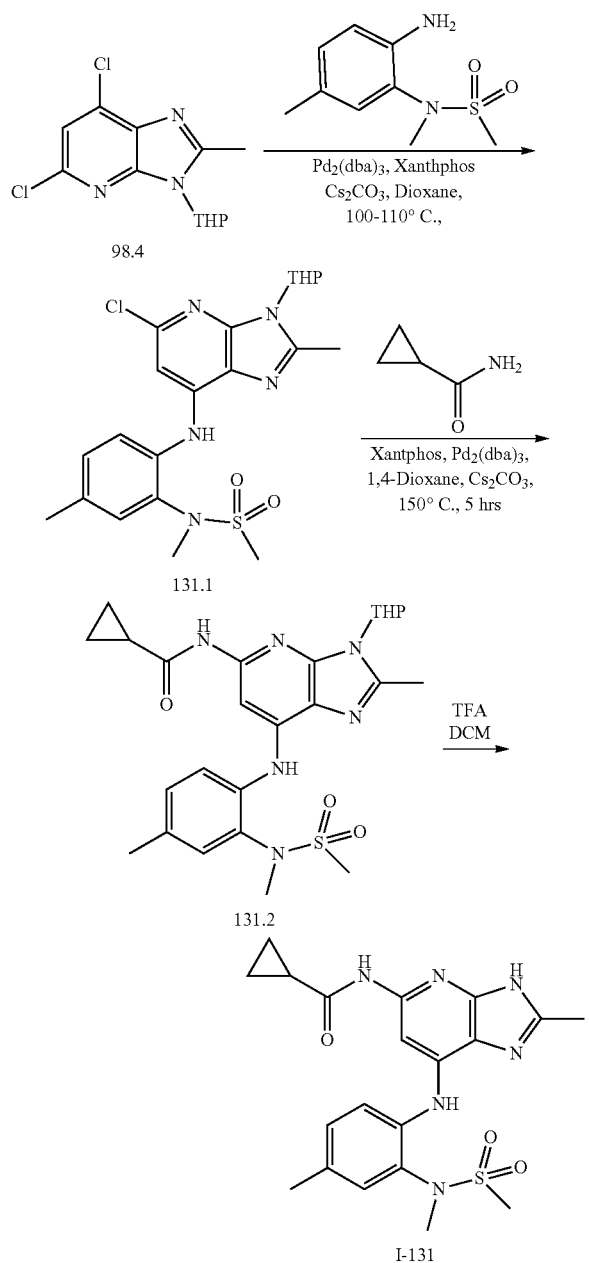

Synthesis of Compound 131.1.

Compound 131.1 was synthesized from 98.4 and 95.1 using general procedure A. (Yield: 34.64%). MS(ES): m/z 464.51 [M+H]+.

Synthesis of Compound 131.2.

Compound was synthesized from 131.1 and cyclopropanecarboxamide using general procedure B. (Yield: 71.20%). MS(ES): m/z 513.26 [M+H]+.

Synthesis of I-131.

Compound I-131 was synthesized from 131.2 using general procedure C. (Yield: 77.05%). MS(ES): m/z: 429.29 [M+H]+, LCMS purity, 96.15%, HPLC purity 95.55%, 1H NMR (DMSO, 400 MHz): 12.35 (s, 1H), 10.42 (s, 1H), 7.74-7.71 (d, J=12 Hz, 2H), 7.46 (s, 2H), 7.25-7.23 (d, J=8 Hz, 1H), 3.17 (s, 3H), 3.09 (s, 3H), 2.48 (s, 3H), 2.36 (s, 3H), 2.00 (s, 1H), 0.76 (s, 4H).

Example 132: Synthesis of N-(2-((5-((5,6-dimethylpyrazin-2-yl)amino)-2-methyl-3H-imidazo[4,5-b]pyridin-7-yl)amino)-5-methylphenyl)-N-methylmethanesulfonamide, I-132

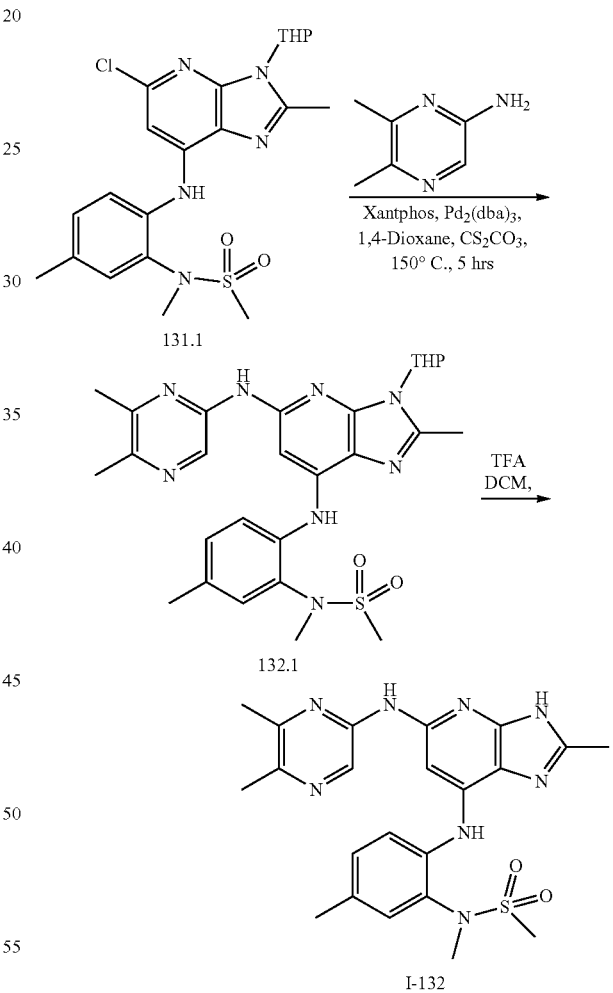

Synthesis of Compound 132.1.

Compound was synthesized from 131.1 and 5,6-dimethylpyrazin-2-amine using general procedure B. (Yield: 61.79%). MS(ES): m/z 551.89 [M+H]+.

Synthesis of I-132.

Compound I-132 was synthesized from 132.1 using general procedure C. (Yield: 75.11%). MS(ES): m/z: 467.35 [M+H]+, LCMS purity, 96.56%, HPLC purity 95.24%, 1H NMR (DMSO, 400 MHz): 12.30 (s, 1H), 9.45 (s, 1H), 8.86

(s, 1H), 7.74 (s, 1H), 7.59-7.57 (d, J=8 Hz, 1H), 7.47 (s, 1H), 7.27-7.25 (m, 2H), 3.19 (s, 3H), 3.11 (s, 3H), 2.47 (s, 3H), 2.37 (s, 6H), 2.36 (s, 3H).

Example 133: Synthesis of N-(7-((3-(2,5-dimethyl-2H-1,2,3-triazol-4-yl)-2-methoxyphenyl)amino)-2-methyl-3H-imidazo[4,5-b]pyridin-5-yl)cyclopropanecarboxamide, I-133

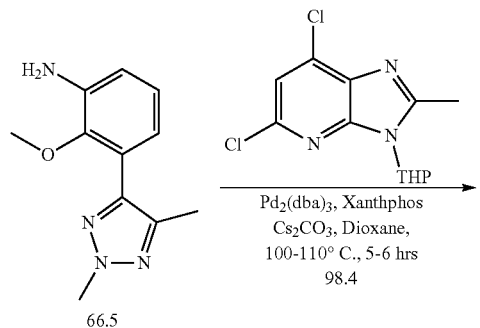

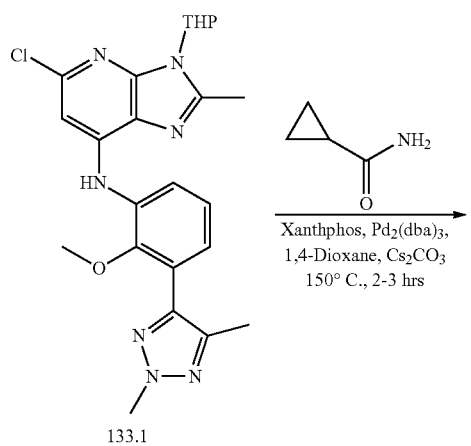

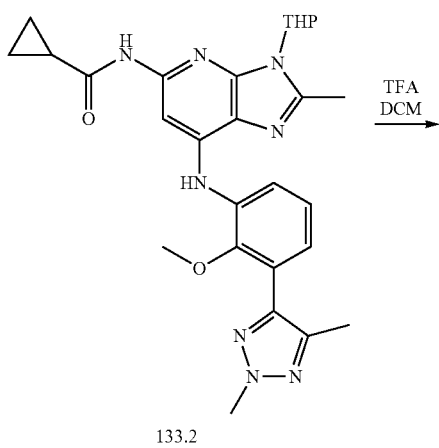

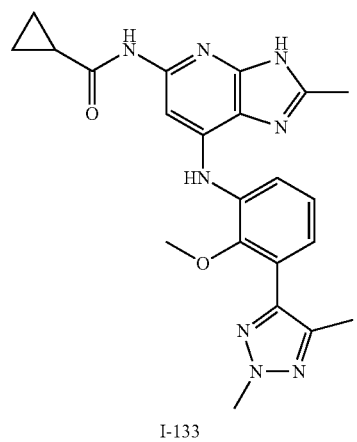

I-133

Synthesis of Compound 133.1.

Compound 133.1 was synthesized from 98.4 and 66.5 using general procedure A. (Yield: 18.66%). MS(ES): m/z 468.71 [M+H]⁺.

Synthesis of Compound 133.2.

Compound 133.2 was synthesized from 133.1 and cyclopropanecarboxamide using general procedure B. (Yield: 62.28%). MS(ES): m/z 517.46 [M+H]⁺.

Synthesis of I-133.

Compound I-133 was synthesized from 133.2 using general procedure C. (Yield: 58.64%). MS(ES): m/z: 433.37 [M+H]⁺, LCMS purity, 97.76%, HPLC purity 98.61%, 1H NMR (DMSO, 400 MHz): 13.56 (s, 1H), 10.66 (s, 1H), 8.26 (s, 1H), 7.77 (s, 1H), 7.60-7.58 (d, J=6.8 Hz, 1H), 7.48-7.47 (d, J=6.4 Hz, 1H), 7.26-7.24 (d, J=7.2 Hz, 1H), 3.86 (s, 3H), 3.72 (s, 3H), 2.62 (s, 3H), 2.47 (s, 3H), 2.47 (m, 1H), 0.78 (s, 4H).

Example 134: Synthesis of N-(5-chloro-2-((5-((6-cyanopyridin-2-yl)amino)-2-methyl-3H-imidazo[4,5-b]pyridin-7-yl)amino)phenyl)-N-methylmethanesulfonamide, I-134

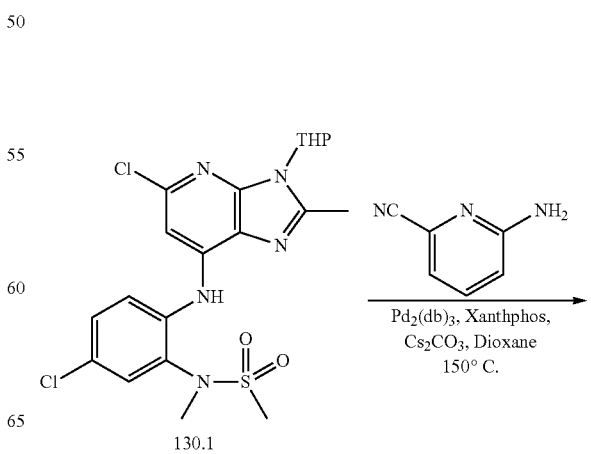

557

-continued

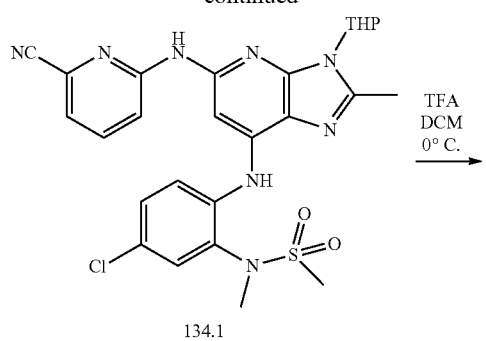

134.1

TFA
DCM
0° C.

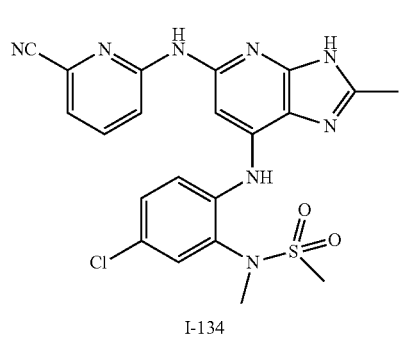

I-134

Synthesis of Compound 134.1.

Compound 134.1 was synthesized from 6-aminopicolinonitrile and 130.1 using general procedure B. (Yield: 25.63%). MS (ES): m/z 568.07 [M+H]$^+$.

Synthesis of Compound I-134.

Compound I-134 was synthesized from 134.1 using general procedure C. (Yield: 66.54%), MS(ES): m/z: 483.26 [M+H]$^+$, LCMS purity: 97.21%, HPLC purity: 96.63%, 1H NMR (DMSO, 400 MHz): 12.77 (s, 1H), 9.96 (s, 1H), 8.15 (s, 1H), 7.99-7.95 (t, J=18 Hz, 2H), 7.85 (m, 2H), 7.75-7.73 (d, J=8.8 Hz, 1H), 7.56-7.53 (m, 1H), 7.44-7.41 (m, 1H), 3.24 (s, 3H), 3.15 (s, 3H), 2.49 (s, 3H).

Example 135: Synthesis of N-(2-(difluoromethyl)-7-((4-(4-methyl-1H-pyrazol-1-yl)-2-(N-methylmethylsulfonamido)phenyl)amino)-3-imidazo[4,5-b]pyridin-5-yl)cyclopropanecarboxamide, I-135

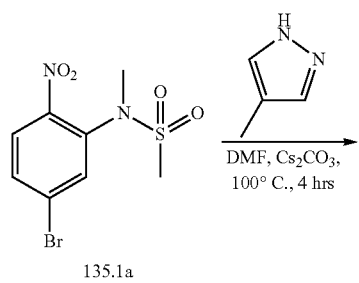

135.1a 1H-pyrazole with methyl

DMF, Cs$_2$CO$_3$,
100° C., 4 hrs

558

-continued

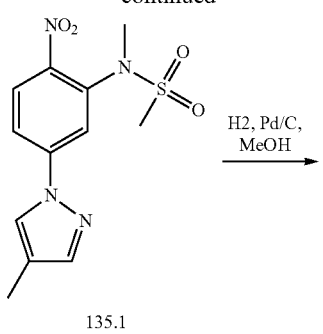

135.1

H2, Pd/C,
MeOH

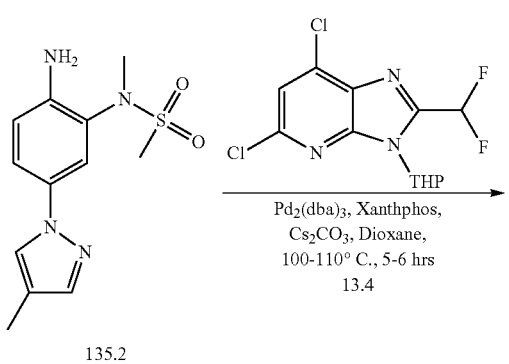

135.2

Pd$_2$(dba)$_3$, Xanthphos,
Cs$_2$CO$_3$, Dioxane,
100-110° C., 5-6 hrs
13.4

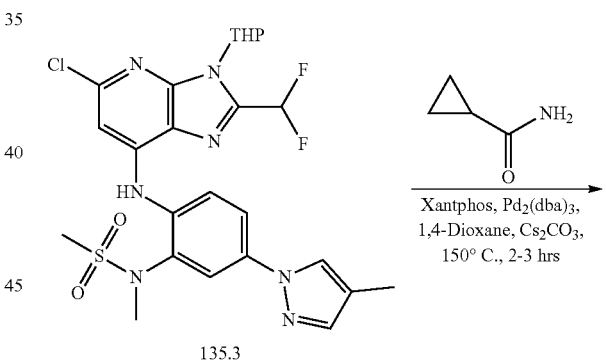

135.3

Xantphos, Pd$_2$(dba)$_3$,
1,4-Dioxane, Cs$_2$CO$_3$,
150° C., 2-3 hrs

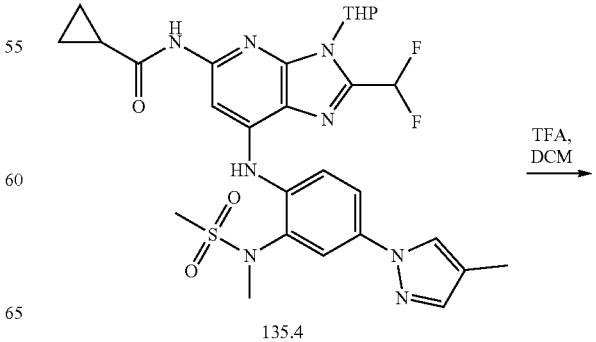

135.4

TFA,
DCM

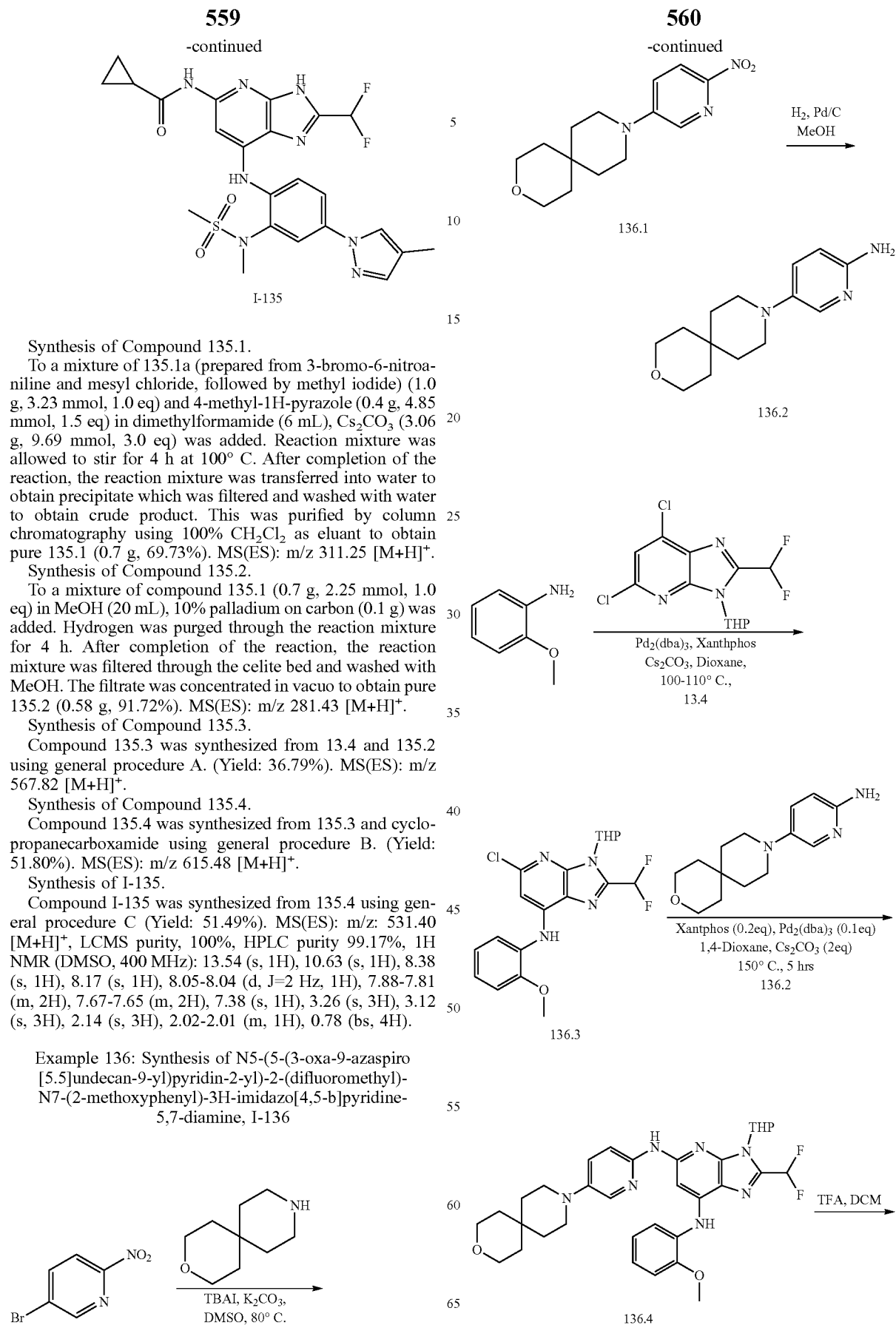

Synthesis of Compound 135.1.

To a mixture of 135.1a (prepared from 3-bromo-6-nitroaniline and mesyl chloride, followed by methyl iodide) (1.0 g, 3.23 mmol, 1.0 eq) and 4-methyl-1H-pyrazole (0.4 g, 4.85 mmol, 1.5 eq) in dimethylformamide (6 mL), $Cs_2CO_3$ (3.06 g, 9.69 mmol, 3.0 eq) was added. Reaction mixture was allowed to stir for 4 h at 100° C. After completion of the reaction, the reaction mixture was transferred into water to obtain precipitate which was filtered and washed with water to obtain crude product. This was purified by column chromatography using 100% $CH_2Cl_2$ as eluant to obtain pure 135.1 (0.7 g, 69.73%). MS(ES): m/z 311.25 [M+H]$^+$.

Synthesis of Compound 135.2.

To a mixture of compound 135.1 (0.7 g, 2.25 mmol, 1.0 eq) in MeOH (20 mL), 10% palladium on carbon (0.1 g) was added. Hydrogen was purged through the reaction mixture for 4 h. After completion of the reaction, the reaction mixture was filtered through the celite bed and washed with MeOH. The filtrate was concentrated in vacuo to obtain pure 135.2 (0.58 g, 91.72%). MS(ES): m/z 281.43 [M+H]$^+$.

Synthesis of Compound 135.3.

Compound 135.3 was synthesized from 13.4 and 135.2 using general procedure A. (Yield: 36.79%). MS(ES): m/z 567.82 [M+H]$^+$.

Synthesis of Compound 135.4.

Compound 135.4 was synthesized from 135.3 and cyclopropanecarboxamide using general procedure B. (Yield: 51.80%). MS(ES): m/z 615.48 [M+H]$^+$.

Synthesis of I-135.

Compound I-135 was synthesized from 135.4 using general procedure C (Yield: 51.49%). MS(ES): m/z: 531.40 [M+H]$^+$, LCMS purity, 100%, HPLC purity 99.17%, 1H NMR (DMSO, 400 MHz): 13.54 (s, 1H), 10.63 (s, 1H), 8.38 (s, 1H), 8.17 (s, 1H), 8.05-8.04 (d, J=2 Hz, 1H), 7.88-7.81 (m, 2H), 7.67-7.65 (m, 2H), 7.38 (s, 1H), 3.26 (s, 3H), 3.12 (s, 3H), 2.14 (s, 3H), 2.02-2.01 (m, 1H), 0.78 (bs, 4H).

Example 136: Synthesis of N5-(5-(3-oxa-9-azaspiro[5.5]undecan-9-yl)pyridin-2-yl)-2-(difluoromethyl)-N7-(2-methoxyphenyl)-3H-imidazo[4,5-b]pyridine-5,7-diamine, I-136

Example 137: Synthesis of 5-((5-(3-oxa-9-azaspiro[5.5]undecan-9-yl)pyridin-2-yl)methyl)-N-(2-methoxyphenyl)-2-methyl-3H-imidazo[4,5-b]pyridin-7-amine, 1-137

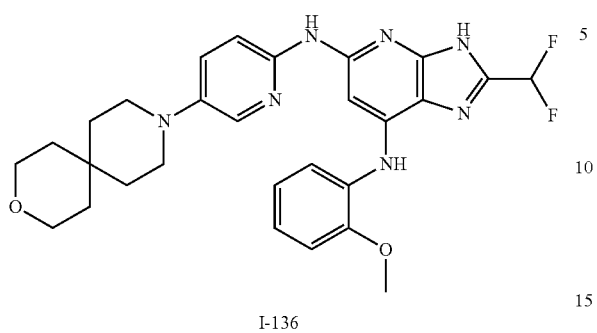

I-136

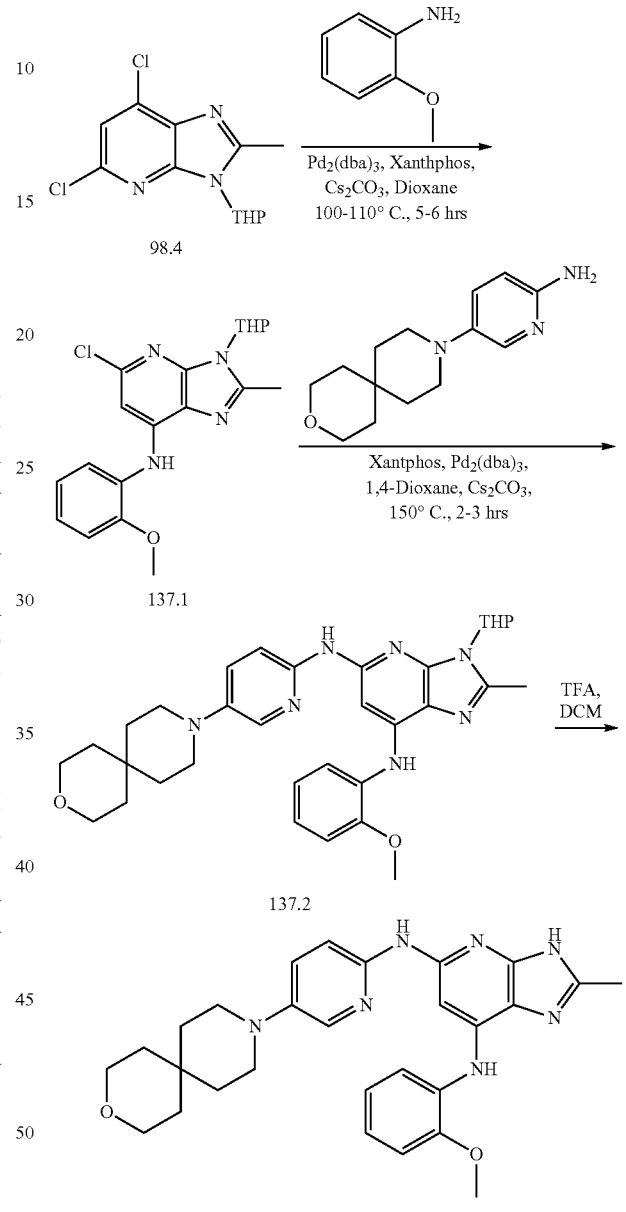

Synthesis of Compound 136.1.

To compound 5-bromo-2-nitropyridine (1.0 g, 49.0 mmol, 1.0 eq) and 3-oxa-9-azaspiro[5.5]undecane (0.841 g, 54 mmol, 1.1 eq) in dimethyl sulfoxide (10 mL), tetrabutylammonium iodide (0.246 g, 73 mmol, 1.5 eq) and potassium carbonate (0.984 g, 98 mmol, 2 eq) were added. Reaction mixture was stirred at 80° C. for 1 hour. Upon completion, reaction mixture was transferred into cold water and then extracted with ethyl acetate. Organic layers were combined, dried over $Na_2SO_4$ and concentrated in vacuo to obtain crude product. This was purified by trituration by hexane to obtain pure 136.1 (1.2 g, 87.84%). MS(ES): m/z 278.32 [M+H]$^+$.

Synthesis of Compound 136.2.

To compound 136.1 (1.2 g, 37 mmol, 1.0 eq) in MeOH (120 mL), 10% Pd/C (0.3 g) was added. Hydrogen was purged through reaction mixture for 4 h. Upon completion, reaction mixture was filtered through celite-bed and washed with MeOH. Filtrate was concentrated in vacuo to obtain 136.2 (1 g, 93.43%). MS(ES): m/z 248.34 [M+H]$^+$.

Synthesis of Compound 136.3.

Compound 136.3 was synthesized from 13.4 and 2-methoxyaniline using general procedure A. (Yield: 37.65%). MS(ES): m/z 409.83 [M+H]$^+$.

Synthesis of Compound 136.4.

Compound 136.4 was synthesized from 136.2 and 136.3 using general procedure A. (Yield: 39.58%). MS(ES): m/z 620.72 [M+H]$^+$.

Synthesis of I-136.

Compound I-136 was synthesized from 136.4 using general procedure C. (Yield: 61.71%). MS(ES): m/z: 536.36 [M+H]$^+$, LCMS purity: 97.99%, HPLC purity: 96.67%, 1H NMR (DMSO, 400 MHz): 9.27 (s, 1H), 8.00 (s, 1H), 7.90 (s, 1H), 7.73 (s, 1H), 7.53-7.51 (d, J=6.4 Hz, 1H), 7.39 (bs, 2H), 7.14 (bs, 3H), 7.05-7.03 (d, J=8 Hz, 2H), 3.88 (s, 3H), 3.59-3.57 (t, J=5.2 Hz, 4H), 3.08 (s, 4H), 1.645-1.69 (t, J=5.2 Hz, 4H), 1.48-1.45 (t, J=5.2 Hz, 4H).

Synthesis of Compound 137.1.

Compound 137.1 was synthesized from 98.4 and 2-methoxyaniline using general procedure A. (Yield: 33.03%). MS(ES): m/z 373.85 [M+H]$^+$.

Synthesis of Compound 137.2.

Compound 137.2 was synthesized from 137.1 and 136.2 using general procedure B. (Yield: 56.21%). MS(ES): m/z 584.74 [M+H]$^+$.

Synthesis of I-137.

Compound I-137 was synthesized from 137.2 using general procedure C (Yield: 59.86%). MS(ES): m/z: 500.46 [M+H]$^+$, LCMS purity: 97.89%, HPLC purity: 97.37%, 1H NMR (DMSO, 400 MHz): 9.27 (s, 1H), 8.0 (s, 1H), 7.87 (s, 1H), 7.60-7.53 (m, 2H), 7.21-7.13 (m, 2H), 7.07-7.03 (t, J=7.2 Hz, 2H), 6.67 (s, 1H), 3.94 (s, 3H), 3.74-3.71 (t, J=4.8 Hz, 3H), 3.16 (s, 4H), 2.60 (s, 4H), 1.76 (s, 4H), 1.59 (s, 4H).

Example 138: Synthesis of N7-(2-methoxy-3-(2-methyl-2H-tetrazol-5-yl)phenyl)-N5-(5-(2-methoxy-propan-2-yl)-6-methylpyrazin-2-yl)-2-methyl-3H-imidazo[4,5-b]pyridine-5,7-diamines, I-138

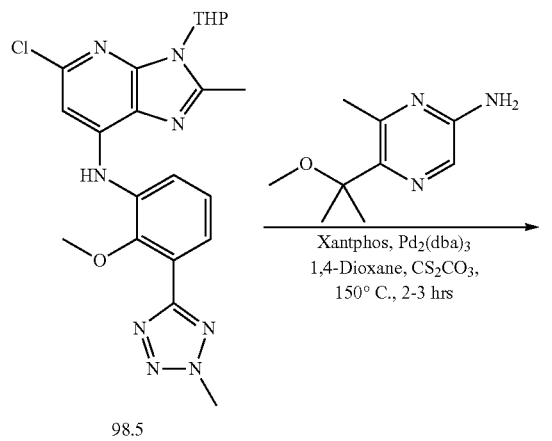

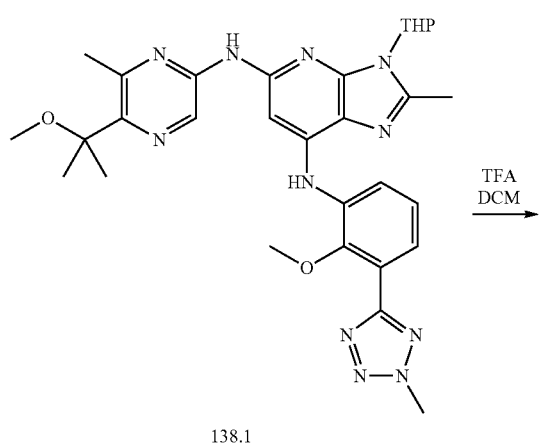

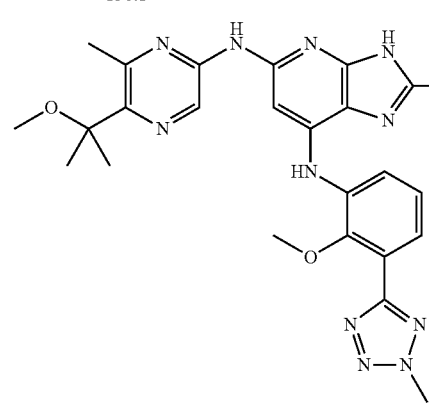

Synthesis of Compound 138.1.

Compound 138.1 was synthesized from 5-(2-methoxy-propan-2-yl)-6-methylpyrazin-2-amine and 98.5 using general procedure B. (Yield: 38.26%). MS(ES): m/z 600.70 [M+H]⁺.

Synthesis of I-138.

Compound I-138 was synthesized from 138.1 using general procedure C. (Yield: 80.22%). MS(ES): m/z: 516.46 [M+H]⁺, LCMS purity 95.18%, HPLC purity 95.14%, 1H NMR (DMSO-d6, 400 MHz): 9.77 (s, 1H), 8.99 (s, 1H), 8.37 (s, 1H), 7.72-7.66 (m, 2H), 7.39-7.34 (m, 2H), 7.16 (s, 1H), 4.46 (s, 3H), 3.75 (s, 3H), 3.34 (s, 3H), 2.95 (s, 3H), 2.33 (s, 3H), 1.489 (s, 6H).

Example 139: Synthesis of N-(2-(difluoromethyl)-7-((4-(3-methyl-1H-pyrazol-1-yl)-2-(N-methylmethylsulfonamido)phenyl)amino)-3H-imidazo[4,5-b]pyridin-5-yl)cyclopropanecarboxamide, I-139

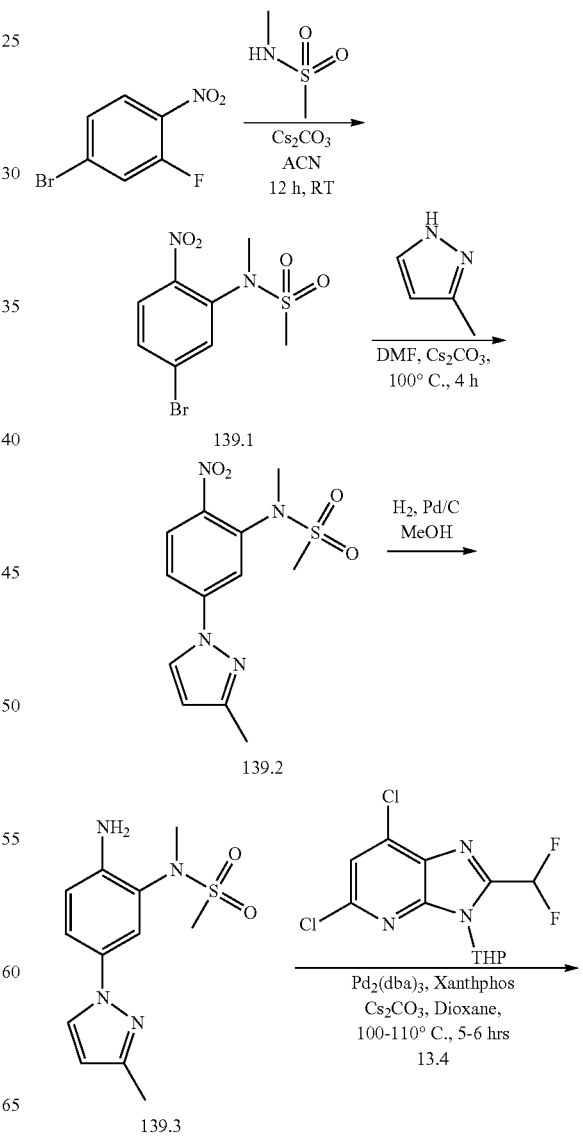

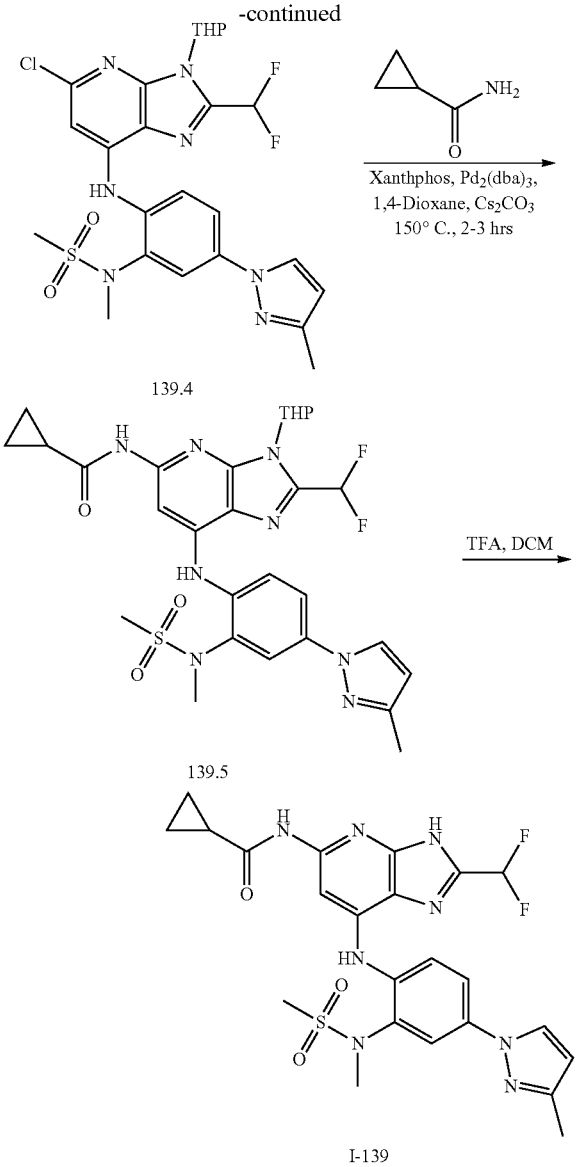

139.4

139.5

I-139

Synthesis of Compound 139.1.

To a suspension of Cs$_2$CO$_3$ (2.8 g, 0.008 mmol, 1.9 eq) in acetonitrile (28 mL), N-methyl methanesulfonamide (0.5 g, 0.004 mmol, 1.1 eq) was added and cooled to 0° C. Then compound 4-bromo-2-fluoro-1-nitrobenzene (1 g, 0.004 mmol, 1 eq) was added dropwise in the reaction mixture within 15 min. Reaction mixture was stirred at r.t. for 12 hours. After completion of the reaction, the reaction mixture was filtered and the filtrate was concentrated in vacuo to obtain 139.1. (0.8 g, 56.930). MS(ES): m/z 310.12 [M+H]$^+$.

Synthesis of Compound 139.2.

To a mixture of compound 139.1 (1.0 g, 3.23 mmol, 1.0 eq) and 3-methyl-1H-pyrazole (0.4 g, 4.85 mmol, 1.5 eq) in N,N-dimethylformamide (6 mL), Cs$_2$CO$_3$ (3.06 g, 9.69 mmol, 3.0 eq) was added. Reaction mixture was allowed to stir for 4 h at 100° C. After completion of the reaction, the reaction mixture was transferred into water to obtain precipitate which was filtered and washed with water to obtain crude product. This was purified by column chromatography using 100% CH$_2$Cl$_2$ as eluant to obtain pure 139.2 (0.7 g, 69.73%). MS(ES): m/z 311.25 [M+H]$^+$.

Synthesis of Compound 139.3.

To a mixture of compound 139.2 (0.7 g, 2.25 mmol, 1.0 eq) in MeOH (20 mL), 100 palladium on carbon (0.1 g) was added. Hydrogen was purged through the reaction mixture for 4 h. After completion of the reaction, the reaction mixture was filtered through the celite bed and washed with MeOH. The filtrate was concentrated in vacuo to obtain pure 139.3 (0.58 g, 91.72%). MS(ES): m/z 281.43 [M+H]$^+$.

Synthesis of Compound 139.4.

Compound 139.4 was synthesized 139.3 and 13.4 using general procedure A. (Yield: 23.77%). MS(ES): m/z 567.48 [M+H]$^+$.

Synthesis of Compound 139.5.

Compound 139.5 was synthesized from 139.4 and cyclopropanecarboxamide using general procedure B. (Yield: 42.97%). MS(ES): m/z 615.47 [M+H]$^+$.

Synthesis of I-139.

Compound I-139 was synthesized from 139.5 using general procedure C. (Yield: 51.72%). MS(ES): m/z: 531.26 [M+H]$^+$, LCMS purity, 95.07%, HPLC purity 91.48%, 1H NMR (CDCl3, 400 MHz): 13.42 (s, 1H), 8.29 (s, 1H), 8.11 (s, 1H), 7.89-7.87 (d, J=6.4 Hz, 3H), 7.66-7.63 (d, J=8.6 Hz, 1H), 7.01 (t, 1H), 6.32 (s, 2H), 3.38 (s, 3H), 3.10 (s, 3H), 2.43 (s, 3H), 2.13 (s, 1H), 1.13 (bs, 2H), 0.95 (bs, 2H).

Example 140: Synthesis of 3-((5-(cyclopropanecarboxamido)-2-(difluoromethyl)-3H-imidazo[4,5-b]pyridin-7-yl)amino)-2-methoxybenzoic acid, I-140

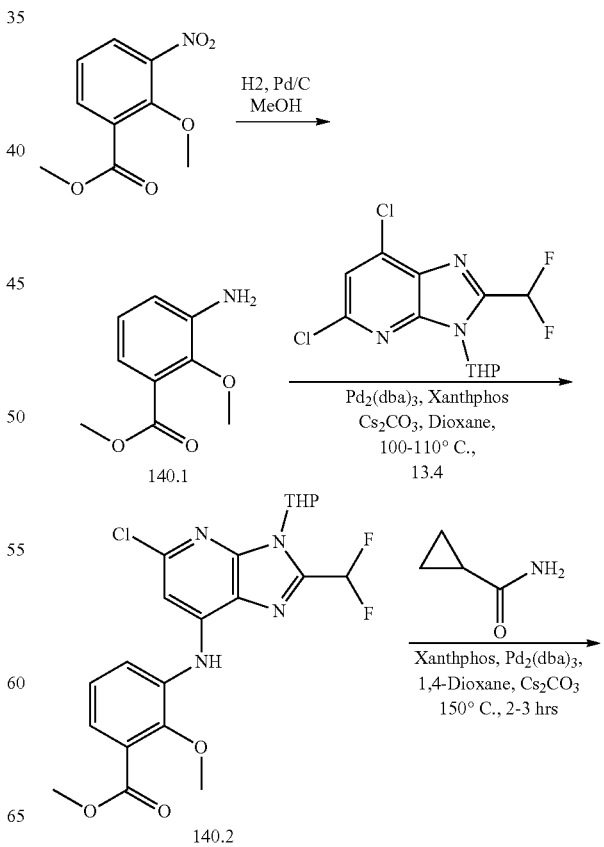

140.1

140.2

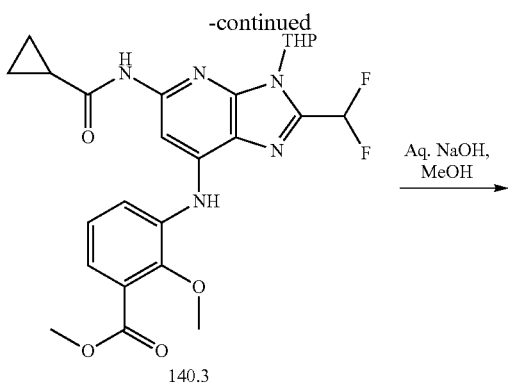

140.3

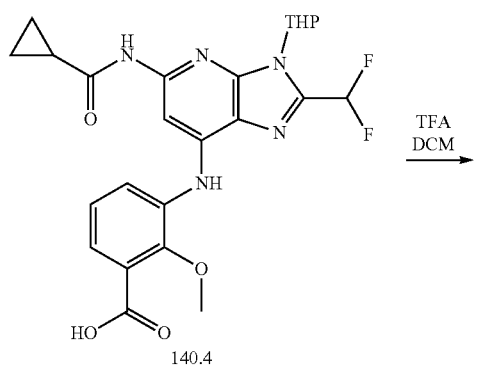

140.4

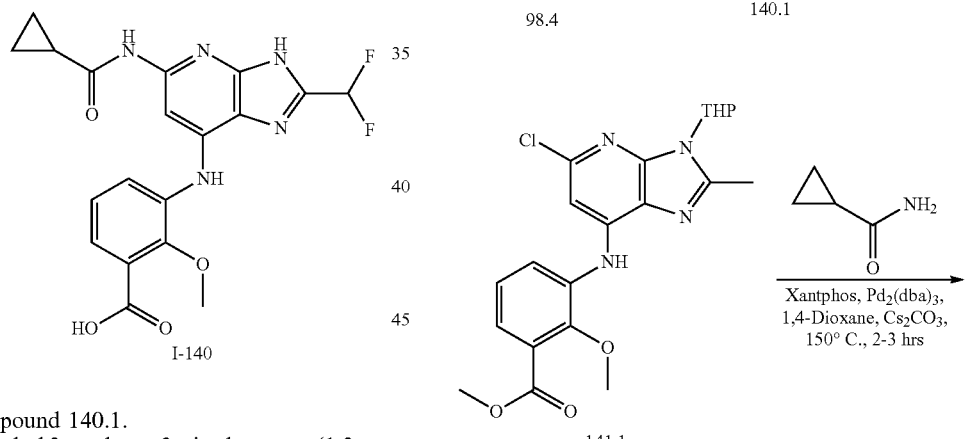

I-140

Synthesis of Compound 140.1.

To a solution of methyl 2-methoxy-3-nitrobenzoate (1.2 g, 5.68 mmol, 1.0 eq) in MeOH (10 mL), 10% palladium in charcoal (0.2 g) was added. Hydrogen was purged through the reaction mixture for 30 min. After completion of the reaction, the reaction mixture was filtered through celite bed and washed with MeOH. Filtrate was concentrated in vacuo to obtain 140.1 (0.8 g, 77.70%). MS(ES): m/z 182.43 [M+H]+.

Synthesis of Compound 140.2.

Compound 140.2 was synthesized from 140.1 and 13.4 using general procedure A. (Yield: 37.95%). MS(ES): m/z 467.38 [M+H]+.

Synthesis of Compound 140.3.

Compound 140.3 was synthesized from 140.2 and cyclopropanecarboxamide using general procedure B. (Yield: 51.87%). MS(ES): m/z 516.49 [M+H]+.

Synthesis of Compound 140.4.

To compound 140.3 (0.070 g, 0.135 mmol, 1.0 eq) in MeOH (0.8 mL), sodium hydroxide (0.027 g, 0.67 mmol, 5.0 eq) in water (0.2 mL) was added. After completion of the reaction, the reaction mixture was concentrated, and then transferred to cold water. pH of the solution was adjusted to 6-7 by using 1N HCl and then extracted with ethyl acetate. Organic layers were combined, dried over anhydrous Na$_2$SO$_4$, filtered and concentrated in vacuo to obtain 140.4 (0.031 g, 52.21%). MS(ES): m/z 502.36 [M+H]+.

Synthesis of I-140.

Compound I-140 was synthesized from 140.4 using general procedure C. (Yield: 93.87%). MS(ES): m/z: 418.34 [M+H]+, LCMS purity, 95.16%, HPLC purity 97.43%, 1H NMR (CDCl3, 400 MHz): 10.66 (s, 1H), 8.45 (s, 1H), 7.59-7.51 (m, 3H), 7.38 (s, 1H), 7.27-7.23 (t, J=7.6 Hz, 2H), 3.87 (s, 3H), 2.01-1.98 (t, J=5.2 Hz, 1H), 0.78-0.76 (m, 4H).

Example 141: Synthesis of 3-((5-(cyclopropanecarboxamido)-2-methyl-3H-imidazo[4,5-b]pyridin-7-yl)amino)-2-methoxybenzoic acid, I-141

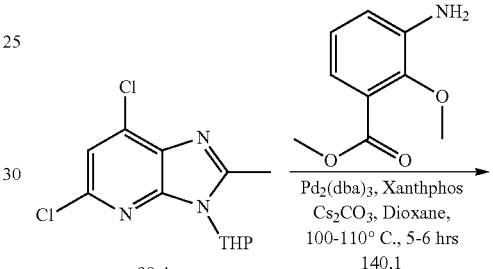

98.4                140.1

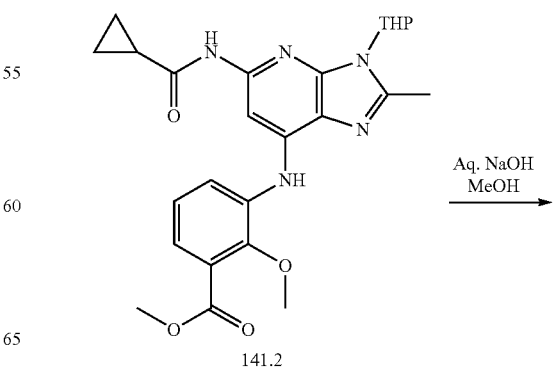

141.1

141.2

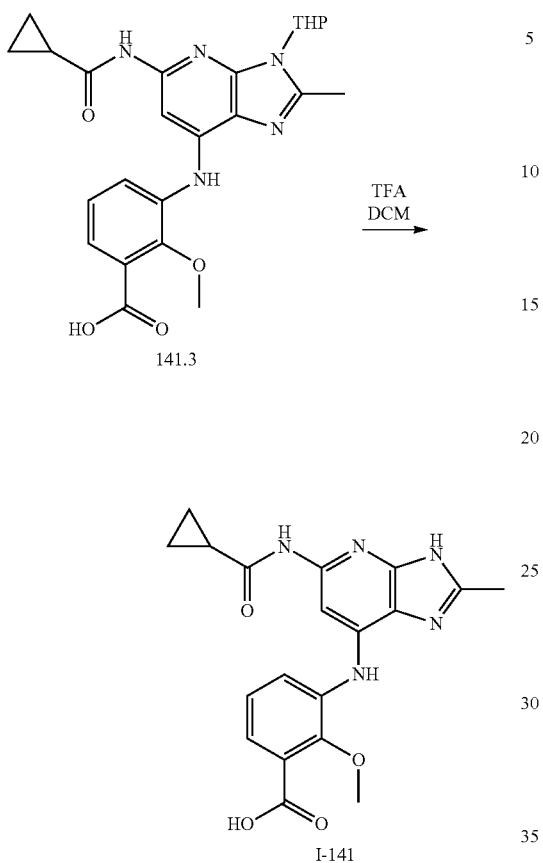

141.3

I-141

Synthesis of Compound 141.1.

Compound 141.1 was synthesized from 11.4 and 140.1 using general procedure A. (Yield: 46.49%). MS(ES): m/z 431.28 [M+H]⁺.

Synthesis of Compound 141.2.

Compound 141.2 was synthesized from 141.1 and cyclopropanecarboxamide using general procedure B. (Yield: 77.02%). MS(ES): m/z 480.56 [M+H]⁺.

Synthesis of Compound 141.3.

To compound 141.2 (0.130 g, 0.27 mmol, 1.0 eq) in MeOH (1.6 mL), sodium hydroxide (0.055 g, 1.35 mmol, 5.0 eq) in water (0.4 mL) was added. After completion of the reaction, the reaction mixture was concentrated, and then transferred to cold water. pH of the solution was adjusted to 6-7 by using 1N HCl and then extracted with ethyl acetate. Organic layers were combined, dried over anhydrous Na₂SO₄, filtered and concentrated in vacuo to obtain 141.3 (0.070 g, 53.22%). MS(ES): m/z 466.27 [M+H]⁺.

Synthesis of I-141.

Compound I-141 was synthesized from 141.3 using general procedure C. (Yield: 88.49%). MS(ES): m/z: 382.33 [M+H]⁺, LCMS purity, 100%, HPLC purity 99.84%, 1H NMR (DMSO, 400 MHz): 13.11 (s, 1H), 10.80 (s, 1H), 8.56 (s, 1H), 7.76 (s, 1H), 7.59-7.57 (d, J=8 Hz, 1H), 7.53-7.51 (d, J=8.4 Hz, 1H), 7.28-7.24 (t, J=8 Hz, 1H), 3.75 (s, 3H), 2.70 (s, 3H), 1.99 (s, 1H), 0.79 (bs, 4H).

Example 142: Synthesis of N-(2-(difluoromethyl)-7-((2-methoxy-4-(1-methyl-1H-imidazol-5-yl)phenyl)amino)-3H-imidazo[4,5-b]pyridin-5-yl)cyclopropanecarboxamide, I-142

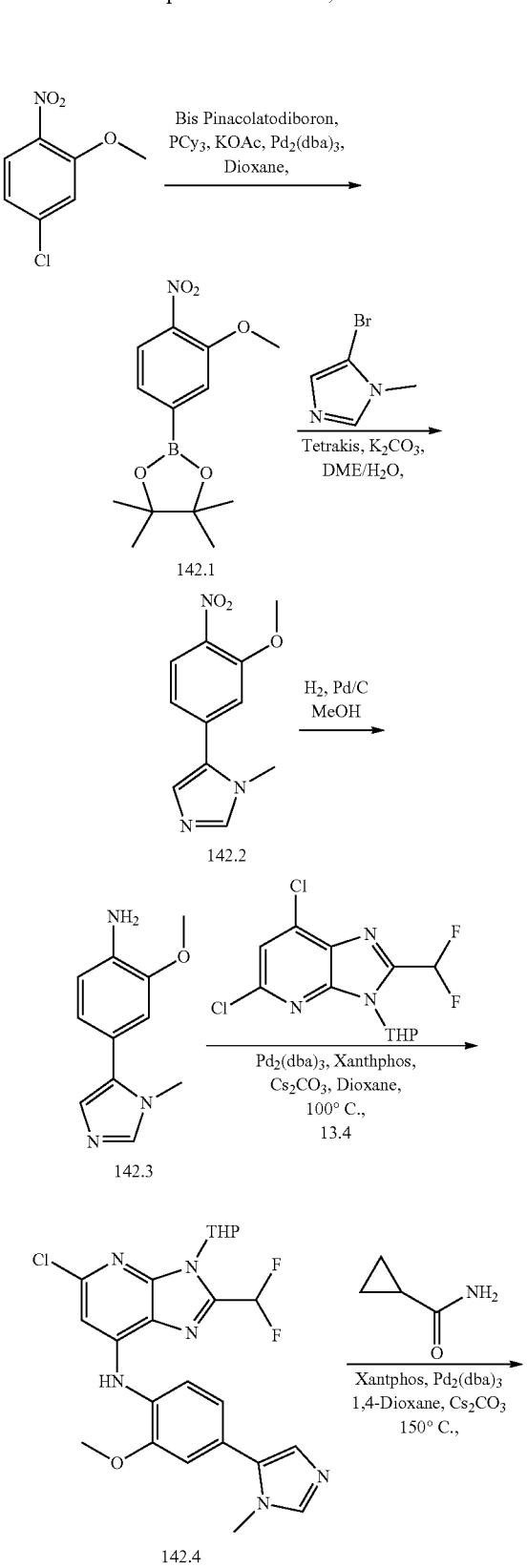

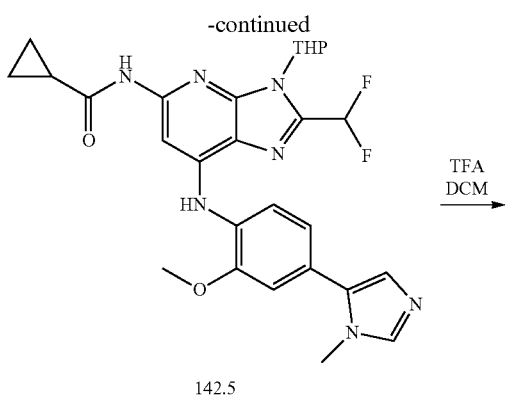

142.5

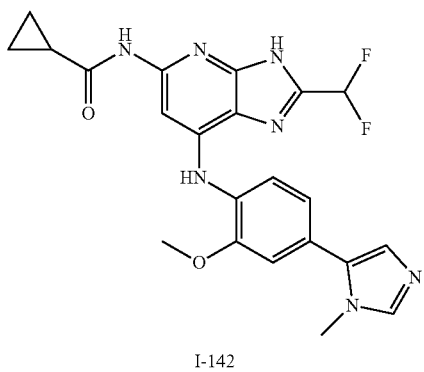

I-142

Synthesis of Compound 142.1.

To a solution of 4-chloro-2-methoxy-1-nitrobenzene (15 g, 79.97 mmol, 1.0 eq), in 1,4-dioxane (150 mL) was added Bis Pinacolatodiboron (30.56 g, 12.03 mmol, 1.5 eq). The reaction mixture was degassed by argon for 30 min. Pd$_2$(dba)$_3$ (7.3 g, 8.02 mmol, 0.1 eq), potassium acetate (2.6 g, 26.47 mmol, 3.3 eq), Tricyclohexylphosphine(4.5 g, 16.04 mmol, 0.2 eq) were added into reaction mixture and again degassed by argon for 30 min. Further reaction mixture was stirred at 85° C. for 3 h. After completion of reaction, water was added to reaction mixture and extracted with ethyl acetate. Organic layers were combined, dried over Na$_2$SO$_4$ and concentrated in vacuo to obtain crude product. This was purified by column chromatography and compound was eluted in 20% ethyl acetate in hexane to obtain pure 142.1 (12 g, 53.77%). MS(ES): m/z 280.10 [M+H]$^+$.

Synthesis of Compound 142.2.

To a solution of 142.1 (12 g, 43.00 mmol, 1.0 eq) in mixture of Dimethoxyethane 90 mL) and water (30 mL) was added 5-bromo-1-methyl-1H-imidazole (8.31 g, 51.59 mmol, 1.2 eq) The reaction mixture was degassed by argon for 30 min. Tetrakis(triphenylphosphine)palladium (4.96 g, 4.30 mmol, 0.1 eq), potassium carbonate (19.6 g, 0.141 mmol, 3.3 eq,) were added into reaction mixture and again degassed by argon for 30 min. Further reaction mixture was stirred at 150° C. for 5 h. After completion of reaction, water was added to reaction mixture and extracted with ethyl acetate. Organic layers were combined, dried over Na$_2$SO$_4$ and concentrated in vacuo to obtain crude product. This was purified by column chromatography and compound was eluted in 20% ethyl acetate in hexane to obtain pure 142.2 (2 g, 19.94%). MS(ES): m/z 234.23 [M+H]$^+$.

Synthesis of Compound 142.3.

To a solution of 142.2 (2 g, 8.58 mmol, 1.0 eq) in MeOH (50 mL), 10% Pd/C (1 g) was added. Hydrogen was purged through reaction mixture for 2-3 h. Upon completion, reaction mixture was filtered through celite-bed and washed with MeOH. Filtrate was concentrated in vacuo to obtain 142.3 (0.750 g, 43.03%). MS(ES): m/z 204.25 [M+H]$^+$.

Synthesis of Compound 142.4.

Compound 142.4 was synthesized using from 13.4 and 142.3 using general procedure A (Yield: 21.96%). MS(ES): m/z 489.92 [M+H]$^+$ Synthesis of Compound 142.5.

Compound 142.5 was synthesized from 142.4 and cyclopropanecarboxamide using general procedure B. (Yield: 45.48%). MS(ES): m/z 538.57 [M+H]$^+$.

Synthesis of I-142.

Compound I-142 was synthesized from 142.5 using general procedure C. (Yield: 11.86%). MS(ES): m/z: 454.4 [M+H]$^+$, LCMS purity, 100%, HPLC purity 100%, 1H NMR (DMSO, 400 MHz): 13.52 (s, 1H), 10.61 (s, 1H), 8.13 (s, 1H), 7.89 (s, 1H), 7.79 (s, 1H), 7.50-7.48 (d, J=8 Hz, 1H), 7.36 (s, 1H), 7.23-7.21 (d, J=8.8 Hz, 2H), 7.17-7.15 (d, J=8 Hz, 1H), 3.91 (s, 3H), 3.77 (s, 3H), 2.03 (s, 1H), 0.78 (s, 4H).

Example 143: Synthesis of 6-((2-(difluoromethyl)-7-((2-methoxy-4-(1-methyl-1H-imidazol-5-yl)phenyl)amino)-3H-imidazo[4,5-b]pyridin-5-yl)amino)picolinonitril, I-143

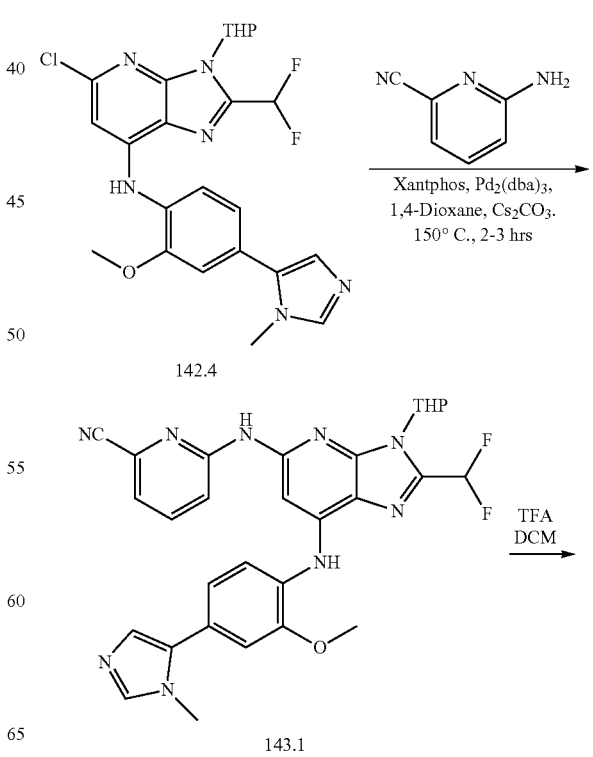

142.4

143.1

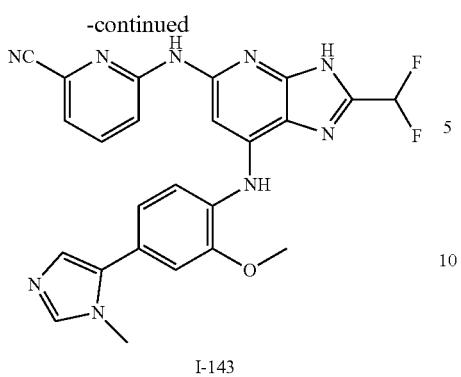

I-143

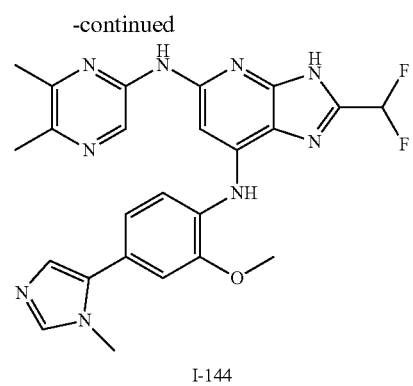

I-144

Synthesis of Compound 143.1.

Compound 143.1 was synthesized from 142.4 and 6-aminopicolinonitrile using general procedure A (Yield: 42.77%). MS(ES): m/z 572.69 [M+H]⁺.

Synthesis of I-143.

Compound I-143 was synthesized from 143.1 using general procedure C. (Yield: 58.63%). MS(ES): m/z: 488.36 [M+H]⁺, LCMS purity: 99.21%, HPLC purity: 98.76%, 1H NMR (DMSO, 400 MHz): 13.53 (s, 1H), 10.13 (s, 1H), 8.14-8.12 (d, J=8.4 Hz, 1H), 8.05 (s, 1H), 7.89-7.85 (t, J=7.6 Hz, 1H), 7.79 (s, 1H), 7.67-7.65 (d, J=8 Hz, 1H), 7.48-7.46 (d, J=6.8 Hz, 2H), 7.24-7.20 (t, J=7.6 Hz, 2H), 7.23 (t, 1H), 7.14 (s, 1H), 3.96 (s, 3H), 3.76 (s, 3H).

Synthesis of Compound 144.1.

Compound was synthesized from 5,6-dimethylpyrazin-2-amine and 142.4 using general procedure B to obtain 1.4. (Yield: 63.70%). MS (ES): m/z 576.62 [M+H]⁺.

Synthesis of Compound I-144.

Compound I-144 was synthesized from 144.1 using general procedure C. (Yield: 39.04%). MS(ES): m/z: 492.36 [M+H]⁺, LCMS purity: 96.07%, HPLC purity: 99.05%, 1H NMR (DMSO, 400 MHz): 13.41 (s, 1H), 9.68 (s, 1H), 8.97 (s, 1H), 7.98 (s, 1H), 7.74-7.71 (d, J=12 Hz, 1H), 7.62-7.59 (d, J=8 Hz, 1H), 7.40-7.34 (t, J=10.8 Hz, 2H), 7.23-7.10 (m, 3H), 3.94 (s, 3H), 3.73 (s, 3H), 3.73 (s, 3H), 2.37 (s, 3H).

Example 144: Synthesis of 2-(difluoromethyl)-N5-(5,6-dimethylpyrazin-2-yl)-N7-(2-methoxy-4-(1-methyl-1H-imidazol-5-yl)phenyl)-3H-imidazo[4,5-b]pyridine-5,7-diamine, I-144

Example 145: Synthesis of N-(2-methyl-7-((4-(4-methyl-1H-pyrazol-1-yl)-2-(N-methylmethylsulfonamido)phenyl)amino)-3H-imidazo[4,5-b]pyridin-5-yl)cyclopropanecarboxamide, I-145

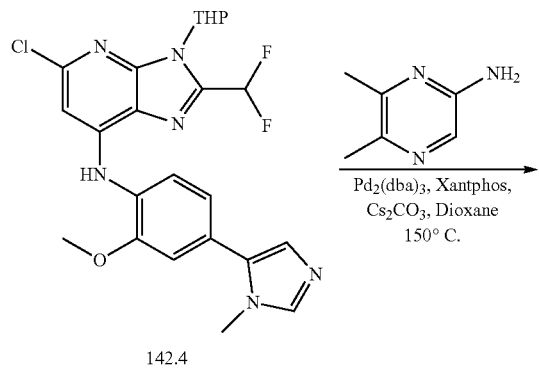

142.4

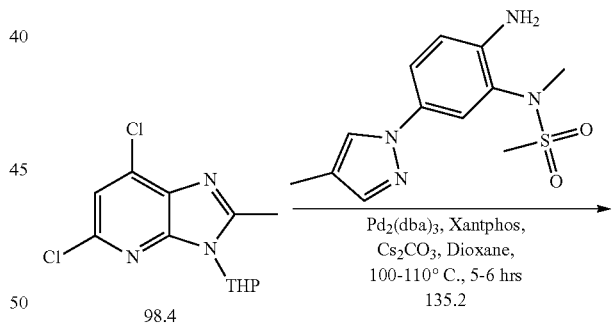

98.4

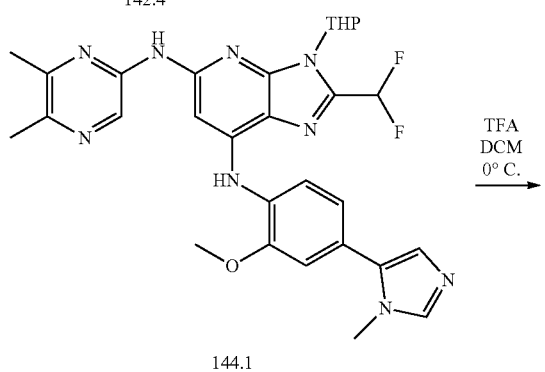

144.1

145.1

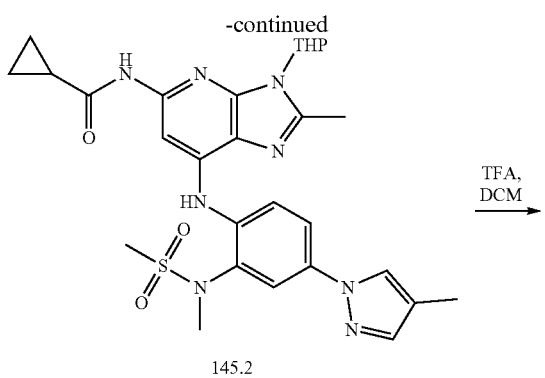

Synthesis of Compound 145.1.

Compound 145.1 was synthesized from 98.4 and 135.2 using general procedure A. (Yield: 26.45%). MS(ES): m/z 531.38 [M+H]$^+$.

Synthesis of Compound 145.2.

Compound 145.1 was synthesized from 145.1 and cyclopropanecarboxamide using general procedure B. (Yield: 48.85%). MS(ES): m/z 579.43 [M+H]$^+$.

Synthesis of Compound I-145.

Compound I-145 was synthesized from 145.2 using general procedure C. (Yield: 58.50%). MS(ES): m/z: 495.36 [M+H]$^+$, LCMS purity, 98.27%, HPLC purity 95.07%, 1H NMR (DMSO-d6, 400 MHz): 10.47 (s, 1H), 8.36 (s, 1H), 8.02-8.01 (d, J=2 Hz, 1H), 7.89-7.82 (m, 2H), 7.76 (s, 1H), 7.64 (s, 1H), 7.60 (s, 1H), 3.26 (s, 3H), 3.15 (s, 3H), 2.49 (s, 3H), 2.09 (s, 3H), 1.98 (s, 1H), 0.76-0.69 (m, 4H).

Example 146: Synthesis of N-(2-(difluoromethyl)-7-((3-(1,4-dimethyl-1H-1,2,3-triazol-5-yl)-2-methoxyphenyl)amino)-3H-imidazo[4,5-b]pyridin-5-yl)cyclopropanecarboxamide, I-146

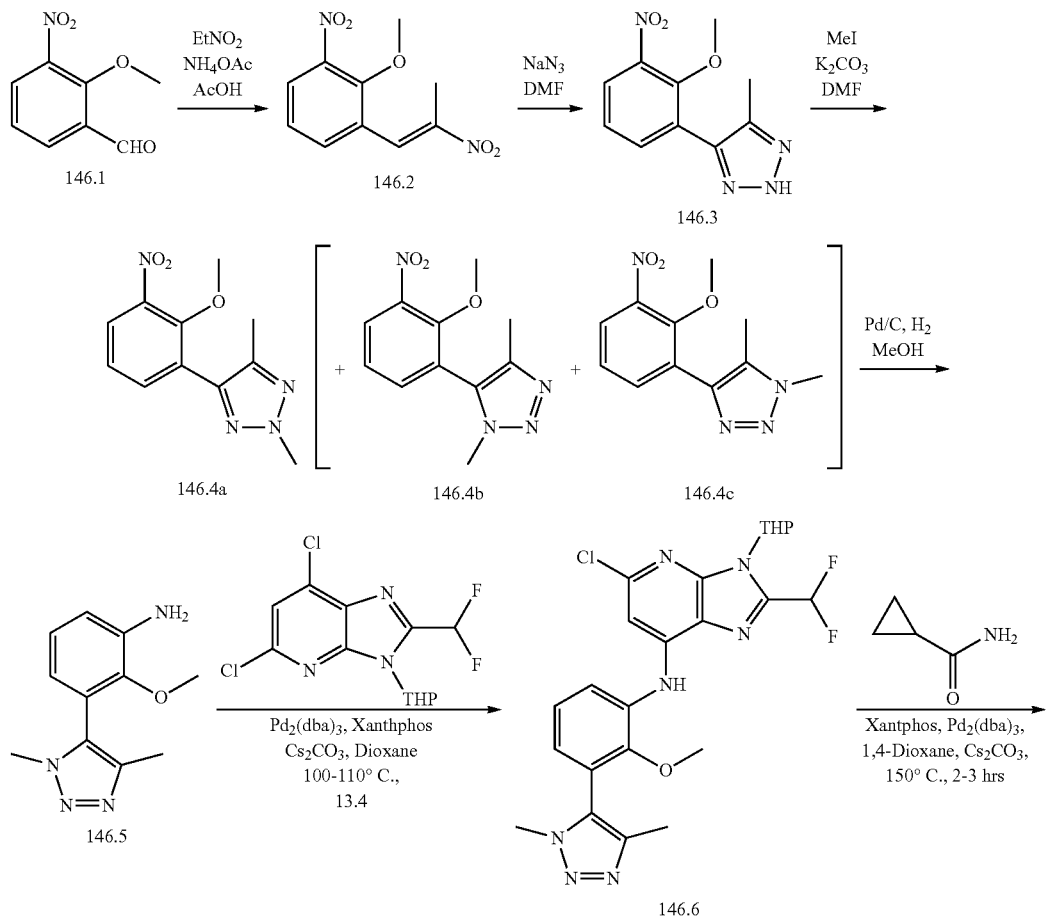

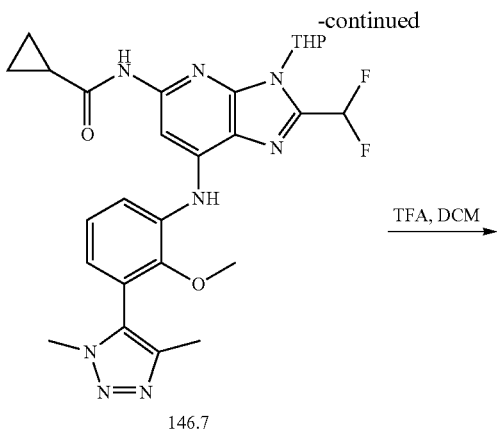

146.7

TFA, DCM →

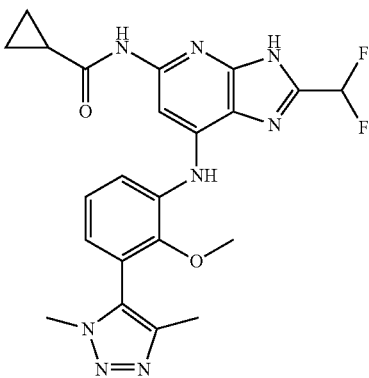

I-146

Synthesis of Compound 146.2.

To a solution of compound 146.1 (7 g, 38.6 mmol, 1.0 eq) in acetic acid (70 mL), nitroethane (3.4 g, 46.4 mmol, 1.2 eq) and ammonium acetate (4.4 g, 58.3 mmol, 1.5 eq) was added. Reaction mixture was stirred at 80° C. for 2 h. After completion of the reaction, the reaction mixture was transferred to water and extracted with ethyl acetate. Organic layer combined, dried over anhydrous sodium sulfate, filtered and concentrated under reduced pressure to obtain pure 146.2 (5 g, 54.32%). MS(ES): m/z 239.56 [M+H]$^+$.

Synthesis of Compound 146.3.

To a solution of compound 146.2 (5 g, 21.08 mmol, 1.0 eq) in N,N-dimethylformamide (50 mL), sodium azide (4.09 g, 63.02 mmol, 3.0 eq) was added. Reaction mixture was stirred at 60° C. for 1 h. After completion of the reaction, the reaction mixture was transferred to water and extracted with ethyl acetate. Organic layer combined, dried over anhydrous sodium sulfate, filtered and concentrated under reduced pressure to obtain the crude material. This was further purified by column chromatography using 5% methanol in dichloromethane to obtain pure 146.3 (4.3 g, 87.46%). MS(ES): m/z 235.48 [M+H]$^+$.

Synthesis of Compound 146.4a.

To a solution of compound 146.3 (4.3 g, 18.3 mmol, 1.0 eq) in N,N'-dimethylformamide (43 mL), potassium carbonate (5.07 g, 36.7 mmol, 2.0 eq) was added. Reaction mixture was stirred at room temperature for 15 min. Then, methyl iodide (3.1 g, 22.0 mmol, 1.2 eq) was added dropwise. Reaction mixture was stirred at room temperature for 3 h. After completion of the reaction, the reaction mixture was transferred to water and extracted with ethyl acetate. Organic layer combined, dried over anhydrous sodium sulfate, filtered and concentrated under reduced pressure to obtain the crude material. This was further purified by column chromatography using 3% methanol in dichloromethane as eluant to obtain pure 146.4a (0.5 g, 10.97%) along with pure 146.4b and pure 146.4c. MS(ES): m/z 249.71 [M+H]$^+$. [00608]

Synthesis of Compound 146.5.

To a solution of compound 146.4a (0.130 g, 0.05 mmol, 1.0 eq) in methanol, 10% palladium on charcoal (0.04 g) was added. Hydrogen was purged through the reaction for 18 h. After completion of the reaction, the reaction mixture was filtered through celite bed and washed with methanol. Filtrate was concentrated under reduced pressure to obtain the crude material. This was further purified by column chromatography using 2.5% methanol in dichloromethane as eluant to obtain pure 146.5 (0.110 g, 96.24%). MS(ES): m/z 219.54 [M+H]$^+$.

Synthesis of Compound 146.6.

Compound 146.6 was synthesized from 146.5 and 13.4 using general procedure A. (Yield: 35.44%). MS(ES): m/z 504.21 [M+H]$^+$.

Synthesis of Compound 146.7.

Compound 146.7 was synthesized from 146.6 and cyclopropanecarboxamide using general procedure B. (Yield: 55.73%). MS(ES): m/z 553.48 [M+H]$^+$.

Synthesis of Compound I-146.

Compound I-146 was synthesized from 146.7 using general procedure C. (Yield: 53.62%). MS(ES): m/z: 469.37 [M+H]$^+$, LCMS purity, 100.00%, HPLC purity 98.46%, 1H NMR (DMSO, 400 MHz): 10.56 (s, 1H), 8.23 (s, 1H), 7.68 (s, 1H), 7.62-7.60 (d, J=7.6 Hz, 1H), 7.47-7.45 (d, J=7.2 Hz, 1H), 7.25-7.22 (t, J=8 Hz, 1H), 7.10 (s, 1H), 6.83 (bs, 1H), 3.85 (s, 3H), 3.69 (s, 3H), 2.47 (s, 3H), 2.01 (s, 1H), 0.76-0.76 (m, 4H).

Example 147: N-(2-(difluoromethyl)-7-((4-(1-methyl-1H-imidazol-5-yl)-2-(N-methylmethylsulfonamido)phenyl)amino)-3H-imidazo[4,5-b]pyridin-5-yl)cyclopropanecarboxamide, I-147

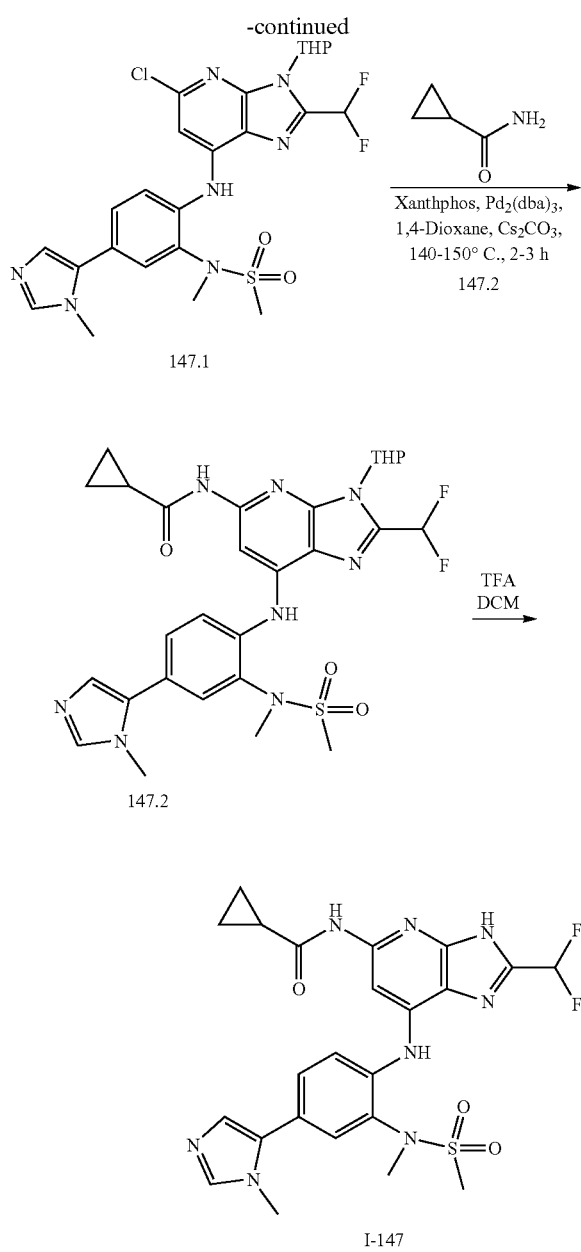

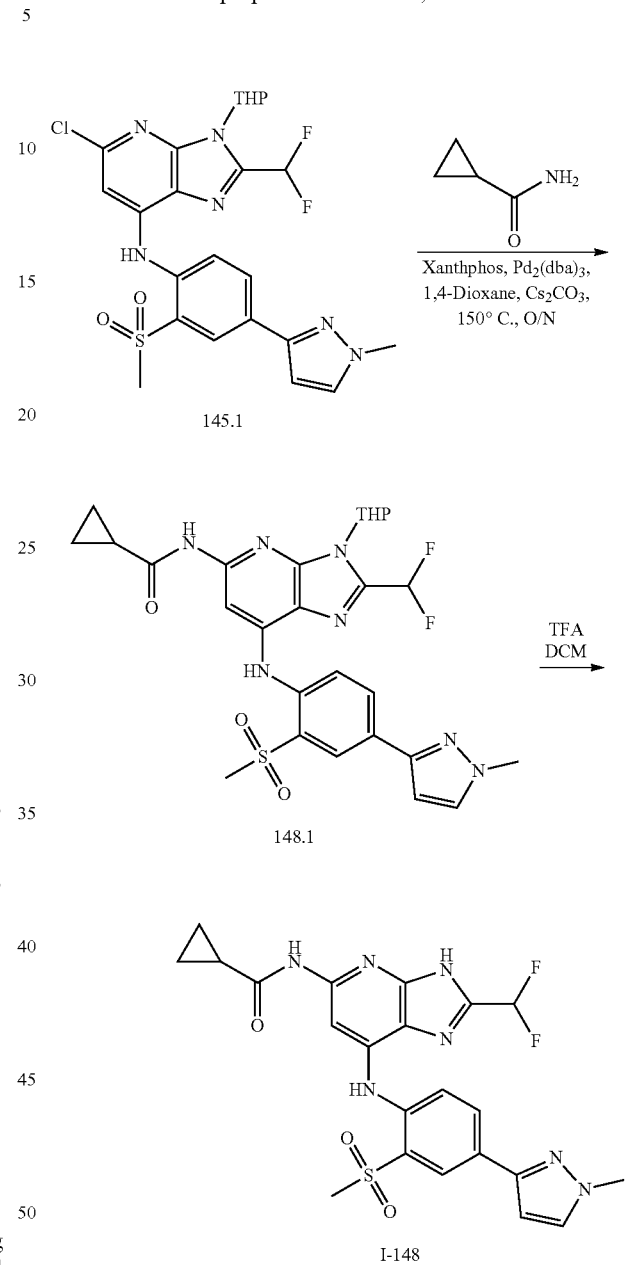

Example 148: Synthesis of N-(2-(difluoromethyl)-7-((4-(1-methyl-1H-pyrazol-3-yl)-2-(methylsulfonyl)phenyl)amino)-3H-imidazo[4,5-b]pyridin-5-yl)cyclopropanecarboxamide, I-148

Synthesis of Compound 147.1

Compound was synthesized from 13.4 and 212.1 using general procedure A. (Yield: 17.79%). MS(ES): m/z 567.84 [M+H]$^+$.

Synthesis of Compound 147.2.

Compound 147.2 was synthesized from 147.1 and cyclopropanecarboxamide using general procedure B. (Yield: 47.88%). MS(ES): m/z 615.48 [M+H]$^+$.

Synthesis of I-147.

Compound I-147 was synthesized from using general procedure C. (Yield: 66.84%). MS(ES): m/z: 531.31 [M+H]$^+$, LCMS purity, 94.81%, HPLC purity 95.06%, 1H NMR (DMSO-d6, 400 MHz): 13.59 (s, 1H), 10.67 (s, 1H), 8.22 (s, 1H), 7.96 (s, 1H), 7.78-7.68 (m, 4H), 7.58-7.57 (d, J=7.6 Hz, 1H), 7.26 (t, 1H), 3.77 (s, 3H), 3.27 (s, 3H), 3.13 (s, 3H), 2.00 (s, 1H), 0.79-0.78 (d, J=5.6 Hz, 4H).

Synthesis of Compound 148.1.

Compound 148.1 was synthesized from 145.1 and cyclopropanecarboxamide using general procedure B. (Yield: 42.79%). MS(ES): m/z 589.64 [M+H]$^+$.

Synthesis of I-148.

Compound I-148 was synthesized from 148.1 using general procedure C. (Yield: 91.75%). MS(ES): m/z: 502.36 [M+H]$^+$, LCMS purity, 98.50%, HPLC purity 97.87%, 1H NMR (DMSO, 400 MHz): 8.93 (s, 1H), 8.36-8.35 (d, J=1.6 Hz, 1H), 8.16-8.13 (d, J=8 Hz 1H), 7.96 (s, 1H), 7.81 (s, 1H), 7.78 (s, 1H), 7.41 (s, 1H), 7.27 (t, 1H), 6.83-6.83 (s, 1H), 3.92 (s, 3H), 3.26 (s, 3H), 1.96 (s, 1H) 0.84 (S, 4H).

Example 149: Synthesis of N-(7-((3-(3,5-dimethyl-1H-1,2,4-triazol-1-yl)-2-methoxyphenyl)amino)-2-methyl-3H-imidazo[4,5-b]pyridin-5-yl)cyclopropanecarboxamide, I-149

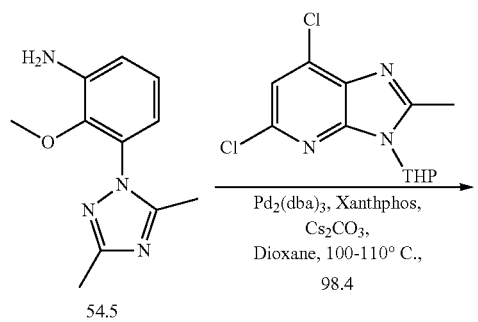

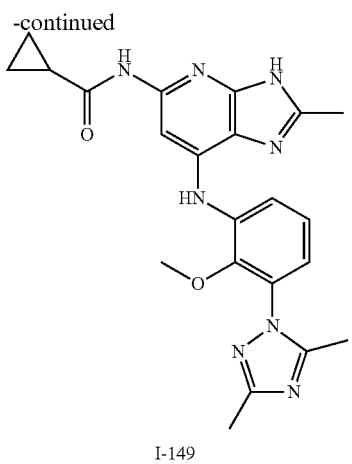

I-149

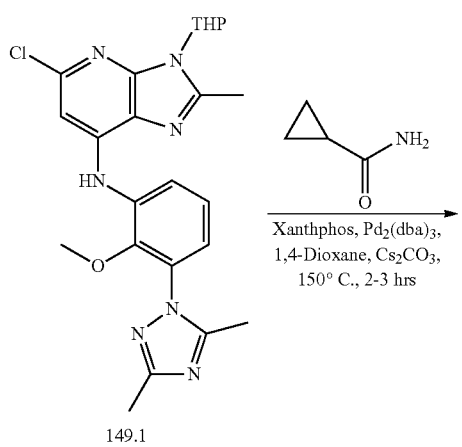

Synthesis of Compound 149.1.
Compound 149.1 was synthesized from 11.4 and 54.5 using general procedure A. (Yield: 23.99%). MS(ES): m/z 468.52 [M+H]$^+$.

Synthesis of Compound 149.2.
Compound 149.2 was synthesized from 149.1 and cyclopropanecarboxamide using general procedure B. (Yield: 78.00%). MS(ES): m/z 517.43 [M+H]$^+$.

Synthesis of 149.
Compound I-149 was synthesized from 149.2 using general procedure C. (Yield: 69.36%). MS(ES): m/z: 433.42 [M+H]$^+$, LCMS purity, 100%, HPLC purity 98.17%, 1H NMR (DMSO, 400 MHz): 12.32 (s, 1H), 10.40 (s, 1H), 8.21 (s, 1H), 7.60-7.50 (m, 2H), 7.29-7.25 (m, 1H), 7.16-7.14 (d, J=8 Hz, 1H), 3.35 (s, 3H), 2.46 (s, 3H), 2.27 (s, 3H), 2.24 (s, 3H), 1.98-1.95 (t, J=5.6 Hz, 1H) 0.74-0.73 (d, J=5.6 Hz, 4H).

Example 150: Synthesis of N-(7-((4-(methoxymethyl)-2-(N-methylmethylsulfonamido)phenyl)amino)-2-methyl-3H-imidazo[4,5-b]pyridin-5-yl)cyclopropanecarboxamide, I-150

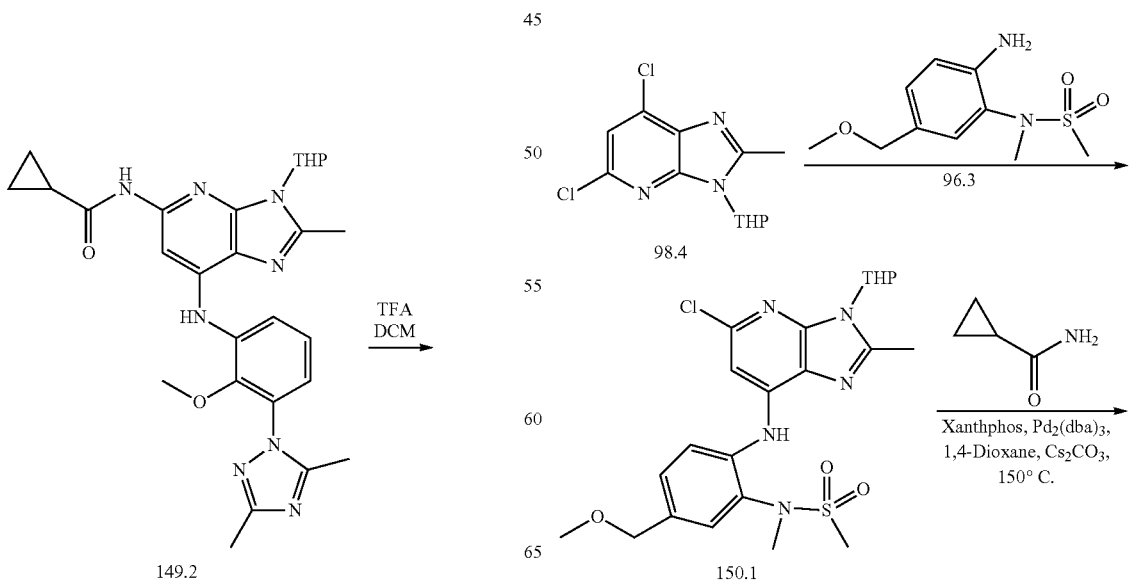

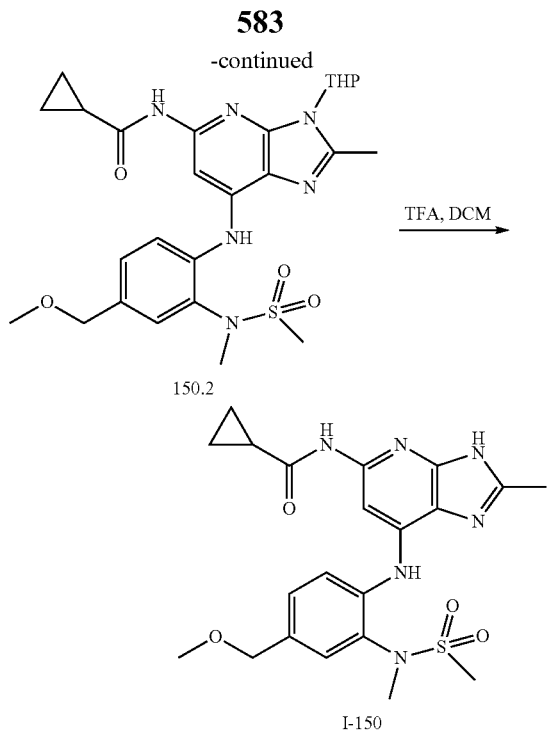

150.2

I-150

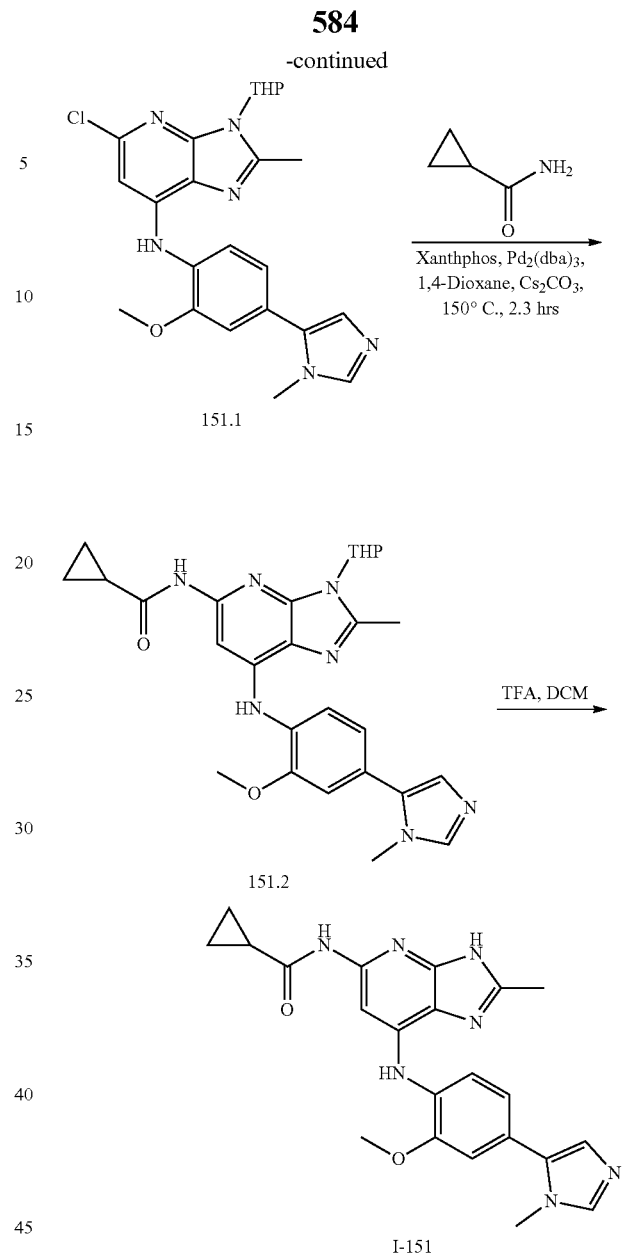

Synthesis of Compound 150.1.

Compound 150.1 was synthesized from 98.4 and 96.3 using general procedure A (Yield: 30.81%). MS(ES): m/z 495.01 [M+H]⁺.

Synthesis of Compound 150.2.

Compound 150.2 was synthesized from 150.1 and cyclopropanecarboxamide using general procedure B. (Yield: 16.69%). MS(ES): m/z 543.66 [M+H]⁺.

Synthesis of I-150.

Compound I-150 was synthesized from 150.2 using general procedure C. (Yield: 69.93%). MS(ES): m/z: 459.46 [M+H]⁺, LCMS purity, 100%, HPLC purity 99.52%, 1H NMR (DMSO, 400 MHz): 12.34 (s, 1H), 10.44 (s, 1H), 7.84-7.80 (d, J=15.6 Hz, 2H), 7.57-7.55 (d, J=15.6 Hz, 2H), 7.36 (s, 1H), 4.43 (s, 3H), 3.19 (s, 3H), 3.09 (s, 3H), 2.55 (s, 2H), 2.47 (s, 3H), 1.96 (s, 1H), 0.85 (s, 4H).

Example 151: Synthesis of N-(7-(((2-methoxy-4-(1-methyl-1H-imidazol-5-yl)phenyl)amino)-2-methyl-3H-imidazo[4,5-b]pyridin-5-yl)cyclopropanecarboxamide, I-151

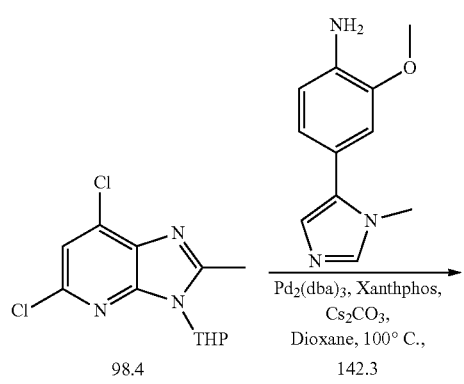

Synthesis of Compound 151.1.

Compound 151.1 was synthesized from 98.4 and 142.3 using general procedure A. (Yield: 31.59%). MS(ES): m/z 553.94 [M+H]⁺.

Synthesis of Compound 151.2.

Compound was synthesized from 151.1 and cyclopropanecarboxamide using general procedure B. (Yield: 13.55%). MS(ES): m/z 502.59 [M+H]⁺.

Synthesis of I-151.

Compound I-151 was synthesized from 151.2 using general procedure (Yield: 72.09%). MS(ES): m/z: 418.3 [M+H]⁺, LCMS purity, 95.14%, HPLC purity 96.17%, 1H NMR (DMSO, 400 MHz): 12.37 (s, 1H), 10.50-10.45 (d, J=18 Hz, 1H), 7.93 (s, 1H), 7.72-7.70 (d, J=8.8 Hz, 2H), 7.52-7.50 (d, J=8 Hz, 1H), 7.41 (s, 1H), 7.20-7.10 (m, 2H), 3.94 (s, 3H), 3.74 (s, 3H), 3.35 (s, 3H), 2.00 (s, 1H) 0.78-0.75 (d, J=9.6 Hz, 4H).

Example 152: Synthesis of N5-(5,6-dimethylpyrazin-2-yl)-N7-(2-methoxy-4-(1-methyl-1H-imidazol-5-yl)phenyl)-2-methyl-3H-imidazo[4,5-b]pyridine-5,7-diamine, I-152

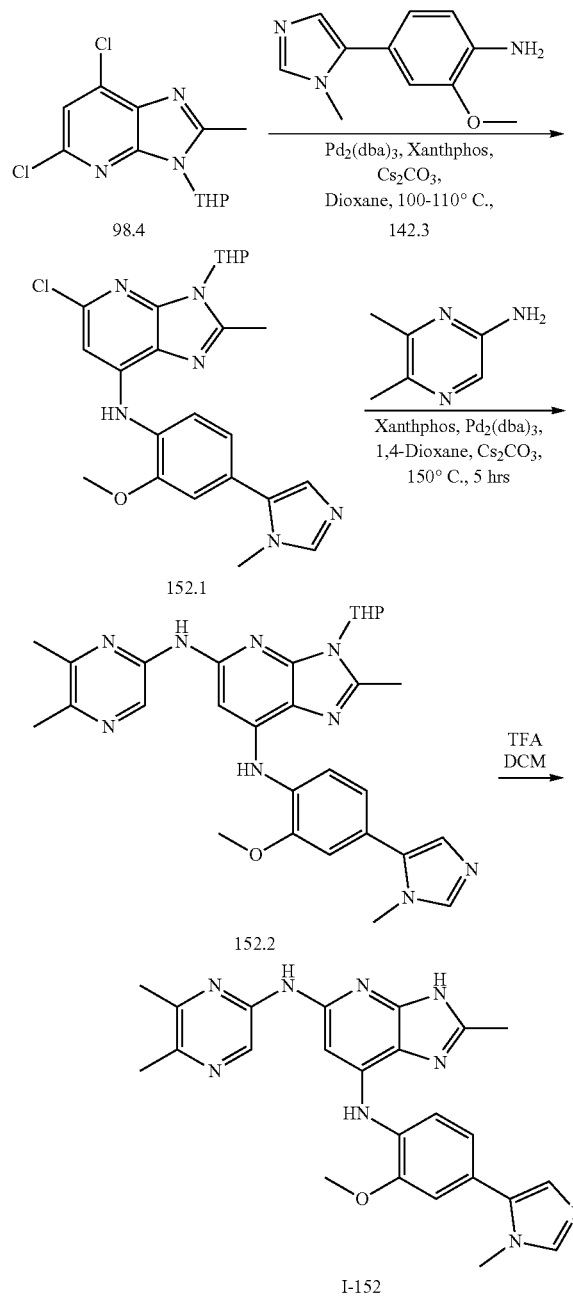

Synthesis of Compound 152.1.

Compound 152.1 was synthesized from 98.4 and 142.3 using general procedure A. (Yield: 33.65%). MS(ES): m/z 453.59 [M+H]$^+$.

Synthesis of Compound 152.2.

Compound 152.2 was synthesized from 5,6-dimethylpyrazin-2-amine and 152.1 using general procedure B. (Yield: 33.57%). MS(ES): m/z 540.25 [M+H]$^+$.

Synthesis of I-152.

Compound I-152 was synthesized from 152.2 using general procedure C. (Yield: 74.04%). MS(ES): m/z: 456.4 [M+H]$^+$, LCMS purity, 100.00%, HPLC purity 96.54%, 1H NMR (DMSO, 400 MHz): 12.29 (s, 1H), 9.47 (s, 1H), 8.85 (s, 1H), 7.70 (s, 1H), 7.64-7.62 (d, J=8 Hz, 2H), 7.46-7.31 (m, 1H), 7.18 (s, 1H), 7.11-7.06 (t, J=8 Hz, 1H), 3.94 (s, 3H), 3.72 (s, 3H), 2.54 (s, 3H), 2.45 (s, 3H), 2.36-2.36 (d, J=3.6 Hz, 3H).

Example 153: Synthesis of N-(2-methyl-7-((4-(1-methyl-1H-imidazol-5-yl)-2-(N-methylmethylsulfonamido)phenyl)amino)-3H-imidazo[4,5-b]pyridin-5-yl)cyclopropanecarboxamide, I-153

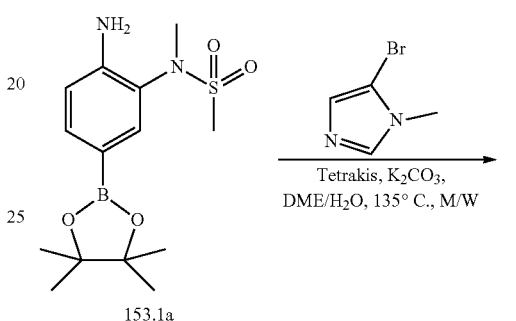

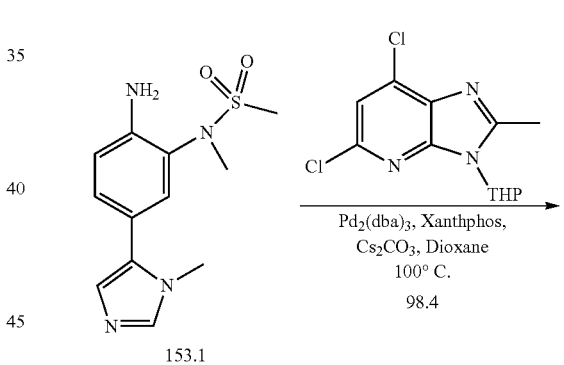

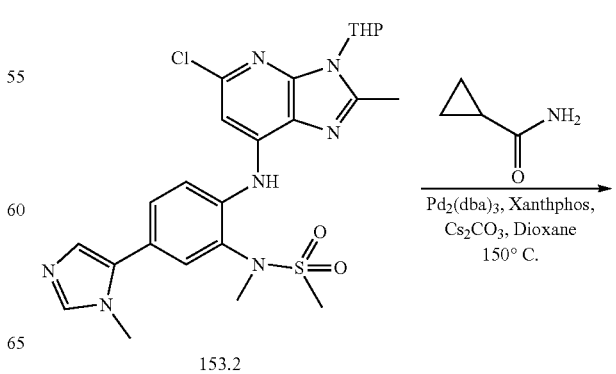

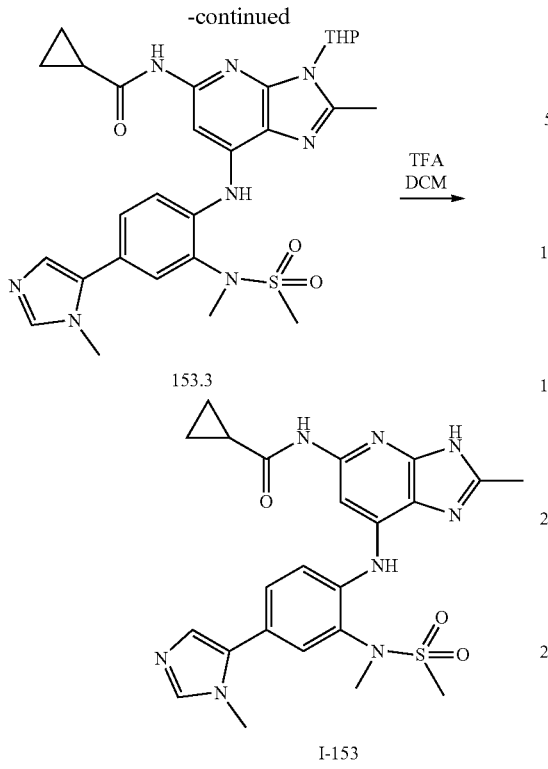

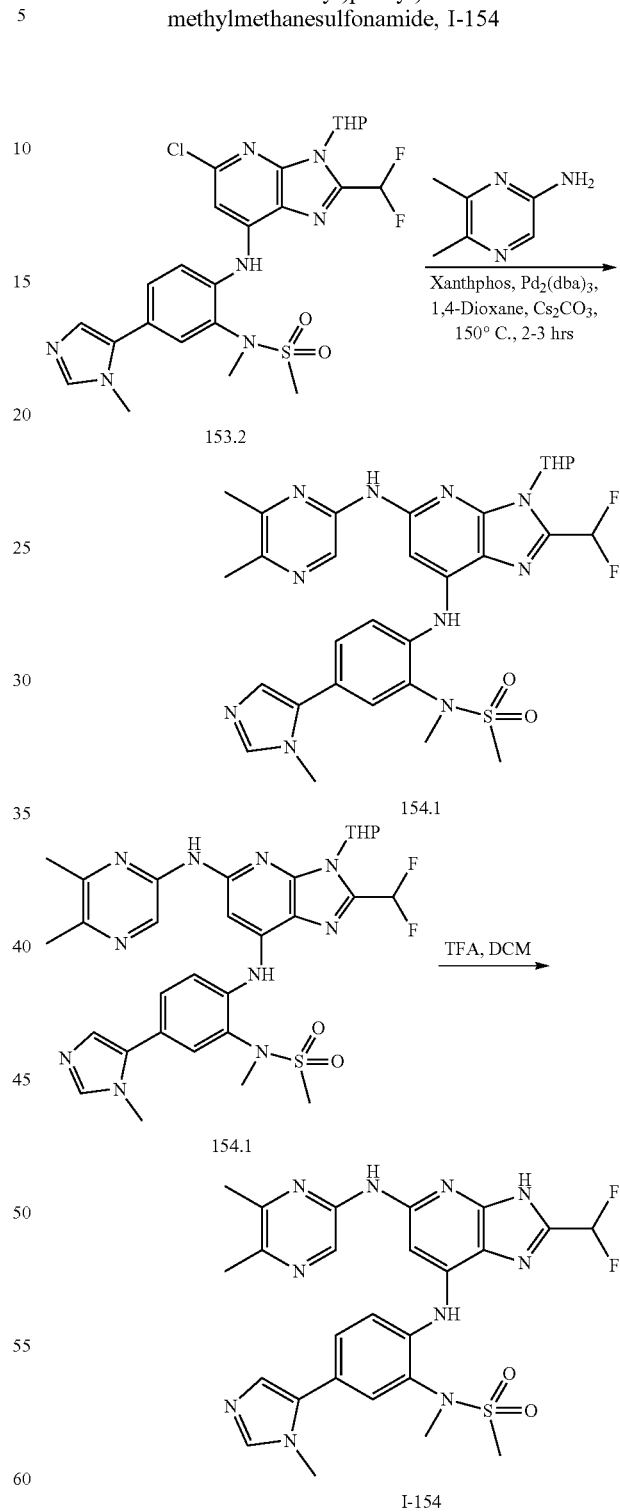

Example 154: Synthesis of N-(2-((2-(difluoromethyl)-5-((5,6-dimethylpyrazin-2-yl)amino)-3H-imidazo[4,5-b]pyridin-7-yl)amino)-5-(1-methyl-1H-imidazol-5-yl)phenyl)-N-methylmethanesulfonamide, I-154

Synthesis of Compound 153.1.

A mixture of 153.1a (prepared from 135.1a by nitro reduction and boronation with $B_2pin_2$ catalyzed by tetrakis Pd) (1 g, 3.07 mmol, 1.0 eq), 5-bromo-1-methyl-1H-imidazole (0.74 g, 4.60 mmol, 1.5 eq), Tetrakis(triphenylphosphine)palladium(0) (0.177 g, 1.53 mmol, 0.05 eq) and potassium carbonate (1.27 g, 9.2 mmol, 3.0 eq) in mixture of Dimethoxyethane (25 mL) and water (09 mL) was degassed with argon for 30 min. Further reaction mixture was irradiated under microwave at 135° C. for 1 h. Upon completion, reaction mixture was cooled to r.t., transferred in water and extracted with ethyl acetate. Combined organic layer dried over $Na_2SO_4$ and concentrated in vacuo to obtain crude product. This was purified by column chromatography and compound was eluted in 15% ethyl acetate in hexane to obtain pure 153.1 (0.500 g, 58.18%). MS(ES): m/z 281.35 $[M+H]^+$.

Synthesis of Compound 153.2.

Compound 153.2 was synthesized from 153.1 and 98.4 using general procedure A. (Yield: 45.84%). MS (ES): m/z 531.04 $[M+H]^+$.

Synthesis of Compound 153.3.

Compound 153.3 was synthesized from 153.2 and cyclopropanecarboxamide using general procedure B. (Yield: 50.73%). MS (ES): m/z 579.69 $[M+H]^+$.

Synthesis of Compound I-153.

Compound I-153 was synthesized from 153.3 using general procedure C. (Yield: 37.38%). MS(ES): m/z: 495.53 $[M+H]^+$, LCMS purity: 100%, HPLC purity: 96.14%, 1H NMR (DMSO, 400 MHz): 12.39 (s, 1H), 10.49 (s, 1H), 7.98 (s, 1H), 7.90 (s, 1H), 7.76-7.75 (d, J=6 Hz, 2H), 7.68-7.66 (d, J=8.4 Hz, 1H), 7.56-7.53 (t, J=8.4 Hz, 1H), 7.14 (s, 1H), 3.76 (s, 3H), 3.30 (s, 3H), 3.19 (s, 3H), 2.56 (s, 3H), 2.00 (s, 1H), 0.77-0.76 (d, J=7.6 Hz, 4H).

Synthesis of compound 154.1 Compound 154.1 was synthesized from 153.2 and 5,6-dimethylpyrazin-2-amine using general procedure B. (Yield: 48.88%). MS(ES): m/z 653.73 $[M+H]^+$.

Synthesis of I-154.

Compound I-154 was synthesized from 154.1 using general procedure C. (Yield: 46.29%). MS(ES): m/z: 569.4 [M+H]+, LCMS purity, 98.65%, HPLC purity 98.39%, 1H NMR (DMSO, 400 MHz): 13.48 (s, 1H), 9.74 (s, 1H), 8.97 (s, 1H), 8.14 (s, 1H), 7.82-7.77 (t, J=10 Hz, 3H), 7.60-7.58 (d, J=8.4 Hz, 1H), 7.47 (s, 1H), 7.23 (t, 1H), 3.78 (s, 3H), 3.28 (s, 3H), 3.11 (s, 3H), 2.39 (s, 6H).

Example 155: Synthesis of N-(2-(difluoromethyl)-7-((3-(1,5-dimethyl-1H-1,2,3-triazol-4-yl)-2-methoxyphenyl)amino)-3H-imidazo[4,5-b]pyridin-5-yl)cyclopropanecarboxamide, I-155

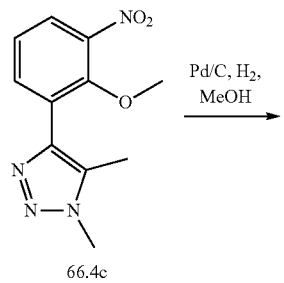

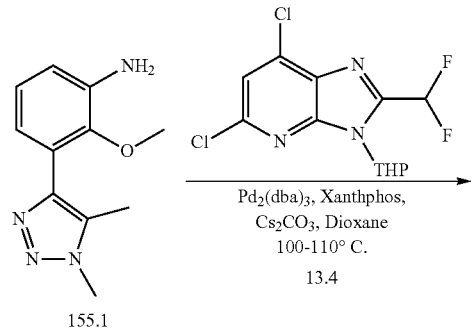

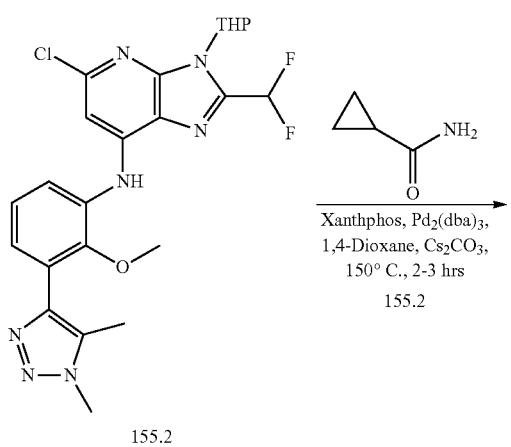

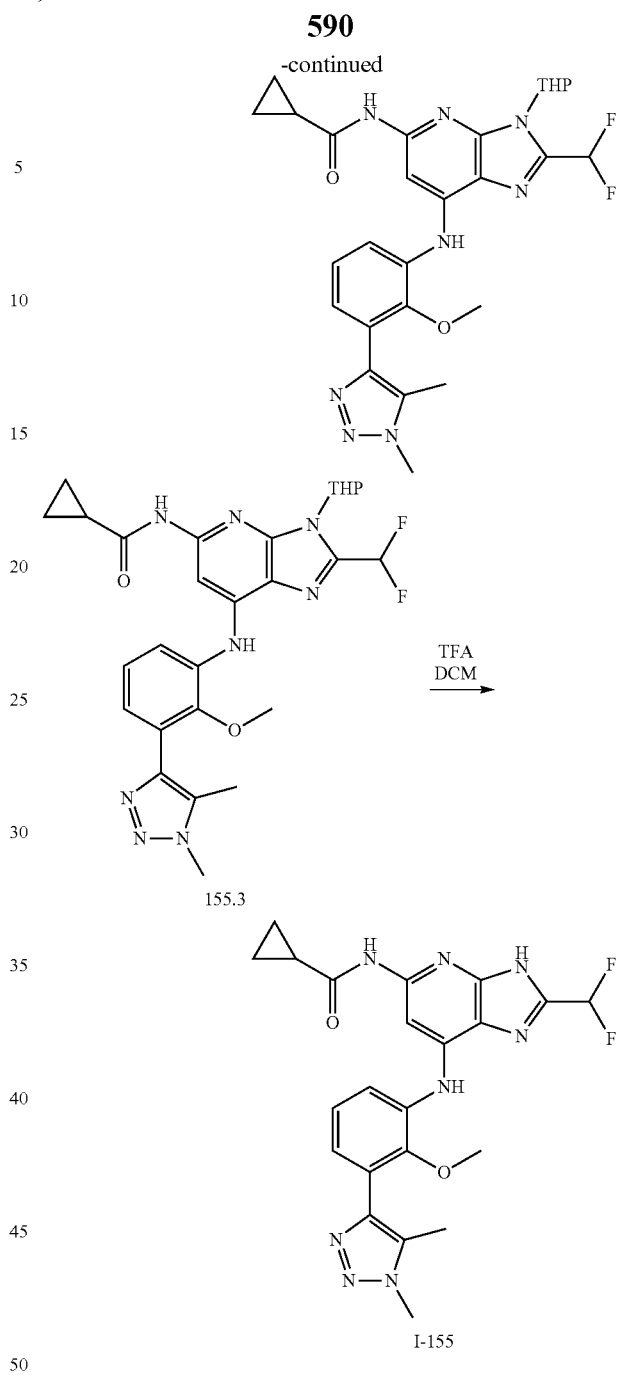

Synthesis of Compound 155.1.

To compound 66.4c (0.180 g, 7.2 mmol, 1.0 eq) in MeOH, 10% Pd/C (0.072 g) was added. Hydrogen was purged through the reaction mixture for 4 h. Upon completion, reaction mixture was filtered through celite-bed and washed with MeOH. Filtrate was concentrated in vacuo to obtain 1.2 (0.130 g, 82.14%). MS(ES): m/z 219.26 [M+H]+.

Synthesis of Compound 155.2.

Compound 155.2 was synthesized from 155.1 and 13.4 using general procedure A. (Yield: 31.65%). MS(ES): m/z 504.94 [M+H]+.

Synthesis of Compound 155.3.

Compound was synthesized from 155.2 and cyclopropanecarboxamide using general procedure B. (Yield: 51.12%). MS(ES): m/z 540.57 [M+H]+.

Synthesis of I-155.

Compound I-155 was synthesized from 155.3 using general procedure C. (Yield: 61.25%). MS(ES): m/z: 469.35 [M+H]$^+$, LCMS purity: 99.12%, HPLC purity: 97.52%, 1H NMR (DMSO, 400 MHz): 13.50 (s, 1H), 10.56 (s, 1H), 8.23 (s, 1H), 7.68 (s, 1H), 7.62-7.60 (d, J=7.6 Hz, 1H), 7.47-7.45 (d, J=7.2 Hz, 1H), 7.25-7.22 (m, 1H), 7.09 (t, 1H), 3.85 (s, 3H), 3.69 (s, 3H), 2.47 (s, 3H), 2.01 (s, 1H), 0.76-0.74 (d, J=7.6 Hz, 4H).

Example 156: Synthesis of N-(2-methyl-7-((4-(1-methyl-1H-imidazol-4-yl)-2-(N-methylmethylsulfonamido)phenyl)amino)-3H-imidazo[4,5-b]pyridin-5-yl)cyclopropanecarboxamide, I-156

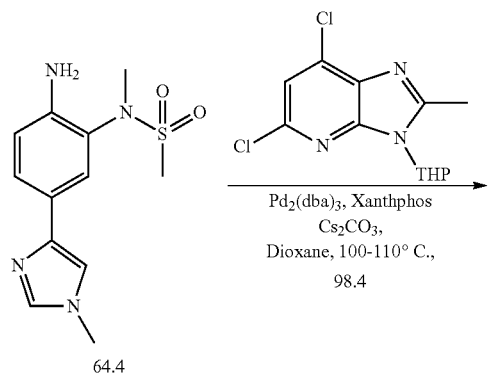

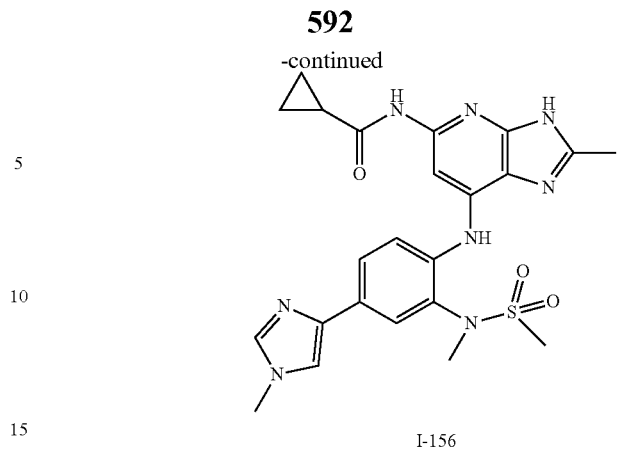

I-156

Synthesis of Compound 156.1.

Compound 156.1 was synthesized from 98.4 and 64.4 using general procedure A. (Yield: 38.08%). MS(ES): m/z 531.48 [M+H]$^+$.

Synthesis of Compound 156.2.

Compound was synthesized from 156.1 and cyclopropanecarboxamide using general procedure B. (Yield: 44.52%). MS(ES): m/z 579.67 [M+H]$^+$.

Synthesis of I-156.

Compound I-156 was synthesized from 156.2 using general procedure C. (Yield: 43.46%). MS(ES): m/z: 495.4 [M+H]$^+$, LCMS purity: 100%, HPLC purity: 99.46%, 1H NMR (DMSO, 400 MHz): 12.48 (s, 1H), 10.51 (s, 1H), 8.27-8.25 (d, J=8.4 Hz 1H), 7.81 (s, 2H), 7.68-7.60 (m, 4H), 3.71 (s, 3H), 3.22 (s, 3H), 3.12 (s, 3H), 2.47 (s, 3H), 1.25 (s, 1H), 0.85 (bs, 4H).

Example 157: Synthesis of N-(7-((3-(1,4-dimethyl-1H-1,2,3-triazol-5-yl)-2-methoxyphenyl)amino)-2-methyl-3H-imidazo[4,5-b]pyridin-5-yl)cyclopropanecarboxamide, I-157

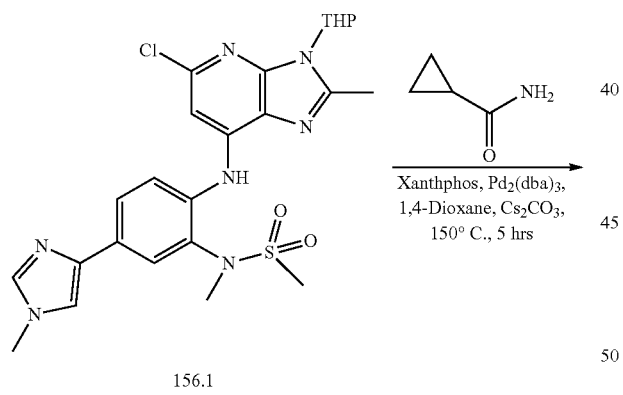

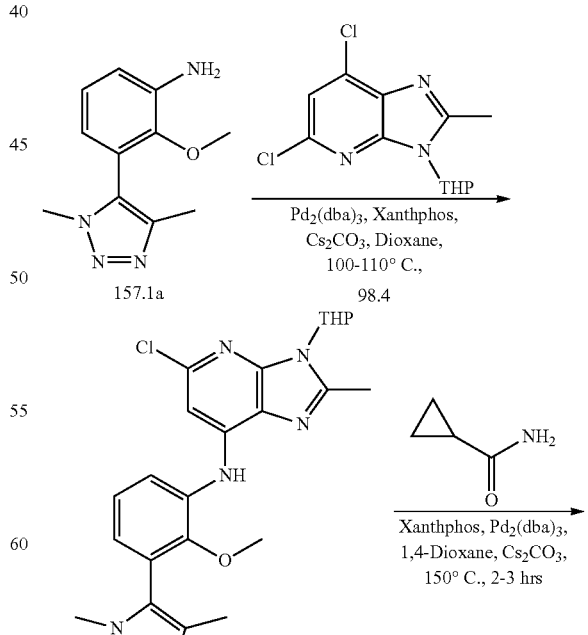

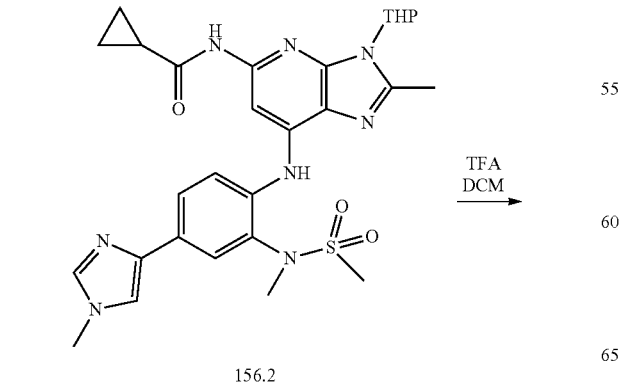

-continued

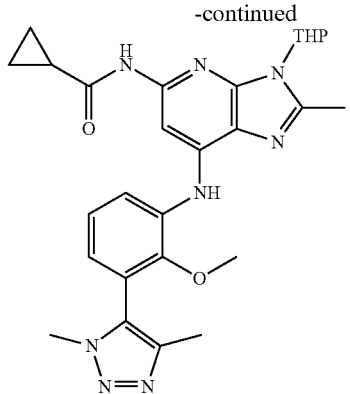

157.2

TFA, DCM →

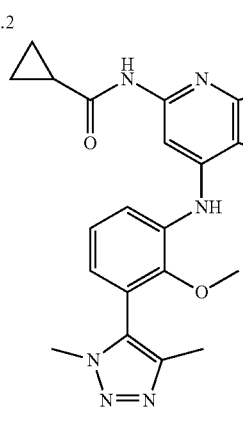

I-157

Synthesis of Compound 157.1.
Compound 157.1 was synthesized 157.1a (prepared by hydrogenation of 66.4b) and 98.4 using general procedure A. (Yield: 34.44%). MS(ES): m/z 468.68 [M+H]$^+$.

Synthesis of Compound 157.2.
Compound 157.2 was synthesized from 157.1 and cyclopropanecarboxamide using general procedure B. (Yield: 54.73%). MS(ES): m/z 517.25 [M+H]$^+$.

Synthesis of I-157.
Compound I-157 was synthesized from using general procedure C. (Yield: 53.55%). MS(ES): m/z: 433.39 [M+H]$^+$, LCMS purity, 99.15%, HPLC purity 99.20%, 1H NMR (DMSO, 400 MHz): 10.55 (s, 1H), 7.78 (s, 1H), 7.54-7.46 (m, 3H), 7.2-7.19 (m, 2H), 4.12 (s, 3H), 3.85 (s, 3H), 3.71 (s, 3H), 3.62 (s, 3H) 1.96 (s, 1H), 0.76 (s, 4H).

Example 158: Synthesis of N-(7-((3-(1,5-dimethyl-1H-1,2,3-triazol-4-yl)-2-methoxyphenyl)amino)-2-methyl-3H-imidazo[4,5-b]pyridin-5-yl)cyclopropanecarboxamide, I-158

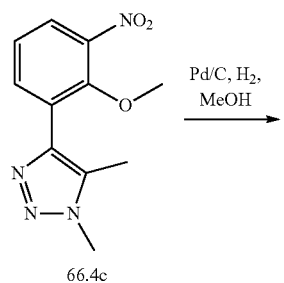

66.4c

Pd/C, H$_2$,
MeOH
→

-continued

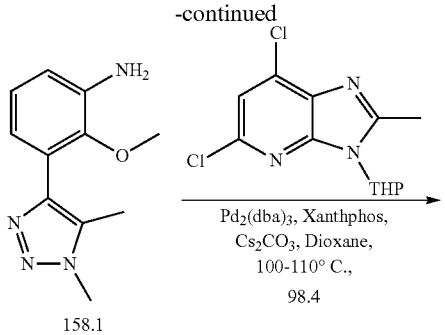

158.1

Pd$_2$(dba)$_3$, Xanthphos,
Cs$_2$CO$_3$, Dioxane,
100-110° C.,
98.4
→

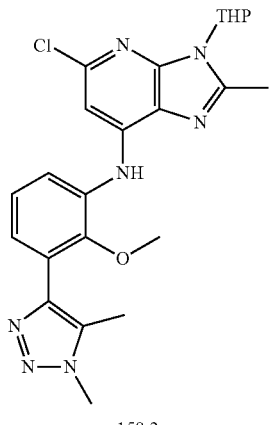

158.2

Xanthphos, Pd$_2$(dba)$_3$,
1,4-Dioxane, Cs$_2$CO$_3$,
150° C., 2-3 hrs
→

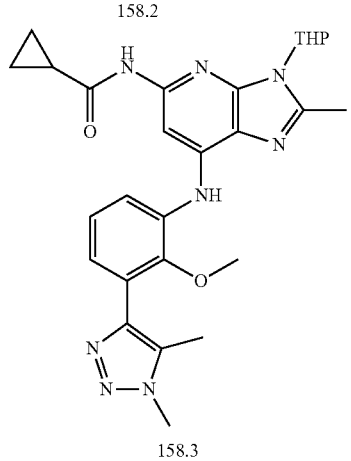

158.3

TFA, DCM →

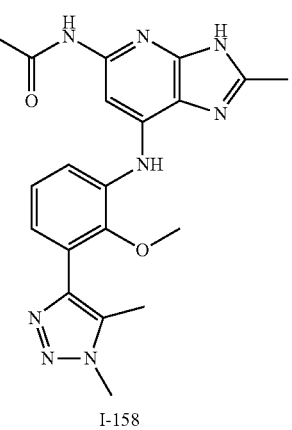

I-158

Synthesis of Compound 158.1.
To compound 66.4c (0.700 g, 28.2 mmol, 1.0 eq) in MeOH, 10% Pd/C (0.280 g) was added. Hydrogen was purged through reaction mixture for 4 h. Upon completion, reaction mixture was filtered through celite-bed and washed with MeOH. Filtrate was concentrated in vacuo to obtain 158.1 (0.470 g, 76.37%). MS(ES): m/z 219.26 [M+H]⁺.

Synthesis of Compound 158.2.

Compound 158.2 was synthesized from 158.1 and 98.4 using general procedure A. (Yield: 22.90%). MS(ES): m/z 467.97 [M+H]⁺.

Synthesis of Compound 158.3.

Compound 158.3 was synthesized from 158.2 and cyclopropanecarboxamide using general procedure B. (Yield: 48.89%). MS(ES): m/z 517.61 [M+H]⁺.

Synthesis of I-158.

Compound I-158 was synthesized from 158.3 using general procedure C. (Yield: 60.85%). MS(ES): m/z: 433.42 [M+H]⁺, LCMS purity: 100.00%, HPLC purity: 97.85%, 1H NMR (DMSO, 400 MHz): 10.66 (s, 1H), 8.26 (s, 1H), 7.77 (s, 1H), 7.60-7.58 (d, J=6.8 Hz, 1H), 7.48-7.47 (d, J=6.4 Hz, 2H), 7.26-7.24 (d, J=7.2 Hz, 1H), 3.86 (s, 3H), 3.72 (s, 3H) 2.62 (s, 3H), 2.47 (s, 3H) 2.02 (s, 1H), 0.78 (bs, 4H).

Example 159: Synthesis of N-(2-(difluoromethyl)-7-((4-(3-methyl-1H-pyrazol-1-yl)-2-(methylsulfonyl)phenyl)amino)-3H-imidazo[4,5-b]pyridin-5-yl)cyclopropanecarboxamide, I-159

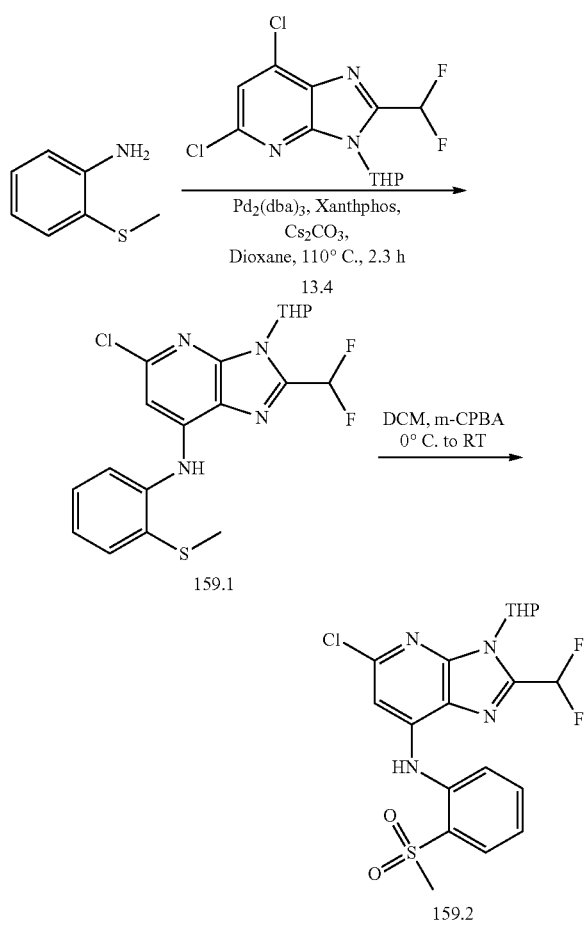

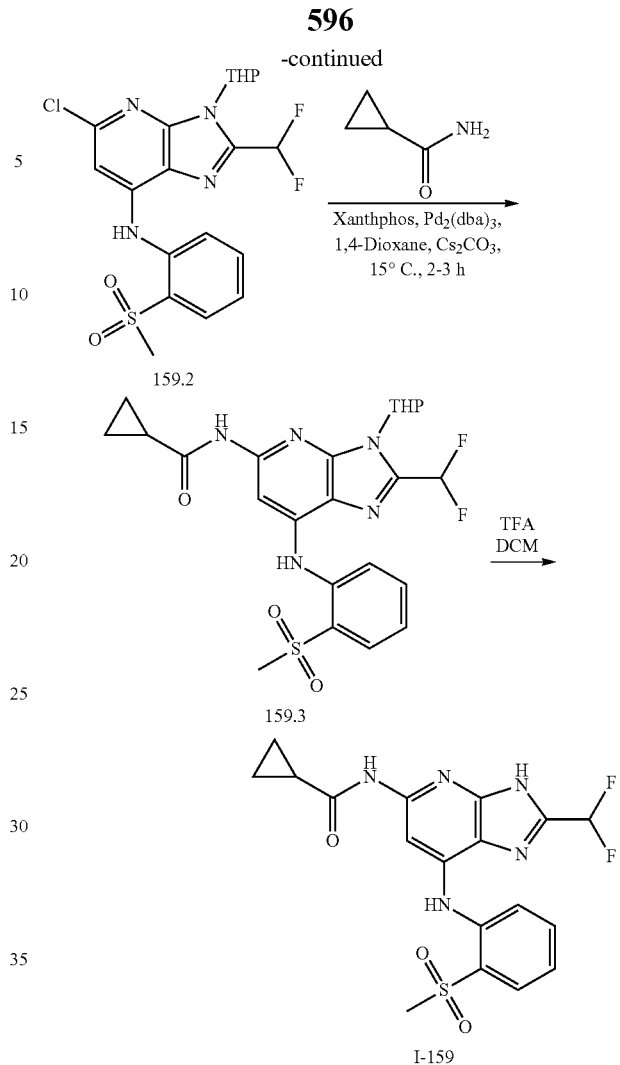

Synthesis of Compound 159.1.

Compound 159.1 was synthesized from 2-(methylthio) aniline and 13.4 using general procedure A. (Yield: 102%). MS(ES): m/z 425.89 [M+H]⁺.

Synthesis of Compound 159.2.

To a solution of 159.1 (0.1 g, 0.235 mmol, 1.0 eq) in CH₂Cl₂ (2 mL) was added meta-chloro perbenzoic acid (0.08 g, 0.470 mmol, 2.0 eq) at 0° C. and stirred the reaction mixture at r.t. for 2 h. Upon completion, reaction mixture was transferred into aqueous solution of NaHCO₃ and extracted with CH₂C12. Organic layer was concentrated in vacuo to obtain crude product. This was purified by column chromatography using 20% ethyl acetate in hexane to obtain pure 159.2 (0.09 g, Yield: 83.70%). MS(ES): m/z 457.89 [M+H]⁺.

Synthesis of Compound 159.3.

Compound 159.3 was synthesized from 159.2 and cyclopropanecarboxamide using general procedure B. (Yield: 40.17%). MS(ES): m/z 506.54 [M+H]⁺.

Synthesis of I-159.

Compound I-159 was synthesized from 159.3 using general procedure C. (Yield: 74.98%). MS(ES): m/z: 422.32 [M+H]⁺, LCMS purity, 97.70%, HPLC purity 97.90%, 1H NMR (DMSO-d6, 400 MHz): 13.68 (s, 1H), 10.75 (s, 1H), 8.79 (s, 1H), 8.08 (s, 1H), 7.95-7.93 (d, J=7.6 Hz, 1H), 7.79-7.79 (d, J=3.2 Hz, 2H), 7.39 (m, 1H), 3.21 (s, 3H) 2.07-2.01 (s, 1H), 0.793 (s, 3H).

Example 160: Synthesis of 6-((7-((2-methoxy-4-(1-methyl-1H-imidazol-5-yl)phenyl)amino)-2-methyl-3H-imidazo[4,5-b]pyridin-5-yl)amino)picolinonitrile, I-160

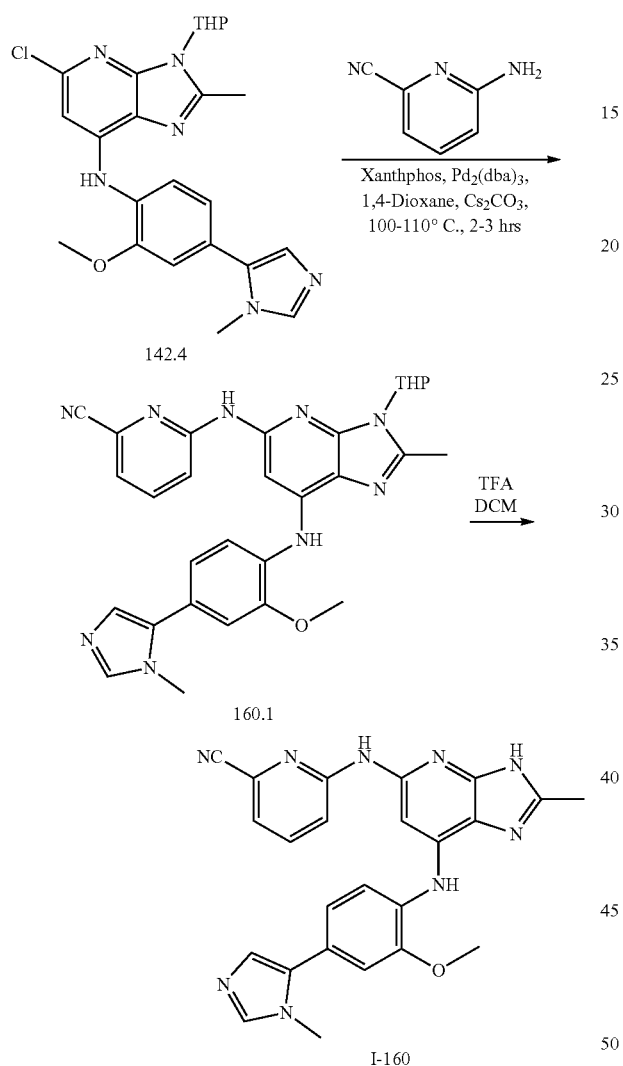

Synthesis of Compound 160.1.

Compound 160.1 was synthesized from 142.4 and 6-aminopicolinonitrile using general procedure B. (Yield: 28.75%). MS(ES): m/z 536.61 [M+H]+.

Synthesis of Compound I-160.

Compound I-160 was synthesized from 160.1 using general procedure C. (Yield: 94.21%). MS(ES): m/z 452.5 [M+H]+, LCMS purity: 97.45%, HPLC purity: 97.96%, 1H NMR (DMSO, 400 MHz): 12.57 (s, 1H), 11.23 (s, 1H), 10.51 (s, 1H), 10.07 (s, 1H), 8.23-8.14 (m, 2H), 7.82-7.80 (t, J=8.4 Hz, 1H), 7.61-7.59 (d, J=11.2 Hz, 1H), 7.51-7.53 (m, 2H), 7.25-7.17 (m, 2H), 3.87 (s, 3H), 3.23 (s, 3H), 2.43 (s, 3H).

Example 161: Synthesis of N-(2-(difluoromethyl)-7-((4-(1,3-dimethyl-1H-1,2,4-triazol-5-yl)-2-methoxyphenyl)amino)-3H-imidazo[4,5-b]pyridin-5-yl)cyclopropanecarboxamide, I-161

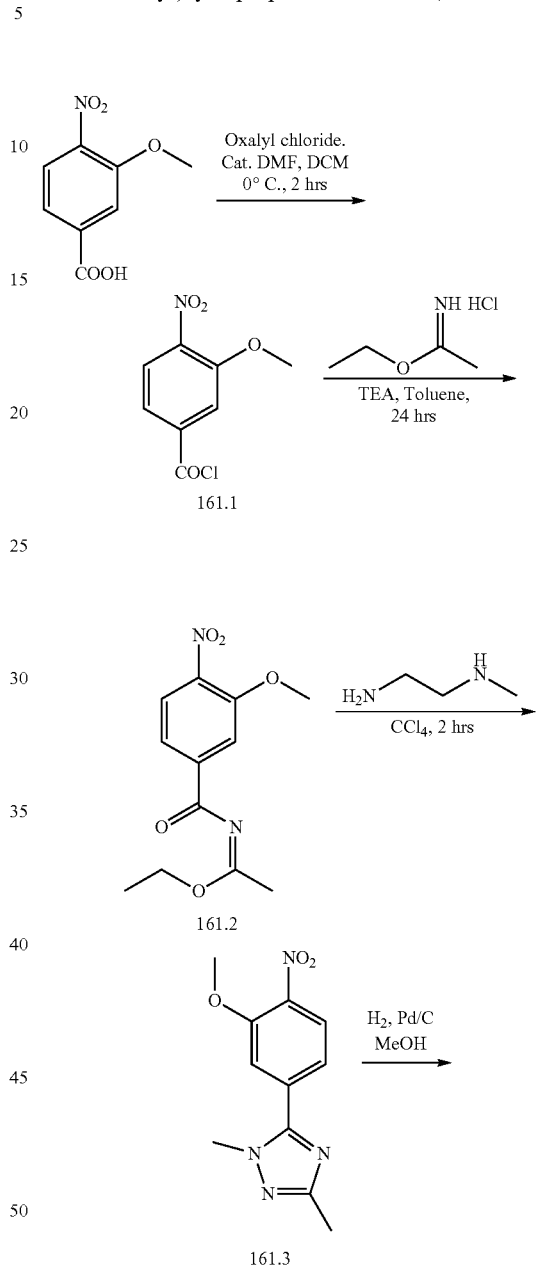

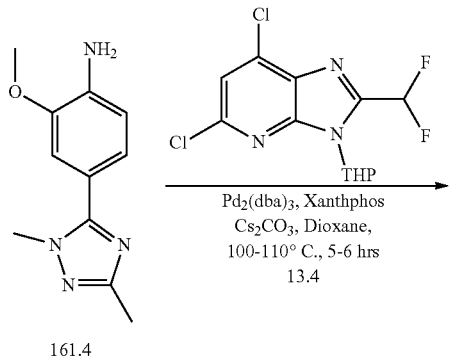

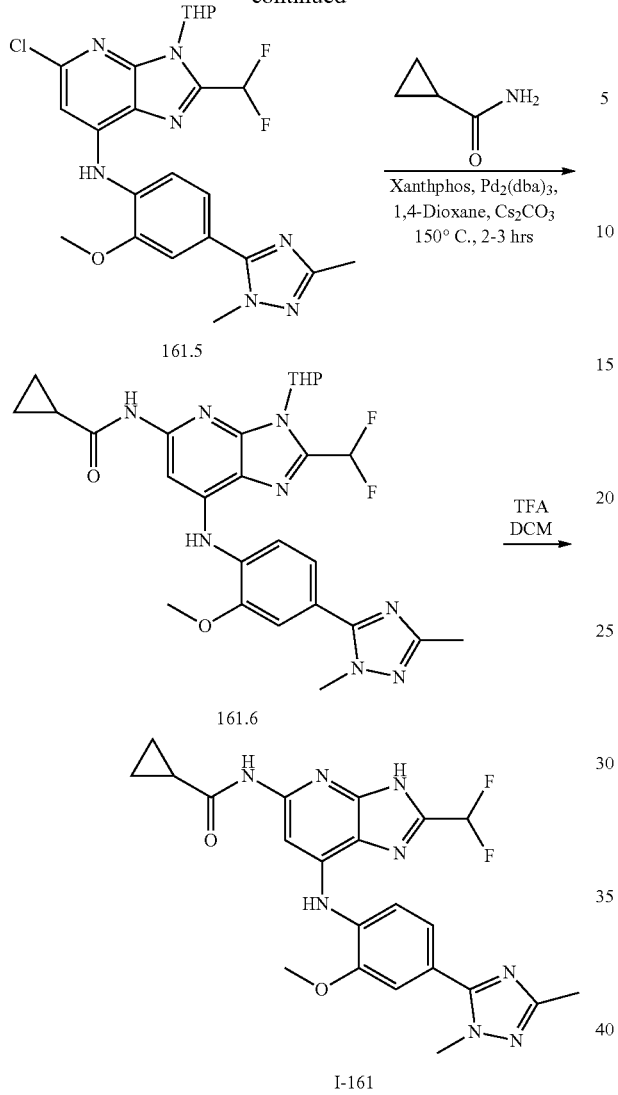

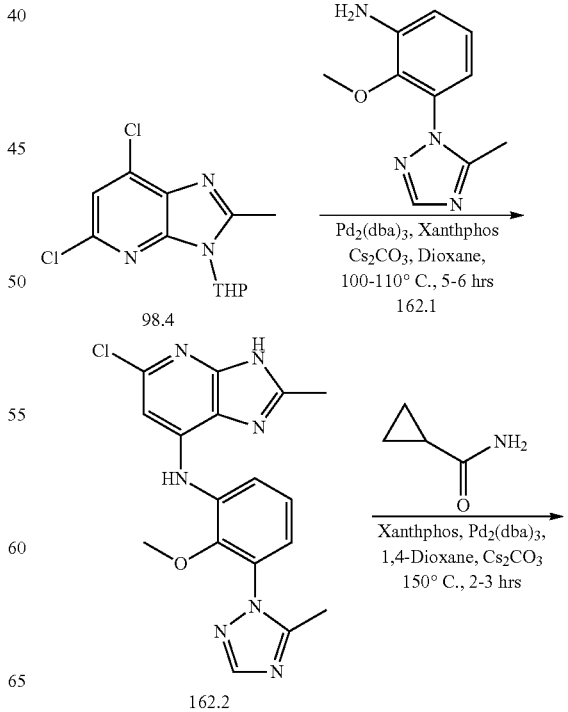

h. Upon completion, reaction mixture was transferred into cold water and extracted with ethyl acetate. Organic layers were combined, dried over Na₂SO₄ and concentrated in vacuo to obtain crude product. This was purified by column chromatography and compound was eluted in 2.5% MeOH in CH₂Cl₂ as eluant to obtain pure 161.3 (5.5 g, 21.07%). MS(ES): m/z 249.24 [M+H]⁺.

Synthesis of Compound 161.4.

To compound 161.3 (5.5 g, 22 mmol, 1.0 eq) in MeOH, 10% Pd/C (1.0 g) was added. Hydrogen was purged through the reaction mixture for 4 h. Upon completion, reaction mixture was filtered through celite-bed and washed with MeOH. Filtrate was concentrated in vacuo to obtain 161.4 (4.5 g, 93.06%). MS(ES): m/z 219.26 [M+H]⁺.

Synthesis of Compound 161.5.

Compound 161.5 was synthesized from 161.4 and 13.4 using general procedure A. (Yield: 13.21%). MS(ES): m/z 504.94 [M+H]⁺.

Synthesis of Compound 161.6.

Compound 161.6 was synthesized from 161.5 and cyclopropanecarboxamide using general procedure B. (Yield: 47.77%). MS(ES): m/z 553.59 [M+H]⁺.

Synthesis of I-161.

Compound I-161 was synthesized from 161.6 using general procedure C. (Yield: 55.76%). MS(ES): m/z: 469.52 [M+H]⁺, LCMS purity: 100%, HPLC purity: 96.23%, 1H NMR (DMSO, 400 MHz): 13.55 (s, 1H), 10.64 (s, 1H), 8.23 (s, 1H), 7.87 (s, 1H), 7.57-7.55 (d, J=8.4 Hz, 1H), 7.46 s, 1H), 7.41-7.39 (d, J=8 Hz, 2H), 3.93 (s, 6H), 2.30 (s, 3H) 2.03-2.01 (d, J=11.2 Hz, 1H), 0.79 (bs, 4H).

Example 162: Synthesis of N-(7-((2-methoxy-3-(5-methyl-1H-1,2,4-triazol-1-yl)phenyl)amino)-2-methyl-3H-imidazo[4,5-b]pyridin-5-yl)cyclopropanecarboxamide, I-162

Synthesis of Compound 161.1.

To a solution of 3-methoxy-4-nitrobenzoic acid (25.0 g, 126 mmol, 1.0 eq) in CH₂Cl₂ at 0° C. added dimethylformamide (0.463 g, 6.3 mmol, 0.05 eq) followed by oxalyl chloride(32.20 g, 253 mmol, 2 eq) dropwise. Reaction mixture was stirred at 0° C. for 2 h. After completion of reaction, oxalyl chloride and CH₂Cl₂ was concentrated in vacuo to obtain crude product. Then reaction mixture was directly used in next step. 161.1 (27 g, 98.76%). MS(ES): m/z 216.59 [M+H]⁺.

Synthesis of Compound 161.2.

To a compound 161.1 (27 g, 125 mmol, 1.0 eq) in toluene (560 ml) added ethyl acetimidate hydrochloride (17.02 g, 137 mmol, 1.1 eq) and triethylamine (31.6 g, 313 mmol, 2.5 eq) at 0° C. Reaction mixture was stirred for 24 h at r.t. Upon completion, reaction mixture was transferred into cold then extracted with ethyl acetate. Organic layers were combined, dried over Na₂SO₄ and concentrated in vacuo to obtain crude 161.2 (28 g, 4.21%). MS(ES): m/z 267.25 [M+H]⁺.

Synthesis of Compound 161.3.

To crude 161.2 (28.0 g, 105 mmol, 1.0 eq) in carbon tetrachloride (560 ml), methyl hydrazine (5.32 g, 115 mmol, 1.1 eq) was added. Reaction mixture was stirred at r.t. for 2

-continued

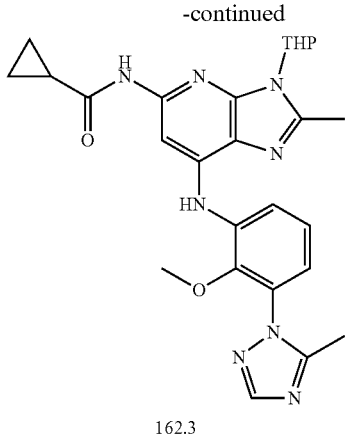

162.3

↓ TFA DCM

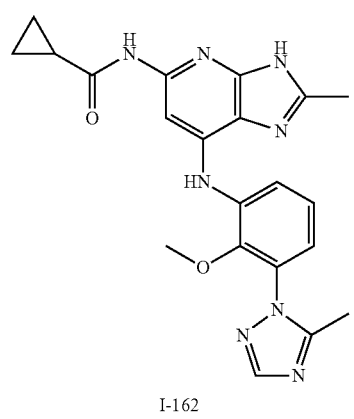

I-162

Synthesis of Compound 162.1.

Compound 162.1 was synthesized as per experimental protocol 1-55

Synthesis of Compound 162.2.

Compound 162.2 was synthesized from 98.4 and 162.1 using general procedure. A (Yield: 30.37%). MS(ES): m/z 370.81 [M+H]⁺.

Synthesis of Compound 162.3.

Compound 162.3 was synthesized from 162.2 and cyclopropanecarboxamide using general procedure. B (Yield: 32.11%). MS(ES): m/z 503.58 [M+H]⁺.

Synthesis of I-162.

Compound I-162 was synthesized from 162.3 using general procedure C. (Yield: 65.06%). MS(ES): m/z: 419.34 [M+H]⁺, LCMS purity, 96.98%, HPLC purity 97.27%, 1H NMR (DMSO, 400 MHz): 12.33 (s, 1H), 10.42 (s, 1H), 8.27 (s, 1H), 8.07 (s, 1H), 7.61 (s, 1H), 7.57-7.55 (d, J=8 Hz, 1H), 7.33-7.29 (t, J=7.6 Hz, 1H), 7.22-7.20 (d, J=7.6 Hz, 1H), 3.35 (s, 3H), 2.48 (s, 3H) 2.32 (s, 3H), 1.10-1.97 (t, J=11.2 Hz, 1H), 0.76 (s, 4H).

Example 163: Synthesis of N-(7-((4-(1,3-dimethyl-1H-1,2,4-triazol-5-yl)-2-methoxyphenyl)amino)-2-methyl-3H-imidazo[4,5-b]pyridin-5-yl)cyclopropanecarboxamide, I-163

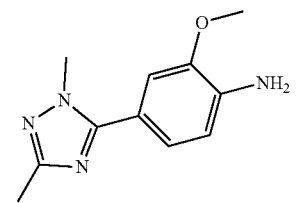

98.4 + 161.4

Pd₂(dba)₃, Xanthphos
Cs₂CO₃, Dioxane,
100-110° C., 5-6 hrs

↓

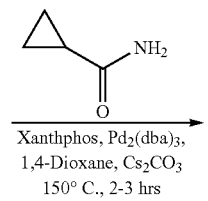

163.1

Xanthphos, Pd₂(dba)₃,
1,4-Dioxane, Cs₂CO₃
150° C., 2-3 hrs

↓

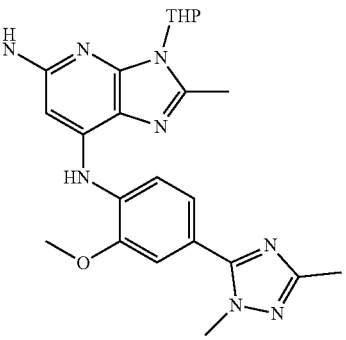

163.2

↓ TFA, DCM

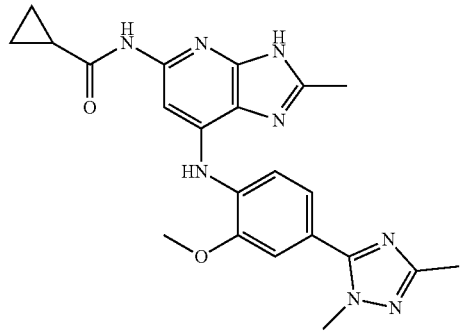

I-163

Synthesis of Compound 163.1.

Compound 163.1 was synthesized from 98.4 and 161.4 using general procedure A. (Yield: 16.32%). MS(ES): m/z 468.51 [M+H]⁺.

Synthesis of Compound 163.2.

Compound 163.2 was synthesized from 163.1 and cyclopropanecarboxamide using general procedure B. (Yield: 45.29%). MS(ES): m/z 517.52 [M+H]+.

Synthesis of I-163.

Compound I-163 was synthesized from 163.2 using general procedure C. (Yield: 79.63%). MS(ES): m/z: 433.4 [M+H]+, LCMS purity, 100%, HPLC purity 100%, 1H NMR (DMSO, 400 MHz): 12.42 (s, 1H), 10.50 (s, 1H), 7.94 (s, 1H), 7.83 (s, 1H), 7.59-7.57 (d, J=8 Hz, 1H), 7.48-7.36 (m, 2H), 3.97 (s, 6H), 2.44 (s, 3H), 2.29 (s, 3H), 2.01 (bs, 1H), 0.81-0.76 (m, 4H).

Example 164: N-(2-(difluoromethyl)-7-((4-(1,3-dimethyl-1H-1,2,4-triazol-5-yl)-2-(N-methylmethylsulfonamido)phenyl)amino)-3H-imidazo[4,5-b]pyridin-5-yl)cyclopropanecarboxamide, I-164

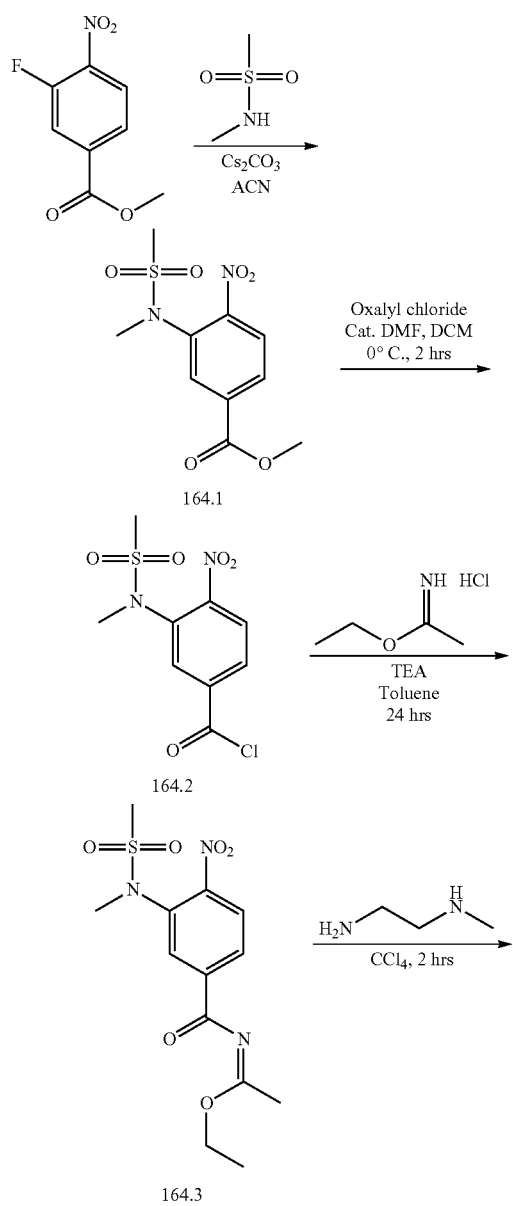

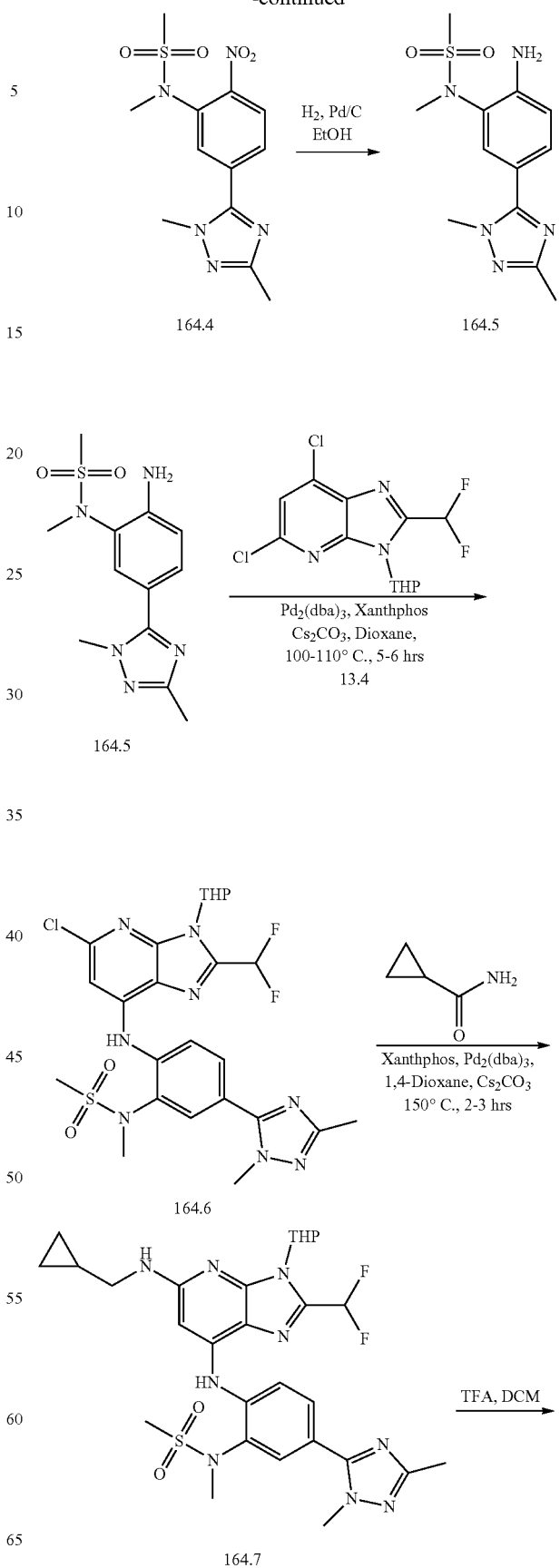

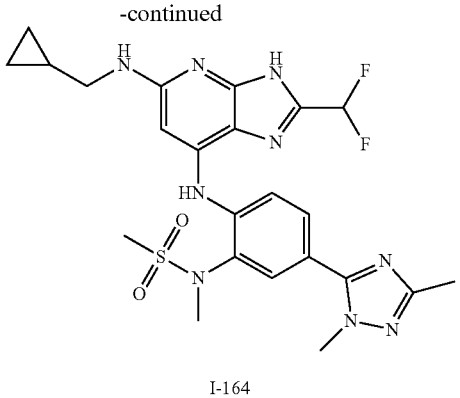

I-164

Synthesis of Compound 164.1.

To a solution of methyl 3-fluoro-4-nitrobenzoate (25 g, 125 mmol, 1.0 eq) in acetonitrile (500 mL), N-methyl methanesulfonamide (15 g, 13.8 mmol, 1.1 eq) and $Cs_2CO_3$ (81.2 g, 250 mmol, 2.0 eq) was added. Reaction mixture was stirred at r.t. for 24 h. After completion of the reaction, the reaction mixture was concentrated, transferred into water and then extracted with ethyl acetate. Organic layer combined, dried over anhydrous $Na_2SO_4$, filtered and concentrated in vacuo to obtain 164.1 (25 g, 69.08%). MS(ES): m/z 289.47 $[M+H]^+$.

Synthesis of Compound 164.2.

To compound 164.1 (25.0 g, 126 mmol, 1.0 eq) in $CH_2Cl_2$ (500 mL) at 0° C. added catalytic dimethylformamide (0.463 g, 6.3 mmol, 0.05 eq) followed by oxalyl chloride (32.20 g, 253 mmol, 2 eq) dropwise. Reaction mixture was stirred at 0° C. for 2 h. After completion of reaction, oxalyl chloride and $CH_2Cl_2$ was concentrated in vacuo to obtain crude product 164.2 (25 g, 98.49%). MS(ES): m/z 293.64 $[M+H]^+$. This crude compound was directly used in next step.

Synthesis of Compound 164.3.

To a compound 164.2 (25 g, 85 mmol, 1.0 eq) in toluene (500 ml) added ethyl acetimidate hydrochloride (8.19 g, 94.2 mmol, 1.1 eq) and triethylamine (21.4 g, 212.3 mmol, 2.5 eq) at 0° C. Reaction mixture was stirred for 24 h at r.t. Upon completion, reaction mixture was transferred into cold then extracted with ethyl acetate. Organic layers were combined, dried over $Na_2SO_4$ and concentrated in vacuo to obtain crude 164.3 (25 g, 85.24%). MS(ES): m/z 344.28 $[M+H]^+$.

Synthesis of Compound 164.4.

To crude compound 164.3 (25.0 g, 72.8 mmol, 1.0 eq) in carbon tetrachloride (500 ml), methyl hydrazine (3.6 g, 81.01 mmol, 1.1 eq) was added. Reaction mixture was stirred at r.t. for 2 h. Upon completion, reaction mixture was transferred into cold water and extracted with ethyl acetate. Organic layers were combined, dried over $Na_2SO_4$ and concentrated in vacuo to obtain crude product. This was purified by column chromatography and compound was eluted in 2.5% MeOH in $CH_2Cl_2$ as eluant to obtain pure 164.4 (6 g, 25.33%). MS(ES): m/z 326.53 $[M+H]^+$.

Synthesis of Compound 164.5.

To compound 164.4 (6 g, 18.2 mmol, 1.0 eq) in MeOH, 10% Pd/C (1.0 g) was added. Hydrogen was purged through the reaction mixture for 4 h. Upon completion, reaction mixture was filtered through celite-bed and washed with MeOH. Filtrate was concentrated in vacuo to obtain 164.5 (4.2 g, 77.11%). MS(ES): m/z 296.58 $[M+H]^+$.

Synthesis of Compound 164.6.

Compound 164.6 was synthesized from 164.5 and 13.4 using general procedure A. (Yield: 20.84%). MS(ES): m/z 582.04 $[M+H]^+$.

Synthesis of compound 164.7 Compound 164.7 was synthesized from 164.6 and cyclopropanecarboxamide using general procedure B. (Yield: 12.38%). MS(ES): m/z 630.69 $[M+H]^+$.

Synthesis of I-164.

Compound I-164 was synthesized from 164.7 using general procedure C (Yield: 56.66%). MS(ES): m/z: 546.36 $[M+H]^+$, LCMS purity, 95.41%, HPLC purity 95.52%, 1H NMR (DMSO, 400 MHz): 13.62 (s, 1H), 10.70 (s, 1H), 8.32 (s, 1H), 8.03 (s, 1H), 7.98 (s, 1H), 7.81-7.73 (m, 2H), 7.25 (t, 1H), 3.95 (s, 3H), 3.27 (s, 3H), 3.14 (s, 3H), 2.29 (s, 3H), 2.04 (m, 1H), 0.79 (s, 4H).

Example 165: Synthesis of N-(7-((4-(1,3-dimethyl-1H-1,2,4-triazol-5-yl)-2-(N-methylmethylsulfonamido)phenyl)amino)-2-methyl-3H-imidazo[4,5-b]pyridin-5-yl)cyclopropanecarboxamide, I-165

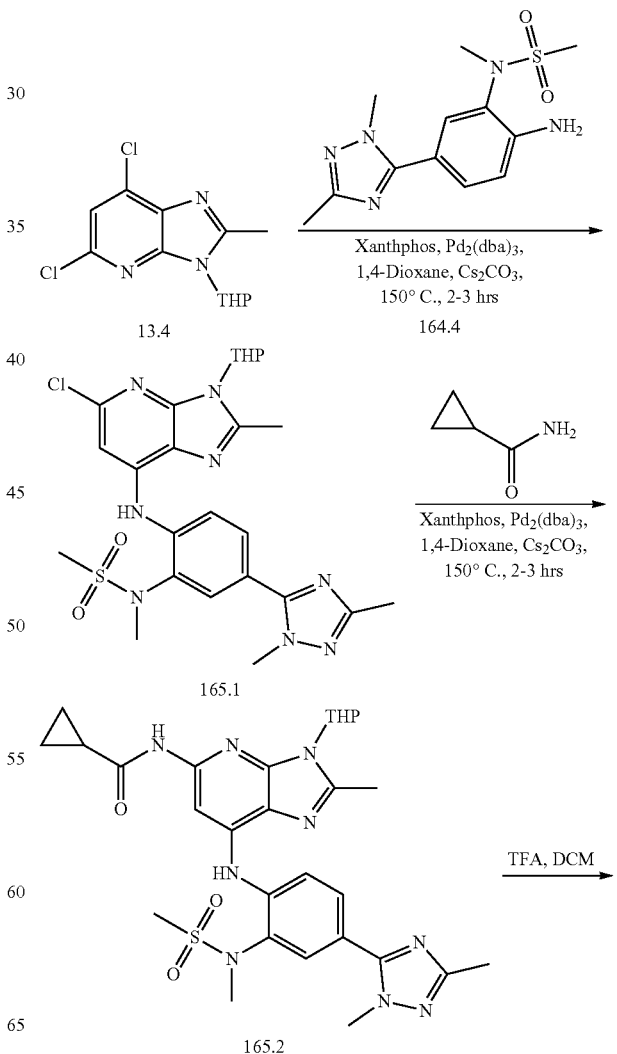

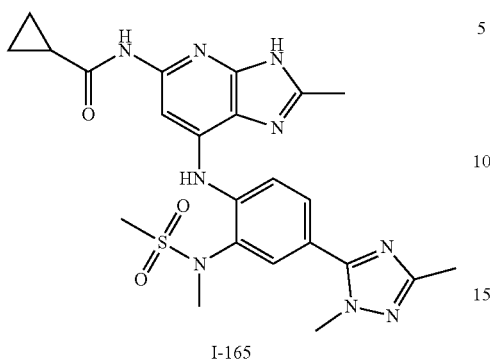

I-165

Synthesis of Compound 165.1.

Compound 165.1 was synthesized from 98.4 and 164.4 using general procedure A. (Yield: 17.88%). MS(ES): m/z 546.06 [M+H]$^+$.

Synthesis of compound 165.2 Compound 165.2 was synthesized from 165.1 and cyclopropanecarboxamide using general procedure B. (Yield: 29.21%). MS(ES): m/z 594.71 [M+H]$^+$.

Synthesis of I-165.

Compound I-165 was synthesized from 165.2 using general procedure C. (Yield: 77.67%). MS(ES): m/z: 510.53 [M+H]$^+$, LCMS purity, 98.65%, HPLC purity 95.05%, 1H NMR (DMSO, 400 MHz): 12.60 (s, 1H), 10.58 (s, 1H), 8.61-8.59 (d, J=9.2 Hz, 1H), 8.15 (s, 1H), 7.77 (s, 2H), 7.69-7.65 (m, 1H), 4.00 (s, 3H), 3.24 (s, 3H), 3.09 (s, 3H), 2.49 (s, 3H), 2.27 (s, 3H), 1.30 (s, 1H), 0.86 (bs, 4H).

Example 166: Synthesis of N-(2-((2-(difluoromethyl)-5-((5,6-dimethylpyrazin-2-yl)amino)-3H-imidazo[4,5-b]pyridin-7-yl)amino)-5-(1,3-dimethyl-1H-1,2,4-triazol-5-yl)phenyl)-N-methyl-methanesulfonamide, I-166

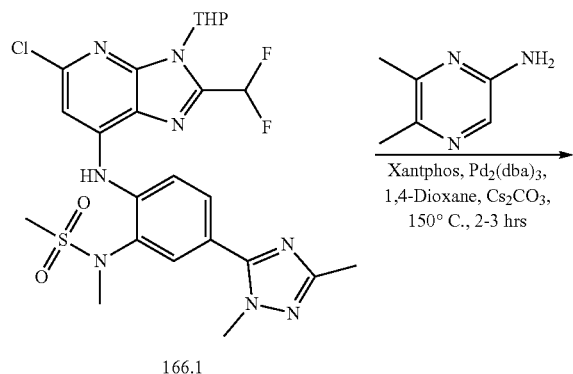

166.1

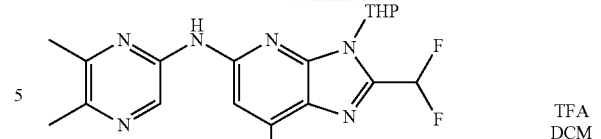

166.2

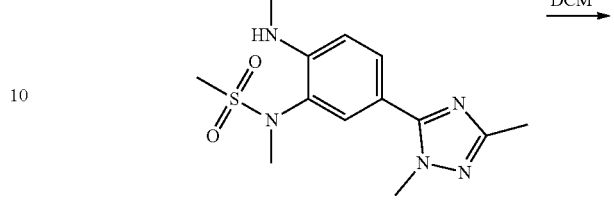

I-166

Synthesis of Compound 166.1.

Compound 166.1 was synthesized as per experimental protocol in 1-164.

Synthesis of Compound 162.1.

Compound 166.2 was synthesized from 166.1 and 5,6-dimethylpyrazin-2-amine using general procedure B. (Yield: 60.91%). MS(ES): m/z 668.74 [M+H]$^+$.

Synthesis of I-166.

Compound I-166 was synthesized from 166.2 using general procedure C. (Yield: 84.99%). MS(ES): m/z: 584.49 [M+H]$^+$, LCMS purity, 98.17%, HPLC purity 95.87%, 1H NMR (DMSO, 400 MHz): 13.52 (s, 1H), 9.78 (s, 1H), 9.01 (s, 1H), 8.24 (s, 1H), 7.99-7.99 (d, J=1.6 Hz, 1H), 7.89-7.80 (m, 2H), 7.52 (s, 1H), 7.23 (t, 1H), 3.96 (s, 3H), 3.29 (s, 3H), 3.17 (s, 3H), 2.39 (s, 6H), 2.30 (s, 3H).

Example 167: Synthesis of 2-(difluoromethyl)-N7-(3-(1,3-dimethyl-1H-1,2,4-triazol-5-yl)-2-methoxyphenyl)-N5-(4-fluoro-5-(3-methoxyazetidin-1-yl)pyridin-2-yl)-3H-imidazo[4,5-b]pyridine-5,7-diamine, I-167

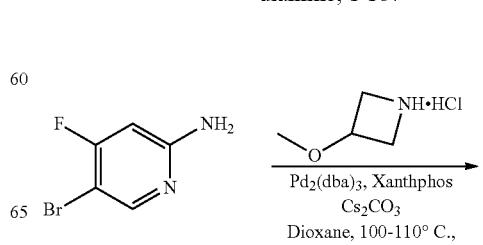

-continued

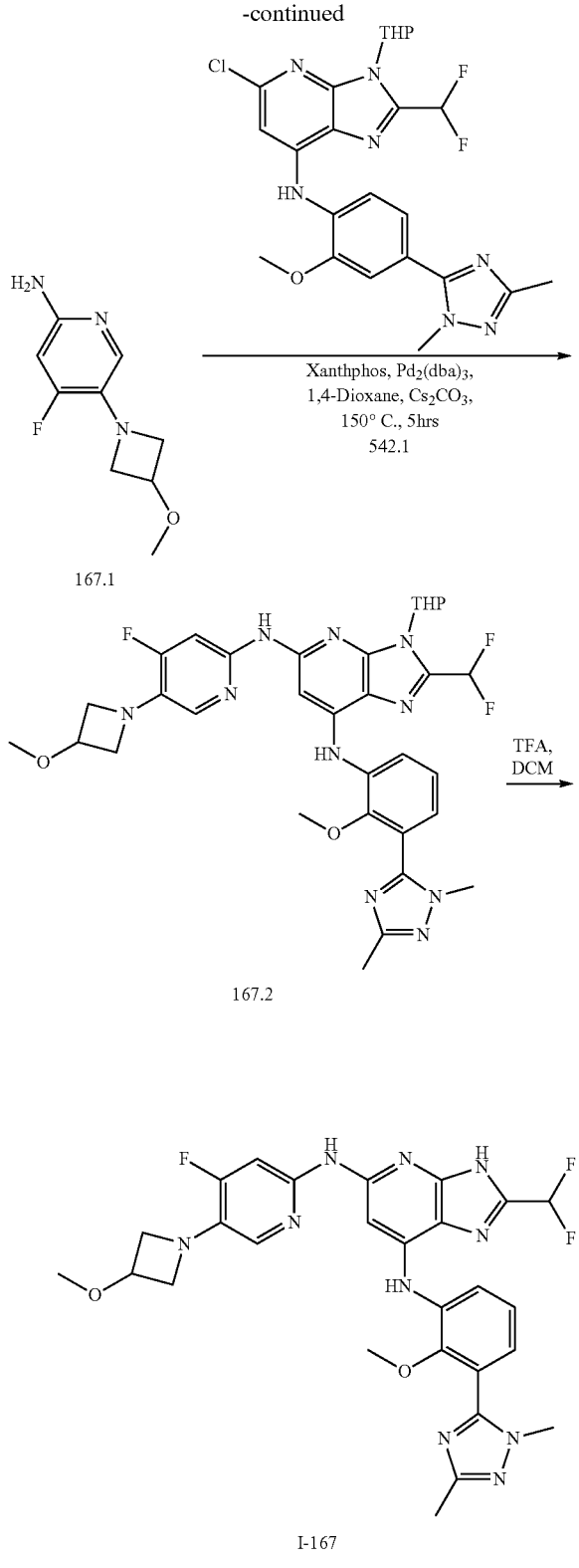

167.1

167.2

I-167

Synthesis of Compound 167.1.

To compound 5-bromo-4-fluoropyridin-2-amine (1.0 g, 5.23 mmol, 1.0 eq) in 1,4-dioxane (25 mL) was added 3-methoxyazetidine hydrochloride (1.29 g, 10.47 mmol, 2.0 eq), $Cs_2CO_3$ (6.84 g, 20.94 mmol, 4.0 eq). The reaction mixture was degassed for 10 min. under argon atmosphere, then $Pd_2(dba)_3$ (0.047 g, 0.52 mmol, 0.1 eq) and Xantphos (0.605 g, 1.047 mmol, 0.2 eq) were added, again degassed for 5 min. The reaction was stirred at 110° C. for 3 h. Upon completion, reaction mixture was cooled to r.t., transferred in water and product was extracted with ethyl acetate. Organic layers were combined, washed with brine, dried over $Na_2SO_4$ and concentrated in vacuo to obtain crude product. This was purified by column chromatography using 2% MeOH in $CH_2Cl_2$ as eluant to obtain pure 167.1 (0.145 g, 14.05%). MS(ES): m/z 198.15 $[M+H]^+$.

Synthesis of Compound 167.2.

Compound 167.2 was synthesized from 167.1 and 542.1 using general procedure B. (Yield: 45.49%). MS(ES): m/z 665.73 $[M+H]^+$.

Synthesis of I-167.

Compound I-167 was synthesized from 167.2 using general procedure C. (Yield: 79.51%). MS(ES): m/z: 581.4 $[M+H]^+$, LCMS purity, 98.59%, HPLC purity 97.07%, 1H NMR (DMSO, 400 MHz): 13.45 (s, 1H), 9.58 (s, 1H), 8.16 (s, 1H), 7.97 (s, 1H), 7.67-7.59 (m, 1H), 7.44-7.38 (t, J=13.6 Hz, 2H), 7.17 (s, 1H), 7.02 (s, 1H), 3.97 (s, 3H), 3.95 (s, 3H), 3.66 (s, 1H), 3.24 (s, 3H), 2.21 (s, 3H), 1.24 (s, 4H).

Example 168: Synthesis of N7-(3-(1,3-dimethyl-1H-1,2,4-triazol-5-yl)-2-methoxyphenyl)-N5-(4-fluoro-5-(3-methoxyazetidin-1-yl)pyridin-2-yl)-2-methyl-3H-imidazo[4,5-b]pyridine-5,7-diamine, I-168

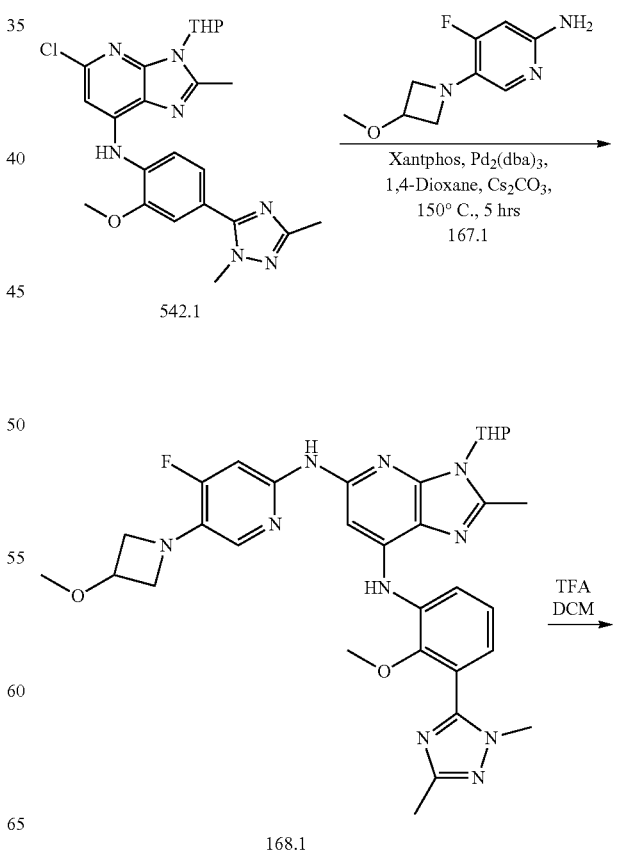

168.1

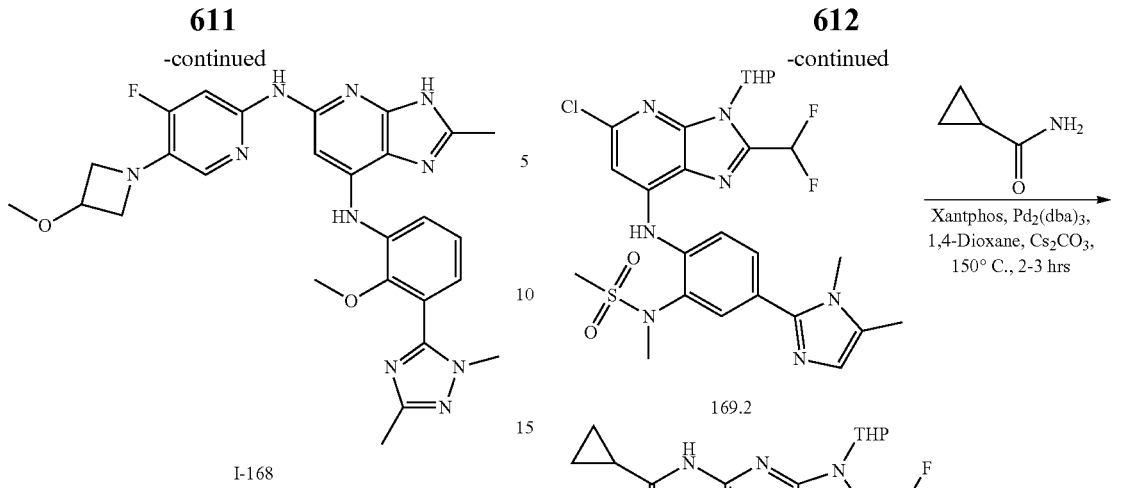

I-168

Synthesis of Compound 168.1.
Compound 186.1 was synthesized from 167.1 and 542.1 using general procedure B. (Yield: 40.32%). MS(ES): m/z 629.71 [M+H]⁺.

Synthesis of I-168.
Compound I-168 was synthesized from 168.1 using general procedure C. (Yield: 45.80%). MS(ES): m/z: 545.46 [M+H]⁺, LCMS purity: 100%, HPLC purity: 96.77%, 1H NMR (DMSO, 400 MHz): 12.35 (s, 1H), 9.37 (s, 1H), 8.07-8.04 (d, J=15.2 Hz, 1H), 7.71-7.67 (m, 2H), 7.60-7.567 (d, J=12.4 Hz, 1H), 7.41-7.37 (m, 2H), 7.09 (s, 1H), 3.94 (s, 6H), 3.24 (s, 3H), 3.18-3.16 (d, J=5.2 Hz, 1H), 2.44 (s, 3H), 2.28 (s, 3H), 1.24 (s, 4H).

Example 169: N-(2-(difluoromethyl)-7-((4-(1,5-dimethyl-1H-imidazol-2-yl)-2-(N-methylmethylsulfonamido)phenyl)amino)-3H-imidazo[4,5-b]pyridin-5-yl)cyclopropanecarboxamide, I-169

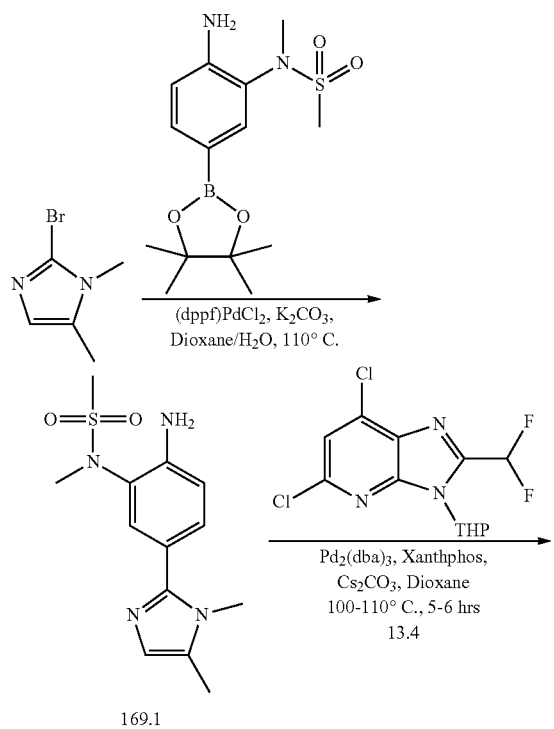

I-169

Synthesis of Compound 169.1.
A mixture of 2-bromo-1,5-dimethyl-1H-imidazole (1.0 g, 5.71 mmol, 1.0 eq) and N-(2-amino-5-(4,4,5,5-tetramethyl-1,3,2-dioxaborolan-2-yl)phenyl)-N-methylmethaneSulfonamide (2.04 g, 6.28 mmol, 1.1 eq) in 1,4-dioxane (10 mL) was degassed with argon for 10 min followed by addition of [1,1'-Bis(diphenylphosphino)ferrocene]palladium(II) dichloride(0.208 g, 0.28 mmol, 0.05 eq) and potassium carbonate(0.236 g, 1.71 mmol, 3.0 eq). Reaction mixture was stirred at 110° C. for 24 h. Upon completion, reaction mixture was transferred into cold water and extracted with ethyl acetate. Organic layer combined, dried over Na₂SO₄ and concentrated in vacuo to obtain crude product. This was purified by column chromatography and compound was eluted in 15% ethyl acetate in hexane as eluant to obtain pure 169.1 (0.4 g, 23.78%). MS(ES): m/z 296.37 [M+H]⁺.

Synthesis of Compound 169.2.
Compound 169.2 was synthesized from 169.1 and 13.4 using general procedure A. (Yield: 39.33%). MS(ES): m/z 581.05 [M+H]⁺.

Synthesis of Compound 169.3.
Compound 169.3 was synthesized from 169.2 and cyclopropanecarboxamide using general procedure B. (Yield: 53.57%). MS(ES): m/z 629.70 [M+H]⁺.

Synthesis of I-169.

Compound I-169 was synthesized from 169.3 using general procedure C. (Yield: 44.90%). MS(ES): m/z: 545.41 [M+H]⁺, LCMS purity, 100%, HPLC purity 100%, 1H NMR (DMSO, 400 MHz): 13.56 (s, 1H), 10.68 (s, 1H), 8.23 (s, 1H), 8.16 (s, 1H), 7.97 (s, 1H), 7.86 (s, 1H), 7.69-7.65 (t, 2H), 7.40 (s, 1H), 3.64 (s, 3H), 3.26 (s, 3H), 3.12 (s, 3H), 2.25 (s, 3H), 2.02-1.99 (m, 1H), 0.78 (m, 4H).

Example 170: N-(7-((4-(1,5-dimethyl-1H-imidazol-2-yl)-2-(N-methylmethyl-sulfonamido)phenyl)amino)-2-methyl-3H-imidazo[4,5-b]pyridin-5-yl)cyclopropanecarboxamide, I-170

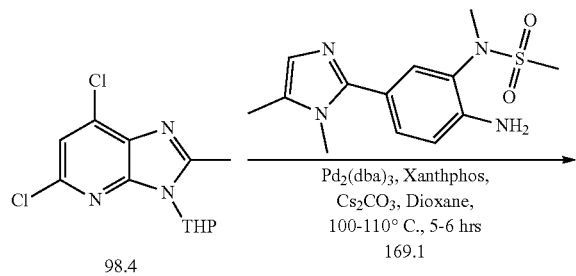

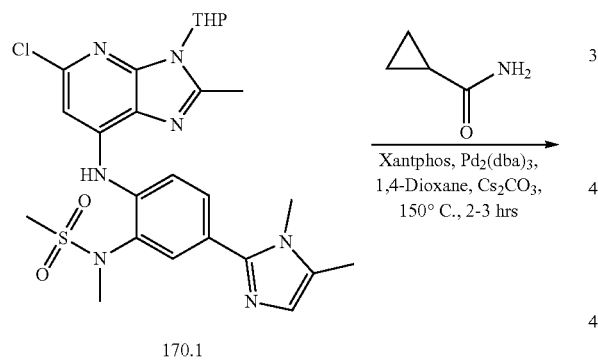

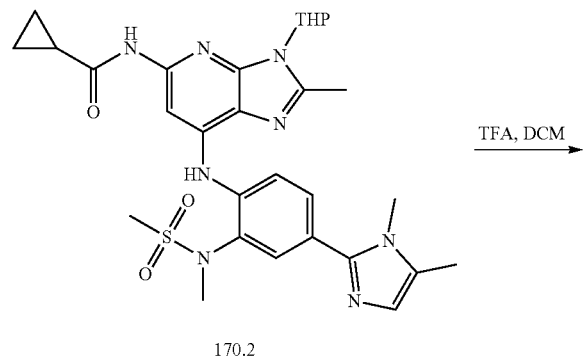

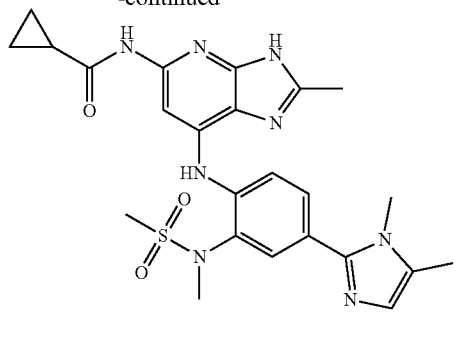

I-170

Synthesis of Compound 170.1.

Compound 170.1 was synthesized from 98.4 and 169.1 as per experimental procedure in 1-169.

Synthesis of Compound 170.2.

Compound 170.2 was synthesized from 170.1 and cyclopropanecarboxamide using general procedure A. (Yield: 35.17%). MS(ES): m/z 545.07 [M+H]⁺.

Synthesis of I-170.

Compound I-170 was synthesized from 170.1 using general procedure C (Yield: 56.39%). MS(ES): m/z: 509.41 [M+H]⁺, LCMS purity, 98.88%, HPLC purity 95.13%, 1H NMR (DMSO, 400 MHz): 12.40 (s, 1H), 10.49 (s, 1H), 7.99 (s, 1H), 7.91 (s, 1H), 7.84 (s, 1H), 7.69-7.65 (m, 2H), 6.79 (s, 1H), 3.64 (s, 3H), 3.25 (s, 3H), 3.15 (s, 3H), 2.48 (s, 3H), 2.24 (s, 3H), 1.99 (s, 1H), 0.76 (m, 4H).

Example 171: Synthesis of N-(2-(difluoromethyl)-7-((4-(1-methyl-1H-pyrazol-3-yl)-2-(N-methyl methylsulfonamido)phenyl)amino)-3H-imidazo[4,5-b]pyridin-5-yl)cyclopropaneCarboxamide, I-171

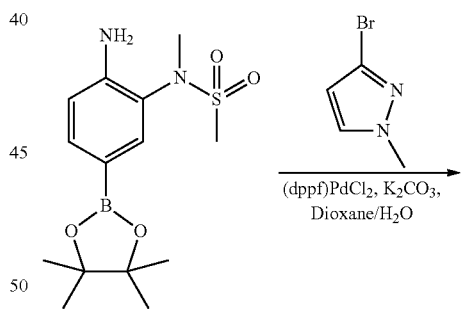

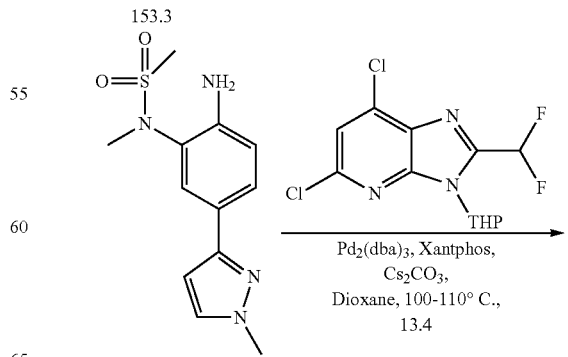

171.1

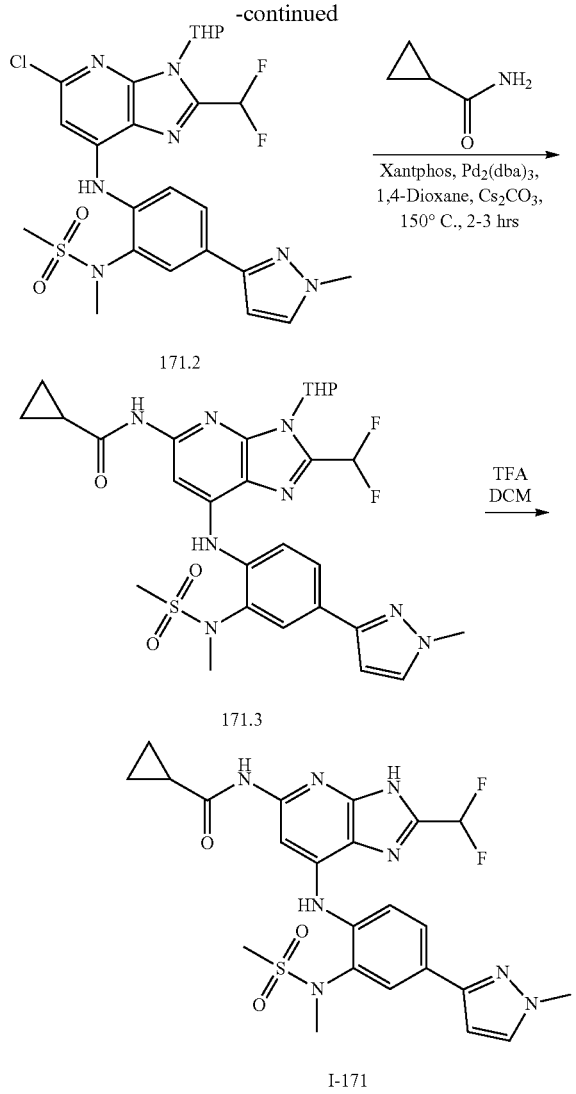

171.2

171.3

I-171

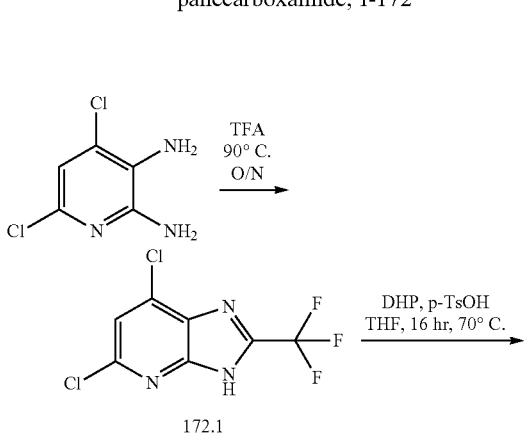

Synthesis of I-171.

Compound I-171 was synthesized from 171.3 using general procedure C. (Yield: 96.55%). MS(ES): m/z: 531.49 [M+H]⁺, LCMS purity: 97.88%, HPLC purity: 97.24%, 1H NMR (DMSO, 400 MHz): 13.54 (s, 1H), 10.64 (s, 1H), 8.15 (s, 1H), 7.99 (s, 1H), 7.87-7.77 (m, 3H), 7.61-7.59 (d, J=8.4 Hz, 1H), 7.25 (t, 1H), 6.81-6.80 (d, J=2.4 Hz, 1H), 3.91 (s, 3H), 3.25 (s, 3H), 3.10 (s, 3H), 1.99 (s, 1H), 0.77 (bs, 4H).

Example 172: Synthesis of N-(7-((2-m ethoxy-3-(2-methyl-2H-tetrazol-5-yl)phenyl)amino)-2-(trifluoromethyl)-3H-imidazo[4,5-b]pyridin-5-yl)cyclopropanecarboxamide, I-172

172.1

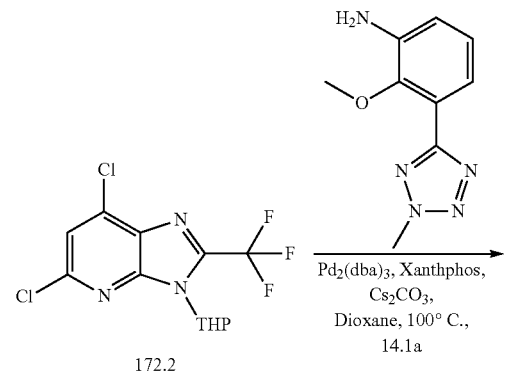

172.2

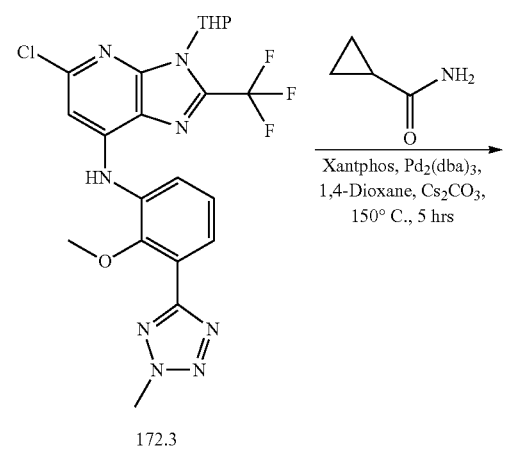

172.3

Synthesis of Compound 171.1.

To a solution of 153.3 (1.0 g, 3.06 mmol, 1.0 eq) and 3-bromo-1-methyl-1H-pyrazole (0.48 g, 3.06 mmol, 1.0 eq) in a mixture of 1,4-dioxane and water, potassium carbonate (0.84 g, 6.13 mmol, 2.0 eq) and [1,1'-Bis(diphenylphosphino)ferrocene]dichloropalladium(II)complex (0.24 g, 0.306 mmol, 0.1 eq) with CH₂Cl₂ were added. Reaction mixture was degassed for 15 min and then stirred at 110° C. for 2 h. After completion of the reaction, reaction mixture was transferred to water and extracted with ethyl acetate. Organic layers were combined, dried over Na₂SO₄, filtered and concentrated in vacuo to obtain the crude material. This was purified by column chromatography using 20% ethyl acetate in hexane as eluant to obtain pure 171.1 (0.450 g, 26.18%). MS (ES): m/z 281.43 [M+H]⁺.

Synthesis of Compound 171.2.

Compound 171.2 was synthesized from 171.1 and 13.4 using general procedure A. (Yield: 37.15%). MS(ES): m/z 567.16 [M+H]⁺.

Synthesis of Compound 171.3.

Compound 171.3 was synthesized from 171.2 and cyclopropanecarboxamide using general procedure B. (Yield: 36.83%). MS(ES): m/z 615.46 [M+H]⁺.

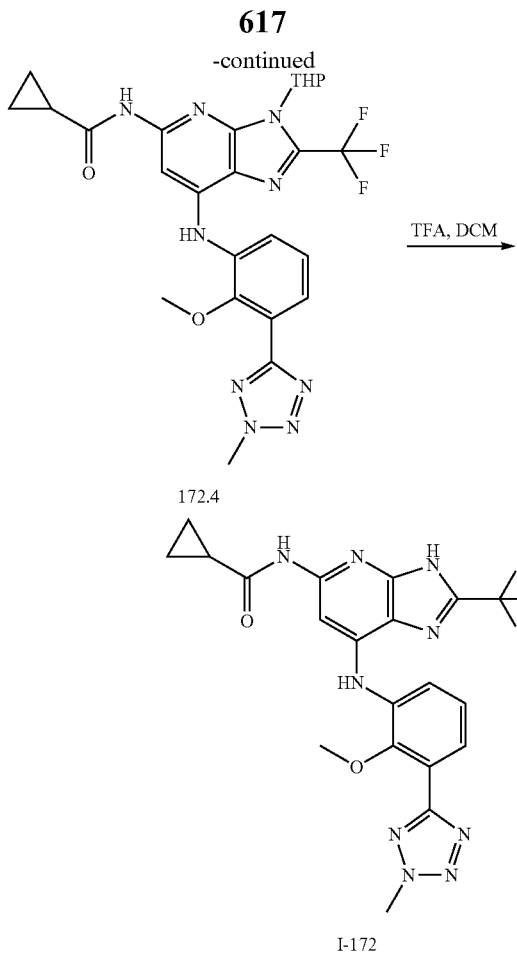

Synthesis of Compound 172.1.

A mixture of 4,6-dichloropyridine-2,3-diamine (0.500 g, 2.81 mmol, 1 eq), and trifluroacetic acid (3.5 mL), was heated at 90° C. for 16 h. After completion of reaction, the reaction mixture was transferred into $NaHCO_3$ solution and extracted with ethyl acetate. Combined Organic layer dried over $Na_2SO_4$ and concentrated in vacuo to obtain crude product. This was purified by column chromatography and compound was eluted in 25% ethyl acetate in hexane to obtain pure 172.1. (0.350 g, 48.67%), MS(ES): m/z 257.01 [M+H]$^+$.

Synthesis of Compound 172.2.

To a solution of 172.1 (0.350 g, 1.37 mmol, 1 eq), in tetrahydrofuran (6.3 mL), was added dihydropyran (0.80 g, 9.5 mmol, 7 eq), and Pyridinium p-toluenesulfonate (0.034 g, 0.13 mmol, 0.1 eq). Reaction mixture was heated at 70° C. for 16 h. After completion of reaction, the reaction mixture was concentrated in vacuo to obtain crude product. This was purified by column chromatography and compound was eluted in 25% ethyl acetate in hexane to obtain pure 172.2. (0.350 g, 43.01%), MS(ES): m/z 341.13 [M+H]$^+$.

Synthesis of Compound 172.3.

Compound 172.3 was synthesized from 172.2 and 14.1a using general procedure A to obtain 1.4. (Yield: 17.14%). MS (ES): m/z 509.89 [M+H]$^+$.

Synthesis of Compound 172.4.

Compound 172.4 was synthesized from 172.3 and cyclopropanecarboxamide using general procedure B. (Yield: 60.13%). MS (ES): m/z 558.54 [M+H]$^+$.

Synthesis of I-172.

Compound I-172 was synthesized from 172.4 using general procedure C. (Yield: 58.55%). MS(ES): m/z: 474.42 [M+H]$^+$, LCMS purity, 98.68%, HPLC purity 99.12%, 1H NMR (DMSO, 400 MHz): 14.02 (s, 1H), 10.61 (s, 1H), 7.76-7.74 (d, J=7.6 Hz, 1H), 7.56-7.54 (d, J=6.8 Hz, 2H), 7.38-7.34 (t, J=8 Hz, 2H), 4.47 (s, 3H), 3.65 (s, 3H), 1.57 (s, 1H), 0.85 (s, 4H).

Example 173: Synthesis of N-(5-(1,3-dimethyl-1H-1,2,4-triazol-5-yl)-2-((5-(((5,6-dimethylpyrazin-2-yl)amino)-2-methyl-3H-imidazo[4,5-b]pyridin-7-yl)amino)phenyl)-N-methylmethanesulfonamide, I-173

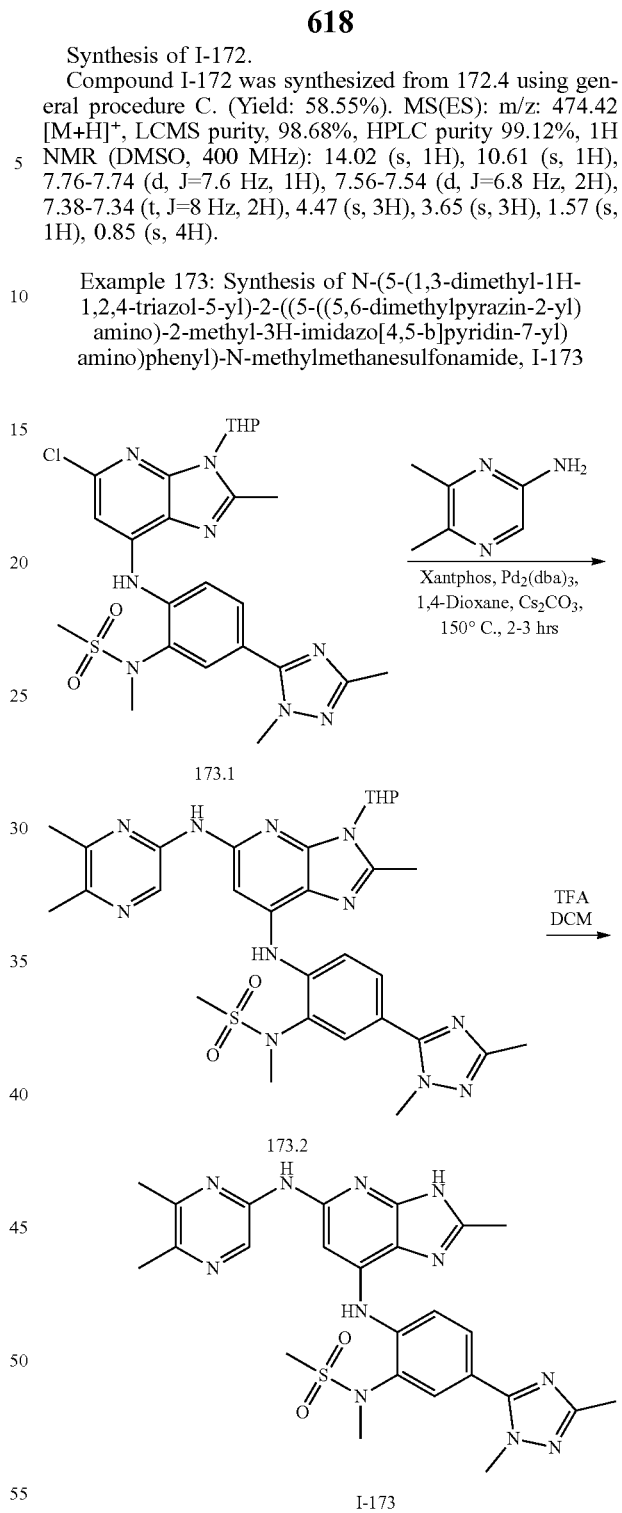

Synthesis of Compound 173.1.

Compound 173.1 was synthesized as per experimental protocol in 1-164.

Synthesis of Compound 173.2.

Compound 173.2 was synthesized from 173.1 and 5,6-dimethylpyrazin-2-amine using general procedure B. (Yield: 47.45%). MS(ES): m/z 632.76 [M+H]$^+$.

Synthesis of I-173.

Compound I-173 was synthesized from 173.2 using general procedure C. (Yield: 58.73%). MS(ES): m/z: 548.42

[M+H]⁺, LCMS purity, 100%, HPLC purity 99.74%, 1H NMR (DMSO, 400 MHz): 12.49 (s, 1H), 9.70 (s, 1H), 8.52-8.47 (m, 2H), 8.12 (s, 1H), 7.94 (s, 1H), 7.85-7.85 (d, J=1.6 Hz, 1H), 7.71-7.69 (d, J=8.4 Hz, 1H), 3.93 (s, 3H), 3.27 (s, 3H), 3.21 (s, 3H), 2.50 (s, 3H), 2.47 (s, 3H), 2.41 (s, 3H), 2.28 (s, 3H).

Example 174: N-(2-methyl-7-((4-(1-methyl-1H-pyrazol-3-yl)-2-(N-methyl-methysulfonamido)phenyl)amino)-3H-imidazo[4,5-b]pyridin-5-yl)cyclopropanecarboxamide, I-174

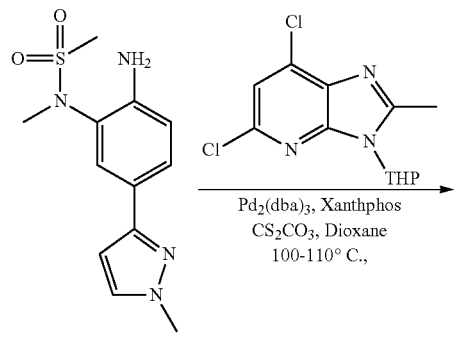

171.1

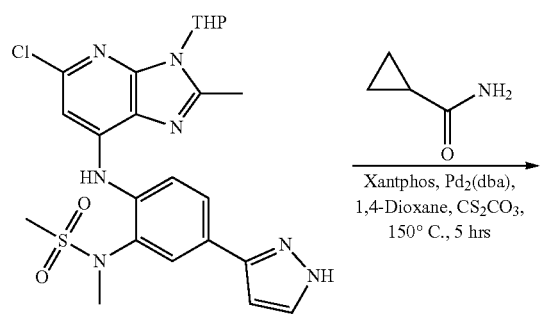

174.1

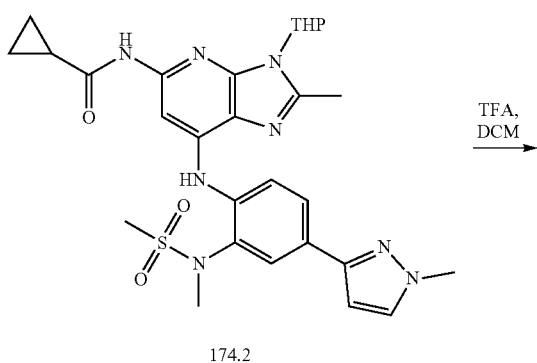

174.2

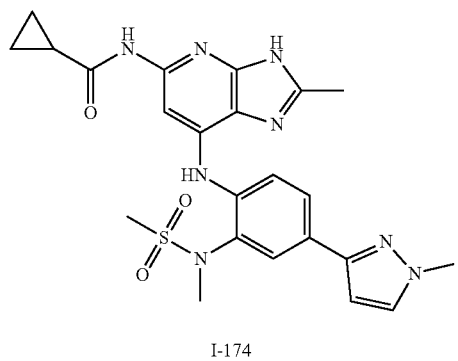 [SMILES: CN(c1cc(-c2ccn(C)n2)ccc1Nc1cc(NC(=O)C2CC2)nc2[nH]c(C(F)F)nc12)S(C)(=O)=O]

I-174

Synthesis of Compound 174.1.

Compound 174.1 was synthesized from 98.4 and 171.1 using general procedure A. (Yield: 33.66%). MS(ES): m/z 531.62 [M+H]⁺.

Synthesis of Compound 174.2.

Compound 174.2 was synthesized from 174.1 and cyclopropanecarboxamide using general procedure B. (Yield: 29.44%). MS(ES): m/z 579.84 [M+H]⁺.

Synthesis of I-174.

Compound I-174 was synthesized from 174.2 using general procedure C. (Yield: 78.01%). MS(ES): m/z: 495.36 [M+H]⁺, LCMS purity: 100%, HPLC purity: 100%, 1H NMR (DMSO, 400 MHz): 12.36 (s, 1H), 10.46 (s, 1H), 7.96-7.96 (d, J=2 Hz, 1H), 7.89 (s, 1H), 7.83-7.76 (m, 3H), 7.61-7.58 (d, J=8.4 Hz, 1H), 6.78-6.78 (d, J=2.4 Hz, 1H), 3.90 (s, 3H), 3.24 (s, 3H), 3.13 (s, 3H), 2.47 (s, 3H), 1.99-1.97 (m, 1H), 0.77-0.73 (m, 4H).

Example 175: Synthesis of N-(2-(difluoromethyl)-7-((4-(1,4-dimethyl-1H-imidazol-2-yl)-2-(N-methyl-methylsulfonamido)phenyl)amino)-3H-imidazo[4,5-b]pyridin-5-yl)cyclopropane-Carboxamide, I-175

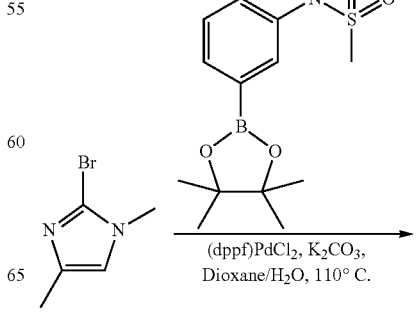

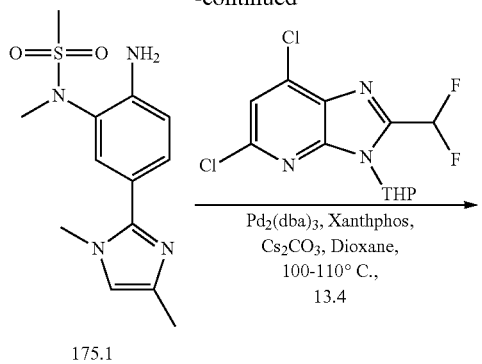

175.1

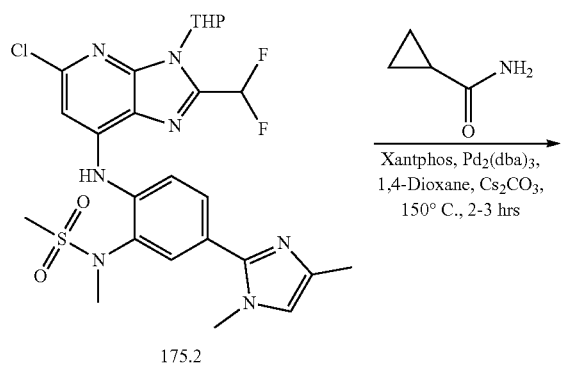

175.2

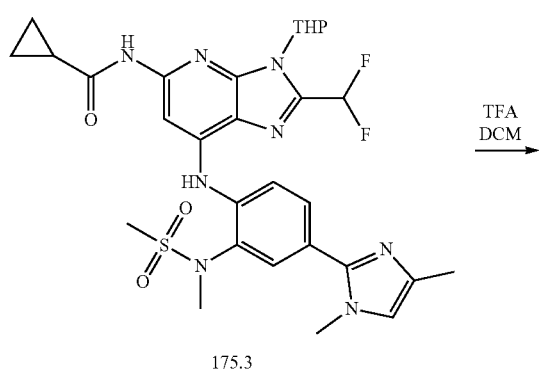

175.3

I-175

Synthesis of Compound 175.1.

To a mixture of compound 2-bromo-1,4-dimethyl-1H-imidazole (1 g, 3.0 mmol, 1.0 eq) and N-(2-amino-5-(4,4,5,5-tetramethyl-1,3,2-dioxaborolan-2-yl)phenyl)-N-methyl-methane-Sulfonamide (0.8 g, 4.5 mmol, 1.5 eq) in a mixture of dioxane (0.8 mL) and water (0.2 mL), potassium carbonate (1.2 g, 0.91 mmol, 3.0 eq) was added. Reaction mixture was degassed for 15 min and then stirred at 110° C. for 2 h. After completion of the reaction, the reaction mixture was transferred to water and extracted with ethyl acetate. Organic layer were combined, dried over $Na_2SO_4$, filtered and concentrated in vacuo to get the crude material. This was purified by column chromatography using 8% ethyl acetate in hexane as eluant to obtain 175.1 (0.4 g, 23.78%). MS(ES): m/z 295.47 $[M+H]^+$.

Synthesis of Compound 175.2.

Compound 175.2 was synthesized from 175.1 and 13.4 using general procedure A. (Yield: 42.94%). MS(ES): m/z 581.05 $[M+H]^+$.

Synthesis of Compound 175.3.

Compound 175.3 was synthesized from 175.2 and cyclopropanecarboxamide using general procedure B. (Yield: 51.16%). MS(ES): m/z 629.70 $[M+H]^+$.

Synthesis of I-175.

Compound I-175 was synthesized from 175.3 using general procedure C. (Yield: 56.78%). MS(ES): m/z: 545.50 $[M+H]^+$, LCMS purity: 98.64%, HPLC purity: 97.84%, 1H NMR (DMSO, 400 MHz): 13.71 (s, 1H), 10.80 (s, 1H), 8.45 (s, 1H), 8.13 (s, 1H), 8.01 (s, 1H), 7.84 (s, 2H), 7.53 (s, 1H), 7.27 (t, 1H), 3.89 (s, 3H), 3.24 (s, 3H), 3.20 (s, 3H), 2.34 (s, 3H), 2.06 (s, 1H), 0.87-0.80 (m, 4H).

Example 176: Synthesis of N-(7-((4-(1,4-dimethyl-1H-imidazol-2-yl)-2-(N-methylmethyl-sulfonamido)phenyl)amino)-2-methyl-3H-imidazo[4,5-b]pyridin-5-yl)cyclopropane-carboxamide, I-176

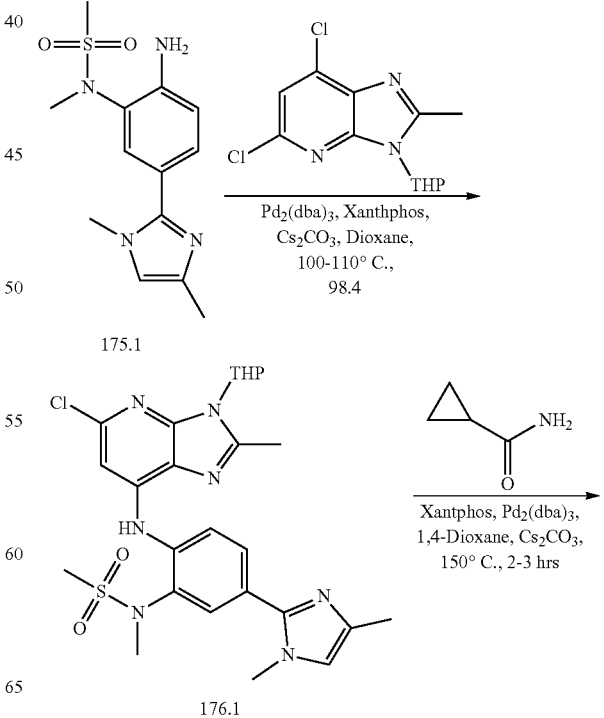

175.1

176.1

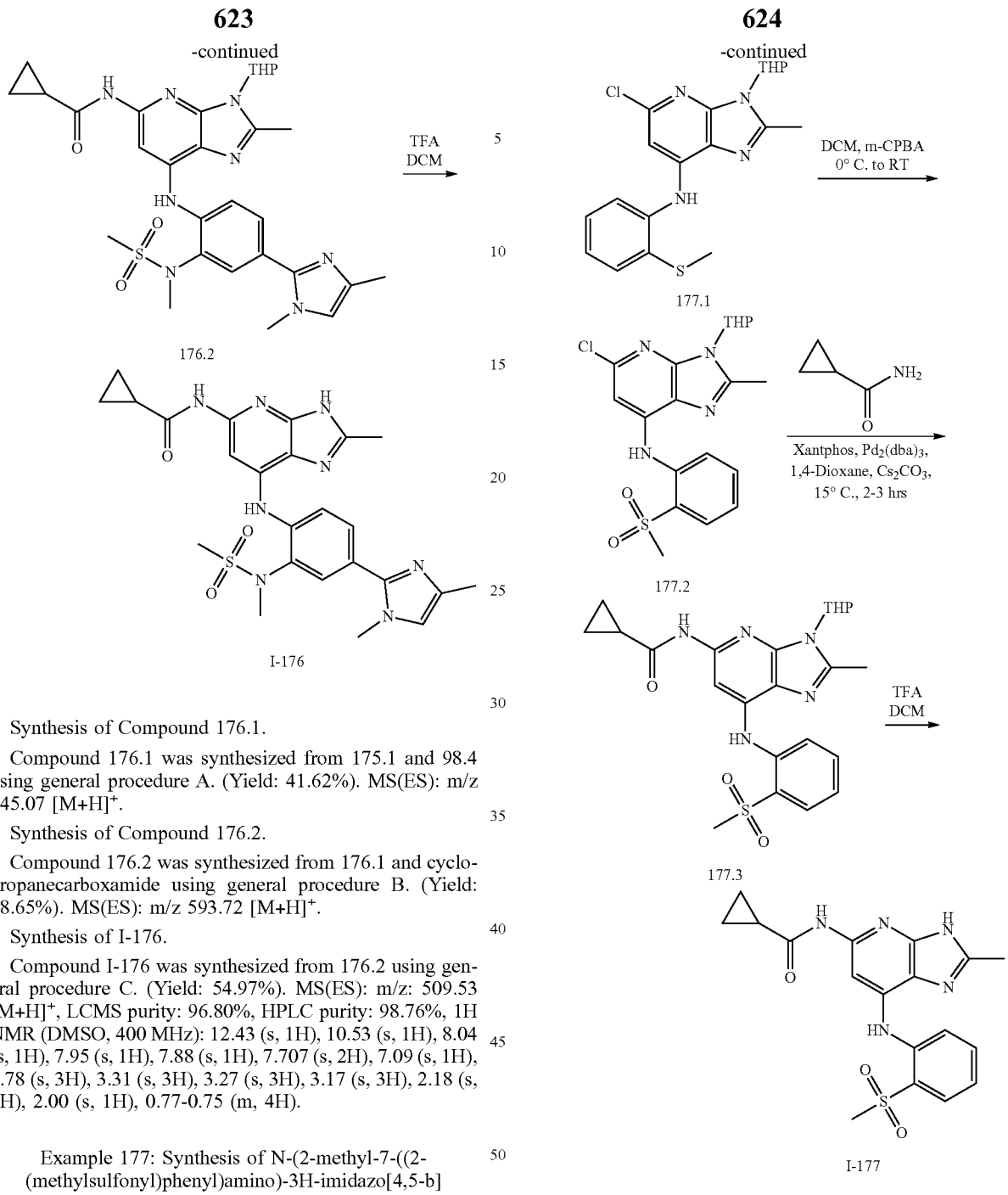

Synthesis of Compound 176.1.

Compound 176.1 was synthesized from 175.1 and 98.4 using general procedure A. (Yield: 41.62%). MS(ES): m/z 545.07 [M+H]⁺.

Synthesis of Compound 176.2.

Compound 176.2 was synthesized from 176.1 and cyclopropanecarboxamide using general procedure B. (Yield: 48.65%). MS(ES): m/z 593.72 [M+H]⁺.

Synthesis of I-176.

Compound I-176 was synthesized from 176.2 using general procedure C. (Yield: 54.97%). MS(ES): m/z: 509.53 [M+H]⁺, LCMS purity: 96.80%, HPLC purity: 98.76%, 1H NMR (DMSO, 400 MHz): 12.43 (s, 1H), 10.53 (s, 1H), 8.04 (s, 1H), 7.95 (s, 1H), 7.88 (s, 1H), 7.707 (s, 2H), 7.09 (s, 1H), 3.78 (s, 3H), 3.31 (s, 3H), 3.27 (s, 3H), 3.17 (s, 3H), 2.18 (s, 3H), 2.00 (s, 1H), 0.77-0.75 (m, 4H).

Example 177: Synthesis of N-(2-methyl-7-((2-(methylsulfonyl)phenyl)amino)-3H-imidazo[4,5-b]pyridin-5-yl)cyclopropanecarboxamide, I-177

Synthesis of Compound 177.1.

Compound 177.1 was synthesized from 2-(methylthio) aniline and 98.4 using general procedure A. (Yield: 8.95%). MS(ES): m/z 389.91 [M+H]⁺.

Synthesis of Compound 177.2.

To a solution of 177.1 (0.11 g, 0.282 mmol, 1.0 eq) in CH₂Cl₂ (2 mL) was added meta-chloro perbenzoic acid (0.097 g, 0.564 mmol, 2.0 eq) at 0° C. and stirred the reaction mixture at r.t. for 2 h. Upon completion, reaction mixture was transferred into aqueous solution of NaHCO₃ and extracted with CH₂Cl₂. Organic layer was concentrated in vacuo to obtain crude product. This was purified by column chromatography using 20% ethyl acetate in hexane to obtain pure 177.2 (0.09 g, Yield: 75.60%). MS(ES): m/z 421.91 [M+H]⁺.

Synthesis of Compound 177.3.

Compound 177.3 was synthesized from 177.2 and cyclopropanecarboxamide using general procedure B. (Yield: 59.76%). MS(ES): m/z 470.56 [M+H]$^+$.

Synthesis of I-177.

Compound I-177 was synthesized from 177.3 using general procedure C. (Yield: 44.79%). MS(ES): m/z: 386.33 [M+H]$^+$, LCMS purity, 97.71%, HPLC purity 93.60%, 1H NMR (DMSO, 400 MHz): 12.52 (s, 1H), 10.61 (s, 1H), 8.62 (s, 1H), 8.02 (s, 1H), 7.93-7.91 (d, J=7.6 Hz, 1H), 7.75 (s, 2H), 7.30 (s, 1H), 3.15 (s, 3H), 2.47 (s, 3H), 2.00 (s, 1H), 0.76 (s, 4H).

Example 178: Synthesis of N-(2-((5-(((6-cyanopyridin-2-yl)amino)-2-(difluoromethyl)-3H-imidazo[4,5-b]pyridin-7-yl)amino)-5-(difluoromethyl)phenyl)-N-methylmethanesulfonamide, I-178

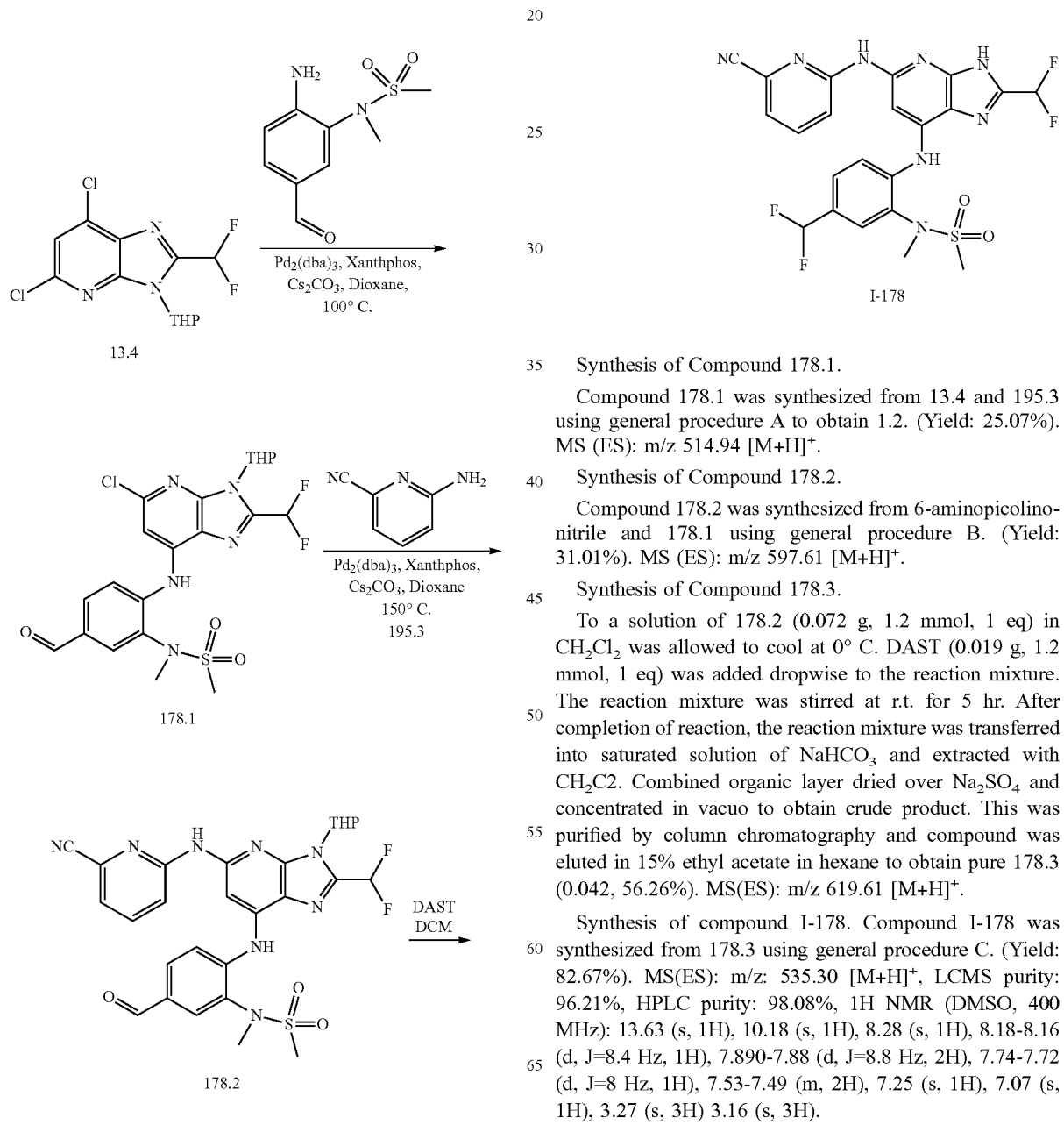

Synthesis of Compound 178.1.

Compound 178.1 was synthesized from 13.4 and 195.3 using general procedure A to obtain 1.2. (Yield: 25.07%). MS (ES): m/z 514.94 [M+H]$^+$.

Synthesis of Compound 178.2.

Compound 178.2 was synthesized from 6-aminopicolinonitrile and 178.1 using general procedure B. (Yield: 31.01%). MS (ES): m/z 597.61 [M+H]$^+$.

Synthesis of Compound 178.3.

To a solution of 178.2 (0.072 g, 1.2 mmol, 1 eq) in CH$_2$Cl$_2$ was allowed to cool at 0° C. DAST (0.019 g, 1.2 mmol, 1 eq) was added dropwise to the reaction mixture. The reaction mixture was stirred at r.t. for 5 hr. After completion of reaction, the reaction mixture was transferred into saturated solution of NaHCO$_3$ and extracted with CH$_2$C2. Combined organic layer dried over Na$_2$SO$_4$ and concentrated in vacuo to obtain crude product. This was purified by column chromatography and compound was eluted in 15% ethyl acetate in hexane to obtain pure 178.3 (0.042, 56.26%). MS(ES): m/z 619.61 [M+H]$^+$.

Synthesis of compound I-178. Compound I-178 was synthesized from 178.3 using general procedure C. (Yield: 82.67%). MS(ES): m/z: 535.30 [M+H]$^+$, LCMS purity: 96.21%, HPLC purity: 98.08%, 1H NMR (DMSO, 400 MHz): 13.63 (s, 1H), 10.18 (s, 1H), 8.28 (s, 1H), 8.18-8.16 (d, J=8.4 Hz, 1H), 7.890-7.88 (d, J=8.8 Hz, 2H), 7.74-7.72 (d, J=8 Hz, 1H), 7.53-7.49 (m, 2H), 7.25 (s, 1H), 7.07 (s, 1H), 3.27 (s, 3H) 3.16 (s, 3H).

Example 179: Synthesis of 3-((5-(cyclopropanecarboxamido)-2-(difluoromethyl)-3H-imidazo[4,5-b]pyridin-7-yl)amino)-2-methoxybenzoic acid, I-179

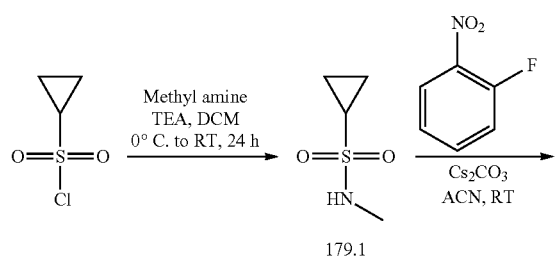

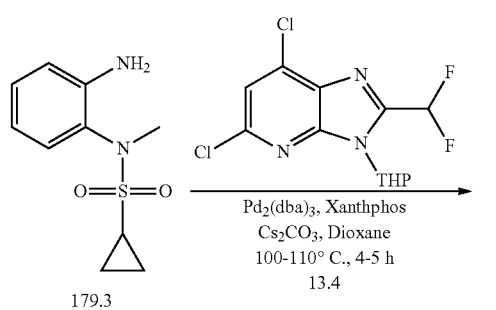

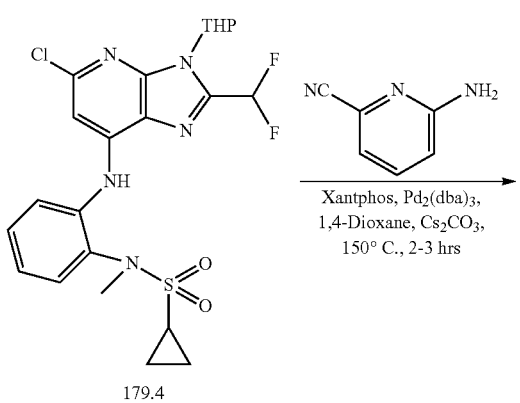

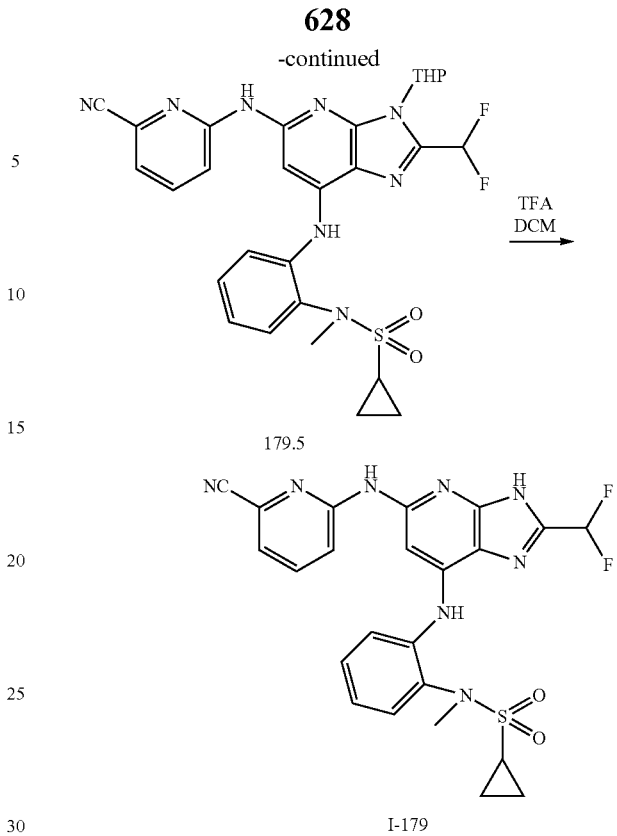

Synthesis of Compound 179.1.

To a solution of cyclopropanesulfonyl chloride (1.0 g, 7.11 mmol, 1.0 eq) in $CH_2Cl_2$ (8 mL) at 0° C., methylamine (2M in tetrahydrofuran) (10.7 mL, 21.4 mmol, 3.0 eq) was added. After 5 min, triethylamine (1.4 mL, 10.7 mmol, 1.5 eq) was added dropwise. Reaction mixture was stirred at r.t. for 24 h. After completion of the reaction, the reaction mixture was transferred into water and extracted with $CH_2Cl_2$. Organic layers were combined, dried over anhydrous $Na_2SO_4$, filtered and concentrated in vacuo to obtain 179.1 (0.9 g, 93.6%). MS(ES): m/z 136.48 [M+H]$^+$.

Synthesis of Compound 179.2.

To compound 179.1 (0.9 g, 6.38 mmol, 1.0 eq) in acetonitrile (10 mL), $Cs_2CO_3$ (3.1 g, 9.57 mmol, 1.5 eq) was added. After 10 min, d 1-fluoro-2-nitrobenzene (1.3 g, 9.57 mmol, 1.5 eq) was added. Reaction mixture was stirred at r.t. for 24 h. After completion of the reaction, the reaction mixture was transferred into water and extracted with ethyl acetate. Organic layers were combined, dried over anhydrous $Na_2SO_4$, filtered and concentrated in vacuo to obtain 179.2 (1.2 g, 73.41%). MS(ES): m/z 257.72 [M+H]$^+$.

Synthesis of Compound 179.3.

To compound 179.2 (1.2 g, 4.68 mmol, 1.0 eq) in MeOH (15 mL), 10% Pd/C (0.3 g) was added. Hydrogen gas was purged into the reaction mixture for 30 min. After completion of the reaction, the reaction mixture was filtered through celite bed and washed with MeOH. Filtrate was concentrated in vacuo to obtain 179.3 (0.9 g, 84.94%). MS(ES): m/z 227.91 [M+H]$^+$.

Synthesis of Compound 179.4.

Compound 179.4 was synthesized from 179.3 and 13.4 using from general procedure A. (Yield: 27.85%). MS(ES): m/z 512.46 [M+H]$^+$.

Synthesis of Compound 179.5.

Compound 179.5 was synthesized from 179.4 and 6-aminopicolinonitrile using general procedure B. (Yield: 44.42%). MS(ES): m/z 595.48 [M+H]$^+$.

Synthesis of I-179.

Compound I-179 was synthesized from 179.5 using general procedure C. (Yield: 53.76%). MS(ES): m/z: 511.31 [M+H]$^+$, LCMS purity, 96.15%, HPLC purity 94.37%, 1H NMR (DMSO-d6, 400 MHz): 13.56 (s, 1H), 10.14 (s, 1H), 8.14-8.11 (m, 2H), 7.90-7.86 (t, J=7.6 Hz, 1H), 7.79-7.72 (m, 2H), 7.54-7.47 (m, 3H), 7.28-7.24 (m, 2H), 3.26 (s, 3H), 2.88 (s, 1H), 1.08-1.06 (d, 2H) 0.91 (s, 2H).

Example 180: Synthesis of N-(2-((5-(((6-cyanopyridin-2-yl)amino)-2-methyl-3H-imidazo[4,5-b]pyridin-7-yl)amino)phenyl)-N-methylcyclopropanesulfonamide, I-180

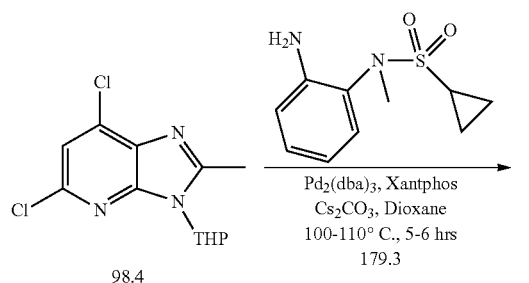

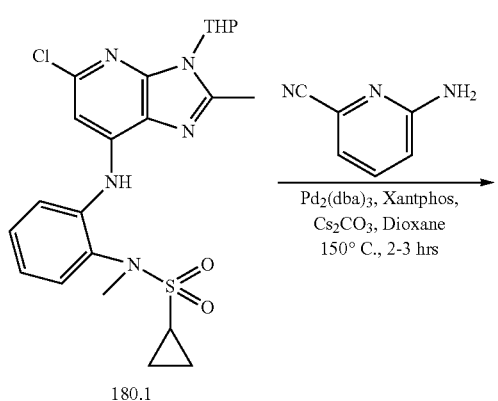

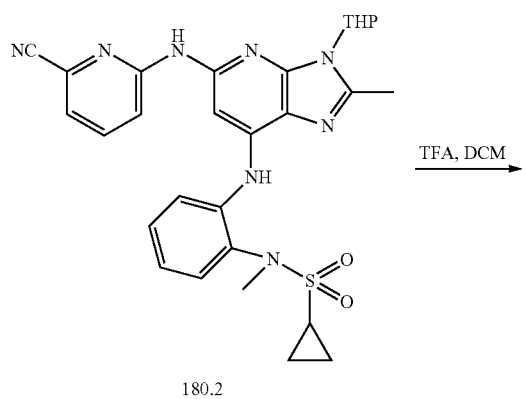

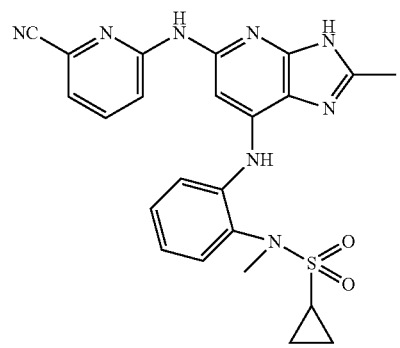

I-180

Synthesis of Compound 180.1.

Compound 180.1 was synthesized from 98.4 and 180.1 using general procedure A. (Yield: 32.09%). MS(ES): m/z 476.99 [M+H]$^+$.

Synthesis of Compound 180.2.

Compound 180.2 was synthesized from 180.1 and cyclopropanecarboxamide using general procedure A. (Yield: 32.09%). MS(ES): m/z 476.99 [M+H]$^+$.

Synthesis of I-180.

Compound I-180 was synthesized from 180.2 using general procedure C. (Yield: 78.48%). MS(ES): m/z: 475.25 [M+H]$^+$, LCMS purity: 97.69%, HPLC purity: 97.32%, 1H NMR (DMSO, 400 MHz): 12.41 (s, 1H), 9.95 (s, 1H), 8.02-8.00 (d, J=8.4 Hz 1H), 7.91 (s, 1H), 7.85-7.77 (m, 2H), 7.71-7.69 (d, J=7.6 Hz, 1H), 7.54-7.50 (m, 2H), 7.43-7.41 (d, J=7.2 Hz, 1H), 7.21-7.17 (t, J=7.6 Hz, 1H), 3.25 (s, 3H), 2.89 (s, 1H), 2.476 (s, 3H), 1.12-1.09 (t, J=6.8 Hz, 2H) 0.93 (bs, 2H).

Example 181: Synthesis of N-(2-((5-(((6-cyanopyridin-2-yl)amino)-2-methyl-3H-imidazo[4,5-b]pyridin-7-yl)amino)phenyl)-N-methylethanesulfonamide, I-181

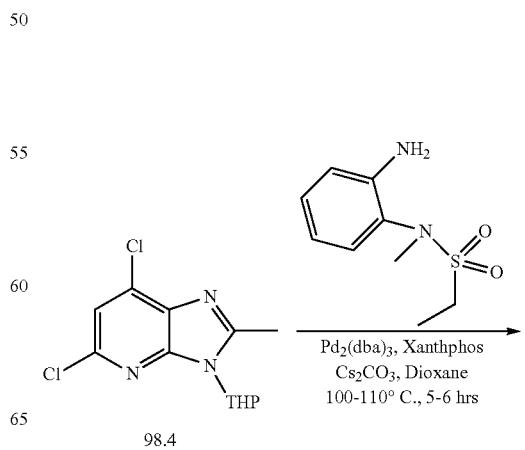

631

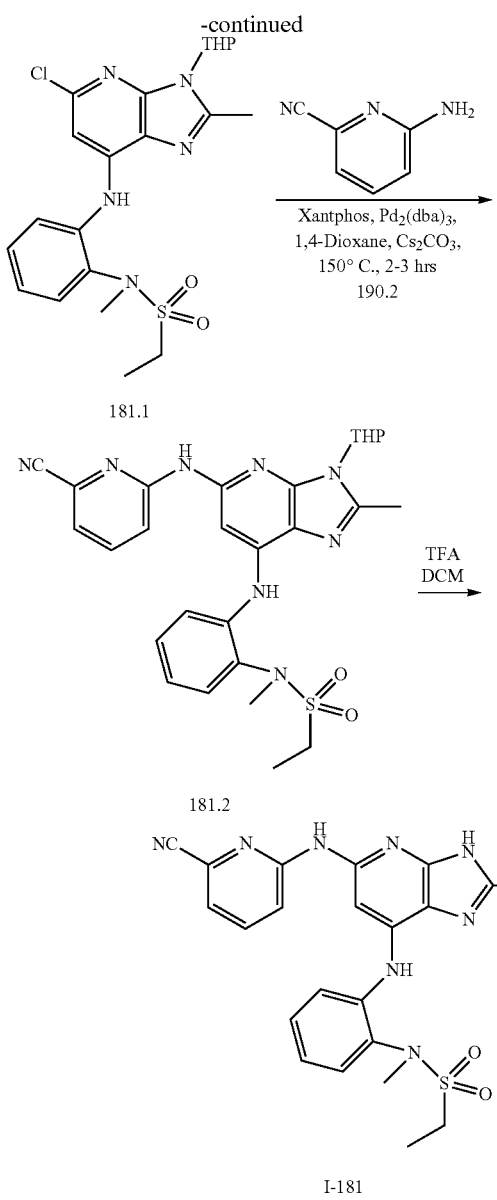

181.1

181.2

I-181

Synthesis of Compound 181.1

Compound 181.1 was synthesized from 98.4 and 190.2 using general procedure A. (Yield: 16.93%). MS(ES): m/z 464.53 [M+H]$^+$.

Synthesis of Compound 181.2.

Compound 181.2 was synthesized from 6-aminopicolinonitrile and 181.1 using general procedure B. (Yield: 50.15%). MS(ES): m/z 547.28 [M+H]$^+$.

Synthesis of I-181.

Compound I-182 was synthesized using from 182.2 general procedure C. (Yield: 99.02%). MS(ES): m/z: 463.30 [M+H]$^+$, LCMS purity, 100%, HPLC purity: 98.31%, 1H NMR (DMSO-d6, 400 MHz): 12.83 (s, 1H), 10.02 (s, 1H), 8.00 (s, 1H), 7.98 (s, 1H), 7.86-7.82 (t, 1H), 7.73-7.71 (d, J=7.6 HZ, 1H), 7.66-7.64 (d, J=7.6 HZ, 1H), 7.54-7.50 (t, 1H), 7.45-7.43 (d, 1H), 7.36 (s, 1H), 7.26-7.22 (t, 1H), 3.40-3.38 (m, 2H), 3.29 (s, 3H), 2.51 (s, 3H), 1.30-1.26 (t, 3H).

632

Example 182: Synthesis of N-(2-(difluoromethyl)-7-((2-(N-methylmethylsulfonamido)-4-(tetrahydro-2H-pyran-4-yl)phenyl)amino)-3H-imidazo[4,5-b]pyridin-5-yl)cyclopropanecarboxamide, I-182

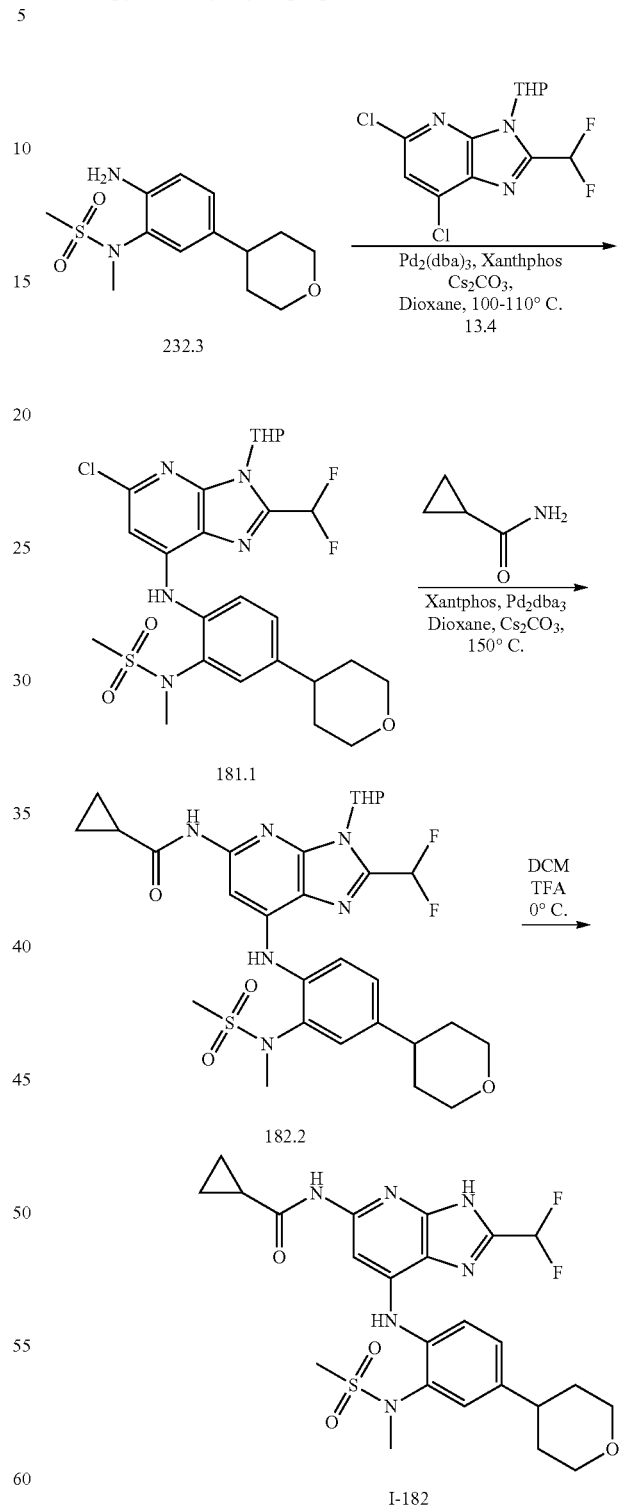

Synthesis of Compound 182.1.

Compound 182.1 was synthesized from 13.4 and 232.3 using general procedure A. (Yield: 54.87%). MS(ES): m/z 571.38 [M+H]$^+$.

Synthesis of Compound 182.2.

Compound 182.2 was synthesized from 182.1 and cyclopropanecarboxyamide using general procedure B. (Yield: 29.32%). MS(ES): m/z 619.51 [M+H]+.

Synthesis of I-182.

Compound I-182 was synthesized from 182.2 using general procedure C. (Yield: 49.60%). MS(ES): m/z: 535.50 [M+H]+, LCMS purity, 99.71%, HPLC purity 99.39%, 1H NMR (DMSO, 400 MHz): 13.54 (s, 1H), 10.63 (s, 1H), 8.06 (s, 1H), 7.86 (s, 1H), 7.60-7.55 (d, J=1.6 Hz, 1H), 7.56-7.53 (d, J=8.4 Hz, 1H), 7.39-7.33 (m, 1H), 7.25 (t, 1H), 4.00-3.97 (d, J=10.8 Hz, 2H), 3.49-3.48 (d, J=3.6 Hz, 2H), 3.24 (s, 3H), 3.08 (s, 3H), 2.84 (m, 1H), 2.04-2.01 (m, 1H), 1.78-1.73 (m, 4H), 0.78-0.77 (d, J=6 Hz, 4H).

Example 183: Synthesis of N-(7-((4-cyclopropyl-2-(N-methylmethylsulfonamido)phenyl)amino)-2-(difluoromethyl)-3H-imidazo[4,5-b]pyridin-5-yl)cyclopropanecarboxamide, I-183

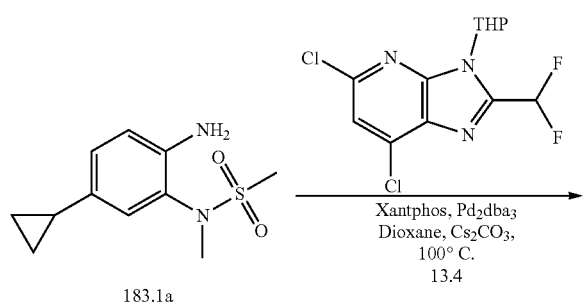

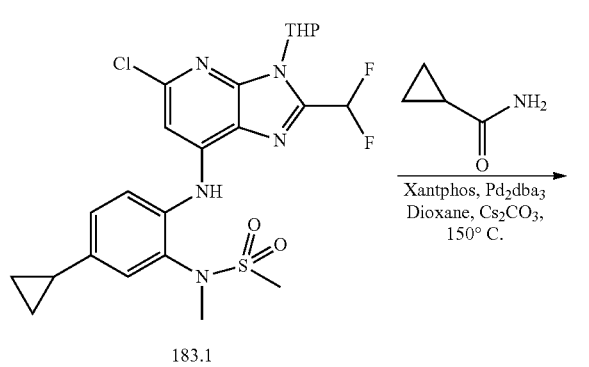

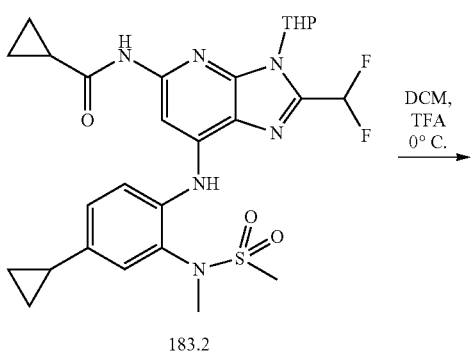

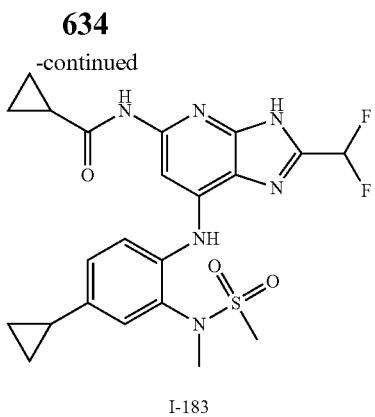

I-183

Synthesis of Compound 183.1.

Compound 183.1 was synthesized from 13.4 and 183.1a using general procedure A. (Yield: 14.62%). MS(ES): m/z 527.00 [M+H]+

Synthesis of Compound 183.2.

Compound 183.2 was synthesized from 183.1 and cyclopropanecarboxamide using general procedure B. (Yield: 51.49%). MS(ES): m/z 575.65 [M+H]+.

Synthesis of I-183.

Compound I-183 was synthesized from 183.2 using general procedure C (Yield: 78.10%). MS(ES): m/z: 491.30 [M+H]+, LCMS purity: 95.14%, HPLC purity: 95.31%, 1H NMR (DMSO, 400 MHz): 13.50 (s, 1H), 10.59 (s, 1H), 8.00 (s, 1H), 7.75 (s, 1H), 7.46-7.43 (d, J=8 Hz, 1H), 7.35 (d, J=1.6 Hz, 2H), 7.23 (t, 1H), 3.17 (m, 3H), 3.05 (s, 3H), 2.00-1.98 (t, J=6.4 Hz, 2H), 1.00-0.98 (m, 2H), 0.77-0.75 (d, J=4.8 Hz, 4H), 0.67-0.66 (d, J=5.6 Hz, 2H).

Example 184: Synthesis of N-(7-((4-cyclopropyl-2-(N-methylmethylsulfonamido)phenyl)amino)-2-methyl-3H-imidazo[4,5-b]pyridin-5-yl)cyclopropanecarboxamidee, I-184

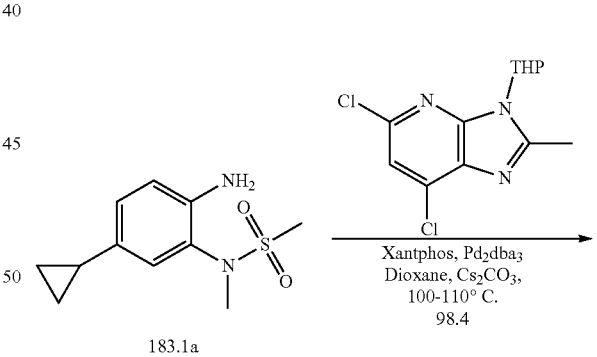

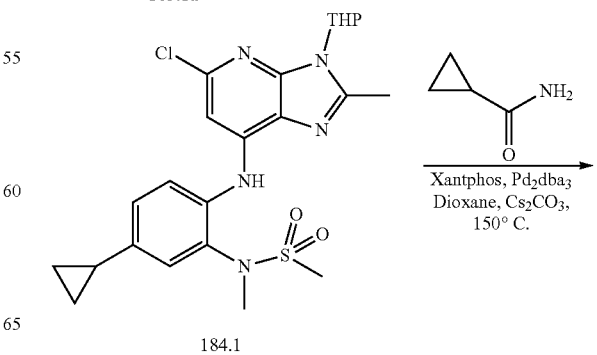

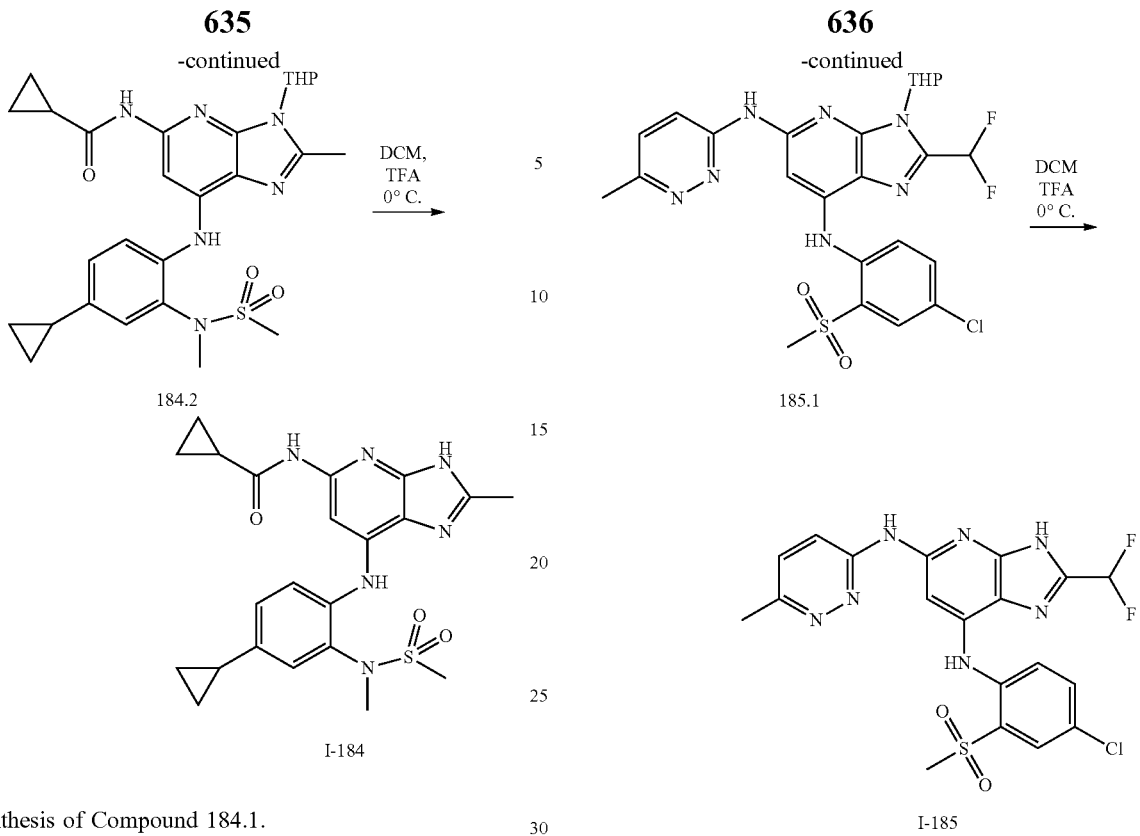

Synthesis of Compound 184.1.

Compound 184.1 was synthesized from 183.1a and 98.4 using general procedure A. (Yield: 21.58%). MS(ES): m/z 491.02 [M+H]⁺.

Synthesis of Compound 184.2.

Compound 184.2 was synthesized from 184.1 and cyclopropanecarboxamide using general procedure B. (Yield: 53.75%). MS(ES): m/z 539.67 [M+H]⁺.

Synthesis of Compound I-184.

Compound I-184 was synthesized from 184.2 using general procedure C. (Yield: 72.92%) MS(ES): m/z: 455.40 [M+H]⁺, LCMS purity: 95.98%, HPLC purity: 95.02%, 1H NMR (DMSO, 400 MHz): 12.32 (s, 1H), 10.42 (s, 1H), 7.74 (s, 1H), 7.69 (s, 1H), 7.44-7.42 (d, J=8 Hz, 1H), 7.33-7.33 (d, J=2 Hz, 1H), 7.13-7.11 (m, 1H), 3.17 (s, 3H), 3.07 (s, 3H), 2.47 (s, 3H), 1.99-1.92 (m, 2H), 1.07-0.95 (m, 2H), 0.75-0.75 (d, J=8.4 Hz, 6H).

Example 185: Synthesis of N7-(4-chloro-2-(methylsulfonyl)phenyl)-2-(difluoromethyl)-N5-(6-methylpyridazin-3-yl)-3H-imidazo[4,5-b]pyridine-5,7-diamine, I-185

Synthesis of Compound 185.1.

Compound 185.1 was synthesized from 58.2 and methylpyridazin-3-amine using general procedure B. (Yield: 35.39%). MS(ES): m/z 565.01 [M+H]⁺.

Synthesis of I-185.

Compound I-185 was synthesized from 185.1 using general procedure C. (Yield: 79.09%). MS(ES): m/z: 480.20 [M+H]⁺, LCMS purity: 96.41%, HPLC purity: 98.01%, 1H NMR (DMSO, 400 MHz): 13.81 (s, 1H), 10.99 (s, 1H), 9.02 (s, 1H), 8.24-8.22 (d, J=8 Hz 1H), 7.97-7.96 (d, J=2 Hz, 2H), 7.91-7.81 (m, 2H), 7.28 (s, 1H), 6.98 (s, 1H), 3.35 (s, 3H), 2.59 (s, 3H).

Example 186: Synthesis of 6-((7-((4-chloro-2-(methylsulfonyl)phenyl)amino)-2-methyl-3H-imidazo[4,5-b]pyridin-5-yl)amino)picolinonitrile, I-186

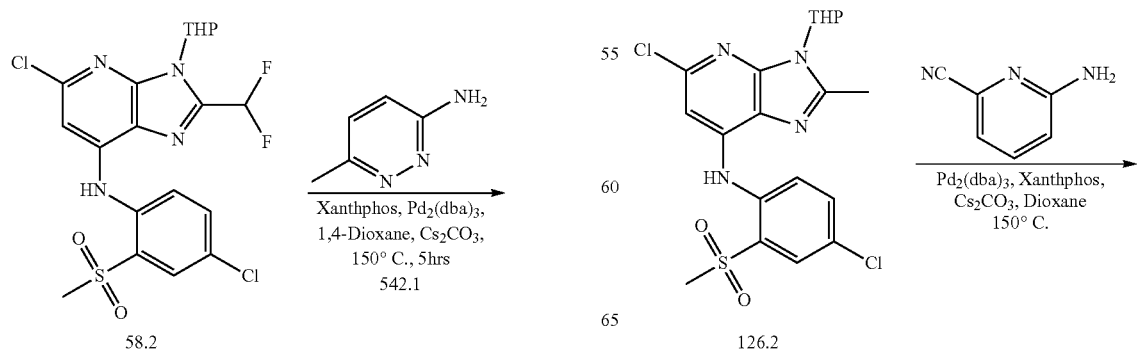

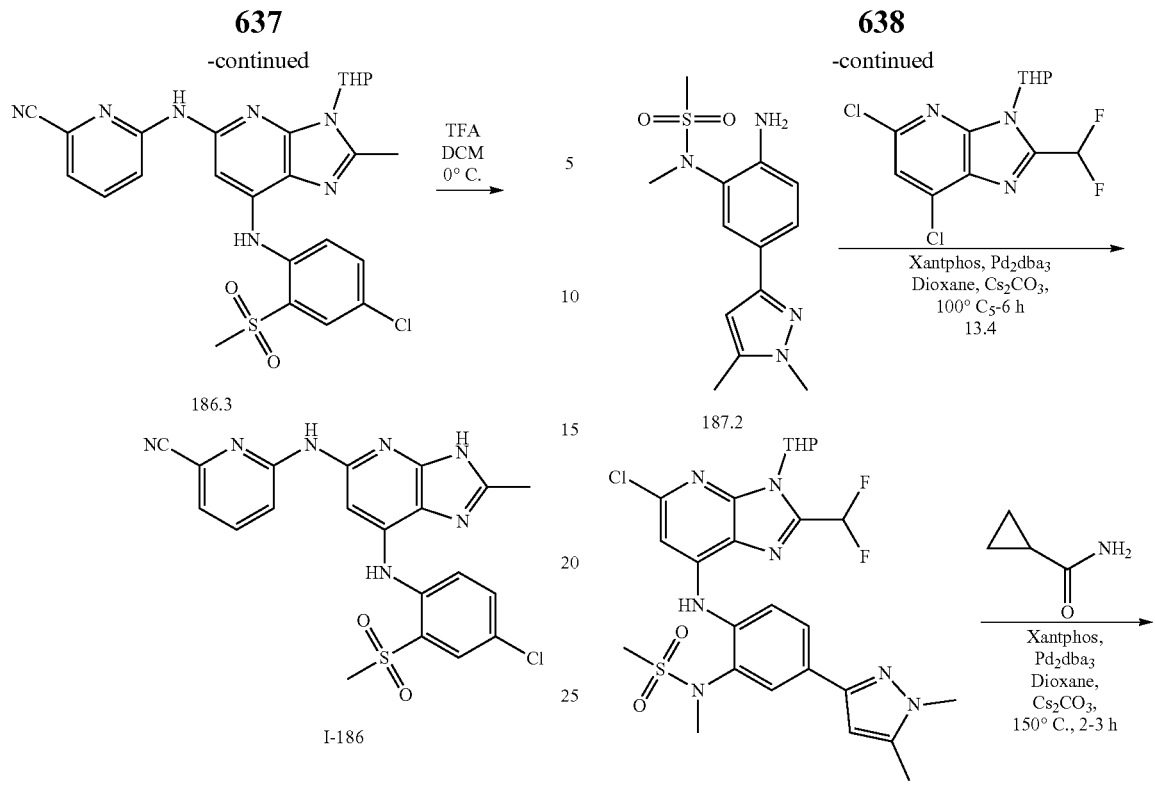

Synthesis of Compound 186.3.

Compound 186.3 was synthesized from 6-aminopicolinonitrile and 126.2 using general procedure B. (Yield: 24.18%). MS (ES): m/z 539.02 [M+H]$^+$.

Synthesis of Compound I-186.

Compound I-186 was synthesized from 186.3 using general procedure C. (Yield: 74.08%). MS(ES): m/z: 454.36 [M+H]$^+$, LCMS purity: 97.59%, HPLC purity: 97.61%, 1H NMR (DMSO, 400 MHz): 10.05 (s, 1H), 8.77 (s, 1H), 7.96-7.94 (d, J=8.4 Hz, 2H), 7.87-7.85 (t, J=3.6 Hz, 3H), 7.64 (s, 1H), 7.49-7.44 (m, 1H), 7.13-7.11 (d, J=8 Hz, 1H), 3.30 (s, 3H) 2.48 (s, 3H).

Example 187: Synthesis of N-(2-(difluoromethyl)-7-((4-(1,5-dimethyl-1H-pyrazol-3-yl)-2-(N-methylmethylsulfonamido)phenyl)amino)-3H-imidazo[4,5-b]pyridin-5-yl)cyclopropanecarboxamide, I-187

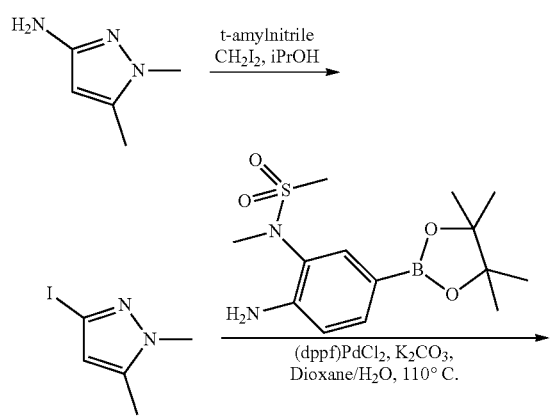

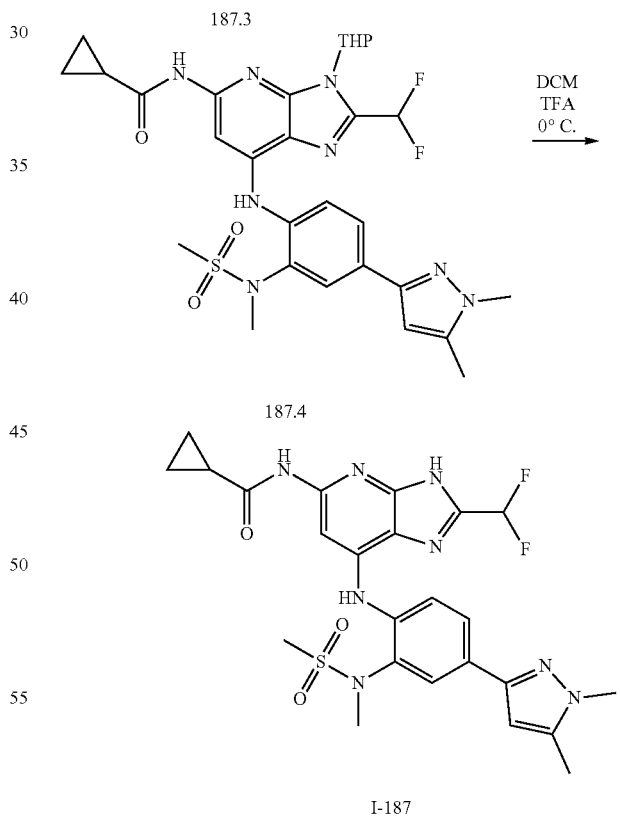

Synthesis of Compound 187.1.

To a solution of 1,5-dimethyl-1H-pyrazol-3-amine (1 g, 9.0 mmol, 1.0 eq), in isopropyl alcohol(20 mL) was added Isoamyl nitrile (1.58 g, 13.50 mmol, 1.5 eq) and Diidomethane (4.21 g, 15.7 mmol, 1.75 eq). The reaction mixture was stirred at 60° C. for 16 h. Upon completion, reaction mixture transferred into 10% HCl solution and washed with hexane. Aqueous layer neutralized by sodium hydroxide solution and extracted with ethyl acetate. Organic layers were combined, dried over Na₂SO₄ and concentrated in vacuo to obtain crude product. This was purified by column chromatography and compound was eluted in 4% ethyl acetate in hexane to obtain pure 187.1 (0.750 g, 37.55%). MS(ES): m/z 223.03 [M+H]⁺.

Synthesis of Compound 187.2.

To a solution of 187.1 (0.750 g, 3.38 mmol, 1.5 eq) in 1,4-dioxane (12 mL) and water(3 mL) was added N-(2-amino-5-(4,4,5,5-tetramethyl-1,3,2-dioxaborolan-2-yl)phenyl)-N-methylmethanesulfonamide (0.740 g, 2.25 mmol, 1 eq), and potassium carbonate (1.4 g, 10.10 mmol, 3 eq). The reaction mixture was degassed by argon for 30 min. [1,1'-Bisdiphenylphosphinoferrocene]palladium(II) dichloride (0.074 g, 1.013 mmol, 0.03 eq), was added into reaction mixture and again reaction mixture was degassed by argon for 30 min. Further reaction mixture was stirred at 110° C. for 3 h. Upon completion, reaction mixture transferred into water and extracted with ethyl acetate. Organic layers were combined, dried over Na₂SO₄ and concentrated in vacuo to obtain crude product. This was purified by column chromatography and compound was eluted in 2% MeOH in CH₂Cl₂ to obtain pure 187.2 (0.500 g, 75.42%). MS(ES): m/z 295.37 [M+H]⁺.

Synthesis of Compound 187.3.

Compound 187.3 was synthesized from 187.2 and 13.4 using general procedure A (Yield: 28.88%). MS(ES): m/z 581.05 [M+H]⁺

Synthesis of Compound 187.4.

Compound 187.4 was synthesized from 187.3 and cyclopropanecarboxamide using general procedure B. (Yield: 46.13%). MS(ES): m/z 629.70 [M+H]⁺.

Synthesis of I-187.

Compound I-187 was synthesized from 187.4 using general procedure C. (Yield: 53.28%). MS(ES): m/z: 545.40 [M+H]⁺, LCMS purity, 100%, HPLC purity 99.78%, 1H NMR (DMSO, 400 MHz): 10.67 (s, 1H), 8.18 (s, 1H), 7.94-7.94 (d, J=1.6 Hz, 1H), 7.82-7.76 (m, 2H), 7.59-7.57 (d, J=8.4 Hz, 1H), 7.39-7.13 (t, 1H), 7.26 (t, 1H), 6.60 (s, 1H), 3.79 (s, 3H), 3.24 (s, 3H), 3.09 (s, 3H), 2.31 (s, 3H), 2.00-1.99 (d, J=6 Hz, 1H), 0.78-0.76 (bs, 4H).

Example 188: Synthesis of N-(7-((4-cyclobutyl-2-(methylsulfonyl)phenyl)amino)-2-methyl-3H-imidazo[4,5-b]pyridin-5-yl)cyclopropanecarboxamide, I-188

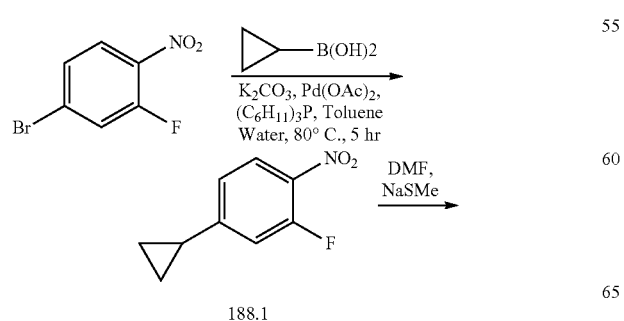

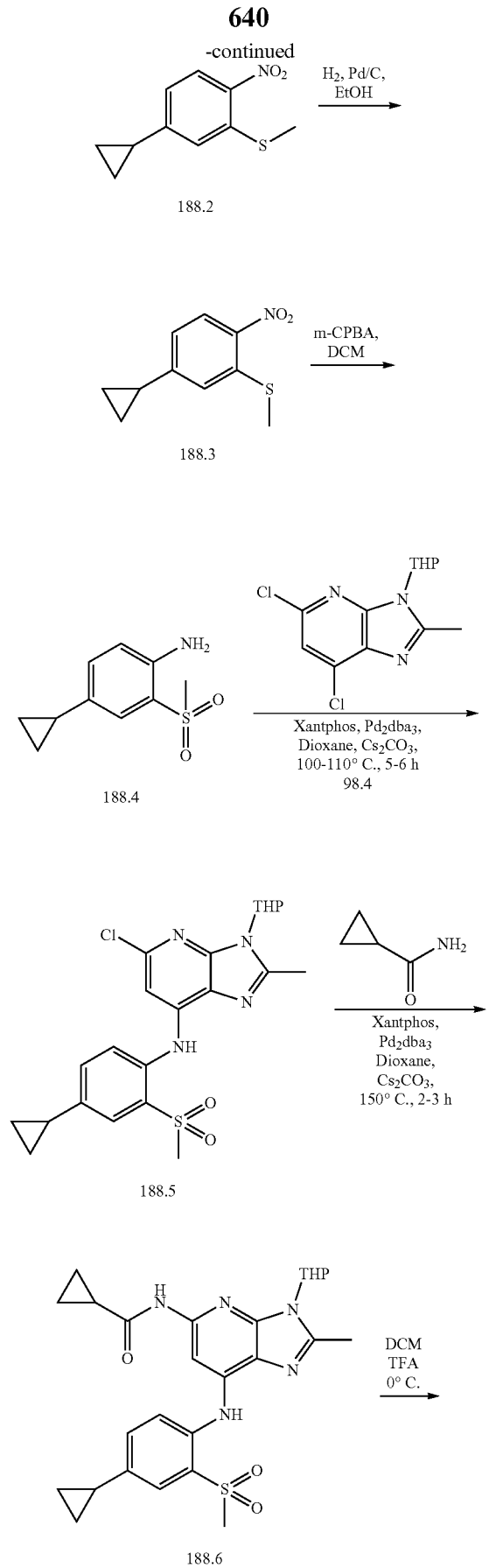

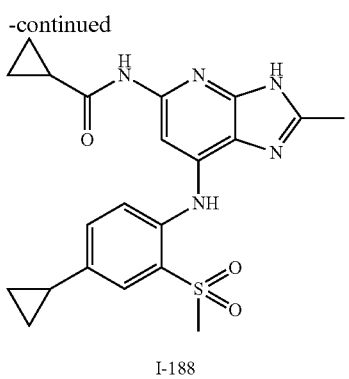

I-188

Synthesis of Compound 188.1.

To a solution of 4-bromo-2-fluoro-1-nitrobenzene (1.0 g, 4.55 mmol, 1.0 eq) in mixture of toluene (12 mL) and water (5 mL) were added cyclopropyl boronic acid (0.51 g, 5.91 mmol, 1.3 eq) and potassium carbonate (1.25 g, 9.1 mmol, 2.0 eq). The reaction mixture was degassed for 10 min under argon atmosphere, and palladium acetate (0.102 g, 0.455 mmol, 0.1 eq) and Tricyclohexylphosphine (0.255 g, 0.91 mmol, 0.2 eq) were added. Reaction mixture was again degassed for 10 min and stirred at 80° C. for 5 h. Upon completion, reaction mixture was transferred into water and extracted with ethyl acetate. Organic layers were combined, dried over $Na_2SO_4$ and concentrated in vacuo to obtain crude product. This was purified by column chromatography and compound was eluted in 10% ethyl acetate in hexane as eluent to obtain 188.1. (0.81 g, 98.36%). MS(ES): m/z 182.17 $[M+H]^+$.

Synthesis of Compound 188.2.

To a solution of 188.1 (0.81 g, 4.47 mmol, 1.0 eq) in N,N-Dimethylformamide (10 mL) was added sodium thiomethoxide (0.313 g, 4.47 mmol, 1.0 eq). Reaction mixture was stirred at 150° C. for 5 h. Upon completion, reaction mixture was transferred into water and extracted with ethyl acetate. Organic layers were combined, dried over $Na_2SO_4$ and concentrated in vacuo to obtain crude product. This was purified by column chromatography and compound was eluted in 15% ethyl acetate in hexane as eluent to obtain 199.2. (0.78 g, 83.37%). MS(ES): m/z 210.26 $[M+H]^+$.

Synthesis of Compound 188.3.

To a solution of 188.2 (0.78 g, 3.73 mmol, 1.0 eq) in ethanol (10 mL), 10% Pd/C (0.060 g) was added. Hydrogen was purged through reaction mixture for 2-3 h. Upon completion, reaction mixture was filtered through celite-bed and washed with ethanol. Filtrate was concentrated in vacuo to obtain 188.3 (0.63 g, 94.28%). MS(ES): m/z 180.28 $[M+H]^+$.

Synthesis of Compound 188.4.

To compound 188.3 (0.63 g, 3.51 mmol, 1.00 eq) in $CH_2Cl_2$ (6 mL) at 0° C., m-chloroperoxybenzoic acid (2.119 g, 12.28 mmol, 3.5 eq) was added portionwise. Reaction mixture was stirred at r.t. for 30 min. After completion of the reaction, the reaction mixture was transferred in water and extracted with ethyl acetate. The organic layer was then washed with $NaHCO_3$. The Organic layers were combined, dried over $Na_2SO_4$, filtered and concentrated in vacuo to obtain 188.4 (0.65 g, 87.55%). MS (ES): m/z 212.28 $[M+H]^+$.

Synthesis of Compound 188.5.

Compound 188.5 was synthesized from 188.4 and 98.4 using general procedure A. (Yield: 28.42%). MS(ES): m/z 461.553 $[M+H]^+$.

Synthesis of Compound 188.6.

Compound 188.6 was synthesized from 188.5 and cyclopropanecarboxamide using general procedure B. (Yield: 39.39%). MS(ES): m/z 510.29 $[M+H]^+$.

Synthesis of I-188.

Compound I-188 was synthesized from 188.6 using general procedure C (Yield: 93.15%). MS(ES): m/z: 426.29 $[M+H]^+$, LCMS purity, 100%, HPLC purity 99.05%, 1H NMR (DMSO-d6, 400 MHz): 12.67 (s, 1H), 10.65 (s, 1H), 8.43 (s, 1H), 7.87 (s, 1H), 7.62-7.60 (t, J=3.6 Hz, 2H), 7.46-7.44 (t, J=2 Hz, 1H), 3.46 (s, 3H), 3.16 (s, 3H), 2.10-2.06 (m, 1H), 2.03-1.91 (m, 1H), 1.02-1.00 (d, J=7.2 Hz, 2H), 0.748 (s, 6H).

Example 189: Synthesis of N7-(4-chloro-2-(methylsulfonyl)phenyl)-2-methyl-N5-(6-methylpyridazin-3-yl)-3H-imidazo[4,5-b]pyridine-5,7-diamine, I-189

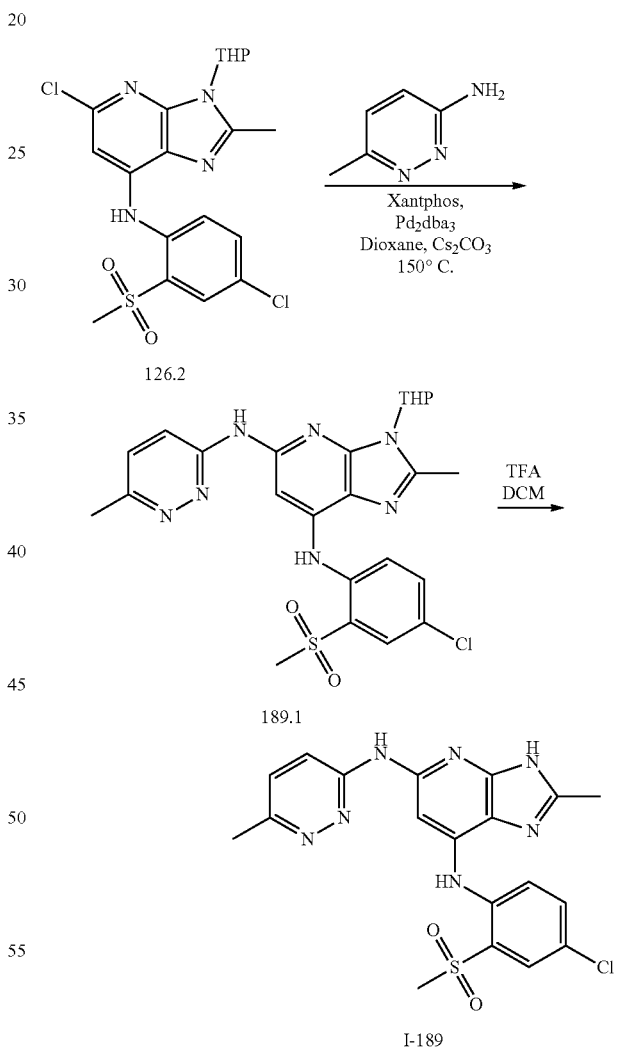

I-189

Synthesis of Compound 189.1.

Compound was synthesized from 6-methylpyridazin-3-amine and 126.2 using general procedure B. (Yield: 22.18%). MS(ES): m/z 528.48 $[M+H]^+$.

Synthesis of I-189.

Compound I-189 was synthesized fro 189.1 using general procedure C. (Yield: 79.03%). MS(ES): m/z: 444.36

[M+H]+, LCMS purity: 97.04%, HPLC purity: 98.11%, 1H NMR (DMSO, 400 MHz): 12.63 (s, 1H), 9.68 (s, 1H), 9.87 (s, 1H), 8.64 (s, 1H), 8.19-8.17 (d, J=9.2 Hz, 1H), 7.88-7.78 (m, 2H), 7.44-7.42 (d, J=9.2 Hz, 1H), 7.34 (s, 1H), 3.29 (s, 3H), 2.46 (s, 3H), 2.45 (s, 3H).

Example 190: Synthesis of N-(2-((5-((6-cyanopyridin-2-yl)amino)-2-(difluoromethyl)-3H-imidazo[4,5-b]pyridin-7-yl)amino)phenyl)-N-methylethanesulfonamide, I-190

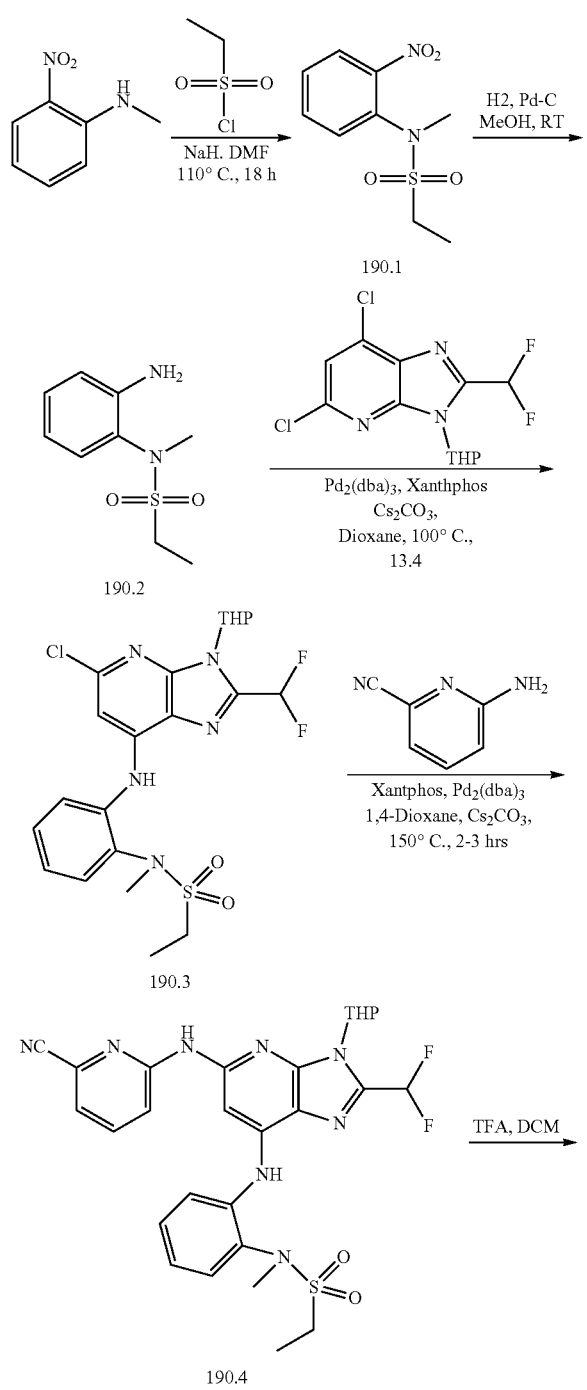

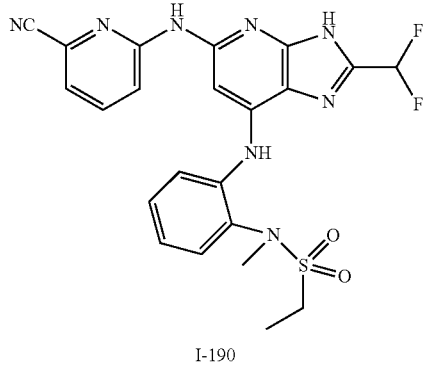

I-190

Synthesis of Compound 190.1.

To a solution of N-methyl-2-nitroaniline (0.5 g, 3.28 mmol, 1.0 eq) in dimethylformamide (10 mL) at 0° C., sodium hydride (0.33 g, 8.2 mmol, 2.5 eq) was added portionwise. Reaction mixture was stirred at 0° C. for 30 min. Then ethanesulfonyl chloride (0.84 g, 6.57 mmol, 2.0 eq) was added dropwise. Reaction mixture was allowed to stir at 110° C. for 18 h. After completion of the reaction, the reaction mixture was transferred into ice-cold water and extracted with ethyl acetate. Organic layers were combined, dried over anhydrous Na₂SO₄, filtered and concentrated in vacuo to obtain crude product. This was purified by column chromatography using 15% ethyl acetate in hexane as eluant to obtain pure 190.1 (0.7 g, 87.21%). MS(ES): m/z 245.16 [M+H]+.

Synthesis of Compound 190.2.

To a solution of 190.1 (0.7 g, 2.86 mmol, 1.0 eq) in MeOH (20 mL), 10% Pd/C (0.180 g) was added. Hydrogen was purged in the reaction mixture for 2 h. After completion of the reaction, the reaction mixture was filtered through celite bed, washed with MeOH and concentrated in vacuo to obtain 190.2 (0.52 g, 84.68%). MS(ES): m/z 215.43 [M+H]+.

Synthesis of Compound 190.3.

Compound 190.3 was synthesized from 13.4 and 190.2 using general procedure A. (Yield: 10.71%). MS(ES): m/z 500.23 [M+H]+.

Synthesis of Compound 190.4.

Compound 190.4 was synthesized from 190.3 and 6-aminopicolinonitrile using general procedure B. (Yield: 38.90%). MS(ES): m/z 583.43 [M+H]+.

Synthesis of I-190.

Compound I-190 was synthesized from 190.4 using general procedure C. (Yield: 89.37%). MS(ES): m/z: 499.43 [M+H]+, LCMS purity, 100%, HPLC purity 99.74%, 1H NMR (DMSO, 400 MHz): 10.14 (s, 1H), 8.09-8.07 (d, J=8 Hz, 1H), 7.99-7.98 (d, J=5.6 Hz, 2H), 7.92-7.88 (t, J=2 Hz, 1H), 7.74-7.72 (d, J=8.4 Hz, 1H), 7.58-7.57 (d, J=7.2 Hz, 1H), 7.54-7.52 (d, J=8 Hz, 1H), 7.43-7.41 (m, 1H), 7.17-7.04 (m, 2H), 3.31-3.30 (q, J=7.2 Hz, 2H), 3.21 (s, 3H), 1.31-1.25 (s, 3H).

Example 191: Synthesis of 6-((7-((4-chloro-2-(methylsulfonyl)phenyl)amino)-2-(difluoromethyl)-3H-imidazo[4,5-b]pyridin-5-yl)amino)picolinonitrile, I-191

Example 192: Synthesis of (1R,2R)—N-(7-((4-chloro-2-(methylsulfonyl)phenyl)amino)-2-methyl-3H-imidazo[4,5-b]pyridin-5-yl)-2-fluorocyclopropane-1-carboxamide, I-192

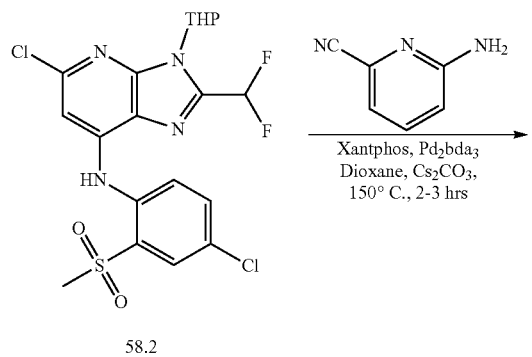

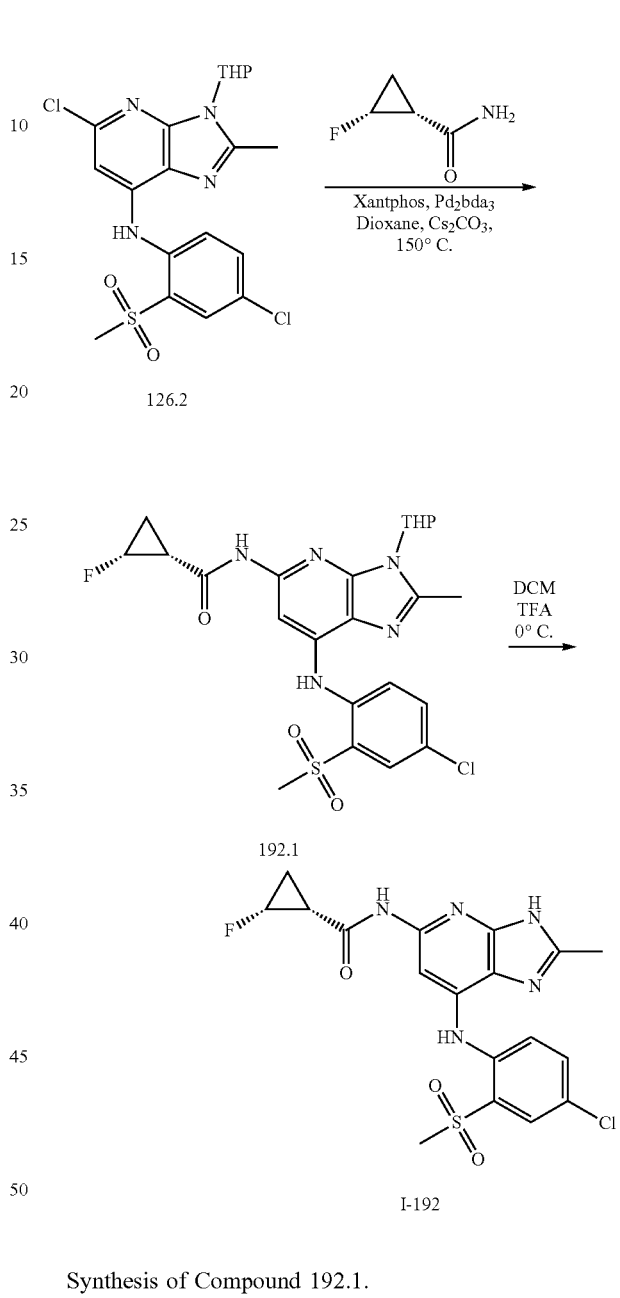

Synthesis of Compound 191.1.

Compound was synthesized from 58.2 and 6-aminopicolinonitrile using general procedure B. (Yield: 23.43%). MS(ES): m/z 490.89 [M+H]+.

Synthesis of I-191.

Compound I-191 was synthesized from compound 191.1 using general procedure C. (Yield: 79.09%) MS(ES): m/z 490.33 [M+H]+, LCMS purity: 99.82%, HPLC purity: 99.66%, 1H NMR (DMSO, 400 MHz): 13.69 (s, 1H), 10.23 (s, 1H), 8.92 (s, 1H), 8.10-8.08 (d, J=8.8 Hz, 1H), 7.97-7.88 (m, 4H), 7.64 (s, 1H), 7.51-7.49 (d, J=7.2 Hz, 1H), 7.24 (t, 1H), 3.32 (s, 3H).

Synthesis of Compound 192.1.

Compound 192.1 was synthesized from (1R,2R)-2-fluorocyclopropane-1-carboxamide and 126.2 using general procedure B. (Yield: 11.84%). MS(ES): m/z 522.38 [M+H]+.

Synthesis of I-192.

Compound I-192 was synthesized from 192.1 using general procedure C. (Yield: 62.74%). MS(ES): m/z: 438.30 [M+H]+, LCMS purity: 95.90%, HPLC purity: 97.33%, Chiral HPLC purity: 94%, 1H NMR (DMSO, 400 MHz): 12.59 (s, 1H), 10.80 (s, 1H), 8.61 (s, 1H), 7.91-7.73 (d, J=8.8 Hz, 4H), 4.95-4.78 (m, 1H), 3.28 (s, 3H), 2.49 (s, 3H), 1.52-1.46 (m, 1H), 1.25-1.20 (m, 2H).

Example 193: Synthesis of N-(7-((4-(1,5-dimethyl-1H-pyrazol-3-yl)-2-(N-methylmethylsulfonamido)phenyl)amino)-2-methyl-3H-imidazo[4,5-b]pyridin-5-yl)cyclopropanecarboxamide, I-193

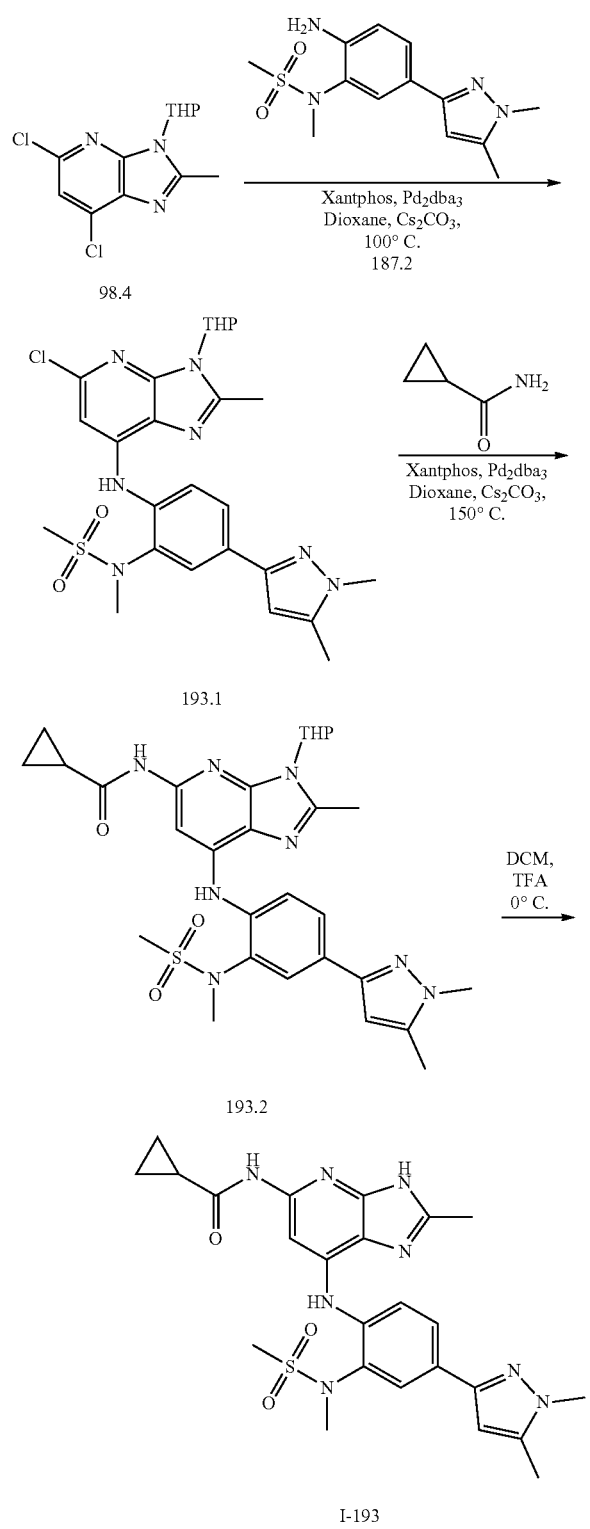

Synthesis of Compound 193.1.

Compound 193.1 was synthesized from 98.4 and 187.2 using general procedure A. (Yield: 29.87%). MS(ES): m/z 545.07 [M+H]$^+$.

Synthesis of compound 193.2 Compound 193.2 was synthesized from 193.1 and cyclopropanecarboxamide using general procedure B. (Yield: 43.96%). MS(ES): m/z 593.72 [M+H]$^+$.

Synthesis of compound I-193.

Compound I-193 was synthesized from 193.2 using general procedure C. (Yield: 46.27%). MS(ES): m/z: 509.41 [M+H]$^+$, LCMS purity: 99.73%, HPLC purity: 99.26%, 1H NMR (DMSO, 400 MHz): 12.49 (s, 1H), 10.54 (s, 1H), 8.32-8.29 (d, J=8.8 Hz, 1H), 7.87 (s, 1H), 7.79-7.78 (d, J=5.6 Hz, 1H), 7.71 (s, 1H), 7.65-7.63 (d, J=8.4 Hz, 1H), 6.50 (s, 1H), 3.77 (s, 3H), 3.22 (s, 3H), 3.12 (s, 3H), 2.47 (s, 3H), 2.30 (s, 3H), 1.57 (m, 1H), 0.89-0.82 (m, 4H).

Example 194: Synthesis of N-(7-((4-(1,3-dimethyl-1H-pyrazol-4-yl)-2-(N-methylmethylsulfonamido)phenyl)amino)-2-methyl-3H-imidazo[4,5-b]pyridin-5-yl)cyclopropanecarboxamide, I-194

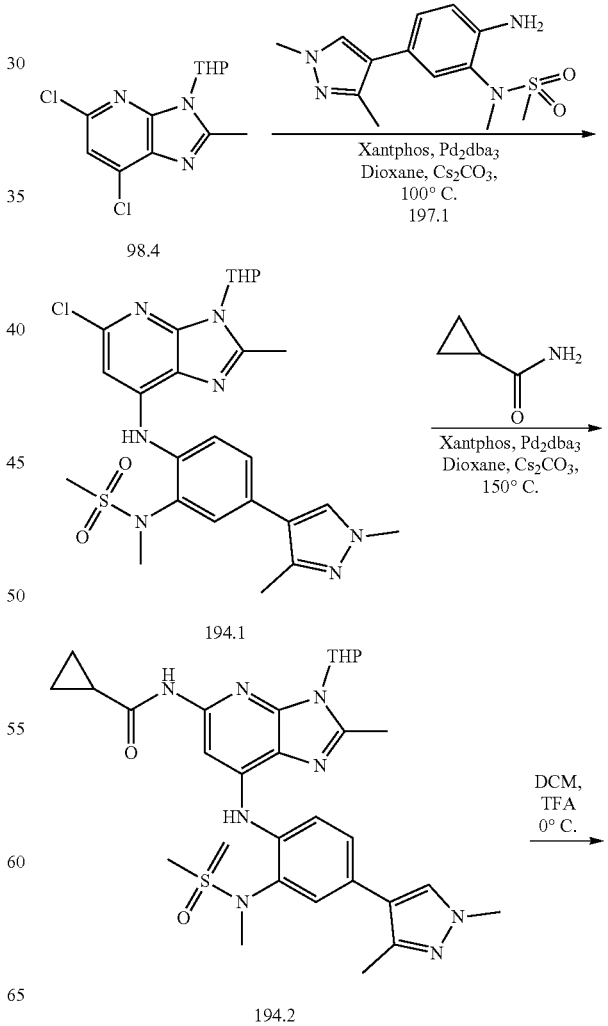

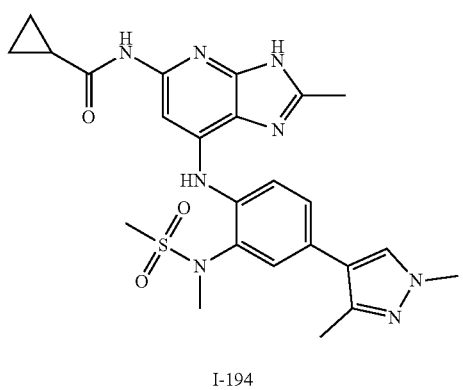

I-194

Synthesis of Compound 194.1.

Compound 194.1 was synthesized from 98.4 and 197.1 using general procedure A. (Yield: 25.67%). MS(ES): m/z 545.07 [M+H]$^+$.

Synthesis of Compound 194.2.

Compound 194.1 was synthesized from 194.1 and cyclopropanecarboxamide using general procedure B. (Yield: 52.67%). MS(ES): m/z 593.72 [M+H]$^+$.

Synthesis of compound I-194.

Compound I-194 was synthesized from 194.2 using general procedure C (Yield: 41.62%). MS(ES): m/z 509.53 [M+H]$^+$, LCMS purity, 100.00%, HPLC purity 96.25%, 1H NMR (DMSO, 400 MHz): 12.47 (s, 1H), 10.53 (s, 1H), 8.31-8.29 (d, J=7.2 Hz, 1H), 7.89 (s, 1H), 7.82 (s, 1H), 7.80 (s, 1H), 7.48-7.48 (d, J=2.0 Hz, 1H), 7.35-7.32 (m, 1H), 3.80 (s, 3H), 3.22 (s, 3H), 3.13 (s, 3H), 2.47 (s, 3H), 2.32 (s, 3H), 1.10 (m, 1H), 0.85-0.82 (m, 4H).

Example 195: Synthesis of N-(2-((5-((6-cyanopyridin-2-yl)amino)-2-methyl-3H-imidazo[4,5-b]pyridin-7-yl)amino)-5-(difluoromethyl)phenyl)-N-methylmethanesulfonamide, I-195

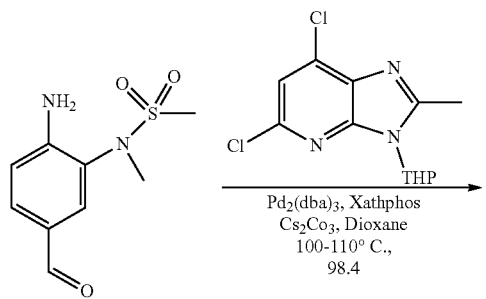

195.3

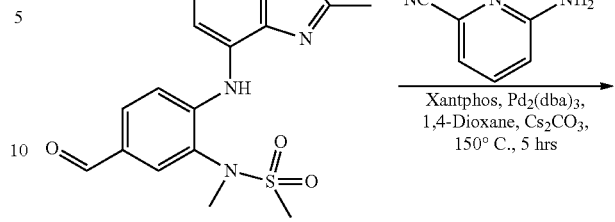

195.1

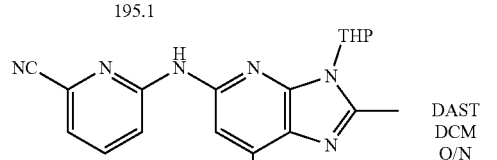

195.2

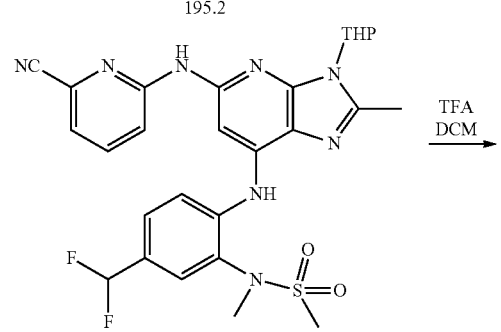

195.3

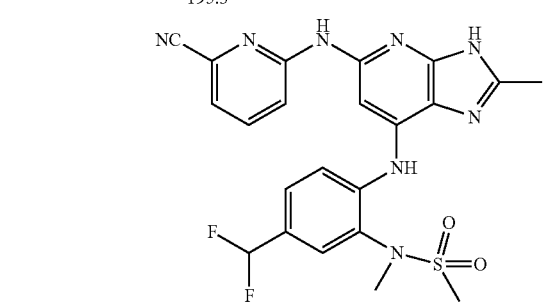

I-195

Synthesis of Compound 195.1.

Compound 195.1 was synthesized from 98.4 and 195.3 using general procedure A. (Yield: 28.26%). MS(ES): m/z 478.54 [M+H]$^+$.

Synthesis of Compound 195.2.

Compound was synthesized from 6-aminopicolinonitrile and 195.1 using general procedure B. (Yield: 31.26%). MS(ES): m/z 561.43 [M+H]$^+$.

Synthesis of Compound 195.3.

To compound 195.2 in CH$_2$Cl$_2$, dimethyl aminosulfurtrichloride was added. Reaction mixture was stirred at r.t. overnight. Reaction mixture was quenched by NaHCO$_3$ and then water was added and extracted with ethyl acetate. Organic layers were combined, dried over anhydrous Na$_2$SO$_4$, filtered and concentrated in vacuo to obtain 195.3 (0.073 g, 54.04%). MS(ES): m/z 583.49 [M+H]$^+$.

Synthesis of I-195.

Compound I-195 was synthesized from 195.3 using general procedure C. (Yield: 35.06%). MS(ES): m/z: 499.36 [M+H]$^+$, LCMS purity: 100%, HPLC purity: 97.33%, 1H NMR (DMSO, 400 MHz): 12.47 (s, 1H), 9.99 (s, 1H), 8.07 (s, 1H), 8.04-8.02 (d, J=8.4 Hz, 1H), 7.90-7.82 (m, 3H), 7.72-7.70 (d, J=8.8 Hz, 1H), 7.56 (s, 1H), 7.45-7.44 (d, J=7.2 Hz, 1H), 3.26 (s, 3H), 3.19 (s, 3H), 2.52 (s, 3H).

Example 196: Synthesis of N-(2-methyl-7-((2-(N-methylmethylsulfonamido)-4-(tetrahydro-2H-pyran-4-yl)phenyl)amino)-3H-imidazo[4,5-b]pyridin-5-yl)cyclopropanecarboxamide, I-196

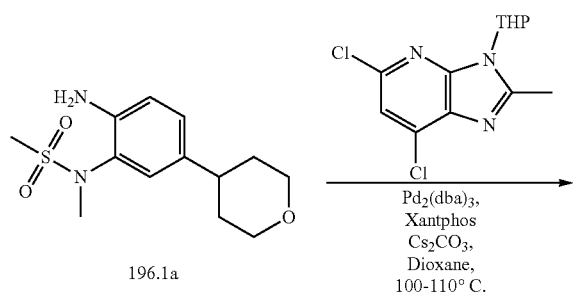

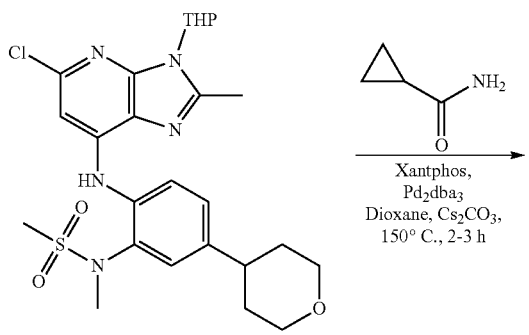

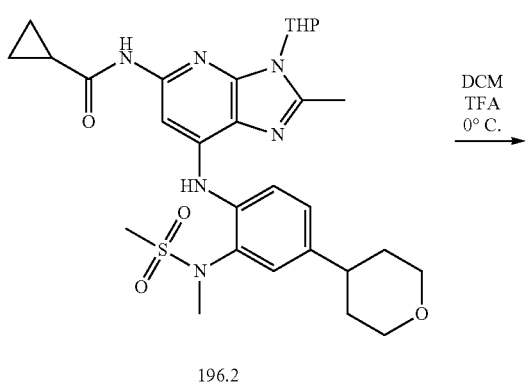

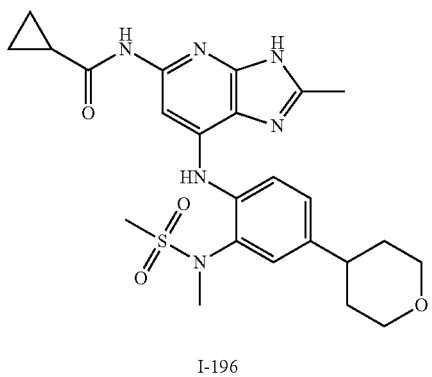

I-196

Synthesis of Compound 196.1.

Compound 196.1 was synthesized from 98.4 and 196.1a using general procedure A. (Yield: 31.21%). MS(ES): m/z 535.67 [M+H]$^+$.

Synthesis of Compound 196.2.

Compound 196.2 was synthesized from 196.1 and cyclopropanecarboxamide using general procedure B. (Yield: 29.65%). MS(ES): m/z 583.42 [M+H]$^+$.

Synthesis of I-196.

Compound I-196 was synthesized from 196.2 using general procedure C. (Yield: 63.75%). MS(ES): m/z: 499.51 [M+H]$^+$, LCMS purity, 98.12%, HPLC purity 98.20%, 1H NMR (DMSO, 400 MHz): 12.34 (s, 1H), 10.45 (s, 1H), 7.78 (s, 2H), 7.56-7.56 (d, J=1.2 Hz, 1H), 7.53-7.51 (d, J=12.4 Hz, 1H), 7.33-7.31 (m, 1H), 3.99-3.96 (d, J=10.8 Hz, 2H), 3.502-3.45 (m, 2H), 3.20 (s, 3H), 3.09 (s, 3H), 2.86-2.78 (m, 1H), 2.48 (s, 3H), 1.99-1.97 (m, 1H), 1.78-1.69 (m, 4H), 0.76 (s, 4H).

Example 197: Synthesis of N-(2-(difluoromethyl)-7-((4-(1,3-dimethyl-1H-pyrazol-4-yl)-2-(N-methylmethylsulfonamido)phenyl)amino)-3H-imidazo[4,5-b]pyridin-5-yl)cyclopropanecarboxamide, 1-197

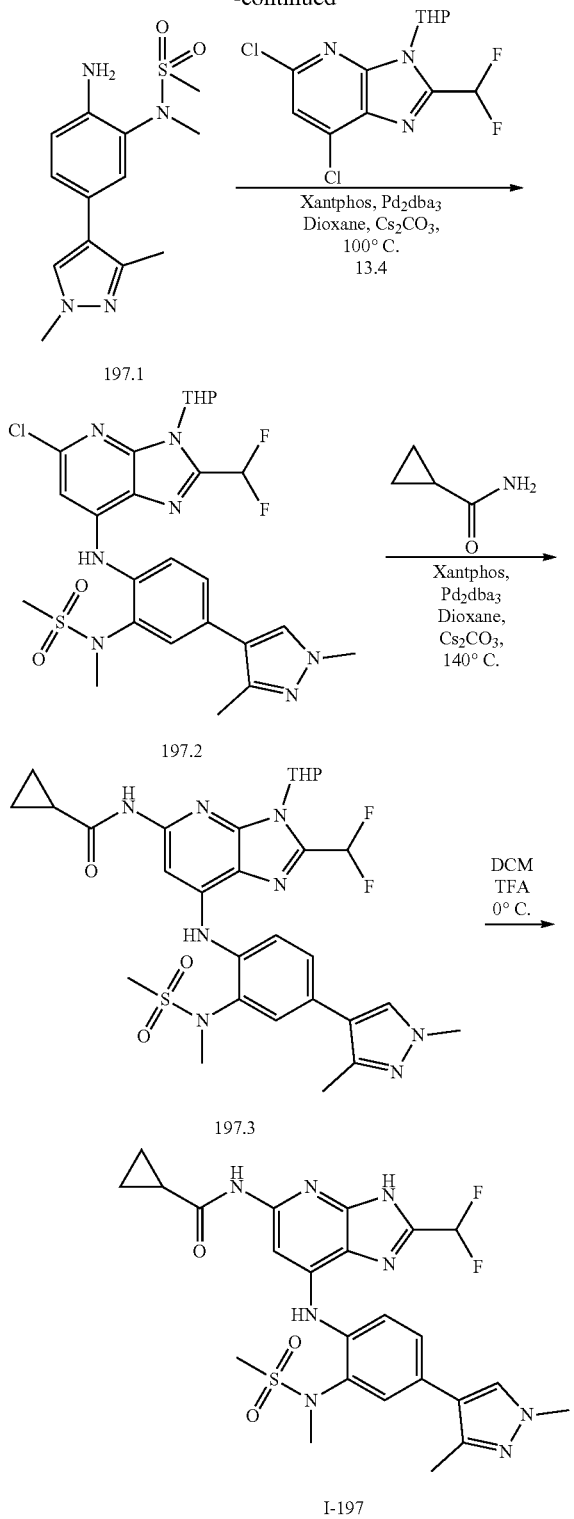

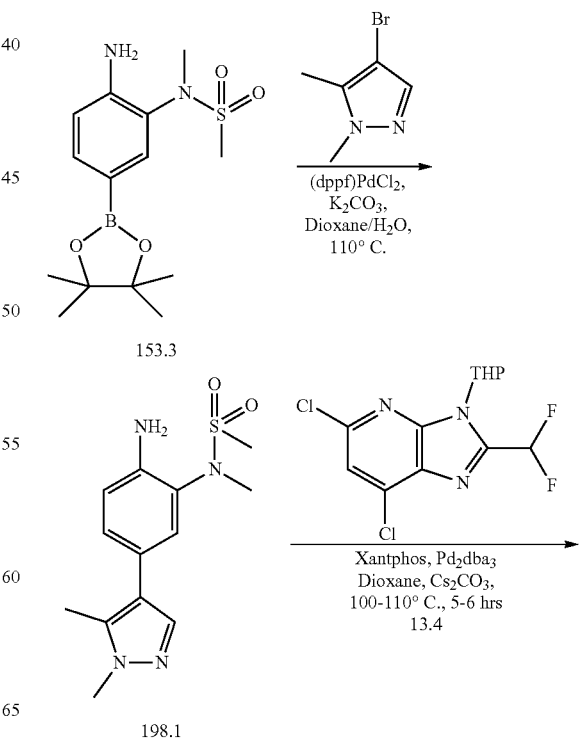

Synthesis of Compound 197.1.

A solution of 153.3 (1 g, 3.07 mmol, 1.0 eq), 4-bromo-1,3-dimethyl-1H-pyrazole (0.650 g, 3.68 mmol, 1.2 eq) in mixture of 1,4-dioxane (20 mL) and water (5 mL) was degassed by argon for 30 min. 1,1'-Bis(diphenylphosphino)ferrocene (0.224 g, 3.067 mmol, 0.1 eq), potassium carbonate (1.39 g, 0.010 mmol, 3.3 eq,) were added into reaction mixture and again reaction mixture was degassed by argon for 30 min. Further reaction mixture was stirred at 110° C. for 5 h. After completion of reaction, water was added to reaction mixture and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 197.1 (0.500 g, 55.41%). MS(ES): m/z 295.37 $[M+H]^+$.

Synthesis of Compound 197.2.

Compound 197.2 was synthesized from 197.1 and 13.4 using general procedure A. (Yield: 24.44%). MS(ES): m/z 581.05 $[M+H]^+$.

Synthesis of Compound 197.3.

Compound 197.3 was synthesized from 197.2 and cyclopropanecarboxamide using general procedure B. (Yield: 40.26%). MS(ES): m/z 629.70 $[M+H]^+$.

Synthesis of compound I-197.

Compound I-197 was synthesized from 197.3 using general procedure C (Yield: 62.53%). MS(ES): m/z: 545.50 $[M+H]^+$, LCMS purity: 95.52%, HPLC purity: 99.04%, 1H NMR (DMSO, 400 MHz): 13.54 (s, 1H), 10.62 (s, 1H), 8.11 (s, 1H), 7.99 (s, 1H), 7.86 (s, 1H), 7.64 (s, 1H), 7.61-7.58 (d, J=8.4 Hz, 1H), 7.48-7.46 (d, J=9.2 Hz, 1H), 7.24 (t, 1H), 3.81 (3H), 3.23 (s, 3H), 3.12 (s, 3H), 2.35 (s, 3H), 2.09 (s, 1H), 0.77-0.76 (m, 4H).

Example 198: Synthesis of N N-(2-(difluoromethyl)-7-((4-(1,5-dimethyl-1H-pyrazol-4-yl)-2-(N-methylmethylsulfonamido)phenyl)amino)-3H-imidazo[4,5-b]pyridin-5-yl)cyclopropanecarboxamide, I-198

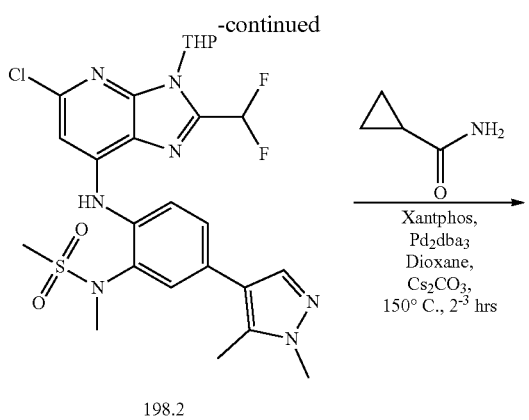

198.2

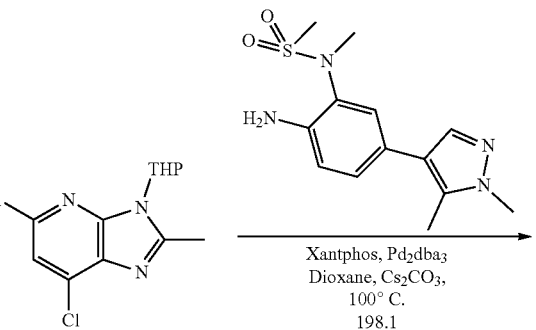

198.3

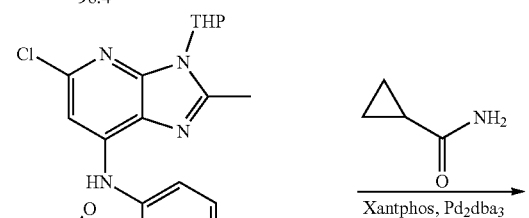

I-198

Synthesis of Compound 198.1.

A mixture of 153.3 (1.0 g, 3.06 mmol, 1.0 eq) and 4-bromo-1,5-dimethyl-1H-pyrazole (0.580 g, 0.366 mmol, 1.1 eq) in 1,4-dioxane (10 mL) was degassed with argon for 10 min. Then [1,1'-Bis(diphenylphosphino)ferrocene]palladium(II) dichloride(0.450 g, 2.28 mmol, 1.1 eq) and potassium carbonate(0.620 g, 1.98 mmol, 3 eq) was added into it. Reaction mixture was stirred at 110° C. for 24 h. Upon completion, reaction mixture was transferred into cold water and extracted with ethyl acetate. Organic layers were combined, dried over $Na_2SO_4$ and concentrated in vacuo to obtain crude product. This was purified by column chromatography and compound was eluted in 15% ethyl acetate in hexane as eluant to obtain pure 198.1 (0.520 g, 57.63%). MS(ES): m/z 295.37 [M+H]⁺.

Synthesis of Compound 198.2.

Compound 198.2 was synthesized from 198.1 and 13.4 using general procedure A. (Yield: 25.78%). MS(ES): m/z 581.05 [M+H]⁺.

Synthesis of Compound 198.3.

Compound was synthesized from 198.2 and cyclopropanecarboxamide using general procedure B. (Yield: 34.87%). MS(ES): m/z 629.70 [M+H]⁺.

Synthesis of I-198.

Compound I-198 was synthesized from 198.3 using general procedure (Yield: 84.18%). MS(ES): m/z: 545.60 [M+H]⁺, LCMS purity: 99.00%, HPLC purity: 99.08%, 1H NMR (DMSO, 400 MHz): 10.61 (s, 1H), 8.10 (s, 1H), 7.85 (s, 1H), 7.67 (s, 2H), 7.62-7.61 (d, J=2 Hz, 1H), 7.60 (s, 1H), 7.47-7.46 (dd, J=2 Hz, J=8.4 Hz, 1H), 7.23 (t, 1H), 3.81 (s, 3H), 3.24 (s, 3H), 3.11 (s, 3H), 2.42 (s, 3H), 2.03-2.00 (m, 1H), 0.77-0.75 (m, 4H).

Example 199: Synthesis of N-(7-((4-(1,5-dimethyl-1H-pyrazol-4-yl)-2-(N-methylmethylsulfonamido)phenyl)amino)-2-methyl-3H-imidazo[4,5-b]pyridin-5-yl)cyclopropanecarboxamide, I-199

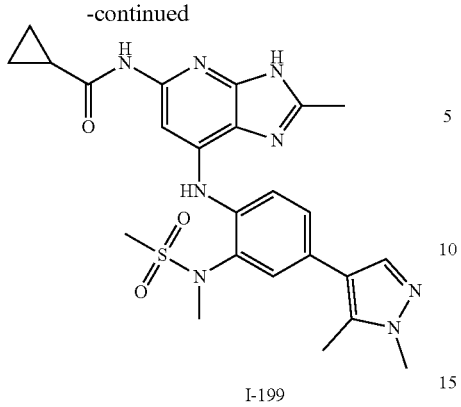

I-199

Synthesis of Compound 199.1.

Compound 199.1 was synthesized from 98.4 and 198.1 using general procedure A. (Yield: 24.24%). MS(ES): m/z 545.1 [M+H]$^+$.

Synthesis of Compound 199.2.

Compound was synthesized from 198.1 and cyclopropanecarboxamide using general procedure B. (Yield: 42.62%). MS(ES): m/z 593.7 [M+H]$^+$.

Synthesis of I-199.

Compound I-199 was synthesized using 199.2 general procedure C. (Yield: 71.7%). MS(ES): m/z: 509.46 [M+H]$^+$, LCMS purity: 98.97%, HPLC purity 100%, 1H NMR (DMSO, 400 MHz): 12.24 (s, 1H), 10.45 (s, 1H), 7.86 (s, 1H), 7.80 (s, 2H), 7.65 (s, 1H), 7.59-7.59 (d, J=1.6 Hz, 1H), 7.44-7.42 (m, 1H), 3.80 (s, 3H), 3.23 (s, 3H), 3.13 (s, 3H), 2.48 (s, 3H), 2.41 (s, 3H), 1.98 (s, 1H), 0.75-0.73 (m, 4H).

Example 200: Synthesis of N-(2-((2-(difluoromethyl)-5-((2,6-dimethylpyrimidin-4-yl)amino)-3H-imidazo[4,5-b]pyridin-7-yl)amino)phenyl)-N-(methyl-d3)methanesulfonamide, I-200

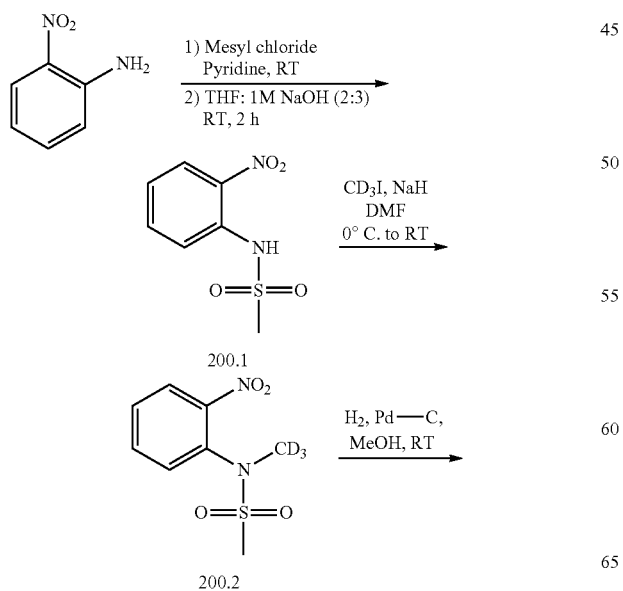

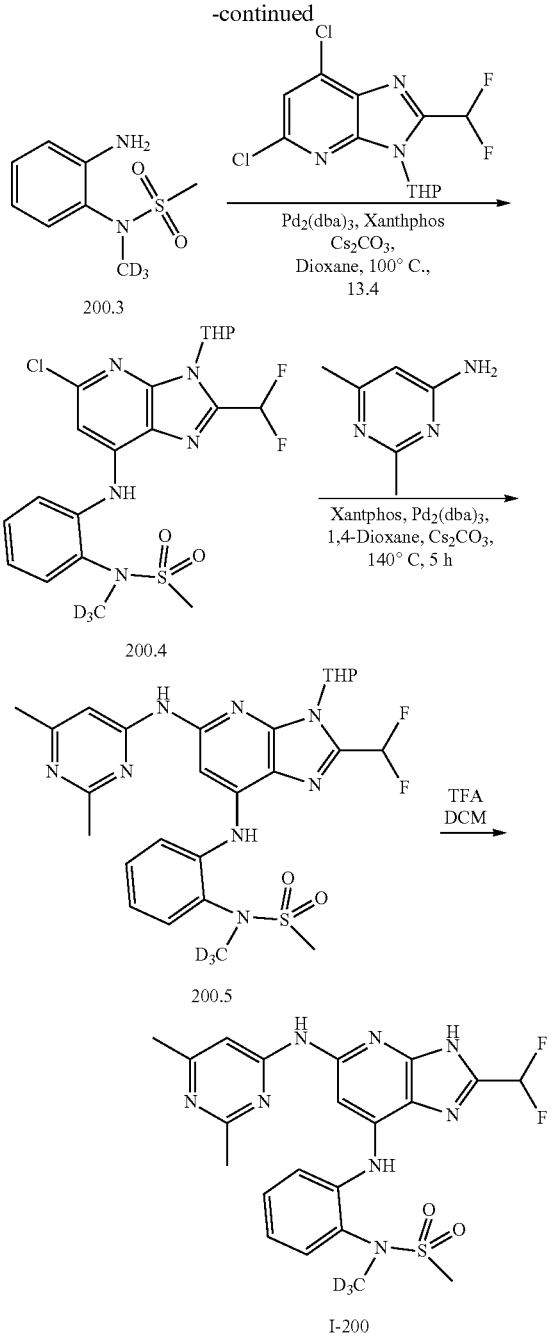

Synthesis of Compound 200.1.

To a solution of 2-nitroaniline (1.0 g, 7.24 mmol, 1.0 eq) in pyridine (2.5 mL) was added mesyl chloride (1.65 g, 14.48 mmol, 2.0 eq) at 0° C. and stirred the reaction mixture at r.t. for 20 h. Upon completion, reaction mixture was transferred into ice cold water, precipitate was formed. Precipitate was further dissolved in mixture of tetrahydrofuran (2 mL) and 1N sodium hydroxide (3 mL) and stirred at r.t. for 2 h. The reaction mixture was transferred into 2N HCl up to pH 7 and extracted with ethyl acetate. Organic layer was washed with brine, dried over Na$_2$SO$_4$ and concentrated in vacuo to obtain crude product. This was purified by column chromatography using 20% ethyl acetate in hexane to obtain pure 200.1 (1.0 g, Yield: 63.88%). MS(ES): m/z 217.21 [M+H]$^+$.

Synthesis of Compound 200.2.

To a solution of 200.1 (1.0 g, 4.63 mmol, 1.0 eq) in N,N-dimethylformamide (10 mL) was added sodium hydride (0.22 g, 9.26 mmol, 2.0 eq) at 0° C. and stirred the reaction mixture 10 min. Added iodomethane-d3 (1.0 g, 6.94 mmol, 1.5 eq) dropwise into reaction mixture at 0° C. Reaction mixture was stirred at r.t. for 2 h. Upon completion, reaction mixture was transferred into ice cold water, solid was formed, filtered solid and concentrated in vacuo to obtain pure 200.2 (0.61 g, Yield: 56.54%). MS(ES): m/z 234.26 [M+H]⁺.

Synthesis of Compound 200.3.

To a solution of 200.2 (0.61 g, 2.62 mmol, 1.0 eq) in MeOH (6 mL), 10% Pd/C (0.3 g) was added. Hydrogen was purged through reaction mixture for 2-3 h. Upon completion, reaction mixture was filtered through celite-bed and washed with ethanol. Filtrate was concentrated in vacuo to obtain 200.3 (0.45 g, 84.65%). MS(ES): m/z 204.27 [M+H]⁺.

Synthesis of Compound 200.4.

Compound 200.4 was synthesized from 200.3 and 13.4 using general procedure A. (Yield: 20.79%). MS(ES): m/z 489.95 [M+H]⁺.

Synthesis of Compound 200.5.

Compound 200.5 was synthesized from 2,6-dimethylpyrimidin-4-amine and 200.4 using general procedure B. (Yield: 46.72%). MS(ES): m/z 576.65 [M+H]⁺.

Synthesis of I-200.

Compound I-200 was synthesized from 200.5 using general procedure C. (Yield: 57.49%). MS(ES): m/z: 492.46 [M+H]⁺, LCMS purity: 98.37%, HPLC purity 99.02%, 1H NMR (MeOD, 400 MHz): 7.79-7.77 (d, J=8 Hz, 1H), 7.64-7.62 (d, J=8 Hz, 1H), 7.52-7.48 (m, 2H), 7.31-7.24 (m, 2H), 3.06 (s, 3H), 2.49 (s, 3H), 2.40 (s, 3H).

Example 201: Synthesis of N-(2-((5-((2,6-dimethylpyrimidin-4-yl)amino)-2-methyl-3H-imidazo[4,5-b]pyridin-7-yl)amino)phenyl)-N-(methyl-d3)methanesulfonamide, I-201

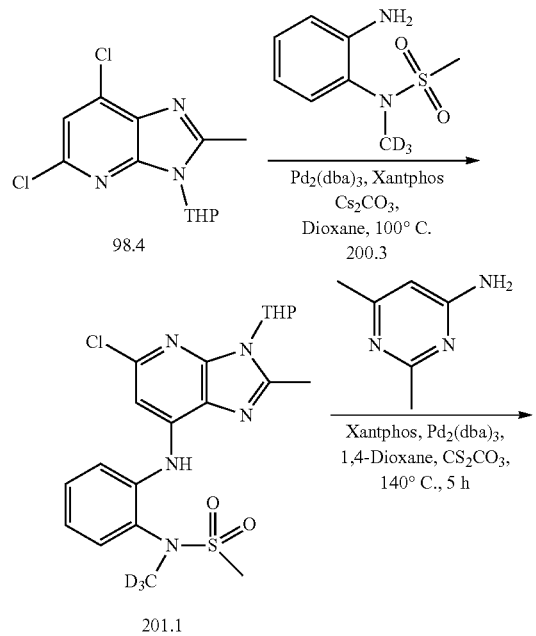

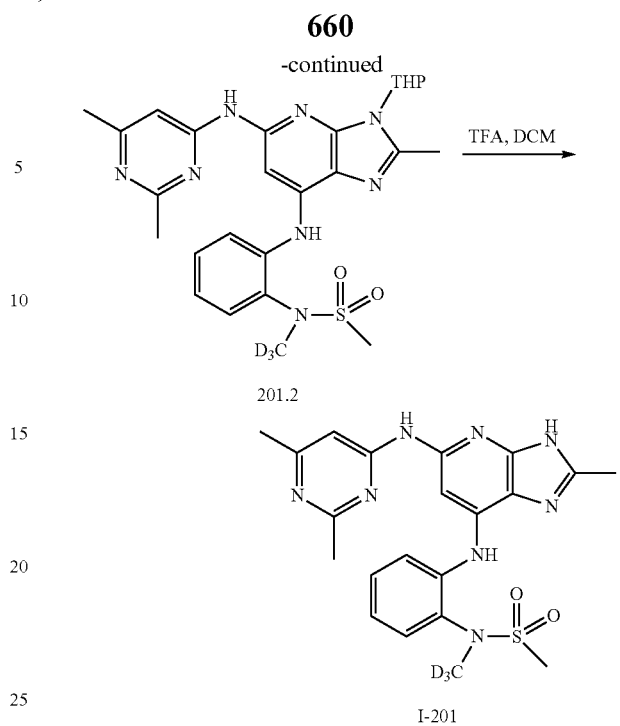

Synthesis of Compound 201.1.

Compound 201.1 was synthesized from 98.4 and 200.3 using general procedure A. (Yield: 20.19%). MS(ES): m/z 453.97 [M+H]⁺.

Synthesis of Compound 201.2.

Compound 201.2 was synthesized from 201.1 and 2,6-dimethylpyrimidin-4-amine using general procedure B. (Yield: 43.83%). MS(ES): m/z 540.67 [M+H]⁺.

Synthesis of compound I-201.

Compound I-201 was synthesized from 201.2 using general procedure C. (Yield: 63.01%). MS(ES): m/z: 456.5 [M+H]⁺, LCMS purity: 98.03%, HPLC purity 98.11%, 1H NMR (DMSO-d6, 400 MHz): 12.46 (s, 1H), 9.74 (s, 1H), 7.88 (s, 1H), 7.73-7.71 (s, J=7.6 Hz, 1H), 7.65-7.63 (d, J=7.6 Hz, 1H), 7.46-7.42 (m, 3H), 7.21-7.18 (m, 1H), 3.11 (s, 3H), 2.46 (s, 3H), 2.39 (s, 3H), 2.29 (s, 3H).

Example 202: Synthesis of N-(5-(difluoromethyl)-2-((2-(difluoromethyl)-5-((1-methyl-1H-pyrazol-3-yl)amino)-3H-imidazo[4,5-b]pyridin-7-yl)amino)phenyl)-N-methylmethanesulfonamide, I-202

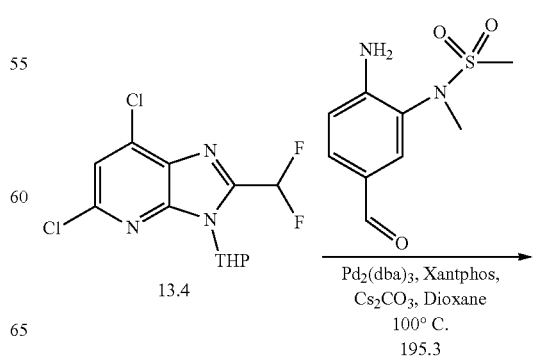

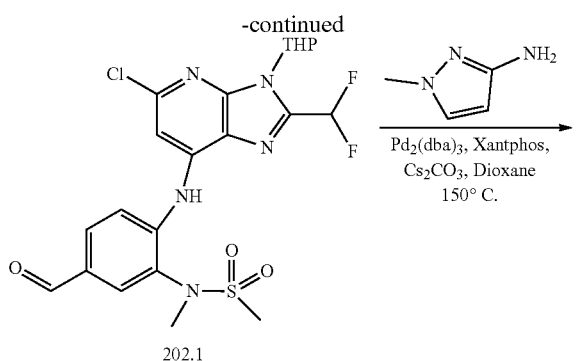

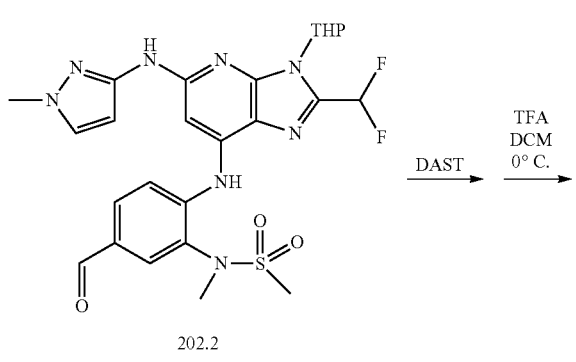

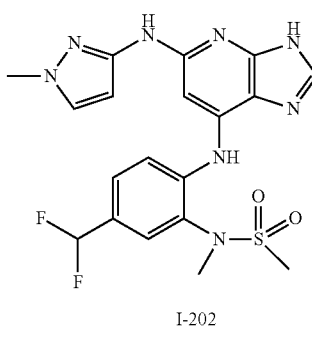

I-202

Synthesis of Compound 202.1.

Compound 202.1 was synthesized from 13.4 and 195.3 using general procedure A. (Yield: 14.33%). MS (ES): m/z 514.94 [M+H]

Synthesis of Compound 202.2.

Compound 202.2 was synthesized from 1-methyl-1H-pyrazol-3-amine and 202.1 using general procedure B. (Yield: 55.90%). MS (ES): m/z 575.61 [M+H]$^+$.

Synthesis of Compound I-202.

Compound I-202 was synthesized from 202.2 by treatment with DAST followed by general procedure C. (Yield: 22.42%). MS(ES): m/z: 513.46 [M−H]+, LCMS purity: 99.68%, HPLC purity: 99.47%, 1H NMR (DMSO, 400 MHz): 13.22 (s, 1H), 9.21 (s, 1H), 8.06 (s, 1H), 7.88 (s, 1H), 7.82-7.80 (d, J=8.4 Hz, 1H), 7.67-7.65 (d, J=8.4 Hz, 1H), 7.53-7.52 (d, J=2 Hz, 1H), 7.31-6.93 (m, 3H), 6.44 (s, 1H), 3.74 (s, 3H), 3.26 (s, 3H), 3.16 (s, 3H).

Example 203: Synthesis of (N-(7-((4-cyclopropyl-2-(methylsulfonyl)phenyl)amino)-2-(difluoromethyl)-3H-imidazo[4,5-b]pyridin-5-yl)cyclopropanecarboxamide, I-203

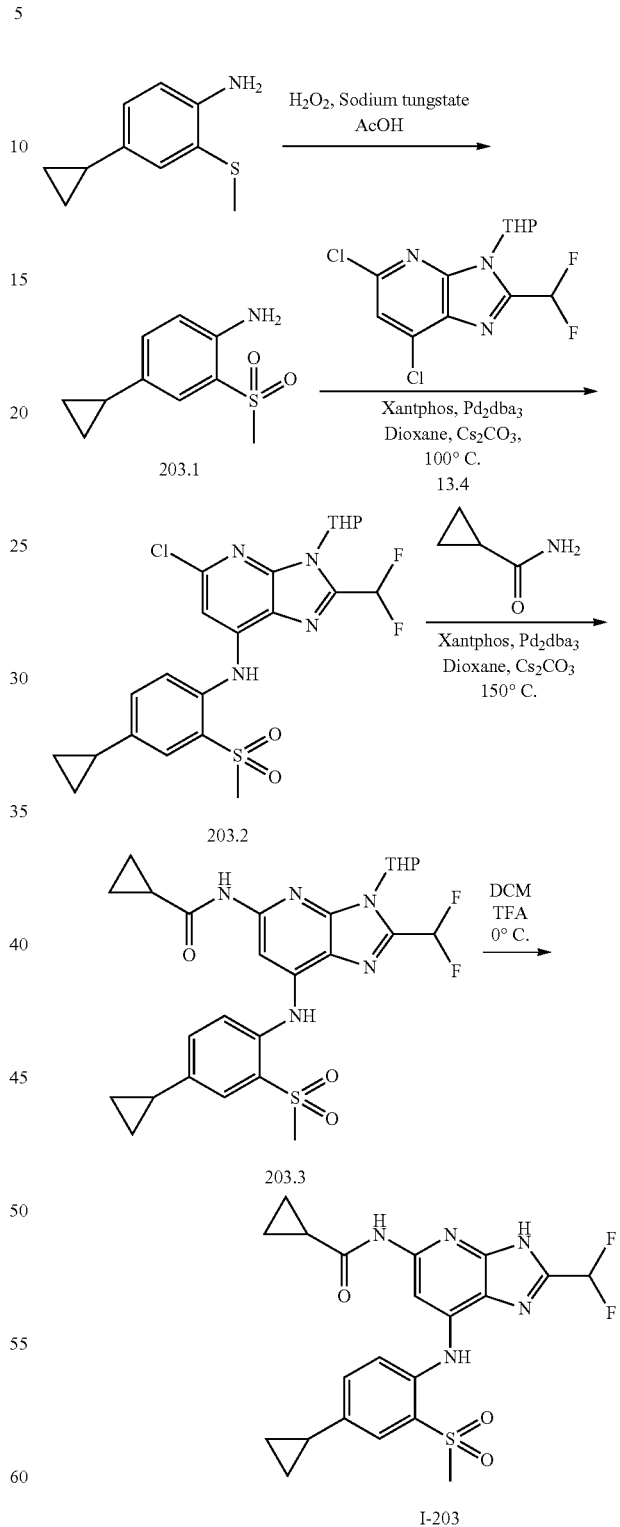

Synthesis of Compound 203.1.

To a solution of 4-cyclopropyl-2-(methylthio)aniline (0.700 g, 3.90 mmol, 1 eq) in acetic acid (0.7 mL) was added 30% hydrogen peroxide (2.65 g, 78.09 mmol, 20.0 eq) and sodium tungstate dihydrate (1.3 g, 3.90 mmol, 1 eq). Reaction mixture was stirred at r.t. for 2 h. Upon completion, reaction mixture was transferred in ice-water and precipitated product was filtered, washed with 50% ethyl acetate in hexane and dried well to obtain 203.1. (0.570 g, Yield: 69.10%). MS(ES): m/z 212.28 [M+H]+

Synthesis of Compound 203.2.

Compound 203.2 was synthesized from 13.4 and 203.1 using general procedure A. (Yield: 20.47%). MS(ES): m/z 497.96 [M+H]$^+$.

Synthesis of Compound 203.3.

Compound 203.3 was synthesized from 203.2 and cyclopropanecarboxamide using general procedure B. (Yield: 34.16%). MS(ES): m/z 546.61 [M+H]$^+$.

Synthesis of I-203

Compound I-203 was synthesized from 203.3 using general procedure C. (Yield: 65.68%). MS(ES): m/z: 462.56 [M+H]$^+$, LCMS purity: 99.13%, HPLC purity: 99.88%, 1H NMR (DMSO, 400 MHz): 13.65 (s, 1H), 10.73 (s, 1H), 8.65 (s, 1H), 7.97 (s, 1H), 7.66-7.64 (d, J=10.4 Hz, 2H), 7.50-7.48 (d, J=7.6 Hz, 1H), 3.19 (s, 3H), 2.09-2.03 (m, 2H), 1.04-1.02 (m, 2H), 0.79-0.78 (m, 6H).

Example 204: Synthesis of 6-((7-(((2-methoxy-3-(2-methyl-2H-tetrazol-5-yl)phenyl)amino)-2-methyl-3H-imidazo[4,5-b]pyridin-5-yl)amino)-3-(2-methoxypropan-2-yl)pyrazine-2-carbonitrile, I-204

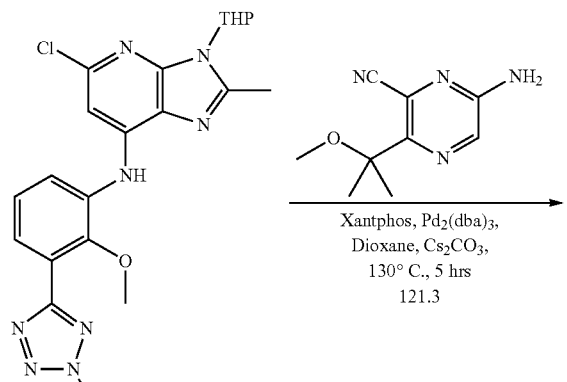

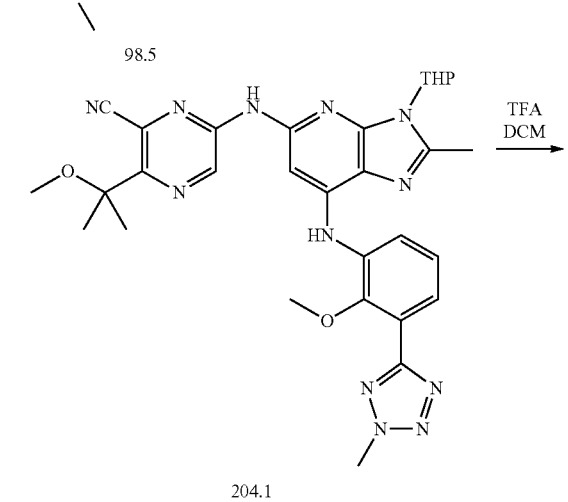

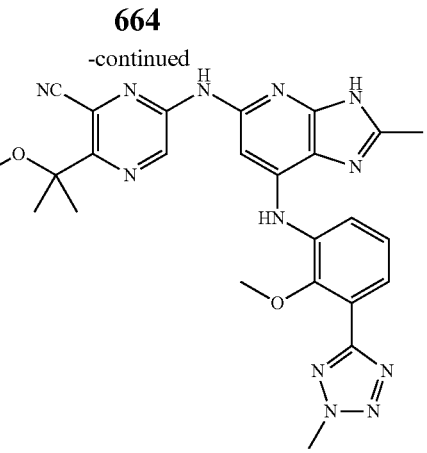

I-204

Synthesis of Compound 204.1.

Compound 204.1 was synthesized from 98.5 and 121.3 using general procedure B. (Yield: 59.59%). MS(ES): m/z 611.68 [M+H]$^+$.

Synthesis of compound I-204. Compound I-204 was synthesized from 204.1 using general procedure C. (Yield: 59.44%). MS(ES): m/z: 527.74 [M+H]$^+$, LCMS purity: 100%, HPLC purity 98.93%, 1H NMR (DMSO-d6, 400 MHz): 12.49 (s, 1H), 10.29 (s, 1H), 9.36 (s, 1H), 8.06 (s, 1H), 7.76-7.74 (d, J=7.2 Hz, 1H), 7.68-7.61 (m, 1H), 7.43-7.39 (t, J=8 Hz, 1H), 7.19-7.17 (d, J=7.6 Hz, 1H), 4.48 (s, 3H), 3.75 (s, 3H), 3.75 (s, 3H), 2.50 (s, 3H), 1.55 (s, 6H).

Example 205: Synthesis of N-(2-(difluoromethyl)-7-((2-(methylsulfonyl)-4-(5-methylthiazol-2-yl)phenyl)amino)-3H-imidazo[4,5-b]pyridin-5-yl)cyclopropanecarboxamide, I-205

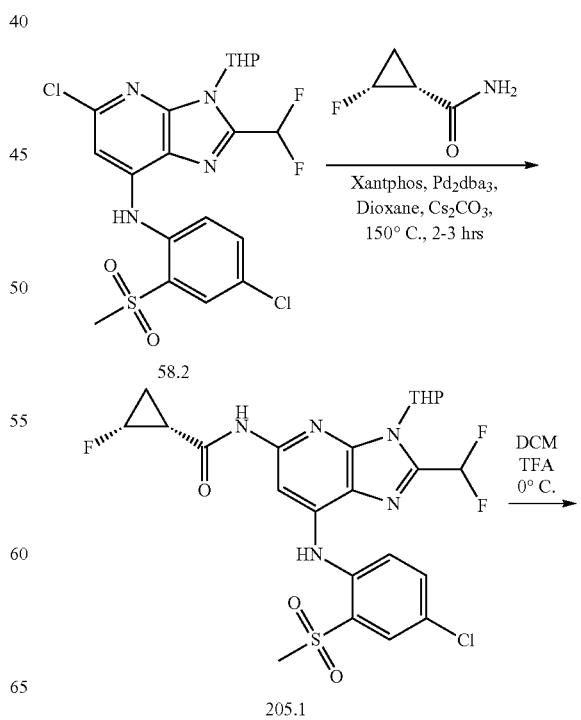

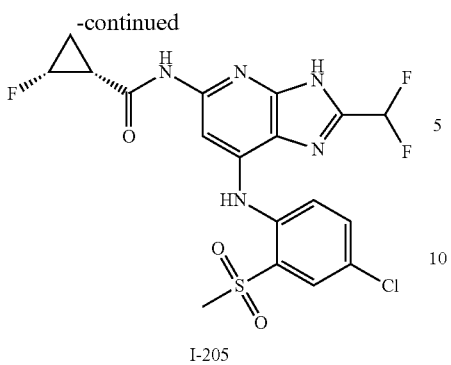

I-205

Synthesis of Compound 205.1.

Compound 205.1 was synthesized from 58.2 and (1R, 2R)-2-fluorocyclopropane-1-carboxamide using general procedure B. (Yield: 26.42%). MS(ES): m/z 558.61 [M+H]⁺.

Synthesis of Compound I-205

Compound I-205 was synthesized from 205.1 using general procedure C. (Yield: 58.88%). MS(ES): m/z: 474.52 [M+H]⁺, LCMS purity: 96.00%, HPLC purity 95.08%, 1H NMR (DMSO, 400 MHz): 13.72 (s, 1H), 10.83 (s, 1H), 8.79 (s, 1H), 8.03 (s, 1H), 7.89-7.86 (m, 2H), 7.25 (t, 1H), 7.08-7.78 (d, J=8.4 Hz, 1H), 5.01-4.84 (s, 1H), 3.30 (s, 3H), 2.23 (s, 1H), 1.20-1.16 (t, J=7.2 Hz, 2H).

Example 206: Synthesis of 2-(difluoromethyl)-N7-(2-methoxy-3-(1-methyl-1H-1,2,4-triazol-3-yl)phenyl)-N5-(1-methyl-5-(trifluoromethyl)-1H-pyrazol-3-yl)-3H-imidazo[4,5-b]pyridine-5,7-diamine, I-206

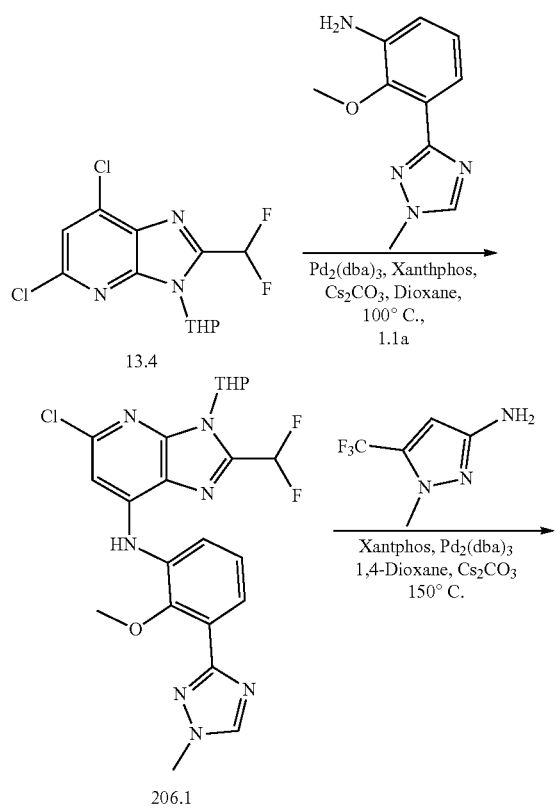

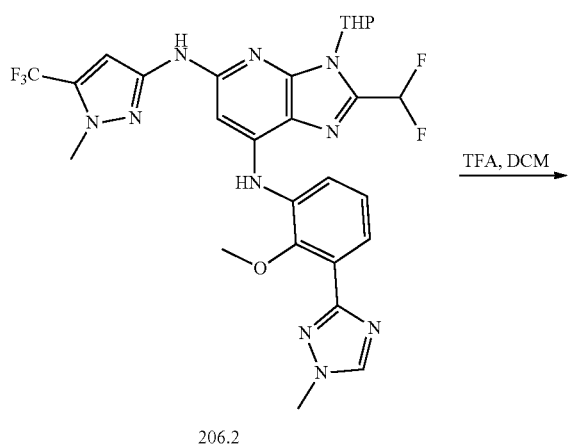

I-206

Synthesis of Compound 206.1.

Compound 206.1 was synthesized from 13.4 and 1.1a using general procedure A. (Yield: 37.26%). MS(ES): m/z 490.91 [M+H]⁺.

Synthesis of Compound 206.2.

Compound 206.2 was synthesized from 206.1 and 1-methyl-5-(trifluoromethyl)-1H-pyrazol-3-amine using general procedure B. (Yield: 27.49%). MS(ES): m/z 619.57 [M+H]⁺.

Synthesis of Compound I-206.

Compound I-206 was synthesized from 206.2 using general procedure C. (Yield: 58.85%). MS(ES): m/z: 535.65 [M+H]⁺, LCMS purity: 98.09%, HPLC purity: 97.47%, 1H NMR (DMSO, 400 MHz): 13.31 (s, 1H), 9.50 (s, 1H), 8.57 (s, 1H), 8.07 (s, 1H), 7.63-7.61 (dd, J=1.6 Hz, J=8 Hz, 1H), 7.56-7.54 (d, J=8 Hz, 1H), 7.29-7.25 (d, J=8 Hz, 1H), 7.20 (s, 1H), 7.16 (t, 1H), 6.56 (s, 1H), 3.95 (s, 3H), 3.78 (s, 3H), 3.71 (s, 3H).

Example 207: Synthesis of (1S,2S)—N-(2-(difluoromethyl)-7-((4-(1-methyl-1H-pyrazol-4-yl)-2-(N-methylmethylsulfonamido)phenyl)amino)-3H-imidazo[4,5-b]pyridin-5-yl)-2-fluorocyclopropane-1-carboxamide, I-207

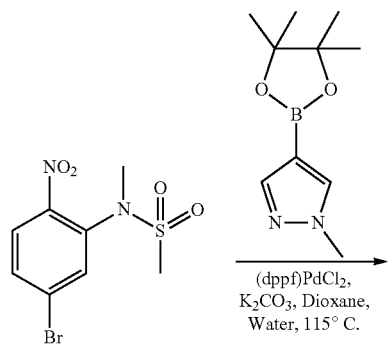

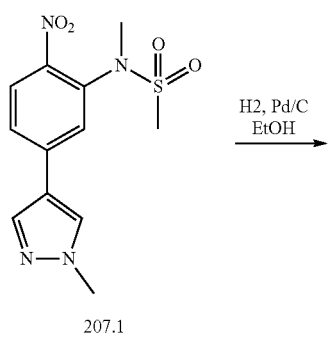

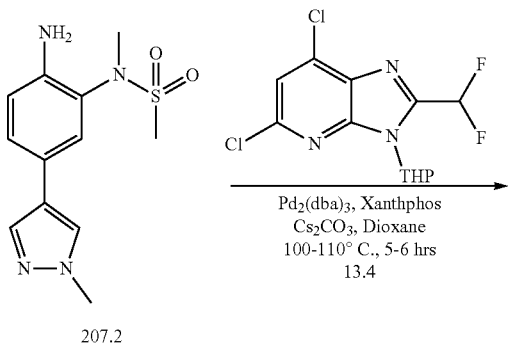

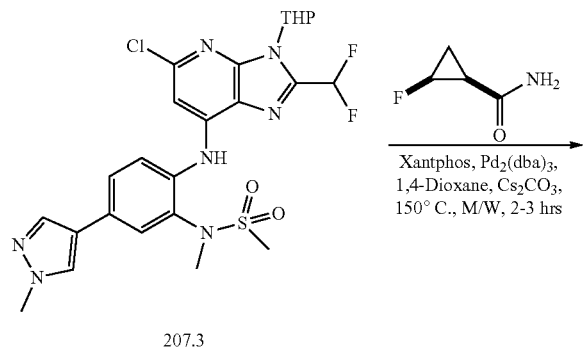

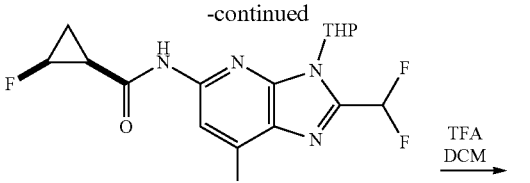

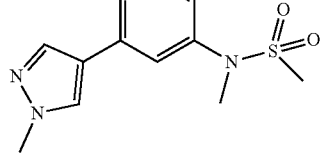

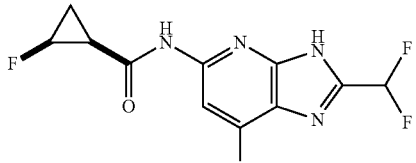

I-207

Synthesis of Compound 207.1.

To a compound of 1 (4.0 g, 13 mmol, 1.0 eq) and 1-methyl-4-(4,4,5,5-tetramethyl-1,3,2-dioxaborolan-2-yl)-1H-pyrazole (2.98 g, 14.3 mmol, 1.1 eq) in a mixture of dioxane (32 mL) and water (8 mL). Reaction mixture was degassed with argon for 10 min. Then [1,1'-Bis(diphenylphosphino)ferrocene]palladium(II) dichloride (2.12 g, 2.60 mmol, 0.2 eq) and potassium carbonate (5.39 g, 39.2 mmol, 3.0 eq) were added. Reaction mixture was stirred at 115° C. for 24 h. Upon completion, reaction mixture was transferred into cold water then extracted with ethyl acetate. Organic layers were combined, dried over Na$_2$SO$_4$ and concentrated in vacuo to obtain crude product. This was purified by column chromatography and compound was eluted in 15% ethyl acetate in hexane as eluant to obtain pure 207.1 (1.2 g, 29.88%). MS(ES): m/z 311.33 [M+H]$^+$.

Synthesis of Compound 207.2.

To compound 207.1 (1.2 g, 3.85 mmol, 1.0 eq) in MeOH, 10% Pd/C (0.224 g) was added. Hydrogen was purged through reaction mixture for 4 h. Upon completion, reaction mixture was filtered through celite-bed and washed with MeOH. Filtrate was concentrated in vacuo to obtain 207.2 (0.800 g, 73.80%). MS(ES): m/z 281.35 [M+H]$^+$.

Synthesis of Compound 207.3.

Compound 207.3 was synthesized from 207.2 and 13.4 using general procedure A. (Yield: 34.67%). MS(ES): m/z 567.02 [M+H]$^+$.

Synthesis of Compound 207.4.

Compound 207.4 was synthesized from 207.3 and (1S,2S)-2-fluorocyclopropane-1-carboxamide using general procedure B. (Yield: 2045%). MS(ES): m/z 633.66 [M+H]$^+$.

Synthesis of I-207.

Compound I-207 was synthesized from 207.4 using general procedure C. (Yield: 54.06%). MS(ES): m/z: 549.65 [M+H]$^+$, LCMS purity: 97.57%, HPLC purity 97.83%, 1H NMR (DMSO, 400 MHz): 13.58 (s, 1H), 10.80 (s, 1H), 8.25 (s, 1H), 8.13 (s, 1H), 7.98 (s, 1H), 7.86-7.85 (d, J=0.4 Hz, 1H), 7.77 (s, 1H), 7.65-7.62 (d, J=1.2 Hz, 1H), 7.56-7.54 (d, J=8 Hz, 1H), 7.26 (t, 1H), 4.94-4.77 (m, 1H), 3.90 (s, 3H), 3.24 (s, 3H), 3.18 (s, 3H), 2.62 (s, 1H), 1.51 (m, 2H).

Example 208: Synthesis of (1S,2S)-2-fluoro-N-(2-methyl-7-((4-(1-methyl-1H-imidazol-5-yl)-2-(N-methylmethylsulfonamido)phenyl)amino)-3H-imidazo[4,5-b]pyridin-5-yl)cyclopropane-1-carboxamide, I-208

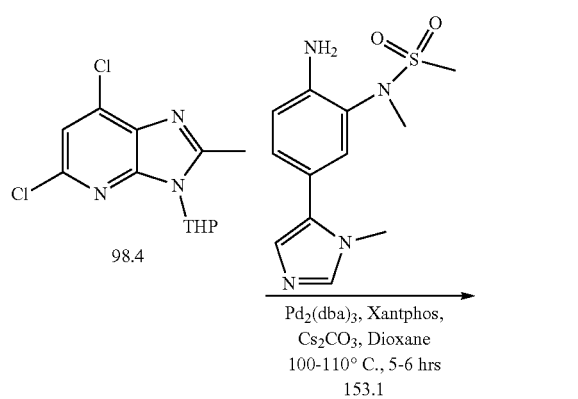

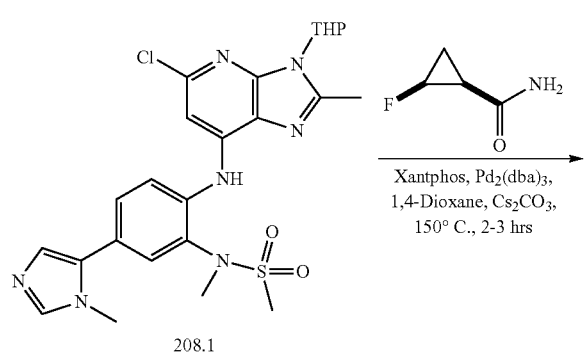

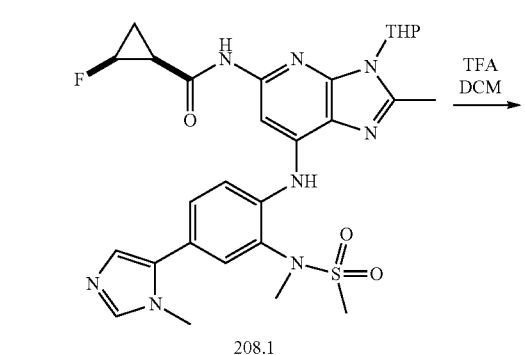

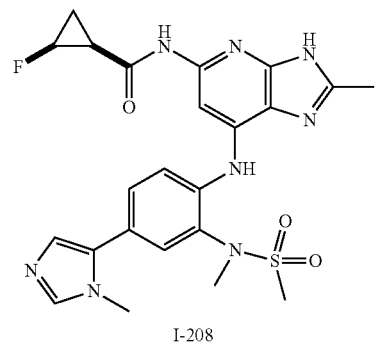

I-208

Synthesis of Compound 208.1.

Compound 208.1 was synthesized from 98.4 and 153.1 using general procedure A. (Yield: 38.99%). MS(ES): m/z 531.28 [M+H]$^+$.

Synthesis of Compound 208.2.

Compound was synthesized from 208.1 and (1S,2S)-2-fluorocyclopropane-1-carboxamide using general procedure B. (Yield: 27.98%). MS(ES): m/z 597.43 [M+H]$^+$.

Synthesis of I-208.

Compound I-208 was synthesized from 208.2 using general procedure C. (Yield: 73.91%). MS(ES): m/z: 513.59 [M+H]$^+$, LCMS purity: 100%, HPLC purity 98.46%, 1H NMR (DMSO-d6, 400 MHz): 12.56 (s, 1H), 10.68 (s, 1H), 8.00 (s, 1H), 7.84 (s, 1H), 7.75-7.74 (m, 2H), 7.67-7.65 (d, J=8.4 Hz, 1H), 7.54-7.52 (d, J=8.4 Hz, 1H), 7.14 (s, 1H), 4.99-4.94 (m, 1H), 3.76 (s, 3H), 3.26 (s, 3H), 3.15 (s, 3H), 2.49 (s, 3H), 1.50-1.44 (m, 1H), 1.25-1.11 (m, 2H).

Example 209: Synthesis of (1S,2S)-2-fluoro-N-(2-methyl-7-((4-(1-methyl-1H-pyrazol-4-yl)-2-(N-methylmethylsulfonamido)phenyl)amino)-3H-imidazo[4,5-b]pyridin-5-yl)cyclopropane-1-carboxamide, I-209

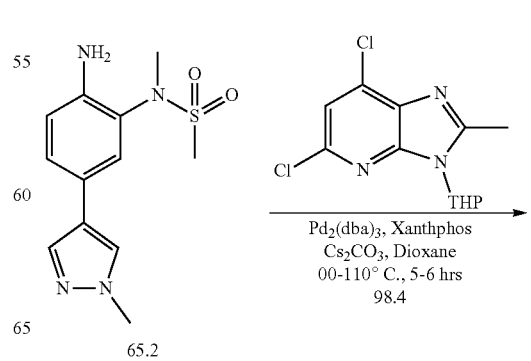

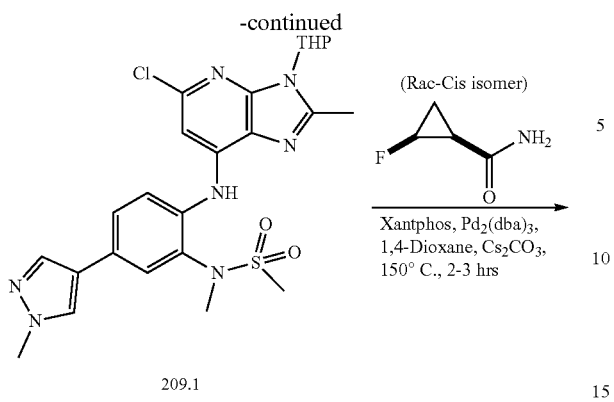

209.1

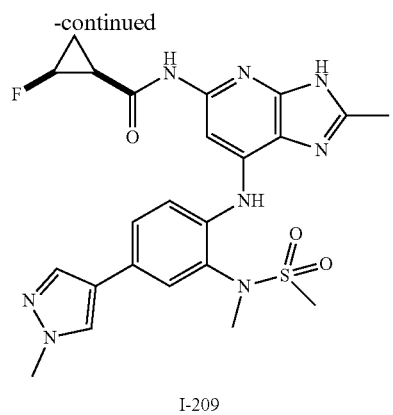

I-209

Synthesis of Compound 209.1.
Compound 209.1 was synthesized from 65.2 and 98.4 using general procedure A. (Yield: 31.41%). MS(ES): m/z 531.76 [M+H]⁺.

Synthesis of Compound 209.2.
Compound 209.2 was synthesized from 209.1 and (1S, 2S)-2-fluorocyclopropane-1-carboxamide using general procedure B. (Yield: 12.75%). MS(ES): m/z 597.76 [M+H]⁺.

Synthesis of I-209.
Compound I-209 was synthesized from 209.2 using general procedure C t. (Yield: 42.33%). MS(ES): m/z: 513.46 [M+H]⁺, LCMS purity: 95.70%, HPLC purity: 95.02%, Chiral HPLC: (69%, 29%), 1H NMR (DMSO, 400 MHz): 12.36 (s, 1H), 10.49 (s, 1H), 8.22 (s, 1H), 7.96 (s, 1H), 7.85 (s, 1H), 7.83-7.83 (d, J=1.6 Hz, 1H), 7.79 (s, 1H), 7.65-7.62 (m, 1H), 7.57-7.55 (d, J=8.4 Hz, 1H), 4.97-4.794 (m, 1H), 3.88 (s, 3H), 3.23 (s, 3H), 3.12 (s, 3H), 2.48 (s, 3H), 1.60-1.54 (m, 1H), 1.22-1.11 (m, 2H).

Example 210: Synthesis of (1S,2S)—N-(2-(difluoromethyl)-7-((4-(1-methyl-1H-pyrazol-3-yl)-2-(methylsulfonyl)phenyl)amino)-3H-imidazo[4,5-b]pyridin-5-yl)-2-fluorocyclopropane-1-carboxamide, I-210

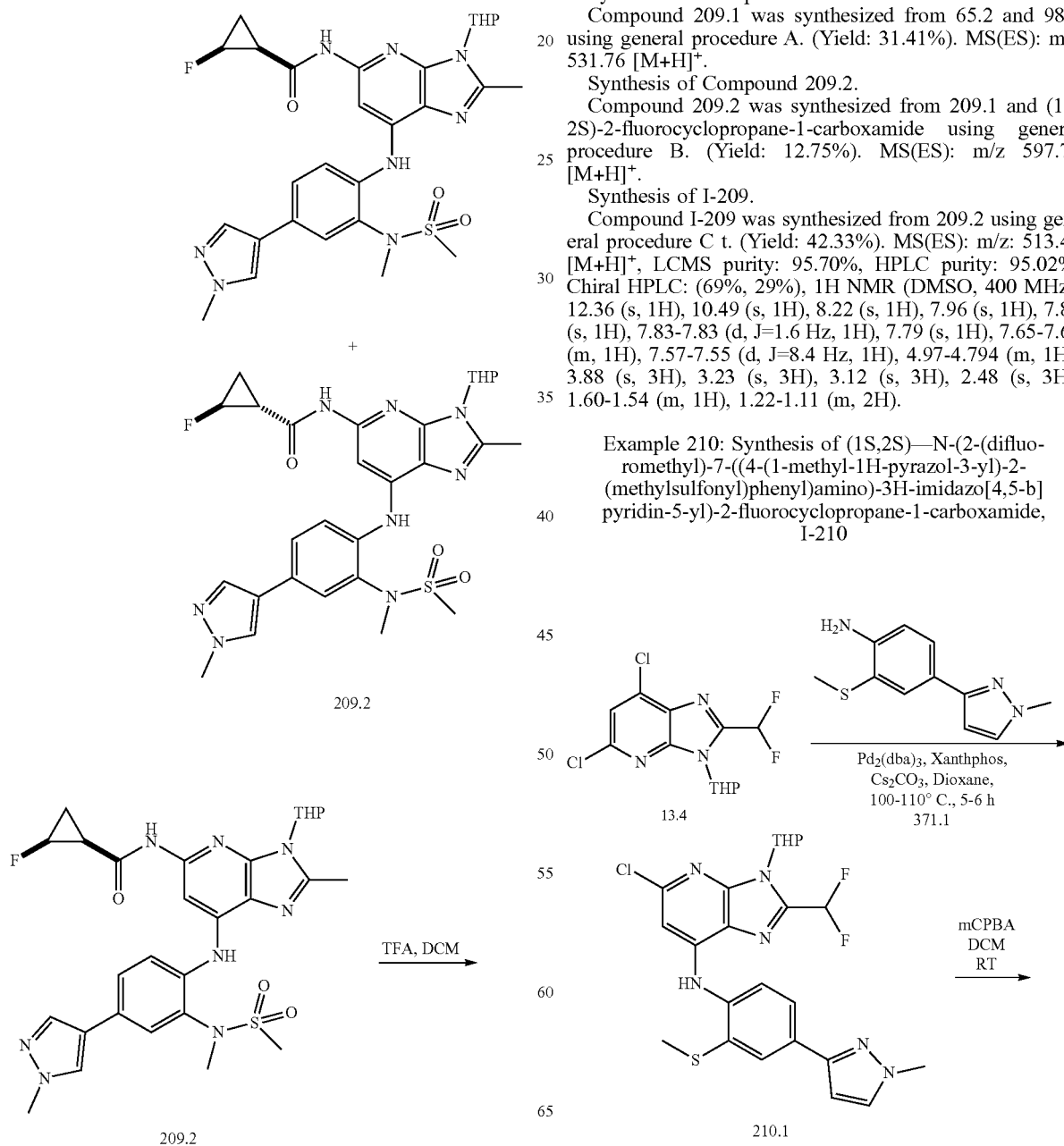

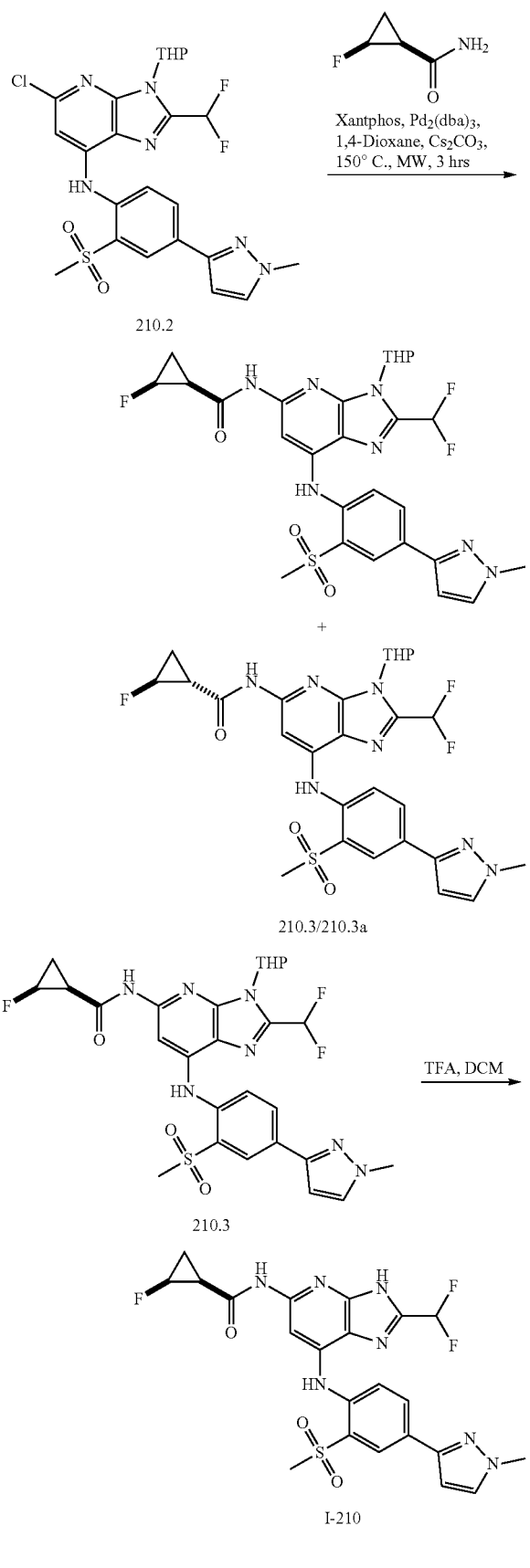

Synthesis of Compound 210.1.

Compound 210.1 was synthesized from 13.4 and 371.1 using general method A. (Yield: 19.98%). MS(ES): m/z 505.98 [M+H]⁺.

Synthesis of Compound 210.2.

To compound 210.1 (0.230 g, 0.4 mmol, 1.0 eq) in CH₂Cl₂ (5 ml), m-chloroperbenzoic acid (0.23 g, 1.3 mmol, 3.0 eq) was added portionwise at 0° C. Reaction mixture was stirred at r.t. for 2 h. Upon completion, reaction mixture was basified using NaHCO₃ solution, transferred to water and then extracted with CH₂Cl₂. Organic layer combined, dried over Na₂SO₄, filtered and concentrated in vacuo to obtain crude product. This was purified by column chromatography using 2.5% MeOH in CH₂Cl₂ as eluant to obtain pure 210.2 (0.190 g, 77.69%). MS(ES): m/z 537.98 [M+H]⁺.

Synthesis of Compound 210.3.

Compound 210.3 was synthesized from 210.2 and (1S, 2S)-2-fluorocyclopropane-1-carboxamide using general procedure B. (Yield: 21.07%). MS(ES): m/z: 603.03 [M+H]⁺.

Synthesis of I-210.

Compound I-210 was synthesized from 210.3 using general procedure C. (Yield: 77.46%). MS(ES): m/z: 520.41 [M+H]⁺, LCMS purity: 95.99%, HPLC purity: 95.30%, Chiral HPLC: (15%, 85%), 1H NMR (DMSO, 400 MHz): 13.69 (s, 1H), 10.78 (s, 1H), 8.65 (s, 1H), 8.32 (s, 1H), 8.10-8.08 (d, J=8.4 Hz, 1H), 7.93 (s, 1H), 7.79 (s, 2H), 7.07 (t, 1H), 6.81-6.80 (d, J=2 Hz, 1H), 4.95-4.78 (m, 1H), 3.92 (s, 3H), 3.24 (s, 3H), 1.50-1.45 (m, 1H), 1.37-1.18 (m, 2H).

Example 211: Synthesis of (1S,2S)-2-fluoro-N-(2-methyl-7-((4-(1-methyl-1H-pyrazol-3-yl)-2-(methylsulfonyl)phenyl)amino)-3H-imidazo[4,5-b]pyridin-5-yl)cyclopropane-1-carboxamide, I-211

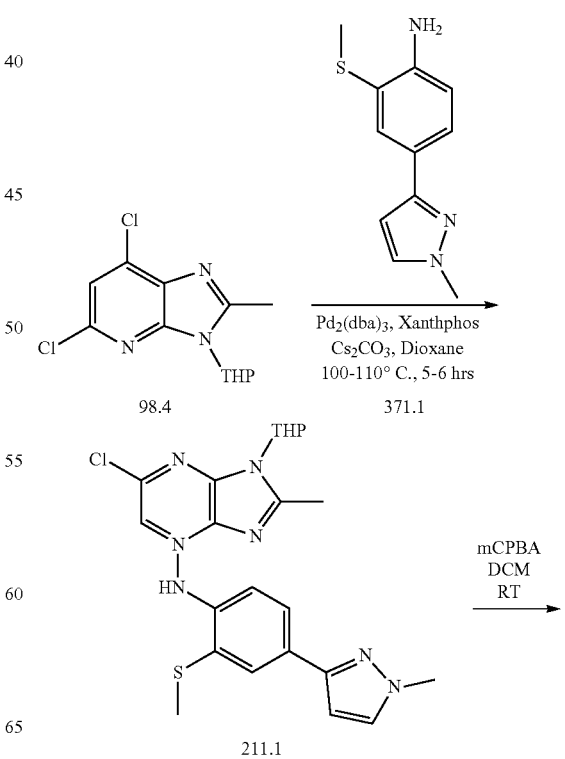

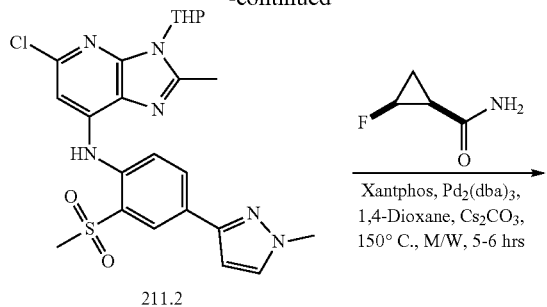

Hz, 2H), 6.815-6.81 (d, J=2 Hz, 1H), 5.01-4.98 (m, 1H), 3.92 (s, 3H), 3.36 (s, 3H), 3.17 (s, 3H), 1.65-1.51 (m, 1H), 1.36-1.11 (m, 2H).

Example 212: Synthesis of (1S,2S)-2-fluoro-N-(2-methyl-7-((4-(1-methyl-1H-imidazol-5-yl)-2-(N-methylmethylsulfonamido)phenyl)amino)-3H-imidazo[4,5-b]pyridin-5-yl)cyclopropane-1-carboxamide, I-212

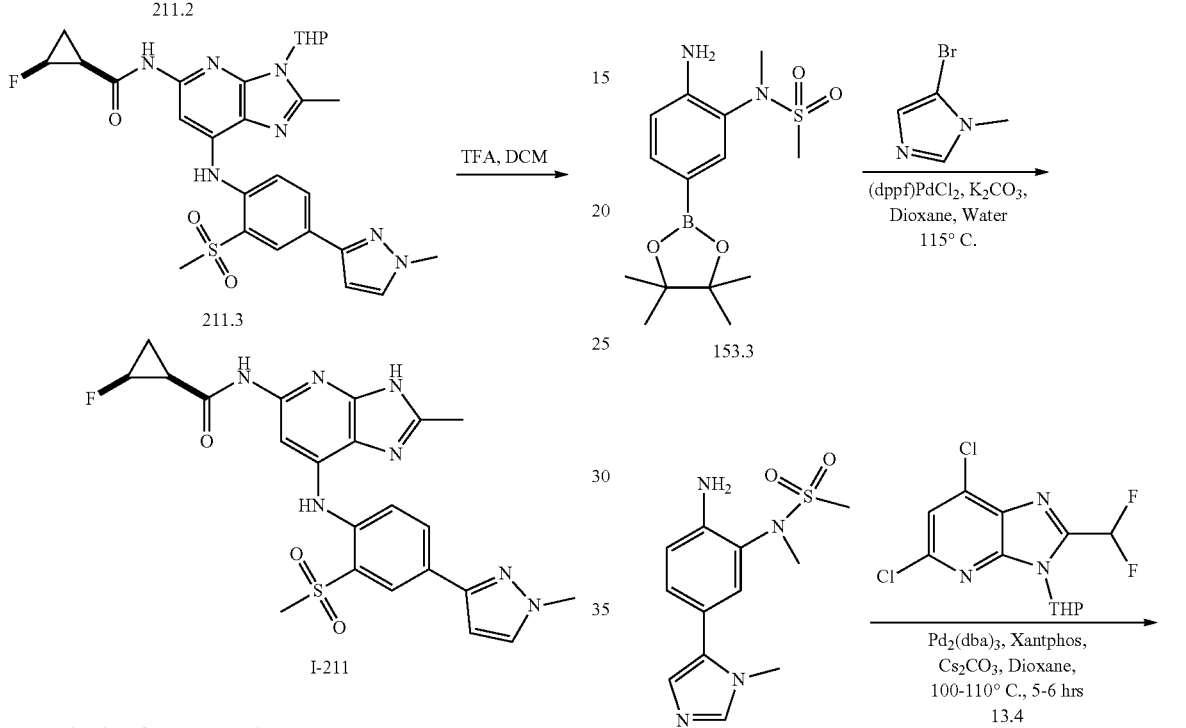

Synthesis of Compound 211.1.

Compound 211.1 was synthesized from 98.4 and 371.1 using general procedure A. (Yield: 28.06%). MS(ES): m/z 470 [M+H]+.

Synthesis of Compound 211.2.

To compound 211.1 (0.3 g, 6.38 mmol, 1.0 eq) in CH$_2$Cl$_2$ (5 ml) was added m-chloroperbenzoic acid (0.33 g, 1.92 mmol, 3.0 eq) portionwise at 0° C. Reaction mixture was stirred at r.t. for 2 h. After completion of reaction, the pH of the reaction mixture was adjusted to 7 using NaHCO$_3$ solution, transferred to water and then extracted with CH$_2$C12. Organic layer combined, dried over Na$_2$SO$_4$ and concentrated in vacuo to obtain crude product. This was purified by column chromatography using 2.5% MeOH in CH$_2$Cl$_2$ as eluant to obtain pure 211.2 (0.200 g, 62.41%). MS(ES): m/z 502.00 [M+H]+.

Synthesis of Compound 211.3.

Compound 211.3 was synthesized from 211.2 and (1S,2S)-2-fluorocyclopropane-1-carboxamide using general procedure B. (Yield: 37.51%). MS(ES): m/z 568.64 [M+H]+.

Synthesis of I-211.

Compound I-211 was synthesized from 211.3 using general procedure C. (Yield: 82.87%). MS(ES): m/z: 484.52 [M+H]+, LCMS purity: 98.34%, HPLC purity 95.21%, Chiral HPLC: (73%, 27%), 1H NMR (DMSO, 400 MHz): 12.60 (s, 1H), 10.66 (s, 1H), 8.63 (s, 1H), 8.33 (s, 1H), 8.14-8.11 (d, J=8.4 Hz, 1H), 8.03 (s, 1H), 7.80-7.79 (d, J=2

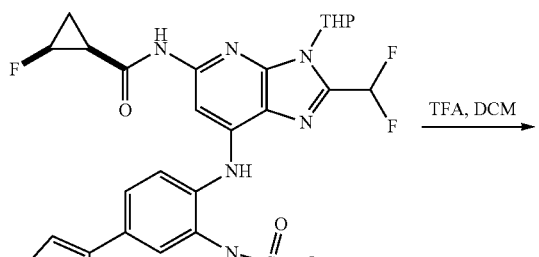

212.3a

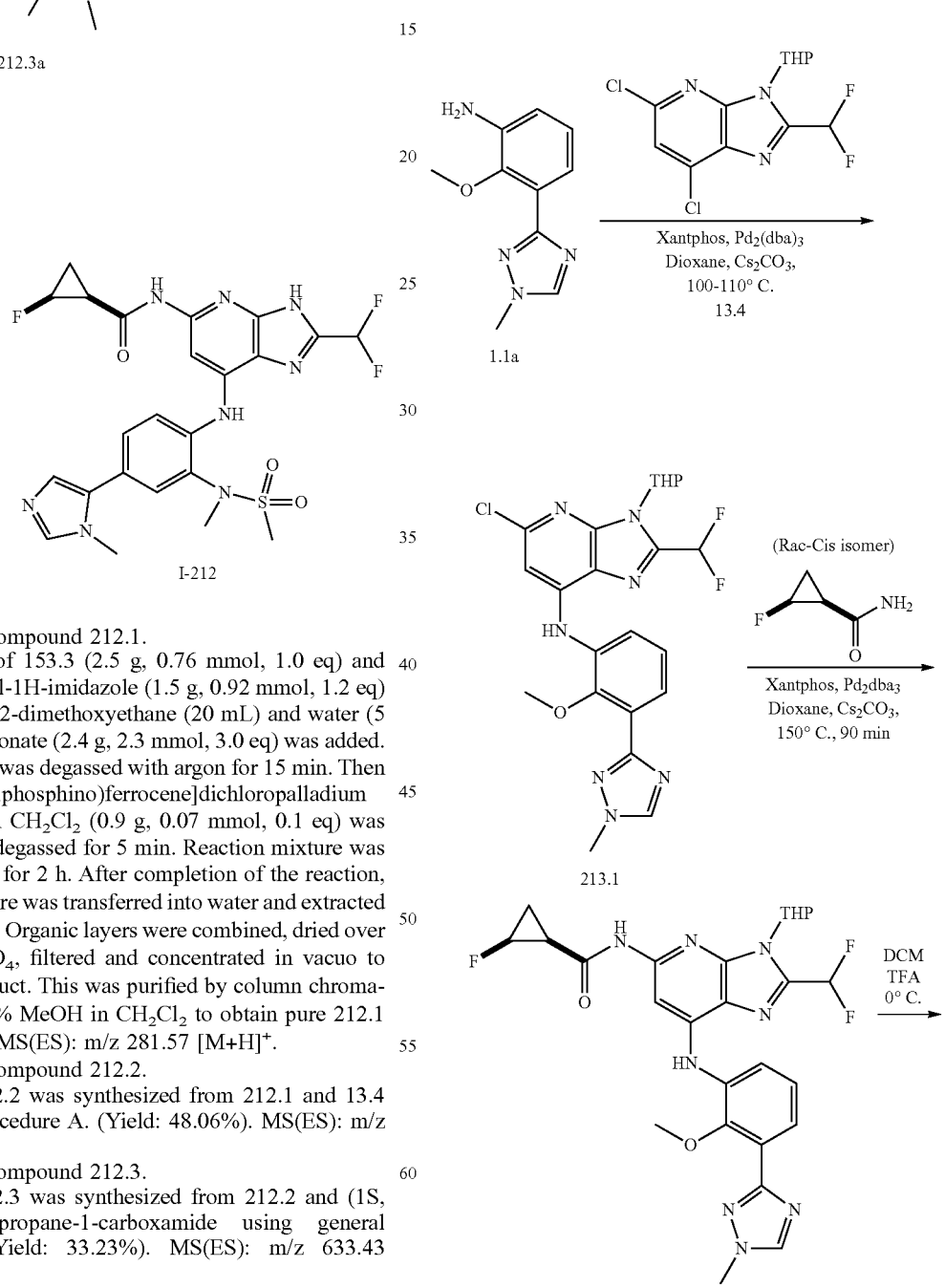

[M+H]⁺, LCMS purity: 100%, HPLC purity 96.86%, Chiral HPLC: (48%, 52%), 1H NMR (MeOD, 400 MHz): 8.52 (s, 1H), 7.87 (s, 2H), 7.7-7.69 (d, J=8 Hz, 1H), 7.65-7.63 (d, J=8 Hz, 1H), 7.32-7.28 (t, J=8 Hz, 1H), 7.24 (t, 1H), 4.76 (s, 1H), 4.05 (s, 3H), 3.73 (s, 3H), 3.39 (s, 3H), 1.60-1.49 (m, 1H), 1.45-1.35 (m, 2H).

Example 213: Synthesis of N-(2-(difluoromethyl)-7-((2-methoxy-3-(1-methyl-1H-1,2,4-triazol-3-yl)phenyl)amino)-3H-imidazo[4,5-b]pyridin-5-yl)-2-fluorocyclopropane-1-carboxamide, I-213

Synthesis of Compound 212.1.

To a solution of 153.3 (2.5 g, 0.76 mmol, 1.0 eq) and 5-bromo-1-methyl-1H-imidazole (1.5 g, 0.92 mmol, 1.2 eq) in a mixture of 1,2-dimethoxyethane (20 mL) and water (5 mL), sodium carbonate (2.4 g, 2.3 mmol, 3.0 eq) was added. Reaction mixture was degassed with argon for 15 min. Then [1,1'-Bis(diphenylphosphino)ferrocene]dichloropalladium (II) complex with CH₂Cl₂ (0.9 g, 0.07 mmol, 0.1 eq) was added and again degassed for 5 min. Reaction mixture was stirred at 115° C. for 2 h. After completion of the reaction, the reaction mixture was transferred into water and extracted with ethyl acetate. Organic layers were combined, dried over anhydrous Na₂SO₄, filtered and concentrated in vacuo to obtain crude product. This was purified by column chromatography using 2% MeOH in CH₂Cl₂ to obtain pure 212.1 (1.3 g, 60.50%). MS(ES): m/z 281.57 [M+H]⁺.

Synthesis of Compound 212.2.

Compound 212.2 was synthesized from 212.1 and 13.4 using general procedure A. (Yield: 48.06%). MS(ES): m/z 567.83 [M+H]⁺.

Synthesis of Compound 212.3.

Compound 212.3 was synthesized from 212.2 and (1S,2S)-2-fluorocyclopropane-1-carboxamide using general procedure B. (Yield: 33.23%). MS(ES): m/z 633.43 [M+H]⁺.

Synthesis of I-212.

Compound I-212 was synthesized from 212.3 using general procedure C. (Yield: 64.70%). MS(ES): m/z: 549.5

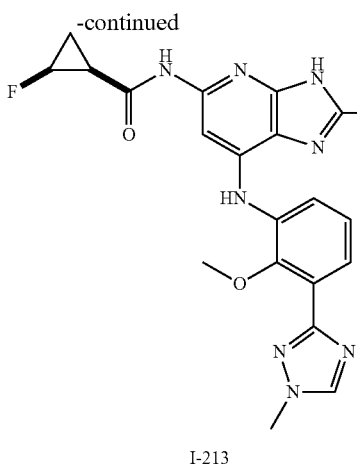

I-213

Synthesis of Compound 213.1.

Compound 213.1 was synthesized from 1.1a and 13.4 using general procedure B. (Yield: 31.27%). MS(ES): m/z 490.23 [M+H]$^+$.

Synthesis of Compound 213.2.

Compound 213.2 was synthesized from (1S,2S)-2-fluorocyclopropane-1-carboxamide and 213.1 using general procedure B. (Yield: 17.61%). MS(ES): m/z 557.42 [M+H]$^+$.

Synthesis of I-213.

Compound I-213 was synthesized from 213.2 using general procedure C. (Yield: 88.35%). MS(ES): m/z: 473.5 [M+H]$^+$, LCMS purity: 99.56%, HPLC purity: 99.17%, Chiral HPLC purity: 76.44%, 1H NMR (MeOD, 400 MHz): 8.52 (s, 1H), 7.93 (s, 1H), 7.75-7.73 (d, J=7.6 Hz, 1H), 7.65-7.63 (t, J=1.2 Hz, 1H), 7.35-7.31 (t, J=8 Hz, 1H), 7.01 (t, 1H), 4.80-4.76 (m, 1H), 4.05 (s, 3H), 3.74 (s, 3H), 1.88-1.78 (m, 1H), 1.22-1.19 (m, 2H).

Example 214: Synthesis of N-(2-(difluoromethyl)-7-((4-(1-methyl-1H-imidazol-5-yl)-2-(methylsulfonyl)phenyl)amino)-3H-imidazo[4,5-b]pyridin-5-yl) cyclopropanecarboxamide, I-214

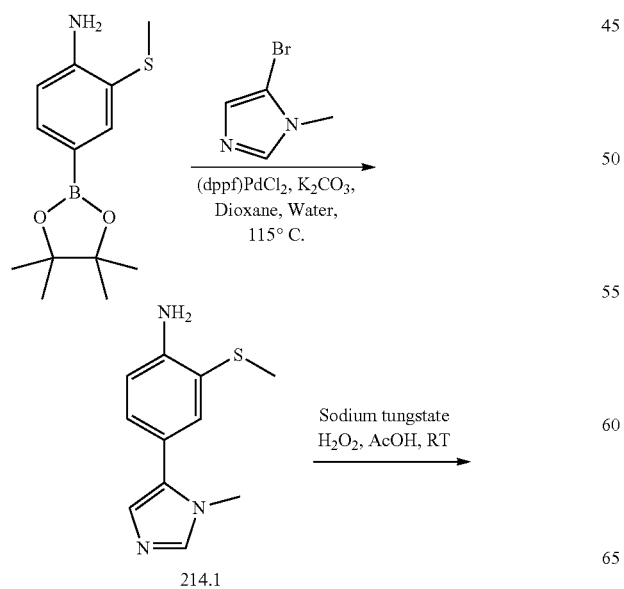

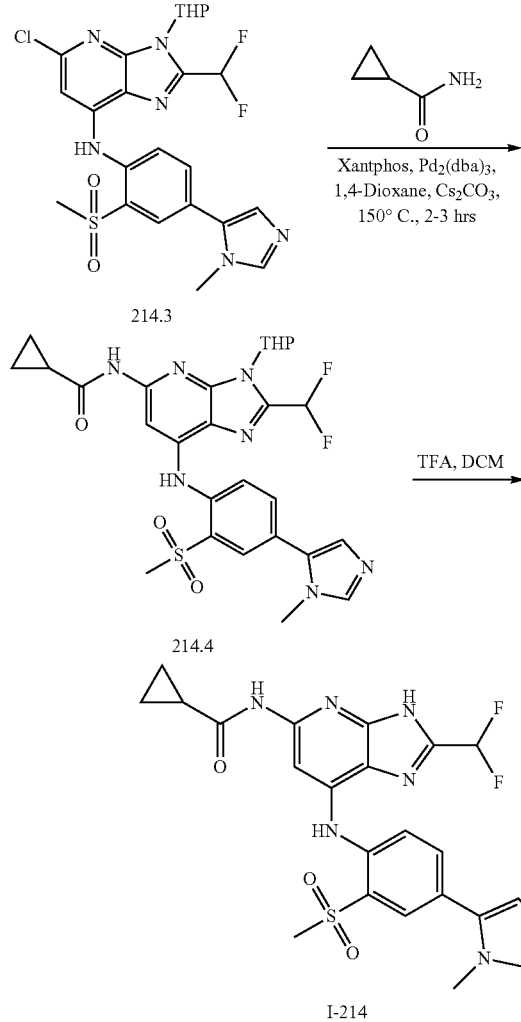

I-214

Synthesis of Compound 214.1.

A mixture of 2-(methylthio)-4-(4,4,5,5-tetramethyl-1,3,2-dioxaborolan-2-yl)aniline (2.8 g, 1.05' mmol, 1.0 eq) and 5-bromo-1-methyl-1H-imidazole 1.1 (2.5 g, 1.58 mmol, 1.5 eq.) in a mixture of dioxane (24 mL) and water (6 mL). Reaction mixture was degassed with argon atmosphere for 10 min. Then [1,1'-Bis(diphenylphosphino)ferrocene]palladium(II) dichloride(0.250 g, 0.31 mmol, 0.03 eq) and potassium carbonate(4.37 g, 3.16 mmol, 3 eq) was added into it. Reaction mixture was stirred at 115° C. for 24 h. Upon completion, reaction mixture was transferred into cold water then extracted with ethyl acetate. Organic layers were combined, dried over Na$_2$SO$_4$ and concentrated in vacuo to obtain crude product. This was purified by column chromatography and compound was eluted in 5% ethyl acetate in hexane as eluant to obtain pure 214.1 (1.5 g, 90.69%). MS(ES): m/z 220.31 [M+H]⁺.

Synthesis of Compound 214.2.

To compound 214.1 (1.5 g, 6.30 mmol, 1.0 eq) in acetic acid (15 mL), sodium tungstate (2 g, 6.30 mmol, 1 eq) was added portion wise. Reaction mixture was allowed to stir at r.t. for 5 min. Then, 30% hydrogen peroxide solution (18 mL) was added dropwise at r.t. Reaction mixture was allowed to stir at r.t. for 10 min. After completion of the reaction, the reaction mixture was transferred to water. The pH of the solution was adjusted to 7 by using saturated NaHCO₃ and then extracted with ethyl acetate. Organic layers were combined, dried over anhydrous Na₂SO₄, filtered and concentrated in vacuo to get the crude material. This was purified by column chromatography using 10-13% ethyl acetate in hexane as eluant to obtain pure 214.2 (1.2 g, 69.81%). MS(ES): m/z 252.30 [M+H]⁺.

Synthesis of Compound 214.3.

Compound 214.3 was synthesized from 13.4 and 214.2 using general procedure A. (Yield: 46.53%). MS(ES): m/z 505.46 [M+H]⁺.

Synthesis of Compound 1.4.

Compound 214.4 was synthesized from 214.3 and cyclopropanecarboxamide using general procedure B. (Yield: 73.35%). MS(ES): m/z 586.64 [M+H]⁺.

Synthesis of I-214.

Compound I-214 was synthesized from 214.4 using general procedure C. (Yield: 72.98%). MS(ES): m/z: 502.41 [M+H]⁺, LCMS purity: 96.66%, HPLC purity 99.09%, 1H NMR (MeOD, 400 MHz): 8.11-8.09 (t, J=7.2 Hz, 2H), 7.98-7.96 (d, J=8.4 Hz, 1H), 7.88-7.85 (dd, J=2 Hz, J=8.8 Hz, 1H), 7.78 (s, 1H), 7.20 (s, 1H), 6.97 (s, 1H), 3.83 (s, 3H), 3.20 (s, 3H), 1.92-1.90 (t, 1H), 0.99-0.98 (d, J=4 Hz, 2H), 0.93-0.91 (d, J=8 Hz, 2H).

Example 215: Synthesis of N-(2-methyl-7-((4-(1-methyl-1H-imidazol-5-yl)-2-(methylsulfonyl)phenyl)amino)-3H-imidazo[4,5-b]pyridin-5-yl)cyclopropanecarboxamide, I-215

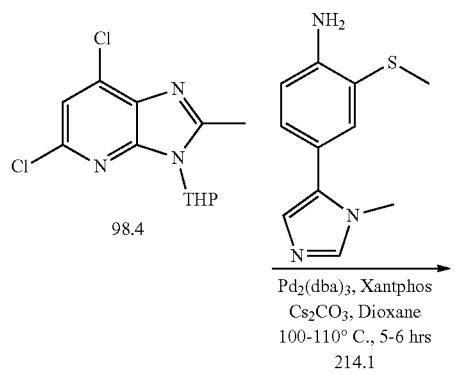

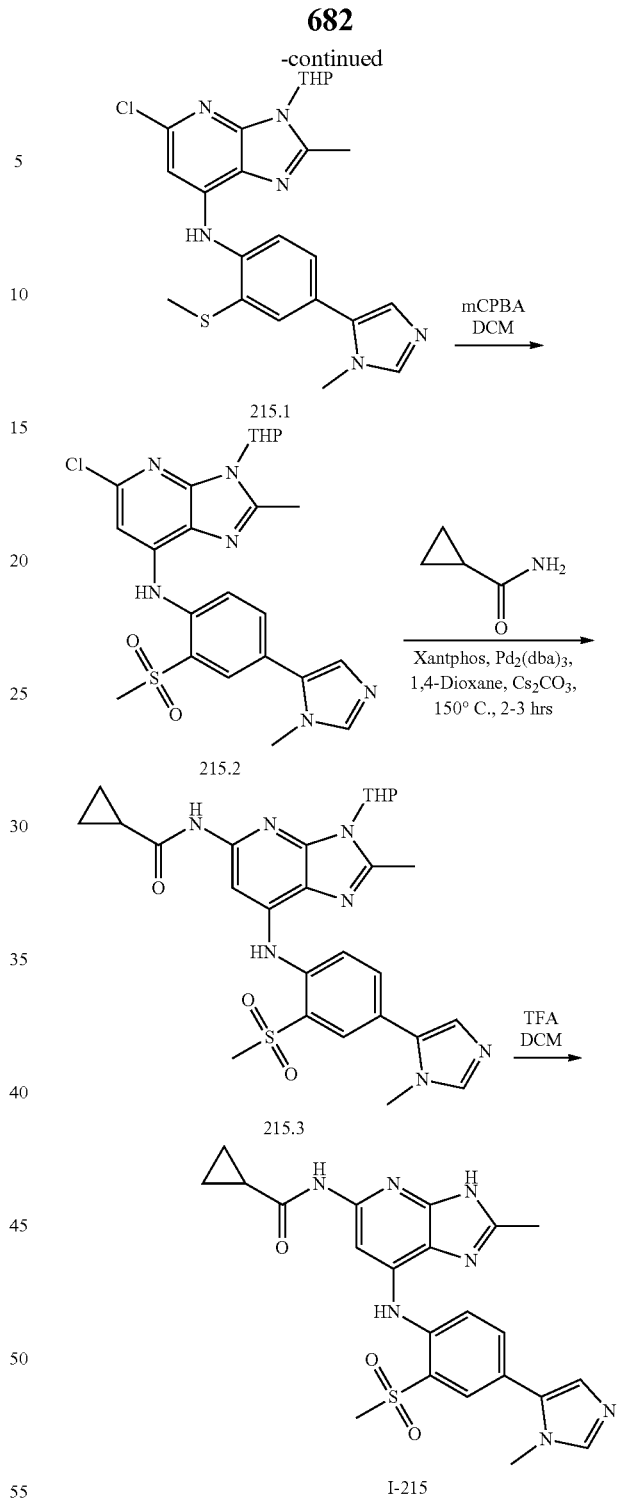

Synthesis of Compound 215.1.

Compound 215.1 was synthesized from 98.4 and 214.1 using general procedure A. (Yield: 33.69%). MS(ES): m/z 470 [M+H]⁺.

Synthesis of Compound 215.2.

To compound 1215.1 (0.610 g, 13 mmol, 1.0 eq) in CH₂Cl₂ (7 mL) was added m-chloroperbenzoic acid (0.67 g, 39 mmol, 3.0 eq) portionwise at 0° C. Reaction mixture was stirred at r.t. for 2 h. Upon completion, reaction mixture was transferred into water and neutralised using saturated NaHCO₃ solution and then extracted with CH₂Cl₂. Organic layers were combined, dried over Na₂SO₄, filtered and concentrated in vacuo to obtain crude product. This was purified by column chromatography and compound was eluted in 2.5% MeOH in CH₂Cl₂ as eluant to obtain pure 215.2 (0.280 g, 42.97%). MS(ES): m/z 502.00 [M+H]⁺.

Synthesis of Compound 215.3.

Compound 215.3 was synthesized 215.2 and cyclopropanecarboxamide using general procedure B. (Yield: 41.78%). MS(ES): m/z 550.65 [M+H]⁺.

Synthesis of I-215.

Compound I-215 was synthesized from 215.3 using general procedure C. (Yield: 70.84%). MS(ES): m/z: 466.57 [M+H]⁺, LCMS purity: 98.35%, HPLC purity: 97.93%, 1H NMR (DMSO, 400 MHz): 9.01 (s, 1H), 8.18 (s, 1H), 8.10 (s, 1H), 8.01 (s, 1H), 7.87 (s, 2H), 7.77 (s, 1H), 7.36 (s, 1H), 7.20 (s, 1H), 3.94 (s, 3H), 3.21 (s, 3H), 2.69 (s, 3H), 2.00-1.98 (d, J=7.6 Hz, 1H), 0.93-0.88 (bs, 4H).

Example 216: Synthesis of N-(2-(difluoromethyl)-7-((4-(1,5-dimethyl-1H-pyrazol-3-yl)-2-(methylsulfonyl)phenyl)amino)-3H-imidazo[4,5-b]pyridin-5-yl)cyclopropanecarboxamide, I-216

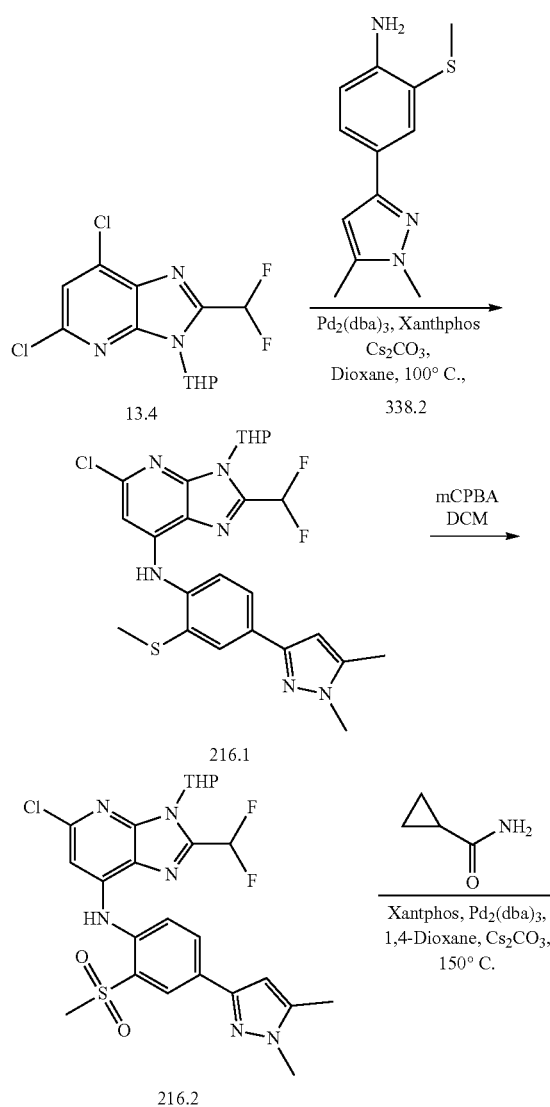

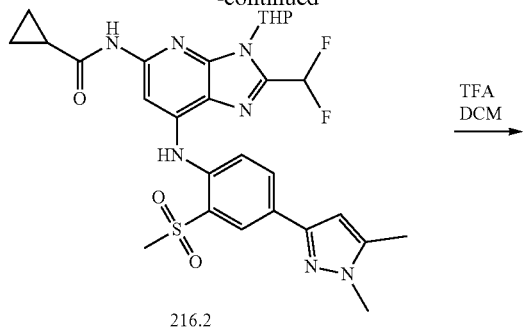

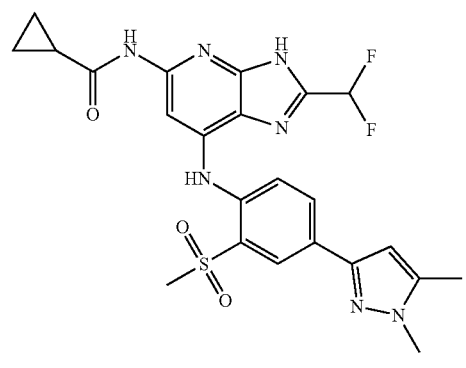

I-216

Synthesis of Compound 216.1.

Compound 216.1 was synthesized from 13.4 and 338.2 using general procedure A. (Yield: 35.86%). MS(ES): m/z 520.01 [M+H]⁺.

Synthesis of Compound 216.2.

To a cooled solution of 216.1 (0.130 g, 250.48 mmol, 1 eq) in CH₂Cl₂ (2 mL) was added meta-Chloroperbenzoic acid (0.151 g, 8.766 mmol, 3.5 eq) portionwise. The reaction mixture was stirred at r.t. for 3 hr. After completion of reaction, the reaction mixture was transferred into saturated NaHCO₃ solution and extracted with CH₂Cl₂. Combined Organic layer dried over Na₂SO₄ and concentrated in vacuo to obtain crude product. This was purified by column chromatography and compound was eluted in 30% ethyl acetate in MeOH to obtain pure 216.2 (0.069 g, 49.99%). MS(ES): m/z 552.01 [M+H]⁺

Synthesis of Compound 216.3.

Compound 216.3 was synthesized from 216.2 and cyclopropanecarboxamide using general procedure B. (Yield: 75.86%). MS(ES): m/z 516.54 [M+H]⁺.

Synthesis of Compound I-216.

Compound I-216 was synthesized from 216.3 using general procedure C. (Yield: 67.21%). MS(ES): m/z: 516.54 [M+H]⁺, LCMS purity: 100.00%, HPLC purity 99.51%, 1H NMR (DMSO, 400 MHz): 13.69 (s, 1H), 10.77 (s, 1H), 8.78 (s, 1H), 8.38 (s, 1H), 8.10 (s, 1H), 8.09-8.07 (d, J=8.8 Hz, 1H), 7.81-7.79 (s, 1H), 6.61 (s, 1H), 3.81 (s, 3H), 3.25 (s, 3H), 2.37 (s, 3H), 2.10-2.05 (m, 1H), 0.87 (bs, 4H).

Example 217: Synthesis of N-(7-((4-(1,5-dimethyl-1H-pyrazol-3-yl)-2-(methylsulfonyl)phenyl)amino)-2-methyl-3H-imidazo[4,5-b]pyridin-5-yl)cyclopropanecarboxamide, I-217

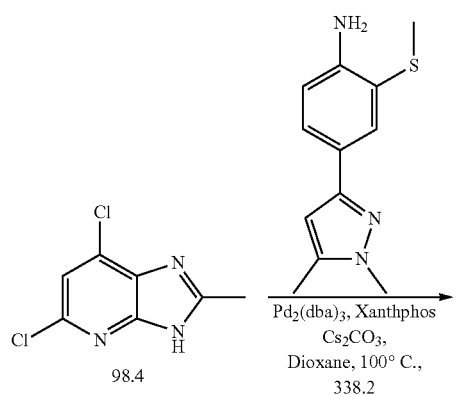

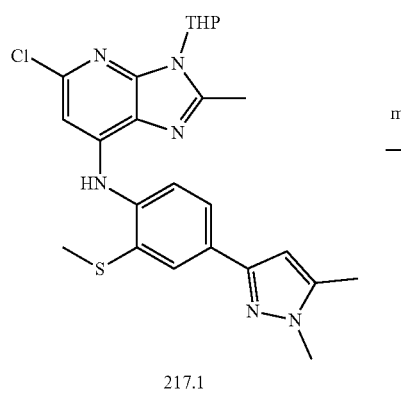

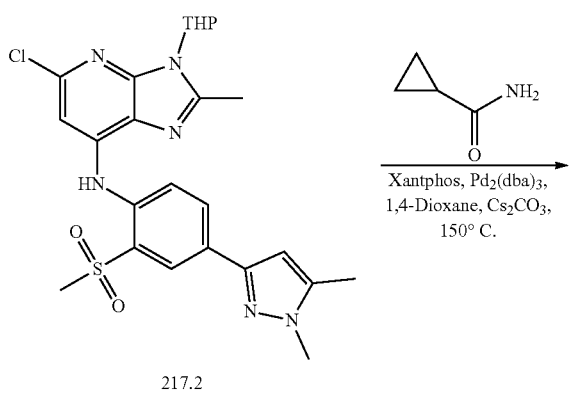

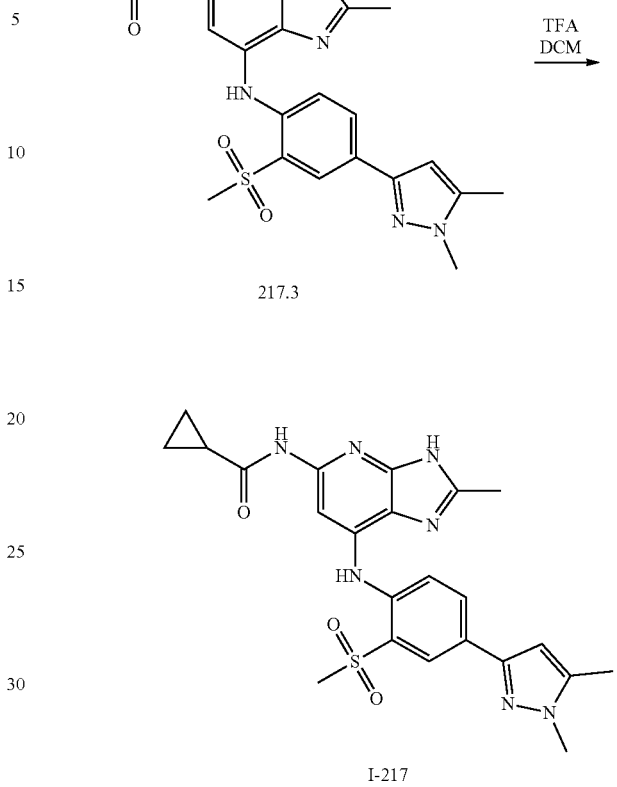

Synthesis of Compound 217.1.

Compound 217.1 was synthesized from 98.4 and 338.2 using general procedure A. (Yield: 21.03%). MS(ES): m/z 484.03 [M+H]$^+$.

Synthesis of Compound 217.2.

To a cooled solution of 217.1 (0.113 g, 233.94 mmol, 1 eq) in CH$_2$Cl$_2$ (2 mL) was added meta-Chloroperbenzoic acid (0.140 g, 8.19 mmol, 3.5 eq) portionwise. The reaction mixture was stirred at r.t. for 3 hr. After completion of reaction, the reaction mixture was transferred into saturated NaHCO$_3$ solution and extracted with CH$_2$Cl$_2$. Combined Organic layer dried over Na$_2$SO$_4$ and concentrated in vacuo to obtain crude product. This was purified by column chromatography and compound was eluted in 30% ethyl acetate in MeOH to obtain pure 217.2. (0.090 g, 74.70%). MS(ES): m/z 516.03 [M+H]$^+$ Synthesis of Compound 217.3.

Compound 217.3 was synthesized from 217.2 and cyclopropanecarboxamide using general procedure B. (Yield: 60.91%). MS(ES): m/z 564.68 [M+H]$^+$.

Synthesis of Compound I-217.

Compound I-217 was synthesized from 217.3 using general procedure C. (Yield: 48.98%). MS(ES): m/z: 480.57 [M+H]$^+$, LCMS purity: 100%, HPLC purity 99.34%, 1H NMR (DMSO, 400 MHz): 13.59 (s, 1H), 10.95 (s, 1H), 8.66 (s, 1H), 8.37-8.37 (d, J=1.6 Hz, 1H), 8.08-8.06 (s, 1H), 7.88 (s, 1H), 7.60-7.57 (d, J=8.4 Hz, 1H), 6.62 (s, 1H), 3.80 (s, 1H), 3.24 (s, 3H), 2.76 (s, 3H), 2.30 (s, 3H), 1.99-1.96 (m, 1H), 0.79-0.77 (d, J=6.8 Hz, 4H).

Example 218/219: Synthesis of (R)—N-(2-(difluoromethyl)-7-((2-(N-methylmethylsulfonamido)-4-(tetrahydro-2H-pyran-2-yl)phenyl)amino)-3H-imidazo[4,5-b]pyridin-5-yl)cyclopropanecarboxamide, I-218 and (S)—N-(2-(difluoromethyl)-7-((2-(N-methylmethylsulfonamido)-4-(tetrahydro-2H-pyran-2-yl)phenyl)amino)-3H-imidazo[4,5-b]pyridin-5-yl)cyclopropanecarboxamide, I-219

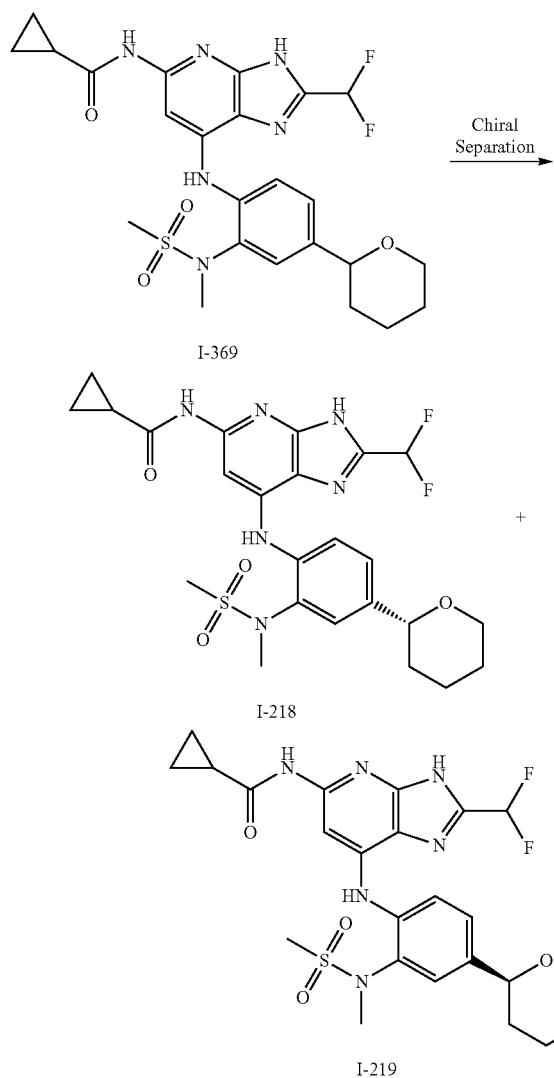

Synthesis of compound I-218 and I-219. Isomers of I-369 (0.100 g) were separated out using column (CHIRAL PAK AD-H (250 mm*4.6 mm, 5u)) and 0.1% TFA in HEX:IPA (80:20) at flow rate of 4 mL/min. to get pure fraction-1 (FR-a) and fraction-2 (FR-b). FR-a was concentrated in vacuo at 30° C. to afford pure I-218 (0.018 g). MS(ES): m/z: 535.65 [M+H]$^+$, LCMS purity: 100%, HPLC purity 100%, Chiral HPLC: 100%, 1H NMR (MeOD, 400 MHz): 7.74 (s, 1H), 7.68-7.66 (d, J=8.4 Hz, 1H), 7.61 (s, 1H), 7.47-7.45 (d, J=8.4 Hz, 1H), 6.99 (t, 1H), 4.46-4.43 (d, J=10.4 Hz, 1H) 4.16-4.13-(d, J=10.8 Hz, 1H), 3.72-3.67 (m, 1H), 3.30 (s, 3H), 3.05 (s, 3H), 1.99 (m, 1H), 1.87-1.63 (m, 6H), 0.96-0.89 (m, 4H). FR-b was concentrated in vacuo at 30° C. to afford pure I-219 (0.017 g). MS(ES): m/z: 535.65 [M+H]$^+$, LCMS purity: 100%, HPLC purity 95.10%, Chiral HPLC: 98.28%, 1H NMR (MeOD, 400 MHz): 7.68-7.61 (m, 3H), 7.62 (s, 1H), 7.00 (t, 1H), 4.46-4.44 (d, J=10 Hz, 1H), 4.16-4.13 (d, J=11.2 Hz, 1H) 3.72-3.67 (m, 1H), 3.30 (s, 3H), 3.05 (s, 3H), 2.06 (m, 1H), 1.97-1.66 (m, 6H), 1.05-0.91 (m, 4H).

Example 220: Synthesis of N-(7-((4-cyclobutyl-2-(methylsulfonyl)phenyl)amino)-2-(difluoromethyl)-3H-imidazo[4,5-b]pyridin-5-yl)cyclopropanecarboxamide, I-220

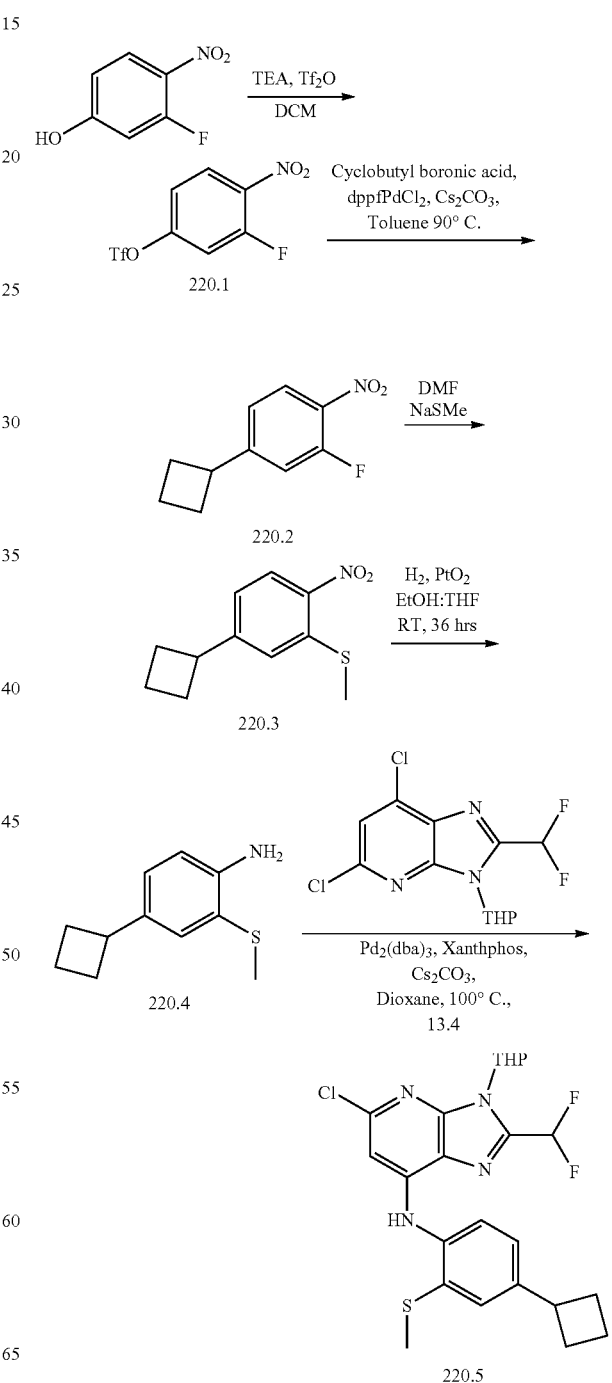

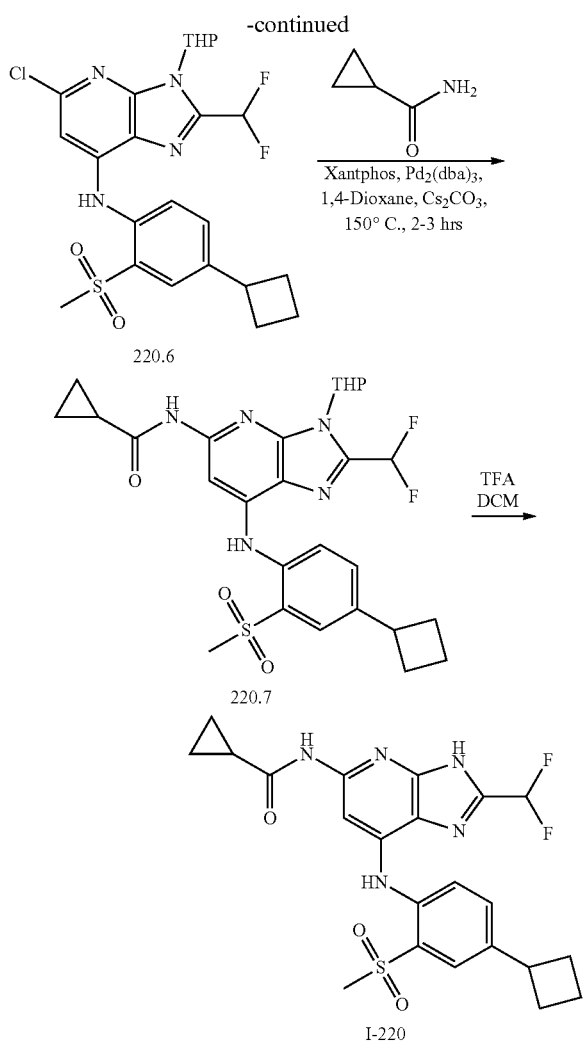

Synthesis of Compound 220.1.

To compound 3-fluoro-4-nitrophenol (5 g, 31.8 mmol, 1.0 eq) in $CH_2Cl_2$ (50 mL), triethylamine (6.5 mL, 47.7 mmol, 1.5 eq) was added at 0° C. Reaction mixture was stirred at 0° C. for 10 min. Then, trifluoromethane sulfonic acid (6.3 mL, 31.8 mmol, 1.0 eq) was added dropwise. Reaction mixture was allowed to stir at 0° C. for 16 h. After completion of the reaction, the reaction mixture was transferred to water and extracted with $CH_2Cl_2$. Organic layers were combined, dried over anhydrous $Na_2SO_4$, filtered and evaporated under vacuum to obtain 220.1 (0.35 g, 83.39%). MS(ES): m/z 204.18 $[M+H]^+$.

Synthesis of Compound 220.2.

To compound 220.1 (3.0 g, 10.3 mmol, 1.0 eq) and cyclopropylboronic acid (1.29 g, 12.93 mmol, 1.25 eq) in toluene (30 mL), $Cs_2CO_3$ (5.0 g, 15.45 mmol, 1.5 eq) was added. Reaction mixture was degassed with argon for 5 min. Then, [1,1'-Bis(diphenylphosphino)ferrocene]dichloropalladium(II), complex with $CH_2Cl_2$ (0.67 g, 0.824 mmol, 0.08 eq) was added and reaction mixture was again degassed with argon for 10 min. Reaction mixture was stirred at 90° C. for 4 h. After completion of the reaction, the reaction mixture was transferred to water and extracted with $CH_2Cl_2$. Organic layers were combined, dried over anhydrous $Na_2SO_4$, filtered and evaporated under vacuum to obtain 220.2 (1.1 g, 54.32%). MS(ES): m/z 196.54 $[M+H]^+$.

Synthesis of Compound 220.3.

To compound 220.2 (1.3 g, 6.66 mmol, 1.0 eq) in dimethylformamide (20 mL), sodium methanethiolate (1.0 g, 14.66 mmol, 2.2 eq) in water was added. Reaction mixture was stirred at 15-20° C. for 5 h. After completion of the reaction, the reaction mixture was transferred in water and extracted with ethyl acetate. Organic layers were combined, dried over $Na_2SO_4$, filtered and concentrated in vacuo to get the crude material. This was purified by column chromatography using 15% ethyl acetate in hexane as eluant to obtain pure 220.3 (1.2 g, 80.69%). MS(ES): m/z 224.38 $[M+H]^+$.

Synthesis of Compound 220.4.

To a solution of 220.3 (1.2 g, 1.74 mmol, 1.0 eq) in MeOH (35 mL), 10% Pd/C (0.42 g) was added. Hydrogen was purged through reaction mixture for 12 h. Upon completion, reaction mixture was filtered through celite-bed and washed with ethanol. Filtrate was concentrated in vacuo to obtain 220.4 (0.8 g, 77.01%). MS(ES): m/z 194.25 $[M+H]^+$.

Synthesis of Compound 220.5.

Compound 220.5 was synthesized from 220.4 and 13.4 using general procedure A. (Yield: 34.98%). MS(ES): m/z 479.83 $[M+H]^+$.

Synthesis of Compound 220.6.

To compound 220.5 (0.5 g, 1.44 mmol, 1.0 eq) in $CH_2Cl_2$ (5 mL) at 0° C., m-chloroperocybenzoic acid (0.5 mL) was added dropwise. Reaction mixture was stirred at r.t. for 10 min. After completion of the reaction, the reaction mixture was transferred in water and extracted with ethyl acetate. The organic layer was then washed with $NaHCO_3$. The Organic layers were combined, dried over $Na_2SO_4$, filtered and concentrated in vacuo to obtain 220.6 (0.3 g, 73.23%). MS(ES): m/z 511.26 $[M+H]^+$.

Synthesis of Compound 220.7.

Compound 220.7 was synthesized from 220.6 and cyclopropanecarboxyamide using general procedure B. (Yield: 32.26%). MS(ES): m/z 560.49 $[M+H]^+$.

Synthesis of I-220.

Compound I-220 was synthesized from 220.7 using general procedure C. (Yield: 57.73%). MS(ES): m/z: 476.35 $[M+H]^+$, LCMS purity: 98.93%, HPLC purity 98.53%, 1H NMR (DMSO+TFA, 400 MHz): 7.19 (s, 2H), 6.95-6.93 (d, J=8 Hz, 1H), 6.84-6.82 (d, J=8 Hz, 1H), 6.22 (t, 1H), 3.11 (s, 1H), 2.92 (m, 1H), 2.29 (s, 3H) 1.63 (bs, 2H), 1.44-1.34 (m, 2H), 1.13 (bs, 1H), 0.97 (s, 2H), 0.31-0.20 (m, 4H).

Example 221: Synthesis of N-(7-((4-cyclobutyl-2-(methylsulfonyl)phenyl)amino)-2-methyl-3H-imidazo[4,5-b]pyridin-5-yl)cyclopropanecarboxamide, I-221

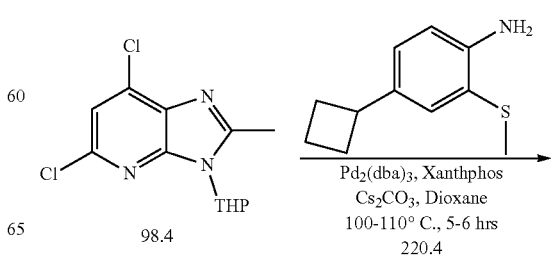

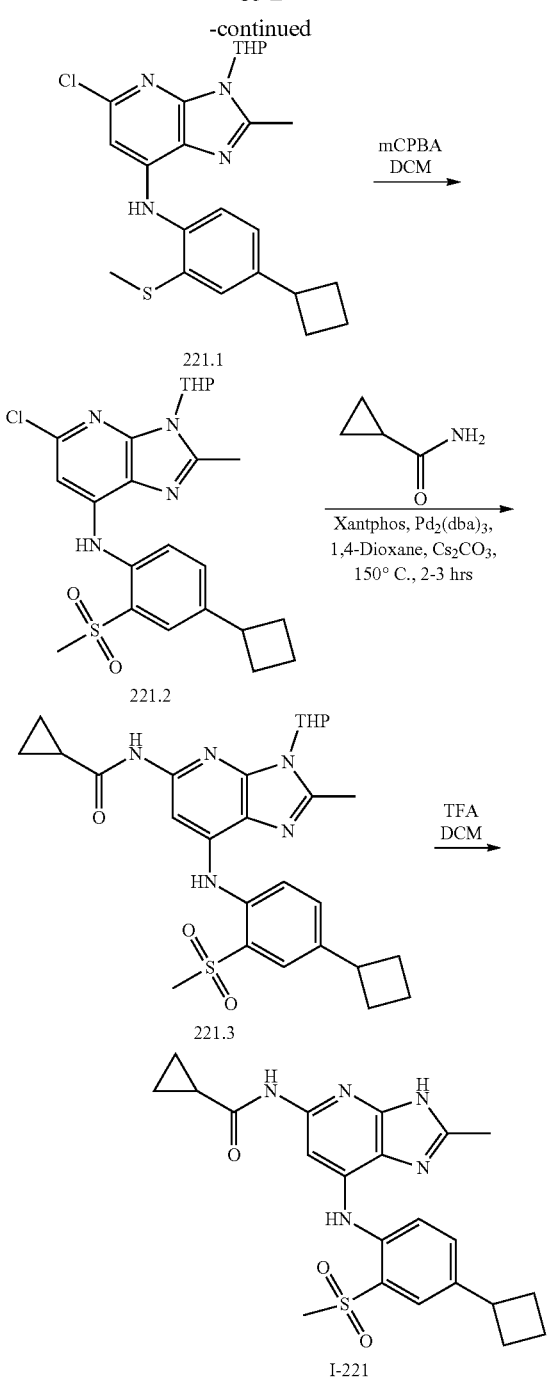

dried over Na$_2$SO$_4$, filtered and concentrated in vacuo to obtain 221.2 (0.170 g, 60.82%). MS(ES): m/z 476.53 [M+H]$^+$.

Synthesis of Compound 221.3.

Compound 221.3 was synthesized from 221.2 and cyclopropanecarboxamide using general procedure B. (Yield: 48.38%). MS(ES): m/z 524.86 [M+H]$^+$.

Synthesis of Compound I-221.

Compound I-221 was synthesized from 221.3 using general procedure C. (Yield: 64.04%). MS(ES): m/z: 440.40 [M+H]$^+$, LCMS purity: 100%, HPLC purity 99.01%, 1H NMR (MeOD, 400 MHz): 7.86-7.86 (d, J=1.6 Hz, 1H), 7.81 (s, 1H), 7.71-7.69 (d, J=8.4 Hz, 1H), 7.65-7.63 (m, 1H), 3.70-3.66 (m, 1H), 3.09 (s, 3H), 2.61 (s, 3H), 2.47-2.4 (m, 2H) 2.26-2.09 (m, 3H), 1.98-1.85 (m, 2H), 0.97-0.95 (m, 4H).

Example 222: Synthesis of N-(2-(difluoromethyl)-7-((4-(methoxymethyl)-2-(methylsulfonyl)phenyl)amino)-3H-imidazo[4,5-b]pyridin-5-yl)cyclopropanecarboxamide, I-222

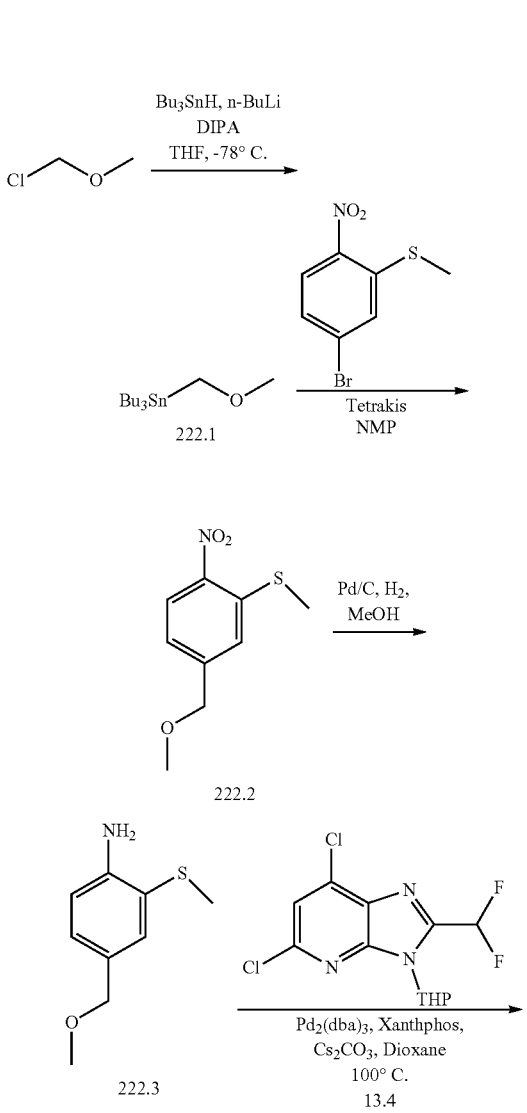

Synthesis of Compound 221.1.

Compound 221.1 was synthesized from 98.4 and 220.4 using general procedure A. (Yield: 33.45%). MS(ES): m/z 444.52 [M+H]$^+$.

Synthesis of Compound 221.2.

To compound 221.1 (0.22 g, 0.5 mmol, 1.00 eq) in CH$_2$Cl$_2$ (4 mL) at 0° C., m-chloroperoxybenzoic acid (0.4 g, 1.75 mmol, 3.5 eq) was added portionwise. Reaction mixture was stirred at r.t. for 10 min. After completion of the reaction, the reaction mixture was transferred in water and extracted with ethyl acetate. The organic layer was then washed with NaHCO$_3$. The Organic layers were combined,

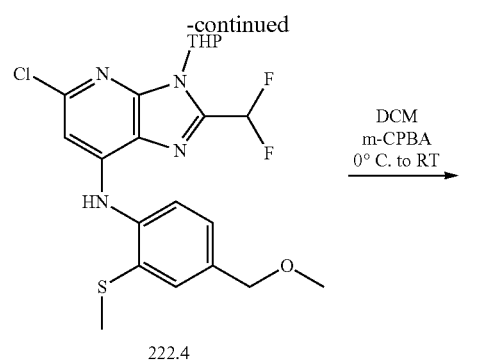

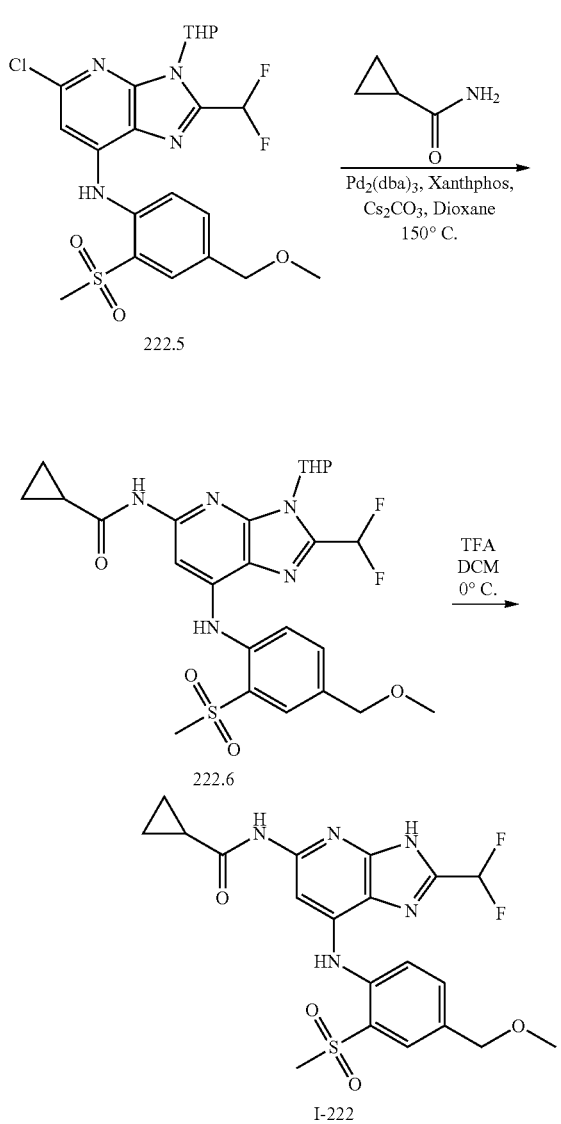

and then maintained 0° C. and stirred for 30 min. The reaction mixture was cooled to −78° C., added chloro(methoxy)methane (10 g, 0.125 mmol, 1.0 eq) and reaction mixture was allowed to warm to r.t. The reaction mixture was stirred at r.t. for 5 h. Upon completion, reaction mixture was transferred in to brine and extracted with diethyl ether. Organic layers were combined, washed with brine, dried over $Na_2SO_4$ and concentrated in vacuo to obtain crude product. This was purified by column chromatography and compound was eluted hexane as eluent to obtain 222.1. (7.0 g, 16.82%). MS(ES): m/z 336.12 $[M+H]^+$.

Synthesis of Compound 222.2.

To a solution of 222.1 (3.7 g, 14.92 mmol, 1.0 eq) in N-methylpyrrolidine (35 mL) was added (5-bromo-2-nitrophenyl)(methyl)sulfane (5.0 g, 14.92 mmol, 1 eq). The reaction mixture was degassed for 10 min. under argon atmosphere. Tetrakis(triphenylphosphine)palladium(0) (1.72 g, 1.49 mmol, 0.1 eq), again reaction mixture was degassed for 10 min. under argon atmosphere. The reaction was stirred at 60° C. for 20 h. Upon completion, reaction mixture was transferred in water and extracted with ethyl acetate. Combined organic layer was washed with brine, dried over $Na_2SO_4$ and concentrated in vacuo to obtain crude product. This was purified by column chromatography using 15% ethyl acetate in hexane to obtain pure 222.2 (2.1 g, 66.00%). MS(ES): m/z 214.25 $[M+H]^+$.

Synthesis of Compound 222.3.

To a solution of 222.2 (2.1 g, 9.85 mmol, 1.0 eq) in MeOH (50 mL), 10% Pd/C (1 g) was added. Hydrogen was purged through reaction mixture for 4 h. Upon completion, reaction mixture was filtered through celite-bed and washed with MeOH. Filtrate was concentrated in vacuo to obtain 222.3. (1.1 g, 60.95%). MS(ES): m/z 184.27 $[M+H]^+$.

Synthesis of Compound 222.4.

Compound 222.4 was synthesized from 222.3 and 13.4 using general procedure A. (Yield: 23.45%). MS (ES): m/z 469.95 $[M+H]^+$.

Synthesis of Compound 222.5.

A solution 222.4 (0.240 g, 5.11 mmol, 1 eq) in $CH_2Cl_2$ (10 mL) was allowed to cool at 0° C. and meta-Chloroperbenzoic acid(0.097 g, 5.62 mmol, 1.1 eq) was added slowly to the reaction mixture. The reaction mixture was stirred at r.t. for 1 hr. After completion of reaction, the reaction mixture was transferred into saturated $NaHCO_3$ solution and extracted with $CH_2Cl_2$. Combined Organic layer dried over $Na_2SO_4$ and concentrated in vacuo to obtain crude product. This was purified by column chromatography and compound was eluted in 2% MeOH in $CH_2Cl_2$ to obtain 222.5 (0.160 g, 62.41%). MS(ES): m/z 501.95 $[M+H]^+$.

Synthesis of Compound 222.6.

Compound was synthesized from 122.5 and cyclopropanecarboxamide using general procedure B. (Yield: 45.57%). MS (ES): m/z 550.59 $[M+H]^+$.

Synthesis of Compound I-222

Compound I-222 was synthesized from 222.6 using general procedure C. (Yield: 59.04%). MS(ES): m/z: 466.35 $[M+H]^+$, LCMS purity: 100%, HPLC purity: 97.55%, 1H NMR (MeOD, 400 MHz): 8.05 (s, 1H), 8.01-8.00 (d, J=1.6 Hz, 1H), 7.87-7.85 (d, J=8.4 Hz, 1H), 7.75-7.73 (d, J=8.4 Hz, 1H), 6.98 (t, 1H), 4.56 (s, 2H), 3.47 (s, 3H), 3.12 (s, 3H), 1.90 (s, 1H), 0.98-0.89 (s, 4H).

Synthesis of Compound 222.1.

To a solution of diisopropyl amine (38.7 g, 0.30 mmol, 2.4 eq) in tetrahydrofuran (200 mL) was cooled to −78° C. followed by n-butyl lithium (19.21 g, 0.30 mmol, 2.4 eq) was added and stirred reaction mixture for 30 min. at the same temperature. Tributyltin hydride (87.03 g, 0.30 mmol, 2.4 eq) was added to reaction mixture at same temperature

Example 223: Synthesis of N-(7-((4-(methoxymethyl)-2-(methylsulfonyl)phenyl)amino)-2-methyl-3H-imidazo[4,5-b]pyridin-5-yl)cyclopropanecarboxamide, I-223

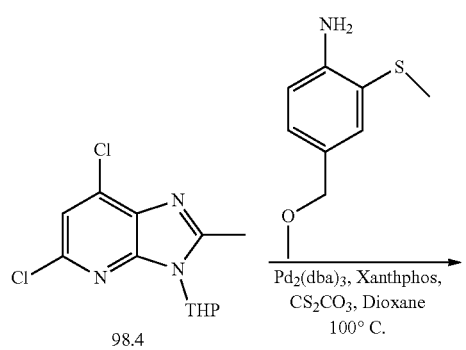

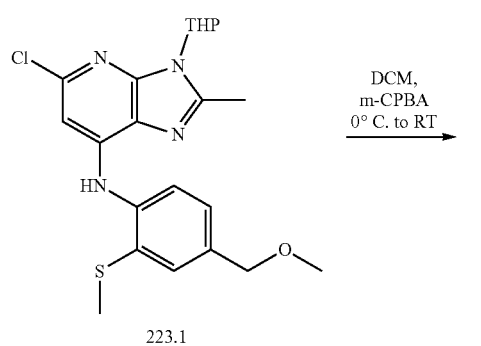

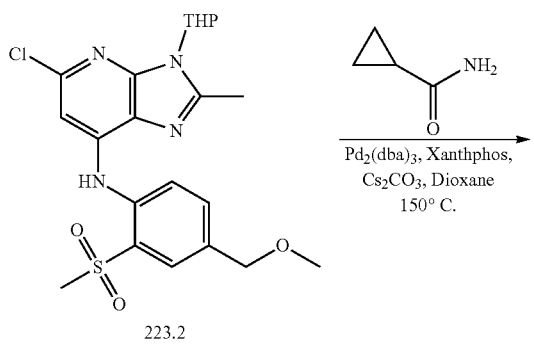

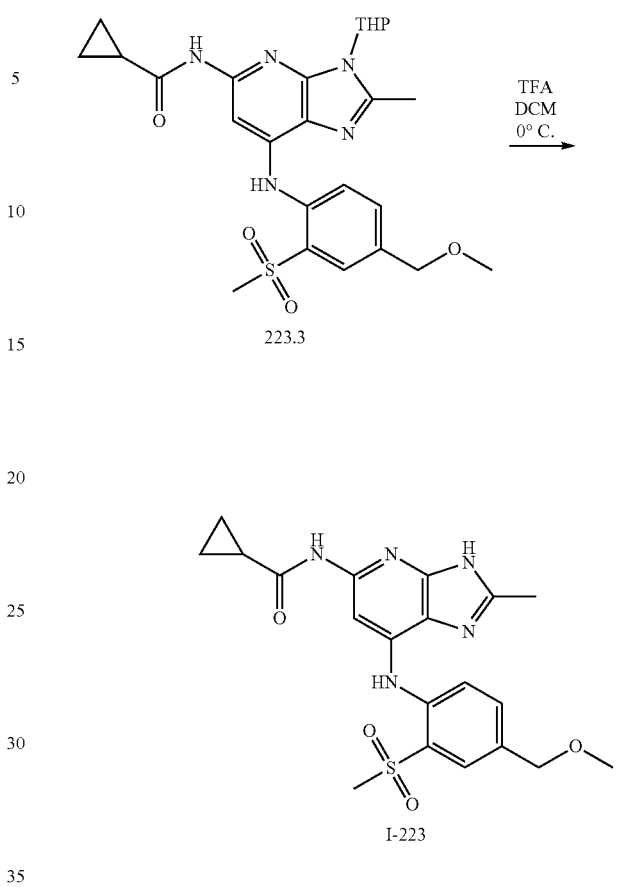

Synthesis of Compound 223.1.

Compound 223.1 was synthesized from 4-(methoxymethyl)-2-(methylthio)aniline and 98.4 using general procedure A. (Yield: 38.00%). MS (ES): m/z 432.97 [M+H]$^+$.

Synthesis of Compound 223.2.

A solution 223.1 (0.240 g, 5.54 mmol, 1 eq) in CH$_2$Cl$_2$ (10 mL) was allowed to cool at 0° C. and meta-Chloroperbenzoic acid(0.104 g, 6.09 mmol, 1.1 eq) was added slowly to the reaction mixture. The reaction mixture was stirred at r.t. for 1 hr. After completion of reaction, the reaction mixture was transferred into saturated NaHCO$_3$ solution and extracted with CH$_2$Cl$_2$. Combined Organic layer dried over Na$_2$SO$_4$ and concentrated in vacuo to obtain crude product. This was purified by column chromatography and compound was eluted in 2% MeOH in CH$_2$Cl$_2$ to obtain pure 223.1. (0.140 g, 56.68%). MS(ES): m/z 465.97 [M+H]$^+$.

Synthesis of Compound 223.3.

Compound was synthesized from 223.2 and cyclopropanecarboxamide using general procedure B. (Yield: 48.50%). MS (ES): m/z 514.61 [M+H]$^+$.

Synthesis of Compound I-223.

Compound I-223 was synthesized from 223.3 using general procedure C. (Yield: 55.81%). MS(ES): m/z 430.55 [M+H]$^+$, LCMS purity: 95.61%, HPLC purity 97.09%, 1H NMR (MeOD, 400 MHz): 7.98 (s, 1H), 7.91 (s, 1H), 7.78 (s, 1H), 7.71-7.69 (d, J=7.6 Hz, 1H), 4.54 (s, 2H), 3.46 (s, 3H), 3.38 (s, 3H), 3.12 (s, 3H), 1.87 (s, 1H), 0.96-0.88 (m, 4H).

Example 224/225: Synthesis of (1S,2S)-2-fluoro-N-(2-methyl-7-((4-(1-methyl-1H-pyrazol-3-yl)-2-(methylsulfonyl)phenyl)amino)-3H-imidazo[4,5-b]pyridin-5-yl)cyclopropane-1-carboxamide, I-224 and (1R,2R)-2-fluoro-N-(2-methyl-7-((4-(1-methyl-1H-pyrazol-3-yl)-2-(methylsulfonyl)phenyl)amino)-3H-imidazo[4,5-b]pyridin-5-yl)cyclopropane-1-carboxamide, I-225

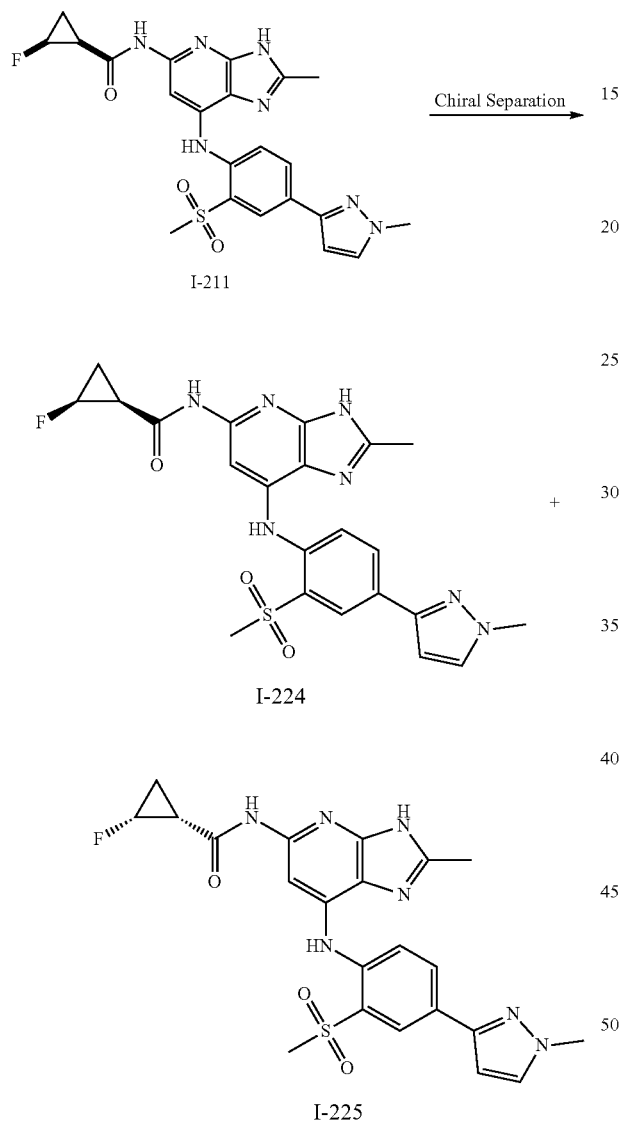

Synthesis of Compound I-224 and I-225.

Isomers of I-211 (0.052 g) were separated out using column (CHIRAL PAK AD-H 250×4.6 mm, 5 µM) 0.1 DEA in IPA:ACN (50:50) as co-solvent with flow rate of 4 mL/min. to get pure fraction-1 (FR-a) and fraction-2 (FR-b). FR-a was concentrated in vacuo at 30° C. to afford pure I-224 (0.024 g). MS(ES): m/z: 484.30 [M+H]$^+$, LCMS purity: 100%, HPLC purity: 98.57%, Chiral HPLC Purity: (100%), 1H NMR (DMSO, 400 MHz): 10.81 (s, 1H), 8.67 (s, 1H), 8.38-8.37 (d, J=1.6 Hz, 1H), 8.15-8.13 (d, J=8.4 Hz, 1H), 7.95 (s, 1H), 7.82-7.81 (d, J=2 Hz, 2H), 7.73-7.71 (d, J=8.8 Hz, 1H), 6.84-6.84 (d, J=2 Hz, 1H), 5.0-4.84 (m, 1H), 3.93 (s, 3H), 3.27 (s, 3H), 2.63 (s, 3H), 2.20 (s, 1H), 1.64-1.58 (m, 1H), 1.19-1.12 (m, 1H). FR-b was concentrated in vacuo at 30° C. to afford pure I-225 (0.004 g) MS(ES): m/z: 484.41 [M+H]$^+$, LCMS purity: 100%, HPLC purity: 100%, Chiral HPLC Purity: (97%), 1H NMR (MeOD, 400 MHz): 8.43-8.42 (d, J=4 Hz, 1H), 8.13-8.11 (d, J=8 Hz, 1H), 7.99 (s, 1H), 7.86 (s, 1H), 7.68-7.67 (d, J=4 Hz, 1H), 6.73-6.72 (d, J=4 Hz, 1H), 4.77 (m, 1H), 3.99 (s, 3H), 3.17 (s, 3H), 2.60 (s, 3H), 2.09 (m, 1H), 1.78-1.72 (m, 1H), 1.19-1.16 (m, 1H).

Example 226: Synthesis of N-(2-methyl-7-((2-(methylsulfonyl)-4-(tetrahydro-2H-pyran-4-yl)phenyl)amino)-3H-imidazo[4,5-b]pyridin-5-yl)cyclopropanecarboxamide, I-226

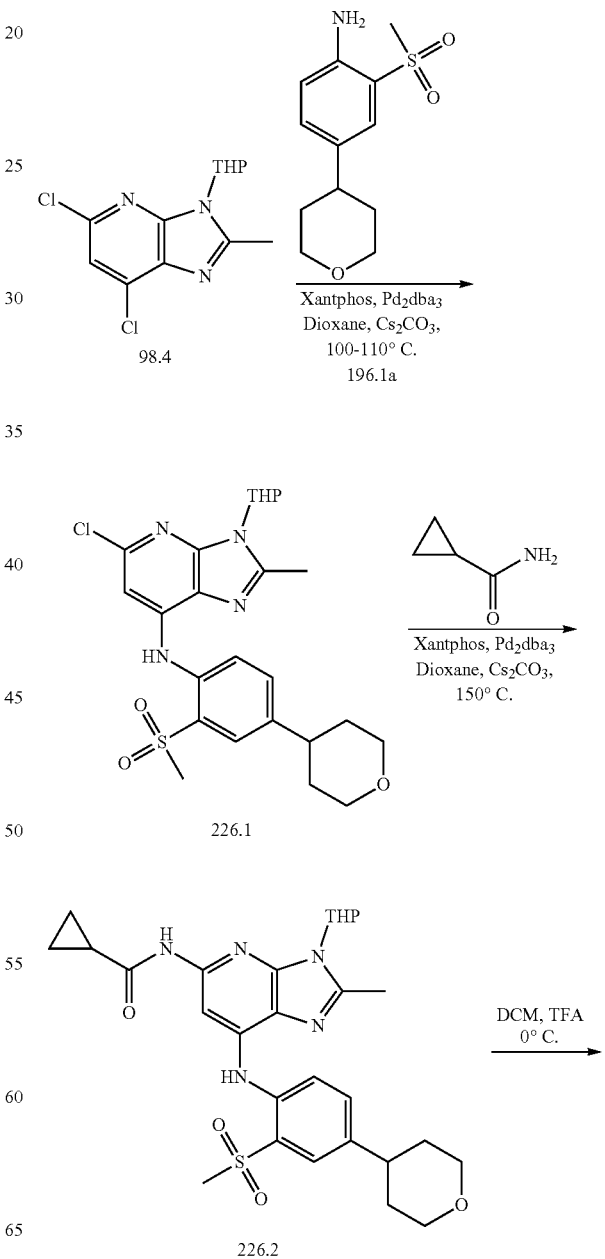

-continued

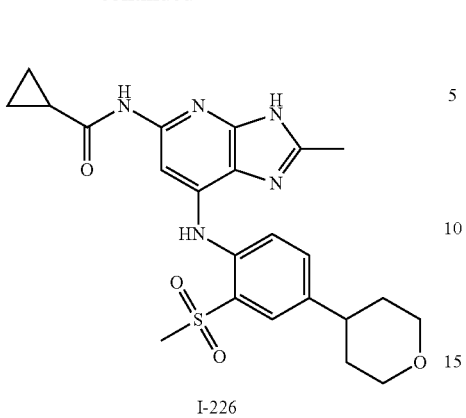

I-226

Synthesis of Compound 226.1.

Compound 226.1 was synthesized from 232.3 and 98.4 using general procedure A. (Yield: 19.45%). MS(ES): m/z 506.03 [M+H]$^+$.

Synthesis of Compound 226.2.

Compound 226.2 was synthesized from 226.1 and cyclopropanecarboxamide using general procedure B. (Yield: 82.09%). MS(ES): m/z 554.68 [M+H]$^+$.

Synthesis of I-226.

Compound I-226 was synthesized from 226.2 using general procedure C (Yield: 75.99%). MS(ES): m/z: 470.52 [M+H]$^+$, LCMS purity: 100%, HPLC purity: 100%, 1H NMR (DMSO-d6, 400 MHz): 12.52 (s, 1H), 10.58 (s, 1H), 8.49 (s, 1H), 7.95 (s, 1H), 7.75 (s, 1H), 7.71-7.66 (m, 2H), 3.99-3.95 (m, 2H), 3.48-3.42 (m, 2H), 3.19-3.17 (m, 6H), 2.93-2.87 (m, 1H), 2.01-1.98 (t, J=11.6 Hz, 1H), 1.78-1.63 (m, 4H), 0.77-0.76 (d, J=4.8 Hz, 4H).

Example 227/228: Synthesis of (R)-2,2-difluoro-N-(2-methyl-7-((4-(1-methyl-1H-imidazol-4-yl)-2-(methylsulfonyl)phenyl)amino)-3H-imidazo[4,5-b]pyridin-5-yl)cyclopropane-1-carboxamide, I-227 and (S)-2,2-difluoro-N-(2-methyl-7-((4-(1-methyl-1H-imidazol-4-yl)-2-(methylsulfonyl) phenyl)amino)-3H-imidazo[4,5-b]pyridin-5-yl)cyclopropane-1-carboxamide, I-228

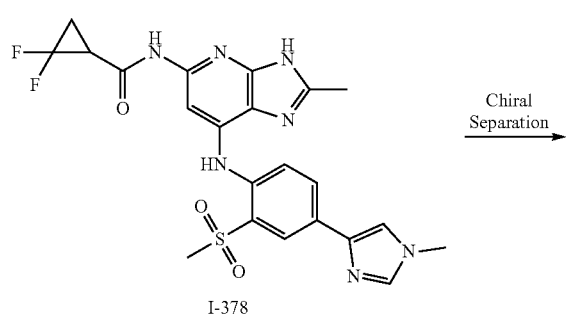

I-378

Chiral Separation →

-continued

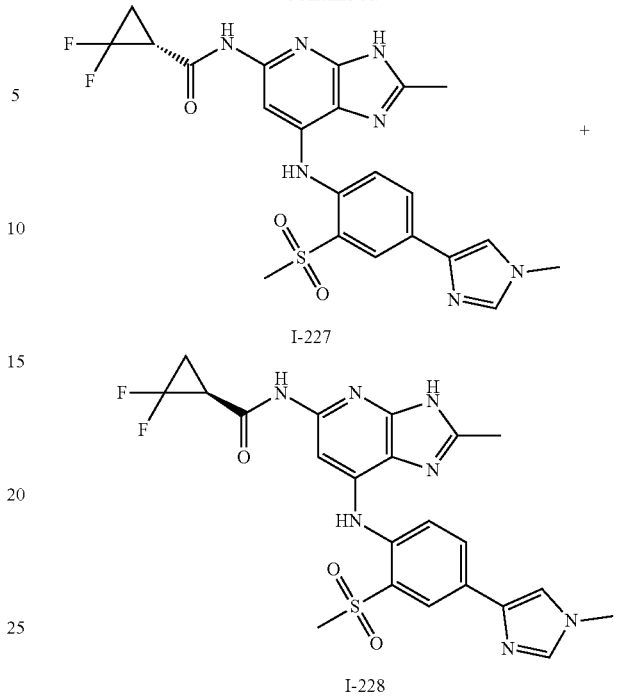

I-227

I-228

Synthesis of Compound I-227 and I-228.

Isomers of 1-378 (0.087 g) were separated out using column (CHIRAL CEL OX-H 250×4.6 mm, 5 µM) 0.1 DEA in IPA as co-solvent with flow rate of 4 mL/min. to get pure fraction-1 (FR-a) and fraction-2 (FR-b). FR-a was concentrated in vacuo at 30° C. to afford pure I-227 (0.025 g). MS(ES): m/z: 502.40 [M+H]$^+$, LCMS purity: 100%, HPLC purity: 99.61%, Chiral HPLC Purity: (100.00%), 1H NMR (MeOD, 400 MHz): 8.37-8.36 (d, J=2 Hz, 1H), 8.05-8.02 (dd, J=1.6 Hz, J=8.4 Hz, 1H), 7.92 (s, 1H), 7.78-7.76 (d, J=8.4 Hz, 1H), 7.72 (s, 1H), 7.59 (s, 1H), 3.81 (s, 3H), 3.14 (s, 3H), 2.81-2.76 (m, 1H), 2.59 (s, 3H), 2.10-2.01 (m, 1H), 1.84-1.82 (m, 1H). FR-b was concentrated in vacuo at 30° C. to afford pure I-228 (0.025 g). MS(ES): m/z: 502.31 [M+H]$^+$, LCMS purity: 100.00%, HPLC purity: 100.00%, Chiral HPLC Purity: (98.04%), 1H NMR (MeOD, 400 MHz): 8.37-8.36 (d, J=2 Hz, 1H), 8.05-8.03 (dd, J=2 Hz, J=8.4 Hz, 1H), 7.92 (s, 1H), 7.78 (m, 1H), 7.70 (s, 1H), 7.59 (s, 1H), 3.81 (s, 3H), 3.14 (s, 3H), 2.84-2.76 (m, 1H), 2.59 (s, 3H), 2.09-2.03 (m, 1H), 1.84-1.82 (m, 1H).

Example 229: Synthesis of N-(2-((5-((6-cyanopyridin-2-yl)amino)-2-(difluoromethyl)-3H-imidazo[4,5-b]pyridin-7-yl)amino)phenyl)-N-(difluoromethyl) methanesulfonamide, I-229

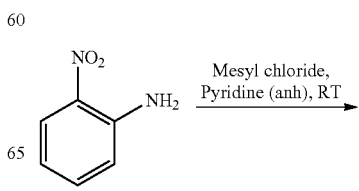

Mesyl chloride, Pyridine (anh), RT →

-continued

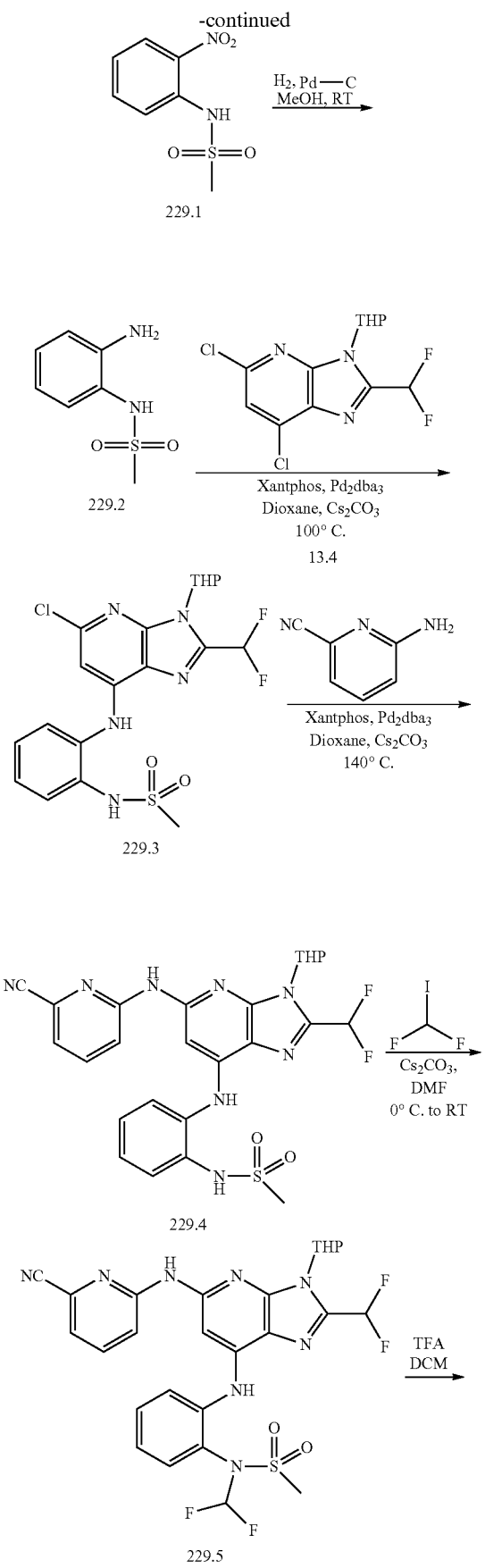

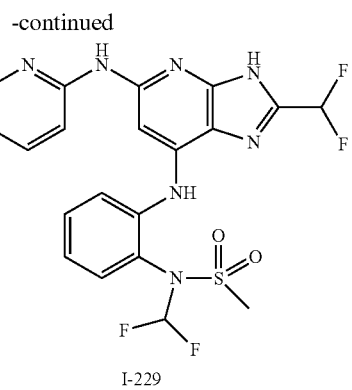

I-229

Synthesis of Compound 229.1.

To compound 2-nitroaniline (5 g, 36.12 mmol, 1.0 eq) in pyridine (50 mL), mesyl chloride (4.95 g, 43.43 mmol, 1.2 eq) was added dropwise. Reaction mixture was stirred at r.t. for 2 h. After completion of the reaction, the reaction mixture was transferred into water and extracted with ethyl acetate. Organic layers were combined, dried over $Na_2SO_4$, filtered and concentrated in vacuo to get the crude material. This was purified by column chromatography using 5% ethyl acetate in hexane as eluant to obtain pure 229.1 (2 g, 25.55%). MS(ES): m/z 217.26 $[M+H]^+$.

Synthesis of Compound 229.2.

To compound 229.1 (2 g, 9.2 mmol, 1.0 eq) in MeOH (30 mL), 10% palladium on carbon (0.7 g) was added. Hydrogen was purged through the reaction mixture for 4 h. Upon completion, reaction mixture was filtered through celite-bed and washed with MeOH. Filtrate was concentrated in vacuo to obtain 229.2 (1.7 g, 54.3%). MS(ES): m/z 187.36 $[M+H]^+$.

Synthesis of Compound 229.3.

Compound 229.3 was synthesized from 229.2 and 13.4 using general procedure A. (Yield: 49.33%). MS(ES): m/z 472.51 $[M+H]^+$.

Synthesis of Compound 229.4.

Compound 229.4 was synthesized from 229.3 and 6-aminonicotinonitrile using general procedure B. (Yield: 51.06%). MS(ES): m/z 555.72 $[M+H]^+$.

Synthesis of Compound 229.5.

To compound 229.4 (0.3 g, 0.54 mmol, 1.0 eq) and difluoroiodomethane (0.192 g, 1.08 mmol, 2.0 eq) in dimethylformamide (1 mL) at 0° C., $Cs_2CO_3$ (0.351 g, 1.08 mmol, 2.0 eq) was added. Reaction mixture was stirred at r.t. for 1 h. After completion of the reaction, the reaction mixture was transferred to water and extracted with ethyl acetate. Organic layers were combined, dried over $Na_2SO_4$, filtered and concentrated in vacuo to obtain 229.5 (0.057 g, 52.29%). MS(ES): m/z 605.26 $[M+H]^+$.

Synthesis of Compound I-229.

Compound I-229 was synthesized from 229.5 using general procedure C. (Yield: 63.75%). MS(ES): m/z: 521.36 $[M+H]^+$, LCMS purity: 96.56%, HPLC purity: 96.47%, 1H NMR (DMSO-d6, 400 MHz): 13.60 (s, 1H), 10.14 (s, 1H), 8.16-8.14 (d, J=8.8 Hz, 1H), 7.90-7.83 (m, 2H), 7.71-7.64 (m, 2H), 7.60-7.58 (d, J=8 Hz, 1H), 7.49-7.46 (s, 2H), 7.36-7.22 (m, 1H), 7.22 (t, 1H), 3.34 (s, 3H).

Example 230/231: Synthesis of (S)—N-(2-(difluoromethyl)-7-((4-(1-methyl-1H-pyrazol-4-yl)-2-(N-methylmethylsulfonamido)phenyl)amino)-3H-imidazo[4,5-b]pyridin-5-yl)-2,2-difluorocyclopropane-1-carboxamide, I-230 and (R)—N-(2-(difluoromethyl)-7-((4-(1-methyl-1H-pyrazol-4-yl)-2-(N-methylmethylsulfonamido)phenyl)amino)-3H-imidazo[4,5-b]pyridin-5-yl)-2,2-difluorocyclopropane-1-carboxamide, I-231

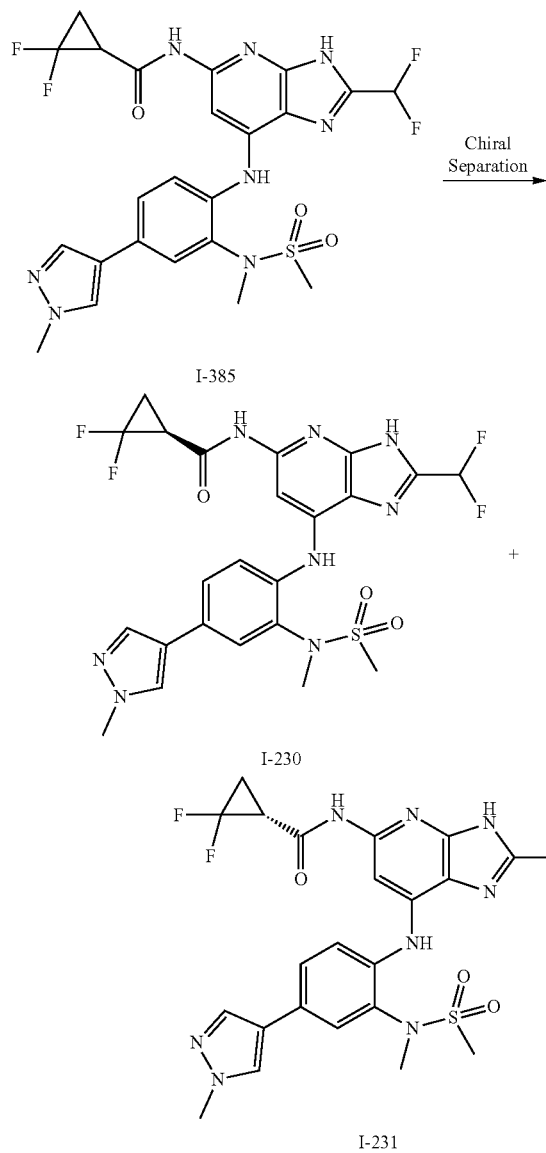

Synthesis of compound I-230 and I-231. Isomers of I-385 (0.100 g) were separated out using column (CHIRAL PAK AD-H 250×4.6 mm, 5 μM) 0.1% DEA in IPA as co-solvent with flow rate of 4 mL/min. to get pure fraction-1 (FR-a) and fraction-2 (FR-b). FR-a was concentrated in vacuo at 30° C. to afford pure I-230 (0.030 g). MS(ES): m/z: 567.56 [M+H]$^+$, LCMS purity: 99.66%, HPLC purity: 97.78%, Chiral HPLC Purity: (100%), 1H NMR (MeOD, 400 MHz): 8.07 (s, 1H), 7.94 (s, 1H), 7.82-7.80 (d, J=6.8 Hz, 2H), 7.72-7.67 (m, 2H), 7.14-6.87 (t, 1H), 3.97 (s, 3H), 3.34 (s, 3H), 3.08 (s, 3H), 2.82-2.80 (d, J=8.4 Hz, 1H). 2.10-2.06 (m, 1H), 1.85-1.83 (m, 1H). FR-b was concentrated in vacuo at 30° C. to afford pure I-231 (0.030 g). MS(ES): m/z: 567.56 [M+H]$^+$, LCMS purity: 98.73%, HPLC purity: 95.06%, Chiral HPLC Purity: (98.28%), 1H NMR (MeOD, 400 MHz): 8.074 (s, 1H), 7.940 (s, 1H), 7.82-7.80 (d, J=7.6 Hz, 2H), 7.72-7.67 (m, 2H), 7.14-6.87 (t, 1H), 3.98 (s, 3H), 3.34 (s, 3H), 3.08 (s, 3H), 2.82-2.80 (d, J=10.0 Hz, 1H). 2.10-2.06 (m, 1H), 1.86-1.83 (m, 1H).

Example 232: Synthesis of N-(2-(difluoromethyl)-7-((2-(methylsulfonyl)-4-(tetrahydro-2H-pyran-4-yl)phenyl)amino)-3H-imidazo[4,5-b]pyridin-5-yl)cyclopropanecarboxamide, I-232

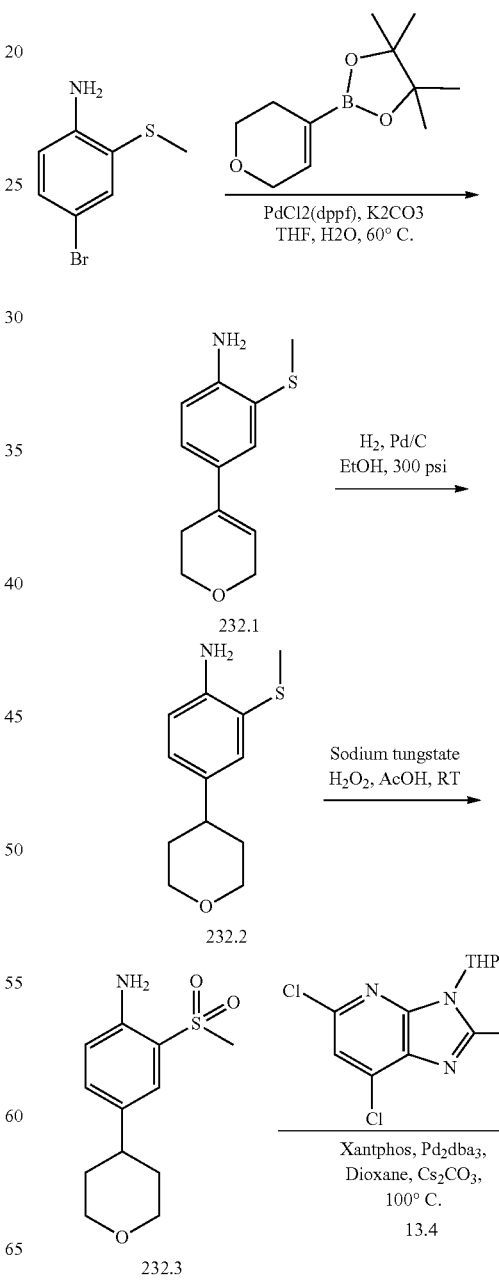

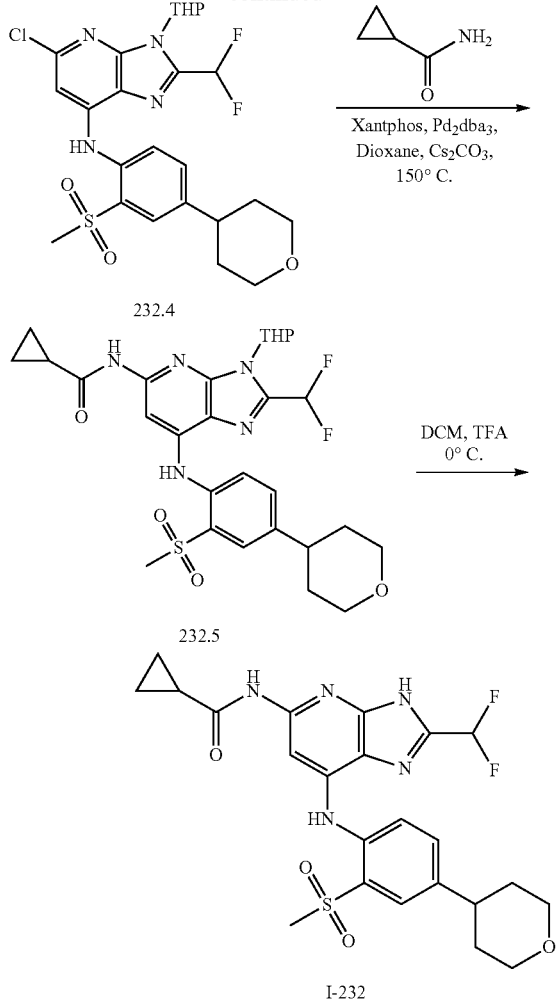

Synthesis of Compound 232.3.

To a solution of 232.2 (0.600 g, 2.69 mmol, 1 eq) in acetic acid (130 mL) was added 30% hydrogen peroxide (0.663 g, 0.195 mmol, 7.26 eq) and sodium tungstate dihydrate (0.711 g, 0.003 mmol, 0.9 eq). Reaction mixture was stirred at r.t. for 2 h. Upon completion, reaction mixture was transferred in ice-water and precipitated product was filtered, washed with 25% ethyl acetate in hexane and dried well to obtain 232.3. (0.520 g, Yield: 75.81%). MS(ES): m/z 256.33 [M+H]$^+$.

Synthesis of Compound 232.4.

Compound 232.4 was synthesized from 13.4 and 232.3 using general procedure A (Yield: 19.85%). MS(ES): m/z 542.01 [M+H]$^+$.

Synthesis of Compound 232.5.

Compound 232.5 was synthesized from 232.4 and cyclopropanecarboxamide using general procedure B. (Yield: 62.56%). MS(ES): m/z 590.66 [M+H]$^+$.

Synthesis of I-232.

Compound I-232 was synthesized from 232.5 using general procedure C. (Yield: 48.21%). MS(ES): m/z: 506.48 [M+H]$^+$, LCMS purity: 95.17%, HPLC purity 97.06%, 1H NMR (DMSO-d6, 400 MHz): 13.78 (s, 1H), 10.76 (s, 1H), 8.72 (s, 1H), 8.06 (s, 1H), 7.79-7.70 (m, 3H), 7.26 (t, 1H), 4.00-3.97 (d, J=10.4 Hz, 2H), 3.52-3.41 (m, 2H), 3.22 (s, 3H), 2.96-2.90 (m, 1H), 2.08-2.02 (m, 1H), 1.80-1.66 (m, 4H), 0.80-0.79 (d, J=6 Hz, 4H).

Example 233/234: Synthesis of (S)-2,2-difluoro-N-(2-methyl-7-((4-(1-methyl-1H-pyrazol-4-yl)-2-(N-methylmethylsulfonamido)phenyl)amino)-3H-imidazo[4,5-b]pyridin-5-yl)cyclopropane-1-carboxamide, I-233 and (R)-2,2-difluoro-N-(2-methyl-7-((4-(1-methyl-1H-pyrazol-4-yl)-2-(N-methylmethylsulfonamido)phenyl)amino)-3H-imidazo[4,5-b]pyridin-5-yl)cyclopropane-1-carboxamide, I-234

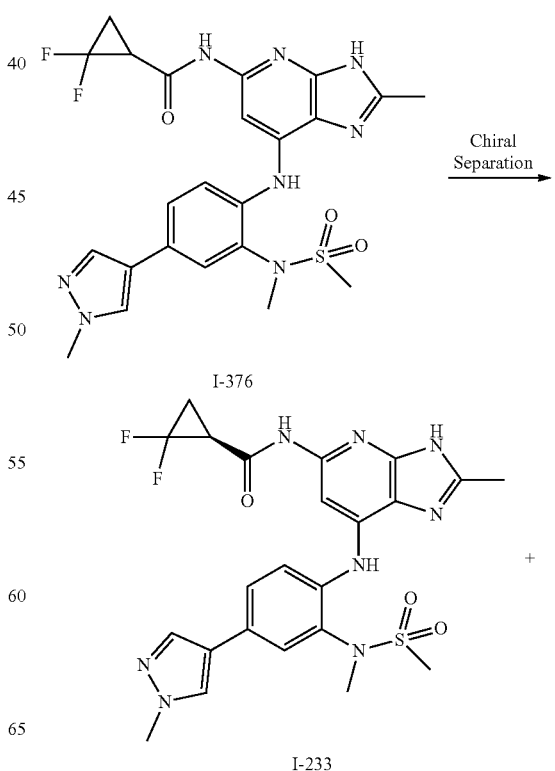

Synthesis of Compound 232.1.

To a solution of 4-bromo-2-(methylthio)aniline (3 g, 13.75 mmol, 1.0 eq), 2-(3,6-dihydro-2H-pyran-4-yl)-4,4,5,5-tetramethyl-1,3,2-dioxaborolane (4.33 g, 20.63 mmol, 1.5 eq) in mixture of tetrahydrofuran (60 mL) and water(10 mL). The reaction mixture was degassed by argon for 30 min. 1,1'-bis(diphenylphosphanyl) ferrocene (1 g, 1.375 mmol, 0.1 eq), potassium carbonate (22.8 mL,) was added into reaction mixture and again reaction mixture was degassed by argon for 30 min. Further reaction mixture was stirred at 70° C. for 3 h. After completion of reaction, water was added to reaction mixture and extracted with ethyl acetate. Organic layers were combined, dried over Na$_2$SO$_4$ and concentrated in vacuo to obtain crude product. This was purified by column chromatography and compound was eluted in 20% ethyl acetate in hexane to obtain pure 232.1 (1.4 g, 45.99%). MS(ES): m/z 222.32 [M+H]$^+$.

Synthesis of Compound 232.2.

To a solution of 232.1 (1.4 g, 6.33 mmol, 1.0 eq) in ethanol (30 mL), 10% Pd/C (0.70 g) was added. Hydrogen was purged through reaction mixture for 2-3 h. Upon completion, reaction mixture was filtered through celite-bed and washed with ethanol. Filtrate was concentrated in vacuo to obtain 232.2 (0.600 g, 42.47%). MS(ES): m/z 224.33 [M+H]$^+$.

I-234

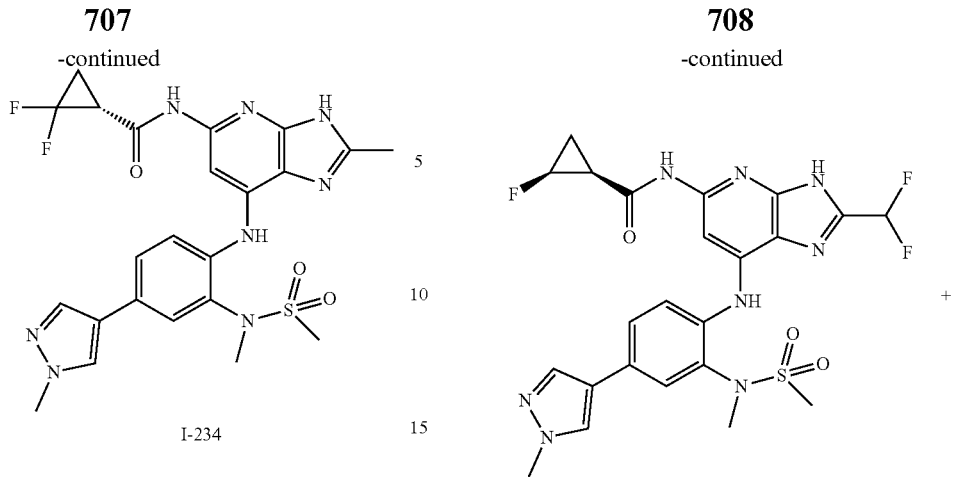

I-235

I-236

Synthesis of Compound I-233 and I-234.

Isomers of 1-376 (0.070 g) were separated out using column (CHIRAL PAK AD-H 250×4.6 mm, 5 µM) 0.1 DEA in IPA as co-solvent with flow rate of 4 mL/min. to get pure fraction-1 (FR-a) and fraction-2 (FR-b). FR-a was concentrated in vacuo at 30° C. to afford pure I-233 (0.026 g). MS(ES): m/z: 531.54 [M+H]+, LCMS purity: 99.63%, HPLC purity 98.52%, Chiral HPLC Purity: (100.00%), 1H NMR (MeOD, 400 MHz): 8.05 (s, 1H), 7.92 (s, 1H), 7.77 (s, 1H), 7.72 (s, 1H), 7.65 (s, 2H), 3.97 (s, 3H), 3.37 (s, 3H), 3.08 (s, 3H), 2.59 (s, 3H), 2.09-2.05 (m, 1H), 1.84-1.81 (m, 2H). FR-b was concentrated in vacuo at 30° C. to afford pure I-234 (0.030 g). MS(ES): m/z: 531.54 [M+H]+, LCMS purity: 98.07%, HPLC purity 97.04%, Chiral HPLC: (100.00%), 1H NMR (MeOD, 400 MHz): 8.05 (s, 1H), 7.92 (s, 1H), 7.77 (s, 1H), 7.72 (s, 1H), 7.65 (s, 2H), 3.97 (s, 3H), 3.39 (s, 3H), 3.08 (s, 3H), 2.64 (s, 3H), 2.18-2.05 (m, 1H), 1.96-1.81 (m, 2H).

Example 235/236: Synthesis of (1S,2S)—N-(2-(difluoromethyl)-7-((4-(1-methyl-1H-pyrazol-4-yl)-2-(N-methylmethylsulfonamido)phenyl)amino)-3H-imidazo[4,5-b]pyridin-5-yl)-2-fluorocyclopropane-1-carboxamide, I-235 and (1R,2R)—N-(2-(difluoromethyl)-7-((4-(1-methyl-1H-pyrazol-4-yl)-2-(N-methylmethylsulfonamido) phenyl) amino)-3H-imidazo[4,5-b]pyridin-5-yl)-2-fluorocyclopropane-1-carboxamide, I-236

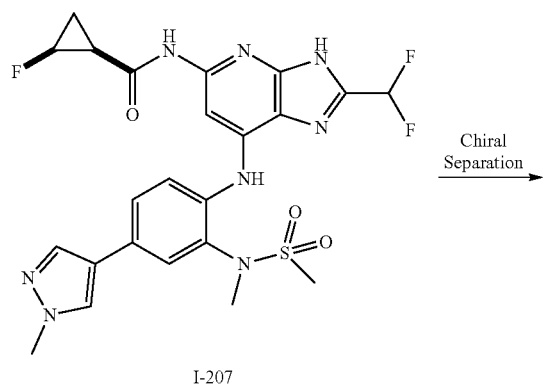

I-207

Chiral Separation →

Synthesis of compounds I-235 and I-236. Isomers of I-207 (0.065 g) were separated out using column (CHIRALCEL OX-H (250 mm*4.6 mm, 5u) and 0.1% DEA IPA:ACN (50:50) flow rate of 3 mL/min. to get pure fraction-1 (FR-a) and fraction-2 (FR-b). FR-a was concentrated in vacuo at 30° C. to afford pure I-235 (0.027 g). MS(ES): m/z: 549.47 [M+H]+, LCMS purity: 97.70%, HPLC purity 99.33%, Chiral HPLC: (100%), 1H NMR (DMSO-d6, 400 MHz): 10.60 (s, 1H), 8.24 (s, 1H), 8.02 (s, 1H), 7.98 (s, 1H), 7.85-7.81 (d, J=13.6 Hz, 2H), 7.66-7.64 (d, J=7.6 Hz, 1H), 7.60-7.58 (d, J=8.4 Hz, 1H), 7.17 (t, 1H), 4.98-4.81 (m, 1H), 3.90 (s, 3H), 3.25 (s, 3H), 3.12 (s, 3H), 1.89 (s, 1H), 1.69-1.56 (m, 2H). FR-b was concentrated in vacuo at 30° C. to afford pure I-236 (0.010 g). MS(ES): m/z: 549.55 [M+H]+, LCMS purity: 99.26%, HPLC purity 98.53%, Chiral HPLC: (100%), 1H NMR (DMSO-d6, 400 MHz): 10.66 (s, 1H), 8.25 (s, 1H), 8.09 (s, 1H), 7.98 (s, 1H), 7.86-7.83 (d, J=11.2 Hz, 2H), 7.67-7.65 (d, J=8.4 Hz, 1H), 7.59-7.57 (d, J=8.4 Hz, 1H), 7.24 (s, 1H), 7.10 (t, 1H), 4.98-4.83 (m, 1H), 3.90 (s, 3H), 3.25 (s, 3H), 3.11 (s, 3H), 2.27 (s, 1H), 1.25 (s, 1H), 1.13 (s, 1H).

Example 237/238: Synthesis of (S)—N-(2-(difluoromethyl)-7-((4-(1-methyl-1H-pyrazol-3-yl)-2-(methylsulfonyl)phenyl)amino)-3H-imidazo[4,5-b]pyridin-5-yl)-2,2-difluorocyclopropane-1-carboxamide, I-237 and (R)—N-(2-(difluoromethyl)-7-((4-(1-methyl-1H-pyrazol-3-yl)-2-(methylsulfonyl)phenyl)amino)-3H-imidazo[4,5-b]pyridin-5-yl)-2,2-difluorocyclopropane-1-carboxamide, I-238

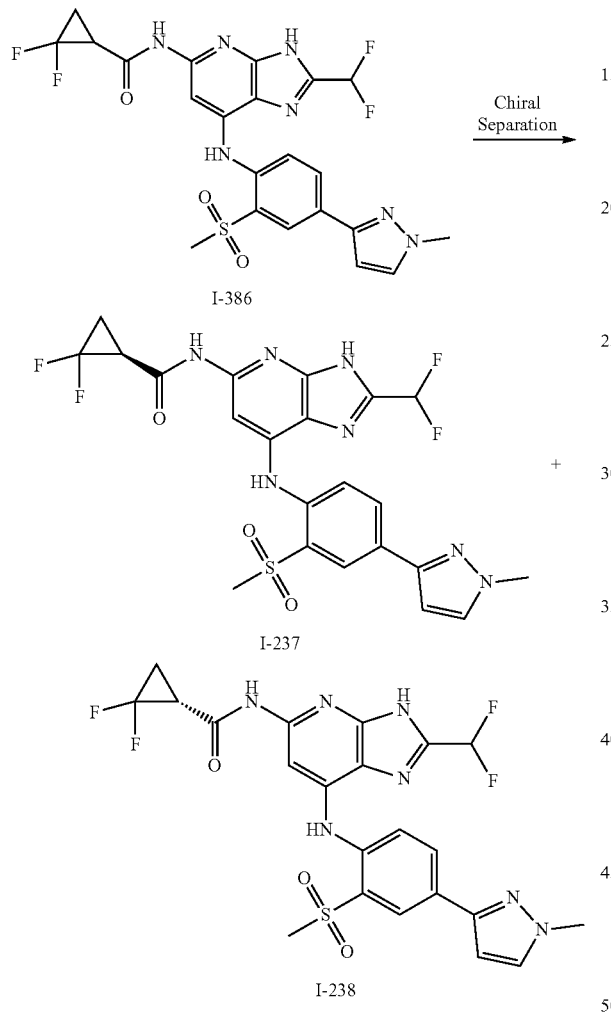

Synthesis of Compound I-237 and I-238.

Isomers of 1-386 (0.095 g) were separated out using column (CHIRAL PAK AD-H 250×4.6 mm, 5 μM) 0.1 DEA in IPA as co-solvent with flow rate of 4 mL/min. to get pure fraction-1 (FR-a) and fraction-2 (FR-b). FR-a was concentrated in vacuo at 30° C. to afford pure I-237 (0.026 g). MS(ES): m/z: 538.35 [M+H]+, LCMS purity: 98.01%, HPLC purity 98.60%, Chiral HPLC: (98.62%), 1H NMR (DMSO-d6, 400 MHz): 13.76 (s, 1H), 10.99 (s, 1H), 8.84 (s, 1H), 8.36-8.36 (d, J=2 Hz, 1H), 8.17-8.15 (d, J=8.4 Hz, 1H), 8.04 (s, 1H), 7.83-7.81 (t, J=7.6 Hz, 1H), 7.40-7.14 (t, 1H), 7.27 (t, 1H), 6.84-6.84 (d, J=2 Hz, 1H), 3.93 (s, 3H), 3.21 (s, 3H), 3.03-3.00 (m, 1H), 2.02-1.99 (m, 2H). FR-b was concentrated in vacuo at 30° C. to afford pure I-238 (0.027 g). MS(ES): m/z: 538.35 [M+H]+, LCMS purity: 98.34%, HPLC purity 97.31%, Chiral HPLC: (98.45%), 1H NMR (DMSO-d6, 400 MHz): 11.01 (s, 1H), 8.85 (s, 1H), 8.36-8.36 (d, J=1.6 Hz, 2H), 8.17-8.15 (d, J=7.2 Hz, 1H), 8.05 (s, 1H), 7.84-7.81 (t, J=8.8 Hz, 2H), 7.42-7.15 (t, 1H), 7.27 (t, 1H), 6.85-6.84 (d, J=2 Hz, 1H), 3.93 (s, 3H), 3.27 (s, 3H), 3.04-3.01 (m, 1H), 2.10-1.99 (m, 2H).

Example 239/240: Synthesis of (S)-2,2-difluoro-N-(2-methyl-7-((4-(1-methyl-1H-pyrazol-3-yl)-2-(methylsulfonyl)phenyl)amino)-3H-imidazo[4,5-b]pyridin-5-yl)cyclopropane-1-carboxamide, I-239 and (R)-2,2-difluoro-N-(2-methyl-7-((4-(1-methyl-1H-pyrazol-3-yl)-2-(methylsulfonyl)phenyl)amino)-3H-imidazo[4,5-b]pyridin-5-yl)cyclopropane-1-carboxamide, I-240

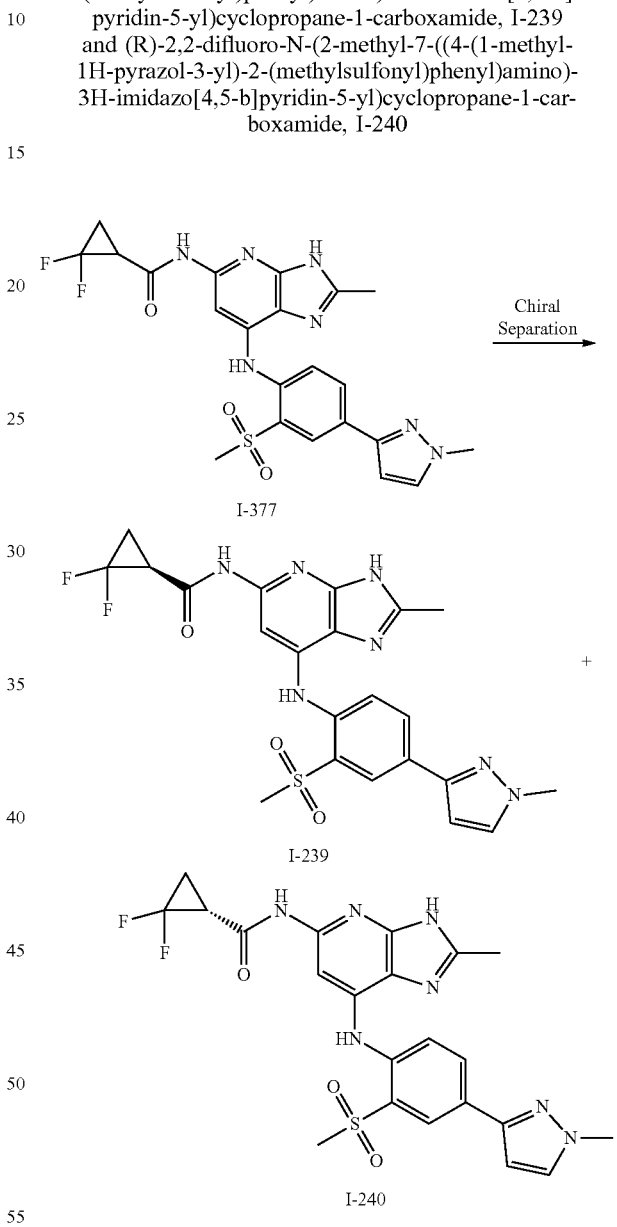

Synthesis of Compound I-239 and I-240.

Isomers of I-377 (0.080 g) were separated out using column (CHIRAL PAK AD-H 250×4.6 mm, 5 μM) 0.1 DEA in IPA as co-solvent with flow rate of 4 mL/min. to get pure fraction-1 (FR-a) and fraction-2 (FR-b). FR-a was concentrated in vacuo at 30° C. to afford pure I-239 (0.025 g). MS(ES): m/z: 502.31 [M+H]+, LCMS purity: 94.90%, HPLC purity: 100%, Chiral HPLC Purity: (96%), 1H NMR (DMSO-d6, 400 MHz): 12.59 (s, 1H), 10.84 (s, 1H), 8.66 (s, 1H), 8.33-8.33 (d, J=2 Hz, 1H), 8.14-8.11 (dd, J=2 Hz, J=8.4 Hz, 1H), 8.00 (s, 1H), 7.81-7.80 (t, J=4.8 Hz, 2H), 6.82-6.82

(d, J=2 Hz, 1H), 3.93 (s, 3H), 3.25 (s, 3H), 3.02-2.94 (m, 1H), 2.51 (s, 3H), 2.04-1.95 (m, 2H). FR-b was concentrated in vacuo at 30° C. to afford pure I-240 (0.026 g) MS(ES): m/z: 502.36 [M+H]⁺, LCMS purity: 99.65%, HPLC: purity: 100%, Chiral HPLC: (99.25%), 1H NMR (DMSO-d6, 400 MHz): 12.59 (s, 1H), 10.84 (s, 1H), 8.66 (s, 1H), 8.33-8.33 (d, J=2 Hz, 1H), 8.14-8.11 (dd, J=1.6 Hz, J=8.4 Hz, 1H), 8.00 (s, 1H), 7.81-7.80 (t, J=4.8 Hz, 2H), 6.82-6.82 (d, J=2 Hz, 1H), 3.93 (s, 3H), 3.25 (s, 3H), 3.00-2.97 (m, 1H), 2.51 (s, 3H), 2.04-1.95 (m, 2H).

Example 241: Synthesis of N-(7-((4-(1,4-dimethyl-1H-pyrazol-3-yl)-2-(methylsulfonyl)phenyl)amino)-2-methyl-3H-imidazo[4,5-b]pyridin-5-yl)cyclopropanecarboxamide, I-241

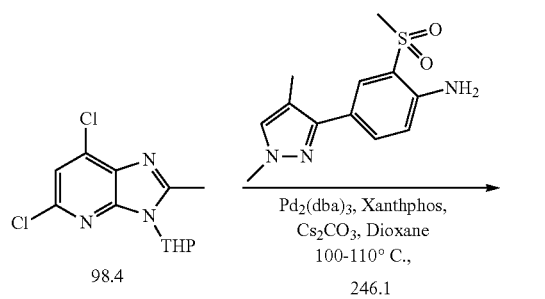

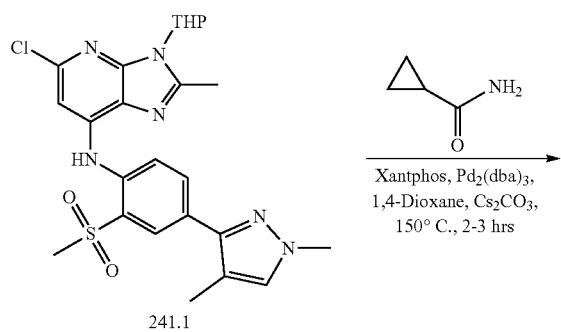

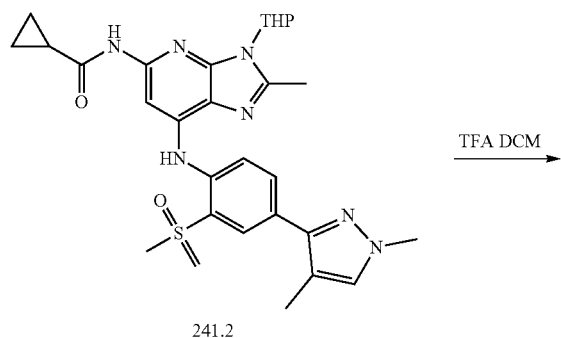

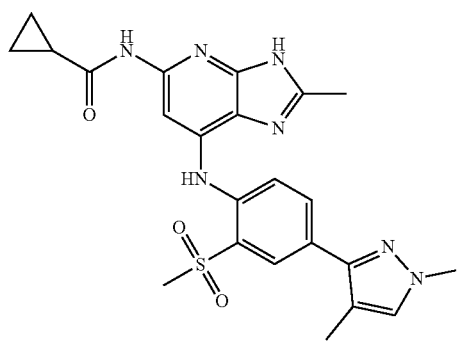

Synthesis of Compound 241.1.
Compound 241.1 was synthesized from 98.4 and 246.1 using general procedure A. (Yield: 34.35%). MS(ES): m/z 516.48 [M+H]⁺.

Synthesis of Compound 241.2
Compound 241.2 was synthesized from 241.1 and cyclopropanecarboxamide using general procedure B. (Yield: 75.38%). MS(ES): m/z 564.13 [M+H]⁺.

Synthesis of I-241.
Compound I-241 was synthesized from 241.2 using general procedure C (Yield: 67.17%). MS(ES): m/z: 480.40 [M+H]⁺, LCMS purity: 100%, HPLC purity 98.78%, 1H NMR (DMSO-d6, 400 MHz): 12.51 (s, 1H), 10.60 (s, 1H), 8.61 (s, 1H), 8.21-8.21 (d, J=2 Hz, 1H), 8.03-7.98 (m, 2H), 7.82-7.80 (d, J=8.8 Hz, 1H), 7.61 (s, 1H), 3.86 (s, 3H), 3.24 (s, 3H), 2.52 (s, 3H), 2.22 (s, 3H), 2.00 (s, 1H), 0.78-0.63 (m, 4H).

Example 242: Synthesis of N-(2-(difluoromethyl)-7-((2-(dimethylphosphoryl)phenyl)amino)-3H-imidazo[4,5-b]pyridin-5-yl)cyclopropanecarboxamide, I-242

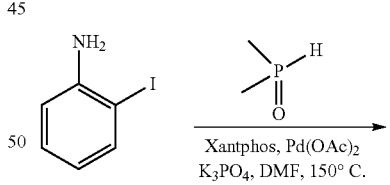

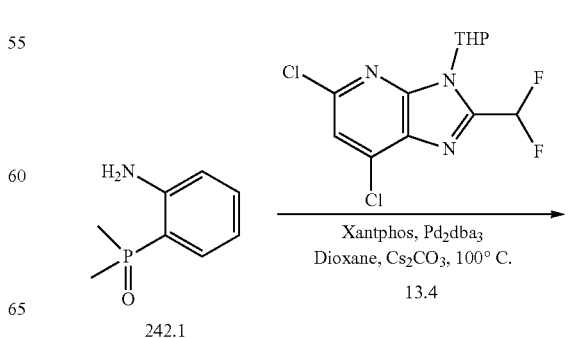

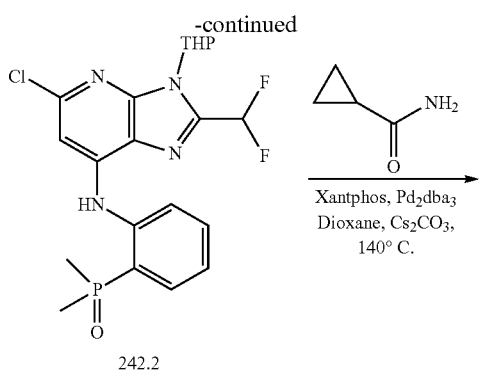

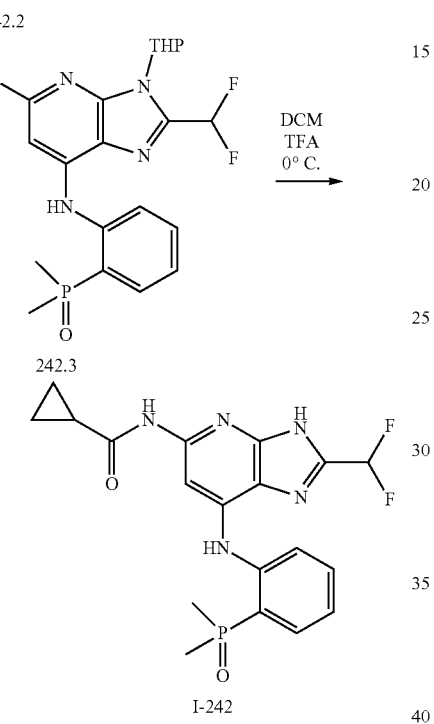

Synthesis of Compound 242.1.

A mixture of 2-iodoaniline (1.5 g, 6.85 mmol, 1.0 eq), dimethyl phosphine oxide (0.590 g, 7.53 mmol, 1.1 eq), Potassium phosphate (1.6 g, 7.53 mmol, 1.1 eq) in dimethylformamide (15 mL) was degassed by argon for 20 min. Xantphos (0.397 g, 0.685 mmol, 0.1 eq), Palladium(II) acetate (0.153 g, 0.685 mmol, 0.1 eq,) was added into reaction mixture and again degassed by argon for 30 min. Further reaction mixture was stirred at 150° C. for 2 h. Upon completion, reaction mixture was transferred into water and extracted with 10% MeOH in $CH_2Cl_2$. Organic layers were combined, dried over $Na_2SO_4$ and concentrated in vacuo to obtain crude product. This was purified by column chromatography and compound was eluted in 5% MeOH in $CH_2Cl_2$ to obtain pure 242.1 (0.700 g, 60.42%). MS(ES): m/z 170.16 $[M+H]^+$.

Synthesis of Compound 242.2.

Compound 242.2 was synthesized from 242.1 and 13.4 using general procedure A. (Yield: 22.26%). MS(ES): m/z 455.84 $[M+H]^+$.

Synthesis of Compound 242.3.

Compound was synthesized from 242.2 and cyclopropanecarboxamide using general procedure B. (Yield: 41.06%). MS(ES): m/z 504.49 $[M+H]^+$.

Synthesis of Compound I-242.

Compound I-242 was synthesized from 242.3 using general procedure C. (Yield: 48.02%). MS(ES): m/z: 420.32 $[M+H]^+$, LCMS purity: 96.81%, HPLC purity: 99.44%, 1H NMR (DMSO-d6, 400 MHz): 13.54 (s, 1H), 10.67 (s, 1H), 10.16 (s, 1H), 8.06 (s, 1H), 7.67-7.56 (m, 3H), 7.35 (s, 1H), 7.22-7.17 (m, 1H), 2.03-2.02 (m, 1H), 1.81 (s, 6H), 0.87 (s, 4H).

Example 243: Synthesis of N-(7-((2-(dimethylphosphoryl)phenyl)amino)-2-methyl-3H-imidazo[4,5-b]pyridin-5-yl)cyclopropanecarboxamide, I-243

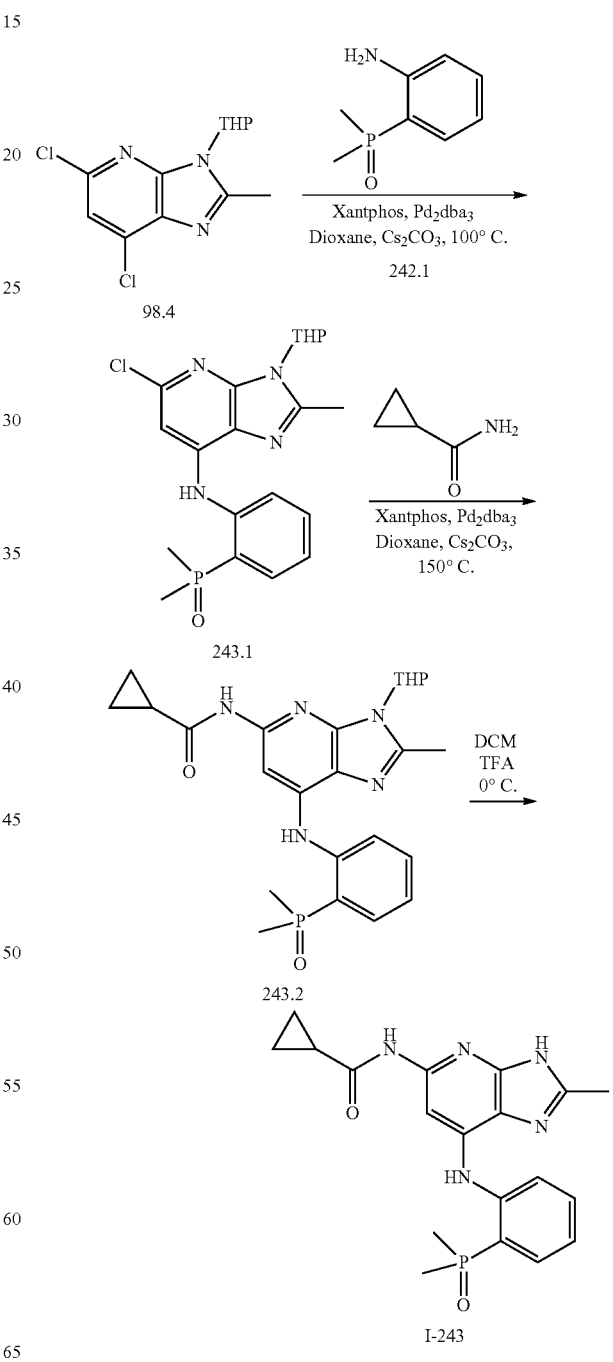

Synthesis of Compound 243.1.

Compound 243.1 was synthesized from 98.4 and 242.2 using general procedure A. (Yield: 39.04%). MS(ES): m/z 519.86 [M+H]$^+$.

Synthesis of Compound 243.2.

Compound 243.2 was synthesized from 242.1 and cyclopropanecarboxamide using general procedure B. (Yield: 36.73%). MS(ES): m/z 568.51 [M+H]$^+$.

Synthesis of Compound I-243.

Compound I-243 was synthesized from 243.2 using general procedure (Yield: 56.51%). MS(ES): m/z: 384.33 [M+H]$^+$, LCMS purity: 98.05%, HPLC purity: 100%, 1H NMR (DMSO-d6, 400 MHz): 12.54 (s, 1H), 10.64 (s, 1H), 10.56 (s, 1H), 8.62-8.59 (m, 1H), 7.53 (s, 1H), 7.50-7.43 (m, 2H), 6.94 (s, 1H), 2.47 (s, 3H), 2.37-2.35 (m, 1H), 1.80 (s, 6H), 0.84 (s, 4H).

Example 244/245: Synthesis of (R)—N-(2-(difluoromethyl)-7-((4-(1-methyl-1H-imidazol-4-yl)-2-(methylsulfonyl)phenyl)amino)-3H-imidazo[4,5-b]pyridin-5-yl)-2,2-difluorocyclopropane-1-carboxamide, I-244 and (S)—N-(2-(difluoromethyl)-7-((4-(1-methyl-1H-imidazol-4-yl)-2-(methylsulfonyl)phenyl)amino)-3H-imidazo[4,5-b]pyridin-5-yl)-2,2-difluorocyclopropane-1-carboxamide, I-245

Synthesis of Compounds I-244 and I-245.

Isomers of I-381 (0.100 g) were separated out using column (CHIRALCEL OX-H (250 mm*4.6 mm, 5u) and 0.1% DEA IPA:ACN (50:50) flow rate of 4 mL/min. to get pure fraction-1 (FR-a) and fraction-2 (FR-b). FR-a was concentrated in vacuo at 30° C. to afford pure I-244 (0.026 g). MS(ES): m/z: 538.55 [M+H]$^+$, LCMS purity: 97.48%, HPLC purity: 96.33%, Chiral HPLC: (100%), 1H NMR (MeOD, 400 MHz): 8.40-8.39 (d, J=2 Hz, 1H), 8.10-8.07 (m, 2H), 7.89-7.86 (d, J=8.4 Hz, 1H), 7.72 (s, 1H), 7.62 (s, 1H), 6.99 (t, 1H), 3.83 (s, 3H), 3.15 (s, 3H), 2.84-2.82 (m, 1H), 2.12-2.05 (m, 1H), 1.95-1.81 (m, 1H). FR-b was concentrated in vacuo at 30° C. to afford pure I-245 (0.027 g). MS(ES): m/z: 538.50 [M+H]$^+$, LCMS purity: 100%, HPLC purity: 99.60%, Chiral HPLC: (99.00%), 1H NMR (MeOD, 400 MHz): 8.40 (s, 1H), 8.10-8.08 (m, 2H), 7.89-7.87 (d, J=8 Hz, 1H), 7.73 (s, 1H), 7.62 (s, 1H), 7.00 (t, 1H), 3.83 (s, 3H), 3.15 (s, 3H), 2.84-2.82 (m, 1H), 2.14-2.07 (m, 1H), 1.87-1.84 (m, 1H).

Example 246: Synthesis of N-(2-(difluoromethyl)-7-((4-(1,4-dimethyl-1H-pyrazol-3-yl)-2-(methylsulfonyl)phenyl)amino)-3H-imidazo[4,5-b]pyridin-5-yl)cyclopropanecarboxamide, I-246

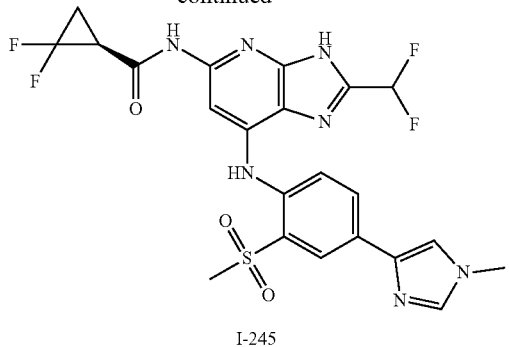
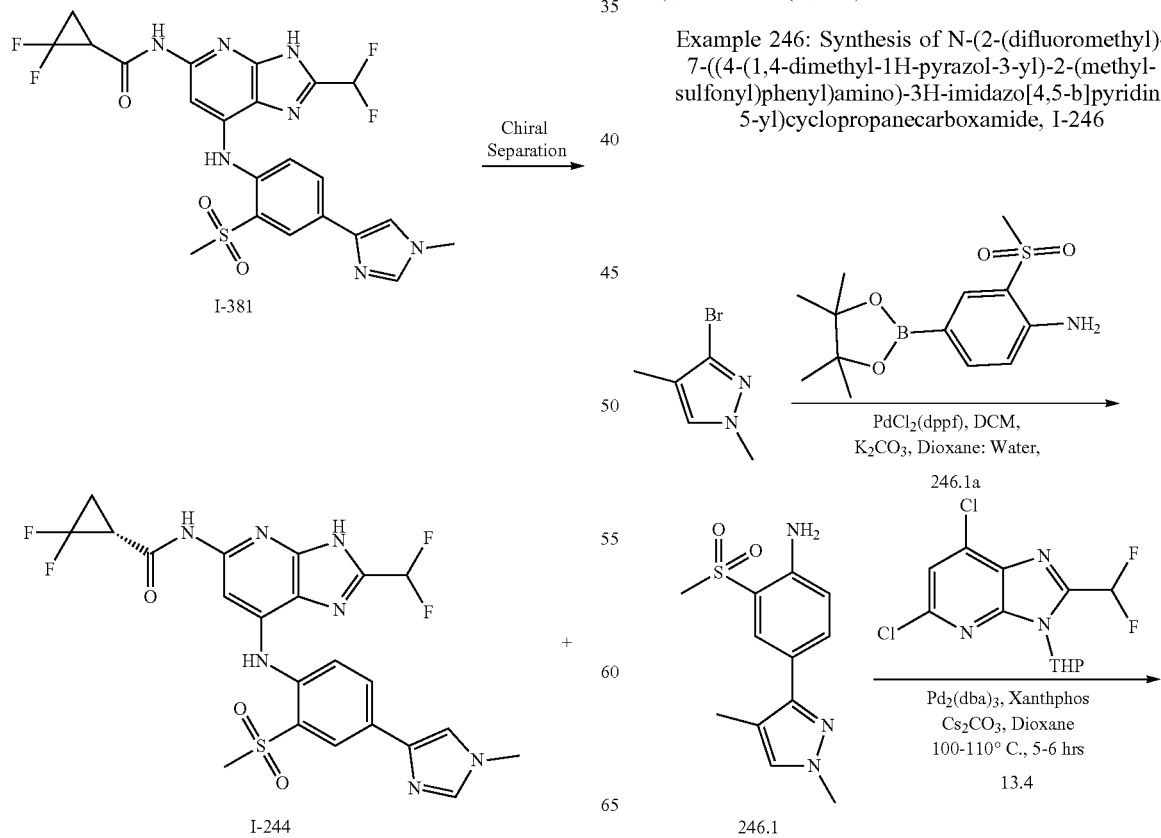

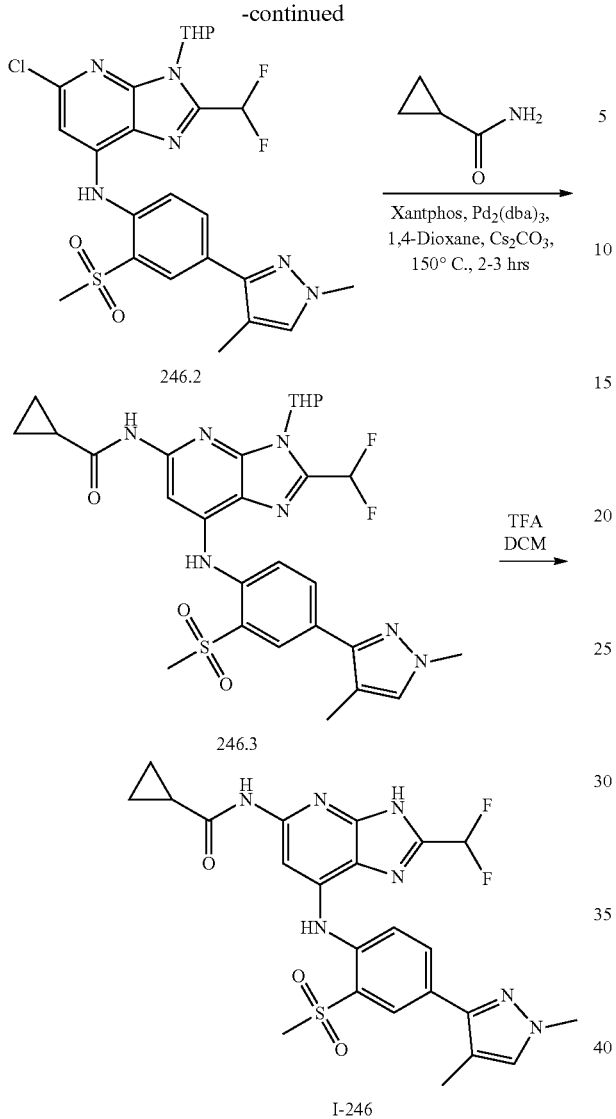

246.2

246.3

I-246

Synthesis of Compound 246.1.

To a solution of 246.1a (1.0 g, 3.36 mmol, 1.0 eq) and 3-bromo-1,4-dimethyl-1H-pyrazole (0.58 g, 3.36 mmol, 1.0 eq) in mixture of 1,4-dioxane (8.0 mL) and water (2.0 mL), potassium carbonate (1.24 g, 9.02 mmol, 2.5 eq) was added. Argon was purged through the reaction mixture for 5 min. Then, [1,1'-bis(diphenylphosphino)ferrocene]dichloropalladium(II) complex with $CH_2Cl_2$ (0.29 g, 0.33 mmol, 0.1 eq) was added and again purged for 5 min. Reaction mixture was stirred at 110° C. for 2 h. After completion of the reaction, the reaction mixture was transferred to water and extracted with ethyl acetate. Organic layers were combined, dried over anhydrous $Na_2SO_4$, filtered and concentrated in vacuo to get the crude material. This was purified by column chromatography using 12% ethyl acetate in hexane as eluant to obtain 246.1 (0.6 g, 39.35%). MS(ES): m/z 266.38 $[M+H]^+$.

Synthesis of Compound 246.2.

Compound 246.2 was synthesized from 246.1 and 13.4 using general procedure A. (Yield: 13.64%). MS(ES): m/z 552.76 $[M+H]^+$.

Synthesis of Compound 246.3.

Compound 246.3 was synthesized from 246.2 and cyclopropanecarboxamide using general procedure B. (Yield: 45.94%). MS(ES): m/z 600.28 $[M+H]^+$.

Synthesis of I-246.

Compound I-246 was synthesized from 246.3 using general procedure C. (Yield: 74.77%). MS(ES): m/z: 516.54 $[M+H]^+$, LCMS purity: 93.73%, HPLC purity 93.67%, 1H NMR (DMSO-d6, 400 MHz): 13.70 (s, 1H), 10.77 (s, 1H), 8.79 (s, 1H), 8.24-8.24 (d, J=2 Hz, 1H), 8.11 (s, 1H), 8.02-8.01 (d, J=2 Hz, 1H), 7.84-7.82 (d, J=8.4 Hz, 1H), 7.62 (s, 1H), 7.27 (t, 1H), 3.87 (s, 3H), 3.26 (s, 3H), 2.25 (s, 3H), 2.05-2.00 (m, 1H), 0.80 (bs, 4H).

Example 247/248: Synthesis of (S)—N-(2-(difluoromethyl)-7-((2-(methylsulfonyl)-4-(tetrahydro-2H-pyran-2-yl)phenyl)amino)-3H-imidazo[4,5-b]pyridin-5-yl)cyclopropanecarboxamide, I-247 and (R)—N-(2-(difluoromethyl)-7-((2-(methylsulfonyl)-4-(tetrahydro-2H-pyran-2-yl)phenyl)amino)-3H-imidazo[4,5-b]pyridin-5-yl)cyclopropanecarboxamide, I-248

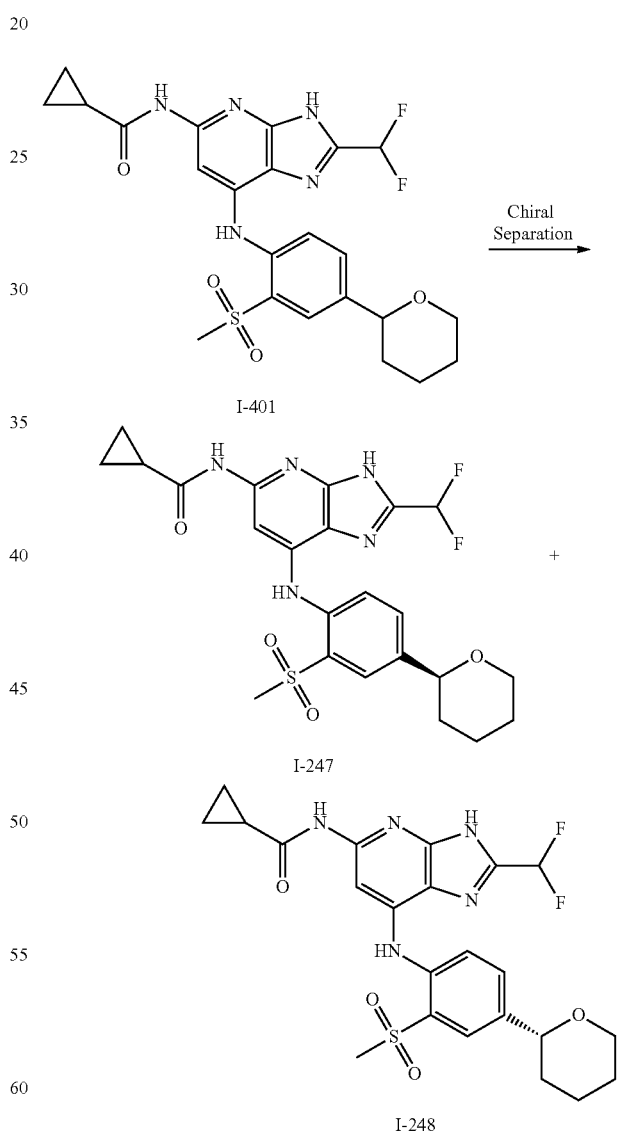

I-401

I-247

I-248

Synthesis of Compounds I-247 and I-248

Isomers of I-401 (0.070 g) were separated out using column (CHIRAL PAK AD-H (250 mm*4.6 mm, 5u)) and 0.1% DEA IPA:ACN (50:50) flow rate of 4 mL/min. to get pure fraction-1 (FR-a) and fraction-2 (FR-b). FR-a was concentrated in vacuo at 30° C. to afford pure I-247 (0.026 g). MS(ES): m/z: 506.53 [M+H], LCMS purity: 99.54%, HPLC purity 99.58%, Chiral HPLC: 100%, 1H NMR (DMSO-d6, 400 MHz): 10.76 (s, 1H), 8.73 (s, 1H), 8.06 (s, 1H), 7.90 (s, 1H), 7.76-7.70 (m, 3H), 7.39-7.13 (t, 1H), 4.46-4.43 (d, J=10.8 Hz, 1H), 4.09-4.06 (d, J=10.8 Hz, 1H), 3.61-3.54 (m, 1H), 3.21 (s, 3H), 2.04-2.02 (d, J=10.8 Hz, 1H), 1.92-1.89 (m, 2H), 1.68-1.61 (m, 2H), 1.50-1.44 (m, 1H), 1.44-1.25 (m, 1H), 0.85 (bs, 4H). FR-b was concentrated in vacuo at 30° C. to afford pure I-248 (0.025 g). MS(ES): m/z: 506.36 [M+H]$^+$, LCMS purity: 95.53%, HPLC purity 95.13%, Chiral HPLC: 99.67%, 1H NMR (DMSO-d6, 400 MHz): 10.75 (s, 1H), 8.72 (s, 1H), 8.06 (s, 1H), 7.90 (s, 1H), 7.76-7.70 (m, 3H), 7.38-7.12 (t, 1H), 4.46-4.43 (d, J=10.8 Hz, 1H), 4.09-4.06 (d, J=11.2 Hz, 1H), 3.60-3.54 (m, 1H), 3.21 (s, 3H), 2.10-2.02 (m, 1H), 1.92-1.89 (m, 2H), 1.70-1.59 (m, 3H), 1.50-1.48 (m, 1H), 0.79 (bs, 4H).

Example 249: Synthesis of N-(2-((5-(((6-cyanopyridin-2-yl) amino)-2-methyl-3H-imidazo[4,5-b]pyridin-7-yl)amino)phenyl)-N-(difluoromethyl)methanesulfonamide, I-249

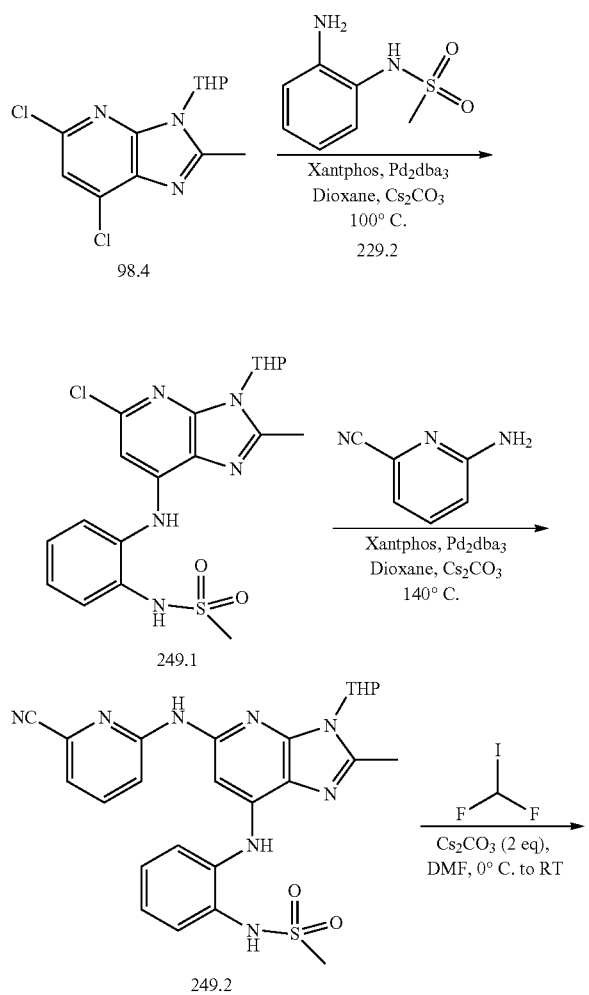

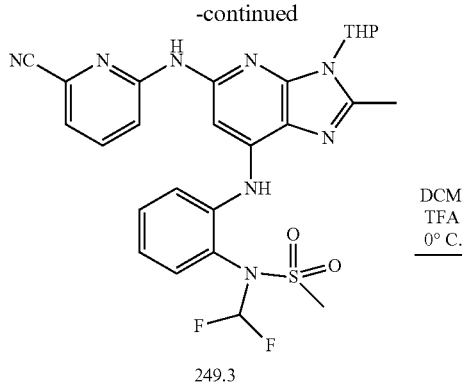

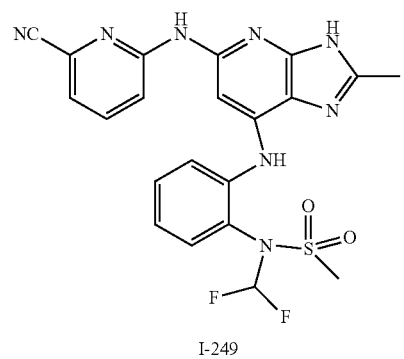

Synthesis of Compound 249.1.

Compound 249.1 was synthesized from 98.4 and 229.2 using general procedure A. (Yield: 32.82%). MS(ES): m/z 436.93 [M+H]$^+$.

Synthesis of Compound 249.2.

Compound 249.2 was synthesized from 249.1 and 6-aminonicotinonitrile using general procedure B. (Yield: 56.04%). MS(ES): m/z 519.60 [M+H]$^+$.

Synthesis of Compound 249.3.

To a solution of 249.2 (0.300 g, 578.48 mmol), 1 eq), in N,N-dimethylformamide (2 mL) was added Cs$_2$CO$_3$ (0.226 g, 6.95 mmol, 1.2 eq) at 0° C. Solution of Difluoroiodomethane (0.123 g, 578.40 mmol, 1.2 eq) in N,N-dimethylformamide (1.5 mL) was added dropwise to the reaction mixture at same temperature. The reaction mixture stirred for 1 h at r.t. Upon completion, reaction mixture was transferred into water and extracted with ethyl acetate. Organic layers were combined, dried over Na$_2$SO$_4$ and concentrated in vacuo to obtain crude product. This was purified by column chromatography and compound was eluted in 1% MeOH in CH$_2$Cl$_2$ as eluent to obtain 249.3 (0.070 g, 21.28%). MS(ES): m/z 569.60 [M+H]$^+$.

Synthesis of Compound I-249.

Compound I-249 was synthesized from 249.3 using general procedure C. (Yield: 16.43%). MS(ES): m/z: 485.41 [M+H]$^+$, LCMS purity: 99.95%, HPLC purity: 99.73%, 1H NMR (DMSO-d6, 400 MHz): 12.45 (s, 1H), 9.96 (s, 1H), 8.04-8.01 (d, J=8.8 Hz, 1H), 7.85-7.81 (m, 2H), 7.69-7.65 (t, J=8.4 Hz, 1H), 7.58-7.51 (m, 2H), 7.46-7.41 (m, 2H), 7.26-7.23 (t, J=7.6 Hz, 1H), 3.39 (s, 3H), 2.47 (s, 3H).

Example 250: Synthesis of (1S,2S)-2-fluoro-N-(2-methyl-7-((4-(1-methyl-1H-imidazol-4-yl)-2-(methylsulfonyl)phenyl)amino)-3H-imidazo[4,5-b]pyridin-5-yl)cyclopropane-1-carboxamide, I-250

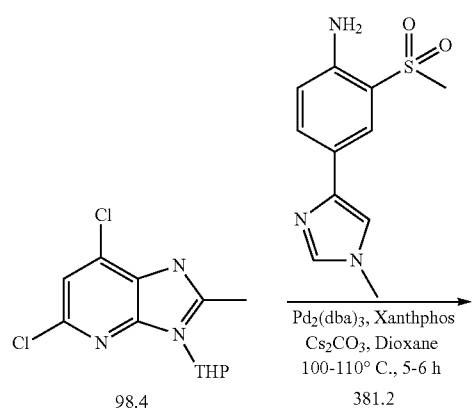

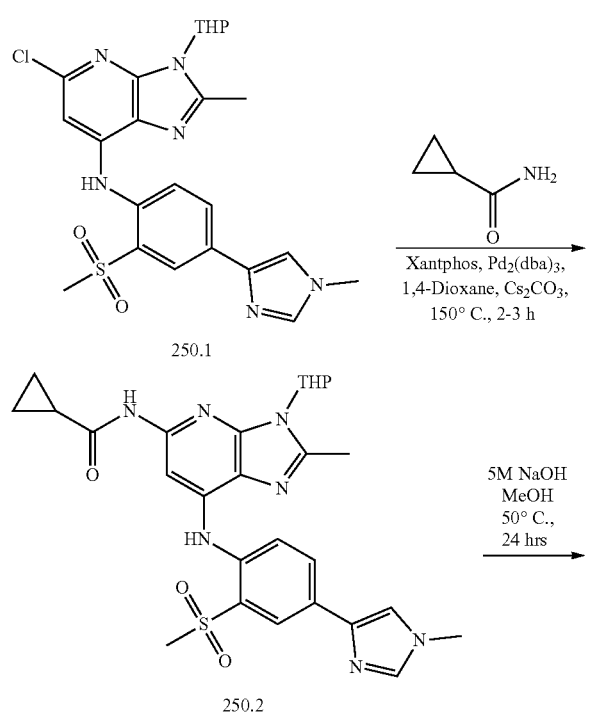

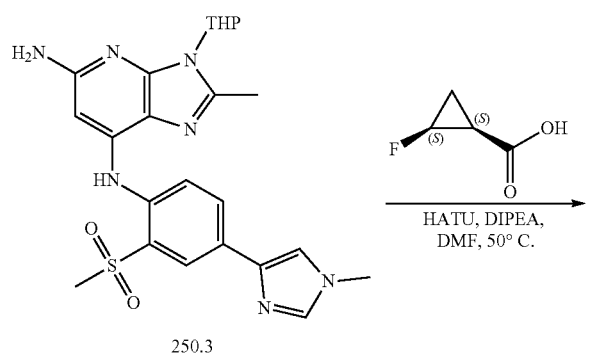

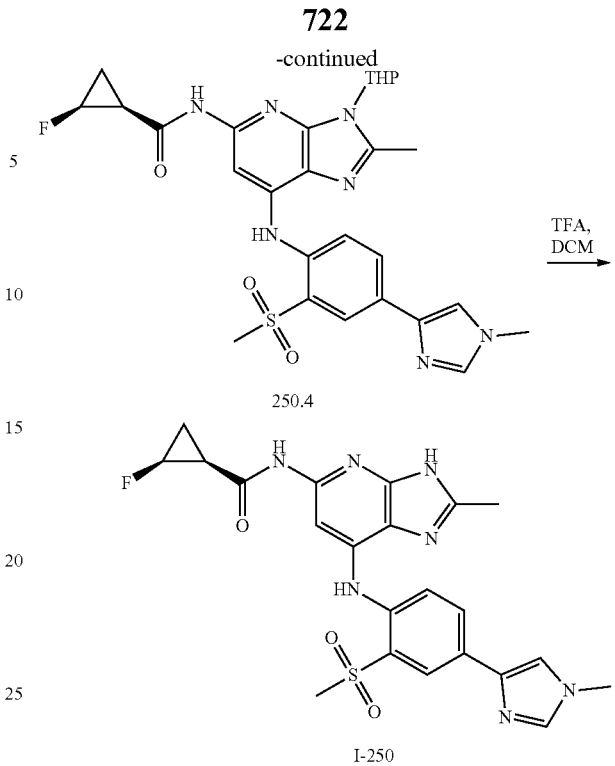

Synthesis of Compound 250.1.

Compound 250.1 was synthesized from 381.2 and 98.4 using general procedure A. (Yield: 38.08%). MS(ES): m/z 502.34 [M+H]$^+$.

Synthesis of Compound 250.2.

Compound 250.2 was synthesized from 250.1 and cyclopropanecarboxamide using general procedure B. (Yield: 56.97%). MS(ES): m/z 550.48 [M+H]$^+$.

Synthesis of Compound 250.3.

To a solution of 250.2 (0.250 g, 0.45 mmol, 1.0 eq) in MeOH (3.0 mL), 5M NaOH (0.091 g, 2.2 mmol, 5.0 eq) was added. Reaction mixture was stirred at 50° C. for 24 hr. Upon completion, reaction mixture was transferred into ice water. The pH of the solution was adjusted to neutral using dilute HCl to obtain solid precipitate which was washed with water and dried well to obtain 250.3. (0.150 g, 68.48%). MS(ES): m/z 482.57 [M+H]$^+$.

Synthesis of Compound 250.4.

To a solution of (1S,2S)-2-fluorocyclopropane-1-carboxylic acid (0.023 g, 0.22 mmol, 1.1 eq) in N,N'-dimethylformamide (1.0 mL) at 0° C., (1-[Bis(dimethylamino)methylene]-1H-1,2,3-triazolo[4,5-b]pyridinium 3-oxid hexafluorophosphate) (0.125 g, 0.33 mmol, 1.5 eq) was added. Reaction mixture was allowed to stir at 0° C. for 30 min. Then, di-isopropylethylamine (0.070 g, 0.55 mmol, 2.5 eq) and compound 250.3 (0.1 g, 0.2 mmol, 1.0 eq) was added. Reaction mixture was allowed to stir at 50° C. for 3 h. After completion of the reaction, the reaction mixture was transferred into water and extracted with ethyl acetate. Organic layer combined, dried over anhydrous Na$_2$SO$_4$, filtered and concentrated in vacuo to obtain the crude material. This was purified by column chromatography using 25% ethyl acetate in hexane to obtain pure 250.4 (0.062 g, 75.14%). MS(ES): m/z: 568.97 [M+H]$^+$.

Synthesis of Compound I-250.

Compound I-250 was synthesized from 250.4 using general procedure C. (Yield: 66.27%). MS(ES): m/z: 484.30 [M+H]$^+$, LCMS purity: 97.81%, HPLC purity: 95.20%, Chiral HPLC Purity: 97.26%, 1H NMR (MeOD, 400 MHz): 8.38-8.37 (d, J=2 Hz, 1H), 8.06-8.03 (dd, J=2 Hz, J=8.4 Hz, 1H), 7.95 (s, 1H), 7.79-7.77 (d, J=7.2 Hz, 1H), 7.71 (s, 1H), 7.59 (s, 1H), 4.79-4.75 (m, 1H), 3.82 (s, 3H), 3.15 (s, 3H), 2.59 (s, 3H), 2.08-2.04 (m, 1H), 1.80-1.69 (m, 1H), 1.21-1.14 (m, 1H).

Example 251: Synthesis of (1R,2R)-2-fluoro-N-(2-methyl-7-((4-(1-methyl-1H-imidazol-4-yl)-2-(methylsulfonyl)phenyl)amino)-3H-imidazo[4,5-b]pyridin-5-yl)cyclopropane-1-carboxamide, I-251

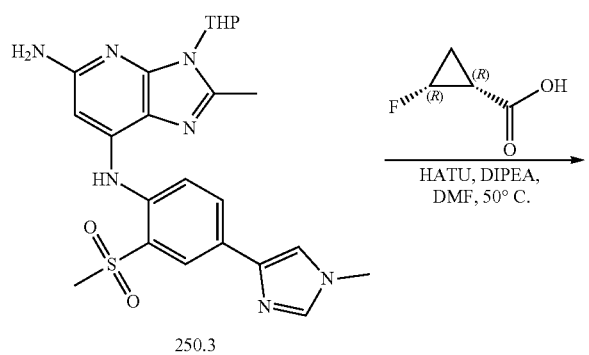

Synthesis of Compound 251.1.

To a solution of (1R,2R)-2-fluorocyclopropane-1-carboxylic acid (0.023 g, 0.22 mmol, 1.1 eq) in N,N'-dimethylformamide (1.0 mL) at 0° C., (1-[Bis(dimethylamino)methylene]-1H-1,2,3-triazolo[4,5-b]pyridinium 3-oxid hexafluorophosphate) (0.125 g, 0.33 mmol, 1.5 eq) was added. Reaction mixture was allowed to stir at 0° C. for 30 min. The, di-isopropylethylamine (0.070 g, 0.55 mmol, 2.5 eq) and 250.3 (0.1 g, 0.2 mmol, 1.0 eq) was added. Reaction mixture was allowed to stir at 50° C. for 3 h. After completion of the reaction, the reaction mixture was transferred into water and extracted with ethyl acetate. Organic layer combined, dried over anhydrous $Na_2SO_4$, filtered and concentrated in vacuo to obtain the crude material. This was purified by column chromatography using 22% ethyl acetate in hexane to obtain pure 251.1 (0.058 g, 44.12%). MS(ES): m/z: 568.54 $[M+H]^+$.

Synthesis of Compound I-251.

Compound I-251 was synthesized from 251.1 using general procedure C. (Yield: 80.96%). MS(ES): m/z: 484.35 $[M+H]^+$, LCMS purity: 98.90%, HPLC purity: 98.14%, Chiral HPLC Purity: (96.00%), 1H NMR (MeOD, 400 MHz): 8.37-8.37 (d, J=1.6 Hz, 1H), 8.05-8.03 (dd, J=2 Hz, J=8.4 Hz, 1H), 7.94 (s, 1H), 7.79 (s, 1H), 7.71 (s, 1H), 7.59 (s, 1H), 4.78-4.74 (m, 1H), 3.82 (s, 3H), 3.15 (s, 3H), 2.59 (s, 3H), 2.08-2.04 (m, 1H), 1.80-1.69 (m, 1H), 1.21-1.14 (m, 1H).

Example 252/253: (R)—N-(2-(difluoromethyl)-7-((2-(methylsulfonyl)-4-(tetrahydro-2H-pyran-3-yl)phenyl)amino)-3H-imidazo[4,5-b]pyridin-5-yl)cyclopropanecarboxamide, I-253 and(S)—N-(2-(difluoromethyl)-7-((2-(methylsulfonyl)-4-(tetrahydro-2H-pyran-3-yl)phenyl)amino)-3H-imidazo[4,5-b]pyridin-5-yl)cyclopropanecarboxamide, I-254

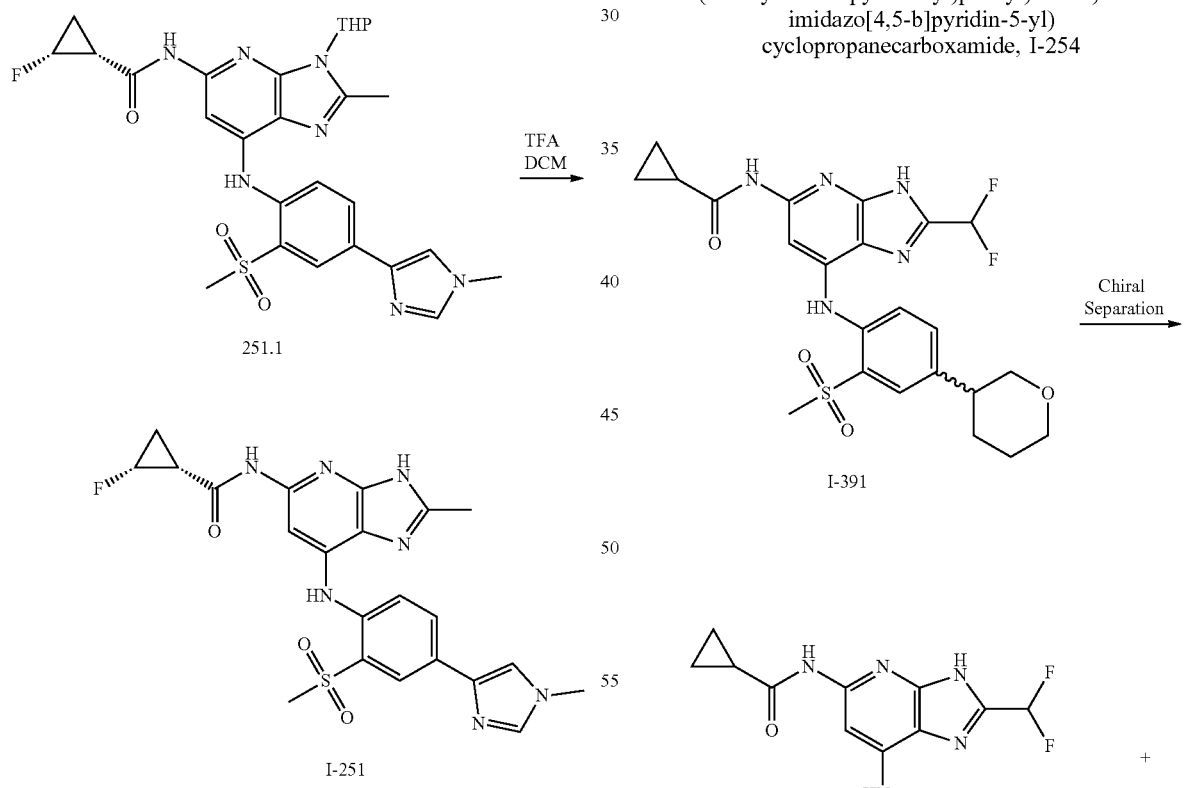

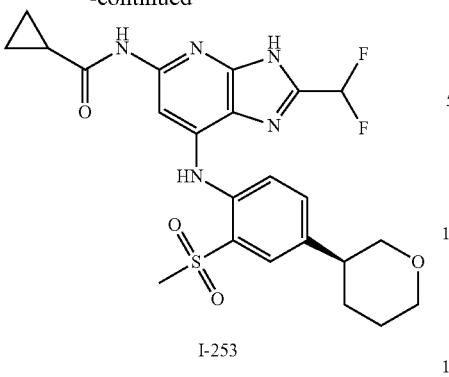

I-253

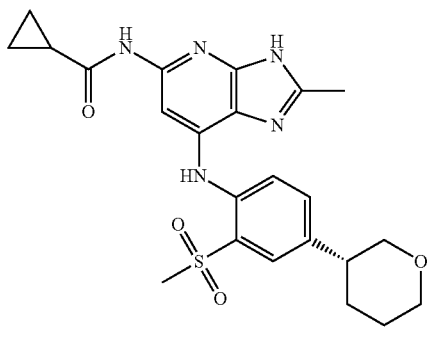

I-254

Synthesis of Compound I-253 and I-254

Isomers of 1-391 (0.070 g) were separated out from 1-391 using column (CHIRAL PAK AD-H (250 mm*4.6 mm, 5u)) and 0.1% DEA in MeOH flow rate of 3 mL/min. to get pure fraction-1 (FR-a) and fraction-2 (FR-b). FR-a was concentrated in vacuo at 30° C. to afford pure I-252 (0.025 g). MS(ES): m/z: 506.36 [M+H]$^+$, LCMS purity: 100%, HPLC purity 98.39%, Chiral HPLC: (100%), 1H NMR (DMSO-d6, 400 MHz): 10.75 (s, 1H), 8.71 (s, 1H), 8.04 (s, 1H), 7.80 (s, 1H), 7.74-7.69 (m, 3H), 7.38-7.11 (t, 1H), 3.89-3.86 (d, J=11.2 Hz, 1H), 3.46-3.39 (m, 2H), 3.21 (s, 3H), 2.91-2.87 (m, 1H), 2.05-1.97 (m, 3H), 1.79-1.67 (m, 3H), 0.79-0.775 (m, 4H). FR-b was concentrated in vacuo at 30° C. to afford pure 1-253 (0.025 g). MS(ES): m/z: 506.31 [M+H]$^+$, LCMS purity: 97.60%, HPLC purity 94.89%, Chiral HPLC: (96.26%), 1H NMR (DMSO-d6, 400 MHz): 13.62 (s, 1H), 10.75 (s, 1H), 8.71 (s, 1H), 8.04 (s, 1H), 7.80 (s, 1H), 7.74-7.69 (m, 2H), 7.38-7.12 (t, 1H), 3.89-3.86 (d, J=10.8 Hz, 2H), 3.51-3.39 (m, 2H), 3.18 (s, 3H), 2.94-2.89 (m, 1H), 2.05-1.97 (m, 2H), 1.80-1.77 (m, 1H), 1.76-1.67 (m, 2H), 0.79-0.77 (m, 4H).

Example 254/255: Synthesis of (R)—N-(2-methyl-7-((2-(methylsulfonyl)-4-(tetrahydro-2H-pyran-3-yl)phenyl)amino)-3H-imidazo[4,5-b]pyridin-5-yl)cyclopropanecarboxamide, I-254 and (S)—N-(2-methyl-7-((2-(methylsulfonyl)-4-(tetrahydro-2H-pyran-3-yl)phenyl)amino)-3H-imidazo[4,5-b]pyridin-5-yl)cyclopropanecarboxamide, I-255

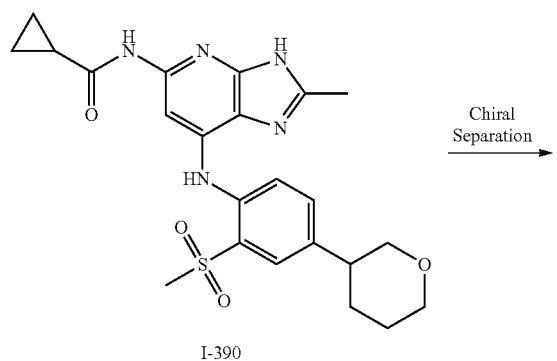

I-390

→ Chiral Separation

I-255

Synthesis of Compound I-254 and I-255.

Isomers of I-390 (0.082 g) were separated out using column (CHIRAL PAK AD-H (250 mm*4.6 mm, 5u)) and 0.1% DEA in MeOH flow rate of 4 mL/min. to get pure fraction-1 (FR-a) and fraction-2 (FR-b). FR-a was concentrated in vacuo at 30° C. to afford pure I-254 (0.022 g). MS(ES): m/z: 470.52 [M+H]$^+$, LCMS purity: 96.87%, HPLC purity 97.50%, Chiral HPLC: (96.22%), 1H NMR (DMSO-d6, 400 MHz): 12.51 (s, 1H), 10.58 (s, 1H), 8.54 (s, 1H), 7.97 (s, 1H), 7.77 (s, 1H), 7.70-7.66 (t, J=6.4 Hz, 2H), 3.88-3.86 (d, J=10.8 Hz, 2H), 3.45-3.38 (m, 2H), 3.19 (s, 3H), 2.92-2.87 (m, 1H), 2.48 (s, 3H), 1.99-1.98 (m, J=5.6 Hz, 2H), 1.82-1.72 (m, 1H), 1.67 (s, 2H), 0.77-0.76 (m, 4H). FR-b was concentrated in vacuo at 30° C. to afford pure I-255 (0.020 g). MS(ES): m/z: 470.52 [M+H]$^+$, LCMS purity: 96.93%, HPLC purity 95.32%, Chiral HPLC: (97.30%), 1H NMR (DMSO-d6, 400 MHz): 12.52 (s, 1H), 10.58 (s, 1H), 8.54 (s, 1H), 7.97 (s, 1H), 7.77 (s, 1H), 7.70-7.66 (m, 2H), 3.88-3.86 (d, J=10.8 Hz, 2H), 3.45-3.42 (m, 2H), 3.21 (s, 3H), 2.92-2.87 (m, 1H), 2.48 (s, 3H), 1.99-1.98 (m, 2H), 1.82-1.75 (m, 1H), 1.67 (s, 2H), 0.77-0.76 (m, 4H).

Example 256/257: Synthesis of (R)-2,2-difluoro-N-(2-methyl-7-((2-(methylsulfonyl)-4-((R)-tetrahydro-2H-pyran-2-yl)phenyl)amino)-3H-imidazo[4,5-b]pyridin-5-yl)cyclopropane-1-carboxamide, I-256 and (S)-2,2-difluoro-N-(2-methyl-7-((2-(methylsulfonyl)-4-((R)-tetrahydro-2H-pyran-2-yl)phenyl)amino)-3H-imidazo[4,5-b]pyridin-5-yl)cyclopropane-1-carboxamide, I-257

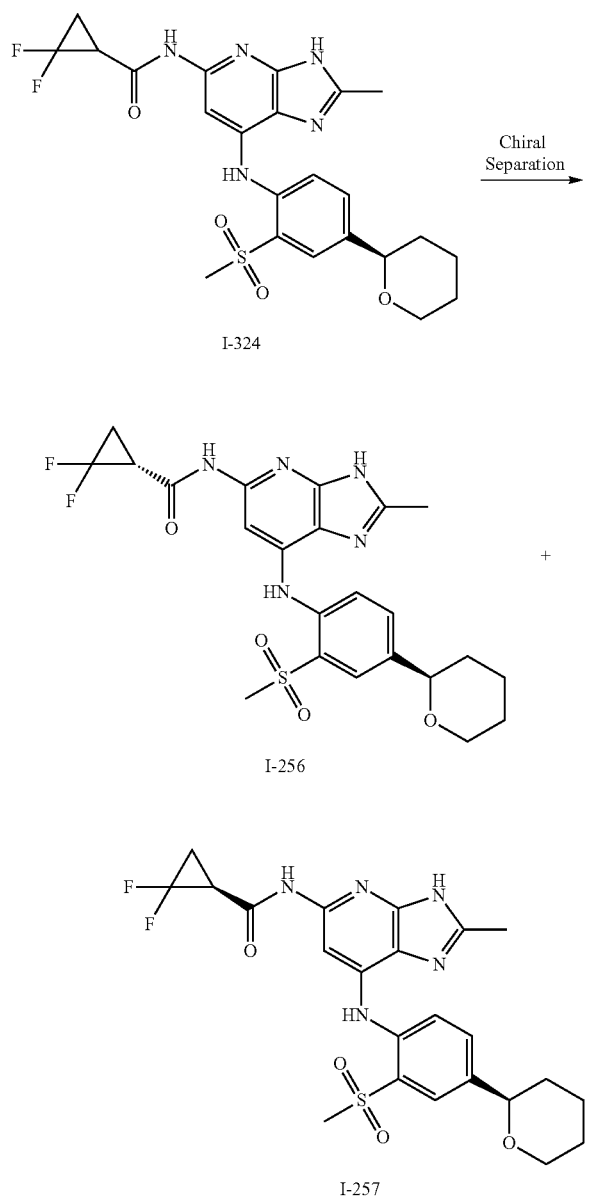 [SMILES: Cc1nc2c(Nc3ccc([C@H]4CCCCO4)cc3S(C)(=O)=O)cc(NC(=O)C3CC3(F)F)nc2[nH]1 ; Cc1nc2c(Nc3ccc([C@H]4CCCCO4)cc3S(C)(=O)=O)cc(NC(=O)[C@H]3CC3(F)F)nc2[nH]1 ; Cc1nc2c(Nc3ccc([C@H]4CCCCO4)cc3S(C)(=O)=O)cc(NC(=O)[C@@H]3CC3(F)F)nc2[nH]1]

Synthesis of Compounds I-256 and I-257.

Isomers of I-324 (0.080 g) were separated out using column (CHIRAL PAK AD-H (250 mm*4.6 mm, 5u)) and 0.1% DEA MEOH flow rate of 4 mL/min. to get pure fraction-1 (FR-a) and fraction-2 (FR-b). FR-a was concentrated in vacuo at 30° C. to afford pure I-256 (0.024 g). MS(ES): m/z: 506.41 [M+H]$^+$, LCMS purity: 98.84%, HPLC purity 98.98%, Chiral HPLC: 98.00%, 1H NMR (DMSO-d6, 400 MHz): 12.55 (s, 1H), 10.80 (s, 1H), 8.57 (s, 1H), 7.93 (s, 1H), 7.87 (s, 1H), 7.74-7.67 (q, J=8.4 Hz, 2H), 4.43-4.41 (d, J=10.4 Hz, 1H), 4.08-4.05 (d, J=11.6 Hz, 1H), 3.59-3.53 (m, 1H), 3.19 (s, 3H), 2.98-2.96 (m, 1H), 2.49 (s, 3H), 1.99-1.87 (m, 4H), 1.67-1.41 (m, 2H), 1.49-1.43 (m, 2H). FR-b was concentrated in vacuo at 30° C. to afford pure I-257 (0.011 g). MS(ES): m/z: 506.46 [M+H]$^+$, LCMS purity: 94.51%, HPLC purity 94.31%, Chiral HPLC: 99.54%, 1H NMR (DMSO-d6, 400 MHz): 12.56 (s, 1H), 10.81 (s, 1H), 8.57 (s, 1H), 7.94 (s, 1H), 7.87 (s, 1H), 7.74-7.67 (q, J=8 Hz, 2H), 4.43-4.41 (d, J=10.8 Hz, 1H), 4.08-4.05 (d, J=11.2 Hz, 1H), 3.59-3.51 (m, 1H), 3.19 (s, 3H), 2.98-2.95 (m, 1H), 2.49 (s, 3H), 1.99-1.88 (m, 4H), 1.65-1.64 (m, 2H), 1.49-1.43 (m, 2H).

Example 258: Synthesis of N-(2-(difluoromethyl)-7-((2-(methylsulfonyl)-4-(trifluoromethyl)phenyl)amino)-3H-imidazo[4,5-b]pyridin-5-yl)cyclopropanecarboxamide, I-258

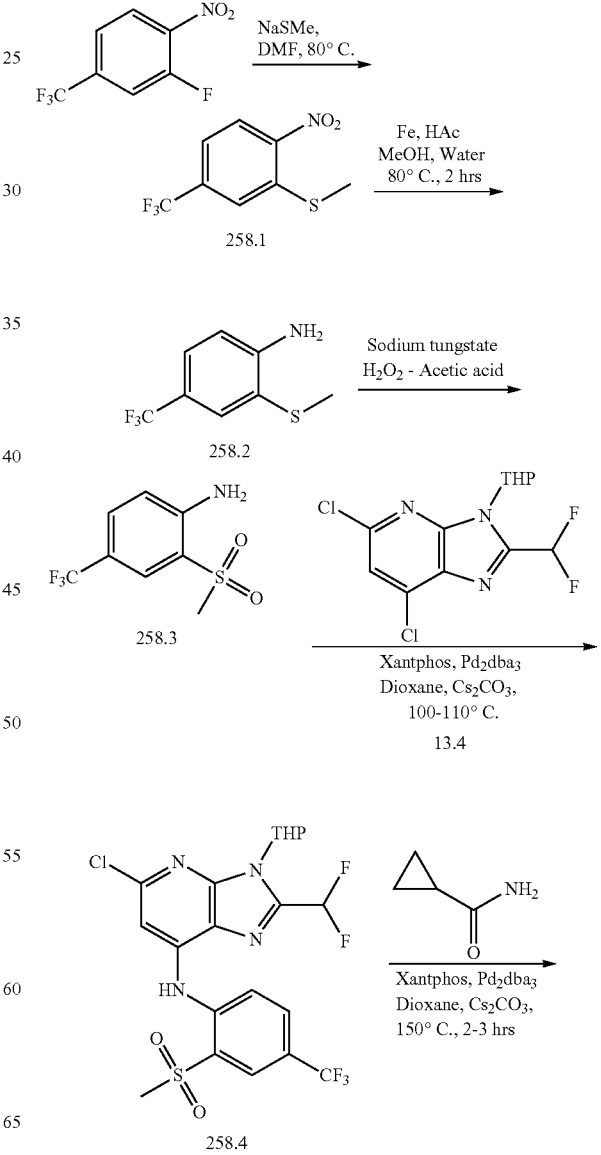

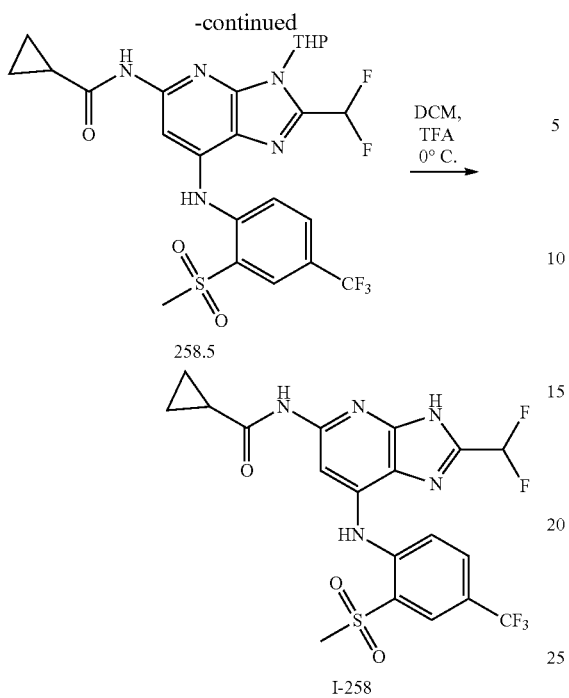

Synthesis of Compound 258.4.

Compound 258.4 was synthesized from 258.3 and 13.4 using general procedure A. (Yield: 18.23%). MS(ES): m/z 525.47 [M+H]+.

Synthesis of Compound 258.5

Compound 258.5 was synthesized from 258.4 and cyclopropanecarboxamide using general procedure B. (Yield: 76.26%). MS(ES): m/z 574.28 [M+H]+.

Synthesis of I-258.

Compound I-258 was synthesized from 258.5 using general procedure C. (Yield: 82.03%). MS(ES): m/z: 490.38 [M+H]+, LCMS purity: 96.08%, HPLC purity: 96.51%, 1H NMR (DMSO-d6, 400 MHz): 13.81 (s, 1H), 10.89 (s, 1H), 9.12 (s, 1H), 8.25 (s, 1H), 8.12 (s, 2H), 7.95-7.93 (d, J=8.4 Hz, 1H), 7.93 (t, 1H), 3.37 (s, 3H), 2.08-2.04 (m, 1H), 0.82 (s, 4H).

Example 259: Synthesis of N-(2-methyl-7-((2-(methylsulfonyl)-4-(trifluoromethyl)phenyl)amino)-3H-imidazo[4,5-b]pyridin-5-yl)cyclopropanecarboxamide, I-259

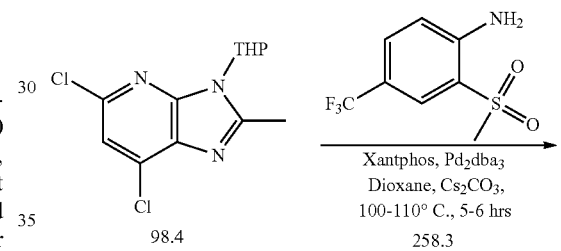

Synthesis of Compound 258.1.

To compound 2-fluoro-1-nitro-4-(trifluoromethyl)benzene (3.0 g, 0.014 mmol, 1.0 eq) in dimethylformamide (60 mL) at 0° C., sodium methanethiolate (1.81 g, 0.025 mmol, 1.8 eq) was added dropwise. Reaction mixture was stirred at 0° C. for 40 min. After completion of the reaction, the solid obtained in the reaction mixture, was filtered and dried under vacuum to obtain 258.1 (3.0 g, 88.15%) MS(ES): m/z 238.45 [M+H]+.

Synthesis of Compound 258.2.

To compound 258.1 (3.0 g, 0.012 mmol, 1.0 eq) in a mixture of MeOH (4 mL) and water (1.1 mL), acetic acid (11.0 g, 0.18 mmol, 15.0 eq) was added. Reaction mixture was allowed to stir at 50-60° C. for 1 h. After 1 h, iron powder (4.96 g, 0.088 mmol, 7.0 eq) was added in portions. Reaction mixture was further allowed to stir at 90° C. for 2 h. After completion of the reaction, the reaction mixture was diluted with MeOH and filtered through celite bed. The filtrate was concentrated in vacuo to get the crude material. This was purified by column chromatography using 15-20% ethyl acetate in hexane as eluant to obtain pure 258.2 (2.1 g, 80.13%). MS(ES): m/z 208.43 [M+H]+.

Synthesis of Compound 258.3.

To compound 258.2 (2.1 g, 4.83 mmol, 1.0 eq) in acetic acid (21 mL), sodium tungstate (1.49 g, 5.07 mmol, 1.005 eq) was added in portions. Reaction mixture was allowed to stir at r.t. for 5 min. Then, 30% hydrogen peroxide solution (18 mL) was added dropwise at r.t. Reaction mixture was allowed to stir at r.t. for 10 min. After completion of the reaction, the reaction mixture was transferred to water. The pH of the solution was adjusted to 7 by using saturated NaHCO3 and then extracted with ethyl acetate. Organic layers were combined, dried over anhydrous Na2SO4, filtered and concentrated in vacuo to get the crude material. This was purified by column chromatography using 10-13% ethyl acetate in hexane as eluant to obtain pure 258.3 (1.2 g, 49.5%). MS(ES): m/z 240.16 [M+H]+.

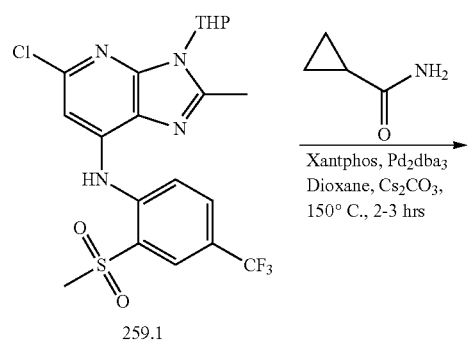

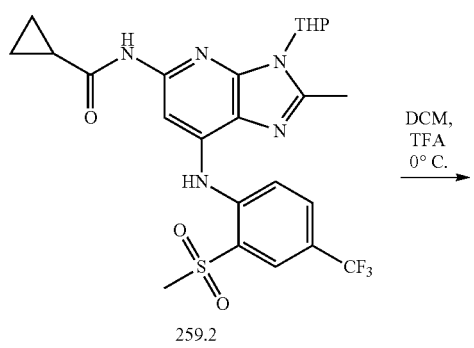

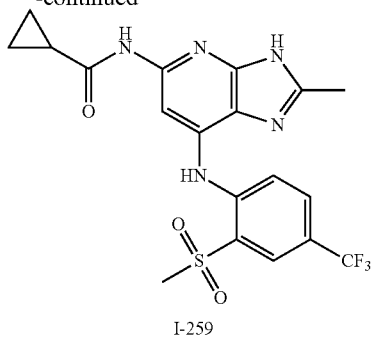

I-259

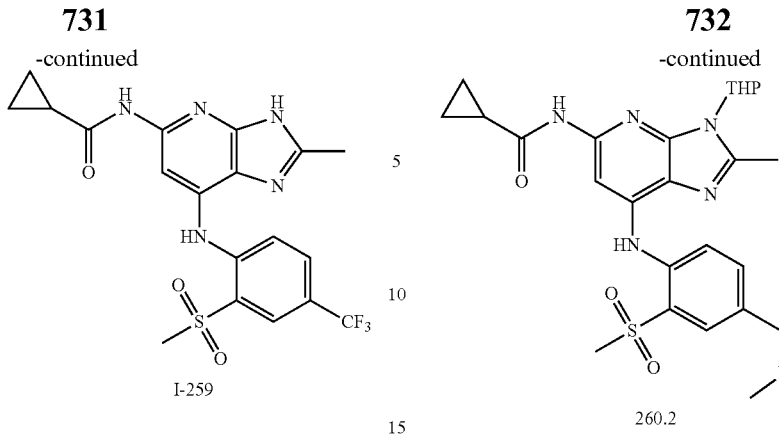

260.2

Synthesis of Compound 259.1.

Compound 259.1 was synthesized from 98.4 and 258.3 using general procedure A. (Yield: 19.57%). MS(ES): m/z 489.51 [M+H]$^+$.

Synthesis of Compound 259.2.

Compound 259.2 was synthesized from 259.1 and cyclopropanecarboxamide using general procedure B. (Yield: 83.37%). MS(ES): m/z 538.47 [M+H]$^+$.

Synthesis of Compound I-259.

Compound I-259 was synthesized from 259.2 using general procedure C. (Yield: 75.44%). MS(ES): m/z: 454.41 [M+H]$^+$, LCMS purity: 100%, HPLC purity 100%, 1H NMR (DMSO-d6, 400 MHz): 12.62 (s, 1H), 10.71 (s, 1H), 8.97 (s, 1H), 8.12-8.06 (m, 3H), 7.90-7.88 (d, J=8.4 Hz, 1H), 3.35 (s, 3H), 2.52 (s, 3H), 2.02-2.00 (d, J=6.8 Hz, 1H), 0.80-0.79 (m, 4H).

Example 260: (1S,2S)-2-fluoro-N-(2-methyl-7-((4-(1-methyl-1H-imidazol-5-yl)-2-(methylsulfonyl)phenyl)amino)-3H-imidazo[4,5-b]pyridin-5-yl)cyclopropane-1-carboxamide, I-260

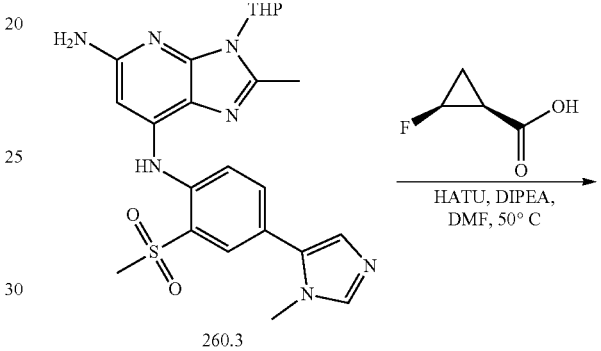

260.3

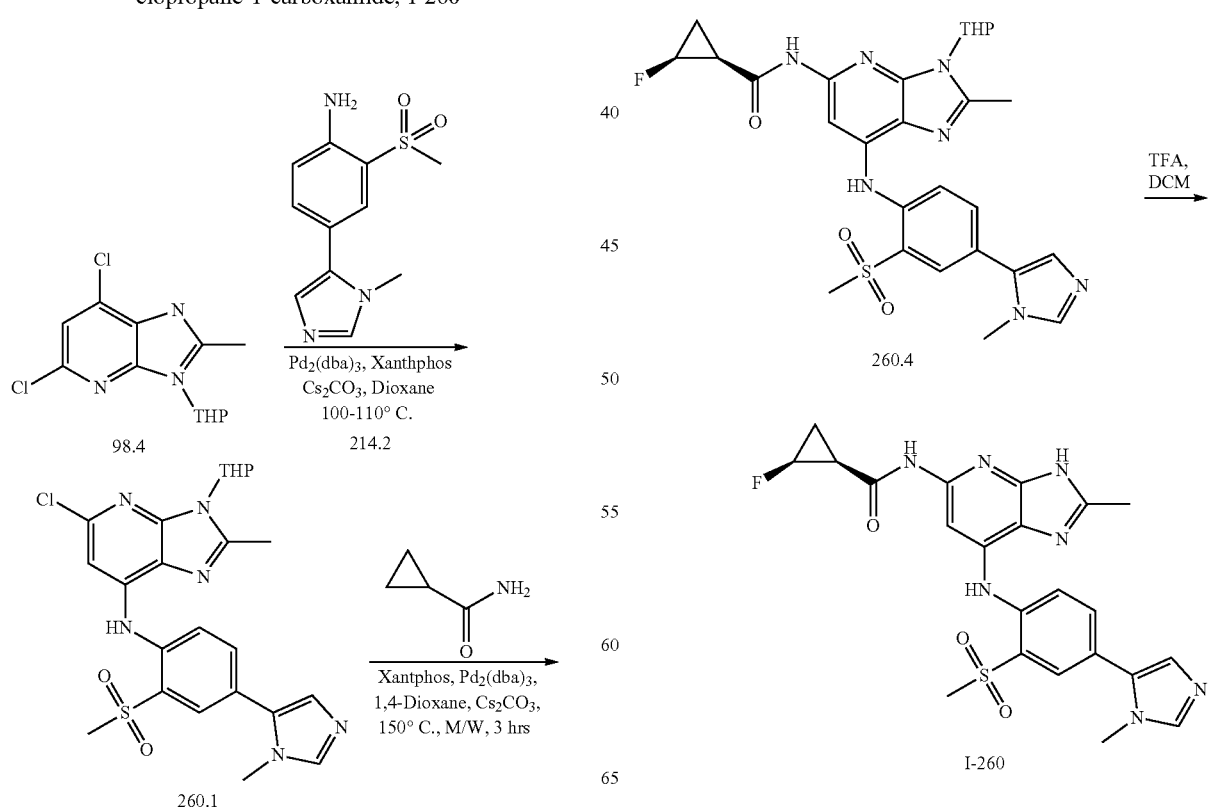

Synthesis of Compound 260.1.

Compound 260.1 was synthesized from 214.2 and 98.4 using general procedure A. (Yield: 25.7%). MS(ES): m/z 502.34 [M+H]$^+$.

Synthesis of Compound 260.2.

Compound 260.2 was synthesized from 260.1 and cyclopropanecarboxamide using general procedure B. (Yield: 63.8%). MS(ES): m/z 550.28 [M+H]$^+$.

Synthesis of Compound 260.3.

To compound 260.2 (0.175 g, 0.31 mmol, 1.0 eq) in MeOH (2 mL), 5M NaOH (0.06 g, 1.5 mmol, 5.0 eq) was added. Reaction mixture was stirred at 50° C. for 36 h. After completion of the reaction, the reaction mixture was concentrated and transferred into water. Then, pH of the solution was adjusted to neutral using dilute HCl solution and then extracted with ethyl acetate. Organic layer combined, dried over anhydrous Na$_2$SO$_4$, filtered and concentrated in vacuo to obtain 260.3 (0.120 g, 78.26%). MS(ES): m/z 550.28 [M+H]$^+$.

Synthesis of Compound 260.4.

To compound (1S,2S)-2-fluorocyclopropane-1-carboxylic acid 1.6 (0.060.0 g, 12 mmol, 1.0 eq) in N,N'-dimethylformamide (1 mL), (1-[Bis(dimethylamino)methylene]-1H-1,2,3-triazolo[4,5-b]pyridinium 3-oxide hexafluorophosphate) (0.094 g, 24 mmol, 2 eq) was added. Reaction mixture was stirred at 0° C. for 15 min. Then, di-isopropylethylamine (0.8 ml, 3.0 mmol 2.5 eq) and compound 260.3 (0.012 g, 12 mmol, 1.0 eq) was added. Reaction mixture was stirred at 50° C. for 3 h. Upon completion, reaction mixture was transferred into cold water and extracted with ethyl acetate. Organic layer combined, dried over Na$_2$SO$_4$, filtered and concentrated in vacuo to obtain crude product. This was purified by column chromatography using 6% MeOH in CH$_2$Cl$_2$ as eluant to obtain pure 260.4 (0.043 g, 60.80%). MS(ES): m/z 568.64 [M+H]$^+$.

Synthesis of I-260.

Compound I-260 was synthesized from 260.4 using general procedure C (Yield: 70.98%). MS(ES): m/z: 484.4 [M+H]$^+$, LCMS purity: 97.64%, HPLC purity: 97.18%, Chiral HPLC Purity: (99.17%), 1H NMR (DMSO-d6, 400 MHz): 10.64 (s, 1H), 8.74 (s, 1H), 8.03 (s, 1H), 7.93-7.89 (m, 3H), 7.84-7.82 (d, J=8 Hz, 1H), 7.76 (s, 1H), 7.18 (s, 1H), 4.50-4.99 (d, J=4.4 Hz, 1H), 3.75 (s, 3H), 3.29 (s, 3H), 2.49 (s, 3H), 2.21 (s, 1H), 1.63-1.58 (m, 1H) 1.18-1.11 (m, 1H).

Example 261: Synthesis of (1R,2R)-2-fluoro-N-(2-methyl-7-((4-(1-methyl-1H-imidazol-5-yl)-2-(methylsulfonyl)phenyl)amino)-3H-imidazo[4,5-b]pyridin-5-yl)cyclopropane-1-carboxamide, I-261

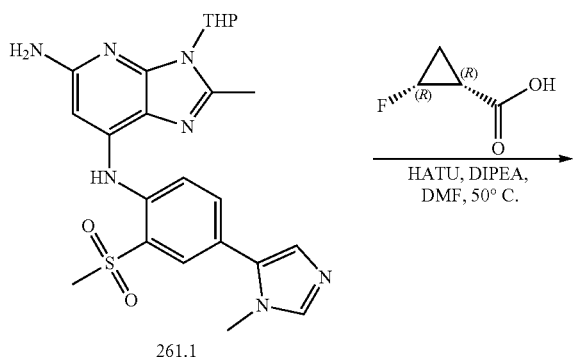

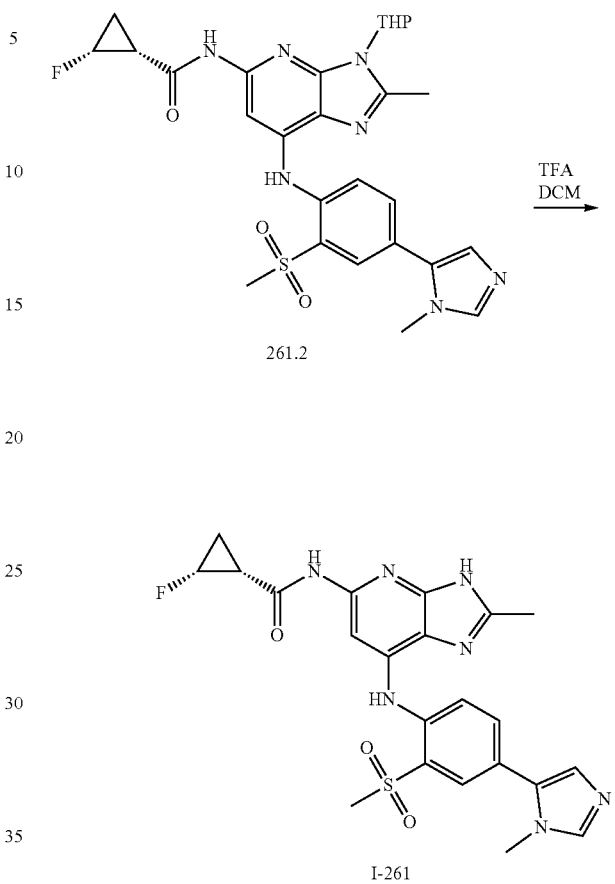

Synthesis of Compound 261.2.

To compound 261.1 (0.060 g, 12 mmol, 1.0 eq) in N,N'-dimethylformamide (1 mL), (1-[Bis(dimethylamino)methylene]-1H-1,2,3-triazolo[4,5-b]pyridinium 3-oxide hexafluorophosphate) (0.094 g, 24 mmol, 2 eq) was added. Reaction mixture was stirred at 0° C. for 15 min. Then, di-isopropylethylamine (0.8 ml, 3.0 mmol 2.5 eq) and compound (1R,2R)-2-fluorocyclopropane-1-carboxylic acid (0.012 g, 12 mmol, 1.0 eq) was added. Reaction mixture was stirred at 50° C. for 3 h. Upon completion, reaction mixture was transferred into cold water and extracted with ethyl acetate. Organic layer combined, dried over Na$_2$SO$_4$, filtered and concentrated in vacuo to obtain crude product. This was purified by column chromatography using 6% MeOH in CH$_2$Cl$_2$ as eluant to obtain pure 261.2 (0.043 g, 60.80%). MS(ES): m/z 568.64 [M+H]$^+$.

Synthesis of I-261.

Compound I-261 was synthesized from 261.2 using general procedure C. (Yield: 70.98%). MS(ES): m/z: 484.4 [M+H]$^+$, LCMS purity: 98.39%, HPLC purity: 98.65%, Chiral HPLC Purity: (99.67%), 1H NMR (DMSO-d6, 400 MHz): 10.63 (s, 1H), 8.70 (s, 1H), 8.02 (s, 1H), 7.92-7.82 (m, 4H), 7.76 (s, 1H), 7.17 (s, 1H), 5.00-4.99 (m, 1H), 3.75 (s, 3H), 3.29 (s, 3H), 2.49 (s, 3H), 2.20 (s, 1H), 1.63-1.57 (m, 1H) 1.18-1.09 (m, 1H).

Example 262: Synthesis of (1S,2S)—N-(7-((4-(1,4-dimethyl-1H-pyrazol-3-yl)-2-(methylsulfonyl)phenyl)amino)-2-methyl-3H-imidazo[4,5-b]pyridin-5-yl)-2-fluorocyclopropane-1-carboxamide, I-262

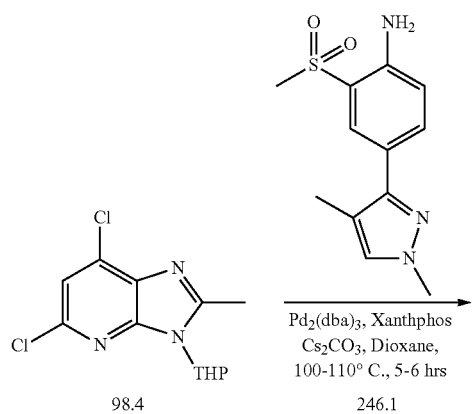

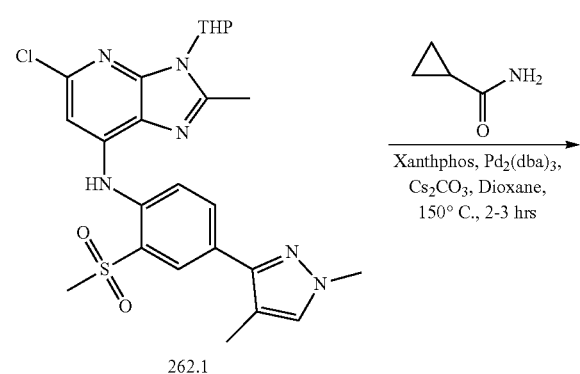

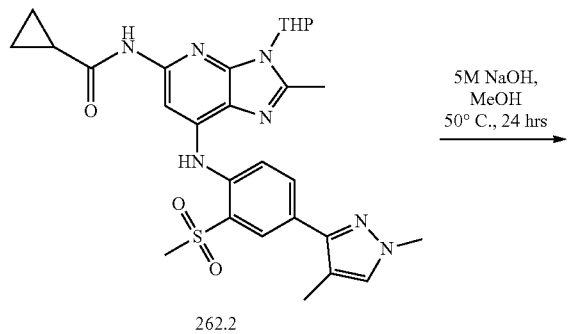

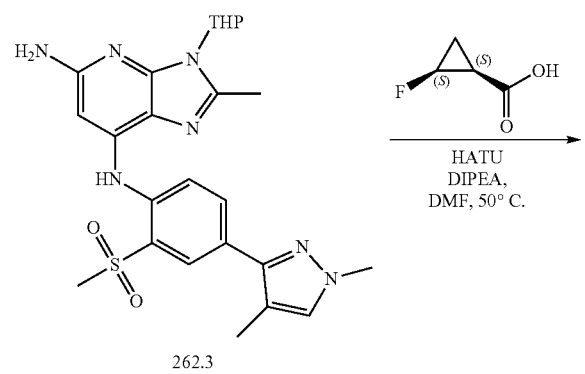

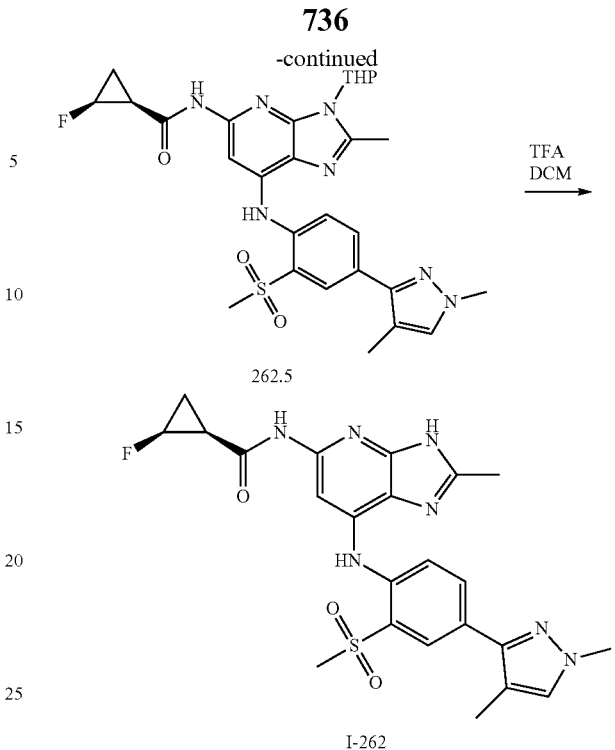

Synthesis of Compound 262.1.
Compound 262.1 was synthesized from 98.4 and 246.1 using general procedure A. (Yield: 20.84%). MS(ES): m/z: 516.29 [M+H]$^+$.

Synthesis of Compound 262.2.
Compound 262.2 was synthesized from 262.1 and cyclopropanecarboxamide using general procedure B. (Yield: 73.10%). MS(ES): m/z: 564.43 [M+H]$^+$.

Synthesis of Compound 262.3.
To compound 262.2 (0.35 g, 0.62 mmol, 1.0 eq) in MeOH (2 mL), 5M NaOH solution (1.5 mL, 3.10 mmol, 5.0 eq) was added dropwise. Reaction mixture was stirred at 80° C. for 24 h. After completion of the reaction, the reaction mixture was transferred into water and extracted with ethyl acetate. Organic layers were combined, dried over anhydrous Na$_2$SO$_4$, filtered and concentrated in vacuo to obtain 262.3 (0.21 g, 68.24%). MS(ES): m/z 500.16 [M+H]$^+$.

Synthesis of Compound 262.4.
To a solution of (1S,2S)-2-fluorocyclopropane-1-carboxylic acid (0.024 g, 0.21 mmol, 1.5 eq) in N,N-dimethylformamide (2 mL) at 0° C., (1-[Bis(dimethylamino)methylene]-1H-1,2,3-triazolo[4,5-b]pyridinium3-oxid hexafluorophosphate) (0.115 g, 0.25 mmol, 2.0 eq) was added. Reaction mixture was stirred at 0° C. for 30 min. Then, compound 1.5 (0.075 g, 0.15 mmol, 1.0 eq) and di-isopropylethylamine (0.059 g, 0.45 mmol, 3.0 eq) was added. Reaction mixture was stirred at 50° C. for 1.5 h. After completion of the reaction, the reaction mixture was transferred to cold water to obtain precipitate which was filtered and dried well to obtain pure 262.4 (0.075 g, 72.71%). MS(ES): m/z 582.47 [M+H]$^+$.

Synthesis of I-262.
Compound I-262 was synthesized from using general procedure C. (Yield: 77.94%). MS(ES): m/z: 498.41 [M+H]$^+$, LCMS purity: 97.28%, HPLC purity 97.94%, Chiral HPLC Purity: (98.05%), 1H NMR (DMSO-d6, 400 MHz): 12.54 (s, 1H), 10.65 (s, 1H), 8.63 (s, 1H), 8.22 (s, 1H), 8.03-8.00 (dd, J=2.8 Hz, J=1.6 Hz, 2H), 7.83-7.81 (d, J=8.4 Hz, 1H), 7.61 (s, 1H), 5.01-4.99 (m, 1H), 3.86 (s, 3H), 3.24 (s, 3H), 2.52 (s, 3H), 2.34 (s, 3H), 1.66-1.61 (m, 1H) 1.60-1.25 (m, 2H).

Example 263: (1R,2R)—N-(7-((4-(1,4-dimethyl-1H-pyrazol-3-yl)-2-(methylsulfonyl)phenyl)amino)-2-methyl-3H-imidazo[4,5-b]pyridin-5-yl)-2-fluorocyclopropane-1-carboxamide, I-263

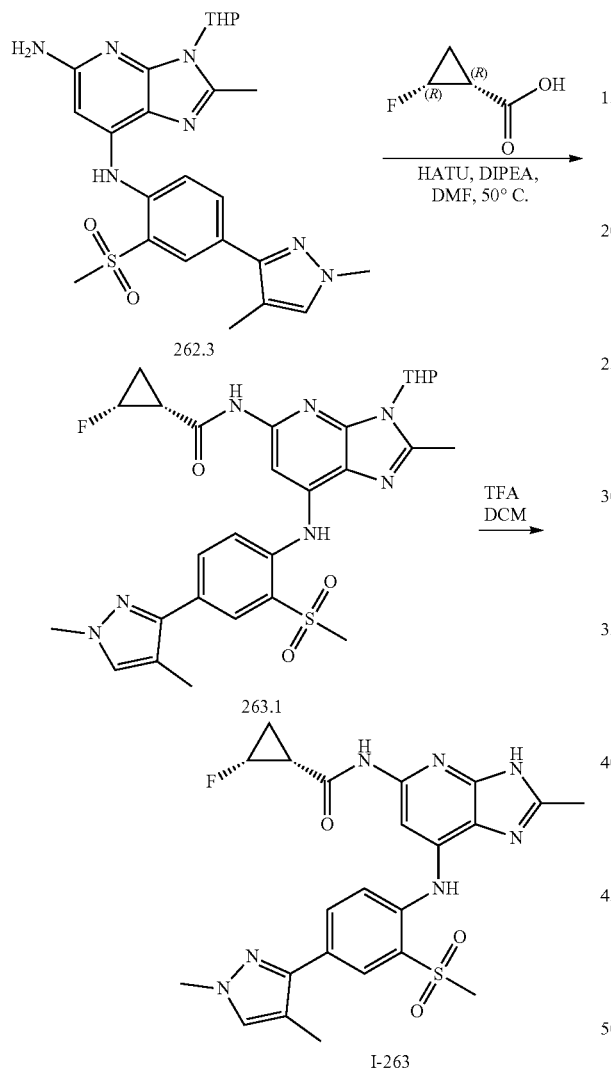

Synthesis of Compound 263.1.

To a solution of 262.3 (0.024 g, 0.21 mmol, 1.5 eq) in N,N-dimethylformamide (2 mL) at 0° C., (1-[Bis(dimethylamino)methylene]-1H-1,2,3-triazolo[4,5-b]pyridinium 3-oxid hexafluorophosphate) (0.115 g, 0.25 mmol, 2.0 eq) was added. Reaction mixture was stirred at 0° C. for 30 min. Then, compound (1R,2R)-2-fluorocyclopropane-1-carboxylic acid (0.075 g, 0.15 mmol, 1.0 eq) and di-isopropylethylamine (0.059 g, 0.45 mmol, 3.0 eq) was added. Reaction mixture was stirred at 50° C. for 1.5 h. After completion of the reaction, the reaction mixture was transferred to cold water to obtain precipitate which was filtered under vacuum, washed with water and dried well to obtain pure 263.1 (0.075 g, 72.71%). MS(ES): m/z 582.47 [M+H]$^+$.

Synthesis of I-263.

Compound I-263 was synthesized from 263.1 using general procedure C. (Yield: 75.95%). MS(ES): m/z: 498.41 [M+H]$^+$, LCMS purity: 99.04%, HPLC purity 99.14%, Chiral HPLC: (98.25%), 1H NMR (DMSO-d6, 400 MHz): 12.54 (s, 1H), 10.65 (s, 1H), 8.63 (s, 1H), 8.22-8.22 (d, J=2 Hz, 1H), 8.02-8.00 (d, J=8.8 Hz, 2H), 7.83-7.81 (d, J=6.8 Hz, 1H), 7.61 (s, 1H), 5.00-4.82 (d, 1H), 3.86 (s, 3H), 3.25 (s, 3H), 2.52 (s, 3H), 2.25 (s, 3H), 1.65-1.59 (m, 1H) 1.16-1.11 (m, 2H).

Example 264: Synthesis of N-(7-((4-cyclobutyl-2-(methylsulfonyl)phenyl)amino)-2-methyl-3H-imidazo[4,5-b]pyridin-5-yl)cyclopropanecarboxamide, I-264

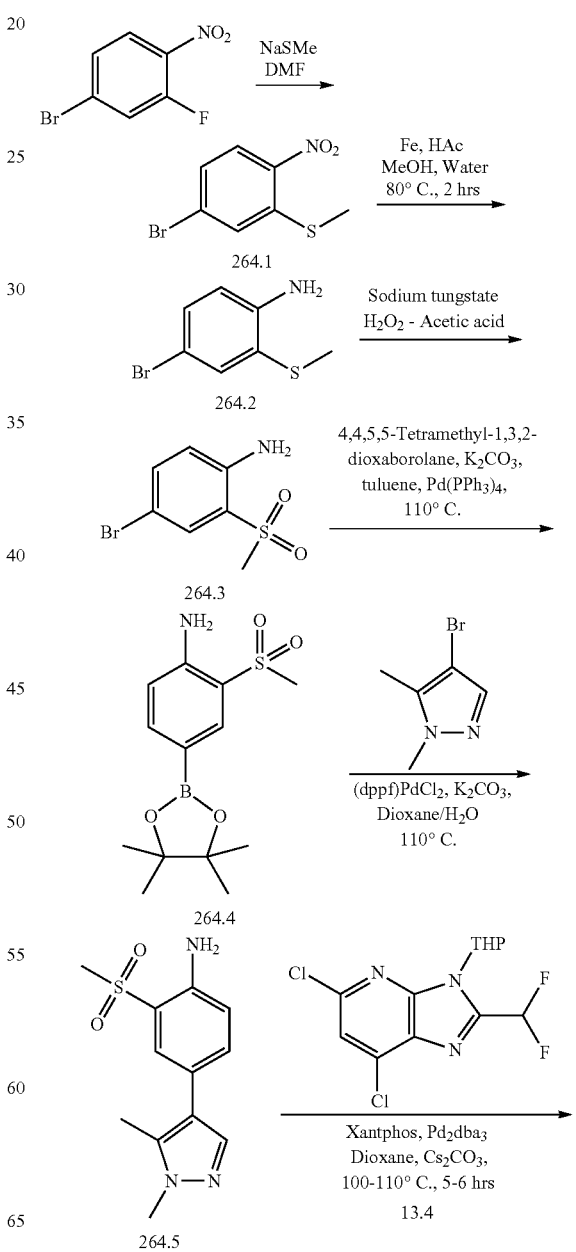

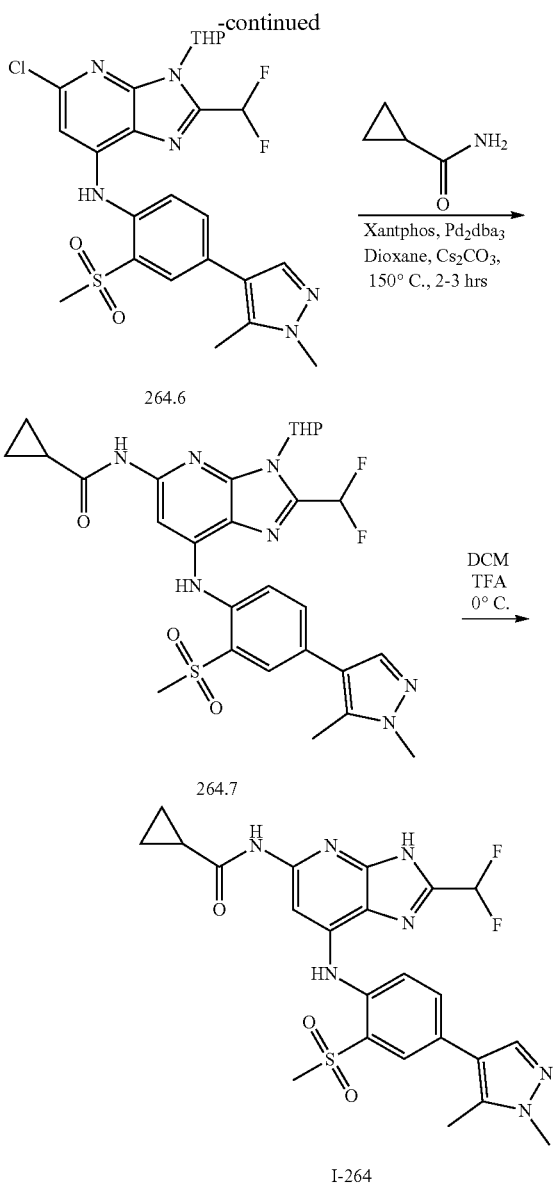

Synthesis of Compound 264.1.

To compound 4-bromo-2-fluoro-1-nitrobenzene (3.0 g, 13.64 mmol, 1.0 eq) in N,N-dimethylformamide (30 mL) at 0° C., sodium methanethiolate (1.72 g, 24.55 mmol, 1.8 eq) was added dropwise. Reaction mixture was stirred at 0° C. for 40 min. After completion of the reaction, the solid obtained in the reaction mixture, was filtered and dried under vacuum to obtain 264.1 (3.0 g, 88.68%) MS(ES): m/z 249.09 [M+H]$^+$.

Synthesis of Compound 264.2.

To compound 264.1 (3.0 g, 12.09 mmol, 1.0 eq) in a mixture of MeOH (4 mL) and water (1.1 mL), acetic acid (10.88 g, 181.35 mmol, 15.0 eq) was added. Reaction mixture was allowed to stir at 50-60° C. for 1 h. After 1 h, iron powder (4.62 g, 84.1 mmol, 7.0 eq) was added in portions. Reaction mixture was further allowed to stir at 80° C. for 2 h. After completion of the reaction, the reaction mixture was diluted with MeOH and filtered through celite bed. The filtrate was concentrated in vacuo to get the crude material. This was purified by column chromatography using 15-20% ethyl acetate in hexane as eluant to obtain pure 264.2 (2.1 g, 79.62%). MS(ES): m/z 219.11 [M+H]$^+$.

Synthesis of Compound 264.3.

To compound 264.2 (2.1 g, 9.63 mmol, 1.0 eq) in acetic acid (21 mL), sodium tungstate (2.84 g, 9.65 mmol, 1.005 eq) was added portionwise. Reaction mixture was allowed to stir at r.t. for 5 min. Then, 30% hydrogen peroxide solution (18 mL) was added dropwise at r.t. Reaction mixture was allowed to stir at r.t. for 10 min. After completion of the reaction, the reaction mixture was transferred to water. The pH of the solution was adjusted to 7 by using saturated NaHCO$_3$ and then extracted with ethyl acetate. Organic layers were combined, dried over anhydrous Na$_2$SO$_4$, filtered and concentrated in vacuo to get the crude material. This was purified by column chromatography using 10-13% ethyl acetate in hexane as eluant to obtain pure 264.3 (1.2 g, 49.83%). MS(ES): m/z 251.11 [M+H]$^+$.

Synthesis of Compound 264.4.

To compound 264.3 (1 g, 4.0 mmol, 1.0 eq) and 4,4,5,5-Tetramethyl-1,3,2-dioxaborolane (1.79 g, 10.1 mmol, 1.5 eq) in tetrahydrofuran (10 mL), potassium carbonate (1.1 g, 8.0 mmol, 2.0 eq) was added. Argon was purged through the reaction mixture for 5 min. Then, [1,1'-Bis(diphenylphosphino)ferrocene]dichloro-palladium(II) (0.29 g, 0.4 mmol, 0.1 eq) was added and again purged for 5 min. Reaction mixture was stirred at 110° C. for 4 h. After completion of the reaction, the reaction mixture was transferred to water and extracted with ethyl acetate. Organic layers were combined, dried over anhydrous Na$_2$SO$_4$, filtered and concentrated in vacuo to get the crude material. This was purified by column chromatography using 12% ethyl acetate in hexane as eluant to obtain 264.4 (0.8 g, 67.33%). MS(ES): m/z 298.18 [M+H]$^+$.

Synthesis of Compound 264.5.

To compound 264.4 (5.0 g, 16 mmol, 1.0 eq) and 4-bromo-1,5-dimethyl-1H-pyrazole (2.74 g, 14 mmol, 0.84 eq) in 1,4-dioxane (40 mL), potassium carbonate (6.96 g, 48 mmol, 3.0 eq) was added. Argon gas was purged through the reaction for 10-15 min. Then, [1,1'-Bis(diphenylphosphino)ferrocene]dichloropalladium(II)] complex with CH$_2$Cl$_2$ (0.41 g, 0.48 mmol, 0.03 eq) was added. Reaction mixture was stirred at 100-110° C. for 3 h. After completion of the reaction, the reaction mixture was transferred to water and extracted with ethyl acetate. Organic layers were combined, dried over anhydrous Na$_2$SO$_4$, filtered and evaporated under vacuum to obtain 264.5 (1.5 g, 33.6%). MS(ES): m/z 266.37 [M+H]$^+$.

Synthesis of Compound 264.6.

Compound 264.6 was synthesized from 264.5 and 13.4 using general procedure A. (Yield: 26.16%). MS(ES): m/z 552.48 [M+H]$^+$.

Synthesis of Compound 264.7.

Compound 264.7 was synthesized from 264.6 and cyclopropanecarboxamide using general procedure B. (Yield: 42.88%). MS(ES): m/z 600.28 [M+H]$^+$.

Synthesis of I-264.

Compound I-264 was synthesized from 267.4 using general procedure C. (Yield: 51.93%). MS(ES): m/z: 516.46 [M+H]$^+$, LCMS purity: 99.65%, HPLC purity 99.04%, 1H NMR (DMSO-d6, 400 MHz): 13.68 (s, 1H), 10.76 (s, 1H), 8.77 (s, 1H), 8.07 (s, 1H), 7.89 (s, 1H), 7.82-7.79 (d, J=8.8 Hz, 2H), 7.71 (s, 1H), 7.27 (t, 1H), 3.82 (s, 3H), 3.26 (s, 3H), 2.43 (s, 3H), 2.06-2.03 (m, 1H), 0.80-0.78 (m, 4H).

Example 265: Synthesis of N-(7-((4-(1,5-dimethyl-1H-pyrazol-4-yl)-2-(methylsulfonyl)phenyl)amino)-2-methyl-3H-imidazo[4,5-b]pyridin-5-yl)cyclopropanecarboxamide, I-265

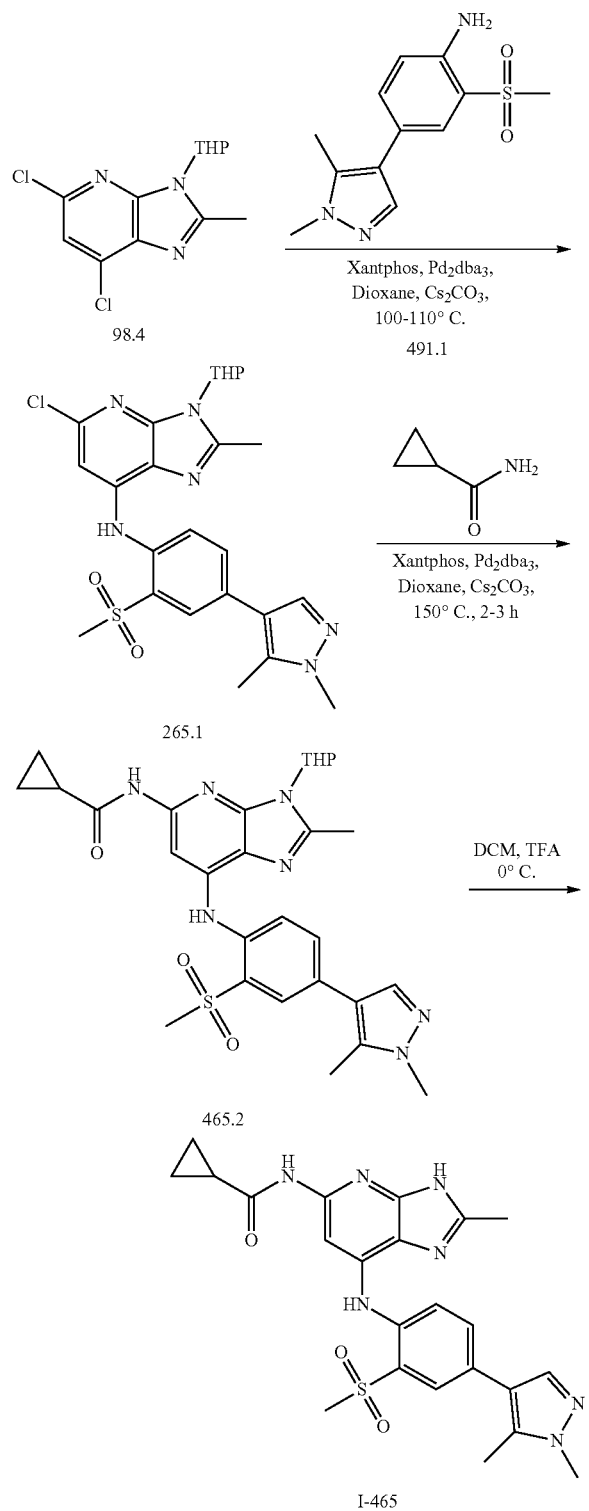

Synthesis of compound 265.2 Compound 265.2 was synthesized from 265.1 and cyclopropanecarboxamide using general procedure. B (Yield: 63.96%). MS(ES): m/z 564.27 [M+H]⁺.

Synthesis of I-265.

Compound was synthesized from 265.2 using general procedure C (Yield: 67.17%). MS(ES): m/z: 480.40 [M+H]⁺, LCMS purity: 98.65%, HPLC purity 95.45%, 1H NMR (DMSO-d6, 400 MHz): 12.501 (s, 1H), 10.59 (s, 1H), 8.59 (s, 1H), 8.00 (s, 1H), 7.86 (s, 1H), 7.79 (s, 2H), 7.69 (s, 1H), 3.82 (s, 3H), 2.62 (s, 3H), 3.24 (s, 3H), 2.43 (s, 3H), 2.01-2.00 (m, 1H), 0.78 (bs, 4H).

Example 266/267: Synthesis of (1S,2S)-2-fluoro-N-(7-((2-methoxy-3-(1-methyl-1H-1,2,4-triazol-3-yl)phenyl)amino)-2-methyl-3H-imidazo[4,5-b]pyridin-5-yl)cyclopropane-1-carboxamide, I-266 and (1R,2R)-2-fluoro-N-(7-((2-methoxy-3-(1-methyl-1H-1,2,4-triazol-3-yl)phenyl)amino)-2-methyl-3H-imidazo[4,5-b]pyridin-5-yl)cyclopropane-1-carboxamide, I-267

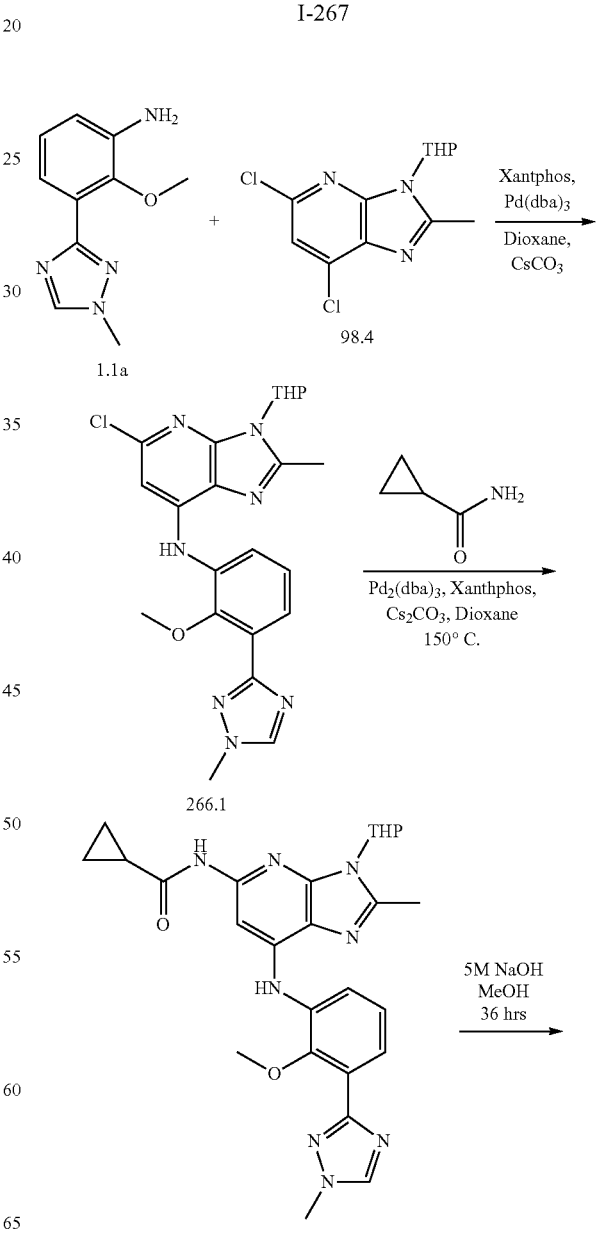

Synthesis of Compound 265.1.

Compound 265.1 was synthesized from 491.1 and 98.4 using general procedure. A (Yield: 20.61%). MS(ES): m/z 516.23 [M+H]⁺.

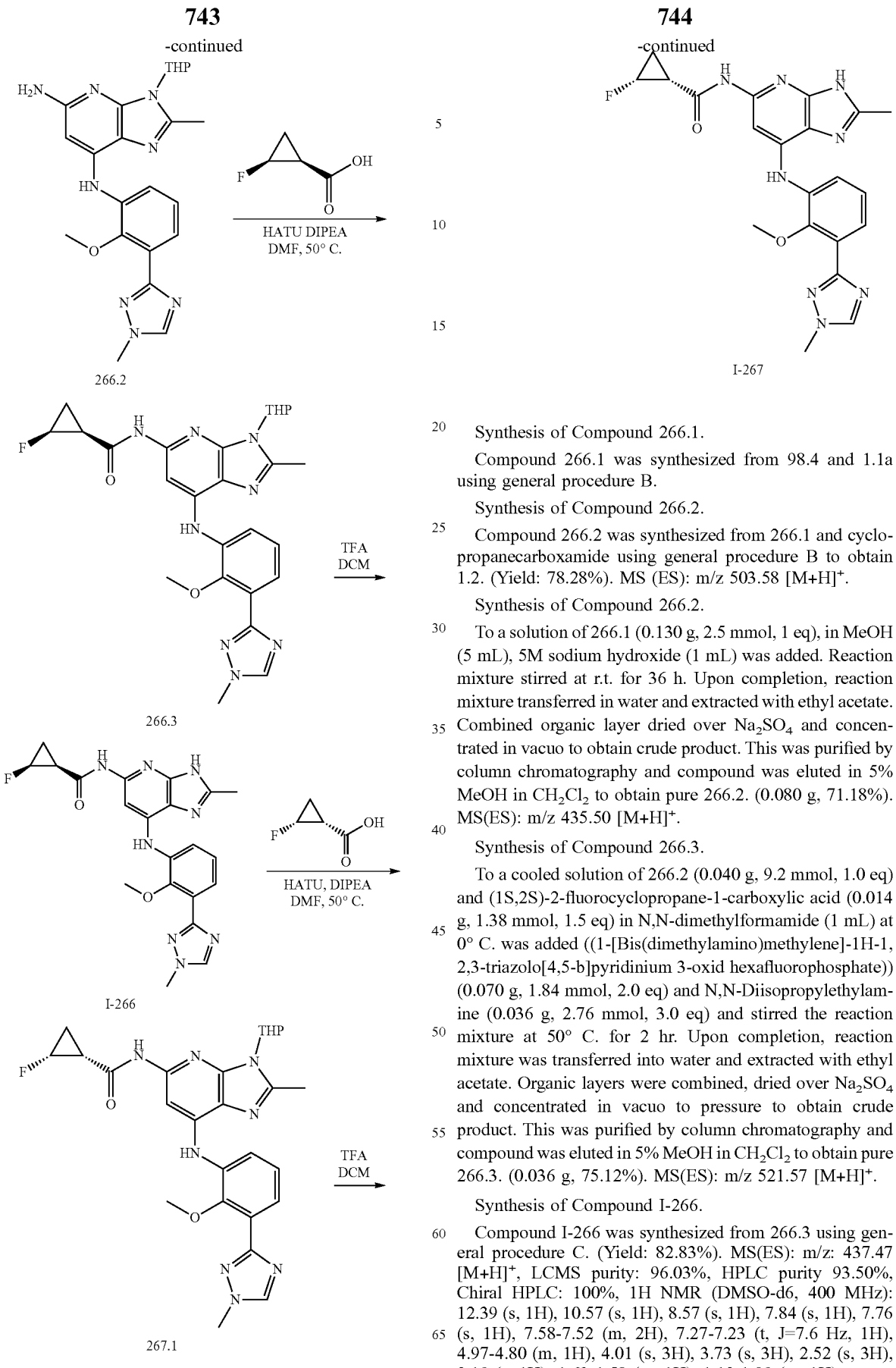

Synthesis of Compound 266.1.

Compound 266.1 was synthesized from 98.4 and 1.1a using general procedure B.

Synthesis of Compound 266.2.

Compound 266.2 was synthesized from 266.1 and cyclopropanecarboxamide using general procedure B to obtain 1.2. (Yield: 78.28%). MS (ES): m/z 503.58 [M+H]$^+$.

Synthesis of Compound 266.2.

To a solution of 266.1 (0.130 g, 2.5 mmol, 1 eq), in MeOH (5 mL), 5M sodium hydroxide (1 mL) was added. Reaction mixture stirred at r.t. for 36 h. Upon completion, reaction mixture transferred in water and extracted with ethyl acetate. Combined organic layer dried over Na$_2$SO$_4$ and concentrated in vacuo to obtain crude product. This was purified by column chromatography and compound was eluted in 5% MeOH in CH$_2$Cl$_2$ to obtain pure 266.2. (0.080 g, 71.18%). MS(ES): m/z 435.50 [M+H]$^+$.

Synthesis of Compound 266.3.

To a cooled solution of 266.2 (0.040 g, 9.2 mmol, 1.0 eq) and (1S,2S)-2-fluorocyclopropane-1-carboxylic acid (0.014 g, 1.38 mmol, 1.5 eq) in N,N-dimethylformamide (1 mL) at 0° C. was added ((1-[Bis(dimethylamino)methylene]-1H-1,2,3-triazolo[4,5-b]pyridinium 3-oxid hexafluorophosphate)) (0.070 g, 1.84 mmol, 2.0 eq) and N,N-Diisopropylethylamine (0.036 g, 2.76 mmol, 3.0 eq) and stirred the reaction mixture at 50° C. for 2 hr. Upon completion, reaction mixture was transferred into water and extracted with ethyl acetate. Organic layers were combined, dried over Na$_2$SO$_4$ and concentrated in vacuo to pressure to obtain crude product. This was purified by column chromatography and compound was eluted in 5% MeOH in CH$_2$Cl$_2$ to obtain pure 266.3. (0.036 g, 75.12%). MS(ES): m/z 521.57 [M+H]$^+$.

Synthesis of Compound I-266.

Compound I-266 was synthesized from 266.3 using general procedure C. (Yield: 82.83%). MS(ES): m/z: 437.47 [M+H]$^+$, LCMS purity: 96.03%, HPLC purity 93.50%, Chiral HPLC: 100%, 1H NMR (DMSO-d6, 400 MHz): 12.39 (s, 1H), 10.57 (s, 1H), 8.57 (s, 1H), 7.84 (s, 1H), 7.76 (s, 1H), 7.58-7.52 (m, 2H), 7.27-7.23 (t, J=7.6 Hz, 1H), 4.97-4.80 (m, 1H), 4.01 (s, 3H), 3.73 (s, 3H), 2.52 (s, 3H), 2.19 (s, 1H), 1.63-1.58 (m, 1H), 1.12-1.09 (m, 1H).

Synthesis of Compound 267.1.

To a solution of 266.2 (0.040 g, 9.2 mmol, 1.0 eq) and (1S,2S)-2-fluorocyclopropane-1-carboxylic acid (0.014 g, 1.38 mmol, 1.5 eq) in N,N-dimethylformamide (1 mL) and cooled at 0° C. Added HATU ((1-[Bis(dimethylamino)methylene]-1H-1,2,3-triazolo[4,5-b]pyridinium 3-oxid hexafluorophosphate)) (0.070 g, 1.84 mmol, 2.0 eq) and N,N-Diisopropylethylamine (0.036 g, 2.76 mmol, 3.0 eq) and stirred the reaction mixture at 50° C. for 2 hr. Upon completion, reaction mixture was transferred into water and extracted with ethyl acetate. Organic layers were combined, dried over $Na_2SO_4$ and concentrated in vacuo to pressure to obtain crude product. This was purified by column chromatography and compound was eluted in 5% MeOH in $CH_2Cl_2$ to obtain pure 267.1. (0.028 g, 58.43%). MS(ES): m/z 521.57 $[M+H]^+$.

Synthesis of Compound I-267.

Compound I-267 was synthesized from 267.1 using general procedure C. (Yield: 93.73%). MS(ES): m/z: 437.60 $[M+H]^+$, LCMS purity: 98.74%, HPLC purity 97.53%, Chiral HPLC: 100%, 1H NMR (DMSO-d6, 400 MHz): 10.49 (s, 1H), 8.57 (s, 1H), 7.85 (s, 1H), 7.78 (s, 1H), 7.58-7.51 (m, 2H), 7.27-7.23 (t, J=8 Hz, 1H), 6.18-6.17 (d, J=5.2 Hz, 1H), 4.97 (s, 1H), 3.97 (s, 3H), 3.73 (s, 3H), 2.52 (s, 3H), 1.63-1.57 (m, 1H), 1.47-1.31 (m, 1H), 1.25 (s, 1H).

Example 268: Synthesis of (1S,2S)-2-fluoro-N-(2-methyl-7-((4-(1-methyl-1H-pyrazol-4-yl)-2-(N-methylmethylsulfonamido)phenyl)amino)-3H-imidazo[4,5-b]pyridin-5-yl)cyclopropane-1-carboxamide, I-268

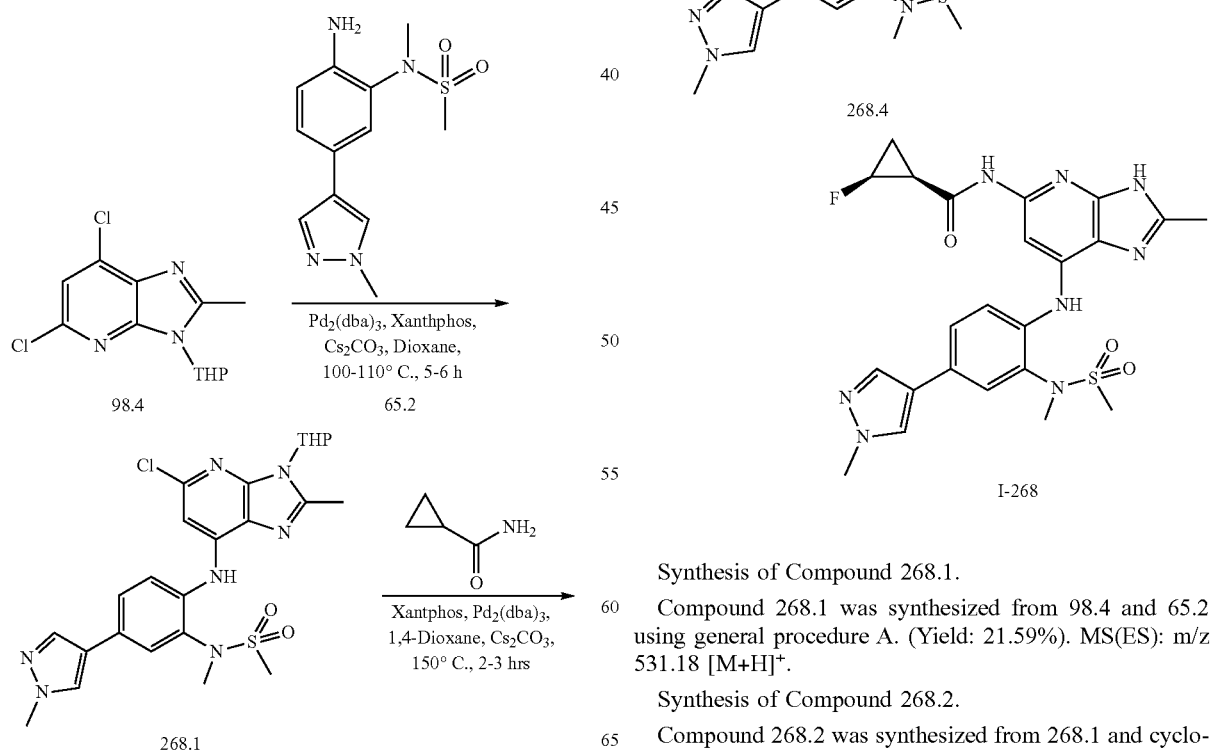

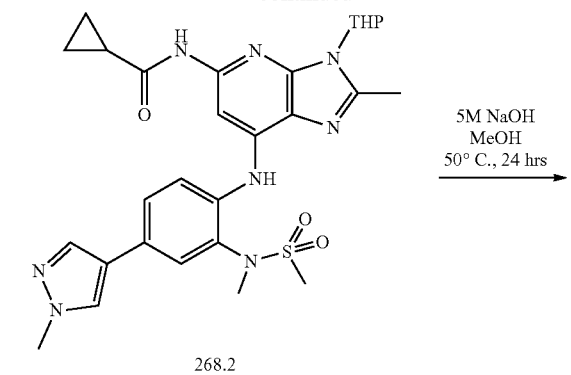

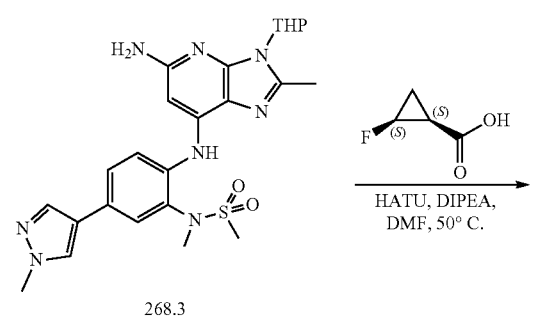

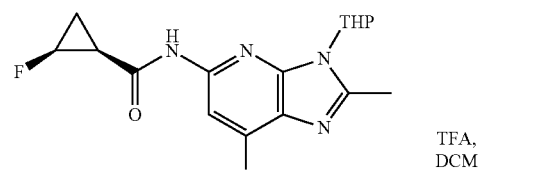

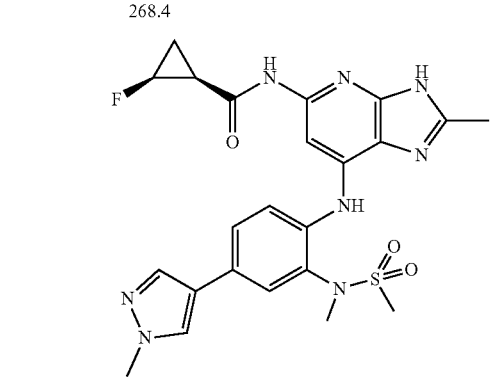

Synthesis of Compound 268.1.

Compound 268.1 was synthesized from 98.4 and 65.2 using general procedure A. (Yield: 21.59%). MS(ES): m/z 531.18 $[M+H]^+$.

Synthesis of Compound 268.2.

Compound 268.2 was synthesized from 268.1 and cyclopropanecarboxamide using general procedure A. (Yield: 51.52%). MS(ES): m/z 579.61 $[M+H]^+$.

Synthesis of Compound 268.3.

To compound 268.2 (0.225 g, 3.89 mmol, 1.0 eq) in MeOH was added 5M sodium hydroxide (3 ml). Reaction mixture was stirred at 50° C. for 24 h. Upon completion, reaction mixture was concentrated. The pH of the reaction mixture was adjusted to neutral using NaHCO₃ solution and then extracted with CH₂Cl₂. Organic layer combined, dried over Na₂SO₄, filtered and concentrated in vacuo to obtain crude product. This was purified by column chromatography using 2.5% MeOH in CH₂Cl₂ as eluant to obtain pure 268.3 (0.120 g, 60.44%). MS(ES): m/z 511.62 [M+H]⁺.

Synthesis of Compound 268.4.

To a solution of (1S,2S)-2-fluorocyclopropane-1-carboxylic acid (0.060 g, 0.11 mmol, 1.0 eq) in N,N'-dimethylformamide (1 mL) at 0° C. (1-[Bis(dimethylamino)methylene]-1H-1,2,3-triazolo[4,5-b]pyridinium 3-oxid hexafluorophosphate) (0.066 g, 0.17 mmol, 1.5 eq) was added into it. Reaction mixture was stirred at 0° C. for 30 min. Then, compound 268.3 (0.036 g, 0.35 mmol, 3.0 eq) and di-isopropylethylamine (0.037 g, 0.29 mmol, 2.5 eq) was added. Reaction mixture was stirred at r.t. for 2 h. After completion of reaction, the reaction mixture was transferred into cold water and extracted with ethyl acetate. Organic layer combined, dried over Na₂SO₄, filtered and concentrated in vacuo to obtain crude product. This was purified by column chromatography using 25% ethyl acetate in hexane as eluant to obtain pure 268.4 (0.038 g, 54.29%). MS(ES): m/z 596.68 [M+H]⁺.

Synthesis of I-268.

Compound I-268 was synthesized from 268.4 using general procedure C. (Yield: 70.46%). MS(ES): m/z: 513.51 [M+H]⁺, LCMS purity: 96.10%, HPLC purity: 96.21%, Chiral HPLC Purity: (100.00%), 1H NMR (MeOD, 400 MHz): 8.05 (s, 1H), 7.92 (s, 1H), 7.77 (s, 1H), 7.75 (s, 1H), 7.66 (s, 2H), 4.76-4.72 (m, 1H), 3.97 (s, 3H), 3.34 (s, 3H), 3.08 (s, 3H), 2.59 (s, 3H), 2.15 (s, 1H), 1.78-1.70 (m, 1H), 1.19-1.13 (m, 1H).

Example 269: Synthesis of (1R,2R)-2-fluoro-N-(2-methyl-7-((4-(1-methyl-1H-pyrazol-4-yl)-2-(N-methylmethylsulfonamido)phenyl)amino)-3H-imidazo[4,5-b]pyridin-5-yl)cyclopropane-1-carboxamide, I-269

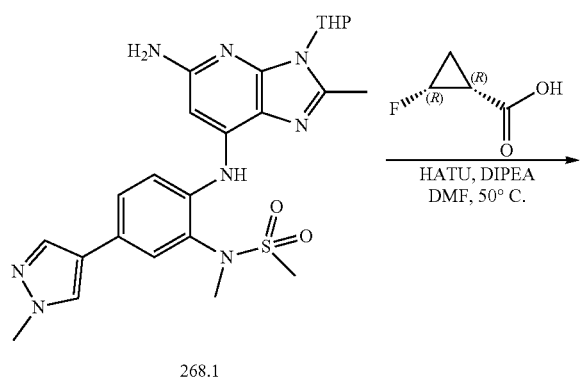

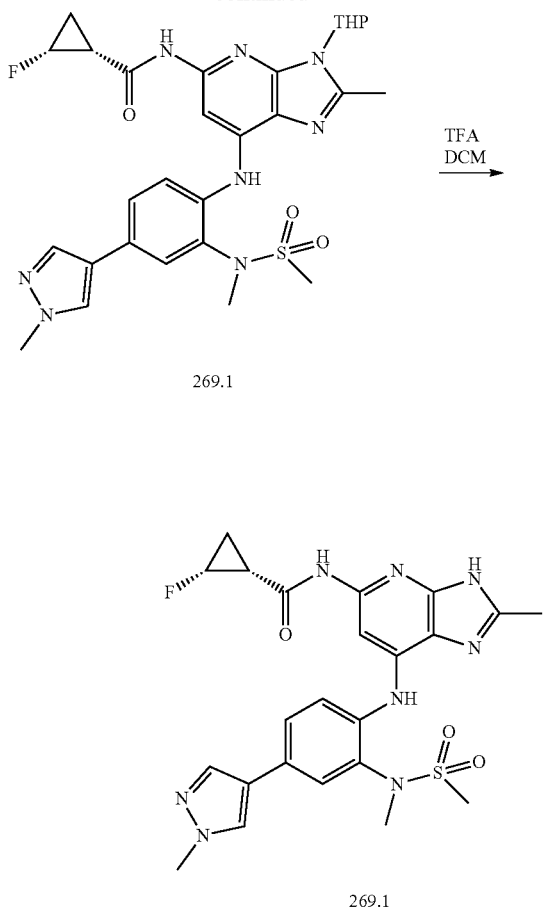

Synthesis of Compound 269.1.

To compound (1R,2R)-2-fluorocyclopropane-1-carboxylic acid (0.060 g, 0.11 mmol, 1.0 eq) in N,N'-dimethylformamide (1 mL) at 0° C., (1-[Bis(dimethylamino)methylene]-1H-1,2,3-triazolo[4,5-b]pyridinium 3-oxid hexafluorophosphate) (0.062 g, 0.16 mmol, 1.5 eq) was added. Reaction mixture was stirred at 0° C. for 30 min. Then, diisopropyl ethyl amine (0.035 g, 0.27 mmol, 2.5 eq) and compound 268.1 (0.014 g, 0.14 mmol, 1.2 eq) was added. Reaction mixture was stirred at 50° C. for 2 h. After completion of reaction, the reaction mixture was transferred into cold water and extracted by ethyl acetate. Organic layers were combined, dried over Na₂SO₄ and concentrated in vacuo to obtain crude product. This was purified by column chromatography and compound was eluted in 25% ethyl acetate in hexane as eluant to obtain pure 1.2 (0.035 g, 49.92%). MS(ES): m/z 597.68 [M+H]⁺.

Synthesis of I-269.

Compound I-269 was synthesized from 269.1 using general procedure C. (Yield: 76.50%). MS(ES): m/z: 513.51 [M+H]⁺, LCMS purity: 96.10%, HPLC purity: 96.21%, Chiral HPLC Purity: (100%), 1H NMR (MeOD, 400 MHz): 8.05 (s, 1H), 7.92 (s, 1H), 7.77 (s, 1H), 7.75 (s, 1H), 7.66 (s, 2H), 4.76-4.72 (m, 1H), 3.97 (s, 3H), 3.34 (s, 3H), 3.08 (s, 3H), 2.59 (s, 3H), 2.15 (s, 1H), 1.78-1.70 (m, 1H), 1.19-1.13 (m, 1H).

Example 270/271: (S)—N-(2-(difluoromethyl)-7-((4-(1-methyl-1H-imidazol-5-yl)-2-(N-methylmethylsulfonamido)phenyl)amino)-3H-imidazo[4,5-b]pyridin-5-yl)-2,2-difluorocyclopropane-1-carboxamide, I-270 and (R)—N-(2-(difluoromethyl)-7-((4-(1-methyl-1H-imidazol-5-yl)-2-(N-methylmethylsulfonamido)phenyl)amino)-3H-imidazo[4,5-b]pyridin-5-yl)-2,2-difluorocyclopropane-1-carboxamide, I-271

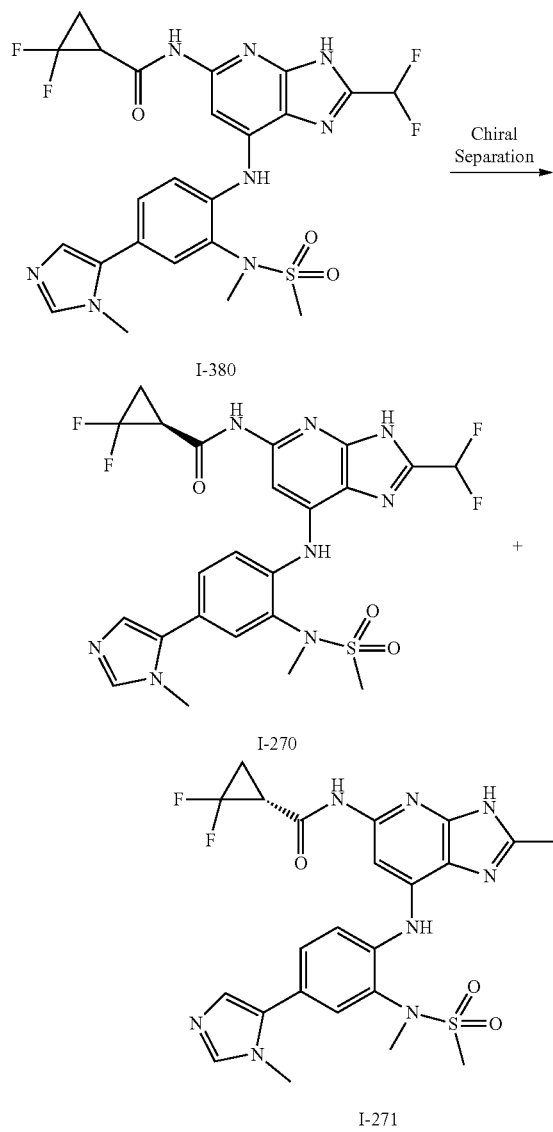

Synthesis of Compound I-270 and I-271.

Isomers of I-380 (0.105 g) were separated out using column (CHIRALPAK AD-H 250×4.6 mm, 5 µM) 0.1% NH3 in MeOH:ACN (30:70) as co-solvent with flow rate of 3 mL/min. to get pure fraction-1 (FR-a) and fraction-2 (FR-b). FR-a was concentrated in vacuo at 30° C. to afford pure I-270 (0.023 g). MS(ES): m/z 567.50 [M+H]$^+$, LCMS purity: 99.35%, HPLC Purity: 98.85%, Chiral HPLC: 100%, 1H NMR (DMSO, 400 MHz): 10.71 (s, 1H), 8.04 (s, 1H), 7.82 (s, 1H), 7.73-7.69 (m, 2H), 7.56-7.54 (m, 1H), 7.13 (s, 1H), 7.05 (t, 1H), 3.76 (s, 2H), 3.27 (s, 3H), 3.16 (s, 3H), 3.00 (s, 1H), 3.09 (s, 1H), 2.52 (s, 3H), 2.01-1.88 (m, 1H). FR-b was concentrated in vacuo at 30° C. to afford pure I-271 (0.027 g). MS(ES): m/z 567.50 [M+H]$^+$, LCMS purity: 99.00%, HPLC Purity: 99.13%, Chiral HPLC: 100%, 1H NMR (DMSO, 400 MHz): 10.71 (s, 1H), 8.12 (s, 1H), 7.84 (s, 1H), 7.75-7.74 (m, 2H), 7.716-7.695 (m, 1H), 7.579-7.558 (d, J=, 1H), 7.15 (t, 1H), 3.81 (s, 2H), 3.20 (s, 3H), 3.16 (s, 3H), 2.11 (s, 1H), 2.02-1.97 (m, 2H), 1.88 (s, 1H), 1.25 (s, 2H).

Example 272: Synthesis of N-(2-(difluoromethyl)-7-((2-(methylsulfonyl)-4-(tetrahydro-2H-pyran-4-yl)phenyl)amino)-3H-imidazo[4,5-b]pyridin-5-yl)-2,2-difluorocyclopropane-1-carboxamide, I-272

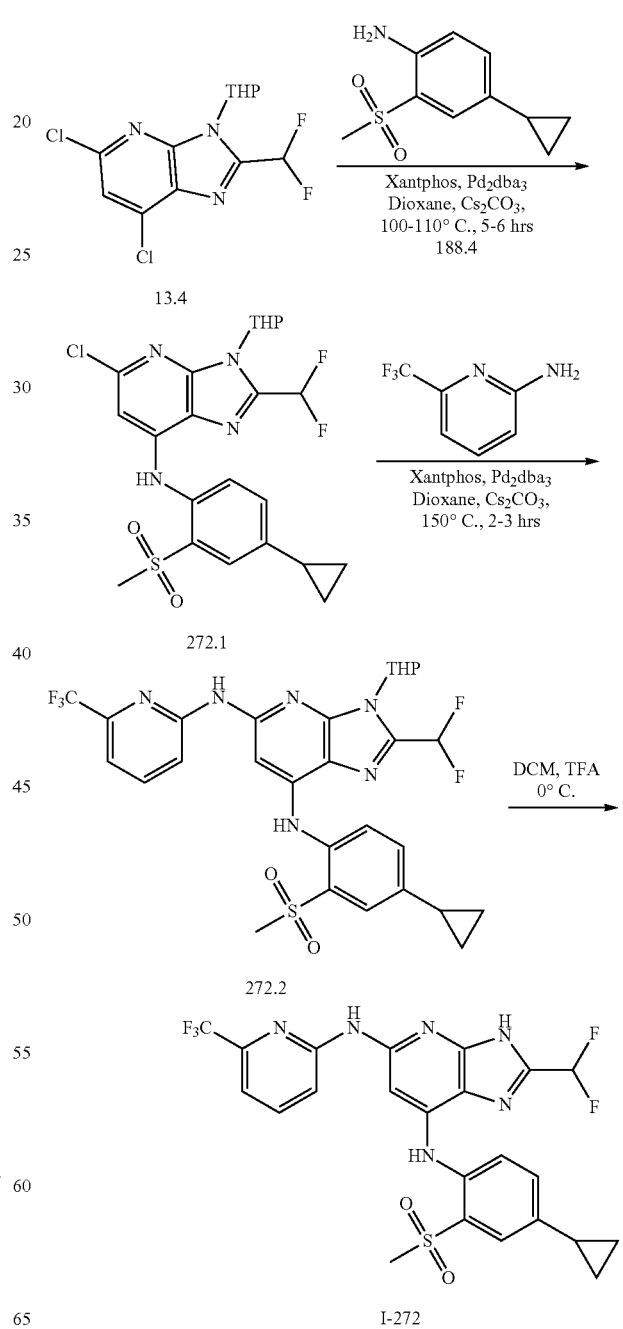

Synthesis of Compound 272.1.

Compound 272.1 was synthesized from 188.4 and 13.4 using general procedure A. (Yield: 17.29%). MS(ES): m/z 497.52 [M+H]⁺.

Synthesis of Compound 272.2.

Compound 272.2 was synthesized from 272.1 and 6-(trifluoromethyl)pyridin-2-amine using general procedure B. (Yield: 66.51%). MS(ES): m/z 623.47 [M+H]⁺.

Synthesis of compound I-272. Compound I-272 was synthesized from 272.2 using general procedure C (Yield: 80.93%). MS(ES): m/z 539.50 [M+H]⁺, LCMS purity: 99.34%, HPLC Purity: 100%, 1H NMR (DMSO-d6, 400 MHz): 13.67 (s, 1H), 9.99 (s, 1H), 8.62 (s, 1H), 8.25-8.23 (d, J=8.4 Hz, 1H), 7.92-7.88 (d, J=1.6 Hz, 1H), 7.75-7.73 (d, J=8.4, 1H), 7.65 (s, 1H), 7.42-7.40 (d, J=8.4 Hz, 2H), 7.28-7.26 (d, J=7.2 Hz, 1H), 7.13 (s, 1H), 3.21 (s, 3H), 2.12-2.06 (m, 1H), 1.07-1.02 (m, 2H), 0.76-0.72 (m, 2H).

Example 273: Synthesis of I-273

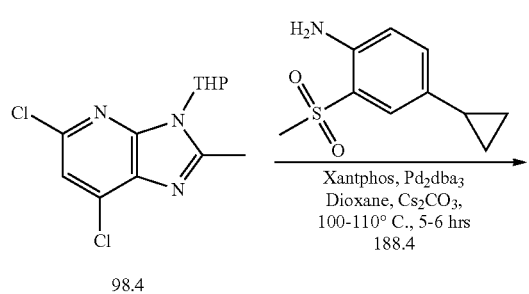

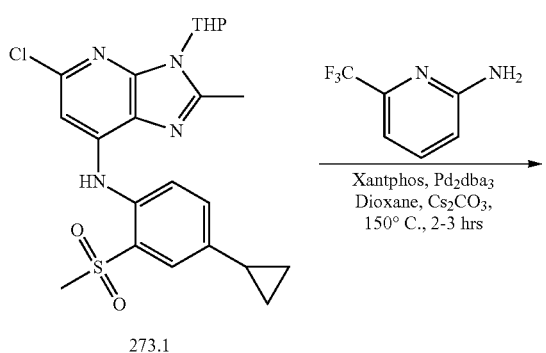

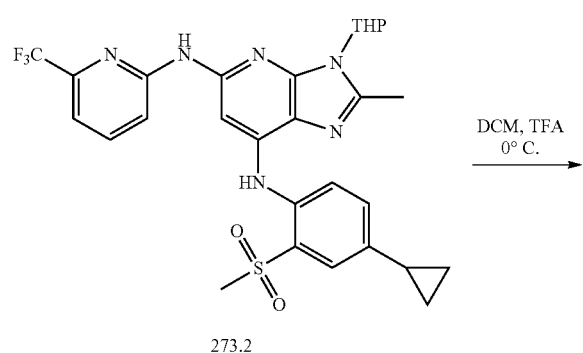

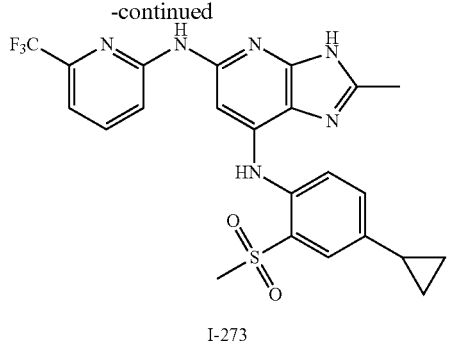

I-273

Synthesis of Compound 273.1.

Compound 273.1 was synthesized from 98.4 and 188.4 using general procedure A. (Yield: 17.29%). MS(ES): m/z 497.52 [M+H]⁺.

Synthesis of Compound 273.2.

Compound 273.2 was synthesized from 273.1 and cyclopropanecarboxamide using general procedure B. (Yield: 65.48%). MS(ES): m/z 587.43 [M+H]⁺.

Synthesis of Compound I-273.

Compound I-273 was synthesized from 273.2 using general procedure C. (Yield: 39.69%). MS(ES): m/z 503.41 [M+H]⁺, LCMS purity: 99.70%, HPLC Purity: 98.45%, 1H NMR (DMSO-d6, 400 MHz): 12.46 (s, 1H), 9.92 (s, 1H), 8.54 (s, 1H), 8.08-8.06 (d, J=8.0 Hz, 1H), 7.88-7.85 (t, J=1.2 Hz, 1H), 7.74-7.72 (s, 1H), 7.64 (s, 1H), 7.44-7.38 (m, 2H), 7.26-7.24 (d, J=8.4 Hz, 1H), 3.18 (s, 3H), 2.33 (s, 3H), 2.07 (s, 1H), 1.04-1.02 (d, J=8.4 Hz, 2H), 0.73-0.72 (d, J=4.0 Hz, 2H).

Example 274/275: Synthesis of (S)-2,2-difluoro-N-(2-methyl-7-((4-(1-methyl-1H-imidazol-5-yl)-2-(N-methylmethylsulfonamido)phenyl)amino)-3H-imidazo[4,5-b]pyridin-5-yl)cyclopropane-1-carboxamide, I-274 and (R)-2,2-difluoro-N-(2-methyl-7-((4-(1-methyl-1H-imidazol-5-yl)-2-(N-methylmethylsulfonamido)phenyl)amino)-3H-imidazo[4,5-b]pyridin-5-yl)cyclopropane-1-carboxamide, I-27

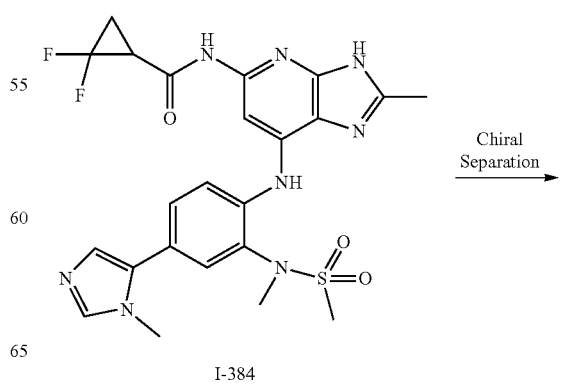

I-384

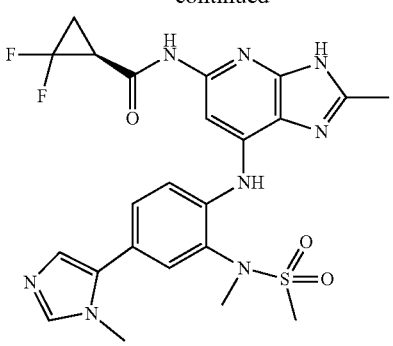

I-274

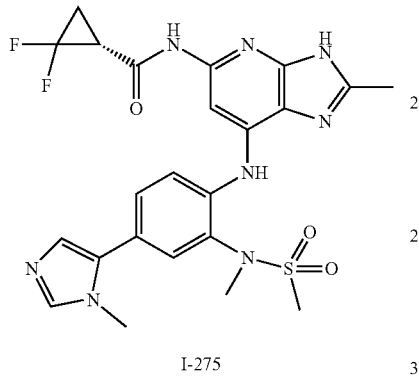

I-275

Synthesis of Compound I-274 and I-275.

Isomers of I-384 (0.090 g) were separated out using column (CHIRALPAK AD-H 250×4.6 mm, 5 μM) 0.1% NH3 in MeOH:ACN (30:70) as co-solvent with flow rate of 3 mL/min. to get pure fraction-1 (FR-a) and fraction-2 (FR-b). FR-a was concentrated in vacuo at 30° C. to afford pure I-274 (0.020 g). MS(ES): m/z 531.6 [M+H]+, LCMS purity: 97.57%, HPLC Purity: 99.85%, Chiral HPLC: 100%, 1H NMR (DMSO, 400 MHz): 10.74 (s, 1H), 8.05 (s, 1H), 7.84 (s, 1H), 7.758-7.745 (d, J=5.2 Hz, 2H), 7.65 (s, 1H), 7.567-7.549 (d, J=7.2 Hz, 1H), 7.14 (s, 1H), 3.76 (s, 3H), 3.26 (s, 3H), 3.14 (s, 3H), 2.99-2.96 (m, 2H), 2.00 (s, 3H), 1.69 (s, 1H), 0.87 (s, 1H). FR-b was concentrated in vacuo at 30° C. to afford pure I-275 (0.023 g). MS(ES): m/z 529.31 [M+H]+, LCMS purity: 98.87%, HPLC Purity: 98.06%, Chiral HPLC: 100%, 1H NMR (DMSO, 400 MHz): 10.73 (s, 1H), 8.06 (s, 1H), 7.83 (s, 1H), 7.75-7.74 (m, 2H), 7.67-7.65 (m, 1H), 7.56-7.54 (m, 1H), 7.14 (s, 1H), 3.76 (s, 3H), 3.26 (s, 3H), 3.14 (s, 3H), 2.04-1.96 (m, 3H), 1.65 (s, 1H), 1.25-1.21 (m, 2H), 1.10-1.08 (s, 1H).

Example 276: Synthesis of 6-((2-(difluoromethyl)-7-((4-(1,5-dimethyl-1H-pyrazol-3-yl)-2-(methylsulfonyl)phenyl)amino)-3H-imidazo[4,5-b]pyridin-5-yl)amino)picolinonitrile, I-276

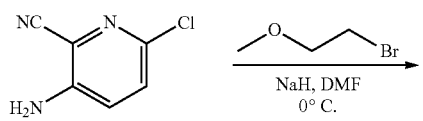

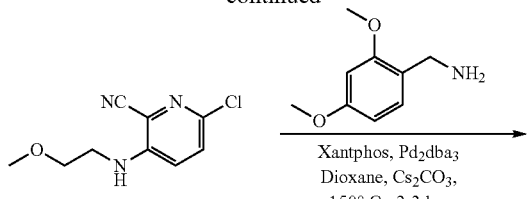

276.1

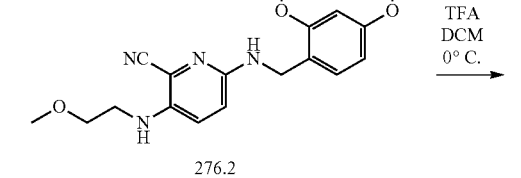

276.2

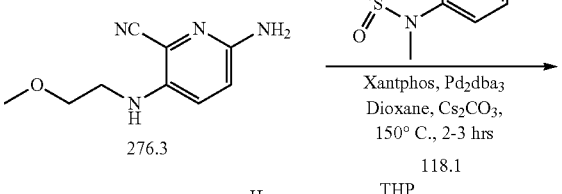

276.3

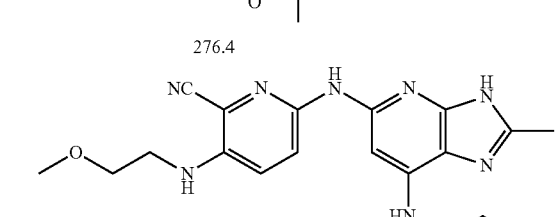

I-276

Synthesis of Compound 276.1.

To compound 3-amino-6-chloropicolinonitrile (3 g, 1.96 mmol, 1.0 eq) in N,N'-dimethylformamide (30 mL) at 0° C., was added compound 1-bromo-2-methoxyethane (3.24 g, 2.35 mmol, 1.2 eq). Then, sodium hydride (0.940 g, 3.92 mmol, 2.0 eq) was added into it. Reaction mixture was stirred at 0° C. for 5 h. After completion of reaction, the reaction mixture was transferred into cold water and with extracted by ethyl acetate. Organic layer combined, dried over Na2SO4 and concentrated in vacuo to obtain crude product. This was purified by column chromatography and compound was eluted in 30% ethyl acetate in hexane as eluant to obtain pure 276.1 (1.8 g, 43.54%). MS(ES): m/z 212.65 [M+H]⁺.

Synthesis of Compound 276.2.

Compound 276.2 was synthesized from 276.1 and (2,4-dimethoxyphenyl)methanamine using general procedure B. (Yield: 20.60%). MS(ES): m/z 343.40 [M+H]⁺.

Synthesis of Compound 276.3

Compound 276.3 was synthesized using from 276.2 general procedure C. (Yield: 57.64%). MS(ES): m/z: 179.20 [M+H]⁺.

Synthesis of Compound 276.4.

Compound was synthesized from 276.3 and 118.1 using general procedure B. (Yield: 30.76%). MS(ES): m/z 606.72 [M+H]⁺.

Synthesis of I-276.

Compound I-276 was synthesized from 276.4 using general procedure C (Yield: 59.94%). MS(ES): m/z 522.56 [M+H]⁺, LCMS purity: 99.52%, HPLC Purity: 99.55%, ¹H NMR (DMSO, 400 MHz): 12.25 (s, 1H), 9.31 (s, 1H), 7.86-7.75 (m, 3H), 7.65-7.63 (d, 1H), 7.53-7.50 (d, 2H), 7.41-7.38 (m, 2H), 7.19-7.15 (d, 1H), 5.72 (s, 1H), 3.50 (s, 3H), 3.29 (s, 3H), 3.22 (s, 3H), 3.13 (s, 3H), 2.45 (s, 3H).

Example 277: Synthesis of N-(2-((5-((6-cyano-5-((2-methoxyethyl)amino)pyridin-2-yl)amino)-2-methyl-3H-imidazo[4,5-b]pyridin-7-yl)amino)phenyl)-N-methylmethanesulfonamide, I-277

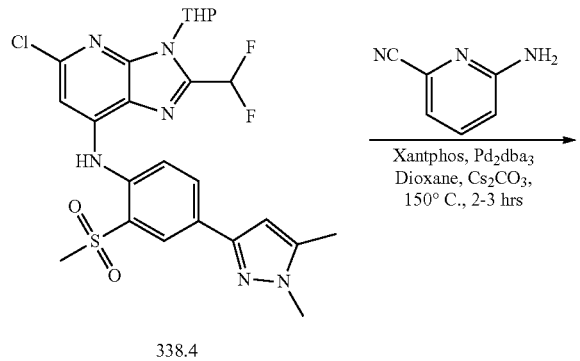

338.4

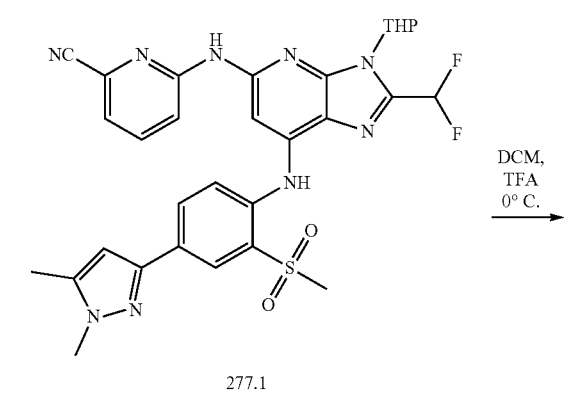

277.1

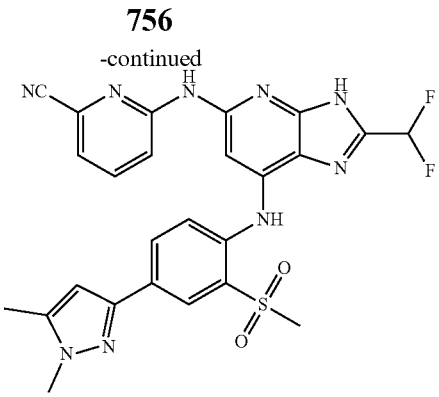

I-277

Synthesis of Compound 277.1.

Compound 277.1 was synthesized from 338.4 and 6-aminopicolinonitrile using general procedure B. (Yield: 10.44%). MS(ES): m/z 634.68 [M+H]⁺.

Synthesis of I-277.

Compound I-277 was synthesized from 277.1 using general procedure C. (Yield: 69.18%). MS(ES): m/z 550.70 [M+H]⁺, LCMS purity: 98.88%, HPLC Purity: 98.11%, 1H NMR (DMSO, 400 MHz): 13.76 (s, 1H), 10.19 (s, 1H), 8.88 (s, 1H), 8.31 (s, 1H), 8.17-8.12 (m, 2H), 7.97-7.87 (m, 2H), 7.6 (s, 1H), 7.49-7.47 (d, J=7.2 Hz, 1H), 6.53 (s, 1H), 3.81 (s, 3H), 3.27 (s, 3H), 2.32 (s, 3H), 1.24 (s, 1H).

Example 278/279: Synthesis of (R)-2,2-difluoro-N-(2-methyl-7-((2-(methylsulfonyl)-4-((S)-tetrahydro-2H-pyran-2-yl)phenyl)amino)-3H-imidazo[4,5-b]pyridin-5-yl)cyclopropane-1-carboxamide, I-278 and (S)-2,2-difluoro-N-(2-methyl-7-((2-(methylsulfonyl)-4-((S)-tetrahydro-2H-pyran-2-yl)phenyl)amino)-3H-imidazo[4,5-b]pyridin-5-yl)cyclopropane-1-carboxamide, I-279

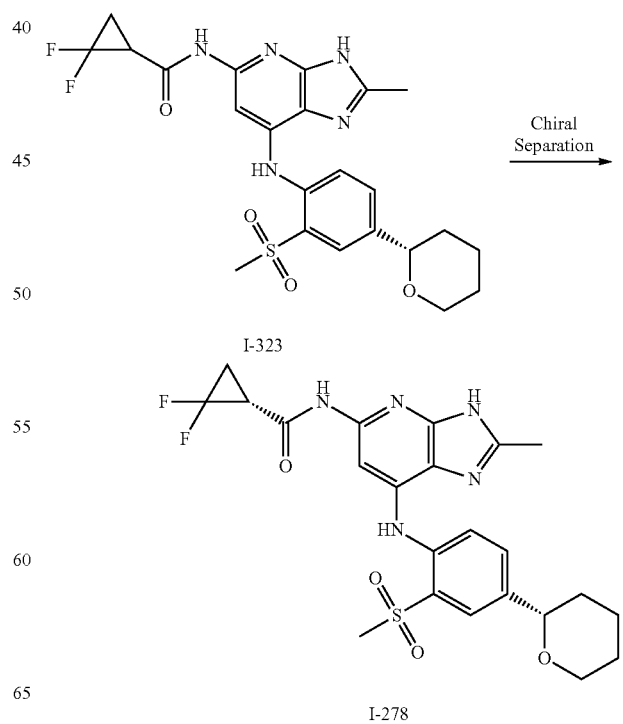

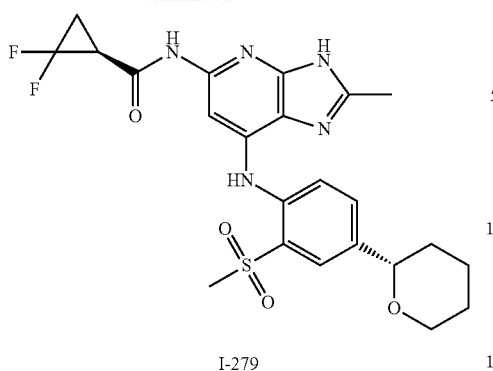

I-279

Synthesis of Compound I-278 and I-279.

Isomers of I-323 (0.075 g) were separated out using column (CHIRAL CEL OX-H 250×4.6 mm, 5 μM) 0.1 DEA in IPA as co-solvent with flow rate of 4 mL/min. to get pure fraction-1 (FR-a) and fraction-2 (FR-b). FR-a was concentrated in vacuo at 30° C. to afford pure I-278 (0.022 g). MS(ES): m/z 506.56 [M+H]$^+$, LCMS purity: 99.54%, HPLC Purity: 99.14%, Chiral HPLC Purity: 97.07%, 1H NMR (DMSO, 400 MHz): 12.57 (s, 1H), 10.82 (s, 1H), 8.57 (s, 1H), 7.94-7.88 (d, J=27.2 Hz, 2H), 7.75-7.68 (m, 2H), 4.44-4.41 (d, J=10.4 Hz, 1H), 4.08-4.05 (d, J=10.8 Hz, 1H), 3.60-3.56 (m, 1H), 3.19 (s, 3H), 2.95 (s, 1H), 1.98 (s, 2H), 1.90 (s, 3H), 1.58 (s, 2H), 1.24 (bs, 4H). FR-b was concentrated in vacuo at 30° C. to afford pure I-279 (0.020 g). MS(ES): m/z 506.68 [M+H]$^+$, LCMS purity: 94.45%, HPLC Purity: 95.96%, Chiral HPLC: 98.15%, 1H NMR (DMSO, 400 MHz): 12.65 (s, 1H), 10.82 (s, 1H), 8.57 (s, 1H), 7.94-7.88 (m, 2H), 7.72-7.70 (m, 2H), 4.44-4.41 (d, J=10.4 Hz, 1H), 4.08-4.05 (d, J=10.8 Hz, 1H), 3.57 (s, 1H), 3.19 (s, 3H), 2.00-1.86 (m, 6H), 1.64-1.58 (m, 2H), 1.24 (bs, 4H).

Example 280/281: Synthesis of (R)—N-(2-(difluoromethyl)-7-((2-(methylsulfonyl)-4-((R)-tetrahydro-2H-pyran-2-yl)phenyl)amino)-3H-imidazo[4,5-b]pyridin-5-yl)-2,2-difluorocyclopropane-1-carboxamide, I-280 and(S)—N-(2-(difluoromethyl)-7-((2-(methylsulfonyl)-4-((R)-tetrahydro-2H-pyran-2-yl)phenyl)amino)-3H-imidazo[4,5-b]pyridin-5-yl)-2,2-difluorocyclopropane-1-carboxamide, I-281

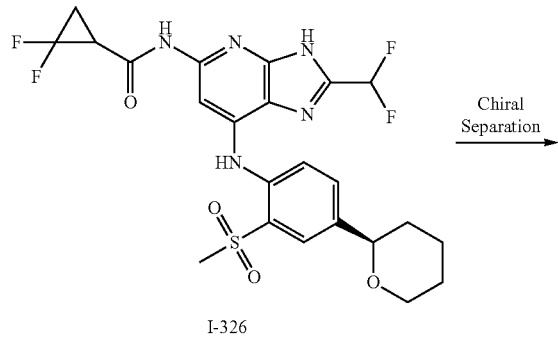

I-326

→ Chiral Separation

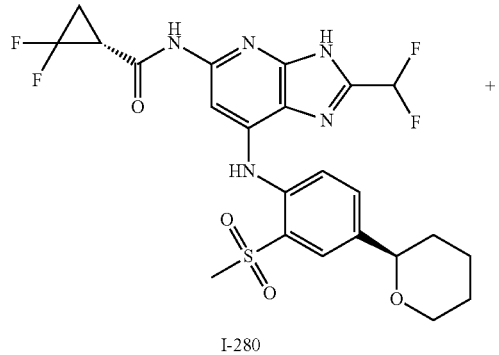

I-280

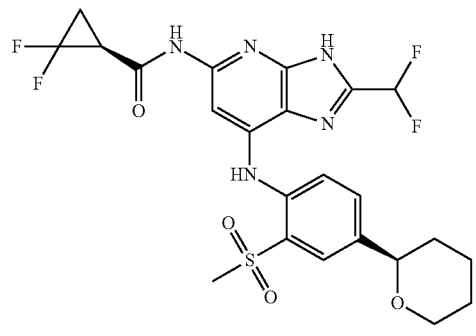

I-281

Synthesis of Compounds I-280 and I-281.

Isomers of I-326 (0.075 g) were separated out using column (CHIRALCEL OX-H (250 mm*4.6 mm, 5u) and 0.1% DEA IPA flow rate of 4 mL/min. to get pure fraction-1 (FR-a) and fraction-2 (FR-b). FR-a was concentrated in vacuo at 30° C. to afford pure I-280 (0.022 g). MS(ES): m/z 542.75 [M+H]$^+$, LCMS purity: 98.84%, HPLC Purity: 99.52%, Chiral HPLC: 97.65%, 1H NMR (DMSO-d6, 400 MHz): 13.78 (s, 1H), 10.97 (s, 1H), 8.76 (s, 1H), 7.99 (s, 1H), 7.91 (s, 1H), 7.77-7.71 (m, 2H), 7.26 (t, 1H), 4.46-4.43 (d, J=7.2 Hz, 1H), 4.09-4.06 (d, J=7.2 Hz, 1H), 3.61-3.54 (s, 1H), 3.21 (s, 3H), 1.99 (bs, 2H), 1.98-1.89 (m, 2H), 1.58 (s, 2H), 1.50-1.44 (m, 1H), 1.24 (s, 2H). FR-b was concentrated in vacuo at 30° C. to afford pure I-281 (0.022 g). MS(ES): m/z 542.75 [M+H]$^+$, LCMS purity: 95.09%, HPLC Purity: 94.35%, Chiral HPLC: 97.58%, 1H NMR (DMSO-d6, 400 MHz): 13.78 (s, 1H), 10.97 (s, 1H), 8.76 (s, 1H), 7.98-7.91 (s, 2H), 7.75-7.71 (m, 2H), 7.26 (t, 1H), 4.46-4.43 (d, J=7.2 Hz, 1H), 4.09-4.06 (d, 1H), 3.58 (s, 1H), 3.21 (s, 3H), 1.98 (bs, 2H), 1.92-1.90 (m, 2H), 1.58 (s, 2H), 1.24 (s, 3H).

Example 282: Synthesis of (1S,2S)—N-(7-((4-(4,4-dimethyl-4,5-dihydrooxazol-2-yl)-2-(methylsulfonyl)phenyl)amino)-2-methyl-3H-imidazo[4,5-b]pyridin-5-yl)-2-fluorocyclopropane-1-carboxamide, I-282

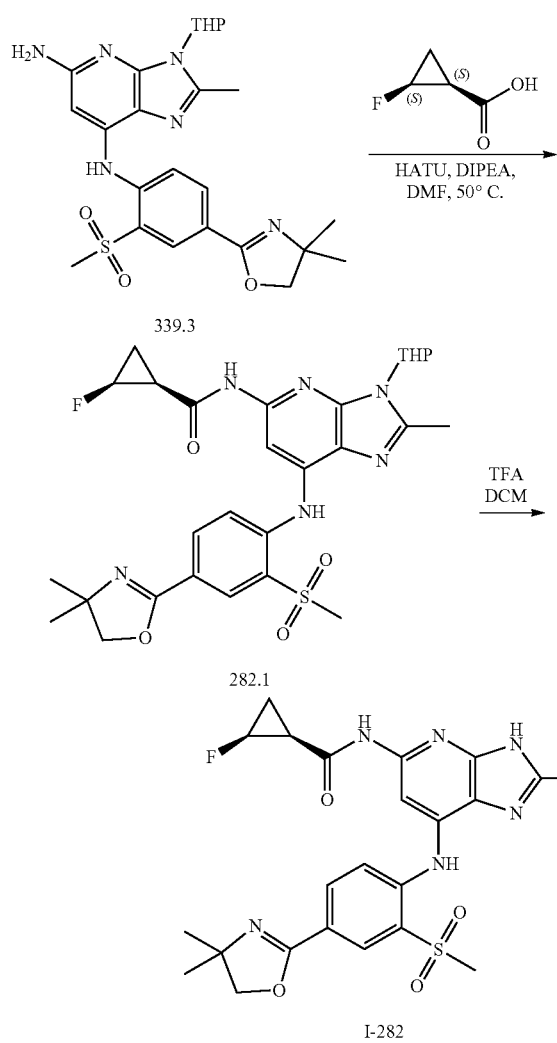

Synthesis of Compound 282.1.

To a solution of (1S,2S)-2-fluorocyclopropane-1-carboxylic acid (0.30 g, 0.27 mmol, 1.5 eq) in N,N-dimethylformamide (3 mL) at 0° C., 1-[Bis(dimethylamino)methylene]-1H-1,2,3-triazolo[4,5-b]pyridinium3-oxid hexafluorophosphate (0.138 g, 0.36 mmol, 2.0 eq) was added. Reaction mixture was allowed to stir for 15 min at 0° C. Then, diisopropylethylamine (0.0070 g, 0.54 mmol, 3.0 eq) and compound 339.3 (0.090 g, 0.18 mmol, 1.0 eq) was added. Reaction mixture was stirred at 50° C. for 5 h. After completion of the reaction, the reaction mixture was transferred to water and extracted with ethyl acetate. Organic layers were combined, dried over anhydrous $Na_2SO_4$, filtered and concentrated in vacuo to get the crude material. This was purified by column chromatography using 2% MeOH in $CH_2Cl_2$ as eluant to obtain pure 283.1 (0.030 g, 28.43%). MS(ES): m/z 585.47 $[M+H]^+$.

Synthesis of Compound I-282.

Compound I-282 was synthesized from 282.1 using general procedure C. (Yield: 83.95%). MS(ES): m/z 501.56 $[M+H]^+$, LCMS purity: 97.65%, HPLC Purity: 94.34%, Chiral HPLC: 95.66%, 1H NMR (DMSO-d6, 400 MHz): 12.60 (s, 1H), 10.71 (s, 1H), 8.83 (s, 1H), 8.31 (s, 1H), 8.07 (s, 2H), 7.82 (s, 1H), 4.99 (s, 1H), 4.82 (s, 1H), 4.15 (s, 2H), 3.28 (s, 3H), 2.20 (s, 1H), 2.09 (s, 1H), 1.65-1.59 (d, J=2.32 Hz, 2H), 1.30 (s, 6H), 1.14 (s, 1H).

Example 283: Synthesis of N-(2-(difluoromethyl)-7-((4-(5,5-dimethyl-4,5-dihydrooxazol-2-yl)-2-(methylsulfonyl)phenyl)amino)-3H-imidazo[4,5-b]pyridin-5-yl)cyclopropanecarboxamide, I-283

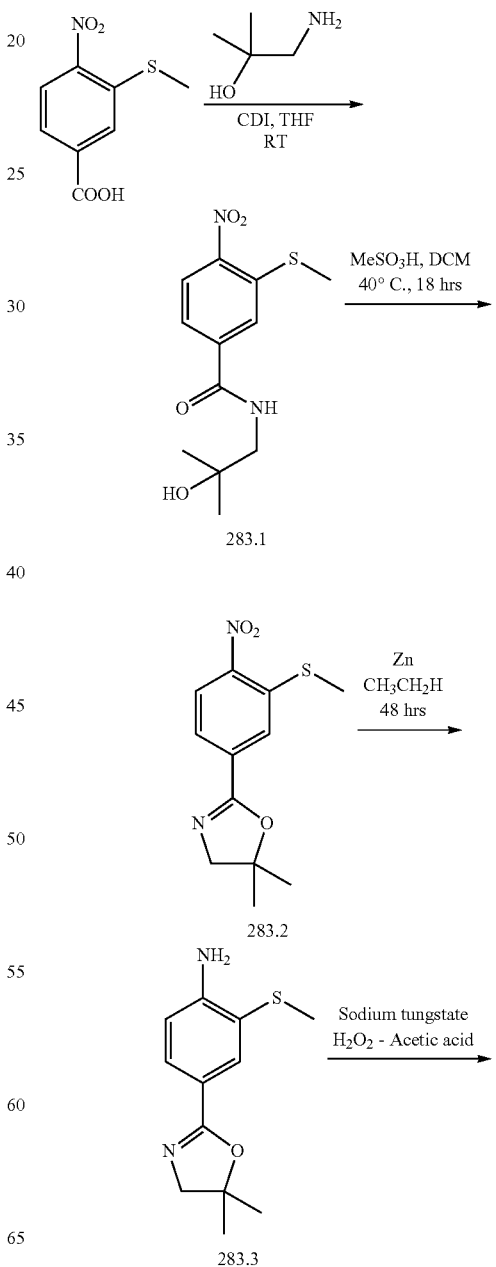

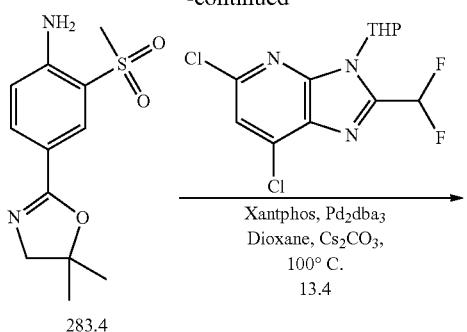

283.4

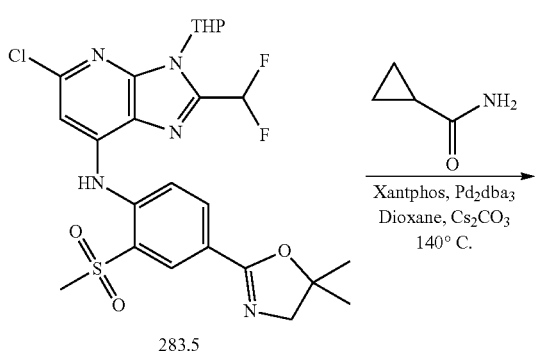

283.5

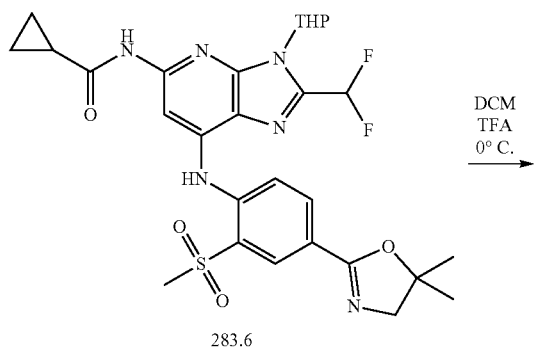

283.6

I-283

Synthesis of Compound 283.1.

A solution of 3-(methylthio)-4-nitrobenzoic acid (5 g, 23.45 mmol, 1 eq), 1,1'-Carbonyldiimidazole (5.70 g, 3.520 mmol, 1.5 eq) in tetrahydrofuran (50 mL) was stirred for 3 h at r.t. 1-amino-2-methylpropan-2-ol (2.51 g, 28.16 mmol, 1.2 eq) was added into the reaction mixture at r.t. Reaction mixture stirred for 30 min. Upon completion, reaction mixture was transferred into ethyl acetate and washed with 0.2M HCl. Organic layer again washed with saturated bicarbonate solution. Organic layers were combined, dried over $Na_2SO_4$ and concentrated in vacuo to obtain crude product. This was purified by column chromatography and compound was eluted in 10% MeOH in $CH_2Cl_2$ as eluent to obtain 283.1 (3.2 g, 47.99%). MS(ES): m/z 285.33 $[M+H]^+$.

Synthesis of Compound 283.2.

To a solution of 283.1 (3 g, 10.55 mmol, 1 eq), in $CH_2Cl_2$ (150 mL), was added methane sulphonic acid (6.08 g, 63.38 mmol, 6 eq), drop wise at 0° C. Reaction mixture was heated at 40° C. for 18 h. Upon completion, reaction mixture was transferred into saturated bicarbonate solution and extracted with $CH_2Cl_2$. Organic layers were combined, dried over $Na_2SO_4$ and concentrated in vacuo to obtain crude product. This was purified by trituration with diethyl ether to obtain 283.2 (2.3 g, 81.85%). MS(ES): m/z 267.32 $[M+H]^+$.

Synthesis of Compound 283.3.

To a solution of 283.2 (2.3 g, 8.64 mmol, 1 eq), in Acetic acid (24 mL), was added zinc dust (2.82 g, 43.23 mmol, 5 eq) portion wise. Reaction mixture was stirred at r.t. for 16 h. After completion of reaction, the reaction mixture was transferred into $NaHCO_3$ solution and extracted with ethyl acetate. Combined Organic layer dried over $Na_2SO_4$ and concentrated in vacuo to obtain crude product. This was purified by trituration with diethyl ether to obtain 283.3 (1.9 g, 93.09%). MS(ES): m/z 237.33 $[M+H]^+$.

Synthesis of Compound 283.4.

To a solution of 283.3 (1.9 g, 8.04 mmol, 1 eq) in acetic acid (19 mL) was added 30% hydrogen peroxide (5.47 g, 0.1610 mmol, 20.0 eq) and sodium tungstate dehydrate (2.35 g, 8.04 mmol, 1 eq). Reaction mixture was stirred at r.t. for 2 h. Upon completion, reaction mixture was transferred in ice-water and precipitated product was filtered, washed with 50% ethyl acetate in hexane and dried well to obtain 283.4 (1.2 g, Yield: 55.63%). MS(ES): m/z 269.33 $[M+H]^+$.

Synthesis of Compound 283.5.

Compound 283.5 was synthesized from 283.4 and 13.4 using general procedure A. (Yield: 19.94%). MS(ES): m/z 555.01 $[M+H]^+$.

Synthesis of Compound 283.6.

Compound 283.6 was synthesized from 283.5 and cyclopropanecarboxamide using general procedure B. (Yield: 45.96%). MS(ES): m/z 603.66 $[M+H]^+$.

Synthesis of Compound I-283.

Compound I-283 was synthesized from 286.3 using general procedure C (Yield: 61.99%). MS(ES): m/z 519.51 $[M+H]^+$, LCMS purity: 94.75%, HPLC Purity: 95.96%, 1H NMR (DMSO, 400 MHz): 13.76 (s, 1H), 10.85 (s, 1H), 8.98 (s, 1H), 8.31 (s, 1H), 8.21 (s, 1H), 8.12-8.11 (d, J=7.6 Hz, 1H), 7.87-7.85 (d, J=8.4 Hz, 1H), 3.74 (s, 2H), 3.30 (s, 3H), 2.05 (s, 2H), 1.47 (s, 6H), 0.82 (bs, 4H).

Example 284: Synthesis of N-(7-((4-(5,5-dimethyl-4,5-dihydrooxazol-2-yl)-2-(methylsulfonyl)phenyl)amino)-2-methyl-3H-imidazo[4,5-b]pyridin-5-yl)cyclopropanecarboxamide, I-284

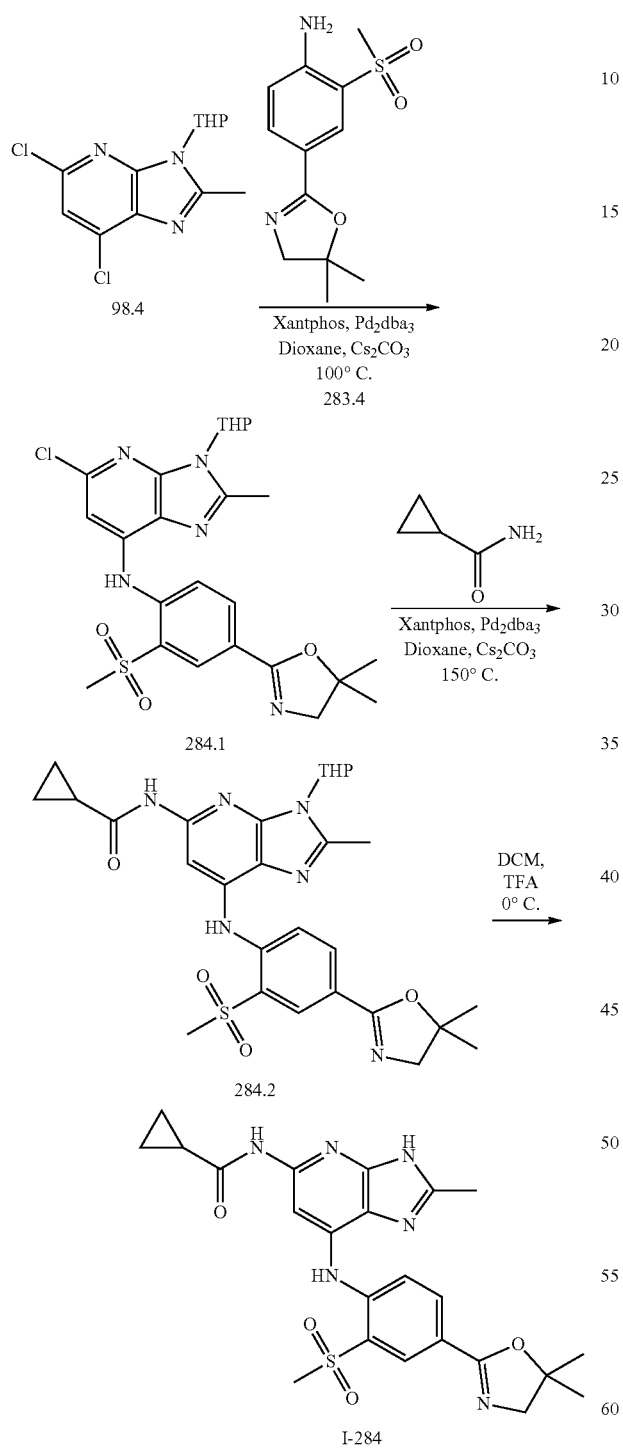

Synthesis of Compound 284.1.

Compound 284.1 was synthesized from 98.4 and 283.4 using general procedure A. (Yield: 25.78%). MS(ES): m/z 519.03 [M+H]$^+$.

Synthesis of Compound 284.2.

Compound 284.2 was synthesized from 284.1 and cyclopropanecarboxamide using general procedure B. (Yield: 45.71%). MS(ES): m/z 567.68 [M+H]$^+$.

Synthesis of Compound I-284.

Compound I-284 was synthesized from 284.2 using general procedure C. (Yield: 50.33%). MS(ES): m/z 482.61 [M−H]+, LCMS purity: 100%, HPLC Purity: 96.35%, 1H NMR (DMSO, 400 MHz): 12.58 (s, 1H), 10.67 (s, 1H), 8.83 (s, 1H), 8.28 (s, 1H), 8.09-8.07 (m, 2H), 7.82-7.80 (d, J=8.8 Hz, 1H), 3.72 (s, 2H), 3.27 (s, 3H), 2.49 (s, 3H), 2.01-2.00 (m, 1H), 1.46 (s, 6H), 0.79-0.77 (s, 4H).

Example 285: Synthesis of N-(7-((4-cyclopropyl-2-(dimethylphosphoryl)phenyl)amino)-2-(difluoromethyl)-3H-imidazo[4,5-b]pyridin-5-yl)cyclopropanecarboxamide, I-285

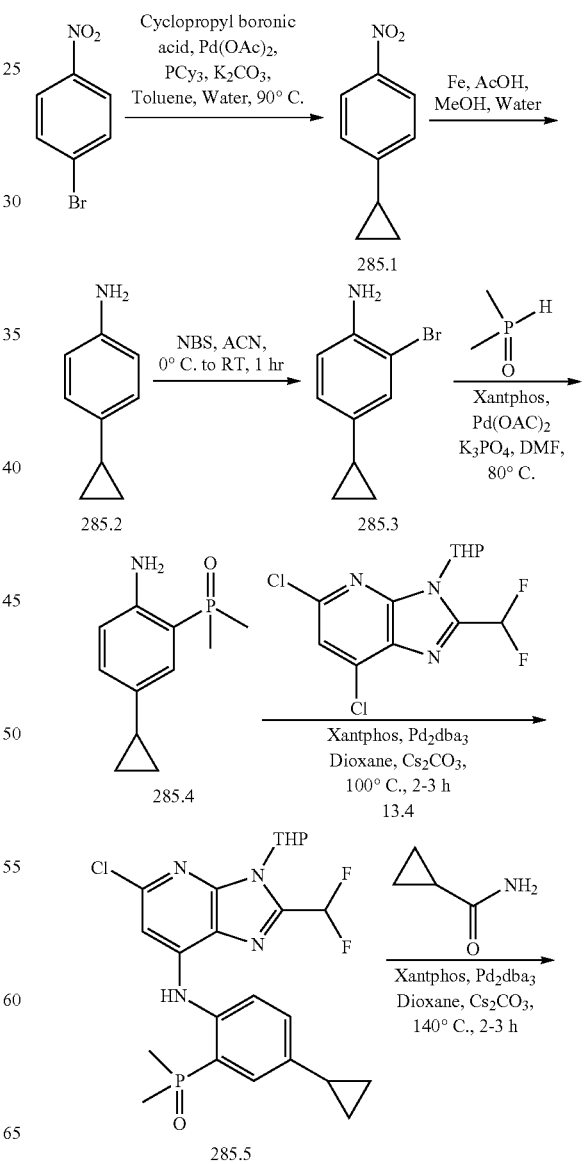

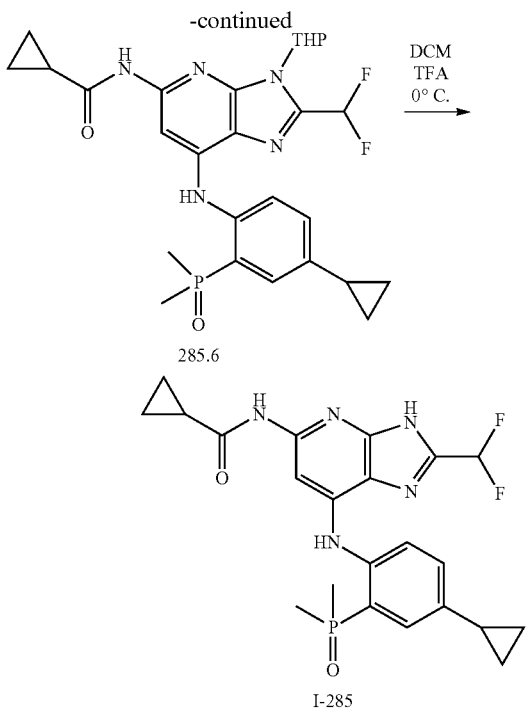

Synthesis of Compound 285.1.

To a solution of 1-bromo-4-nitrobenzene (5.0 g, 24.75 mmol, 1.0 eq) and cyclopropyl boronic acid (3.19 g, 37.12 mmol, 1.5 eq) in toluene (40 mL) and water (10 mL) was added potassium carbonate (10.24 g, 74.25 mmol, 3.0 eq). The reaction mixture was degassed for 10 min. under argon atmosphere. To this palladium acetate (0.56 g, 2.475 mmol, 0.1 eq) and Tricyclohexylphosphine (1.39 g, 4.95 mmol, 0.2 eq) were added, again degassed for 10 min. under argon atmosphere. The reaction was stirred at 100° C. for 3 h. Upon completion, reaction mixture was transferred in water and extracted with ethyl acetate. Combined organic layer was washed with brine, dried over $Na_2SO_4$ and concentrated in vacuo to obtain crude product. This was purified by column chromatography using 5% ethyl acetate in hexane to obtain pure 285.1 (3.0 g, 74.28%). MS(ES): m/z 164.18 [M+H]$^+$.

Synthesis of Compound 285.2.

To a solution of 285.1 (2.5 g, 15.32 mmol, 1.0 eq) in mixture of MeOH (20 mL) and water (5 mL) was added acetic acid (5 mL) followed by iron powder (3.0 g). Reaction mixture was stirred at 100° C. for 2 h. Upon completion, reaction mixture was transferred into water and extracted with ethyl acetate. Combined organic layer was washed with brine, dried over $Na_2SO_4$ and concentrated in vacuo to obtain crude product. This was purified by column chromatography using 30% ethyl acetate in hexane to obtain pure 285.2 (2.0 g, 98.01%). MS(ES): m/z 134.19 [M+H]$^+$.

Synthesis of Compound 285.3.

To a solution of 285.2 (1.4 g, 10.51 mmol, 1.0 eq) in acetonitrile (20 mL) was added N-Bromosuccinimide (2.43 g, 13.66 mmol, 1.3 eq) at 0° C. Reaction mixture was stirred at r.t. for 2 h. Upon completion, reaction mixture was transferred into water and extracted with ethyl acetate. Combined organic layer was washed with brine, dried over $Na_2SO_4$ and concentrated in vacuo to obtain crude product. This was purified by column chromatography using 5% ethyl acetate in hexane to obtain pure 285.3 (1.8 g, 80.74%). MS(ES): m/z 213.09 [M+H]$^+$.

Synthesis of Compound 285.4.

To a solution of 285.3 (1.3 g, 6.13 mmol, 1.0 eq) and dimethyl phosphine oxide (0.526 g, 6.74 mmol, 1.1 eq) in N,N-dimethylformamide (13 mL) was added potassium phosphate (2.6 g, 12.26 mmol, 2.0 eq). The reaction mixture was degassed for 10 min. under argon atmosphere. The palladium acetate (0.13 g, 0.613 mmol, 0.1 eq) and Xantphos (0.71 g, 1.226 mmol, 0.2 eq) were added, again reaction mixture was degassed for 10 min. under argon atmosphere. The reaction was stirred at 100° C. for 3 h. Upon completion, reaction mixture was transferred in water and extracted with ethyl acetate. Combined organic layer was washed with brine, dried over $Na_2SO_4$ and concentrated in vacuo to obtain crude product. This was purified by column chromatography using 5% MeOH in $CH_2Cl_2$ to obtain pure 285.4 (0.56 g, 43.67%). MS(ES): m/z 210.23 [M+H]$^+$.

Synthesis of Compound 285.5.

Compound 285.5 was synthesized from 285.4 and 13.4 using general procedure A. (Yield: 18.60%). MS(ES): m/z 495.91 [M+H]$^+$.

Synthesis of Compound 285.6.

Compound 285.6 was synthesized from 285.5 and cyclopropanecarboxamide using general procedure B. (Yield: 74.50%). MS(ES): m/z 544.56 [M+H]$^+$.

Synthesis of I-285.

Compound I-285 was synthesized from 285.6 using general procedure C. (Yield: 56.53%). MS(ES): m/z 460.71 [M+H]$^+$, LCMS purity: 98.61%, HPLC Purity: 97.50%, 1H NMR (DMSO, 400 MHz): 13.49 (s, 1H), 10.62 (s, 1H), 9.92 (s, 1H), 7.93 (s, 1H), 7.49-7.46 (m, 1H), 7.34-7.30 (m, 1H), 7.265-7.244 (d, J=8.4 Hz, 1H), 2.01-1.94 (s, 3H), 1.782-1.698 (d, J=3.6 Hz, 6H), 0.98-0.94 (d, J=18.8 Hz, 2H), 0.76-0.73 (m, 6H).

Example 286: Synthesis of N-(7-((4-cyclopropyl-2-(dimethylphosphoryl)phenyl)amino)-2-methyl-3H-imidazo[4,5-b]pyridin-5-yl)cyclopropanecarboxamide, I-286

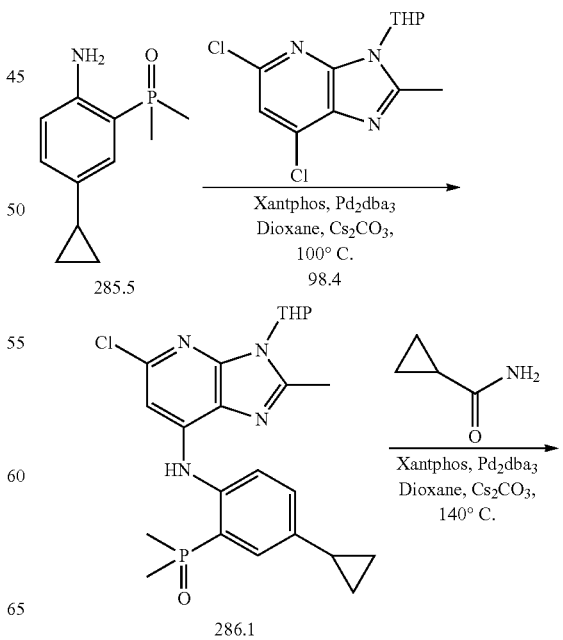

767

-continued

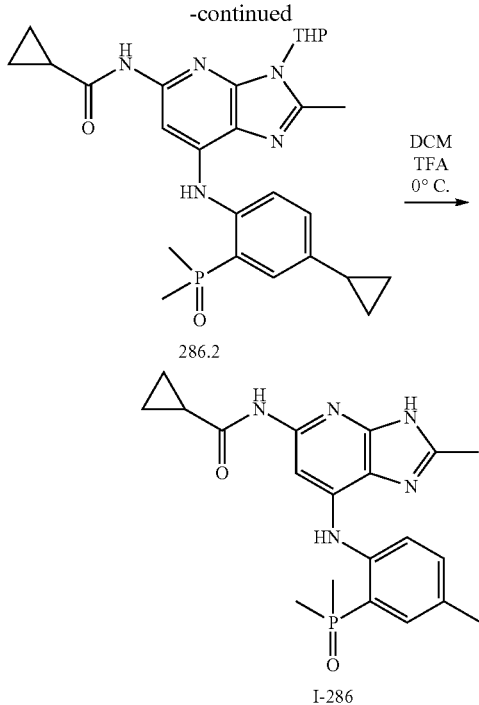

286.2

DCM
TFA
0° C.

I-286

Synthesis of Compound 286.1.

Compound 286.1 was synthesized from 285.4 and 98.4 using general procedure A. (Yield: 18.24%). MS(ES): m/z 459.93 [M+H]⁺.

Synthesis of Compound 286.2.

Compound 286.2 was synthesized from 286.1 and cyclopropanecarboxamide using general procedure B. (Yield: 76.85%). MS(ES): m/z 508.57 [M+H]⁺.

Synthesis of I-286.

Compound I-286 was synthesized from 286.2 using general procedure C. (Yield: 50.77%). MS(ES): m/z 424.60 [M+H]⁺, LCMS purity: 96.17%, HPLC Purity: 97.56%, 1H NMR (DMSO, 400 MHz): 12.31 (s, 1H), 10.44 (s, 1H), 9.59 (s, 1H), 7.80 (s, 1H), 7.44-7.38 (m, 2H), 7.28-7.21 (m, 2H), 2.45 (s, 3H), 1.980-1.969 (m, 2H), 1.734-1.663 (d, J=28.4 Hz, 6H), 0.968-0.952 (d, J=6.4 Hz, 2H), 0.889-0.855 (t, J=13.6 Hz, 1H), 0.74 (s, 4H).

Example 287: Synthesis of N-(7-((4-(1-cyclopropyl-1H-pyrazol-3-yl)-2-(methylsulfonyl)phenyl)amino)-2-(difluoromethyl)-3H-imidazo[4,5-b]pyridin-5-yl)cyclopropanecarboxamide, I-287

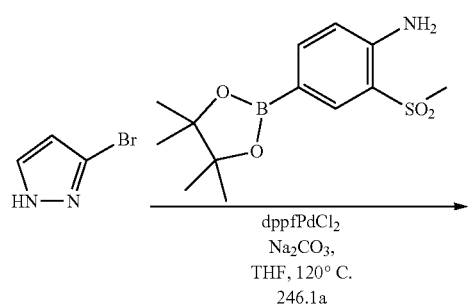

dppfPdCl₂
Na₂CO₃,
THF, 120° C.
246.1a

768

-continued

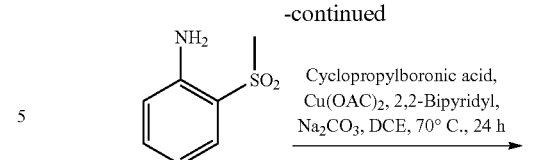

287.1

Cyclopropylboronic acid,
Cu(OAc)₂, 2,2-Bipyridyl,
Na₂CO₃, DCE, 70° C., 24 h

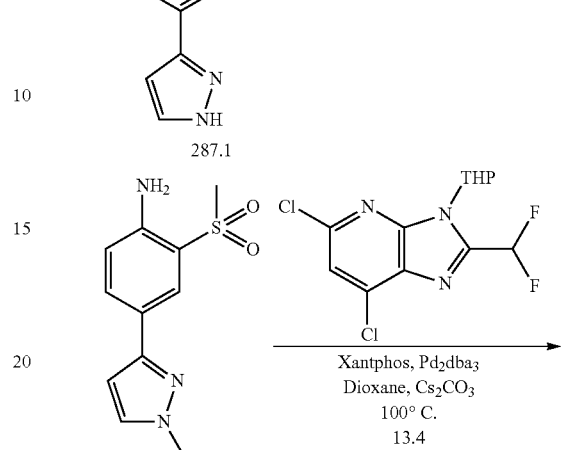

287.2

Xantphos, Pd₂dba₃
Dioxane, Cs₂CO₃
100° C.
13.4

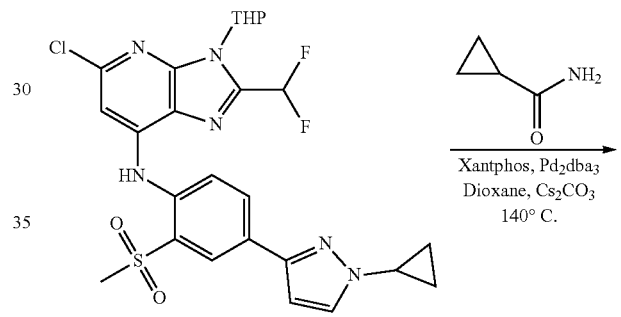

287.3

Xantphos, Pd₂dba₃
Dioxane, Cs₂CO₃
140° C.

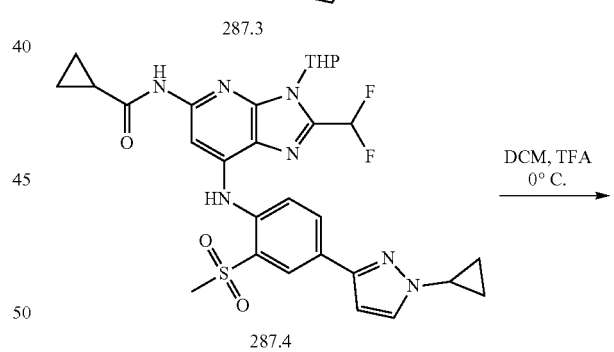

287.4

DCM, TFA
0° C.

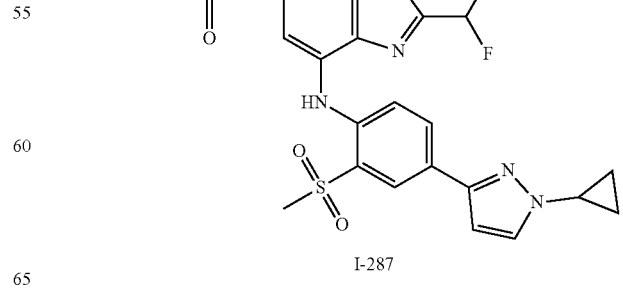

I-287

Synthesis of Compound 287.1

To compound 246.1a (4 g, 15.9 mmol, 1.0 eq) and compound 1.2 (3.69 g, 17.5 mmol, 1.1 eq) in tetrahydrofuran (32 mL), sodium carbonate (4.3 g, 31.8 mmol, 2.0 eq) was added. Reaction mixture was degassed for 5 min. Then, [1,1'-Bis(diphenylphosphino)ferrocene]dichloropalladium (II) (1.16 g, 1.59 mmol, 0.1 eq) was added and again degassed for 5 min. Reaction mixture was stirred at 120° C. for 4 h. After completion of the reaction, the reaction mixture was transferred to water and extracted with ethyl acetate. Organic layers were combined, dried over anhydrous Na$_2$SO$_4$, filtered and concentrated in vacuo to get the crude material. This was purified by column chromatography using 13% ethyl acetate in hexane as eluant to obtain 287.1 (2.0 g, 15.49%). MS(ES): m/z 238.46 [M+H]$^+$.

Synthesis of Compound 287.2.

To compound 287.1 (0.28 g, 1.18 mmol, 1.0 eq) in dichloroethane (8 mL), cyclopropyl boronic acid (0.2 g, 2.36 mmol, 2.0 eq), copper acetate (0.21 g, 1.18 mmol, 1.0 eq), 2,2'-bipyridine (0.18 g, 1.18 mmol, 1.0 eq) were added. Oxygen was purged through the reaction mixture for 10-15 min at r.t. Reaction mixture was stirred at 80° C. for 24 h. After completion of the reaction, the reaction mixture was filtered and washed with ethyl acetate. Filtrate was concentrated in vacuo to obtain 287.2 (0.114 g, 34.83%). MS(ES): m/z 278.43 [M+H]$^+$.

Synthesis of Compound 287.3.

Compound 287.3 was synthesized from 287.2 and 13.4 using general procedure A. (Yield: 13.14%). MS(ES): m/z 564.45 [M+H]$^+$.

Synthesis of Compound 287.4.

Compound 287.4 was synthesized from 287.3 and cyclopropanecarboxamide using general procedure B. (Yield: 64.43%). MS(ES): m/z 612.57 [M+H]$^+$.

Synthesis of Compound I-287.

Compound I-287 was synthesized from 287.4 using general procedure C. (Yield: 92.76%). MS(ES): m/z 528.56 [M+H]$^+$, LCMS purity: 99.24%, HPLC Purity: 99.41%, 1H NMR (DMSO-d6, 400 MHz): 13.68 (s, 1H), 10.77 (s, 1H), 8.81 (s, 1H), 8.32 (s, 1H), 8.14-8.10 (m, 2H), 7.88 (s, 1H), 7.82-7.79 (d, J=8.4 Hz, 1H), 7.26 (s, 1H), 6.38 (s, 1H), 3.81-3.77 (m, 1H), 3.25 (s, 3H), 2.04 (s, 1H), 1.11 (s, 2H), 1.02-1.00 (d, J=5.6 Hz, 2H), 0.79 (s, 4H).

Example 288: Synthesis of N-(2-(difluoromethyl)-7-((2-(methylsulfonyl)-4-(4-methylthiazol-2-yl)phenyl)amino)-3H-imidazo[4,5-b]pyridin-5-yl)cyclopropanecarboxamide, I-288

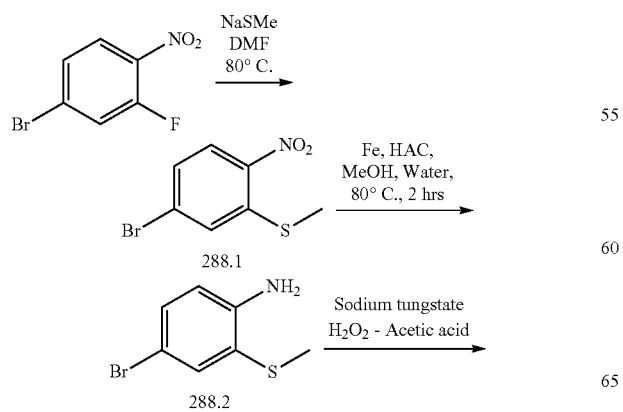

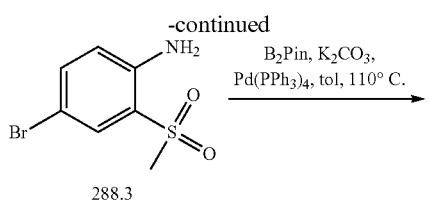

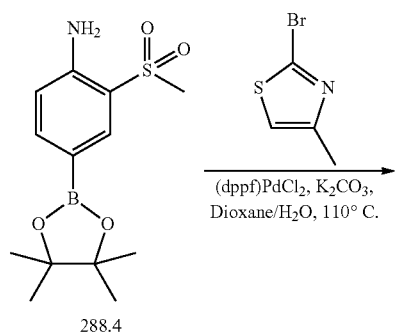

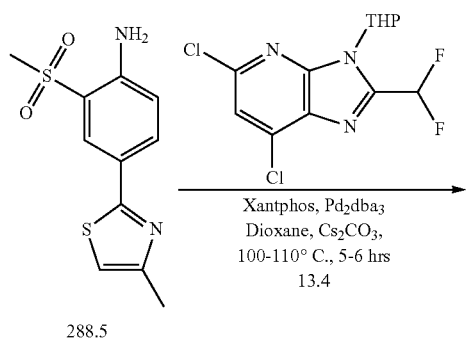

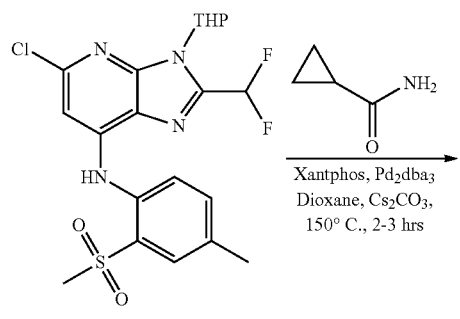

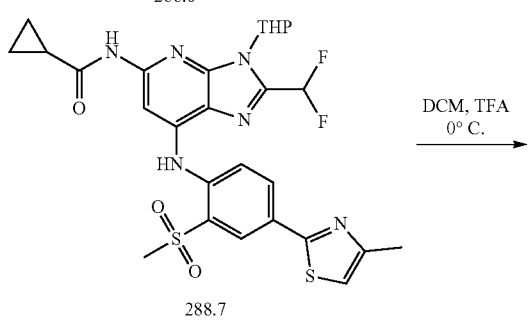

-continued

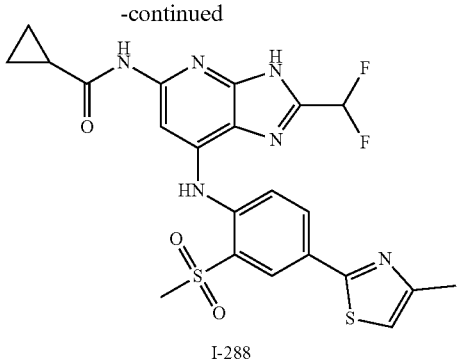

I-288

Synthesis of Compound 281.1.

To a solution of 4-bromo-2-fluoro-1-nitrobenzene (3.0 g, 13.64 mmol, 1.0 eq) in N,N-dimethylformamide (30 mL) at 0° C., sodium methanethiolate (1.72 g, 24.55 mmol, 1.8 eq) was added dropwise. Reaction mixture was stirred at 0° C. for 40 min. After completion of the reaction, the solid obtained in the reaction mixture, was filtered and dried under vacuum to obtain 288.1 (3.0 g, 88.68%) MS(ES): m/z 249.09 [M+H]$^+$.

Synthesis of Compound 288.2.

To compound 288.1 (3.0 g, 12.09 mmol, 1.0 eq) in a mixture of MeOH (4 mL) and water (1.1 mL), acetic acid (10.88 g, 181.35 mmol, 15.0 eq) was added. Reaction mixture was allowed to stir at 50-60° C. for 1 h. After 1 h, iron powder (4.62 g, 84.1 mmol, 7.0 eq) was added in portions. Reaction mixture was further allowed to stir at 90° C. for 2 h. After completion of the reaction, the reaction mixture was diluted with MeOH and filtered through celite bed. The filtrate was concentrated in vacuo to get the crude material. This was purified by column chromatography using 15-20% ethyl acetate in hexane as eluant to obtain pure 288.2 (2.1 g, 79.62%). MS(ES): m/z 219.11 [M+H]$^+$.

Synthesis of Compound 288.3.

To compound 288.2 (2.1 g, 9.63 mmol, 1.0 eq) in acetic acid (21 mL), sodium tungstate (2.84 g, 9.65 mmol, 1.005 eq) was added portionwise. Reaction mixture was allowed to stir at r.t. for 5 min. Then, 30% hydrogen peroxide solution (18 mL) was added dropwise at r.t. Reaction mixture was allowed to stir at r.t. for 10 min. After completion of the reaction, the reaction mixture was transferred to water. The pH of the solution was adjusted to 7 by using saturated NaHCO$_3$ and then extracted with ethyl acetate. Organic layers were combined, dried over anhydrous Na$_2$SO$_4$, filtered and concentrated in vacuo to get the crude material. This was purified by column chromatography using 10-13% ethyl acetate in hexane as eluant to obtain pure 288.3 (1.2 g, 49.83%). MS(ES): m/z 251.11 [M+H]$^+$.

Synthesis of Compound 288.4.

To compound 288.3 (1 g, 4.0 mmol, 1.0 eq) and 4,4,5,5-Tetramethyl-1,3,2-dioxaborolane (1.79 g, 10.1 mmol, 1.5 eq) in tetrahydrofuran (10 mL), potassium carbonate (1.1 g, 8.0 mmol, 2.0 eq) was added. Argon was purged through the reaction mixture for 5 min. Then, [1,1'-Bis(diphenylphosphino)ferrocene]dichloro-palladium(II) (0.29 g, 0.4 mmol, 0.1 eq) was added and again purged for 5 min. Reaction mixture was stirred at 120° C. for 4 h. After completion of the reaction, the reaction mixture was transferred to water and extracted with ethyl acetate. Organic layers were combined, dried over anhydrous Na$_2$SO$_4$, filtered and concentrated in vacuo to get the crude material. This was purified by column chromatography using 12% ethyl acetate in hexane as eluant to obtain 288.4 (0.8 g, 67.33%). MS(ES): m/z 298.18 [M+H]$^+$.

Synthesis of Compound 288.5.

To compound 1 (2 g, 6.7 mmol, 1.0 eq) and compound 1.5 (1.79 g, 10.1 mmol, 1.5 eq) in mixture of 1,4-dioxane (16 mL) and water (4 mL), sodium carbonate (1.41 g, 13.4 mmol, 2.0 eq) was added. Argon was purged through the reaction mixture for 5 min. Then, [1,1'-Bis(diphenylphosphino)ferrocene]dichloropalladium(II) (0.54 g, 0.67 mmol, 0.1 eq) was added and again purged for 5 min. Reaction mixture was stirred at 120° C. for 4 h. After completion of the reaction, the reaction mixture was transferred to water and extracted with ethyl acetate. Organic layers were combined, dried over anhydrous Na$_2$SO$_4$, filtered and concentrated in vacuo to get the crude material. This was purified by column chromatography using 12% ethyl acetate in hexane as eluant to obtain 288.5 (0.9 g, 66.45%). MS(ES): m/z 269.46 [M+H]$^+$.

Synthesis of Compound 288.6.

Compound 288.6 was synthesized from 13.4 and 288.5 using general procedure A. (Yield: 23.65%). MS(ES): m/z 555.38 [M+H]$^+$.

Synthesis of Compound 288.7.

Compound 288.7 was synthesized from 288.6 and cyclopropanecarboxamide using general procedure B. (Yield: 46.72%). MS(ES): m/z 603.37 [M+H]$^+$.

Synthesis of I-288.

Compound I-288 was synthesized from 288.7 using general procedure C. (Yield: 56.24%). MS(ES): m/z 519.56 [M+H]$^+$, LCMS purity: 99.24%, HPLC Purity: 99.41%, 1H NMR (DMSO-d6, 400 MHz): 13.76 (s, 1H), 10.85 (s, 1H), 8.98 (s, 1H), 8.45 (s, 1H), 8.24-8.21 (d, 2H), 7.90-7.88 (d, J=8.4 Hz 1H), 7.41 (s, 1H), 7.15 (t, 1H), 3.32 (s, 3H), 2.47 (s, 3H), 2.06 (bs, 1H), 0.82 (bs, 4H).

Example 289: Synthesis of N-(2-methyl-7-((2-(methylsulfonyl)-4-(4-methylthiazol-2-yl)phenyl)amino)-3H-imidazo[4,5-b]pyridin-5-yl)cyclopropanecarboxamide, I-289

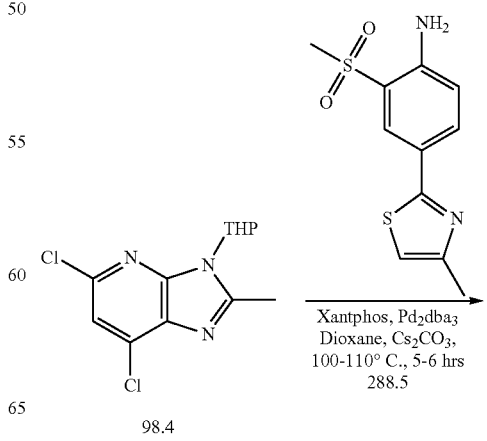

-continued

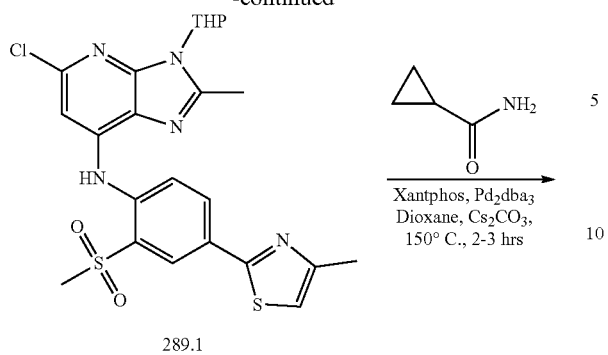

289.1

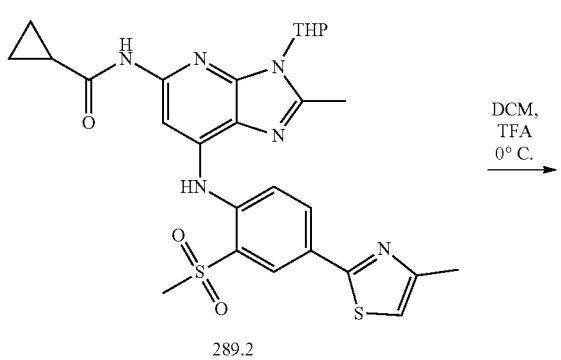

289.2

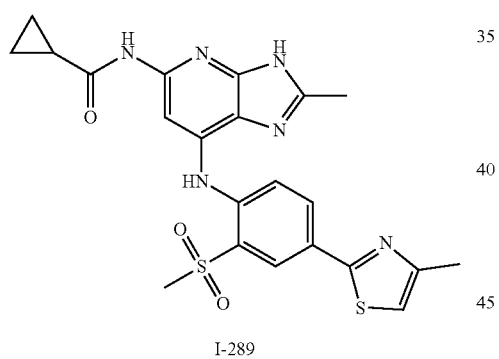

I-289

Synthesis of Compound 289.1.

Compound 289.1 was synthesized from 98.4 and 288.5 using general procedure A. (Yield: 26.12%). MS(ES): m/z 519.47 [M+H]⁺.

Synthesis of Compound 289.2.

Compound 289.2 was synthesized from 289.1 and cyclopropanecarboxamide using general procedure B. (Yield: 54.08%). MS(ES): m/z 567.28 [M+H]⁺.

Synthesis of Compound I-289.

Compound I-289 was synthesized from 289.2 using general procedure C. (Yield: 68.50%). MS(ES): m/z 483.62 [M+H]⁺, LCMS purity: 98.31%, HPLC Purity: 98.61%, 1H NMR (DMSO-d6, 400 MHz): 13.12 (s, 1H), 10.75 (s, 1H), 8.76 (s, 1H), 8.19-8.17 (d, J=6.8 Hz, 1H), 8.04 (s, 1H), 7.76-7.74 (d, J=8.4 Hz, 1H), 7.38 (s, 1H), 3.30 (s, 3H), 2.57 (s, 3H), 2.45 (s, 4H), 2.01-1.96 (m, 1H), 0.79 (s, 4H).

Example 290: Synthesis of 2-(difluoromethyl)-N7-(4-(1,5-dimethyl-1H-pyrazol-3-yl)-2-(methylsulfonyl)phenyl)-N5-(6-(trifluoromethyl)pyridin-2-yl)-3H-imidazo[4,5-b]pyridine-5,7-diamine, I-290

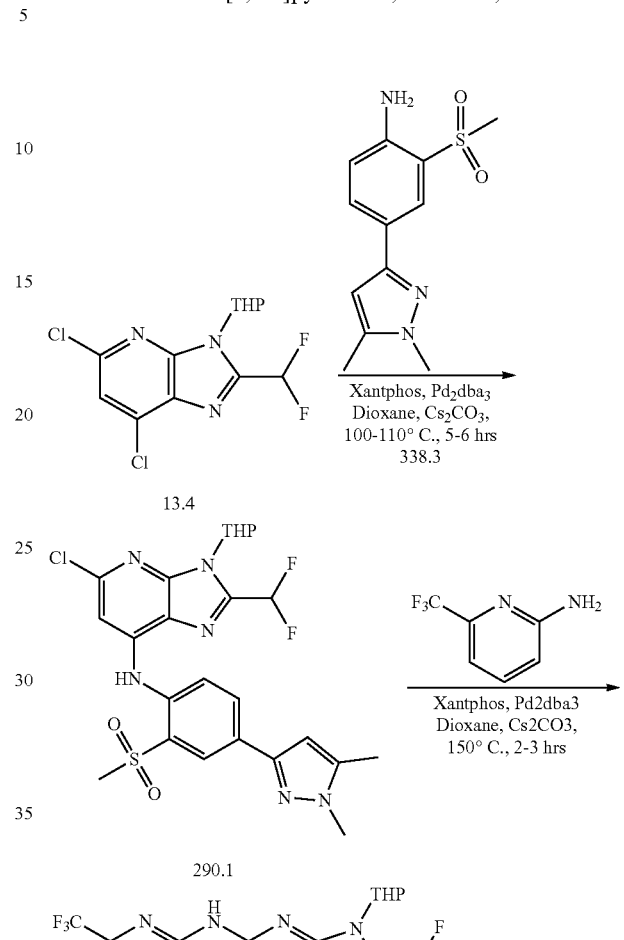

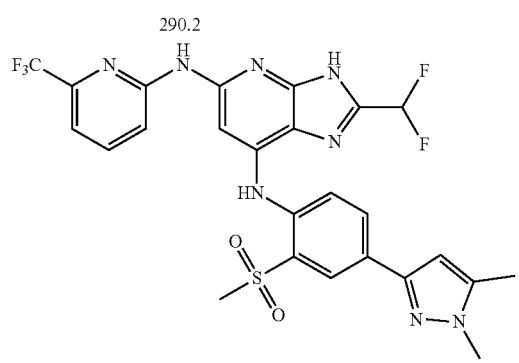

I-290

Synthesis of Compound 290.1.

Compound 290.1 was synthesized from 338.3 and 13.4 using general procedure A. (Yield: 17.89%). MS(ES): m/z 552.01 [M+H]⁺.

Synthesis of Compound 290.2.

Compound 290.2 was synthesized from 290.1 and 6-(trifluoromethyl)pyridin-2-amine using general procedure B. (Yield: 56.37%). MS(ES): m/z 677.67 [M+H]⁺.

Synthesis of I-290.

Compound I-290 was synthesized from 290.2 using general procedure C. (Yield: 88.82%). MS(ES): m/z 593.54 [M+H]⁺, LCMS purity: 97.21%, HPLC Purity: 95.56%, 1H NMR (DMSO, 400 MHz): 13.67 (s, 1H), 10.18 (s, 1H), 8.88 (s, 1H), 8.31-8.25 (m, 2H), 8.06-8.04 (d, J=8.4 Hz, 1H), 7.97-7.87 (m, 2H), 7.55 (s, 1H), 7.34-7.32 (d, J=8.4 Hz, 1H), 6.57 (s, 1H), 3.81 (s, 3H), 3.27 (s, 3H), 2.33 (s, 3H), 1.24-1.17 (m, 1H).

Example 291/292: Synthesis of (S)—N-(2-methyl-7-((2-(methylsulfonyl)-4-(tetrahydrofuran-3-yl)phenyl)amino)-3H-imidazo[4,5-b]pyridin-5-yl)cyclopropanecarboxamide, I-291 and (R)—N-(2-methyl-7-((2-(methylsulfonyl)-4-(tetrahydrofuran-3-yl)phenyl)amino)-3H-imidazo[4,5-b]pyridin-5-yl)cyclopropanecarboxamide, I-292

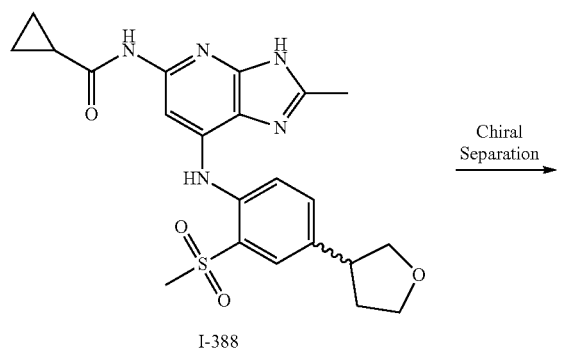

I-388

Chiral Separation →

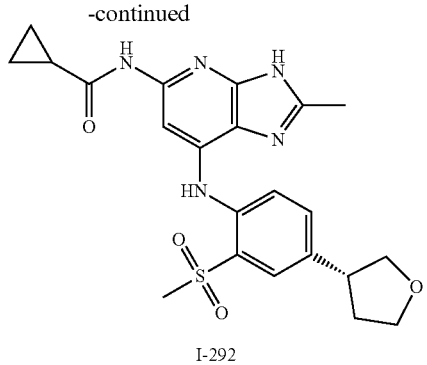

I-292

Synthesis of Compound I-291 and I-292.

Isomers of I-388 (0.094 g) were separated out using column (CHIRALCEL OX-H 250×4.6 mm, 5 μM) 0.1 DEA in IPA:ACN (50:50) as co-solvent with flow rate of 4 mL/min. to get pure fraction-1 (FR-a) and fraction-2 (FR-b). FR-a was concentrated in vacuo at 30° C. to afford pure I-291 (0.027 g). MS(ES): m/z 456.50 [M+H]⁺, LCMS purity: 100%, HPLC Purity: 99.83%, Chiral HPLC Purity: 100%, 1H NMR (DMSO-d6, 400 MHz): 12.46 (s, 1H), 10.57 (s, 1H), 8.52 (s, 1H), 7.96 (s, 1H), 7.77-7.65 (m, 3H), 4.00-3.95 (m, 2H), 3.18 (s, 3H), 3.14 (s, 3H), 2.36-2.34 (m, 1H), 1.99-0.89 (m, 2H), 1.24 (s, 2H), 1.71 (s, 1H), 0.71 (s, 4H). FR-b was concentrated in vacuo at 30° C. to afford pure I-292 (0.025 g). MS(ES): m/z 456.61 [M+H]⁺, LCMS purity: 100%, HPLC Purity: 100%, Chiral HPLC Purity: 98.23%, 1H NMR (DMSO-d6, 400 MHz): 12.46 (s, 1H), 10.57 (s, 1H), 8.52 (s, 1H), 7.97 (s, 1H), 7.77 (s, 1H), 7.27-7.65 (m, 2H), 4.00-3.95 (m, 2H), 3.84-3.78 (m, 1H), 3.61-3.58 (m, 1H), 3.51-3.47 (m, 1H), 3.31 (s, 2H), 3.18 (s, 3H), 2.50 (s, 3H), 2.40-2.34 (m, 1H), 1.99-1.90 (m, 2H), 0.89-0.84 (m, 2H).

Example 293/294: Synthesis of (S)—N-(2-(difluoromethyl)-7-((2-(methylsulfonyl)-4-(tetrahydro-2H-pyran-4-yl)phenyl)amino)-3H-imidazo[4,5-b]pyridin-5-yl)-2,2-difluorocyclopropane-1-carboxamide, I-293 and (R)—N-(2-(difluoromethyl)-7-((2-(methylsulfonyl)-4-(tetrahydro-2H-pyran-4-yl)phenyl)amino)-3H-imidazo[4,5-b]pyridin-5-yl)-2,2-difluorocyclopropane-1-carboxamide, I-294

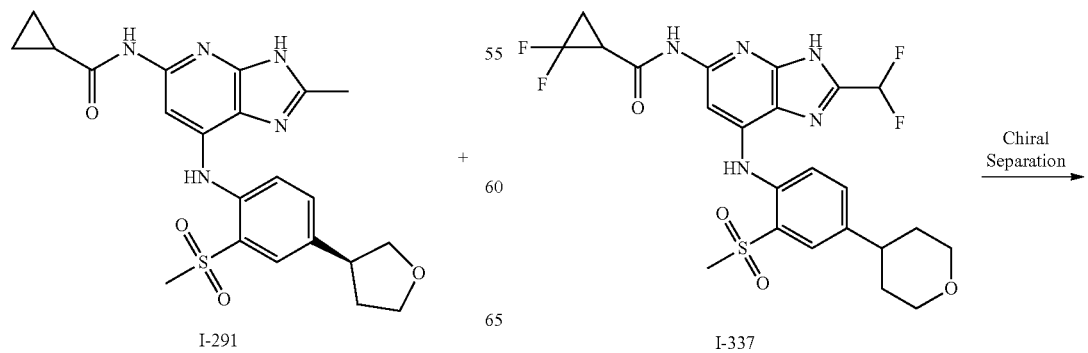

I-291 + I-337

Chiral Separation →

-continued

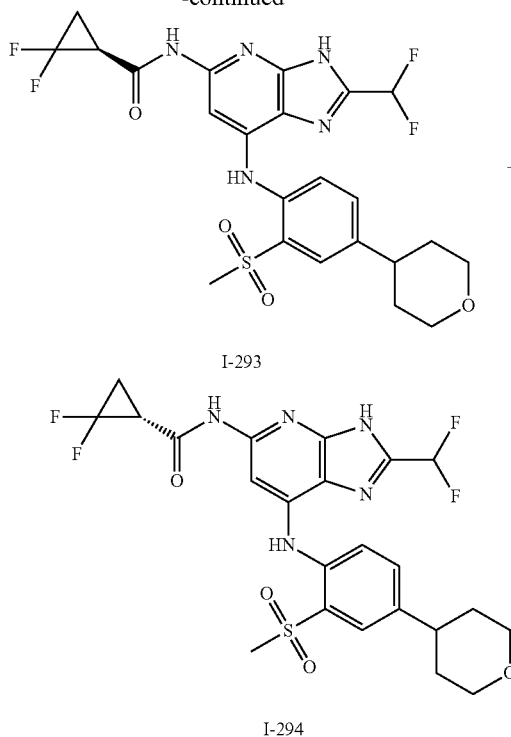

I-293

I-294

Synthesis of Compound I-293 and I-294.

Isomers of 1-337 (0.095 g) were separated out using column (CHIRALCEL OX-H 250×4.6 mm, 5 μM) 0.1 DEA in IPA as co-solvent with flow rate of 3 mL/min. to get pure fraction-1 (FR-a) and fraction-2 (FR-b). FR-a was concentrated in vacuo at 30° C. to afford pure I-293 (0.028 g). MS(ES): m/z 542.56 [M+H]$^+$, LCMS purity: 94.64%, HPLC Purity: 96.67%, Chiral HPLC: 98.13%, 1H NMR (DMSO-d6, 400 MHz): 13.77 (s, 1H), 10.94 (s, 1H), 7.97 (s, 1H), 7.79-7.72 (m, 3H), 7.26 (t, 2.4 Hz, 1H), 3.98-3.96 (d, J=8.4 Hz, 2H), 3.45 (s, 2H), 3.21 (s, 3H), 2.93-2.92 (d, J=6.8 Hz, 2H), 1.99-1.97 (d, J=7.2 Hz, 3H), 1.76-1.68 (m, 4H). FR-b was concentrated in vacuo at 30° C. to afford pure I-294 (0.024 g). MS(ES): m/z 542.56 [M+H]$^+$, LCMS purity: 100%, HPLC Purity: 99.88%, Chiral HPLC: 98.55%, 1H NMR (DMSO-d6, 400 MHz): 13.71 (s, 1H), 10.96 (s, 1H), 7.96 (s, 1H), 7.79-7.72 (m, 3H), 7.26 (t, 4.2 Hz, 1H), 3.98-3.96 (d, J=8.0 Hz, 3H), 3.48-3.42 (t, J=2.2 Hz, 3H), 3.21 (s, 3H), 2.99-2.89 (m, 4H), 1.99-1.97 (m, 3H).

Example 295: Synthesis of N-(2-((5-((6-cyano-5-((2-methoxyethyl)amino)pyridin-2-yl)amino)-2-(difluoromethyl)-3H-imidazo[4,5-b]pyridin-7-yl)amino)phenyl)-N-methylmethane sulfonamide, I-295

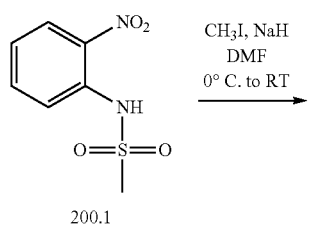

-continued

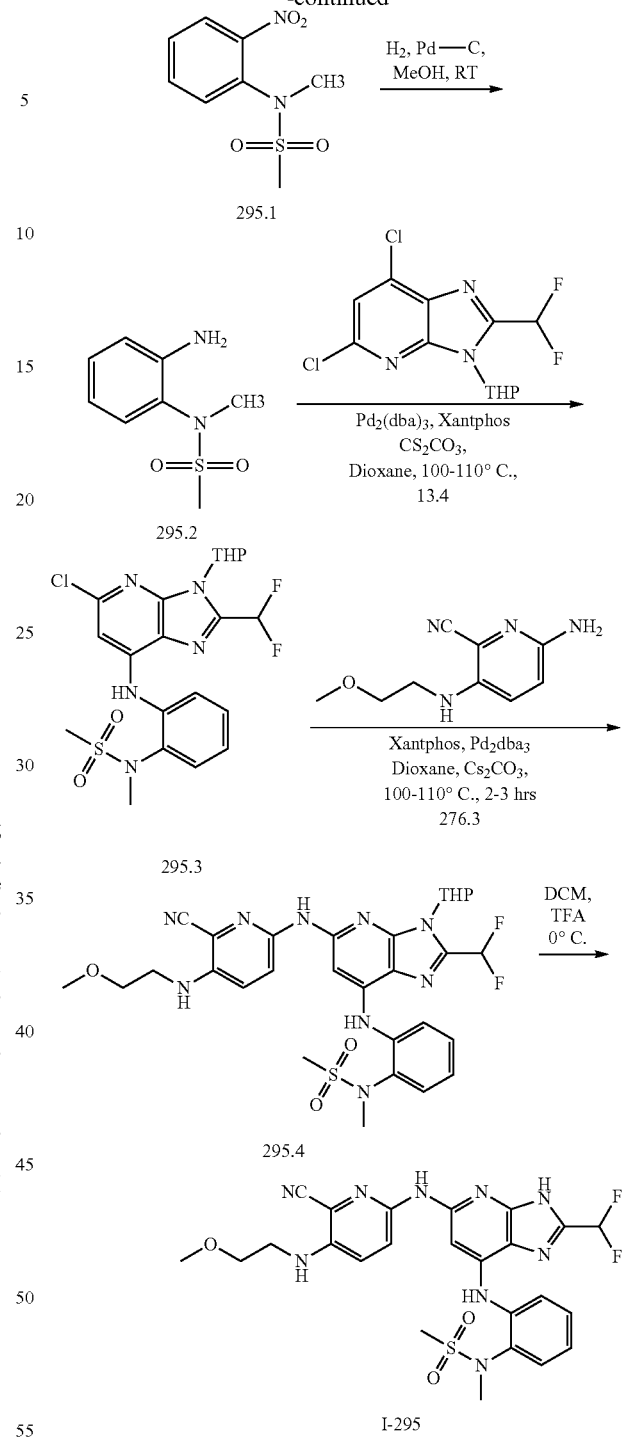

Synthesis of Compound 295.1.

To a solution of 200.1 (1.0 g, 4.63 mmol, 1.0 eq) in N,N-dimethylformamide (10 mL) was added sodium hydride (0.22 g, 9.26 mmol, 2.0 eq) at 0° C. and stirred the reaction mixture 10 min. Added iodomethane (0.97 g, 6.94 mmol, 1.5 eq) dropwise into reaction mixture at 0° C. Reaction mixture was stirred at r.t. for 2 h. Upon completion, reaction mixture was transferred into ice cold water, precipitated solid filtered and dried well to obtain pure 295.1 (0.7 g, Yield: 65.74%). MS(ES): m/z 231.26 [M+H]$^+$.

Synthesis of Compound 295.2.

To a solution of 295.1 (0.7 g, 3.04 mmol, 1.0 eq) in MeOH (7 mL), 10% Pd/C (0.3 g) was added. Hydrogen was purged through reaction mixture for 2-3 h. Upon completion, reaction mixture was filtered through celite-bed and washed with MeOH. Filtrate was concentrated in vacuo to obtain 295.2 (0.5 g, 82.12%). MS(ES): m/z 201.47 [M+H]⁺.

Synthesis of Compound 295.3.

Compound 295.3 was synthesized from 295.2 and 13.4 using general procedure A (Yield: 30.54%). MS(ES): m/z 486.92 [M+H]⁺.

Synthesis of Compound 295.4.

Compound 295.4 was synthesized from 295.3 and 276.3 using general procedure A. (Yield: 34.71%). MS(ES): m/z 642.70 [M+H]⁺.

Synthesis of Compound I-295.

Compound I-295 was synthesized from 295.4 using general procedure C. (Yield: 52.31%). MS(ES): m/z 558.62 [M+H]⁺, LCMS purity: 94.67%, HPLC Purity: 98.43%, 1H NMR (DMSO, 400 MHz): 13.40 (s, 1H), 9.53 (s, 1H), 8.03 (s, 1H), 7.92-7.89 (d, J=8.0 Hz, 1H), 7.76-7.74 (d, J=8.0 Hz, 1H), 7.68-7.66 (d, J=8.0 Hz, 1H), 7.55-7.52 (t, J=8.0 Hz, 1H), 7.43-7.34 (m, 3H), 7.26-7.20 (s, 1H), 3.49 (s, 2H), 3.38 (s, 2H), 3.29 (s, 3H), 3.18 (s, 3H), 3.15 (s, 3H), 1.35-1.24 (m, 1H).

Example 296: Synthesis of (1S,2S)—N-(2-(difluoromethyl)-7-((2-methoxy-3-(1-methyl-1H-1,2,4-triazol-3-yl)phenyl)amino)-3H-imidazo[4,5-b]pyridin-5-yl)-2-fluorocyclopropane-1-carboxamide, I-296

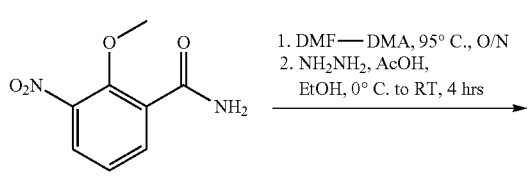

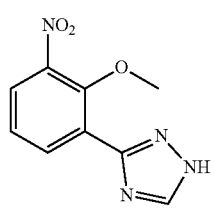

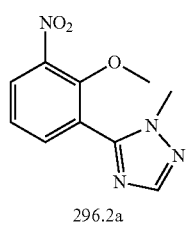 AND 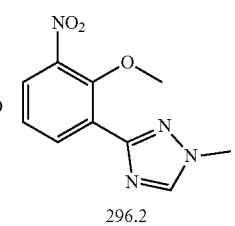

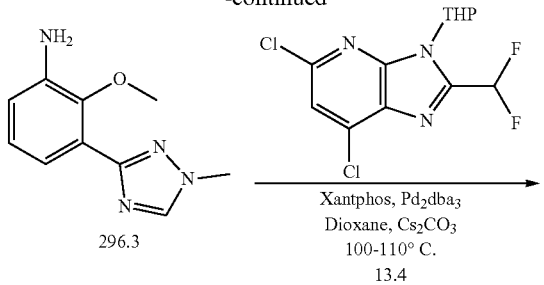

296.3

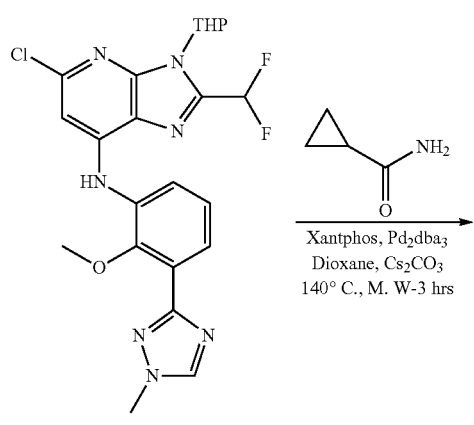

296.4

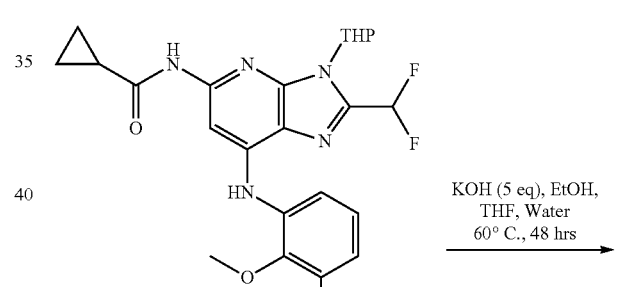

296.5

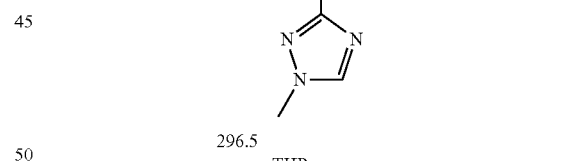

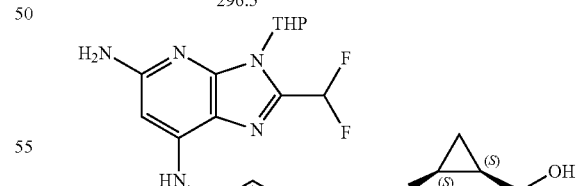

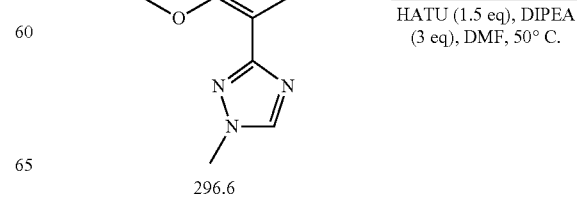

296.6

-continued

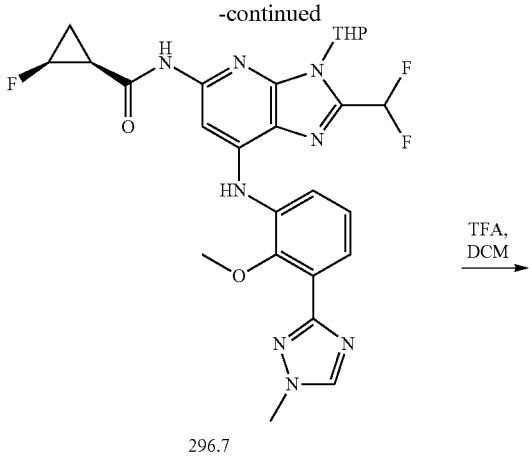

296.7

I-296

Synthesis of Compound 296.1.

To compound 2-methoxy-3-nitrobenzamide (10 g, 51.0 mmol, 1.0 eq) in dimethylformamide dimethyl acetal (75 mL) was added. Reaction mixture was stirred at 95° C. for 24 h. Then, ethanol (100 mL) was added and cooled to 0° C. Then, hydrazine hydrate (28.57 g, 510.0 mmol, 10 eq) and acetic acid (50 mL) was added and reaction mixture was allowed to stir at r.t. for 4 h. After completion of the reaction, the reaction mixture was concentrated, transferred to water and extracted with ethyl acetate. Organic layer combined, dried over anhydrous Na$_2$SO$_4$, filtered and concentrated in vacuo to obtain 296.1 (8 g, 71.27%). MS(ES): m/z 221.55 [M+H]$^+$.

Synthesis of Compound 296.2.

To compound 296.1 (8 g, 36.36 mmol, 1.0 eq) in dimethylformamide (80 mL) at 0° C., potassium carbonate (15.05 g, 109.09 mmol, 3.0 eq) and methyl iodide (7.69 g, 54.54 mmol, 1.5 eq) was added. Reaction mixture was stirred at r.t. for 24 h. After completion of reaction, the reaction mixture was transferred into cold water and extracted by ethyl acetate. Organic layer combined, dried over Na$_2$SO$_4$ and concentrated in vacuo to obtain crude product. This was purified by column chromatography and compound was eluted in 25% ethyl acetate in hexane as eluant to obtain pure 296.2 (3.0 g, 35.25%) MS(ES): m/z 235.84 [M+H]$^+$. And regioisomer 296.2a Synthesis of Compound 296.3.

To a compound of 296.2 (3 g, 12.8 mmol, 1.0 eq) in MeOH (30 mL) 10% Pd/C (1.5 g) was added. Hydrogen was purged through the reaction mixture for 24 h. After completion of the reaction, the reaction mixture was filtered through celite bed, washed with MeOH and concentrated in vacuo to obtain crude product. This was purified by column chromatography using 20% ethyl acetate in hexane to obtain pure 296.3 (2.5 g, 95.57%). MS(ES): m/z 205.84 [M+H]$^+$.

Synthesis of Compound 296.4.

Compound 296.4 was synthesized from 13.4 and 296.3 using general procedure A. (Yield: 27.79%). MS(ES): m/z 490.58 [M+H]$^+$.

Synthesis of Compound 296.5.

Compound 296.5 was synthesized from 296.4 and cyclopropanecarboxamide using general procedure B. (Yield: 42.23%). MS(ES): m/z 539.67 [M+H]$^+$.

Synthesis of Compound 296.6.

To a compound of 296.5 (0.130 g, 0.24 mmol, 1.0 eq) in a mixture of ethanol, water and tetrahydrofuran (80 mL), potassium hydroxide (0.1 g, 0.72 mmol, 3.0 eq) was added. Reaction mixture was stirred at 60° C. for 48 h. After completion of reaction, the reaction mixture was transferred into cold water and extracted by ethyl acetate. Organic layer combined, dried over Na$_2$SO$_4$ and concentrated in vacuo to obtain crude product. This was purified by column chromatography and compound was eluted in 20% ethyl acetate in hexane as eluant to obtain pure 296.6 (0.050 g, 44.03%). MS(ES): m/z 471.57 [M+H]$^+$.

Synthesis of Compound 296.7.

To a compound of 296.6 (0.013 g, 0.13 mmol, 1.2 eq) in dimethylformamide (1 mL) at 0° C., (1-[Bis(dimethylamino)methylene]-1H-1,2,3-triazolo[4,5-b]pyridinium-3-oxid hexafluorophosphate) (0.060 g, 0.15 mmol, 1.5 eq) was added. Reaction mixture was stirred at 0° C. for 30 min. Then, compound 1.9 (0.050 g, 0.10 mmol, 1.0 eq) and diisopropylethylamine (0.034 g, 0.26 mmol, 2.5 eq) was added. Reaction mixture was stirred at 50° C. for 3 h. After completion of reaction, the reaction mixture was transferred into cold water and extracted by ethyl acetate. Organic layer combined, dried over Na$_2$SO$_4$ and concentrated in vacuo to obtain crude product. This was purified by column chromatography and compound was eluted in 20% ethyl acetate in hexane as eluant to obtain pure 296.7 (0.045 g, 76.08%). MS(ES): m/z 557.84 [M+H]$^+$.

Synthesis of Compound I-296.

Compound I-296 was synthesized from 296.7 using general procedure C. (Yield: 20.94%). MS(ES): m/z 473.72 [M+H]$^+$, LCMS purity: 100%, HPLC Purity: 99.22%, Chiral HPLC: 98.13%, 1H NMR (MeOD, 400 MHz): 12.72 (s, 1H), 8.52 (s, 1H), 7.94 (s, 1H), 7.75-7.73 (d, J=7.6 Hz, 1H), 7.65-7.6 (d, J=7.6 Hz, 1H), 7.35-7.31 (m, 1H), 7.01 (t, 1H), 4.05 (s, 3H), 3.74 (s, 3H), 2.09 (s, 2H), 1.80-1.73 (m, 1H), 1.22-1.17 (m, 2H).

Example 297/298: Synthesis of (S)—N-(2-(difluoromethyl)-7-((2-(methylsulfinyl)phenyl)amino)-3H-imidazo[4,5-b]pyridin-5-yl)cyclopropanecarboxamide, I-297 and (R)—N-(2-(difluoromethyl)-7-((2-(methylsulfinyl)phenyl)amino)-3H-imidazo[4,5-b]pyridin-5-yl)cyclopropanecarboxamide, I-298

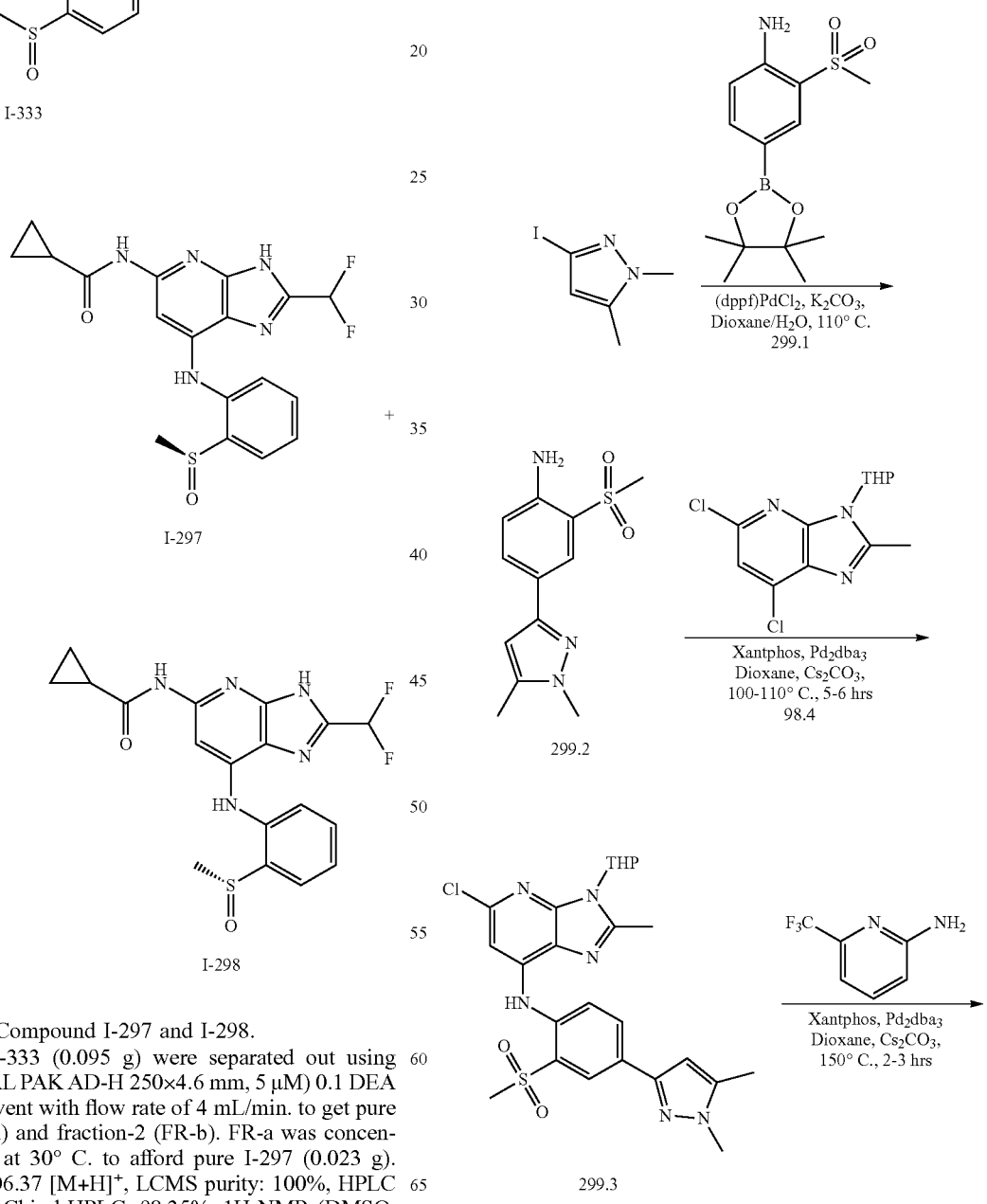

Synthesis of Compound I-297 and I-298.

Isomers of 1-333 (0.095 g) were separated out using column (CHIRAL PAK AD-H 250×4.6 mm, 5 μM) 0.1 DEA in IPA as co-solvent with flow rate of 4 mL/min. to get pure fraction-1 (FR-a) and fraction-2 (FR-b). FR-a was concentrated in vacuo at 30° C. to afford pure I-297 (0.023 g). MS(ES): m/z 406.37 [M+H]$^+$, LCMS Purity: 99.78%, Chiral HPLC: 98.35%, 1H NMR (DMSO, 400 MHz): 10.54 (s, 1H), 9.08 (s, 1H), 7.83-7.81 (d, J=7.6 Hz, 1H), 7.62-7.59 (m, 1H), 7.50-7.44 (m, 3H), 7.17 (s, 1H). 5.77 (s, 1H), 2.68 (s, 3H), 1.99-1.90 (m, 1H), 0.73 (bs, 4H). FR-b was concentrated in vacuo at 30° C. to afford pure I-298 (0.030 g). MS(ES): m/z 406.37 [M+H]$^+$, LCMS purity: 100%, HPLC Purity: 99.69%, Chiral HPLC: 100%, 1H NMR (DMSO, 400 MHz): 10.51 (s, 1H), 9.06 (s, 1H), 7.81-7.79 (d, J=7.2 Hz, 1H), 7.62-7.58 (m, 1H), 7.48-7.43 (m, 3H), 7.13 (s, 1H), 2.74 (s, 3H), 2.00-1.96 (m, 1H), 1.24 (s, 1H), 0.73 (bs, 4H).

Example 299: N7-(4-(1,5-dimethyl-1H-pyrazol-3-yl)-2-(methylsulfonyl)phenyl)-2-methyl-N5-(6-(trifluoromethyl)pyridin-2-yl)-3H-imidazo[4,5-b]pyridine-5,7-diamine, I-299

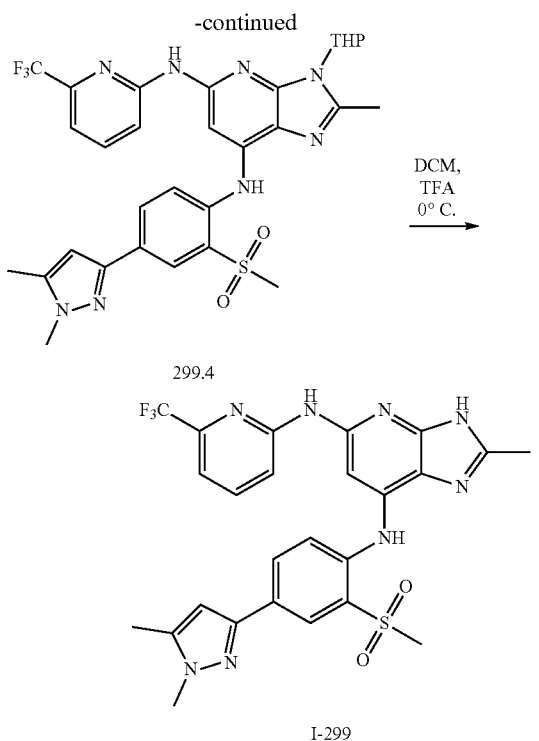

299.4

I-299

Synthesis of Compound 299.1.

Compound 299.1 was synthesized as per 1-288.

Synthesis of Compound 299.2.

To compound 3-iodo-1,5-dimethyl-1H-pyrazole (1.0 g, 4.5 mmol, 1.0 eq) in a mixture of dioxane (8 mL) and water (2 mL), compound 299.1 (1.47 g, 4.95 mmol, 1.1 eq) was added. Reaction mixture was degassed with argon for 10 minutes. Then [1,1'-Bis(diphenylphosphino)ferrocene]palladium(II) dichloride (0.65 g, 0.9 mmol, 0.2 eq) and potassium carbonate (1.86 g, 13.5 mmol, 3 eq) was added into it. Reaction mixture was stirred at 110° C. for 24 h. Upon completion, reaction mixture was transferred into cold water then extracted with ethyl acetate. Organic layers were combined, dried over Na$_2$SO$_4$, filtered and concentrated in vacuo to obtain crude product. This was purified by column chromatography using 15% ethyl acetate in hexane as eluant to obtain pure 299.2 (0.700 g, 58.58%). MS(ES): m/z 266.33 [M+H]$^+$.

Synthesis of Compound 299.3.

Compound 299.3 was synthesized from 98.4 and 299.2 using general procedure A. (Yield: 26.79%). MS(ES): m/z 516.03 [M+H]$^+$.

Synthesis of Compound 299.4.

Compound 299.4 was synthesized from 299.3 and 6-(trifluoromethyl)pyridin-2-amine using general procedure B. (Yield: 43.29%). MS(ES): m/z 641.69 [M+H]$^+$.

Synthesis of Compound I-299.

Compound I-299 was synthesized from 299.4 using general procedure C. (Yield: 65.78%). MS(ES): m/z 557.80 [M+H]$^+$, LCMS purity: 97.08%, HPLC Purity: 95.96%, 1H NMR (DMSO, 400 MHz): 12.51 (s, 1H), 9.98 (s, 1H), 8.73 (s, 1H), 8.27 (s, 1H), 8.13-8.11 (d, J=8.8 Hz, 1H), 8.03-8.00 (d, J=8.4 Hz, 1H), 7.91-7.87 (m, 2H), 7.54 (s, 1H), 7.28-7.26 (d, J=7.2 Hz, 1H), 6.54 (s, 1H), 3.81 (s, 3H), 3.25 (s, 3H), 2.48 (s, 3H), 2.32 (s, 3H).

Example 300: Synthesis of 2-(difluoromethyl)-N7-(4-(1,5-dimethyl-1H-pyrazol-3-yl)-2-(methylsulfonyl)phenyl)-N5-(5,6-dimethylpyrazin-2-yl)-3H-imidazo[4,5-b]pyridine-5,7-diamine, I-300

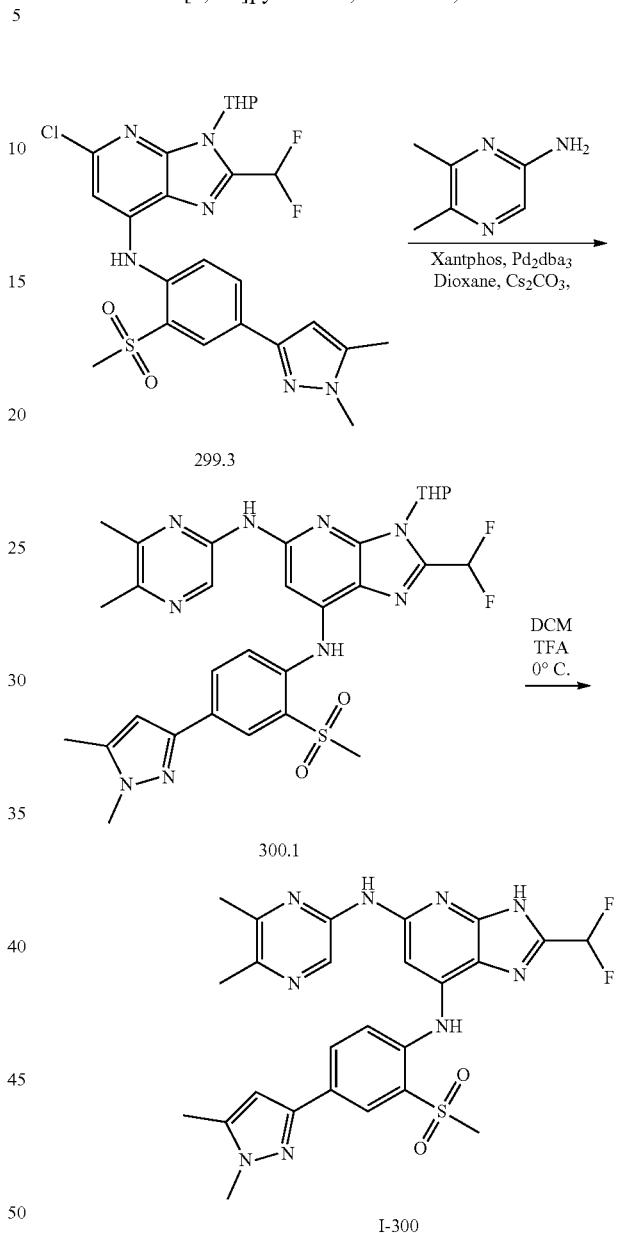

299.3

300.1

I-300

Synthesis of Compound 300.1.

Compound 300.1 was synthesized from 299.3 and 5,6-dimethylpyrazin-2-amine using general procedure A. (Yield: 56.16%). MS(ES): m/z 638.71 [M+H]$^+$.

Synthesis of Compound I-300.

Compound I-300 was synthesized using general procedure C. (Yield: 67.34%). MS(ES): m/z 554.55 [M+H]$^+$, LCMS purity: 95.28%, HPLC Purity: 96.18%, 1H NMR (DMSO, 400 MHz): 13.57 (s, 1H), 9.81 (s, 1H), 9.00 (s, 1H), 8.82 (s, 1H), 8.30 (s, 1H), 8.10-8.08 (d, J=10 Hz, 1H), 7.92-7.90 (d, J=8.4 Hz, 1H), 7.54 (s, 1H), 7.23 (s, 1H), 6.59 (s, 1H), 3.81 (s, 3H), 3.27 (s, 3H), 2.40-2.38 (d, J=6 Hz, 6H), 2.32 (s, 3H).

Example 301: Synthesis of (1R,2R)—N-(2-(difluoromethyl)-7-((4-(1-methyl-1H-imidazol-4-yl)-2-(methylsulfonyl)phenyl)amino)-3H-imidazo[4,5-b]pyridin-5-yl)-2-fluorocyclopropane-1-carboxamide, I-301

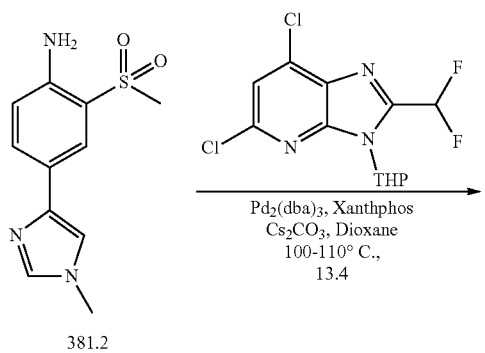

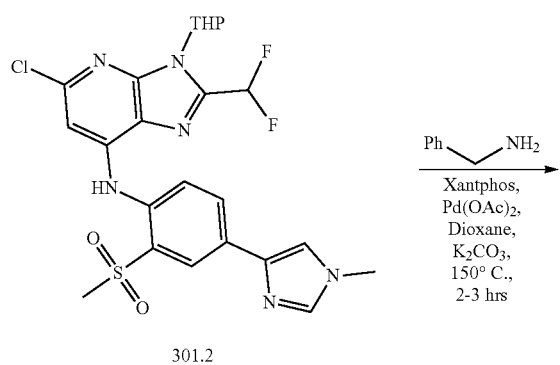

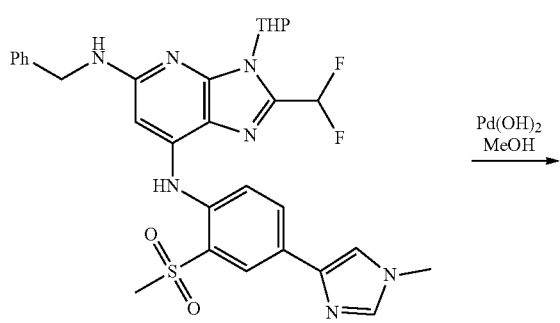

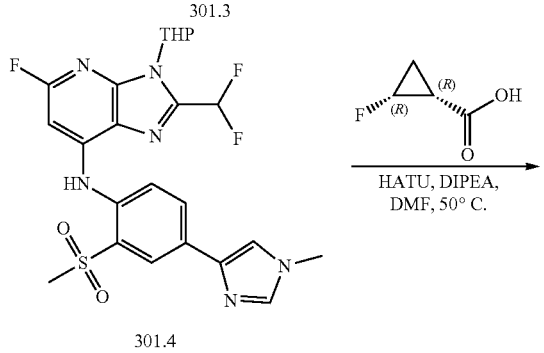

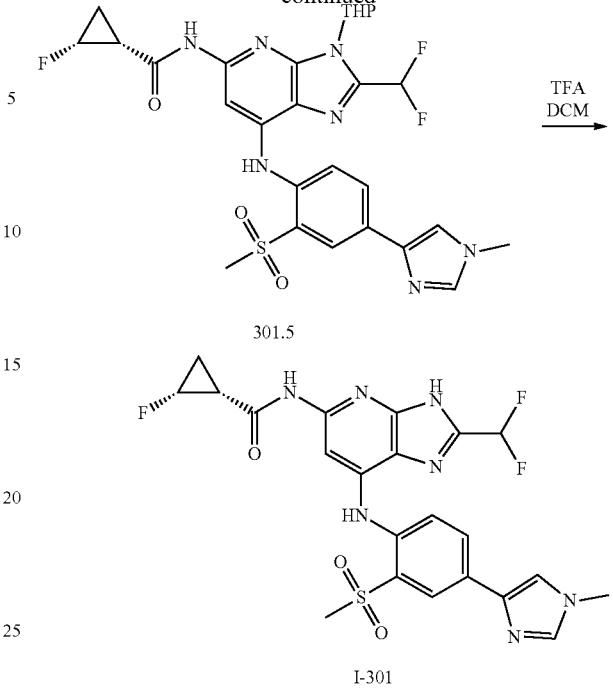

Synthesis of Compound 301.2.

Compound 301.2 was synthesized from 381.2 and 13.4 using general procedure A. (Yield: 39.99%). MS(ES): m/z 537.42 [M+H]⁺.

Synthesis of Compound 301.3.

Compound 301.3 was synthesized from 301.2 and benzylamine using general procedure B. (Yield: 20.68%). MS(ES): m/z 608.57 [M+H]⁺.

Synthesis of Compound 301.4.

To a solution of 301.3 (0.2 g, 0.34 mmol, 1.0 eq) in MeOH (2.0 mL), palladium acetate (0.15 g, 0.68 mmol, 2.0 eq) was added. Reaction mixture was stirred at 50° C. for 24 h. Upon completion, reaction mixture was transferred into ice water and extracted with ethyl acetate. Organic layer combined, dried over anhydrous Na$_2$SO$_4$, filtered and concentrated in vacuo to obtain 301.4 (0.1 g, 67.09%). MS(ES): m/z 518.37 [M+H]⁺.

Synthesis of Compound 301.5.

To compound (1R,2R)-2-fluorocyclopropane-1-carboxylic acid 1.7 (0.014 g, 1.32 mmol, 1.2 eq) in N,N'-dimethylformamide (1.0 mL) at 0° C., (1-[Bis(dimethylamino)methylene]-1H-1,2,3-triazolo[4,5-b]pyridinium 3-oxide hexafluoro-phosphate) (0.062 g, 1.65 mmol, 1.5 eq) was added. Reaction mixture was allowed to stir at 0° C. for 30 min. The, di-isopropylethylamine (0.035 g, 2.71 mmol, 2.5 eq) and compound 301.4 (0.60 g, 1.13 mmol, 1.0 eq) was added. Reaction mixture was allowed to stir at 50° C. for 3 h. After completion of the reaction, the reaction mixture was transferred into water and extracted with ethyl acetate. Organic layer combined, dried over anhydrous Na$_2$SO$_4$, filtered and concentrated in vacuo to obtain the crude material. This was purified by column chromatography using 25% ethyl acetate in hexane to obtain pure 301.5 (0.040 g, 57.16%). MS(ES): m/z: 604.38 [M+H]⁺.

Synthesis of Compound I-301.

Compound I-301 was synthesized from 301.5 using general procedure C. (Yield: 36.31%). MS(ES): m/z 520.51 [M+H]⁺, LCMS purity: 95.59%, HPLC Purity: 95.45%, Chiral HPLC: 97.04%, 1H NMR (DMSO, 400 MHz): 13.70 (s, 1H), 10.81 (s, 1H), 8.75 (s, 1H), 8.33 (s, 1H), 8.12-8.06 (m, 2H), 7.81-7.74 (m, 3H), 7.28 (s, 1H), 5.01-4.84 (d, J=68 Hz, 1H), 3.73 (s, 3H), 3.24 (s, 3H), 2.24 (s, 1H), 1.64-1.59 (m, 1H), 1.15 (bs, 1H).

Example 302: Synthesis of 6-((2-(difluoromethyl)-7-((4-(1,5-dimethyl-1H-pyrazol-4-yl)-2-(methylsulfonyl)phenyl)amino)-3H-imidazo[4,5-b]pyridin-5-yl)amino)picolinonitrile, I-302

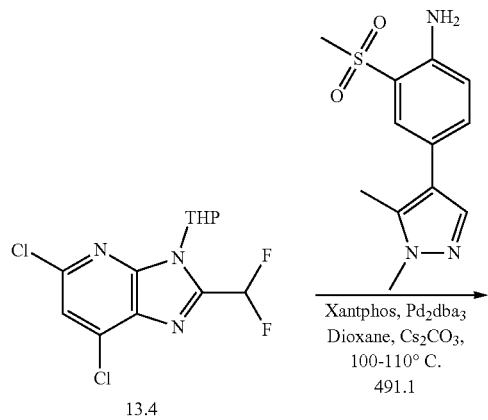

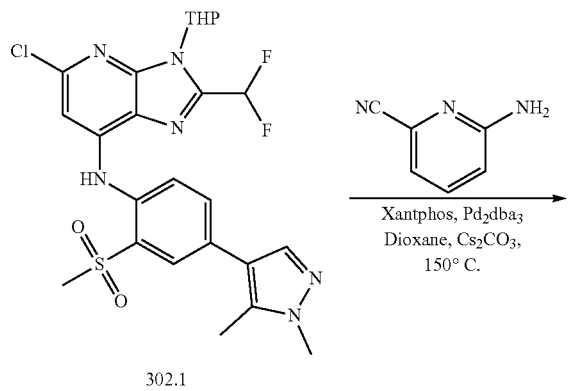

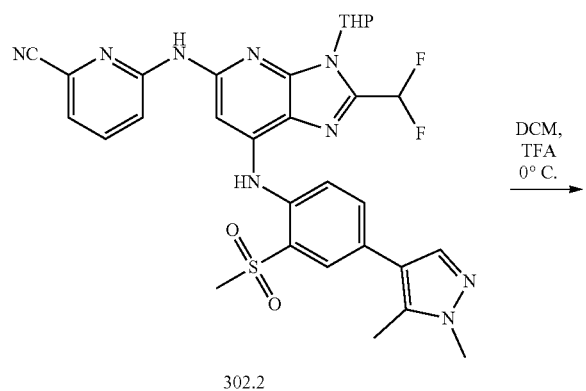

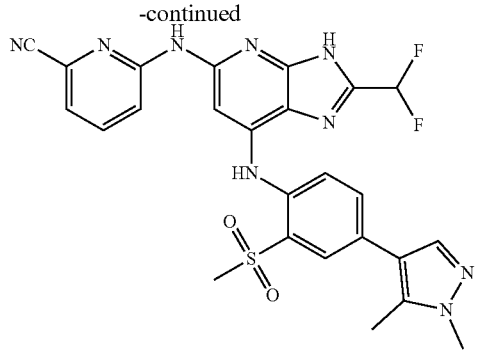

I-302

Synthesis of Compound 302.1.

Compound 302.1 was synthesized from 491.1 and 13.4 using general procedure A. (Yield: 30.40%). MS(ES): m/z 552.13 [M+H]$^+$.

Synthesis of Compound 302.2.

Compound 302.2 was synthesized from 302.1 and 6-aminopicolinonitrile using general procedure B. (Yield: 60.20%). MS(ES): m/z 634.53 [M+H]$^+$.

Synthesis of I-302.

Compound I-302 was synthesized from 303.2 using general procedure C (Yield: 70.47%). MS(ES): m/z 550.50 [M+H]$^+$, LCMS purity: 100%, HPLC Purity: 96.96%, 1H NMR (DMSO, 400 MHz): 13.66 (s, 1H), 10.23 (s, 1H), 8.93 (s, 1H), 8.05-7.99 (m, 2H), 7.91-7.86 (m, 3H), 7.73 (s, 1H), 7.67 (s, 1H), 7.50-7.49 (d, J=11.2 Hz, 1H), 7.263 (s, 1H), 3.83 (s, 3H), 3.28 (s, 3H), 2.44 (s, 3H).

Example 303: Synthesis of 6-((2-(difluoromethyl)-7-((4-(1,5-dimethyl-1H-pyrazol-3-yl)-2-(methylsulfonyl)phenyl)amino)-3H-imidazo[4,5-b]pyridin-5-yl)amino)-3-methylpicolinonitrile, I-303

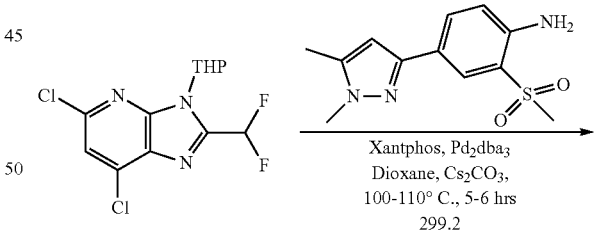

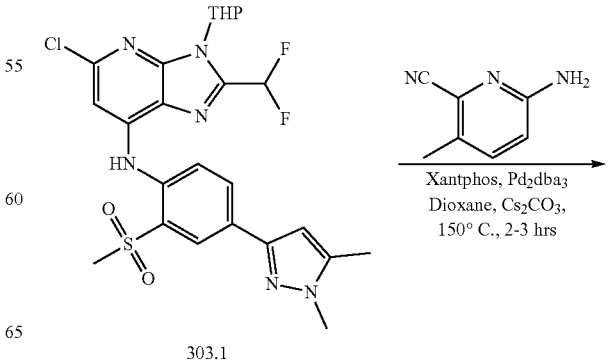

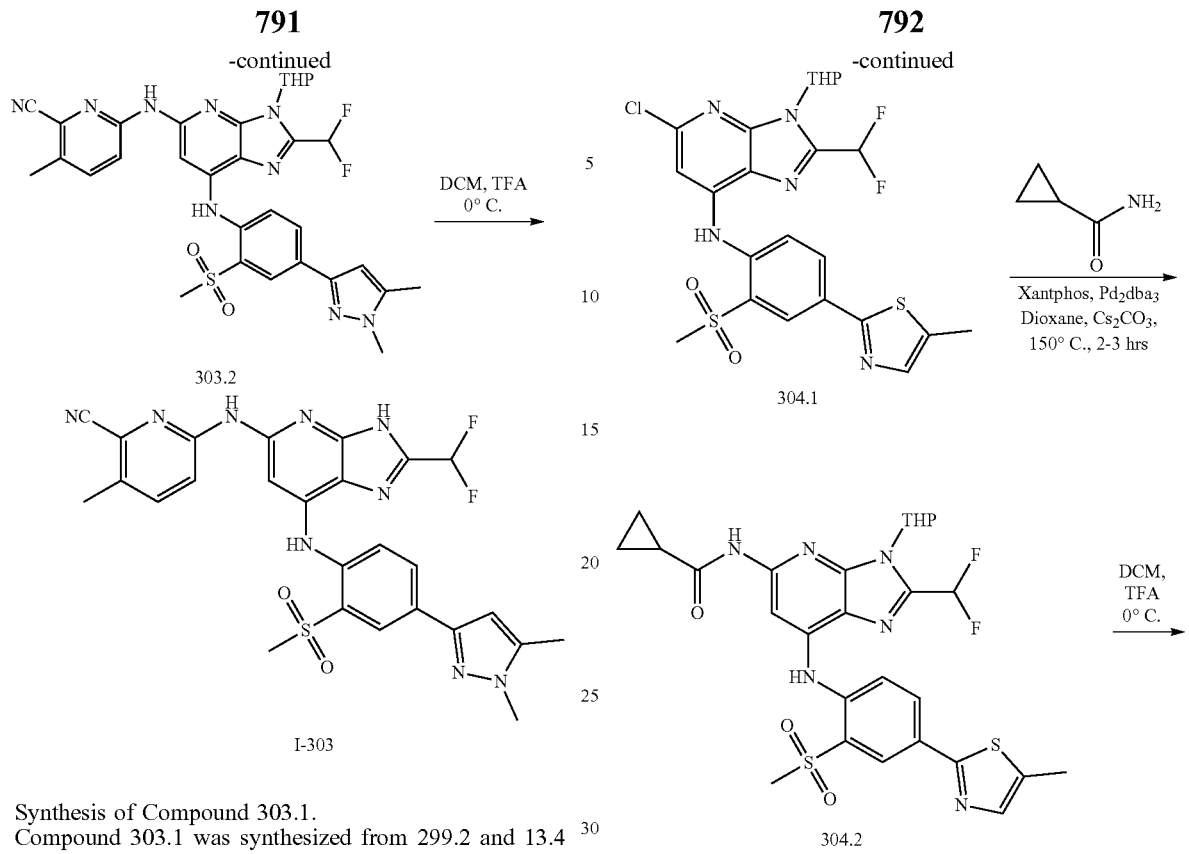

Synthesis of Compound 303.1.

Compound 303.1 was synthesized from 299.2 and 13.4 using general procedure A. (Yield: 38.52%). MS(ES): m/z 552.01 [M+H]⁺.

Synthesis of Compound 303.2.

Compound 303.3 was synthesized from 303.1 and 6-amino-3-methylpicolinonitrile using general procedure B. (Yield: 59.55%). MS(ES): m/z 648.71 [M+H]⁺.

Synthesis of I-303.

Compound I-303 was synthesized from 303.2 using general procedure C (Yield: 73.88%). MS(ES): m/z 564.81 [M+H]⁺, LCMS purity: 95.72%, HPLC Purity: 96.18%, 1H NMR (DMSO, 400 MHz): 13.64 (s, 1H), 10.09 (s, 1H), 8.90 (s, 1H), 8.31 (s, 1H), 8.15-8.13 (d, J=8.4 Hz, 1H), 8.07-8.05 (d, J=8.8 Hz, 1H), 7.97-7.94 (d, J=8.4 Hz, 1H), 7.81-7.79 (d, J=8.8 Hz, 1H), 7.62 (s, 1H), 7.24 (s, 1H), 6.53 (s, 1H), 3.81 (s, 3H), 3.26 (s, 3H), 2.41 (s, 3H), 2.32 (s, 3H).

Example 304: Synthesis of N-(2-(difluoromethyl)-7-((2-(methylsulfonyl)-4-(5-methylthiazol-2-yl)phenyl)amino)-3H-imidazo[4,5-b]pyridin-5-yl)cyclopropanecarboxamide, I-304

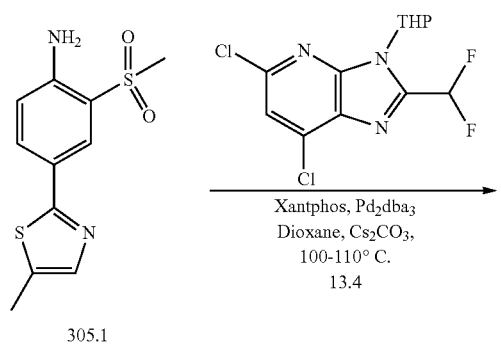

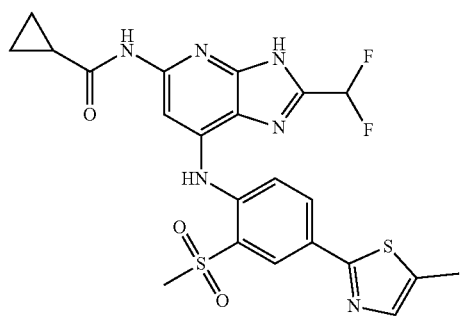

Synthesis of Compound 304.1.

Compound 304.1 was synthesized from 13.4 and 305.1 using general procedure A. (Yield: 19.37%). MS(ES): m/z 555.03 [M+H]⁺.

Synthesis of Compound 304.2.

Compound 304.2 was synthesized from 304.1 and cyclopropanecarboxamide using general procedure B. (Yield: 61.29%). MS(ES): m/z 603.68 [M+H]⁺.

Synthesis of I-304.

Compound I-304 was synthesized from 304.2 using general procedure C. (Yield: 43.58%). MS(ES): m/z 519.74 [M+H]⁺, LCMS Purity: 95.27%, HPLC Purity: 94.12%, 1H NMR (DMSO, 400 MHz): 13.76 (s, 1H), 10.85 (s, 1H), 8.96 (s, 1H), 8.40-8.40 (d, J=2 Hz, 1H), 8.20-8.18 (m, 2H), 7.89-7.87 (d, J=8.4 Hz, 1H), 7.67 (s, 1H), 7.28 (s, 1H), 3.23 (s, 3H), 2.51 (s, 3H), 2.07-2.05 (m, 1H), 0.82 (s, 4H).

Example 1-305: Synthesis of N-(2-methyl-7-((2-(methylsulfonyl)-4-(5-methylthiazol-2-yl)phenyl)amino)-3H-imidazo[4,5-b]pyridin-5-yl)cyclopropanecarboxamide, I-305

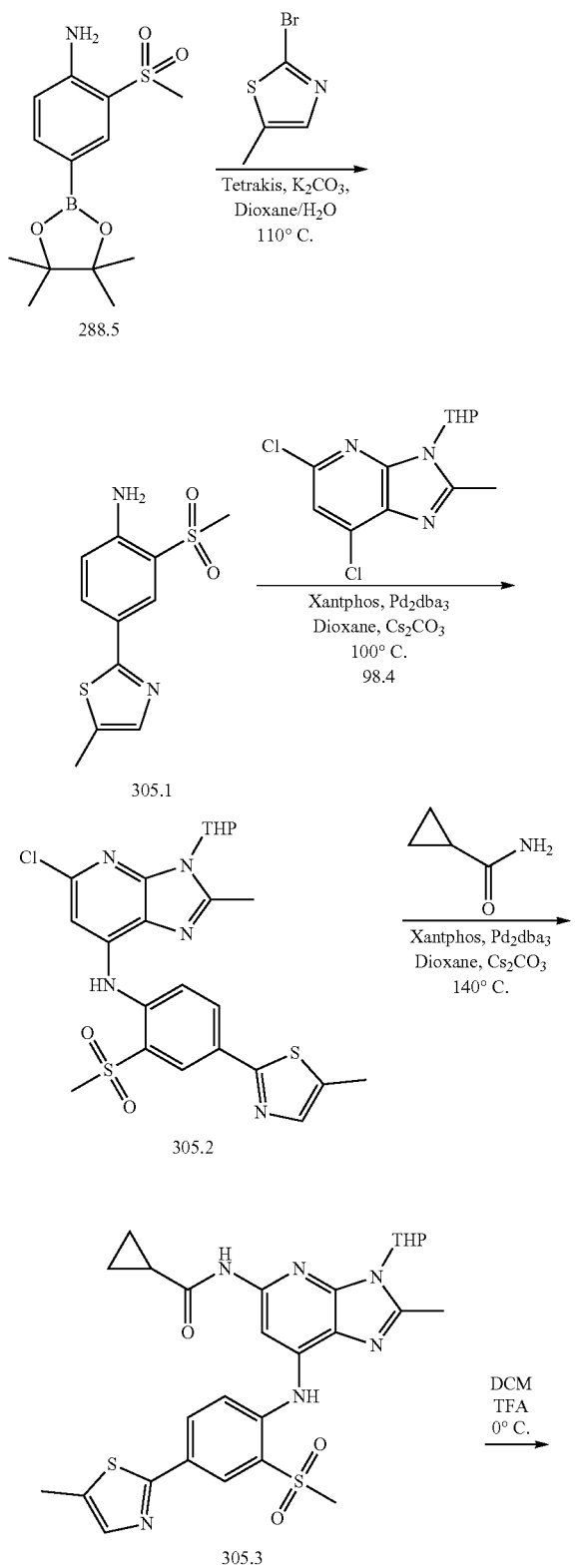

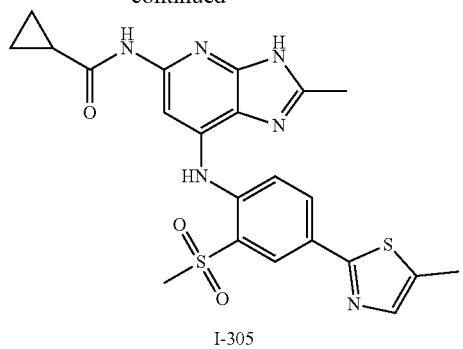

I-305

Synthesis of Compound 305.1.

To compound 288.5 (2 g, 11.23 mmol, 1.0 eq) and compound 1 (5 g, 16.85 mmol, 1.5 eq) in mixture of 1,4-dioxane (16 mL) and water (4 mL), sodium carbonate (2.38 g, 22.46 mmol, 2.0 eq) was added. Argon was purged through the reaction mixture for 5 min. Then, [1,1′-Bis(diphenylphosphino)ferrocene]dichloropalladium(II) (0.819 g, 1.12 mmol, 0.1 eq) was added and again degassed for 5 min. Reaction mixture was stirred at 120° C. for 4 h. After completion of the reaction, the reaction mixture was transferred into water and extracted with ethyl acetate. Organic layers were combined, dried over anhydrous $Na_2SO_4$, filtered and concentrated in vacuo to obtain the crude material. This was purified by column chromatography using 12% ethyl acetate in hexane as eluant to obtain 1.2 (1.1 g, 36.49%). MS(ES): m/z 269.35 [M+H]$^+$.

Synthesis of Compound 305.2.

Compound 305.2 was synthesized from 98.4 and 305.1 using general procedure A. (Yield: 17.27%). MS(ES): m/z 519.05 [M+H]$^+$.

Synthesis of Compound 305.3.

Compound 305.3 was synthesized from 305.2 and cyclopropanecarboxamide using general procedure B. (Yield: 54.85%). MS(ES): m/z 567.70 [M+H]$^+$.

Synthesis of I-305.

Compound I-305 was synthesized from 305.3 using general procedure C. (Yield: 58.72%). MS(ES): m/z 483.45 [M+H]$^+$, LCMS purity: 95.71%, HPLC Purity: 95.47%, 1H NMR (DMSO-d6, 400 MHz): 12.57 (s, 1H), 10.66 (s, 1H), 8.79 (s, 1H), 8.37 (s, 1H), 8.16-8.09 (m, 2H), 7.85-7.83 (d, J=8.8 Hz, 1H), 7.65 (s, 1H), 3.30 (s, 3H), 2.51 (s, 6H), 2.01 (bs, 1H). 0.79-0.77 (m, 4H).

Example 306/307: Synthesis of (S)—N-(2-(difluoromethyl)-7-((2-(methylsulfonyl)-4-((R)-tetrahydrofuran-2-yl)phenyl)amino)-3H-imidazo[4,5-b]pyridin-5-yl)-2,2-difluorocyclopropane-1-carboxamide, I-306 and (R)—N-(2-(difluoromethyl)-7-((2-(methylsulfonyl)-4-((R)-tetrahydrofuran-2-yl)phenyl)amino)-3H-imidazo[4,5-b]pyridin-5-yl)-2,2-difluorocyclopropane-1-carboxamide, I-307

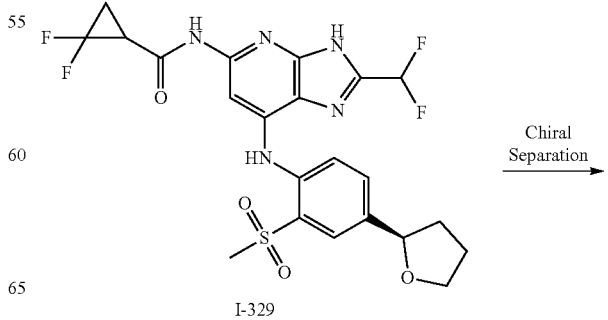

I-329

795
-continued

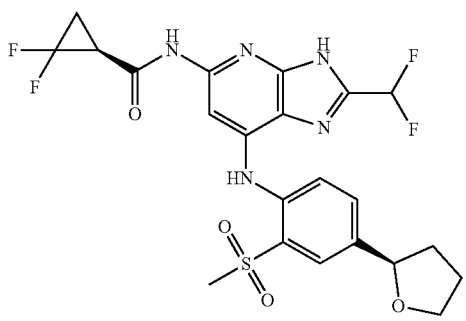

I-306

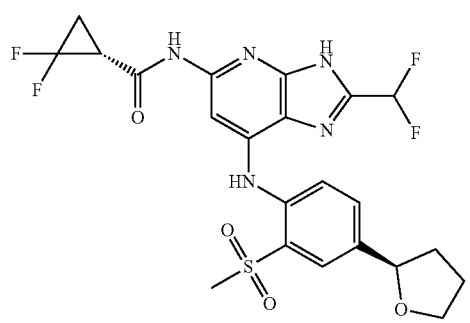

I-307

Synthesis of Compound I-306 and I-307.

Isomers of I-329 (0.085 g) were separated out using column (CHIRALCEL OX-H 250×4.6 mm, 5 μM) 0.1 DEA in IPA as co-solvent with flow rate of 4 mL/min. to get pure fraction-1 (FR-a) and fraction-2 (FR-b). FR-a was concentrated in vacuo at 30° C. to afford pure I-306 (0.025 g). MS(ES): m/z 528.89 [M+H]$^+$, LCMS purity: 100%, HPLC Purity: 97.26%, Chiral HPLC: 100%, 1H NMR (DMSO, 400 MHz): 13.74 (s, 1H), 10.97 (s, 1H), 8.77 (s, 1H), 7.99 (s, 1H), 7.88 (s, 1H), 7.77-7.70 (m, 2H), 4.92-4.89 (t, J=14.4 Hz, 1H), 4.13-4.00 (m, 2H), 3.21 (s, 3H), 3.17-3.16 (d, J=5.2 Hz, 1H), 2.99 (s, 1H), 2.42-2.34 (s, 2H), 2.09-1.96 (m, 4H). FR-b was concentrated in vacuo at 30° C. to afford pure I-307 (0.025 g). MS(ES): m/z 528.61 [M+H]$^+$, LCMS purity: 98.87%, HPLC Purity: 99.23%, Chiral HPLC: 100%, 1H NMR (DMSO, 400 MHz): 13.74 (s, 1H), 10.97 (s, 1H), 8.77 (s, 1H), 7.99 (s, 1H), 7.88 (s, 1H), 7.77-7.70 (m, 2H), 4.92-4.89 (t, J=14.4 Hz, 1H), 4.13-4.10 (m, 2H), 3.21 (s, 3H), 3.17-3.16 (d, J=5.2 Hz, 1H), 2.99 (s, 1H), 2.42-2.34 (s, 2H), 2.08-1.95 (m, 4H).

796

Example 308/309: Synthesis of (S)—N-(2-(difluoromethyl)-7-((4-(1,5-dimethyl-1H-pyrazol-4-yl)-2-(methylsulfonyl)phenyl)amino)-3H-imidazo[4,5-b]pyridin-5-yl)-2,2-difluorocyclopropane-1-carboxamide, I-308 and (R)—N-(2-(difluoromethyl)-7-((4-(1,5-dimethyl-1H-pyrazol-4-yl)-2-(methylsulfonyl)phenyl)amino)-3H-imidazo[4,5-b]pyridin-5-yl)-2,2-difluorocyclopropane-1-carboxamide, I-309

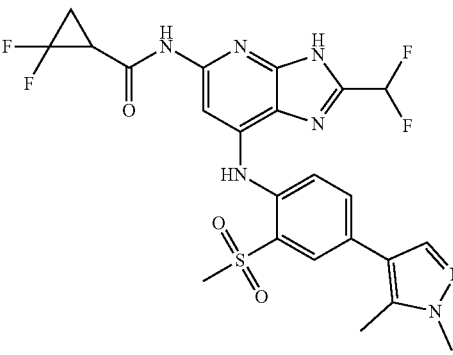

I-331

Chiral separation →

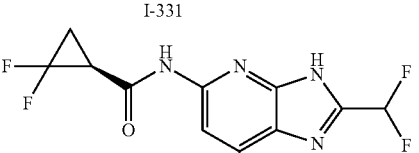

I-308
+

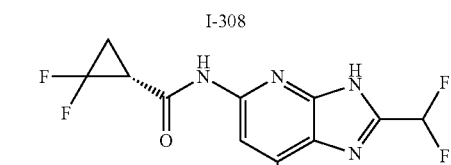

I-309

Synthesis of Compound I-308 and I-309.

Isomers of I-331 (0.1 g) were separated out using column (CHIRAL PAK AD-H 250×4.6 mm, 5 μM) 0.1 DEA in IPA as co-solvent with flow rate of 4 mL/min. to get pure fraction-1 (FR-a) and fraction-2 (FR-b). FR-a was concentrated in vacuo at 30° C. to afford pure I-308 (0.027 g). MS(ES): m/z 552.77 [M+H]$^+$, LCMS purity: 100%, HPLC Purity: 97.83%, Chiral HPLC: 100%, 1H NMR (DMSO, 400 MHz): 13.74 (s, 1H), 10.96 (s, 1H), 8.77 (s, 1H), 7.98 (s, 1H), 7.90 (s, 1H), 7.82-7.81 (m, 2H), 7.71 (s, 1H), 7.26 (s, 1H), 3.87-3.77 (t, 3H), 3.26 (s, 3H), 3.02-2.99 (s, 1H), 2.43 (s, 3H), 2.20-1.92 (m, 2H). FR-b was concentrated in vacuo at 30° C. to afford pure I-309 (0.027 g). MS(ES): m/z 552.667 [M+H]$^+$, LCMS purity: 97.11%, HPLC Purity: 96.67%, Chiral HPLC: 98.27%, 1H NMR (DMSO, 400 MHz): 13.74 (s, 1H), 10.96 (s, 1H), 8.79 (s, 1H), 7.98 (s, 1H), 7.90 (s, 1H), 7.85-7.76 (m, 2H), 7.71 (s, 1H), 7.27 (s, 1H), 3.82 (s, 3H), 3.26 (s, 3H), 3.03-2.99 (s, 1H), 2.43 (s, 3H), 2.02-1.96 (m, 2H).

Example 310/311: Synthesis of (R)—N-(2-(difluoromethyl)-7-((2-(methylsulfonyl)-4-((R)-tetrahydro-2H-pyran-3-yl)phenyl)amino)-3H-imidazo[4,5-b]pyridin-5-yl)-2,2-difluorocyclopropane-1-carboxamide, I-310 or (S)—N-(2-(difluoromethyl)-7-((2-(methylsulfonyl)-4-((R)-tetrahydro-2H-pyran-3-yl)phenyl)amino)-3H-imidazo[4,5-b]pyridin-5-yl)-2,2-difluorocyclopropane-1-carboxamide, I-311

Purity: 98.00%, Chiral HPLC Purity: 100%, 1H NMR (DMSO, 400 MHz): 8.02 (s, 1H), 7.91 (s, 1H), 7.83-7.81 (d, J=8.4 Hz, 1H), 7.71-7.69 (d, J=10.4 Hz, 1H), 6.97 (s, 1H), 4.01-3.98 (s, 1H), 3.58-3.48 (m, 2H), 3.10 (s, 3H), 3.06-2.97 (m, 1H), 2.83-2.80 (m, 1H), 2.11-2.06 (s, 2H), 1.89-1.79 (m, 4H), 0.92-0.90 (m, 4H). FR-b was concentrated in vacuo at 30° C. to afford pure I-311 (0.028 g). MS(ES): m/z 542.55 [M+H]$^+$, LCMS purity: 99.47%, HPLC Purity: 99.51%, Chiral HPLC Purity: 97.43%, 1H NMR (DMSO, 400 MHz): 8.02 (s, 1H), 7.91 (s, 1H), 7.83-7.81 (d, J=8.4 Hz, 1H), 7.71-7.69 (d, J=, 1H), 4.01-3.98 (s, 2H), 3.58-3.48 (m, 2H), 3.10 (s, 3H), 3.06-2.97 (m, 1H), 2.82-2.80 (m, 1H), 2.11-2.06 (s, 2H), 1.89-1.79 (m, 4H), 0.92-0.90 (m, 4H).

Example 312: Synthesis of N-(7-((4-(4,5-dimethylthiazol-2-yl)-2-(methylsulfonyl)phenyl)amino)-2-methyl-3H-imidazo[4,5-b]pyridin-5-yl)cyclopropanecarboxamide, I-312

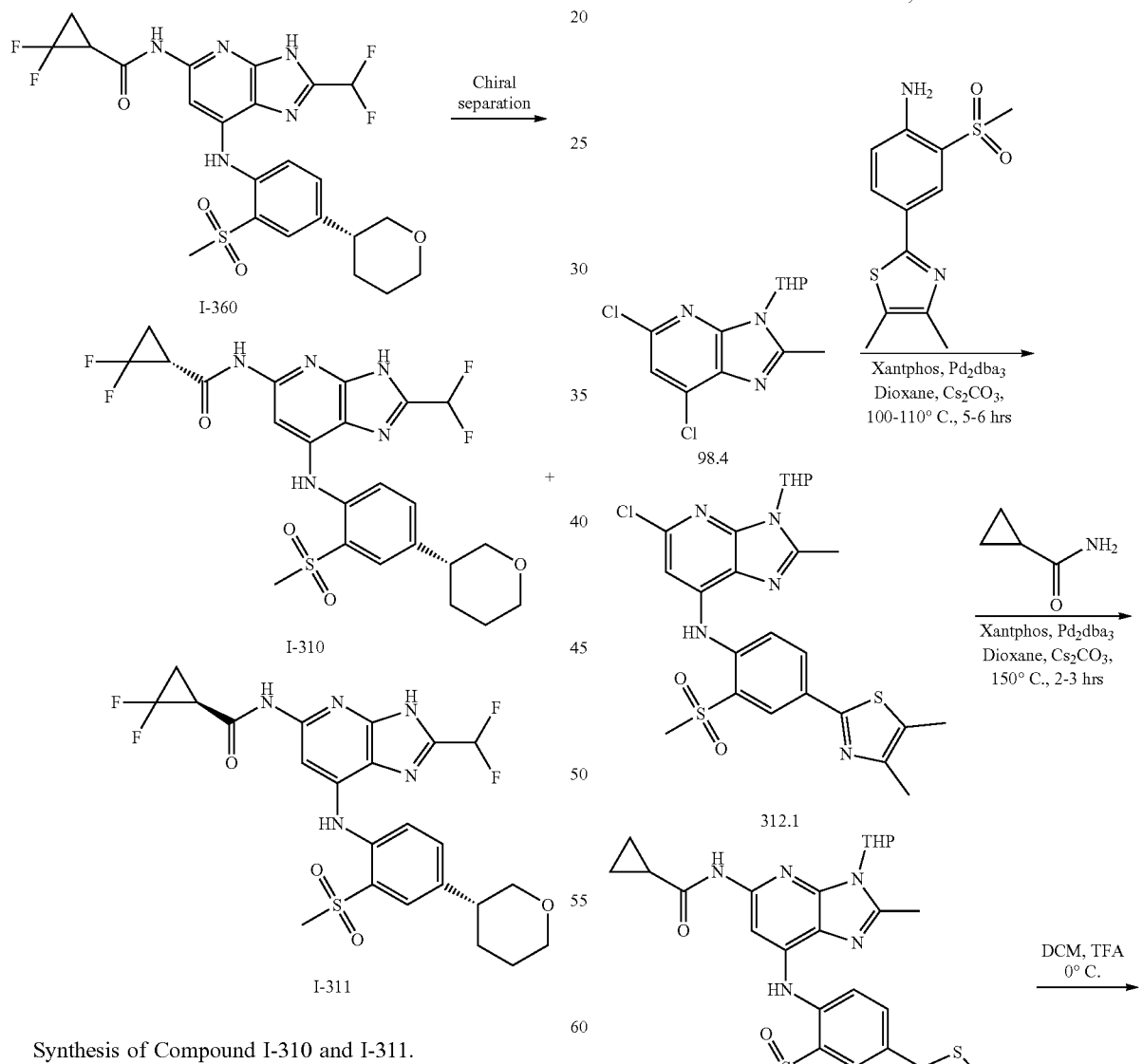

Synthesis of Compound I-310 and I-311.

Isomers of I-360 (0.080 g) were separated out using column (CHIRALCEL OX-H 250×4.6 mm, 5 µM) 0.1 DEA in IPA as co-solvent with flow rate of 4 mL/min. to get pure fraction-1 (FR-a) and fraction-2 (FR-b). FR-a was concentrated in vacuo at 30° C. to afford pure I-310 (0.028 g). MS(ES): m/z 542.55 [M+H]$^+$, LCMS purity: 98.03%, HPLC

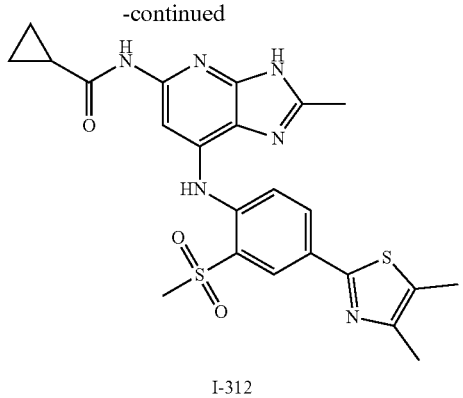

I-312

Synthesis of Compound 312.1.

Compound 312.1 was synthesized from 465.2 and 98.4 using general procedure A. (Yield: 28.66%). MS(ES): m/z 533.07 [M+H]⁺.

Synthesis of Compound 312.2.

Compound was synthesized from 312.1 and cyclopropanecarboxamide using general procedure B. (Yield: 33.93%). MS(ES): m/z 581.72 [M+H]⁺.

Synthesis of I-312.

Compound I-312 was synthesized from 312.2 using general procedure C (Yield: 58.47%). MS(ES): m/z 497.46 [M+H]⁺, LCMS purity: 100%, HPLC Purity: 99.49%, $^1$H NMR (DMSO, 400 MHz): 12.56 (s, 1H), 10.66 (s, 1H), 8.78 (s, 1H), 8.36 (s, 1H), 8.09 (s, 2H), 7.84-7.83 (m, 1H), 3.30 (s, 3H), 2.52 (s, 3H), 2.42-2.35 (d, 6H), 2.02 (s, 1H), 0.80 (bs, 4H).

Example 313/314: Synthesis of (S)—N-(2-(difluoromethyl)-7-((4-(1,5-dimethyl-1H-pyrazol-3-yl)-2-(methylsulfonyl)phenyl)amino)-3H-imidazo[4,5-b]pyridin-5-yl)-2,2-difluorocyclopropane-1-carboxamide, I-313 and (R)—N-(2-(difluoromethyl)-7-((4-(1,5-dimethyl-1H-pyrazol-3-yl)-2-(methylsulfonyl)phenyl)amino)-3H-imidazo[4,5-b]pyridin-5-yl)-2,2-difluorocyclopropane-1-carboxamide, I-314

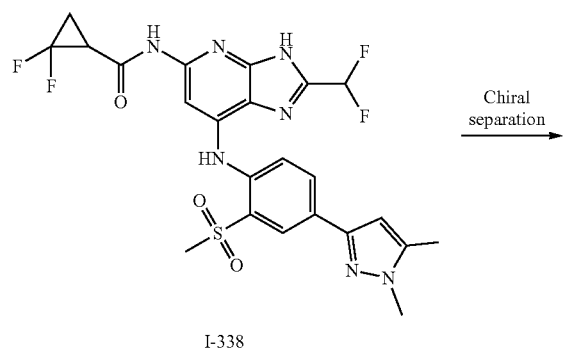

I-338

Chiral separation →

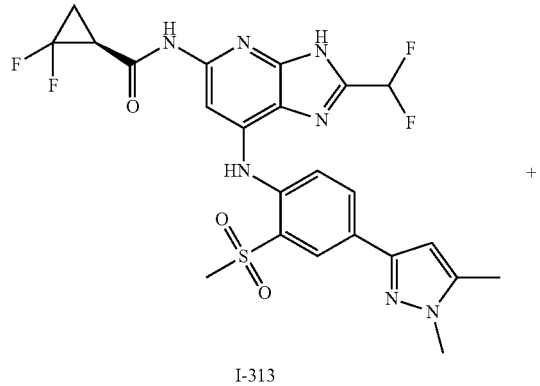

I-313

I-314

Synthesis of Compound I-313 and I-314.

Isomers of I-338 (0.1 g) were separated out using column (CHIRALCEL OX-H 250×4.6 mm, 5 μM) 0.1 DEA in IPA and acetonitrile (50:50) as co-solvent with flow rate of 4 mL/min. to get pure fraction-1 (FR-a) and fraction-2 (FR-b). FR-a was concentrated in vacuo at 30° C. to afford pure I-313 (0.022 g). MS(ES): m/z 552.85 [M+H]⁺, LCMS purity: 98.69%, HPLC Purity: 96.87%, Chiral HPLC Purity: 100%, 1H NMR (DMSO, 400 MHz): 13.79 (s, 1H), 10.81 (s, 1H), 8.64 (s, 1H), 8.28 (s, 1H), 8.06-8.04 (d, J=8.8 Hz, 1H), 7.93 (s, 1H), 7.82-7.79 (d, J=8.8 Hz, 1H), 7.21 (t, 1H), 6.59 (s, 1H), 3.80 (s, 2H), 3.24 (s, 3H), 2.31 (s, 3H), 2.02-1.96 (s, 2H). FR-b was concentrated in vacuo at 30° C. to afford pure I-314 (0.009 g). MS(ES): m/z 552.80 [M+H]⁺, LCMS purity: 97.21%, HPLC Purity: 99.41%, Chiral HPLC Purity: 96%, 1H NMR (DMSO, 400 MHz): 13.75 (s, 1H), 10.98 (s, 1H), 8.80 (s, 1H), 8.30 (s, 1H), 8.09-8.02 (m, 2H), 7-7.785 (d, J=8.4 Hz, 1H), 7.26 (t, 1H), 7.13 (s, 1H), 6.61 (s, 1H), 4.05 (s, 3H), 3.24 (s, 3H), 2.31 (s, 3H), 2.00 (s, 2H).

Example 315: Synthesis of 2-(difluoromethyl)-N7-(4-(1,4-dimethyl-1H-pyrazol-3-yl)-2-(methylsulfonyl)phenyl)-N5-(5,6-dimethylpyrazin-2-yl)-3H-imidazo[4,5-b]pyridine-5,7-diamine, I-315

Example 316/317: Synthesis of (S)—N-(2-(difluoromethyl)-7-((2-(methylsulfonyl)-4-((S)-tetrahydrofuran-2-yl)phenyl)amino)-3H-imidazo[4,5-b]pyridin-5-yl)-2,2-difluorocyclopropane-1-carboxamide, I-316 and (R)—N-(2-(difluoromethyl)-7-((2-(methylsulfonyl)-4-((S)-tetrahydrofuran-2-yl)phenyl)amino)-3H-imidazo[4,5-b]pyridin-5-yl)-2,2-difluorocyclopropane-1-carboxamide, I-317

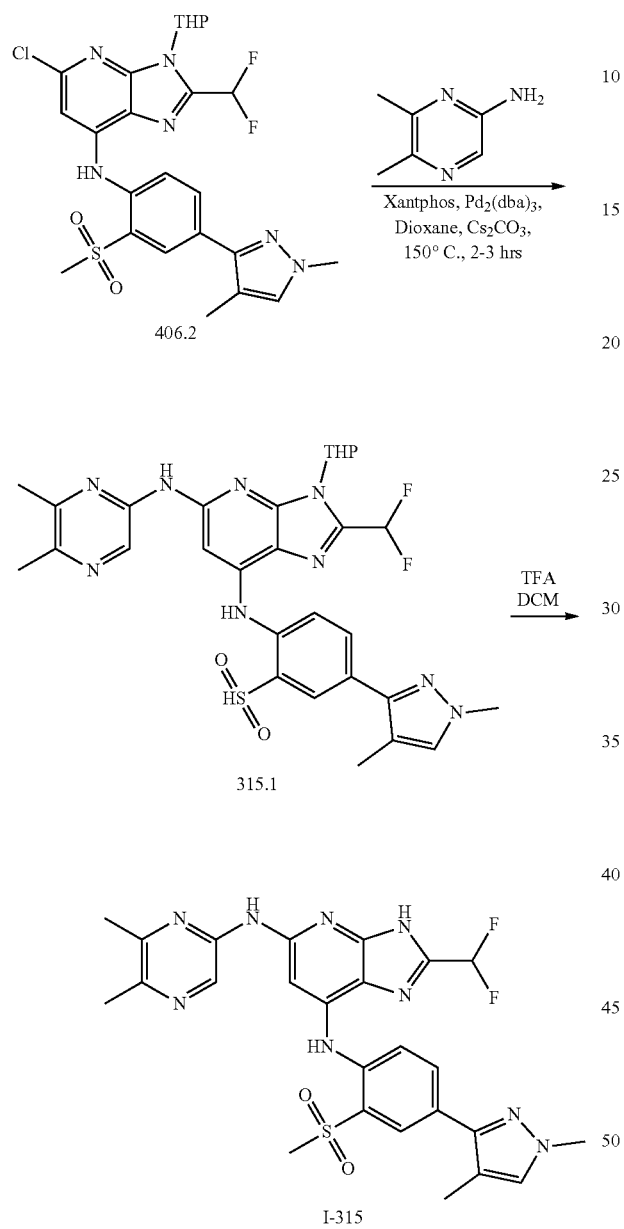

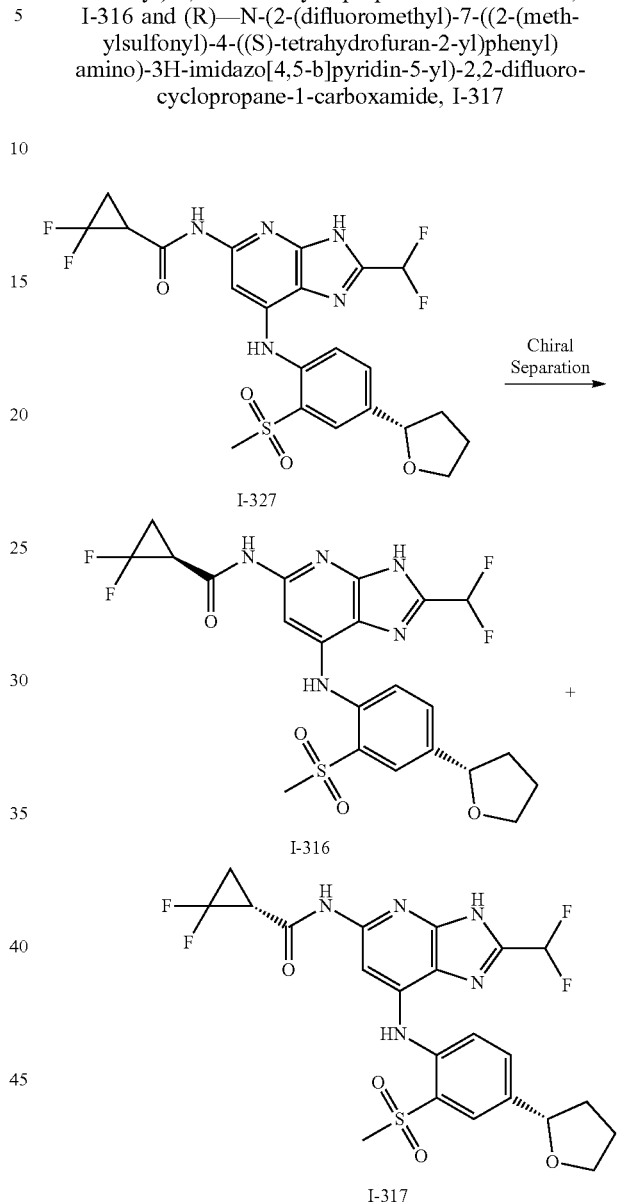

Synthesis of Compound 315.1.

Compound 315.1 was synthesized from 406.2 and 5,6-dimethylpyrazin-2-amine using general procedure B. (Yield: 43.2%). MS(ES): m/z 638.43 [M+H]⁺.

Synthesis of I-315.

Compound I-315 was synthesized from 315.1 using general procedure C. (Yield: 80.64%). MS(ES): m/z 554.52 [M+H]⁺, LCMS purity: 98.31%, HPLC Purity: 95.14%, 1H NMR (DMSO, 400 MHz): 13.58 (s, 1H), 9.83 (s, 1H), 8.99 (s, 1H), 8.87 (s, 1H), 8.26 (s, 1H), 8.06-7.95 (m, 2H), 7.62-7.61 (d, J=5.6 Hz, 2H), 7.24 (s, 1H), 3.87 (s, 3H), 3.27 (s, 3H), 2.40 (s, 6H), 2.26 (s, 3H).

Synthesis of Compound I-316 and I-317.

Isomers of I-327 (0.105 g) were separated out using column (CHIRAL PAK AD-H 250×4.6 mm, 5 μM) 0.1 DEA in IPA as co-solvent with flow rate of 4 mL/min. to get pure fraction-1 (FR-a) and fraction-2 (FR-b). FR-a was concentrated in vacuo at 30° C. to afford pure I-316 (0.025 g). MS(ES): m/z 528.79 [M+H]⁺, LCMS purity: 99.65%, HPLC Purity: 99.63%, Chiral HPLC: 100%, 1H NMR (DMSO, 400 MHz): 13.65 (s, 1H), 11.10 (s, 1H), 8.71 (s, 1H), 8.20-8.18 (d, J=30 Hz, 1H), 7.81 (s, 2H), 7.63-7.60 (d, J=10.4 Hz, 1H), 4.89-4.85 (t, J=14.4 Hz, 1H), 4.05-3.99 (m, 1H), 3.86-3.81 (m, 1H), 3.23 (s, 3H), 2.10-2.01 (m, 2H), 1.99-1.92 (m, 2H), 1.35-1.28 (m, 4H). FR-b was concentrated in vacuo at 30° C. to afford pure I-317 (0.024 g). MS(ES): m/z 528.79 [M+H]⁺, LCMS purity: 99.69%, HPLC Purity: 99.72%, Chiral HPLC: 100%, 1H NMR (DMSO, 400 MHz): 13.69 (s, 1H), 11.12 (s, 1H), 8.72 (s, 1H), 8.19-8.17 (d, J=8.4 Hz, 1H), 7.81 (s, 2H), 7.63-7.60 (d, J=10.4 Hz, 1H), 7.19 (s, 1H), 4.89-4.85 (t, J=14.4 Hz, 1H), 4.05-3.98 (m, 1H), 3.85-3.51 (m, 1H), 3.23 (s, 3H), 3.18-3.17 (m, 1H), 2.46-2.38 (m, 1H), 2.19-2.01 (m, 2H), 2.05-1.92 (m, 2H), 1.70-1.68 (m, 1H).

Example 318/319: Synthesis of (S)—N-(7-((4-cyclobutyl-2-(methylsulfonyl)phenyl)amino)-2-(difluoromethyl)-3H-imidazo[4,5-b]pyridin-5-yl)-2,2-difluorocyclopropane-1-carboxamide, I-318 and (R)—N-(7-((4-cyclobutyl-2-(methylsulfonyl)phenyl)amino)-2-(difluoromethyl)-3H-imidazo[4,5-b]pyridin-5-yl)-2,2-difluorocyclopropane-1-carboxamide, I-319

DEA in IPA as co-solvent with flow rate of 4 mL/min. to get pure fraction-1 (FR-a) and fraction-2 (FR-b). FR-a was concentrated in vacuo at 30° C. to afford pure I-318 (0.030 g). MS(ES): m/z 512.64 [M+H]$^+$, LCMS purity: 100%, HPLC Purity: 100%, 1H NMR (DMSO, 400 MHz): 13.71 (s, 1H), 10.94 (s, 1H), 8.74 (s, 1H), 7.94 (s, 1H), 7.76-7.67 (m, 3H), 3.69-3.61 (m, 1H), 3.21 (s, 3H), 3.02-2.99 (m, 2H), 2.39-2.33 (m, 2H), 2.21-2.13 (m, 2H), 2.07-1.98 (s, 3H), 1.89-.182 (m, 1H). FR-b was concentrated in vacuo at 30° C. to afford pure I-319 (0.030 g) MS(ES): m/z 512.64 [M+H]$^+$, LCMS purity: 100%, HPLC Purity: 99.59%, Chiral HPLC Purity: 99.56%, 1H NMR (DMSO, 400 MHz): 13.70 (s, 1H), 10.94 (s, 1H), 8.69 (s, 1H), 7.93 (s, 1H), 7.76-7.66 (m, 3H), 7.25 (s, 1H), 3.67-3.60 (m, 1H), 3.21 (s, 3H), 3.02 (s, 1H), 2.36-2.32 (m, 2H), 2.20-2.13 (s, 2H), 2.07-1.98 (m, 3H), 1.89-1.84 (m, 1H).

Example 320: Synthesis of N-(2-(difluoromethyl)-7-((2-methoxy-3-(4-methylthiazol-2-yl)phenyl)amino)-3H-imidazo[4,5-b]pyridin-5-yl)cyclopropanecarboxamide, I-320

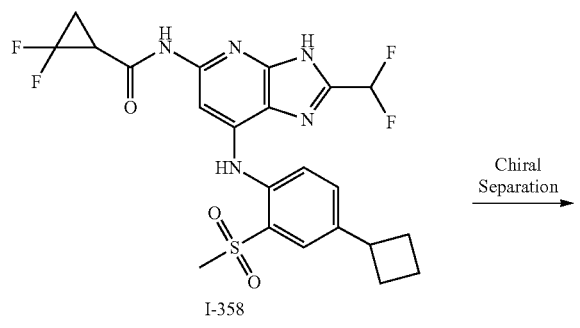

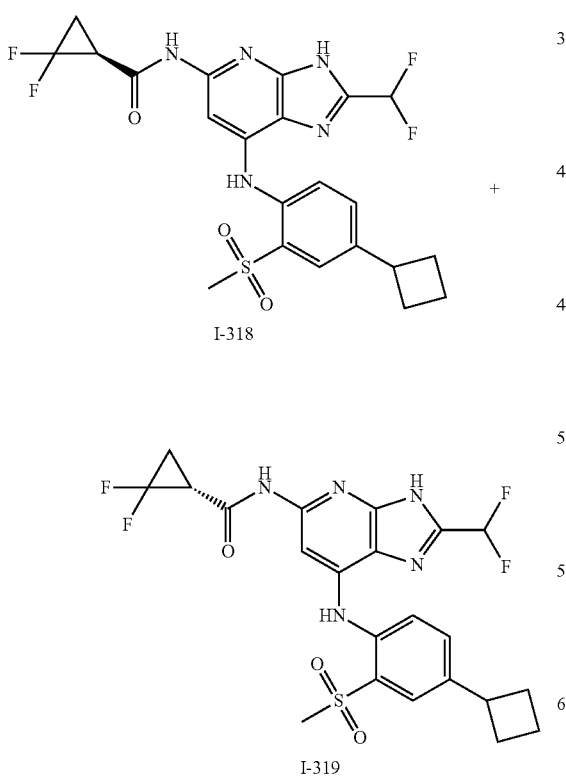

Synthesis of Compound I-318 and I-319.
Isomers of I-358 (0.085 g) were separated out using column (CHIRAL PAK AD-H 250×4.6 mm, 5 μM) 0.1%

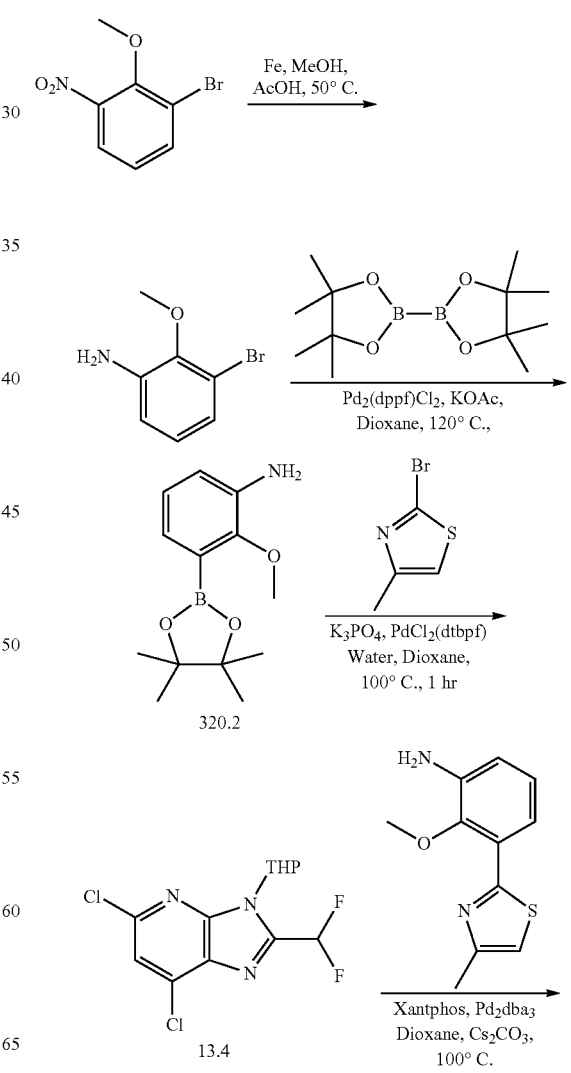

-continued

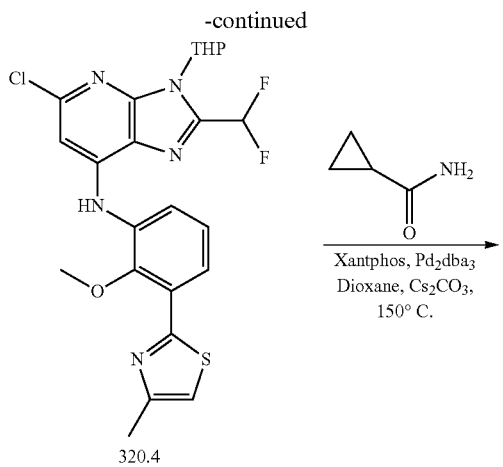

320.4

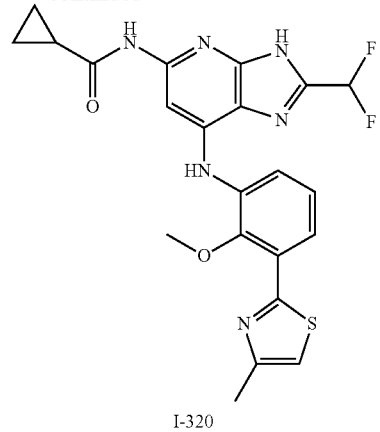

I-320

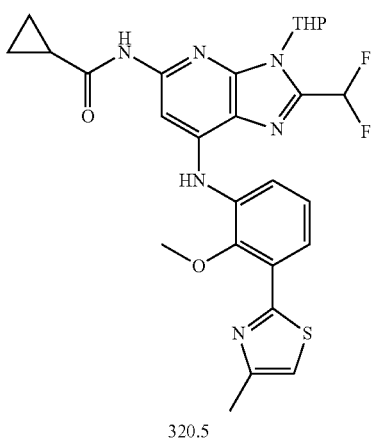

320.5

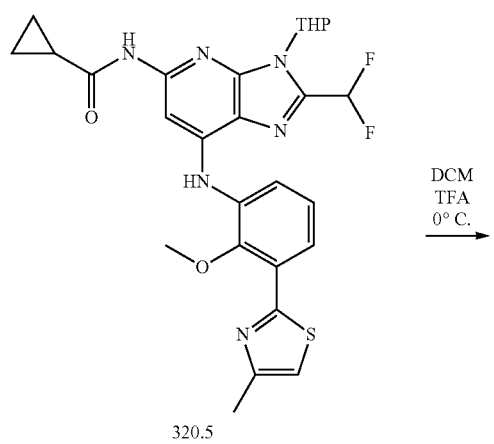

320.5

Synthesis of Compound 320.1.

To a solution of 1-bromo-2-methoxy-3-nitrobenzene (5 g, 21.55 mmol, 1 eq) in MeOH (25 mL) was added iron (6.03 g, 107.7 mmol, 5 eq), and acetic acid (25 mL). The reaction mixture was stirred for 12 h at 50° C. Upon completion, reaction mixture was filtered and washed with MeOH and concentrated in vacuo. Crude material transferred into saturated bicarbonate solution and extracted with ethyl acetate. Organic layers were combined, dried over $Na_2SO_4$ and concentrated in vacuo to obtain crude product. This was purified by column chromatography and compound was eluted in 10% ethyl acetate in hexane to obtain pure 320.1 (4 g, 91.87%). MS(ES): m/z 203.05 $[M+H]^+$.

Synthesis of Compound 320.2.

To a solution of 320.1 (4 g, 19.80 mmol, 1 eq) in 1,4-dioxane (40 mL) was added 4,4,4',4',5,5,5',5'-octamethyl-2,2'-bi(1,3,2-dioxaborolane) (25.14 g, 98.98 mmol, 5 eq), and potassium acetate (5.82 g, 59.40 mmol, 3 eq). The reaction mixture was degassed by argon for 30 min. [1,1'-Bisdiphenylphosphinoferrocene]palladium(II) dichloride (0.434 g, 5.09 mmol, 0.03 eq), was added into reaction mixture and again degassed by argon for 30 min. Further reaction mixture was stirred at 120° C. for 2 h. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 5% ethyl acetate in hexane to obtain pure 320.2 (2.7 g, 54.75%). MS(ES): m/z 250.12 $[M+H]^+$.

Synthesis of Compound 320.3.

To a solution of 320.2 (2.7 g, 10.84 mmol, 1 eq) in 1,4-dioxane (20 mL) and water (4 mL), was added 2-bromo-4-methylthiazole (2.89 g, 16.26 mmol, 1.5 eq), and potassium phosphate (6.9 g, 32.53 mmol, 3 eq). The reaction mixture was degassed by argon for 30 min. [1,1'-Bis(di-tert-butylphosphino)ferrocene]palladium(II) dichloride (0.212 g, 3.25 mmol, 0.03 eq), was added into reaction mixture and again degassed by argon for 30 min. Further reaction mixture was stirred at 120° C. for 2 h. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 5% ethyl acetate in hexane to obtain pure 320.3 (0.6 g, 27.37%). MS(ES): m/z 203.26 $[M+H]^+$.

807

Synthesis of Compound 320.4.

Compound 320.4 was synthesized from 320.3 and 13.4 using general procedure A (Yield: 22.28%). MS(ES): m/z 506.97 [M+H]⁺

Synthesis of Compound 320.5.

Compound 320.5 was synthesized from 320.4 and cyclopropanecarboxamide using general procedure B. (Yield: 43.44%). MS(ES): m/z 555.62 [M+H]⁺.

Synthesis of I-320.

Compound I-320 was synthesized from 320.4 using general procedure C. (Yield: 70.73%). MS(ES): m/z 471.17 [M+H]⁺, LCMS purity: 100%, HPLC Purity: 98.93%, 1H NMR (DMSO, 400 MHz): 13.46 (s, 1H), 10.52 (s, 1H), 8.66 (s, 1H), 8.10-8.08 (d, J=7.6 Hz, 1H), 7.48-7.34 (m, 3H), 7.27-7.21 (m, 1H), 7.06 (t, 1H), 3.73 (s, 3H), 2.47 (s, 3H), 2.00-1.97 (t, J=11.2 Hz, 1H), 0.71 (bs, 4H).

Example 321: Synthesis of N-(7-((2-methoxy-3-(4-methylthiazol-2-yl)phenyl)amino)-2-methyl-3H-imidazo[4,5-b]pyridin-5-yl)cyclopropanecarboxamide, I-321

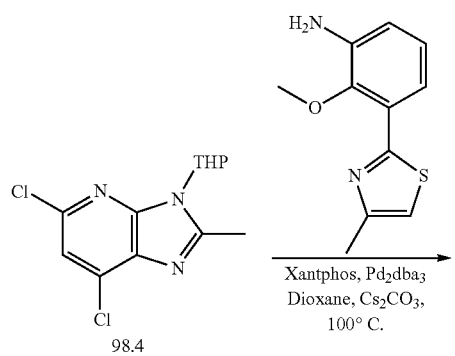

98.4

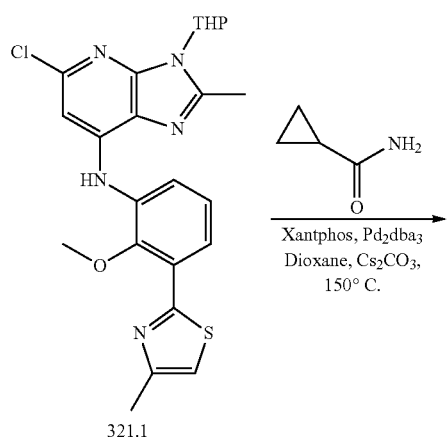

321.1

808

-continued

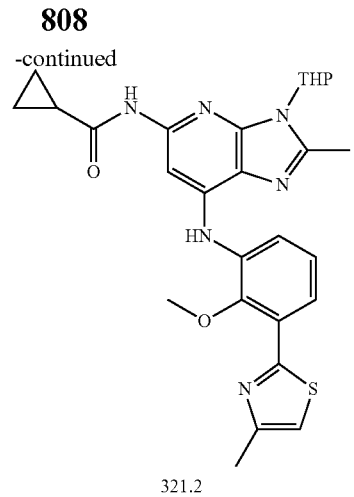

321.2

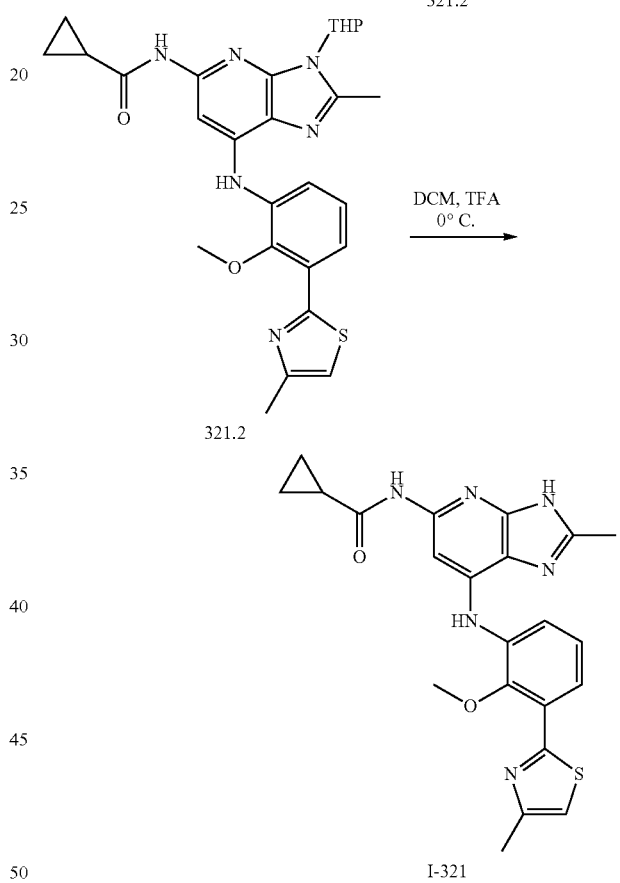

Synthesis of Compound 321.1.

Compound 321.1 was synthesized from 320.3 and 98.4 using general procedure A to obtain 1.2. (Yield: 20.88%). MS (ES): m/z 470.99 [M+H]⁺.

Synthesis of Compound 321.2.

Compound 321.2 was synthesized from 321.1 and cyclopropanecarboxamide using general procedure B. (Yield: 54.37%). MS (ES): m/z 519.64 [M+H]⁺.

Synthesis of Compound I-321.

Compound I-321 was synthesized from 321.2 using general procedure C. (Yield: 58.02%). MS(ES): m/z 435.44 [M+H]⁺, LCMS purity: 98.97%, HPLC Purity: 98.54%, 1H NMR (DMSO, 400 MHz): 10.80 (s, 1H), 8.81 (s, 1H), 8.08-8.08 (d, J=0.4 Hz, 1H), 7.71 (s, 1H), 7.48-7.43 (m, 3H), 7.34-7.30 (m, 1H), 3.76 (s, 3H), 2.70 (s, 3H), 2.47 (s, 3H), 1.99-1.96 (t, J=10.8 Hz, 1H), 0.77 (bs, 4H).

Example 322: Synthesis of (1S,2S)—N-(2-(difluoromethyl)-7-((4-(1-methyl-1H-imidazol-4-yl)-2-(methylsulfonyl)phenyl)amino)-3H-imidazo[4,5-b]pyridin-5-yl)-2-fluorocyclopropane-1-carboxamide, I-322

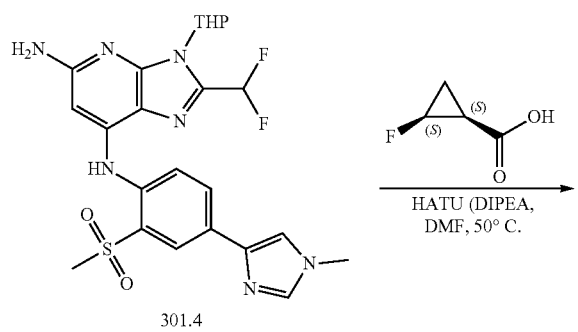

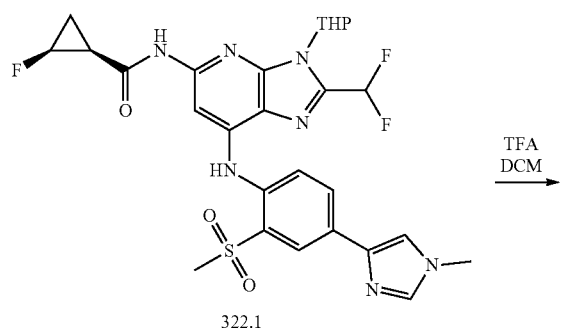

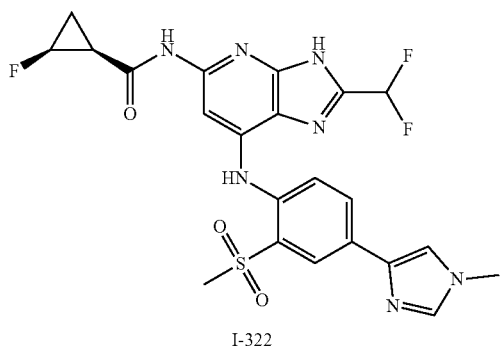

Synthesis of Compound 322.1.

To a solution of (1S,2S)-2-fluorocyclopropane-1-carboxylic acid (0.018 g, 0.173 mmol, 1.5 eq) in N,N-dimethylformamide (0.5 mL) at 0° C., ((1-[Bis(dimethylamino)methylene]-1H-1,2,3-triazolo[4,5-b]pyridinium 3-oxid hexa fluoro phosphate)) (0.066 g, 0.173 mmol, 1.5 eq) was added. Reaction mixture was stirred at 0° C. for 30 min. Then, N,N-Diisopropylethylamine (0.044 g, 3.48 mmol, 3.0 eq) and compound 301.4 (0.060 g, 0.115 mmol, 1.0 eq) was added. Reaction mixture was stirred at 50° C. for 5 hr. Upon completion, reaction mixture was transferred into ice water and extracted with ethyl acetate. Organic layers were combined, dried over Na$_2$SO$_4$ and concentrated in vacuo to pressure to obtain crude product. This was purified by column chromatography and compound was eluted in 5% MeOH in CH$_2$Cl$_2$ to obtain pure 322.1 (0.042 g, 60.02%). MS(ES): m/z 604.62 [M+H]$^+$.

Synthesis of Compound I-322.

Compound I-322 was synthesized from 322.1 using general procedure C. (Yield: 74.69%). MS(ES): m/z 520.64 [M+H]$^+$, LCMS purity: 95.17%, HPLC Purity: 96.43%, Chiral HPLC Purity: 98.45%, 1H NMR (DMSO, 400 MHz): 13.70 (s, 1H), 10.80 (s, 1H), 8.74 (s, 1H), 8.33 (s, 1H), 8.11-8.06 (m, 2H), 7.80-7.73 (m, 3H), 7.27 (t, 1H), 3.72 (s, 3H), 3.24 (s, 3H), 2.24 (s, 2H), 1.66-1.60 (d, J=23.2 Hz, 1H), 1.25 (s, 1H).

Example 323: Synthesis of 2,2-difluoro-N-(2-methyl-7-((2-(methylsulfonyl)-4-((S)-tetrahydro-2H-pyran-2-yl)phenyl)amino)-3H-imidazo[4,5-b]pyridin-5-yl)cyclopropane-1-carboxamide, I-323

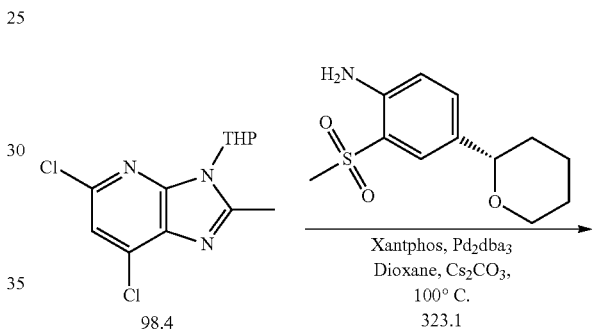

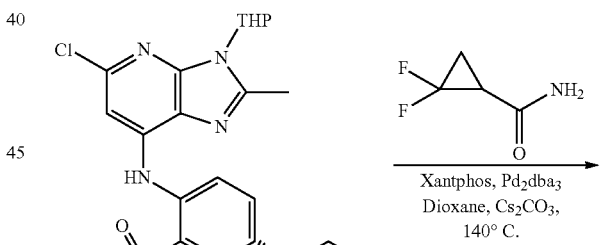

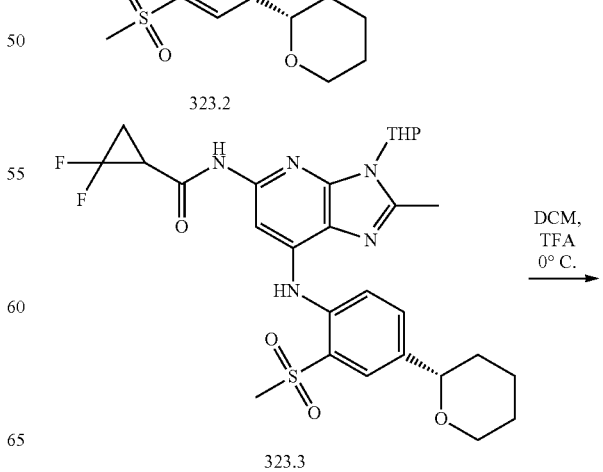

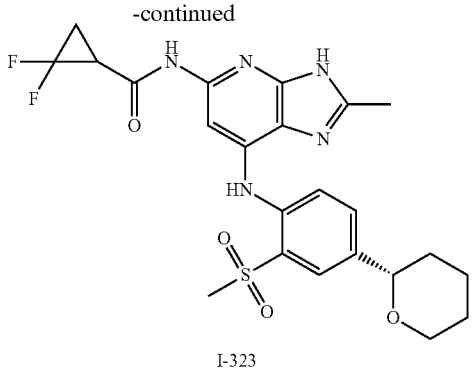

I-323

Synthesis of Compound 323.1.
Compound 323.1 was synthesized as per 1-325
Synthesis of Compound 323.2.
Compound 323.2 was synthesized from 98.4 and 323.1 using general procedure A. (Yield: 38.89%). MS(ES): m/z 506.03 [M+H]$^+$.
Synthesis of Compound 323.3.
Compound was synthesized from 323.2 and 2,2-difluorocyclopropane-1-carboxamide using general procedure B. (Yield: 47.11%). MS(ES): m/z 590.66 [M+H]$^+$.
Synthesis of I-323.
Compound I-323 was synthesized from 323.3 using general procedure C (Yield: 79.53%). MS(ES): m/z: 506.41 [M+H]$^+$, LCMS purity: 98.61%, HPLC purity 97.83%, Chiral HPLC: (52.00%, 48.00%), 1H NMR (DMSO-d6, 400 MHz): 12.55 (s, 1H), 10.80 (s, 1H), 8.57 (s, 1H), 7.94 (s, 1H), 7.87 (s, 1H), 7.74-7.68 (m, 2H), 4.43-4.41 (d, J=10.8 Hz, 1H), 4.08-4.02 (m, 1H), 3.59 (s, 3H), 3.19 (s, 3H), 2.98-2.95 (m, 1H), 2.02-1.97 (m, 2H), 1.93-1.88 (m, 2H), 1.67-1.57 (m, 2H), 1.49-1.44 (m, 2H), 1.24-1.16 (m, 1H).

Example 324: Synthesis of 2,2-difluoro-N-(2-methyl-7-((2-(methylsulfonyl)-4-((R)-tetrahydro-2H-pyran-2-yl)phenyl)amino)-3H-imidazo[4,5-b]pyridin-5-yl)cyclopropane-1-carboxamide, I-324

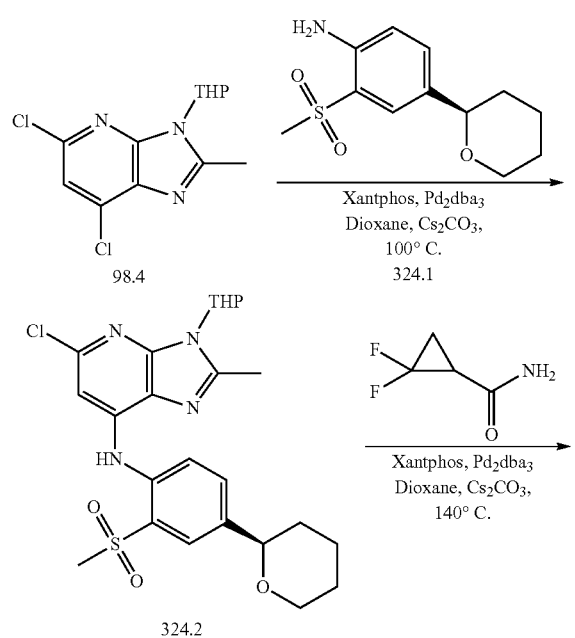

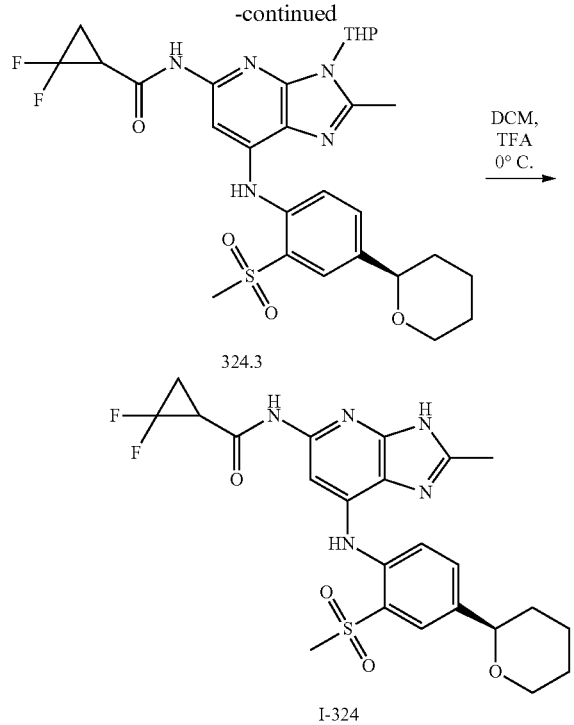

I-324

Synthesis of Compound 324.1.
Compound 324.1 was synthesized as per 1-325.
Synthesis of Compound 324.2.
Compound 324.2 was synthesized from 98.4 and 324.1 using general procedure A. (Yield: 33.71%). MS(ES): m/z 506.03 [M+H]$^+$.
Synthesis of Compound 324.3.
Compound 324.3 was synthesized from 324.2 and 2,2-difluorocyclopropane-1-carboxamide using general procedure B. (Yield: 47.11%). MS(ES): m/z 590.66 [M+H]$^+$.
Synthesis of I-324.
Compound I-324 was synthesized from 324.3 using general procedure C. (Yield: 95.43%). MS(ES): m/z: 506.36 [M−H]+, LCMS purity: 97.08%, HPLC purity 95.29%, Chiral HPLC: (52.00%, 48.00%), 1H NMR (DMSO-d6, 400 MHz): 10.82 (s, 1H), 8.58 (s, 1H), 7.94 (s, 1H), 7.88 (s, 1H), 7.75-7.68 (m, 3H), 4.44-4.41 (d, J=10.4 Hz, 1H), 4.09-4.06 (d, J=11.6 Hz, 1H), 3.82 (s, 1H), 3.60-3.57 (d, J=11.2 Hz, 1H), 3.19 (s, 3H), 3.02-2.97 (m, 1H), 2.68-2.65 (m, 1H), 2.50 (s, 3H), 2.10-1.84 (m, 4H), 1.66-1.58 (m, 2H).

Example 325: Synthesis of N-(2-(difluoromethyl)-7-((2-(methylsulfonyl)-4-((S)-tetrahydro-2H-pyran-2-yl)phenyl)amino)-3H-imidazo[4,5-b]pyridin-5-yl)-2,2-difluorocyclopropane-1-carboxamide, I-325

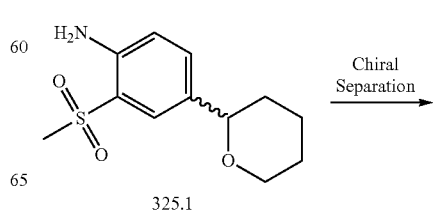

325.1

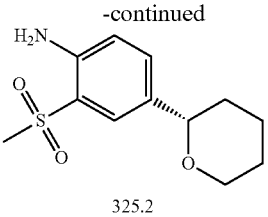

325.2

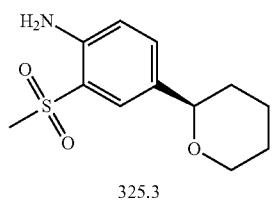

325.3

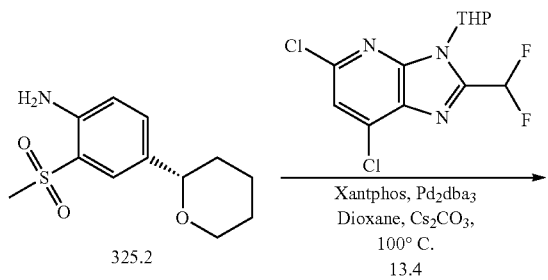

325.2    13.4

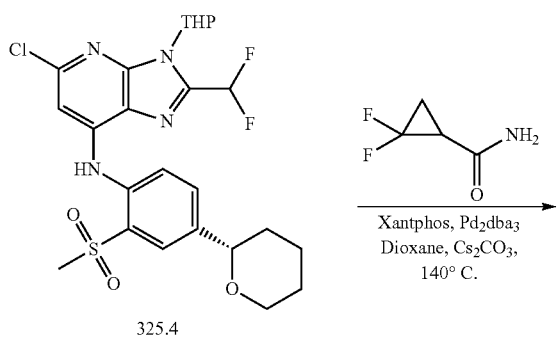

325.4

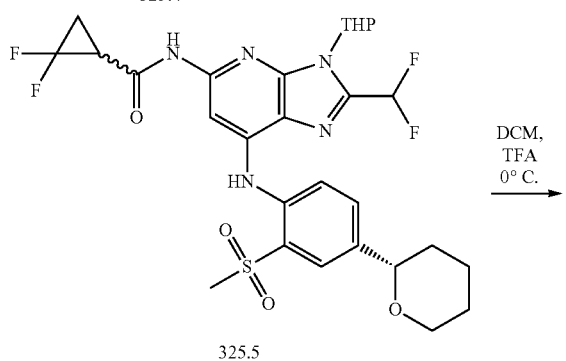

325.5

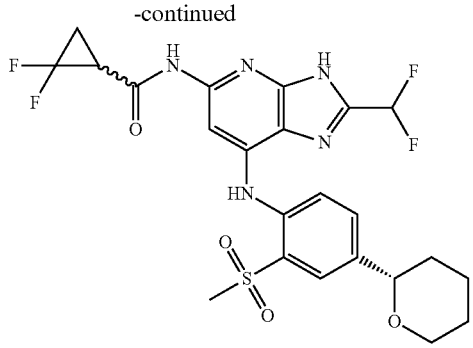

I-325

Synthesis of Compound 325.1.

Compound 325.1 was synthesized as per I-391.

Synthesis of Compound 325.2/325/3.

Isomers of compound 325.1 (1.2 g) were separated out using column (CHIRAL CEL OX-H 250×4.6 mm, 5 μM) 0.1 DEA in IPA as co-solvent with flow rate of 4 mL/min. to get pure fraction-1 (FR-a) and fraction-2 (FR-b). FR-a was concentrated in vacuo at 30° C. to afford pure compound 325.2 (0.3 g, 25.0%). MS(ES): m/z: 256.40 [M+H]$^+$ Synthesis of Compound 325.4.

Compound 325.4 was synthesized from 13.4 and 325.2 using general procedure A. (Yield: 31.46%). MS(ES): m/z 542.16 [M+H]$^+$.

Synthesis of Compound 325.5.

Compound 325.5 was synthesized from 325.4 and 2,2-difluorocyclopropane-1-carboxamide using general procedure B. (Yield: 47.56%). MS(ES): m/z 626.48 [M+H]$^+$.

Synthesis of I-325.

Compound I-325 was synthesized from 325.5 using general procedure C. (Yield: 63.02%). MS(ES): m/z: 542.50 [M+H]$^+$, LCMS purity: 95.56%, HPLC purity 96.96%, Chiral HPLC: (45.00%, 44.00%), 1H NMR (MeOD, 400 MHz): 8.05-8.04 (d, J=5.2 Hz, 1H), 7.86-7.84 (m, 1H), 7.77-7.76 (m, 2H), 7.12-6.86 (t, 1H), 4.51-4.48 (d, J=11.6 Hz, 1H), 4.17-4.15 (d, J=9.6 Hz, 1H), 3.74-3.68 (m, 1H), 3.38 (s, 1H), 3.11 (s, 3H), 2.84-2.79 (m, 1H), 2.13-2.08 (m, 1H), 1.99-1.90 (m, 2H), 1.88-1.78 (m, 2H), 1.75-1.66 (m, 1H), 1.62-1.59 (m, 1H).

Example 326: Synthesis of N-(2-(difluoromethyl)-7-((2-(methylsulfonyl)-4-((R)-tetrahydro-2H-pyran-2-yl)phenyl)amino)-3H-imidazo[4,5-b]pyridin-5-yl)-2,2-difluorocyclopropane-1-carboxamide, I-326

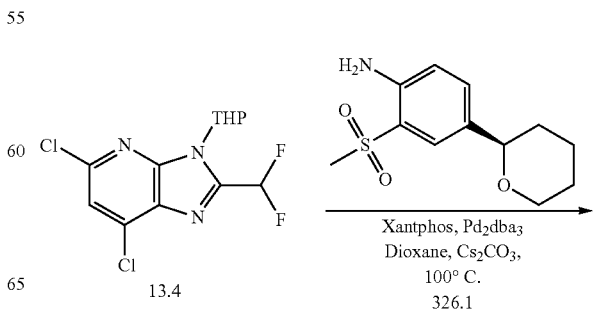

13.4    326.1

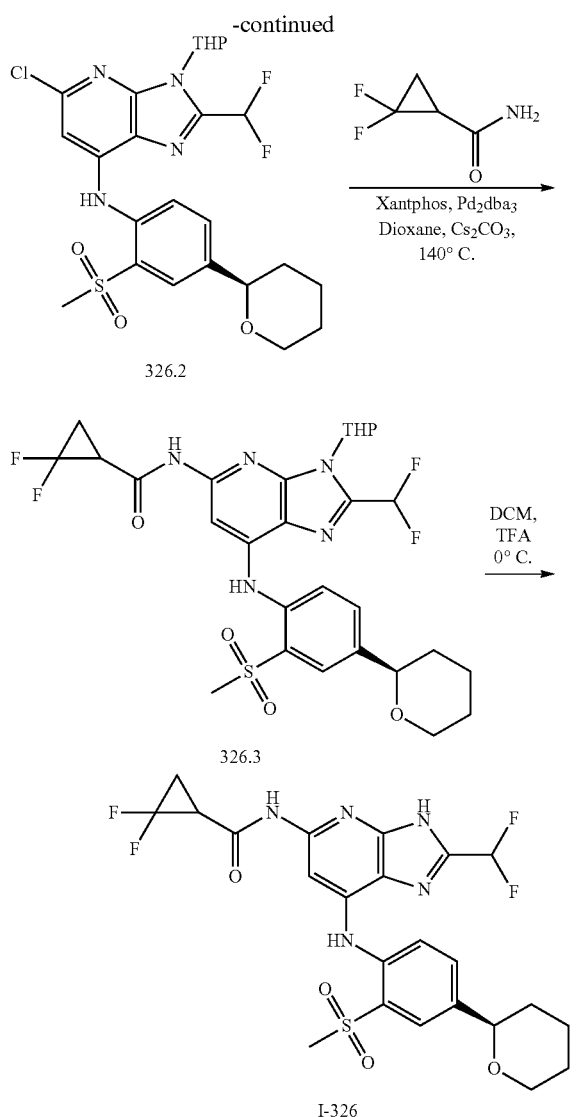

I-326

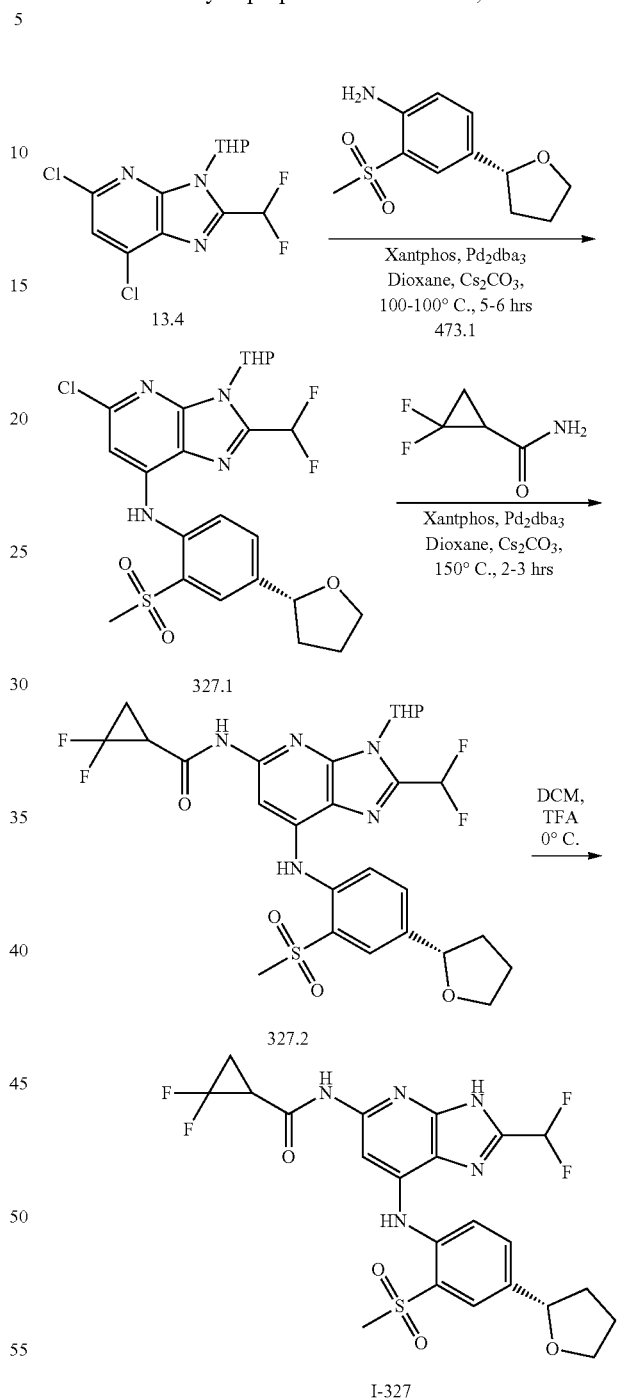

Example 327: Synthesis of N-(2-(difluoromethyl)-7-((2-(methylsulfonyl)-4-((S)-tetrahydrofuran-2-yl)phenyl)amino)-3H-imidazo[4,5-b]pyridin-5-yl)-2,2-difluorocyclopropane-1-carboxamide, I-327

Synthesis of Compound 326.1.

Compound 326.1 was synthesized as per I-325.

Synthesis of Compound 326.2.

Compound 326.2 was synthesized from 13.4 and 326.1 using general procedure A. (Yield: 28.73%). MS(ES): m/z 542.01 [M+H]$^+$.

Synthesis of Compound 326.3.

Compound 326.3 was synthesized from 326.2 and 2,2-difluorocyclopropane-1-carboxamide using general procedure B. (Yield: 67.94%). MS(ES): m/z 626.64 [M+H]$^+$.

Synthesis of I-326.

Compound I-326 was synthesized from 326.3 using general procedure C (Yield: 89.28%). MS(ES): m/z: 542.65 [M+H]$^+$, LCMS purity: 97.70%, HPLC purity 96.81%, Chiral HPLC: (50.00%, 48.44%), 1H NMR (DMSO-d6, 400 MHz): 13.74 (s, 1H), 10.97 (s, 1H), 8.77 (s, 1H), 7.99 (s, 1H), 7.90 (s, 1H), 7.74-7.71 (m, 2H), 7.26 (t, 1H), 4.46-4.43 (d, J=10.4 Hz, 1H), 4.08-4.05 (d, J=11.2 Hz, 1H), 3.60-3.57 (m, 1H), 3.21 (s, 3H), 2.09-1.81 (m, 4H), 1.80-1.60 (m, 3H), 1.58-1.35 (m, 1H) 1.24 (s, 1H).

Synthesis of Compound 327.1.

Compound 327.1 was synthesized from 13.4 and 473.1 using general procedure A. (Yield: 24.66%). MS(ES): m/z 527.98 [M+H]$^+$.

Synthesis of Compound 327.2.

Compound was synthesized from 327.1 and 2,2-difluorocyclopropane-1-carboxamide using general procedure B. (Yield: 58.47%). MS(ES): m/z 612.61 [M+H]$^+$.

Synthesis of Compound I-327.

Compound I-327 was synthesized from 327.2 using general procedure C. (Yield: 91.54%). MS(ES): m/z 528.51 [M+H]$^+$, LCMS purity: 98.62%, HPLC Purity: 100%, Chiral HPLC Purity: 48.19% and 51.80%, 1H NMR (DMSO, 400 MHz): 13.75 (s, 1H), 10.99 (s, 1H), 8.78 (s, 1H), 8.00 (s, 1H), 7.88 (m, 2H), 7.78-7.72 (m, 2H), 4.93-4.90 (t, 1H), 4.06-4.01 (m, 1H), 3.86-3.83 (m, 1H), 3.22 (s, 3H), 3.02-3.00 (m, 1H), 2.42-2.35 (m, 1H), 2.02-1.96 (m, 4H), 1.76-1.69 (m, 1H).

Example 328: Synthesis of N-(7-((2-(N,S-dimethyl-sulfonimidoyl)phenyl)amino)-2-methyl-3H-imidazo[4,5-b]pyridin-5-yl)cyclopropanecarboxamide, I-328

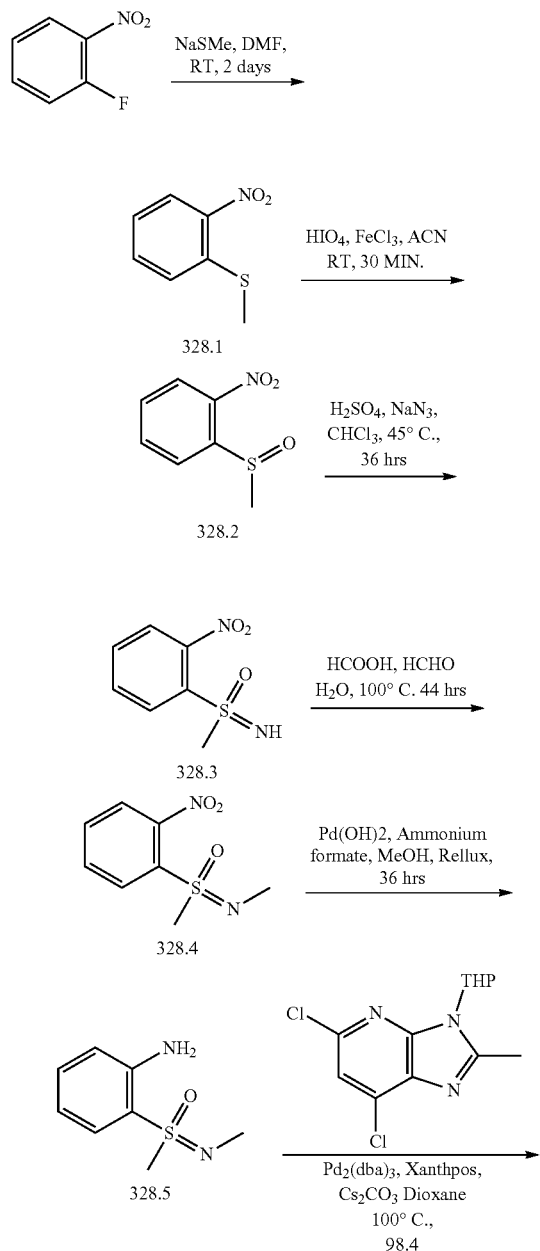

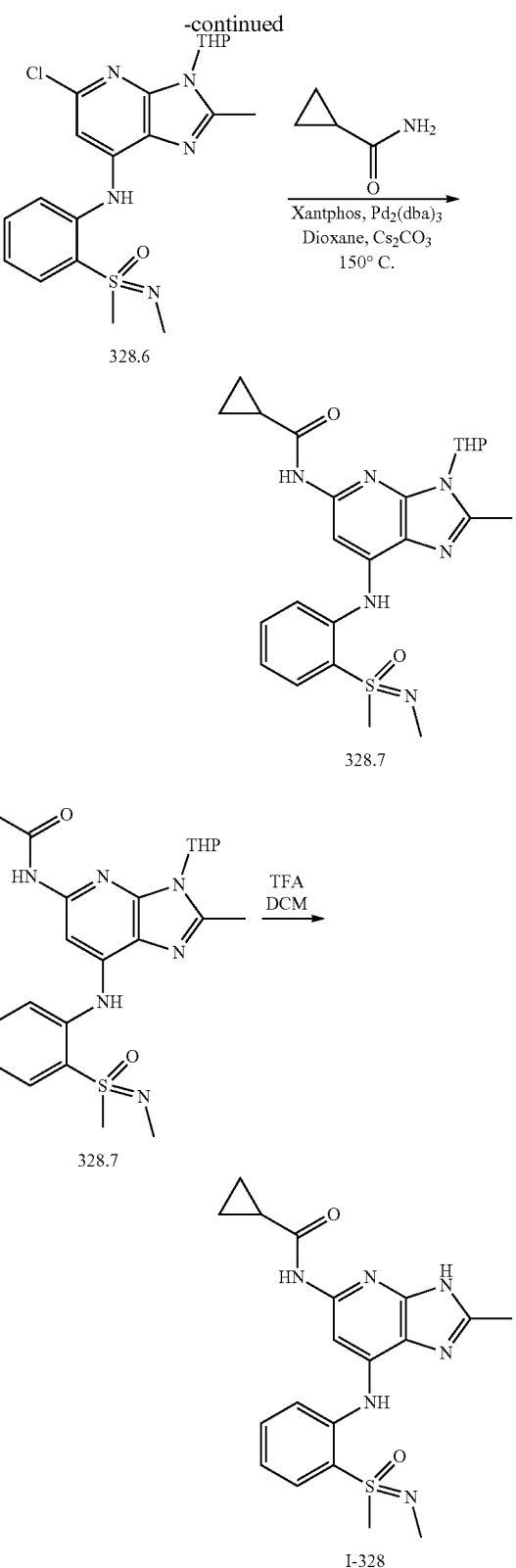

Synthesis of Compound 328.1.

To compound 1-fluoro-2-nitrobenzene 1 (10 g, 70.9 mmol, 1.0 eq) in N,N'-dimethylformamide (100 mL), sodium methanethiolate (5.95 g, 85.1 mmol, 1.2 eq) was added. Reaction mixture was stirred at r.t. for 48 h. After completion of the reaction, the reaction mixture was transferred into water and extracted with ethyl acetate. Organic layer combined, dried over anhydrous Na$_2$SO$_4$, filtered and concentrated in vacuo to obtain 328.1 (10 g, 83.39%). MS(ES): m/z 170.53 [M+H]$^+$.

Synthesis of Compound 328.2.

To compound 328.1 (10 g, 59.17 mmol, 1.0 eq) in acetonitrile (100 mL), periodic acid (5.65 g, 29.5 mmol, 0.5 eq) and iron chloride (4.77 g, 29.5 mmol, 0.5 eq) were added. Reaction mixture was stirred at r.t. for 30 min. After completion of the reaction, acetonitrile was concentrated and reaction mixture was transferred into water, extracted with ethyl acetate. Organic layer combined, dried over anhydrous Na$_2$SO$_4$, filtered and concentrated in vacuo to obtain the crude material. This was purified by column chromatography using 15% ethyl acetate in hexane to obtain 328.2 (9 g, 82.22%). MS(ES): m/z 186.96 [M+H]$^+$.

Synthesis of Compound 328.3.

To compound 328.2 (5 g, 27.02 mmol, 1.0 eq) in chloroform (50 mL) sodium azide (3.51 g, 54.04 mmol, 2.0 eq) and concentrated nitric acid (0.52 g, 54.0 mmol, 0.2 eq) were added. Reaction mixture was stirred at 45° C. for 36 h. After completion of the reaction, the reaction mixture was transferred into water and extracted with CH$_2$Cl$_2$. Organic layer combined, dried over anhydrous Na$_2$SO$_4$, filtered and concentrated in vacuo to obtain crude product. This was purified by column chromatography using 2% MeOH in CH$_2$Cl$_2$ as eluant to obtain pure 328.3 (3 g, 55.50%). MS(ES): m/z 201.49 [M+H]$^+$.

Synthesis of Compound 328.4.

To a suspension of compound 328.3 (3 g, 13.9 mmol, 1.0 eq) in water (30 mL), formaldehyde (0.5 g, 16.6 mmol, 1.2 eq) and formic acid (0.32 g, 6.9 mmol, 0.5 eq) were added. Reaction mixture was stirred at 100° C. for 44 h. After completion of the reaction, the reaction mixture was cooled to r.t., transferred into water and extracted with ethyl acetate. Organic layer combined, dried over anhydrous Na$_2$SO$_4$, filtered and concentrated in vacuo to obtain crude product. This was purified by column chromatography using 40% ethyl acetate in hexane as eluant to obtain 328.4. MS(ES): m/z 215.43 [M+H]$^+$.

Synthesis of Compound 328.5.

To compound 328.4 (2 g, 93.02 mmol, 1.0 eq) in MeOH (20 mL), palladium hydroxide (0.49 g, 4.6 mmol, 0.5 eq) and ammonium formate (1.17 g, 18.6 mmol, 2.0 eq) were added. Reaction mixture was stirred at 80° C. for 36 h. After completion of the reaction, the reaction mixture was transferred into water and extracted with ethyl acetate. Organic layer combined, dried over anhydrous Na$_2$SO$_4$, filtered and concentrated in vacuo to obtain the crude material. This was purified by 5% MeOH in CH$_2$Cl$_2$ as eluant to obtain pure 328.5 (0.8 g, 40.53%). MS(ES): m/z 185.16 [M+H]$^+$.

Synthesis of Compound 328.6.

Compound 328.6 was synthesized from 328.5 and 98.4 using general procedure A. (Yield: 42.20%). MS(ES): m/z 434.96 [M+H]$^+$.

Synthesis of Compound 328.7.

Compound 328.7 was synthesized from 328.6 and cyclopropanecarboxamide using general procedure B. (Yield: 44.96%). MS(ES): m/z 483.60 [M+H]$^+$.

Synthesis of I-328.

Compound I-328 was synthesized from 328.7 using general procedure C. (Yield: 54.50%). MS(ES): m/z 399.49 [M+H]$^+$, LCMS purity: 99.24%, HPLC Purity: 97.26%, Chiral HPLC: 49.38% and 50.10% 1H NMR (DMSO, 400 MHz): 12.52 (s, 1H), 10.53 (s, 1H), 9.64 (s, 1H), 8.06 (s, 1H), 7.880-7.861 (d, J=29.6 Hz, 1H), 7.74-7.66 (m, 2H), 7.25-7.21 (m, 1H), 3.06 (s, 3H), 2.65 (s, 3H), 2.45 (s, 3H), 2.02-1.98 (s, 1H), 0.81-0.62 (m, 4H).

Example 329: Synthesis of N-(2-(difluoromethyl)-7-((2-(methylsulfonyl)-4-((R)-tetrahydrofuran-2-yl)phenyl)amino)-3H-imidazo[4,5-b]pyridin-5-yl)-2,2-difluorocyclopropane-1-carboxamide, I-329

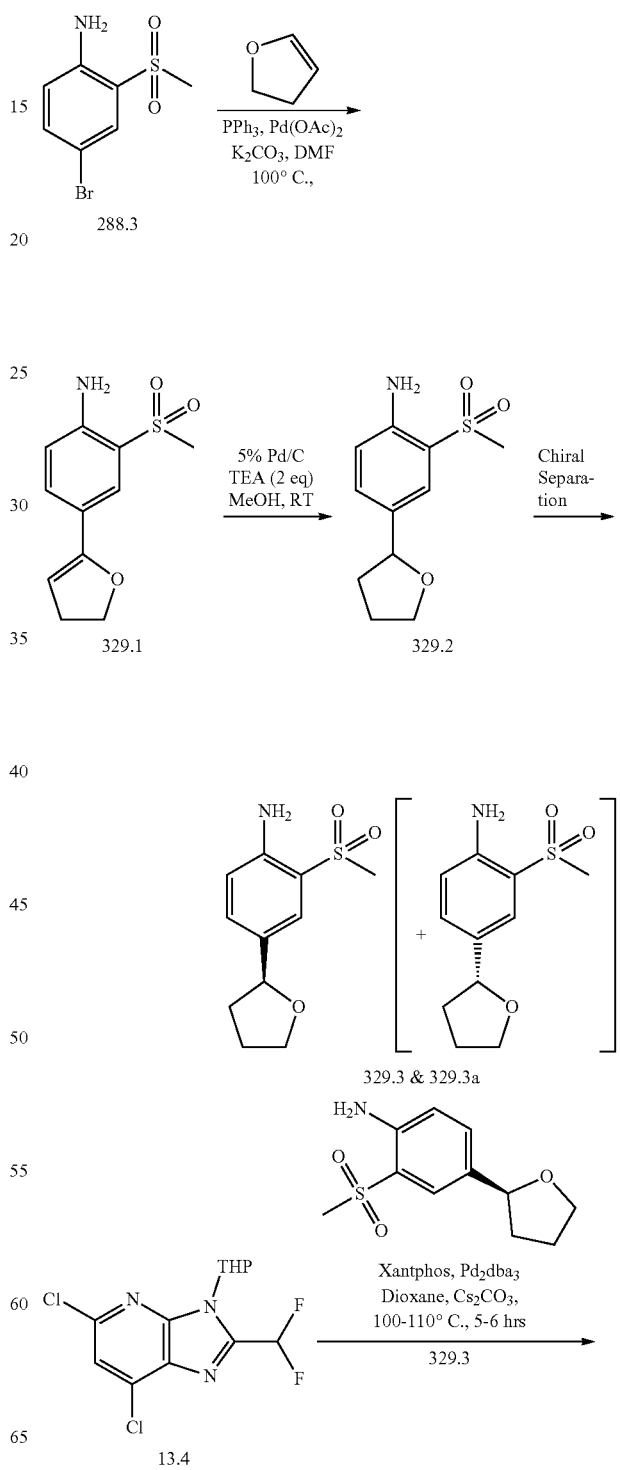

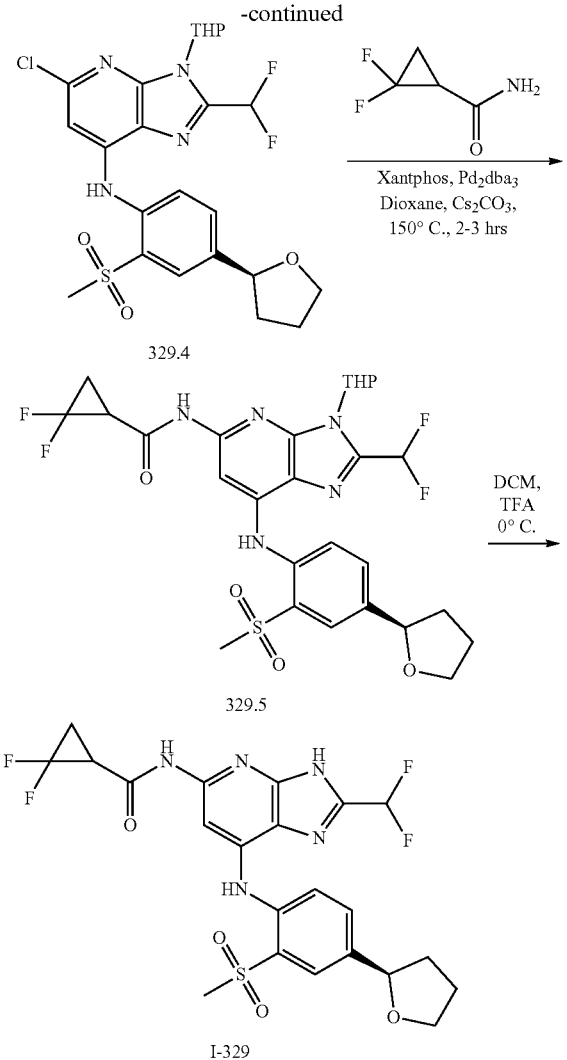

Synthesis of Compound 329.1.

To a solution of 288.3 (10 g, 45.85 mmol, 1 eq) in dimethylformamide (100 mL) was added 2,3-dihydropyran (16 g, 229.24 mmol, 5 eq), and potassium carbonate (19 g, 137.61 mmol, 3 eq), Triphenylphosphine (2.4 g, 9.17 mmol, 0.2 eq). The reaction mixture was degassed by argon for 30 min. Palladium(II) acetate (1 g, 4.58 mmol, 0.1 eq), was added into reaction mixture and again reaction mixture was degassed by argon for 30 min. Further reaction mixture was stirred at 100° C. for 15 h. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 329.1 (5.5 g, 50.13%). MS(ES): m/z 240.29 $[M+H]^+$.

Synthesis of Compound 329.2.

To a solution of 329.1 (5 g, 20.90 mmol, 1.0 eq) in MeOH (90 mL), 10% Pd/C (0.400 g), Triethylamine (6.3 g, 62.76 mmol, 3 eq) was added. Hydrogen was purged through reaction mixture for 2-3 hr at r.t. Upon completion, reaction mixture was filtered through celite-bed and washed with ethanol. Filtrate was concentrated in vacuo to obtain 329.2 (3 g, 59.50%). MS(ES): m/z 242.31 $[M+H]^+$.

Synthesis of Compound 329.3.

Isomers of compound 329.2 (0.9 g) were separated out using column (CHIRAL CEL OX-H 250×4.6 mm, 5 μM) AND 0.1% DEA in IPA as co-solvent with flow rate of 4 mL/min. to get pure fraction-1 (FR-a) and fraction-2 (FR-b). FR-b was concentrated in vacuo at 30° C. to afford pure 329.3 (0.30 g, 33.25%). MS(ES): m/z 242.32 $[M+H]^+$.

Synthesis of Compound 329.4.

Compound 329.4 was synthesized from 329.3 and 13.4 using general procedure A. (Yield: 24.30%). MS(ES): m/z 527.98 $[M+H]^+$.

Synthesis of Compound 329.5.

Compound 329.5 was synthesized from 329.4 and difluorocyclopropane-1-carboxamide using general procedure B. (Yield: 68.68%). MS(ES): m/z 612.61 $[M+H]^+$.

Synthesis of Compound I-329.

Compound I-329 was synthesized from 329.5 using general procedure C. (Yield: 89.80%). MS(ES): m/z 528.61 $[M+H]^+$, LCMS purity: 98.87%, HPLC Purity: 99.23%, Chiral HPLC Purity: 50.15% and 49.84%, 1H NMR (DMSO, 400 MHz): 13.74 (s, 1H), 10.97 (s, 1H), 7.97 (s, 1H), 7.87 (s, 1H), 7.74-7.72 (m, 2H), 4.90 (s, 1H), 4.0.2 (s, 1H), 4.01 (s, 1H), 3.21 (s, 3H), 3.17-3.16 (d, J=5.2 Hz, 3H), 2.42-2.34 (m, 2H), 2.01-1.95 (m, 4H).

Example 330: Synthesis of N-(7-((4-(5,5-dimethyl-tetrahydrofuran-2-yl)-2-(methylsulfonyl)phenyl)amino)-2-methyl-3H-imidazo[4,5-b]pyridin-5-yl)cyclopropanecarboxamide, I-330

823
-continued

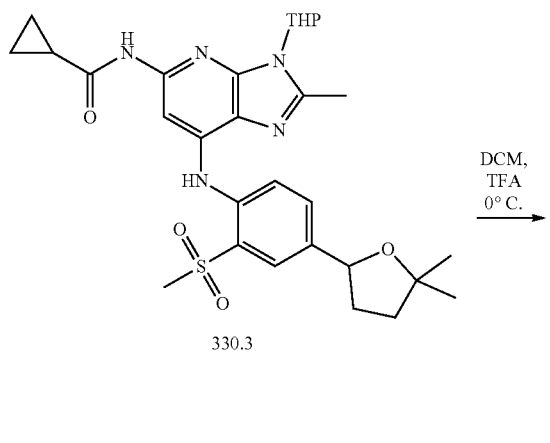

330.3

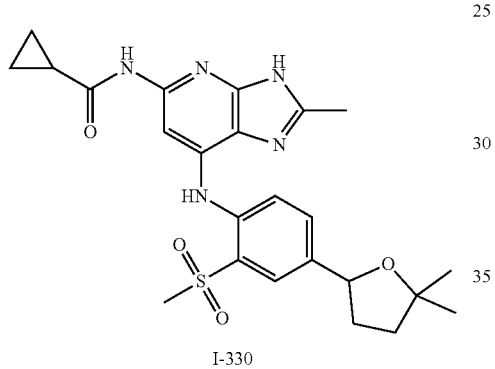

I-330

Synthesis of Compound 330.1.

Compound 330.1 was synthesized as per experimental section in I-332

Synthesis of Compound 330.2.

Compound 330.2 was synthesized from 98.4 and 330.1 using general procedure A. (Yield: 24.26%). MS(ES): m/z 520.06 [M+H]$^+$.

Synthesis of Compound 330.3.

Compound 330.3 was synthesized from 330.2 and cyclopropanecarboxamide using general procedure B. (Yield: 60.26%). MS(ES): m/z 568.71 [M+H]$^+$.

Synthesis of I-330.

Compound I-330 was synthesized from 330.3 using general procedure C. (Yield: 89.06%). MS(ES): m/z 483.61 [M−H]+, LCMS purity: 97.64%, HPLC purity: 96.78%, Chiral HPLC: 49.32%, 49.14%, 1H NMR (DMSO, 400 MHz): 13.11 (s, 1H), 10.70 (s, 1H), 8.53 (s, 1H), 7.91 (s, 2H), 7.68 (s, 2H), 5.0 (s, 1H), 3.20 (s, 3H), 2.59 (s, 3H), 2.41 (s, 1H), 2.0 (s, 1H), 1.85 (s, 3H), 1.349-1.311 (d, J=15.2 Hz, 6H), 0.80 (bs, 4H).

824

Example 331: Synthesis of N-(2-(difluoromethyl)-7-((4-(1,5-dimethyl-1H-pyrazol-4-yl)-2-(methylsulfonyl)phenyl)amino)-3H-imidazo[4,5-b]pyridin-5-yl)-2,2-difluorocyclopropane-1-carboxamide, I-331

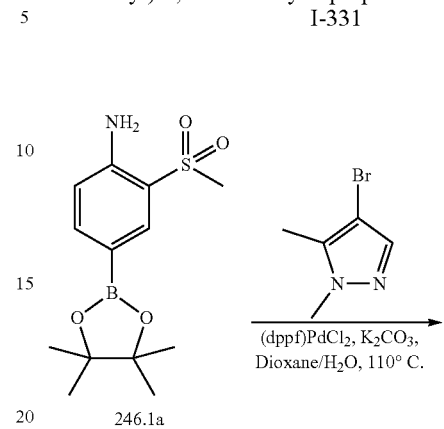

246.1a

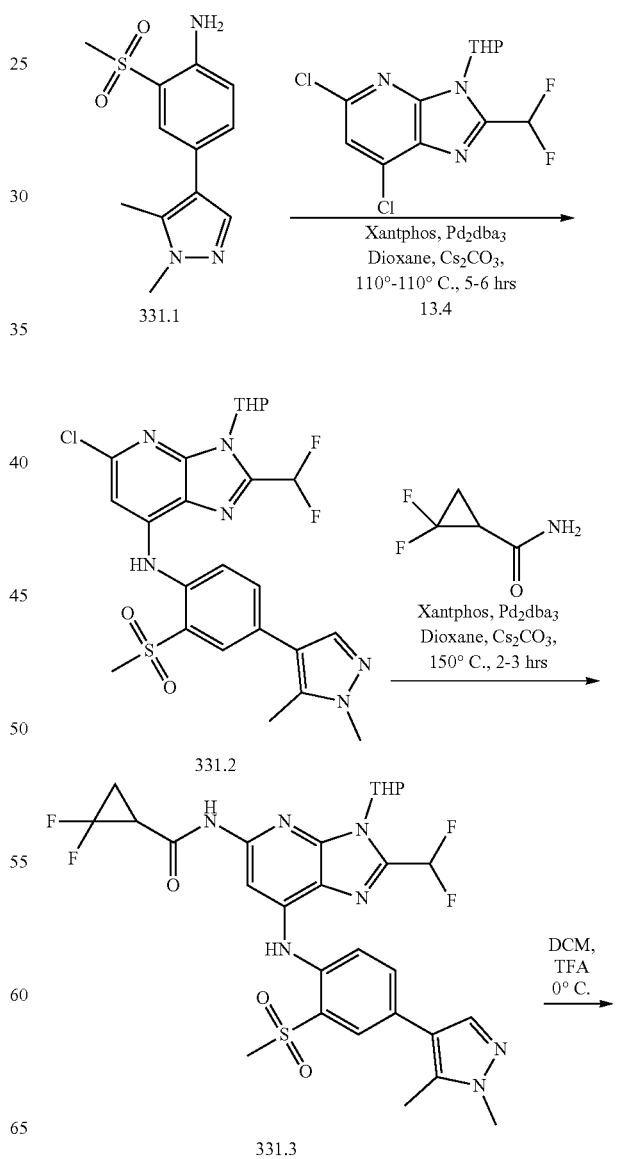

331.1  13.4

331.2

331.3

-continued

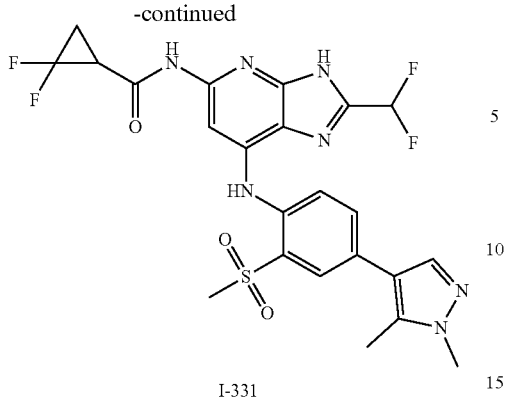

I-331

Synthesis of Compound 331.1.

To compound 4-bromo-1,5-dimethyl-1H-pyrazole (1.5 g, 5.05 mmol, 1.0 eq) in a mixture of dioxane (12 mL) and water (3 mL), compound 2-(methylsulfonyl)-4-(4,4,5,5-tetramethyl-1,3,2-dioxaborolan-2-yl)aniline (0.97 g, 5.5 mmol, 1.1 eq) was added. Reaction mixture was degassed with argon for 10 minute. Then [1,1'-Bis(diphenylphosphino)ferrocene]palladium(II) dichloride (0.82 g, 1.0 mmol, 0.2 eq) and potassium carbonate (2.09 g, 15.1 mmol, 3.0 eq) was added into it. Reaction mixture was stirred at 110° C. for 24 h. Upon completion, reaction mixture was transferred into cold water then extracted with ethyl acetate. Organic layers were combined, dried over Na$_2$SO$_4$ and concentrated in vacuo to obtain crude product. This was purified by column chromatography and compound was eluted in 15% ethyl acetate in hexane as eluant to obtain pure 331.1 (0.7 g, 39.20%). MS(ES): m/z 266.33 [M+H]$^+$.

Synthesis of Compound 331.2.

Compound 331.2 was synthesized from 331.1 and 13.4 using general procedure A. (Yield: 24.08%). MS(ES): m/z 552.01 [M+H]$^+$.

Synthesis of Compound 331.3.

Compound 331.3 was synthesized from 331.2 and 2,2-difluorocyclopropane-1-carboxamide using general procedure B. (Yield: 60.68%). MS(ES): m/z 636.64 [M+H]$^+$.

Synthesis of I-331.

Compound I-331 was synthesized from 331.3 using general procedure C. (Yield: 90.56%). MS(ES): m/z 552.50 [M+H]$^+$, LCMS purity: 97.73%, HPLC Purity: 97.27%, Chiral HPLC: 47.95% and 49.65%, 1H NMR (DMSO, 400 MHz): 13.75 (s, 1H), 10.98 (s, 1H), 8.81 (s, 1H), 8.00 (s, 1H), 7.90 (s, 1H), 7.85-7.72 (m, 3H), 3.82 (s, 3H), 3.26 (s, 3H), 3.18-3.17 (d, J=5.2 Hz, 1H), 2.43 (s, 3H), 1.92-1.77 (m, 2H), 1.31 (s, 1H).

Example 332: Synthesis of (S)—N-(2-methyl-7-((2-(methylsulfonyl)-4-(tetrahydrofuran-2-yl)phenyl)amino)-3H-imidazo[4,5-b]pyridin-5-yl)cyclopropanecarboxamide, I-332

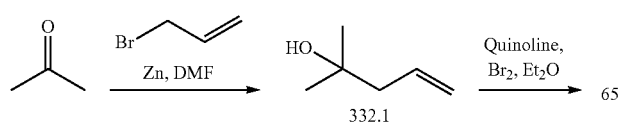

332.1

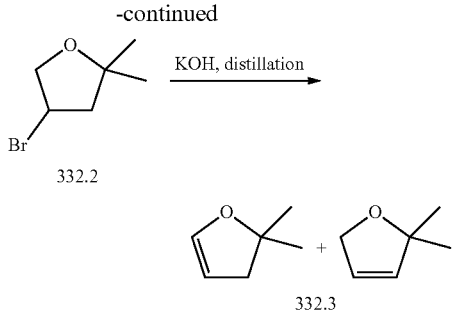

332.2

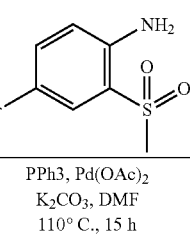

332.3

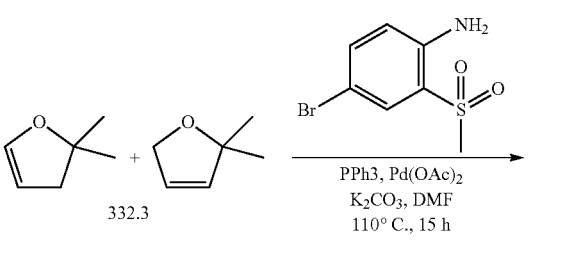

332.4 → 332.5

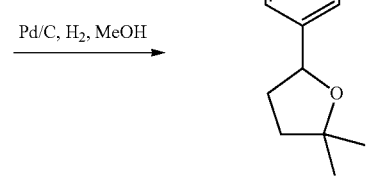

332.5

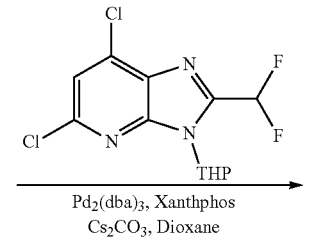

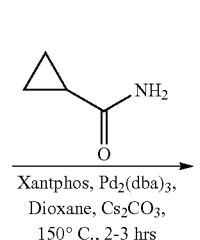

332.6

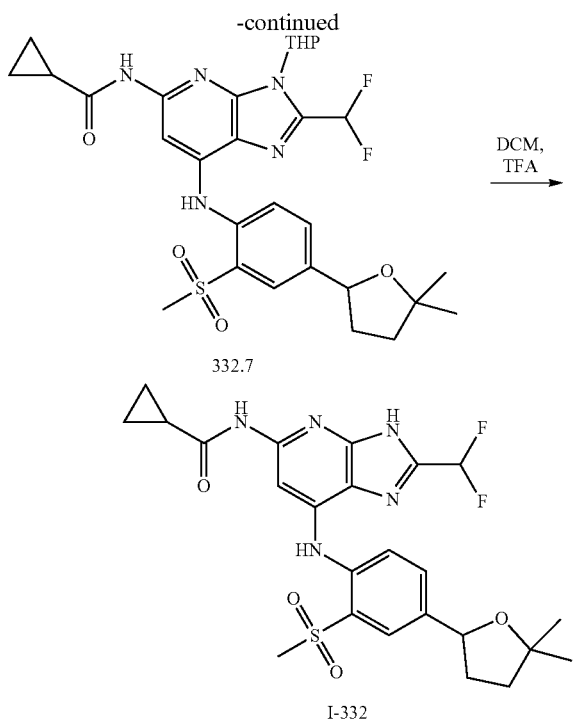

Synthesis of Compound 332.1.

To compound acetone (25 g, 431 mmol, 1.0 eq) in N,N-dimethylformamide (250 mL), 3-bromoprop-1-ene (77.5 g, 646 mmol, 1.5 eq) and zinc powder (14.0 g, 215 mmol, 0.5 eq) were added. Reaction mixture was stirred at 120° C. for 24 h. After completion of the reaction, the reaction mixture was transferred to water and extracted with ethyl acetate. Organic layer combined, dried over anhydrous Na$_2$SO$_4$, filtered and concentrated in vacuo to obtain 332.1 (15 g, 34.79%). MS(ES): m/z 101.37 [M+H]$^+$.

Synthesis of Compound 332.2.

To compound 332.1 (15 g, 148 mmol, 1.0 eq) in CH$_2$Cl$_2$ (150 mL), quinoline (19.1 g, 148 mmol, 1.0 eq) was added followed by dropwise addition of bromine solution (9 mL, 148 mmol, 1.0 eq). Reaction mixture was stirred at r.t. for 5 h. After completion of the reaction, the reaction mixture was transferred into water and extracted with CH$_2$Cl$_2$. Organic layer combined, dried over anhydrous Na$_2$SO$_4$, filtered and concentrated in vacuo to obtain crude product. This was purified by column chromatography using 20% ethyl acetate in hexane to obtain pure 332.2 (10 g, 37.29%). MS(ES): m/z 180.27 [M+H]$^+$.

Synthesis of Compound 332.3.

To compound 332.2 (10 g, 55.5 mmol, 1.0 eq) in dimethylformamide (100 mL), potassium hydroxide (6.25 g, 1.11 mmol, 2.0 eq) was added. After completion of the reaction, reaction mixture neutralised with 1N HCl and extracted with ethyl acetate. Organic layer combined, dried over anhydrous Na$_2$SO$_4$, filtered and concentrated in vacuo to obtain 332.3 (3 g, 5.73%). MS(ES): m/z 99.26 [M+H]$^+$.

Synthesis of Compound 332.4.

To compound 332.3 (3 g, 30.6 mmol, 1.0 eq) in N,N-dimethylformamide (30 mL), 4-bromo-2-(methylsulfonyl) aniline (7.65 g, 30.61 mmol, 1.0 eq) was added. Reaction mixture was degassed by argon for 15 min. Then potassium carbonate (12.6 g, 91.83 mmol, 3.0 eq), palladium acetate (1.37 g, 6.12 mmol, 0.2 eq) and triphenylphosphine (4 g, 15.3 mmol, 0.5 eq) was added. Reaction mixture was again degassed with argon for 5 min and stirred at 110° C. for 15 h. After completion of the reaction, the reaction mixture was transferred into water and extracted with ethyl acetate. Organic layer combined, dried over anhydrous Na$_2$SO$_4$, filtered and concentrated in vacuo to obtain 332.4 (1 g, 12.24%). MS(ES): m/z 267.43 [M+H]$^+$.

Synthesis of Compound 332.5.

To compound 332.4 (1 g, 3.74 mmol, 1.0 eq) in MeOH (20 mL), 10% palladium in charcoal (0.2 g) was added. Hydrogen was purged through the reaction mixture for 5 h. After completion of the reaction, the reaction mixture was filtered through celite bed and washed with MeOH. Filtrate was concentrated in vacuo to obtain 332.5 (0.450 g, 54.49%). MS(ES): m/z 689.89 [M+H]$^+$.

Synthesis of Compound 332.6.

Compound 332.6 was synthesized from 13.4 nd 332.5 using general procedure A. (Yield: 23.57%). MS(ES): m/z 556.34 [M+H]$^+$.

Synthesis of Compound 332.7.

Compound 332.7 was synthesized from 332.6 and cyclopropanecarboxamide using general procedure B. (Yield: 70.13%). MS(ES): m/z 604.59 [M+H]$^+$.

Synthesis of I-332.

Compound I-332 was synthesized from 332.7 using general procedure C. (Yield: 98.31%). MS(ES): m/z 520.61 [M+H]$^+$, LCMS purity: 98.77%, HPLC purity: 98.34%, Chiral HPLC: 49.57%, 50.52%, 1H NMR (DMSO, 400 MHz): 13.68 (s, 1H), 10.76 (s, 1H), 8.72 (s, 1H), 8.05 (s, 1H), 7.90 (s, 1H), 7.77-7.70 (m, 2H), 7.401-7.136 (t, J=106 Hz, 1H), 5.03-5.00 (m, 1H), 3.20 (s, 3H), 2.43-2.40 (m, 1H), 2.03 (m, 1H), 1.84 (m, 3H), 1.347-1.247 (d, J=40 Hz, 6H), 0.79 (bs, 4H).

Example 333: Synthesis of N-(2-(difluoromethyl)-7-((2-(methylsulfinyl)phenyl)amino)-3H-imidazo[4,5-b]pyridin-5-yl)cyclopropanecarboxamide, I-333

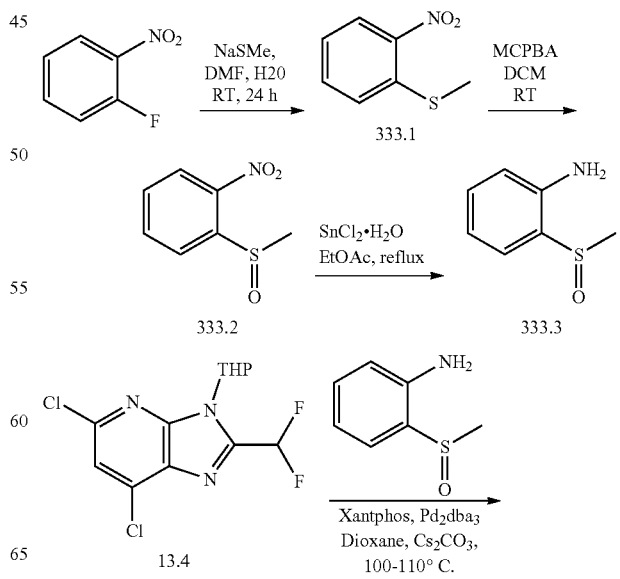

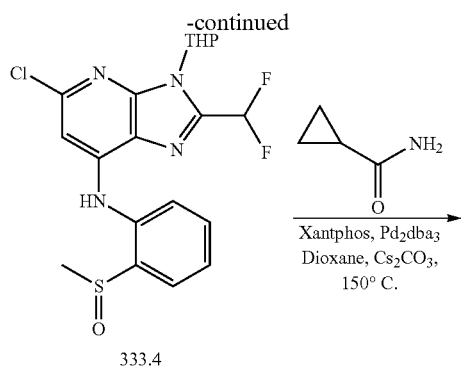

333.4

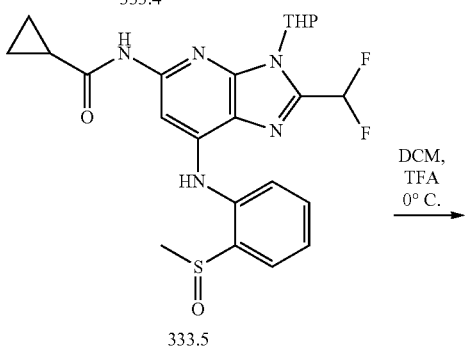

333.5

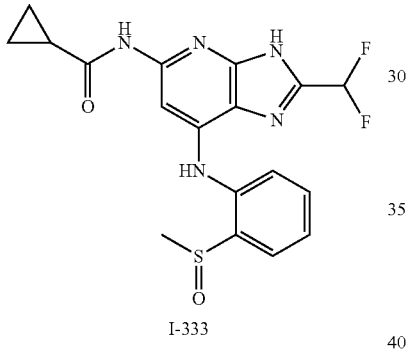

I-333

Synthesis of Compound 333.1.

To compound 2-fluoronitrobenzene (5 g, 3.54 mmol, 1 eq) in a mixture of dimethylformamide (50 ml) and water (10 mL), was added sodium thiomethoxide (3.72 g, 5.31 mmol, 1.5 eq). Reaction mixture was stirred at r.t. for 24 h. After completion of the reaction, the reaction mixture was transferred into cold water and extracted by ethyl acetate. Organic layer was concentrated in vacuo to obtain 333.1. (4.2 g, 70.05%). MS(ES): m/z 170.20 [M+H]⁺.

Synthesis of Compound 333.2.

To a compound of 333.1 (4.2 g, 35.9 mmol, 1.0 eq) in CH₂Cl₂ (50 ml) was added m-chloroperbenzoic acid (9.30 g, 53.9 mmol, 1.5 eq) portionwise at 0° C. Reaction mixture was stirred at r.t. for 2 h. Upon completion, reaction mixture was transferred to water and basified by NaHCO₃ and extracted with CH₂Cl₂. Organic layers were combined, dried over Na₂SO₄ and concentrated in vacuo to obtain crude product. This was purified by column chromatography and compound was eluted in 2.5% MeOH in CH₂Cl₂ as eluant to obtain pure 333.2 (3.6 g, 79.83%). MS(ES): m/z 186.20 [M+H]⁺.

Synthesis of Compound 333.3.

To compound 333.2 (3.67 g, 1.97 mmol, 1 eq) in ethyl acetate was added tin(II) chloride hydrate (4.4 g, 2.16 mmol, 1.1 eq). Reaction mixture was refluxed at 80° C. After completion of the reaction, the reaction mixture transferred into cold water and extracted by ethyl acetate. Organic layer combined, dried over anhydrous Na₂SO₄ and concentrated in vacuo to obtain 333.3 (2.1 g, 68.27%). MS(ES): m/z 156.22 [M+H]⁺.

Synthesis of Compound 333.4.

Compound 333.4 was synthesized from 333.3 and 13.4 using general procedure A. (Yield: 40.19%). MS(ES): m/z 441.89 [M+H]⁺.

Synthesis of Compound 333.5.

Compound 333.5 was synthesized from 333.4 and cyclopropanecarboxamide using general procedure B. (Yield: 65.50%). MS(ES): m/z 490.54 [M+H]⁺.

Synthesis of I-333.

Compound I-333 was synthesized from 333.5 using general procedure C (Yield: 95.59%). MS(ES): m/z 406.47 [M+H]⁺, LCMS purity: 100%, HPLC Purity: 99.56%, Chiral HPLC: 49.28% and 50.71%, 1H NMR (DMSO, 400 MHz): 13.50 (s, 1H), 10.57 (s, 1H), 9.16 (s, 1H), 7.84-7.82 (d, J=6.8 Hz, 1H), 7.63-7.60 (d, J=13.6 Hz, 1H), 7.52-7.45 (m, 3H), 7.07 (s, 1H), 2.73 (s, 3H), 2.00-1.97 (t, 1H), 0.74-0.72 (bs, 4H).

Example 334: Synthesis of N-(2-methyl-7-((2-(methylsulfonyl)-4-(tetrahydrofuran-2-yl)phenyl)amino)-3H-imidazo[4,5-b]pyridin-5-yl)cyclopropanecarboxamide, I-334

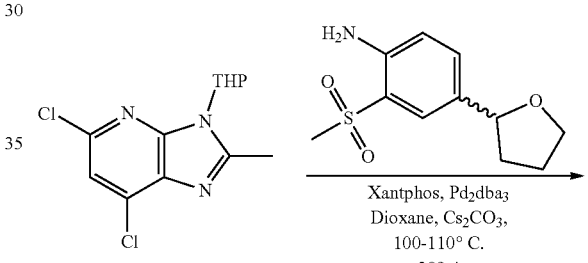

98.4    389.4

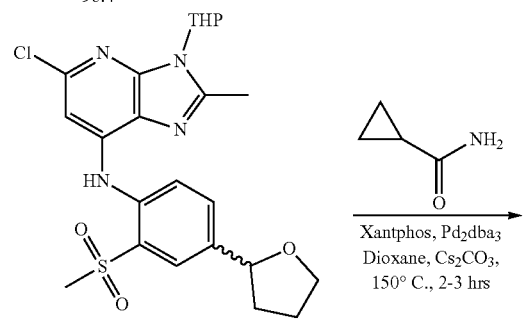

334.1

334.2

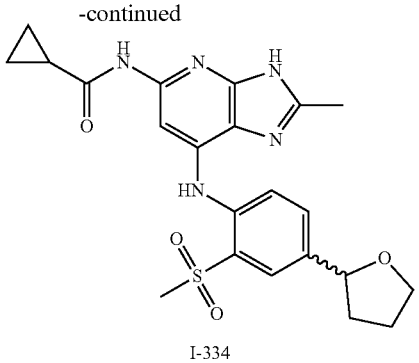

I-334

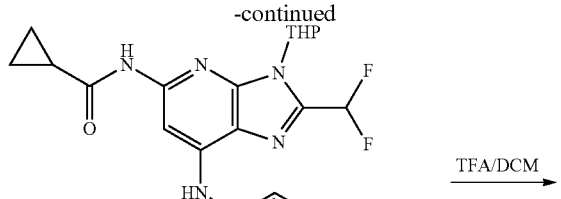

335.2

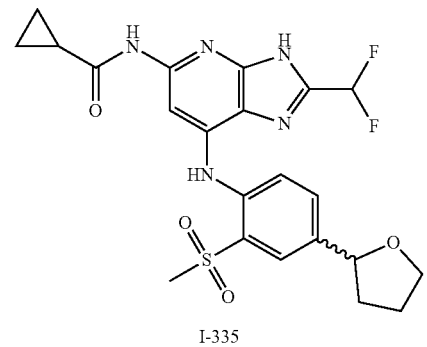

I-335

Synthesis of Compound 334.1.

Compound 334.1 was synthesized from 98.4 and 389.4 using general procedure A. (Yield: 22.93%). MS(ES): m/z 492.38 [M+H]⁺.

Synthesis of Compound 334.2.

Compound 334.2 was synthesized from 334.1 and cyclopropanecarboxamide using general procedure B. (Yield: 84.49%). MS(ES): m/z 540.28 [M+H]⁺.

Synthesis of I-334.

Compound I-334 was synthesized from 334.2 using general procedure C. (Yield: 91.13%). MS(ES): m/z 456.71 [M+H]⁺, LCMS purity: 99.19%, HPLC Purity: 98.48%, 1H NMR (DMSO, 400 MHz): 12.72 (s, 1H), 10.63 (s, 1H), 8.52 (s, 1H), 7.95 (s, 1H), 7.86 (s, 1H), 7.72-7.67 (m, 2H), 4.91-4.87 (m, 1H), 4.06-4.00 (m, 1H), 3.88-3.82 (s, 1H), 3.2 (s, 6H), 2.51-2.33 (m, 1H), 2.02-1.95 (s, 3H), 1.75-1.68 (m, 1H), 0.78-0.76 (s, 4H).

Example 335: Synthesis of N-(2-(difluoromethyl)-7-((2-(methylsulfonyl)-4-(tetrahydrofuran-2-yl)phenyl)amino)-3H-imidazo[4,5-b]pyridin-5-yl)cyclopropanecarboxamide, I-335

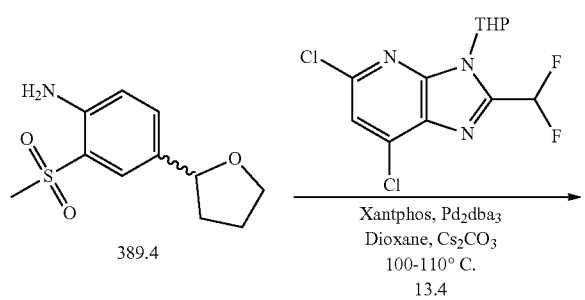

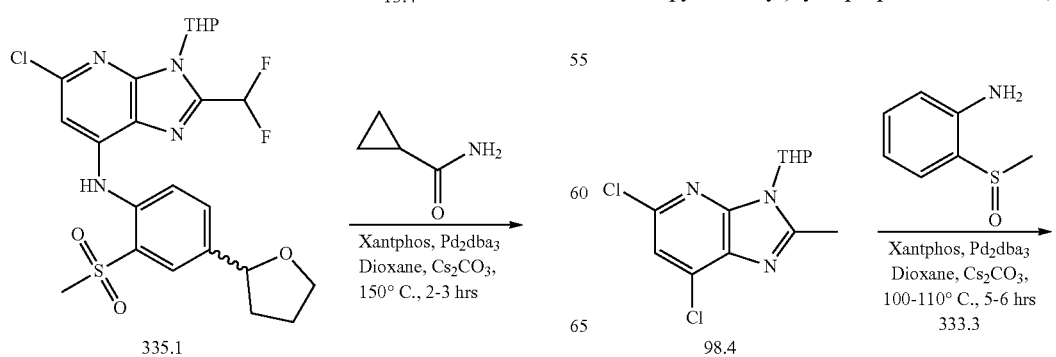

Synthesis of Compound 335.1.

Compound 335.1 was synthesized from 389.4 and using general procedure A. (Yield: 22.89%). MS(ES): m/z 527.34 [M+H]⁺.

Synthesis of Compound 335.2.

Compound 335.2 was synthesized from 335.1 and cyclpropanecarboxamide using general procedure B. (Yield: 68.66%). MS(ES): m/z 576.48 [M+H]⁺.

Synthesis of 1.335.

Compound I-335 was synthesized from 335.2 using general procedure C. (Yield: 78.08%). MS(ES): m/z 492.51 [M+H]⁺, LCMS purity: 95.59%, HPLC Purity: 100%, Chiral HPLC Purity: 43.54% and 51.84%, 1H NMR (DMSO, 400 MHz): 13.68 (s, 1H), 10.74 (s, 1H), 8.72 (s, 1H), 8.05 (m, 1H), 7.87 (s, 1H), 7.77-7.70 (m, 2H), 7.24 (s, 1H), 4.92-4.89 (t, J=14.4 Hz, 1H), 4.048-4.029 (d, J=7.6 Hz, 1H), 3.86-3.84 (d, J=7.2 Hz, 1H), 3.21 (s, 3H), 2.68 (s, 1H), 2.42-2.34 (m, 1H), 2.02-1.97 (m, 3H), 1.74-1.71 (m, 1H), 0.79 (s, 3H).

Example 336: Synthesis of N-(2-methyl-7-((2-(methylsulfinyl)phenyl)amino)-3H-imidazo[4,5-b]pyridin-5-yl)cyclopropanecarboxamide, I-336

833

-continued

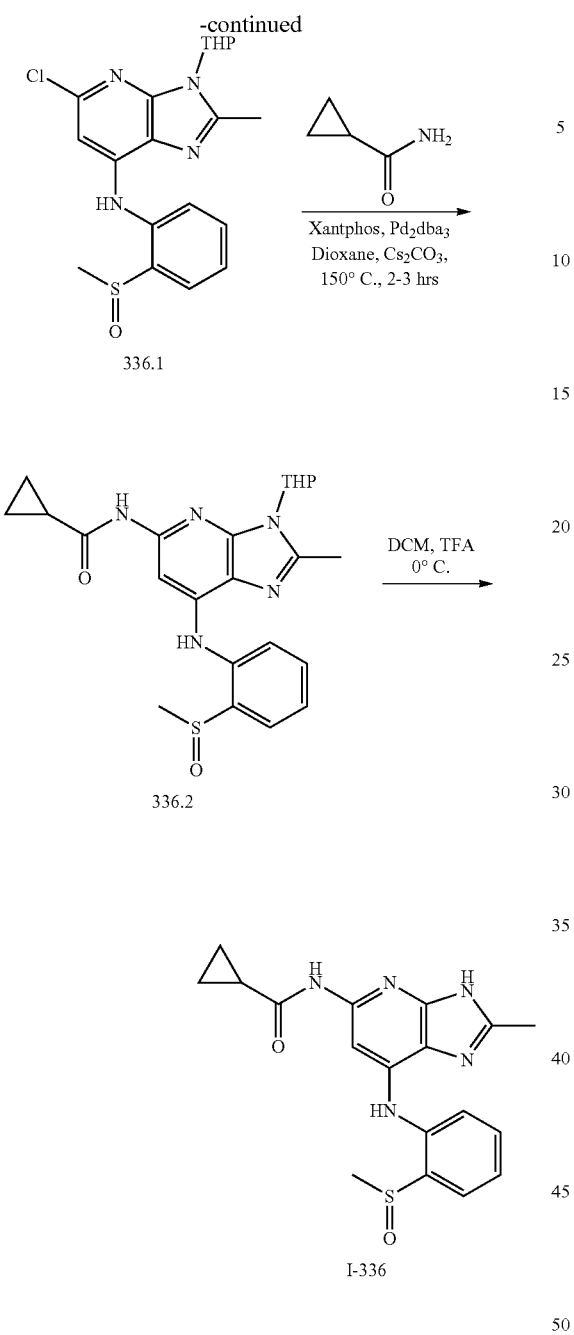

Synthesis of Compound 336.1.

Compound 336.1 was synthesized from 98.4 and 333.3 using general procedure A. (Yield: 21.98%). MS(ES): m/z 405.91 [M+H]⁺.

Synthesis of Compound 336.2.

Compound 336.2 was synthesized from 336.1 using general procedure B. (Yield: 67.47%). MS(ES): m/z 454.56 [M+H]⁺.

Synthesis of I-336.

Compound I-336 was synthesized from 336.2 using general procedure C (Yield: 94.44%). MS(ES): m/z 370.43 [M+H]⁺, LCMS purity: 98.14%, HPLC Purity: 99.74%, Chiral HPLC: 100%, 1H NMR (DMSO, 400 MHz): 12.33 (s, 1H), 10.40 (s, 1H), 8.88 (s, 1H), 7.78 (d, J=7.6 Hz, 1H), 7.60-7.56 (t, J=14.4 Hz, 1H), 7.46-7.40 (m, 3H), 2.74 (s, 3H), 2.47 (s, 3H), 1.97-1.94 (t, 1H), 0.72 (bs, 4H).

834

Example 337: Synthesis of N-(2-(difluoromethyl)-7-((2-(methylsulfonyl)-4-(tetrahydro-2H-pyran-4-yl)phenyl)amino)-3H-imidazol[4,5-b]pyridin-5-yl)-2,2-difluorocyclopropane-1-carboxamide, I-337

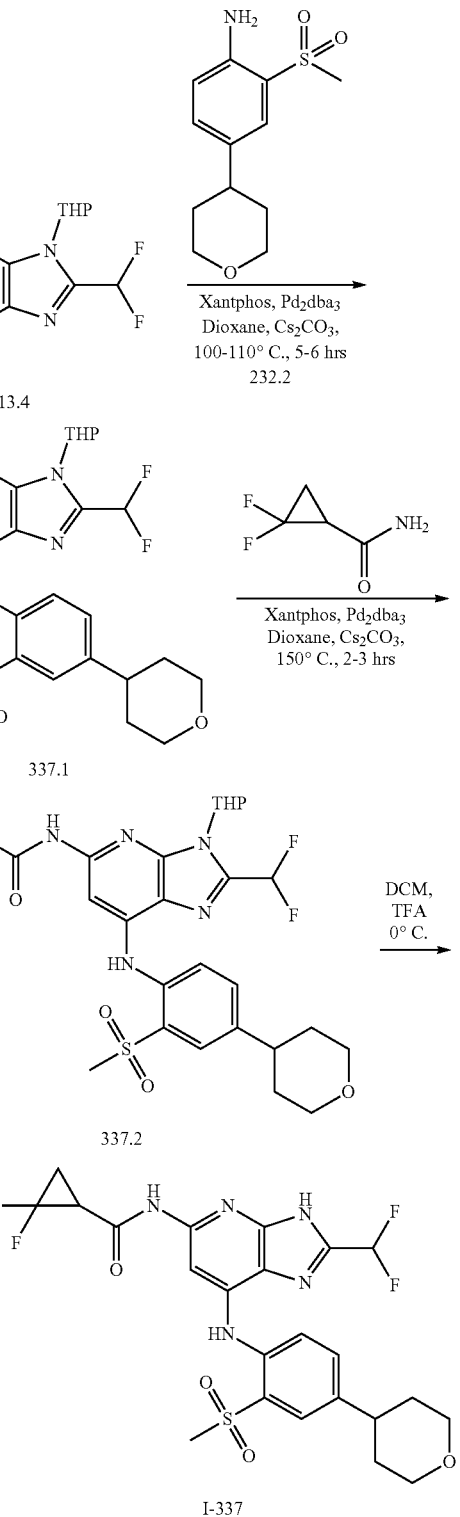

Synthesis of Compound 337.1.

Compound 337.1 was synthesized from 13.4 and 232.2 using general procedure A. (Yield: 26.74%). MS(ES): m/z 542.75 [M+H]⁺.

Synthesis of Compound 337.2.

Compound 337.2 was synthesized from 337.1 and 2,2-difluorocyclopropane-1-carboxamide using general procedure B. (Yield: 57.65%). MS(ES): m/z 626.84 [M+H]⁺.

Synthesis of Compound I-337.

Compound I-337 was synthesized from 337.2 using general procedure C. (Yield: 51.93%). MS(ES): m/z: 542.65 [M+H]⁺, LCMS purity: 99.65%, HPLC purity: 99.04%, Chiral HPLC purity: 50.39%, 49.60%, 1H NMR (DMSO-d6, 400 MHz): 13.68 (s, 1H), 10.76 (s, 1H), 8.77 (s, 1H), 8.07 (s, 1H), 7.89 (s, 1H), 7.82-7.79 (d, J=8.8 Hz, 2H), 7.71 (1H), 7.27 (t, 1H), 3.82 (s, 3H), 3.26 (s, 3H), 2.43 (s, 3H), 2.06-2.03 (m, 1H), 0.80-0.78 (m, 4H).

Example 338: Synthesis of N-(2-(difluoromethyl)-7-((4-(1,5-dimethyl-1H-pyrazol-3-yl)-2-(methylsulfonyl)phenyl)amino)-3H-imidazo[4,5-b]pyridin-5-yl)-2,2-difluorocyclopropane-1-carboxamide, I-338

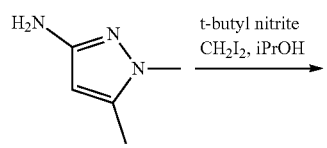

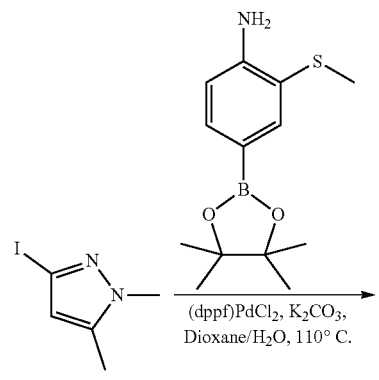

338.1

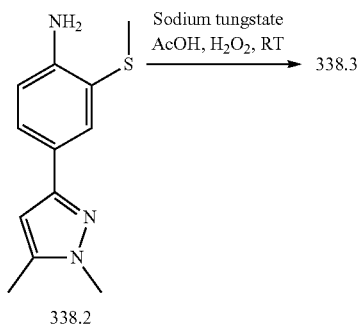

338.2

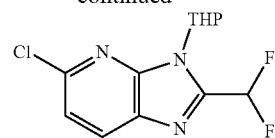

338.3

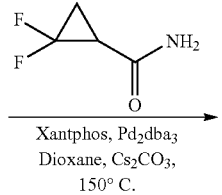

338.4

338.5

I-338

Synthesis of Compound 338.1.

To compound 1,5-dimethyl-1H-pyrazol-3-amine (4 g. 3.6 mmol, 1.0 eq) in isopropyl alcohol (20 mL), t-butyl nitrite (5.56 g, 5.4 mmol, 1.5 eq) and di-iodomethane (5.1 mL, 6.3 mmol, 1.75 eq) were added at r.t. Reaction mixture was stirred at 55° C. for 5 h. After completion of the reaction, the reaction mixture was transferred in water. The pH of the solution was adjusted to 8-10 by using 10N NaOH and then extracted with ethyl acetate. Organic layers were combined, dried over $Na_2SO_4$, filtered and concentrated in vacuo to get the crude material. This was purified by column chromatography using 10% ethyl acetate in hexane as eluant to obtain pure 338.1 (3.0 g, 37.55%). MS(ES): m/z 223.32 $[M+H]^+$.

Synthesis of Compound 338.2.

To compound 338.1 (2 g. 9.0 mmol, 1.0 eq) and 2-(methylthio)-4-(4,4,5,5-tetramethyl-1,3,2-dioxaborolan-2-yl)aniline (1.78 g, 5.9 mmol, 0.6 eq) in dioxane (20 mL), potassium carbonate (3.72 g, 27 mmol, 3.0 eq) was added. Reaction mixture was degassed for 5 min and then [1,1'-Bis(diphenylphosphino)ferrocene]dichloropalladium(II), complex with $CH_2Cl_2$ (0.22 mL, 0.27 mmol, 0.03 eq) was added. Reaction mixture was again degassed for 5 min and stirred at 110° C. for 2 h. After completion of the reaction, the reaction mixture was transferred in water and extracted with ethyl acetate. Organic layers were combined, dried over $Na_2SO_4$, filtered and concentrated in vacuo to get the crude material. This was purified by column chromatography using 15% ethyl acetate in hexane as eluant to obtain pure 338.2 (1.0 g, 47.58%). MS(ES): m/z 234.48 $[M+H]^+$.

Synthesis of Compound 338.3.

To a solution of 338.2 (0.18 g. 0.78 mmol, 1.0 eq) in acetic acid (2 mL), sodium tungstate (0.257 g, 0.78 mmol, 1.0 eq) and hydrogen peroxide (1.83 mL, 15.6 mmol, 20 eq) were added. Reaction mixture was stirred at r.t. for 5 min. After completion of the reaction, the reaction mixture was transferred to water. The pH ~7 was adjusted by using saturated $NaHCO_3$ and extracted with ethyl acetate. Organic layers were combined, dried over $Na_2SO_4$, filtered and concentrated in vacuo to get the crude material. This was purified by column chromatography using 20% ethyl acetate in hexane as eluant to obtain pure 338.3 (1.0 g, 77.31%). MS(ES): m/z 266.75 $[M+H]^+$.

Synthesis of Compound 338.4.

Compound 338.4 was synthesized from 338.3 and 13.4 using general procedure A. (Yield: 18.45%). MS(ES): m/z 552.68 $[M+H]^+$.

Synthesis of Compound 338.5.

Compound 338.5 was synthesized from 338.4 and 2,2-difluorocyclopropane-1-carboxamide using general procedure B. (Yield: 56.35%). MS(ES): m/z 636.43 $[M+H]^+$.

Synthesis of I-338.

Compound I-338 was synthesized from 338.5 using general procedure C. (Yield: 93.7%). MS(ES): m/z 552.55 $[M+H]^+$, LCMS purity: 98.87%, HPLC Purity: 98.51%, Chiral HPLC: (47.72%, 48.74%), 1H NMR (DMSO, 400 MHz): 10.72 (s, 1H), 8.55 (s, 1H), 8.26 (s, 1H), 8.03-8.011 (d, J=10.0 Hz, 1H), 7.87 (s, 1H), 7.81-7.79 (d, J=8.8 Hz, 1H), 6.96 (s, 1H), 6.56 (s, 1H), 3.79 (s, 3H), 3.22 (s, 3H), 2.98-2.93 (m, 1H), 2.30 (s, 3H), 2.01-1.88 (m, 2H), 1.23 (s, 1H).

Example 339: Synthesis of (1R,2R)—N-(7-((4-(4,4-dimethyl-4,5-dihydrooxazol-2-yl)-2-(methylsulfonyl) phenyl)amino)-2-methyl-3H-imidazo[4,5-b]pyridin-5-yl)-2-fluorocyclopropane-1-carboxamide, I-339

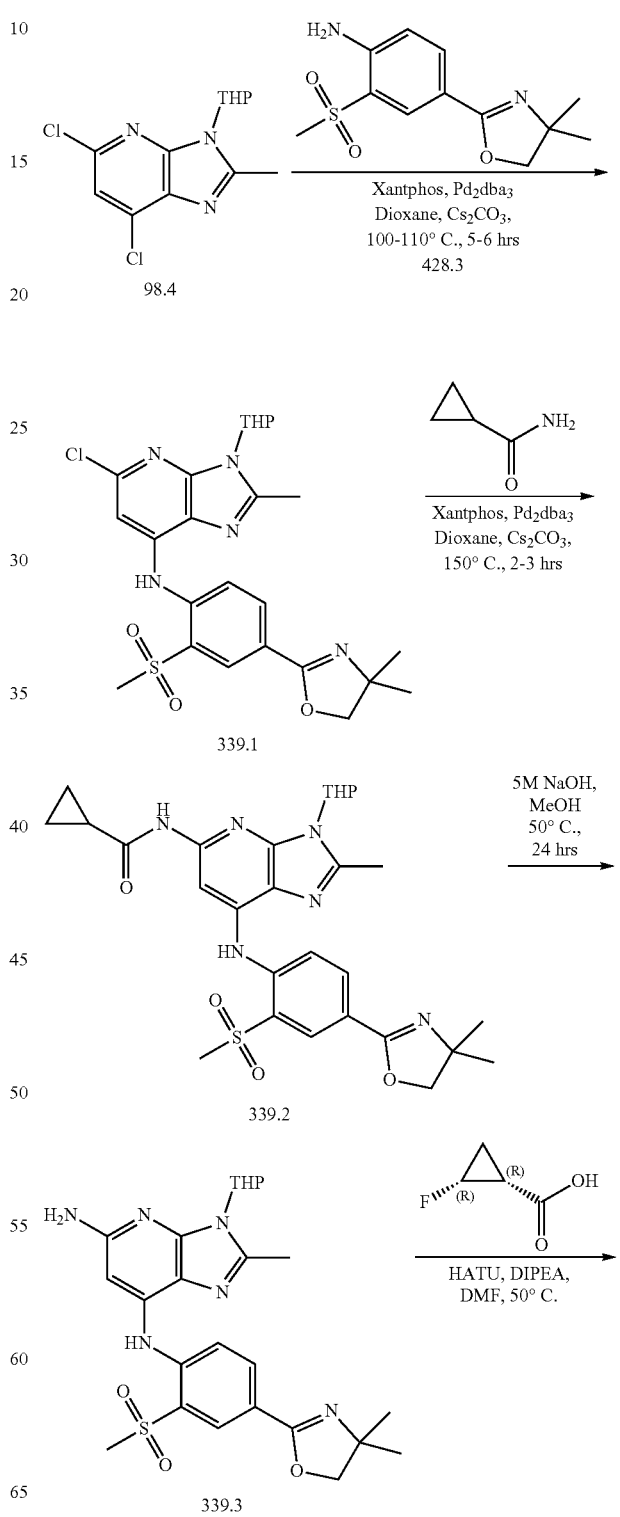

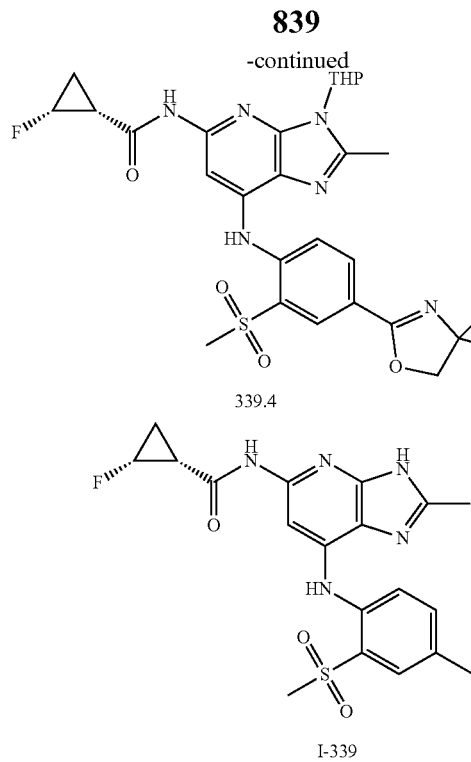

339.4

I-339

Synthesis of Compound 339.1.

Compound 339.1 was synthesized from 98.4 and 428.3 using general procedure A. (Yield: 34.04%). MS(ES): m/z 519.46 [M+H]$^+$.

Synthesis of Compound 339.2.

Compound 339.2 was synthesized from 339.1 and cyclopropanecarboxamide using general procedure B. (Yield: 71.54%). MS(ES): m/z 567.12 [M+H]$^+$.

Synthesis of Compound 339.3.

To compound 339.2 (0.260 g, 0.45 mmol, 1.0 eq) in MeOH (3.0 mL), 5M NaOH solution (4.0 mL) was added. Reaction mixture was stirred at 50° C. for 24 h. After completion of the reaction, the reaction mixture was transferred to water and extracted with ethyl acetate. Organic layers were combined, dried over anhydrous Na$_2$SO$_4$, filtered and concentrated in vacuo to obtain 339.3 (0.180 g, 77.03%). MS(ES): m/z 499.51 [M+H]$^+$.

Synthesis of Compound 339.4.

To a solution of (1R,2R)-2-fluorocyclopropane-1-carboxylic acid (0.30 g, 0.27 mmol, 1.5 eq) in N,N-dimethylformamide (3 mL) at 0° C., 1-[Bis(dimethylamino)methylene]-1H-1,2,3-triazolo[4,5-b]pyridinium3-oxid hexafluorophosphate (0.138 g, 0.36 mmol, 2.0 eq) was added. Reaction mixture was allowed to stir for 15 min at 0° C. Then, diisopropylethylamine (0.07 g, 0.54 mmol, 3.0 eq) and compound 339.3 (0.090 g, 0.18 mmol, 1.0 eq) was added. Reaction mixture was stirred at 50° C. for 5 h. After completion of the reaction, the reaction mixture was transferred to water and extracted with ethyl acetate. Organic layers were combined, dried over anhydrous Na$_2$SO$_4$, filtered and concentrated in vacuo to get the crude material. This was purified by column chromatography using 2% MeOH in CH$_2$Cl$_2$ as eluant to obtain pure 339.4 (0.030 g, 28.43%). MS(ES): m/z 585.47 [M+H]$^+$.

Synthesis of Compound I-339.

Compound I-339 was synthesized from using general procedure C. (Yield: 69.02%). MS(ES): m/z 501.51 [M+H]$^+$, LCMS purity: 95.19%, HPLC Purity: 95.18%, Chiral HPLC: 97.40%, 1H NMR (DMSO-d6, 400 MHz): 10.73 (s, 1H), 8.84 (s, 1H), 8.31 (s, 1H), 8.08 (s, 2H), 7.81 (s, 1H), 5.02-4.98 (m, 1H), 4.84-4.81 (m, 1H), 4.16 (s, 3H), 3.29 (s, 3H), 2.21 (s, 2H), 1.67-1.60 (d, J=2.72 Hz, 2H), 1.32 (s, 6H), 1.17-1.08 (m, 1H).

Example 340: Synthesis of 2,2-difluoro-N-(2-methyl-7-((2-(methylsulfonyl)-4-((R)-tetrahydrofuran-2-yl)phenyl)amino)-3H-imidazo[4,5-b]pyridin-5-yl)cyclopropane-1-carboxamide, I-340

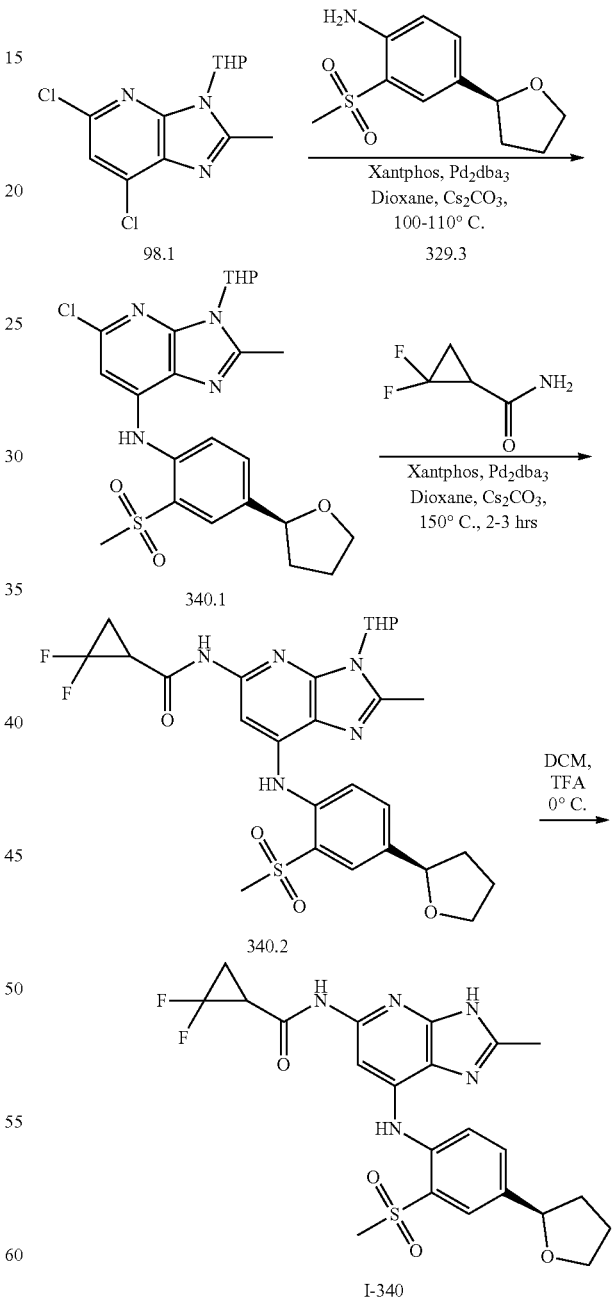

Synthesis of Compound 340.1.

Compound 340.1 was synthesized from 98.1 and 329.3 using general procedure A. (Yield: 31%). MS(ES): m/z 494.02 [M+H]$^+$.

Synthesis of Compound 340.2.

Compound 340.2 was synthesized from 340.1 and 2,2-difluorocyclopropane-1-carboxamide using general procedure B. (Yield: 49.59%). MS(ES): m/z 576.63 [M+H]⁺.

Synthesis of I-340.

Compound I-340 was synthesized from 340.2 using general procedure C (Yield: 95.82%). MS(ES): m/z 492.41 [M+H]⁺, LCMS purity: 97.41%, HPLC Purity: 96.62%, Chiral HPLC Purity: 43.43% and 44.28%, 1H NMR (DMSO, 400 MHz): 12.56 (s, 1H), 10.81 (s, 1H), 8.58 (s, 1H), 7.95 (s, 1H), 7.86 (s, 1H), 7.76-7.69 (m, 2H), 4.91-4.88 (t, J=8.4 Hz, 1H), 4.12-4.09 (m, 2H), 3.88-3.82 (m, 1H), 3.20-3.17 (m, 3H), 2.97 (s, 1H), 2.52 (s, 3H), 2.41-2.35 (m, 1H), 2.00-1.97 (t, 3H), 1.76-1.67 (s, 1H).

Example 346: Synthesis of (N-(7-((4-(4,4-dimethyl-4,5-dihydrothiazol-2-yl)-2-(methylsulfonyl)phenyl)amino)-2-methyl-3H-imidazo[4,5-b]pyridin-5-yl)-2,2-difluorocyclopropane-1-carboxamide, I-346

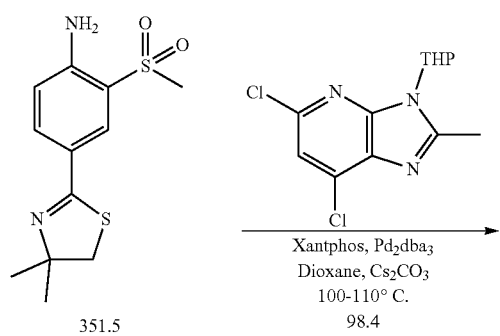

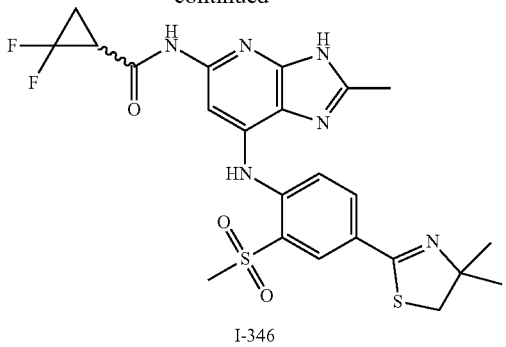

Synthesis of Compound 346.1.

Compound 346.1 was synthesized from 98.4 and 351.5 using general procedure A. (Yield: 30.24%). MS(ES): m/z 535.09 [M+H]⁺.

Synthesis of Compound 346.2.

Compound 346.2 was synthesized from 346.1 and 2,2-difluorocyclopropane-1-carboxamide using general procedure B. (Yield: 29.72%). MS(ES): m/z 619.72 [M+H]⁺.

Synthesis of I-346.

Compound I-346 was synthesized from 346.2 using general procedure C (Yield: 72.33%). MS(ES): m/z 534.51 [M+H]⁺, LCMS purity: 98.58%, HPLC Purity: 98.19%, Chiral HPLC Purity: 49.31% and 49.75%, 1H NMR (DMSO, 400 MHz): 13.83 (s, 1H), 11.06 (s, 1H), 9.01 (s, 1H), 8.25 (s, 1H), 8.14 (s, 1H), 8.03-8.01 (d, J=8.8 Hz, 1H), 7.87-7.85 (d, J=8.8 Hz, 2H), 7.27 (s, 1H), 3.30 (s, 3H), 3.03-3.01 (s, 1H), 2.50 (s, 2H), 2.03-2.00 (m, 3H), 1.14 (s, 6H).

Example 348: Synthesis of 2,2-difluoro-N-(2-methyl-7-((2-(methylsulfonyl)-4-((S)-tetrahydrofuran-2-yl)phenyl)amino)-3H-imidazo[4,5-b]pyridin-5-yl)cyclopropane-1-carboxamide, I-348

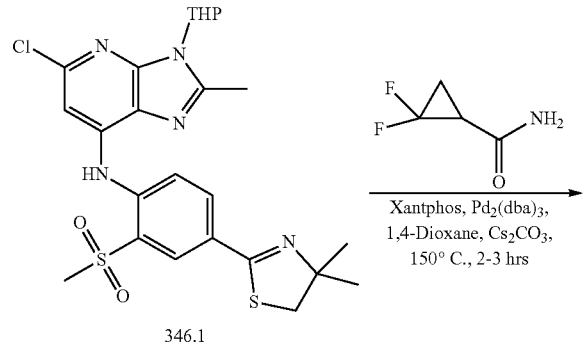

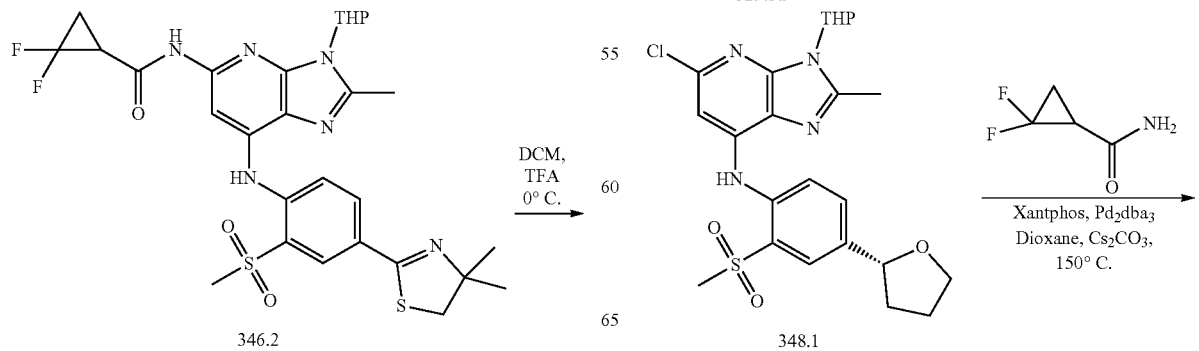

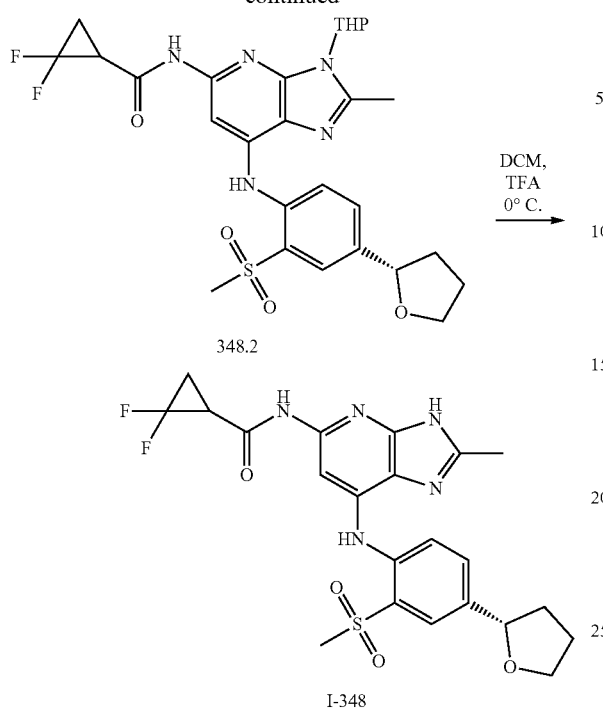

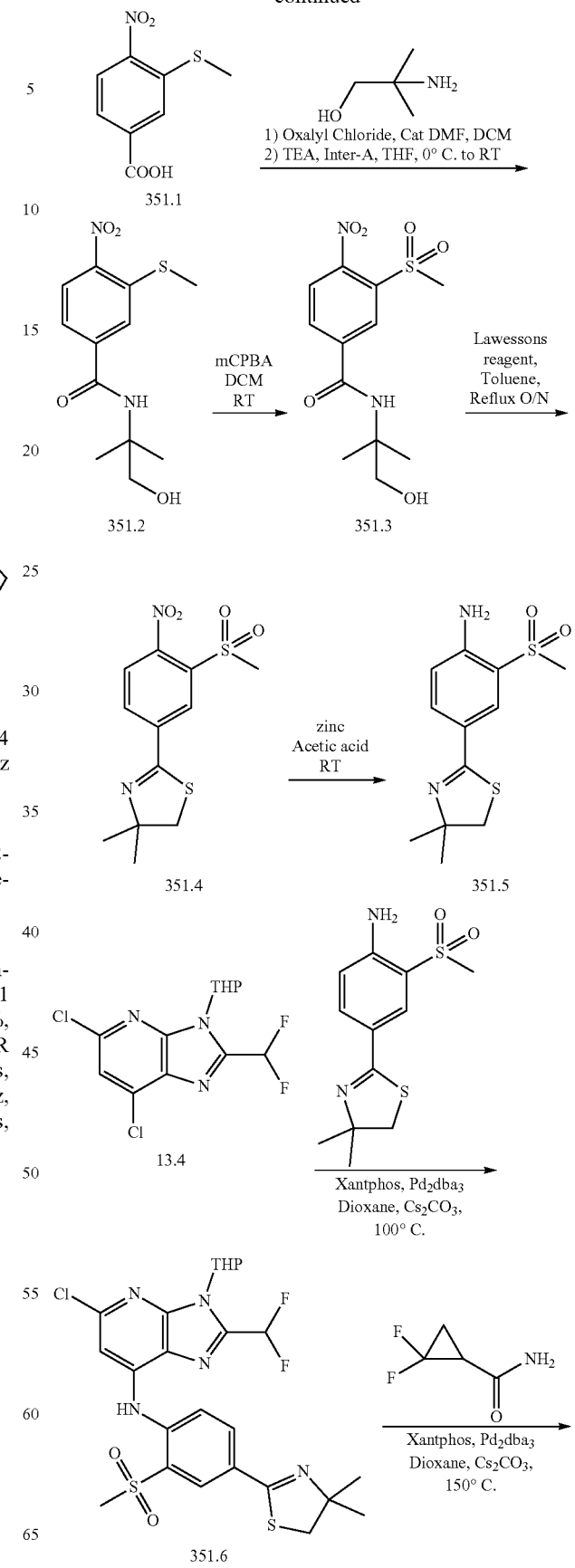

Synthesis of Compound 348.1.

Compound 348.1 was synthesized from 329.3a and 98.4 using general procedure A. (Yield: 26.11%). MS(ES): m/z 492.00 [M+H]⁺.

Synthesis of Compound 348.2.

Compound 348.2 was synthesized from 348.1 and 2,2-difluorocyclopropane-1-carboxamide using general procedure B. (Yield: 62.72%). MS(ES): m/z 576.63 [M+H]⁺.

Synthesis of I-348.

Compound I-348 was synthesized from 348.2 using general procedure C. (Yield: 79.64%). MS(ES): m/z 492.51 [M+H]⁺, LCMS purity: 97.64%, HPLC Purity: 95.32%, CHIRAL HPLC Purity: 47.49% & 48.21%, 1H NMR (DMSO, 400 MHz): 12.56 (s, 1H), 10.81 (s, 1H), 8.88 (s, 1H), 7.948-7.858 (d, J=36 Hz, 2H), 7.76-7.74 (d, J=8.4 Hz, 2H), 4.89 (s, 2H), 4.11-4.02 (m, 2H), 3.20 (s, 4H), 2.96 (s, 1H), 2.37 (s, 2H), 1.98 (s, 4H), 1.73-1.71 (s, 1H).

Example 351: Synthesis of N-(2-(difluoromethyl)-7-((4-(4,4-dimethyl-4,5-dihydrothiazol-2-yl)-2-(methylsulfonyl)phenyl)amino)-3H-imidazo[4,5-b]pyridin-5-yl)-2,2-difluorocyclopropane-1-carboxamide, I-351

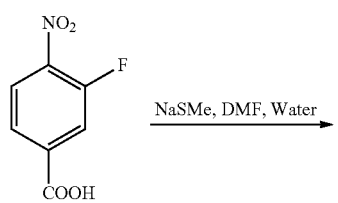

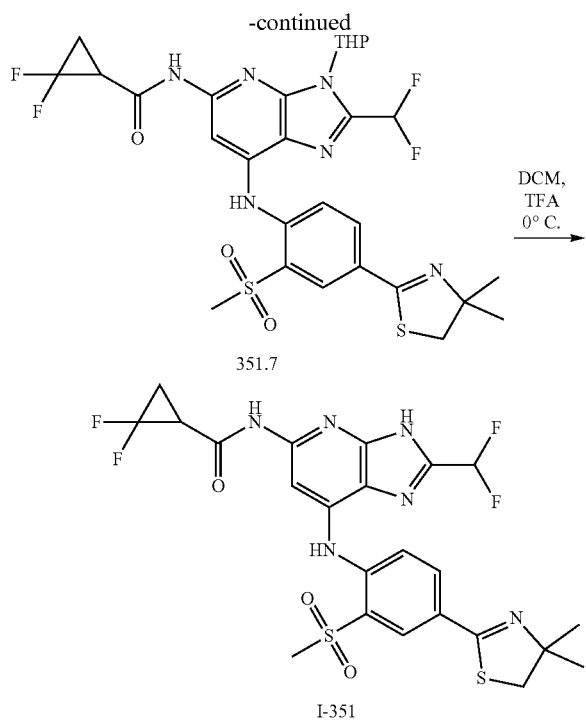

Synthesis of Compound 351.1.

To a solution of 3-fluoro-4-nitrobenzoic acid (20 g, 108.04 mmol, 1.0 eq) in mixture of N—N-dimethylformamide (200 mL) and water (50 mL) was added dropwise sodium thiomethoxide water solution (16.64 g, 23.78 mmol, 2.2 eq) at 0° C. The reaction was stirred at 15-20° C. for 1 h. Upon completion, reaction mixture was transferred in water and extracted with ethyl acetate. Combined organic layer was washed with brine, dried over $Na_2SO_4$ and concentrated in vacuo to obtain crude product. This was purified by column chromatography using 5% ethyl acetate in hexane to obtain pure 1.1 (18 g, 78.14%). MS(ES): m/z 214.21 [M+H]$^+$.

Synthesis of Compound 351.2.

To a solution of 351.1 (5 g, 23.45 mmol, 1 eq), in $CH_2Cl_2$ (100 mL), was added oxalyl chloride (14.78 g, 117.3 mmol, 5 eq) and N—N-dimethylformamide (catalytic amount) at 0° C. Reaction mixture was stirred at r.t. for 4 h. Upon completion, reaction mixture was concentrated in vacuo to obtain crude product. A solution of 1.2 (3.14 g, 35.18 mmol, 1.5 eq) and Triethylamine (7.11 g, 70.42 mmol, 3 eq), in Tetrahydrofuran (50 mL), was added into crude material at 0° C. and stirred the reaction mixture at r.t. for 3 h. Upon completion, reaction mixture was transferred into water and extracted with ethyl acetate. Organic layers were combined, dried over $Na_2SO_4$ and concentrated in vacuo to obtain crude product. This was purified by column chromatography and compound was eluted in 30% ethyl acetate in hexane as eluent to obtain pure 351.2. (4 g, 59.99%). MS(ES): m/z 285.33 [M+H]$^+$.

Synthesis of Compound 351.3.

To a cooled solution of 351.2 (4 g, 17.59 mmol, 1 eq) in $CH_2Cl_2$ (100 mL) at 0° C. was added meta-Chloroperbenzoic acid (10.59 g, 61.61 mmol, 3.5 eq) slowly portionwise. The reaction mixture was stirred at r.t. for 3 h. After completion of reaction, the reaction mixture was transferred into saturated $NaHCO_3$ solution and extracted with $CH_2Cl_2$. Combined Organic layer dried over $Na_2SO_4$ and concentrated in vacuo to obtain crude product. This was purified by column chromatography and compound was eluted in 30% ethyl acetate in MeOH to obtain pure 351.3 (3.5 g, 62.92%). MS(ES): m/z 317.33 [M+H]$^+$ Synthesis of Compound 351.4.

To a solution of 351.3 (2.5 g, 7.90 mmol, 1.0 eq) in Toluene (25 mL) was added lawessons reagent(6.39 g, 15.82 mmol, 2 eq) and reflux the reaction mixture for 18 h. Upon completion, reaction mixture was transferred into water and extracted with ethyl acetate. Organic layers were combined, dried over $Na_2SO_4$ and concentrated in vacuo to obtain crude product. This was purified by column chromatography and compound was eluted in 15% ethyl acetate in hexane as eluent to obtain pure 351.4 (1.2 g, 48.30%). MS(ES): m/z 315.37 [M+H]$^+$.

Synthesis of Compound 351.5.

To a solution of 351.4 (1.2 g, 3.82 mmol, 1 eq), in Acetic acid (1.2 mL), was added zinc dust (1.26 g, 19.10 mmol, 5 eq) portion wise. Reaction mixture was stirred at r.t. for 8 h. After completion of reaction, the reaction mixture was transferred into $NaHCO_3$ solution and extracted with ethyl acetate. Combined Organic layer dried over $Na_2SO_4$ and concentrated in vacuo to obtain crude product. This was purified by column chromatography and compound was eluted in 30% ethyl acetate in hexane to obtain pure 351.5 (0.320 g, 29.48%). MS(ES): m/z 285.39 [M+H]$^+$.

Synthesis of Compound 351.6.

Compound 351.6 was synthesized from 13.4 and 351.5 using general procedure A. (Yield: 21.31%). MS (ES): m/z 571.07 [M+H]

Synthesis of Compound 351.7.

Compound 351.7 was synthesized from 2,2-difluorocyclopropane-1-carboxamide and 351.6 using general procedure B. (Yield: 36.28%). MS (ES): m/z 655.70 [M+H]$^+$.

Synthesis of Compound I-351.

Compound I-351 was synthesized from 351.7 using general procedure C. (Yield: 76.50%). MS(ES): m/z 571.50 [M+H]$^+$, LCMS purity: 98.30%, HPLC Purity: 98.09%, Chiral HPLC: 43.33%, 55.95%, 1H NMR (DMSO, 400 MHz): 13.85 (s, 1H), 11.08 (s, 1H), 9.021 (s, 1H), 8.26 (s, 1H), 8.15 (s, 1H), 8.042-8.022 (d, J=8 Hz, 1H), 7.886-7.864 (d, J=8.8 Hz, 1H), 7.28 (t, 1H), 3.31 (s, 3H), 3.02 (s, 1H), 2.03 (s, 2H), 1.422 (s, 6H).

Example 358: Synthesis of N-(7-((4-cyclobutyl-2-(methylsulfonyl)phenyl)amino)-2-(difluoromethyl)-3H-imidazo[4,5-b]pyridin-5-yl)-2,2-difluorocyclopropane-1-carboxamide, I-358

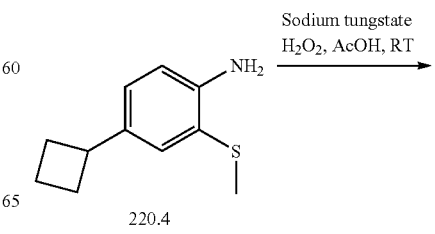

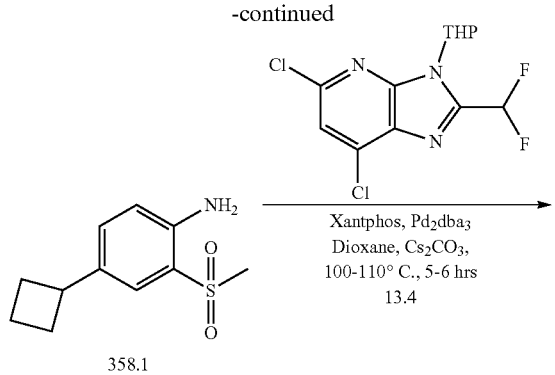

358.1

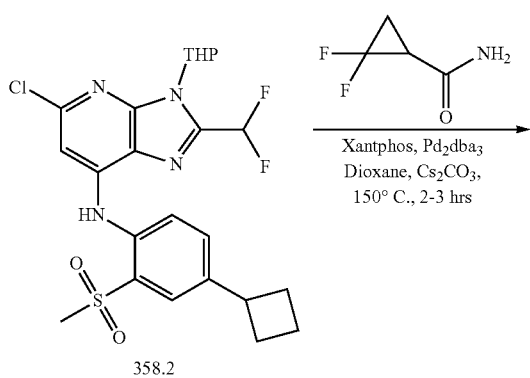

358.2

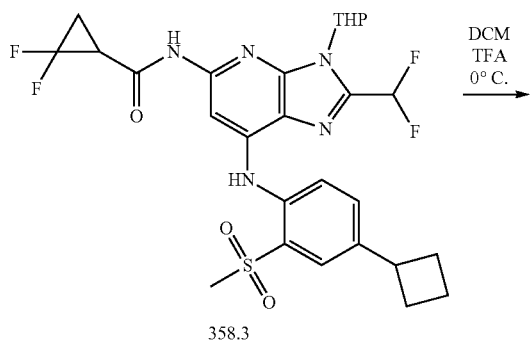

358.3

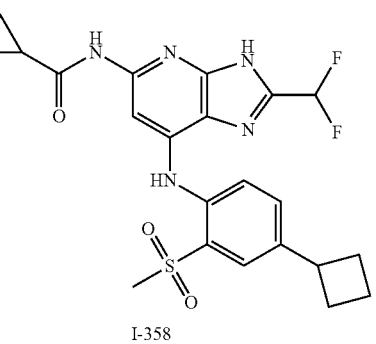

I-358

Synthesis of Compound 358.1.

To compound 220.4 (6.6 g, g, 34.19 mmol, 1.0 eq) in acetic acid (66 mL), hydrogen peroxide (79 mL, 684 mmol, 20 eq) was added. Then, sodium tungstate (11.28 g, 34.19 mmol, 1.0 eq) was added in portions within 15 min. Reaction mixture was stirred at r.t. for 10 min. After completion of the reaction, the reaction mixture was transferred into ice cold water and extracted with ethyl acetate. Organic layer combined, dried over anhydrous Na$_2$SO$_4$, filtered and concentrated in vacuo to obtain the crude material. This was purified by column chromatography using 7% ethyl acetate in hexane as eluant to obtain pure 358.1 (1.8 g, 23.40%). MS(ES): m/z 226.83 [M+H]$^+$.

Synthesis of Compound 358.2

Compound 358.2 was synthesized from 358.1 and 13.4 using general procedure A. (Yield: 34.67%). MS(ES): m/z 511.48 [M+H]$^+$.

Synthesis of Compound 358.3.

Compound 358.3 was synthesized from 358.2 and 2,2-difluorocyclopropane-1-carboxamide using general procedure B. (Yield: 64.34%). MS(ES): m/z 596.26 [M+H]$^+$.

Synthesis of I-358.

Compound I-358 was synthesized from 358.3 using general procedure C. (Yield: 77.63%). MS(ES): m/z 512.46 [M+H]$^+$, LCMS purity: 98.90%, HPLC Purity: 97.93%, 1H NMR (DMSO, 400 MHz): 13.73 (s, 1H), 10.97 (s, 1H), 8.72 (s, 1H), 7.96 (s, 1H), 7.76-7.67 (m, 3H), 7.72 (s, 1H), 4.12 (s, 1H), 3.67-3.63 (m, 1H), 3.21 (s, 3H), 3.17 (s, 2H), 3.029-3.00 (m, 1H), 2.83-2.32 (m, 2H), 2.18-2.11 (m, 2H), 1.89-1.82 (m, 1H).

Example 359: Synthesis of N-(2-(difluoromethyl)-7-((2-(methylsulfonyl)-4-((S)-tetrahydro-2H-pyran-3-yl)phenyl)amino)-3H-imidazo[4,5-b]pyridin-5-yl)-2,2-difluorocyclopropane-1-carboxamide, I-359

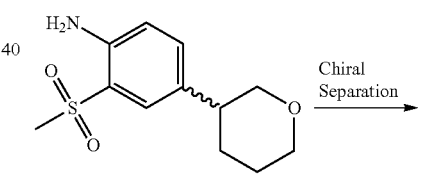

391.2

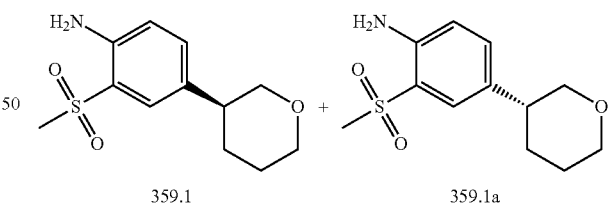

359.1      359.1a

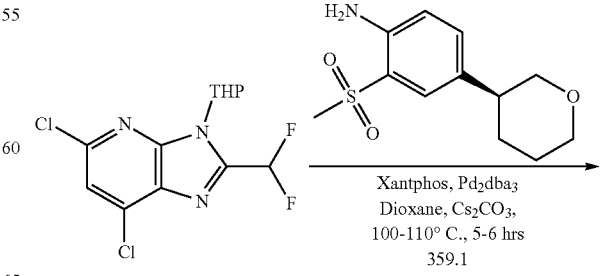

359.1

-continued

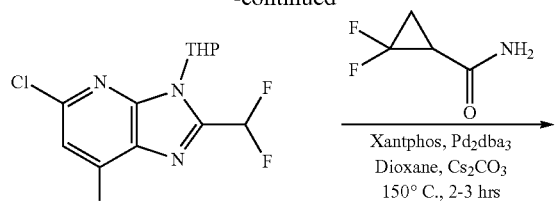

359.2

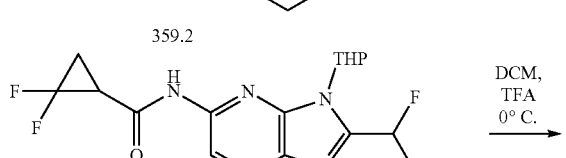

359.3

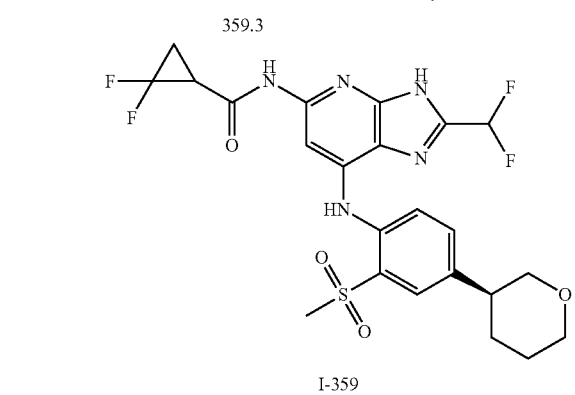

I-359

Synthesis of Compound 359.1.

Isomers of compound 391.2 (0.9 g) were separated out using column (CHIRAL PAK AD-H 250×4.6 mm, 5 μM) 0.1% DEA in IPA as co-solvent with flow rate of 4 mL/min. to get pure fraction-1 (FR-a) and fraction-2 (FR-b). FR-b was concentrated in vacuo at 30° C. to afford pure 359.1 (0.3 g). MS(ES): m/z: 256.37 [M+H]$^+$.

Synthesis of Compound 359.2.

Compound 359.2 was synthesized from 13.4 and 359.1 using general procedure A. (Yield: 25.07%). MS(ES): m/z 542.01 [M+H]$^+$.

Synthesis of Compound 359.3.

Compound 359.3 was synthesized from 359.2 and 2,2-difluorocyclopropane-1-carboxamide using general procedure B. (Yield: 64.85%). MS(ES): m/z 626.64 [M+H]$^+$.

Synthesis of Compound I-359.

Compound I-359 was synthesized from 359.3 using general procedure C. (Yield: 77.02%). MS(ES): m/z 542.60 [M+H]$^+$, LCMS purity: 97.76%, HPLC Purity: 95.32%, Chiral HPLC: 48.92% and 50.81%, 1H NMR (MeOD, 400 MHz): 13.12 (s, 1H), 8.04 (s, 1H), 7.92 (s, 1H), 7.84-7.82 (d, J=8.4 Hz, 1H), 7.72-7.69 (d, J=10.4 Hz, 1H), 6.98 (s, 1H), 4.01-3.99 (m, 2H), 3.59-3.51 (m, 2H), 3.11 (s, 3H), 3.01-2.94 (m, 1H), 2.86-2.81 (m, 1H), 2.12-2.07 (m, 2H), 1.90-1.80 (m, 4H).

Example 360: Synthesis of N-(2-(difluoromethyl)-7-((2-(methylsulfonyl)-4-((R)-tetrahydro-2H-pyran-3-yl)phenyl)amino)-3H-imidazo[4,5-b]pyridin-5-yl)-2,2-difluorocyclopropane-1-carboxamide, I-360

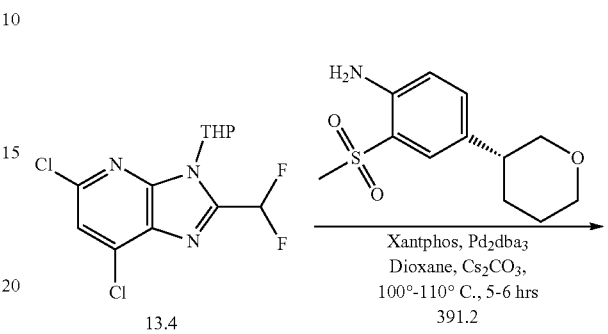

391.2

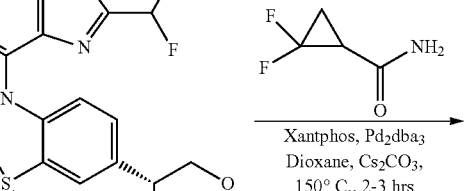

360.1

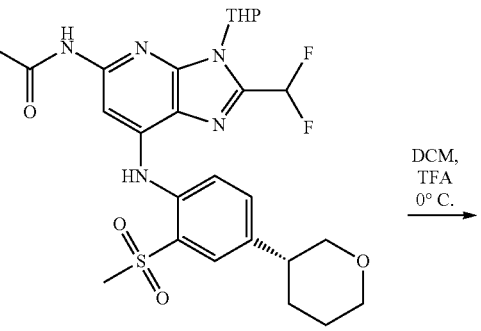

360.2

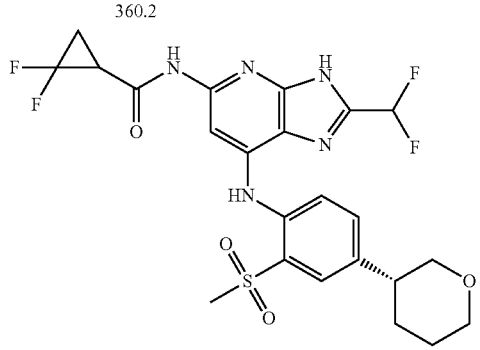

I-360

Synthesis of Compound 360.1.

Compound 360.1 was synthesized from 13.4 and 391.2 using general procedure A. (Yield: 31.76%). MS(ES): m/z 542.01 [M+H]$^+$.

Synthesis of Compound 360.2.

Compound 360.2 was synthesized from 360.1 and 2,2-difluorocyclopropane-1-carboxamide using general procedure B. (Yield: 59.45%). MS(ES): m/z 626.64 [M+H]⁺.

Synthesis of I-360.

Compound I-360 was synthesized from 360.2 using general procedure C (Yield: 94.53%). MS(ES): m/z 542.55 [M+H]⁺, LCMS purity: 94.72%, HPLC Purity: 97.11%, Chiral HPLC: 49.17, 50.17%, 1H NMR (DMSO, 400 MHz): 8.04 (s, 1H), 7.92 (s, 1H), 7.85-7.70 (m, 3H), 6.98 (s, 1H), 4.01-3.90 (m, 2H), 3.59-3.51 (m, 2H), 3.11 (s, 2H), 3.02-2.96 (m, 1H), 2.84-2.82 (m, 1H), 2.12-2.07 (m, 2H), 1.90-1.80 (s, 4H), 1.29-1.25 (s, 2H), 0.93 (bs, 1H).

Example 361: Synthesis of N-(7-((4-cyclobutyl-2-(methylsulfonyl)phenyl)amino)-2-methyl-3H-imidazo[4,5-b]pyridin-5-yl)-2,2-difluorocyclopropane-1-carboxamide, I-361

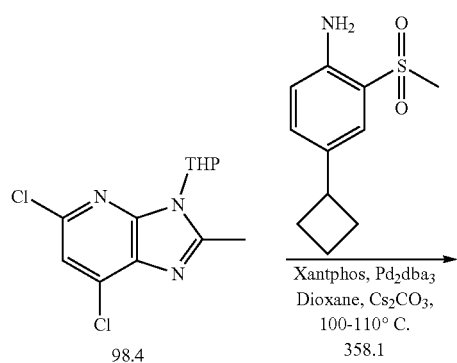

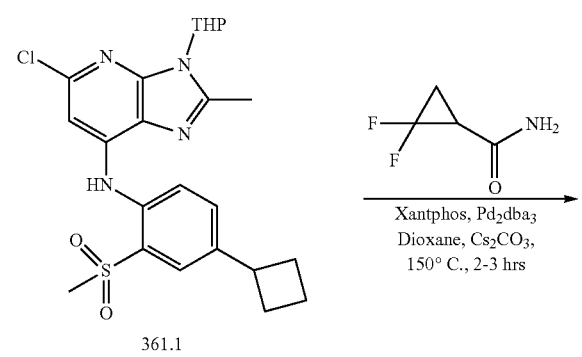

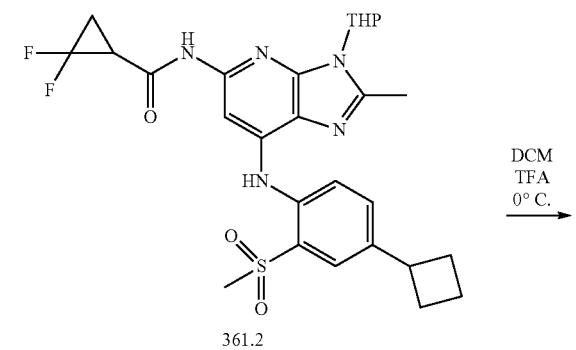

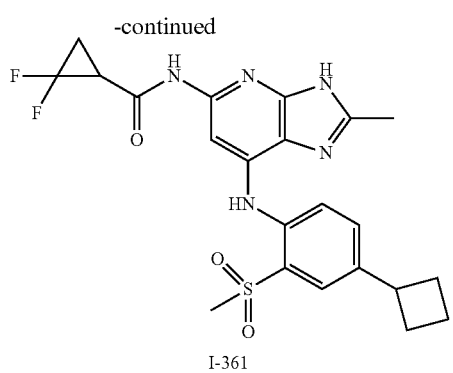

Synthesis of Compound 361.1.

Compound 361.1 was synthesized from 98.4 and 358.1 using general procedure A. (Yield: 30.12%). MS(ES): m/z 476.58 [M+H]⁺.

Synthesis of Compound 361.2.

Compound 361.2 was synthesized from 361.1 and 2,2-difluorocyclopropane-1-carboxamide using general procedure B. (Yield: 63.66%). MS(ES): m/z 560.46 [M+H]⁺.

Synthesis of I-361.

Compound I-361 was synthesized from 361.2 using general procedure C (Yield: 94.15%). MS(ES): m/z 476.67 [M+H]⁺, LCMS purity: 95.16%, HPLC Purity: 99.53%, Chiral HPLC Purity: 49.33% and 49.60%, 1H NMR (DMSO-d6, 400 MHz): 12.65 (s, 1H), 10.81 (s, 1H), 8.48 (s, 1H), 7.86 (s, 1H), 7.72-7.55 (m, 1H), 7.43 (m, 3H), 3.78-3.58 (m, 1H), 3.41-3.35 (m, 1H), 3.18 (s, 3H), 3.17 (s, 1H), 3.08-2.95 (m, 1H), 2.37-2.30 (m, 2H), 2.25-2.13 (m, 2H), 2.19-2.01 (m, 3H), 1.83-1.80 (m, 1H).

Example 363: Synthesis of N-(7-((4-(1,4-dimethyl-1H-pyrazol-3-yl)-2-(methylsulfonyl)phenyl)amino)-2-methyl-3H-imidazo[4,5-b]pyridin-5-yl)-2,2-dimethylcyclopropane-1-carboxamide, I-363

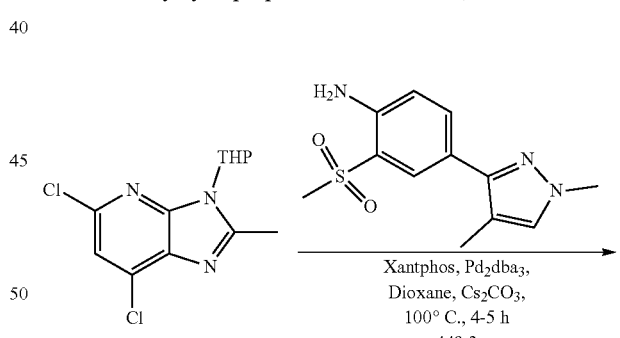

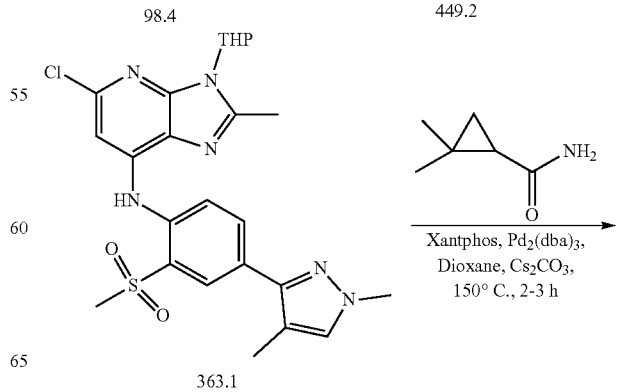

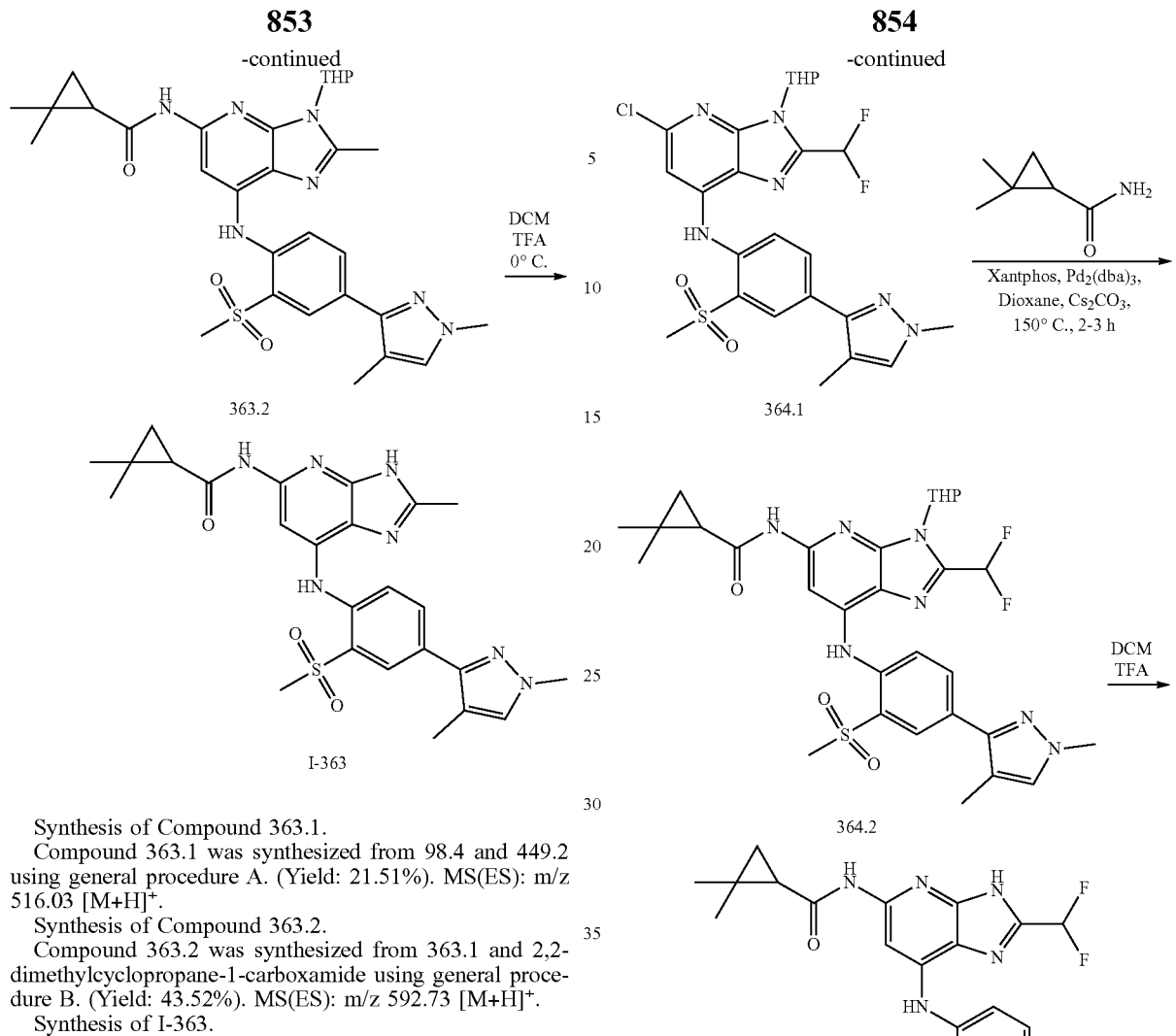

Synthesis of Compound 363.1.

Compound 363.1 was synthesized from 98.4 and 449.2 using general procedure A. (Yield: 21.51%). MS(ES): m/z 516.03 [M+H]⁺.

Synthesis of Compound 363.2.

Compound 363.2 was synthesized from 363.1 and 2,2-dimethylcyclopropane-1-carboxamide using general procedure B. (Yield: 43.52%). MS(ES): m/z 592.73 [M+H]⁺.

Synthesis of I-363.

Compound I-363 was synthesized from 363.2 using general procedure C. (Yield: 83.27%). MS(ES): m/z 508.51 [M+H]⁺, LCMS purity: 99.91%, HPLC purity: 99.67%, Chiral HPLC: 48.08%, 51.68%, 1H NMR (DMSO-d6, 400 MHz): 12.49 (s, 1H), 10.42 (s, 1H), 8.63 (s, 1H), 8.20 (s, 1H), 8.04-7.98 (m, 2H), 7.82-7.80 (m, 1H), 7.60 (s, 1H), 3.85 (s, 3H), 3.25 (s, 3H), 2.49 (s, 3H), 2.24 (s, 3H), 1.91-1.88 (m, 1H), 1.14-1.13 (m, 6H), 0.97 (s, 1H), 0.78-0.76 (d, J=4.8 Hz, 1H).

Example 364: Synthesis of N-(2-(difluoromethyl)-7-((4-(1,4-dimethyl-1H-pyrazol-3-yl)-2-(methylsulfonyl)phenyl)amino)-3H-imidazo[4,5-b]pyridin-5-yl)-2,2-dimethylcyclopropane-1-carboxamide, I-364

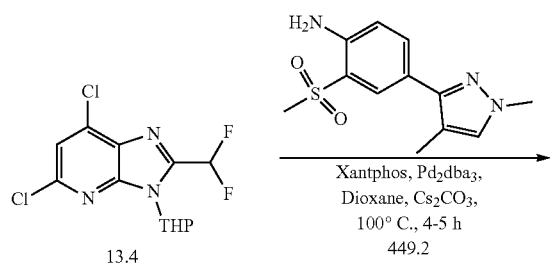

Synthesis of Compound 364.1.

Compound 364.1 was synthesized from 13.4 and 449.2 using general procedure A. (Yield: 25.72%). MS(ES): m/z 552.01 [M+H]⁺.

Synthesis of Compound 364.2.

Compound 364.2 was synthesized from 364.1 and 2,2-dimethylcyclopropane-1-carboxamide using general procedure B. (Yield: 51.87%). MS(ES): m/z 628.71 [M+H].

Synthesis of I-364.

Compound I-364 was synthesized from 364.2 using general procedure C (Yield: 75.50%). MS(ES): m/z 544.56 [M+H]⁺, LCMS purity: 100%, HPLC purity: 99.54%, Chiral HPLC: 49.49%, 50.50%, 1H NMR (DMSO-d6, 400 MHz): 13.67 (s, 1H), 10.61 (s, 1H), 8.81 (s, 1H), 8.82 (s, 1H), 8.11 (s, 1H), 8.04-8.01 (dd, J=1.0 Hz, 1H), 7.85-7.83 (d, J=8.4 Hz, 1H), 7.61 (s, 1H), 7.40-7.13 (t, J=1.0 Hz, 1H), 3.86 (s, 3H), 3.27 (s, 3H), 2.24 (s, 3H), 1.94-1.91 (t, J=1.2 Hz, 1H), 1.15-1.13 (d, 6H), 0.981 (s, 1H), 0.80-0.77 (m, 1H).

Example 365: Synthesis of 2-(difluoromethyl)-N7-(2-(methylsulfonyl)-4-(tetrahydro-2H-pyran-2-yl)phenyl)-N5-(6-(trifluoromethyl)pyridin-2-yl)-3H-imidazo[4,5-b]pyridine-5,7-diamine, I-365

Example 366: Synthesis of 2-(difluoromethyl)-N5-(2,6-dimethylpyrimidin-4-yl)-N7-(2-(methylsulfonyl)-4-(tetrahydro-2H-pyran-2-yl)phenyl)-3H-imidazo[4,5-b]pyridine-5,7-diamine, I-366

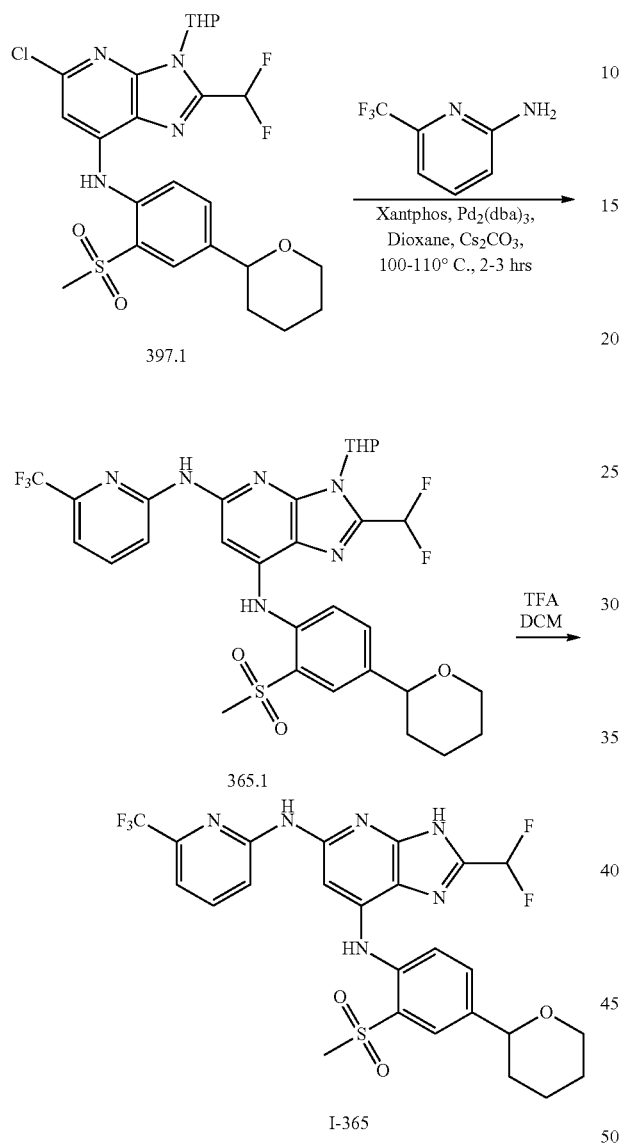
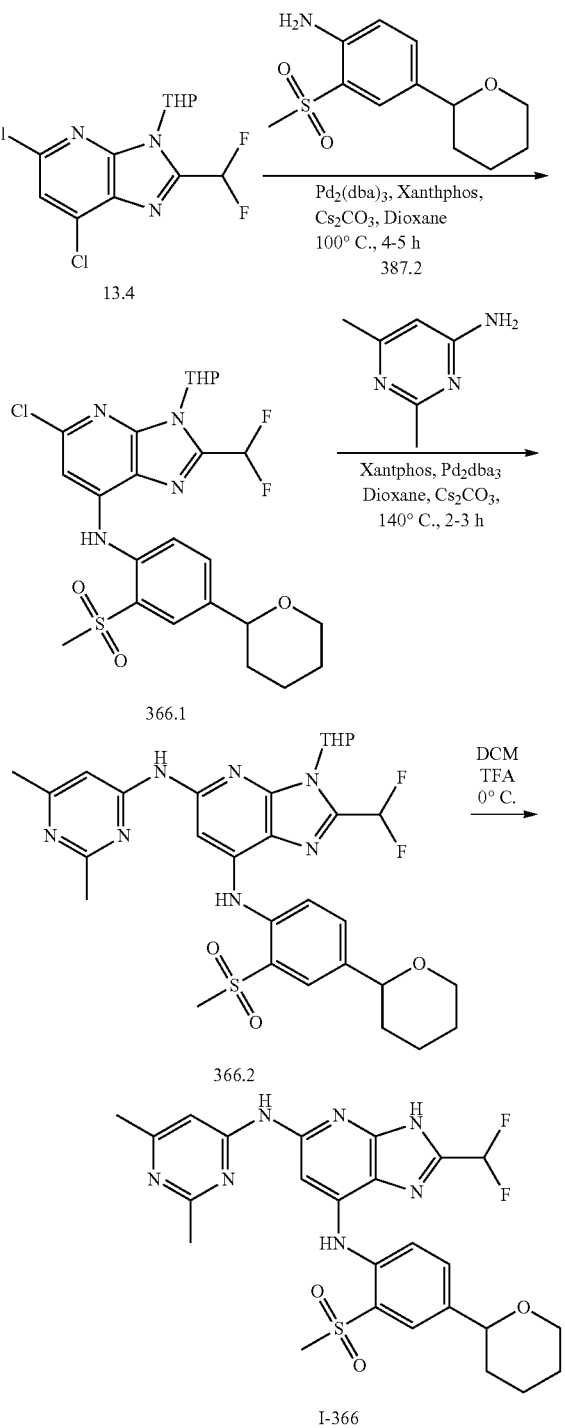

Synthesis of Compound 365.1.

Compound 365.1 was synthesized from 397.1 and 6-(trifluoromethyl)pyridin-2-amine using general procedure A. (Yield: 53.56%). MS(ES): m/z 667.67 [M+H]+.

Synthesis of Compound I-365.

Compound I-365 was synthesized from 365.1 using general procedure C (Yield: 82.36%). MS(ES): m/z 583.76 [M+H]+, LCMS purity: 98.82%, HPLC Purity: 96.18%, Chiral HPLC Purity: (49.3%, 49%), H NMR (DMSO, 400 MHz): 10.15 (s, 1H), 8.81 (s, 1H), 8.24-8.22 (d, J=8.0 Hz, 1H), 7.94-7.91 (m, 2H), 7.83-7.81 (d, J=8.0 Hz, 1H), 7.69-7.67 (d, J=8.4 Hz, 1H), 7.5 (s, 1H), 7.32-7.30 (d, J=5.2 Hz, 1H), 3.58 (s, 1H), 3.21 (s, 3H), 1.91-1.88 (m, 2H), 1.68-1.67 (m, 2H), 1.58 (s, 2H), 1.48-1.42 (m, 2H), 1.22 (s, 2H).

Synthesis of Compound 366.1

Compound 366.1 was synthesized from 13.4 and 387.2 and using general procedure A. (Yield: 20.10%). MS(ES): m/z 542.01 [M+H]+.

Synthesis of Compound 366.2.

Compound 366.2=was synthesized from 366.1 and 2,6-dimethylpyrimidin-4-amine using general procedure B. (Yield: 64.64%). MS(ES): m/z 628.71 [M+H]⁺.

Synthesis of I-366.

Compound I-366 was synthesized from 366.2 using general procedure C. (Yield: 76.98%). MS(ES): m/z 544.56 [M+H]⁺, LCMS purity: 95.30%, HPLC purity: 97.01%, 1H NMR (DMSO-d6, 400 MHz): 13.66 (s, 1H), 10.03 (s, 1H), 8.82 (s, 1H), 7.92 (s, 1H), 7.87-7.85 (m, 1H), 7.74-7.72 (d, J=8.4 Hz, 1H), 7.63 (s, 1H), 7.56 (s, 1H), 4.47-4.45 (d, J=10.8 Hz, 1H), 4.10-4.07 (d, J=11.2 Hz, 1H), 3.62-3.55 (m, 1H), 3.23 (s, 3H), 2.41 (s, 3H), 2.32 (s, 3H), 1.92-1.89 (d, J=11.2 Hz, 2H), 1.70-1.67 (m, 1H), 1.59 (s, 2H), 1.48-1.40 (m, 2H).

Example 367: Synthesis of N5-(2,6-dimethylpyrimidin-4-yl)-2-methyl-N7-(2-(methylsulfonyl)-4-(tetrahydro-2H-pyran-2-yl)phenyl)-3H-imidazo[4,5-b]pyridine-5,7-diamine, I-367

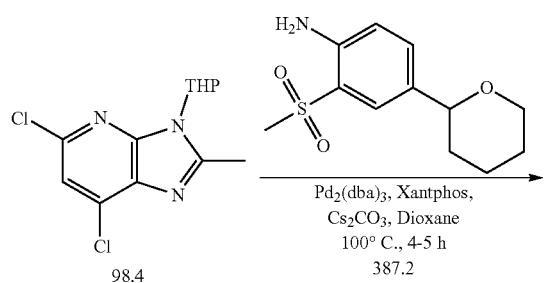

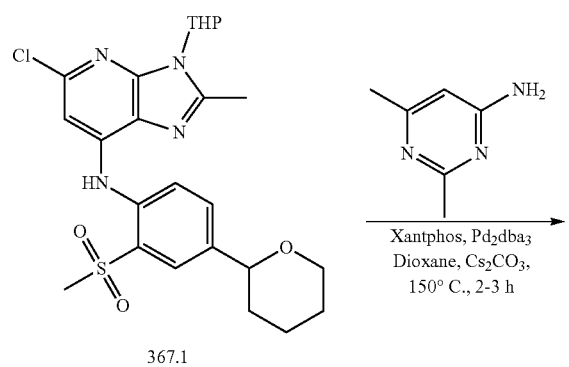

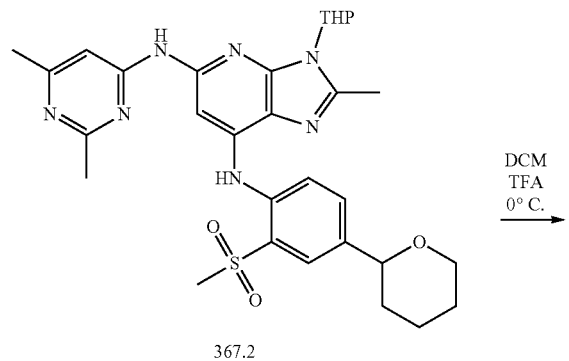

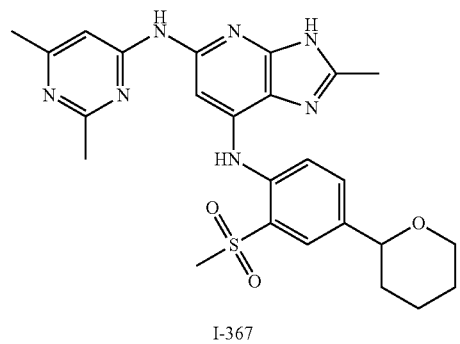

Synthesis of Compound 367.1.

Compound was synthesized from 98.4 and 387.2 using general procedure A. (Yield: 21.10%). MS(ES): m/z 506.03 [M+H]⁺.

Synthesis of Compound 367.2.

Compound was synthesized from 367.1 and 2,6-dimethylpyrimidin-4-amine using general procedure B. (Yield: 52.83%). MS(ES): m/z 592.73 [M+H]⁺.

Synthesis of I-367.

Compound I-367 was synthesized from 367.2 using general procedure C. (Yield: 89.67%). MS(ES): m/z 508.61 [M+H]⁺, LCMS purity: 97.46%, HPLC purity: 98.98%, 1H NMR (DMSO-d6, 400 MHz): 12.51 (s, 1H), 9.83 (s, 1H), 8.65 (s, 1H), 7.89-7.85 (m, 2H), 7.71-7.68 (d, J=8.8 Hz, 1H), 7.59 (s, 1H), 7.44 (s, 1H), 4.45-4.43 (d, J=10.8 Hz, 1H), 3.20 (s, 3H), 3.18-3.17 (m, 2H), 2.47 (s, 3H), 2.40 (s, 3H), 2.30 (s, 3H), 1.91-1.88 (d, J=10.4 Hz, 2H), 1.59 (s, 2H), 1.48-1.40 (m, 2H).

Example I-368: Synthesis of 2-fluoro-N-(7-((2-methoxy-3-(1-methyl-1H-1,2,4-triazol-3-yl)phenyl)amino)-2-methyl-3H-imidazo[4,5-b]pyridin-5-yl)cyclopropane-1-carboxamide, I-368

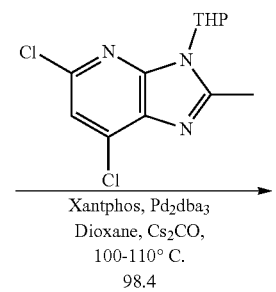

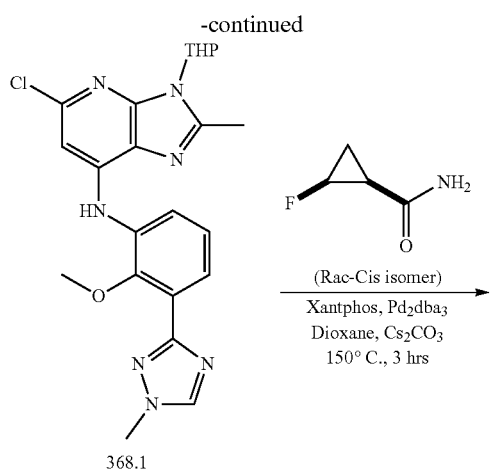

Synthesis of Compound 368.2.

Compound 368.2 was synthesized from 368.1 and (1S, 2S)-2-fluorocyclopropane-1-carboxamide using general procedure B. (Yield: 19.62%). MS(ES): m/z 521.38 [M+H]$^+$.

Synthesis of I-368.

Compound I-368 was synthesized from 368.2 using general procedure C. (Yield: 66.26%). MS(ES): m/z: 437.65 [M+H]$^+$, LCMS purity: 98.02%, HPLC purity: 98.09%, Chiral HPLC purity: (69%, 28%), 1H NMR (DMSO, 400 MHz): 12.12 (s, 1H), 10.49 (s, 1H), 8.58 (s, 1H), 7.85 (s, 1H), 7.76 (s, 1H), 7.58-7.46 (m, 2H), 7.27-7.23 (m, 1H), 4.97-4.78 (m, 1H), 3.96 (s, 3H), 3.74 (s, 3H), 2.50 (s, 3H), 2.18 (m, 1H), 1.63-1.58 (m, 1H), 1.47-1.41 (m, 1H).

Example 369: Synthesis of N-(2-(difluoromethyl)-7-((2-(N-methylmethylsulfonamido)-4-(tetrahydro-2H-pyran-2-yl)phenyl)amino)-3H-imidazo[4,5-b]pyridin-5-yl)cyclopropanecarboxamide, I-369

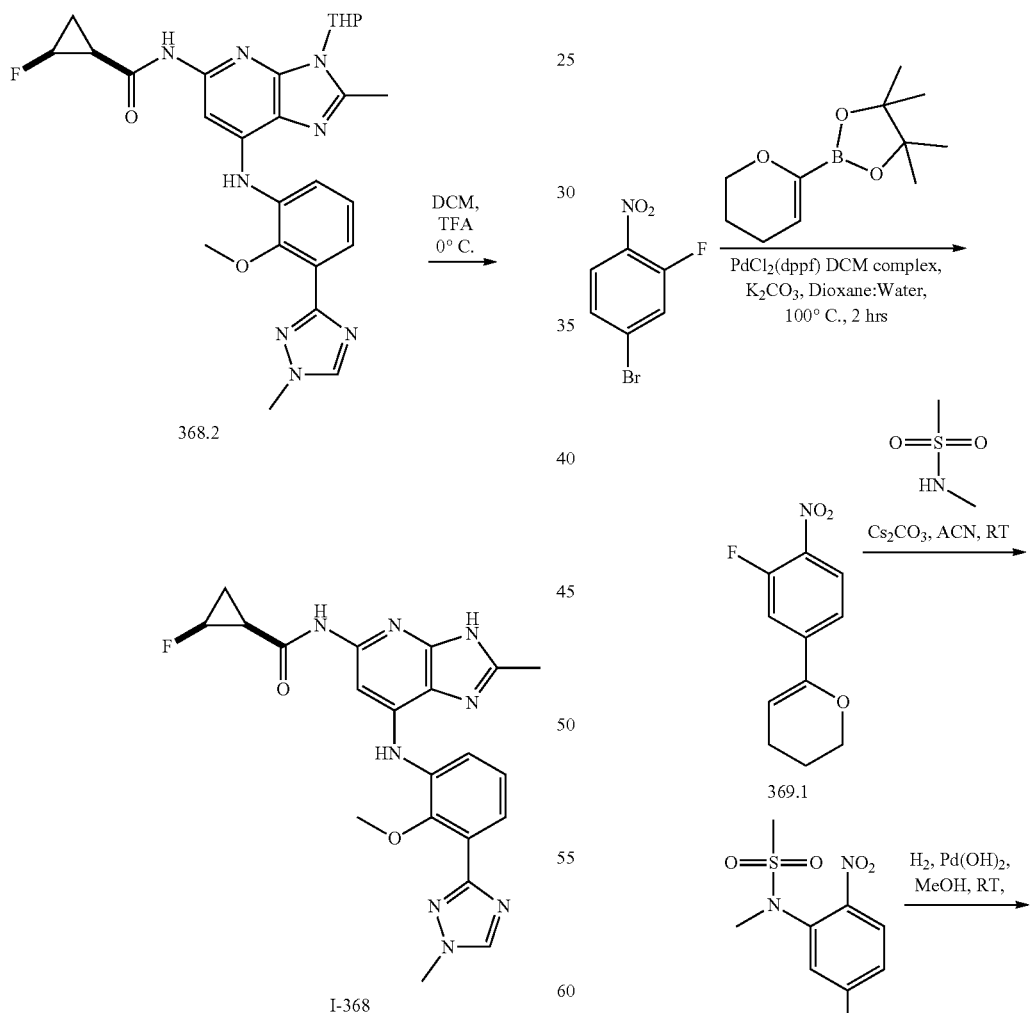

Synthesis of Compound 368.1.

Compound 368.1 was synthesized from 98.4 and 1.1a using general procedure A. (Yield: 31.49%). MS(ES): m/z 454.16 [M+H]$^+$.

861

-continued

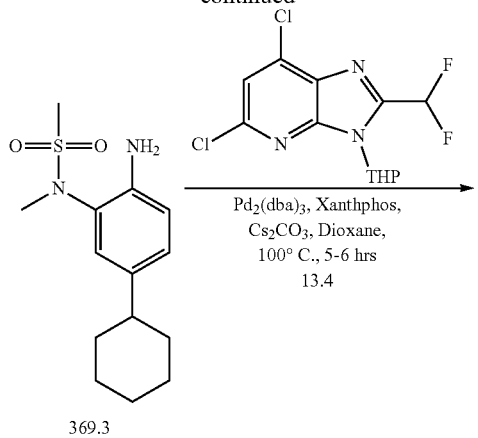

369.3

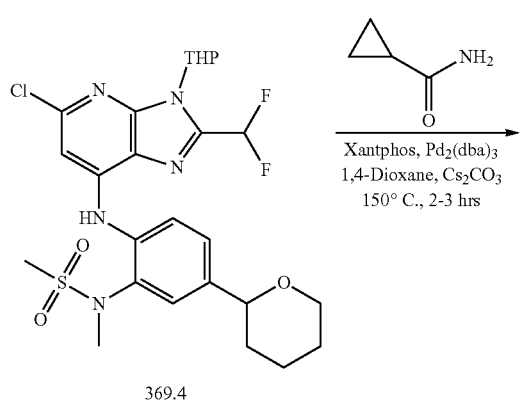

369.4

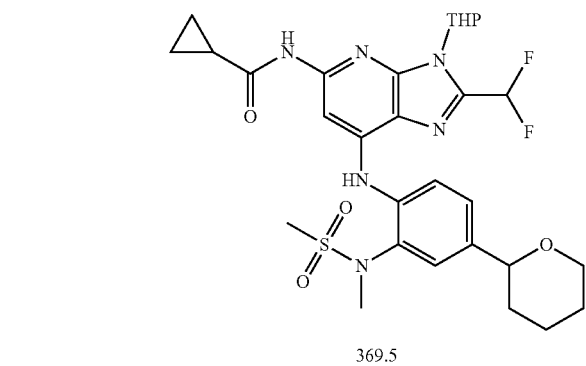

369.5

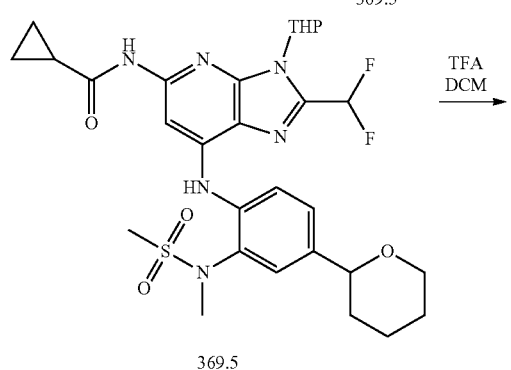

369.5

862

-continued

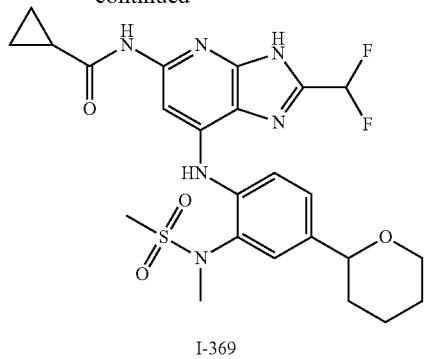

I-369

Synthesis of Compound 369.1.

To a solution of 4-bromo-2-fluoro-1-nitrobenzene (3 g, 13.64 mmol, 1 eq) in 1,4-dioxane (24 mL) and water(6 mL) was added 2-(3,4-dihydro-2H-pyran-6-yl)-4,4,5,5-tetramethyl-1,3,2-dioxaborolane (5.74 g, 27.27 mmol, 2 eq), and potassium carbonate (5.64 g, 40.90 mmol, 3 eq). The reaction mixture was degassed by argon for 30 min. [1,1'-Bisdiphenylphosphinoferrocene]palladium(II) dichloride complex with CH$_2$Cl$_2$ (0.333 g, 4.09 mmol, 0.03 eq), was added into reaction mixture and again reaction mixture was degassed by argon for 30 min. Further reaction mixture was stirred at 100° C. for 2 h. Upon completion, reaction mixture transferred into water and extracted with ethyl acetate. Organic layers were combined, dried over Na$_2$SO$_4$ and concentrated in vacuo to obtain crude product. This was purified by column chromatography and compound was eluted in 5% ethyl acetate in hexane to obtain pure 369.1 (2.4 g, 78.85%). MS(ES): m/z 223.20 [M+H]$^+$.

Synthesis of Compound 369.2.

To a solution of 369.1 (2.4 g, 10.75 mmol, 1 eq), in acetonitrile (70 mL) was added Cs$_2$CO$_3$ (10.54 g, 32.43 mmol, 3 eq) (20 mL) N-methylmethanesulfonamide (1.3 g, 11.83 mmol, 1.1 eq) at r.t. Reaction mixture was stirred for 16 h. Upon completion, reaction mixture was filtered through celite bed and concentrated in vacuo. Crude material was transferred into water and extracted with ethyl acetate. Organic layers were combined, dried over Na$_2$SO$_4$ and concentrated in vacuo to obtain crude product. This was purified by column chromatography and compound was eluted in 10% ethyl acetate in hexane to obtain pure 369.2 (Yield: 59.55%). MS(ES): m/z 313.34 [M+H]$^+$.

Synthesis of Compound 369.3.

To a solution of 369.2 (2 g, 6.40 mmol, 1.0 eq) in MeOH (40 mL), 10% palladium hydroxide on charcoal (0.140 g) was added. Hydrogen was purged through reaction mixture for 2-3 h. Upon completion, reaction mixture was filtered through celite-bed and washed with ethanol. Filtrate was concentrated in vacuo to obtain 369.3 (0.600 g, 42.47%). MS(ES): m/z 224.33 [M+H]$^+$.

Synthesis of Compound 369.4.

Compound 369.4 was synthesized from 369.3 and 13.4 using general procedure A (Yield: 42.95%). MS(ES): m/z 571.05 [M+H]$^+$.

Synthesis of Compound 369.5.

Compound 369.5 was synthesized from 369.4 and cyclopropanecarboxamide using general procedure B. (Yield: 35.16%). MS(ES): m/z 619.70 [M+H]$^+$.

Synthesis of I-369.

Compound I-369 was synthesized from 369.5 using general procedure C. (Yield: 79.82%). MS(ES): m/z: 535.45 [M+H]$^+$, LCMS purity: 99.15%, HPLC purity: 95.20%, Chiral HPLC: (52:48), 1H NMR (MeOD, 400 MHz): 7.71 (s, 1H), 7.65-7.63 (d, J=8.4 Hz, 1H), 7.55-7.53 (d, J=8 Hz, 1H) 7.10 (t, 1H), 6.77 (s, 1H), 4.51-4.49 (d, J=10 Hz, 1H), 4.18-4.15 (d, J=11.2 Hz, 1H), 3.29 (s, 3H), 3.04 (s, 3H), 2.03-1.95 (m, 2H), 1.81-1.57 (m, 4H), 1.11-1.09 (m, 2H), 1.02-1.00 (m, 4H).

Example 370: Synthesis of (1R,2S)—N-(2-(difluoromethyl)-7-((4-(1-methyl-1H-imidazol-5-yl)-2-(N-methylmethylsulfonamido)phenyl)amino)-3H-imidazo[4,5-b]pyridin-5-yl)-2-fluorocyclopropane-1-carboxamide, I-370

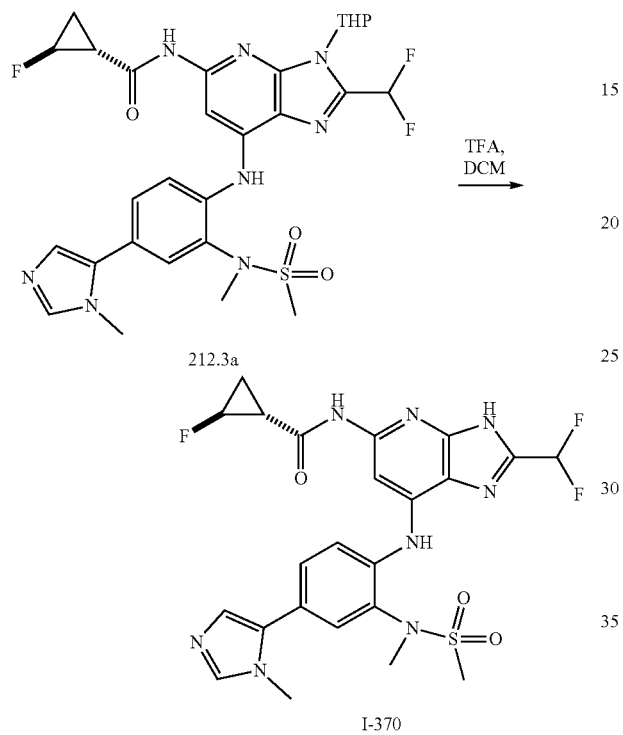

Synthesis of I-370.

Compound I-370 was synthesized from 212.3a using general procedure C. (Yield: 65.62%). MS(ES): m/z: 549.40 [M+H]$^+$, LCMS purity: 98.62%, HPLC purity 96.37%, 1H NMR (MeOD, 400 MHz): 8.52 (s, 1H), 7.87 (s, 2H), 7.71-7.69 (d, J=8 Hz, 1H), 7.65-7.63 (d, J=8 Hz, 1H), 7.32-7.28 (t, J=8 Hz, 1H), 7.02 (t, 1H), 4.76 (s, 1H), 4.05 (s, 3H), 3.73 (s, 3H), 3.39 (s, 3H), 1.60-1.45 (m, 1H), 1.40-1.23 (m, 2H).

Example 371: Synthesis of (1R,2S)—N-(2-(difluoromethyl)-7-((4-(1-methyl-1H-pyrazol-3-yl)-2-(methylsulfonyl)phenyl)amino)-3H-imidazo[4,5-b]pyridin-5-yl)-2-fluorocyclopropane-1-carboxamide, I-371

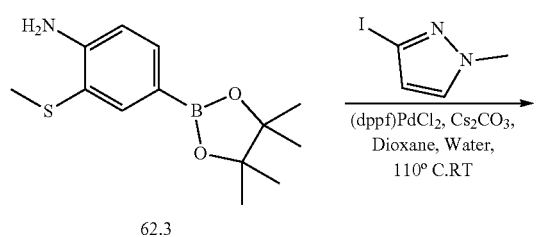

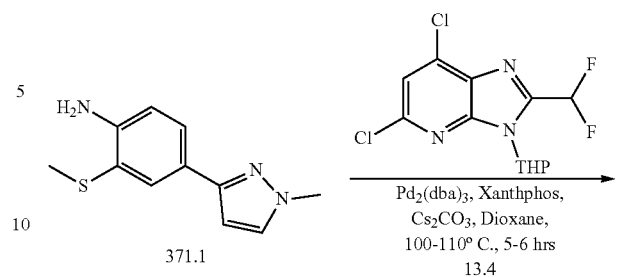

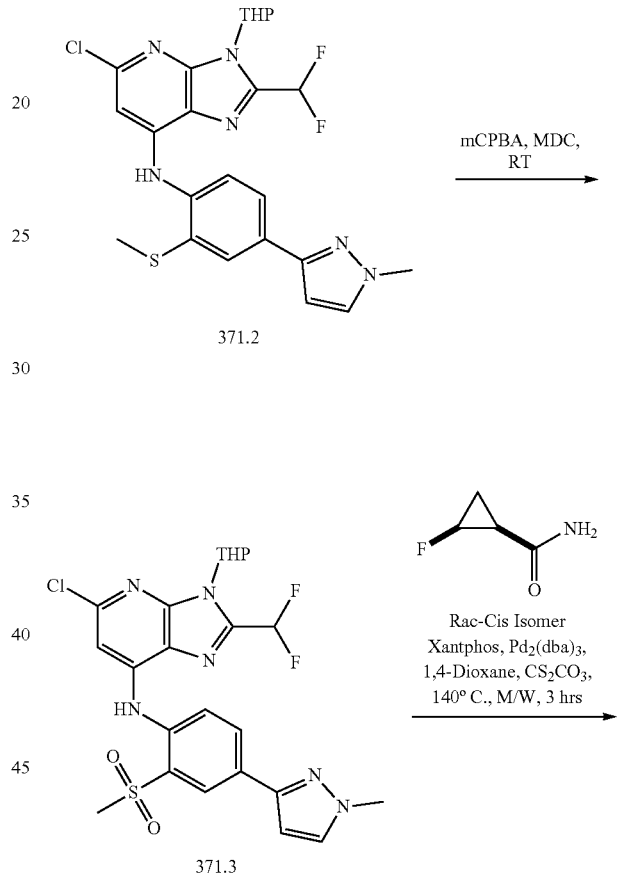

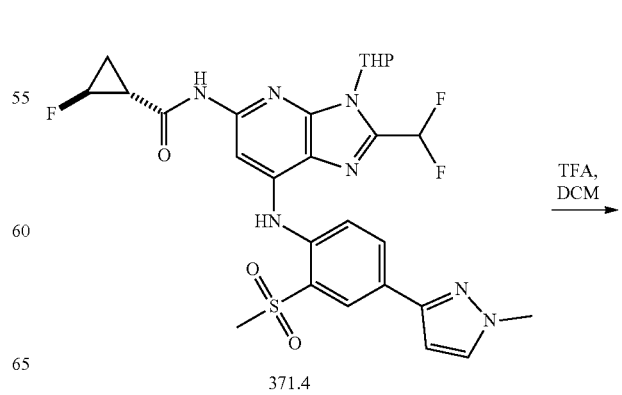

865

-continued

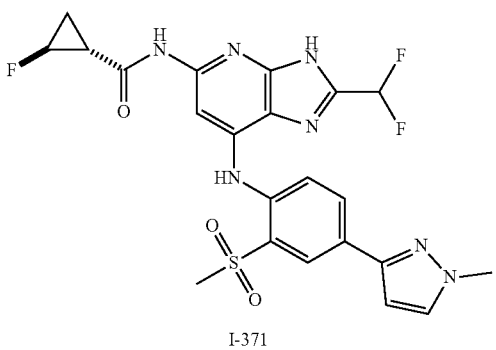 [SMILES: Cn1ccc(-c2ccc(Nc3cc(NC(=O)[C@H]4C[C@@H]4F)nc4[nH]c(C(F)F)nc34)c(S(C)(=O)=O)c2)n1]

I-371

Synthesis of Compound 371.1.

To compound 62.3 (2.2 g, 8.3 mmol, 1.0 eq) in a mixture of 1,4-dioxane (18 mL) and water (4 mL), 3-iodo-1-methyl-1H-pyrazole (2.07 g, 9.9 mmol, 1.2 eq) and $Cs_2CO_3$ (8.09 g, 24.9 mmol, 3.0 eq) were added. Reaction mixture was degassed by argon for 15 min. Then, 1,1'-Bis-(diphenylphosphino) ferrocene]palladium(II) dichloride (1.35 g, 1.6 mmol, 0.2 eq) was added and again degassed for 5 min. Reaction mixture was stirred at 110° C. for 4 h. After completion of the reaction, the reaction mixture was transferred into water and extracted with ethyl acetate. Organic layer combined, dried over anhydrous $Na_2SO_4$, filtered and concentrated in vacuo to obtain the crude material. This was purified by column chromatography using 15% ethyl acetate in hexane to obtain 371.1 (1 g, 54.96%). MS(ES): m/z 220.61 $[M+H]^+$.

Synthesis of Compound 371.2.

Compound 371.2 was synthesized from 371.1 and 13.4 using general procedure A. (Yield: 19.98%). MS(ES): m/z 505.48 $[M+H]^+$.

Synthesis of Compound 371.3.

To compound 371.2 (0.23 g, 0.45 mmol, 1.00 eq) in $CH_2Cl_2$ (4 mL) at 0° C., m-chloroperoxybenzoic acid (0.27 g, 1.59 mmol, 3.5 eq) was added portionwise. Reaction mixture was stirred at r.t. for 10 min. After completion of the reaction, the reaction mixture was transferred into water and extracted with ethyl acetate. The organic layer was then washed with $NaHCO_3$. The organic layer combined, dried over $Na_2SO_4$, filtered and concentrated in vacuo to obtain 371.3 (0.190 g, 77.62%). MS(ES): m/z 537.42 $[M+H]^+$.

Synthesis of Compound 371.4.

Compound 371.4 was synthesized from 371.3 and (1S,2S)-2-fluorocyclopropane-1-carboxamide using general procedure B. (Yield: 25.75%). MS(ES): m/z 604.18 $[M+H]^+$.

Synthesis of I-371.

Compound I-371 was synthesized from 371.4 using general procedure C (Yield: 84.04%). MS(ES): m/z: 520.46 $[M+H]^+$, LCMS purity: 95.15%, HPLC purity: 98.76%, Chiral HPLC: (72%), 1H NMR (DMSO, 400 MHz): 13.72 (s, 1H), 10.80 (s, 1H), 8.78 (s, 1H), 8.17-8.15 (d, J=8.4 Hz, 2H), 8.08 (s, 1H), 7.84-7.80 (m, 2H), 7.24 (s, 1H), 6.84-6.79 (m, 1H), 5.01-4.83 (m, 1H), 3.98 (s, 3H), 3.35 (s, 3H), 1.66-1.59 (s, 1H), 1.25-1.12 (m, 2H).

866

Example 372: Synthesis of (1R,2S)-2-fluoro-N-(2-methyl-7-((4-(1-methyl-1H-pyrazol-4-yl)-2-(N-methylmethylsulfonamido)phenyl)amino)-3H-imidazo[4,5-b]pyridin-5-yl)cyclopropane-1-carboxamide, I-372

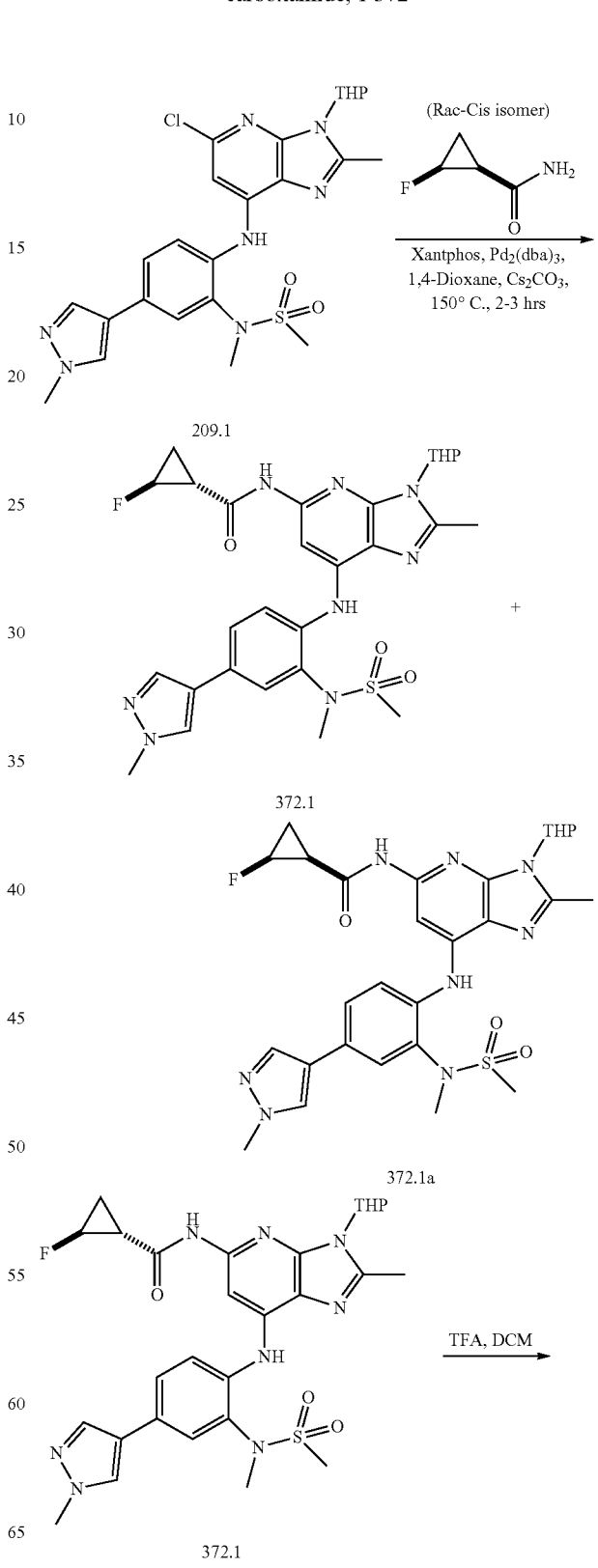

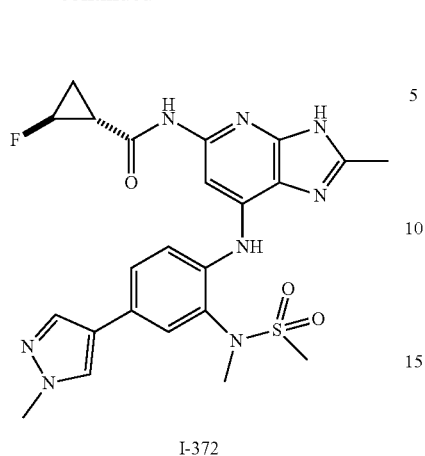

I-372

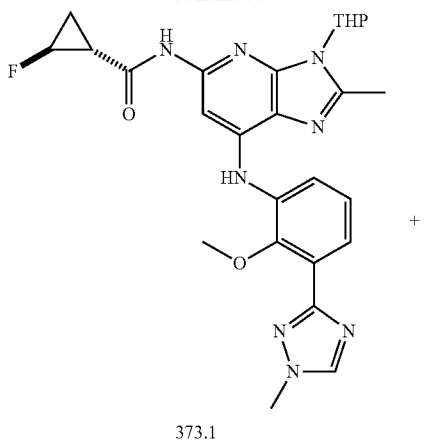

373.1

Synthesis of Compound 372.1.

Compound 372.1 was synthesized from 209.1 and (1S,2S)-2-fluorocyclopropane-1-carboxamide using general procedure B. (Yield: 15.75%). MS(ES): m/z 597.76 [M+H]$^+$.

Synthesis of I-372.

Compound I-372 was synthesized from 372.1 using general procedure C. (Yield: 42.33%). MS(ES): m/z: 513.41 [M+H]$^+$, LCMS purity: 95.15%, HPLC purity: 92.15%, Chiral HPLC Purity: (23%, 67%), 1H NMR (DMSO, 400 MHz): 12.41 (s, 1H), 10.63 (s, 1H), 8.22 (s, 1H), 7.95 (s, 1H), 7.84-7.82 (d, J=9.6 Hz, 2H), 7.71 (s, 1H), 7.61-7.59 (d, J=8.4 Hz, 1H), 7.53 (s, 1H), 4.91-4.76 (m, 1H), 3.88 (s, 3H), 3.22 (s, 3H), 3.17 (s, 3H), 3.11 (s, 3H), 1.47-1.42 (m, 1H) 1.2-1.15 (m, 2H).

Example 373: Synthesis of (1R,2S)-2-fluoro-N-(7-((2-methoxy-3-(1-methyl-1H-1,2,4-triazol-3-yl)phenyl)amino)-2-methyl-3H-imidazo[4,5-b]pyridin-5-yl)cyclopropane-1-carboxamide, I-373

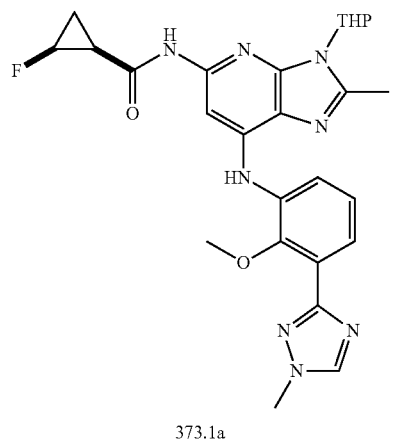 [SMILES: COc1c(Nc2cc(NC(=O)[C@H]3C[C@@H]3F)nc3[nH]c(C)nc23)cccc1-c1ncn(C)n1]

373.1a

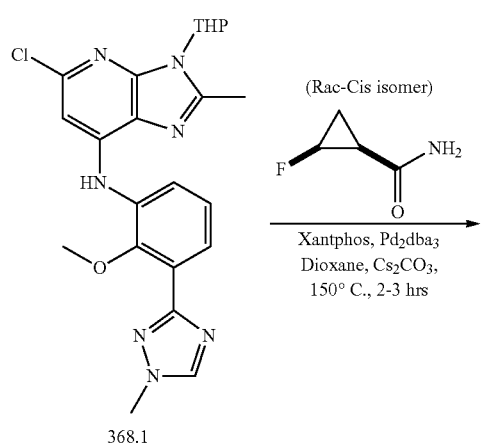

368.1

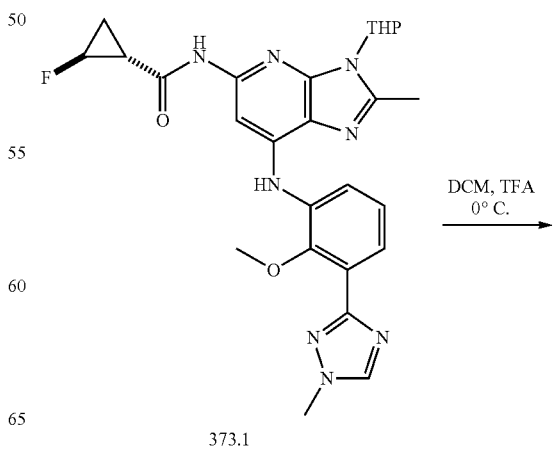

373.1

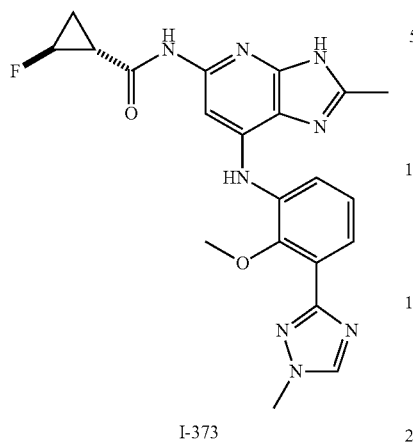

I-373

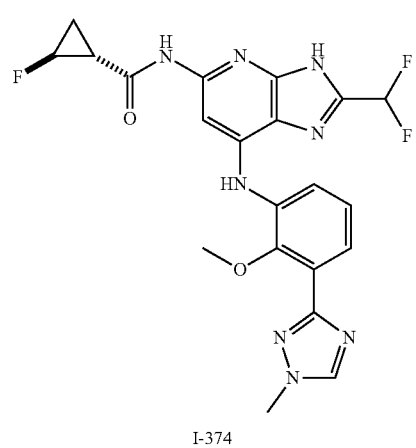

I-374

Synthesis of Compound 373.1.

Compound 373.1 was synthesized from 368.1 and (1S, 2S)-2-fluorocyclopropane-1-carboxamide using general procedure B. (Yield: 14.53%). MS(ES): m/z: 521.73 [M+H]⁺.

Synthesis I-373.

Compound I-373 was synthesized from 373.1 using general procedure C. (Yield: 71.56%). MS(ES): m/z: 437.65 [M+H]⁺, LCMS purity: 98.49%, HPLC purity: 96.40%, Chiral HPLC Purity: (26%, 74%), 1H NMR (DMSO, 400 MHz): 12.50 (s, 1H), 10.64 (s, 1H), 8.57 (s, 1H), 7.93 (s, 1H), 7.71 (s, 1H), 7.57-7.55 (d, J=6.8 Hz, 1H), 7.49-7.47 (d, J=6.8 Hz, 1H), 7.24-7.20 (t, 1H), 3.96 (s, 3H), 3.68 (s, 3H), 2.52 (s, 3H), 1.48-1.41 (m, 2H), 1.24-1.18 (m, 1H) 1.21 (t, 1H).

Example 1-374: Synthesis of N-(2-(difluoromethyl)-7-((2-methoxy-3-(1-methyl-1H-1,2,4-triazol-3-yl)phenyl)amino)-3H-imidazo[4,5-b]pyridin-5-yl)-2-fluorocyclopropane-1-carboxamide, I-374

Synthesis of I-374.

Compound I-374 was synthesized from 374.1 using general procedure C. (Yield: 82.46%). MS(ES): m/z: 473.5 [M+H]⁺, LCMS purity: 99.31%, HPLC purity: 97.95%, Chiral HPLC purity: 75.53%, 1H NMR (MeOD, 400 MHz): 8.52 (s, 1H), 7.87 (s, 1H), 7.71-7.6 (d, J=8 Hz, 1H), 7.65-7.63 (d, J=8 Hz, 1H), 7.32-7.15 (t, J=8 Hz, 1H), 7.01 (t, 1H), 4.76 (s, 1H), 4.05 (s, 3H), 3.73 (s, 3H), 1.60-1.51 (m, 1H), 1.48-1.27 (m, 2H).

Example 375: Synthesis of N-(2-methyl-7-((2-(N-methylmethylsulfonamido)-4-(tetrahydro-2H-pyran-2-yl)phenyl)amino)-3H-imidazo[4,5-b]pyridin-5-yl) cyclopropanecarboxamide, I-375

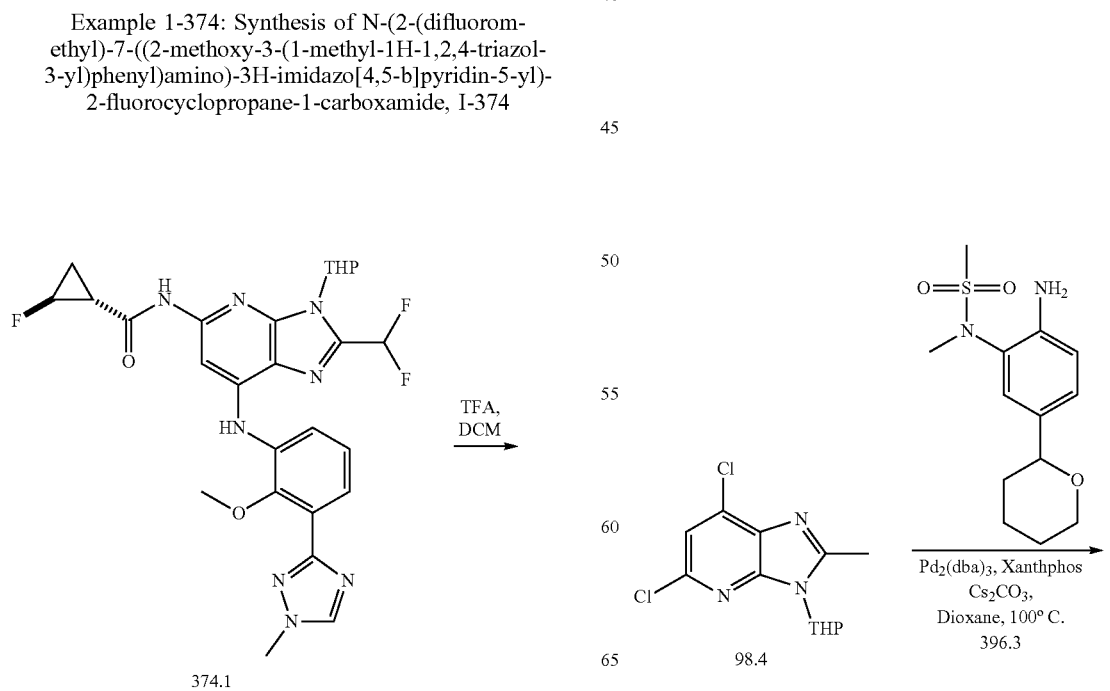

871

-continued

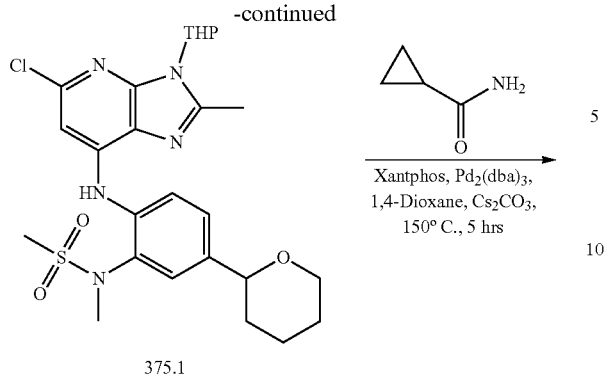

Synthesis of Compound 375.1.

Compound 375.1 was synthesized from 98.4 and 369.3 using general procedure A. (Yield: 32.29%). MS(ES): m/z 535.07 [M+H]+.

Synthesis of Compound 375.2.

Compound 375.2 was synthesized from 375.1 and cyclopropanecarboxamide using general procedure B. (Yield: 34.37%). MS(ES): m/z 583.72 [M+H]+.

Synthesis of Compound I-375.

Compound I-375 was synthesized from 375.2 using general procedure C. (Yield: 68.17%). MS(ES): m/z: 499.46 [M+H]+, LCMS purity: 99.54%, HPLC purity: 99.27%, 1H NMR (MeOD, 400 MHz): 7.63 (s, 1H), 7.60-7.58 (d, J=8.4 Hz, 1H), 7.48-7.46 (d, J=8.4 Hz, 1H), 7.36 (s, 1H), 4.47-4.45 (d, J=9.6 Hz, 1H), 4.16-4.14 (d, J=11.2 Hz, 1H), 3.73-3.67 (m, 1H), 3.30 (s, 3H), 3.04 (s, 3H), 2.66 (s, 3H), 2.01-2.01 (m, 2H), 1.83-1.59 (m, 6H), 1.00-0.92 (m, 4H).

872

Example 376: Synthesis of 2,2-difluoro-N-(2-methyl-7-((4-(1-methyl-1H-pyrazol-4-yl)-2-(N-methylmethylsulfonamido)phenyl)amino)-3H-imidazo[4,5-b]pyridin-5-yl)cyclopropane-1-carboxamide, I-376

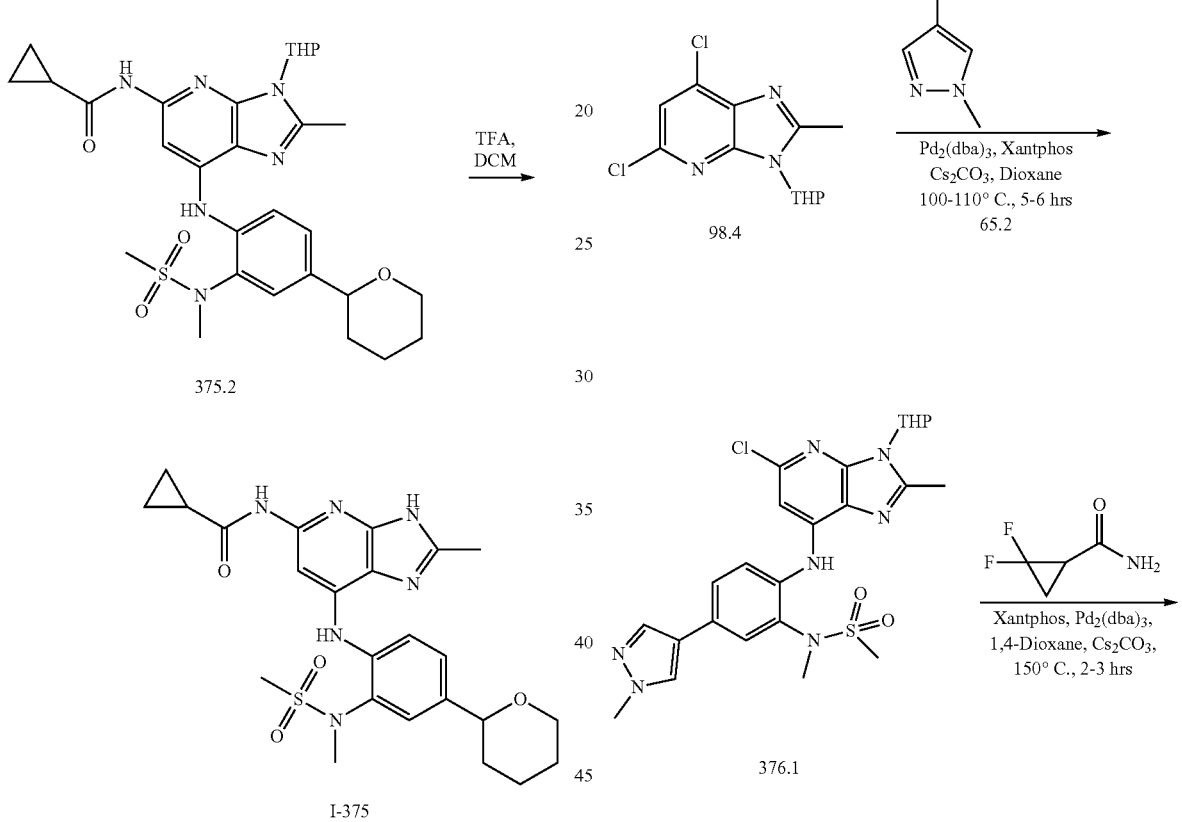

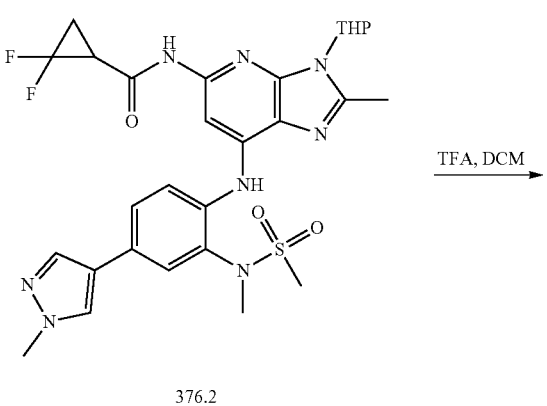

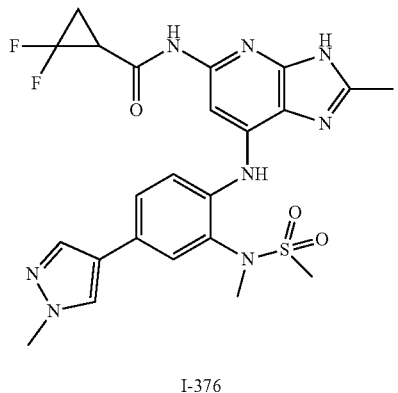

I-376

Synthesis of Compound 376.1.

Compound 376.1 was synthesized from 98.4 and 65.2 using general procedure A. (Yield: 17.63%). MS(ES): m/z 531.04 [M+H]+.

Synthesis of Compound 376.2.

Compound 376.2 was synthesized from 376.1 and 2,2-difluorocyclopropane-1-carboxamide using general procedure B. (Yield: 11.73%). MS(ES): m/z 615.67 [M+H]+.

Synthesis of I-376.

Compound I-376 was synthesized from 376.2 using general procedure C. (Yield: 42.16%). MS(ES): m/z: 531.40 [M+H]+, LCMS purity: 98.50%, HPLC purity: 95.06%, Chiral HPLC: (49%, 38%), 1H NMR (MeOD, 400 MHz): 8.22-8.20 (d, J=8.8 Hz, 1H), 8.00 (s, 1H), 7.87 (s, 1H), 7.68-7.68 (d, J=8 Hz, 1H), 7.56-7.54 (d, J=8.4 Hz, 2H), 3.96 (s, 3H), 3.69 (s, 3H), 3.07 (s, 3H), 2.58 (s, 3H), 2.19 (s, 1H), 1.43 (s, 2H).

Example 377: Synthesis of 2,2-difluoro-N-(2-methyl-7-((4-(1-methyl-1H-pyrazol-3-yl)-2-(methylsulfonyl)phenyl)amino)-3H-imidazo[4,5-b]pyridin-5-yl)cyclopropane-1-carboxamide, I-377

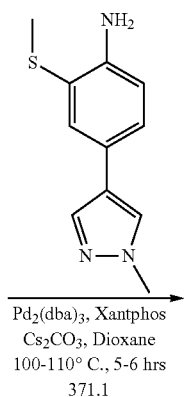

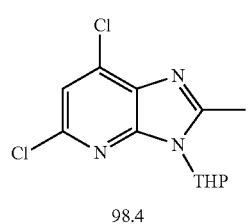

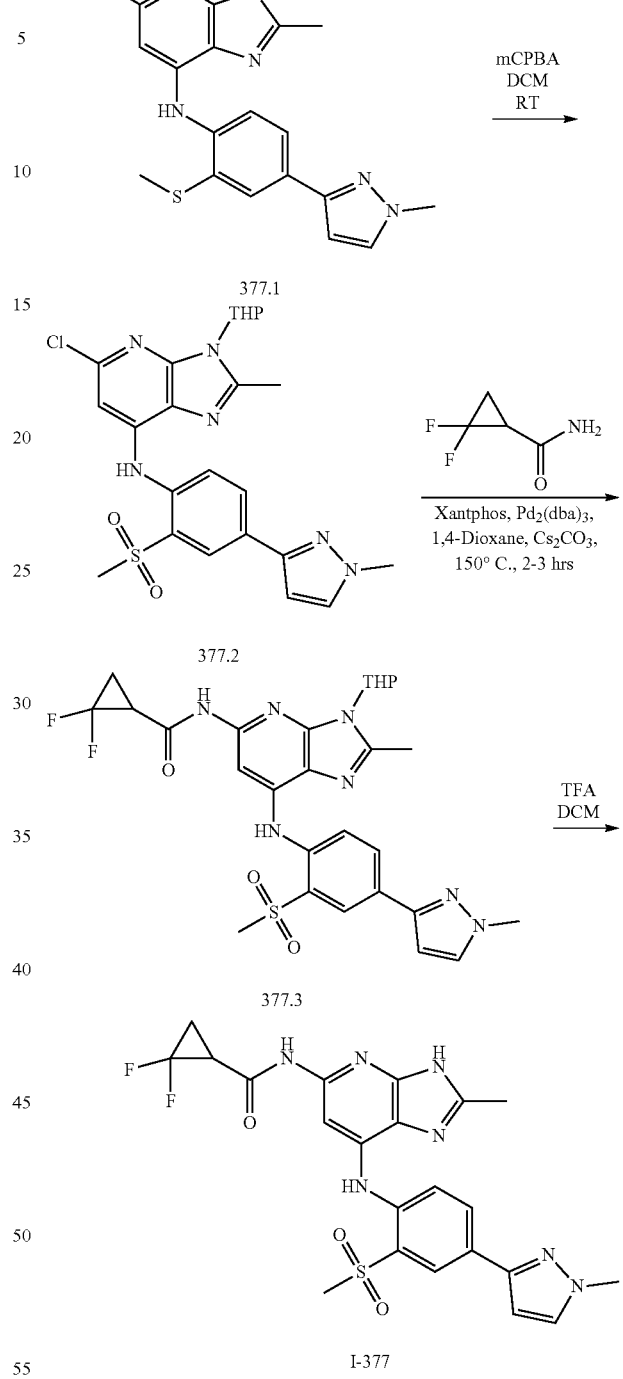

I-377

Synthesis of Compound 377.1.

Compound 377.1 was synthesized from 98.4 and 371.1 using general procedure A. (Yield: 38.72%). MS(ES): m/z 470.00 [M+H]+.

Synthesis of Compound 377.2.

To a compound 377.1 (0.265 g, 5.63 mmol, 1.0 eq) in CH$_2$Cl$_2$ (5 ml), m-chloroperbenzoic acid (0.29 g, 1.69 mmol, 3.0 eq) was added portionwise at 0° C. Reaction mixture was stirred at r.t. for 2 h. After completion of reaction, the pH of the reaction mixture was adjusted to neutral using NaHCO$_3$ solution and then extracted using CH$_2$Cl$_2$. Organic layers were combined, dried over Na$_2$SO$_4$, filtered and concentrated in vacuo to obtain crude product. This was purified by column chromatography using 2.5% MeOH in CH$_2$Cl$_2$ as eluant to obtain pure 377.2 (0.200 g, 70.65%). MS(ES): m/z 502.00 [M+H]$^+$.

Synthesis of Compound 377.3.

Compound 377.3 was synthesized from 377.2 and 2,2-difluorocyclopropane-1-carboxamide using general procedure B. (Yield: 32.51%). MS(ES): m/z 586.63 [M+H]$^+$.

Synthesis of I-377.

Compound 377.3 was synthesized using general procedure C. (Yield: 19.97%). MS(ES): m/z: 502.36 [M+H]$^+$, LCMS purity: 99.35%, HPLC purity 99.28%, Chiral HPLC: (50%, 50%), 1H NMR (MeOD, 400 MHz): 8.47-8.47 (d, J=2 Hz, 1H), 8.16-8.16 (d, J=2 Hz, 1H), 8.03 (s, 1H), 7.72-7.69 (m, 2H), 6.76-6.75 (d, J=2 Hz, 1H), 3.99 (s, 3H), 3.19 (s, 3H), 2.83 (s, 3H), 2.10-2.07 (m, 1H), 1.32-1.31 (m, 2H).

Example 378: Synthesis of N-(7-((4-(112-imidazol-4-yl)-2-(methylsulfonyl)phenyl)amino)-2-methyl-3H-imidazo[4,5-b]pyridin-5-yl)-2,2-difluorocyclopropane-1-carboxamide, I-378

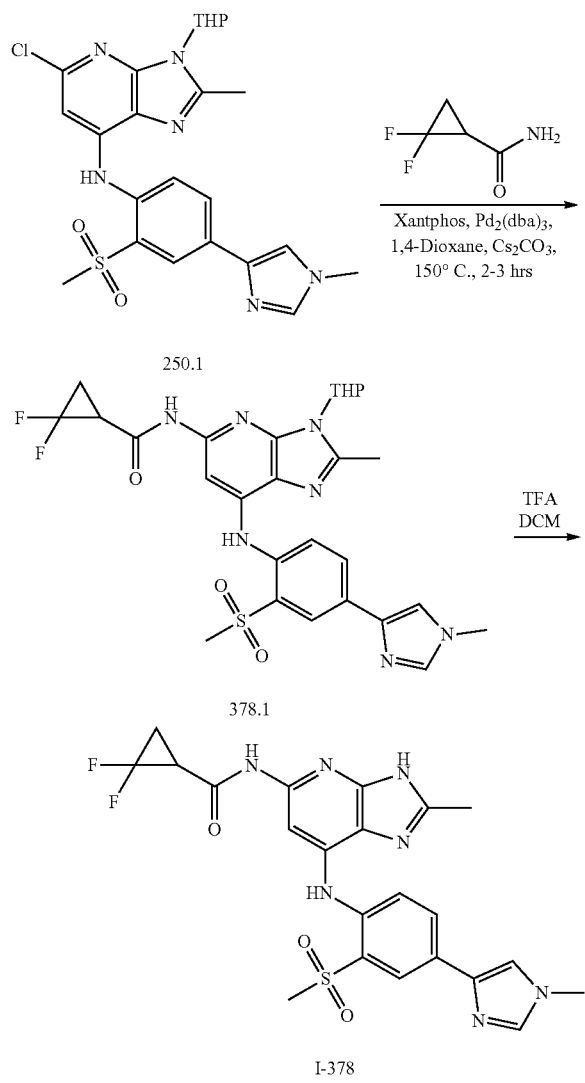

Synthesis of Compound 578.1.

Compound 378.1 was synthesized from 250.1 and 2,2-difluorocyclopropane-1-carboxamide using general procedure A. (Yield: 62.74%). MS(ES): m/z 586.63 [M+H]$^+$.

Synthesis of I-378,

Compound was synthesized from 378.1 using general procedure C. (Yield: 95.21%). MS(ES): m/z: 502.5 [M+H]$^+$, LCMS purity: 100%, HPLC purity: 96.02%, Chiral HPLC: (49%, 48%), 1H NMR (MeOD, 400 MHz): 8.38-8.37 (d, J=2 Hz, 1H), 8.06-8.04 (d, J=8.4 Hz, 1H), 7.93 (s, 1H), 7.8 (s, 1H), 7.71 (s, 1H), 7.60 (s, 1H), 3.82 (s, 3H), 3.15 (s, 3H), 2.60 (s, 3H), 2.07-2.04 (m, 1H), 1.37-1.27 (m, 2H).

Example 379: Synthesis of N-(2-(difluoromethyl)-7-((4-(1-methyl-1H-imidazol-5-yl)-2-(methylsulfonyl)phenyl)amino)-3H-imidazo[4,5-b]pyridin-5-yl)-2,2-difluorocyclopropane-1-carboxamide, I-379

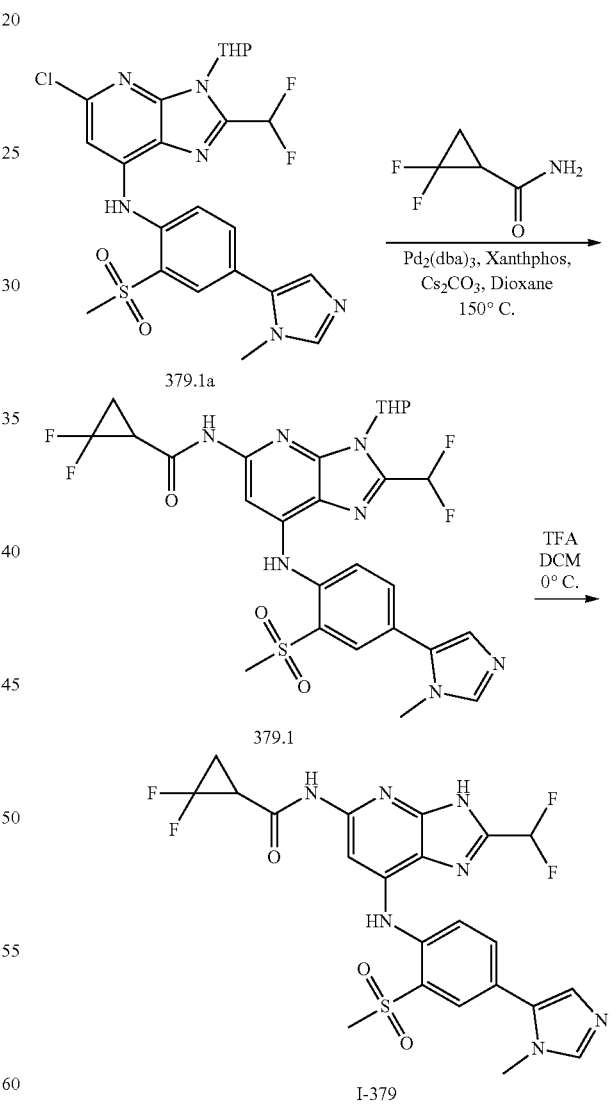

Synthesis of Compound 379.1.

Compound was synthesized from 2,2-difluorocyclopropane-1-carboxamide and 379.1a (prepared in a manner analogous to 382.2) using general procedure B. (Yield: 38.87%). MS (ES): m/z 622.61 [M+H]$^+$.

Synthesis of Compound I-379.

Compound I-379 was synthesized from 379.1 using general procedure C. (Yield: 96.38%). MS(ES): m/z: 538.55 [M+H]$^+$, LCMS purity: 98.37%, HPLC purity: 98.50%, 1H NMR (MeOD, 400 MHz): 8.17 (s, 1H), 8.11-8.11 (d, J=2 Hz, 1H), 8.01-7.99 (d, J=8.4 Hz, 1H), 7.91-7.89 (m, 1H), 7.89 (s, 1H), 7.22 (s, 1H), 7.00 (t, 1H), 3.84 (s, 3H), 3.20 (s, 3H), 2.19-2.09 (m, 1H), 1.32-1.25 (m, 2H).

Example 380: Synthesis of N-(2-(difluoromethyl)-7-((4-(1-methyl-1H-imidazol-5-yl)-2-(N-methylmethylsulfonamido)phenyl)amino)-3H-imidazo[4,5-b]pyridin-5-yl)-2,2-difluorocyclopropane-1-carboxamide, I-380

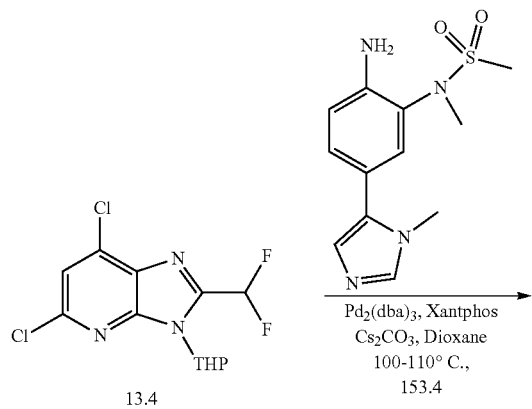

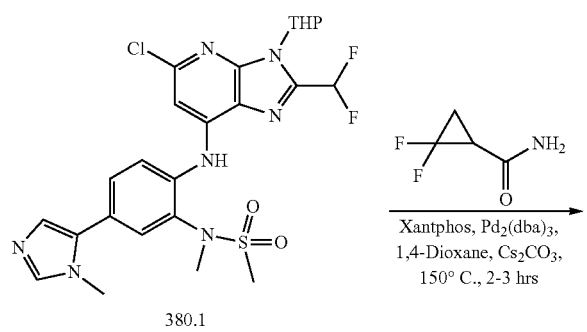

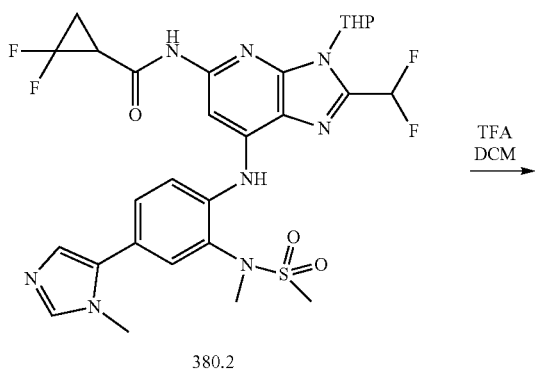

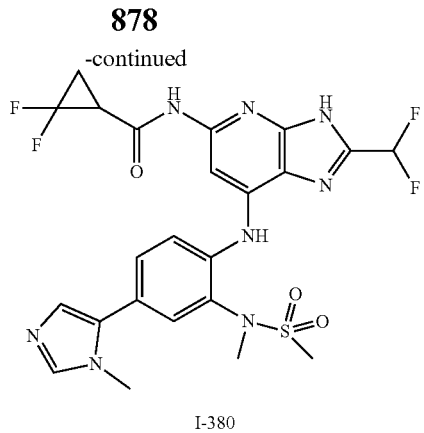

I-380

Synthesis of Compound 380.1.

Compound 380.1 was synthesized from 13.4 and 153.4 using general procedure A. (Yield: 10.67%). MS(ES): m/z 567.84 [M+H]$^+$.

Synthesis of Compound 380.2

Compound 380.2 was synthesized from 380.1 and 2,2-difluorocyclopropane-1-carboxamide using general procedure B. (Yield: 43.50%). MS(ES): m/z 651.48 [M+H]$^+$.

Synthesis of I-380.

Compound I-380 was synthesized from 380.2 using general procedure C. (Yield: 63.80%). MS(ES): m/z: 567.51 [M+H]$^+$, LCMS purity: 98.88%, HPLC purity: 94.90%, Chiral HPLC: (50%, 50%), 1H NMR (DMSO, 400 MHz): 13.67 (s, 1H), 10.91 (s, 1H), 8.30 (s, 1H), 7.90 (s, 1H), 7.79-7.76 (d, J=1.2 Hz, 2H), 7.71-7.69 (d, J=4.0 Hz, 1H), 7.60-7.58 (d, J=7.6 Hz, 1H), 7.28 (t, 1H), 7.17 (s, 1H), 3.77 (s, 3H), 3.27 (s, 3H), 3.13 (s, 3H), 2.00 (s, 1H), 1.2 (s, 2H).

Example 381: Synthesis of N-(2-(difluoromethyl)-7-((4-(1-methyl-1H-imidazol-4-yl)-2-(methylsulfonyl)phenyl)amino)-3H-imidazo[4,5-b]pyridin-5-yl)-2,2-difluorocyclopropane-1-carboxamide, I-381

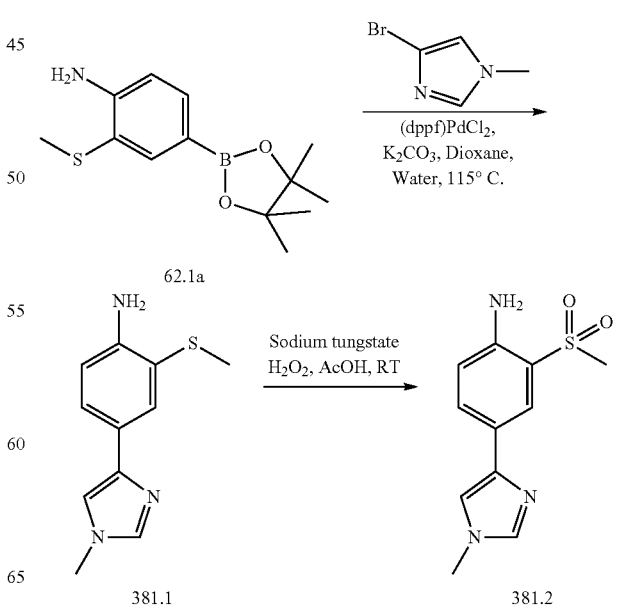

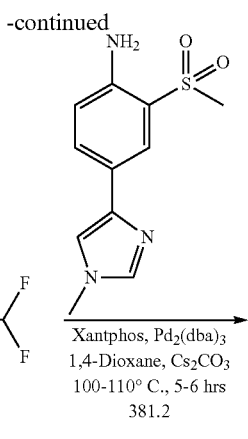

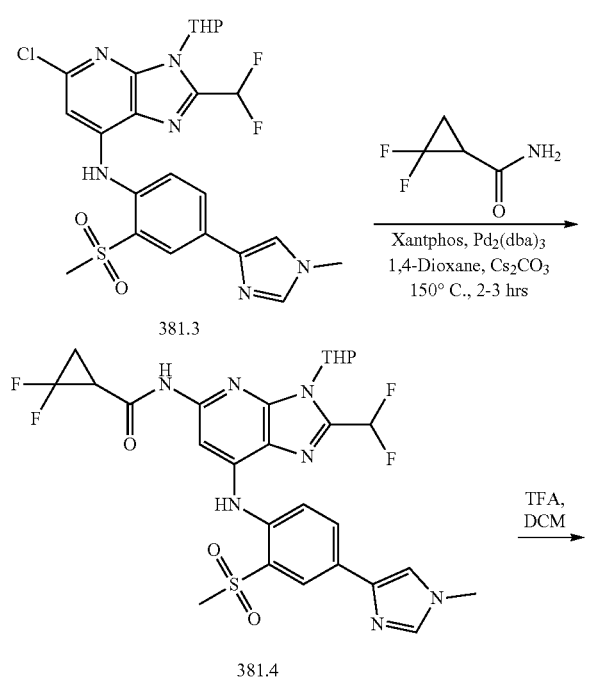

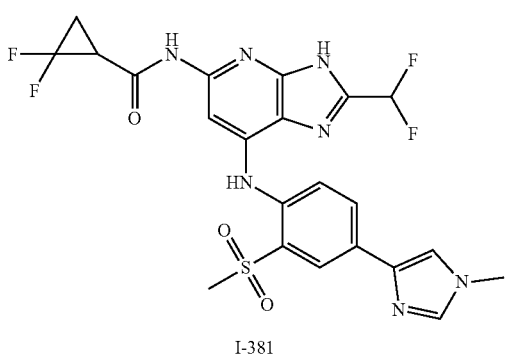

Synthesis of Compound 381.1.

To compound 62.1a (6 g, 22.64 mmol, 1.0 eq) in a mixture of 1,4-dioxane (50 mL) and water (10 mL), 4-bromo-1-methyl-1H-imidazole (4.0 g, 24.9 mmol, 1.1 eq) and potassium carbonate (9.3 g, 67.9 mmol, 3.0 eq) were added. Reaction mixture was degassed by argon for 15 min. Then, 1,1'-Bis-(diphenylphosphino)ferrocene]palladium(II) dichloride (3.6 g, 4.5 mmol, 0.2 eq) was added and again degassed for 5 min. Reaction mixture was stirred at 110° C. for 4 h. After completion of the reaction, the reaction mixture was transferred into water and extracted with ethyl acetate. Organic layer combined, dried over anhydrous Na$_2$SO$_4$, filtered and concentrated in vacuo to obtain the crude material. This was purified by column chromatography using 15% ethyl acetate in hexane to obtain 381.1 (3.2 g, 64.49%). MS(ES): m/z 220.48 [M+H]$^+$.

Synthesis of Compound 381.2.

To compound 381.1 (3 g, 13.6 mmol, 1.0 eq) in acetic acid (8 mL), sodium tungstate (4.01 g, 13.6 mmol, 1.0 eq) and hydrogen peroxide (9.24 mL, 272 mmol, 20 eq) were added. Reaction mixture was stirred at r.t. for 15 min. After completion of the reaction, the reaction mixture was transferred to water. The pH ~7 was adjusted by using saturated NaHCO$_3$ and extracted with ethyl acetate. Organic layers were combined, dried over Na$_2$SO$_4$, filtered and concentrated in vacuo to get the crude material. This was purified by column chromatography using 20% ethyl acetate in hexane as eluant to obtain pure 381.2 (1.3 g, 37.82%). MS(ES): m/z 252.76 [M+H]$^+$.

Synthesis of Compound 381.3.

Compound 381.3 was synthesized from 13.4 and 381.2 using general procedure B. (Yield: 24.85%). MS(ES): m/z 537.46 [M+H]$^+$.

Synthesis of Compound 381.4.

Compound 381.4 was synthesized from 381.3 and 2,2-difluorocyclopropane-1-carboxamide using general procedure B. (Yield: 29.70%). MS(ES): m/z 622.61 [M+H]$^+$.

Synthesis of I-381.

Compound I-381 was synthesized from 381.4 using general procedure C. (Yield: 77.80%). MS(ES): m/z: 538.40 [M+H]$^+$, LCMS purity: 99.25%, HPLC purity: 95.35%, Chiral HPLC: (52%, 48%), 1H NMR (MeOD, 400 MHz): 8.40-8.39 (d, J=2 Hz, 1H), 8.10-8.07 (m, 2H), 7.88-7.86 (d, J=8.4 Hz, 1H), 7.72 (s, 1H), 7.62 (s, 1H), 6.99 (t, 1H), 3.82 (s, 3H), 3.15 (s, 3H), 2.84 (bs, 1H), 2.12-2.07 (m, 1H), 1.88-1.82 (m, 1H).

Example 382: Synthesis of 2,2-difluoro-N-(2-methyl-7-((4-(1-methyl-1H-imidazol-5-yl)-2-(methylsulfonyl)phenyl)amino)-3H-imidazo[4,5-b]pyridin-5-yl)cyclopropane-1-carboxamide, I-382

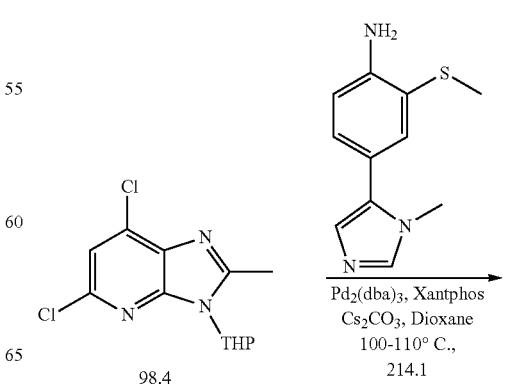

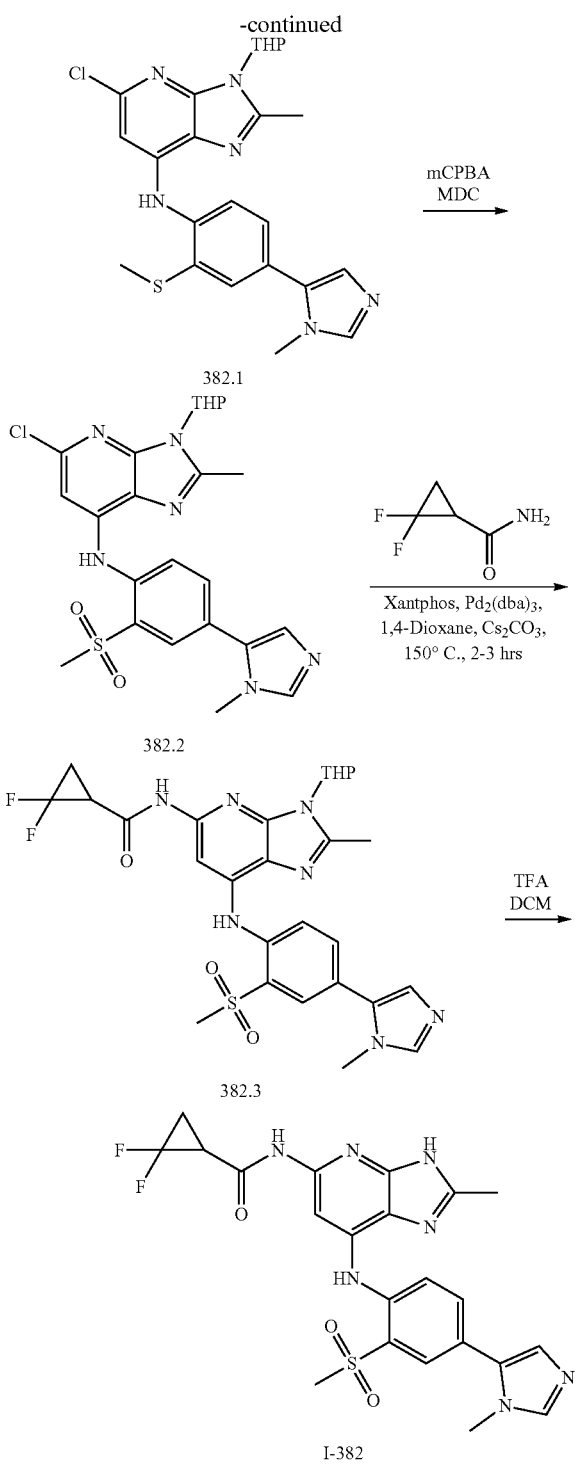

382.1

382.2

382.3

I-382

Synthesis of Compound 382.1.

Compound 382.1 was synthesized from 98.4 and 214.1 using general procedure A. (Yield: 33.56%). MS(ES): m/z 470.28 [M+H]$^+$.

Synthesis of Compound 382.2.

To compound 382.1 (0.61 g, 1.28 mmol, 1.0 eq) in CH$_2$Cl$_2$ (1 mL) at 0° C., m-chloroperoxybenzoic acid (0.770 g, 4.48 mmol, 3.5 eq) was added. Reaction mixture was stirred at r.t. for 4 h. After completion of the reaction, the reaction mixture was transferred into water and extracted with CH$_2$Cl$_2$. Organic layer combined, dried over anhydrous Na$_2$SO$_4$, filtered and concentrated in vacuo to obtain crude product. This was purified by column chromatography using 5% ethyl acetate in hexane to obtain pure 382.2 (0.28 g, 42.97%). MS(ES): m/z 502.37 [M+H]$^+$.

Synthesis of Compound 382.3.

Compound 382.3 was synthesized from 382.2 and 2,2-difluorocyclopropane-1-carboxamide using general procedure B. (Yield: 38.21%). MS(ES): m/z 586.17 [M+H]$^+$.

Synthesis of I-382.

Compound I-382 was synthesized from 382.3 using general procedure C. (Yield: 81.92%). MS(ES): m/z: 502.4 [M+H]$^+$, LCMS purity: 98.70%, HPLC purity 99.70%, 1H NMR (DMSO, 400 MHz): 12.61 (s, 1H), 10.86 (s, 1H), 8.78 (s, 1H), 8.03-7.78 (m, 5H), 7.19 (s, 1H), 3.75 (s, 3H), 3.29 (s, 3H), 2.98 (s, 3H), 2.00-1.98 (m, 1H), 1.15-1.24 (m, 2H).

Example 383: Synthesis of 5-methoxy-2-methyl-N-(4-(1-methyl-1H-pyrazol-3-yl)-2-(methylsulfonyl)phenyl)-3H-imidazo[4,5-b]pyridin-7-amine, I-383

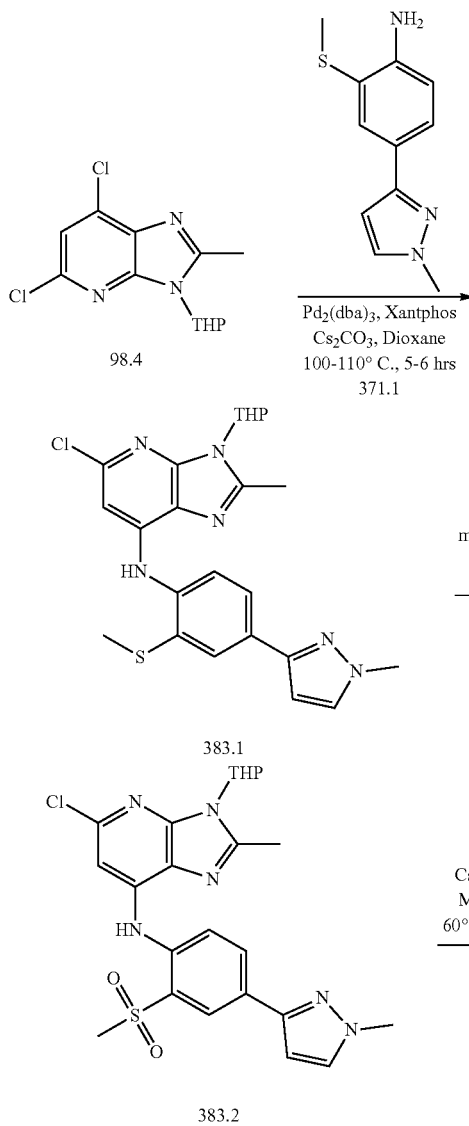

383.1

383.2

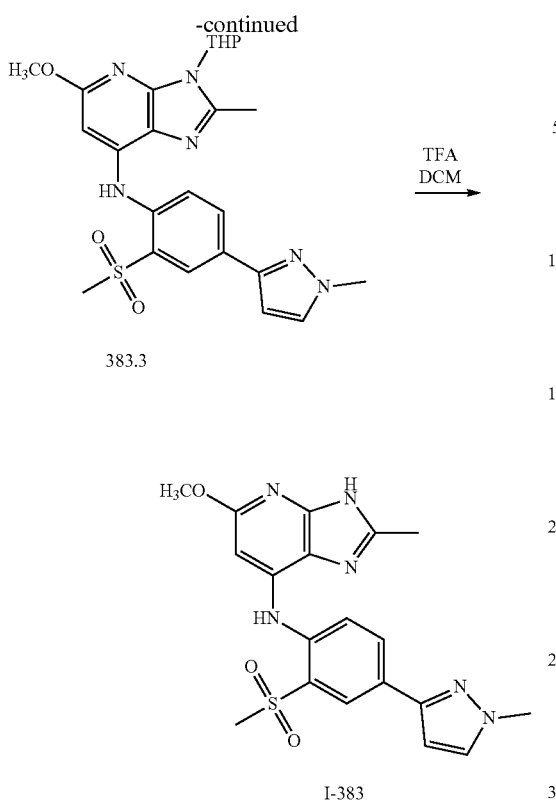

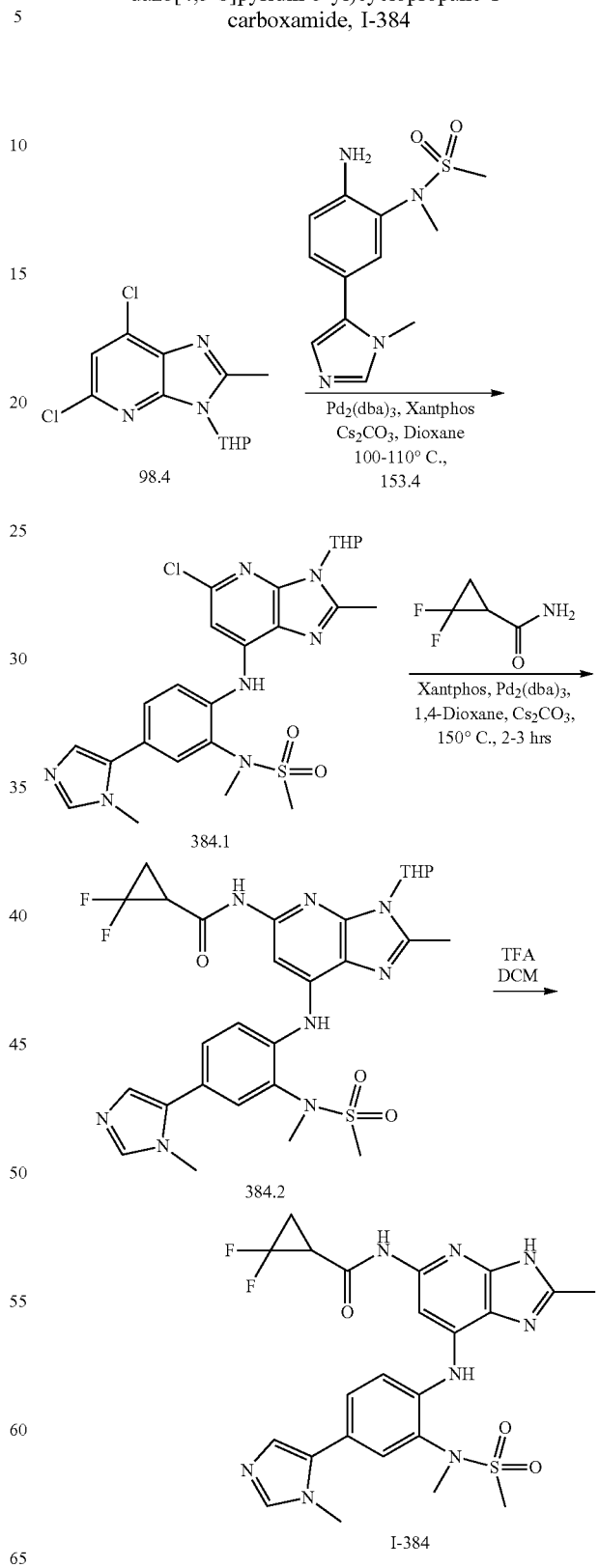

Example 384: Synthesis of 2,2-difluoro-N-(2-methyl-7-((4-(1-methyl-1H-imidazol-5-yl)-2-(N-methylmethylsulfonamido)phenyl)amino)-3H-imidazo[4,5-b]pyridin-5-yl)cyclopropane-1-carboxamide, I-384

Synthesis of Compound 383.1.

Compound 383.1 was synthesized from 98.4 and 371.1 using general procedure A. (Yield: 38.72%). MS(ES): m/z 470.00 [M+H]$^+$.

Synthesis of Compound 383.2.

To compound 383.1 (0.265 g, 0.563 mmol, 1.0 eq) in CH$_2$Cl$_2$ (5 ml), m-chloroperbenzoic acid (0.29 g, 1.69 mmol, 3.0 eq) was added portionwise at 0° C. Reaction mixture was stirred at r.t. for 2 h. After completion of reaction, the pH of the reaction mixture was adjusted to neutral using NaHCO$_3$ solution and then extracted using CH$_2$Cl$_2$. Organic layers were combined, dried over Na$_2$SO$_4$, filtered and concentrated in vacuo to obtain crude product. This was purified by column chromatography using 2.5% MeOH in CH$_2$Cl$_2$ as eluant to obtain pure 383.2 (0.200 g, 70.65%). MS(ES): m/z 502.00 [M+H]$^+$.

Synthesis of Compound 383.3.

To compound 383.2 (0.100 g, 0.199 mmol, 1.0 eq) in MeOH (5 mL) was added Cs$_2$CO$_3$ (0.064 g, 0.199 mmol, 1.0 eq) and heated at 60° C. for 1 h. Upon completion, reaction mixture concentrated in vacuo, transferred into water and extracted with ethyl acetate. Organic layers were combined, dried over Na$_2$SO$_4$, filtered and concentrated in vacuo to obtain 383.3 (Yield: 80.71%). MS(ES): m/z 497.6 [M+H]$^+$.

Synthesis of Compound I-383.

Compound I-383 was synthesized from 383.3 using general procedure C. (Yield: 36.43%). MS(ES): m/z: 413.29 [M+H]$^+$, LCMS purity: 95.50%, HPLC purity 95.00%, 1H NMR (DMSO, 400 MHz): 12.60 (s, 1H), 8.60 (s, 1H), 8.29-8.28 (d, J=1.6 Hz, 1H), 8.10-8.07 (dd, 1H), 7.81-7.78 (m, 2H), 6.75-6.74 (d, J=1.6 Hz Hz, 1H), 6.36 (s, 1H), 3.91 (s, 3H), 3.83 (s, 3H), 3.22 (s, 3H), 2.44 (s, 3H).

Synthesis of Compound 384.1.

Compound 384.1 was synthesized from 98.4 and 153.4 using general procedure A. (Yield: 30.85%). MS(ES): m/z 531.24 [M+H]⁺.

Synthesis of Compound 384.2.

Compound 384.2 was synthesized from 384.1 and 2,2-difluorocyclopropane-1-carboxamide using general procedure B. (Yield: 41.39%). MS(ES): m/z 615.48 [M+H]⁺.

Synthesis of I-384.

Compound I-384 was synthesized using general procedure C. (Yield: 86.89%). MS(ES): m/z: 531.7 [M+H]⁺, LCMS purity: 96.94%, HPLC purity: 95.06%, Chiral HPLC: (51.62%, 48.37%), 1H NMR (DMSO, 400 MHz): 12.48 (s, 1H), 10.73 (s, 1H), 8.03 (s, 1H), 7.85 (s, 1H), 7.76-7.74 (d, J=8 Hz, 2H), 7.69-7.67 (d, J=7.6 Hz, 1H), 7.57-7.55 (d, 1H), 7.14 (s, 1H), 3.76 (s, 3H), 3.26 (s, 3H), 3.15 (s, 3H), 2.52 (s, 3H), 1.97 (bs, 2H).

Example 385: Synthesis of N-(2-(difluoromethyl)-7-((4-(1-methyl-1H-pyrazol-4-yl)-2-(N-methylmethylsulfonamido)phenyl)amino)-3H-imidazo[4,5-b]pyridin-5-yl)-2,2-difluorocyclopropane-1-carboxamide, I-385

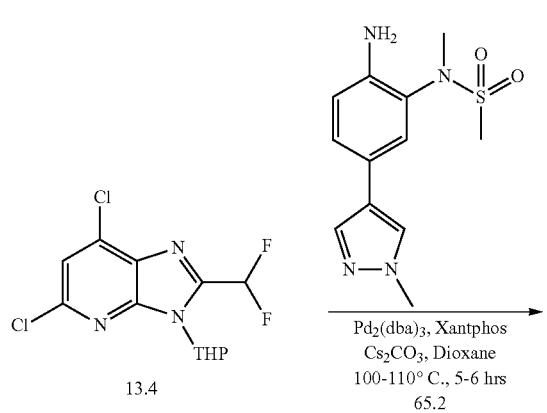

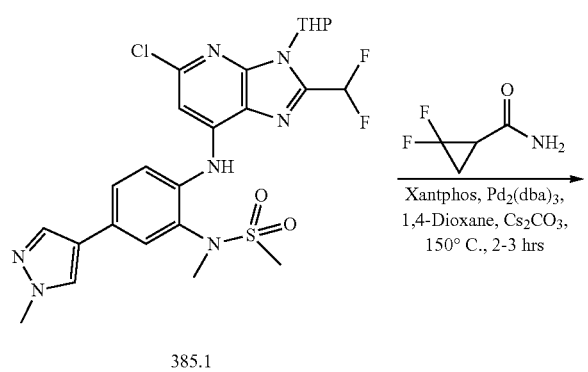

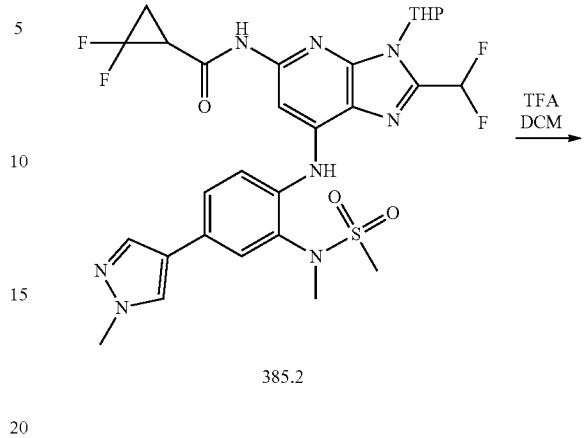

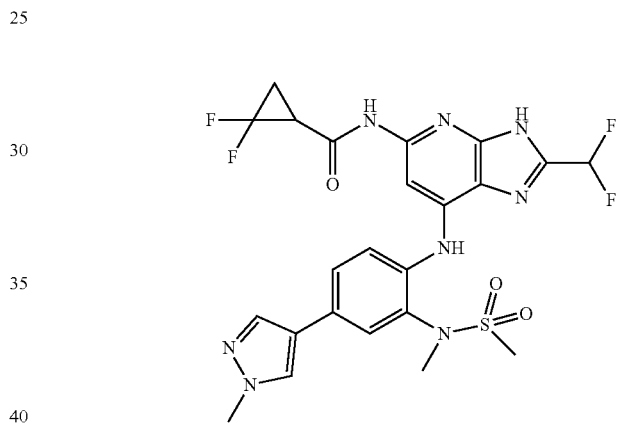

Synthesis of Compound 385.1.

Compound 385.1 was synthesized from 13.4 and 65.2 using general procedure A. (Yield: 32.34%). MS(ES): m/z 567.02 [M+H]⁺.

Synthesis of Compound 385.2.

Compound 385.2 was synthesized from 385.1 and 2,2-difluorocyclopropane-1-carboxamide using general procedure B. (Yield: 65.84%). MS(ES): m/z 651.28 [M+H]⁺.

Synthesis of I-385.

Compound I-385 was synthesized from 385.3 using general procedure C (Yield: 76.57%). MS(ES): m/z: 567.32 [M+H]⁺, LCMS purity: 98.88%, HPLC purity: 96.13%, Chiral HPLC Purity: (54%, 46%), 1H NMR (DMSO-d6, 400 MHz): 13.60 (s, 1H), 10.85 (s, 1H), 8.25 (s, 1H), 8.17 (s, 1H), 7.99 (s, 1H), 7.86 (s, 1H), 7.79 (s, 1H), 7.67-7.65 (t, J=7.6 Hz, 1H), 7.59-7.56 (d, J=8.4 Hz, 1H), 7.27 (t, 1H), 3.90 (s, 3H), 3.25 (s, 3H), 3.10 (s, 3H), 3.02-2.99 (m, 1H), 1.99-1.95 (m, 2H).

Example 386: Synthesis of N-(2-(difluoromethyl)-7-((4-(1-methyl-1H-pyrazol-3-yl)-2-(methylsulfonyl)phenyl)amino)-3H-imidazo[4,5-b]pyridin-5-yl)-2,2-difluorocyclopropane-1-carboxamide, I-386

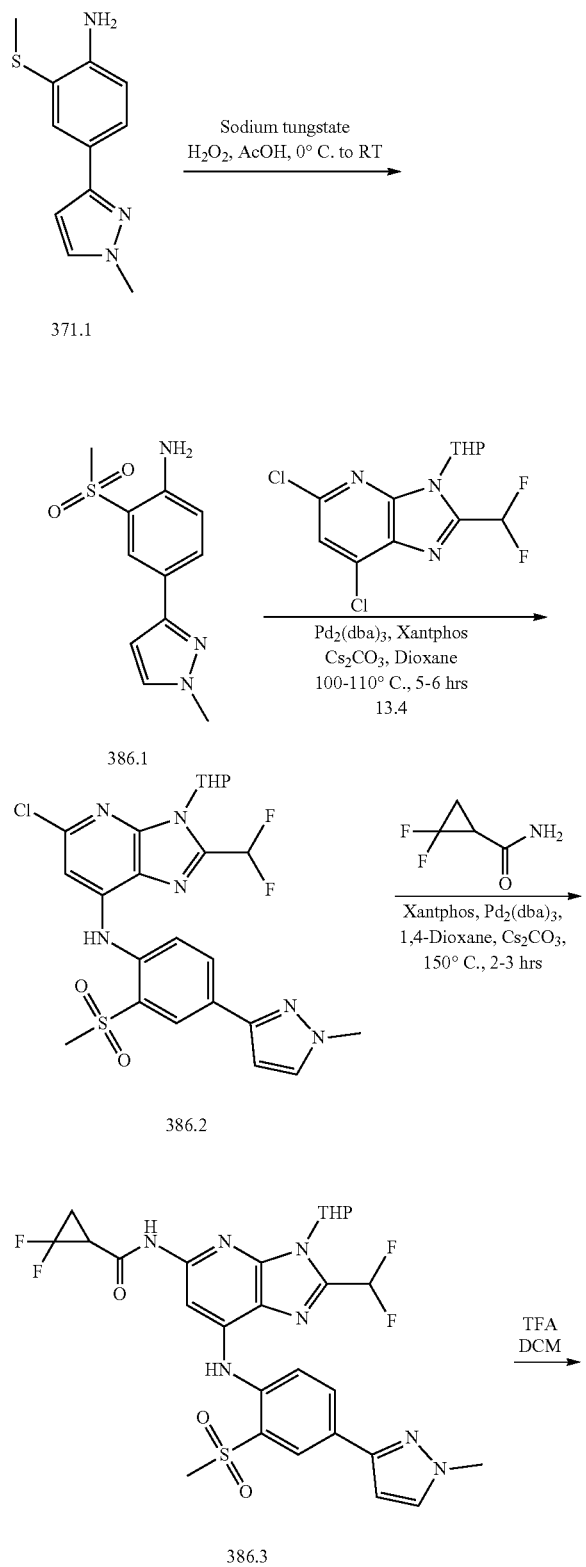

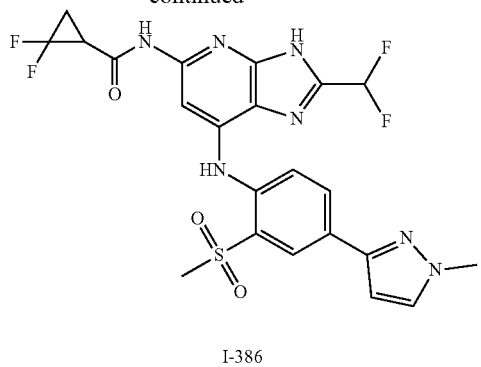

I-386

Synthesis of Compound 386.1.

To compound 371.1 (2.25 g, 1.02 mmol, 1.0 eq) in acetic acid (4 mL), sodium tungstate (2.9 g, 1.02 mmol, 1.0 eq) and hydrogen peroxide (2.5 mL, 20.4 mmol, 20 eq) were added. Reaction mixture was stirred at r.t. for 15 min. After completion of the reaction, the reaction mixture was transferred to water. The pH ~7 was adjusted by using saturated NaHCO$_3$ and extracted with ethyl acetate. Organic layers were combined, dried over Na$_2$SO$_4$, filtered and concentrated in vacuo to get the crude material. This was purified by column chromatography using 20% ethyl acetate in hexane as eluant to obtain pure 386.1 (1.4 g, 44.24%). MS(ES): m/z 252.30 [M+H]$^+$ Synthesis of Compound 386.2.

Compound 386.2 was synthesized from 386.1 and 13.4 using general procedure A. (Yield: 23.87%). MS(ES): m/z 537.98 [M+H]$^+$.

Synthesis of Compound 386.3.

Compound 386.3 was synthesized from 386.2 and 2,2-difluorocyclopropane-1-carboxamide using general procedure B. (Yield: 44.92%). MS(ES): m/z 622.61 [M+H]$^+$.

Synthesis of I-386.

Compound I-386 was synthesized from 386.3 using general procedure C. (Yield: 84.51%). MS(ES): m/z: 538.35 [M+H]$^+$, LCMS purity: 95.97%, HPLC purity: 98.34%, Chiral HPLC: (50%, 50%), 1H NMR (DMSO, 400 MHz): 13.77 (s, 1H), 11.01 (s, 1H), 8.85 (s, 1H), 8.37-8.36 (d, J=1.6 Hz, 1H), 8.17-8.15 (d, 1H), 8.06 (s, 1H), 7.84-7.81 (m, 2H), 7.28 (t, 1H), 6.85-6.84 (d, J=2 Hz, 1H), 3.93 (s, 3H), 3.27 (s, 3H), 3.04-3.01 (m, 1H), 2.02-2.00 (m, 2H).

Example 387: Synthesis of N-(2-methyl-7-((2-(methylsulfonyl)-4-(tetrahydro-2H-pyran-2-yl)phenyl)amino)-3H-imidazo[4,5-b]pyridin-5-yl)cyclopropanecarboxamide, I-387

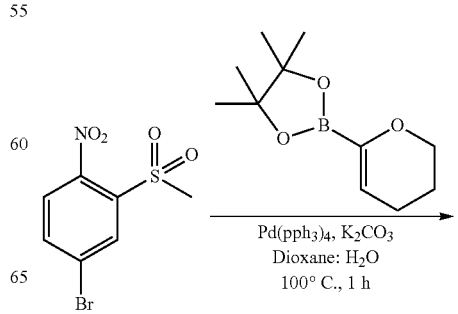

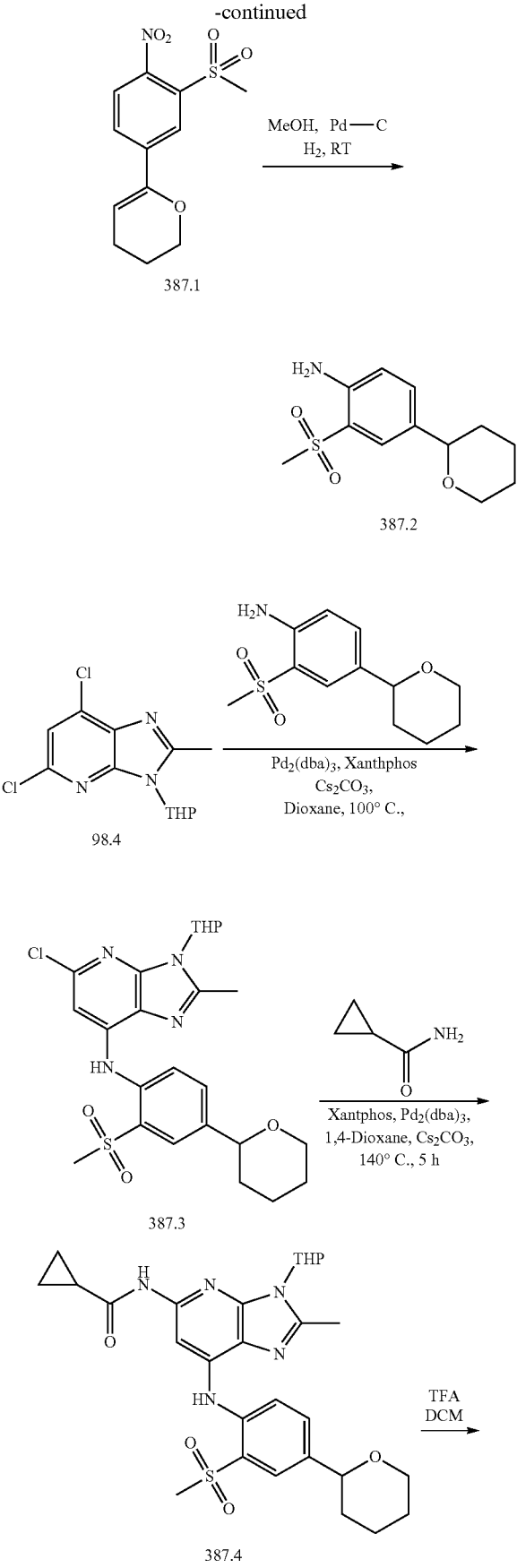

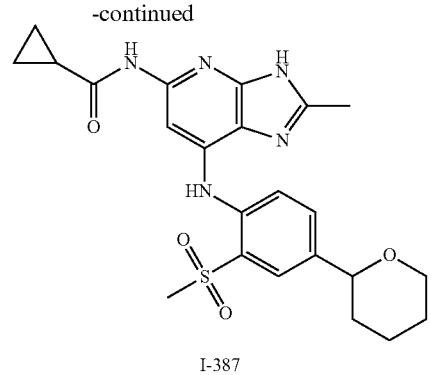

I-387

Synthesis of Compound 387.1

To a solution of 4-bromo-2-(methylsulfonyl)-1-nitrobenzene (3.5 g, 12.50 mmol, 1.0 eq) and 2-(3,4-dihydro-2H-pyran-6-yl)-4,4,5,5-tetramethyl-1,3,2-dioxaborolane (2.63 g, 12.50 mmol, 1.0 eq) in mixture of 1,4-dioxane (8 mL) and water (2 mL) was added potassium carbonate (3.45 g, 25 mmol, 2.0 eq). The reaction mixture was degassed for 10 min. under argon atmosphere. Then tetrakis(triphenylphosphine)palladium(0) (1.44 g, 1.25 mmol, 0.1 eq) was added, again degassed for 10 min. under argon atmosphere. The reaction mixture was stirred at 100° C. for 1 h. Upon completion, reaction mixture was transferred in water and extracted with ethyl acetate. Combined organic layer was washed with brine, dried over $Na_2SO_4$ and concentrated in vacuo to obtain crude product. This was purified by column chromatography using 9% ethyl acetate in hexane to obtain pure 387.1 (3.2 g, 90.39%). MS(ES): m/z 284.30 $[M+H]^+$.

Synthesis of Compound 387.2.

To a solution of 387.1 (3.2 g, 11.30 mmol, 1.0 eq) in MeOH (30 mL), 10% Pd/C (1.5 g) was added. Hydrogen was purged through reaction mixture for 2-3 h. Upon completion, reaction mixture was filtered through celite-bed and washed with ethanol. Filtrate was concentrated in vacuo to obtain 387.2 (1.7 g, 58.94%). MS(ES): m/z 256.33 $[M+H]^+$.

Synthesis of Compound 387.3.

Compound 387.3 was synthesized from 387.2 and 98.4 using general procedure A. (Yield: 31.60%). MS(ES): m/z 506.03 $[M+H]^+$.

Synthesis of Compound 387.4.

Compound 387.4 was synthesized from 387.3 and cyclopropanecarboxamide using general procedure B. (Yield: 60.20%). MS(ES): m/z 554.68 $[M+H]^+$.

Synthesis of I-387.

Compound I-387 was synthesized from 387.4 using general procedure C. (Yield: 85.76). MS(ES): m/z: 470.42 $[M+H]^+$, LCMS purity: 98.71%, HPLC purity 99.06%, 1H NMR (DMSO-d6, 400 MHz): 12.48 (s, 1H), 10.58 (s, 1H), 8.53 (s, 1H), 7.98 (s, 1H), 7.86-7.86 (d, J=1.2 Hz, 1H), 7.73-7.66 (m, 2H), 4.42-4.40 (d, J=10.4 Hz, 1H), 4.07-4.04 (d, J=11.2 Hz, 1H), 3.59-3.53 (m, 1H), 3.18 (s, 3H), 2.48 (s, 3H), 1.99-1.96 (m, 1H), 1.90-1.87 (d, J=11.2 Hz, 2H), 1.67-1.41 (m, 4H), 0.77-0.75 (m, 4H).

Example 388: Synthesis of N-(2-methyl-7-((2-(methylsulfonyl)-4-(tetrahydrofuran-3-yl)phenyl)amino)-3H-imidazo[4,5-b]pyridin-5-yl)cyclopropanecarboxamide, I-388

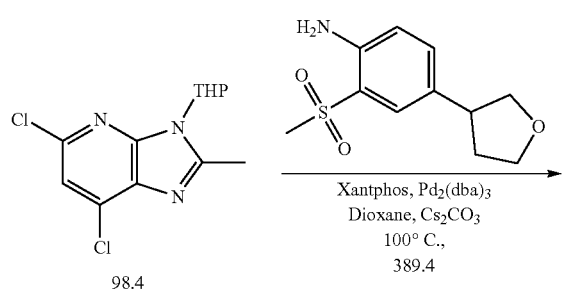

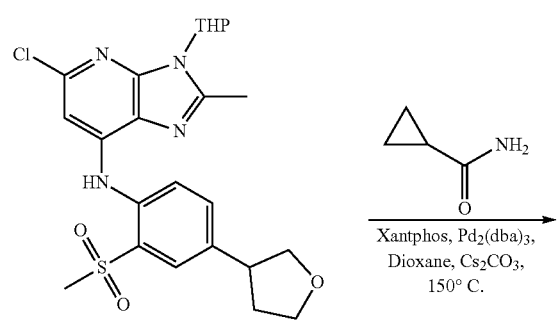

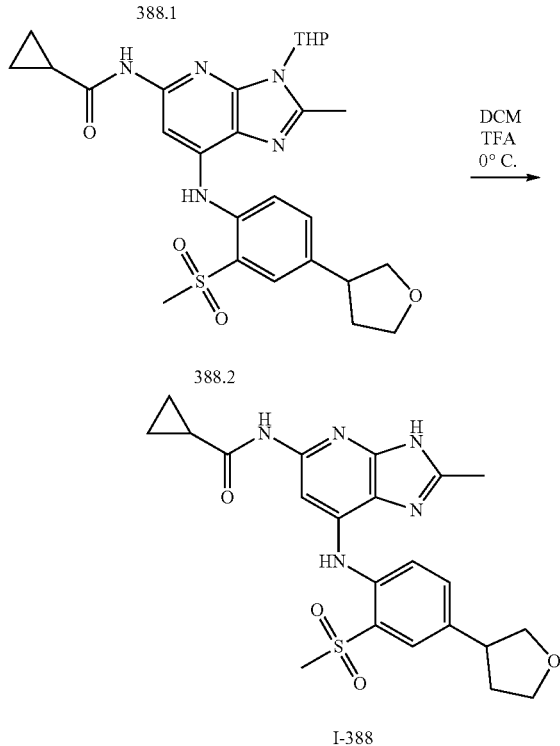

Synthesis of Compound 388.1.

Compound 388.1 was synthesized from 98.4 and 389.4 using general procedure A. (Yield: 17.00%). MS(ES): m/z 492.00 [M+H]⁺.

Synthesis of Compound 388.2.

Compound 388.2 was synthesized from 388.1 and cyclopropanecarboxamide using general procedure B. (Yield: 60.83%). MS(ES): m/z 540.65 [M+H]⁺.

Synthesis of I-388.

Compound I-388 was synthesized from 388.2 using general procedure C. (Yield: 95.18%). MS(ES): m/z: 456.51 [M+H]⁺, LCMS purity: 97.19%, HPLC purity: 99.26%, Chiral HPLC: (49.00%, 51.00%), 1H NMR (DMSO-d6, 400 MHz): 12.56 (s, 1H), 10.67 (s, 1H), 8.48 (s, 1H), 7.94 (s, 1H), 7.77-7.77 (d, J=2 Hz, 1H), 7.71-7.64 (m, 2H), 4.05-4.03 (m, 1H), 4.01-3.97 (m, 1H), 3.84-3.78 (q, J=7.6 Hz, 1H), 3.62-3.58 (t, J=7.6 Hz, 1H), 3.53-3.46 (q, J=7.6 Hz, 1H), 3.19 (s, 3H), 2.47 (s, 3H), 2.42-2.32 (m, 1H), 1.99-1.90 (m, 2H), 0.77-0.67 (m, 4H).

Example 389: Synthesis of N-(2-(difluoromethyl)-7-((2-(methylsulfonyl)-4-(tetrahydrofuran-3-yl)phenyl)amino)-3H-imidazo[4,5-b]pyridin-5-yl)cyclopropanecarboxamide, I-389

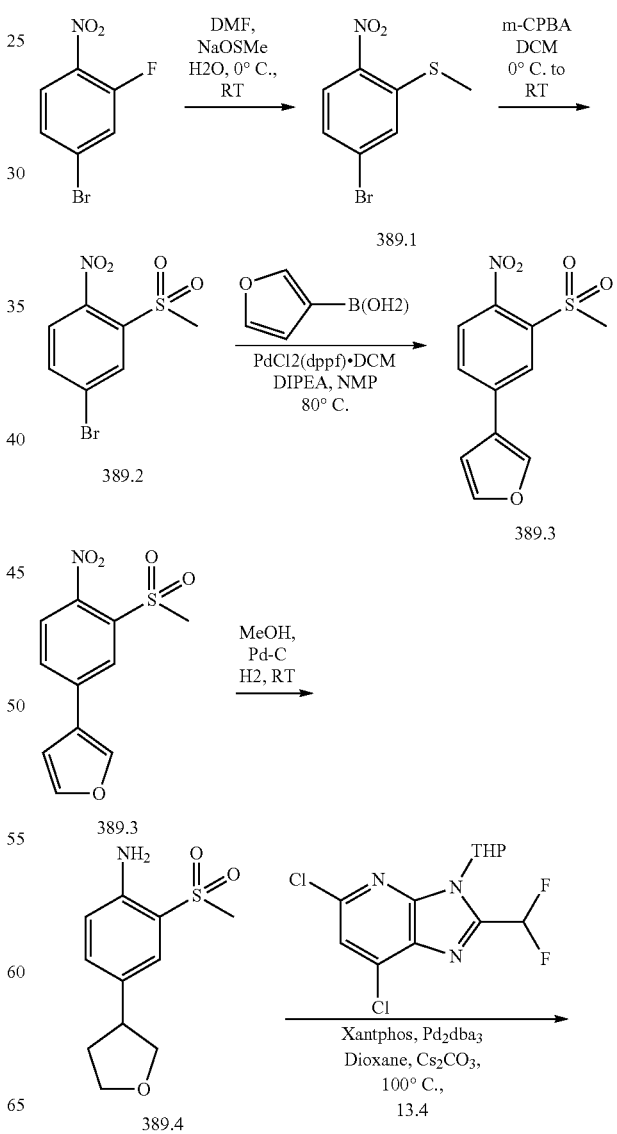

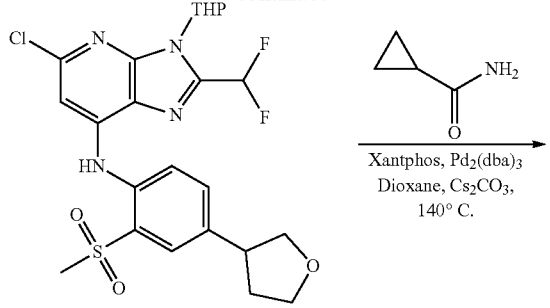

389.5

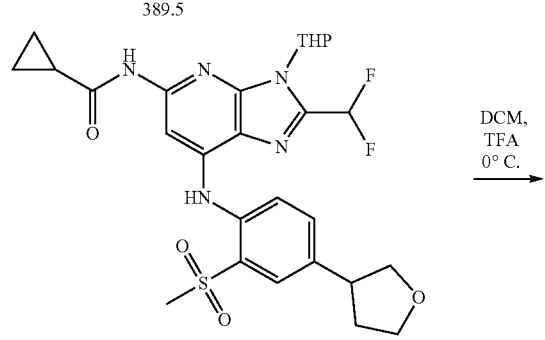

389.6

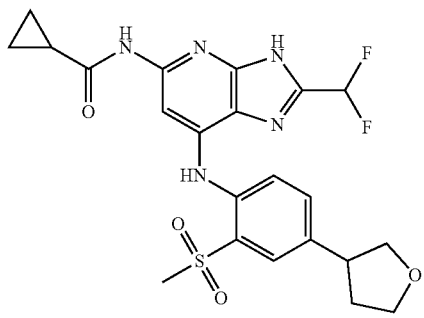

I-389

Synthesis of Compound 389.1.

To a solution of 4-bromo-2-fluoro-1-nitrobenzene (20 g, 90.9 mmol, 1.0 eq) in N,N'-dimethylformamide (200 mL) at 0° C., sodium methylsulfonate (23.1 g, 272.7 mmol, 3.0 eq) was added. Reaction mixture was stirred at r.t. for 3 h. After completion of the reaction, the reaction mixture was transferred to water and extracted with ethyl acetate. Organic layer combined, dried over anhydrous $Na_2SO_4$, filtered and concentrated in vacuo to obtain the crude material. This was purified by column chromatography using 30% ethyl acetate in hexane as eluant to obtain 389.1 (15 g, 66.51%). MS(ES): m/z 249.35 [M+H]$^+$.

Synthesis of Compound 389.2.

To compound 389.1 (15 g, 60.48 mmol, 1.0 eq) in $CH_2Cl_2$ (150 mL) at 0° C., m-chloroperoxybenzoic acid (36.41 g, 211.69 mmol, 3.5 eq) was added. Reaction mixture was stirred at r.t. for 4 h. After completion of the reaction, the reaction mixture was transferred into water and extracted with $CH_2Cl_2$. Organic layer combined, dried over anhydrous $Na_2SO_4$, filtered and concentrated in vacuo to obtain crude product. This was purified by column chromatography using 5% ethyl acetate in hexane to obtain pure 389.2 (13 g, 76.77%). MS(ES): m/z 281.13 [M+H]$^+$.

Synthesis of Compound 389.3.

To compound 389.2 (5 g, 17.85 mmol, 1.0 eq) in $CH_2Cl_2$ (50 mL), furan-3-yl(14-oxidaneylidene)borane (1.86 g, 19.63 mmol, 1.1 eq), diisopropylethylamine (5.7 g, 44.6 mmol, 2.5 eq) and N-methylpyrrolidine (3.03 g, 35.7 mmol, 2.0 eq) was added. Reaction mixture was degassed with argon for 15 min. Then, 1,1'-Bis(diphenylphosphino)ferrocene-palladium(II)dichloride (2.9 g, 3.5 mmol, 0.2 eq) was added and again degassed for 5 min. Reaction mixture was stirred at 80° C. for 2 h. After completion of the reaction, the reaction mixture was transferred to water and extracted with $CH_2Cl_2$. Organic layer combined, dried over anhydrous $Na_2SO_4$, filtered and concentrated in vacuo to obtain the crude material. This was purified by column chromatography using 12% ethyl acetate in hexane to obtain pure 389.3 (2.2 g, 48.52%). MS(ES): m/z 268.19 [M+H]$^+$.

Synthesis of Compound 389.4.

To compound 389.3 (2.2 g, 8.23 mmol, 1.0 eq) in MeOH (30 mL), 10% Pd/C (0.65 g) was added. Hydrogen was purged through the reaction mixture for 3-4 h. After completion of the reaction, the reaction mixture was filtered through celite bed and washed with MeOH. Filtrate was concentrated in vacuo to obtain 389.4 (1.1 g, 55.38%). MS(ES): m/z 242.57 [M+H]$^+$.

Synthesis of Compound 389.5.

Compound 389.5 was synthesized from 389.4 and 13.4 using general procedure A. (Yield: 19.16%). MS(ES): m/z 530.48 [M+H]$^+$.

Synthesis of Compound 389.6.

Compound 389.6 was synthesized from 389.5 and cyclopropanecarboxamide using general procedure B. (Yield: 45.995%). MS(ES): m/z 576.18 [M+H]$^+$.

Synthesis of I-389.

Compound I-389 was synthesized from 389.6 using general procedure C. (Yield: 94.81%). MS(ES): m/z: 492.36 [M+H]$^+$, LCMS purity: 98.62%, HPLC purity 97.73%, 1H NMR (DMSO-d6, 400 MHz): 13.68 (s, 1H), 10.74 (s, 1H), 8.70 (s, 1H), 8.04 (s, 1H), 7.81 (s, 1H), 7.76-7.70 (m, 2H), 7.37-7.12 (t, 1H), 4.09-3.97 (m, 2H), 3.86-3.80 (m, 1H), 3.64-3.51 (m, 2H), 3.22 (s, 3H), 2.43-2.35 (m, 1H), 2.06-1.92 (m, 2H), 0.80 (bs, 4H).

Example 390: N-(2-methyl-7-((2-(methylsulfonyl)-4-(tetrahydro-2H-pyran-3-yl)phenyl)amino)-3H-imidazo[4,5-b]pyridin-5-yl)cyclopropanecarboxamide, I-390

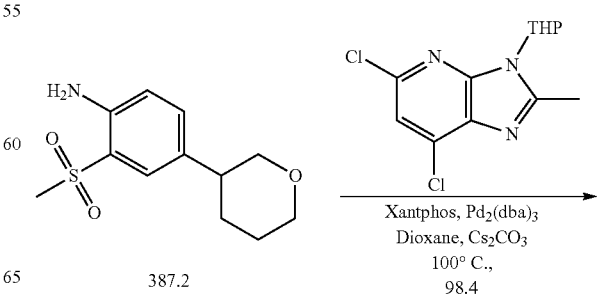

387.2

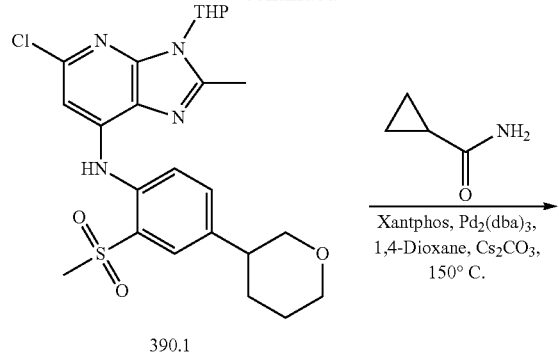

390.1

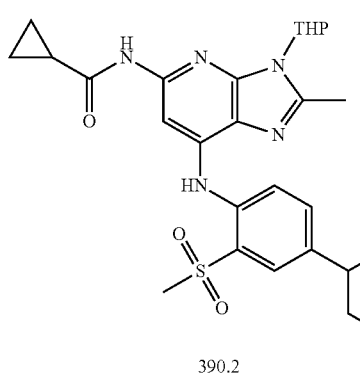

390.2

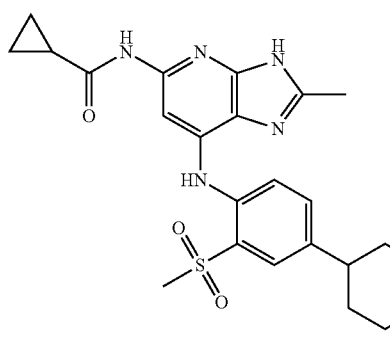

I-390

Synthesis of Compound 390.1.

Compound was synthesized from 387.2 and 98.4 using general procedure A. (Yield: 28.31%). MS(ES): m/z 506.03 [M+H]⁺.

Synthesis of Compound 390.2.

Compound was synthesized from 390.1 and cyclopropanecarboxamide using general procedure B. (Yield: 84.70%). MS(ES): m/z 554.68 [M+H]⁺.

Synthesis of I-390.

Compound I-390 was synthesized from 390.2 using general procedure C. (Yield: 83.45%). MS(ES): m/z: 470.52 [M+H]⁺, LCMS purity: 96.82%, HPLC purity 94.00%, Chiral HPLC: (46.00%, 52.00%), 1H NMR (DMSO-d6, 400 MHz): 12.48 (s, 1H), 10.58 (s, 1H), 8.54 (s, 1H), 7.97 (s, 1H), 7.77 (s, 1H), 7.72-7.66 (m, 2H), 3.89-3.86 (d, J=11.2 Hz, 2H), 3.45-3.38 (m, 2H), 3.19 (s, 3H), 2.92-2.87 (m, 1H), 2.48 (s, 3H), 1.99-1.97 (m, 2H), 1.79-1.72 (m, 3H), 0.77-0.76 (d, J=4.4 Hz, 4H).

Example 391: Synthesis of N-(2-(difluoromethyl)-7-((2-(methylsulfonyl)-4-(tetrahydro-2H-pyran-3-yl)phenyl)amino)-3H-imidazo[4,5-b]pyridin-5-yl)cyclopropanecarboxamide, I-391

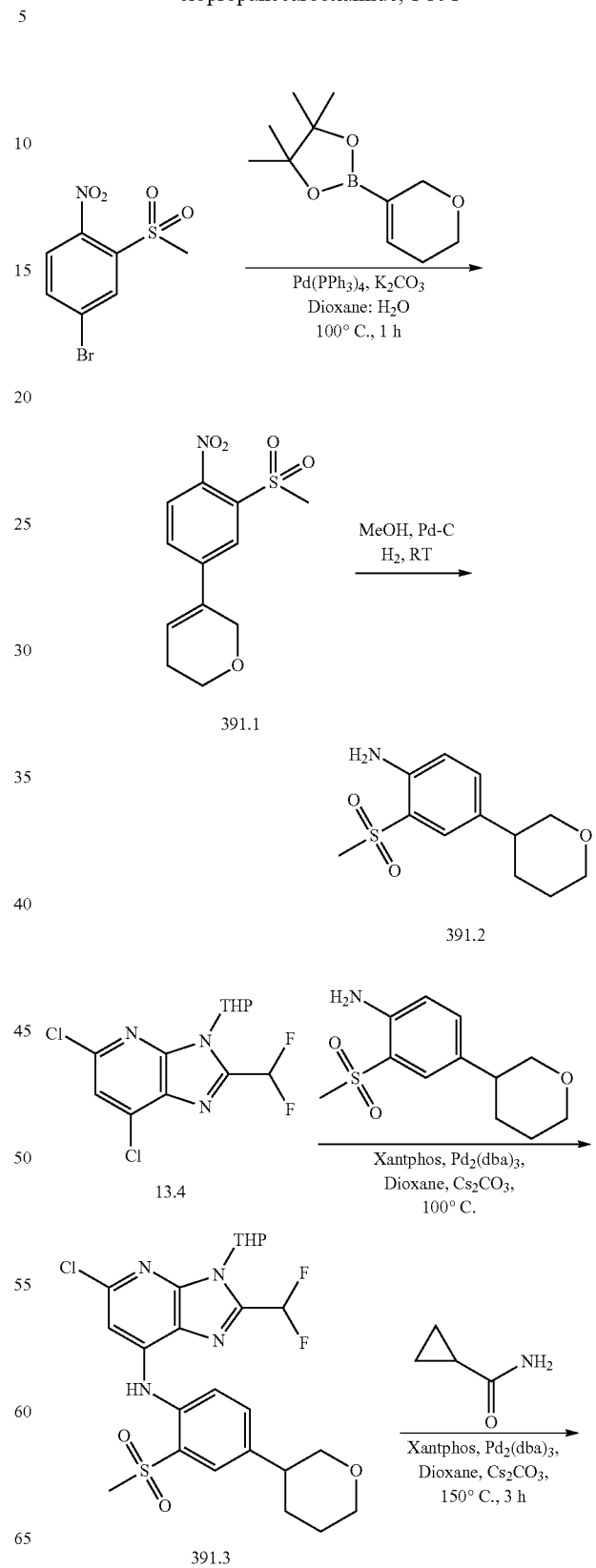

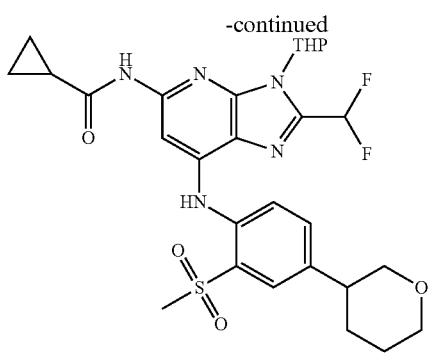

Synthesis of Compound 391.1.

To a solution of 4-bromo-2-(methylsulfonyl)-1-nitrobenzene (1.0 g, 3.57 mmol, 1.0 eq) and 2-(5,6-dihydro-2H-pyran-3-yl)-4,4,5,5-tetramethyl-1,3,2-dioxaborolane (0.75 g, 3.57 mmol, 1.0 eq) in mixture of 1,4-dioxane (8 mL) and water (2 mL) was added potassium carbonate (0.98 g, 7.14 mmol, 2.0 eq). The reaction mixture was degassed for 10 min. under argon atmosphere. The tetrakis(triphenylphosphine)palladium(0) (0.412 g, 0.357 mmol, 0.1 eq) was added, again reaction mixture was degassed for 10 min. under argon atmosphere. The reaction was stirred at 100° C. for 1 h. Upon completion, reaction mixture was transferred in water and extracted with ethyl acetate. Combined organic layer was washed with brine, dried over $Na_2SO_4$ and concentrated in vacuo to obtain crude product. This was purified by column chromatography using 5% ethyl acetate in hexane to obtain pure 391.1 (0.71 g, 70.20%). MS(ES): m/z 284.30 $[M+H]^+$.

Synthesis of Compound 391.2.

To a solution of 391.1 (0.71 g, 2.51 mmol, 1.0 eq) in MeOH (10 mL), 10% Pd/C (0.4 g) was added. Hydrogen was purged through reaction mixture for 2-3 h. Upon completion, reaction mixture was filtered through celite-bed and washed with ethanol. Filtrate was concentrated in vacuo to obtain 391.2 (0.53 g, 82.82%). MS(ES): m/z 256.33 $[M+H]^+$.

Synthesis of Compound 391.3.

Compound 391.3 was synthesized from 391.2 and 13.4 using general procedure A. (Yield: 24.92%). MS(ES): m/z 542.01 $[M+H]^+$.

Synthesis of Compound 391.4.

Compound 391.4 was synthesized from 391.3 and cyclopropanecarboxamide using general procedure B. (Yield: 76.46%). MS(ES): m/z 590.66 $[M+H]^+$.

Synthesis of I-391.

Compound I-391 was synthesized from 391.4 using general procedure C. (Yield: 84.83%). MS(ES): m/z: 506.36 $[M+H]^+$, LCMS purity: 97.02%, HPLC purity 96.33%, Chiral HPLC: (49.65%, 50.34%), 1H NMR (MeOD, 400 MHz): 13.68 (s, 1H), 10.76 (s, 1H), 8.73 (s, 1H), 8.06 (s, 1H), 7.80 (s, 1H), 7.75-7.70 (m, 2H), 7.39-7.12 (t, 1H), 3.89-3.86 (d, J=11.2 Hz, 2H), 3.46-3.45 (d, J=5.2 Hz, 2H), 3.21 (s, 3H), 2.95-2.89 (m, 1H), 2.05-1.97 (m, 2H), 1.83-1.73 (m, 1H), 1.73 (s, 2H), 0.79-0.78 (d, J=6 Hz, 4H).

Example 397: Synthesis of 2-(difluoromethyl)-N5-(5,6-dimethylpyrazin-2-yl)-N7-(2-(methylsulfonyl)-4-(tetrahydro-2H-pyran-2-yl)phenyl)-3H-imidazo[4,5-b]pyridine-5,7-diamine, I-397

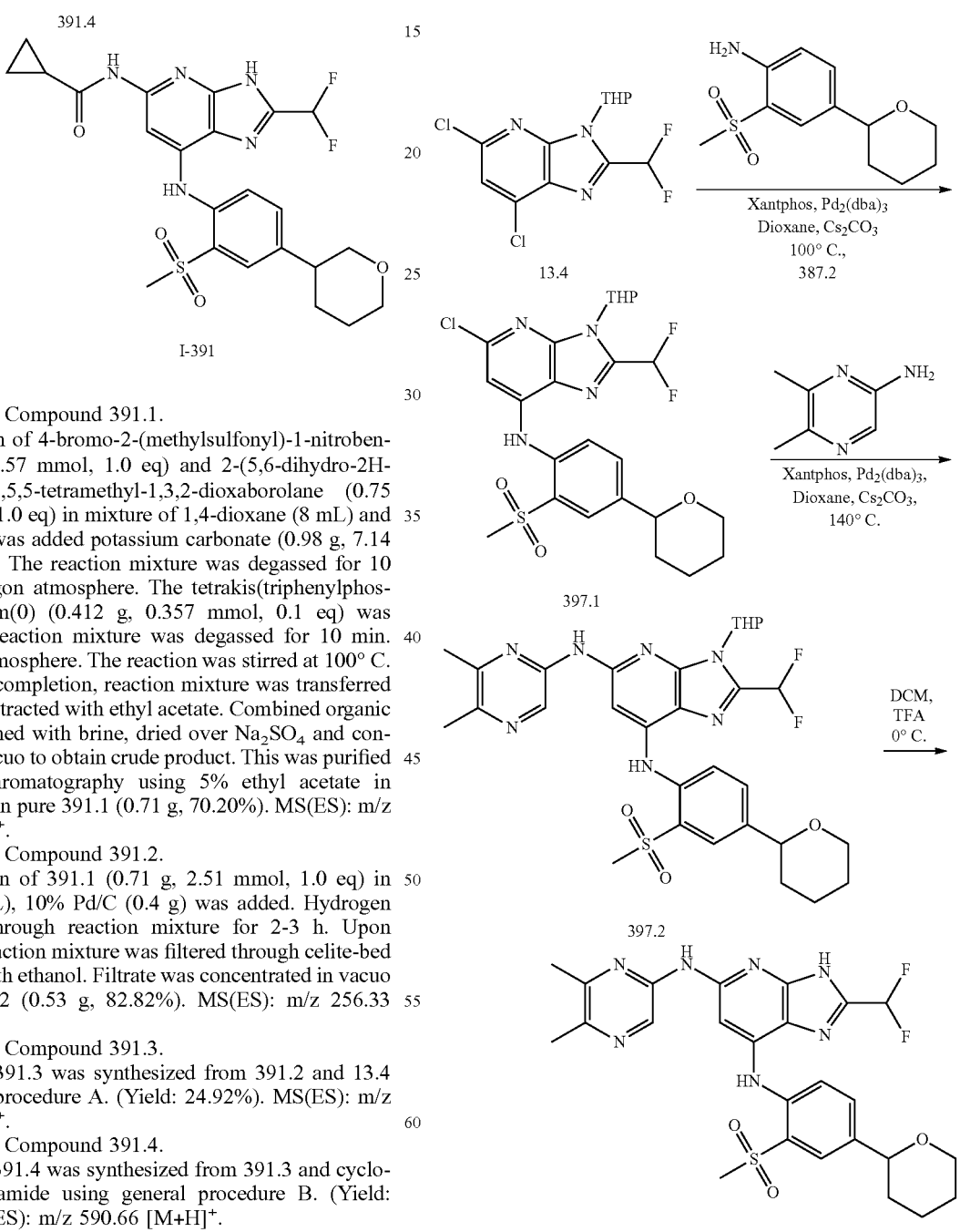

899

Synthesis of Compound 397.1.

Compound 397.1 was synthesized from 387.2 and 13.4 using general procedure A. (Yield: 23.60%). MS(ES): m/z 542.01 [M+H]⁺.

Synthesis of Compound 397.2.

Compound was synthesized from 397.2 and 5,6-dimethylpyrazin-2-amine using general procedure B. (Yield: 51.71%). MS(ES): m/z 628.71 [M+H]⁺.

Synthesis of I-397.

Compound I-397 was synthesized from 397.2 using general procedure C. (Yield: 97.19%). MS(ES): m/z 544.60 [M+H]⁺, LCMS purity: 95.85%, HPLC purity: 97.37%, 1H NMR (DMSO-d6, 400 MHz): 13.56 (s, 1H), 9.80 (s, 1H), 8.98 (s, 1H), 8.76 (s, 1H), 7.92 (s, 1H), 7.86-7.84 (m, 1H), 7.74-7.72 (d, J=8.4 Hz, 1H), 7.49 (s, 1H), 7.23 (s, 1H), 4.47-4.45 (d, J=10.4 Hz, 1H), 4.10-4.07 (d, J=11.6 Hz, 1H), 3.59-3.55 (m, 1H), 3.22 (s, 3H), 2.40 (s, 2H), 2.37 (s, 3H), 1.92-1.89 (d, J=10.8 Hz, 2H), 1.65 (s, 1H), 1.59-41 (m, 2H), 1.24 (s, 2H).

Example 398: Synthesis of N5-(5,6-dimethylpyrazin-2-yl)-2-methyl-N7-(2-(methylsulfonyl)-4-(tetrahydro-2H-pyran-2-yl)phenyl)-3H-imidazo[4,5-b]pyridine-5,7-diamine, I-398

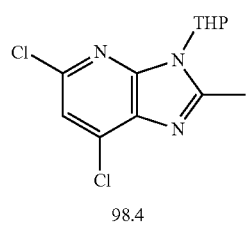

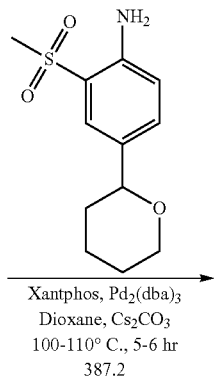

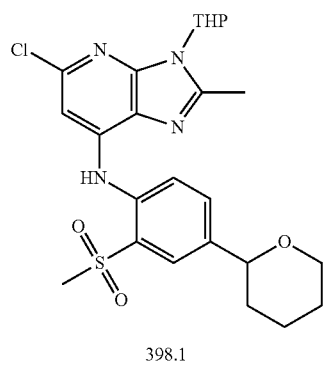

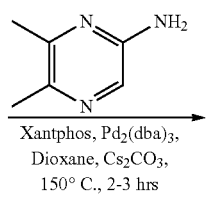

900

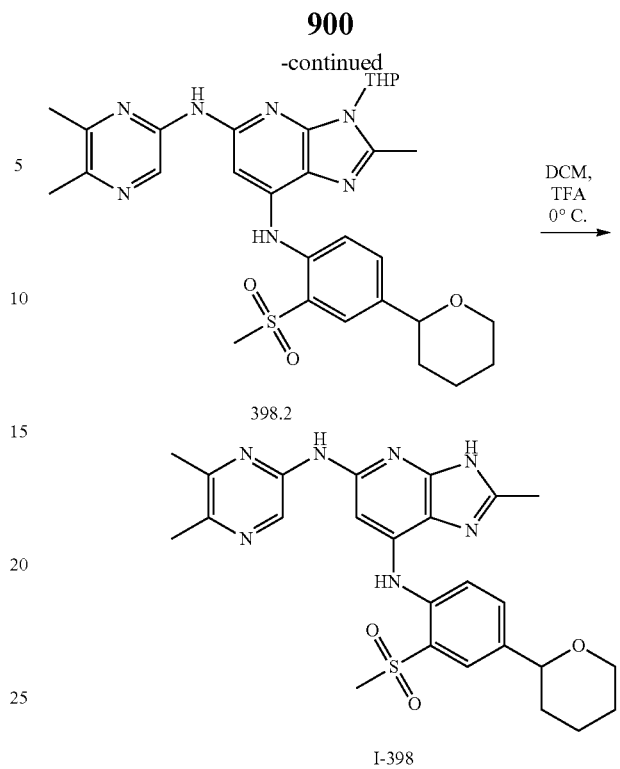

Synthesis of Compound 398.1.

Compound 398.1 was synthesized from 98.4 and 387.2 using general procedure A. (Yield: 28.99%). MS(ES): m/z 506.03 [M+H]⁺.

Synthesis of Compound 398.2.

Compound 398.2 was synthesized from 398.1 and 5,6-dimethylpyrazin-2-amine using general procedure B. (Yield: 60.96%). MS(ES): m/z 592.73 [M+H]⁺.

Synthesis of I-398.

Compound I-398 was synthesized from 398.2 using general procedure C (Yield: 45.49%). MS(ES): m/z 508.61 [M+H]⁺, LCMS purity: 97.45%, HPLC purity: 97.96%, 1H NMR (DMSO, 400 MHz): 12.41 (s, 1H), 9.57 (s, 1H), 8.87 (s, 1H), 8.60 (s, 1H), 7.88-7.84 (m, 2H), 7.70-7.68 (d, J=8.4 Hz, 1H), 7.50 (s, 1H), 4.45-4.42 (d, J=11.2 Hz, 1H), 4.09-4.06 (d, J=11.6 Hz, 1H), 3.20 (s, 3H), 2.46 (s, 4H), 2.38-2.37 (d, J=4 Hz, 6H), 1.91-1.88 (d, J=11.6 Hz, 2H), 1.67 (s, 1H), 1.59 (s, 2H), 0.86 (bs, 1H).

Example 400: Synthesis of N-(7-((4-(1-methoxyethyl)-2-(methylsulfonyl)phenyl)amino)-2-methyl-3H-imidazo[4,5-b]pyridin-5-yl)cyclopropanecarboxamide, I-400

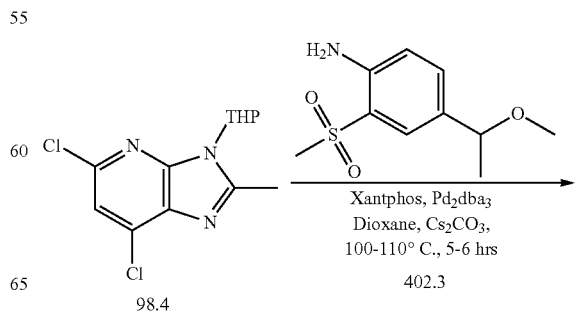

-continued

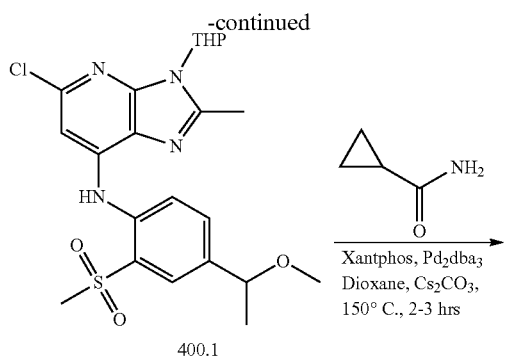

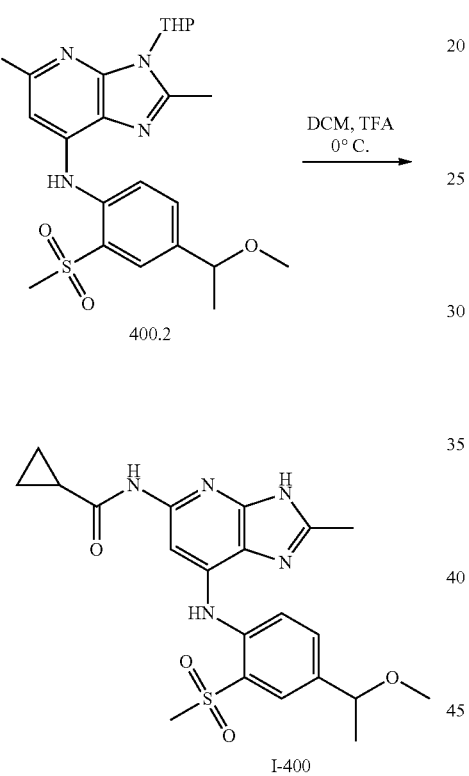

Example 401: Synthesis of N-(2-(difluoromethyl)-7-((2-(methylsulfonyl)-4-(tetrahydro-2H-pyran-2-yl)phenyl)amino)-3H-imidazo[4,5-b]pyridin-5-yl)cyclopropanecarboxamide, I-401

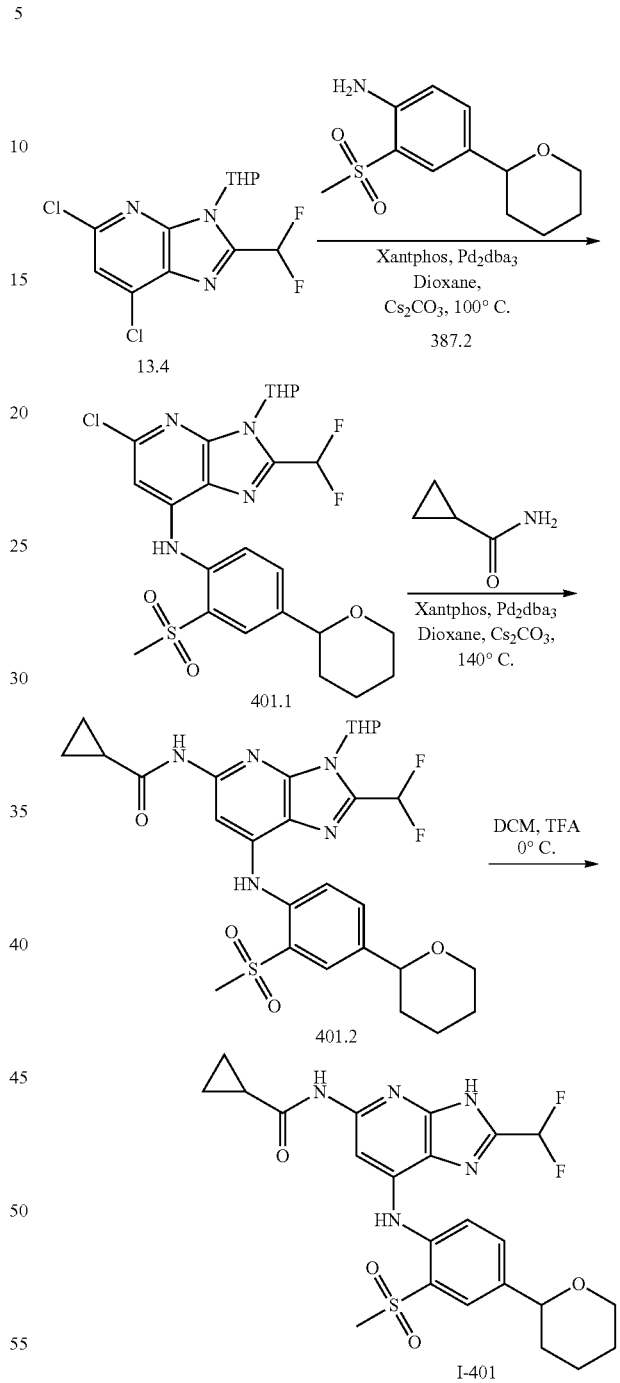

Synthesis of Compound 400.1.

Compound 400.1 was synthesized from and 402.3 and 98.4 using general procedure A. (Yield: 22.19%). MS(ES): m/z 479.99 [M+H]$^+$.

Synthesis of Compound 400.2.

Compound 400.2 was synthesized from 400.1 and cyclopropanecarboxamide using general procedure B. (Yield: 80.31%). MS(ES): m/z 528.64 [M+H]$^+$.

Synthesis of I-400.

Compound I-400 was synthesized from 400.2 using general procedure C. (Yield: 93.10%). MS(ES): m/z: 444.42 [M+H]$^+$, LCMS purity: 95.22%, HPLC purity: 100%, 1H NMR (MeOD, 400 MHz): 7.96 (s, 1H), 7.92 (s, 1H), 7.70 (s, 1H), 7.68 (s, 1H), 4.47-4.45 (d, J=6.4 Hz, 1H), 3.30 (s, 3H), 3.13 (s, 3H), 2.59 (s, 3H), 1.88 (s, 1H), 1.47 (s, 3H), 0.97-0.89 (m, 4H).

Synthesis of Compound 401.1.

Compound 401.1 was synthesized from 13.4 and 387.2 using general procedure B. (Yield: 12.98%). MS(ES): m/z 542.01 [M+H]$^+$.

Synthesis of Compound 401.2.

Compound 401.2 was synthesized from 401.1 and cyclopropanecarboxamide using general procedure B. (Yield: 45.87%). MS(ES): m/z 590.66 [M+H]$^+$.

Synthesis of I-401.

Compound I-401 was synthesized from 401.2 using general procedure C. (Yield: 95.43%). MS(ES): m/z: 506.31 [M+H]$^+$, LCMS purity: 97.06%, HPLC purity 97.03%, Chiral HPLC: (50.00%, 48.00%), 1H NMR (DMSO-d6, 400 MHz): 13.69 (s, 1H), 10.77 (s, 1H), 8.73 (s, 1H), 8.07 (s, 1H), 8.07 (s, 1H), 7.77-7.71 (m, 2H), 7.40-7.14 (t, 1H), 4.46-4.43 (d, J=10.8 Hz, 1H), 4.09-4.06 (d, J=11.6 Hz, 1H), 3.58 (s, 1H), 3.21 (s, 3H), 2.04 (s, 1H), 1.92-1.90 (d, J=10.0 Hz, 2H), 1.68-1.45 (m, 4H), 0.80 (s, 4H).

Example 402: Synthesis of N-(2-(difluoromethyl)-7-((4-(1-methoxyethyl)-2-(methylsulfonyl)phenyl)amino)-3H-imidazo[4,5-b]pyridin-5-yl)cyclopropanecarboxamide, I-402

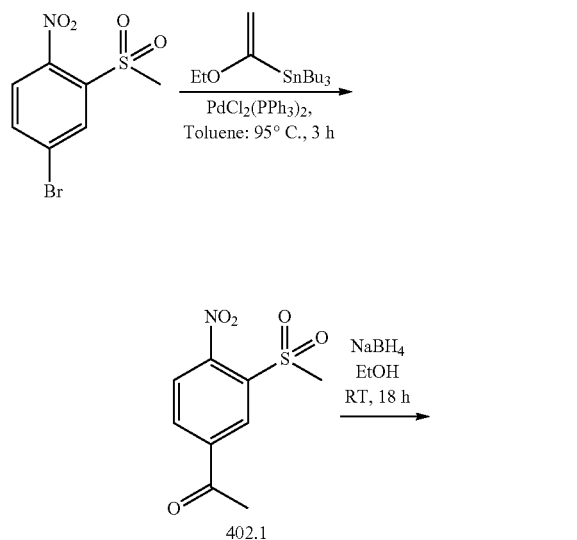

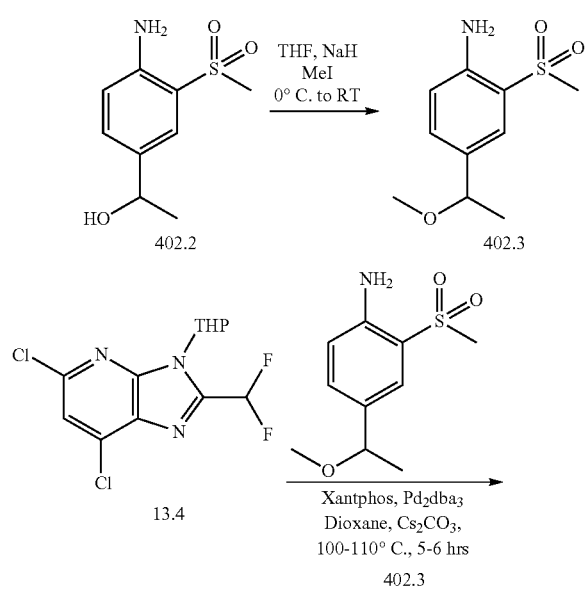

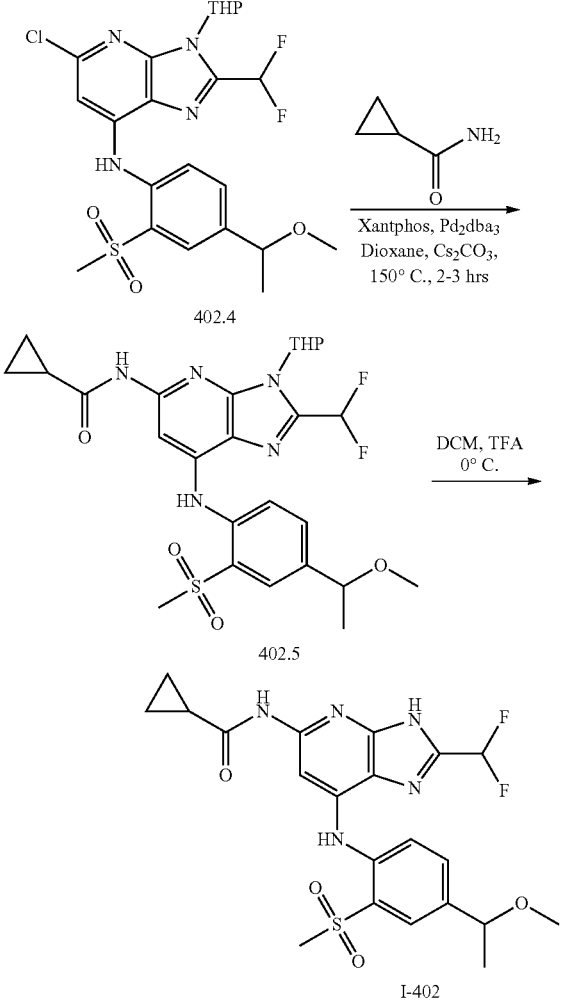

Synthesis of Compound 402.1.

To compound 4-bromo-2-(methylsulfonyl)-1-nitrobenzene (5 g, 17.8 mmol, 1.0 eq) in a mixture of toluene (150 mL), tributyl(1-ethoxyvinyl)stannane (7.74 g, 21.42 mmol, 1.2 eq) and Bis(triphenylphosphine)palladium chloride (1.25 g, 1.78 mmol, 0.1 eq) was added. Reaction mixture was stirred at 95° C. for 3 h. After completion of the reaction, the reaction mixture was transferred into water and extracted with ethyl acetate. Organic layer combined, dried over anhydrous Na$_2$SO$_4$, filtered and concentrated in vacuo to get the crude product. This was purified by column chromatography using 20% ethyl acetate in hexane as eluant to obtain 402.1 (3.5 g, 80.61%). MS(ES): m/z 244.64 [M+H]$^+$.

Synthesis of Compound 402.2.

To compound 402.1 (2.8 g, 11.52 mmol, 1.0 eq) in ethanol (60 mL), sodium borohydride (1.75 g, 46.09 mmol, 4.0 eq) was added. Reaction mixture was stirred at r.t. for 18 h. After completion of the reaction, the reaction mixture was concentrated in vacuo, transferred to water and extracted with ethyl acetate to obtain crude product. This was purified by column chromatography using 2% MeOH in CH$_2$Cl$_2$ to obtain pure 402.2 (2.2 g, 77.93%). MS(ES): m/z 246.84 [M+H]$^+$.

Synthesis of Compound 402.3.

To compound 402.2 (2.2 g, 10.23 mmol, 1.0 eq) in tetrahydrofuran (50 mL) at 0° C., sodium hydride (0.49 g, 20.46 mmol, 2.0 eq) was added. Reaction mixture was stirred at 0° C. for 20 min. Then, methyl iodide (4.35 g, 30.69 mmol, 3.0 eq) was added. Reaction mixture was stirred at r.t. for 2.5 h. After completion of the reaction, the reaction mixture was transferred into water and extracted with ethyl acetate. Organic layer combined, dried over anhydrous Na$_2$SO$_4$, filtered and concentrated in vacuo to obtain 402.3 (1.1 g, 47.29%). MS(ES): m/z 260.58 [M+H]$^+$.

Synthesis of Compound 402.4.

Compound 402.4 was synthesized from 402.3 and 13.4 using general procedure A. (Yield: 16.54%). MS(ES): m/z 515.42 [M+H]$^+$.

Synthesis of Compound 402.5.

Compound 402.5 was synthesized from 402.4 and cyclopropanecarboxamide using general procedure B. (Yield: 49.20%). MS(ES): m/z 564.38 [M+H]$^+$.

Synthesis of Compound I-402.

Compound I-402 was synthesized from 402.5 using general procedure C. (Yield: 75.56%). MS(ES): m/z: 480.47 [M+H]$^+$, LCMS purity: 97.68%, HPLC purity: 95.08%, Chiral HPLC: (48.00%, 50.00%), 1H NMR (MeOD, 400 MHz): 8.06 (s, 1H), 7.98 (s, 1H), 7.89-7.87 (d, J=8.4 Hz, 1H), 7.74-7.72 (d, J=8.4 Hz, 1H), 7.12-6.86 (t, 1H), 4.50-4.45 (m, 1H), 3.31 (s, 3H), 3.13 (s, 3H), 1.90-1.90 (d, J=4 Hz, 1H), 1.43 (s, 3H), 0.98-0.90 (m, 4H).

Example 403: Synthesis of 3-((3-chloropropyl)amino)-6-((7-((2-methoxy-3-(2-methyl-2H-tetrazol-5-yl)phenyl)amino)-2-methyl-3H-imidazo[4,5-b]pyridin-5-yl)amino)picolinonitrile, I-403

Synthesis of I-403.

Compound I-403 was synthesized from 403.1 (prepared from 98.5 and 40.3 using general procedure B) using general procedure C. (Yield: 58.88%). MS(ES): m/z: 545.26 [M+H]$^+$, LCMS purity, 97.61%, HPLC purity: 96.86%, 1H NMR (DMSO, 400 MHz): 9.40 (s, 1H), 7.88-7.86 (d, J=8.8 Hz 1H), 7.780-7.76 (d, J=7.6 Hz 2H), 7.61-7.59 (d, J=7.6 Hz 1H), 7.42-7.346 (m, 2H), 7.28 (s, 1H), 6.02 (s, 1H), 4.47 (s, 3H), 3.75 (s, 3H), 3.34 (s, 3H) 3.73 (s, 2H), 3.17 (s, 2H), 2.02-1.99 (t, J=6.4 Hz 2H).

Example 404: Synthesis of 2-(difluoromethyl)-N7-(4-(1-methyl-1H-imidazol-5-yl)-2-(methylsulfonyl)phenyl)-3-(tetrahydro-2H-pyran-2-yl)-3H-imidazo[4,5-b]pyridine-5,7-diamine, I-404

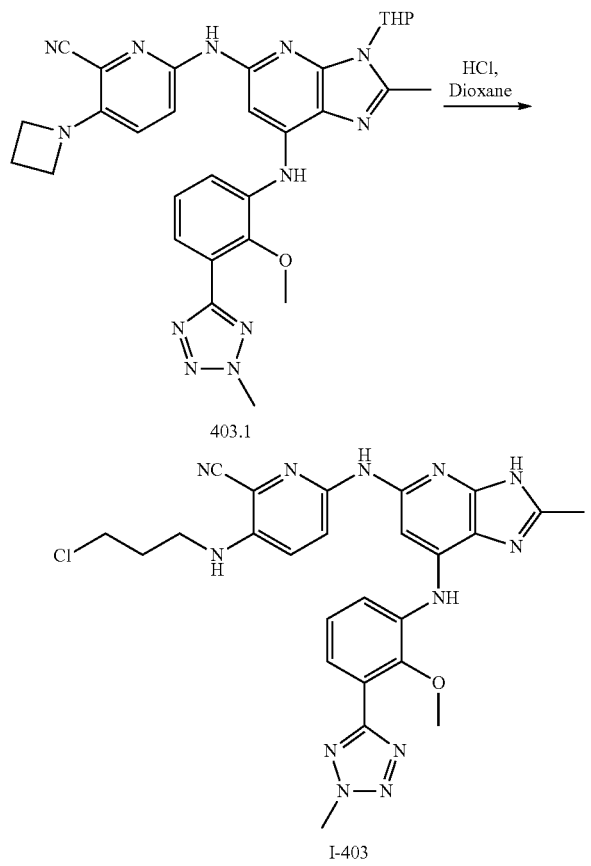

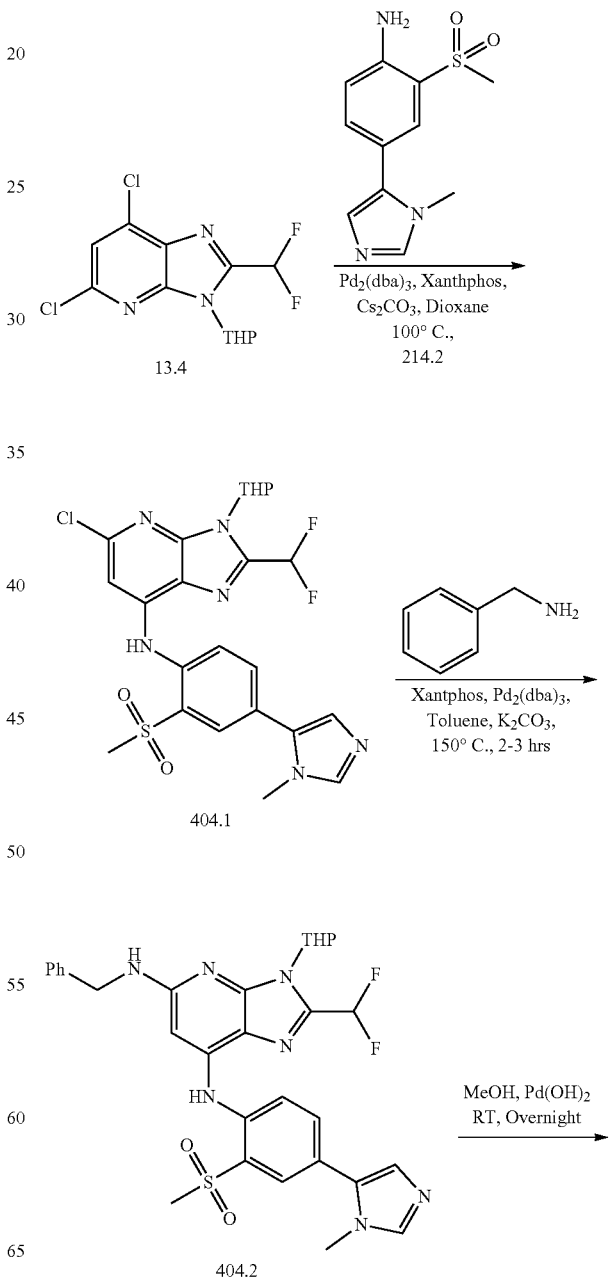

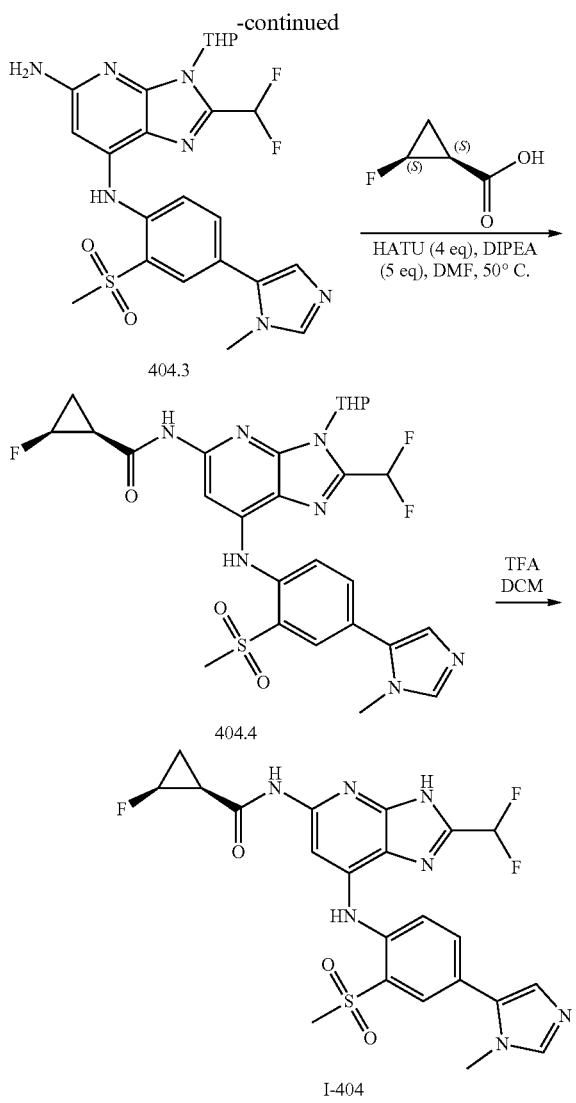

404.3

404.4

I-404

Synthesis of Compound 404.1.

Compound was synthesized from 13.4 and 214.2 using general procedure A. (Yield: 35.57%). MS(ES): m/z 537.25 [M+H]+.

Synthesis of Compound 404.2.

Compound was synthesized from 404.1 and benzylamine using general procedure A. (Yield: 67.44%). MS(ES): m/z 608.43 [M+H]+.

Synthesis of Compound 404.3.

To compound 404.2 (0.29 g, 0.47 mmol, 1.0 eq) in MeOH (10 mL), palladium hydroxide (0.1 g) was added. Reaction mixture was stirred at r.t. for 24 hours. After completion of the reaction, the reaction mixture was filtered through celite bed and washed with MeOH. Filtrate was concentrated in vacuo to obtain 404.3 (0.16 g, 64.78%). MS(ES): m/z 518.43 [M+H].

Synthesis of Compound 404.4.

To compound (1S,2S)-2-fluorocyclopropane-1-carboxylic acid (0.048 g, 0.46 mmol, 3.0 eq) in N,N-dimethylformamide (2 mL) at 0° C., (1-[Bis(dimethylamino)methylene]-1H-1,2,3-triazolo[4,5-b]pyridinium 3-oxid hexafluorophosphate) (0.235 g, 0.61 mmol, 4.0 eq) was added. Reaction mixture was stirred at 0° C. for 30 min. Then, compound 404.3 (0.080 g, 0.15 mmol, 1.0 eq) and di-isopropylethylamine (0.099 g, 0.77 mmol, 5.0 eq) was added. Reaction mixture was stirred at 50° C. for 1.5 h. After completion of the reaction, the reaction mixture was transferred to cold water to obtain precipitate which was filtered and dried well to obtain pure 404.4 (0.04 g, 42.87%). MS(ES): m/z 604.47 [M+H]+.

Synthesis of I-404.

Compound I-404 was synthesized from 404.4 using general procedure C (Yield: 74.69%). MS(ES): m/z 520.74 [M+H]+, LCMS purity: 95.76%, HPLC purity: 97.66%, Chiral HPLC Purity: 99.69%, 1H NMR (DMSO, 400 MHz): 13.75 (s, 1H), 10.85 (s, 1H), 8.93 (s, 1H), 8.14 (s, 1H), 7.96-7.87 (m, 3H), 7.77 (m, 1H), 7.21 (t, 1H), 3.76 (s, 3H), 3.30 (s, 3H), 2.25 (s, 1H), 1.654-1.594 (d, J=2.4, 2H), 1.20-1.12 (m, 2H).

Example 405: Synthesis of (1R,2R)—N-(2-(difluoromethyl)-7-((4-(1-methyl-1H-imidazol-5-yl)-2-(methylsulfonyl)phenyl)amino)-3H-imidazo[4,5-b]pyridin-5-yl)-2-fluorocyclopropane-1-carboxamide, I-405

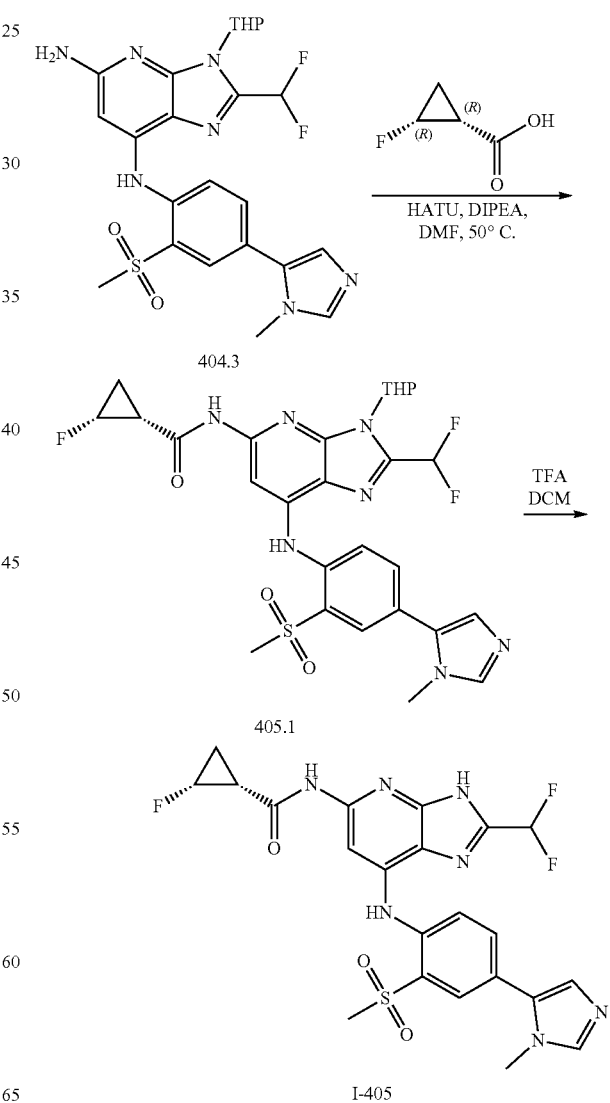

404.3

405.1

I-405

Synthesis of Compound 405.1.

To compound (1R,2R)-2-fluorocyclopropane-1-carboxylic acid (0.019 g, 0.18 mmol, 1.2 eq) in N,N'-dimethylformamide (1 mL) at 0° C., (1-[Bis(dimethylamino)methylene]-1H-1,2,3-triazolo[4,5-b]pyridinium 3-oxid hexafluorophosphate) (0.087 g, 0.23 mmol, 1.5 eq) was added into it. After 30 min, di-isopropylethylamine (0.049 g, 0.45 mmol, 3.0 eq) and 404.3 (0.080 g, 0.15 mmol, 1.0 eq) was added. Reaction mixture was stirred at 50° C. for 2 h. After completion of reaction, the reaction mixture was transferred into cold water and extracted by ethyl acetate. Organic layer combined, dried over Na$_2$SO$_4$ and concentrated in vacuo to obtain crude product. This was purified by column chromatography and compound was eluted in 25% ethyl acetate in hexane as eluant to obtain pure 405.1 (0.040 g, 42.87%). MS(ES): m/z 604.62 [M+H]$^+$.

Synthesis of I-405.

Compound I-405 was synthesized from 405.1 using general procedure C (Yield: 87.14%). MS(ES): m/z 520.59 [M+H]$^+$, LCMS purity: 100%, HPLC purity: 98.20%, Chiral HPLC Purity: 99.39%, 1H NMR (DMSO, 400 MHz): 13.75 (s, 1H), 10.86 (s, 1H), 8.93 (s, 1H), 8.15 (s, 1H), 7.97-7.88 (m, 3H), 7.87 (s, 1H), 7.28-7.14 (m, 2H), 5.02 (s, 1H), 3.76 (s, 3H), 3.31 (s, 3H), 2.24 (s, 1H), 1.24-1.08 (m, 2H).

Example 406: Synthesis of (1 S,2S)—N-(2-(difluoromethyl)-7-((4-(1,4-dimethyl-1H-pyrazol-3-yl)-2-(methylsulfonyl)phenyl)amino)-3H-imidazo[4,5-b]pyridin-5-yl)-2-fluorocyclopropane-1-carboxamide, I-406

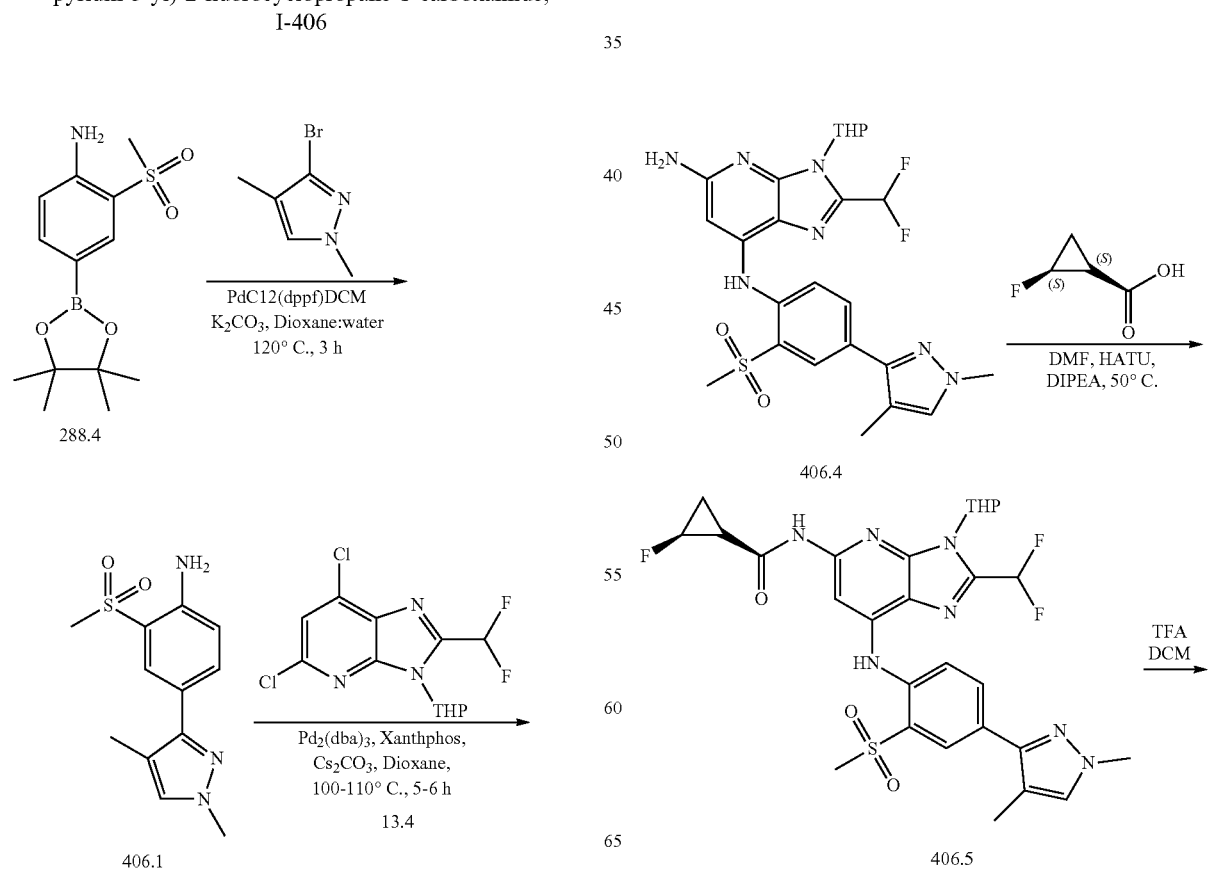

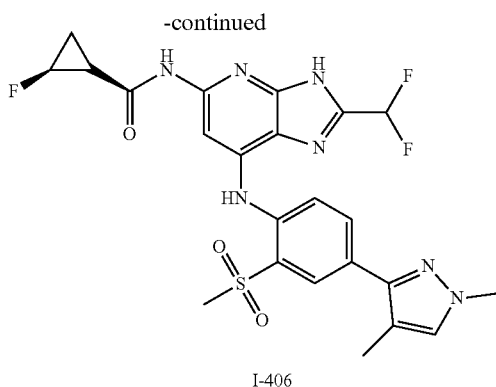

I-406

Synthesis of Compound 406.1.

To a solution of 288.4 (1.76 g, 10.1 mmol, 1.5 eq), 3-bromo-1,4-dimethyl-1H-pyrazole (2 g, 6.73 mmol, 1.0 eq) in a mixture of 1,4-dioxane (40 mL) and water (10 mL), potassium carbonate (2.8 g, 20.2 mmol, 3.0 eq) was added. Reaction mixture was degassed using argon for 15 min. Then, [1,1'-Bis(diphenylphosphino) ferrocene]dichloropalladium(II) complex with CH$_2$Cl$_2$ (0.27 g, 0.33 mmol, 0.05 eq) was added and again degassed for 5 min. Reaction mixture was stirred at 120° C. for 3 h. After completion of the reaction, the reaction mixture was transferred to water and extracted with ethyl acetate. Organic layers were combined, dried over Na$_2$SO$_4$, filtered and concentrated in vacuo to obtain 406.1 (0.98 g, 32.32%). MS(ES): m/z 266.47 [M+H]$^+$.

Synthesis of Compound 406.2.

Compound 406.2 was synthesized from 406.1 and 13.4 using general procedure A. (Yield: 32.10%). MS(ES): m/z 552.43 [M+H]$^+$.

Synthesis of Compound 406.3.

To compound 406.2 (0.180 g, 0.347 mmol, 1.0 eq) in 1,4-dioxane (3.5 mL) was added N-benzyl amine (0.053 g, 0.49 mmol, 1.5 eq), potassium carbonate (0.135 g, 0.98 mmol, 3.0 eq). The reaction mixture was degassed for 10 min. under argon atmosphere, then Pd$_2$(dba)$_3$ (0.030 g, 0.032 mmol, 0.1 eq) and Xantphos (0.038 g, 0.065 mmol, 0.2 eq) were added, again degassed for 5 min. The reaction was stirred at 150° C. for 2-3 h. Upon completion, reaction mixture was cooled to r.t., transferred in water and product was extracted with ethyl acetate. Organic layers were combined, washed with brine, dried over Na$_2$SO$_4$ and concentrated in vacuo to obtain crude product. This was purified by combi flash using 3% MeOH in CH$_2$Cl$_2$ as eluant to obtain pure 406.2 (0.130 g, 64.01%). MS(ES): m/z 622.57 [M+H]$^+$.

Synthesis of Compound 406.4.

To a solution of 406.3 (0.120 g, 0.19 mmol, 1.0 eq) in MeOH (5 mL), palladium hydroxide (0.180 g, 0.28 mmol, 1.5 eq) was added. Hydrogen was purged through the reaction mixture for 24 h. After completion of the reaction, the reaction mixture was filtered through celite bed and washed with MeOH. Filtrate was concentrated to obtain 406.4 (0.075 g, 73.10%). MS(ES): m/z 532.18 [M+H]$^+$.

Synthesis of Compound 406.5.

To a solution of (1S,2S)-2-fluorocyclopropane-1-carboxylic acid (0.022 g, 0.221 mmol, 1.5 eq) in N,N-dimethylformamide (2 mL) at 0° C., 1(1-[Bis(dimethylamino)methylene]-1H-1,2,3-triazolo[4,5-b]pyridinium 3-oxid hexafluoro phosphate) (0.107 g, 0.28 mmol, 2.0 eq) was added. Reaction mixture was allowed to stir for 15 min at 0° C. Then, diisopropylethylamine (0.055 g, 0.43 mmol, 3.0 eq) and 406.4 (0.075 g, 0.14 mmol, 1.0 eq) was added. Reaction mixture was stirred at 50° C. for 5 h. After completion of the reaction, the reaction mixture was transferred to water and extracted with ethyl acetate. Organic layers were combined, dried over anhydrous Na$_2$SO$_4$, filtered and concentrated in vacuo to get the crude material. This was purified by column chromatography using 2% MeOH in CH$_2$Cl$_2$ as eluant to obtain pure 406.5 (0.045 g, 48.41%). MS(ES): m/z 618.45 [M+H]$^+$.

Synthesis of Compound I-406.

Compound I-406 was synthesized from 406.5 using general procedure C. (Yield: 69.46%). MS(ES): m/z 534.74 [M+H]$^+$, LCMS purity: 99.52%, HPLC purity: 97.26%, Chiral HPLC Purity: 100%, 1H NMR (DMSO-d6, 400 MHz): 13.72 (s, 1H), 10.82 (s, 1H), 8.81 (s, 1H), 8.24 (s, 1H), 8.10-8.03 (m, 2H), 7.85-7.83 (d, J=1.0, 1H), 7.62 (s, 1H), 7.28 (t, 4.2 Hz, 1H), 5.01-4.83 (d, J=7.0, 1H) 3.86 (s, 3H), 3.26 (s, 3H), 2.25 (s, 3H), 1.66-1.59 (d, J=2.68, 1H), 1.22-1.13 (d, J=3.84, 2H).

Example 407: Synthesis of (1R,2R)—N-(2-(difluoromethyl)-7-((4-(1,4-dimethyl-1H-pyrazol-3-yl)-2-(methylsulfonyl)phenyl)amino)-3H-imidazo[4,5-b]pyridin-5-yl)-2-fluorocyclopropane-1-carboxamide, I-407

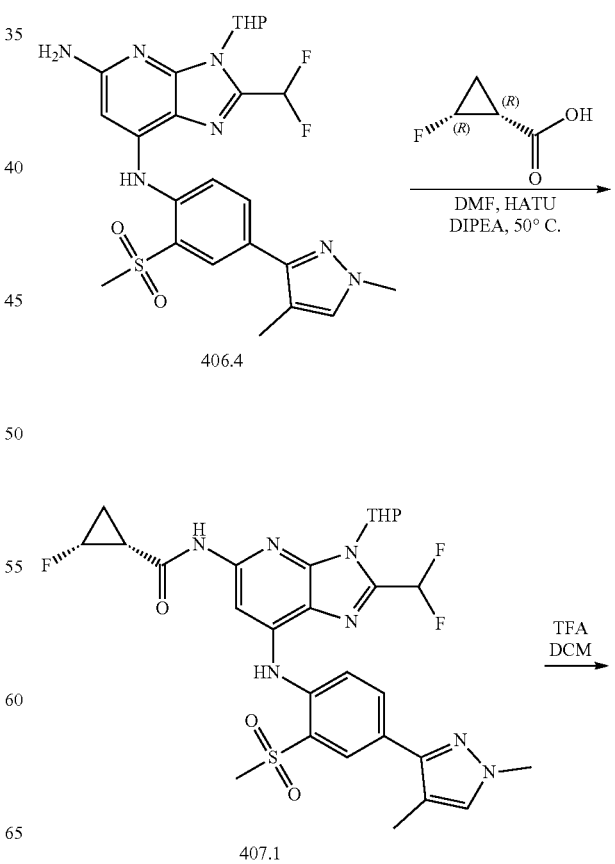

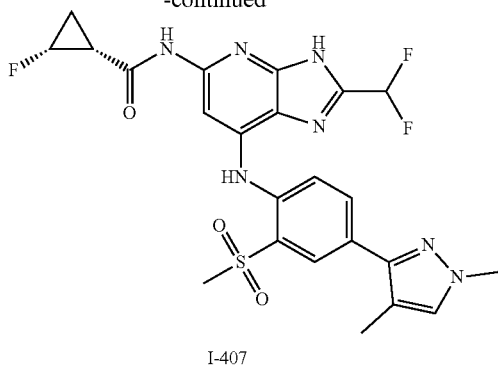

I-407

Synthesis of Compound 407.1.

To a solution of 406.4 (0.018 g, 0.18 mmol, 1.2 eq) in N,N-dimethylformamide (2 mL) at 0° C., (1-[Bis(dimethylamino)methylene]-1H-1,2,3-triazolo[4,5-b]pyridinium 3-oxid hexafluorophosphate) (0.114 g, 0.34 mmol, 2.0 eq) was added. Reaction mixture was stirred at 0° C. for 30 min. Then, compound (1R,2R)-2-fluorocyclopropane-1-carboxylic acid 1 (0.080 g, 0.15 mmol, 1.0 eq) and di-isopropylethylamine (0.05 g, 0.45 mmol, 3.0 eq) was added. Reaction mixture was stirred at 50° C. for 1.5 h. After completion of the reaction, the reaction mixture was transferred to cold water to obtain precipitate which was filtered and dried well to obtain 407.1 (0.055 g, 59.17%). MS(ES): m/z 618.45 [M+H]+.

Synthesis of I-407.

Compound I-407 was synthesized from 406.1 using general procedure C. (Yield: 63.15%). MS(ES): m/z 534.50 [M+H]+, LCMS purity: 96.75%, HPLC purity: 96.85%, 1H NMR (DMSO, 400 MHz): 13.73 (s, 1H), 10.83 (s, 1H), 8.81 (s, 1H), 8.24 (s, 1H), 8.10 (s, 1H), 8.05-8.03 (d, J=8.4, 1H), 7.85-7.83 (d, J=8.0, 1H), 7.28 (s, 1H), 5.00 (s, 1H), 4.83 (s, 1H), 3.85 (s, 3H), 3.22 (s, 3H), 2.16 (s, 3H), 1.65-1.60 (d, J=3.6 Hz, 1H), 1.18-1.12 (m, 2H).

Example 408: Synthesis of N-(2-(difluoromethyl)-7-((2-(dimethylphosphoryl)-4-(tetrahydro-2H-pyran-4-yl)phenyl)amino)-3H-imidazo[4,5-b]pyridin-5-yl)cyclopropanecarboxamide, I-408

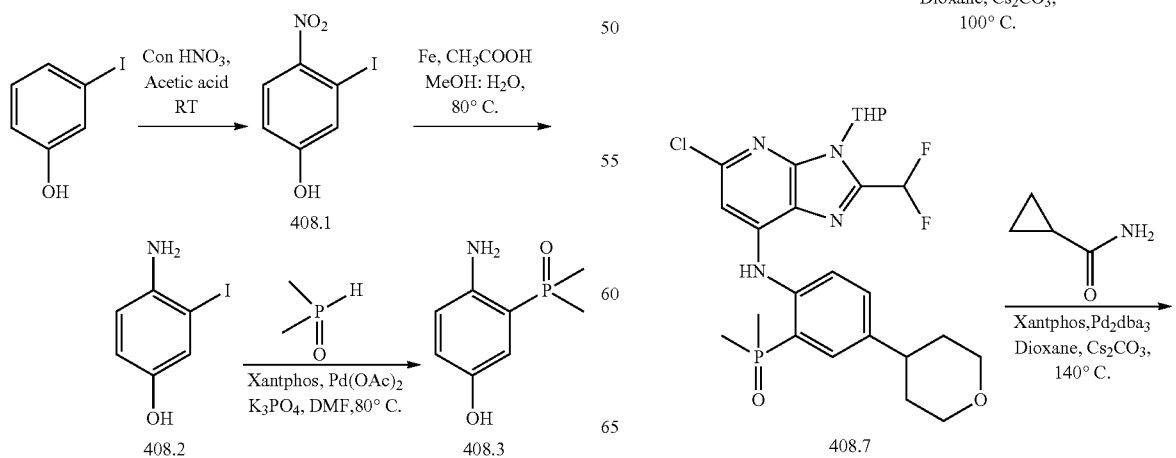

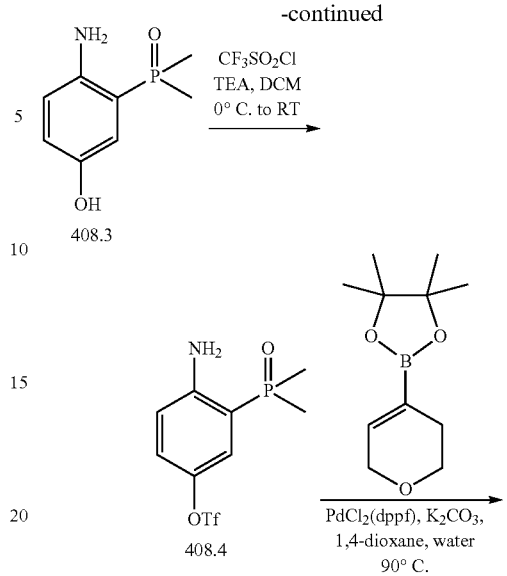

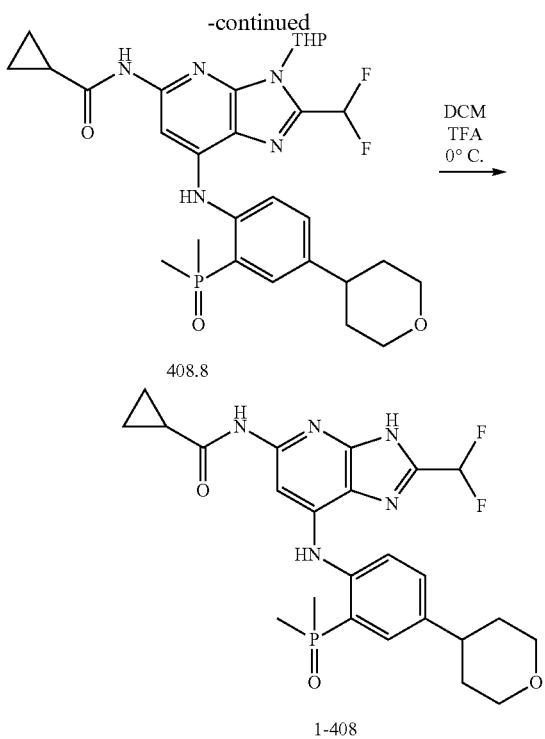

Synthesis of Compound 408.1.

To compound, 3-iodonitrobenzene (20 g, 90.9 mmol, 1.0 eq) in glacial acetic acid (96 mL) at 10° C., concentrated nitric acid (6.3 g, 99.9 mmol, 1.1 eq) was added dropwise. Reaction mixture was stirred at r.t. for 1 h. After completion of the reaction, the reaction mixture was concentrated in vacuo, transferred into water and extracted with $CH_2Cl_2$. Organic layer combined, dried over anhydrous $Na_2SO_4$, filtered and concentrated in vacuo to obtain the crude material. This was purified by column chromatography using 20% $CH_2Cl_2$ in hexane as eluant to obtain pure 408.1 (1 g, 45.66%). MS(ES): m/z 266.35 [M+H]$^+$.

Synthesis of Compound 408.2.

To compound 408.1 (1 g, 46.8 mmol, 1.0 eq) in a mixture of MeOH (88 mL) and water (22 mL), acetic acid (42.12 g, 702.1 mmol, 15 eq) was added. Reaction mixture was stirred at 40° C. for 30 min. Then, iron powder (18.34 g, 327.6 mmol, 7 eq) was added in portions and the reaction mixture was stirred at 90° C. for 1 h. Upon completion, reaction mixture was transferred into cold water and extracted with ethyl acetate. Organic layers were combined, dried over $Na_2SO_4$ and concentrated in vacuo to obtain crude product. This was purified by column chromatography and compound was eluted in 2% MeOH in $CH_2Cl_2$ as eluant to obtain pure 408.2 (7.0 g, 71.75%). MS(ES): m/z 236.54 [M+H]$^+$.

Synthesis of Compound 408.3.

To compound 408.2 (5 g, 21.2 mmol, 1.0 eq) in N,N'-dimethylformamide (50 mL), potassium phosphate (4.96 g, 23.4 mmol, 1.1 eq) and dimethylphosphine oxide was added. Reaction mixture was degassed by argon for 15 min. Then, palladium acetate (0.47 g, 0.21 mmol, 0.1 eq) and 4 Xantphos (1.29 g, 2.12 mmol, 0.1 eq) was added and again degassed for 10 min. Reaction mixture was stirred at 80° C. for 3 h. After completion of the reaction, the reaction mixture was transferred into water and extracted with ethyl acetate. Organic layer combined, dried over anhydrous $Na_2SO_4$, filtered and evaporated under vacuum to obtain the crude material. This was purified by column chromatography using 10% MeOH in $CH_2Cl_2$ as eluant to obtain pure 408.3 (3 g, 76.16%). MS(ES): m/z 186.54 [M+H]$^+$.

Synthesis of Compound 408.4.

To compound 408.4 (1.6 g, 8.64 mmol, 1.0 eq) in $CH_2Cl_2$ (16 mL) at 0° C., triethylamine (40 mL, 20.6 mmol, 3.2 eq) was added. Then, trifluoromethanesulfonyl chloride (2.0 mL, 6.17 mmol, 1.4 eq) was added dropwise. Reaction mixture was stirred at 0° C. for 1 h. After completion of the reaction, the reaction mixture was transferred into water and extracted with $CH_2Cl_2$. Organic layer combined, dried over anhydrous $Na_2SO_4$, filtered and concentrated in vacuo to obtain the crude material. This was purified by column chromatography using 1% MeOH in $CH_2Cl_2$ as eluant to obtain pure 408.4 (0.9 g, 32.83%). MS(ES): m/z 318.43 [M+H]$^+$.

Synthesis of Compound 408.5.

To compound 408.4 (0.75 g, 3.02 mmol, 1.0 eq) in a mixture of 1,4-dioxane (6 mL) and water (1.5 mL), 2-(3,6-dihydro-2H-pyran-4-yl)-4,4,5,5-tetramethyl-1,3,2-dioxaborolane (0.95 g, 4.5 mmol, 1.5 eq) and potassium carbonate (1.25 g, 9.07 mmol, 3.0 eq) was added. Reaction mixture was degassed with argon for 15 min. Then, (1,1'-Bis(diphenylphosphino)ferrocene)palladium(II) dichloride (0.24 g, 0.30 mmol, 0.1 eq) was added and again degassed for 5 min. Reaction mixture was stirred at 90° C. for 3 h. After completion of the reaction, the reaction mixture was transferred into water and extracted with ethyl acetate. Organic layer combined, dried over anhydrous $Na_2SO_4$, filtered and concentrated in vacuo to obtain the crude material. This was purified by column chromatography using 17% ethyl acetate in hexane as eluant to obtain pure 408.5 (0.75 g, 67.40%). MS(ES): m/z 252.34 [M+H]$^+$.

Synthesis of Compound 408.6.

To compound 408.5 (0.7 g, 2.7 mmol, 1.0 eq) in MeOH, 10% Pd/C (0.1 g) was added. Hydrogen was purged through reaction mixture for 48 h. Upon completion, reaction mixture was filtered through celite-bed and washed with MeOH. Filtrate was concentrated in vacuo to obtain 408.6 (0.35 g, 69.44%). MS(ES): m/z 254.28 [M+H]$^+$.

Synthesis of Compound 408.7.

Compound 408.7 was synthesized from 408.6 and 13.4 using general procedure B. (Yield: 42.69%). MS(ES): m/z 539.47 [M+H]$^+$.

Synthesis of Compound 408.8.

Compound 408.8 was synthesized from 408.7 and cyclopropanecarboxamide using general procedure B. (Yield: 51.98%). MS(ES): m/z 588.61 [M+H]$^+$.

Synthesis of I-408.

Compound I-408 was synthesized from 408.8 using general procedure C/(Yield: 65.91%). MS(ES): m/z 504.61 [M+H]$^+$, LCMS purity: 98.39%, HPLC purity: 97.69%, 1H NMR (DMSO, 400 MHz): 13.51 (s, 1H), 10.64 (s, 1H), 10.06 (s, 1H), 8.00 (s, 1H), 7.57-7.45 (m, 3H), 7.21 (s, 1H), 3.98-3.95 (d, J=19.6 Hz, 2H), 3.47-3.43 (m, 2H), 2.83-2.79 (m, 1H), 2.03-0.99 (m, 1H), 1.75-1.72 (m, 10H), 0.78-0.76 (m, 4H).

Example 409: Synthesis of N7-(4-cyclopropyl-2-(methylsulfonyl)phenyl)-2-(difluoromethyl)-N5-(5,6,7,8-tetrahydro-4H-pyrazolo[1,5-a]azepin-2-yl)-3H-imidazo[4,5-b]pyridine-5,7-diamine, I-409

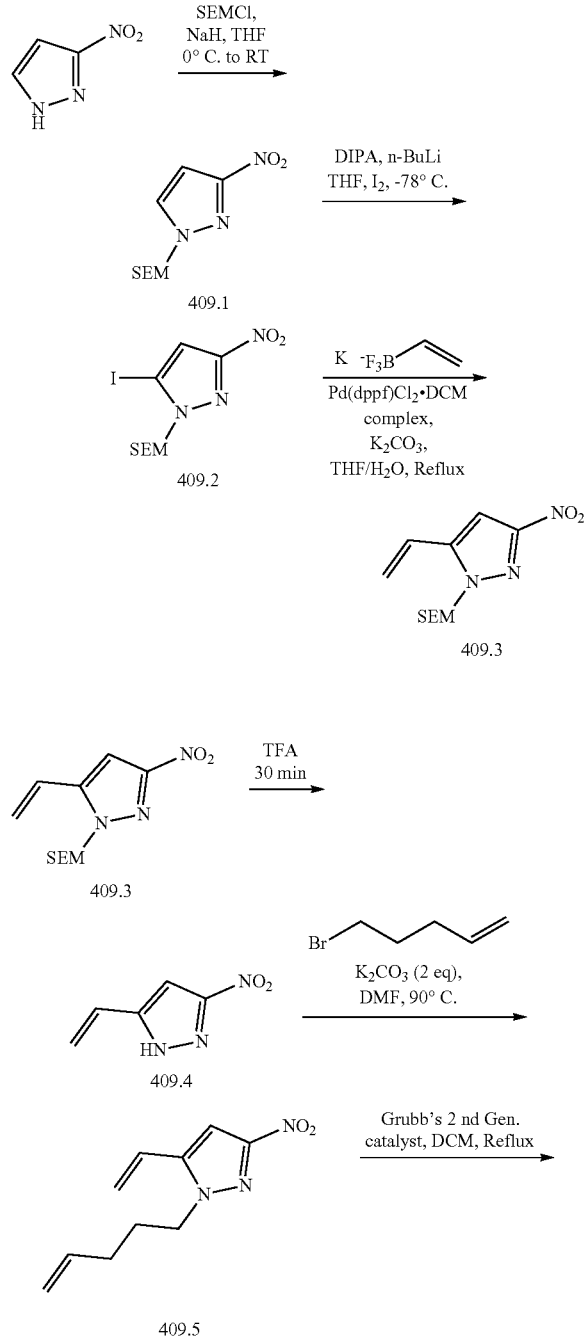

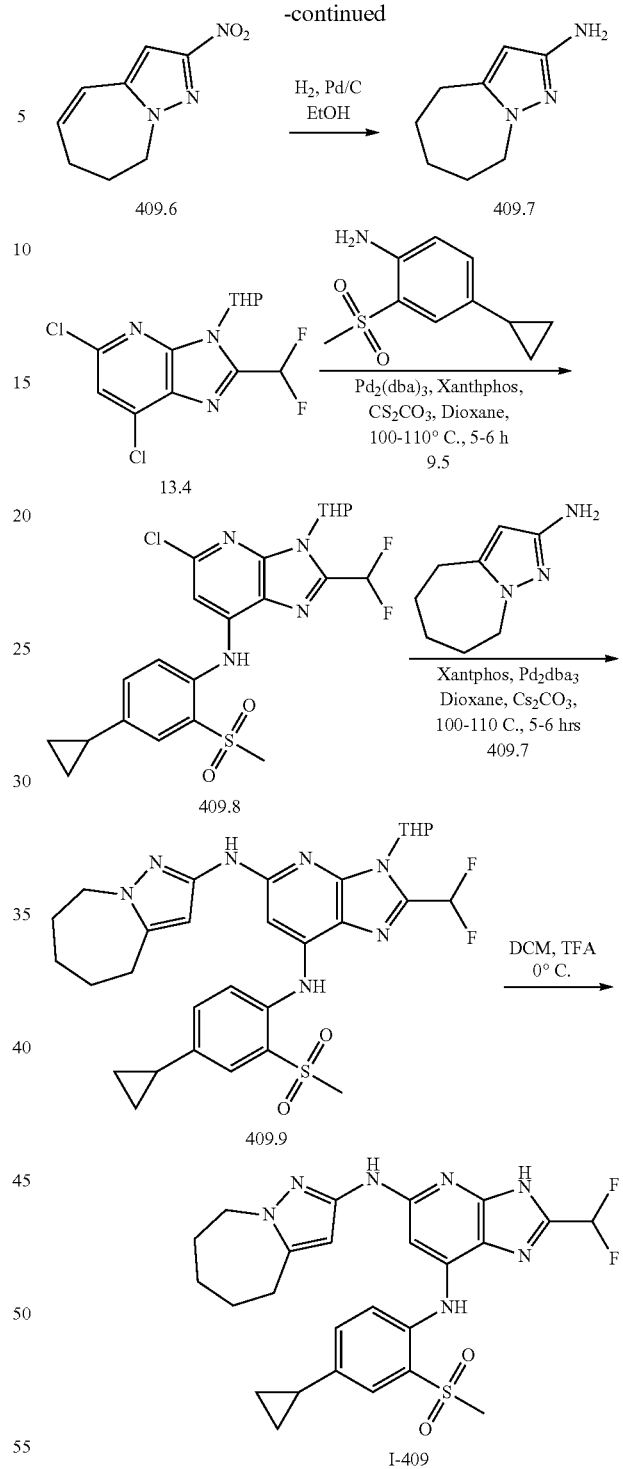

Synthesis of Compound 409.1.

To compound 3-nitro-1H-pyrazole 1 (10 g, 88.4 mmol, 1.0 eq) in tetrahydrofuran (100 mL) at 0° C., sodium hydride (6.3 g, 265.3 mmol, 3.0 eq) was added. Reaction mixture was allowed to stir for 30 min at 0° C. Then, 2-(trimethylsilyl) ethoxymethyl chloride (17.6 g, 106.0 mmol, 1.2 eq) was added. Reaction mixture was allowed to stir for 3 h at r.t. After completion of the reaction, the reaction mixture was transferred into water and extracted with ethyl acetate. Organic layer combined, dried over anhydrous Na$_2$SO$_4$, filtered and concentrated in vacuo to obtain the crude material. This was purified by column chromatography using 20% ethyl acetate in hexane to obtain pure 409.1 (9 g, 41.82%). MS(ES): m/z 244.43 [M+H]⁺.

Synthesis of Compound 409.2.

To a solution of diisopropylamine (8.7 mL, 61.2 mmol, 1.5 eq) in tetrahydrofuran (40 mL) at −78° C., n-butyl lithium (38.3 mL, 57.5 mmol, 1.4 eq) was added dropwise. Reaction mixture was at r.t. for 30 min and then again cooled to −78° C. Solution of compound 409.1 (10 g, 41.2 mmol, 1.0 eq) in tetrahydrofuran (30 mL) was added dropwise at −78° C. Reaction mixture was stirred at −78° C. for 1 h. Then, iodine (12.5 g, 49.8 mmol, 1.2 eq) in tetrahydrofuran (30 mL) was added dropwise at −78° C. and the reaction mixture was stirred at r.t. for 24 h. After completion of reaction, the reaction mixture was transferred to ice cooled solution of sodium thiosulfate and extracted with ethyl acetate. Organic layer combined, dried over anhydrous $Na_2SO_4$, filtered and concentrated in vacuo to obtain the crude material. This was purified by column chromatography using 20% ethyl acetate in hexane as eluant to obtain pure 409.2 (6.1 g, 40.20%). MS(ES): m/z 370.53 [M+H]⁺.

Synthesis of Compound 409.3

To compound 409.2 (6.1 g, 16.52 mmol, 1.0 eq) in a mixture of tetrahydrofuran (60 mL) and water (12 mL), compound Potassium vinyl trifluoroborate (3.98 g, 29.73 mmol, 1.8 eq) and potassium carbonate (6.8 g, 49.56 mmol, 3.0 eq) was added. Reaction mixture was purged by argon for 15 min. Then, 1,1'-Bis(diphenylphosphino)ferrocene-palladium(II)dichloride (0.67 g, 0.82 mmol, 0.05 eq) was added. Reaction mixture was stirred at 100° C. for 24 h. After completion of the reaction, the reaction mixture was transferred to water and extracted with ethyl acetate. Organic layer combined, dried over anhydrous $Na_2SO_4$, filtered and concentrated in vacuo to obtain the crude material. This was purified by column chromatography using 10% ethyl acetate in hexane to obtain pure 409.3 (3.9 g, 87.64%). MS(ES): m/z 270.68 [M+H]⁺.

Synthesis of Compound 409.4.

The solution of compound 409.3 (3.9 g, 14.5 mmol, 1.0 eq) in trifluoroacetic acid (39 mL) is stirred at r.t. for 30 min. After completion of the reaction, the reaction mixture is concentrated in vacuo, transferred to aqueous saturated $NaHCO_3$ solution and extracted with ethyl acetate. Organic layer combined, dried over anhydrous $Na_2SO_4$, filtered and concentrated in vacuo to obtain 409.4 (2.0 g, 99.30%). MS(ES): m/z 140.53 [M+H]⁺.

Synthesis of Compound 409.5.

To compound 1.5 (0.9 g, 6.47 mmol, 1.0 eq) in N,N'-dimethylformamide (9 mL), compound 5-bromopent-1-ene (1.06 g, 7.12 mmol, 1.1 eq) and potassium carbonate (2.68 g, 19.42 mmol, 3.0 eq) was added. Reaction mixture was stirred at 120° C. for 24 h. After completion of the reaction the reaction mixture was transferred to water and extracted with ethyl acetate. Organic layer combined, dried over anhydrous $Na_2SO_4$, filtered and concentrated in vacuo to obtain the crude material. This was purified by column chromatography using 10% ethyl acetate in hexane to obtain pure 409.5 (0.6 g, 44.75%). MS(ES): m/z 208.73 [M+H]⁺.

Synthesis of Compound 409.6.

To compound 409.5 (0.6 g, 2.89 mmol, 1.0 eq) in $CH_2Cl_2$ (6 mL), Grubb's second generation catalyst (0.17 g, 0.28 mmol, 0.1 eq) was added. Reaction mixture was stirred at 50° C. for 24 h. After completion of the reaction, the reaction mixture was concentrated in vacuo and purified by column chromatography using 15% ethyl acetate in hexane as eluant to obtain pure 409.6 (0.45 g, 86.74%). MS(ES): m/z 180.46 [M+H]⁺.

Synthesis of Compound 409.7.

To compound 409.6 (0.4 g, 2.23 mmol, 1.0 eq) in MeOH (5 mL), 10% Pd/C (0.2 g) was added. Hydrogen was purged through the reaction for 6 h. After completion of the reaction, the reaction mixture was filtered through celite bed, washed with MeOH and concentrated in vacuo to obtain 409.7 (0.3 g, 88.87%). MS(ES): m/z 152.84 [M+H]⁺.

Synthesis of Compound 409.8.

Compound 409.8 was synthesized from 13.4 and 9.5 using general procedure A. (Yield: 21.20%). MS(ES): m/z 497.96 [M+H]⁺.

Synthesis of Compound 409.9.

Compound 409.9 was synthesized from 409.8 and 409.7 using general procedure B. (Yield: 45.25%). MS(ES): m/z 612.84 [M+H]⁺.

Synthesis of I-409.

Compound I-409 was synthesized from 409.9 using general procedure C. Yield: 62.43%). MS(ES): m/z 528.66 [M+H]⁺, LCMS purity: 99.01%, HPLC purity: 97.71%, 1H NMR (DMSO, 400 MHz): 13.30 (s, 1H), 9.07 (s, 1H), 8.52 (s, 1H), 7.74-7.72 (d, J=8.4 Hz, 2H), 7.64 (s, 1H), 7.47-7.45 (d, J=8.4 Hz, 1H), 7.15 (s, 1H), 7.05 (s, 1H), 6.24 (s, 1H), 4.10 (s, 1H), 3.19 (s, 3H), 2.69 (s, 2H), 2.13-2.06 (m, 1H), 1.79 (s, 2H), 1.66-1.60 (d, J=22.8 Hz, 4H), 1.10-1.01 (d, J=34 Hz, 2H), 0.76-0.72 (d, J=15.4 Hz, 2H).

Example 410: Synthesis of N7-(4-cyclopropyl-2-(methylsulfonyl)phenyl)-2-methyl-N5-(5,6,7,8-tetra-hydro-4H-pyrazolo[1,5-a]azepin-2-yl)-3H-imidazo[4,5-b]pyridine-5,7-diamine, I-410

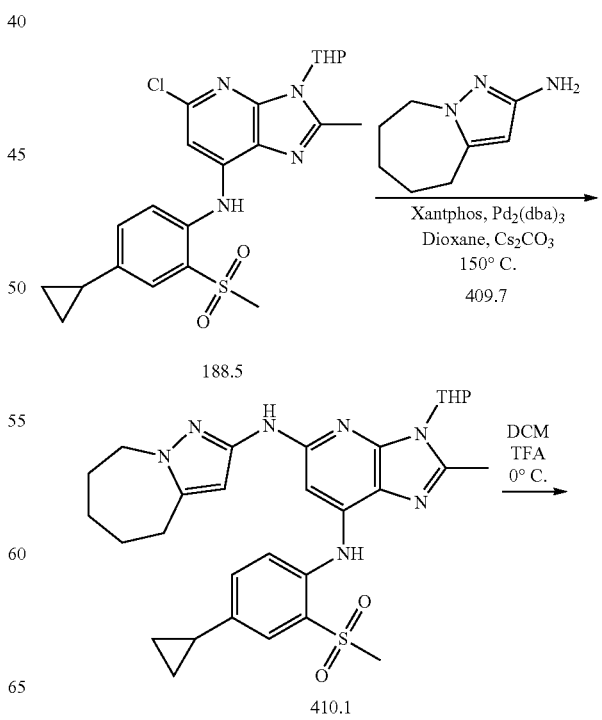

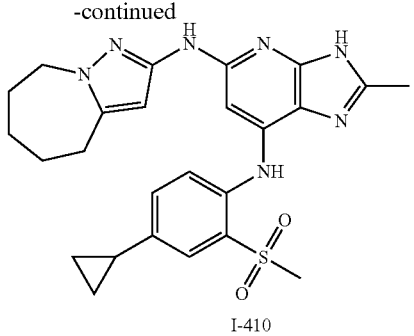

I-410

Synthesis of Compound 410.1.

Compound 410.1 was synthesized from 188.5 and 409.7 using general procedure B. (Yield: 36.70%). MS(ES): m/z 576.73 [M+H]⁺.

Synthesis of Compound I-410.

Compound I-410 was synthesized from 410.1 using general procedure C. (Yield: 61.75%). MS(ES): m/z 492.61 [M+H]⁺, LCMS purity: 96.87%, HPLC purity: 98.82%, 1H NMR (DMSO, 400 MHz): 12.17 (s, 1H), 8.75 (s, 1H), 8.37 (s, 1H), 7.73-7.71 (d, J=8.4 Hz, 1H), 7.61 (s, 1H), 7.44-7.42 (d, J=8.4 Hz, 1H), 7.02 (s, 1H), 6.16 (s, 1H), 4.06-4.04 (m, 2H), 3.17 (s, 3H), 2.68 (s, 2H), 2.43 (s, 3H), 2.10-2.04 (m, 1H), 1.79 (s, 2H), 1.66-1.60 (d, 4H), 1.04-1.01 (d, 2H), 0.73-0.72 (d, 2H).

Example 411/412: (S)—N-(7-((4-cyclobutyl-2-(methylsulfonyl)phenyl)amino)-2-methyl-3H-imidazo[4,5-b]pyridin-5-yl)-2,2-difluorocyclopropane-1-carboxamide, I-411 and (R)—N-(7-((4-cyclobutyl-2-(methylsulfonyl)phenyl)amino)-2-methyl-3H-imidazo[4,5-b]pyridin-5-yl)-2,2-difluorocyclopropane-1-carboxamide, I-412

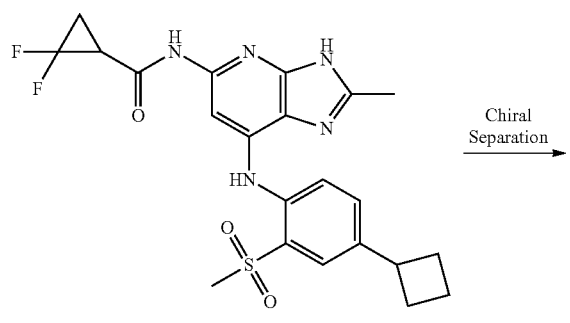

I-361

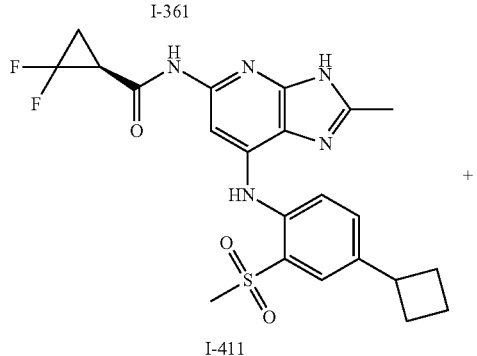

I-411

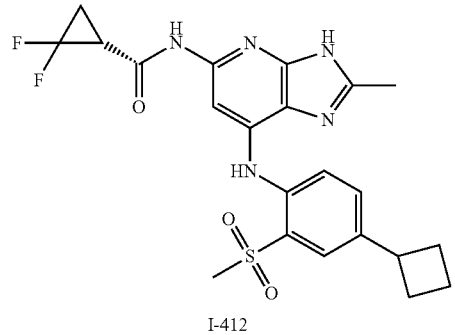

I-412

Synthesis of Compound I-411 and I-412.

Isomers of I-361 (0.105 g) were separated out using column (CHIRALCEL OX-H (250 mm*4.6 mm, 5u)) and 0.1% DEA in IPA:ACN (50:50) flow rate of 4 mL/min. to get pure fraction-1 (FR-a) and fraction-2 (FR-b). FR-a was concentrated in vacuo at 30° C. to afford pure I-411 (0.028 g). MS(ES): m/z 476.62 [M+H]⁺, LCMS purity: 99.73%, HPLC purity: 99.40%, Chiral HPLC purity: 100%, 1H NMR (DMSO, 400 MHz): 12.55 (s, 1H), 10.80 (s, 1H), 8.52 (s, 1H), 7.91 (s, 1H), 7.72-7.64 (m, 3H), 3.67-3.59 (m, 1H), 3.19 (s, 3H), 3.01-2.93 (m, 1H), 2.49 (s, 3H), 2.37-2.31 (m, 2H), 2.20-2.10 (m, 2H), 2.04-1.97 (m, 3H), 1.88-1.84 (m, 1H). FR-b was concentrated in vacuo at 30° C. to afford pure I-412 (0.022 g). MS(ES): m/z 476.45 [M+H]⁺, LCMS purity: 99.07%, HPLC purity: 96.82%, Chiral HPLC purity: 98.73%, 1H NMR (DMSO, 400 MHz): 12.53 (s, 1H), 10.78 (s, 1H), 8.51 (s, 1H), 7.90 (s, 1H), 7.71-7.63 (m, 3H), 3.64-3.60 (s, 1H), 3.18 (s, 3H), 2.98-2.95 (dd, J=10.8 Hz, 1H), 2.504 (s, 3H), 2.37-2.30 (m, 2H), 2.18-2.16 (m, 2H), 2.03-1.96 (m, 3H), 1.87-1.83 (m, 1H).

Example 413: Synthesis of (1R,2R)—N-(7-((4-cyclobutyl-2-(methylsulfonyl)phenyl)amino)-2-methyl-3H-imidazo[4,5-b]pyridin-5-yl)-2-fluorocyclopropane-1-carboxamide, I-413

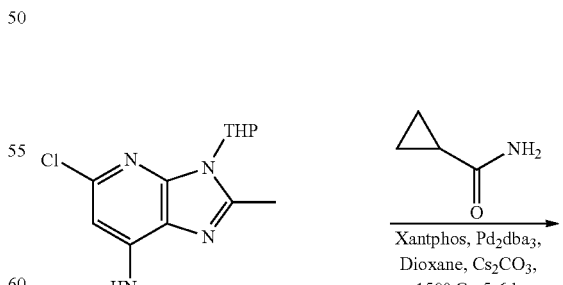

221.2

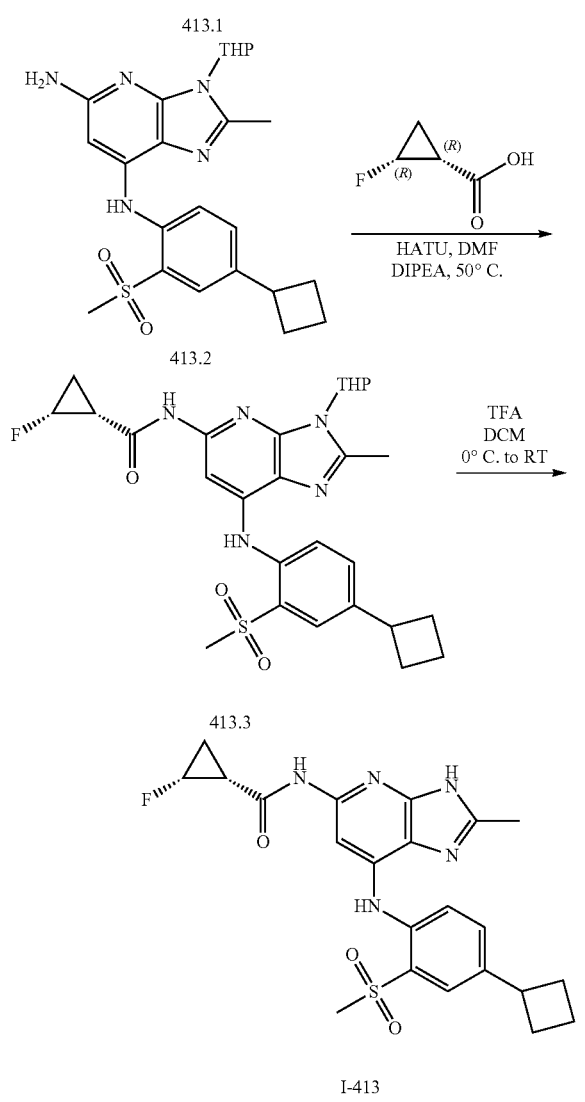

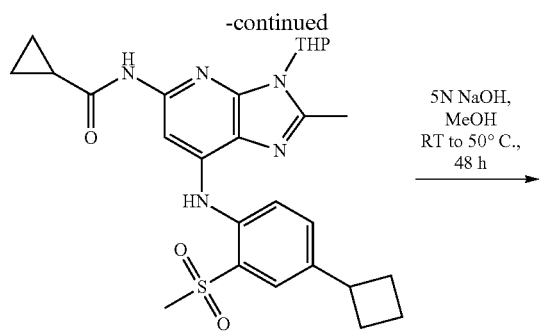

Synthesis of Compound 413.1.

Compound 413.1 was synthesized from 221.2 and cyclopropanecarboxamide using general procedure B. (Yield: 75.59%). MS(ES): m/z 524.16 [M+H]$^+$.

Synthesis of Compound 413.2.

To compound 413.1 (0.350 g, 0.66 mmol, 1.0 eq) in MeOH (5 mL), 5N NaOH solution (0.67 mL, 3.33 mmol, 5.0 eq) was added dropwise at r.t. Reaction mixture was stirred at 70° C. for 48 h. After completion of the reaction, the reaction mixture was transferred to water. The pH of the solution was adjusted to 6-7 by using dil. HCl. Precipitated solid filtered, washed with water, dried well to obtain pure 413.2. (0.28 g, 84.69%). MS(ES): m/z 456.18 [M+H]$^+$.

Synthesis of Compound 413.3.

To compound (1R,2R)-2-fluorocyclopropane-1-carboxylic acid 1.4 (0.024 g, 0.23 mmol, 1.5 eq) in N,N-dimethylformamide (2 mL) at 0° C., (1-[Bis(dimethylamino)methylene]-1H-1,2,3-triazolo[4,5-b]pyridinium 3-oxid hexafluoro phosphate) (0.14 g, 0.38 mmol, 2.5 eq) was added. Reaction mixture was stirred at 0° C. for 30 min. Then, compound 413.2 (0.070 g, 0.15 mmol, 1.0 eq) and di-isopropylethylamine (0.09 mL, 0.53 mmol, 3.5 eq) was added. Reaction mixture was stirred at 50° C. for 1.5 h. After completion of the reaction, the reaction mixture was transferred to cold water to get solid precipitates. These were further filtered under vacuum and washed with water to get pure 413.3 (Yield: 60.98%). MS(ES): m/z 541.46 [M+H]$^+$.

Synthesis of I-413.

Compound I-413 was synthesized from 413.3 using general procedure C (Yield: 55.11%). MS(ES): m/z 458.50 [M+H]$^+$, LCMS purity: 95.64%, HPLC purity: 97.25%, Chiral HPLC purity: 97%, 1H NMR (DMSO-d6, 400 MHz): 12.49 (s, 1H), 10.61 (s, 1H), 8.49 (s, 1H), 7.94 (s, 1H), 7.72-7.70 (m, 2H), 7.64 (m, 1H), 3.64-3.60 (m, 1H), 3.18 (s, 3H), 2.48 (s, 3H), 2.37-2.33 (m, 2H), 2.19-2.09 (m, 3H), 2.01-1.97 (m, 2H), 1.88-1.83 (m, 1H), 1.57-1.54 (d, J=1.8 Hz, 1H), 1.20-1.14 (m, 1H).

Example 414: Synthesis of (1S,2S)—N-(7-((4-cyclobutyl-2-(methylsulfonyl)phenyl)amino)-2-methyl-3H-imidazo[4,5-b]pyridin-5-yl)-2-fluorocyclopropane-1-carboxamide, I-414

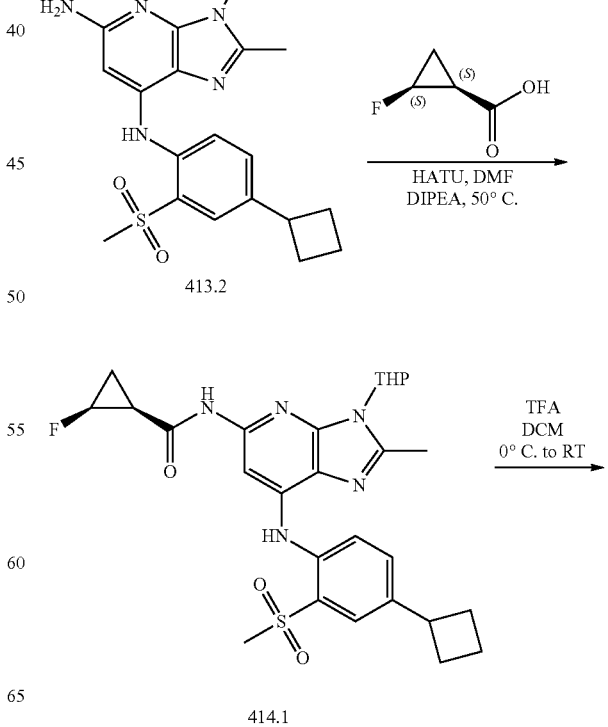

-continued

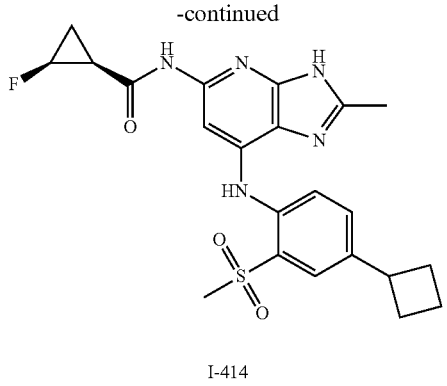

I-414

Synthesis of Compound 414.1.

To a solution of (1S,2S)-2-fluorocyclopropane-1-carboxylic acid (0.024 g, 0.23 mmol, 1.5 eq) in N,N-dimethylformamide (2 mL) at 0° C., (1-[Bis(dimethylamino)methylene]-1H-1,2,3-triazolo[4,5-b]pyridinium 3-oxid hexafluoro phosphate) (0.14 g, 0.38 mmol, 2.5 eq) was added. Reaction mixture was stirred at 0° C. for 30 min. Then, compound 413.2 (0.070 g, 0.15 mmol, 1.0 eq) and di-isopropylethylamine (0.09 mL, 0.53 mmol, 3.5 eq) was added. Reaction mixture was stirred at 50° C. for 1.5 h. After completion of the reaction, the reaction mixture was transferred to cold water to get solid precipitates. These were further filtered under vacuum and washed with water to get pure 414.1 (Yield: 65.19%). MS(ES): m/z 541.46 [M+H]$^+$.

Synthesis of I-414.

Compound I-414 was synthesized from 414.1 using general procedure C (Yield: 47.74%). MS(ES): m/z 458.50 [M+H]$^+$, LCMS purity: 99.46%, HPLC purity: 97.72%, Chiral HPLC Purity: 100%, 1H NMR (DMSO-d6, 400 MHz): 12.50 (s, 1H), 10.61 (s, 1H), 8.48 (s, 1H), 7.94 (s, 1H), 7.71-7.64 (m, 3H), 4.11 (s, 1H), 3.66-3.57 (m, 1H), 3.18-3.17 (s, 4H), 2.36-2.30 (m, 3H), 2.18-2.08 (m, 3H), 2.03-1.94 (m, 2H), 1.87-1.80 (m, 1H), 1.62-1.55 (d, 1H), 1.16-1.15 (m, 1H).

Example 415: Synthesis of N-(2-(difluoromethyl)-7-((4-(4,5-dimethylthiazol-2-yl)-2-(methylsulfonyl)phenyl)amino)-3H-imidazo[4,5-b]pyridin-5-yl)cyclopropanecarboxamide, I-415

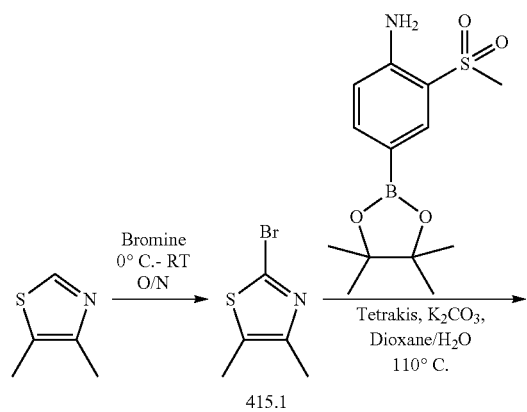

415.1

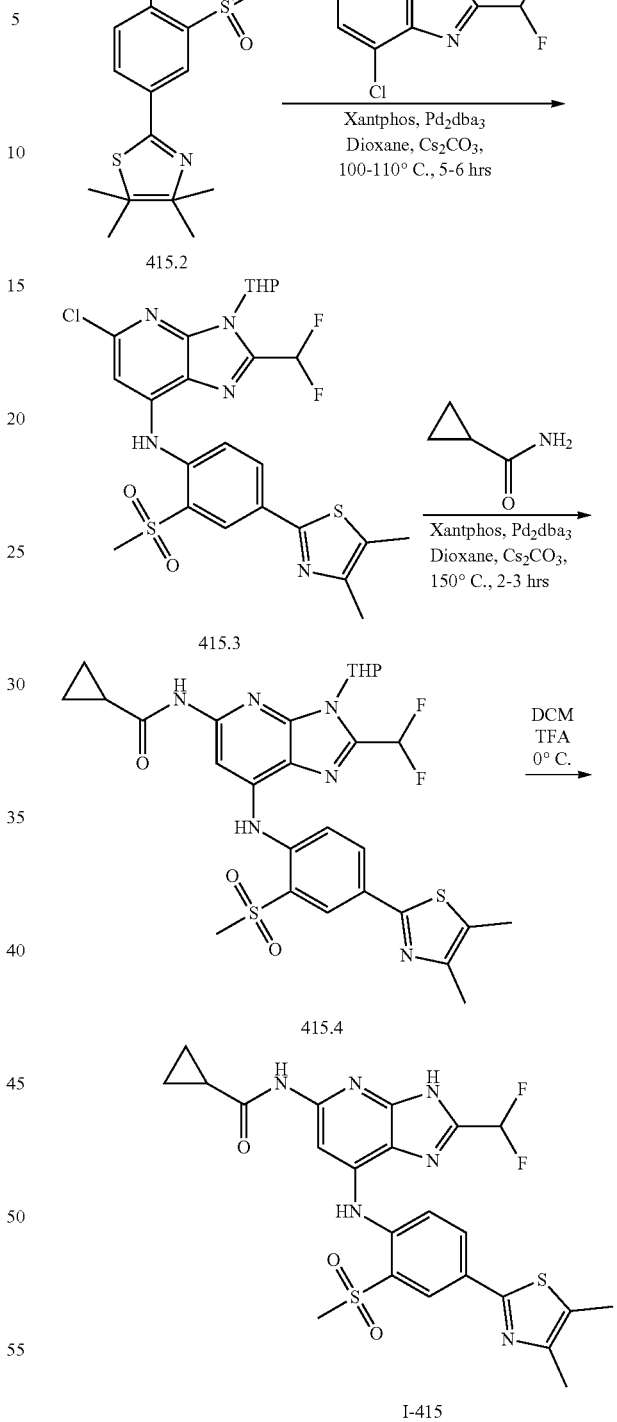

I-415

Synthesis of Compound 415.1.

To a solution of 4,5-dimethylthiazole (5 g, 44.23 mmol, 1.0 eq) in CH$_2$Cl$_2$ (20 mL) at 0° C., bromine solution (3.5 mL, 221.2 mmol, 5.0 eq) was added. Reaction mixture was stirred at r.t. for 24 h. After completion of the reaction, the reaction mixture was quenched using sodium thiosulphate solution, transferred into water and extracted with CH$_2$Cl$_2$. Organic layer combined, dried over anhydrous Na$_2$SO$_4$, filtered and concentrated in vacuo to obtain 415.1 (2.0 g, 23.57%). MS(ES): m/z 193.58 [M+H]⁺.

Synthesis of Compound 415.2.

To compound 415.1 (2 g, g, 8.3 mmol, 1.0 eq) in a mixture of 1,4-dioxane (16 mL) and water (4 mL), compound 246.1a (2.97 g, 10.2 mmol, 1.2 eq) and potassium carbonate (3.4 g, 24.9 mmol, 3.0 eq) was added. Reaction mixture was degassed by argon for 15 min. Then, tetrakis(triphenylphosphine)palladium(0) (1.9 g, 1.6 mmol, 0.2 eq) was added and again degassed for 5 min. After completion of the reaction, the reaction mixture was transferred into water and extracted with ethyl acetate. Organic layer combined, dried over anhydrous Na₂SO₄, filtered and concentrated in vacuo to obtain the crude material. This was purified by column chromatography using 13% ethyl acetate in hexane to obtain pure 415.2 (1.0 g, 34.01%). MS(ES): m/z 283.47 [M+H]⁺.

Synthesis of Compound 415.3.

Compound 415.3 was synthesized from 415.2 and 13.4 using general procedure A. (Yield: 47.14%). MS(ES): m/z 193.25 [M+H]⁺.

Synthesis of Compound 415.4.

Compound 415.4 was synthesized from 415.3 and cyclopropanecarboxamide using general procedure B. (Yield: 55.72%). MS(ES): m/z 617.57 [M+H]⁺.

Synthesis of I-415.

Compound I-415 was synthesized 415.4 from using general procedure C. (Yield: 67.55%). MS(ES): m/z 533.69 [M+H]⁺, LCMS purity: 100%, HPLC purity: 100%, 1H NMR (DMSO, 400 MHz): 13.75 (s, 1H), 10.80 (s, 1H), 8.89 (s, 1H), 8.38 (s, 1H), 8.15-8.12 (m, 2H), 7.87-7.84 (m, 1H), 7.24 (s, 1H), 3.31 (s, 3H), 2.42-2.35 (d, J=27.2 Hz, 6H), 2.05-2.03 (t, 1H), 0.81 (s, 4H).

Example 416: Synthesis of N7-(4-cyclopropyl-2-(methylsulfonyl)phenyl)-2-(difluoromethyl)-N5-(2, 6-dimethylpyrimidin-4-yl)-3H-imidazo[4,5-b]pyridine-5,7-diamine, I-416

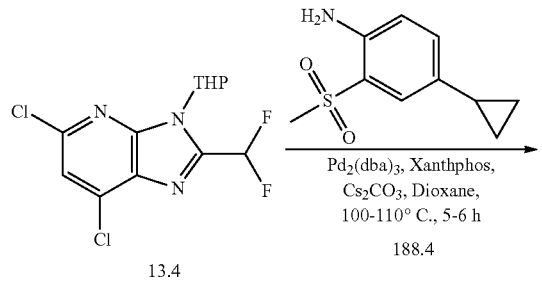

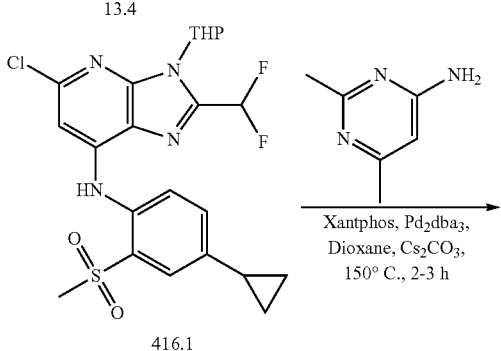

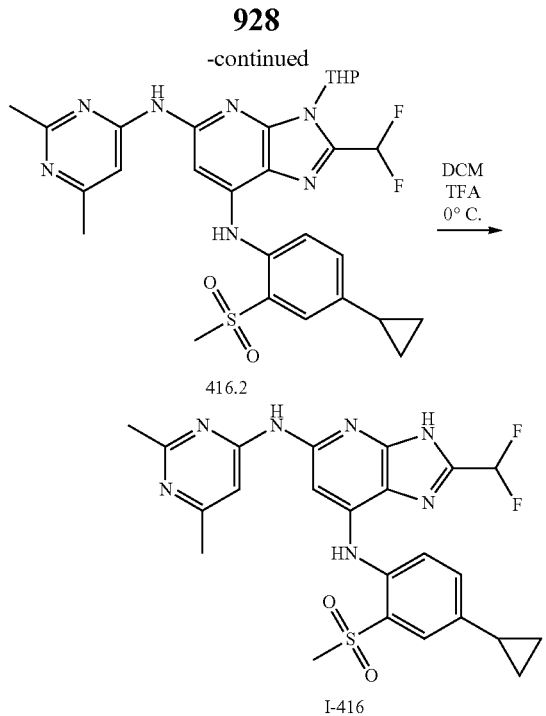

Synthesis of Compound 416.1.

Compound 416.1 was synthesized from 188.4 And 13.4 using general procedure A. (Yield: 21.20%). MS(ES): m/z 497.96 [M+H]⁺.

Synthesis of Compound 416.2.

Compound 416.2 was synthesized from 416.1 and 2,6-dimethylpyrimidin-4-amine using general procedure B. (Yield: 41.86%). MS(ES): m/z 584.43 [M+H]⁺.

Synthesis of I-416.

Compound I-416 was synthesized from 416.2 using general procedure C. (Yield: 49.50%). MS(ES): m/z 500.63 [M+H]⁺, LCMS purity: 96.02%, HPLC purity: 96.07%, 1H NMR (DMSO-d6, 400 MHz): 13.61 (s, 1H), 9.98 (s, 1H), 8.72 (s, 1H), 7.77-7.74 (d, J=8.4 Hz, 1H), 7.66 (s, 1H), 7.56-7.47 (m, 3H), 7.22 (t, J=2.4 Hz, 1H), 3.20 (s, 3H), 2.39 (s, 3H), 2.31 (s, 3H), 2.11-2.09 (t, J=9.6 Hz, 1H), 1.05-1.03 (d, J=6.4 Hz, 2H), 0.75-0.74 (m, 2H).

Example 417: Synthesis of N7-(4-cyclopropyl-2-(methylsulfonyl)phenyl)-2-(difluoromethyl)-N5-(5, 6-dimethylpyrazin-2-yl)-3H-imidazo[4,5-b]pyridine-5,7-diamine, I-417

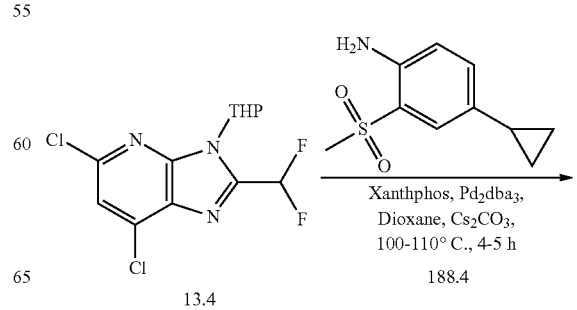

929

-continued

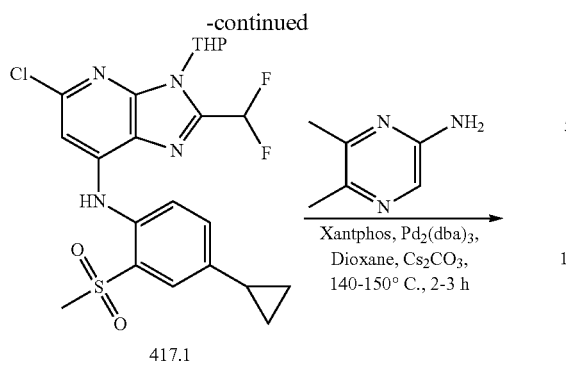

417.1

Xantphos, Pd₂(dba)₃,
Dioxane, Cs₂CO₃,
140-150° C., 2-3 h

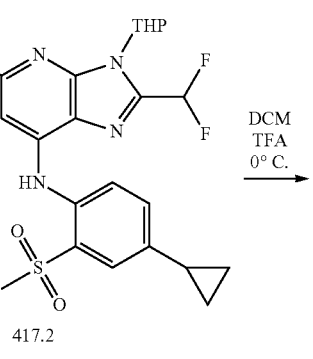

417.2

DCM
TFA
0° C.

I-417

Synthesis of Compound 417.1.

Compound 417.1 was synthesized from 13.4 and 188.4 using general procedure A. (Yield: 42.42%). MS(ES): m/z 461.98 [M+H]⁺.

Synthesis of Compound 417.2.

Compound was synthesized from 417.1 and 5,6-dimethylpyrazin-2-amine using general procedure B. (Yield: 38.32%). MS(ES): m/z 584.66 [M+H]⁺.

Synthesis of I-417.

Compound I-471 was synthesized from 417.2 using general procedure C. (Yield: 56.26%). MS(ES): m/z 500.63 [M+H]⁺, LCMS purity: 99.13%, HPLC purity: 99.62%, 1H NMR (DMSO-d6, 400 MHz): 9.72 (s, 1H), 8.95 (s, 1H), 8.63 (s, 1H), 8.40 (s, 1H), 7.76-7.74 (d, J=8.4 Hz, 1H), 7.65 (s, 1H), 7.48-7.45 (d, J=1.2 Hz, 1H), 7.40 (s, 1H), 3.19 (s, 3H), 2.38 (s, 3H), 2.35 (s, 3H), 2.12-2.08 (m, 1H), 1.12-1.08 (s, 2H), 1.05 (s, 1H), 1.03-1.02 (d, J=0.6 Hz, 2H).

930

Example 418: Synthesis of N-(2-(difluoromethyl)-7-((4-(5-methylfuran-2-yl)-2-(methylsulfonyl)phenyl)amino)-3H-imidazo[4,5-b]pyridin-5-yl)cyclopropanecarboxamide, I-418

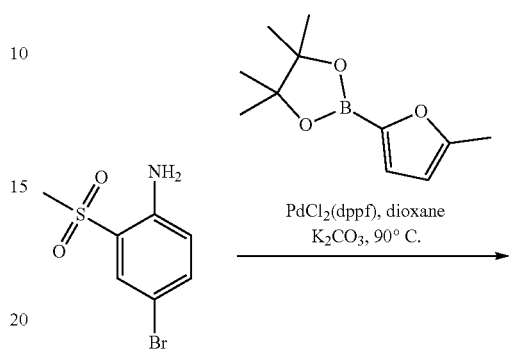

PdCl₂(dppf), dioxane
K₂CO₃, 90° C.

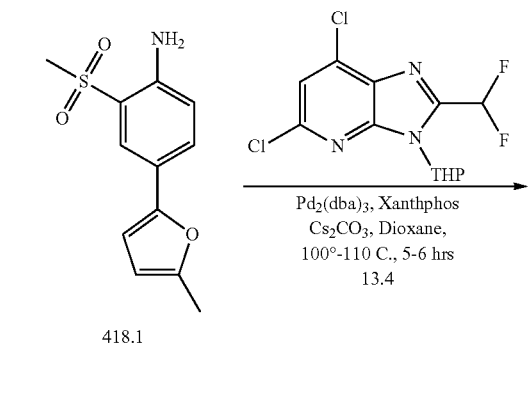

418.1

Pd₂(dba)₃, Xanthphos
Cs₂CO₃, Dioxane,
100°-110 C., 5-6 hrs
13.4

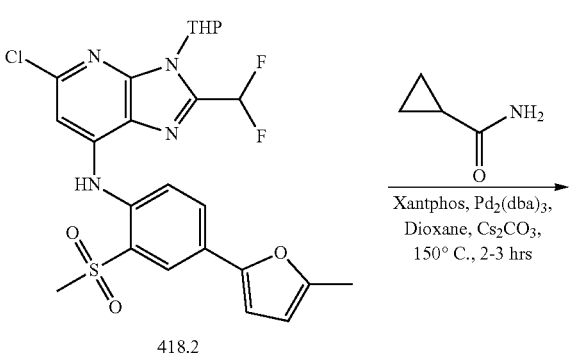

418.2

Xantphos, Pd₂(dba)₃,
Dioxane, Cs₂CO₃,
150° C., 2-3 hrs

931

-continued

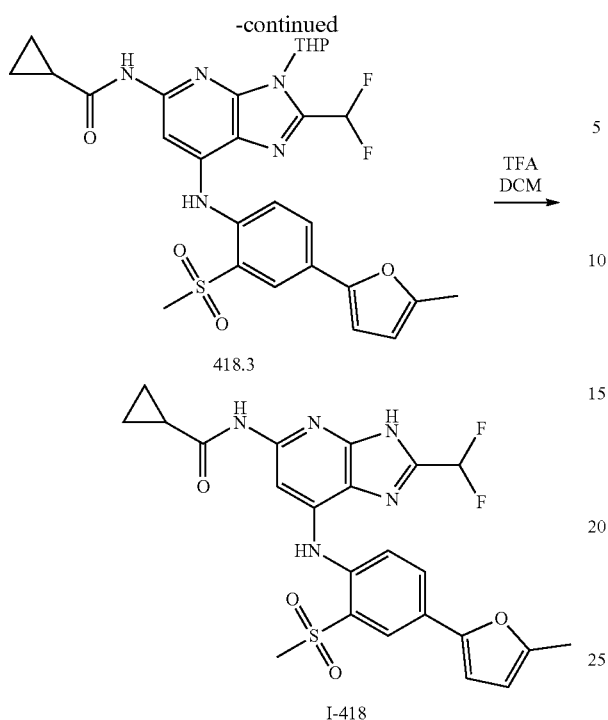

418.3

I-418

Synthesis of Compound 418.1.

To compound 4-bromo-2-(methylsulfonyl)aniline (1.0 g, 4.01 mmol, 1.0 eq) in dioxane (10 mL), compound 4,4,5,5-tetramethyl-2-(5-methylfuran-2-yl)-1,3,2-dioxaborolane (0.990 g, 4.01 mmol, 1.0 eq) was added. Reaction mixture was degassed with argon atmosphere for 10 min. Then [1,1′-Bis(diphenylphosphino) ferrocene]palladium(II)dichloride (0.249 g, 0.40 mmol, 0.1 eq) and potassium carbonate (0.480 g, 8.02 mmol, 2 eq) was added into it. Reaction mixture was stirred at 90° C. for 24 h. Upon completion, reaction mixture was transferred into cold water and extracted with ethyl acetate. Organic layer combined, dried over $Na_2SO_4$ and concentrated in vacuo to obtain crude product. This was purified by column chromatography and compound was eluted in 3% MeOH in $CH_2Cl_2$ as eluant to obtain pure 418.1 (0.900 g, 89.57%). MS(ES): m/z 252.30 [M+H]$^+$.

Synthesis of Compound 418.2

Compound 418.2 was synthesized using from 418.1 and 13.4 general procedure A. (Yield: 13.37%). MS(ES): m/z 537.98 [M+H]$^+$.

Synthesis of Compound 418.3.

Compound 418.3 was synthesized from 418.2 and cyclopropanecarboxamide using general procedure B. (Yield: 59.60%). MS(ES): m/z 586.63 [M+H]$^+$.

Synthesis of I-418.

Compound I-418 was synthesized from 418.3 using general procedure C. (Yield: 71.86%). MS(ES): m/z 502.58 [M+H]$^+$, LCMS purity: 95.83%, HPLC purity: 97.21%, 1H NMR (DMSO, 400 MHz): 13.70 (s, 1H), 10.72 (s, 1H), 8.75 (s, 1H), 8.10-8.01 (m, 3H), 7.82-7.80 (d, J=8.8 Hz, 1H), 7.20 (t, 1H), 6.97 (s, 1H), 6.26 (s, 1H), 3.26 (s, 3H), 2.39 (s, 3H), 2.04 (s, 1H), 0.79 (bs, 4H).

932

Example 419: Synthesis of N-(2-methyl-7-((4-(5-methylfuran-2-yl)-2-(methylsulfonyl)phenyl)amino)-3H-imidazo[4,5-b]pyridin-5-yl)cyclopropanecarboxamide, I-419

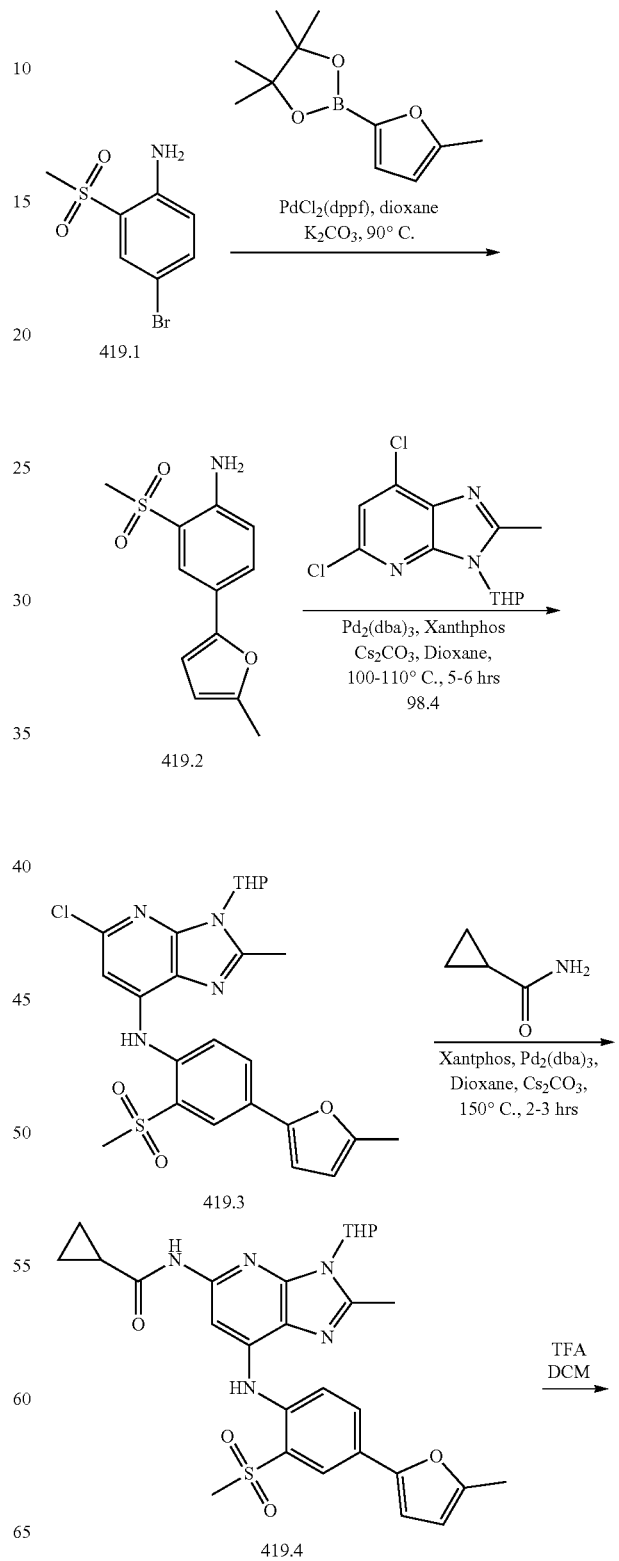

419.1

419.2

419.3

419.4

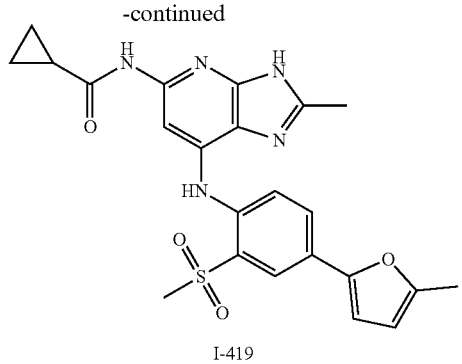

I-419

Synthesis of Compound 419.1.

Compound 419.1 was synthesized as per 1-388.

Synthesis of Compound 419.2.

To compound 419.1 (1 g, 4 mmol, 1.0 eq) in 1,4-dioxane (10 mL), 4,4,5,5-tetramethyl-2-(5-methylfuran-2-yl)-1,3,2-dioxaborolane 1.1 (0.915 g, 4.4 mmol, 1.1 eq) was added. Reaction mixture was degassed using argon for 15 min. Then, potassium carbonate (1.65 g, 12.0 mmol, 3.0 eq) and (1,1'-Bis (diphenylphosphino)ferrocene)palladium(II) dichloride (0.65 g, 0.8 mmol, 0.2 eq) was added. Reaction mixture was stirred at 90° C. for 3 h. After completion of the reaction, reaction mixture was transferred into water and extracted by ethyl acetate. Organic layer combined, dried over Na$_2$SO$_4$, filtered and concentrated in vacuo to obtain the crude material. This was purified by column chromatography using 10% ethyl acetate in hexane to obtain pure 419.2 (0.9 g, 89.57%). MS(ES): m/z 252.07 [M+H]$^+$.

Synthesis of Compound 419.3.

Compound 419.3 was synthesized from 419.2 and 98.4 using general procedure A. (Yield: 21.69%). MS(ES): m/z 502.00 [M+H]$^+$.

Synthesis of Compound 419.4.

Compound 419.4 was synthesized from 418.3 and cyclopropanecarboxamide using general procedure B. (Yield: 42.73%). MS(ES): m/z 550.65 [M+H]$^+$.

Synthesis of I-419.

Compound I-419 was synthesized from 418.4 using general procedure C. (Yield: 70.84%). MS(ES): m/z 466.50 [M+H]$^+$, LCMS purity: 98.69%, HPLC purity: 97.38%, 1H NMR (DMSO, 400 MHz): 12.55 (s, 1H), 10.61 (s, 1H), 8.62 (s, 1H), 8.09-7.99 (m, 3H), 7.78-7.76 (d, J=8.4 Hz, 1H), 6.94 (s, 1H), 6.25 (s, 1H), 3.25 (s, 3H), 2.51 (s, 3H), 2.38 (s, 3H), 2.01-1.99 (t, J=5.2 Hz, 1H), 0.78 (bs, 4H).

Example 420: N-(2-(difluoromethyl)-7-((4-(4,5-dimethylfuran-2-yl)-2-(methylsulfonyl)phenyl)amino)-3H-imidazo[4,5-b]pyridin-5-yl)cyclopropanecarboxamide, I-420

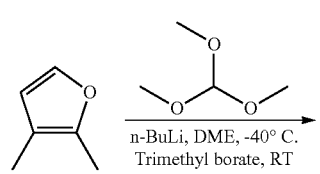

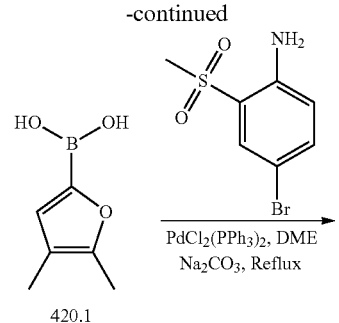

420.1

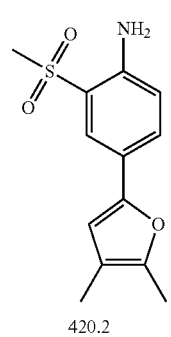

420.2

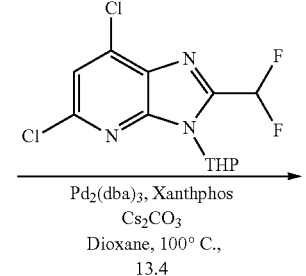

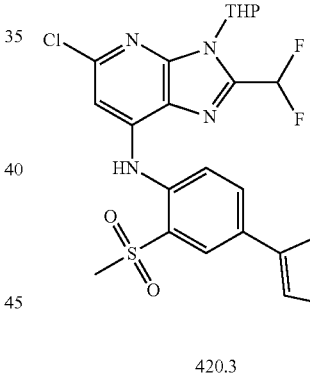

420.3

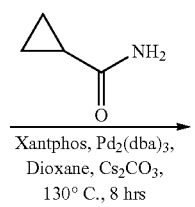

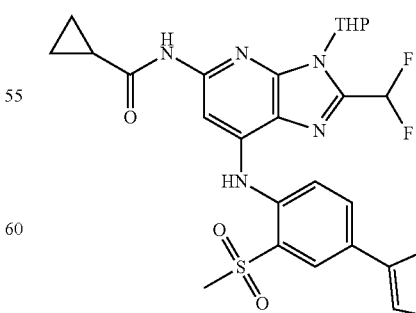

420.4

935

-continued

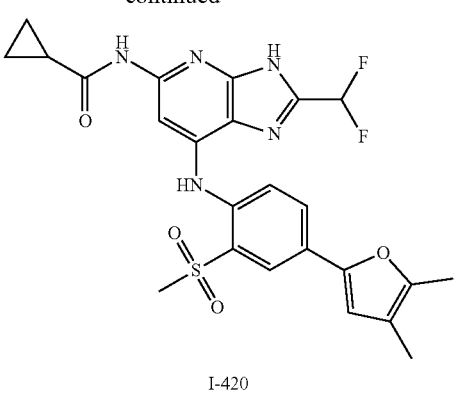

I-420

Synthesis of Compound 420.1.

To a solution of 2,3-dimethylfuran (1.0 g, 10.40 mmol, 1.0 eq) in dimethoxyethane (10 mL) was added n-butyl lithium (5 mL, 12.48 mmol, 1.2 eq) at −78° C. and stirred the reaction mixture at r.t. for 3 h. Reaction mixture again cooled at −78° C. and trimethylborate (1.3 g, 12.48 mmol, 1.2 eq) was added. Reaction mixture was stirred at r.t. for 20 h. Upon completion, reaction mixture was transferred into aqueous solution of potassium carbonate and stirred for 1 h. Solvent was concentrated in vacuo to obtain crude 420.1 (1.0 g, 68.69%). MS(ES): m/z 140.95 [M+H]$^+$.

Synthesis of Compound 420.2.

To a solution of 4-bromo-2-(methylsulfonyl) aniline (1.49 g, 7.15 mmol, 1.2 eq) and 420.1 (1.0 g, 5.95 mmol, 1.0 eq) in dimethoxyethane (10 mL) was added sodium carbonate (1.25 g, 11.9 mmol, 2.0 eq). The reaction mixture was degassed for 10 min. under argon atmosphere. The Bis (triphenylphosphine)palladium chloride (0.417 g, 0.595 mmol, 0.1 eq) was added, again reaction mixture was degassed for 10 min. under argon atmosphere. The reaction was stirred at 100° C. for 3 h. Upon completion, reaction mixture was transferred in water and extracted with ethyl acetate. Combined organic layer was washed with brine, dried over Na$_2$SO$_4$ and concentrated in vacuo to obtain crude product. This was purified by column chromatography using 20% ethyl acetate in hexane to obtain pure 420.2 (0.410 g, 25.95%). MS(ES): m/z 266.33 [M+H]$^+$.

Synthesis of Compound 420.3.

Compound 420.3 was synthesized from 420.2 and 13.4 using general procedure A. (Yield: 31.30%). MS(ES): m/z 552.01 [M+H]$^+$.

Synthesis of Compound 420.4.

Compound 420.4 was synthesized from 420.3 and cyclopropanecarboxamide using general procedure B. (Yield: 56.55%). MS(ES): m/z 600.65 [M+H]$^+$.

Synthesis of I-420.

Compound I-420 was synthesized from 420.4 using general procedure C. (Yield: 58.16%). MS(ES): m/z 516.51 [M+H]$^+$, LCMS purity: 100%, HPLC purity: 95.12%, 1H NMR (DMSO, 400 MHz): 13.70 (s, 1H), 10.78 (s, 1H), 8.79 (s, 1H), 8.07 (s, 1H), 8.00-7.98 (d, J=8.4 Hz, 1H), 7.80-7.78 (d, J=8.4 Hz, 1H), 7.26 (t, 1H), 6.89 (s, 1H), 3.26 (s, 3H), 2.30 (s, 3H), 2.02 (m, 1H) 1.98 (s, 3H), 0.80-0.78 (d, 4H).

936

Example 421 Synthesis of N-(7-((4-(4,5-dimethyl-furan-2-yl)-2-(methylsulfonyl)phenyl)amino)-2-methyl-3H-imidazo[4,5-b]pyridin-5-yl)cyclopropanecarboxamide, I-421

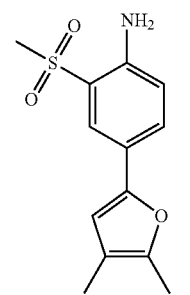

98.4

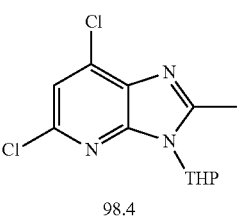

Pd$_2$(dba)$_3$, Xanthphos, Cs$_2$CO$_3$ Dioxane
100° C.-110° C., 2-3 h
420.2

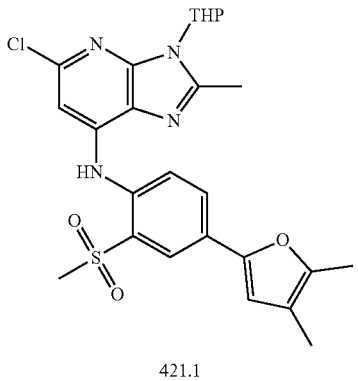

421.1

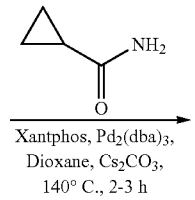

Xantphos, Pd$_2$(dba)$_3$,
Dioxane, Cs$_2$CO$_3$,
140° C., 2-3 h

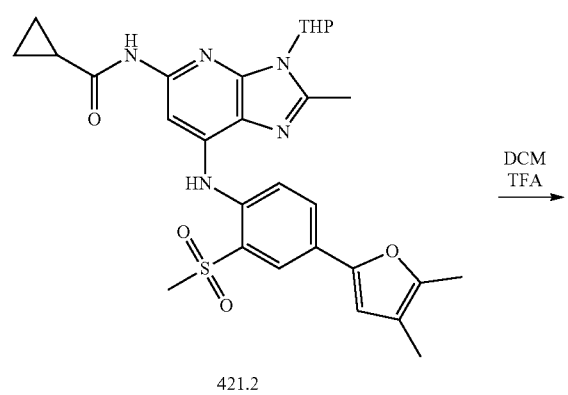

421.2

DCM
TFA

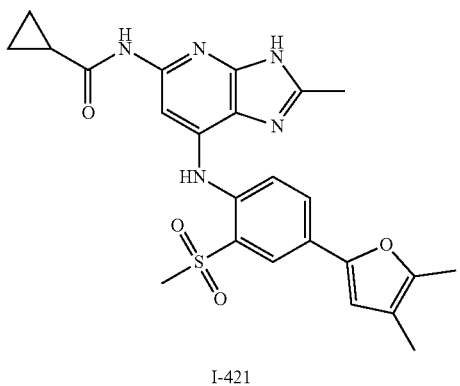 [SMILES: Cc1cc(-c2ccc(Nc3cc(NC(=O)C4CC4)nc4[nH]c(C(F)F)nc34)c(S(C)(=O)=O)c2)oc1C]

I-421

Synthesis of Compound 421.1.

Compound 421.1 was synthesized from 98.4 and 420.2 using general procedure A. (Yield: 42.66%). MS(ES): m/z 516.03 [M+H]⁺.

Synthesis of Compound 421.2.

Compound 421.2 was synthesized from 421.1 and cyclopropanecarboxamide using general procedure B. (Yield: 54.96%). MS(ES): m/z 564.67 [M+H]⁺.

Synthesis of I-421.

Compound I-421 was synthesized from 421.2 using general procedure C. (Yield: 51.42%). MS(ES): m/z 480.20 [M+H]⁺, LCMS purity: 100%, HPLC purity: 95.12%, 1H NMR (DMSO, 400 MHz): 12.51 (s, 1H), 10.61 (s, 1H), 8.79 (s, 1H), 8.04-7.95 (dd, J=38.4 Hz, 2H), 7.78-7.76 (d, J=8.4 Hz, 1H), 6.85 (s, 1H), 3.24 (s, 3H), 2.49 (s, 3H), 2.29 (s, 3H), 1.98 (s, 3H), 0.78 (bs, 4H).

Example 422/423: Synthesis of (S)-2,2-difluoro-N-(2-methyl-7-((2-(methylsulfonyl)-4-((R)-tetrahydrofuran-2-yl)phenyl)amino)-3H-imidazo[4,5-b]pyridin-5-yl)cyclopropane-1-carboxamide, I-422 and (R)-2,2-difluoro-N-(2-methyl-7-((2-(methylsulfonyl)-4-((R)-tetrahydrofuran-2-yl)phenyl)amino)-3H-imidazo[4,5-b]pyridin-5-yl)cyclopropane-1-carboxamide, I-423

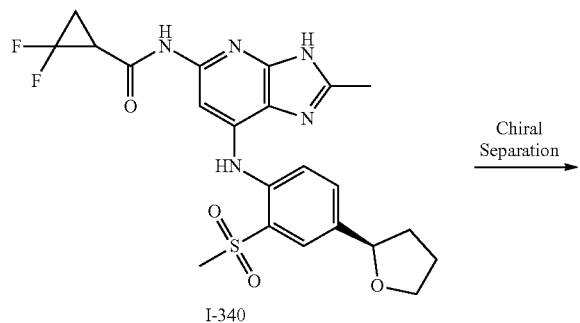

I-340

Chiral Separation →

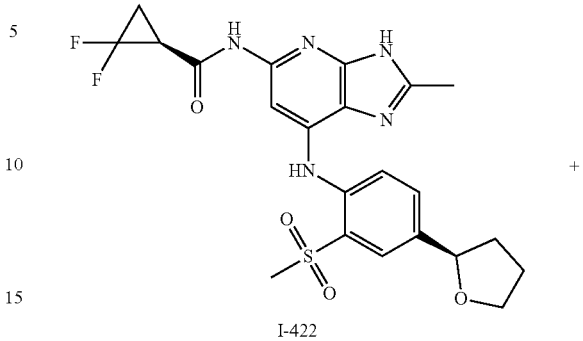

I-422

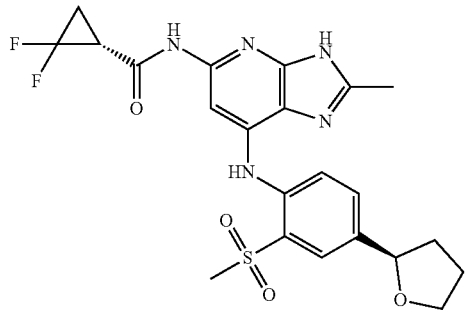

I-423

Synthesis of Compound I-422 and I-423.

Isomers of I-340 (0.090 g) were separated out using column (CHIRALCEL OX-H 250×4.6 mm, 5 μM) 0.1% DEA in MeOH as co-solvent with flow rate of 4 mL/min. to get pure fraction-1 (FR-a) and fraction-2 (FR-b). FR-a was concentrated in vacuo at 30° C. to afford pure I-422 (0.027 g). MS(ES): m/z 492.56 [M+H]⁺, LCMS purity: 100%, HPLC purity: 100%, Chiral HPLC: 100%, 1H NMR (DMSO, 400 MHz): 12.58 (s, 1H), 10.82 (s, 1H), 8.58 (s, 1H), 7.94 (s, 1H), 7.85 (s, 1H), 7.74-7.68 (m, 2H), 4.91-4.87 (t, J=14.4 Hz, 1H), 4.04-4.00 (m, 1H), 3.87-3.82 (m, 1H), 3.20 (s, 3H), 2.498 (s, 3H), 2.39-2.35 (m, 2H), 2.00-1.97 (t, J=12 Hz, 4H), 1.75-1.66 (m, 1H). FR-b was concentrated in vacuo at 30° C. to afford pure I-423 (0.025 g). MS(ES): m/z 492.61 [M+H]⁺, LCMS purity: 99.39%, HPLC purity: 100%, Chiral HPLC: 95.57%, 1H NMR (DMSO, 400 MHz): 12.59 (s, 1H), 10.82 (s, 1H), 8.57 (s, 1H), 7.94 (s, 1H), 7.85 (s, 1H), 7.76-7.68 (q, 2H), 4.91-4.87 (t, J=14.4 Hz, 1H), 4.06-4.00 (m, 1H), 3.87-3.82 (m, 1H), 3.46 (s, 3H), 3.20 (s, 3H), 3.01-2.96 (m, 1H), 2.41-2.35 (m, 1H), 2.02-1.95 (m, 3H), 1.73-1.66 (m, 1H), 1.24 (s, 1H).

Example 424 and 425: Synthesis of (S)—N-(2-(difluoromethyl)-7-((2-(methylsulfonyl)-4-(tetrahydrofuran-2-yl)phenyl)amino)-3H-imidazo[4,5-b]pyridin-5-yl)cyclopropanecarboxamide, I-424 and (R)—N-(2-(difluoromethyl)-7-((2-(methylsulfonyl)-4-(tetrahydrofuran-2-yl)phenyl)amino)-3H-imidazo[4,5-b]pyridin-5-yl)cyclopropanecarboxamide, I-425

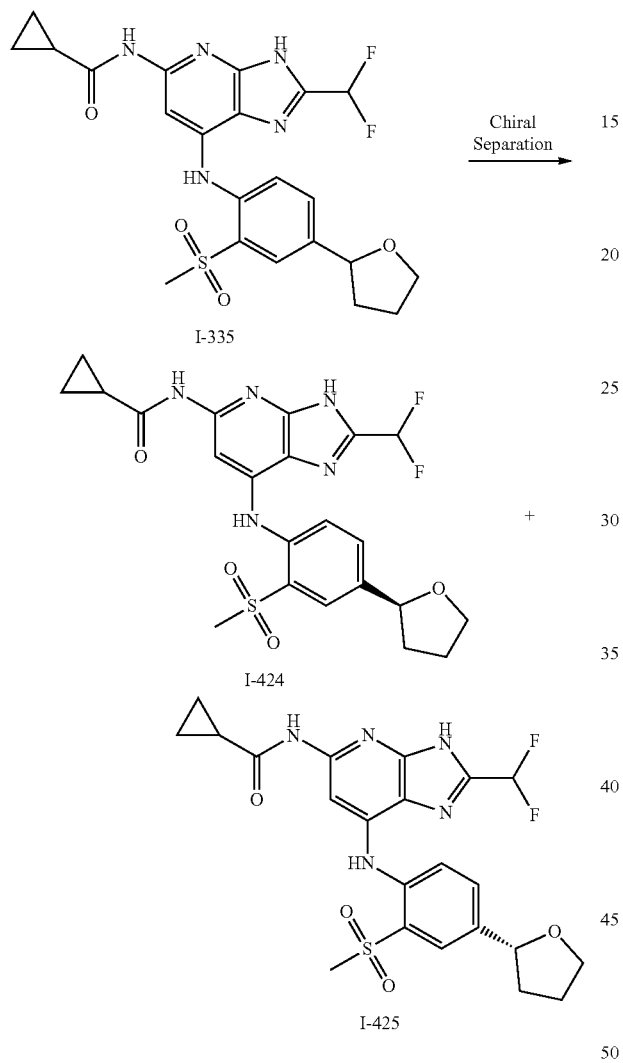

Synthesis of Compound I-424 & I-425.

Isomers of I-335 (0.070 g) were separated out using column (CHIRALCEL OJ-H (250 mm*4.6 mm, 5u) and 0.1% DEA IPA:MEOH (50:50) flow rate of 4 mL/min. to get pure fraction-1 (FR-a) and fraction-2 (FR-bFR-a was concentrated in vacuo at 30° C. to afford pure I-424 (0.025 g). MS(ES): m/z 492.83 [M+H]$^+$, LCMS purity: 97.85%, HPLC purity: 96.92%, Chiral HPLC: 98.65%, 1H NMR (DMSO-d6, 400 MHz): 13.68 (s, 1H), 10.75 (s, 1H), 8.70 (s, 1H), 8.04 (s, 1H), 7.87 (s, 1H), 7.77-7.69 (q, 2H), 7.24 (t, 1H), 4.92-4.88 (t, J=14.4 Hz, 1H), 4.06-4.01 (m, 1H), 3.88-3.82 (m, 1H), 3.09 (s, 3H), 2.42-2.34 (m, 1H), 2.05-1.97 (m, 3H), 1.74-1.69 (m, 1H), 0.79-0.78 (m, 4H). FR-b was concentrated in vacuo at 30° C. to afford pure I-425 (0.020 g). MS(ES): m/z 492.83 [M+H]$^+$, LCMS purity: 99.34%, HPLC purity: 99.48%, Chiral HPLC: 99.41%, 1H NMR (DMSO-d6, 400 MHz): 13.66 (s, 1H), 10.73 (s, 1H), 8.69 (s, 1H), 8.04 (s, 1H), 7.87 (s, 1H), 7.77-7.70 (q, 2H), 4.92-4.89 (t, J=14.4 Hz, 1H), 4.06-4.01 (m, 1H), 3.88-3.83 (m, 1H), 3.21 (s, 3H), 2.40-2.34 (m, 1H), 2.03-1.96 (m, 3H), 1.74-1.69 (m, 1H), 1.25 (s, 1H), 0.79-0.78 (m, 4H).

Example 426/427 Synthesis of (S)-2,2-difluoro-N-(2-methyl-7-((2-(methylsulfonyl)-4-((S)-tetrahydrofuran-2-yl)phenyl)amino)-3H-imidazo[4,5-b]pyridin-5-yl)cyclopropane-1-carboxamide, I-426 and (R)-2,2-difluoro-N-(2-methyl-7-((2-(methylsulfonyl)-4-((S)-tetrahydrofuran-2-yl)phenyl)amino)-3H-imidazo[4,5-b]pyridin-5-yl)cyclopropane-1-carboxamide

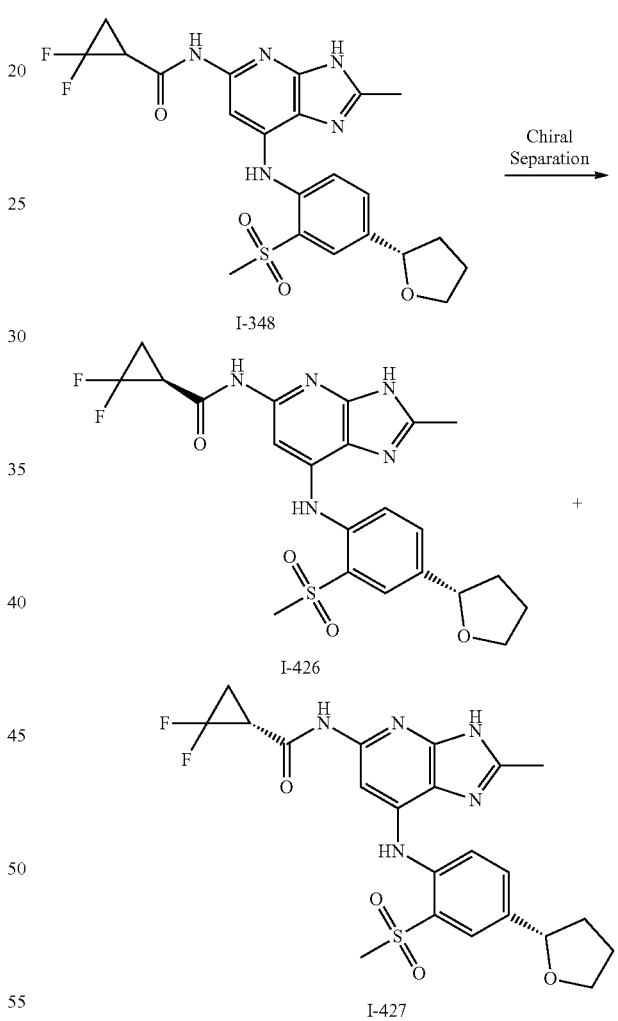

Synthesis of Compound I-426 and I-427.

Isomers of I-348 (0.085 g) were separated out using column (CHIRALCEL OX-H (250 mm*4.6 mm, 5u)) and 0.1% DEA MEOH flow rate of 4 mL/min. to get pure fraction-1 (FR-a) and fraction-2 (FR-b). FR-a was concentrated in vacuo at 30° C. to afford pure I-426 (0.027 g). MS(ES): m/z 492.51 [M+H]$^+$, LCMS purity: 97.97%, HPLC purity: 99.32%, Chiral HPLC: 99.41%, 1H NMR (DMSO, 400 MHz): 12.57 (s, 1H), 10.81 (s, 1H), 8.58 (s, 1H), 7.94 (s, 1H), 7.85 (s, 1H), 7.76-7.68 (q, 2H), 4.91-4.87 (t, J=14.4

Hz, 1H), 4.06-4.00 (m, 1H), 3.87-3.82 (m, 1H), 3.20 (s, 3H), 3.18-3.17 (m, 1H), 2.99-2.94 (m, 1H), 2.49 (s, 3H), 2.41-2.33 (m, 1H), 2.00-1.97 (t, J=14 Hz, 4H) FR-b was concentrated in vacuo at 30° C. to afford pure I-427 (0.026 g). MS(ES): m/z 492.56 [M+H]$^+$, LCMS purity: 99.47%, HPLC purity: 99.44%, Chiral HPLC: 99.47%, 1H NMR (DMSO, 400 MHz): 12.57 (s, 1H), 10.83 (s, 1H), 8.58 (s, 1H), 7.95 (s, 1H), 7.85 (s, 1H), 7.76-7.68 (q, 2H), 4.91-4.87 (t, J=14.4 Hz, 1H), 4.05-4.00 (m, 1H), 3.87-3.82 (m, 1H), 3.20 (s, 3H), 3.18-3.17 (m, 1H), 2.99-2.96 (m, 1H), 2.49 (s, 3H), 2.41-2.33 (m, 1H), 2.00-1.96 (t, J=14 Hz, 4H).
Example 428: Synthesis of (1S,2S)—N-(2-(difluoromethyl)-7-((4-(4,4-dimethyl-4,5-dihydrooxazol-2-yl)-2-(methylsulfonyl)phenyl)amino)-3H-imidazo[4,5-b]pyridin-5-yl)-2-fluorocyclopropane-1-carboxamide, I-428
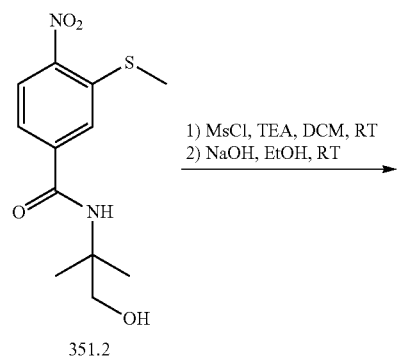
351.2
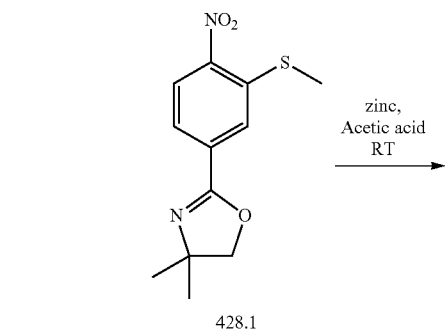
428.1
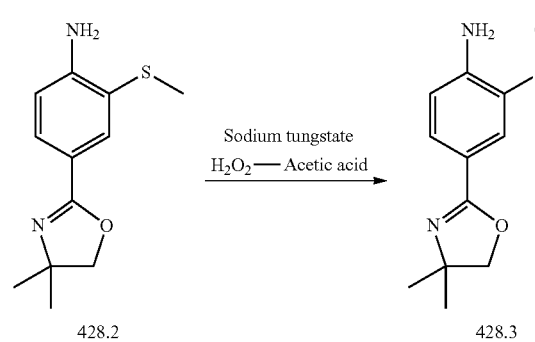
428.2    428.3
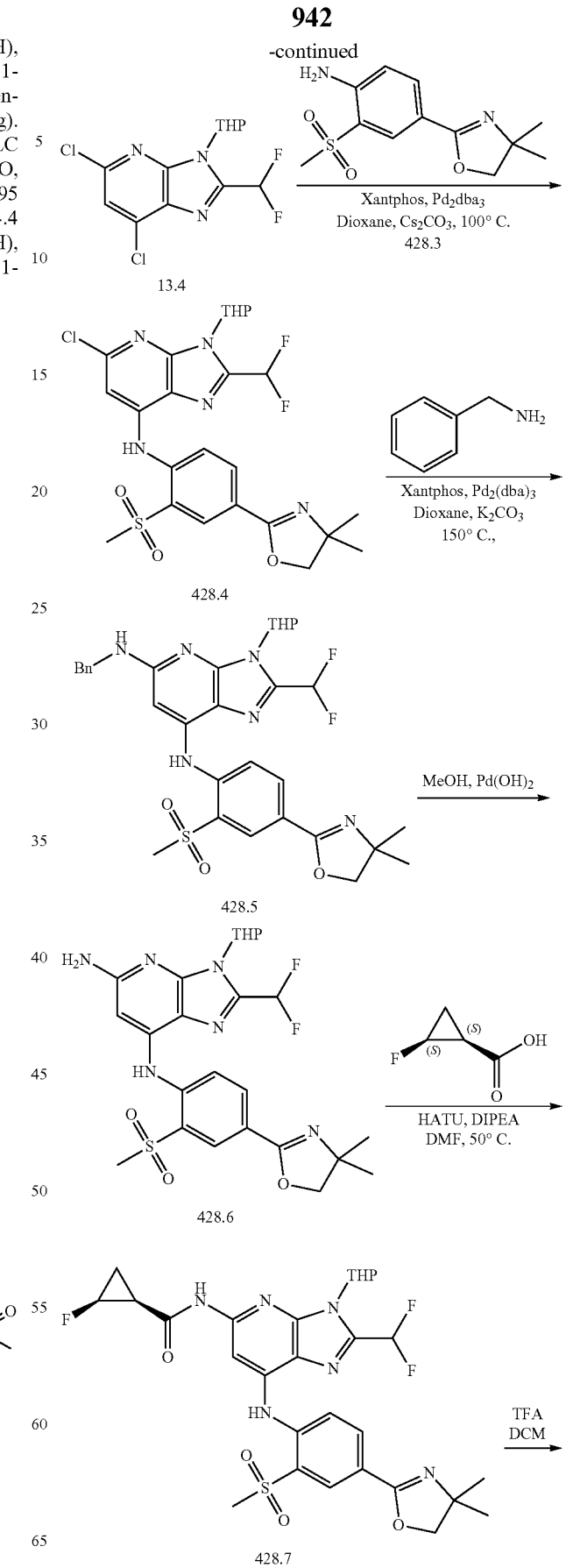

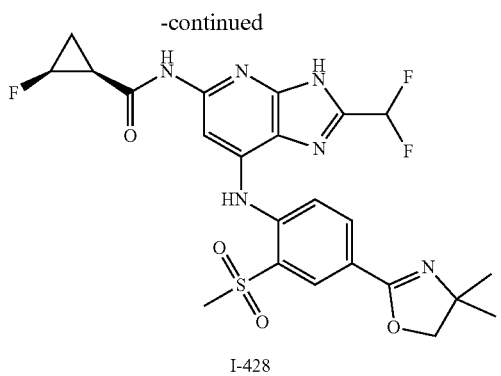

I-428

Synthesis of Compound 428.1.

To a solution of 351.2 (2 g, 7.03 mmol, 1.0 eq) in CH$_2$Cl$_2$ (50 mL) was added dropwise triethylamine (1.7 g, 16.83 mmol, 2.39 eq) and methane sulfonyl chloride (1.73 g, 15.21 mmol, 2.16 eq) was added at 0° C. Reaction mixture was stirred at r.t. for 1 h. Upon completion, reaction mixture was transferred into water and extracted with CH$_2$Cl$_2$. Organic layers were combined, dried over Na$_2$SO$_4$ and concentrated in vacuo to obtain crude product. To this crude material was added 1M sodium hydroxide (1.45 g, 35.21 mmol, 5 eq) and ethanol (20 mL). Reaction mixture was stirred at r.t. for 18 h. Upon completion, reaction mixture was transferred into water and extracted with ethyl acetate. Organic layers were combined, dried over Na$_2$SO$_4$ and concentrated in vacuo to obtain crude product. This was purified by column chromatography and compound was eluted in 30% ethyl acetate in hexane as eluent to obtain intermediate 428.1. (1.6 g, 85.41%). MS(ES): m/z 267.32 [M+H]$^+$.

Synthesis of Compound 428.2.

To a solution of 428.1 (1.6 g, 6.01 mmol, 1 eq), in Acetic acid (1.7 mL), was added zinc dust (1.98 g, 30.07 mmol, 5 eq) portion wise Reaction mixture was stirred at r.t. for 8 h. After completion of reaction, the reaction mixture was transferred into NaHCO$_3$ solution and extracted with ethyl acetate. Combined organic layer dried over Na$_2$SO$_4$ and concentrated in vacuo to obtain crude product. This was purified by column chromatography and compound was eluted in 30% ethyl acetate in hexane to obtain pure 428.2 (1.4 g, 98.60%). MS(ES): m/z 237.33 [M+H]$^+$.

Synthesis of Compound 428.3.

To a solution of 428.2 (1.4 g, 5.92 mmol, 1 eq) in acetic acid (1.6 mL) was added 30% hydrogen peroxide (4.03 g, 0.118 mmol, 20.0 eq) and sodium tungstate dihydrate (1.95 g, 5.92 mmol, 1 eq). Reaction mixture was stirred at r.t. for 2 h. Upon completion, reaction mixture was transferred in ice-water and precipitated product was filtered, washed with 50% ethyl acetate in hexane and dried well to obtain 428.3 (0.700 g, Yield: 44.04%). MS(ES): m/z 269.33 [M+H]$^+$ Synthesis of Compound 428.4.

Compound 428.4 was synthesized from 428.3 and 13.4 using general procedure A to obtain 1.5. (Yield: 31.01%). MS (ES): m/z 55.01 [M+H]$^+$.

Synthesis of Compound 428.5.

Compound was synthesized from 428.4 and benzylamine using general procedure B. (Yield: 60.97%). MS (ES): m/z 625.71 [M+H]$^+$.

Synthesis of Compound 428.6.

To a solution of 428.5 (0.220 g, 352.13 mmol, 1 eq), in MeOH (10 mL), palladium hydroxide on carbon was added at r.t. The reaction mixtures stirred at 60° C. for 30 min. Upon completion, reaction mixture was filtered on celite bed, washed with MeOH and concentrated in vacuo to obtain crude product. This was purified by column chromatography and compound was eluted in 5% MeOH in CH$_2$Cl$_2$ to obtain pure 1.7. (0.100 g, 53.12%). MS(ES): m/z 535.58 [M+H]$^+$.

Synthesis of Compound 428.7.

To a solution 428.6 and (1S,2S)-2-fluorocyclopropane-1-carboxylic acid (0.018 g, 1.82 mmol, 1.5 eq) in N,N-dimethylformamide (0.5 mL) and cooled at 0° C. Added ((1-[Bis(dimethylamino)methylene]-1H-1,2,3-triazolo[4,5-b]pyridinium 3-oxid hexafluorophosphate)) (0.092 g, 2.43 mmol, 2.0 eq) and N,N-Diisopropylethylamine (0.047 g, 3.65 mmol, 3.0 eq) and stirred the reaction mixture at 50° C. for 36 hr. Upon completion, reaction mixture was transferred into ice water and extracted with ethyl acetate. Organic layers were combined, dried over Na$_2$SO$_4$ and concentrated in vacuo to pressure to obtain crude product. This was purified by column chromatography and compound was eluted in 5% MeOH in CH$_2$Cl$_2$ to obtain pure 428.7. (0.040 g, 53.00%). MS(ES): m/z 621.65 [M+H]$^+$.

Synthesis of Compound I-428.

Compound I-428 was synthesized from 428.7 using general procedure C. (Yield: 66.64%). MS(ES): m/z 537.60 [M+H]$^+$, LCMS purity: 95.75%, HPLC purity: 96.95%, Chiral HPLC: 100%, 1H NMR (DMSO, 400 MHz): 13.79 (s, 1H), 10.90 (s, 1H), 9.00 (s, 1H), 8.34 (s, 1H), 8.20 (s, 1H), 8.14-8.12 (d, J=8.8 Hz, 1H), 7.88-7.86 (d, J=8.4 Hz, 1H), 5.02 (s, 1H), 4.85 (s, 1H), 4.17 (s, 2H), 3.30 (s, 3H), 2.25 (s, 1H), 1.62-1.61 (d, J=3.6 Hz, 1H), 1.32 (s, 6H), 1.16 (s, 1H).

Example 429: Synthesis of N-(2-(difluoromethyl)-7-((2-(dimethylphosphoryl)-4-(1-methyl-1H-pyrazol-3-yl)phenyl)amino)-3H-imidazo[4,5-b]pyridin-5-yl)cyclopropanecarboxamide, I-429

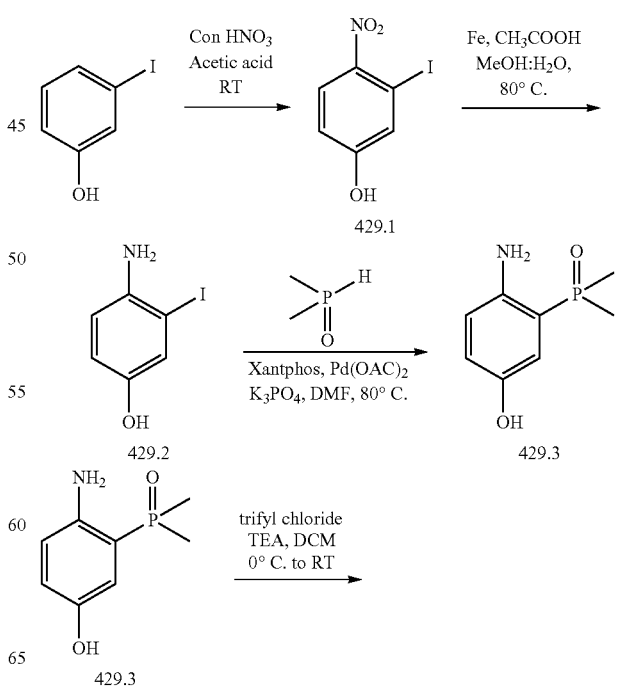

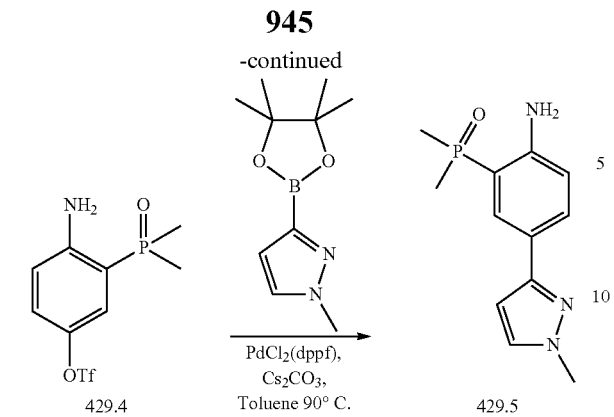

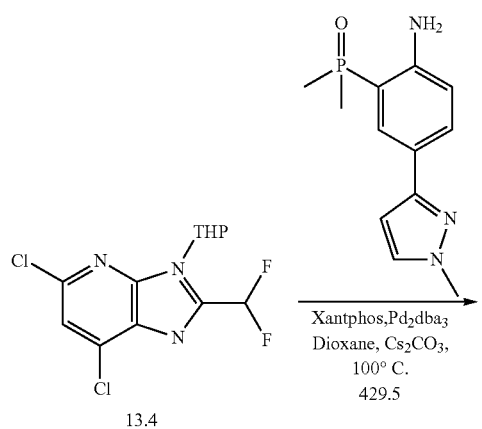

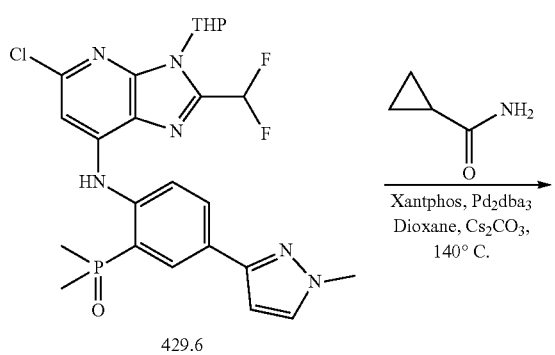

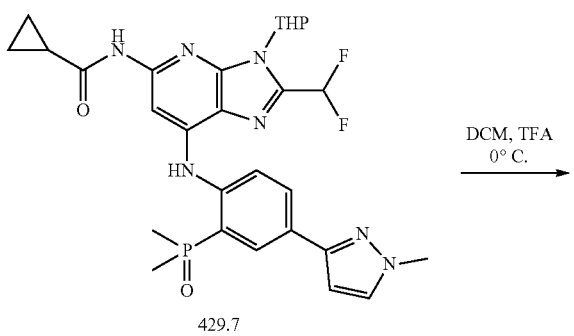

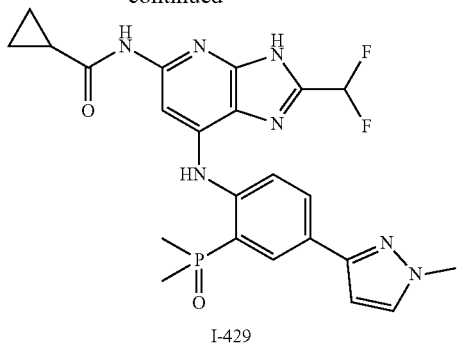

I-429

Synthesis of Compound 429.1.

To a solution of 3-iodophenol (25 g, 113.63 mmol, 1.0 eq) in acetic acid (50 mL), concentrated nitric acid (5 mL, 113.63 mmol, 1 eq) was added at r.t. Reaction mixture was stirred at r.t. for 2 h. Upon completion, reaction mixture transferred into water and extracted with ethyl acetate. Organic layer combined, dried over $Na_2SO_4$, filtered and concentrated in vacuo to obtain crude product. This was purified by column chromatography and compound was eluted in 4% MeOH in $CH_2Cl_2$ to obtain pure 429.1 (12 g, 39.85%). MS(ES): m/z 266.01 $[M+H]^+$.

Synthesis of Compound 429.2.

To a solution of 429.1 (12 g, 113.63 mmol, 1.0 eq) in mixture of MeOH (50 mL) and water (10 mL) was added acetic acid (10 mL). The reaction mixture was stirred at 50° C. for 1 h. Then added iron powder (7.49 g, 136 mmol, 1.2 eq) portion wise into the reaction mixture and stirred the reaction mixture at 80° C. for 2 h. Upon completion, reaction mixture was transferred to water and extracted with ethyl acetate. Organic layers were combined, dried over $Na_2SO_4$, filtered and concentrated in vacuo to obtain crude product. This was purified by column chromatography and compound was eluted in 15% ethyl acetate in hexane to obtain pure 429.2 (9 g, 84.57%). MS(ES): m/z 234.58 $[M+H]^+$.

Synthesis of Compound 429.3.

To a solution of 429.2 (9 g, 38.29 mmol, 1.0 eq) (0.787 g, in N,N-dimethylformamide (90 mL), dimethylphosphine oxide (4.0 g, 38.29 mmol, 1.0 eq) was added. The reaction mixture was degassed with argon for 30 min. Then, palladium (II) acetate (0.230 g, 3.15 mmol, 0.1 eq) and potassium phosphate (1.5 g, 4.7 mmol, 1.5 eq,) were added and the reaction mixture was again degassed with argon for 30 min. Further, reaction mixture was stirred at 80° C. for 5 h. Upon completion, reaction mixture was transferred into water and extracted with ethyl acetate. Organic layers were combined, dried over $Na_2SO_4$, filtered and concentrated in vacuo to obtain crude product. This was purified by column chromatography and compound was eluted in 3.5% MeOH in $CH_2Cl_2$ to obtain pure 429.3 (5.2 g, 70.52%). MS(ES): m/z 186.51 $[M+H]^+$.

Synthesis of Compound 429.4.

To a solution of 429.3 (5.2 g, 28.08 mmol, 1.0 eq) in $CH_2Cl_2$ (50 mL), triethylamine (5.7 g, 56.21 mmol, 2 eq) was added at 0° C. Then, trifluoromethanesulphonyl chloride (5.14 g, 34.28 mmol, 1.2 eq) was added dropwise at 0° C. Reaction mixture stirred at r.t. for 1 hr. Upon completion, reaction mixture transferred into water and extracted with $CH_2Cl_2$. Organic layers were combined, dried over $Na_2SO_4$ and concentrated in vacuo to obtain crude product. This was purified by column chromatography and compound was eluted in 4% MeOH in CH$_2$Cl$_2$ to obtain pure 429.4 (1.6 g, 17.96%). MS(ES): m/z 318.22 [M+H]$^+$.

Synthesis of Compound 429.5.

To a solution of 429.4 (1 g, 3.15 mmol, 1.0 eq) in mixture of toluene (12 mL) and water (3 mL), 1-methyl-3-(4,4,5,5-tetramethyl-1,3,2-dioxaborolan-2-yl)-1H-pyrazole (0.787 g, 3.78 mmol, 1.2 eq) was added. The reaction mixture was degassed with argon for 30 min. Then, [1,1'-Bis-(diphenylphosphino) ferrocene]palladium(II) dichloride (0.230 g, 3.15 mmol, 0.1 eq), Cs$_2$CO$_3$ (1.5 g, 4.7 mmol, 1.5 eq) was added into reaction mixture and again degassed by argon for 30 min. Reaction mixture was stirred at 150° C. for 5 h. Upon completion, reaction mixture transferred into water and extracted with ethyl acetate. Organic layers were combined, dried over Na$_2$SO$_4$ and concentrated in vacuo to obtain crude product. This was purified by column chromatography and compound was eluted in 30% ethyl acetate in hexane to obtain pure 429.5 (0.400 g, 50.91%). MS(ES): m/z 250.25 [M+H]$^+$.

Synthesis of Compound 429.6

Compound 429.6 was synthesized from 13.4 and 429.5 using general procedure A. (Yield: 27.96%). MS(ES): m/z 535.93 [M+H]$^+$.

Synthesis of Compound 429.7.

Compound 429.7 was synthesized from 429.6 and cyclopropanecarboxamide using general procedure B. (Yield: 53.47%). MS(ES): m/z 584.58 [M+H]$^+$.

Synthesis of I-429.

Compound I-429 was synthesized from 429.7 using general procedure C. (Yield: 58.42%). MS(ES): m/z 500.78 [M+H]$^+$, LCMS purity: 99.10%, HPLC purity: 98.17%, 1H NMR (DMSO, 400 MHz): 13.56 (s, 1H), 10.68 (s, 1H), 10.15 (s, 1H), 8.063 (s, 1H), 7.79-7.94 (d, J=10.8 Hz, 2H), 7.77 (s, 1H), 7.66-7.63 (m, 1H), 6.80 (s, 1H), 3.84 (s, 3H), 1.922 (s, 3H), 1.810 (s, 3H), 1.776-1.773 (m, 2H), 1.46-1.30 (m, 4H).

Example 430: Synthesis of N-(7-((2-(dimethylphosphoryl)-4-(1-methyl-1H-pyrazol-3-yl)phenyl)amino)-2-methyl-3H-imidazo[4,5-b]pyridin-5-yl)cyclopropanecarboxamide, I-430

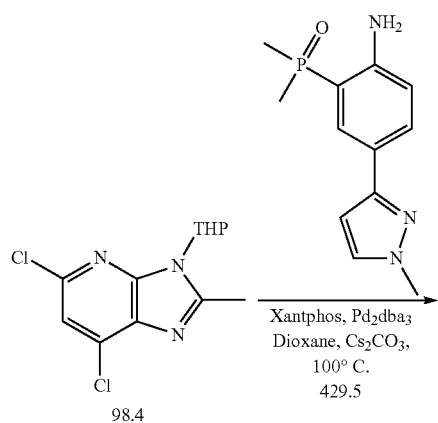

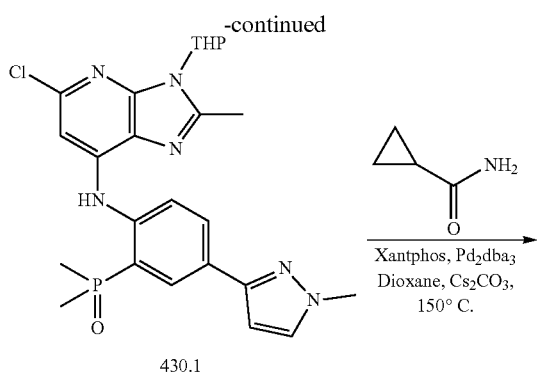

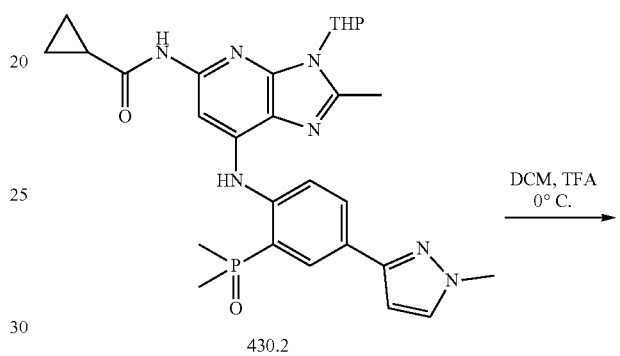

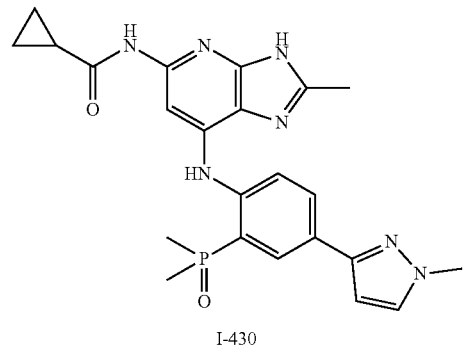

Synthesis of Compound 430.1.

Compound 430.1 was synthesized from 429.5 and 98.4 using general procedure A. (Yield: 28.18%). MS(ES): m/z 499.95 [M+H]$^+$.

Synthesis of Compound 430.2.

Compound 430.2 was synthesized from 430.1 using general procedure B. (Yield: 48.38%). MS(ES): m/z 548.60 [M+H]$^+$.

Synthesis of Compound I-430.

Compound I-430 was synthesized from 430.2 using general procedure C. (Yield: 78.77%). MS(ES): m/z 464.72 [M+H]$^+$, LCMS purity: 99.23%, HPLC purity: 97.95%, 1H NMR (DMSO, 400 MHz): 12.49 (s, 1H), 10.52 (s, 1H), 9.79 (s, 1H), 7.92 (bs, 3H), 7.76 (s, 1H), 7.60 (s, 1H), 6.78 (s, 1H), 3.90 (s, 3H), 2.49 (s, 3H), 1.98 (s, 1H), 1.81-1.77 (d, J=13.6 Hz, 6H), 0.77 (bs, 4H).

Example 431: Synthesis of N-(7-((2-(dimethylphosphoryl)-4-(tetrahydro-2H-pyran-4-yl)phenyl)amino)-2-methyl-3H-imidazo[4,5-b]pyridin-5-yl)cyclopropanecarboxamide, I-431

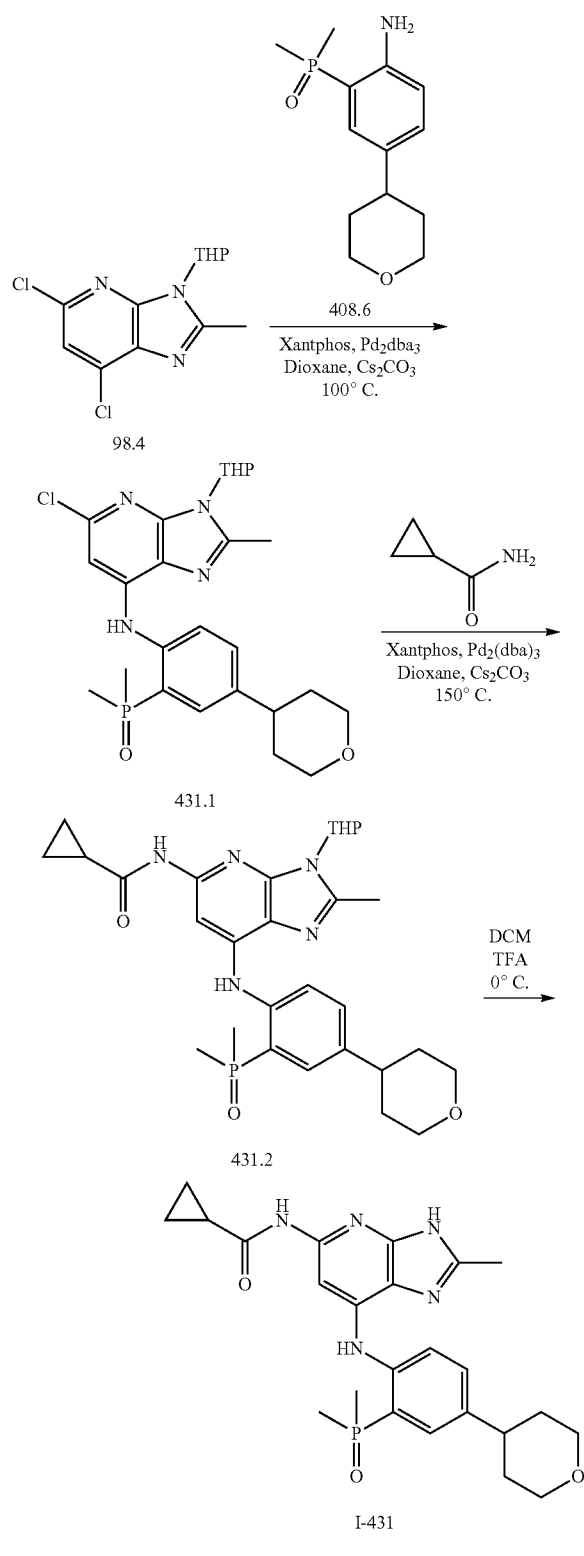

Synthesis of Compound 431.1.

Compound 431.1 was synthesized from 94.8 and 408.6 using general procedure A. (Yield: 27.09%). MS(ES): m/z 503.98 [M+H]$^+$.

Synthesis of Compound 431.2.

Compound 431.2 was synthesized from 431.1 using general procedure B. (Yield: 63.83%). MS(ES): m/z 552.63 [M+H]$^+$.

Synthesis of Compound I-431.

Compound I-431 was synthesized from 431.2 using general procedure C (Yield: 84.28%). MS(ES): m/z 468.77 [M+H]$^+$, LCMS purity: 100%, HPLC purity: 99.40%, 1H NMR (DMSO, 400 MHz): 12.49 (s, 1H), 10.49 (s, 1H), 9.71 (s, 1H), 7.87 (s, 1H), 7.60-7.43 (m, 3H), 3.99-3.96 (d, J=10.8 Hz, 2H), 3.47 (s, 3H), 2.82-2.79 (t, J=13.6 Hz, 1H), 2.48 (s, 3H), 2.00-1.97 (t, 1H), 1.76-1.72 (d, 9H), 0.76 (bs, 4H).

Example 432: Synthesis of (1R,2R)—N-(7-((4-cyclobutyl-2-(methylsulfonyl)phenyl)amino)-2-(difluoromethyl)-3H-imidazo[4,5-b]pyridin-5-yl)-2-fluorocyclopropane-1-carboxamide, I-432

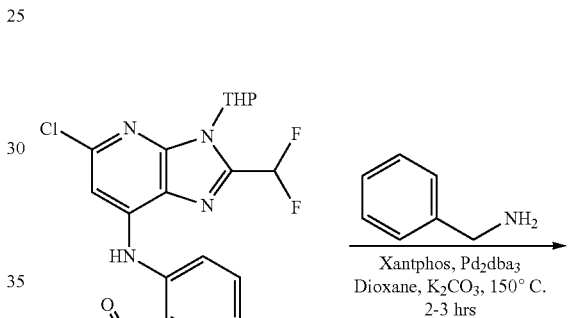

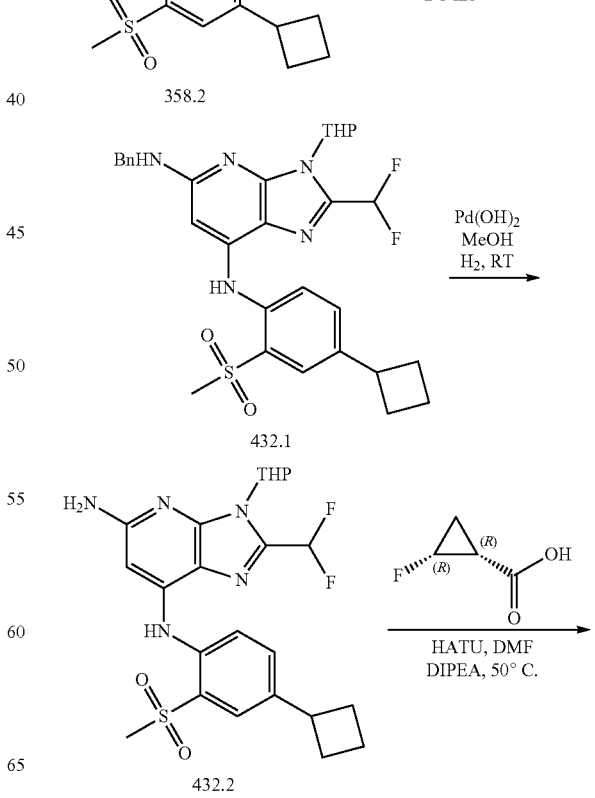

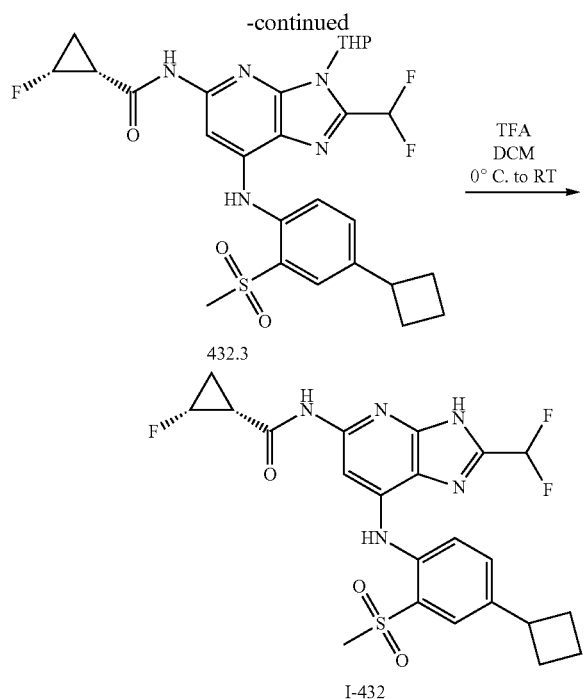

I-432

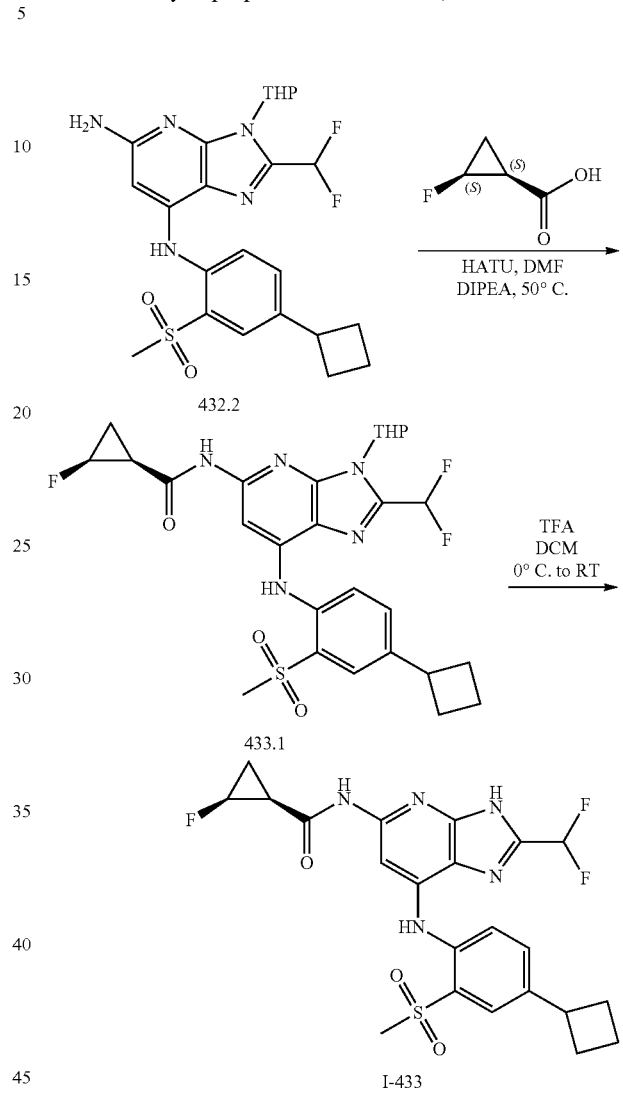

Example 433: Synthesis of (1S,2S)—N-(7-((4-cyclobutyl-2-(methylsulfonyl)phenyl)amino)-2-(difluoromethyl)-3H-imidazo[4,5-b]pyridin-5-yl)-2-fluorocyclopropane-1-carboxamide, I-433

Synthesis of Compound 432.1.

Compound was synthesized from 358.2 and benzylamine using general procedure B. (0.250 g, 62.75%). MS(ES): m/z 582.68 [M+H]⁺.

Synthesis of Compound 432.2.

To compound 432.1 (0.250 g, 2.66 mmol, 1.0 eq) in MeOH (5 mL), palladium hydroxide (0.037 g) was added. Hydrogen was purged through reaction mixture for 4 h. Upon completion, reaction mixture was filtered through celite-bed and washed with MeOH. Filtrate was concentrated in vacuo to obtain 432.2 (0.150 g, 71.00%). MS(ES): m/z 492.56 [M+H]⁺.

Synthesis of Compound 432.2.

To compound (1R,2R)-2-fluorocyclopropane-1-carboxylic acid 1.3 (0.075 g, 0.152 mmol, 1.0 eq) in N,N'-dimethylformamide (1 mL) at 0° C., (1-[Bis(dimethylamino)methylene]-1H-1,2,3-triazolo[4,5-b]pyridinium 3-oxid hexafluorophosphate) (0.079 g, 0.228 mmol, 1.5 eq) was added into it. After 30 min, diisopropyl ethyl amine (0.5 g, 0.38 mmol, 2.5 eq) and compound 432.2 (0.048 g, 0.45 mmol, 3 eq) was added. Reaction mixture was stirred at 50° C. for 2 h. After completion of reaction, the reaction mixture was transferred into cold water and extracted by ethyl acetate. Organic layer combined, dried over Na₂SO₄ and concentrated in vacuo to obtain crude product. This was purified by column chromatography and compound was eluted in 25% ethyl acetate in hexane as eluant to obtain pure 1.5 (0.050 g, 56.73%). MS(ES): m/z 578.62 [M+H]⁺.

Synthesis of Compound I-432.

Compound I-432 was synthesized from 432.3 using general procedure C. (Yield: 70.23%). MS(ES): m/z 494.56 [M+H]⁺, LCMS purity: 98.91%, HPLC purity: 98.07%, Chiral HPLC: 98.93%, 1H NMR (DMSO, 400 MHz): 13.69 (s, 1H), 10.80 (s, 1H), 8.69 (s, 1H), 8.02 (s, 1H), 7.75-7.68 (m, 3H), 7.40-7.13 (t, 1H), 7.26 (t, 1H), 5.00-4.81 (d, J=7.6 Hz, 1H), 3.69-3.60 (m, 1H), 3.21 (s, 3H), 2.38-2.32 (s, 2H), 2.23-2.11 (m, 2H), 2.07-1.98 (m, 1H), 1.88-1.84 (m, 1H), 1.63-1.57 (m, 1H), 1.15-1.11 (m, 1H).

Synthesis of Compound 433.1.

To (1S,2S)-2-fluorocyclopropane-1-carboxylic acid (0.047 g, 0.458 mmol, 3 eq) in N,N-dimethylformamide (3 mL) at 0° C., 1-[Bis(dimethylamino)methylene]-1H-1,2,3-triazolo[4,5-b]pyridinium 3-oxid hexafluorophosphate (0.23 g, 0.61 mmol, 4 eq) was added. Reaction mixture was allowed to stir for 15 min at 0° C. Then, di-isopropylethylamine (0.098 g, 0.76 mmol, 5 eq) and compound 432.2 (0.075 g, 0.152 mmol, 1.0 eq) was added. Reaction mixture was stirred at 50° C. for 5 h. After completion of the reaction, the reaction mixture was transferred into water and extracted with ethyl acetate. Organic layers were combined, dried over anhydrous Na₂SO₄, filtered and concentrated in vacuo to obtain crude product. This was purified by column chromatography using 2% MeOH in CH₂Cl₂ as eluant to obtain pure 433.1 (0.050 g, 56.73%). MS(ES): m/z 578.62 [M+H]⁺.

Synthesis of I-433.

Compound I-433 was synthesized from 433.1 using general procedure C. (Yield: 69.02%). MS(ES): m/z 494.61

[M+H]+, LCMS purity: 100%, HPLC purity: 98.92%, Chiral HPLC: 99.71%, 1H NMR (DMSO-d6, 400 MHz): 13.69 (s, 1H), 10.80 (s, 1H), 8.69 (s, 1H), 8.02 (s, 1H), 7.75-7.68 (m, 3H), 7.13 (s, 1H), 5.00-4.83 (d, J=7.6 Hz, 1H), 3.67-3.62 (m, 1H), 3.18 (s, 3H), 2.38-2.33 (s, 2H), 2.32-2.14 (m, 3H), 2.11-2.10 (m, 1H), 2.05-1.98 (m, 1H), 1.89-1.84 (m, 1H), 1.63 (m, 1H).

Example 434: Synthesis of N7-(4-cyclopropyl-2-(methylsulfonyl)phenyl)-N5-(2,6-dimethylpyrimidin-4-yl)-2-methyl-3H-imidazo[4,5-b]pyridine-5,7-diamine, I-434

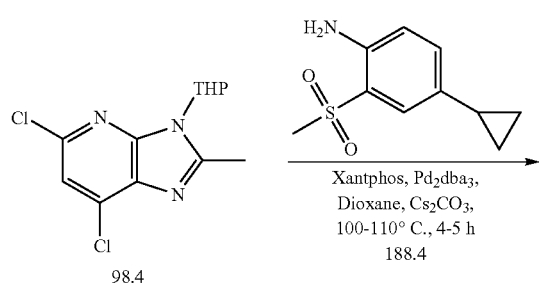

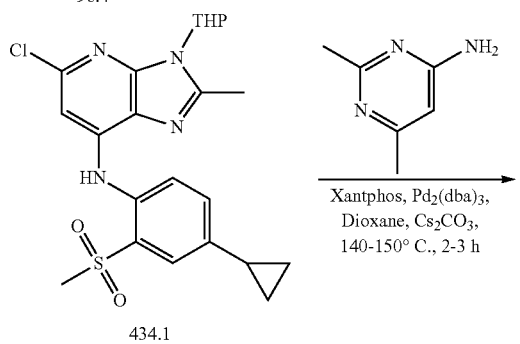

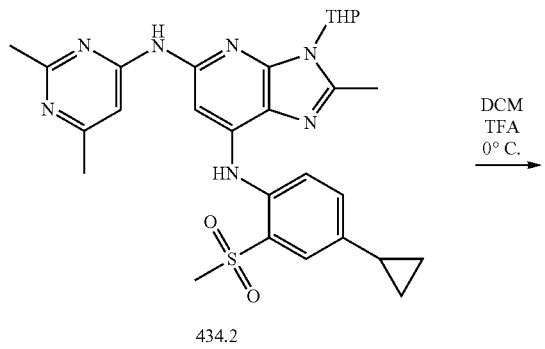

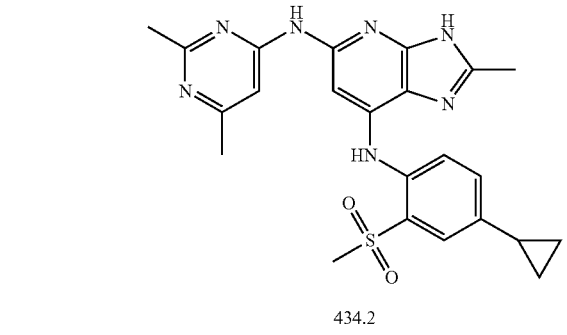

Synthesis of Compound 434.1.

Compound 434.1 was synthesized from 98.4 and 188.4 using general procedure A. (Yield: 42.42%). MS(ES): m/z 461.98 [M+H]+.

Synthesis of Compound 434.2.

Compound 434.2 was synthesized from 334.1 and 2,6-dimethylpyrimidin-4-amine using general procedure B. (Yield: 31.56%). MS(ES): m/z 548.68 [M+H]+.

Synthesis of I-434.

Compound I-434 was synthesized from 334.2 using general procedure C. (Yield: 53.56%). MS(ES): m/z 464.62 [M+H]+, LCMS purity: 98.32%, HPLC purity: 100%, 1H NMR (DMSO-d6, 400 MHz): 13.12 (s, 1H), 11.29 (s, 1H), 8.66 (s, 1H), 7.68-7.65 (m, 3H), 7.50-7.48 (d, J=8.4 Hz, 1H), 3.21 (s, 3H), 2.56-2.55 (d, J=2.8 Hz, 6H), 2.52-2.48 (d, J=1.2 Hz, 4H), 2.14-2.10 (m, 1H), 1.12-1.04 (m, 2H), 0.77-0.75 (d, J=0.84 Hz, 2H).

Example 435: Synthesis of N7-(4-cyclopropyl-2-(methylsulfonyl)phenyl)-N5-(5,6-dimethylpyrazin-2-yl)-2-methyl-3H-imidazo[4,5-b]pyridine-5,7-diamine, I-435

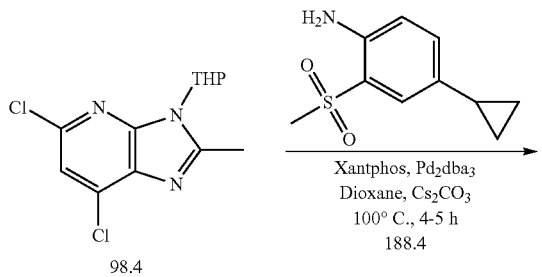

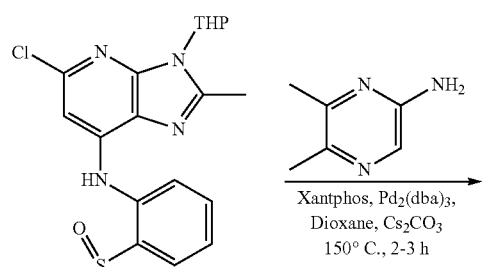

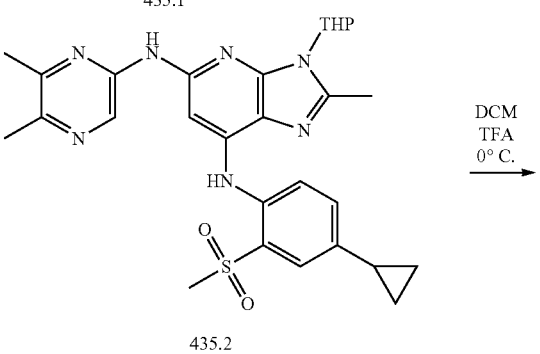

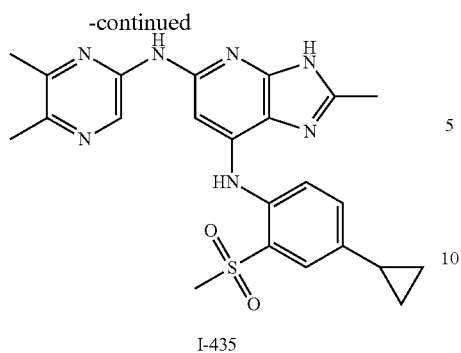

I-435

Synthesis of Compound 435.1.

Compound 435.1 was synthesized from 98.4 and 188.4 using general procedure A. (Yield: 27.22%). MS(ES): m/z 461.98 [M+H]⁺.

Synthesis of Compound 435.2.

Compound 435.2 was synthesized from 435.1 and 5,6-dimethylpyrazin-2-amine using general procedure B. (Yield: 29.46%). MS(ES): m/z 548.68 [M+H]⁺.

Synthesis of Compound I-435.

Compound I-435 was synthesized from 435.2 using general procedure C. (Yield: 62.45%). MS(ES): m/z 464.50 [M+H]⁺, LCMS purity: 98.83%, HPLC purity: 98.41%, 1H NMR (DMSO-d6, 400 MHz): 12.15 (s, 1H), 9.70 (s, 1H), 8.78 (s, 1H), 8.52 (s, 1H), 7.70-7.66 (m, 2H), 7.47-7.45 (m, 1H), 7.32 (s, 1H), 3.18 (s, 3H), 2.53 (s, 3H), 2.37 (s, 3H), 2.33 (s, 3H), 2.13-2.07 (m, 1H), 1.07-1.02 (m, 2H), 0.76-0.72 (m, 2H).

Example 436: Synthesis of N7-(4-cyclopropyl-2-(methylsulfonyl)phenyl)-2-(difluoromethyl)-N5-(6,7-dihydro-4H-pyrazolo[5,1-c][1,4]oxazin-2-yl)-3H-imidazo[4,5-b]pyridine-5,7-diamine, I-435

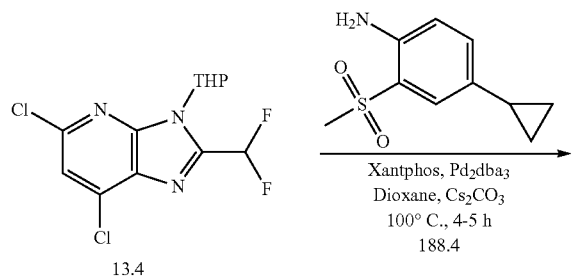

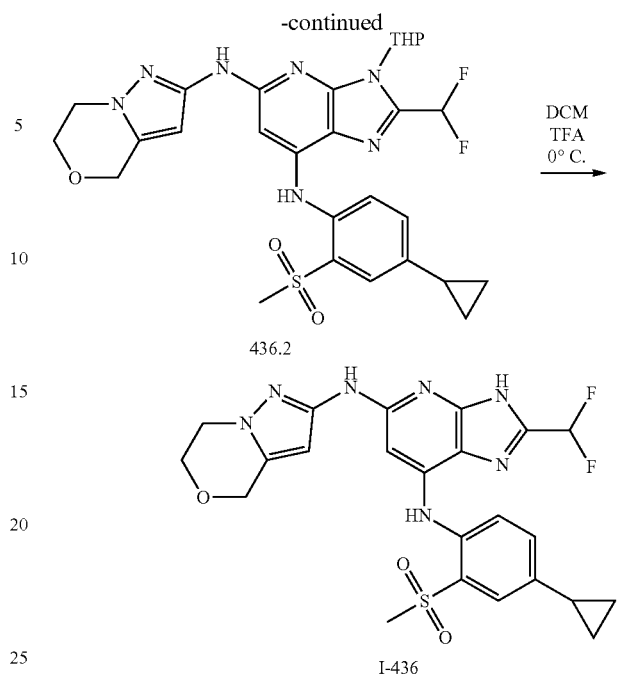

I-436

Synthesis of Compound 436.1.

Compound 436.1 was synthesized from 13.4 and 188.4 using general procedure A. (Yield: 27.22%). MS(ES): m/z 461.98 [M+H]⁺.

Synthesis of Compound 436.2.

Compound 436.2 was synthesized from 435.1 and 6,7-dihydro-4H-pyrazolo[5,1-c][1,4]oxazin-2-amine using general procedure B. (Yield: 27.62%). MS(ES): m/z 600.66 [M+H]⁺.

Synthesis of Compound I-436.

Compound I-436 was synthesized from 436.2 using general procedure C. (Yield: 66.88%). MS(ES): m/z 516.66 [M+H]⁺, LCMS purity: 99.45%, HPLC purity: 99.18%, 1H NMR (DMSO-d6, 400 MHz): 13.35 (s, 1H), 9.28 (s, 1H), 8.56 (s, 1H), 7.75-7.73 (d, J=8.4 Hz, 1H), 7.63 (s, 1H), 7.50-7.48 (d, J=8.4 Hz, 1H), 7.16 (s, 1H), 7.06 (s, 1H), 4.77 (s, 2H), 4.08-4.06 (t, J=1.0 Hz, 2H), 3.97-3.96 (d, J=4.8 Hz, 2H), 3.33 (s, 1H), 3.20 (s, 3H), 2.11-2.06 (m, 1H), 1.08-1.01 (m, 2H), 0.75-0.74 (m, 2H).

Example 437: Synthesis of N7-(4-cyclopropyl-2-(methylsulfonyl)phenyl)-N5-(6,7-dihydro-4H-pyrazolo[5,1-c][1,4]oxazin-2-yl)-2-methyl-3H-imidazo[4,5-b]pyridine-5,7-diamine, I-437

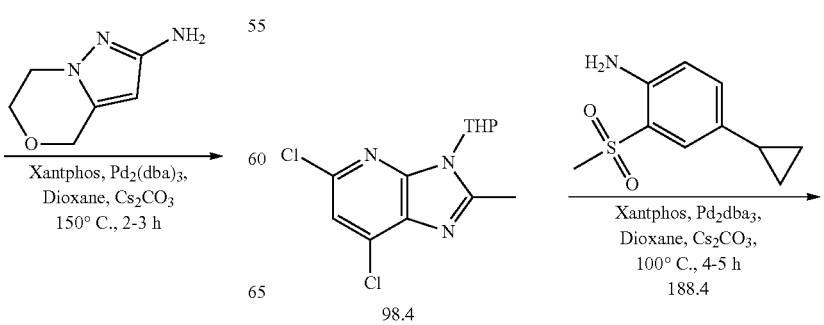

957

-continued

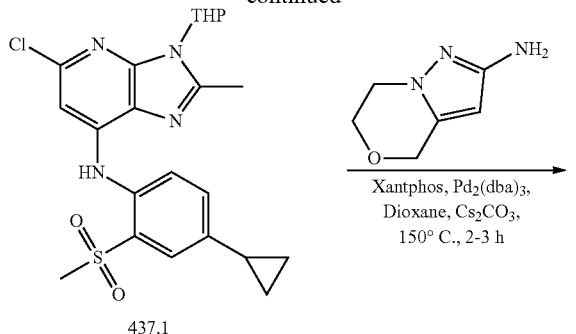

437.1

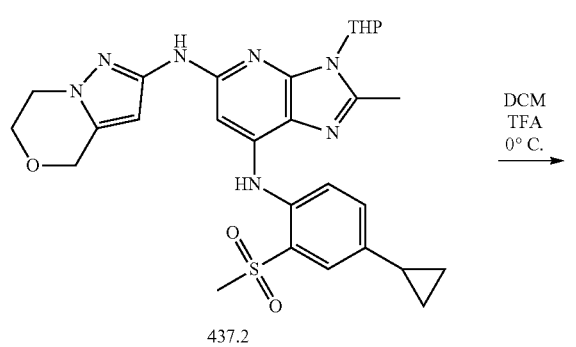

437.2

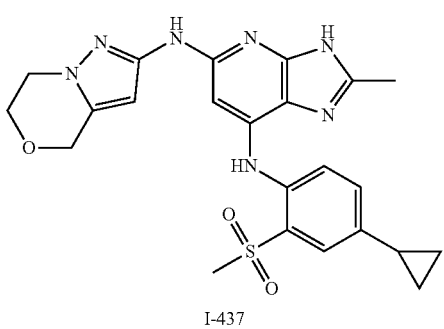

I-437

Synthesis of Compound 437.1.

Compound 437.1 was synthesized 98.4 and 188.4 using general procedure A. (Yield: 27.22%). MS(ES): m/z 461.98 [M+H]$^+$.

Synthesis of Compound 437.2.

Compound 437.2 was synthesized from 437.1 and 6,7-dihydro-4H-pyrazolo[5,1-c][1,4]oxazin-2-amine using general procedure B. (Yield: 47.71%). MS(ES): m/z 564.68 [M+H]$^+$.

Synthesis of Compound I-437.

Compound I-437 was synthesized from 437.2 using general procedure C. (Yield: 50.37%). MS(ES): m/z 480.65 [M+H]$^+$, LCMS purity: 99.05%, HPLC purity: 98.05%, 1H NMR (DMSO-d6, 400 MHz): 12.22 (s, 1H), 8.98 (s, 1H), 8.41 (s, 1H), 7.75-7.73 (d, J=8.4 Hz, 1H), 7.60 (s, 1H), 7.47-7.45 (d, J=8.4 Hz, 1H), 7.05 (s, 1H), 6.32 (s, 1H), 4.75 (s, 2H), 4.06 (s, 2H), 3.96 (s, 2H), 3.18 (s, 3H), 2.41 (s, 3H), 2.09-2.07 (t, J=0.92 Hz, 1H), 1.03-1.02 (d, J=6.8 Hz, 2H), 0.74-0.73 (d, J=4.8 Hz, 2H).

958

Example 438/439: (S)—N-(2-(difluoromethyl)-7-((2-(methylsulfonyl)-4-((S)-tetrahydro-2H-pyran-3-yl)phenyl)amino)-3H-imidazo[4,5-b]pyridin-5-yl)-2,2-difluorocyclopropane-1-carboxamide, I-438 and (R)—N-(2-(difluoromethyl)-7-((2-(methylsulfonyl)-4-((S)-tetrahydro-2H-pyran-3-yl)phenyl)amino)-3H-imidazo[4,5-b]pyridin-5-yl)-2,2-difluorocyclopropane-1-carboxamide, I-439

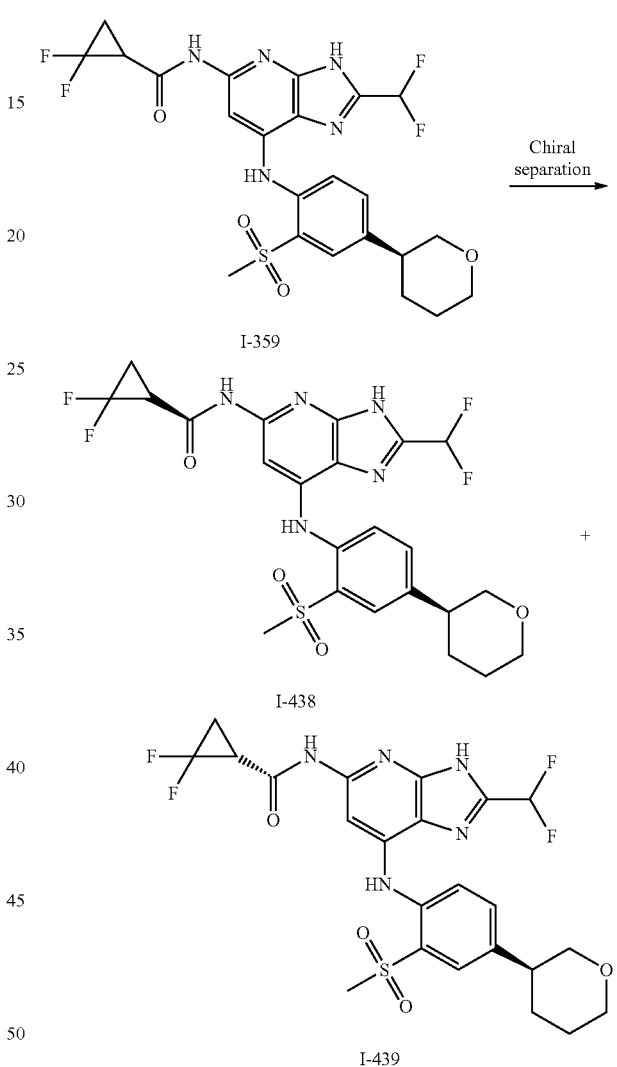

Synthesis of Compound I-438 and I-439.

Isomers of I-359 (0.090 g) were separated out using column (CHIRALCEL OX-H (250 mm*4.6 mm, 5u)) and 0.1% DEA IPA flow rate of 4 mL/min. to get pure fraction-1 (FR-a) and fraction-2 (FR-b). FR-a was concentrated in vacuo at 30° C. to afford pure I-438 (0.025 g). MS(ES): m/z 542.80 [M+H]$^+$, LCMS purity: 100%, HPLC purity: 100%, Chiral HPLC: 100%, 1H NMR (DMSO, 400 MHz): 8.04 (s, 1H), 7.92 (s, 1H), 7.84-7.82 (d, J=8.4 Hz, 1H), 7.72-7.70 (d, J=10.4 Hz, 1H), 4.02-3.99 (m, 2H), 3.59-3.49 (m, 2H), 3.11 (s, 3H), 3.02-2.96 (m, 1H), 2.84-2.82 (m, 1H), 2.12-2.06 (m, 2H), 1.93-1.810 (m, 4H), 1.35 (s, 3H), 0.99-0.97 (m, 1H). FR-b was concentrated in vacuo at 30° C. to afford pure I-439 (0.025 g). MS(ES): m/z 542.80 [M+H]$^+$, LCMS purity: 96.13%, HPLC purity: 94.16%, Chiral HPLC: 98.00%, 1H NMR (DMSO, 400 MHz): 8.03 (s, 1H), 7.92 (s, 1H), 7.84-7.82 (d, J=8.4 Hz, 1H), 7.72-7.69 (d, J=10.4 Hz, 1H), 4.04-3.99 (m, 2H), 3.59-3.49 (m, 2H), 3.11 (s, 3H), 3.02-2.98 (m, 1H), 2.84-2.82 (m, 1H), 2.12-2.06 (m, 2H), 1.90-1.807 (m, 4H), 1.31 (s, 3H), 0.99-0.94 (m, 1H).

Example 440: Synthesis of (1R,2R)—N-(2-(difluoromethyl)-7-((2-methoxy-3-(1-methyl-Ill-1,2,4-triazol-3-yl)phenyl)amino)-3H-imidazo[4,5-b]pyridin-5-yl)-2-fluorocyclopropane-1-carboxamide, I-440

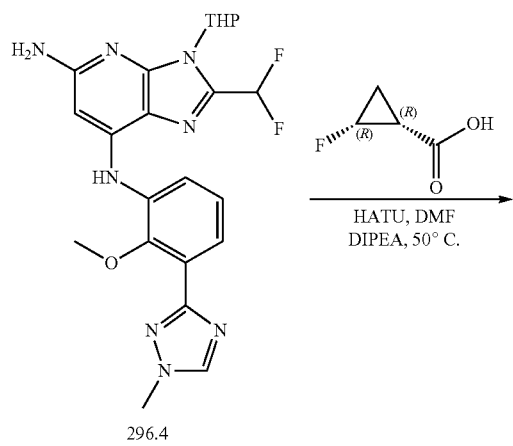

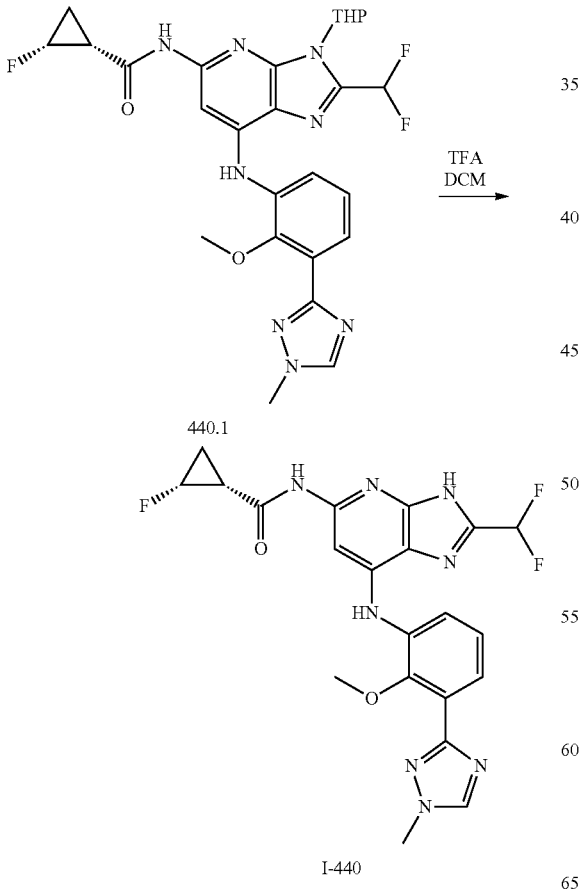

Synthesis of Compound 440.1.

To a solution of (1R,2R)-2-fluorocyclopropane-1-carboxylic acid (0.023 g, 0.22 mmol, 1.2 eq) in N,N'-dimethylformamide (3 mL) at 0° C., (1-[Bis(dimethylamino)methylene]-1H-1,2,3-triazolo[4,5-b]pyridinium 3-oxid hexafluorophosphate) (0.10 g, 0.28 mmol, 1.5 eq) was added. After 30 min, diisopropyl ethyl amine (0.061 g, 0.47 mmol, 2.5 eq) and compound 296.4 (0.090 g, 0.19 mmol, 1.0 eq) was added. Reaction mixture was stirred at 50° C. for 2 h. After completion of reaction, the reaction mixture was transferred into cold water and extracted by ethyl acetate. Organic layer combined, dried over $Na_2SO_4$ and concentrated in vacuo to obtain crude product. This was purified by column chromatography and compound was eluted in 25% ethyl acetate in hexane as eluant to obtain pure 1.2 (0.050 g, 46.96%). MS(ES): m/z 557.55 [M+H]$^+$.

Synthesis of Compound I-440.

Compound I-440 was synthesized using general procedure C. (Yield: 65.97%). MS(ES): m/z 473.50 [M+H]$^+$, LCMS purity: 94.50%, HPLC purity: 99.59%, Chiral HPLC: 98.84%, 1H NMR (DMSO, 400 MHz): 12.12 (s, 1H), 8.52 (s, 1H), 7.93 (s, 1H), 7.75-7.73 (d, J=8.0 Hz, 1H), 7.65-7.62 (d, J=9.2 Hz, 1H), 7.35-7.31 (m, 1H), 7.15 (s, 1H), 7.02 (s, 1H), 6.85 (s, 1H), 4.80-4.76 (m, 1H), 4.05 (s, 3H), 3.74 (s, 3H), 2.09 (s, 1H), 1.82-1.72 (m, 1H), 1.26-1.20 (m, 1H).

Example 441: Synthesis of (S)—N-(2-methyl-7-((2-(methylsulfinyl)phenyl)amino)-3H-imidazo[4,5-b]pyridin-5-yl)cyclopropanecarboxamide, I-441

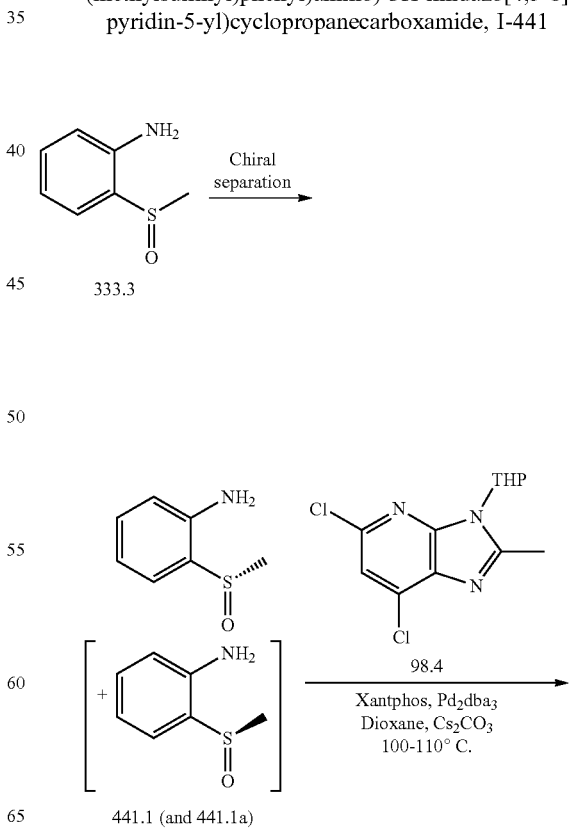

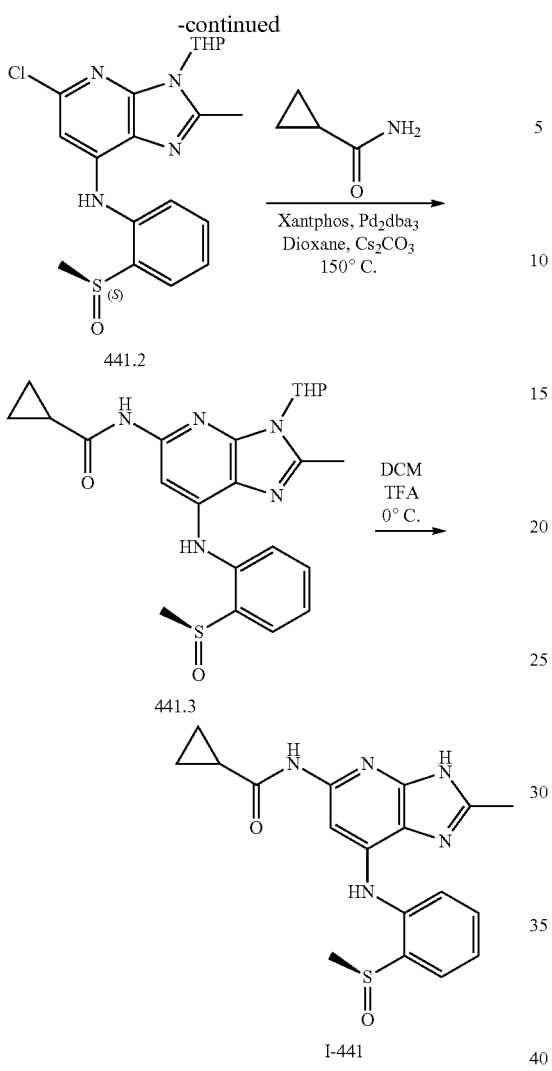

441.2

441.3

I-441

Synthesis of Compound 441.1.

Isomers of compound 333.3 (0.9 g) were separated out using column (CHIRAL PAK AD-H 250×4.6 mm, 5 μM) 0.1% DEA in IPA as co-solvent with flow rate of 4 mL/min. to get pure fraction-1 (FR-a) and fraction-2 (FR-b). FR-a was concentrated in vacuo at 30° C. to afford pure 441.1 (0.250 g, 27.78%). MS(ES): m/z: 156.49 [M+H]$^+$. FR-b was concentrated in vacuo at 30° C. to afford pure 441.1a (0.250 g, 27.78%). MS(ES): m/z: 156.49 [M+H]$^+$.

Synthesis of Compound 441.2.

Compound 441.2 was synthesized from 441.1 and 98.4 using general procedure A. (Yield: 42.40%). MS(ES): m/z 405.91 [M+H]$^+$.

Synthesis of Compound 441.3.

Compound 441.3 was synthesized from 441.2 and cyclopropanecarboxamide using general procedure B. (Yield: 33.92%). MS(ES): m/z 454.56 [M+H]$^+$.

Synthesis of Compound I-441.

Compound I-441 was synthesized from 441.3 using general procedure C (Yield: 53.85%). MS(ES): m/z 370.44 [M+H]$^+$, LCMS purity: 97.60%, HPLC purity: 95.05%, Chiral HPLC: 98.60%, 1H NMR (DMSO, 400 MHz): 12.32 (s, 1H), 10.39 (s, 1H), 8.86 (s, 1H), 7.77-7.75 (d, J=7.2 Hz, 1H), 7.59-7.55 (m, 1H), 7.44-7.39 (m, 3H), 2.73 (s, 3H), 2.46 (s, 3H), 1.95-1.92 (m, 1H), 0.72-0.70 (m, 4H).

Example 442: Synthesis of (R)—N-(2-methyl-7-((2-(methylsulfinyl)phenyl)amino)-3H-imidazo[4,5-b]pyridin-5-yl)cyclopropanecarboxamide, I-442

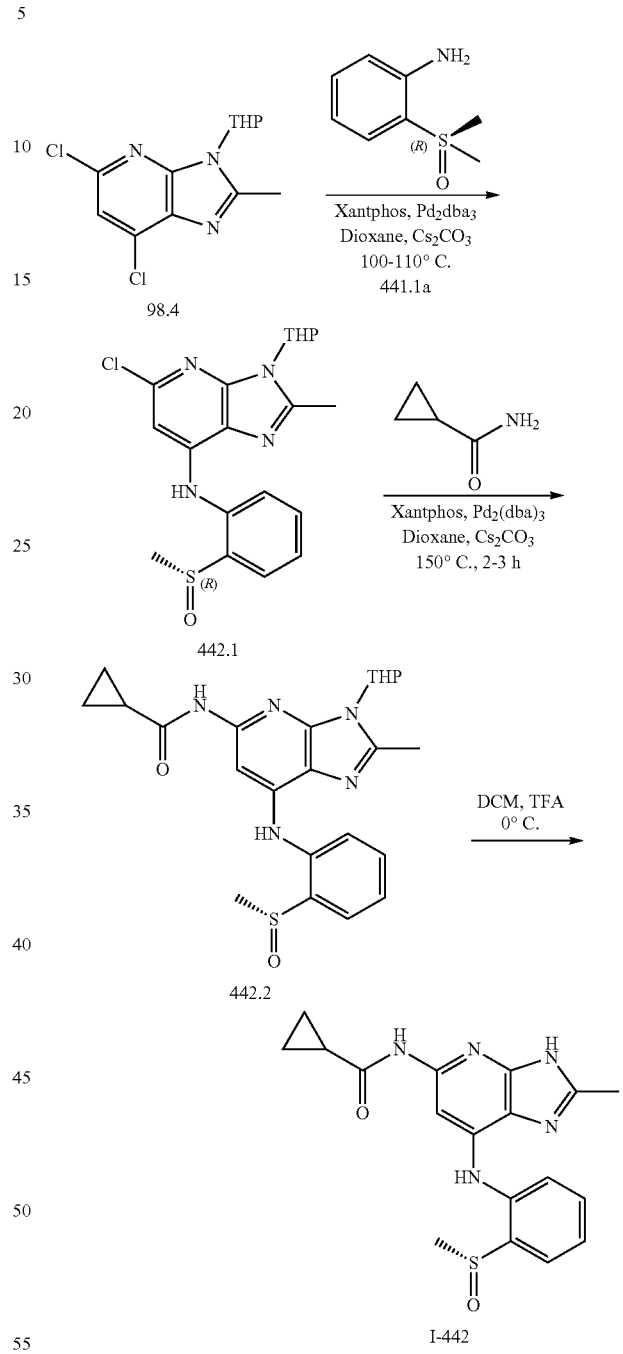

441.1a 442.1

442.2

I-442

Synthesis of Compound 442.1.

Compound 442.1 was synthesized from 98.4 and 441.1a using general procedure A. (Yield: 35.31%). MS(ES): m/z 405.91 [M+H]$^+$.

Synthesis of Compound 442.2.

Compound 442.2 was synthesized from 442.1 and cyclopropanecarboxamide using general procedure B. (Yield: 45.48%). MS(ES): m/z 454.56 [M+H]$^+$.

Synthesis of Compound I-442.

Compound I-442 was synthesized from 442.2 using general procedure C (Yield: 56.19%). MS(ES): m/z 370.53

[M+H]+, LCMS purity: 100%, HPLC purity: 99.39%, Chiral HPLC: 97.27%, 1H NMR (DMSO, 400 MHz): 12.32 (s, 1H), 10.40 (s, 1H), 8.87 (s, 1H), 7.77-7.75 (d, J=7.2 Hz, 1H), 7.59-7.55 (m, 1H), 7.44-7.39 (m, 3H), 2.73 (s, 3H), 2.46 (s, 3H), 1.95-1.92 (m, 1H), 1.40-1.34 (m, 2H), 1.23-1.22 (m, 1H), 0.71-0.70 (m, 1H).

Example 443: Synthesis of N-(7-((4-fluoro-2-(methylsulfonyl)phenyl)amino)-2-methyl-3H-imidazo[4,5-b]pyridin-5-yl)cyclopropanecarboxamide, I-443

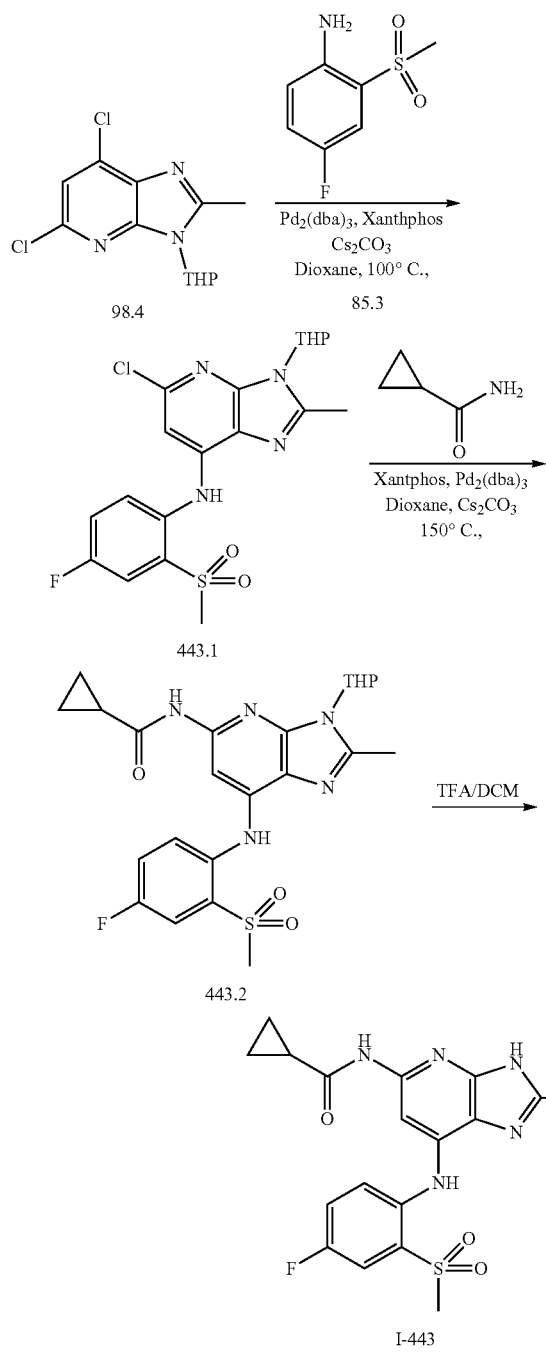

Synthesis of Compound 443.1.

Compound 443.1 was synthesized from 85.3 and 98.4 using general procedure A. (Yield: 42.20%). MS(ES): m/z 439.90 [M+H]+.

Synthesis of Compound 443.2.

Compound 443.2 was synthesized from 443.1 and cyclopropanecarboxamide using general procedure B. (Yield: 54.80%). MS(ES): m/z 488.31 [M+H]+.

Synthesis of Compound I-443.

Compound I-443 was synthesized from 443.2 using general procedure C. (Yield: 60.43%). MS(ES): m/z 404.54 [M+H]+, LCMS purity: 98.63%, HPLC purity: 98.15%, 1H NMR (DMSO, 400 MHz): 12.48 (s, 1H), 10.57 (s, 1H), 8.41 (s, 1H), 7.87 (s, 1H), 7.76 (s, 1H), 7.68 (m, 2H), 3.24 (s, 3H), 2.48 (s, 3H), 2.00-1.98 (t, J=8 Hz, 1H), 0.77-0.75 (m, 4H).

Example 444: Synthesis of N-(7-((4-cyclobutyl-2-(dimethylphosphoryl) phenyl)amino)-2-(difluoromethyl)-3H-imidazo[4,5-b]pyridin-5-yl)cyclopropane carboxamide, I-444

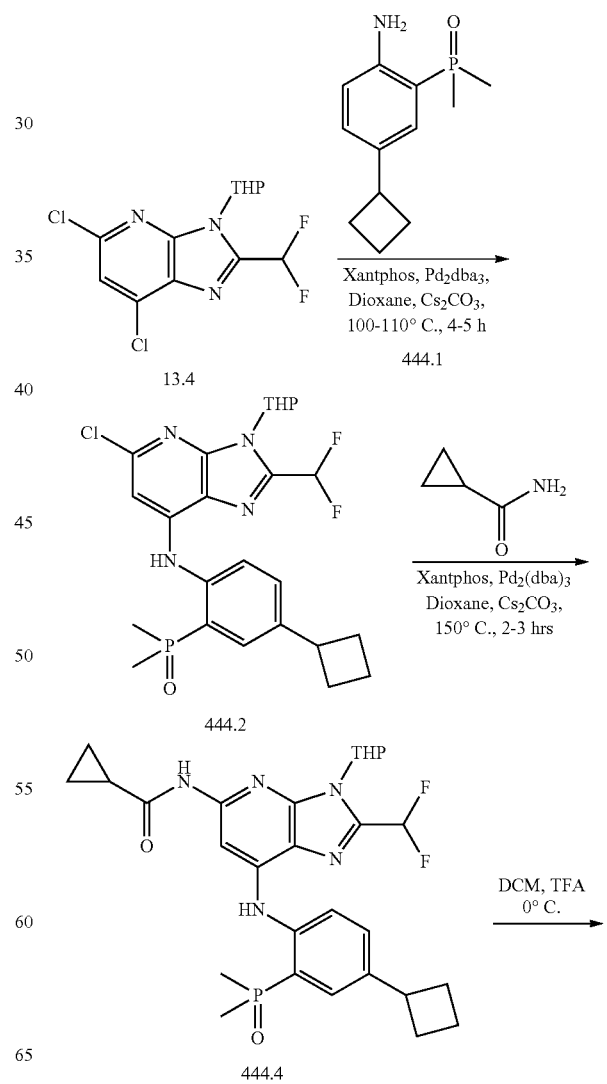

-continued

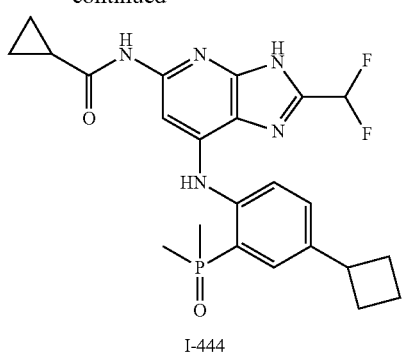

I-444

Synthesis of Compound 444.1.

Starting from 2-bromo-4-cyclobutyl-aniline, compound 444.1 was synthesized similar to the cyclopropyl analog, 285.4.

Synthesis of Compound 444.2.

Compound 444.2 was synthesized from 444.1 and 13.4 using general procedure A. (Yield: 23.62%). MS(ES): m/z 509.43 [M+H]$^+$.

Synthesis of Compound 444.3.

Compound 444.3 was synthesized from 444.2 and cyclopropanecarboxamide using general procedure B. (Yield: 48.90%). MS(ES): m/z 558.62 [M+H]$^+$.

Synthesis of I-444.

Compound I-444 was synthesized from 444.3 using general procedure C. (Yield: 47.11%). MS(ES): m/z 474.52 [M+H]$^+$, LCMS purity: 100%, HPLC purity: 98.87%, 1H NMR (DMSO-d6, 400 MHz): 13.51 (s, 1H), 10.64 (s, 1H), 9.99 (s, 1H), 7.97 (s, 1H), 7.57-7.54 (m, 1H), 7.48 (s, 2H), 3.58-3.53 (m, 1H), 3.42-3.38 (m, 1H), 2.34-2.28 (m, 2H), 2.19-2.14 (m, 2H), 2.04-1.95 (m, 2H), 1.85-1.83 (m, 2H), 1.75-1.72 (d, J=1.32 Hz, 6H), 1.12-1.09 (t, J=1.4 Hz, 1H), 0.78-0.77 (m, 2H).

Example 445: Synthesis of N-(7-((4-cyclobutyl-2-(dimethylphosphoryl)phenyl)amino)-2-methyl-3H-imidazo[4,5-b]pyridin-5-yl)cyclopropanecarboxamide, I-445

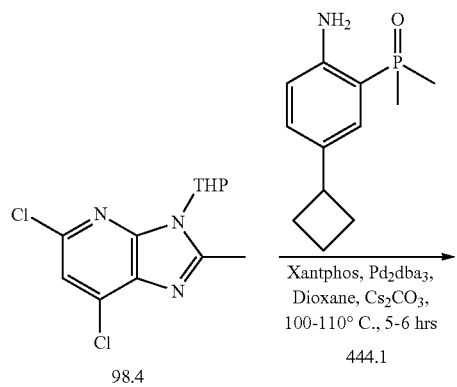

98.4    444.1

-continued

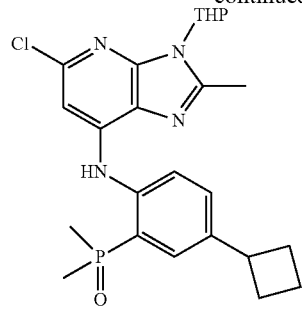

445.1

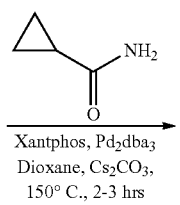

Xantphos, Pd$_2$dba$_3$
Dioxane, Cs$_2$CO$_3$,
150° C., 2-3 hrs

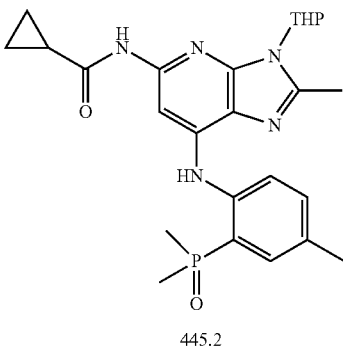

445.2

DCM, TFA
0° C.

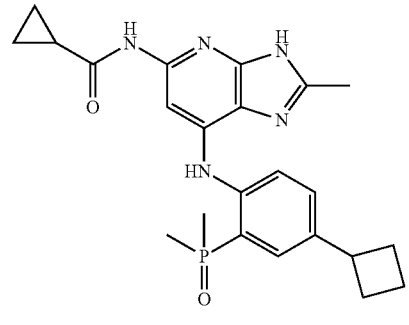

I-445

Synthesis of Compound 445.1.

Compound 445.1 was synthesized from 98.4 and 444.1 using general procedure A. (Yield: 26.33%). MS(ES): m/z 473.95 [M+H]$^+$.

Synthesis of Compound 445.2.

Compound 445.2 was synthesized from 445.1 and cyclopropanecarboxamide using general procedure B. (Yield: 46.90%). MS(ES): m/z 522.60 [M+H]$^+$.

Synthesis of I-445.

Compound I-445 was synthesized from 445.2 using general procedure C. (Yield: 60.41%). MS(ES): m/z 438.52 [M+H]$^+$, LCMS purity: 97.11%, HPLC purity: 96.19%, 1H NMR (DMSO, 400 MHz): 12.33 (s, 1H), 10.46 (s, 1H), 9.65 (s, 1H), 7.84 (s, 1H), 7.51 (s, 1H), 7.45-7.40 (m, 2H), 3.56-3.52 (m, 1H), 2.46 (s, 3H), 2.31-2.27 (m, 2H), 2.18-2.13 (m, 2H), 2.01-1.95 (m, 2H), 1.87-1.82 (m, 1H), 1.75-1.71 (d, J=13.6 Hz, 6H), 0.76 (bs, 4H).

Example 446: Synthesis of N-(2-(difluoromethyl)-7-((2-(methylsulfonyl)-4-(1,3,5-trimethyl-1H-pyrazol-4-yl)phenyl)amino)-3H-imidazo[4,5-b]pyridin-5-yl)cyclopropanecarboxamide, I-446

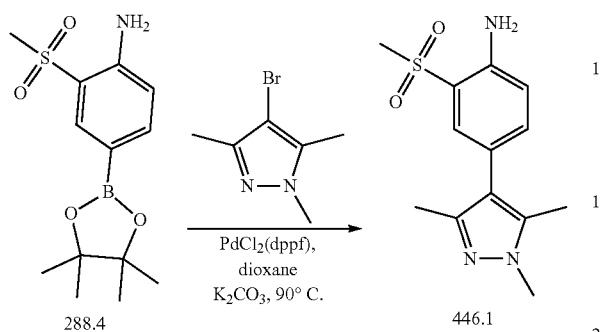

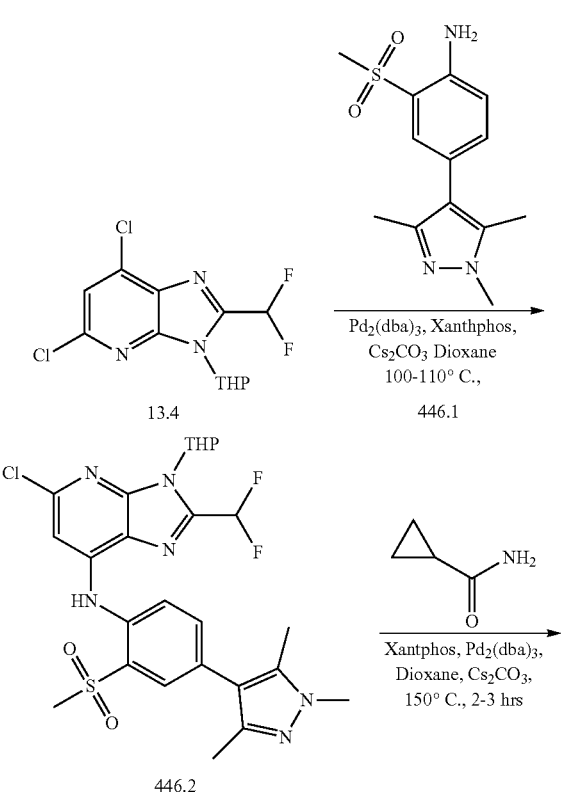

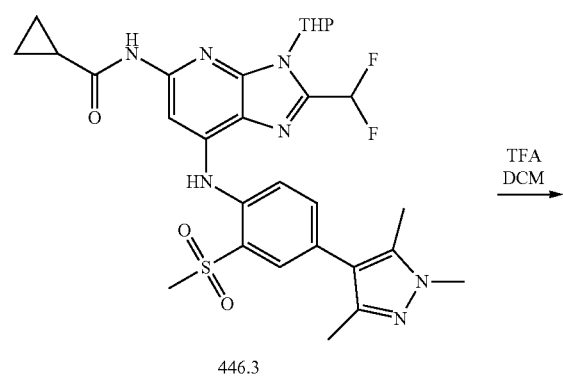

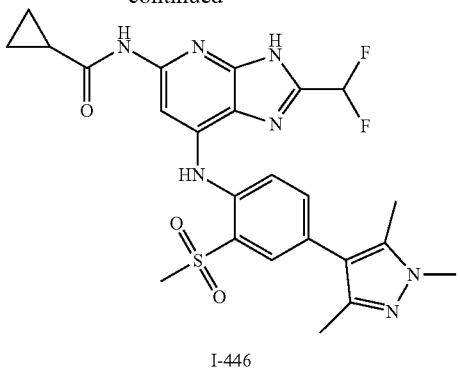

I-446

Synthesis of Compound 446.1.

To compound 288-4 (2.0 g, 6.73 mmol, 1.0 eq) in dioxane (20 mL), 4-bromo-1,3,5-trimethyl-1H-pyrazole (1.91 g, 10.10 mmol, 1.5 eq) was added. Reaction mixture was degassed with argon for 10 min. Then [1,1'-Bis(diphenylphosphino)ferrocene]palladium(II) dichloride (0.984 g, 1.34 mmol, 0.2 eq) and potassium carbonate (2.78 g, 20.19 mmol, 3 eq) was added into it. Reaction mixture was stirred at 110° C. for 24 h. Upon completion, reaction mixture was transferred into cold water then extracted with ethyl acetate. Organic layer combined, dried over Na$_2$SO$_4$ and concentrated in vacuo to obtain crude product. This was purified by column chromatography and compound was eluted in 15% ethyl acetate in hexane as eluant to obtain pure 446.1 (0.950 g, 50.53%). MS(ES): m/z 280.36 [M+H]$^+$.

Synthesis of Compound 446.2.

Compound 446.2 was synthesized from 13.4 and 446.1 using general procedure A. (Yield: 36.73%). MS(ES): m/z 566.04 [M+H]$^+$.

Synthesis of Compound 446.3.

Compound 446.3 was synthesized from 446.2 and cyclopropanecarboxamide using general procedure B. (Yield: 23.02%). MS(ES): m/z 614.68 [M+H]$^+$.

Synthesis of I-446.

Compound I-446 was synthesized from 446.3 using general procedure C. (Yield: 80.23%). MS(ES): m/z 530.65 [M+H]$^+$, LCMS purity: 99.42%, HPLC purity: 98.86%, 1H NMR (DMSO, 400 MHz): 13.70 (s, 1H), 10.78 (s, 1H), 8.80 (s, 1H), 8.11 (s, 1H), 7.84-7.82 (d, J=8.4 Hz, 1H), 7.75 (s, 1H), 7.70-7.68 (d, J=8.0 Hz, 1H), 7.28 (t, 1H), 3.73 (s, 3H), 3.27 (s, 3H), 2.29 (s, 3H), 2.19 (s, 3H), 2.0 (m, 1H), 0.78 (bs, 4H).

Example 447: Synthesis of N-(2-methyl-7-((2-(methylsulfonyl)-4-(1,3,5-trimethyl-1H-pyrazol-4-yl)phenyl)amino)-3H-imidazo[4,5-b]pyridin-5-yl)cyclopropanecarboxamide, I-447

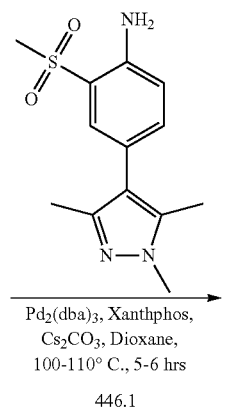

969

-continued

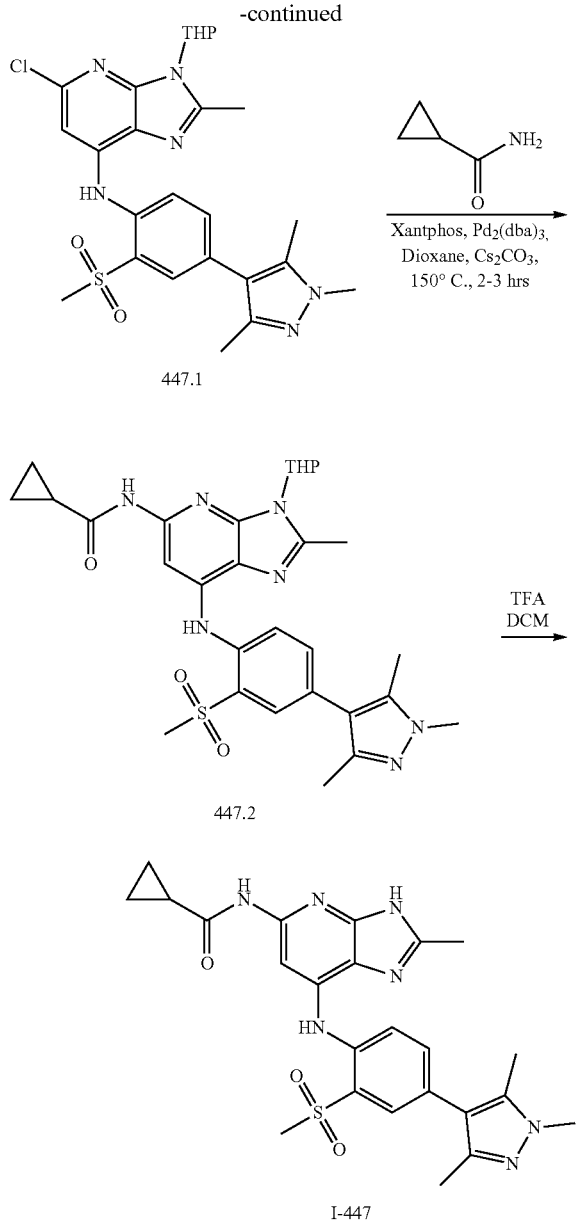

447.1

447.2

I-447

Synthesis of Compound 447.1.

Compound 447.1 was synthesized from 98.4 and 446.1 using general procedure A. (Yield: 34.70%). MS(ES): m/z 530.06 [M+H]⁺.

Synthesis of Compound 447.2.

Compound 447.2 was synthesized from 447.1 and cyclopropanecarboxamide using general procedure B. (Yield: 54.95%). MS(ES): m/z 578.70 [M+H]⁺.

Synthesis of I-447.

Compound I-447 was synthesized from 447.2 using general procedure C (Yield: 81.93%). MS(ES): m/z 494.66 [M+H]⁺, LCMS purity: 95.29%, HPLC purity: 95.86%, 1H NMR (DMSO, 400 MHz): 12.58 (s, 1H), 10.62 (s, 1H), 8.66-8.60 (m, 1H), 8.01 (s, 1H), 7.80-7.73 (m, 1H), 7.72 (s, 1H), 7.66-7.64 (m, 1H), 3.73 (s, 3H), 3.25 (s, 3H), 2.50 (s, 3H), 2.28 (s, 3H), 2.18 (s, 3H), 2.02-1.99 (t, J=12 Hz, 1H), 0.78-0.76 (m, 4H).

970

Example 448: Synthesis of N-(2-((2-(difluoromethyl)-5-((2,6-dimethylpyrimidin-4-yl)amino)-3H-imidazo[4,5-b]pyridin-7-yl)amino)phenyl)-N-methylmethanesulfonamide-d3, I-448

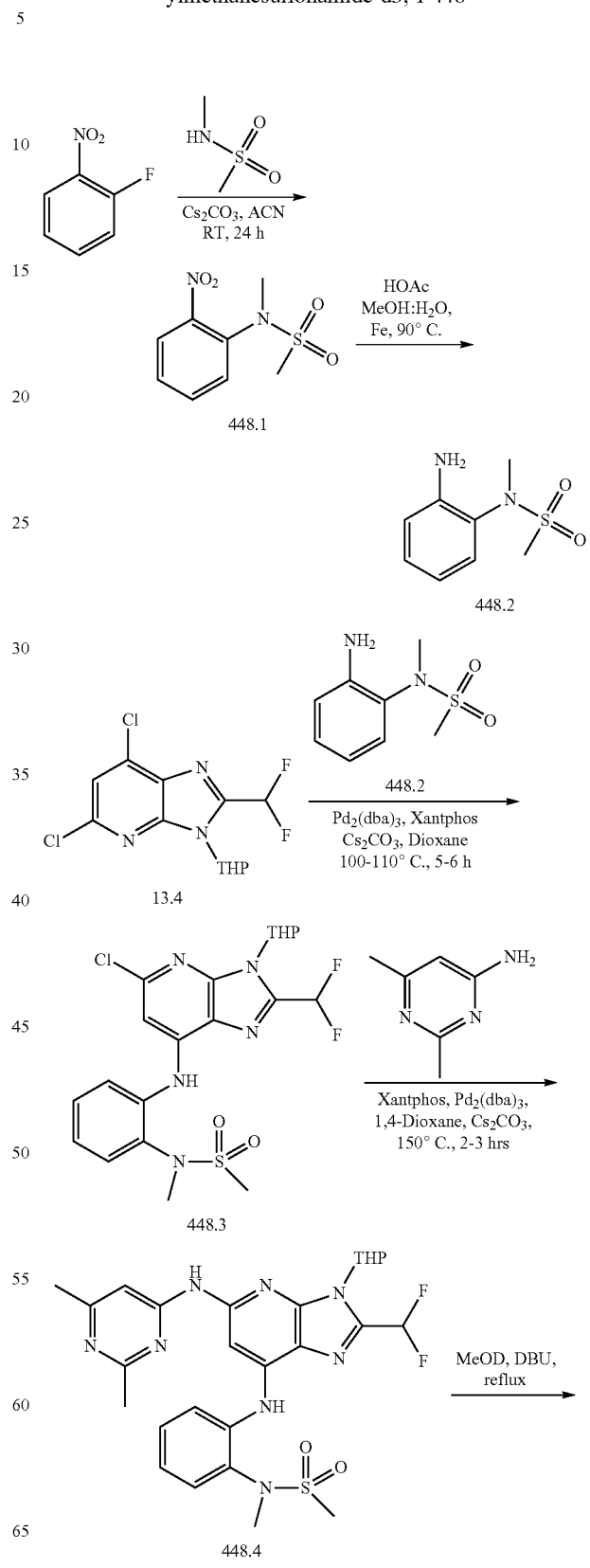

448.1

448.2

13.4

448.3

448.4

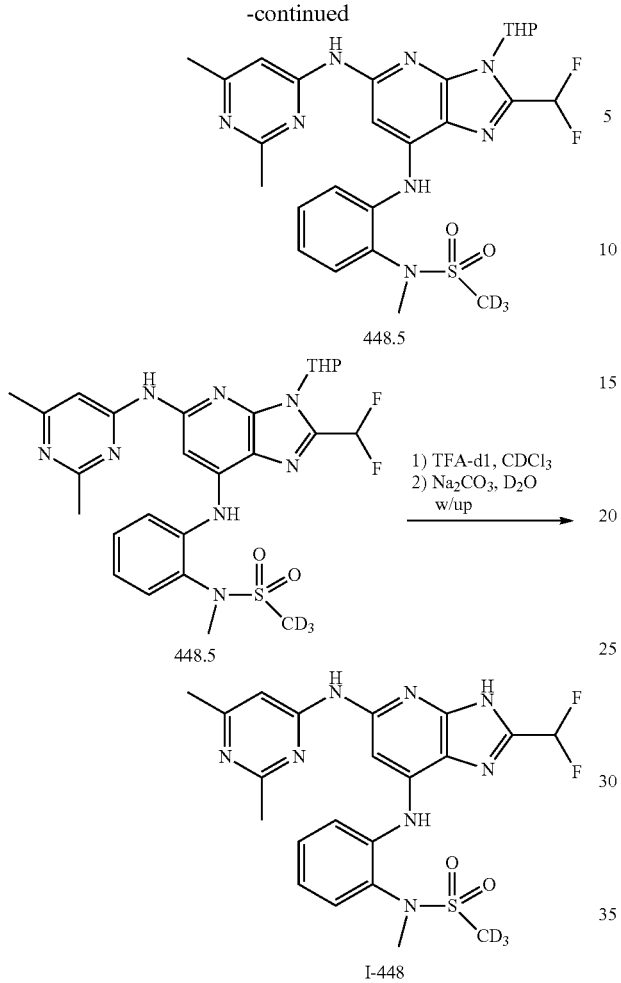

Synthesis of Compound 448.1.

To a solution of 1-fluoro-2-nitrobenzene 1 (5 g, 35.4 mmol, 1.0 eq) in acetonitrile (50 mL), $Cs_2CO_3$ (23.04 g, 70.92 mmol, 2.0 eq) and N-methyl sulfonamide (4.64 g, 42.5 mmol, 1.2 eq) was added. Reaction mixture was stirred at r.t. for 24 h. After completion of the reaction, the reaction mixture was concentrated in vacuo, transferred into water and then extracted with ethyl acetate. Organic layer combined, dried over anhydrous $Na_2SO_4$, filtered and concentrated in vacuo to obtain the crude material. This was purified by column chromatography using 30% ethyl acetate in hexane to obtain pure 448.1 (2 g, 24.51%). MS(ES): m/z 231.51 $[M+H]^+$.

Synthesis of Compound 448.2.

To compound 448.1 (2 g, 8.6 mmol, 1.0 eq) in a mixture of MeOH (16 mL) and water (4 mL), glacial acetic acid (111 mL, 130.4 mmol, 15 eq) was added. Reaction mixture was stirred at 50° C. for 3 h. Then, the reaction mixture was cooled to r.t. and iron powder (3.37 g, 60.4 mmol, 7 eq) was added in portions. Then the reaction mixture was stirred at 90° C. for 2 h. After completion of the reaction, the reaction mixture was transferred into water and extracted with ethyl acetate. Organic layer combined, dried over anhydrous $Na_2SO_4$, filtered and concentrated in vacuo to obtain the crude material. This was purified by column chromatography using 25% ethyl acetate in hexane as eluant to obtain pure 448.2 (1 g, 57.49%). MS(ES): m/z 201.37 $[M+H]^+$.

Synthesis of Compound 448.3.

Compound 448.3 was synthesized from 448.2 and 13.4 using general procedure A. (Yield: 19.78%). MS(ES): m/z 486.35 $[M+H]^+$.

Synthesis of Compound 448.4.

Compound 448.4 was synthesized from 448.3 and 2,6-dimethylpyrimidin-4-amine using general procedure B. (Yield: 67.18%). MS(ES): m/z 573.46 $[M+H]^+$.

Synthesis of Compound 448.5.

To compound 448.4 (0.077 g, 0.13 mmol, 1.0 eq) in deuterated MeOH (2 mL), 1,8-Diazabicyclo[5.4.0]undec-7-ene (0.002 g, 0.01 mmol, 0.1 eq) was added. Reaction mixture was stirred at 60° C. for 48 h. After completion of the reaction, the reaction mixture was concentrated in vacuo, transferred to deuterium oxide and extracted with ethyl acetate. Organic layer combined, dried over anhydrous $Na_2SO_4$, filtered and concentrated in vacuo to obtain 448.5 (0.058 g, 60.73%). MS(ES): m/z 576.27 $[M+H]^+$.

Synthesis of I-448.

Compound I-448 was synthesized from 448.5 using general procedure C. (Yield: 60.58 MS(ES): m/z 492.46 $[M+H]^+$, LCMS purity: 96.74%, HPLC purity: 97.44%, 1H NMR (MeOD, 400 MHz): 7.77-7.75 (d, J=8 Hz, 1H), 7.65-7.64 (d, J=7.2 Hz, 1H), 7.53-7.49 (t, J=17.6 Hz, 1H), 7.34-7.30 (t, J=15.2 Hz, 1H), 7.26 (s, 1H), 7.12 (s, 1H), 6.99 (t, 1H), 6.85 (s, 1H), 3.33 (s, 3H), 2.50 (s, 2H), 2.41 (s, 3H), 1.35 (s, 3H).

Example 449: Synthesis of N7-(4-(1,4-dimethyl-1H-pyrazol-3-yl)-2-(methylsulfonyl)phenyl)-N5-(5,6-dimethylpyrazin-2-yl)-2-methyl-3H-imidazo[4,5-b]pyridine-5,7-diamine, I-449

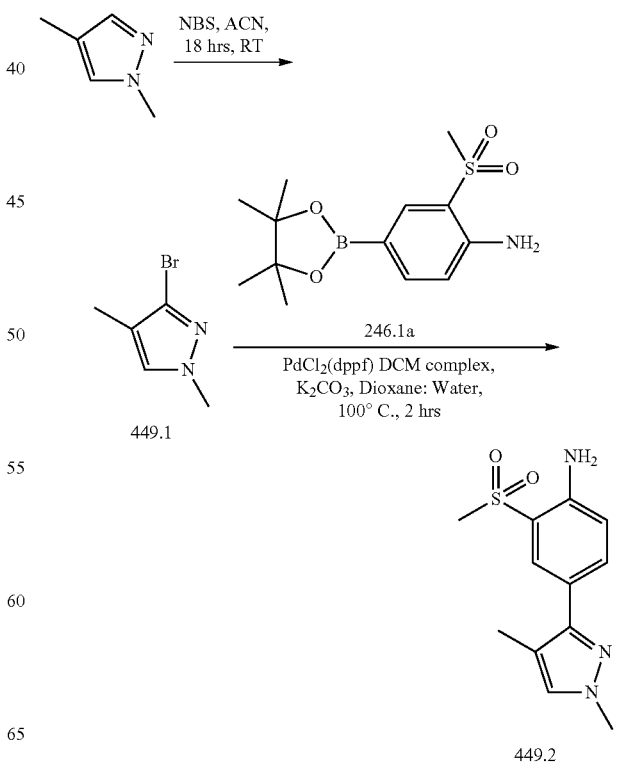

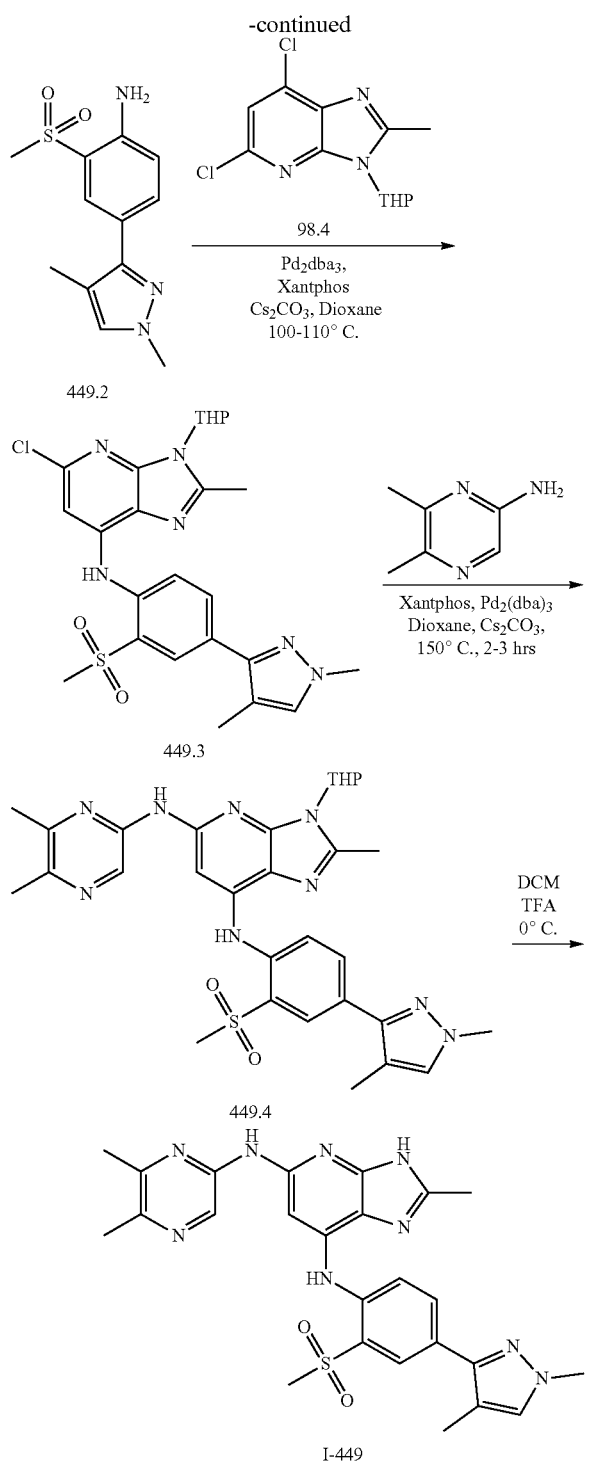

Synthesis of Compound 449.1

To compound 1,4-dimethyl-1H-pyrazole (5.0 g, 5.20 mmol, 1.0 eq) in acetonitrile (50 mL) at 0° C., N-Bromosuccinimide (13.0 g, 7.89 mmol, 1.5 eq) was added dropwise. Reaction mixture was stirred at r.t. for 20 h. After completion of the reaction, the reaction mixture was transferred to water and extracted with ethyl acetate. Organic layers were combined, dried over anhydrous $Na_2SO_4$, filtered and evaporated under vacuum to obtain 449.1 (2.5 g, 27.46%). MS(ES): m/z 176.53 [M+H]$^+$.

Synthesis of Compound 449.2.

To a solution of 449.1 (2.94 g, 0.99 mmol, 1.0 eq) and compound 1.2 (2.5 g, 1.48 mmol, 1.5 eq) in a mixture of 1,4-dioxane (50 mL) and water (10 mL), potassium carbonate (4.1 g, 2.9 mmol, 3.0 eq) was added. Reaction mixture was degassed with argon for 15 min. Then [1,1'-Bis(diphenylphosphino)ferrocene]dichloropalladium(II) complex with $CH_2Cl_2$ (0.40 g, 0.049 mmol, 0.05 eq) was added and again degassed for 5 min. Reaction mixture was stirred at 100° C. for 2 h. After completion of the reaction, the reaction mixture was transferred to water and extracted with ethyl acetate. Organic layer combined, dried over anhydrous $Na_2SO_4$, filtered and concentrated in vacuo to obtain crude product. This was purified by column chromatography using 25% ethyl acetate in hexane to obtain pure 449.2 (2.3 g, 60.69%). MS(ES): m/z 266.49 [M+H]$^+$.

Synthesis of Compound 449.3

Compound 449.3 was synthesized from 449.2 and 98.4 using general procedure A. (Yield: 26.15%). MS(ES): m/z 516.37 [M+H]$^+$.

Synthesis of Compound 449.4.

Compound 449.4 was synthesized from 449.3 and 5,6-dimethylpyrazin-2-amine using general procedure B. (Yield: 13.91%). MS(ES): m/z 602.34 [M+H]$^+$.

Synthesis of I-449.

Compound was synthesized from 449.4 using general procedure C. (Yield: 53.65%). MS(ES): m/z 518.61 [M+H]$^+$, LCMS purity: 99.13%, HPLC purity: 97.84%, 1H NMR (DMSO, 400 MHz): 12.43 (s, 1H), 9.61 (s, 1H), 8.87 (s, 1H), 8.72 (s, 1H), 8.24 (s, 1H), 8.03-7.96 (m, 2H), 7.61 (m, 2H), 3.87 (s, 3H), 3.25 (s, 3H), 2.48 (s, 3H), 2.40-2.38 (d, J=5.2 Hz, 6H), 2.25 (s, 3H).

Example 450: Synthesis of N-(2-(difluoromethyl)-7-((4-(1,4-dimethyl-1H-imidazol-2-yl)-2-(methylsulfonyl)phenyl)amino)-3H-imidazo[4,5-b]pyridin-5-yl)cyclopropanecarboxamide, I-450

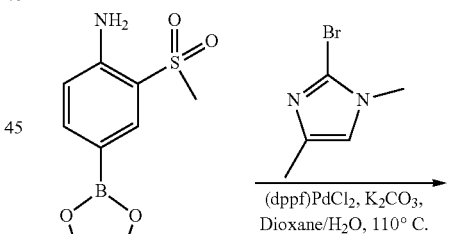

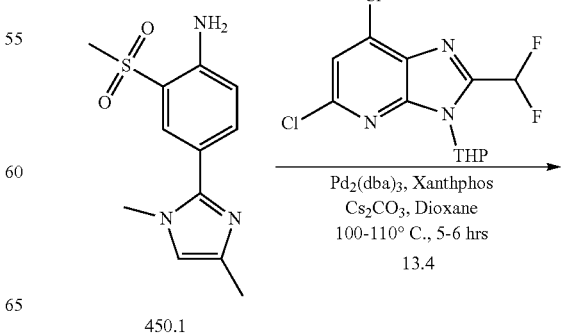

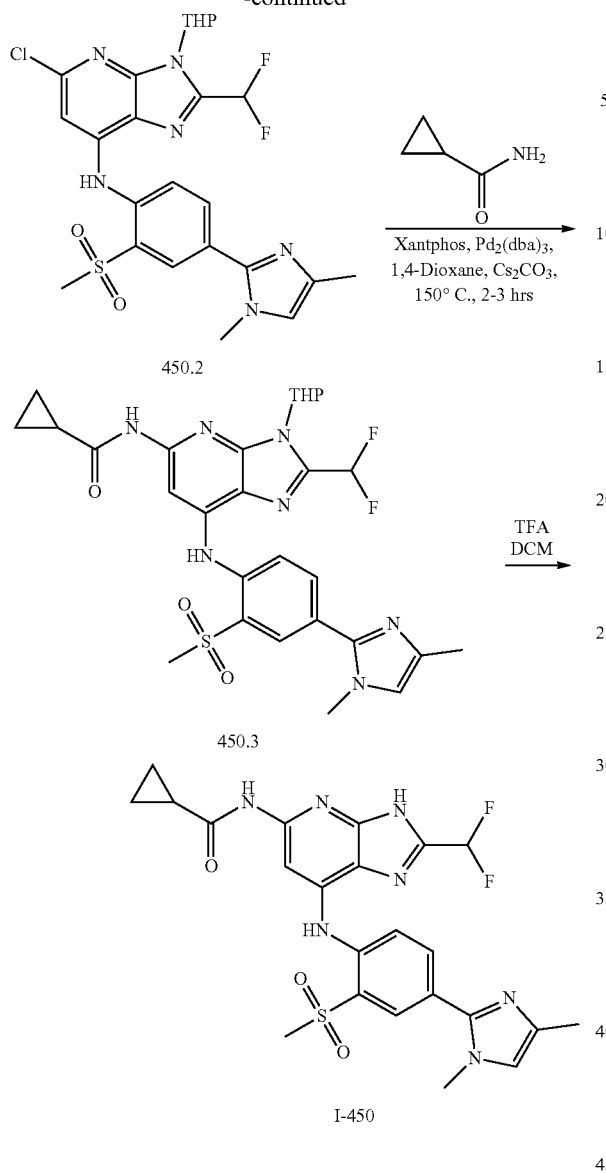

Synthesis of Compound 450.3.

Compound 450.3 was synthesized from 450.2 and cyclopropanecarboxamide using general procedure B. (Yield: 36.75%). MS(ES): m/z 600.66 [M+H]$^+$.

Synthesis of I-450.

Compound I-450 was synthesized from 450.3 using general procedure C (Yield: 72.70%). MS(ES): m/z 516.46 [M+H]$^+$, LCMS purity: 99.87%, HPLC purity: 98.89%, 1H NMR (DMSO, 400 MHz): 10.82 (s, 1H), 8.95 (s, 1H), 8.23-8.23 (d, J=1.6 Hz, 2H), 8.09-8.06 (d, J=10.4 Hz, 1H), 7.89-7.86 (d, J=2.1 Hz, 1H), 7.28 (s, 1H), 7.06 (s, 1H), 3.79 (s, 3H), 3.30 (s, 4H), 2.17 (s, 3H), 2.07-2.04 (s, 1H), 0.81 (bs, 4H).

Example 451: Synthesis of N-(2-(difluoromethyl)-7-((4-(1,5-dimethyl-1H-imidazol-2-yl)-2-(methylsulfonyl)phenyl)amino)-3H-imidazo[4,5-b]pyridin-5-yl)cyclopropaneCarboxamide, I-451

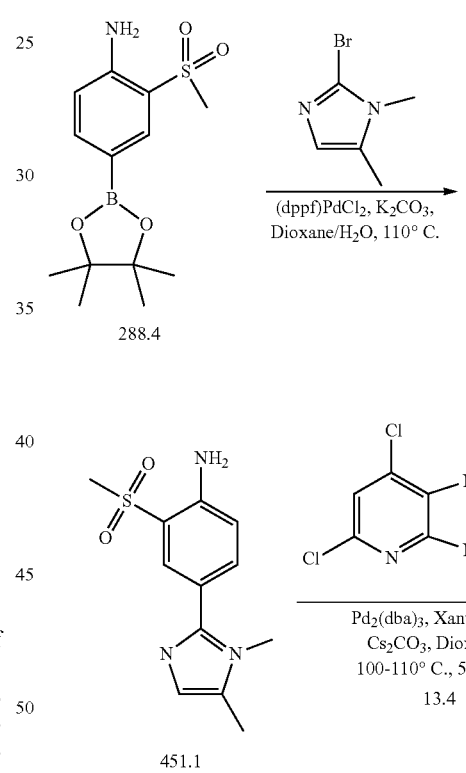

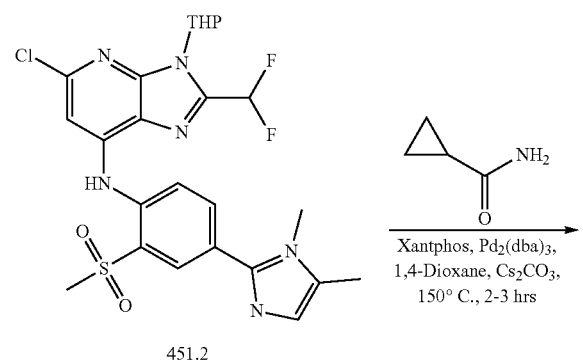

Synthesis of Compound 450.1.

To 288.4 (2.0 g, 1.05 mmol, 1.0 eq) in a mixture of dioxane (16 mL) and water (4 mL), compound 2-bromo-1,4-dimethyl-1H-imidazole (1.75 g, 1.58 mmol, 1.5 eq) was added. Reaction mixture was degassed with argon atmosphere for 10 min. Then [1,1'-Bis(diphenylphosphino)ferrocene]palladium(II)dichloride (0.250 g, 0.31 mmol, 0.03 eq) and potassium carbonate (1.5 g, 3.16 mmol, 3 eq) was added into it. Reaction mixture was stirred at 115° C. for 24 h. Upon completion, reaction mixture was transferred into cold water and extracted with ethyl acetate. Organic layers were combined, dried over Na$_2$SO$_4$ and concentrated in vacuo to obtain crude product. This was purified by column chromatography and compound was eluted in 3% MeOH in CH$_2$Cl$_2$ as eluant to obtain pure 450.1 (1.3 g, 42.88%). MS(ES): m/z 266.33 [M+H]$^+$.

Synthesis of Compound 450.2.

Compound 450.2 was synthesized from 450.1 and 13.4 using general procedure A. (Yield: 28.89%). MS(ES): m/z 552.01 [M+H].

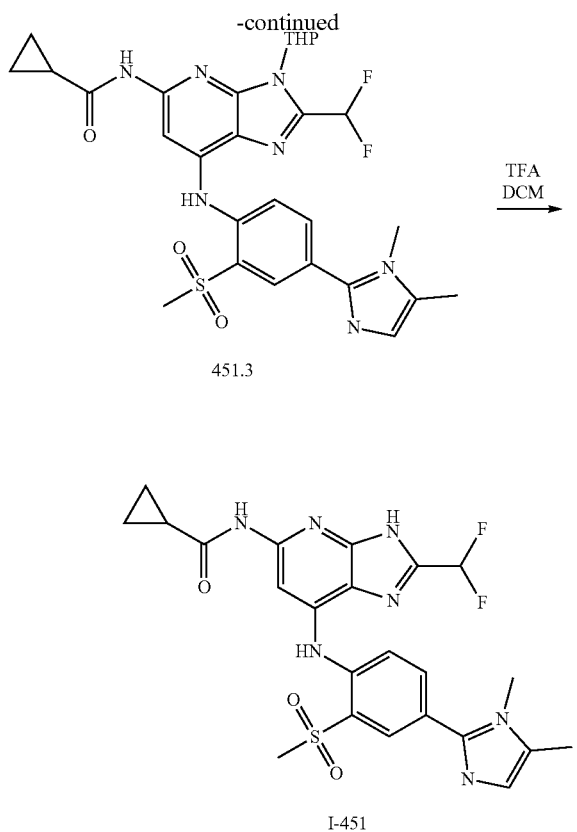

451.3

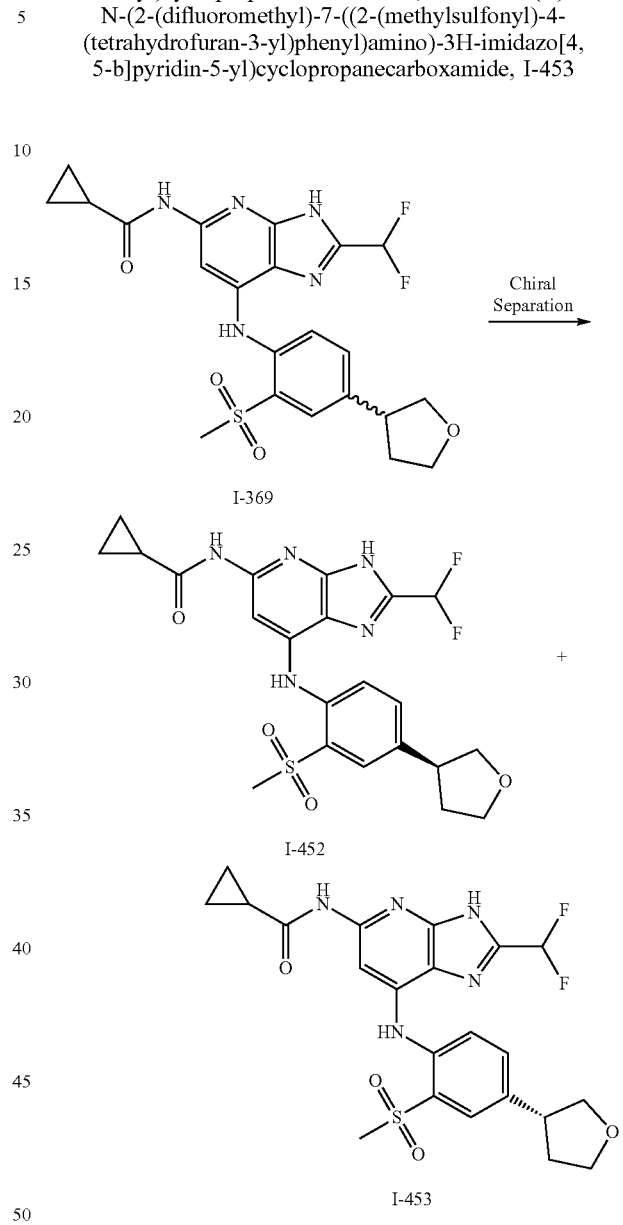

I-451

Synthesis of Compound 451.1

A mixture of 288.4 (2. g, 1.05' mmol, 1.0 eq) and 2-bromo-1,5-dimethyl-1H-imidazole (1.75 g, 1.58 mmol, 1.5. eq) in a mixture of dioxane (16 mL) and water (4 mL) was degassed with argon for 10 min. Then [1,1'-Bis(diphenylphosphino)ferrocene]palladium(II)dichloride (0.250 g, 0.31 mmol, 0.03 eq) and carbonate (1.5 g, 3.16 mmol, 3 eq) was added into it. Reaction mixture was stirred at 115° C. for 24 h. Upon completion, reaction mixture was transferred into cold water then extracted with ethyl acetate. Organic layers were combined, dried over $Na_2SO_4$ and concentrated in vacuo to obtain crude product. This was purified by column chromatography and compound was eluted in 3% MeOH in $CH_2Cl_2$ as eluant to obtain pure 451.1 (1.4 g, 78.40%). MS(ES): m/z 266.33 [M+H]$^+$.

Synthesis of Compound 451.2.

Compound 451.2 was synthesized from 451.1 and 13.4 using general procedure A. (Yield: 19.26%). MS(ES): m/z 552.01 [M+H]$^+$.

Synthesis of Compound 451.3.

Compound was synthesized from 451.2 using general procedure B. (Yield: 55.13%). MS(ES): m/z 600.66 [M+H]$^+$.

Synthesis of I-451.

Compound I-451 was synthesized from 451.3 using general procedure C. (Yield: 77.54%). MS(ES): m/z 516.54 [M+H]$^+$, LCMS purity: 96.41%, HPLC purity: 95.67%, 1H NMR (DMSO, 400 MHz): 13.73 (s, 1H), 10.80 (s, 1H), 8.92 (s, 1H), 8.17 (s, 2H), 8.04-8.02 (m, 1H), 7.27 (t, 1H), 6.82 (s, 2H), 3.67 (s, 3H), 3.29 (s, 3H), 2.26 (s, 3H), 2.05 (s, 1H), 0.81 (bs, 4H).

Example 452/453 Synthesis of (S)—N-(2-(difluoromethyl)-7-((2-(methylsulfonyl)-4-(tetrahydrofuran-3-yl)phenyl)amino)-3H-imidazo[4,5-b]pyridin-5-yl)cyclopropanecarboxamide, I-452 and (R)—N-(2-(difluoromethyl)-7-((2-(methylsulfonyl)-4-(tetrahydrofuran-3-yl)phenyl)amino)-3H-imidazo[4,5-b]pyridin-5-yl)cyclopropanecarboxamide, I-453

Synthesis of Compound I-452 and I-453.

Isomers of I-369 (0.085 g) were separated out using column (CHIRALPAK IC (250 mm*4.6 mm, 5u)) and 0.1% DEA MEOH flow rate of 4 mL/min. to get pure fraction-1 (FR-a) and fraction-2 (FR-b). FR-a was concentrated in vacuo at 30° C. to afford pure I-452 (0.032 g). MS(ES): m/z 492.46 [M+H]$^+$, LCMS purity: 100%, HPLC purity: 100%, Chiral HPLC: 100%, 1H NMR (DMSO, 400 MHz): 13.79 (s, 1H), 10.74 (s, 1H), 8.71 (s, 1H), 8.04 (s, 2H), 7.81 (m, 1H), 7.75-7.68 (m, 2H), 4.05-4.01 (m, 1H), 4.00-3.96 (m, 1H), 3.84-3.78 (m, 1H), 3.63-3.59 (m, 1H), 3.53-3.48 (m, 1H), 3.20 (s, 3H), 2.41-2.33 (m, 1H), 2.04-1.91 (m, 2H), 0.79-0.77 (m, 4H). FR-b was concentrated in vacuo at 30° C. to afford pure I-453 (0.034 g). MS(ES): m/z 492.46 [M+H]$^+$, LCMS purity: 99.24%, HPLC purity: 99.55%, Chiral HPLC: 99.77%, 1H NMR (DMSO, 400 MHz): 13.67 (s, 1H), 10.74 (s, 1H), 8.71 (s, 1H), 8.04 (s, 2H), 7.81 (s, 1H), 7.53-7.69 (m, 2H), 4.04-3.96 (m, 2H), 3.84-3.78 (m, 1H), 3.63-3.59 (m, 1H), 3.55-3.48 (m, 1H), 3.20 (s, 3H), 2.41-2.33 (m, 1H), 2.05-1.91 (m, 2H), 0.79-0.77 (m, 4H).

Example 454/455: (R)—N-(2-(difluoromethyl)-7-((4-(1-methoxyethyl)-2-(methylsulfonyl)phenyl)amino)-3H-imidazo[4,5-b]pyridin-5-yl)cyclopropanecarboxamide, I-454 and (S)—N-(2-(difluoromethyl)-7-((4-(1-methoxyethyl)-2-(methylsulfonyl)phenyl)amino)-3H-imidazo[4,5-b]pyridin-5-yl)cyclopropanecarboxamide, I-455

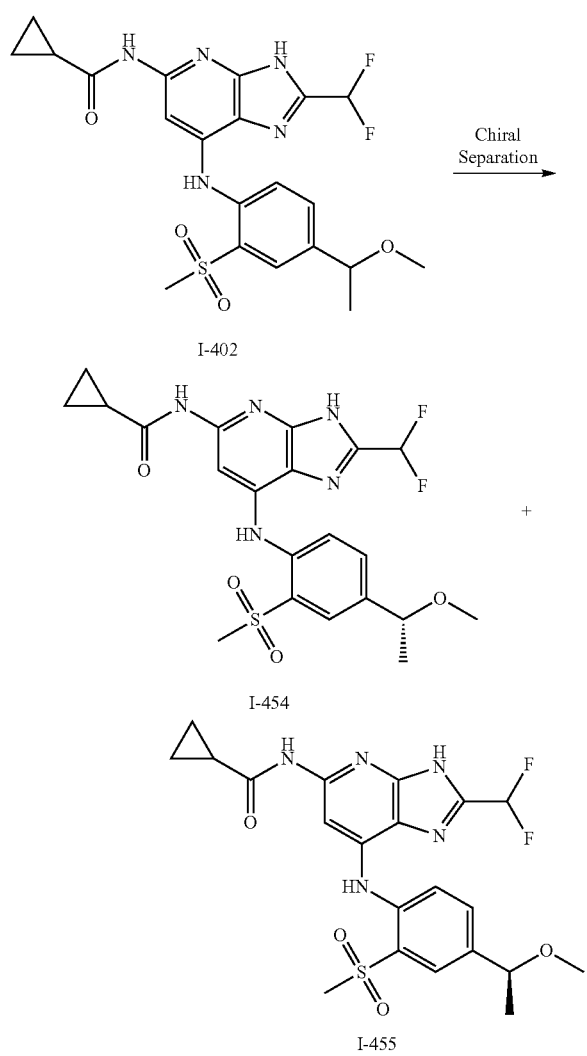

Synthesis of I-454 and I-455.

Isomers of I-402 (0.075 g) were separated out using column (CHIRALCEL OX-H (250 mm*4.6 mm, 5u)) and 0.1% DEA IPA:ACN (50:50) flow rate of 4 mL/min. to get pure fraction-1 (FR-a) and fraction-2 (FR-b). FR-a was concentrated in vacuo at 30° C. to afford pure I-454 (0.023 g). MS(ES): m/z 480.41 [M+H]$^+$, LCMS purity: 98.94%, HPLC purity: 98.40%, Chiral HPLC purity: 99%, 1H NMR (DMSO, 400 MHz): 13.67 (s, 1H), 10.72 (s, 1H), 8.72 (s, 1H), 8.05 (s, 1H), 7.85 (s, 1H), 7.79-7.77 (m, 1H), 7.70-7.68 (m, 1H), 4.43-4.42 (m, 1H), 3.22-3.19 (d, J=9.2 Hz, 6H), 2.03 (m, 1H), 1.39-1.38 (d, J=9.2 Hz, 3H), 1.23 (s, 1H), 0.78 (bs, 4H). FR-b was concentrated in vacuo at 30° C. to afford pure I-455 (0.028 g). MS(ES): m/z 480.46 [M+H]$^+$, LCMS purity: 98.12%, HPLC purity: 97.17%, Chiral HPLC purity: 100%, 1H NMR (DMSO, 400 MHz): 13.65 (s, 1H), 10.71 (s, 1H), 8.70 (s, 1H), 8.05 (s, 1H), 7.85 (s, 1H), 7.80-7.77 (m, 1H), 7.71-7.69 (m, 1H), 4.46-4.4 (m, 1H), 3.23-3.20 (d, J=9.2 Hz, 6H), 2.04 (m, 1H), 1.40-1.39 (d, J=9.2 Hz, 3H), 1.25 (s, 1H), 0.79 (bs, 4H).

Example 456: Synthesis of N-(2-((5-((2,6-dimethylpyrimidin-4-yl)amino)-2-methyl-3H-imidazo[4,5-b]pyridin-7-yl)amino)phenyl)-N-methylmethanesulfonamide-d3, I-456

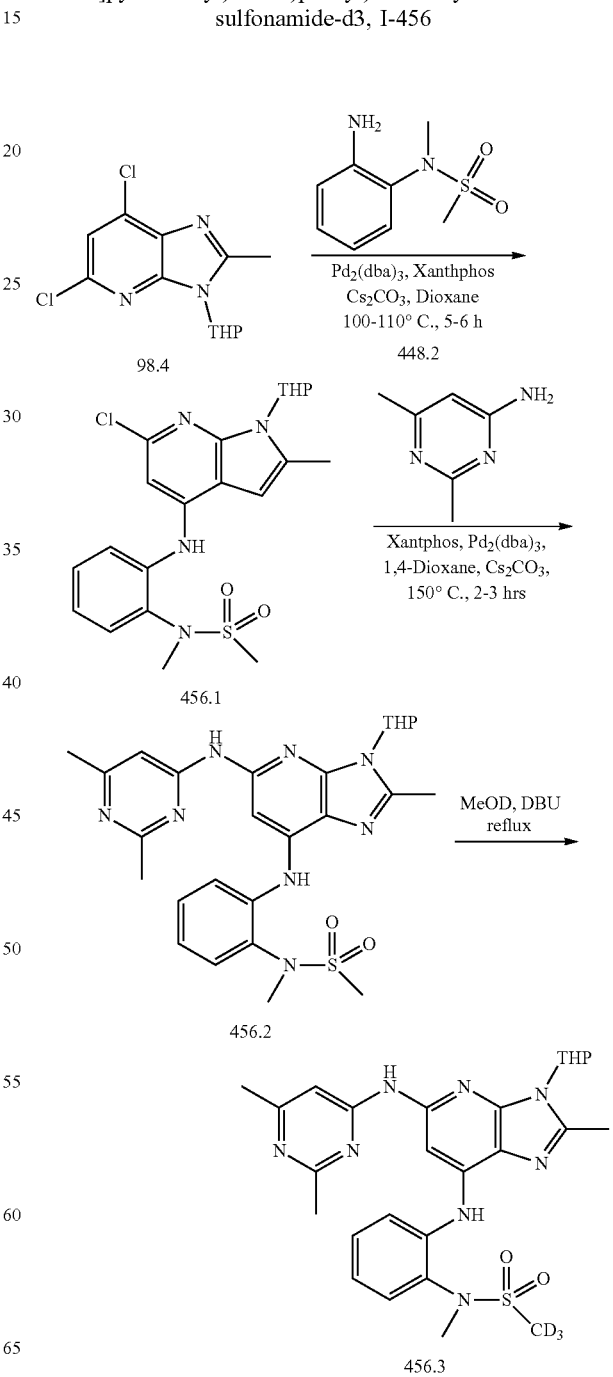

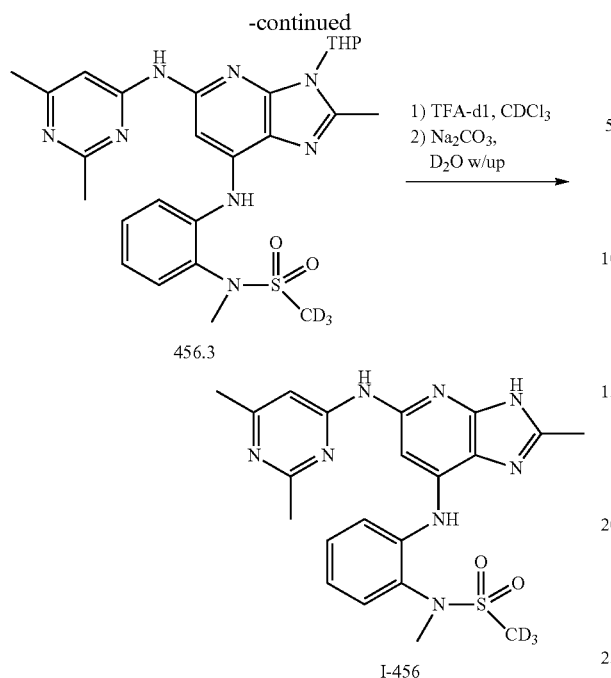

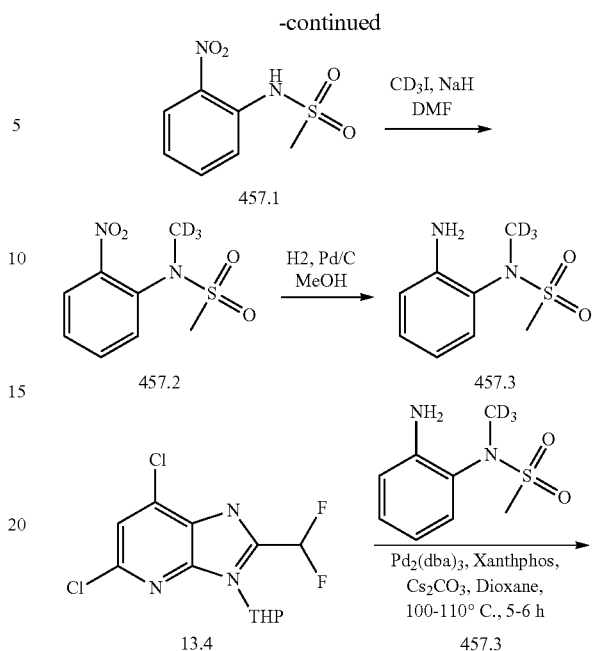

Synthesis of Compound 456.1.
Compound 456.1 was synthesized from 448.2 and 98.4 using general procedure A. (Yield: 45.79%). MS(ES): m/z 450.86 [M+H]⁺.

Synthesis of Compound 456.2.
Compound 456.2 was synthesized from 456.1 and 2,6-dimethylpyrimidin-4-amine using general procedure B. (Yield: 58.23%). MS(ES): m/z 537.28 [M+H]⁺.

Synthesis of Compound 456.3.
To compound 456.2 (0.12 g, 0.2 mmol, 1.0 eq) in deuterated MeOH (2 mL), 1,8-Diazabicyclo[5.4.0]undec-7-ene (0.03 g, 0.02 mmol, 0.1 eq) was added. Reaction mixture was stirred at 60° C. for 48 h. After completion of the reaction, the reaction mixture was concentrated in vacuo, transferred to deuterium oxide and extracted with ethyl acetate. Organic layer combined, dried over anhydrous Na₂SO₄, filtered and concentrated in vacuo to obtain 456.3 (0.120 g, 99.44%). MS(ES): m/z 540.27 [M+H]⁺.

Synthesis of I-456.
Compound I-456 was synthesized from 456.3 using general procedure C. (Yield: 49.36%). MS(ES): m/z 456.66 [M+H]⁺, LCMS purity: 97.82%, HPLC purity: 96.35%, 1H NMR (DMSO, 400 MHz): 12.40 (s, 1H), 9.76 (s, 1H), 7.90 (s, 1H), 7.75-7.64 (m, 2H), 7.49-7.43 (m, 2H), 7.23-7.19 (t, J=14.8 Hz, 1H), 3.33 (s, 1H), 3.21 (s, 3H), 2.47 (s, 3H), 2.41 (s, 3H), 2.30 (s, 3H).

Example 457: Synthesis of N-(2-((2-(difluoromethyl)-5-((2,6-dimethylpyrimidin-4-yl)amino)-3H-imidazo[4,5-b]pyridin-7-yl)amino)phenyl)-N-(methyl-d3)methanesulfonamide-d3, I-457

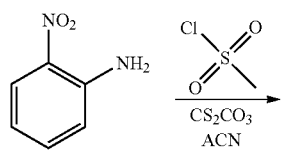

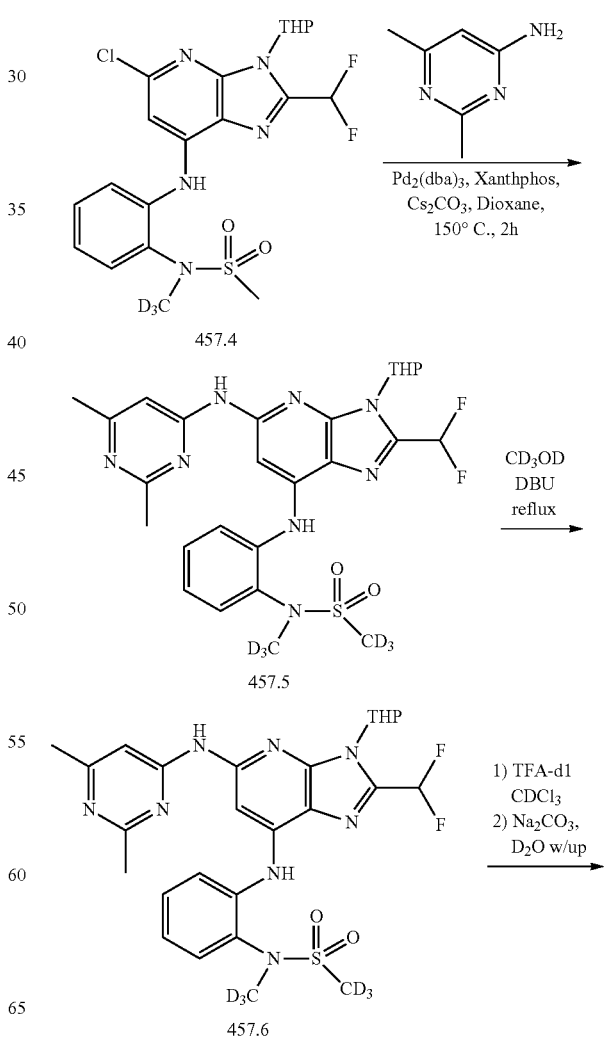

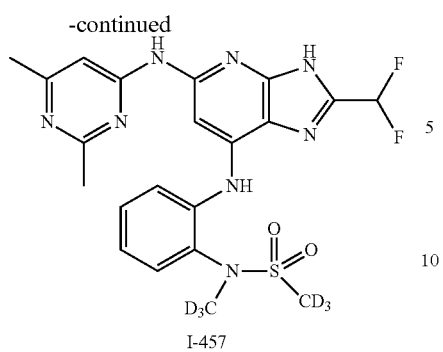

I-457

Synthesis of Compound 457.1.

To compound 2-nitroaniline (4.0 g, 28.9 mmol, 1.0 eq) in pyridine (10 mL), methanesulfonyl chloride (2.7 mL, 34.6 mmol, 1.2 eq) was added. Reaction mixture was stirred at r.t. for 24 h. After completion of the reaction, the reaction mixture was transferred into water to obtain precipitate which was filtered, washed with water and dried well to obtain 457.1 (5.6 g, 89.44%). MS(ES): m/z 217.54 [M+H]$^+$.

Synthesis of Compound 457.2.

To compound 457.1 (1.0 g, 4.6 mmol, 1.0 eq) in N,N-dimethylformamide (10 mL) at 0° C., sodium hydride (0.37 g, 9.2 mmol, 2.0 eq) was added. Reaction mixture was stirred at 0° C. for 30 min and iodomethane-d3 (1.0 g, 6.9 mmol, 1.5 eq) was added. Reaction mixture was stirred at r.t. for 3 h. After completion of reaction, the reaction mixture was transferred into ice cold water and extracted with ethyl acetate. Organic layer combined, dried over anhydrous Na$_2$SO$_4$, filtered and concentrated in vacuo to obtain the crude material. This was purified by trituration using diethyl ether to obtain pure 457.2 (0.75 g, 69.52%). MS(ES): m/z 234.16 [M+H]$^+$.

Synthesis of Compound 457.3.

To compound 457.2 (0.72 g, 3.09 mmol, 1.0 eq) in MeOH (10 mL), 10% Pd/C (0.2 g) was added. Hydrogen was purged through the reaction mixture for 1 h. After completion of the reaction, the reaction mixture was filtered through celite bed and washed with MeOH. Filtrate was concentrated in vacuo to obtain the crude material. This was purified by trituration using diethyl ether to obtain pure 457.3 (0.525 g, 83.67%). MS(ES): m/z 234.16 [M+H]$^+$.

Synthesis of Compound 457.4.

Compound 457.4 was synthesized from 457.3 and 13.4 using general procedure A. (Yield: 34.26%). MS(ES): m/z 489.53 [M+H]$^+$.

Synthesis of Compound 457.5.

Compound 457.5 was synthesized from 457.4 and 2,6-dimethylpyrimidin-4-amine using general procedure B. (Yield: 52.58%). MS(ES): m/z 576.43 [M+H]$^+$.

Synthesis of Compound 457.6.

To compound 457.5 (0.12 g, 0.2 mmol, 1.0 eq) in deuterated MeOH (2 mL), 1,8-Diazabicyclo[5.4.0]undec-7-ene (0.03 g, 0.02 mmol, 0.1 eq) was added. Reaction mixture was stirred at 60° C. for 48 h. After completion of the reaction, the reaction mixture was concentrated in vacuo, transferred into deuterium oxide and extracted with ethyl acetate. Organic layer combined, dried over anhydrous Na$_2$SO$_4$, filtered and concentrated in vacuo to obtain 457.6 (0.095 g, 84.26%). MS(ES): m/z 579.81 [M+H]$^+$.

Synthesis of I-457.

Compound I-457 was synthesized from 457.7 using general procedure C. (Yield: 54.60%). MS(ES): m/z 495.76 [M+H]$^+$, LCMS purity: 95.65%, HPLC purity: 95.35%, 1H NMR (MeOD, 400 MHz): 7.77-7.76 (d, J=7.6 Hz, 1H), 7.65-7.63 (d, J=8.0 Hz, 1H), 7.53-7.49 (t, J=15.2 Hz, 1H), 7.34-7.30 (t, J=15.2 Hz, 1H), 7.12 (s, 1H), 6.99 (t, 1H), 6.85 (s, 1H), 2.50 (s, 3H), 2.41 (s, 3H).

Example 458: Synthesis of N-(2-((5-((2,6-dimethylpyrimidin-4-yl)amino)-2-methyl-3H-imidazo[4,5-b]pyridin-7-yl)amino)phenyl)-N-(methyl-d3)methanesulfonamide-d3, I-458

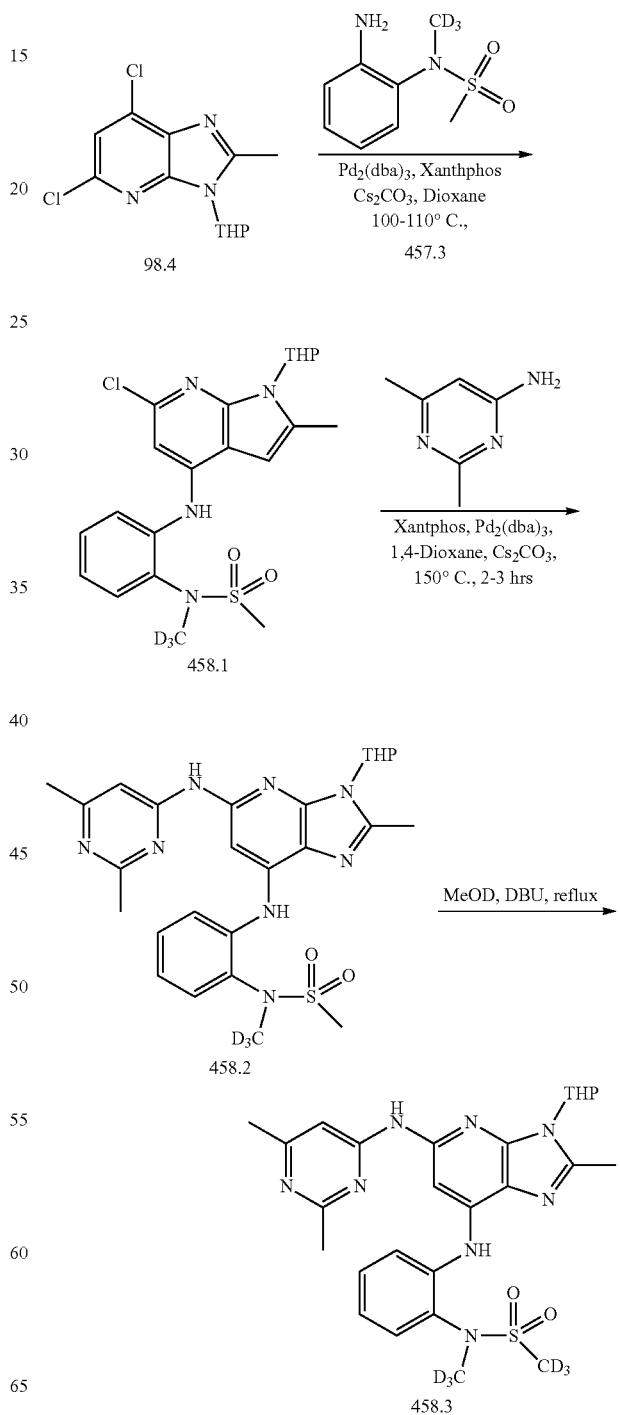

985
-continued

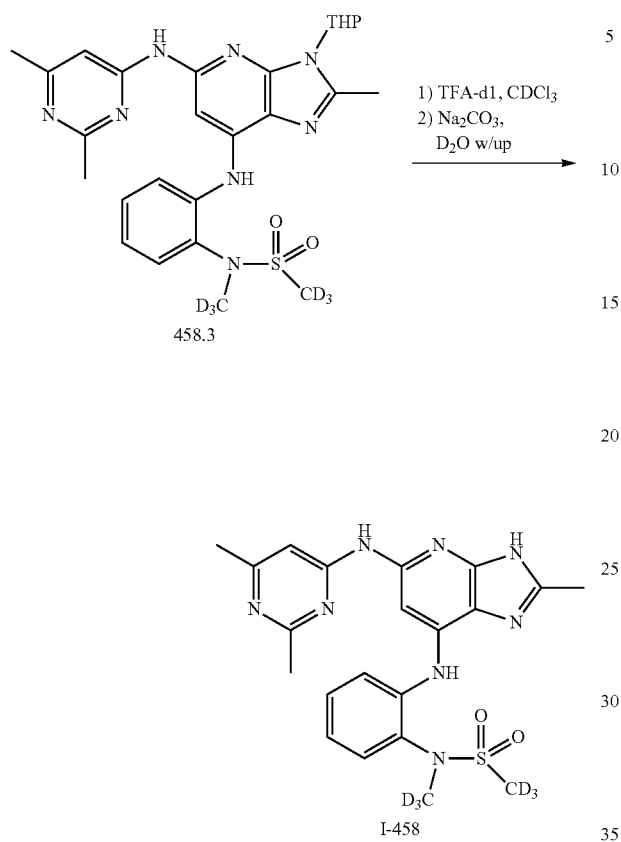

Synthesis of Compound 458.1.

Compound 458.1 was synthesized 457.3 and 98.4 from using general procedure A. (Yield: 42.96%). MS(ES): m/z 453.67 [M+H]⁺.

Synthesis of Compound 458.2.

Compound 458.2 was synthesized from 458.1 and 2,6-dimethylpyrimidin-4-amine using general procedure B. (Yield: 59.25%). MS(ES): m/z 540.16 [M+H]⁺.

Synthesis of Compound 458.3.

To compound 458.2 (0.14 g, 0.2 mmol, 1.0 eq) in deuterated MeOH (2 mL), 1,8-Diazabicyclo[5.4.0]undec-7-ene (0.03 g, 0.02 mmol, 0.1 eq) was added. Reaction mixture was stirred at 60° C. for 48 h. After completion of the reaction, the reaction mixture was concentrated in vacuo, transferred to deuterium oxide and extracted with ethyl acetate. Organic layer combined, dried over anhydrous Na₂SO₄, filtered and concentrated in vacuo to obtain 458.3 (0.130 g, 89.16%). MS(ES): m/z 543.67 [M+H]⁺.

Synthesis of I-458.

Compound I-458 was synthesized using 458.3 general procedure C. (Yield: 32.28%). MS(ES): m/z 459.66 [M+H]⁺, LCMS purity: 99.66%, HPLC purity: 99.34%, 1H NMR (DMSO, 400 MHz): 12.40 (s, 1H), 9.71 (s, 1H), 7.86 (s, 1H), 7.73-7.71 (d, J=8.0 Hz, 1H), 7.64-7.62 (d, J=7.2 Hz, 1H), 7.43-7.41 (m, 3H), 7.20-7.16 (t, J=15.2 Hz, 1H), 2.45-2.39 (d, J=24.8 Hz, 6H), 2.28 (s, 3H).

986

Example 459/460: Synthesis of (R)—N-(2-(difluoromethyl)-7-((4-(1,4-dimethyl-1H-pyrazol-3-yl)-2-(methylsulfonyl)phenyl)amino)-3H-imidazo[4,5-b]pyridin-5-yl)-2,2-dimethylcyclopropane-1-carboxamide, I-459 and (S)—N-(2-(difluoromethyl)-7-((4-(1,4-dimethyl-1H-pyrazol-3-yl)-2-(methylsulfonyl)phenyl)amino)-3H-imidazo[4,5-b]pyridin-5-yl)-2,2-dimethylcyclopropane-1-carboxamide, I-460

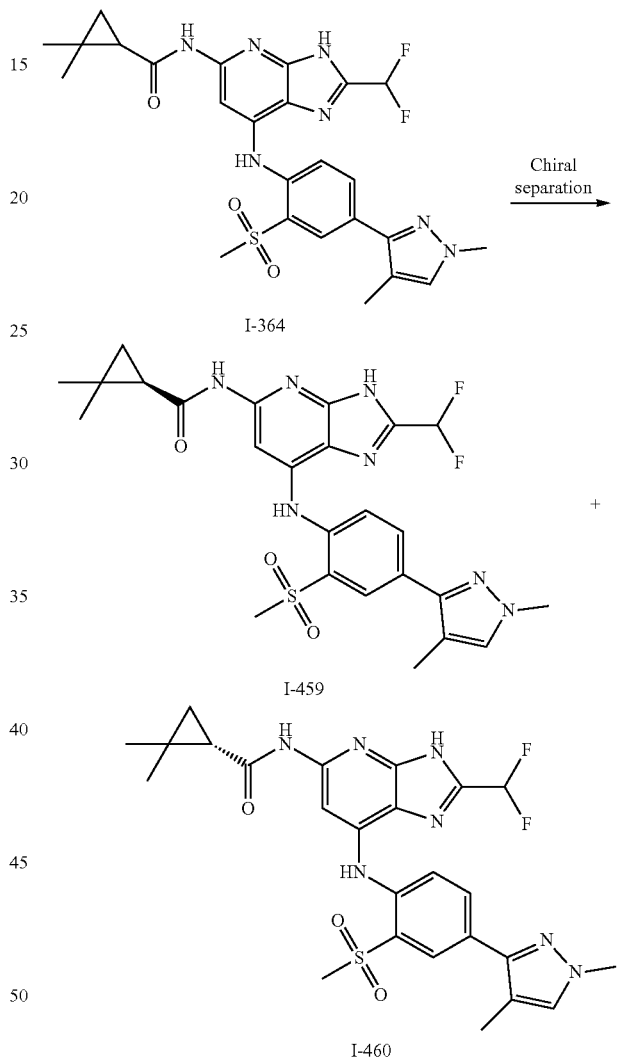

Synthesis of Compound I-459 and I-460.

Isomers of I-364 (0.085 g) were separated out using column (CHIRALCEL OX-H (250 mm*4.6 mm, 5u)) and 0.1% DEA IPA:ACN (50:50) flow rate of 4 mL/min. to get pure fraction-1 (FR-a) and fraction-2 (FR-b). FR-a was concentrated in vacuo at 30° C. to afford pure I-459 (0.025 g). MS(ES): m/z 544.61 [M+H]⁺, LCMS purity: 98.73%, HPLC purity: 98.65%, Chiral HPLC: 95.15%, 1H NMR (DMSO, 400 MHz): 13.71 (s, 1H), 10.57 (s, 1H), 8.77 (s, 1H), 8.23 (d, J=8.0 Hz, 1H), 8.08-8.00 (m, 2H), 7.84-7.82 (d, J=8.4 Hz, 1H), 7.61 (s, 1H), 7.23 (t, 1H), 3.86 (s, 3H), 3.26 (s, 3H), 2.24 (s, 3H), 1.93-1.90 (t, J=13.2 Hz, 1H), 1.14-1.13 (d, 6H), 1.05-1.04 (m, 1H), 0.98-0.96 (m, 1H) FR-b was concentrated in vacuo at 30° C. to afford pure I-460 (0.025 g). MS(ES): m/z 544.70 [M+H]+, LCMS purity: 99.63%, HPLC purity: 100%, Chiral HPLC: 99.50%, 1H NMR (DMSO, 400 MHz): 13.36 (s, 1H), 10.58 (s, 1H), 8.77 (s, 1H), 8.23 (s, 1H), 8.09 (s, 2H), 8.03-8.01 (d, J=8.8 Hz, 1H), 7.84-7.82 (d, J=8.4 Hz, 1H), 7.61 (s, 1H), 7.24 (t, 1H), 3.86 (s, 3H), 3.26 (s, 3H), 2.24 (s, 3H), 1.92 (s, 1H), 1.14-1.13 (d, J=23.2 Hz, 6H), 0.97 (s, 1H).

Example 461: Synthesis of N-(7-((4-(1,4-dimethyl-1H-imidazol-2-yl)-2-(methylsulfonyl)phenyl)amino)-2-methyl-3H-imidazo[4,5-b]pyridin-5-yl)cyclopropanecarboxamide, I-461

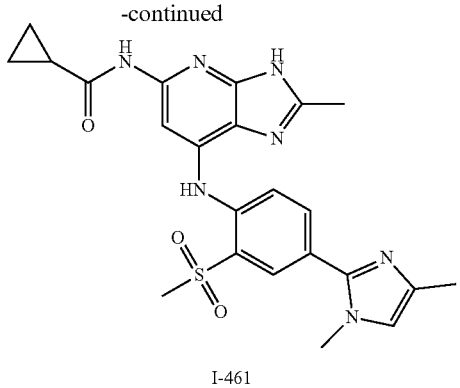

I-461

Synthesis of Compound 461.1.
Compound 461.1 was synthesized from 450.1 and 98.4 using general procedure A. (Yield: 22.22%). MS(ES): m/z 516.03 [M+H]+.

Synthesis of Compound 461.2.
Compound 461.2 was synthesized from 461.1 and cyclopropanecarboxamide using general procedure B. (Yield: 36.55%). MS(ES): m/z 564.68 [M+H]+.

Synthesis of Compound I-461.
Compound I-461 was synthesized from 461.2 using general procedure C (Yield: 51.42%). MS(ES): m/z 480.82 [M+H]+, LCMS purity: 96.21%, HPLC purity: 95.74%, 1H NMR (DMSO, 400 MHz): 12.55 (s, 1H), 10.65 (s, 1H), 8.80 (s, 1H), 8.10-8.03 (m, 2H), 7.86-7.84 (d, J=, 1H), 7.07 (s, 1H), 3.78 (s, 3H), 3.28 (s, 3H), 2.50 (s, 3H), 2.17 (s, 3H), 2.02-2.0 (s, 2H), 0.79 (bs, 4H).

Example 462: Synthesis of N-(7-((4-(1,5-dimethyl-1H-imidazol-2-yl)-2-(methylsulfonyl)phenyl)amino)-2-methyl-3H-imidazo[4,5-b]pyridin-5-yl)cyclopropanecarboxamide, I-462

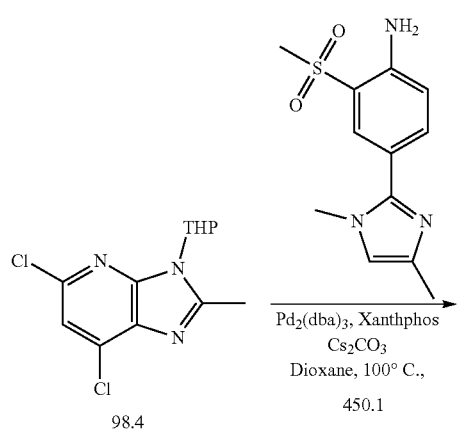

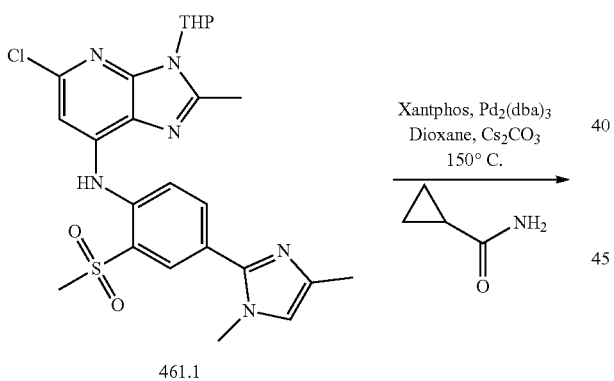

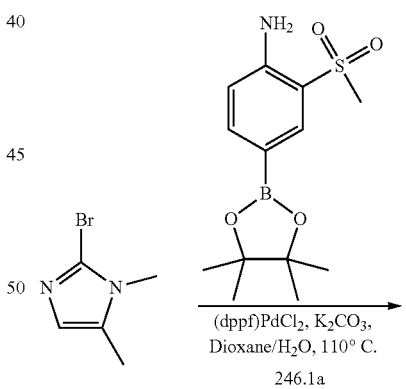

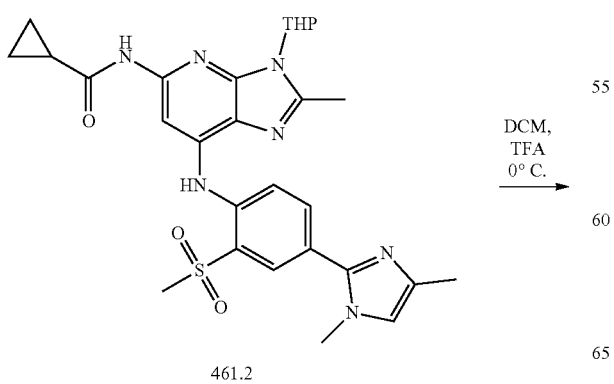

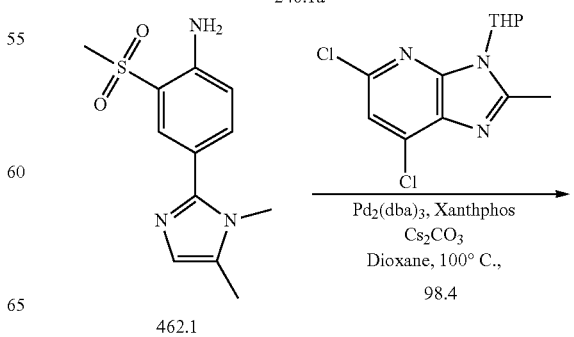

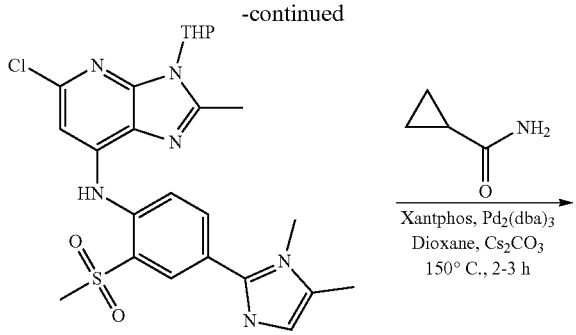

462.2

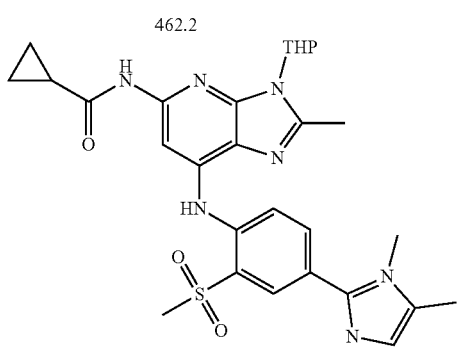

462.3

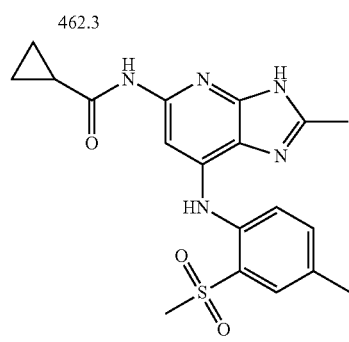

I-462

Synthesis of Compound 462.1.

A mixture of 2-bromo-1,5-dimethyl-1H-imidazole (1.0 g, 5.71 mmol, 1.0 eq) and 246.1a (1.86 g, 6.28 mmol, 1.1 eq) in 1,4-dioxane (10 mL) was degassed with argon for 10 min followed by addition of [1,1'-Bis(diphenylphosphino)ferrocene]palladium(II) dichloride(0.208 g, 0.28 mmol, 0.05 eq) and potassium carbonate (0.236 g, 1.71 mmol, 3.0 eq). Reaction mixture was stirred at 110° C. for 24 h. Upon completion, reaction mixture was transferred into cold water and extracted with ethyl acetate. Organic layer combined, dried over Na$_2$SO$_4$ and concentrated in vacuo to obtain crude product. This was purified by column chromatography and compound was eluted in 15% ethyl acetate in hexane as eluant to obtain pure 462.1 (0.4 g, 23.78%). MS(ES): m/z 266.48 [M+H]$^+$.

Synthesis of Compound 462.2.

Compound 462.2 was synthesized from 462.1 and 98.4 using general procedure A. (Yield: 23.34%). MS(ES): m/z 516.03 [M+H]$^+$.

Synthesis of Compound 462.3.

Compound 462.3 was synthesized from 462.2 and cyclopropanecarboxamide using general procedure B. (Yield: 59.39%). MS(ES): m/z 564.68 [M+H]$^+$.

Synthesis of Compound I-462.

Compound I-462 was synthesized from 462.3 using general procedure C (Yield: 79.57%). MS(ES): m/z 480.51 [M+H]$^+$, LCMS purity: 96.69%, HPLC purity: 96.81%, 1H NMR (DMSO, 400 MHz): 12.53 (s, 1H), 10.62 (s, 1H), 8.74 (s, 1H), 8.12 (s, 1H), 8.07 (s, 1H), 7.99-7.97 (d, J=8.8 Hz, 1H), 7.84-7.82 (d, J=8.8 Hz, 1H), 6.80 (s, 1H), 3.65 (s, 3H), 3.26 (s, 3H), 3.17-3.16 (d, J=5.2 Hz, 1H), 2.50 (s, 3H), 2.24 (s, 3H), 0.77 (bs, 4H).

Example 463: Synthesis of 2-(difluoromethyl)-N5-(5,6-dimethylpyrazin-2-yl)-N7-(2-(methylsulfonyl)-4-(4-methylthiazol-2-yl)phenyl)-3H-imidazo[4,5-b]pyridine-5,7-diamine, I-463

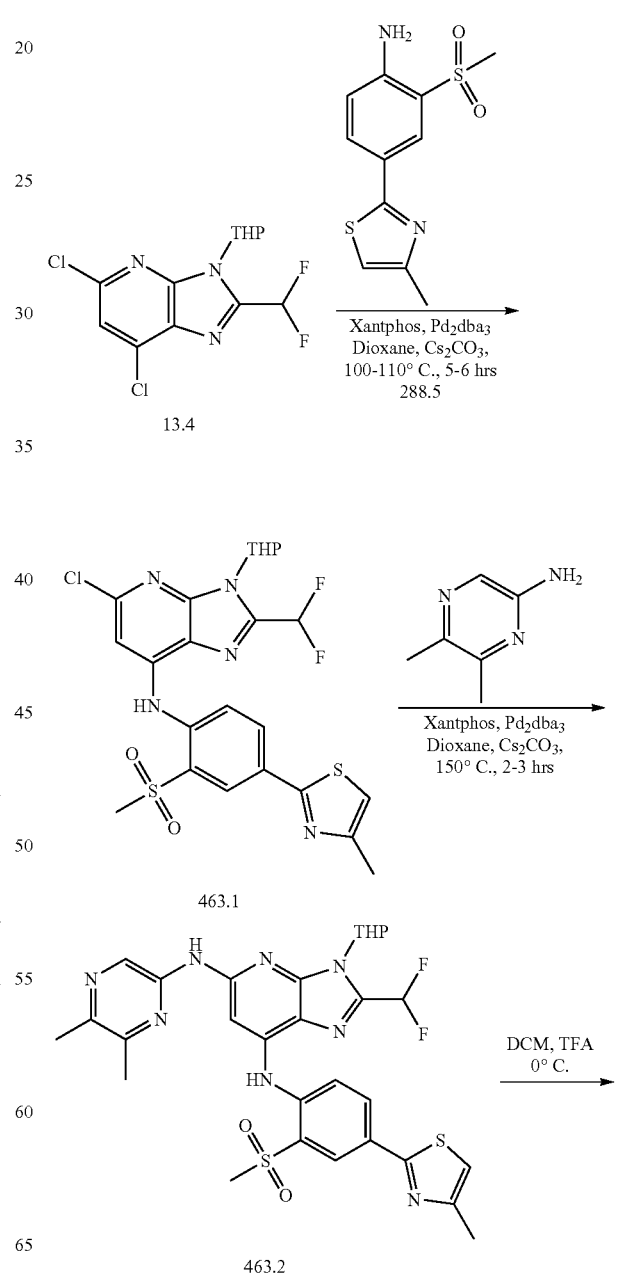

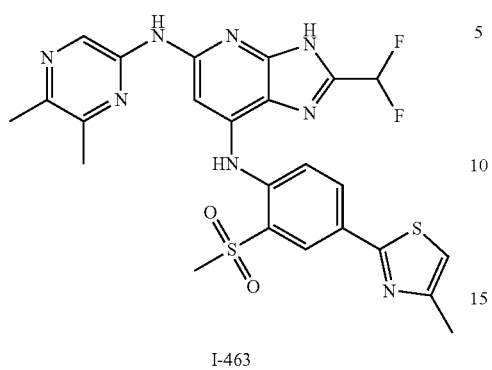

I-463

Synthesis of Compound 463.1.

Compound 463.1 was synthesized from 13.4 and 288.5 using general procedure A. (Yield: 19.62%). MS(ES): m/z 555.67 [M+H]⁺

Synthesis of Compound 463.2.

Compound was synthesized from 463.1 and 5,6-dimethylpyrazin-2-amine using general procedure B. (Yield: 41.24%). MS(ES): m/z 641.43 [M+H]⁺.

Synthesis of I-463.

Compound I-463 was synthesized from 463.2 using general procedure C (Yield: 55.70%). MS(ES): m/z 557.47 [M+H]⁺, LCMS purity: 99.59%, HPLC purity: 97.30%, 1H NMR (DMSO-d6, 400 MHz): 9.85 (s, 1H), 9.02 (s, 2H), 8.44 (s, 1H), 8.23-8.21 (d, J=8.4 Hz, 1H), 8.00-7.98 (d, J=8.0 Hz, 1H), 7.62 (s, 1H), 7.40 (s, 1H), 7.24 (t, 3.2 Hz, 1H), 3.35 (s, 3H), 3.17 (s, 1H), 2.46 (s, 3H), 2.39 (s, 6H).

Example 464: Synthesis of N5-(5,6-dimethylpyrazin-2-yl)-2-methyl-N7-(2-(methylsulfonyl)-4-(4-methylthiazol-2-yl)phenyl)-3H-imidazo[4,5-b]pyridine-5,7-diamine, I-464

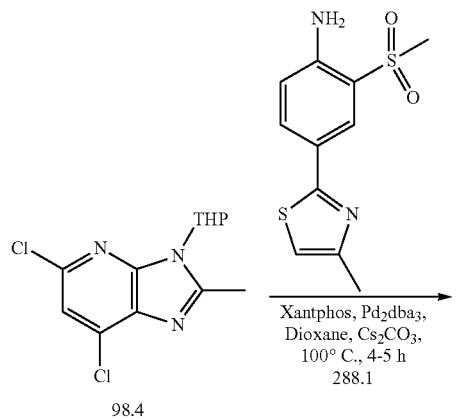

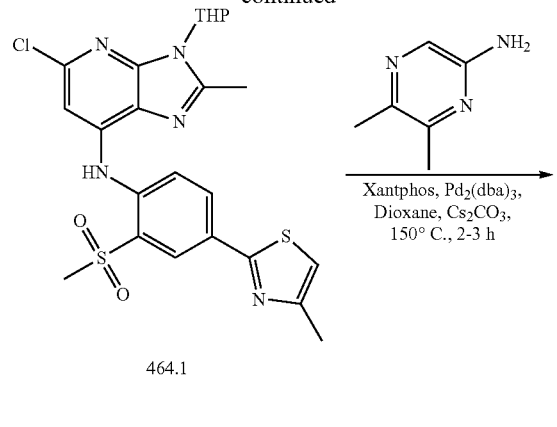

464.1

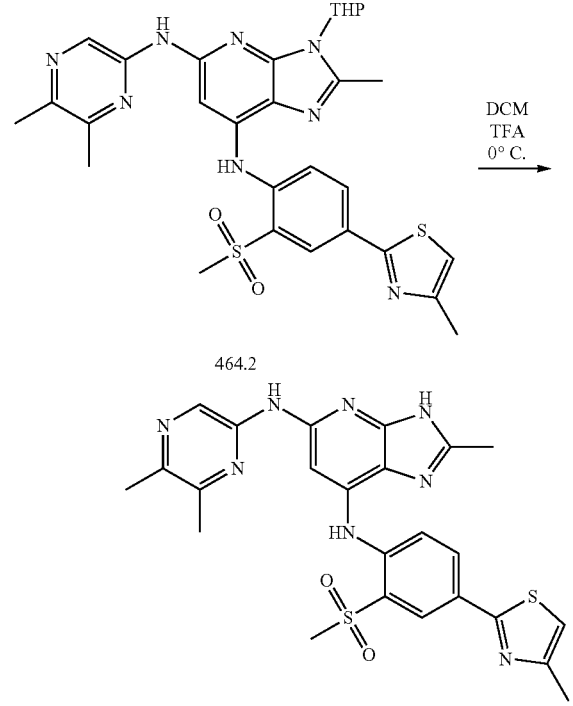

464.2

I-464

Synthesis of Compound 464.1.

Compound 464.1 was synthesized from 98.4 and 288.1 using general procedure A. (Yield: 36.82%). MS(ES): m/z 519.05 [M+H]⁺.

Synthesis of Compound 464.2.

Compound was synthesized from 464.1 and 5,6-dimethylpyrazin-2-amine using general procedure B. (Yield: 42.83%). MS(ES): m/z 605.75 [M+H]⁺.

Synthesis of I-464.

Compound I-464 was synthesized from 464.2 using general procedure C. (Yield: 60.01%). MS(ES): m/z 521.56 [M+H]⁺, LCMS purity: 100%, HPLC purity: 98.64%, 1H NMR (DMSO-d6, 400 MHz): 12.48 (s, 1H), 9.64 (s, 1H), 8.91-8.88 (m, 2H), 8.41 (s, 1H), 8.20-8.18 (m, 1H), 7.99-7.97 (m, 1H), 7.59 (s, 1H), 7.38 (s, 1H), 3.31 (s, 3H), 2.47-2.45 (d, J=5.2 Hz, 6H), 2.38 (s, 6H).

Example 465: Synthesis of N5-(5,6-dimethylpyrazin-2-yl)-2-methyl-N7-(2-(methylsulfonyl)-4-(4-methylthiazol-2-yl)phenyl)-3H-imidazo[4,5-b]pyridine-5,7-diamine, I-465

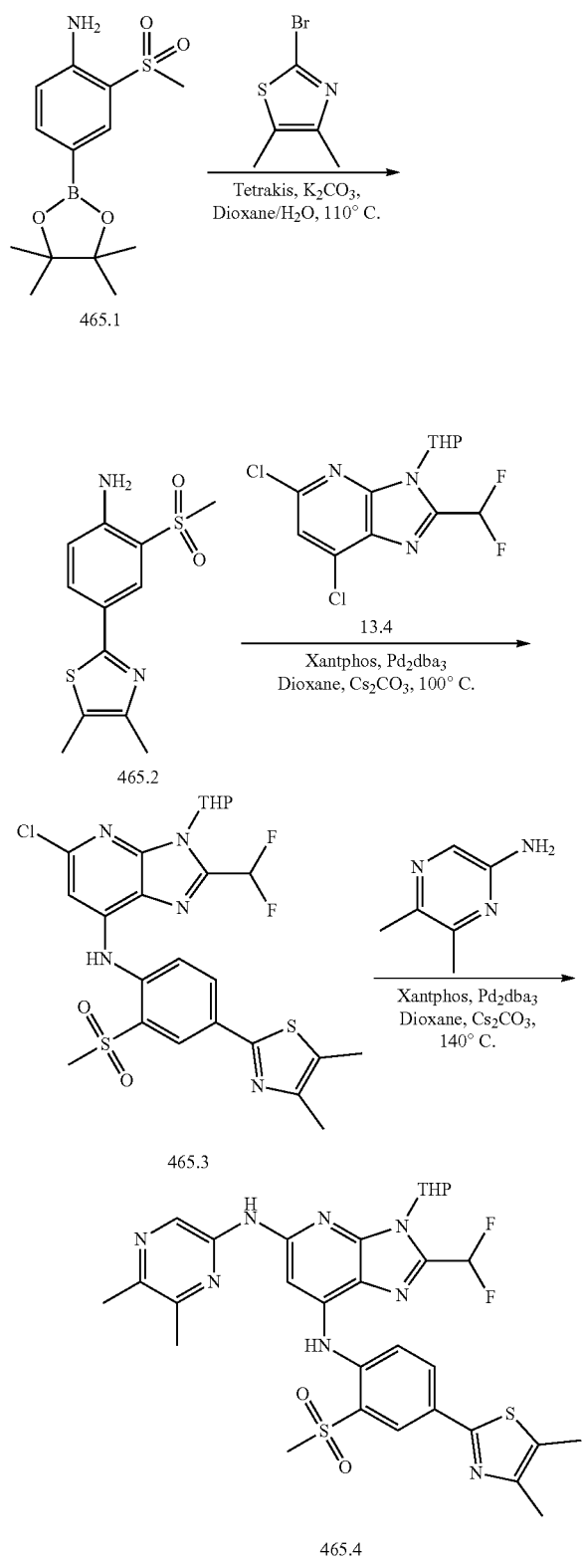

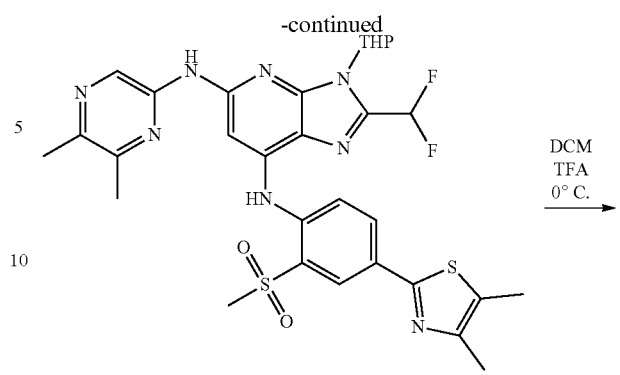

Synthesis of Compound 465.1.

Compound 465.1 was synthesized as per 288.2.

Synthesis of Compound 465.2.

To compound 465.1 (3 g, 10.1 mmol, 1.0 eq) in 1,4-dioxane (30 mL), 2-bromo-4,5-dimethylthiazole (2.3 g, 12.1 mmol, 1.2 eq) was added. Reaction mixture was degassed using argon for 20 min. Then, potassium carbonate (4.18 g, 30.3 mmol, 3.0 eq) and tetrakis(triphenylphosphine)palladium(0) (5.8 g, 5.05 mmol, 0.5 eq) was added and degassed for 5 min. Reaction mixture was stirred at 110° C. for 2 h. After completion of the reaction, the reaction mixture was transferred into water and extracted with ethyl acetate. Organic layer combined, dried over anhydrous $Na_2SO_4$, filtered and evaporated under vacuum to obtain the crude material. This was purified by column chromatography using 13% ethyl acetate in hexane as eluant to obtain pure 465.2 (2 g, 70.16%). MS(ES): m/z 283.38 [M+H]$^+$.

Synthesis of Compound 465.3.

Compound 465.3 was synthesized from 465.2 and 13.4 using general procedure A. (Yield: 18.89%). MS(ES): m/z 569.53 [M+H]$^+$.

Synthesis of compound 465.4 Compound 465.4 was synthesized from 465.3 and 5,6-dimethylpyrazin-2-amine using general procedure B. (Yield: 47.72%). MS(ES): m/z 655.38 [M+H]$^+$.

Synthesis of I-465.

Compound I-465 was synthesized from 465.4 using general procedure C (Yield: 62.59%). MS(ES): m/z 571.8 [M+H]$^+$, LCMS purity: 97.30%, HPLC purity: 98.79%, 1H NMR (DMSO, 400 MHz): 12.48 (s, 1H), 9.63 (s, 1H), 8.90 (s, 1H), 8.35 (s, 1H), 8.14-8.09 (d, J=8.4 Hz, 1H), 7.96-7.94 (d, J=4.2 Hz, 1H), 7.58 (s, 1H), 7.06 (t, 1H), 3.91-3.96 (d, J=9.6 Hz, 1H), 3.30 (s, 3H), 2.47 (s, 3H), 2.41-2.35 (t, 9H).

Example 466: Synthesis of N5-(5,6-dimethylpyrazin-2-yl)-N7-(4-(4,5-dimethylthiazol-2-yl)-2-(methylsulfonyl)phenyl)-2-methyl-3H-imidazo[4,5-b]pyridine-5,7-diamine, I-466

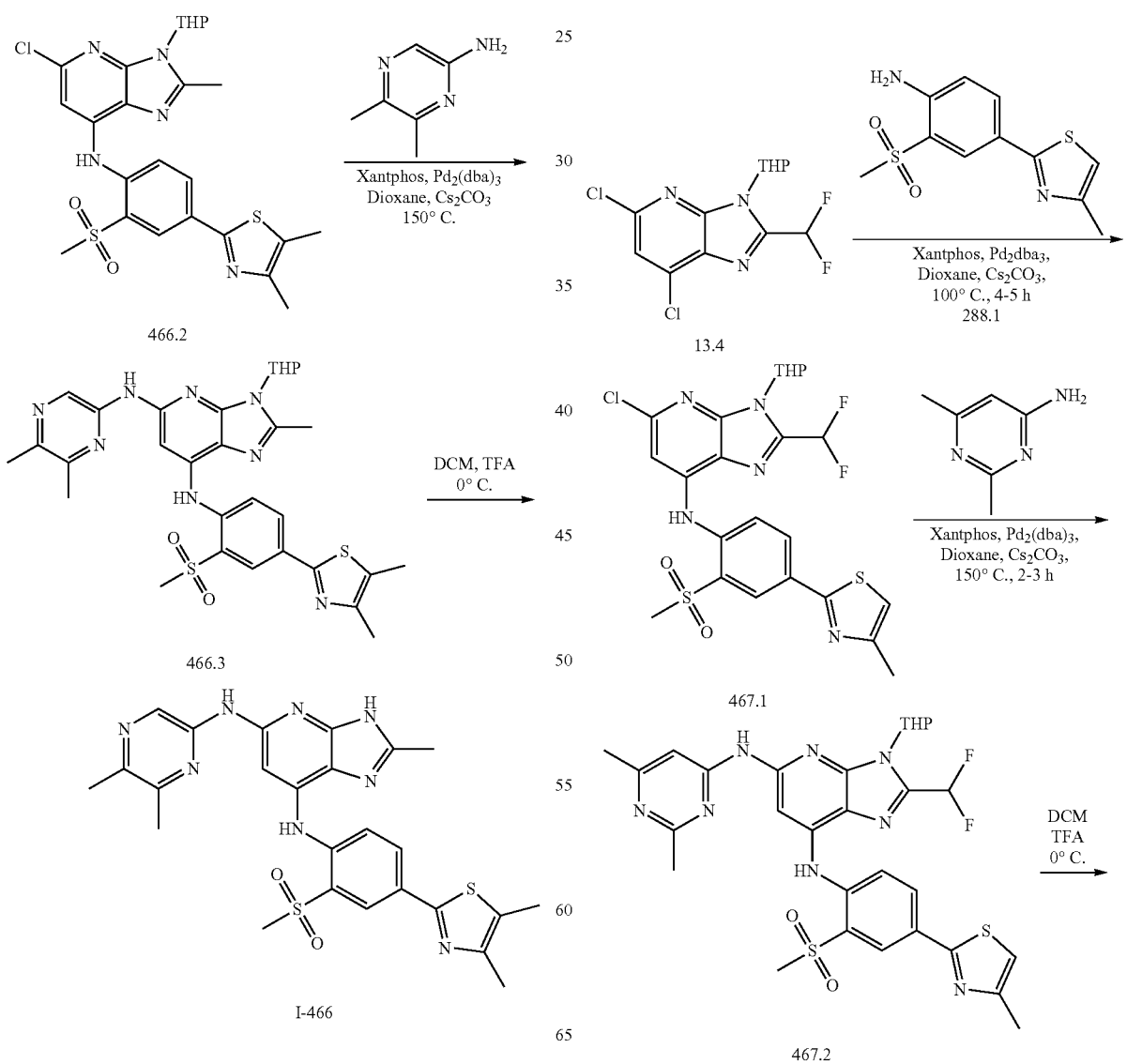

Synthesis of Compound 466.2.

Compound 466.2 was synthesized from 98.4 and 466.1 using general procedure A. (Yield: 17.21%). MS(ES): m/z 533.07 [M+H]$^+$.

Synthesis of Compound 466.3.

Compound 466.3 was synthesized from 466.2 5,6-dimethylpyrazin-2-amine using general procedure B. (Yield: 44.71%). MS(ES): m/z 619.78 [M+H]$^+$.

Synthesis of I-466.

Compound was synthesized using general procedure C. (Yield: 66.77%). MS(ES): m/z 535.60 [M+H]$^+$, LCMS purity: 95.77%, HPLC purity: 98.35%, 1H NMR (DMSO, 400 MHz): 12.48 (s, 1H), 9.64 (s, 1H), 8.91 (s, 1H), 8.85 (s, 1H), 8.37 (s, 1H), 8.13-8.11 (d, J=8.4 Hz, 1H), 7.98-7.96 (d, J=8.8 Hz, 1H), 7.60 (s, 1H), 3.46 (s, 6H), 2.68 (s, 6H), 2.39-2.34 (m, 6H).

Example 467: Synthesis of 2-(difluoromethyl)-N5-(2,6-dimethylpyrimidin-4-yl)-N7-(2-(methylsulfonyl)-4-(4-methylthiazol-2-yl)phenyl)-3H-imidazo[4,5-b]pyridine-5,7-diamine, I-467

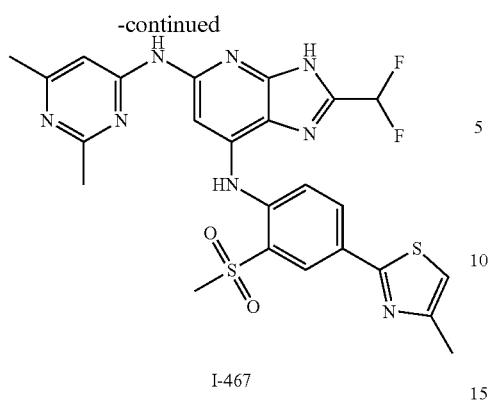

I-467

Synthesis of Compound 467.1.

Compound 467.1 was synthesized from 13.4 and 288.1 using general procedure A. (Yield: 21.90%). MS(ES): m/z 555.03 [M+H]$^+$.

Synthesis of Compound 467.2.

Compound 467.2 was synthesized from 467.1 and 2,6-dimethylpyrimidin-4-amine using general procedure B. (Yield: 41.90%). MS(ES): m/z 641.73 [M+H]$^+$.

Synthesis of I-467.

Compound I-467 was synthesized from 467.2 using general procedure C (Yield: 60.30%). MS(ES): m/z 557.60 [M+H]$^+$, LCMS purity: 100%, HPLC purity: 98.57%, 1H NMR (DMSO-d6, 400 MHz): 13.73 (s, 1H), 10.10 (s, 1H), 9.06 (s, 1H), 8.44 (s, 1H), 8.24-8.22 (d, J=8.8 Hz, 1H), 8.02-7.99 (d, J=8.8 Hz, 1H), 7.77 (s, 1H), 7.60 (s, 1H), 7.40 (s, 1H), 7.25 (t, 1H), 3.34 (s, 3H), 2.46-2.44 (d, 6H), 2.33 (s, 3H).

Example 468: Synthesis of N5-(2,6-dimethylpyrimidin-4-yl)-2-methyl-N7-(2-(methylsulfonyl)-4-(4-methylthiazol-2-yl)phenyl)-3H-imidazo[4,5-b]pyridine-5,7-diamine, I-468

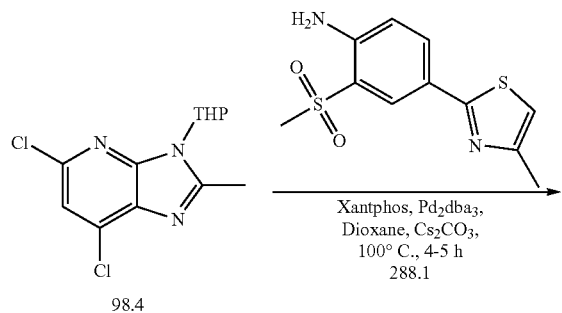

98.4

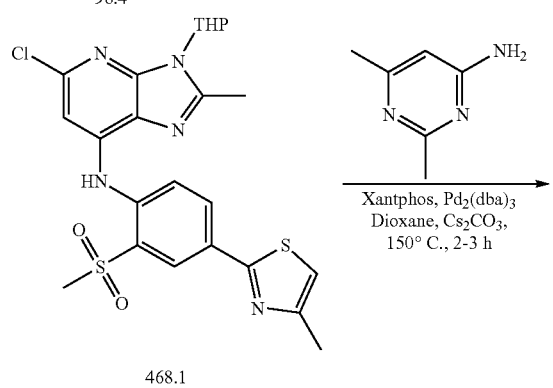

468.1

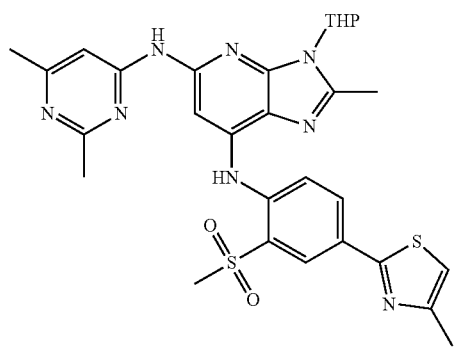

468.2

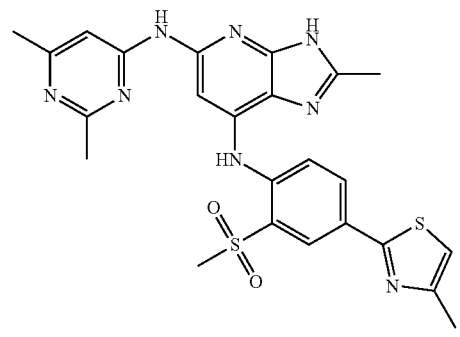

I-468

Synthesis of Compound 468.1.

Compound 468.1 was synthesized from 98.4 and 288.1 using general procedure A. (Yield: 25.30%). MS(ES): m/z 519.05 [M+H]$^+$.

Synthesis of Compound 468.2.

Compound 468.2 was synthesized from 468.1 and 2,6-dimethylpyrimidin-4-amine using general procedure B. (Yield: 41.40%). MS(ES): m/z 605.75 [M+H]$^+$.

Synthesis of I-468.

Compound I-468 was synthesized from 468.2 using general procedure C (Yield: 56.08%). MS(ES): m/z 521.54 [M+H]$^+$, LCMS purity: 100%, HPLC purity: 99.11%, 1H NMR (DMSO-d6, 400 MHz): 12.57 (s, 1H), 9.90 (s, 1H), 8.92 (s, 1H), 8.42 (s, 1H), 8.21-8.18 (d, J=8.4 Hz, 1H), 7.99-7.98 (d, J=8.4 Hz, 1H), 7.71 (s, 1H), 7.47 (s, 1H), 7.38 (s, 1H), 3.32 (s, 3H), 2.48 (s, 3H), 2.45 (s, 3H), 2.42 (s, 3H), 2.31 (s, 3H).

Example 469: Synthesis of 2-(difluoromethyl)-N5-(2,6-dimethylpyrimidin-4-yl)-N7-(4-(4,5-dimethyl-thiazol-2-yl)-2-(methylsulfonyl)phenyl)-3H-imidazo[4,5-b]pyridine-5,7-diamine, I-469

Example 470: Synthesis of N5-(2,6-dimethylpyrimidin-4-yl)-N7-(4-(4,5-dimethylthiazol-2-yl)-2-(methylsulfonyl)phenyl)-2-methyl-3H-imidazo[4,5-b]pyridine-5,7-diamine, I-470

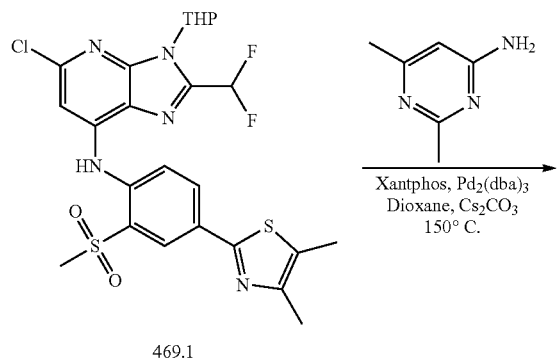

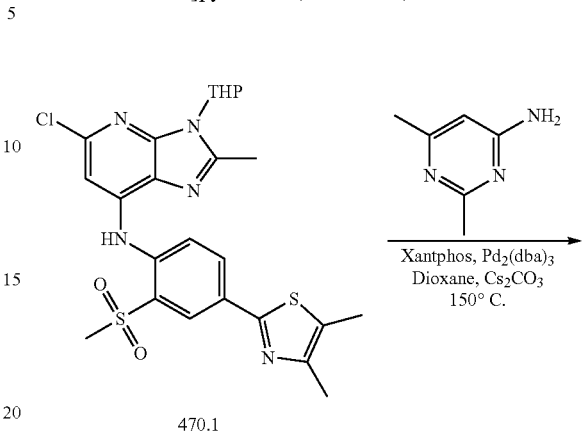

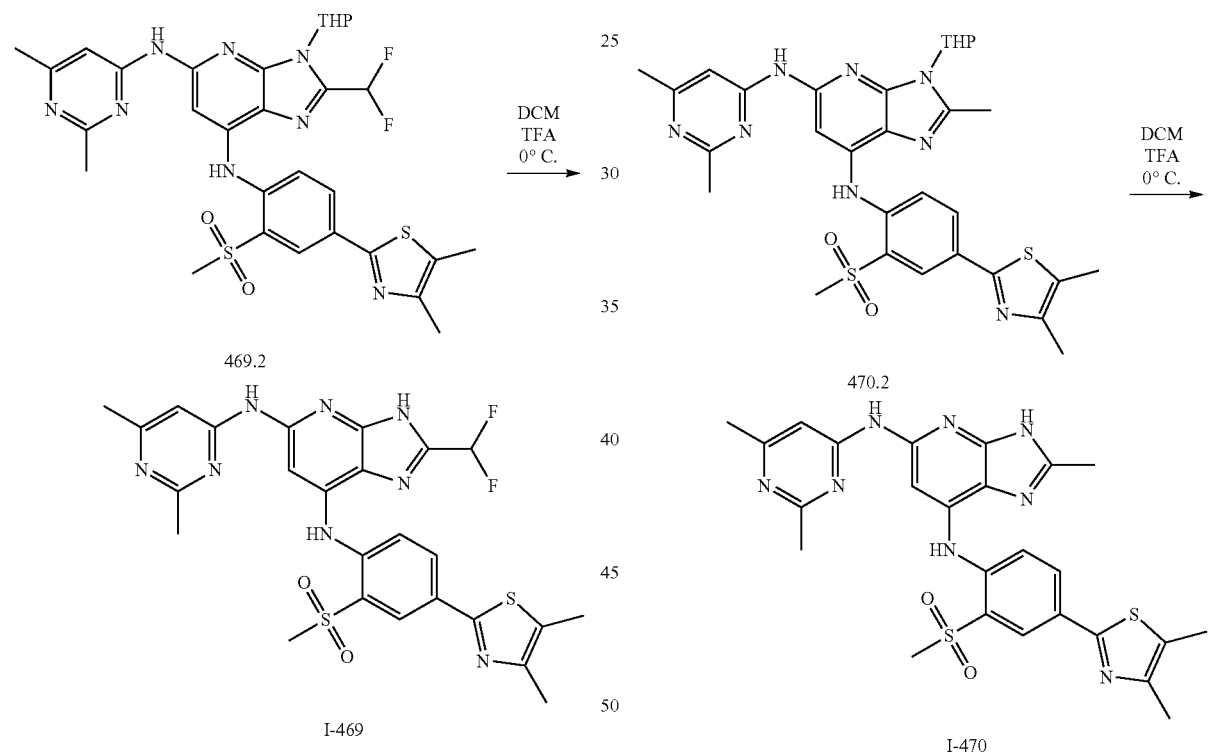

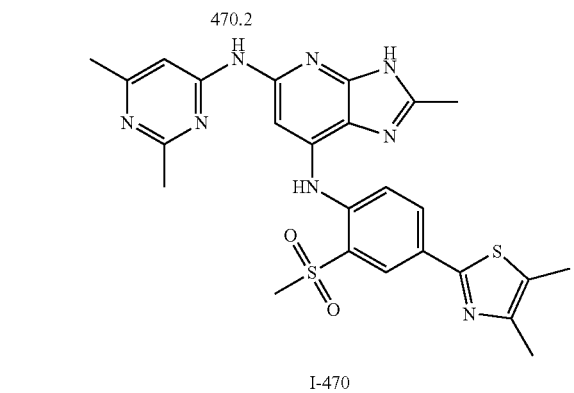

Synthesis of Compound 469.2.

Compound 469.2 was synthesized from 469.1 and 2,6-dimethylpyrimidin-4-amine using general procedure B. (Yield: 53.79%). MS(ES): m/z 655.76 [M+H]$^+$.

Synthesis of I-469.

Compound was synthesized from 469.2 using general procedure C. (Yield: 83.28%). MS(ES): m/z 571.61 [M+H]$^+$, LCMS purity: 100%, HPLC purity: 98.71%, 1H NMR (DMSO, 400 MHz): 9.57 (s, 1H), 8.75 (s, 1H), 8.32 (s, 1H), 8.06-8.03 (m, 1H), 7.98-7.96 (m, 1H), 7.77 (s, 1H), 7.33 (s, 1H), 7.08-7.07 (d, J=5.2 Hz, 1H), 6.82 (t, 1H), 6.81 (s, 1H), 3.29 (s, 3H), 2.40 (s, 6H), 2.34-2.30 (d, 6H).

Synthesis of Compound 470.2.

Compound 470.2 was synthesized from 470.1 and 2,6-dimethylpyrimidin-4-amine using general procedure B. (Yield: 47.29%). MS(ES): m/z 619.78 [M+H]$^+$.

Synthesis of I-470.

Compound I-470 was synthesized from 470.2 using general procedure C. (Yield: 67.34%). MS(ES): m/z 535.8 [M+H]$^+$, LCMS purity: 95.88%, HPLC purity: 97.62%, 1H NMR (DMSO, 400 MHz): 12.62 (s, 1H), 8.88 (s, 1H), 8.36 (s, 1H), 8.12-8.09 (m, 1H), 7.93 (s, 1H), 7.53-7.36 (d, J=6.8 Hz, 1H), 7.13 (s, 1H), 6.83-6.81 (d, J=7.6 Hz, 1H), 3.21 (s, 3H), 2.51-2.50 (m, 6H), 2.45 (s, 3H), 2.41-2.35 (d, 6H).

Example 471: Synthesis of (1R,2R)—N-(2-(difluoromethyl)-7-((4-(4,4-dimethyl-4,5-dihydrooxazol-2-yl)-2-(methylsulfonyl)phenyl)amino)-3H-imidazo[4,5-b]pyridin-5-yl)-2-fluorocyclopropane-1-carboxamide, I-471

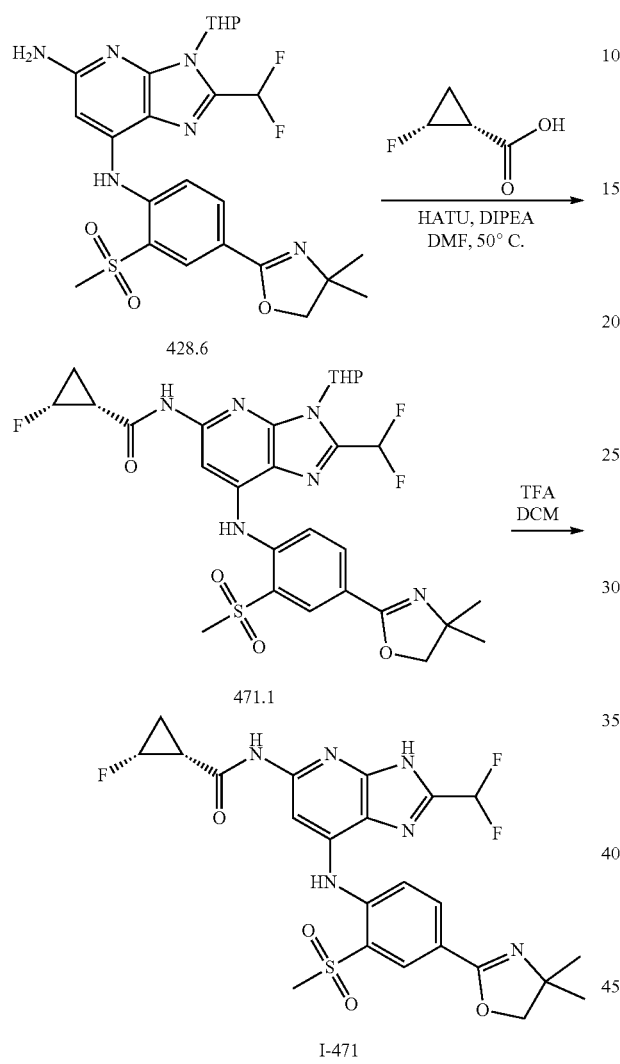

Synthesis of Compound 471.1.

To a solution of 428.6 (0.120 g, 2.24 mmol, 1.0 eq) and (1S,2S)-2-fluorocyclopropane-1-carboxylic acid (0.070 g, 673.42 mmol, 3 eq) in N,N-dimethylformamide (0.5 mL) at 0° C. was added ((1-[Bis(dimethylamino)methylene]-1H-1,2,3-triazolo[4,5-b]pyridinium 3-oxid hexafluorophosphate)) (0.341 g, 8.98 mmol, 4.0 eq) and N,N-Diisopropylethylamine (0.144 g, 0.001 mmol, 5.0 eq). Reaction mixture was stirred at 50° C. for 36 hr. Upon completion, reaction mixture was transferred into ice water and extracted with ethyl acetate. Organic layers were combined, dried over Na$_2$SO$_4$ and concentrated in vacuo to pressure to obtain crude product. This was purified by column chromatography and compound was eluted in 5% MeOH in CH$_2$Cl$_2$ to obtain pure 1 (0.060 g, 43.07%). MS(ES): m/z 621.65 [M+H]$^+$.

Synthesis of Compound I-471.

Compound I-471 was synthesized from 471.1 using general procedure C. (Yield: 50.13%). MS(ES): m/z 537.75 [M+H]$^+$, LCMS purity: 95.53%, HPLC purity: 95.18%, Chiral HPLC: 96.51%, 1H NMR (DMSO, 400 MHz): 13.75 (s, 1H), 10.88 (s, 1H), 8.99 (s, 1H), 8.33 (s, 1H), 8.19 (s, 1H), 8.132-8.112 (d, J=8 Hz, 1H), 7.869-7.848 (d, J=8.4 Hz, 1H), 7.26 (s, 1H), 5.011-4.836 (d, J=70 Hz, 1H), 4.16 (s, 1H), 3.29 (s, 3H), 2.33 (s, 1H), 2.24 (s, 1H), 1.662-1.612 (d, J=20 Hz, 1H), 1.31 (s, 6H), 1.15 (m, 1H).

Example 472: Synthesis of (S)—N-(2-methyl-7-((2-(methylsulfonyl)-4-(tetrahydrofuran-2-yl)phenyl)amino)-3H-imidazo[4,5-b]pyridin-5-yl)cyclopropanecarboxamide, I-472

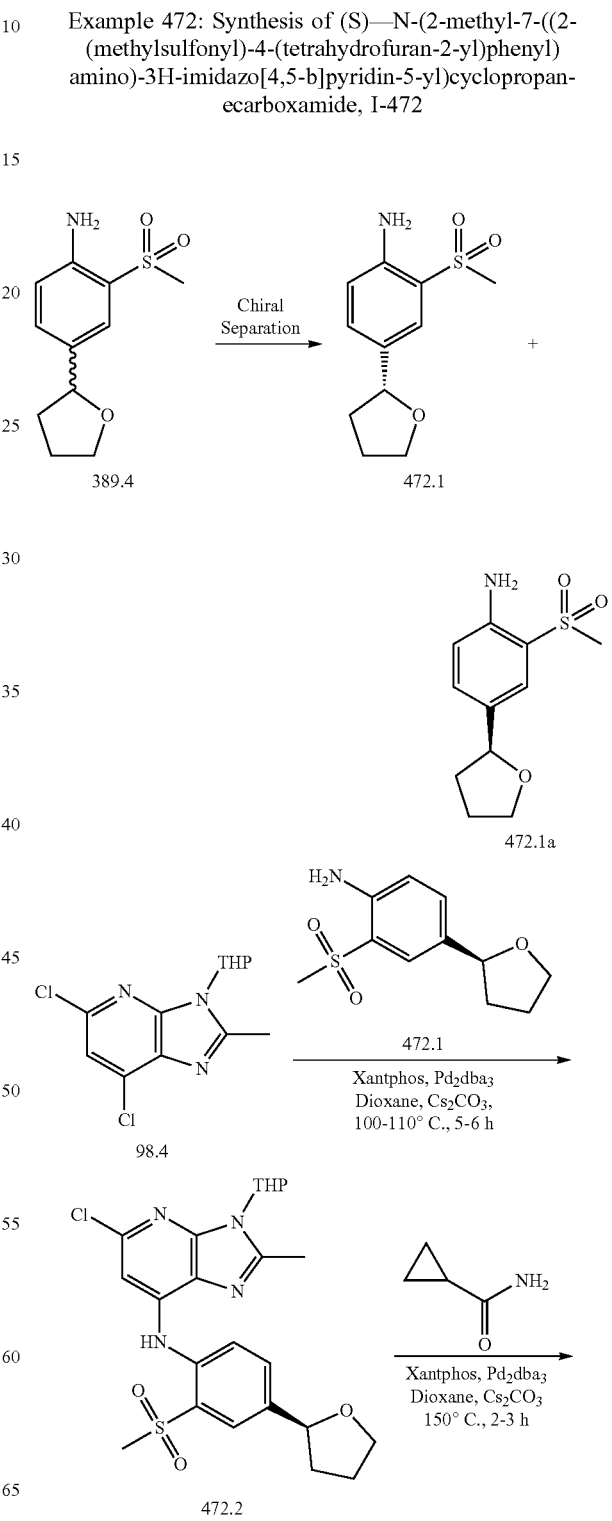

-continued

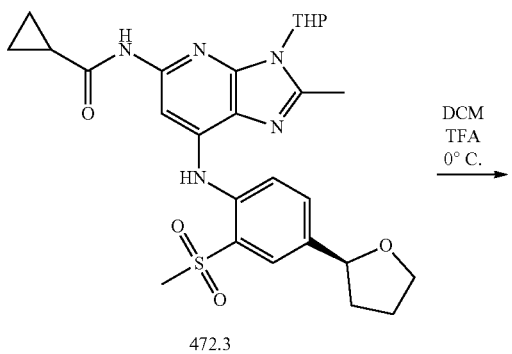

472.3

↓ DCM TFA 0° C.

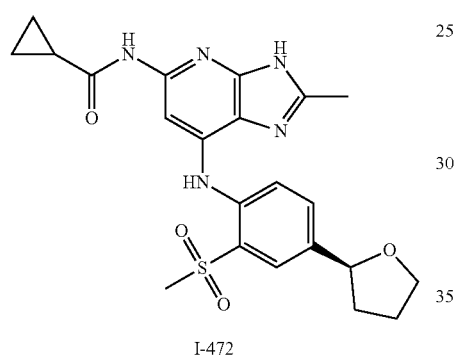

I-472

Synthesis of Compound 472.1.

Isomers of compound 389.4 (0.9 g) were separated out using column (CHIRAL CEL OX-H 250×4.6 mm, 5 μM) AND 0.1% DEA in IPA as co-solvent with flow rate of 4 mL/min. to get pure fraction-1 (FR-a) and fraction-2 (FR-b). FR-b was concentrated in vacuo at 30° C. to afford pure 472.1 (0.270 g, 30.00%). MS(ES): m/z 242.32 [M+H]$^+$.

Synthesis of Compound 472.2.

Compound 472.2 was synthesized from 472.1 and 98.4 using general procedure A. (Yield: 32.38%). MS(ES): m/z 492.37 [M+H]$^+$.

Synthesis of Compound 472.3.

Compound 472.3 was synthesized from 472.2 and cyclopropanecarboxamide using general procedure B. (Yield: 60.66%). MS(ES): m/z 540.28 [M+H]$^+$.

Synthesis of Compound I-472.

Compound I-472 was synthesized from 472.3 using general procedure C. (Yield: 71.08%). MS(ES): m/z 456.56 [M+H]$^+$, LCMS purity: 100%, HPLC purity: 99.25%, Chiral HPLC purity: 99%, 1H NMR (DMSO, 400 MHz): 12.52 (s, 1H), 10.59 (s, 1H), 8.53 (s, 1H), 7.98 (s, 1H), 7.85 (s, 1H), 7.71-7.66 (t, J=8 Hz, 2H), 4.90-4.87 (t, J=8 Hz, 1H), 4.05-4.00 (m, 1H), 3.87-3.82 (m, 2H), 3.19 (s, 3H), 2.41-2.33 (m, 2H), 2.00-1.96 (m, 3H), 1.77-1.66 (m, 2H), 0.77 (bs, 4H).

Example 473: Synthesis of (R)—N-(2-methyl-7-((2-(methylsulfonyl)-4-(tetrahydrofuran-2-yl)phenyl)amino)-3H-imidazo[4,5-b]pyridin-5-yl)cyclopropanecarboxamide, I-473

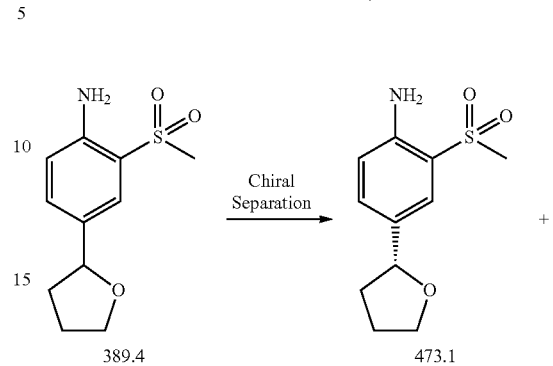

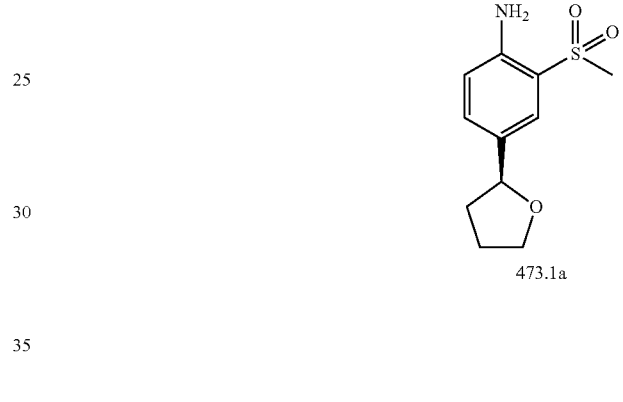

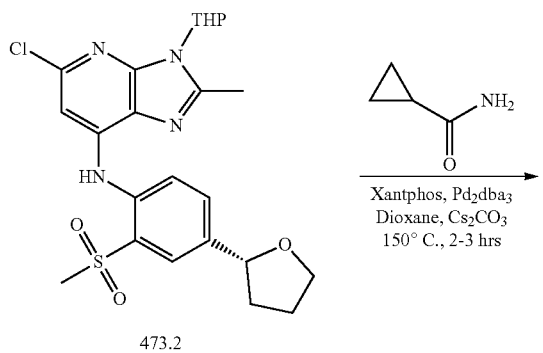

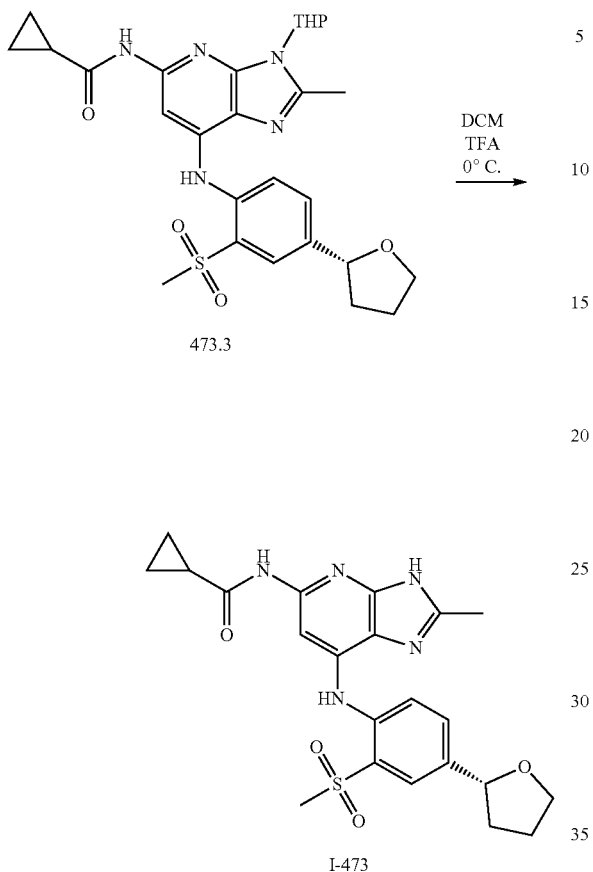

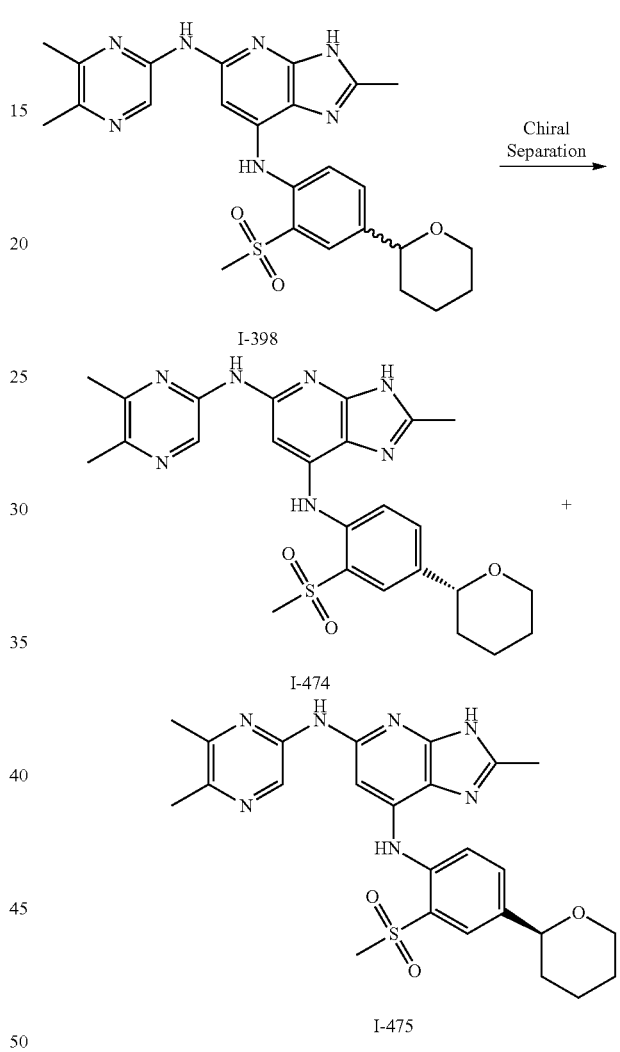

Example 474/475: Synthesis of (R)—N5-(5,6-dimethylpyrazin-2-yl)-2-methyl-N7-(2-(methylsulfonyl)-4-(tetrahydro-2H-pyran-2-yl)phenyl)-3H-imidazo[4,5-b]pyridine-5,7-diamine, I-474 and (S)—N5-(5,6-dimethylpyrazin-2-yl)-2-methyl-N7-(2-(methylsulfonyl)-4-(tetrahydro-2H-pyran-2-yl)phenyl)-3H-imidazo[4,5-b]pyridine-5,7-diamine, I-475

Synthesis of Compound 473.1.

Isomers of compound 389.4 (0.9 g) were separated out using column (CHIRAL CEL OX-H 250×4.6 mm, 5 μM) AND 0.1% DEA in IPA as co-solvent with flow rate of 4 mL/min. to get pure fraction-1 (FR-a) and fraction-2 (FR-b). FR-a was concentrated in vacuo at 30° C. to afford pure 473.1 (0.290 g, 32.22%). MS(ES): m/z 242.32 [M+H]⁺.

Synthesis of Compound 473.2.

Compound 473.2 was synthesized from 473.1 and 98.4 using general procedure A. (Yield: 23.84%). MS(ES): m/z 492.00 [M+H]⁺.

Synthesis of Compound 473.3.

Compound 473.3 was synthesized from 473.2 and cyclopropanecarboxamide using general procedure B. (Yield: 54.59%). MS(ES): m/z 540.65 [M+H]⁺.

Synthesis of I-473.

Compound I-473 was synthesized using general procedure C. (Yield: 72.51%). MS(ES): m/z 456.70 [M+H]⁺, LCMS purity: 99.06%, HPLC purity: 98.50%, Chiral HPLC purity: 99.0%, 1H NMR (DMSO, 400 MHz): 10.57 (s, 1H), 8.53 (s, 1H), 7.98 (s, 1H), 7.83 (s, 1H), 7.74-7.72 (d, J=8.4 Hz, 1H), 7.68-7.66 (d, J=8.4 Hz, 1H), 4.89-4.86 (d, J=14.4 Hz, 1H), 4.04-3.99 (m, 1H), 3.86-3.81 (m, 1H), 3.18 (s, 3H), 2.48 (s, 3H), 2.40-2.32 (m, 2H), 2.01-1.94 (m, 3H), 1.74-1.65 (m, 1H), 0.77-0.75 (s, 4H).

Synthesis of Compounds I-474 and I-475.

Isomers of I-398 (0.110 g) were separated out using column (CHIRALCEL OX-H (250 mm*4.6 mm, 5u) and (0.1% DEA_in HEX_IPA:ACN (70:30) flow rate of 4 mL/min. to get pure fraction-1 (FR-a) and fraction-2 (FR-b). FR-a was concentrated in vacuo at 30° C. to afford pure I-474 (0.035 g). MS(ES): m/z 508.71 [M+H]⁺, LCMS purity: 100%, HPLC purity: 99.82%, Chiral HPLC: 98.56%, 1H NMR (DMSO, 400 MHz): 12.40 (s, 1H), 9.56 (s, 1H), 8.86 (s, 1H), 8.59 (s, 1H), 7.88-7.83 (m, 2H), 7.70-7.67 (d, J=8.4 Hz, 1H), 7.49 (s, 1H), 3.19 (s, 3H), 2.45 (s, 4H), 2.37-2.36 (d, J=4.0 Hz, 6H), 1.90-1.87 (d, J=10.8 Hz, 3H), 1.68-1.64 (m, 2H), 1.58 (s, 2H), 1.48-1.46 (m, 1H). FR-b was concentrated in vacuo at 30° C. to afford pure I-475 (0.030 g). MS(ES): m/z 508.76 [M+H]⁺, LCMS purity: 99.36%, HPLC purity: 98.84%, Chiral HPLC: 95.89%, 1H NMR (DMSO, 400 MHz): 12.42 (s, 1H), 9.58 (s, 1H), 8.87 (s, 1H), 8.60 (s, 1H), 7.88-7.84 (m, 2H), 7.70-7.68 (d, J=8.4 Hz, 1H), 7.50 (s, 1H), 4.45-4.42 (d, J=10.8 Hz, 1H), 4.09-4.06 (d, J=11.6 Hz, 1H), 3.61-3.55 (m, 1H), 3.20 (s, 3H), 2.46 (s, 3H), 2.38-2.37 (d, J=4.0 Hz, 6H), 1.91-1.86 (d, J=18.8 Hz, 2H), 1.69-1.61 (m, 1H), 1.59 (s, 2H), 1.46-1.40 (m, 1H).

Example 476: Synthesis of 2-(difluoromethyl)-N5-(5,6-dimethylpyrazin-2-yl)-N7-(2-(methylsulfonyl)-4-(4-methylthiazol-2-yl)phenyl)-3H-imidazo[4,5-b]pyridine-5,7-diamine, I-476

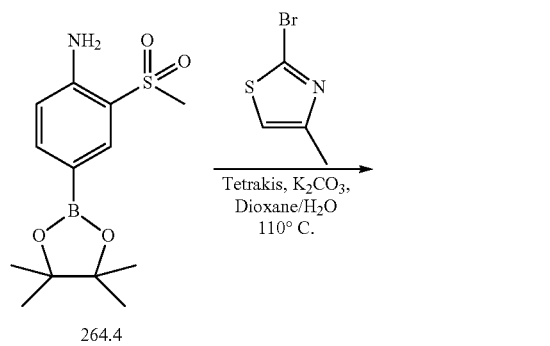

264.4

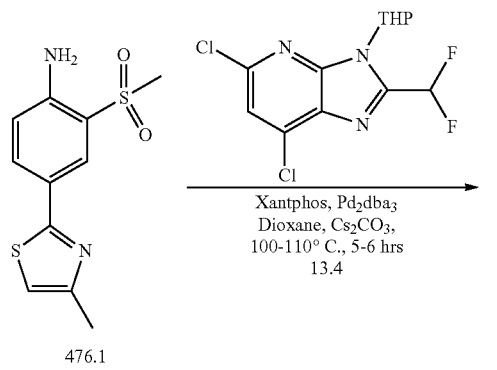

476.1

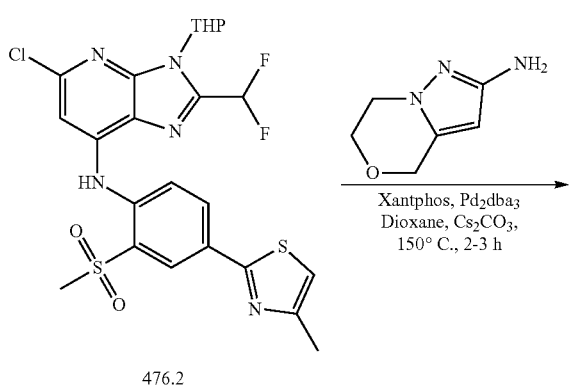

476.2

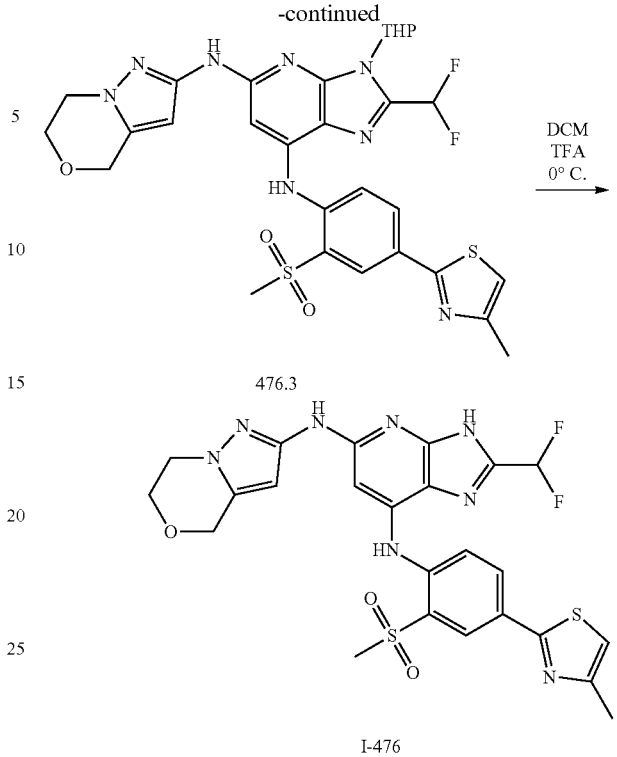

476.3

I-476

Synthesis of Compound 476.1.

To compound 264.4 (2 g, 11.23 mmol, 1.0 eq) and 2-bromo-4-methylthiazole (5 g, 16.85 mmol, 1.5 eq) in mixture of 1,4-dioxane (16 mL) and water (4 mL), sodium carbonate (2.38 g, 22.46 mmol, 2.0 eq) was added. Argon was purged through the reaction mixture for 5 min. Then, [1,1'-Bis(diphenylphosphino)ferrocene]dichloropalladium (II) (0.819 g, 1.12 mmol, 0.1 eq) was added and again purged for 5 min. Reaction mixture was stirred at 120° C. for 4 h. After completion of the reaction, the reaction mixture was transferred to water and extracted with ethyl acetate. Organic layers were combined, dried over anhydrous Na$_2$SO$_4$, filtered and concentrated in vacuo to get the crude material. This was purified by column chromatography using 12% ethyl acetate in hexane as eluant to obtain 476.1 (1.1 g, 36.49%). MS(ES): m/z 269.35 [M+H]$^+$.

Synthesis of Compound 476.2.

Compound 476.2 was synthesized from 476.1 and 13.4 using general procedure A. (Yield: 25.13%). MS(ES): m/z 555.03 [M+H]$^+$.

Synthesis of Compound 476.3.

Compound 476.3 was synthesized from 476.2 and 6,7-dihydro-4H-pyrazolo[5,1-c][1,4]oxazin-2-amine using general procedure B. (Yield: 42.18%). MS(ES): m/z 657.81 [M+H]$^+$.

Synthesis of I-476.

Compound I-476 was synthesized using general procedure C. (Yield: 64.99%). MS(ES): m/z 573.66 [M+H]$^+$, LCMS purity: 97.69%, HPLC purity: 95.09%, 1H NMR (DMSO-d6, 400 MHz): 13.51 (s, 1H), 9.58 (s, 1H), 9.00 (s, 1H), 8.45 (s, 1H), 8.25-8.24 (d, J=7.6 Hz, 1H), 7.95-7.93 (d, J=8.4 Hz, 1H), 7.41 (s, 1H), 7.21 (s, 2H), 6.30 (s, 1H), 4.78 (s, 2H), 4.08-4.01 (d, J=2.9 Hz, 4H), 3.34 (s, 3H), 2.47 (s, 3H).

1009

Example 477: Synthesis of N5-(6,7-dihydro-4H-pyrazolo[5,1-c][1,4]oxazin-2-yl)-2-methyl-N7-(2-(methylsulfonyl)-4-(4-methylthiazol-2-yl)phenyl)-3H-imidazo[4,5-b]pyridine-5,7-diamine, I-477

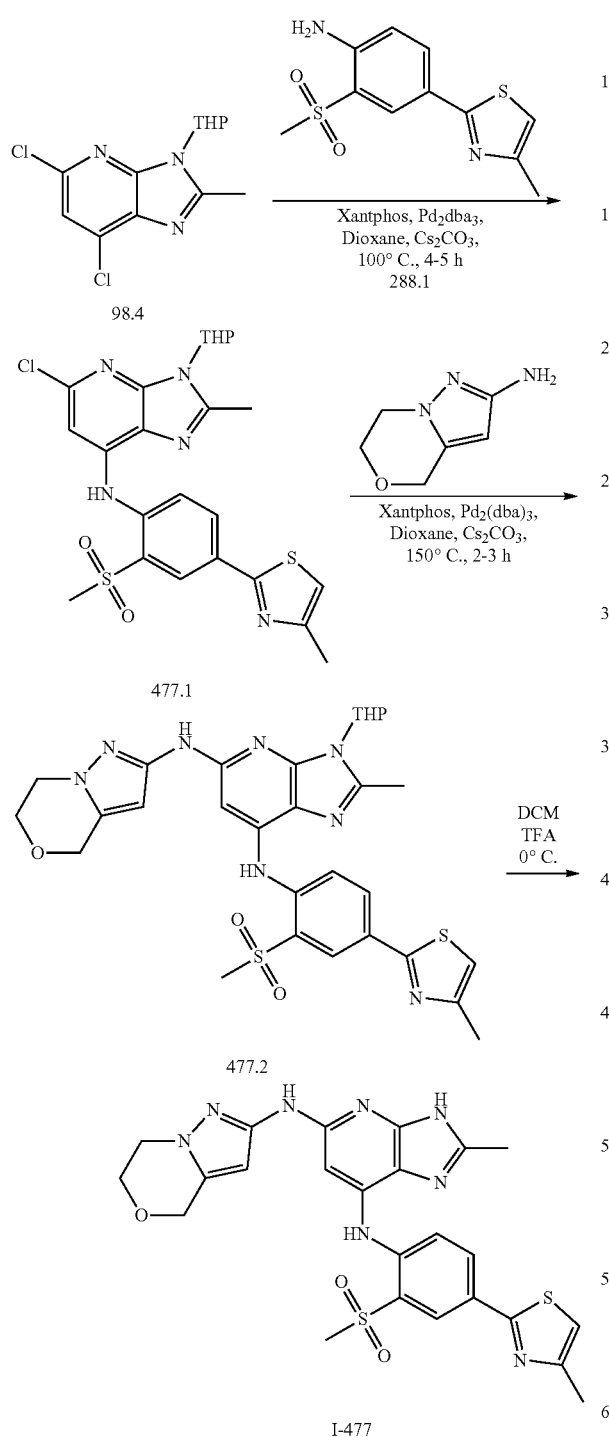

Synthesis of Compound 477.1

Compound 477.1 was synthesized from 98.4 and 288.1 using general procedure A. (Yield: 23.15%). MS(ES): m/z 519.05 [M+H]⁺.

1010

Synthesis of Compound 477.2.

Compound 477.2 was synthesized from 477.1 and 6,7-dihydro-4H-pyrazolo[5,1-c][1,4]oxazin-2-amine using general procedure B. (Yield: 41.03%). MS(ES): m/z 621.75 [M+H]⁺.

Synthesis of I-477.

Compound I-477 was synthesized from 477.2 using general procedure C (Yield: 49.01%). MS(ES): m/z 537.75 [M+H]⁺, LCMS purity: 95.88%, HPLC purity: 95.63%, 1H NMR (DMSO-d6, 400 MHz): 12.41 (s, 1H), 9.14 (s, 1H), 8.76 (s, 1H), 8.40 (s, 1H), 8.19-8.16 (d, J=1.08 Hz, 1H), 7.89-7.87 (d, J=6.4 Hz, 1H), 7.37 (s, 1H), 7.16 (s, 2H), 6.26 (s, 1H), 4.76 (s, 2H), 4.06-3.96 (d, J=3.88 Hz, 4H), 3.31 (s, 3H), 2.43 (s, 3H), 2.44 (s, 2H).

Example 478/479: Synthesis of (R)—N-(7-((4-(1,4-dimethyl-1H-pyrazol-3-yl)-2-(methylsulfonyl)phenyl)amino)-2-methyl-3H-imidazo[4,5-b]pyridin-5-yl)-2,2-dimethylcyclopropane-1-carboxamide, I-478 and (S)—N-(7-((4-(1,4-dimethyl-1H-pyrazol-3-yl)-2-(methylsulfonyl)phenyl)amino)-2-methyl-3H-imidazo[4,5-b]pyridin-5-yl)-2,2-dimethylcyclopropane-1-carboxamide, I-479

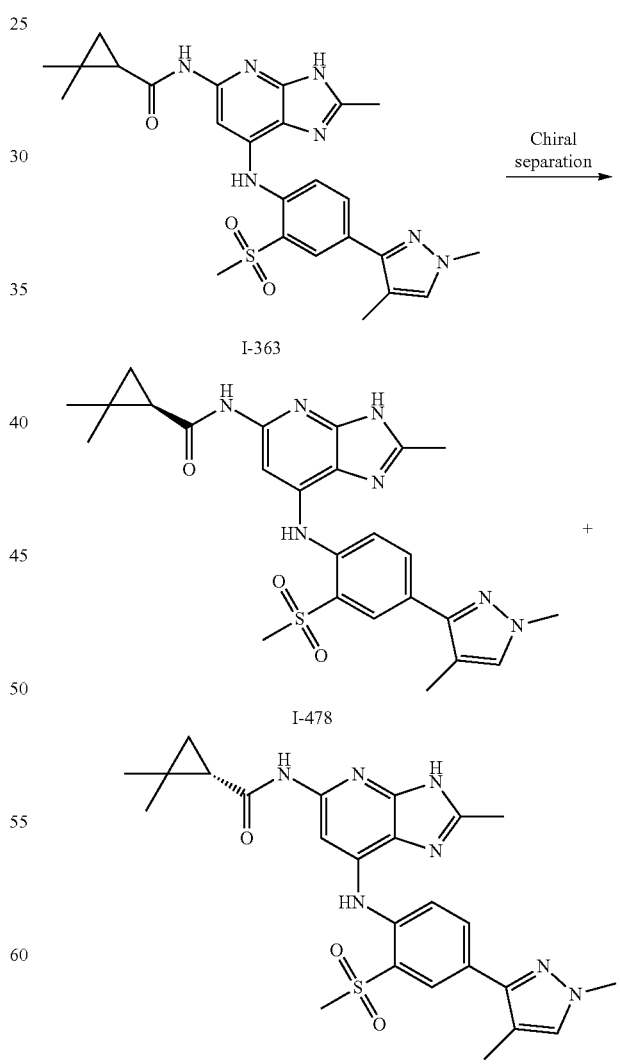

Synthesis of Compounds I-478 and I-479.

Isomers of 1-363 (0.0.085 g) were separated out using column (CHIRALCEL OX-H (250 mm*4.6 mm, 5u) and (0.1% DEA IPA:MEOH (50:50) flow rate of 4 mL/min. to get pure fraction-1 (FR-a) and fraction-2 (FR-b). FR-a was concentrated in vacuo at 30° C. to afford pure I-478 (0.025 g). MS(ES): m/z 508.68 [M+H]$^+$, LCMS purity: 100%, HPLC purity: 100%, Chiral HPLC: 98.78%, 1H NMR (DMSO, 400 MHz): 12.52 (s, 1H), 10.43 (s, 1H), 8.62 (s, 1H), 8.30 (s, 1H), 8.21-8.20 (d, J=8.2 Hz, 2H), 8.00-7.98 (d, J=8.0 Hz, 1H), 7.60 (s, 1H), 3.85 (s, 3H), 3.25 (s, 3H), 2.49 (s, 3H), 2.23 (s, 3H), 1.91-1.88 (m, 1H), 1.1 (s, 6H), 1.09-1.06 (t, 2H). FR-b was concentrated in vacuo at 30° C. to afford pure 1-479 (0.024 g). MS(ES): m/z 508.76 [M+H]$^+$, LCMS purity: 100%, HPLC purity: 99.43%, Chiral HPLC: 99.00%, 1H NMR (DMSO, 400 MHz): 12.48 (s, 1H), 10.42 (s, 1H), 8.63 (s, 1H), 8.20 (s, 1H), 8.03-7.98 (d, 2H), 7.82 (s, 1H), 7.60 (s, 1H), 3.85 (s, 3H), 3.25 (s, 3H), 2.49 (s, 3H), 2.24 (s, 3H), 1.90-1.87 (m, 1H), 1.14 (s, 6H), 0.98-0.96 (t, 2H).

Example 480: Synthesis of 2-(difluoromethyl)-N5-(6,7-dihydro-4H-pyrazolo[5,1-c][1,4]oxazin-2-yl)-N7-(4-(4,5-dimethylthiazol-2-yl)-2-(methylsulfonyl)phenyl)-3H-imidazo[4,5-b]pyridine-5,7-diamine, I-480

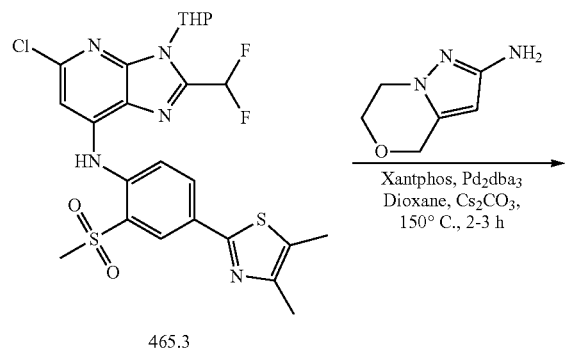

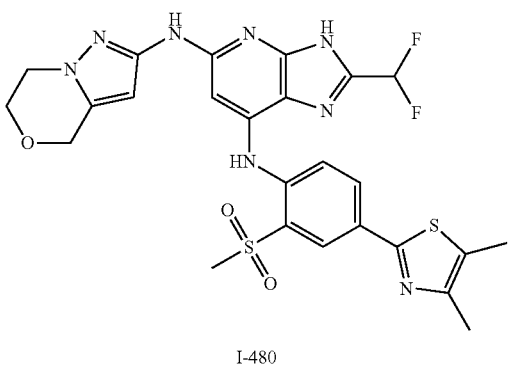

Synthesis of Compound 480.1.

Compound 480.1 was synthesized from 465.3 and 6,7-dihydro-4H-pyrazolo[5,1-c][1,4]oxazin-2-amine using general procedure B. (Yield: 38.11%). MS(ES): m/z 671.75 [M+H]$^+$.

Synthesis of I-480.

Compound I-480 was synthesized from 480.1 using general procedure C. (Yield: 71.14%). MS(ES): m/z 587.6 [M+H]$^+$, LCMS purity: 95.88%, HPLC purity: 97.62%, 1H NMR (DMSO, 400 MHz): 13.42 (s, 1H), 9.37 (s, 1H), 8.87 (s, 1H), 8.36 (s, 1H), 8.14-8.11 (d, J=10.4 Hz, 1H), 7.93-7.91 (d, J=8.4 Hz, 1H), 7.22 (s, 1H), 7.17 (t, 1H), 6.36 (s, 1H), 4.77 (s, 2H), 4.08 (s, 3H), 3.96 (s, 3H), 3.31 (s, 3H), 2.41-2.39 (t, 2H), 2.35-2.33 (t, 2H).

Example 481: Synthesis of N-(2-(difluoromethyl)-7-((4-(2,5-dimethylthiazol-4-yl)-2-(methylsulfonyl)phenyl)amino)-3H-imidazo[4,5-b]pyridin-5-yl)cyclopropanecarboxamide, I-481

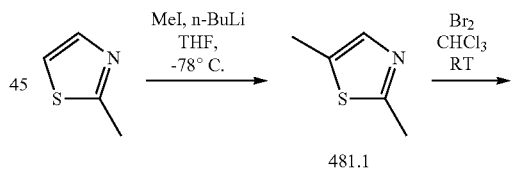

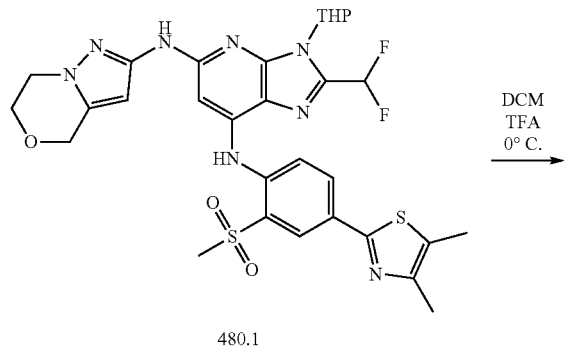

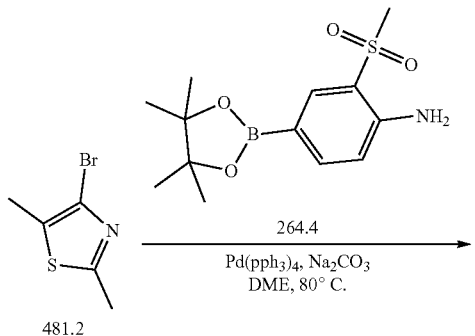

1013
-continued

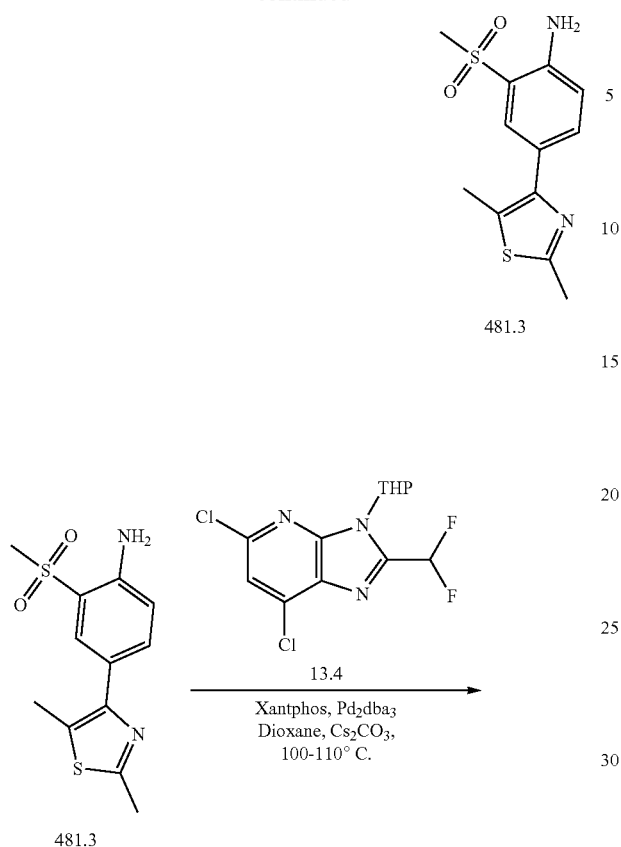

481.3

1014
-continued

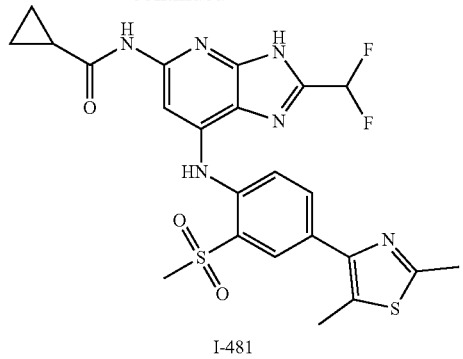

I-481

Synthesis of Compound 481.1.

To a solution of 2-methylthiazole (3.0 g, 30.2 mmol, 1.0 eq) in tetrahydrofuran (90 mL) at −78° C., N-butyl lithium (13.5 mL, 13.33 mmol, 1.1 eq) was added dropwise. Reaction mixture was stirred at −78° C. for 30 min. Then, iodomethane (4.8 g, 33.3 mmol, 1.1 eq) was added. Reaction mixture was stirred at r.t. for 2 h. After completion of the reaction, the reaction mixture was transferred to water and extracted with ethyl acetate. Organic layers were combined, dried over anhydrous $Na_2SO_4$, filtered and concentrated in vacuo to obtain 481.1 (2.1 g, 58.40%). MS(ES): m/z 114.52 $[M+H]^+$.

Synthesis of Compound 481.2.

To compound 481.1 (2.93 g, 11.9 mmol, 1.0 eq) in $CH_2Cl_2$ (23 mL), bromine solution in dicholoromethane (2.3 g, 14.3 mmol, 1.2 eq) was added. Reaction mixture was stirred at r.t. for 3 h. After completion of the reaction, the reaction mixture was transferred to a solution of sodium sulphite and extracted with ethyl acetate. Organic layer combined, dried over anhydrous $Na_2SO_4$, filtered and concentrated in vacuo to obtain pure 481.2 (1.6 g, 47.88%). MS(ES): m/z 193.62 $[M+H]^+$.

Synthesis of Compound 481.3.

To compound 481.2 (1.27 g, 0.65 mmol, 1.3 eq) and 264.4 (1.5 g, 0.50 mmol, 1.0 eq) in a mixture of 1,4-dioxane (25 mL) and water (4 mL), potassium carbonate (2.1 g, 15.1 mmol, 3.0 eq) was added. Reaction mixture was degassed with argon for 15 min. Then, [1,1'-Bis(diphenylphosphino)ferrocene]dichloropalladium(11) complex with dicholoromethane (0.20 g, 0.25 mmol, 0.05 eq) was added. Reaction mixture was stirred at 80° C. for 3 h. After completion of the reaction, the reaction mixture was transferred to water and extracted with ethyl acetate. Organic layers were combined, dried over anhydrous $Na_2SO_4$, filtered and concentrated in vacuo to get the crude material. This was purified by column chromatography using 12% ethyl acetate in hexane to obtain pure 481.3 (1.6 g, 47.88%). MS(ES): m/z 193.62 $[M+H]^+$.

Synthesis of Compound 481.4.

Compound 481.4 was synthesized from 481.3 and 13.4 using general procedure A. (Yield: 33.14%). MS(ES): m/z 569.42 $[M+H]^+$.

Synthesis of Compound 481.5.

Compound 481.5 was synthesized from 481.4 and cyclopropanecarboxamide using general procedure B. (Yield: 46.06%). MS(ES): m/z 617.28 $[M+H]^+$.

Synthesis of I-481.

Compound I-481 was synthesized from 481.5 using general procedure C. (Yield: 61.76%). MS(ES): m/z 533.46 $[M+H]^+$, LCMS purity: 97.17%, HPLC purity: 95.40%, 1H

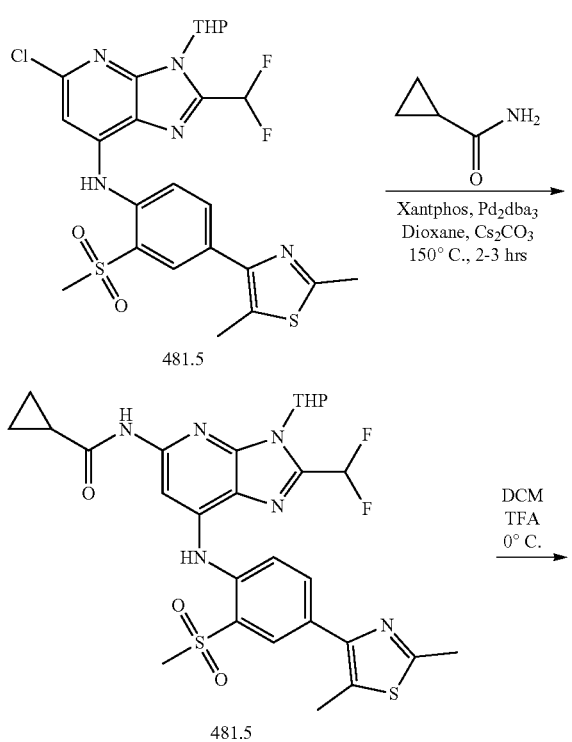

481.5

NMR (DMSO, 400 MHz): 13.60 (s, 1H), 10.72 (s, 1H), 8.80 (s, 1H), 8.24 (s, 1H), 8.10-8.02 (m, 2H), 7.87-7.85 (d, J=8.8 Hz, 1H), 7.24 (t, 1H), 3.27 (s, 3H), 2.66 (s, 3H), 2.58 (s, 3H), 1.35-1.18 (m, 1H), 0.84 (s, 4H).

Example I-482/I-483: Synthesis of (R)—N-(2-(difluoromethyl)-7-((4-(4,4-dimethyl-4,5-dihydrothiazol-2-yl)-2-(methylsulfonyl)phenyl)amino)-3H-imidazo[4,5-b]pyridin-5-yl)-2,2-difluorocyclopropane-1-carboxamide, I-482 and (S)—N-(2-(difluoromethyl)-7-((4-(4,4-dimethyl-4,5-dihydrothiazol-2-yl)-2-(methylsulfonyl)phenyl)amino)-3H-imidazo[4,5-b]pyridin-5-yl)-2,2-difluorocyclopropane-1-carboxamide, I-483

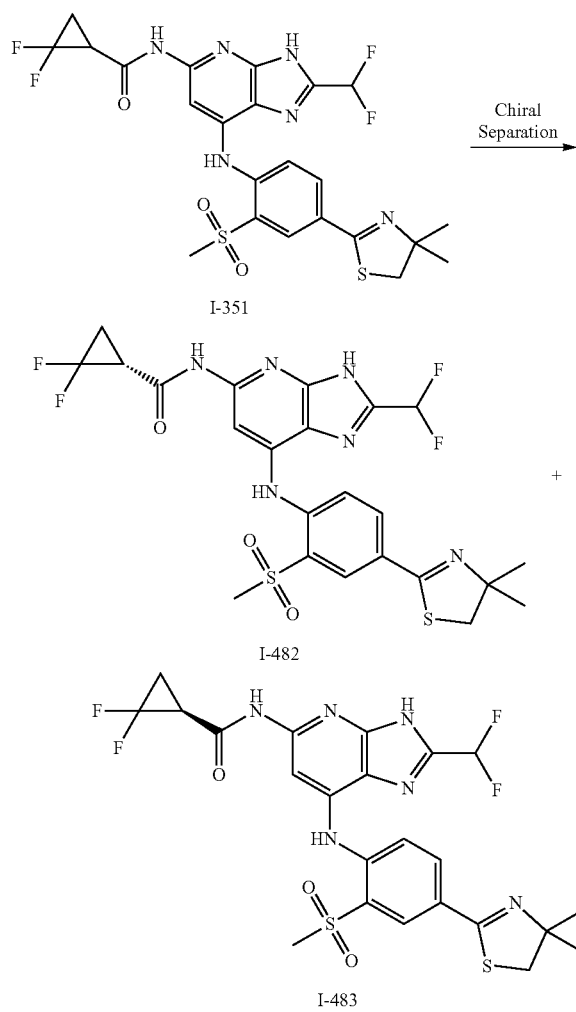

Resolution of Compounds I-482 and I-483.

Isomers of I-351 (0.120 g) were separated out using column (CHIRAL PAK AD-H (250 mm*4.6 mm, 5u)) and 0.1% DEA in IPA:ACN (50:50) flow rate of 4 mL/min. to get pure fraction-1 (FR-a) and fraction-2 (FR-b). FR-a was concentrated in vacuo at 30° C. to afford pure I-482 (0.025 g). MS(ES): m/z 571.66 [M+H]$^+$, LCMS purity: 96.50%, HPLC purity: 95.82%, Chiral HPLC: 100%, 1H NMR (DMSO, 400 MHz): 13.83 (s, 1H), 11.07 (s, 1H), 8.26 (s, 1H), 8.14 (s, 1H), 8.14 (s, 1H), 8.038-8.016 (d, J=8.8 Hz, 1H), 7.87 (s, 1H), 7.27 (s, 1H), 3.31 (s, 2H), 3.04-3.01 (m, 1H), 2.09-1.92 (m, 2H), 1.42 (s, 6H), 1.24 (s, 3H). FR-b was concentrated in vacuo at 30° C. to afford pure I-483 (0.025 g). MS(ES): m/z 571.67 [M+H]$^+$, LCMS purity: 97.72%, HPLC purity: 97.05%, Chiral HPLC: 97.97%, 1H NMR (DMSO, 400 MHz): 13.83 (s, 1H), 11.07 (s, 1H), 9.01 (s, 1H), 8.27 (s, 1H), 8.15 (s, 1H), 8.038-8.020 (d, J=4.0 Hz, 1H), 7.884-7.863 (d, J=8.4, 1H), 7.28 (s, 1H), 3.31 (s, 3H), 3.04-3.02 (m, 1H), 2.49 (s, 2H), 2.044-2.008 (s, 2H), 1.42 (s, 6H).

Example 484/485: Synthesis of (R)—N-(7-((4-(4,4-dimethyl-4,5-dihydrothiazol-2-yl)-2-(methylsulfonyl)phenyl)amino)-2-methyl-3H-imidazo[4,5-b]pyridin-5-yl)-2,2-difluorocyclopropane-1-carboxamide, I-484 and (S)—N-(7-((4-(4,4-dimethyl-4,5-dihydrothiazol-2-yl)-2-(methylsulfonyl)phenyl)amino)-2-methyl-3H-imidazo[4,5-b]pyridin-5-yl)-2,2-difluorocyclopropane-1-carboxamide, I-485

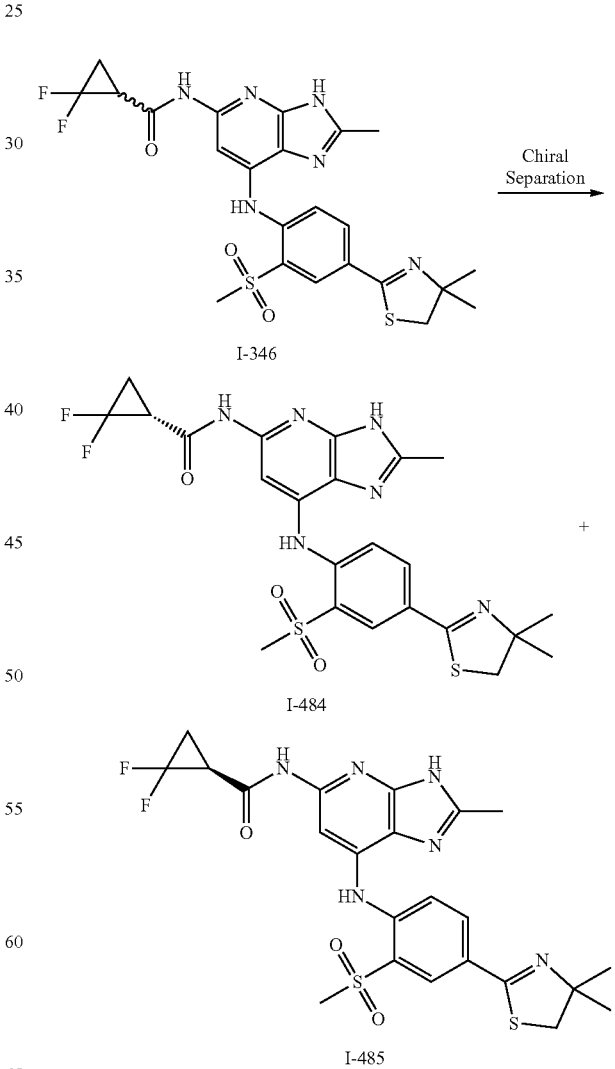

Synthesis of Compound I-484 and I-485.

Isomers of 1-346 (0.110 g) were separated out using column (CHIRALCEL OX-H 250×4.6 mm, 5 μM) 0.1% DEA in MeOH as co-solvent with flow rate of 4 mL/min. to get pure fraction-1 (FR-a) and fraction-2 (FR-b). FR-a was concentrated in vacuo at 30° C. to afford pure I-484 (0.032 g). MS(ES): m/z 535.50 [M+H]$^+$, LCMS purity: 100%, HPLC Purity: 98.93%, Chiral HPLC Purity: 100%, 1H NMR (DMSO, 400 MHz): 12.65 (s, 1H), 10.89 (s, 1H), 8.86 (s, 1H), 8.24 (s, 1H), 8.10 (s, 1H), 8.01-7.98 (d, J=10.4 Hz, 1H), 7.83-7.81 (d, J=8.4 Hz, 1H), 3.29 (s, 3H), 3.19-3.17 (d, J=5.2 Hz, 1H), 2.01 (s, 3H), 1.41 (s, 6H), 0.89-0.86 (m, 4H). FR-b was concentrated in vacuo at 30° C. to afford pure I-485 (0.030 g). MS(ES): m/z 535.55 [M+H]$^+$, LCMS purity: 97.89%, HPLC Purity: 96.33%, Chiral HPLC Purity: 98.59%, 1H NMR (DMSO, 400 MHz): 12.64 (s, 1H), 10.88 (s, 1H), 8.85 (s, 1H), 8.24-8.23 (d, J=2.0 Hz, 1H), 8.10 (s, 1H), 8.00-7.98 (d, J=8.4 Hz, 1H), 7.83-781 (d, J=8.4 Hz, 1H), 3.29 (s, 3H), 3.19-3.17 (m, 1H), 2.97 (s, 2H), 2.01 (s, 2H), 1.41 (s, 6H), 0.89-0.86 (m, 4H).

Example 486/487: Synthesis of (R)-2-(difluoromethyl)-N5-(5,6-dimethylpyrazin-2-yl)-N7-(2-(methylsulfonyl)-4-(tetrahydro-2H-pyran-2-yl)phenyl)-3H-imidazo[4,5-b]pyridine-5,7-diamine, I-486 and (S)-2-(difluoromethyl)-N5-(5,6-dimethylpyrazin-2-yl)-N7-(2-(methylsulfonyl)-4-(tetrahydro-2H-pyran-2-yl)phenyl)-3H-imidazo[4,5-b]pyridine-5,7-diamine, I-487

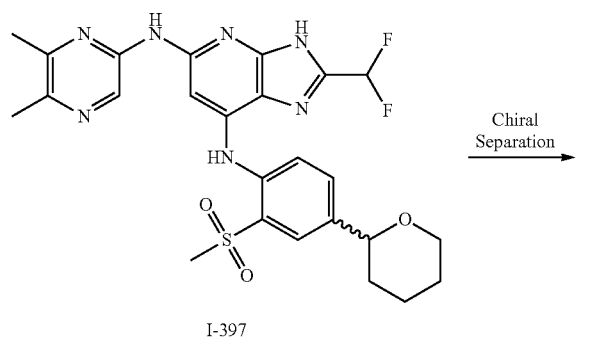

I-397

Chiral Separation →

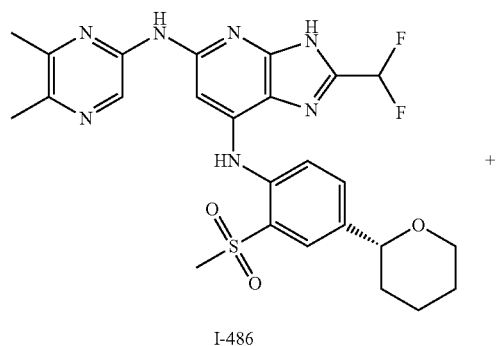

I-486

+

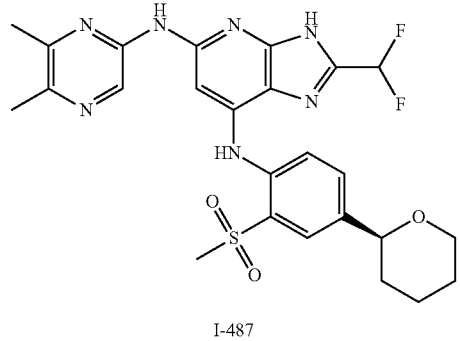

I-487

Synthesis of Compounds I-486 and I-487.

Isomers of 1-397 (0.085 g) were separated out using column (CHIRALCEL OX-H (250 mm*4.6 mm, 5u) and 0.1% DEA MEOH flow rate of 4 mL/min. to get pure fraction-1 (FR-a) and fraction-2 (FR-b). FR-a was concentrated in vacuo at 30° C. to afford pure I-486 (0.012 g). MS(ES): m/z 544.51 [M+H]$^+$, LCMS purity: 99.73%, HPLC purity: 99.44%, Chiral HPLC: 100%, 1H NMR (DMSO, 400 MHz): 9.78 (s, 1H), 8.98 (s, 1H), 8.76 (s, 1H), 7.911-7.851 (d, J=2.4 Hz, 2H), 7.72 (s, 1H), 7.50 (s, 1H), 7.22 (t, 1H), 4.45 (s, 1H), 4.09 (s, 1H), 3.22 (s, 3H), 2.38 (s, 4H), 1.89 (s, 2H), 1.58 (s, 3H), 1.24 (s, 3H), 0.86 (s, 1H). FR-b was concentrated in vacuo at 30° C. to afford pure I-487 (0.015 g). MS(ES): m/z 544.56 [M+H]$^+$, LCMS purity: 95.25%, HPLC purity: 94.09%, Chiral HPLC: 99.73%, 1H NMR (DMSO, 400 MHz): 13.57 (s, 1H), 9.79 (s, 1H), 8.98 (s, 1H), 8.76 (s, 1H), 7.97 (s, 1H), 7.74 (s, 1H), 7.50 (s, 1H), 7.22 (t, 1H), 4.07 (s, 1H), 3.58 (s, 1H), 3.22 (s, 3H), 2.38 (s, 4H), 1.90 (s, 2H), 1.59 (s, 3H), 1.24 (s, 3H), 0.86 (s, 1H).

Example 488: Synthesis of N-(7-((4-(2,5-dimethylthiazol-4-yl)-2-(methylsulfonyl)phenyl)amino)-2-methyl-3H-imidazo[4,5-b]pyridin-5-yl)cyclopropanecarboxamide, I-488

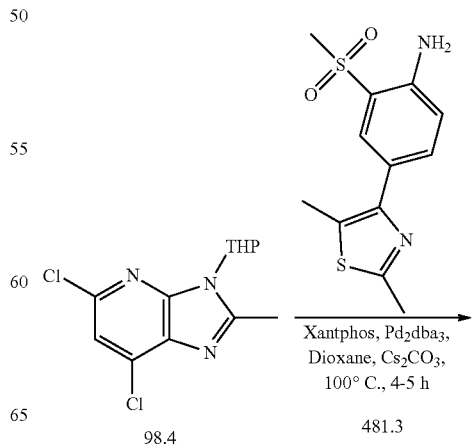

98.4        481.3

Xantphos, Pd$_2$dba$_3$, Dioxane, Cs$_2$CO$_3$, 100° C., 4-5 h

-continued

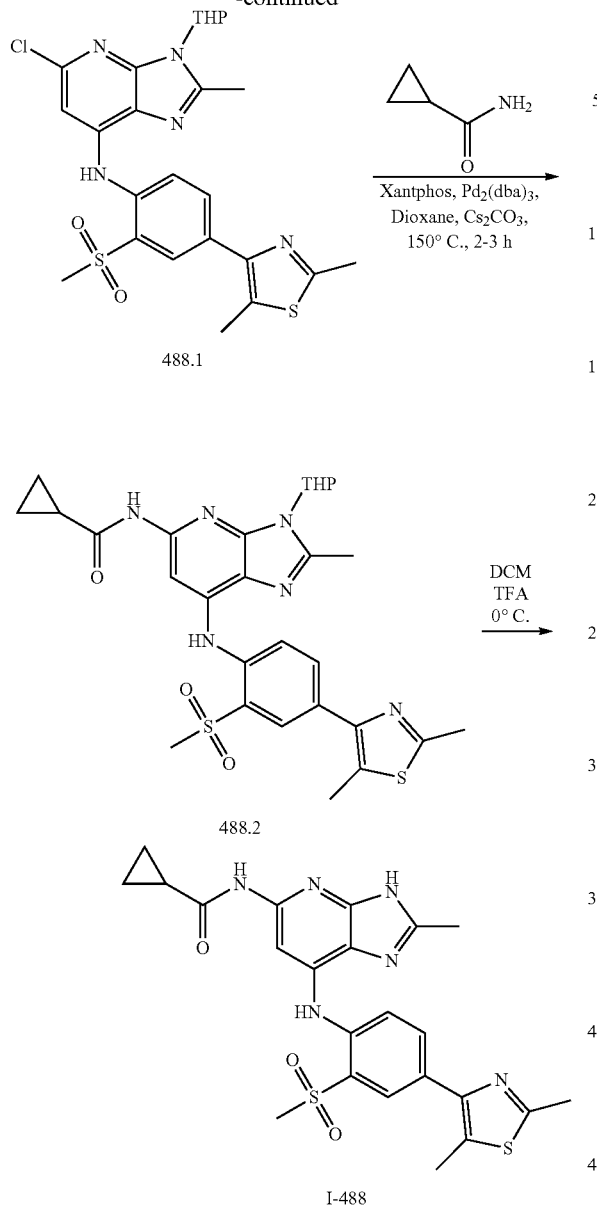

488.1

488.2

I-488

Synthesis of Compound 488.1.

Compound 488.1 was synthesized from 98.4 and 481.3 using general procedure A. (Yield: 34.66%). MS(ES): m/z 533.07 [M+H]⁺.

Synthesis of Compound 488.2.

Compound 488.2 was synthesized from 488.1 and cyclopropanecarboxamide using general procedure B. (Yield: 20.54%). MS(ES): m/z 581.72 [M+H]⁺.

Synthesis of I-488.

Compound I-488 was synthesized from 488.2 using general procedure C (Yield: 71.96%). MS(ES): m/z 497.56 [M+H]⁺, LCMS purity: 100%, HPLC purity: 98.52%, 1H NMR (DMSO-d6, 400 MHz): 12.52 (s, 1H), 10.61 (s, 1H), 8.69 (s, 1H), 8.23-8.22 (d, J=2.4 Hz, 1H), 8.06 (s, 1H), 8.07-8.01 (d, J=2.4 Hz, 1H), 7.85-7.83 (d, J=8.8 Hz, 1H), 3.27 (s, 3H), 2.66 (s, 3H), 2.58 (s, 3H), 2.51 (s, 3H), 2.01 (s, 1H), 0.77 (bs, 4H).

Example 489: Synthesis of 6-((2-(difluoromethyl)-7-((2-(methylsulfonyl)phenyl)amino)-3H-imidazo[4,5-b]pyridin-5-yl)amino)-3-isopropylpicolinonitrile, I-489

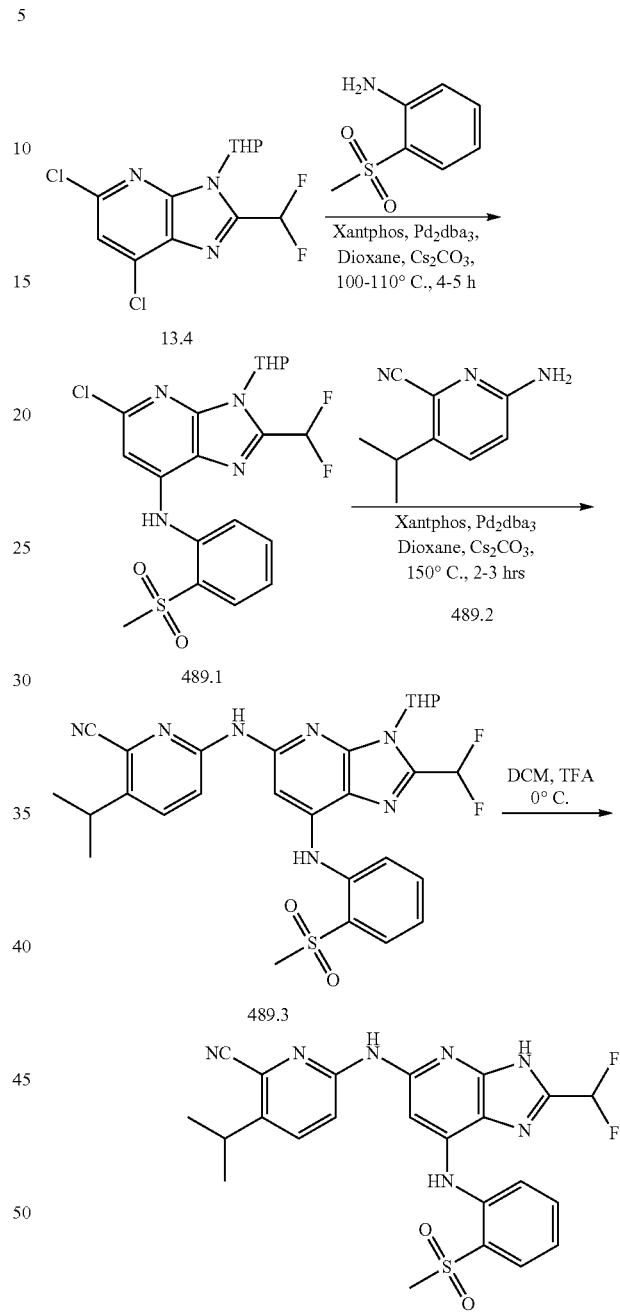

13.4

489.1

489.2

489.3

I-489

Synthesis of Compound 489.1.

Compound 489.1 was synthesized from 13.4 and 2-(methylsulfonyl)aniline using general procedure A. (Yield: 21.25%). MS(ES): m/z 457.7 [M+H]⁺.

Synthesis of Compound 489.3.

Compound 489.3 was synthesized from 489.1 and 489.2 using general procedure B. (Yield: 51.06%). MS(ES): m/z 582.66 [M+H]⁺.

Synthesis of I-489.

Compound I-489 was synthesized from 489.3 using general procedure C. (Yield: 44.96%). MS(ES): m/z 498.46

[M+H]+, LCMS purity: 98.63%, HPLC purity: 98.53%, 1H NMR (DMSO, 400 MHz): 13.64 (s, 1H), 10.11 (s, 1H), 8.93 (s, 1H), 8.08-8.06 (d, J=8.8 Hz, 1H), 7.96-7.84 (m, 4H), 7.63 (s, 1H), 7.39-7.36 (t, J=14.8 Hz, 1H), 7.24 (s, 1H), 3.23 (s, 3H), 2.56 (s, 1H), 1.28-1.26 (d, J=6.8 Hz, 6H).

Example 490: Synthesis of 3-isopropyl-6-((2-methyl-7-((2-(methylsulfonyl)phenyl)amino)-3H-imidazo[4,5-b]pyridin-5-yl)amino)picolinonitrile, I-490

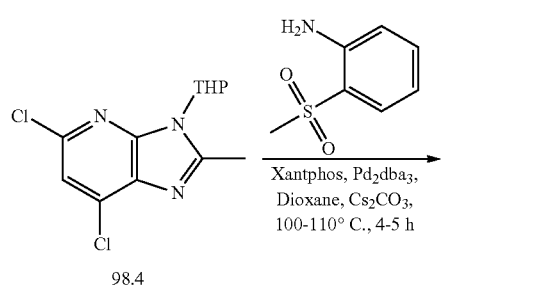

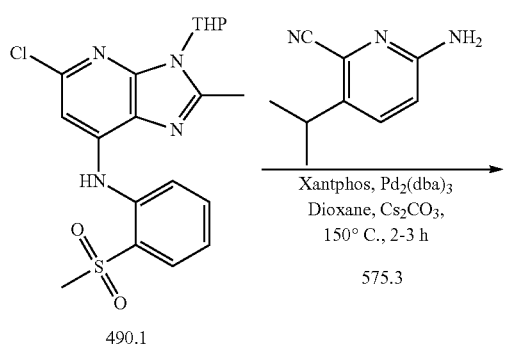

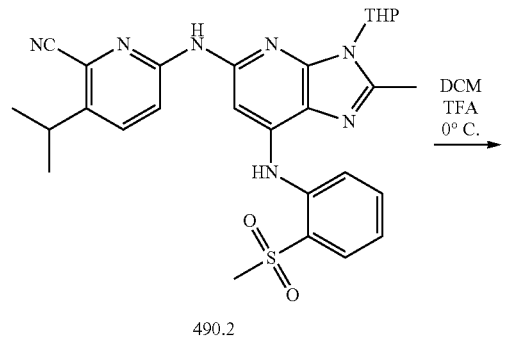

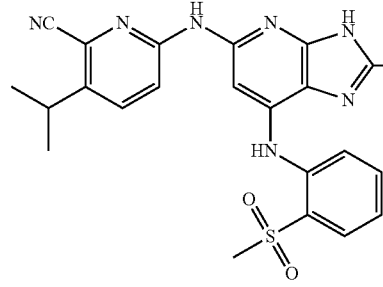

Synthesis of Compound 490.1.

Compound 490.1 was synthesized from 98.4 and 2-(methylsulfonyl)aniline using general procedure B. (Yield: 57.85%). MS(ES): m/z 546.66 [M+H]+.

Synthesis of compound 490.2 Compound 490.2 was synthesized from 490.1 and 575.3 using general method B.

Synthesis of I-490.

Compound I-490 was synthesized from compound 490.2 using general procedure C. (Yield: 70.94%). MS(ES): m/z 462.45 [M+H]+, LCMS purity: 100%, HPLC purity: 98.85%, 1H NMR (DMSO-d6, 400 MHz): 12.50 (s, 1H), 9.89 (s, 1H), 8.75 (s, 1H), 7.97-7.81 (m, 5H), 7.59 (s, 1H), 7.34-7.30 (t, J=1.52 Hz, 1H), 3.21 (s, 1H), 2.50 (s, 3H), 2.43 (s, 3H), 1.27-1.25 (d, J=0.68 Hz, 6H).

Example 491: Synthesis of 2-(difluoromethyl)-N5-(6,7-dihydro-4H-pyrazolo[5,1-c][1,4]oxazin-2-yl)-N7-(4-(1,5-dimethyl-1H-pyrazol-4-yl)-2-(methylsulfonyl)phenyl)-3H-imidazo[4,5-b]pyridine-5,7-diamine, I-491

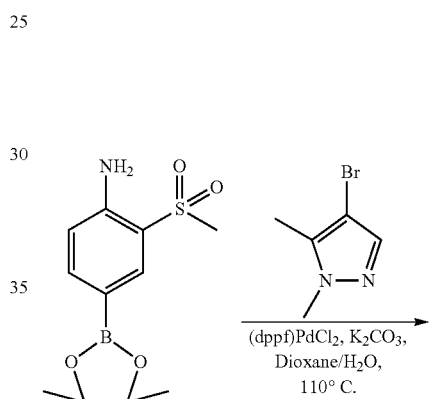

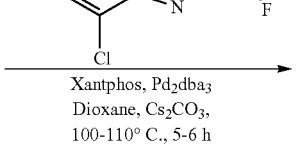

1023

-continued

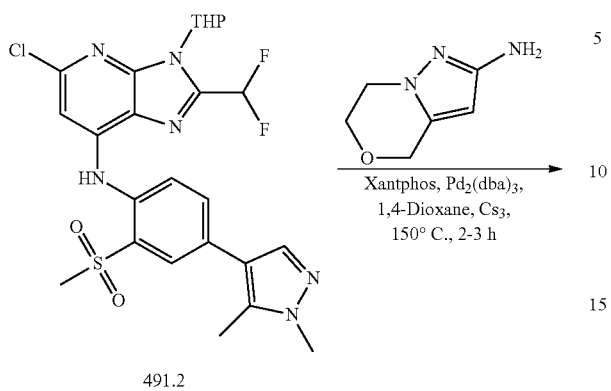

491.2

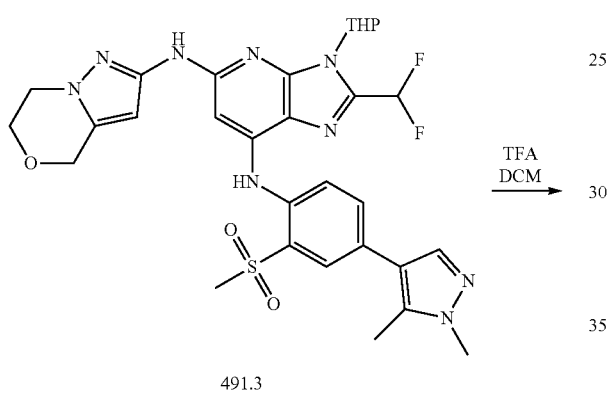

491.3

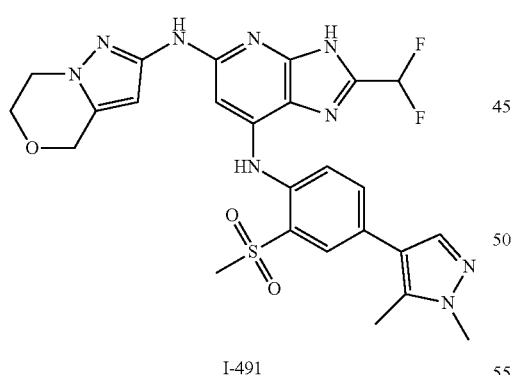

I-491

Synthesis of Compound 491.2.

Compound 491.2 was synthesized from 331.1 and 13.4 using general procedure A. (Yield: 26.16%). MS(ES): m/z 552.48 [M+H]$^+$.

Synthesis of Compound 491.3.

Compound 491.3 was synthesized from 491.2 and 6,7-dihydro-4H-pyrazolo[5,1-c][1,4]oxazin-2-amine using general procedure B. (Yield: 25.05%). MS(ES): m/z 654.76 [M+H]$^+$.

1024

Synthesis of I-491.

Compound I-491 was synthesized from 491.3 using general procedure C. 3 (Yield: 57.38%). MS(ES): m/z 570.47 [M+H]$^+$, LCMS purity: 97.15%, HPLC purity: 96.86%, 1H NMR (DMSO-d6, 400 MHz): 13.37 (s, 1H), 9.32 (s, 1H), 8.72 (s, 1H), 7.92-7.69 (m, 3H), 7.69 (s, 1H), 7.22-7.18 (d, J=1.52 Hz, 2H), 6.31 (s, 1H), 4.77 (s, 2H), 4.07-3.97 (d, J=3.76 Hz, 4H), 3.83 (s, 3H), 3.27 (s, 3H), 2.44 (s, 3H).

Example 492: Synthesis of N5-(6,7-dihydro-4H-pyrazolo[5,1-c][1,4]oxazin-2-yl)-N7-(4-(1,5-dimethyl-1H-pyrazol-4-yl)-(methylsulfonyl)phenyl)-2-methyl-3H-imidazo[4,5-b]pyridine-5,7-diamine, I-492

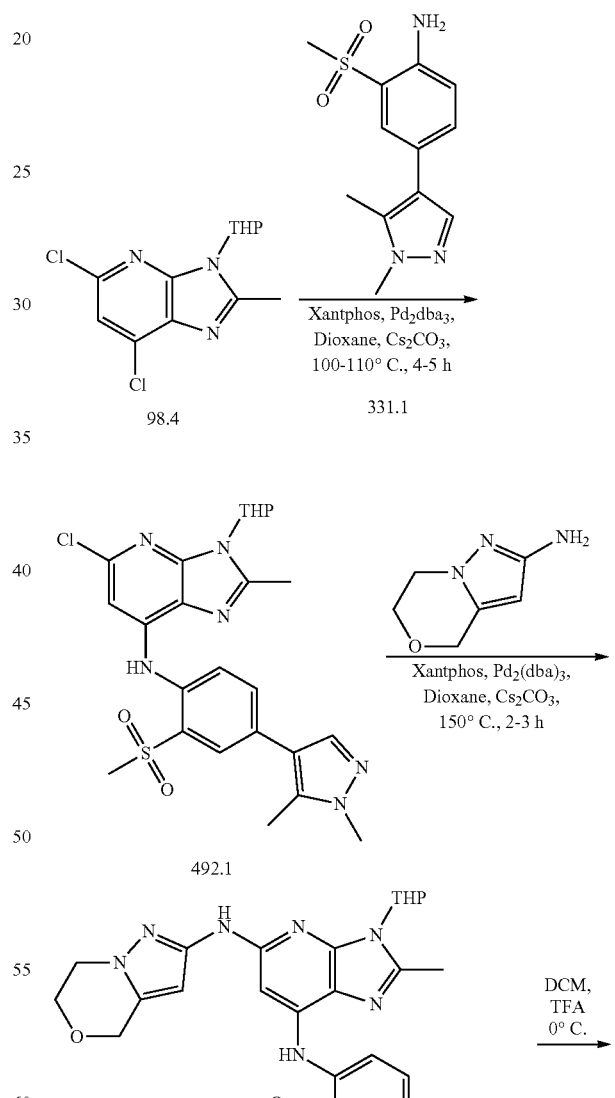

492.1

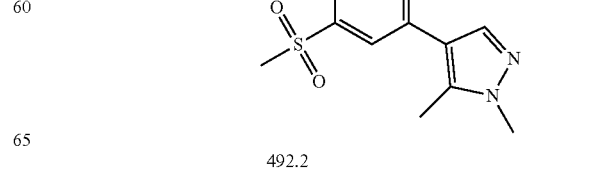

492.2

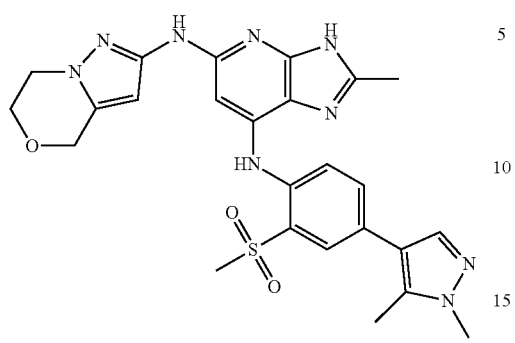

I-492

Synthesis of Compound 492.1.

Compound 492.1 was synthesized from 98.4 and 331.1 using general procedure A. (Yield: 23.34%). MS(ES): m/z 516.03 [M+H]⁺.

Synthesis of Compound 492.2.

Compound 492.2 was synthesized from 492.1 and 6,7-dihydro-4H-pyrazolo[5,1-c][1,4]oxazin-2-amine using general procedure B. (Yield: 37.72%). MS(ES): m/z 618.73 [M+H]⁺.

Synthesis of I-492.

Compound I-492 was synthesized from 492.2 using general procedure C. (Yield: 63.97%). MS(ES): m/z 534.51 [M+H]⁺, LCMS purity: 100%, HPLC purity: 100%, 1H NMR (DMSO-d6, 400 MHz): 1.26 (s, 1H), 9.31 (s, 1H), 8.62 (s, 1H), 7.90-7.82 (m, 3H), 7.70 (s, 1H), 6.97 (s, 1H), 6.17 (s, 1H), 4.76 (s, 2H), 4.08-3.98 (d, J=4.0 Hz, 4H), 3.83 (s, 3H), 3.27 (s, 3H), 2.51 (s, 3H), 2.44 (s, 3H).

Example 493: Synthesis of 2-(difluoromethyl)-N7-(4-(1,5-dimethyl-1H-pyrazol-4-yl)-2-(methylsulfonyl)phenyl)-N5-(6-(trifluoromethyl)pyridin-2-yl)-3H-imidazo[4,5-b]pyridine-5,7-diamine, I-493

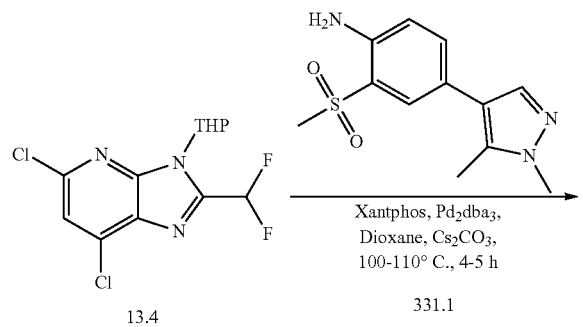

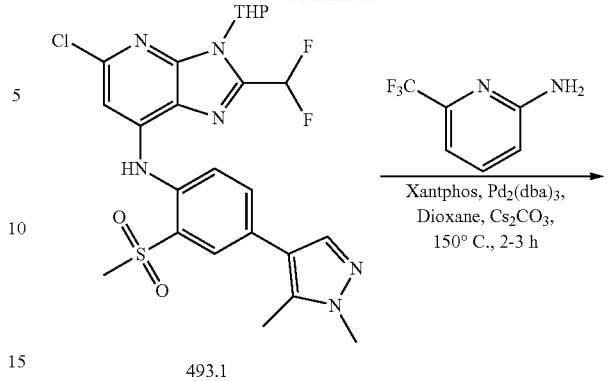

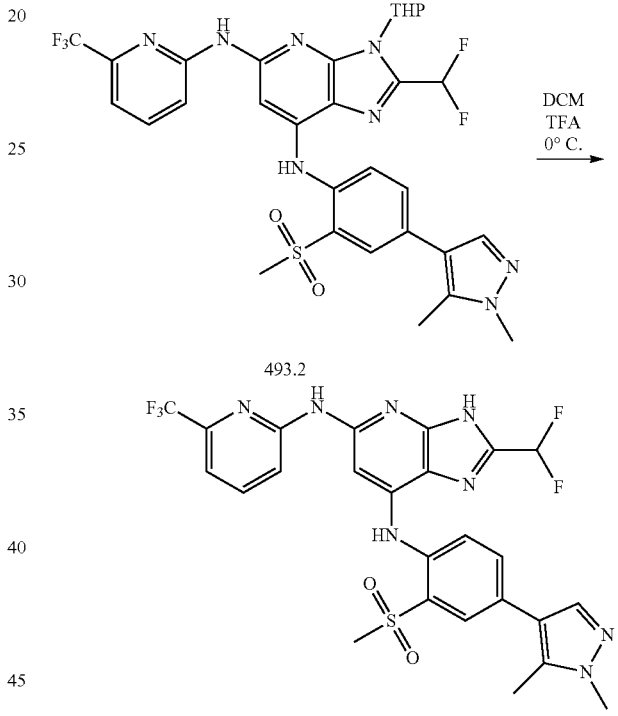

Synthesis of Compound 493.1.

Compound 493.1 was synthesized from 13.4 and 331.1 using general procedure A. (Yield: 18.10%). MS(ES): m/z 552.01 [M+H]⁺.

Synthesis of Compound 493.2.

Compound 493.2 was synthesized from 491.2 and 6-(trifluoromethyl)pyridin-2-amine using general procedure B. (Yield: 37.23%). MS(ES): m/z 577.67 [M+H]⁺.

Synthesis of I-493.

Compound I-493 was synthesized from 493.2 using general procedure C (Yield: 62.81%). MS(ES): m/z 593.47 [M+H]⁺, LCMS purity: 100%, HPLC purity: 100%, 1H NMR (DMSO-d6, 400 MHz): 13.65 (s, 1H), 10.17 (s, 1H), 8.84 (s, 1H), 8.22-8.20 (d, J=8.8 Hz, 1H), 7.96-7.89 (m, 3H), 7.78-7.76 (d, J=1.0 Hz, 1H), 7.68 (s, 1H), 7.58 (s, 1H), 7.38-7.31 (m, 1H), 7.25 (s, 1H), 3.83 (s, 3H), 3.28 (s, 3H), 2.45 (s, 3H).

Example 494: Synthesis of (R)-2-(difluoromethyl)-N5-(2,6-dimethylpyrimidin-4-yl)-N7-(2-(methylsulfonyl)-4-(tetrahydro-2H-pyran-2-yl)phenyl)-3H-imidazo[4,5-b]pyridine-5,7-diamine, I-494

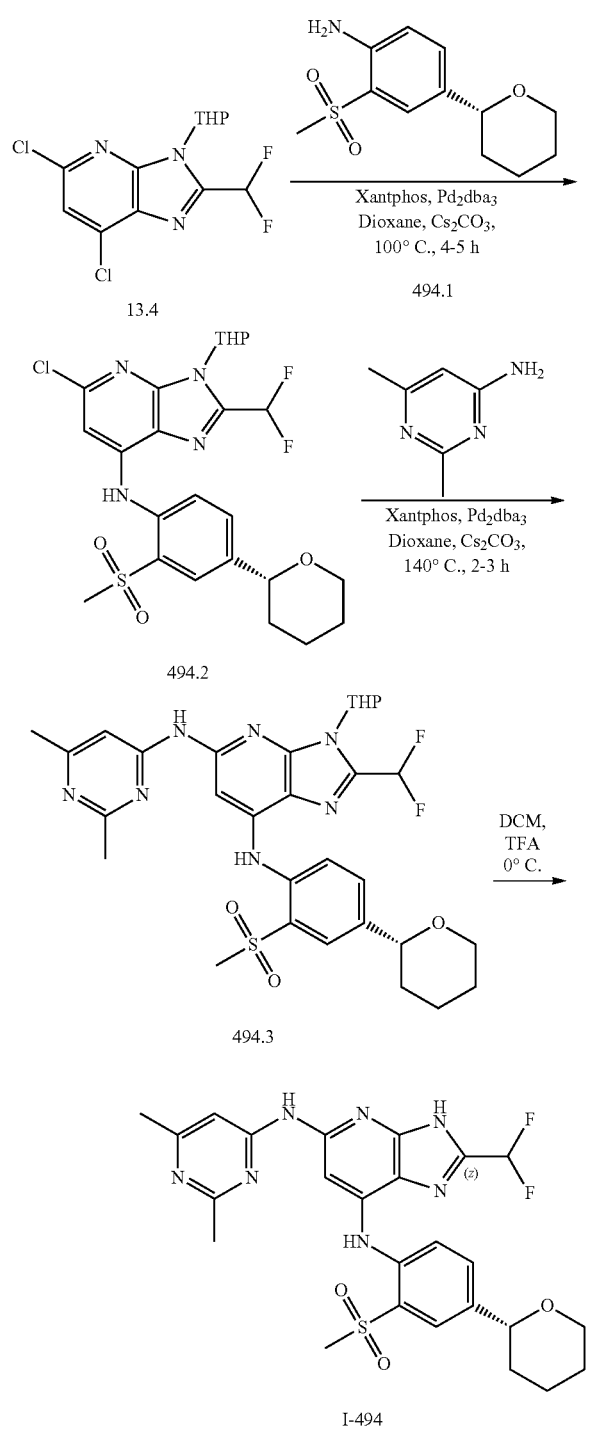

Synthesis of Compound 494.2.

Compound 494.2 was synthesized from 13.4 and 494.1 using general procedure A. (Yield: 42.14%). MS(ES): m/z 542.01 [M+H]+.

Synthesis of Compound 494.3.

Compound 494.3 was synthesized from 494.2 and 2,6-dimethylpyrimidin-4-amine using general procedure B. (Yield: 28.17%). MS(ES): m/z 628.71 [M+H]+.

Synthesis of I-494.

Compound I-494 was synthesized from 494.3 using general procedure C (Yield: 56.33%). MS(ES): m/z 544.56 [M+H]+, LCMS purity: 98.29%, HPLC purity: 97.51%, Chiral HPLC: 98.9%, 1H NMR (DMSO-d6, 400 MHz): 13.65 (s, 1H), 10.04 (s, 1H), 8.82 (s, 1H), 7.92 (s, 1H), 7.87-7.85 (d, J=8.4 Hz, 1H), 7.74-7.72 (d, J=7.6 Hz, 1H), 7.621-7.572 (d, 3H), 5.77 (s, 1H), 3.22 (m, 3H), 2.41 (s, 3H), 2.35 (s, 3H), 1.92-1.89 (d, J=11.2 Hz, 2H), 1.59 (s, 6H).

Example 495: Synthesis of 2-(difluoromethyl)-N5-(6,7-dihydro-4H-pyrazolo[5,1-c][1,4]oxazin-2-yl)-N7-(2-(methylsulfonyl)-4-(5-methylthiazol-2-yl)phenyl)-3H-imidazo[4,5-b]pyridine-5,7-diamine, I-495

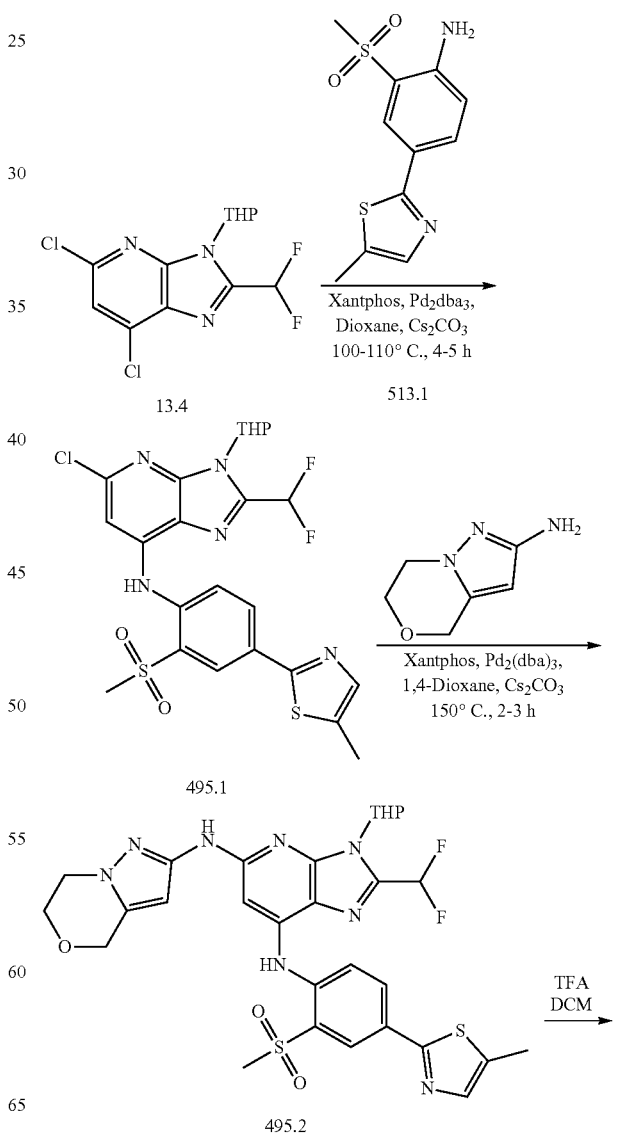

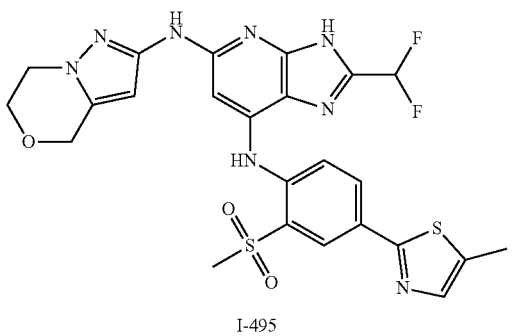

I-495

Synthesis of Compound 495.1.

Compound 495.1 was synthesized from 13.4 and 513.1 using general procedure A. (Yield: 17.44%). MS(ES): m/z 555.03 [M+H]$^+$.

Synthesis of Compound 495.2.

Compound 495.2 was synthesized from 495.1 and 6,7-dihydro-4H-pyrazolo[5,1-c][1,4]oxazin-2-amine using general procedure B. (Yield: 48.34%). MS(ES): m/z 657.76 [M+H]$^+$.

Synthesis of I-495.

Compound I-495 was synthesized from 495.2 using general procedure C. (Yield: 47.96%). MS(ES): m/z 573.51 [M+H]$^+$, LCMS purity: 100%, HPLC purity: 100%, 1H NMR (DMSO-d6, 400 MHz): 13.50 (s, 1H), 9.48 (s, 1H), 8.98 (s, 1H), 8.40 (s, 1H), 8.22-8.20 (d, J=8.0 Hz, 1H), 7.96-7.93 (d, J=8.4 Hz, 1H), 7.68 (s, 1H), 7.21 (t, 1H), 6.32 (s, 1H), 4.78 (s, 2H), 4.08 (bs, 2H), 4.00 (bs, 2H), 3.34 (s, 3H), 2.53 (s, 3H).

Example 496: Synthesis of N5-(6,7-dihydro-4H-pyrazolo[5,1-c][1,4]oxazin-2-yl)-2-methyl-N7-(2-(methylsulfonyl)-4-(5-methylthiazol-2-yl)phenyl)-3H-imidazo[4,5-b]pyridine-5,7-diamine, I-496

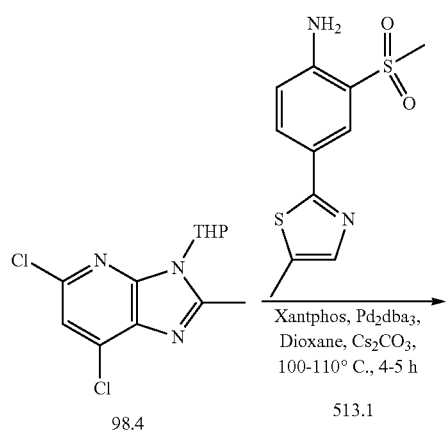

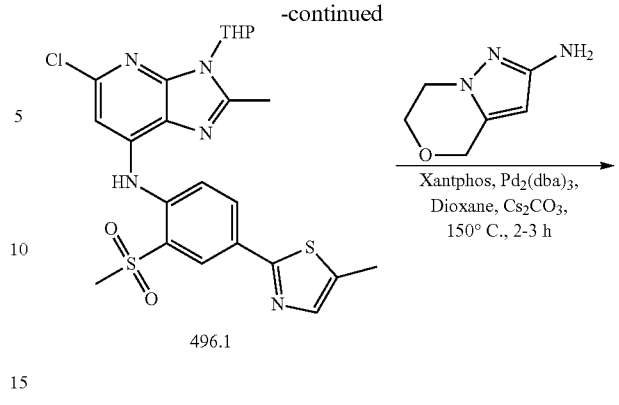

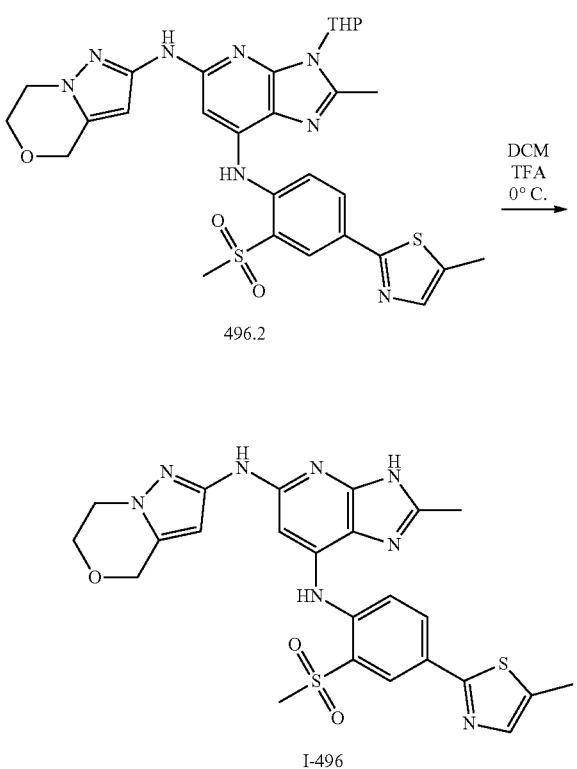

Synthesis of Compound 496.1.

Compound 496.1 was synthesized from 98.4 and 513.1 using general procedure A. (Yield: 34.52%). MS(ES): m/z 519.05 [M+H]$^+$.

Synthesis of Compound 496.2

Compound 496.2 was synthesized from 6,7-dihydro-4H-pyrazolo[5,1-c][1,4]oxazin-2-amine and 496.1 using general procedure B. (Yield: 50.07%). MS(ES): m/z 621.75 [M+H]$^+$.

Synthesis of I-496.

Compound I-496 was synthesized from 496.2 using general procedure C. (Yield: 70.69%). MS(ES): m/z 537.50 [M+H]$^+$, LCMS purity: 100%, HPLC purity: 97.11%, 1H NMR (DMSO-d6, 400 MHz): 13.29 (s, 2H), 9.54 (s, 1H), 8.76 (s, 1H), 8.42 (s, 1H), 8.20-8.18 (d, J=8.4 Hz, 1H), 7.78-7.68 (m, 2H), 6.99 (s, 1H), 4.78 (s, 2H), 4.08-4.06 (d, J=5.2 Hz, 4H), 3.33 (s, 3H), 2.57 (s, 3H), 2.51 (s, 3H).

1031

Example 497: Synthesis of 2-(difluoromethyl)-N5-(6,7-dihydro-4H-pyrazolo[5,1-c][1,4]oxazin-2-yl)-N7-(4-(1,5-dimethyl-1H-pyrazol-4-yl)-2-(methylsulfonyl)phenyl)-3H-imidazo[4,5-b]pyridine-5,7-diamine, I-497

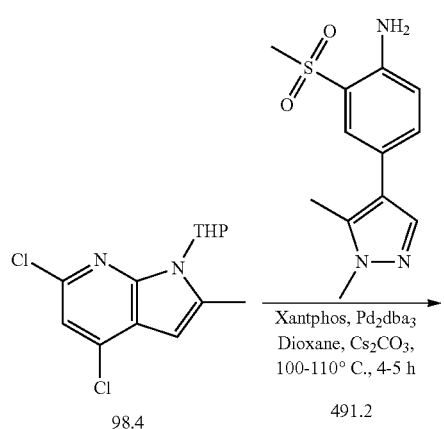

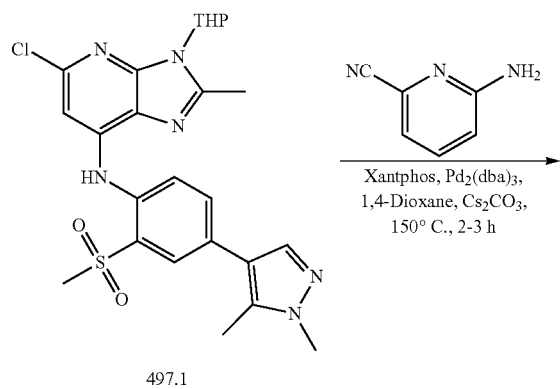

1032

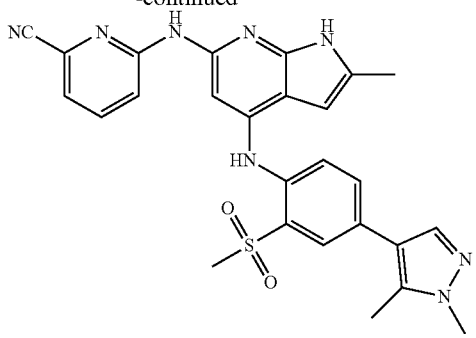

I-497

Synthesis of Compound 497.1.

Compound 497.1 was synthesized from 98.4 and 491.2 using general procedure A. (Yield: 17.92%). MS(ES): m/z 516.94 [M+H]⁺.

Synthesis of Compound 497.2.

Compound 497.2 was synthesized from 497.1 and 6-aminopicolinonitrile using general procedure B. (Yield: 47.39%). MS(ES): m/z 598.32 [M+H]⁺.

Synthesis of I497.

Compound I-497 was synthesized from 497.2 using general procedure C. (Yield: 57.13%). MS(ES): m/z 514.64 [M+H]⁺, LCMS purity: 98.46%, HPLC purity: 97.59%, 1H NMR (DMSO-d6, 400 MHz): 12.52 (s, 1H), 10.01 (s, 1H), 8.74 (s, 1H), 7.98-7.96 (d, 1H), 7.92 (s, 1H), 7.87-7.85 (m, 2H), 7.82 (s, 1H), 7.68 (s, 1H), 7.64 (s, 1H), 7.44-7.42 (d, J=7.2 Hz, 1H), 3.81 (s, 3H), 3.25 (s, 3H), 2.42 (s, 6H).

Example 498/499: Synthesis of (R)—N-(2-(difluoromethyl)-7-((4-(5,5-dimethyltetrahydrofuran-2-yl)-2-(methylsulfonyl)phenyl)amino)-3H-imidazo[4,5-b]pyridin-5-yl)cyclopropanecarboxamide, I-498 and (S)—N-(2-(difluoromethyl)-7-((4-(5,5-dimethyltetrahydrofuran-2-yl)-2-(methylsulfonyl)phenyl)amino)-3H-imidazo[4,5-b]pyridin-5-yl)cyclopropanecarboxamide, I-499

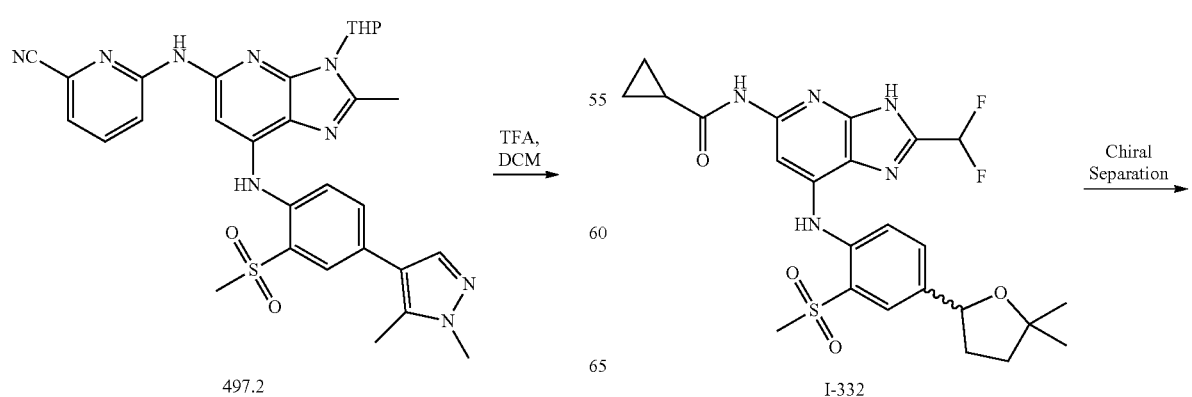

1033

-continued

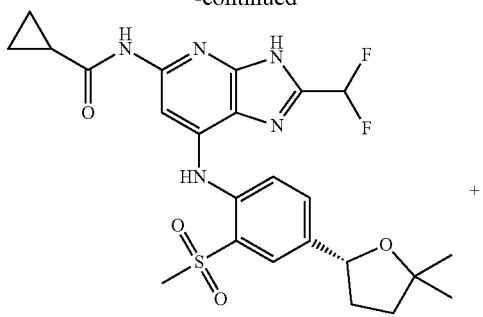

I-498

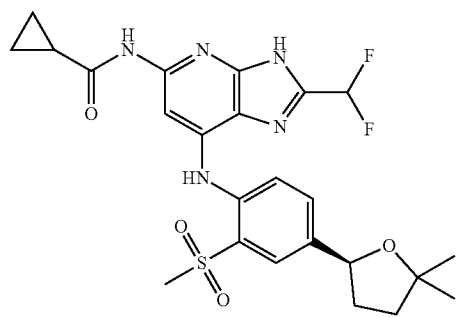

I-499

Synthesis of Compound I-498 and I-499.

Isomers of I-332 (0.095 g) were separated out using column (CHIRAL PAK AD-H 250×4.6 mm, 5 μM) 0.1% DEA in IPA as co-solvent with flow rate of 4 mL/min. to get pure fraction-1 (FR-a) and fraction-2 (FR-b). FR-a was concentrated in vacuo at 30° C. to afford pure I-498 (0.032 g). MS(ES): m/z 520.56 [M+H]+, LCMS purity: 96.48%, HPLC purity: 96.69%, Chiral HPLC: 100%, 1H NMR (DMSO, 400 MHz): 10.69 (s, 1H), 8.65 (s, 1H), 8.00 (s, 1H), 7.89 (m, 1H), 7.76-7.68 (s, 2H), 7.20 (s, 1H), 5.03-5.01 (t, J=7.6 Hz, 1H), 3.20 (s, 3H), 2.40 (s, 1H), 2.03 (s, 2H), 1.88-1.81 (s, 2H), 1.3-1.310 (d, 6H), 1.25 (s, 1H), 0.78 (bs, 4H). FR-b was concentrated in vacuo at 30° C. to afford pure I-499 (0.027 g) MS(ES): m/z 520.59 [M+H]+, LCMS purity: 100%, HPLC purity: 99.12%, Chiral HPLC: 100%, 1H NMR (DMSO, 400 MHz): 13.60 (s, 1H), 10.73 (s, 1H), 8.69 (s, 1H), 8.03 (s, 1H), 7.90 (s, 1H), 7.71-7.69 (m, 2H), 7.25 (s, 1H), 3.20 (s, 3H), 2.44-2.34 (m, 2H), 2.10-2.02 (m, 1H), 1.88-1.77 (m, 3H), 1.35-1.31 (d, 6H), 0.80 (bs, 4H).

Example 500: Synthesis of N-(2-(difluoromethyl)-7-((4-(4-(methoxymethyl)-5-methylthiazol-2-yl)-2-(methylsulfonyl)phenyl)amino)-3H-imidazo[4,5-b]pyridin-5-yl)cyclopropanecarboxamide, I-500

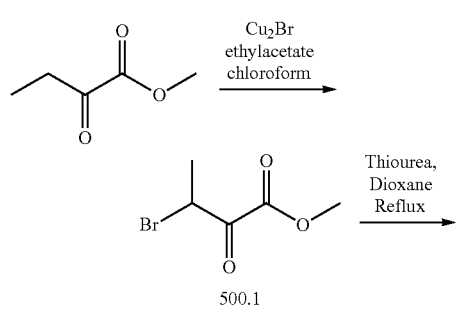

1034

-continued

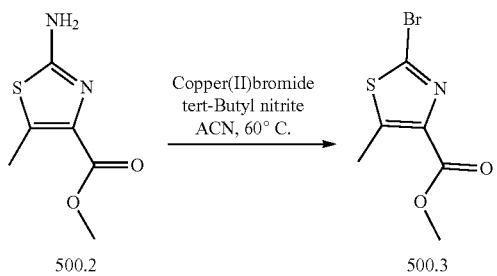

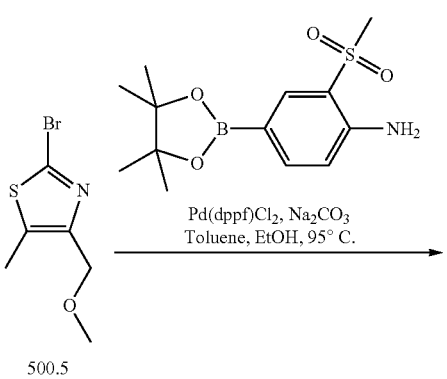

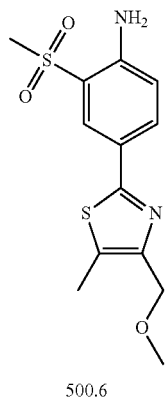

500.6

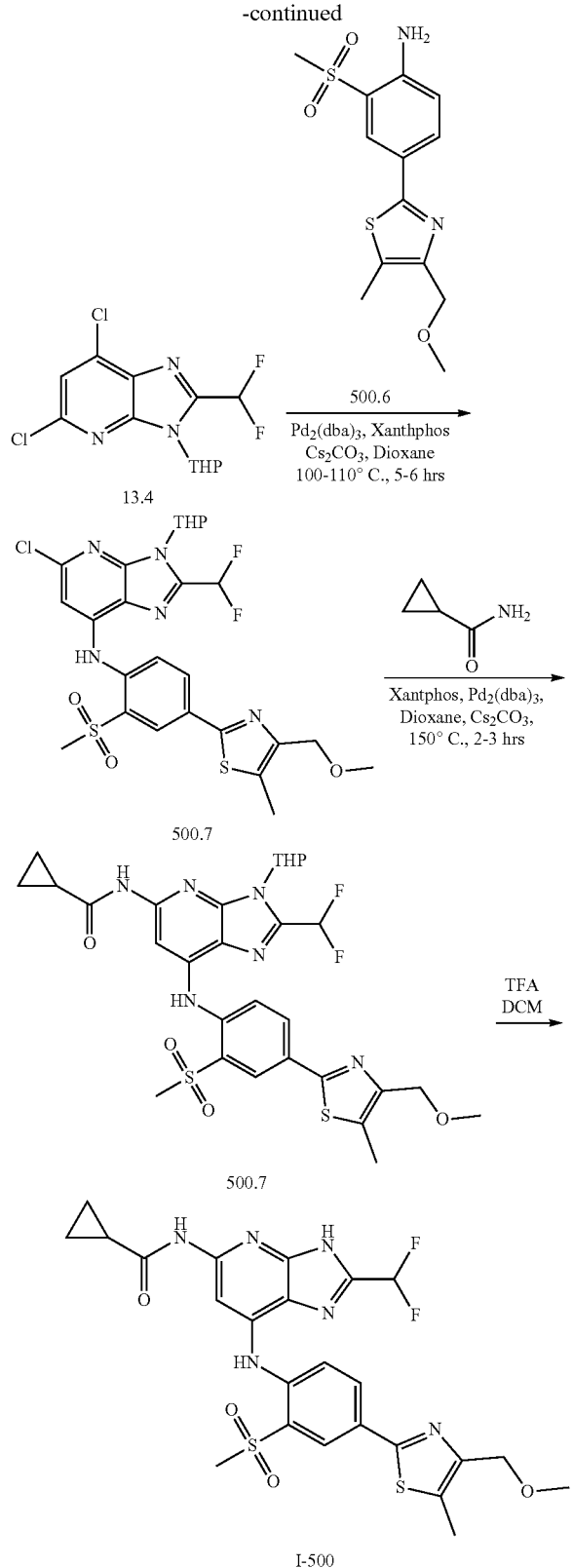

Synthesis of Compound 500.1.

To a solution of copper(II)bromide (19.19 g, 8.61 mmol, 2 eq) in ethyl acetate (10 ml) was added methyl 2-oxobutanoate (5 g, 4.30 mmol, 1 eq) in chloroform (50 mL). Reaction mixture was stirred at 75° C. for 1 h. After completion of the reaction, reaction mixture was filtered through celite bed, washed with chloroform and dried well to obtain crude product. This was purified by column chromatography using 25% ethyl acetate in hexane to obtain pure 500.1. (6 g, 71.45%). MS(ES): m/z 196.01 [M+H]$^+$.

Synthesis of Compound 500.2.

To compound 500.1 (6 g, 30.77 mmol, 1.0 eq) in dioxane (5 ml) was added thiourea (3.51 g, 46.15 mmol, 1.5 eq). Reaction mixture was stirred at 100° C. for 2 h. Upon completion, reaction mixture was transferred into cold water and extracted by ethyl acetate. Organic layer combined, dried over Na$_2$SO$_4$ and concentrated in vacuo to obtain crude product. This was purified by column chromatography and compound was eluted in 2.5% MeOH in CH$_2$Cl$_2$ as eluant to obtain pure 500.2 (4.2 g, 79.27%). MS(ES): m/z 173.20 [M+H]$^+$.

Synthesis of Compound 500.3.

To compound 1.2 (3.7 g, 2.07 mmol, 1 eq) in acetonitrile (40 mL) at 0° C., tert butyl nitrite (4.2 g, 4.15 mmol, 2 eq) and copper(II) bromide (9.26 g, 4.15 mmol, 2 eq) was added. Reaction mixture was stirred at 80° C. for 2 h. After completion of the reaction, the reaction mixture was transferred into cold water and extracted by ethyl acetate. Organic layer combined, dried over anhydrous Na$_2$SO$_4$, filtered and concentrated in vacuo to obtain 500.3. (3.2 g, 67.03%). MS(ES): m/z 237.08 [M+H]$^+$.

Synthesis of Compound 500.4.

To compound 500.3 (3.2 g, 5.63 mmol, 1.0 eq) in ethanol (5 ml) was added sodium borohydride (0.319 g, 8.44 mmol, 1.5 eq) at 0° C. Reaction mixture was stirred at r.t. for 1 h. Upon completion, reaction mixture was transferred into cold water and extracted by ethyl acetate. Organic layer combined, dried over Na$_2$SO$_4$ and concentrated in vacuo to obtain crude product. This was purified by column chromatography and compound was eluted in 2.5% MeOH in CH$_2$Cl$_2$ as eluant to obtain pure 500.4 (1.8 g, 63.82%). MS(ES): m/z 209.07 [M+H]$^+$.

Synthesis of Compound 500.5.

To compound 500.4 (1.8 g, 3.09 mmol, 1.0 eq) in dimethylformamide (5 ml) was added sodium hydride (0.285 g, 4.06 mmol, 1.5 eq) at 0° C. Then, methyl iodide (1.2 g, 3.68 mmol, 1.3 eq) was added. Reaction mixture was stirred at r.t. for 1 h. Upon completion, reaction mixture was transferred into cold water and extracted by ethyl acetate. Organic layer combined, dried over Na$_2$SO$_4$ and concentrated in vacuo to obtain crude product. This was purified by column chromatography and compound was eluted in 2% MeOH in CH$_2$Cl$_2$ as eluant to obtain pure 500.5 (1.1 g, 57.25%). MS(ES): m/z 223.10 [M+H]$^+$.

Synthesis of Compound 500.6.

To compound 500.5 (1.1 g, 6.10 mmol, 1.0 eq) in a mixture of toluene (9 mL) and ethanol (3 mL) was added 2-(methylsulfonyl)-4-(4,4,5,5-tetramethyl-1,3,2-dioxaborolan-2-yl)aniline (0.988 g, 6.42 mmol, 1.1 eq). Reaction mixture was degassed with argon atmosphere for 10 min. Then 1,1'-Bis (diphenyl phosphino)ferrocene] di chloro palladium(II) (0.208 g, 0.28 mmol, 0.05 eq) and sodium carbonate (1.93 g, 18.3 mmol, 3 eq) was added into it. Reaction mixture was stirred at 95° C. for 24 h. Upon completion, reaction mixture was transferred into cold water then extracted with ethyl acetate. Organic layer combined, dried over Na$_2$SO$_4$ and concentrated in vacuo to obtain crude product. This was purified by column chromatography and compound was eluted in 5% MeOH in CH$_2$Cl$_2$ as eluant to obtain pure 500.6 (0.800 g, 51.70%). MS(ES): m/z 313.40 [M+H]$^+$.

Synthesis of Compound 500.7.

Compound 500.7 was synthesized from 500.6 and 13.4 using general procedure A. (Yield: 28.73%). MS(ES): m/z 598.08 [M+H]+.

Synthesis of Compound 500.8.

Compound 500.8 was synthesized from 500.7 and cyclopropanecarboxamide using general procedure B. (Yield: 37.83%). MS(ES): m/z 647.13 [M+H]+.

Synthesis of I-500.

Compound I-500 was synthesized from 500.8 using general procedure C. (Yield: 63.86%). MS(ES): m/z 563.61 [M+H]+, LCMS purity: 97.50%, HPLC purity: 96.76%, 1H NMR (DMSO, 400 MHz): 13.53 (s, 1H), 10.83 (s, 1H), 8.96 (s, 1H), 8.40 (s, 1H), 8.20-8.15 (m, 2H), 7.89-7.87 (d, J=8.4 Hz, 1H), 7.27 (s, 1H), 4.51 (s, 2H), 3.34-3.32 (d, J=6.8 Hz, 6H), 2.51 (s, 3H), 2.06 (s, 1H), 0.81 (bs, 4H).

Example 501: Synthesis of N-(2-(difluoromethyl)-7-((4-(1-(3-methoxypropyl)-1H-pyrazol-3-yl)-2-(methylsulfonyl)phenyl)amino)-3H-imidazo[4,5-b]pyridin-5-yl)cyclopropanecarboxamide, I-501

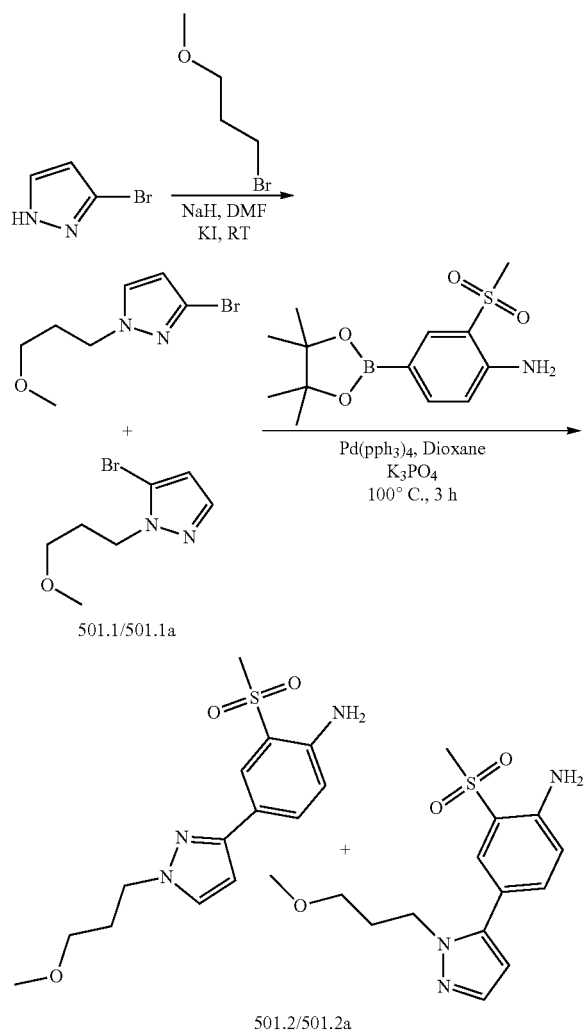

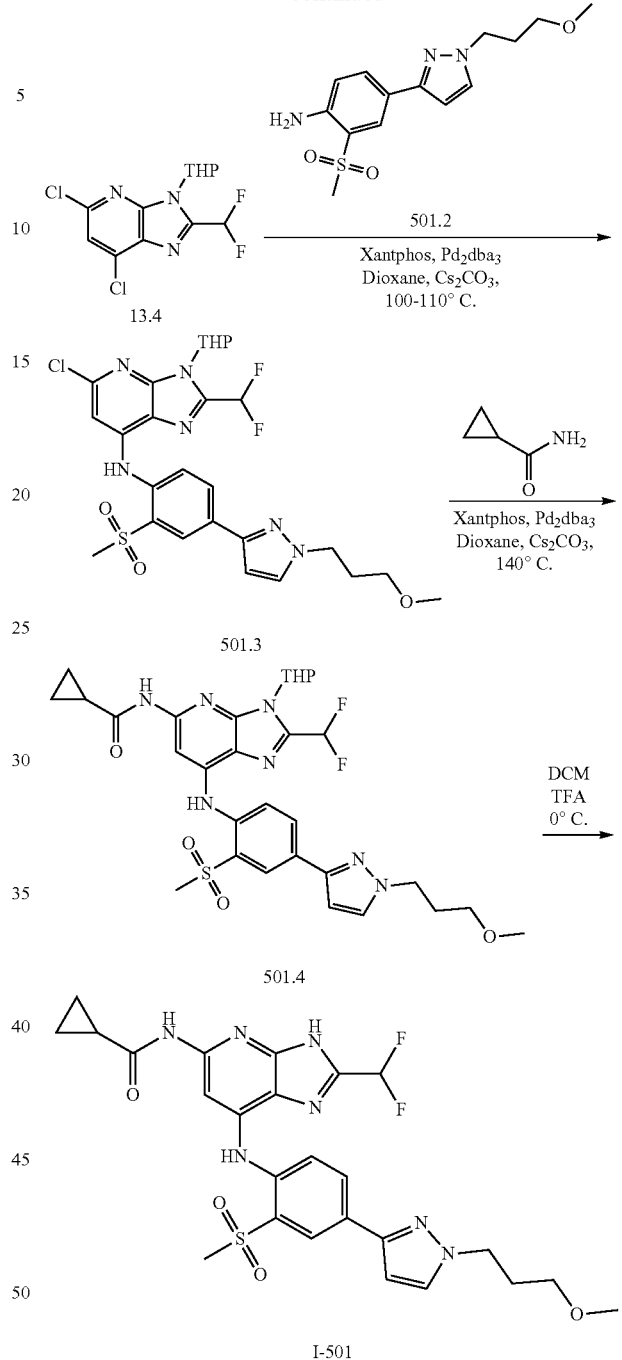

Synthesis of Compound 501.1.

To a solution of 3-bromo-1H-pyrazole (2 g, 13.6 mmol, 1.0 eq) in N,N'-dimethylformamide (20 mL) at 0° C., sodium hydride (0.81 g, 34.5 mmol, 2.5 eq) was added followed by addition of 1-bromo-3-methoxypropane (2.51 g, 16.4 mmol, 1.2 eq) and potassium iodide (0.22 g, 1.36 mmol, 0.1 eq). Reaction mixture was stirred at r.t. for 3 h. After completion of the reaction, the reaction mixture was transferred into water and extracted with ethyl acetate. Organic layer combined, dried over anhydrous Na$_2$SO$_4$, filtered and concentrated in vacuo to obtain 501.1 (2.1 g, 70.44%). MS(ES): m/z 220.35 [M+H]+.

Synthesis of Compound 501.2.

To compound 501.1 (1 g, 4.5 mmol, 1.0 eq) in 1,4-dioxane (10 mL), compound 2-(methylsulfonyl)-4-(4,4,5,5-tetramethyl-1,3,2-dioxaborolan-2-yl)aniline (1.49 g, 5.0 mmol, 1.1 eq) and potassium phosphate (1.03 g, 13.5 mmol, 3.0 eq) were added. Reaction mixture was degassed using argon for 15 min. Then, Tetrakis(triphenylphosphine)palladium(0) (1.03 g, 0.92 mmol, 0.2 eq) was added and again degassed for 5 min. Reaction mixture was stirred at 100° C. for 3 h. After completion of the reaction, the reaction mixture was transferred into water and extracted with ethyl acetate. Organic layer combined, dried over anhydrous $Na_2SO_4$, filtered and concentrated in vacuo to obtain 501.2 (0.8 g, 56.65%). MS(ES): m/z 310.54 $[M+H]^+$.

Synthesis of Compound 501.3.

Compound 501.3 was synthesized from 501.2 and 13.4 using general procedure A. (Yield: 39.37%). MS(ES): m/z 596.87 $[M+H]^+$.

Synthesis of Compound 501.4.

Compound 501.4 was synthesized from 501.3 and cyclopropanecarboxamide using general procedure B. (Yield: 64.71%). MS(ES): m/z 644.23 $[M+H]^+$.

Synthesis of I-501.

Compound I-501 was synthesized from 501.4 using general procedure C. (Yield: 69.02%). MS(ES): m/z 560.75 $[M+H]^+$, LCMS purity: 100%, HPLC purity: 98.56%, 1H NMR (DMSO, 400 MHz): 13.68 (s, 1H), 10.77 (s, 1H), 8.80 (s, 1H), 8.34 (s, 1H), 8.16-8.11 (m, 2H), 7.84-7.81 (d, J=12.0 Hz, 2H), 6.83 (s, 1H), 4.25-4.21 (t, J=14.0 Hz, 2H), 3.26 (s, 6H), 2.08-2.03 (m, 3H), 1.24 (s, 3H), 0.80 (bs, 4H).

Example 502: Synthesis of N-(7-((4-(1-(3-methoxypropyl)-1H-pyrazol-3-yl)-2-(methylsulfonyl)phenyl)amino)-2-methyl-3H-imidazo[4,5-b]pyridin-5-yl)cyclopropanecarboxamide, I-502

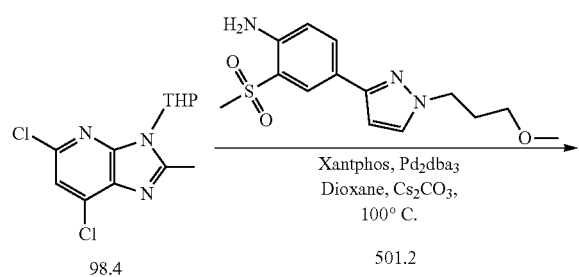

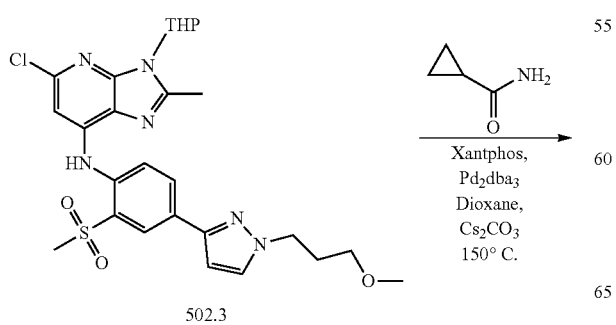

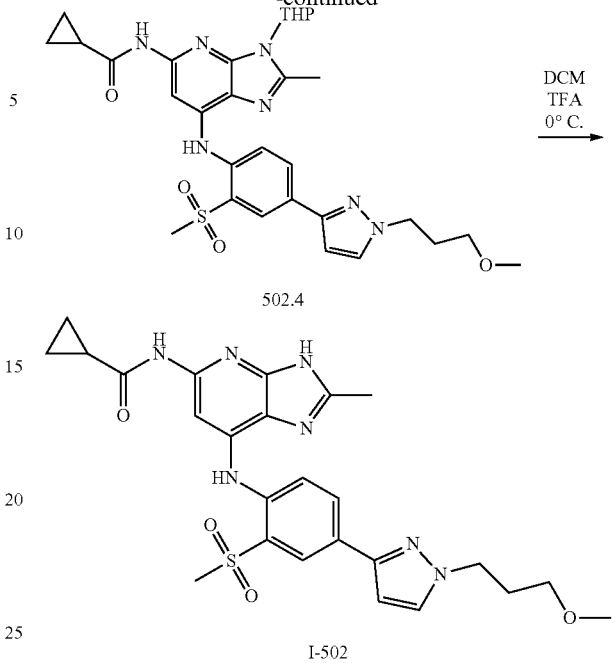

Synthesis of Compound 502.3

Compound 502.3 was synthesized from 502.2 and 98.4 using general procedure A. (Yield: 29.78%). MS(ES): m/z 560.08 $[M+H]^+$.

Synthesis of Compound 502.3.

Compound 503.3 was synthesized from 502.2 and cyclopropanecarboxamide using general procedure B. (Yield: 59.80%). MS(ES): m/z 608.73 $[M+H]^+$.

Synthesis of I-502.

Compound was synthesized from 503.3 using general procedure C. (Yield: 85.71%). MS(ES): m/z 522.76 [M−H]+, LCMS purity: 100%, HPLC purity: 98.62%, 1H NMR (DMSO, 400 MHz): 12.56 (s, 1H), 10.59 (s, 1H), 8.62 (s, 1H), 8.32 (s, 1H), 8.12-8.03 (m, 2H), 7.82-7.78 (m, 2H), 6.80 (s, 1H), 4.24-4.21 (t, J=14.0 Hz, 2H), 3.31 (s, 2H), 3.25-3.24 (d, J=7.6 Hz, 6H), 2.50 (s, 3H), 2.08-2.00 (m, 3H), 0.79-0.76 (m, 4H).

Example 503: Synthesis of 6-((2-methyl-7-((2-(methylsulfonyl)-4-(5-methylthiazol-2-yl)phenyl)amino)-3H-imidazo[4,5-b]pyridin-5-yl)amino)picolinonitrile, I-503

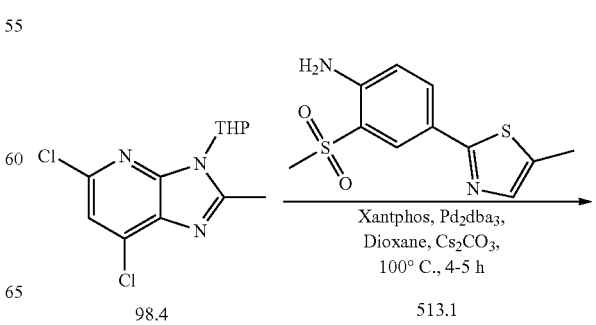

-continued

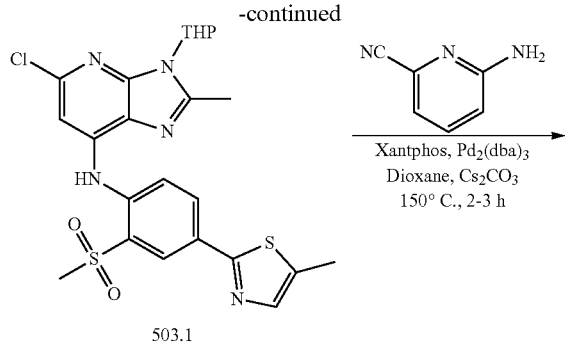

503.1

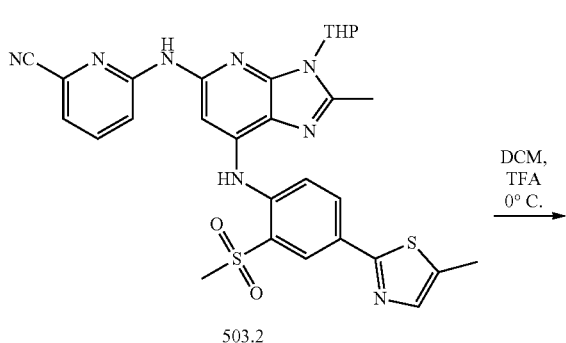

503.2

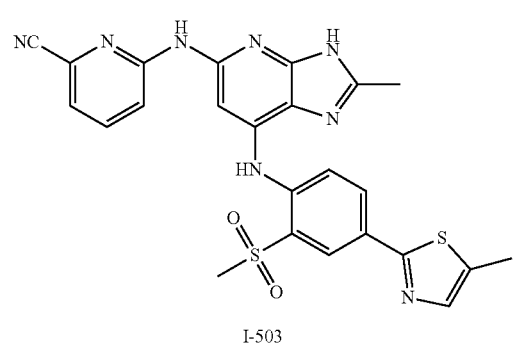

I-503

Synthesis of Compound 503.1.

Compound was synthesized using general procedure A. (Yield: 22.14%). MS(ES): m/z 519.05 [M+H]⁺.

Synthesis of Compound 503.2.

Compound 503.2 was synthesized from 503.1 and 6-aminopicolinonitrile using general procedure B. (Yield: 51.74%). MS(ES): m/z 601.72 [M+H]⁺.

Synthesis of I-503.

Compound I-503 was synthesized from 503.2 using general procedure C. (Yield: 67.83%). MS(ES): m/z 517.51 [M+H]⁺, LCMS purity: 98.92%, HPLC purity: 98.10%, 1H NMR (DMSO-d6, 400 MHz): 8.41 (s, 1H), 7.94-7.90 (t, 2H), 7.65-7.63 (d, J=7.6 Hz, 1H), 7.57 (s, 1H), 7.49-7.47 (d, J=7.6 Hz, 1H), 7.39-7.37 (d, J=7.6 Hz, 1H), 6.96 (s, 1H), 3.01 (s, 3H), 2.68 (s, 3H), 2.38 (s, 3H).

Example 504: Synthesis of 6-((2-methyl-7-((2-(methylsulfonyl)-4-(4-methylthiazol-2-yl)phenyl)amino)-3H-imidazo[4,5-b]pyridin-5-yl)amino)picolinonitrile, I-504

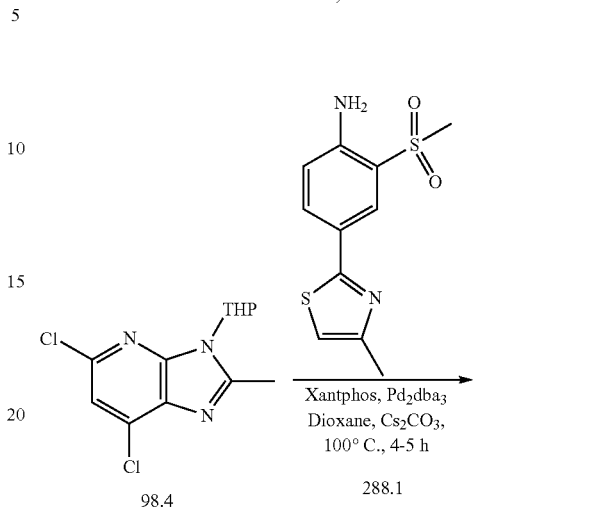

288.1

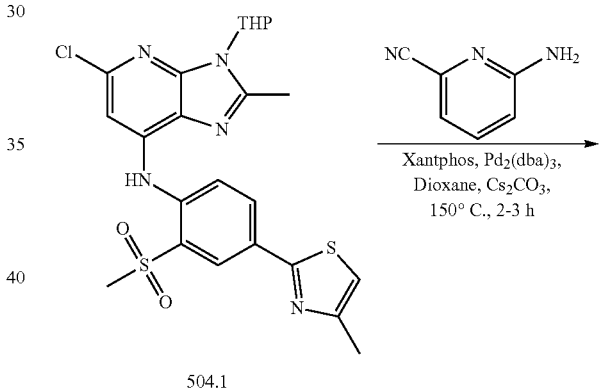

504.1

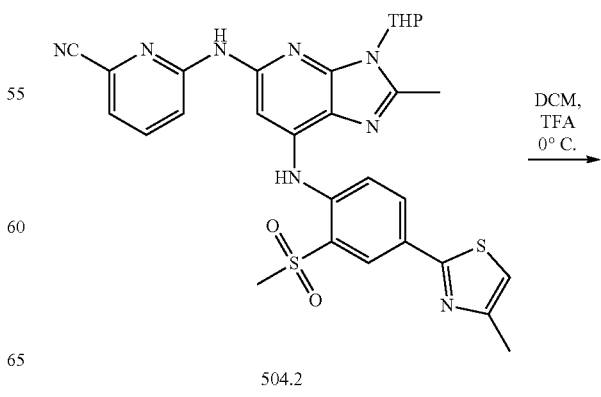

504.2

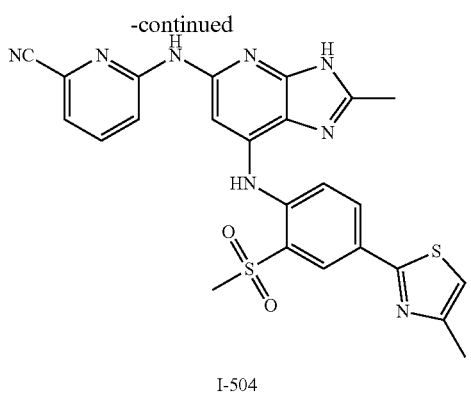

I-504

Synthesis of Compound 504.1.

Compound 504.1 was synthesized from 98.4 and 288.1 using general procedure A. (Yield: 26.51%). MS(ES): m/z 519.05 [M+H]$^+$.

Synthesis of Compound 504.2

Compound 504.2 was synthesized 6-aminopicolinonitrile and 504.1 using general procedure B. (Yield: 48.87%). MS(ES): m/z 600.72 [M+H]$^+$.

Synthesis of I-504.

Compound I-504 was synthesized from 504.2 using general procedure C. (Yield: 51.30%). MS(ES): m/z 517.59 [M+H]$^+$, LCMS purity: 99.06%, HPLC purity: 97.25%, 1H NMR (DMSO-d6, 400 MHz): 12.55 (s, 1H), 10.06 (s, 1H), 8.99 (s, 1H), 8.46 (s, 1H), 8.28-8.26 (d, J=8.4 Hz, 1H), 8.07-8.05 (d, J=8.8 Hz, 1H), 7.96-7.94 (d, J=8.8 Hz, 1H), 7.87-7.83 (t, J=1.6 Hz, 1H), 7.76 (s, 1H), 7.46-7.44 (d, J=7.2 Hz, 1H), 7.37 (s, 1H), 3.32 (s, 3H), 2.49 (s, 3H), 2.46 (s, 3H).

Example 505: Synthesis of (S)-2-(difluoromethyl)-N5-(2,6-dimethylpyrimidin-4-yl)-N7-(2-(methylsulfonyl)-4-(tetrahydro-2H-pyran-2-yl)phenyl)-3H-imidazo[4,5-b]pyridine-5,7-diamine, I-505

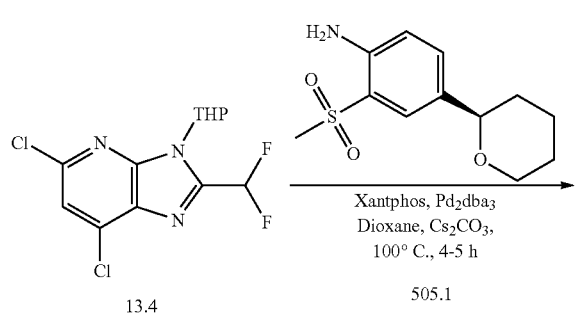

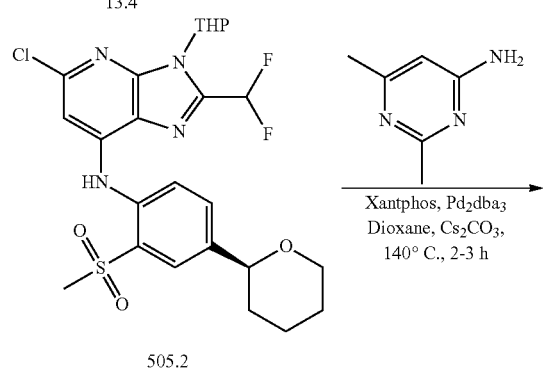

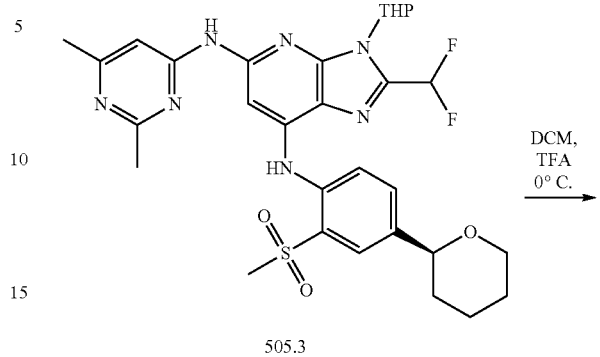

505.3

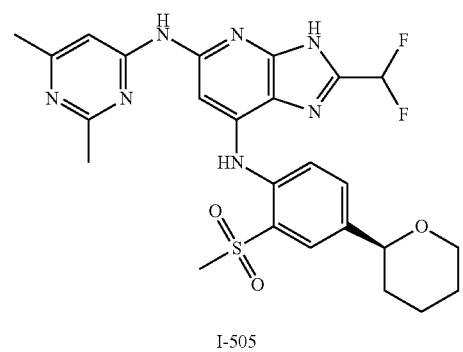

I-505

Synthesis of Compound 505.2.

Compound 505.2 was synthesized from 13.4 and 505.1 using general procedure A. (Yield: 29.50%). MS(ES): m/z 542.01 [M+H]$^+$.

Synthesis of Compound 505.3.

Compound 505.3 was synthesized from 505.2 and 2,6-dimethylpyrimidin-4-amine using general procedure B. (Yield: 57.46%). MS(ES): m/z 628.71 [M+H]$^+$.

Synthesis of I-505.

Compound was synthesized from 505.3 using general procedure C. (Yield: 80.83%). MS(ES): m/z 544.60 [M+H]$^+$, LCMS purity: 99.77%, HPLC purity: 100%, Chiral HPLC: 100%, 1H NMR (DMSO-d6, 400 MHz): 13.65 (s, 1H), 10.01 (s, 1H), 8.81 (s, 1H), 7.91-7.84 (m, 2H), 7.73-7.71 (d, J=8.4 Hz, 1H), 7.61-7.55 (d, J=24.4 Hz, 1H), 7.23 (s, 1H), 5.76 (s, 2H), 4.46-4.44 (d, J=10.8 Hz, 1H), 4.09-4.06 (d, J=11.2 Hz, 1H), 3.22 (s, 3H), 2.40 (s, 3H), 2.31 (S, 3H), 1.91-1.88 (d, J=10.8 Hz, 2H), 1.68-1.67 (m, 1H), 1.58 (s, 2H), 1.45-1.42 (m, 1H).

Example 506: Synthesis of 6-((7-((4-(4,5-dimethyl-thiazol-2-yl)-2-(methylsulfonyl)phenyl)amino)-2-methyl-3H-imidazo[4,5-b]pyridin-5-yl)amino)picolinonitrile, I-506

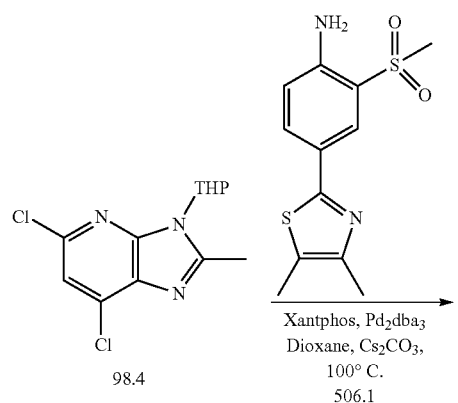

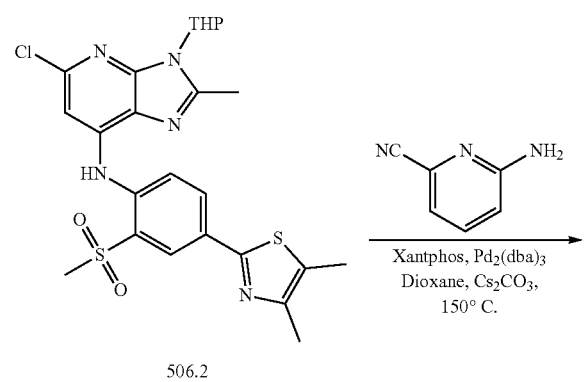

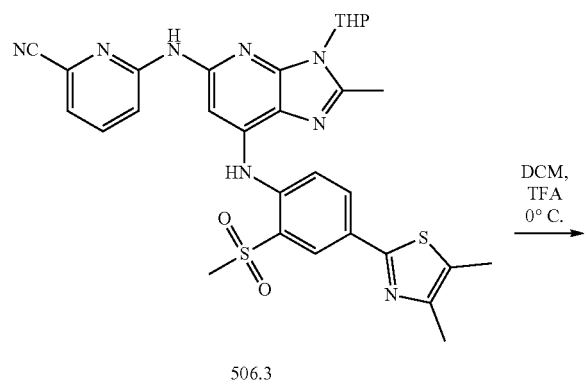

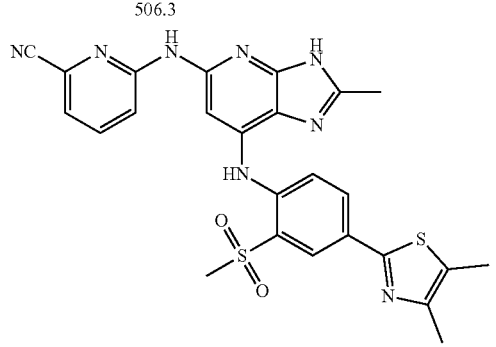

Synthesis of Compound 506.2.

Compound 506.2 was synthesized from 98.4 and 506.1 using general procedure A. (Yield: 21.51%). MS(ES): m/z 533.07 [M+H]+.

Synthesis of Compound 506.3.

Compound 506.3 was synthesized from 506.2 and 6-aminopicolinonitrile using general procedure B. (Yield: 36.06%). MS(ES): m/z 615.74 [M+H]+.

Synthesis of I-506.

Compound I-506 was synthesized from 506.3 using general procedure C (Yield: 57.93%). MS(ES): m/z 531.6 [M+H]+, LCMS purity: 95.91%, 1H NMR (DMSO, 400 MHz): 12.55 (s, 1H), 10.07 (s, 1H), 8.95 (s, 1H), 8.40 (s, 1H), 8.20-8.18 (d, J=8.4 Hz, 1H), 8.05-8.02 (d, J=8.8 Hz, 1H), 7.95-7.96 (d, J=8.8 Hz, 1H), 7.87-7.85 (t, J=16.0 Hz, 1H), 7.75 (s, 1H), 7.46-7.44 (d, J=7.2 Hz, 1H), 3.30 (s, 3H), 2.35 (s, 3H), 2.30 (s, 3H), 1.24 (s, 3H).

Example 507: Synthesis of 6-((2-(difluoromethyl)-7-((4-(4,5-dimethylthiazol-2-yl)-2-(methylsulfonyl)phenyl)amino)-3H-imidazo[4,5-b]pyridin-5-yl)amino)picolinonitrile, I-507

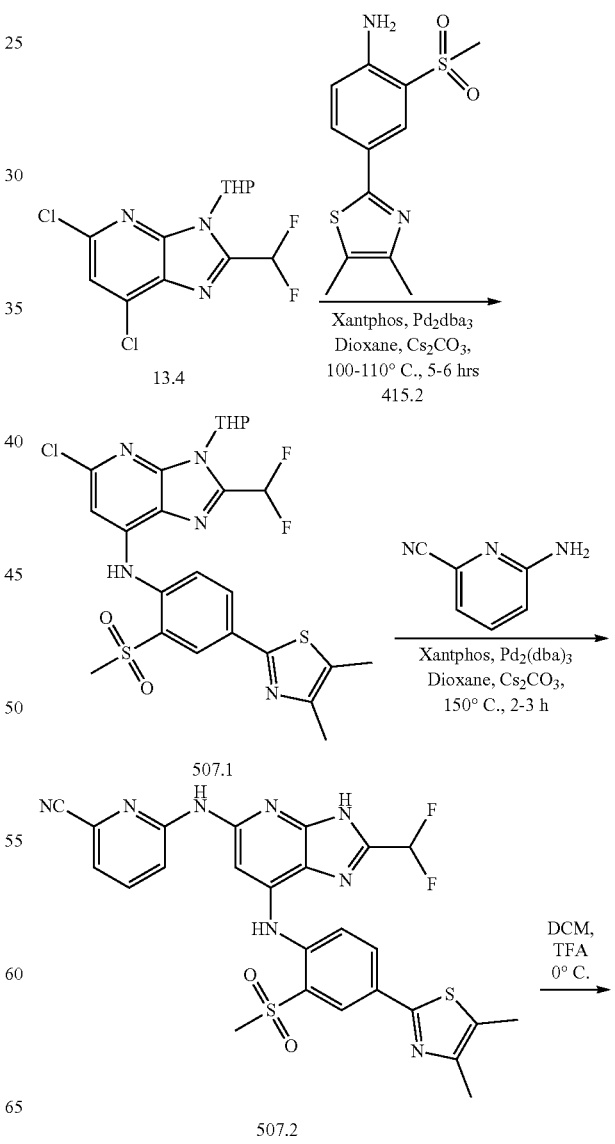

-continued

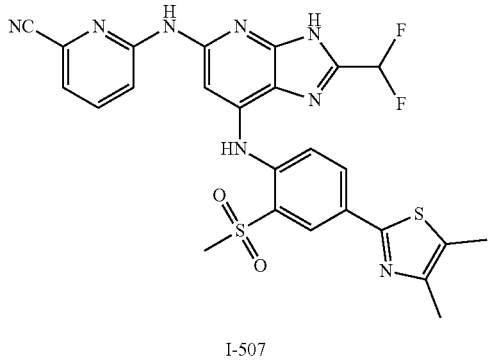

I-507

Synthesis of Compound 507.1.

Compound 507.1 was synthesized from 13.4 and 415.2 using general procedure A. (Yield: 37.81%). MS(ES): m/z 569.05 [M+H]$^+$.

Synthesis of Compound 507.2.

Compound 507.2 was synthesized from 507.1 and 6-aminopicolinonitrile using general procedure B. (Yield: 45.12%). MS(ES): m/z 667.61 [M+H]$^+$.

Synthesis of I-507.

Compound I-507 was synthesized from 507.2 using general procedure C. (Yield: 55.56%). MS(ES): m/z 567.52 [M+H]$^+$, LCMS purity: 99.69%, HPLC Purity: 99.49%, 1H NMR (DMSO-d6, 400 MHz): 13.70 (s, 1H), 10.24 (s, 1H), 9.07 (s, 1H), 8.42 (s, 1H), 8.22-8.19 (d, J=1.04 Hz, 1H), 8.08-8.03 (d, J=2.28 Hz, 2H), 7.91-7.87 (d, J=1.6 Hz, 1H), 7.76 (s, 1H), 7.50-7.48 (d, J=7.2 Hz, 1H), 7.24 (s, 1H), 3.27 (s, 3H), 2.39 (s, 3H), 2.32 (s, 3H).

Example 508: Synthesis of N7-(4-(1,5-dimethyl-1H-pyrazol-3-yl)-2-(methylsulfonyl)phenyl)-N5-(5,6-dimethylpyrazin-2-yl)-2-methyl-3H-imidazo[4,5-b]pyridine-5,7-diamine, I-508

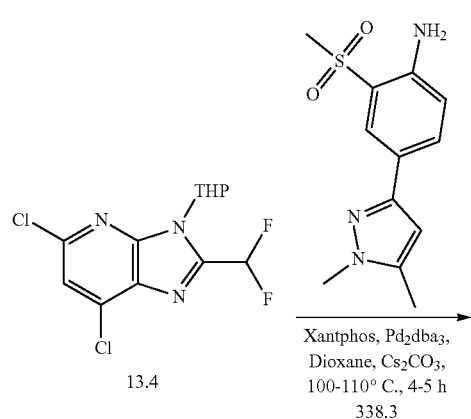

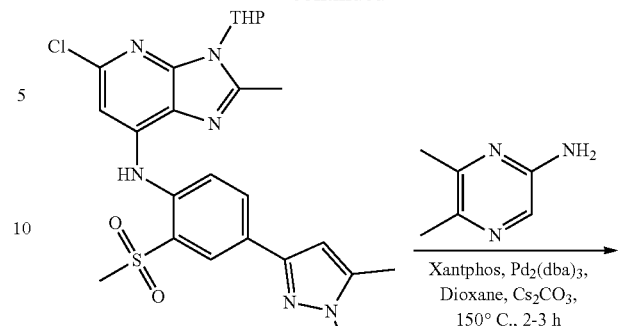

508.1

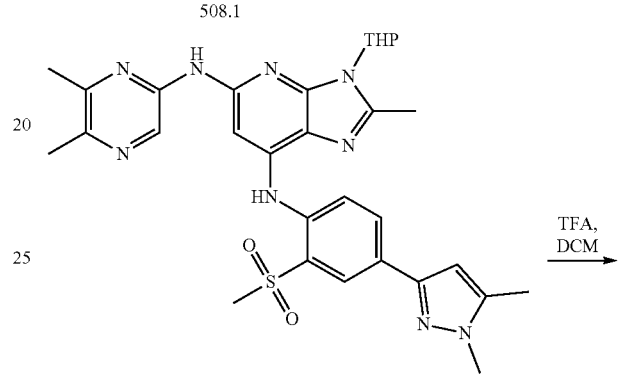

508.2

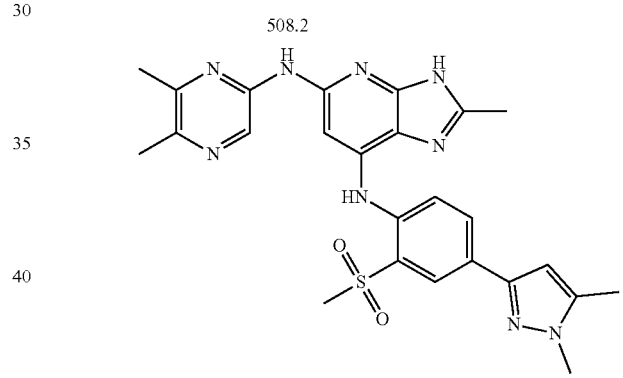

I-508

Synthesis of Compound 508.1.

Compound 508.1 was synthesized from 338.3 and 13.4 using general procedure A. (Yield: 36.49%). MS(ES): m/z 516.03 [M+H]$^+$.

Synthesis of Compound 508.2.

Compound 508.2 was synthesized from 508.1 and 5,6-dimethylpyrazin-2-amine using general procedure B. (Yield: 52.10%). MS(ES): m/z 602.73 [M+H]$^+$.

Synthesis of I-508.

Compound I-508 was synthesized from 508.2 using general procedure C. (Yield: 58.13%). MS(ES): m/z 518.66 [M+H]$^+$, LCMS purity: 100%, HPLC Purity: 100%, 1H NMR (DMSO-d6, 400 MHz): 12.28 (s, 1H), 10.34 (s, 1H), 8.78 (s, 1H), 8.71 (s, 1H), 8.41 (s, 1H), 8.14-8.12 (d, J=8 Hz, 1H), 7.67-7.65 (d, J=8 Hz, 1H), 7.13 (s, 1H), 6.62 (s, 1H), 3.80 (s, 3H), 2.76 (s, 3H), 2.52 (s, 3H), 2.43 (s, 3H), 2.35-2.32 (d, J=1.24 Hz, 6H).

Example 509: Synthesis of N7-(4-(1,5-dimethyl-1H-pyrazol-3-yl)-2-(methylsulfonyl)phenyl)-N5-(2,6-dimethylpyrimidin-4-yl)-2-methyl-3H-imidazo[4,5-b]pyridine-5,7-diamine, I-509

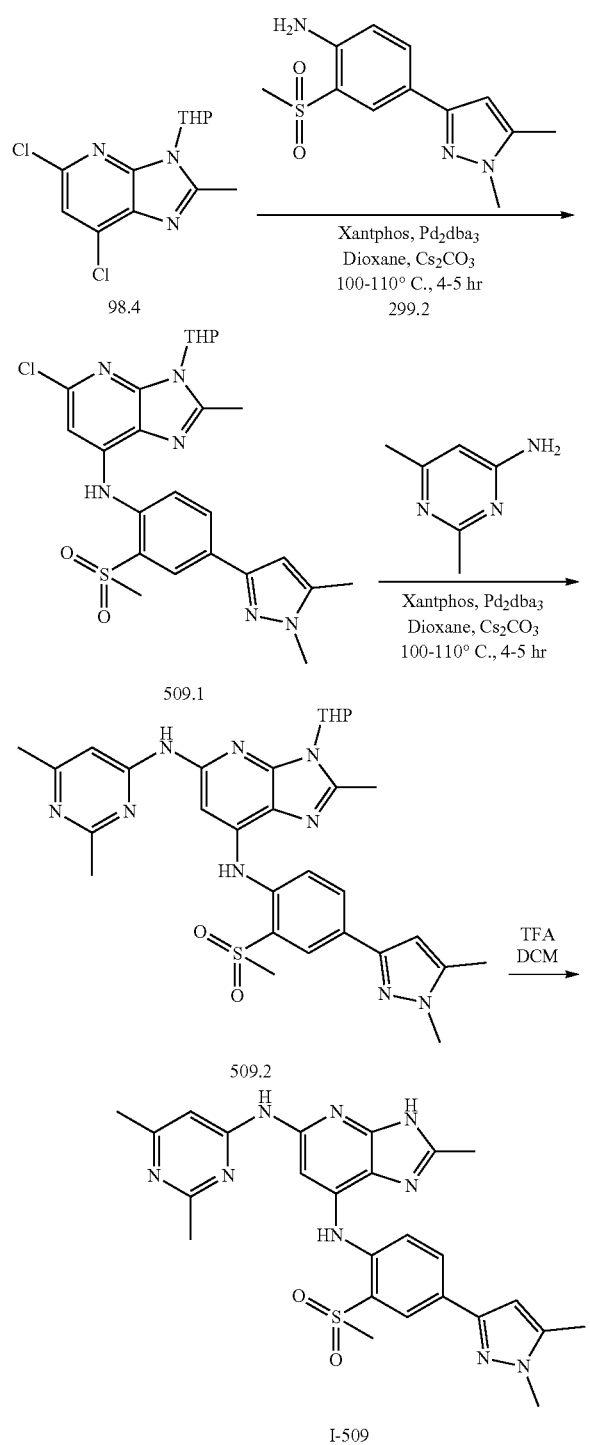

Synthesis of Compound 509.1.

Compound 509.1 was synthesized from 98.4 and 299.2 using general procedure A. (Yield: 21.12%). MS(ES): m/z 516.03 [M+H]$^+$.

Synthesis of Compound 509.2.

Compound 509.2 was synthesized from 509.1 and 2,6-dimethylpyrimidin-4-amine using general procedure B. (Yield: 53.59%). MS(ES): m/z 602.73 [M+H]$^+$.

Synthesis of I-509.

Compound I-509 was synthesized from 509.2 using general procedure C. (Yield: 56.51%). MS(ES): m/z 518.59 [M+H]$^+$, LCMS purity: 99.81%, HPLC Purity: 99.51%, 1H NMR (DMSO-d6, 400 MHz): 12.57 (s, 1H), 9.76 (s, 1H), 8.65 (s, 1H), 8.26 (s, 1H), 8.05-8.03 (d, J=1.0 Hz, 1H), 7.90-7.88 (d, J=2.3 Hz, 1H), 7.53-7.49 (d, J=1.6 Hz, 2H), 6.55 (s, 1H), 3.80 (s, 3H), 3.25 (s, 3H), 2.46-2.41 (d, J=2.3 Hz, 6H), 2.32-2.31 (d, J=2.3 Hz, 6H).

Example 510: Synthesis of 2-(difluoromethyl)-N7-(4-(1,4-dimethyl-1H-pyrazol-3-yl)-2-(methylsulfonyl)phenyl)-N5-(2,6-dimethylpyrimidin-4-yl)-3H-imidazo[4,5-b]pyridine-5,7-diamine, I-510

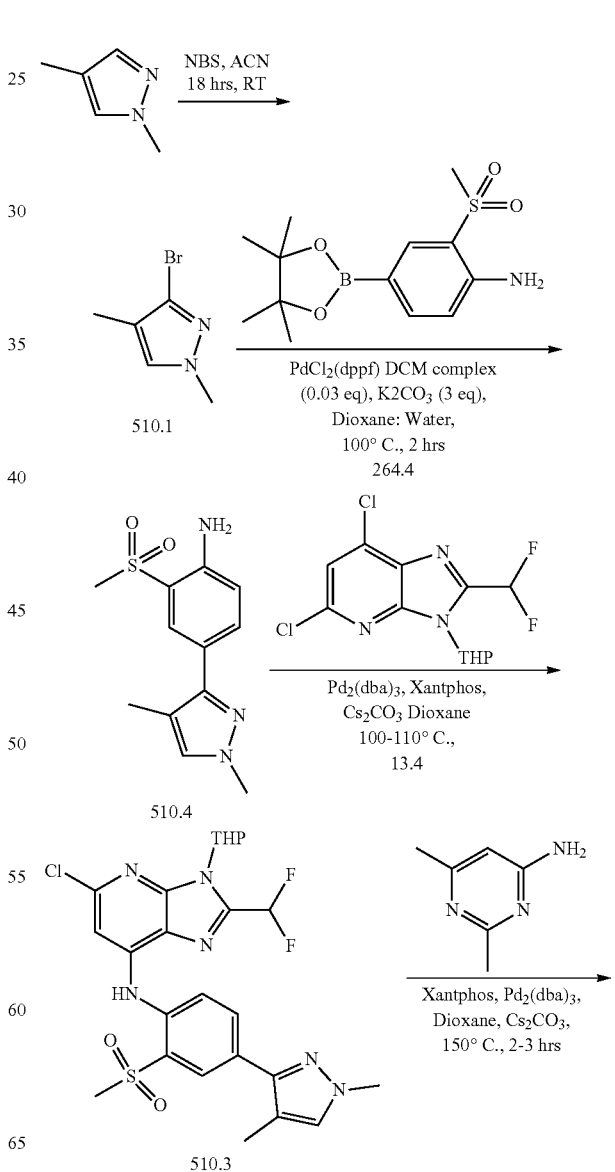

NMR (DMSO, 400 MHz): 13.60 (s, 1H), 10.05 (s, 1H), 8.92 (s, 1H), 8.27 (s, 1H), 8.06-7.96 (dd, J=4.0 Hz, 2H), 7.74 (s, 1H), 7.62-7.56 (m, 2H), 7.25 (t, 1H), 3.87 (s, 3H), 3.28 (s, 3H), 2.44 (s, 3H), 2.33 (s, 3H), 2.26 (s, 3H).

Example 511: Synthesis of N7-(4-(1,4-dimethyl-1H-pyrazol-3-yl)-2-(methylsulfonyl)phenyl)-N5-(2,6-dimethylpyrimidin-4-yl)-2-methyl-3H-imidazo[4,5-b]pyridine-5,7-diamine, I-511

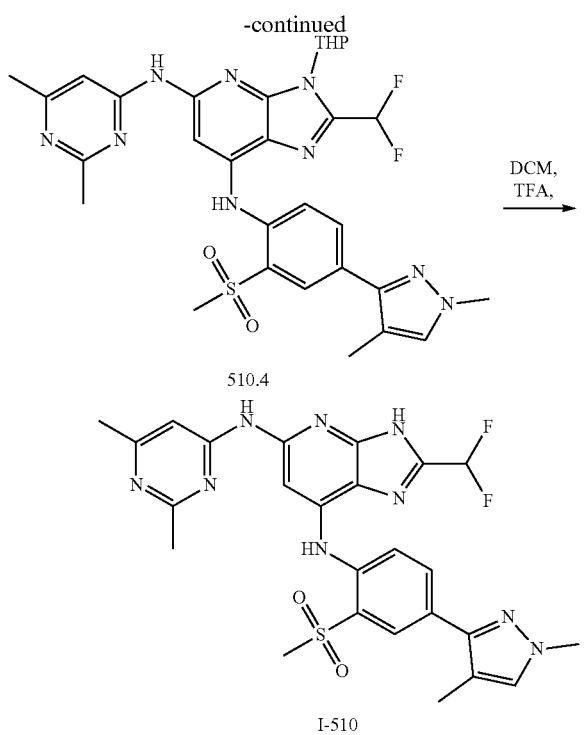

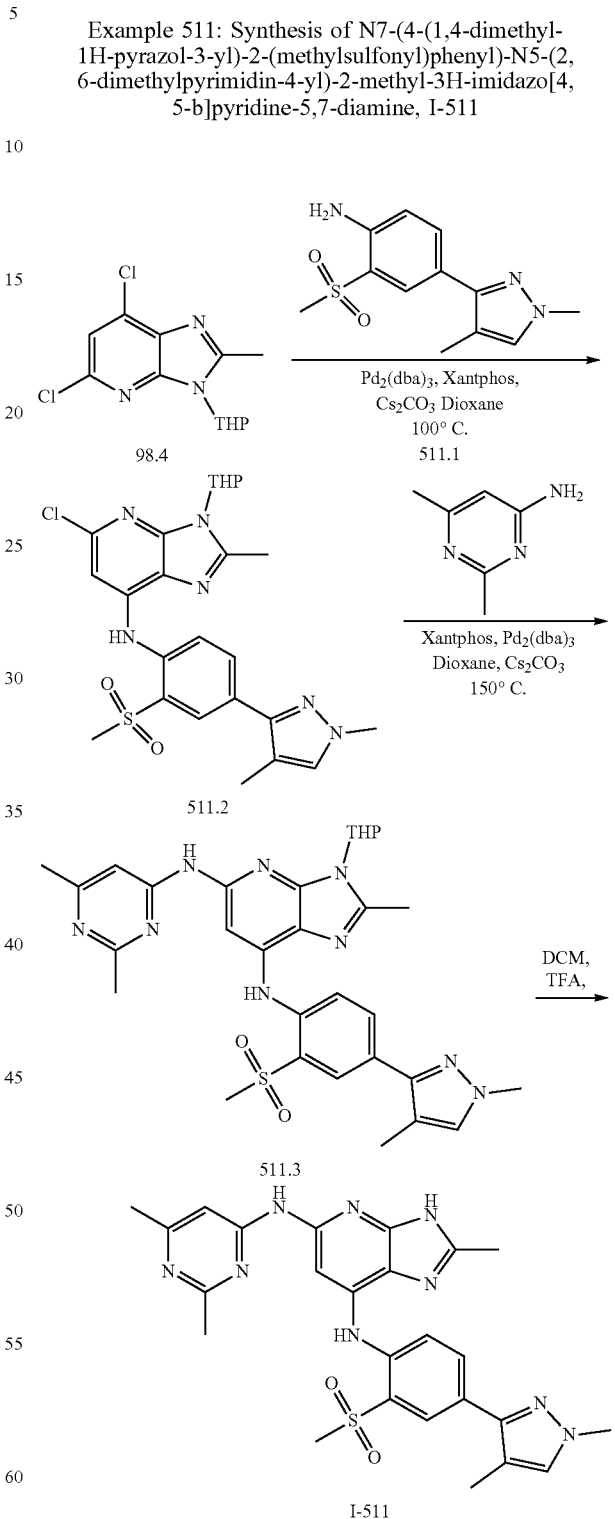

Synthesis of Compound 510.1.

To a solution of 1,4-dimethyl-1H-pyrazole (5.0 g, 5.2 mmol, 1.0 eq) in acetonitrile (50 mL), N-Bromosuccinimide (13.0 g, 7.8 mmol, 1.5 eq) was added. Reaction mixture was stirred at r.t. for 18 h. After completion of the reaction, the reaction mixture was transferred into water and extracted with ethyl acetate. Organic layer combined, dried over anhydrous $Na_2SO_4$, filtered and concentrated in vacuo to obtain pure 510.1 (2.6 g, 27.46%). MS(ES): m/z 176.43 $[M+H]^+$.

Synthesis of Compound 510.2.

To compound 510.1 (2.6 g, 1.4 mmol, 1.5 eq) and compound 264.4 (2.9 g, 0.99 mmol, 1.0 eq) in a mixture of 1,4-dioxane (60 mL) and water (10 mL), potassium carbonate (4.1 g, 2.9 mmol, 3.0 eq) was added. Reaction mixture was degassed with argon for 15 min. Then, [1,1'-Bis(diphenylphosphino)ferrocene]dichloropalladium(II) complex with dicholoromethane (0.40 g, 0.04 mmol, 0.05 eq) was added. Reaction mixture was stirred at 100° C. for 2 h. After completion of the reaction, the reaction mixture was transferred to water and extracted with ethyl acetate. Organic layers were combined, dried over anhydrous $Na_2SO_4$, filtered and concentrated in vacuo to get the crude material. This was purified by column chromatography using 12% ethyl acetate in hexane to obtain pure 510.2 (2.3 g, 58.35%). MS(ES): m/z 266.35 $[M+H]^+$.

Synthesis of Compound 510.3.

Compound 510.3 was synthesized from 510.2 and 13.4 using general procedure A. (Yield: 23.39%). MS(ES): m/z 552.37 $[M+H]^+$.

Synthesis of Compound 510.4.

Compound 510.4 was synthesized from 510.3 and 2,6-dimethylpyrimidin-4-amine using general procedure B. (Yield: 38.88%). MS(ES): m/z 639.47 $[M+H]^+$.

Synthesis of I-510.

Compound I-510 was synthesized from 510.4 using general procedure C. (Yield: 64.00%). MS(ES): m/z 554.62 $[M+H]^+$, LCMS purity: 99.61%, HPLC Purity: 97.8%, 1H Synthesis of Compound 511.2.

Compound 511.2 was synthesized from 98.4 and 511.1 using general procedure A. (Yield: 21.11%). MS(ES): m/z 516.03 $[M+H]^+$.

Synthesis of Compound 511.3.

Compound 511.3 was synthesized from 511.2 and 2,6-dimethylpyrimidin-4-amine using general procedure B. (Yield: 45.05%). MS(ES): m/z 602.73 [M+H]+.

Synthesis of I-511.

Compound I-511 was synthesized from 511.3 using general procedure C (Yield: 69.75%). MS(ES): m/z 517.86 [M+H]+, LCMS purity: 100%, HPLC Purity: 98.20%, 1H NMR (DMSO, 400 MHz): 12.52 (s, 1H), 9.86 (s, 1H), 8.76 (s, 1H), 8.24 (s, 1H), 8.03-7.95 (dd, 2H), 7.70 (s, 1H), 7.61 (s, 1H), 7.44 (s, 1H), 3.86 (s, 3H), 3.25 (s, 3H), 2.43 (s, 6H), 2.31-2.24 (d, 6H).

Example 512: Synthesis of N-(7-((4-(4-(methoxymethyl)-5-methylthiazol-2-yl)-2-(methylsulfonyl)phenyl)amino)-2-methyl-3H-imidazo[4,5-b]pyridin-5-yl)cyclopropanecarboxamide, I-512

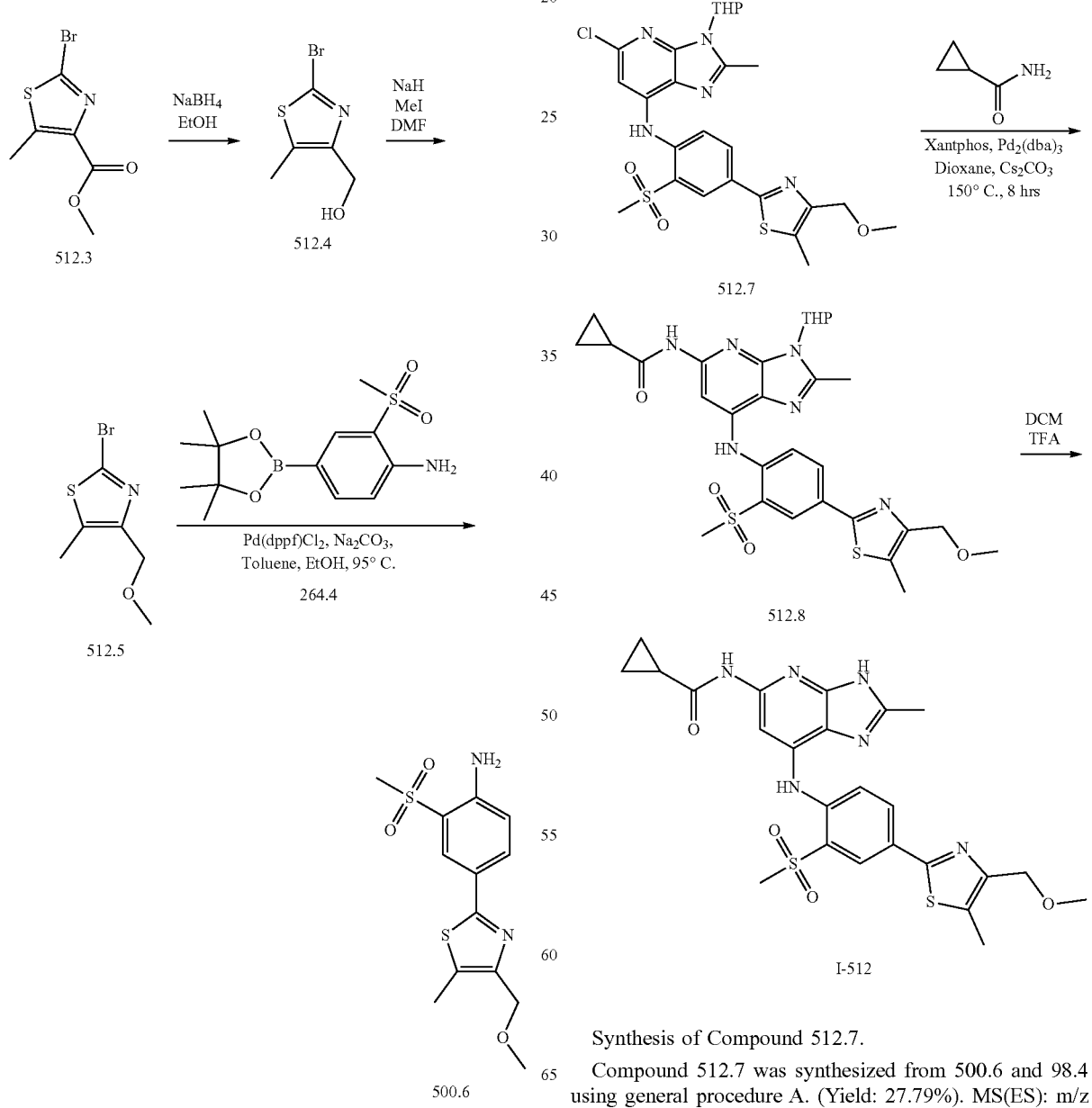

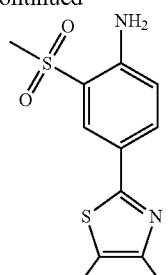

Synthesis of Compound 512.7.

Compound 512.7 was synthesized from 500.6 and 98.4 using general procedure A. (Yield: 27.79%). MS(ES): m/z 563.10 [M+H]+.

Synthesis of Compound 512.8.

Compound 512.8 was synthesized from 512.7 and cyclopropanecarboxamide using general procedure B. (Yield: 46.02%). MS(ES): m/z 611.75 [M+H]+.

Synthesis of I-512.

Compound I-512 was synthesized from 512.8 using general procedure C (Yield: 57.99%). MS(ES): m/z 527.51 [M+H]+, LCMS purity: 96.98%, HPLC Purity: 95.23%, 1H NMR (DMSO, 400 MHz): 12.55 (s, 1H), 10.64 (s, 1H), 8.79 (s, 1H), 8.37 (s, 1H), 8.13-8.08 (m, 2H), 7.846-7.824 (d, J=8.8 Hz, 1H), 4.49 (s, 2H), 3.31 (s, 6H), 3.29 (s, 1H), 2.04-1.99 (d, J=18.8 Hz, 6H), 0.78 (bs, 4H).

Example 513: Synthesis of 6-((2-(difluoromethyl)-7-((2-(methylsulfonyl)-4-(5-methylthiazol-2-yl)phenyl)amino)-3H-imidazo[4,5-b]pyridin-5-yl)amino)picolinonitrile, I-513

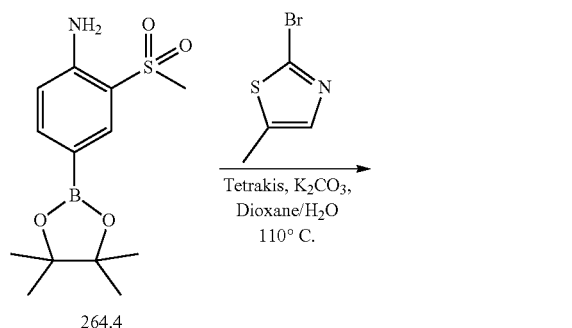

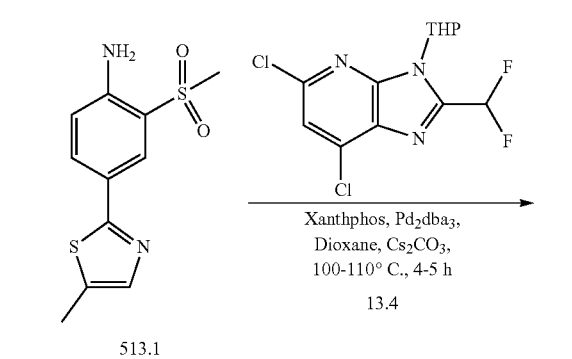

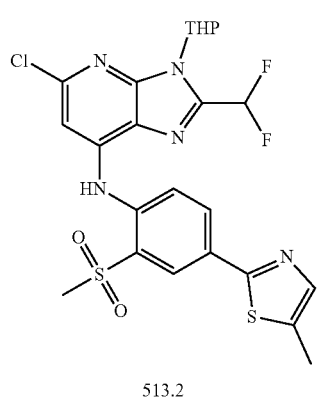

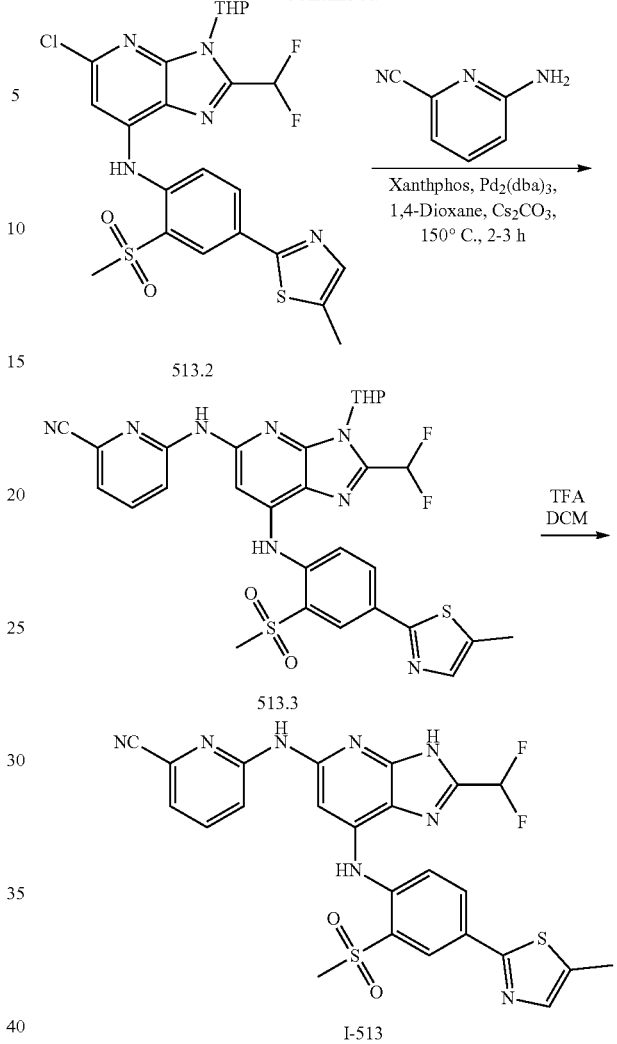

Synthesis of Compound 513.1.

To a solution of 264.4 (2 g, 11.23 mmol, 1.0 eq) and 2-bromo-5-methylthiazole (5 g, 16.85 mmol, 1.5 eq) in mixture of 1,4-dioxane (16 mL) and water (4 mL), sodium carbonate (2.38 g, 22.46 mmol, 2.0 eq) was added. Argon was purged through the reaction mixture for 5 min. Then, [1,1'-Bis(diphenylphosphino)ferrocene]dichloropalladium (II) (0.819 g, 1.12 mmol, 0.1 eq) was added and again degassed for 5 min. Reaction mixture was stirred at 120° C. for 4 h. After completion of the reaction, the reaction mixture was transferred into water and extracted with ethyl acetate. Organic layers were combined, dried over anhydrous Na2SO4, filtered and concentrated in vacuo to obtain the crude material. This was purified by column chromatography using 12% ethyl acetate in hexane as eluant to obtain 513.1 (1.1 g, 36.49%). MS(ES): m/z 269.35 [M+H]+.

Synthesis of Compound 513.2.

Compound 513.2 was synthesized from 513.1 and 13.4 using general procedure A. (Yield: 17.44%). MS(ES): m/z 555.03 [M+H]+.

Synthesis of Compound 513.3.

Compound 513.3 was synthesized from 6-aminopicolinonitrile and 513.2 using general procedure B. (Yield: 48.34%). MS(ES): m/z 637.70 [M+H]+.

Synthesis of I-513.

Compound I-513 was synthesized from 513.3 using general procedure C. (Yield: 69.13%). MS(ES): m/z 553.50 [M+H]$^+$, LCMS purity: 99.24%, HPLC Purity: 98.60%, 1H NMR (DMSO-d6, 400 MHz): 13.74 (s, 1H), 10.26 (s, 1H), 9.09 (s, 1H), 8.42 (s, 1H), 8.27-8.25 (d, J=1.8 Hz, 1H), 8.07-8.05 (m, 2H), 7.91-7.87 (d, J=1.8 Hz, 1H), 7.78 (s, 1H), 7.50-7.48 (d, J=1.8 Hz, 1H), 7.25 (s, 1H), 3.32 (s, 3H), 2.52 (s, 3H), 1.99 (s, 1H).

Example 514: Synthesis of N5-(6,7-dihydro-4H-pyrazolo[5,1-c][1,4]oxazin-2-yl)-N7-(4-(1,5-dimethyl-1H-pyrazol-3-yl)-2-(methylsulfonyl)phenyl)-2-methyl-3H-imidazo[4,5-b]pyridine-5,7-diamine, I-514

Synthesis of Compound 514.3

Compound 514.3 was synthesized from 514.1 and 514.2 using general procedure B. (Yield: 50.70%). MS(ES): m/z 548.64 [M+H]$^+$.

Synthesis of I-514.

Compound I-514 was synthesized from 514.3 using general procedure C. (Yield: 49.66%). MS(ES): m/z 534.64 [M+H]$^+$, LCMS purity: 100%, HPLC Purity: 95.74%, 1H NMR (DMSO, 400 MHz): 12.24 (s, 1H), 9.01 (s, 1H), 8.57 (s, 1H), 8.26 (s, 1H), 8.05-8.03 (d, J=10.0 Hz, 1H), 7.87-7.85 (d, J=8.4 Hz, 1H), 7.13 (s, 1H), 6.56 (s, 1H), 6.26 (s, 1H), 4.77 (s, 2H), 4.10-4.05 (m, 2H), 3.97-3.94 (m, 2H), 3.80 (s, 3H), 3.24 (s, 3H), 2.43 (s, 3H), 2.32 (s, 3H).

Example 515: Synthesis of (R)-2-(difluoromethyl)-N5-(6,7-dihydro-4H-pyrazolo[5,1-c][1,4]oxazin-2-yl)-N7-(2-(methylsulfonyl)-4-(tetrahydro-2H-pyran-2-yl)phenyl)-3H-imidazo[4,5-b]pyridine-5,7-diamine, I-515

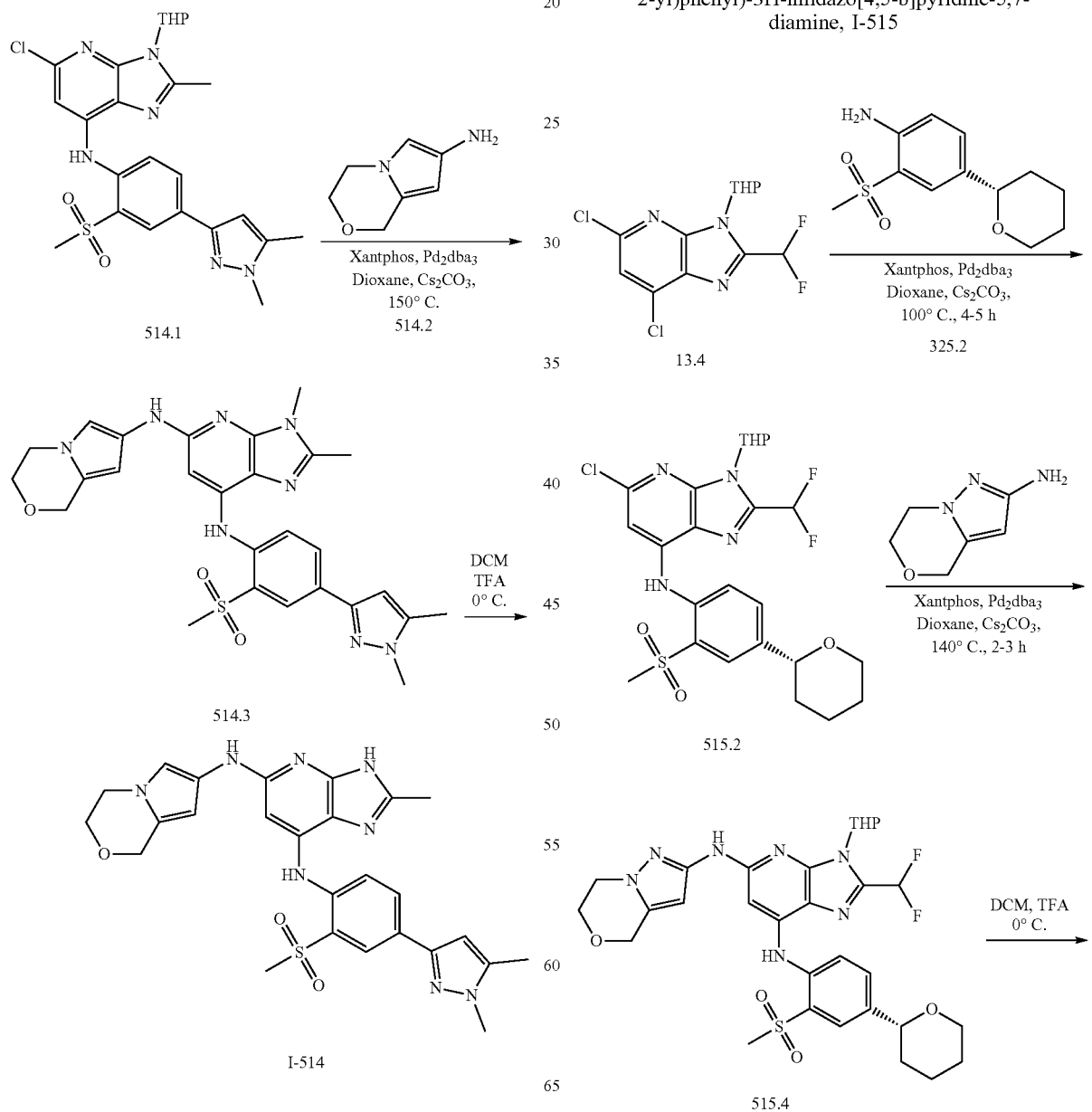

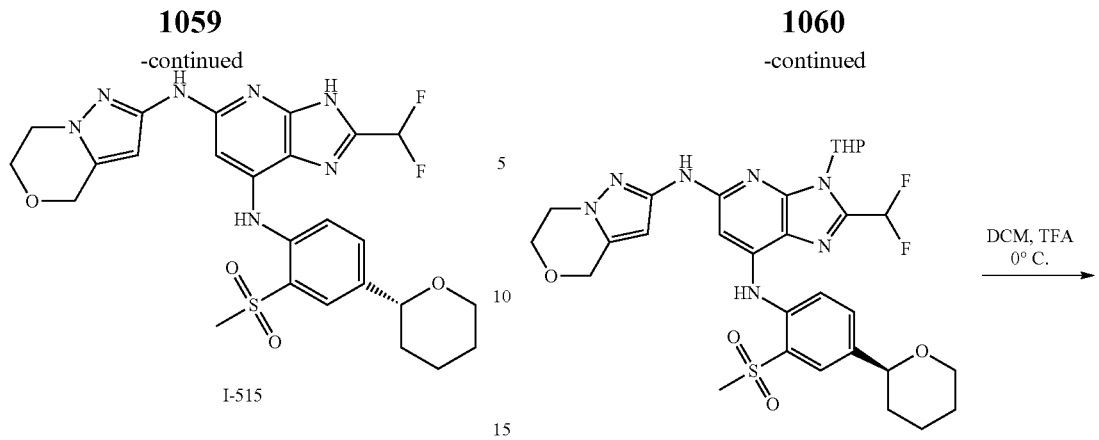

I-515

Synthesis of Compound 515.2.

Compound 515.2 was synthesized from 13.4 and 325.2 using general procedure A. (Yield: 19.97%). MS(ES): m/z 542.01 [M+H]⁺.

Synthesis of Compound 515.4.

Compound 515.4 was synthesized from 515.2 and 6,7-dihydro-4H-pyrazolo[5,1-c][1,4]oxazin-2-amine using general procedure B. (Yield: 42.02%). MS(ES): m/z 644.71 [M+H]⁺.

Synthesis of I-515.

Compound I-515 was synthesized from 515.4 using general procedure C. (Yield: 48.10%). MS(ES): m/z 560.57 [M+H]⁺, LCMS purity: 97.67%, HPLC Purity: 94.05%, 1H NMR (DMSO, 400 MHz): 13.36 (s, 1H), 9.28 (s, 1H), 8.65 (s, 1H), 7.90 (s, 1H), 7.83-781 (d, J=8.4 Hz, 1H), 7.72-7.70 (d, J=2.1 Hz, 1H), 6.33 (s, 1H), 4.71 (s, 2H), 4.07 (s, 2H), 3.96 (s, 2H), 3.62 (s, 1H), 3.21 (s, 3H), 1.92-1.89 (m, 2H), 1.66-1.64 (m, 4H), 1.49-1.41 (m, 2H), 1.25 (s, 2H).

Example 516: Synthesis of (S)-2-(difluoromethyl)-N5-(6,7-dihydro-4H-pyrazolo[5,1-c][1,4]oxazin-2-yl)-N7-(2-(methylsulfonyl)-4-(tetrahydro-2H-pyran-2-yl)phenyl)-3H-imidazo[4,5-b]pyridine-5,7-diamine, I-516

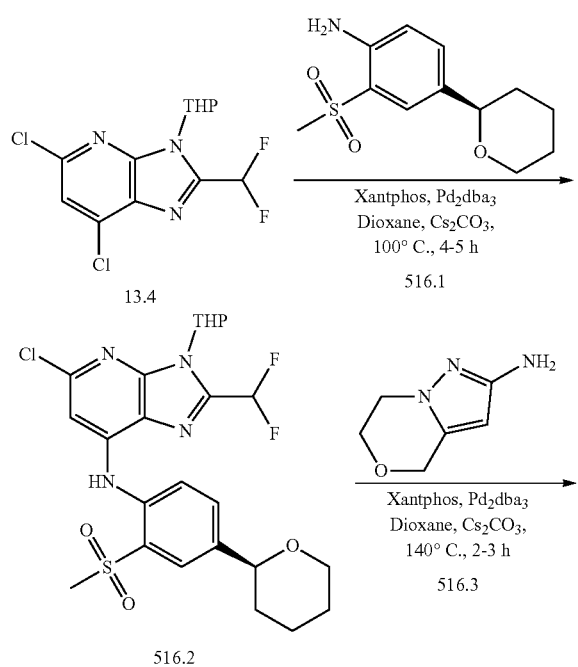

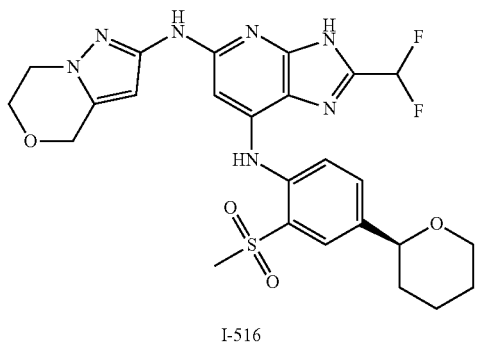

I-516

Synthesis of Compound 516.2.

Compound 516.2 was synthesized from 13.4 and 516.1 using general procedure A. (Yield: 18.50%). MS(ES): m/z 542.01 [M+H]⁺.

Synthesis of Compound 516.4.

Compound 516.4 was synthesized from 516.2 and 516.3 using general procedure B. (Yield: 34.30%). MS(ES): m/z 644.71 [M+H]⁺.

Synthesis of I-516.

Compound I-516 was synthesized from 516.4 using general procedure C. (Yield: 66.14%). MS(ES): m/z 560.62 [M+H]⁺, LCMS purity: 95.79%, HPLC Purity: 96.65%, Chiral HPLC Purity: 99%, 1H NMR (DMSO-d6, 400 MHz): 13.36 (s, 1H), 9.29 (s, 1H), 8.65 (s, 1H), 7.90 (s, 1H), 7.84-7.81 (d, J=8.4 Hz, 1H), 7.73-7.71 (d, J=8.4 Hz, 1H), 7.17-7.12 (d, J=16.8 Hz, 2H), 6.34 (s, 1H), 4.77 (s, 2H), 4.46-4.43 (d, J=11.2 Hz, 1H), 4.06 (s, 3H), 3.98 (s, 2H), 3.21 (s, 3H), 1.92-1.89 (d, J=10.8 Hz, 2H), 1.623 (s, 2H), 1.50-1.41 (m, 2H), 0.89-0.83 (m, 1H).

Example 517/518: Synthesis of (R)-2-(difluoromethyl)-N7-(2-(methylsulfonyl)-4-(tetrahydro-2H-pyran-2-yl)phenyl)-N5-(6-(trifluoromethyl)pyridin-2-yl)-3H-imidazo[4,5-b]pyridine-5,7-diamine, I-517 and (S)-2-(difluoromethyl)-N7-(2-(methylsulfonyl)-4-(tetrahydro-2H-pyran-2-yl)phenyl)-N5-(6-(trifluoromethyl)pyridin-2-yl)-3H-imidazo[4,5-b]pyridine-5,7-diamine, I-518

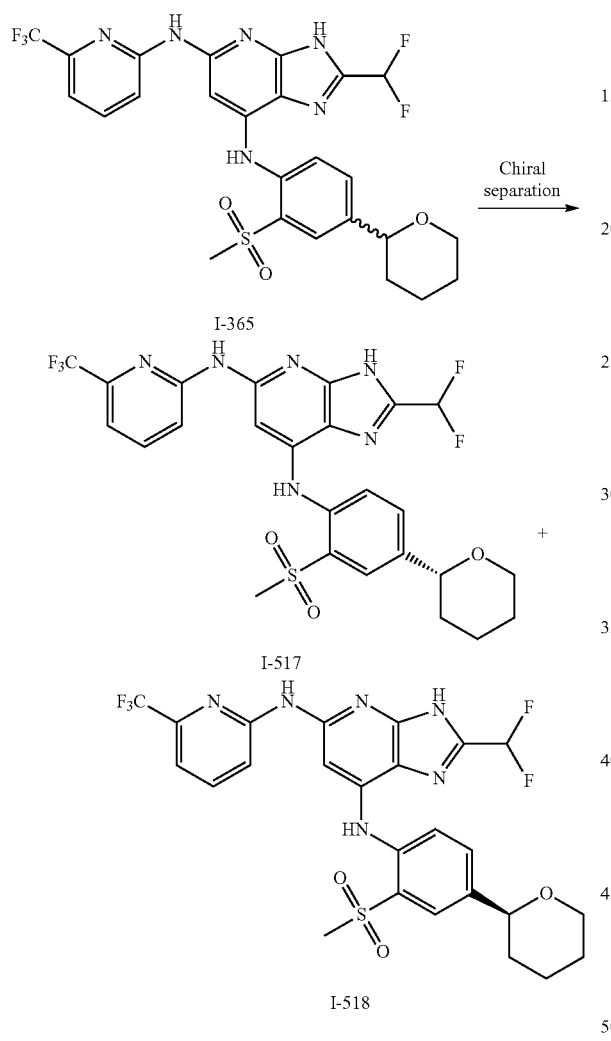

Synthesis of Compound I-517 and I-518.

Isomers of I-365 (0.080 g) were separated out using column (CHIRAL PAK AD-H 250×4.6 mm, 5 μM) 0.1 DEA in IPA as co-solvent with flow rate of 4 mL/min. to get pure fraction-1 (FR-a) and fraction-2 (FR-b). FR-a was concentrated in vacuo at 30° C. to afford pure I-517 (0.020 g). MS(ES): m/z 583.61 [M+H]+, LCMS purity: 100%, HPLC Purity: 98.46%, 1H NMR (DMSO, 400 MHz): 13.64 (s, 1H), 10.15 (s, 1H), 8.81 (s, 1H), 8.25-8.22 (d, J=7.2 Hz, 1H), 7.96-7.92 (m, 2H), 7.84-7.82 (d, J=8.0 Hz, 1H), 7.70-7.68 (d, J=7.6 Hz, 1H), 7.51 (s, 1H), 7.37-7.31 (m, 1H), 4.48-4.45 (d, J=11.2 Hz, 1H), 4.10-4.08 (d, J=10.4 Hz, 1H), 3.59 (s, 1H), 3.22 (s, 3H), 1.92-1.89 (d, J=11.6 Hz, 2H), 1.69 (s, 1H), 1.59 (s, 2H), 1.49-1.44 (s, 2H). FR-b was concentrated in vacuo at 30° C. to afford pure I-518 (0.025 g). MS(ES): m/z 583.61 [M+H]+, LCMS purity: 99.0%, HPLC Purity: 97.0%, 1H NMR (DMSO, 400 MHz): 13.64 (s, 1H), 10.15 (s, 1H), 8.81 (s, 1H), 8.25-8.22 (d, J=8.4 Hz, 1H), 7.96-7.92 (m, 2H), 7.84-7.82 (d, J=8.4 Hz, 1H), 7.70-7.68 (d, J=7.2 Hz, 1H), 7.51 (s, 1H), 7.33-7.31 (d, J=7.2 Hz, 1H), 4.10-4.08 (d, J=11.2 Hz, 1H), 3.60 (s, 1H), 3.22 (s, 3H), 1.92-1.90 (d, J=10.8 Hz, 2H), 1.69 (s, 1H), 1.59 (s, 2H), 1.43 (s, 1H), 1.25 (s, 2H).

Example 519: Synthesis of 2-(difluoromethyl)-N7-(4-(1,5-dimethyl-1H-pyrazol-3-yl)-2-(methylsulfonyl) phenyl)-N5-(2,6-dimethylpyrimidin-4-yl)-3H-imidazo[4,5-b]pyridine-5,7-diamine, I-519

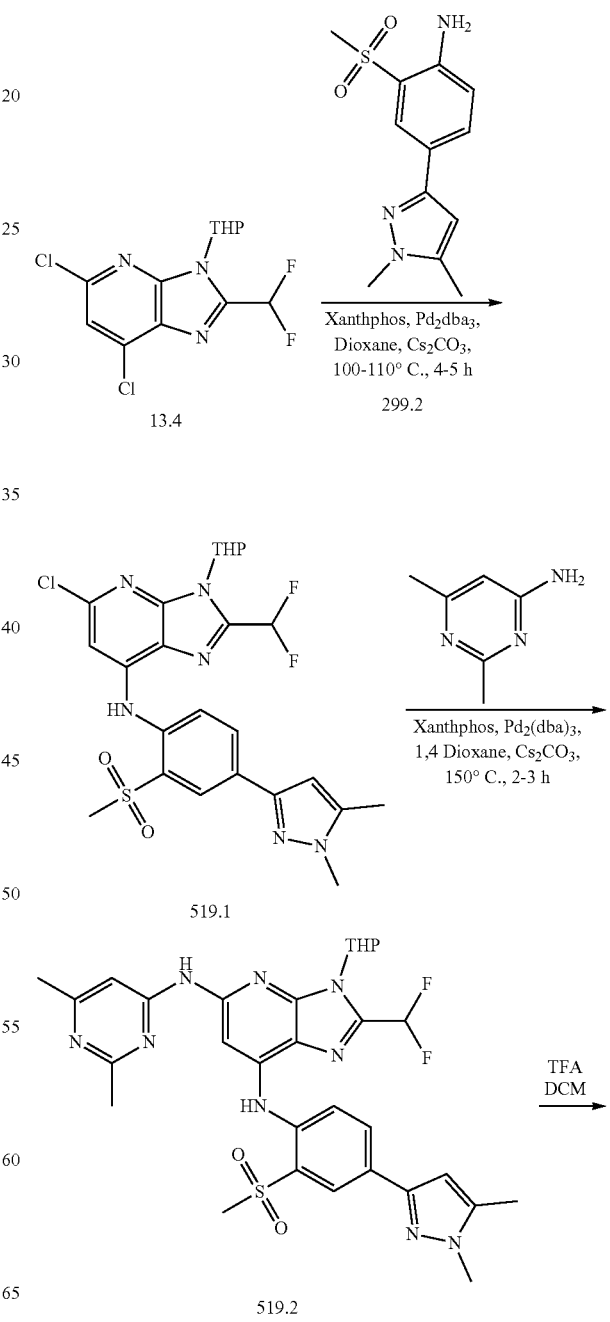

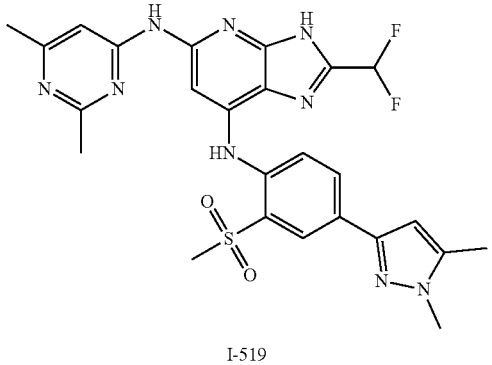

I-519

Synthesis of Compound 519.1.

Compound 519.1 was synthesized from 13.4 and 299.2 using general procedure A. (Yield: 35.08%). MS(ES): m/z 552.01 [M+H]$^+$.

Synthesis of Compound 519.2.

Compound 519.2 was synthesized from 2,6-dimethylpyrimidin-4-amine and 519.1 using general procedure B. (Yield: 48.96%). MS(ES): m/z 638.71 [M+H]$^+$.

Synthesis of I-519.

Compound I-519 was synthesized from 519.2 using general procedure C. (Yield: 59.29%). MS(ES): m/z 554.70 [M+H]$^+$, LCMS purity: 98.02%, HPLC Purity: 96.97%, 1H NMR (DMSO-d6, 400 MHz): 13.74 (s, 1H), 10.41 (s, 1H), 8.91 (s, 1H), 8.32 (s, 1H), 8.11-8.09 (d, J=7.6 Hz, 1H), 7.90-7.88 (d, J=8.4 Hz, 1H), 7.67-7.60 (m, 2H), 7.26 (s, 1H), 6.59 (s, 1H), 3.81 (s, 3H), 3.27 (s, 3H), 2.46 (s, 3H), 2.38 (s, 3H), 2.32 (s, 3H).

Example 536: Synthesis of N-(7-((4-(5,5-dimethyltetrahydro-2H-pyran-2-yl)-2-(methylsulfonyl)phenyl)amino)-2-methyl-3H-imidazo[4,5-b]pyridin-5-yl)cyclopropanecarboxamide, I-536

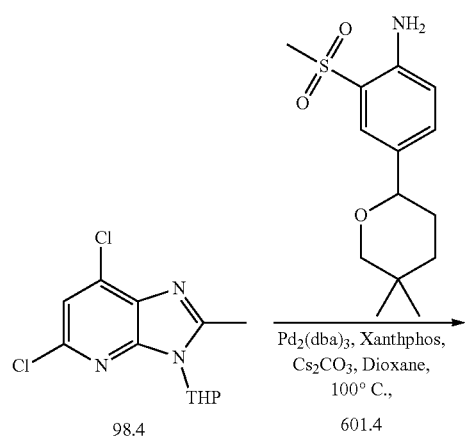

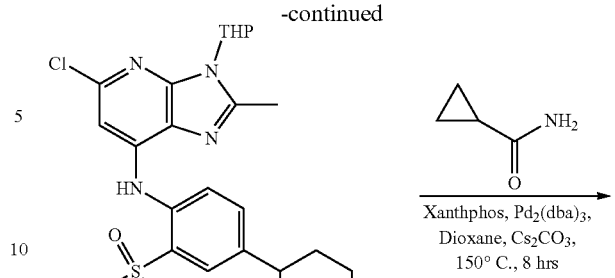

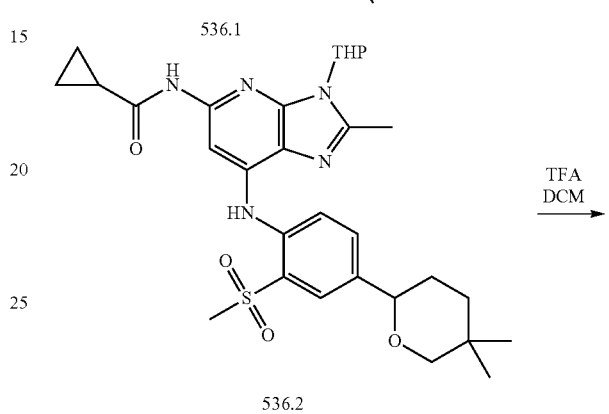

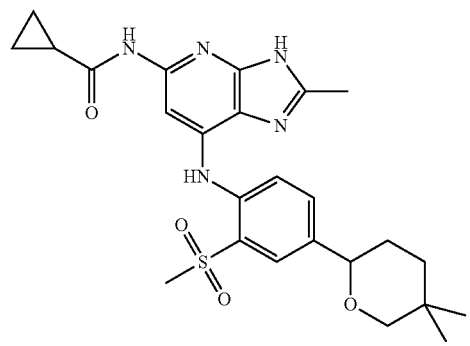

I-536

Synthesis of Compound 536.1.

Compound 536.1 was synthesized from 98.4 and 601.4 using general procedure A (Yield: 35.79%). MS(ES): m/z 534.08 [M+H]$^+$.

Synthesis of Compound 536.2.

Compound 536.2 was synthesized from 536.1 and cyclopropanecarboxamide using general procedure B. (Yield: 68.73%). MS(ES): m/z 582.73 [M+H]$^+$.

Synthesis of I-536.

Compound I-536 was synthesized from 536.2 using general procedure C (Yield: 77.94%). MS(ES): m/z: 498.68 [M+H]$^+$, LCMS purity: 100%, HPLC purity: 98.44%, Chiral HPLC: (51%, 49%), 1H NMR (DMSO, 400 MHz): 12.49 (s, 1H), 10.58 (s, 1H), 8.54 (s, 1H), 7.99 (s, 1H), 7.89 (s, 1H), 7.72-7.70 (d, J=8.4 Hz, 2H), 4.36-4.33 (d, J=10.8 Hz, 1H), 3.58-3.55 (d, J=11.6 Hz, 2H), 3.2 (s, 3H), 2.49 (s, 3H), 2.00 (s, 2H), 1.80 (s, 1H), 1.58 (s, 2H), 1.09 (s, 3H), 0.87 (s, 3H), 0.78-0.76 (m, 4H).

Example 537: Synthesis of N-(7-((4-(1-cyclopropyl-5-methyl-1H-pyrazol-4-yl)-2-(methylsulfonyl)phenyl)amino)-2-(difluoromethyl)-3H-imidazo[4,5-b]pyridin-5-yl)cyclopropanecarboxamide, I-537

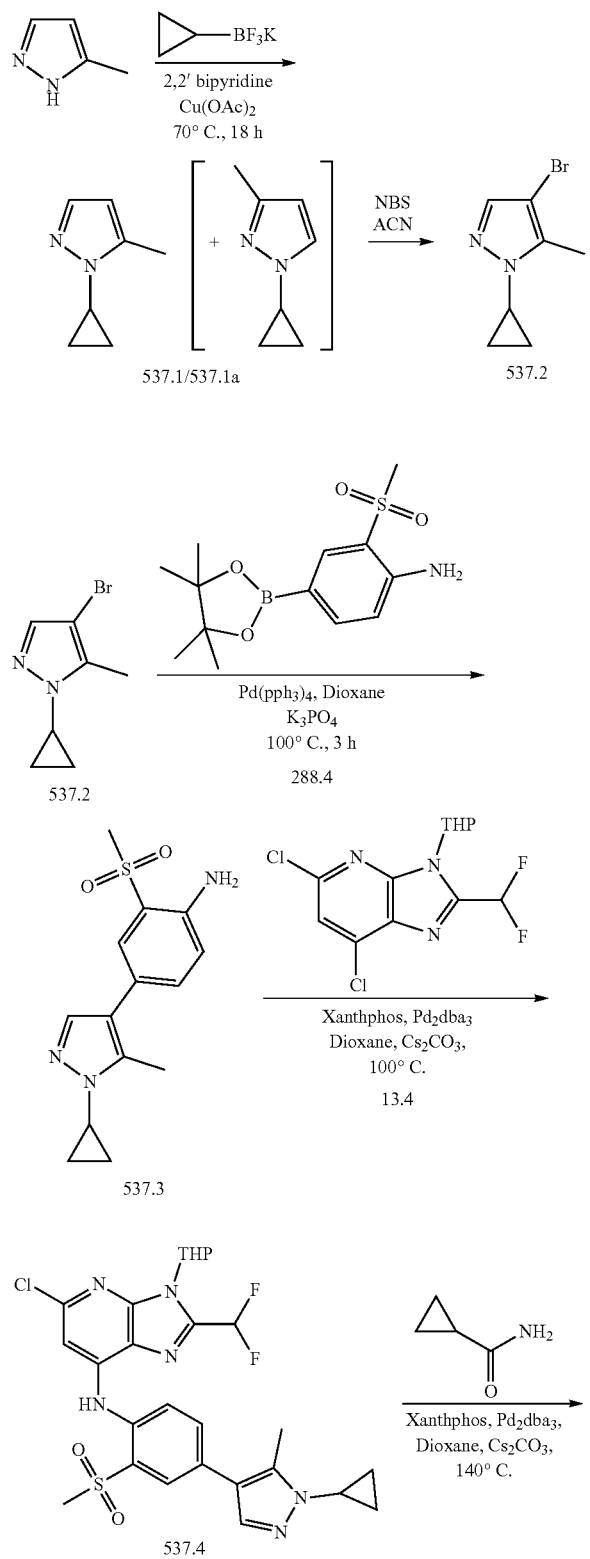

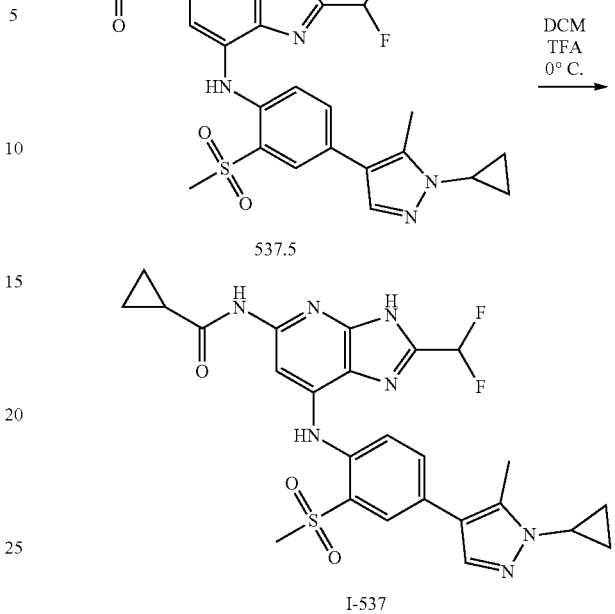

Synthesis of Compound 537.1.

To a solution of 5-methyl-1H-pyrazole 1 (5 g, 60.90 mmol, 1.0 eq) in 2,2-bipyridine (50 mL) was added cyclopropyltrifluoro-14-borane, potassium salt 1.1 (9 g, 60.90 mmol, 1 eq), copper acetate (22 g, 0.121 mmol, 2 eq) at r.t. Reaction mixture heated at 70° C. for 18 hr. Upon completion, reaction mixture was transferred into water and extracted with ethyl acetate. Combined Organic layer dried over $Na_2SO_4$ and concentrated in vacuo to obtain crude product. This was purified by column chromatography and compound was eluted in 10% ethyl acetate in hexane to obtain pure 537.1 (3.2 g, 43.01%). MS(ES): m/z 123.17 [M+H]$^+$.

Synthesis of Compound 537.2.

To a solution of 537.1 (3.2 g, 26.19 mmol, 1.0 eq) in acetonitrile (32 mL) was added N-Bromosuccinimide (5.1 g, 28.85 mmol, 1.1 eq) at 0° C. Reaction mixture stirred at 0° C. for 30 min. Upon completion, reaction mixture was transferred into saturated bicarbonate solution and extracted with ethyl acetate. Combined Organic layer dried over $Na_2SO_4$ and concentrated in vacuo to obtain 537.2 (1.6 g, 30.38%). MS(ES): m/z 202.07 [M+H]$^+$.

Synthesis of Compound 537.3.

Compound 537.3 was synthesized from 537.2 and 288.4 using general method A.

Synthesis of Compound 537.4.

To a solution of 537.3 (1.6 g, 7.96 mmol, 1 eq) in 1,4-dioxane (16 mL) and water (4 mL) was added 13.4 (2.36 g, 7.96 mmol, 1.0 eq), and potassium phosphate (5 g, 23.88 mmol, 3 eq). The reaction mixture was degassed by argon for 30 min. [1,1'-Bisdiphenylphosphinoferrocene]palladium (II)dichloride $CH_2Cl_2$ complex. (1.94 g, 2.38 mmol, 0.03 eq), was added into reaction mixture and again reaction mixture was degassed by argon for 30 min. Further reaction mixture was stirred at 100° C. for 4 h. Upon completion, reaction mixture transferred into water and extracted with ethyl acetate. Organic layers were combined, dried over $Na_2SO_4$ and concentrated in vacuo to obtain crude product.

This was purified by column chromatography and compound was eluted in 20% ethyl acetate in hexane to obtain pure 537.4 (0.200 g, 23.00%). MS(ES): m/z 292.37 [M+H]+.

Synthesis of Compound 537.5.

Compound 537.5 was synthesized from 537.4 and cyclopropanecarboxamide using general procedure B. (Yield: 53.80%). MS(ES): m/z 626.70 [M+H]+.

Synthesis of I-537.

Compound I-537 was synthesized from 537.5 using general procedure C. (Yield: 66.02%). MS(ES): m/z: 542.70 [M+H]+, LCMS purity: 98.48%, HPLC purity: 99.51%, 1H NMR (DMSO, 400 MHz): 13.69 (s, 1H), 10.75 (s, 1H), 8.78 (s, 1H), 7.99 (s, 1H), 7.88 (s, 1H), 7.80 (s, 2H), 7.66 (s, 1H), 7.19 (t, 1H), 3.60-3.57 (m, 1H), 3.26 (s, 3H), 2.50 (s, 3H), 2.06-2.03 (m, 1H), 1.09-1.05 (m, 4H), 0.80-0.79 (m, 4H).

Example 538: Synthesis of N-(2-(difluoromethyl)-7-((4-(1,4-dimethyl-1H-pyrazol-3-yl)-3-fluoro-2-methoxyphenyl)amino)-3H-imidazo[4,5-b]pyridin-5-yl)cyclopropanecarboxamide, I-538

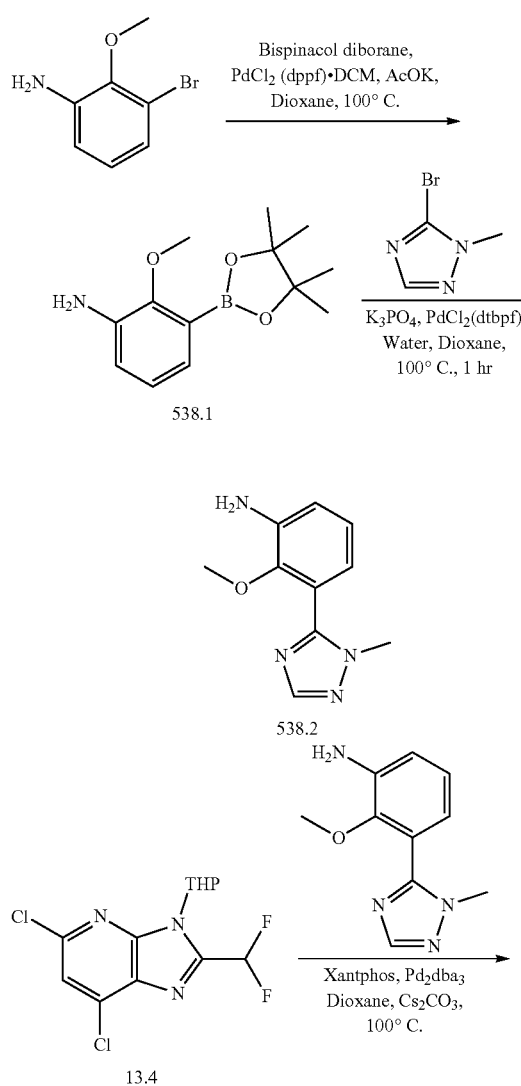

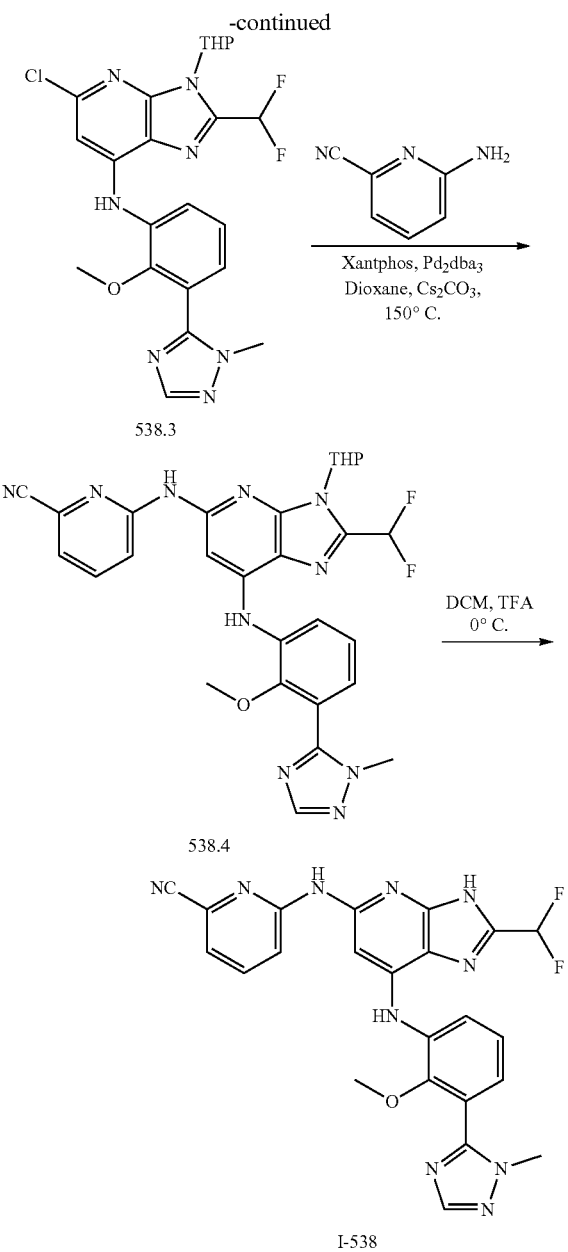

Synthesis of Compound 538.1.

To a solution of 3-bromo-2-methoxyaniline (2 g, 9.90 mmol, 1.0 eq), in 1,4-dioxane (70 mL) was added Bis (pinacolato)diboron (5 g, 19.80 mmol, 2 eq), potassium acetate (2.4 g, 24.75 mmol, 2.5 eq). The reaction mixture was degassed by argon for 30 min. [1,1'-Bis(diphenylphosphino)ferrocene] dichloropalladium(II)CH$_2$Cl$_2$ complex (0.242 g, 2.97 mmol, 0.03 eq) was added into the reaction mixture and again degassed by argon for 20 min. Further reaction mixture was stirred at 100° C. for 5 hr. Upon completion, reaction mixture transferred into water and extracted with ethyl acetate. Organic layers were combined, dried over Na$_2$SO$_4$ and concentrated in vacuo to obtain crude product. This was purified by column chromatography and compound was eluted in 8% ethyl acetate in hexane to obtain pure 538.1 (1.3 g, 52.72%). MS(ES): m/z 250.12 [M+H]+.

1069

Synthesis of Compound 538.2.

To a solution of 5-bromo-1-methyl-1H-1,2,4-triazole 1.2 (1 g, 6.17 mmol, 1.0 eq), in 1,4-dioxane (16 mL) and water (4 mL) was added 538.1 (1.7 g, 6.79 mmol, 1.1 eq), potassium phosphate (2.6 g, 12.34 mmol, 2.0 eq). The reaction mixture was degassed by argon for 30 min. [1,1'-Bis(di-tert-butylphosphino)ferrocene]dichloropalladium(II) (0.602 g, 0.925 mmol, 0.15 eq) was added into the reaction mixture and again degassed by argon for 20 min. Further reaction mixture was stirred at 100° C. for 1 hr. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 40% ethyl acetate in hexane to obtain pure 538.2 (0.400 g, 31.73%). MS(ES): m/z 205.23 [M+H]$^+$.

Synthesis of Compound 538.3.

Compound 538.3 was synthesized from 538.2 and 13.4 using general procedure A (Yield: 39.45%). MS(ES): m/z 490.91 [M+H]$^+$.

Synthesis of Compound 538.4.

Compound 538.4 was synthesized from 538.3 and 6-aminopicolinonitrile using general procedure B. (Yield: 42.78%). MS(ES): m/z 573.58 [M+H]$^+$.

Synthesis of I-538.

Compound I-538 was synthesized from 538.4 using general procedure C (Yield: 58.61%). MS(ES): m/z: 489.50 [M+H]$^+$, LCMS purity: 100%, HPLC purity: 100%, 1H NMR (DMSO, 400 MHz): 13.51 (s, 1H), 10.08 (s, 1H), 8.45 (s, 1H), 8.25-8.23 (d, J=8.8 Hz, 1H), 8.10 (s, 1H), 7.89-7.85 (t, J=7.6 Hz, 1H), 7.72-7.70 (d, J=8.0 Hz, 1H), 7.46-7.28 (m, 4H), 7.12 (t, 1H), 3.77 (s, 3H), 3.44 (s, 3H).

Example 539: Synthesis of 6-((7-((2-methoxy-3-(1-methyl-1H-1,2,4-triazol-5-yl)phenyl)amino)-2-methyl-3H-imidazo[4,5-b]pyridin-5-yl)amino)picolinonitrile, I-539

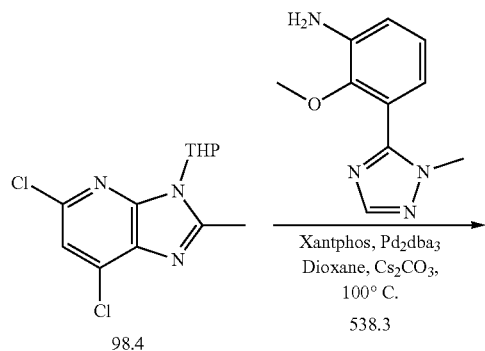

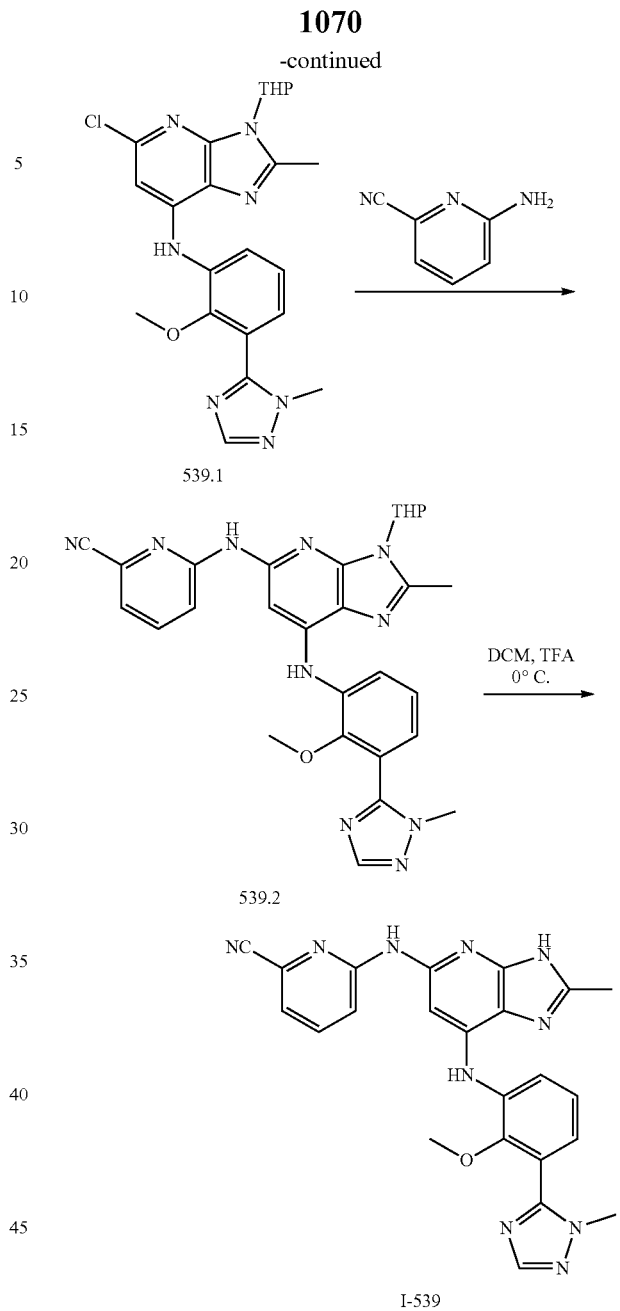

Synthesis of Compound 539.1.

Compound 539.1 was synthesized from 98.4 and 538.3 using general procedure A (Yield: 39.40%). MS(ES): m/z 454.93 [M+H]$^+$.

Synthesis of Compound 539.2.

Compound 539.2 was synthesized from 539.1 and 6-aminopicolinonitrile using general procedure B. (Yield: 53.58%). MS(ES): m/z 573.60 [M+H]$^+$.

Synthesis of I-539.

Compound I-539 was synthesized from 539.2 using general procedure C. (Yield: 54.61%). MS(ES): m/z: 453.50 [M+H]$^+$, LCMS purity: 97.91%, HPLC purity: 95.60%, 1H NMR (DMSO, 400 MHz): 12.40 (s, 1H), 9.93 (s, 1H), 8.08 (s, 2H), 7.85-7.77 (m, 2H), 7.42-7.31 (m, 4H), 7.22-7.20 (d, J=6.0 Hz, 1H), 3.77 (s, 3H), 3.46 (s, 3H), 2.51 (s, 3H).

Example 540: Synthesis of 6-((7-((2-methoxy-3-(2-methyl-2H-1,2,3-triazol-4-yl)phenyl)amino)-2-methyl-3H-imidazo[4,5-b]pyridin-5-yl)amino)picolinonitrile, I-540

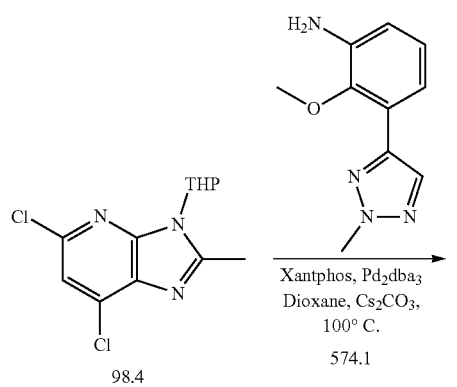

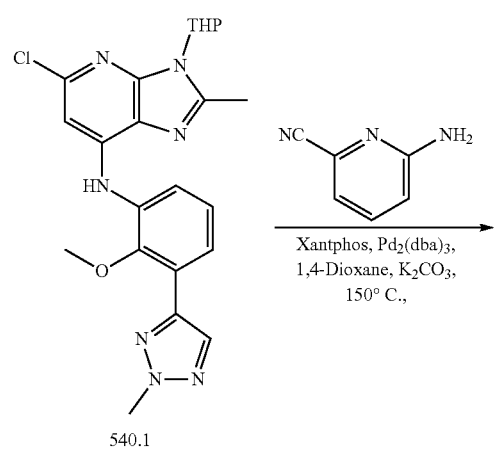

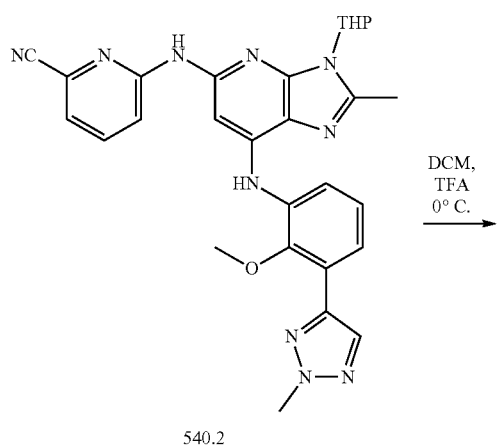

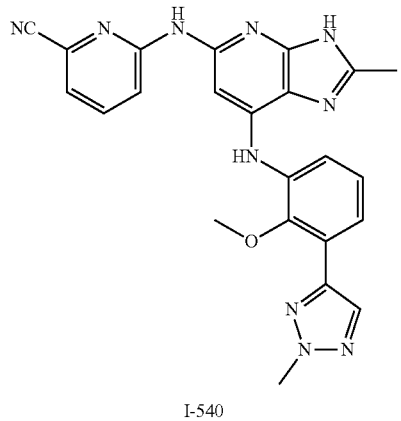

I-540

Synthesis of Compound 540.1.

Compound 540.1 was synthesized from 98.1 and 574.1 using general procedure A. (Yield: 34.67%). MS (ES): m/z 454.93 [M+H]+

Synthesis of Compound 540.2.

Compound 540.2 was synthesized from 540.1 and 6-aminopicolinonitrile using general procedure A. (Yield: 46.14%). MS (ES): m/z 537.60 [M+H]+.

Synthesis of compound I-540.

Compound I-540 was synthesized from 540.2 using general procedure C. (Yield: 55.34%). MS(ES): m/z 453.48 [M+H]+. LCMS purity: 99.59%, HPLC purity: 97.57%, 1H NMR (DMSO-d6, 400 MHz): 12.42 (s, 1H), 9.91 (s, 1H), 8.13 (s, 1H), 8.11 (s, 1H), 7.99 (s, 1H), 7.83-7.79 (t, 1H), 7.62-7.58 (t, 2H), 7.41-7.39 (d, 1H), 7.33-7.29 (t, 1H), 7.25 (s, 1H), 4.24 (s, 3H), 3.65 (s, 3H), 2.50 (s, 3H).

Example 541: Synthesis of 6-((2-(difluoromethyl)-7-((3-(1,3-dimethyl-1H-1,2,4-triazol-5-yl)-2-methoxyphenyl)amino)-3H-imidazo[4,5-b]pyridin-5-yl)amino)picolinonitrile, I-541

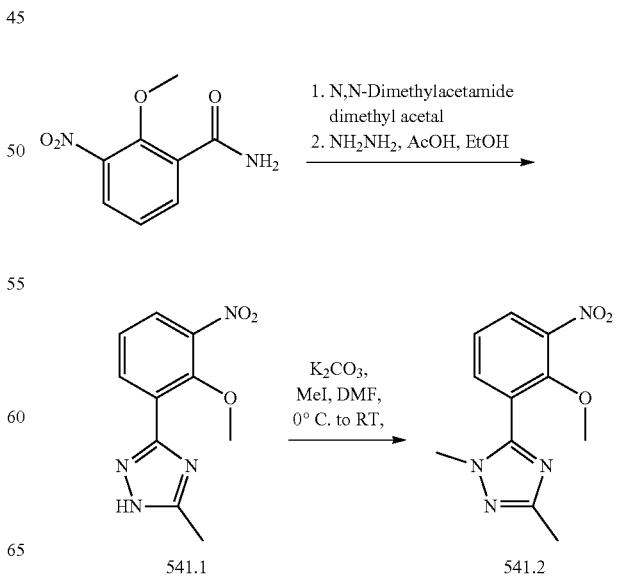

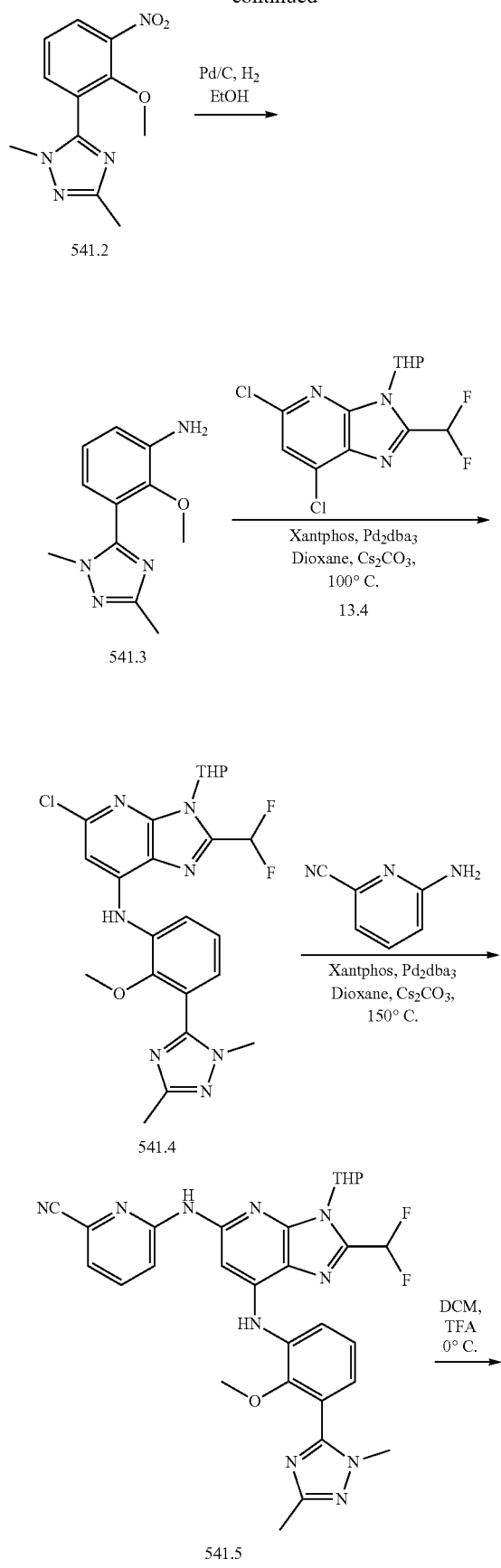

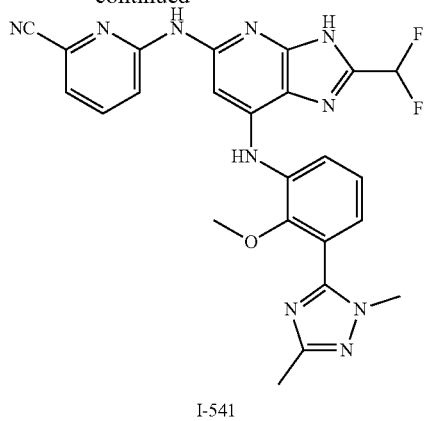

I-541

Synthesis of Compound 541.1.

A solution of 2-methoxy-3-nitrobenzamide 1 (7 g, 35.68 mmol, 1 eq) in DMAc dimethyl acetal (50 mL) was heated at 95° C. to obtain clear solution. Reaction mixture was concentrated under reduce pressure. To the residue ethanol (140 mL) was added at 0° C. followed by addition of acetic acid (40 mL) and hydrazine hydride (17.8 gm, 0.357 mmol, 10 eq). Reaction mixture was stirred at r.t. for 4 h. Upon completion, reaction mixture was transferred into water to obtain solid precipitate, which was filtered, washed with water and dried well to obtain 541.1. (5 g, 59.82%). MS(ES): m/z 235.22 [M+H]$^+$.

Synthesis of Compound 541.2.

To a solution of 541.1 (5 g, 21.35 mmol, 1 eq) in Dimethylformamide (30 mL) was added potassium carbonate (8.8 g, 63.82 mmol, 3 eq) at 0° C. Then methyl Iodide (3.94 g, 27.77 mmol, 1.3 eq) in Dimethylformamide (10 mL) was added into the reaction mixture at 0° C. Further reaction mixture was stirred at r.t. for 14 h. Upon completion, reaction mixture transferred into water and extracted with ethyl acetate. Organic layers were combined, dried over Na$_2$SO$_4$ and concentrated in vacuo to obtain crude product. This was purified by column chromatography and compound was eluted in 30% ethyl acetate in hexane to obtain pure 541.2 (0.620 g, 11.70%). MS(ES): m/z 249.24 [M+H]$^+$.

Synthesis of Compound 541.3.

To a solution of 541.2 (0.620 g, 2.50 mmol, 1.0 eq) in ethanol (25 mL), 10% Pd/C (0.200 g) was added. Hydrogen was purged through reaction mixture for 2-3 h at r.t. Upon completion, reaction mixture was filtered through celite-bed and washed with ethanol. Filtrate was concentrated in vacuo to obtain 541.3 (0.520 g, 95.39%). MS(ES): m/z 219.26 [M+H]$^+$.

Synthesis of Compound 541.4.

Compound 541.4 was synthesized from 541.3 and 13.4 using general procedure A. (Yield: 29.50%). MS (ES): m/z 504.94 [M+H]$^+$.

Synthesis of Compound 541.5.

Compound was synthesized from 541.4 and 6-aminopicolinonitrile using general procedure B. (Yield: 50.11%). MS (ES): m/z 587.61 [M+H]$^+$.

Synthesis of compound I-541. Compound I-541 was synthesized from 541.5 using general procedure C: 98.69%, 1H NMR (DMSO-d6, 400 MHz): 13.50 (s, 1H), 10.08 (s, 1H), 8.44 (s, 1H), 8.24-8.22 (d, J=8.0 Hz, 1H), 7.88-7.84 (t, J=16.0 Hz, 1H), 7.70-7.68 (d, J=8.0 Hz, 1H), 7.46-7.44 (d, J=8.0 Hz, 1H), 7.38-7.32 (m, 2H), 7.28-7.26 (d, J=8.0 Hz, 1H), 7.12 (t, 1H), 3.68 (s, 3H), 3.44 (s, 3H), 2.30 (s, 3H).

Example 542: Synthesis of 6-((7-((3-(1,3-dimethyl-1H-1,2,4-triazol-5-yl)-2-methoxyphenyl)amino)-2-methyl-3H-imidazo[4,5-b]pyridin-5-yl)amino)picolinonitrile, I-542

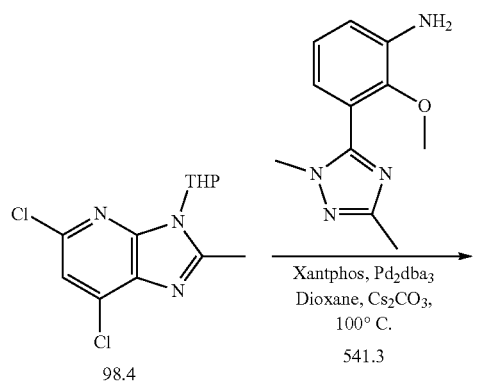

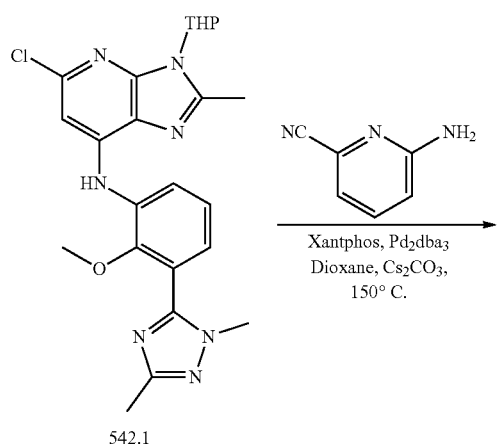

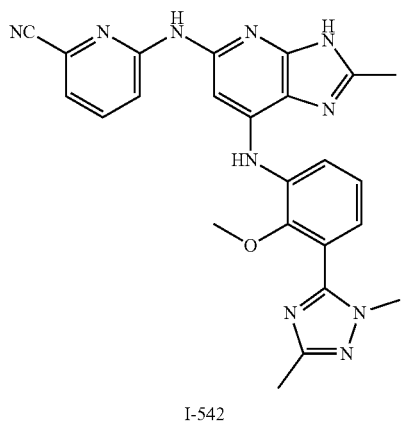

Synthesis of Compound 542.1.

Compound 542.1 was synthesized from 541.3 and 98.4 using general procedure A. (Yield: 23.52%). MS (ES): m/z 468.96 [M+H]$^+$.

Synthesis of Compound 542.2.

Compound 542.2 was synthesized from 542.2 and 6-aminopicolinonitrile using general procedure B. (Yield: 50.99%). MS (ES): m/z 551.63 [M+H]$^+$.

Synthesis of compound I-542. Compound I-542 was synthesized from 542.2 using general procedure C. (Yield: 59.03%). [M+H]$^+$ MS(ES): m/z: 467.67 [M+H]$^+$, LCMS purity: 100%, HPLC purity: 98.61%, 1H NMR (DMSO-d6, 400 MHz): 13.78 (s, 1H), 9.95 (s, 1H), 9.88 (s, 1H), 8.11-8.09 (d, J=8.0 Hz, 1H), 8.01 (s, 1H), 7.83-7.74 (m, 2H), 7.40-7.29 (m, 2H), 7.17-7.15 (d, J=8.0 Hz, 1H), 3.68 (s, 3H), 3.46 (s, 3H), 2.45 (s, 3H), 2.30 (s, 3H).

Example 543: Synthesis of 6-((7-((2-methoxy-3-(4-methylthiazol-2-yl)phenyl)amino)-2-methyl-3H-imidazo[4,5-b]pyridin-5-yl)amino)picolinonitrile, I-543

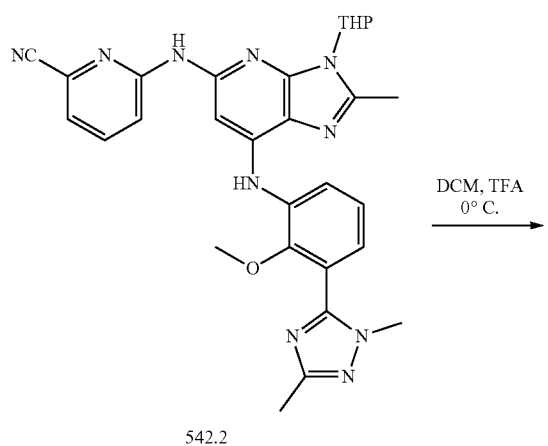

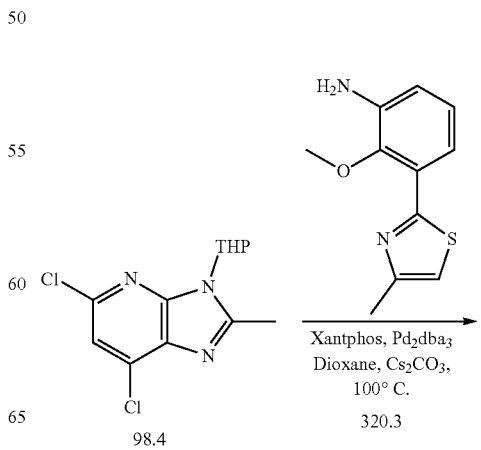

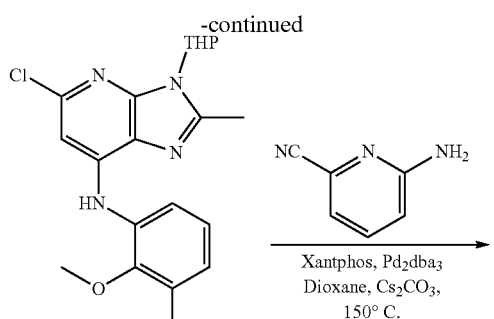

543.1

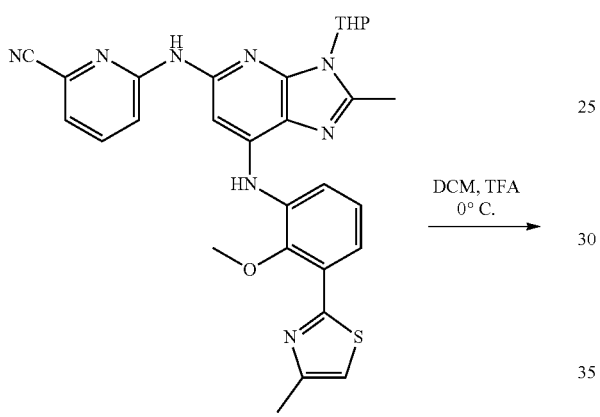

543.2

I-543

Synthesis of Compound 543.1.

Compound 543.1 was synthesized from 98.4 and 320.3 using general procedure A. (Yield: 22.98%). MS(ES): m/z 470.99 [M+H]+.

Synthesis of Compound 543.2.

Compound 543.2 was synthesized from 543.1 and 6-aminopicolinonitrile using general procedure B. (Yield: 68.03%). MS(ES): m/z 553.66 [M+H]+.

Synthesis of I-543.

Compound I-543 was synthesized from 543.2 using general procedure C. (Yield: 66.35%). MS(ES): m/z: 469.57 [M+H]+, LCMS purity: 100%, HPLC purity: 98.72%, 1H NMR (DMSO, 400 MHz): 12.40 (s, 1H), 9.88 (s, 1H), 8.20-8.15 (t, J=8.8 Hz, 2H), 8.01-7.99 (d, J=7.6 Hz, 1H), 7.84-7.80 (t, J=7.6 Hz, 1H), 7.59-7.58 (d, J=7.2 Hz, 1H), 7.40 (s, 2H), 7.35-7.31 (t, J=7.6 Hz, 1H), 7.03 (s, 1H), 3.78 (s, 3H), 2.50 (s, 3H), 2.48 (s, 3H).

Example 544: Synthesis of 6-((2-methyl-7-((2-(methylsulfonyl)-4-(tetrahydrofuran-2-yl)phenyl)amino)-3H-imidazo[4,5-b]pyridin-5-yl)amino)picolinonitrile, I-544

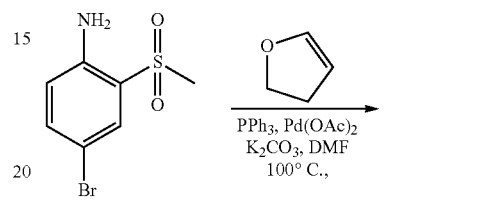

288.3

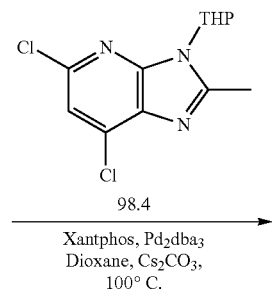

544.1

544.2

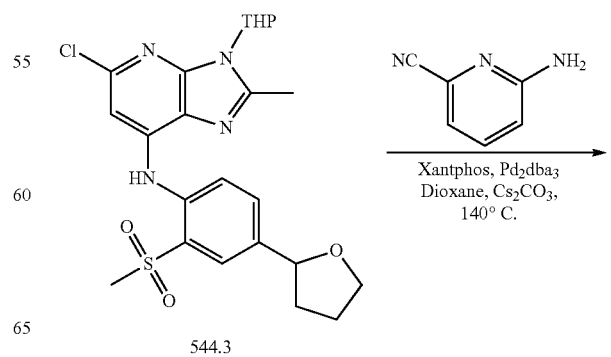

544.3

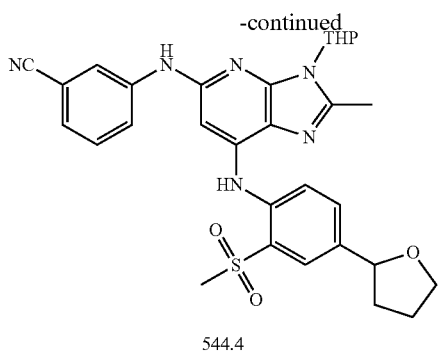

544.4

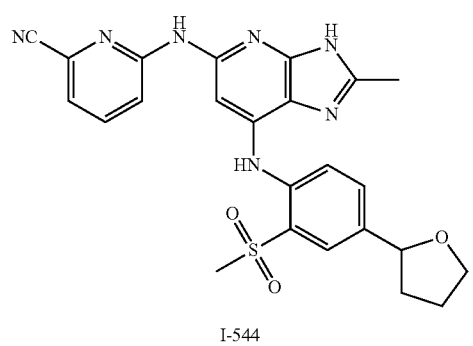 [SMILES: Cc1nc2c(Nc3ccc(C4CCCO4)cc3S(C)(=O)=O)cc(Nc3cccc(C#N)n3)nc2[nH]1]

I-544

Synthesis of Compound 544.1.

To a solution of 288.3 (10 g, 45.85 mmol, 1 eq) in Dimethylformamide (100 mL) was added 2,3-dihydrofuran 1.1 (16 g, 229.24 mmol, 5 eq), potassium carbonate (19 g, 137.61 mmol, 3 eq), and triphenylphosphine (2.4 g, 9.17 mmol, 0.2 eq). The reaction mixture was degassed by argon for 30 min. Palladium(II) acetate (1 g, 4.58 mmol, 0.1 eq), was added into reaction mixture and again reaction mixture was degassed by argon for 30 min. Further reaction mixture was stirred at 100° C. for 15 h. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 544.1 (5.5 g, 50.13%). MS(ES): m/z 240.29 $[M+H]^+$.

Synthesis of Compound 544.2.

To a solution of 544.1 (5 g, 20.90 mmol, 1.0 eq) in MeOH (90 mL), 10% Pd/C (0.400 g), Triethylamine (6.3 g, 62.76 mmol, 3 eq) was added. Hydrogen was purged through reaction mixture for 2-3 h at r.t. Upon completion, reaction mixture was filtered through celite-bed and washed with ethanol. Filtrate was concentrated in vacuo to obtain 544.2 (3 g, 59.50%). MS(ES): m/z 242.31 $[M+H]^+$.

Synthesis of Compound 544.3.

Compound 544.3 was synthesized from 544.2 and 98.4 using general procedure A. (Yield: 40.80%). MS (ES): m/z 492.00 $[M+H]^+$.

Synthesis of Compound 544.4.

Compound 544.4 was synthesized from 544.3 and 6-aminopicolinonitrile using general procedure B. (Yield: 39.13%). MS (ES): m/z 574.67 $[M+H]^+$.

Synthesis of Compound I-544.

Compound was synthesized using from 544.4 general procedure C. (Yield: 80.56%). MS(ES): m/z: 490.45 $[M+H]^+$, LCMS purity: 100%, HPLC purity: 98.48%, Chiral HPLC Purity: 49.52% and 50.54%, 1H NMR (DMSO-d6, 400 MHz): 12.52 (s, 1H), 9.95 (s, 1H), 8.64 (s, 1H), 7.99-7.97 (d, J=8.2 Hz, 1H), 7.92-7.90 (d, J=8.4 Hz, 1H), 7.86-7.82 (m, 2H), 7.75-7.75 (m, 1H), 7.54 (s, 1H), 7.42-7.40 (d, J=8.8 Hz, 1H), 4.92-4.88 (t, 1H), 4.05-4.00 (m, 1H), 3.88-3.82 (m, 1H), 3.21 (s, 3H), 2.47 (s, 3H), 2.38 (m, 1H), 2.02-1.95 (m, 2H), 1.79-1.75 (m, 1H).

Example 545: Synthesis of N-(2-(difluoromethyl)-7-((2-(methylsulfonyl)-4-(2-methylthiazol-4-yl)phenyl)amino)-3H-imidazo[4,5-b]pyridin-5-yl)cyclopropanecarboxamide, I-545

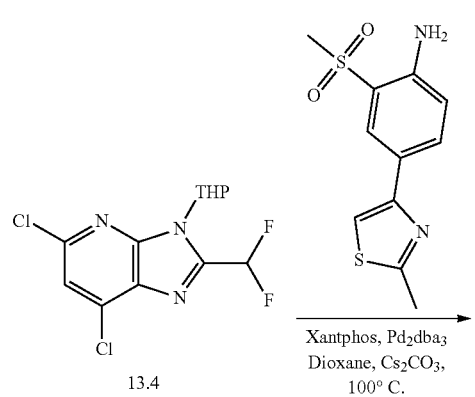

545.1

545.2

-continued

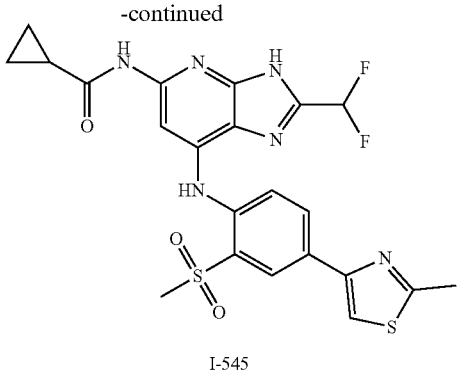

I-545

Synthesis of Compound 545.1.
Compound 545.1 was synthesized from 545.1a and 13.4 using general procedure A. (Yield: 29.06%). MS (ES): m/z 555.10 [M+H]⁺.

Synthesis of Compound 545.2.
Compound 545.2 was synthesized from 545.1 and cyclopropanecarboxamide using general procedure B. (Yield: 61.29%). MS (ES): m/z 603.6 [M+H]⁺.

Synthesis of Compound I-545.
Compound I-545 was synthesized from 545.2 using general procedure C. (Yield: 72.64%). MS(ES): m/z 519.6 [M+H]⁺, LCMS purity: 98.29%, HPLC purity: 98.46%, 1H NMR (DMSO-d6, 400 MHz): 13.70 (s, 1H), 10.78 (s, 1H), 8.87 (s, 1H), 8.50 (s, 1H), 8.31-8.29 (d, J=8.4 Hz, 1H), 8.15-8.12 (d, J=8.0 Hz, 2H), 7.86-7.84 (d, J=8.0 Hz, 1H), 7.26 (t, 1H), 3.26 (s, 3H), 2.75 (s, 3H), 2.09 (s, 1H), 0.80 (s, 4H).

Example 546: Synthesis of 2-(difluoromethyl)-N5-(6-ethynylpyridin-2-yl)-N7-(2-(methylsulfonyl)phenyl)-3H-imidazo[4,5-b]pyridine-5,7-diamine, I-546

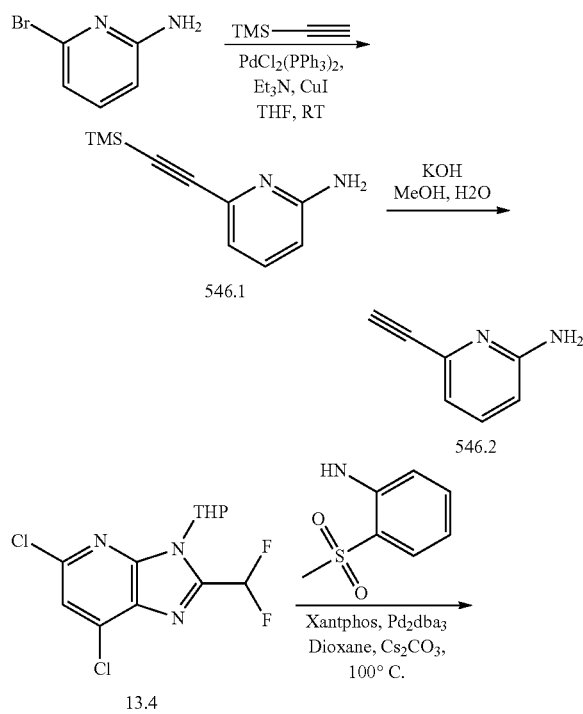

-continued

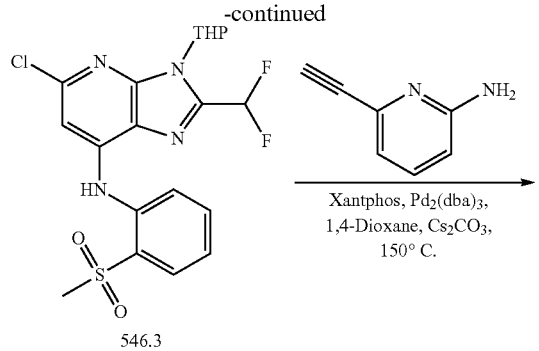

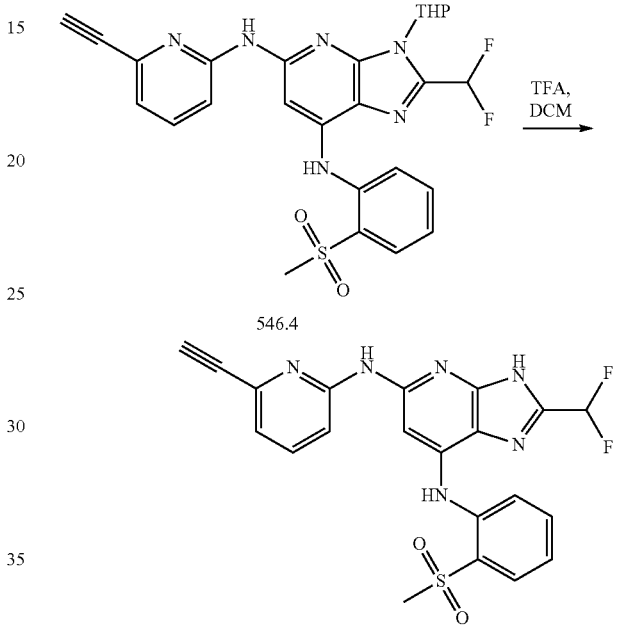

I-546

Synthesis of Compound 546.1.
To a solution of 6-bromopyridin-2-amine (10 g, 57.80 mmol, 1 eq) in Tetrahydrofuran (50 mL), was added Bis(triphenylphosphine)palladium chloride (1.2 g, 1.73 mmol, 0.03 eq), Copper iodide (0.550 g, 2.89 mmol, 0.05 eq) at r.t. Reaction mixture was purged with Argon for 30-40 min. Triethyl amine (20 mL) was added dropwise into the reaction mixture at 0° C. After 5 min, ethynyltrimethylsilane (6.75 g, 68.72 mmol, 1.18 eq) was added dropwise into the reaction mixture at 0° C. Reaction mixture stirred at r.t. for 16 hr. Upon completion, reaction mixture was filtered through Alumina-bed and washed with tetrahydrofuran. Filtrate was concentrated in vacuo to obtain crude product. This was purified by column chromatography and compound was eluted in 5% MeOH in CH₂Cl₂ to obtain pure 546.1 (10 g, 90.91%). MS(ES): m/z 191.32 [M+H]⁺.

Synthesis of Compound 546.2.
To a solution of 546.1 (2.2 g, 11.56 mmol, 1 eq) in 20% potassium hydroxide in MeOH (230 mL) was added water (500 mL). Further reaction mixture was stirred at r.t. for 4 hr. Upon completion, reaction mixture transferred into water and extracted with ethyl acetate. Organic layers were combined, dried over Na₂SO₄ and concentrated in vacuo to obtain crude product. This was purified by trituration with pentane to obtain pure 546.2 (1 g, 73.33%). MS(ES): m/z 119.14 [M+H]⁺.

Synthesis of Compound 546.3.

Compound 546.3 was synthesized from 546.2 and 2-(methylsulfonyl)aniline using general procedure A. (Yield: 11.99%). MS (ES): m/z 457.89 [M+H]+.

Synthesis of Compound 546.4.

Compound 546.4 was synthesized from 546.3 and 546.2 using general procedure B. (Yield 31.81%). MS (ES): m/z 539.57 [M+H]+.

Synthesis of Compound I-546.

Compound I-546 was synthesized from 546.4 using general procedure C. (Yield: 67.16%). MS(ES): m/z: 455.61 [M+H]+, LCMS purity: 100%, HPLC purity: 100%, 1H NMR (DMSO-d6, 400 MHz): 13.67 (s, 1H), 10.03 (s, 1H), 8.95 (s, 1H), 7.97-7.95 (d, J=8.0 Hz, 1H), 7.92-7.90 (m, 1H), 7.85-7.81 (m, 2H), 7.73-7.69 (t, J=12.4 Hz, 1H), 7.50 (s, 1H), 7.38 (s, 1H), 7.24 (s, 1H), 7.11-7.08 (t, 1H), 4.34 (s, 1H), 3.23 (s, 3H).

Example 547: Synthesis of N5-(6-ethynylpyridin-2-yl)-2-methyl-N7-(2-(methylsulfonyl)phenyl)-3H-imidazo[4,5-b]pyridine-5,7-diamine, I-547

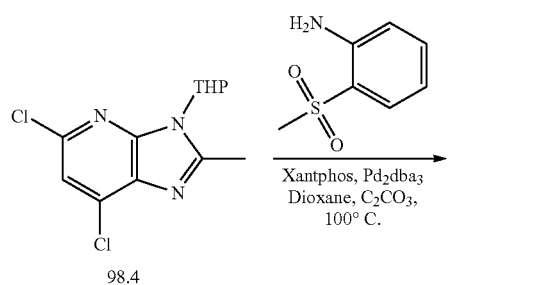

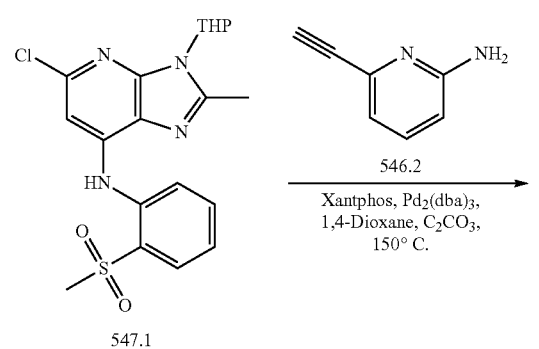

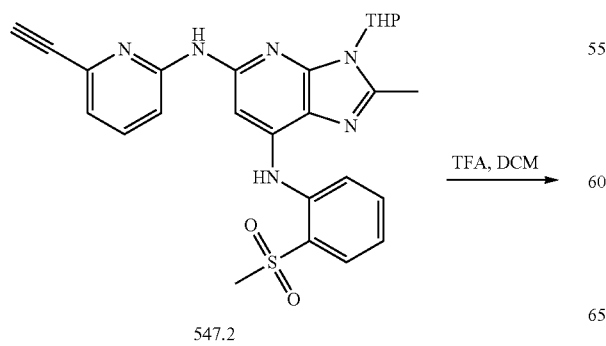

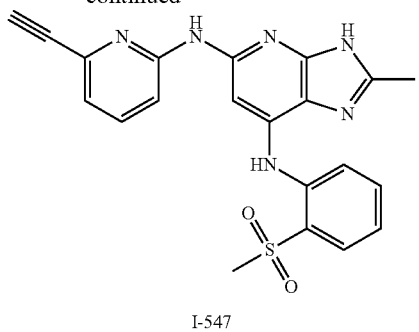

I-547

Synthesis of Compound 547.1.

Compound 547.1 was synthesized from 98.4 and 2-(methylsulfonyl)aniline using general procedure A. (Yield: 23.79%). MS (ES): m/z 421.91 [M+H]+.

Synthesis of Compound 547.2.

Compound 547.2 was synthesized from 547.1 and 546.2 using general procedure B to obtain 1.4. (Yield: 31.11%). MS (ES): m/z 503.59 [M+H]+.

Synthesis of Compound I-547.

Compound I-547 was synthesized 547.2 using general procedure C. (Yield: 64.67%). MS(ES): m/z: 419.62 [M+H]+, LCMS purity: 99.12%, HPLC purity: 98.60%, 1H NMR (DMSO-d6, 400 MHz): 12.42 (s, 1H), 10.13 (s, 1H), 8.01-7.99 (d, J=8.0 Hz, 1H), 7.85-7.82 (m, 1H), 7.77-7.75 (m, 2H), 7.73-7.69 (m, 1H), 7.63 (s, 1H), 7.48 (s, 1H), 7.10 (s, 1H), 4.33 (s, 1H), 3.22 (s, 3H), 2.63 (s, 3H), 1.11-1.07 (m, 1H).

Example 548/549 Synthesis of (S)—N-(7-((2-(N,S-dimethylsulfonimidoyl)phenyl)amino)-2-methyl-3H-imidazo[4,5-b]pyridin-5-yl)cyclopropanecarboxamide, I-548 and N-(7-((2-(N,S-dimethylsulfonimidoyl)phenyl)amino)-2-methyl-3H-imidazo[4,5-b]pyridin-5-yl)cyclopropanecarboxamide, I-549

1085

-continued

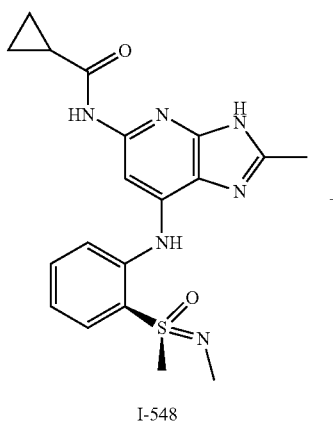

I-548

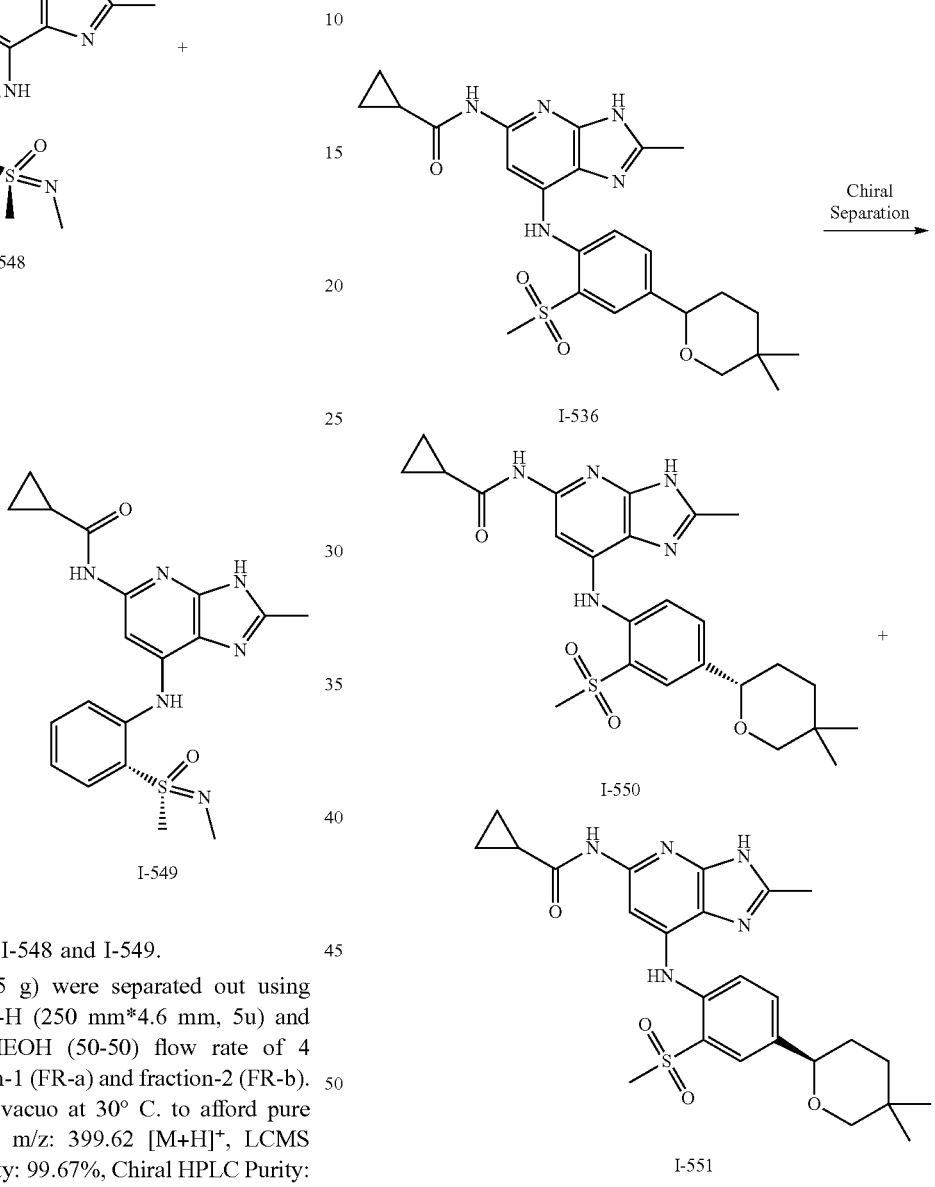

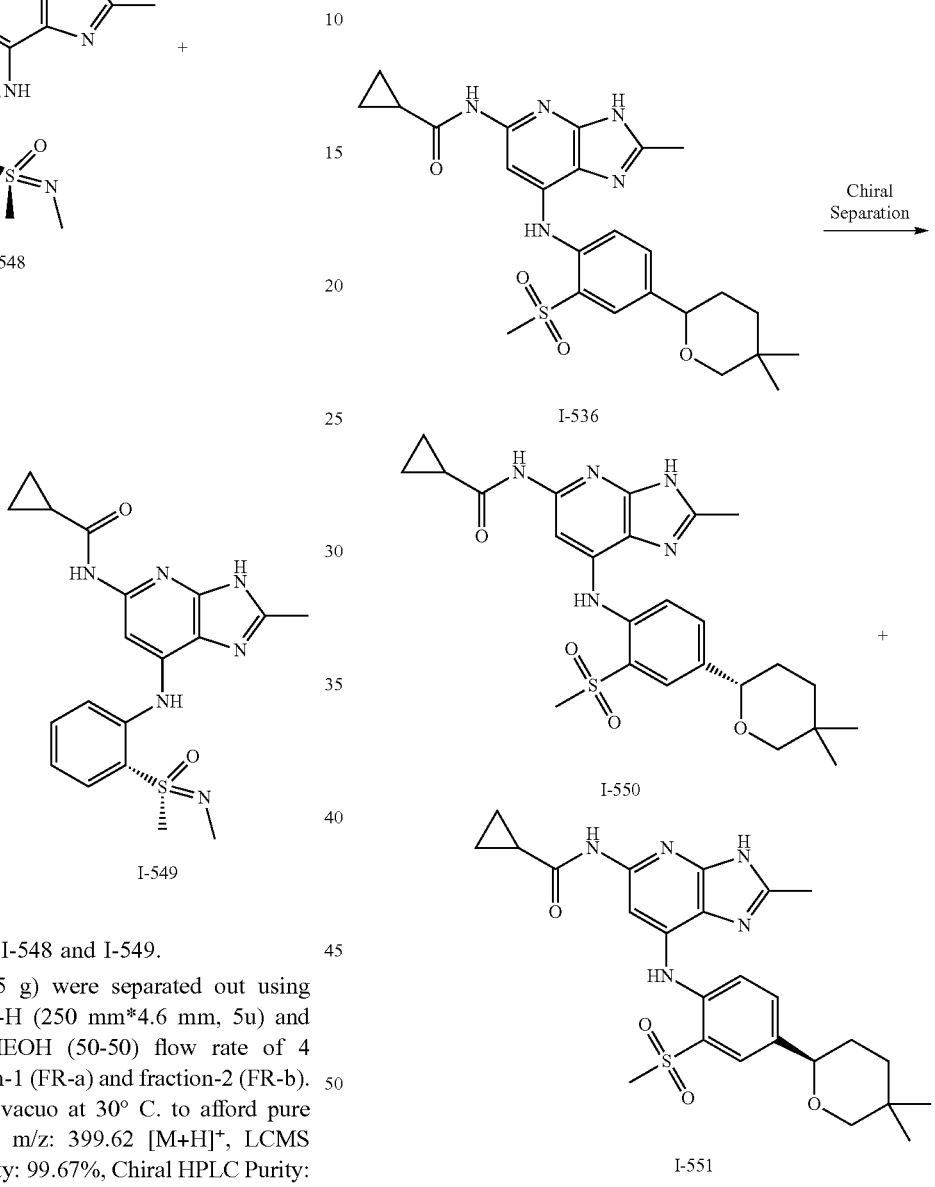

I-549

Synthesis of Compound I-548 and I-549.

Isomers of I-328 (0.105 g) were separated out using column CHIRALPAK AD-H (250 mm*4.6 mm, 5u) and 0.1% D EA_HEX_IPA-MEOH (50-50) flow rate of 4 mL/min. to get pure fraction-1 (FR-a) and fraction-2 (FR-b). FR-a was concentrated in vacuo at 30° C. to afford pure I-548 (0.025 g). MS(ES): m/z: 399.62 [M+H]$^+$, LCMS purity: 98.93%, HPLC purity: 99.67%, Chiral HPLC Purity: 99.51%, 1H NMR (DMSO-d6, 400 MHz): 12.45 (s, 1H), 10.56 (s, 1H), 9.67 (s, 1H), 8.06 (s, 1H), 7.87-7.85 (d, J=8.4 Hz, 1H), 7.76-7.74 (d, J=8.1 Hz, 1H), 7.70-7.66 (m, 1H), 7.22 (s, 1H), 3.10 (s, 3H), 2.68 (s, 3H), 2.48 (s, 3H), 2.00 (s, 1H), 0.81-0.76 (m, 4H). FR-b was concentrated in vacuo at 30° C. to afford pure I-549 (0.028 g). MS(ES): m/z: 399.57 [M+H]$^+$, LCMS purity: 99.16%, HPLC purity: 98.90%, Chiral HPLC Purity: 99.78%, 1H NMR (DMSO-d6, 400 MHz): 12.44 (s, 1H), 10.56 (s, 1H), 9.68 (s, 1H), 8.06 (s, 1H), 7.87-7.85 (d, J=8.4 Hz, 1H), 7.76-7.74 (d, J=8.1 Hz, 1H), 7.68 (s, 1H), 7.22 (s, 1H), 3.10 (s, 3H), 2.68 (s, 3H), 2.48 (s, 3H), 2.01 (s, 1H), 0.89-0.76 (m, 4H).

1086

Example 550/551: Synthesis of (S)—N-(7-((4-(5,5-dimethyltetrahydro-2H-pyran-2-yl)-2-(methylsulfonyl)phenyl)amino)-2-methyl-3H-imidazo[4,5-b]pyridin-5-yl)cyclopropanecarboxamide, I-550 and (R)—N-(7-((4-(5,5-dimethyltetrahydro-2H-pyran-2-yl)-2-(methylsulfonyl)phenyl)amino)-2-methyl-3H-imidazo[4,5-b]pyridin-5-yl)cyclopropanecarboxamide, I-551

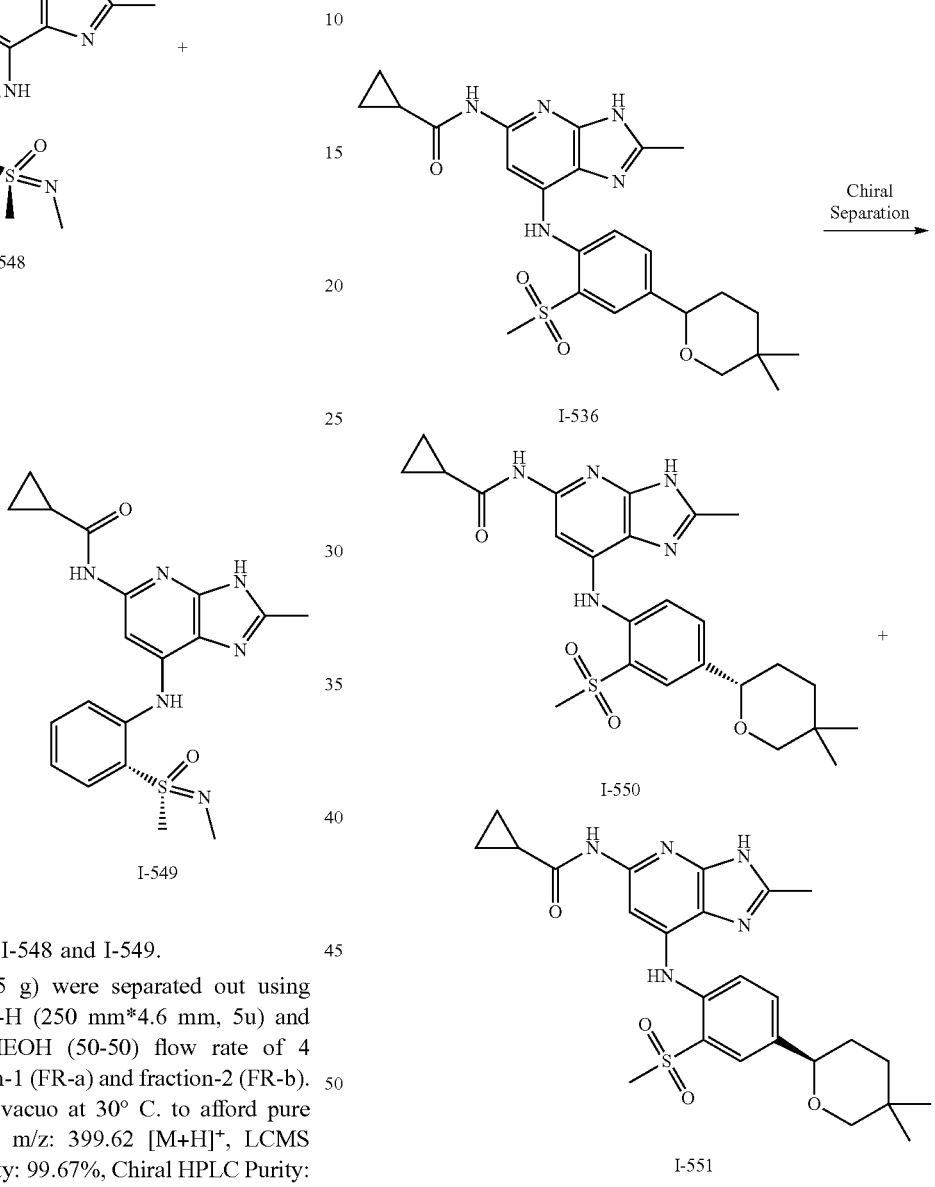

Synthesis of Compound I-550 and I-551.

Isomers of I-536 (0.090 g) were separated out using column CHIRALPAK AD-H (250 mm*4.6 mm, 5u) and 0.1% DEA in MeOH, flow rate of 4 mL/min to get pure fraction-1 (FR-a) and fraction-2 (FR-b). FR-a was concentrated in vacuo at 30° C. to afford pure I-550 (0.030 g). MS(ES): m/z: 498.63 [M+H]$^+$, LCMS purity: 99.49%, HPLC purity 97.16%, Chiral HPLC: (100%), 1H NMR (DMSO, 400 MHz): 12.49 (s, 1H), 10.57 (s, 1H), 8.54 (s, 1H), 7.95 (s, 1H), 7.88 (s, 1H), 7.71 (s, 2H), 4.35-4.33 (d, J=8.8 Hz, 1H), 3.58-3.55 (d, J=11.2 Hz, 2H), 3.19 (s, 3H), 2.51 (s, 3H), 2.00 (s, 2H), 1.80 (s, 1H), 1.58 (s, 2H), 1.09 (s, 3H), 0.87 (s, 3H), 0.77-0.76 (m, 4H). FR-b was concentrated in vacuo at 30° C. to afford pure I-551 (0.035 g). MS(ES): m/z: 498.63 [M+H]⁺, LCMS purity: 100%, HPLC purity 99.91%, Chiral HPLC: (100%), 1H NMR (DMSO, 400 MHz): 12.59 (s, 1H), 10.55 (s, 1H), 8.54 (s, 1H), 7.96 (s, 1H), 7.88 (s, 1H), 7.70 (s, 2H), 4.35-4.33 (d, J=8.8 Hz, 1H), 3.58-3.55 (d, J=12 Hz, 2H), 3.19 (s, 3H), 2.48 (s, 3H), 1.99 (s, 2H), 1.77 (s, 1H), 1.58 (s, 2H), 1.08 (s, 3H), 0.87 (s, 3H), 0.77-0.75 (m, 4H).

Example 552: Synthesis of 6-((2-(difluoromethyl)-7-((4-fluoro-2-(methylsulfonyl)phenyl)amino)-3H-imidazo[4,5-b]pyridin-5-yl)amino)picolinonitrile, I-552

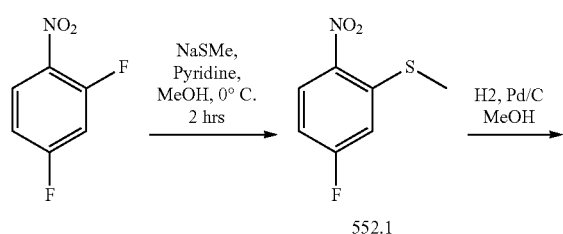

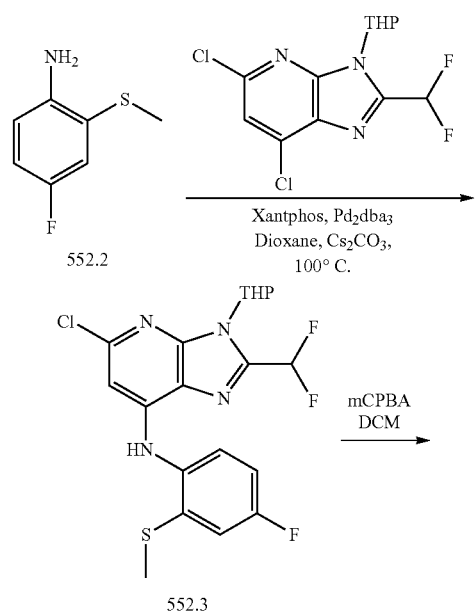

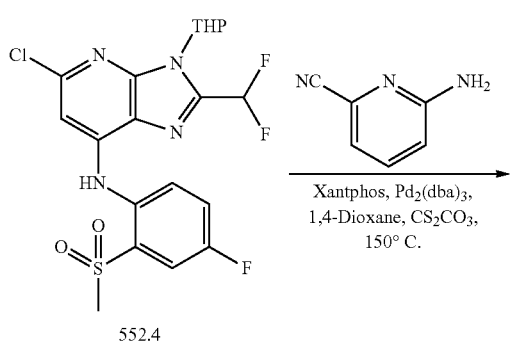

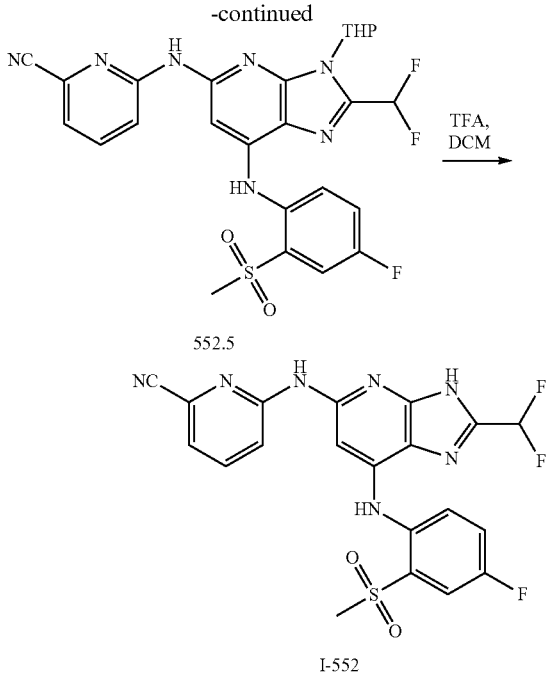

Synthesis of Compound 552.1.
To a solution of 2,4-difluoro-1-nitrobenzene (5 g, 31.43 mmol, 1.0 eq) in MeOH (20 mL) was added Pyridine (6.2 g, 78.6 mmol, 2.5 eq) at r.t. Sodiumthiomethoxide (8.3 g, 34.59 mmol, 1.1 eq) in MeOH (10 mL) solution was added dropwise into the reaction mixture at 0° C. The reaction was stirred at 0° C. for 15 min. Upon completion, reaction mixture was transferred into ice cold water to obtain precipitate which was filtered, washed with water and dried well to obtained 552.1 (5 g, 84.99%). MS(ES): m/z 188.19 [M+H]⁺.

Synthesis of Compound 552.2.
To a solution of 552.1 (2 g, 10.68 mmol, 1.0 eq) in MeOH (90 mL), 10% Pd/C (1.5 g) was added. Hydrogen was purged through reaction mixture for 2-3 hr at r.t. Upon completion, reaction mixture was filtered through celite-bed and washed with ethanol. Filtrate was concentrated in vacuo to obtain 552.2 (0.8 g, 47.63%). MS(ES): m/z 158.21 [M+H]⁺.

Synthesis of Compound 552.3.
Compound 552.3 was synthesized from 552.2 and 13.4 using general procedure A. (Yield: 36.37%). MS(ES): m/z 443.89 [M+H]⁺.

Synthesis of Compound 552.4.
To a solution 552.3 (0.200 g, 451.51 mmol, 1 eq) in CH₂Cl₂ (10 mL) was allowed to r.t. Meta-Chloroperbenzoic acid (0.271 g, 1.58 mmol, 3.5 eq) was added slowly to the reaction mixture at 0° C. The reaction mixture was stirred at r.t. for 3 hr. After completion of reaction, the reaction mixture was transferred into saturated NaHCO₃ solution and extracted with CH₂Cl₂. Combined Organic layer dried over Na₂SO₄ and concentrated in vacuo to obtain crude product. This was purified by column chromatography and compound was eluted in 30% ethyl acetate in hexane to obtain pure 552.4 (0.140 g, 65.28%). MS(ES): m/z 475.88 [M+H]⁺.

Synthesis of Compound 552.5.
Compound 552.5 was synthesized from 552.4 and 6-aminopicolinonitrile using general procedure B. (Yield: 33.46%). MS(ES): m/z 558.55 [M+H]⁺.

Synthesis of I-552.

Compound I-552 was synthesized from 552.5 using general procedure C. (Yield: 57.81%). MS(ES): m/z: 474.52 [M+H]$^+$, LCMS purity: 100%, HPLC purity: 98.70%, 1H NMR (DMSO, 400 MHz): 13.62 (s, 1H), 10.14 (s, 1H), 8.72 (s, 1H), 8.12-8.10 (d, J=8.8 Hz, 1H), 7.95-7.86 (m, 2H), 7.77-7.69 (m, 2H), 7.48-7.45 (m, 2H), 7.22 (t, 1H), 3.29 (s, 3H).

Example 553: Synthesis of 6-((7-((4-fluoro-2-(methylsulfonyl)phenyl)amino)-2-methyl-3H-imidazo[4,5-b]pyridin-5-yl)amino)picolinonitrile, I-553

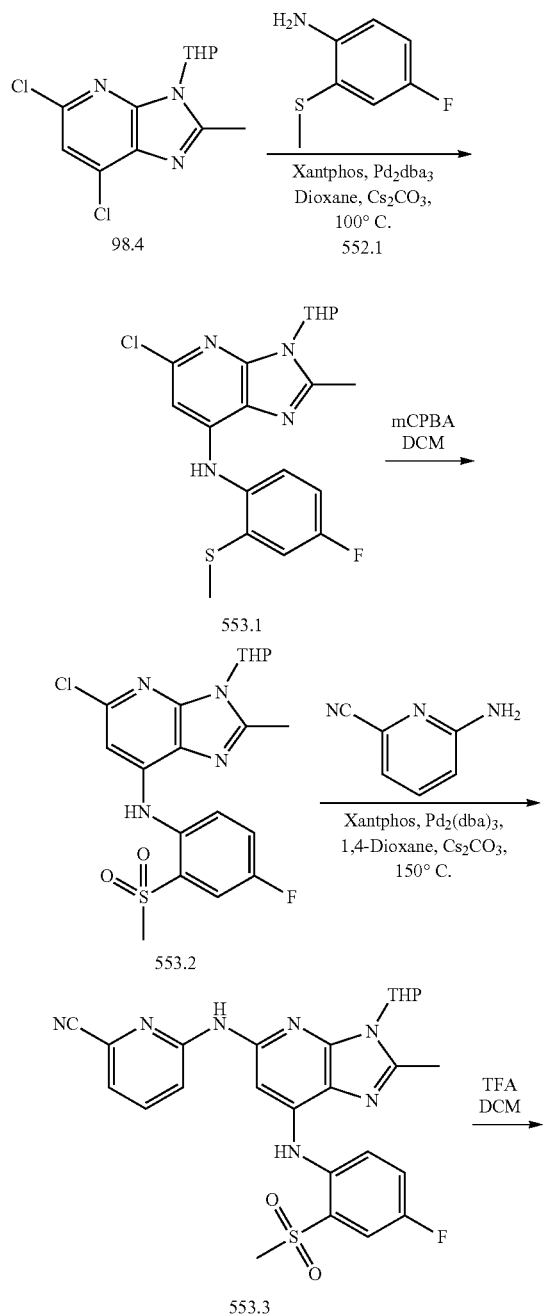

Synthesis of Compound 553.1.

Compound 553.1 was synthesized from 98.4 and 552.1 using general procedure A. (Yield: 38.68%). MS(ES): m/z 407.90 [M+H]$^+$.

Synthesis of Compound 553.2.

To a solution 553.1 (0.220 g, 540.67 mmol, 1 eq) in CH$_2$Cl$_2$ (10 mL) was allowed to r.t. Meta-Chloroperbenzoic acid (0.325 g, 1.89 mmol, 3.5 eq) was added slowly to the reaction mixture at 0° C. The reaction mixture was stirred at r.t. for 3 hr. After completion of reaction, the reaction mixture was transferred into saturated NaHCO$_3$ solution and extracted with CH$_2$Cl$_2$. Combined Organic layer dried over Na$_2$SO$_4$ and concentrated in vacuo to obtain crude product. This was purified by column chromatography and compound was eluted in 30% ethyl acetate in MeOH to obtain pure 553.2. (0.170 g, 71.64%). MS(ES): m/z 439.90 [M+H]$^+$.

Synthesis of Compound 553.3.

Compound 553.3 was synthesized from 553.2 and 6-aminopicolinonitrile using general procedure B. (Yield: 29.70%). MS(ES): m/z 522.57 [M+H]$^+$.

Synthesis of I-553.

Compound I-553 was synthesized using from 553.3 general procedure C. (Yield: 51.67%). [M+H]$^+$. MS(ES): m/z: 438.44 [M+H]$^+$, LCMS purity: 100%, HPLC purity: 96.91%, 1H NMR (DMSO, 400 MHz): 12.45 (s, 1H), 9.98 (s, 1H), 7.99-7.97 (d, J=8.4 Hz, 1H), 7.92 (s, 1H), 7.85-7.81 (t, J=7.2 Hz, 1H), 7.74-7.67 (m, 2H), 7.50 (s, 1H), 7.43-7.42 (d, J=7.2 Hz, 1H), 3.27 (s, 3H), 2.48 (s, 3H).

Example 554: Synthesis of N-(2-(difluoromethyl)-7-((4-(1,4-dimethyl-1H-pyrazol-3-yl)-2-methoxyphenyl)amino)-3H-imidazo[4,5-b]pyridin-5-yl)cyclopropanecarboxamide, I-554

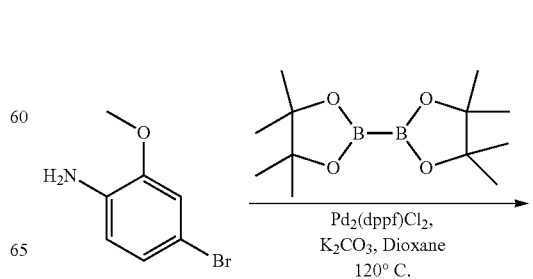

1091

-continued

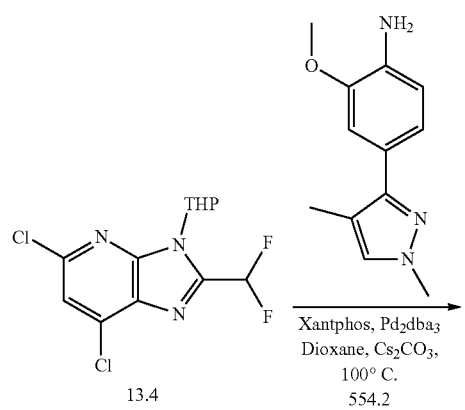

554.1    554.2

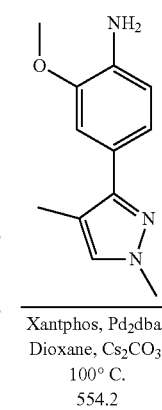

13.4    554.2

554.3

554.4

1092

-continued

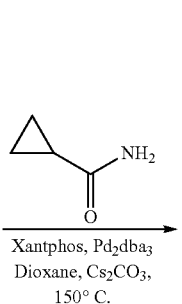

I-554

Synthesis of Compound 554.1.

To a solution of 4-bromo-2-methoxyaniline 1 (3 g, 14.85 mmol, 1 eq) in Dioxane (30 mL) was added 4,4,4',4',5,5,5',5'-octamethyl-2,2'-bi(1,3,2-dioxaborolane) (5.65 g, 22.27 mmol, 1.5 eq) and potassium carbonate (6.14 g, 44.55 mmol, 3 eq). The reaction mixture was degassed by argon for 30 min. DCM [1,1'-Bis(diphenylphosphino)ferrocene]dichloropalladium(II) (0.363 g, 4.45 mmol, 0.03 eq), was added into reaction mixture and again reaction mixture was degassed by argon for 30 min. Further reaction mixture was stirred at 120° C. for 4 h. Upon completion, reaction mixture transferred into water and extracted with ethyl acetate. Organic layers were combined, dried over Na$_2$SO$_4$ and concentrated in vacuo to obtain crude product. This was purified by column chromatography and compound was eluted in 20% ethyl acetate in hexane to obtain pure 554.1 (2.1 g, 56.77%). MS(ES): m/z 250.12 [M+H]$^+$.

Synthesis of Compound 554.2.

To a solution of 554.1 (1 g, 4.01 mmol, 1 eq) in Dioxane (20 mL) and water (3 mL) was added 3-bromo-1,4-dimethyl-1H-pyrazole (1.4 g, 8.03 mmol, 2 eq), and potassium carbonate (1.7 g, 12.0 mmol, 3 eq). The reaction mixture was degassed by argon for 30 min. DCM [1,1'-Bis(diphenylphosphino)ferrocene]dichloropalladium(II) (0.327 g, 4.01 mmol, 0.1 eq), was added into reaction mixture and again reaction mixture was degassed by argon for 30 min. Further reaction mixture was stirred at 120° C. for 2 h. Upon completion, reaction mixture transferred into water and extracted with ethyl acetate. Organic layers were combined, dried over Na$_2$SO$_4$ and concentrated in vacuo to obtain crude product. This was purified by column chromatography and compound was eluted in 20% ethyl acetate in hexane to obtain pure 554.2 (0.500 g, 57.33%). MS(ES): m/z 218.27 [M+H]$^+$.

Synthesis of Compound 554.3.

Compound 554.3 was synthesized from 554.2 and 13.4 using general procedure A. (Yield: 51.24%). MS (ES): m/z 503.95 [M+H]$^+$.

Synthesis of Compound 554.4.

Compound 554.4 was synthesized from 554.3 and cyclopropanecarboxamide using general procedure B. (Yield: 31.00%). MS (ES): m/z 552.60 [M+H]$^+$.

Synthesis of compound I-554. Compound I-554 was synthesized from 554.4 using general procedure C. (Yield: 78.08%). MS(ES): m/z: 468.55 [M+H]$^+$, LCMS purity: 96.05%, HPLC purity: 97.00%, 1H NMR (DMSO-d6, 400 MHz): 10.54 (s, 1H), 8.09 (s, 1H), 7.70 (s, 1H), 7.56 (s, 1H), 7.41 (s, 1H), 7.37 (s, 2H), 7.27-7.22 (m, 2H), 3.79 (s, 6H), 2.23 (s, 3H), 2.00 (bs, 1H), 0.78-0.75 (m, 4H).

Example 555: Synthesis of N-(7-((4-(1,4-dimethyl-1H-pyrazol-3-yl)-2-methoxyphenyl)amino)-2-methyl-3H-imidazo[4,5-b]pyridin-5-yl)cyclopropanecarboxamide, I-555

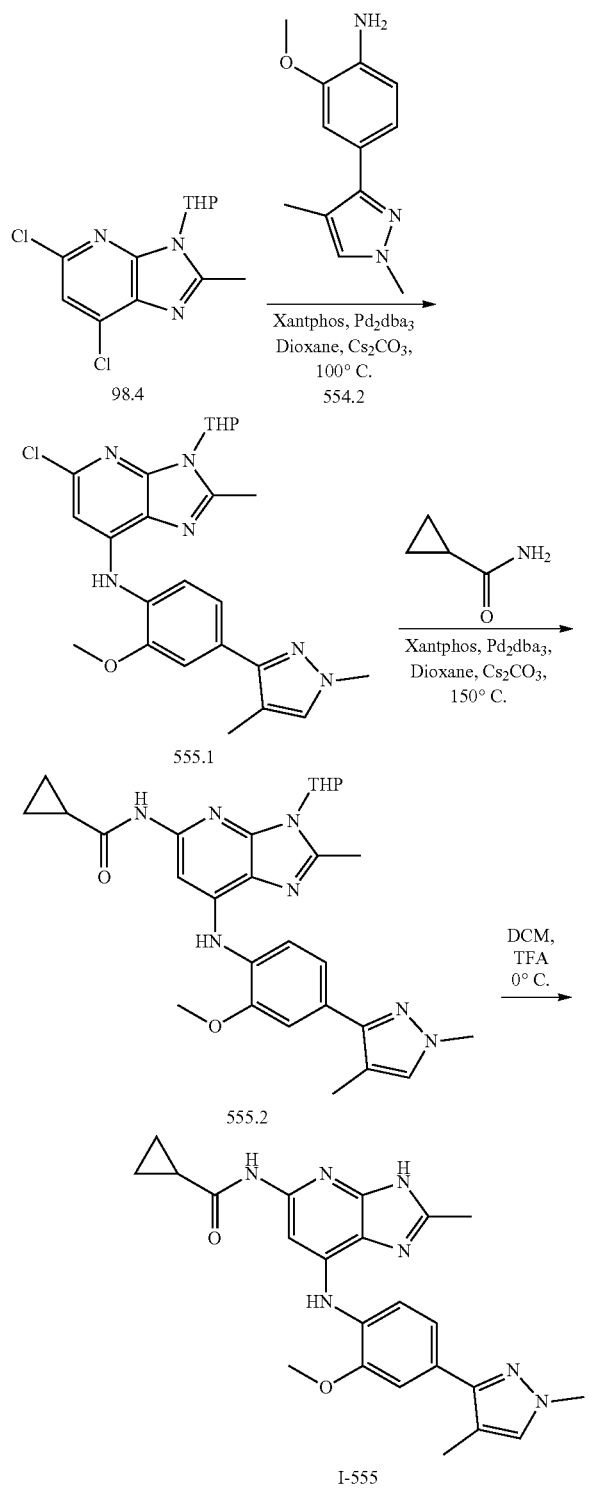

Synthesis of Compound 555.1.

Compound 555.1 was synthesized from 98.4 and 554.2 using general procedure A. (Yield: 51.47%). MS (ES): m/z 567.97 [M+H]$^+$.

Synthesis of Compound 555.2.

Compound 555.2 was synthesized from 555.1 and cyclopropanecarboxamide using general procedure B. (Yield: 53.52%). MS (ES): m/z 516.62 [M+H]$^+$.

Synthesis of compound I-555. Compound I-555 was synthesized from 555.2 using general procedure C t. (Yield: 91.92%). MS(ES): m/z: 432.54 [M+H]$^+$, LCMS purity: 98.69%, HPLC purity: 97.02%, 1H NMR (DMSO-d6, 400 MHz): 12.37 (s, 1H), 10.42 (s, 1H), 7.79 (s, 1H), 7.69 (s, 1H), 7.55 (s, 1H), 7.46-7.44 (d, J=8.0 Hz, 1H), 7.35 (s, 1H), 7.25-7.23 (d, J=8.0 Hz, 1H), 3.91 (s, 3H), 3.84 (s, 3H), 2.49 (s, 3H), 2.23 (s, 3H), 0.85 (s, 1H), 0.78-0.74 (m, 4H).

Example 556: Synthesis of N-(2-(difluoromethyl)-7-((4-(1,4-dimethyl-1H-pyrazol-3-yl)-3-fluoro-2-methoxyphenyl)amino)-3H-imidazo[4,5-b]pyridin-5-yl)cyclopropanecarboxamide, I-556

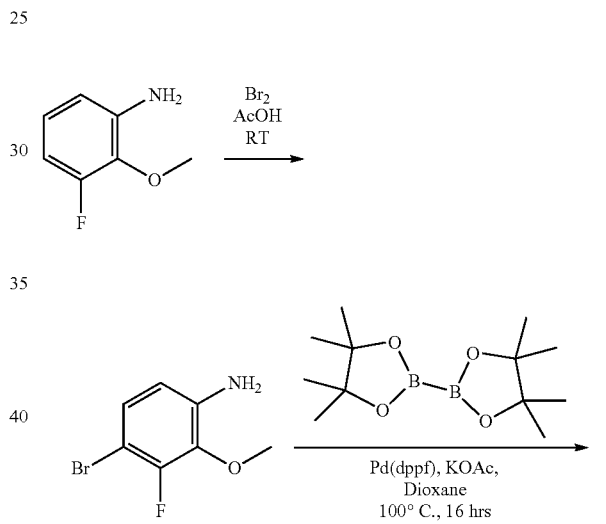

-continued

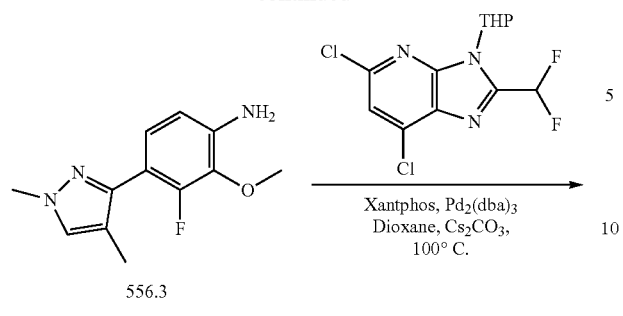

556.3

Xantphos, Pd₂(dba)₃
Dioxane, Cs₂CO₃,
100° C.

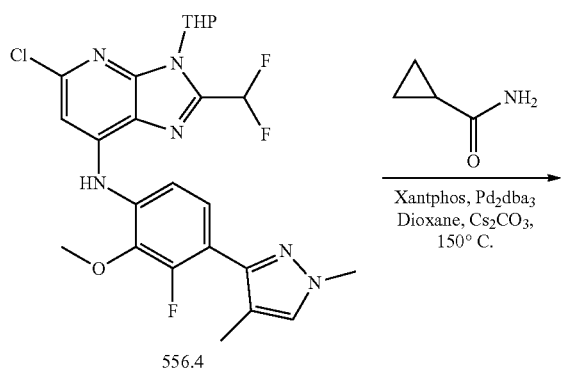

556.4

Xantphos, Pd₂dba₃
Dioxane, Cs₂CO₃,
150° C.

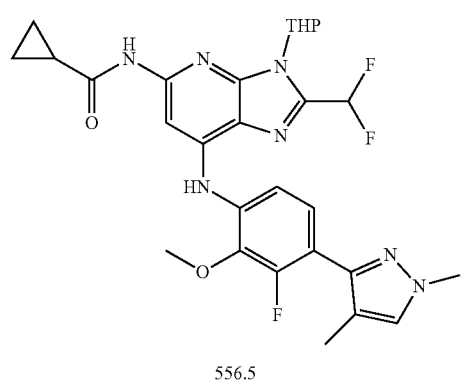

556.5

DCM, TFA
0° C.

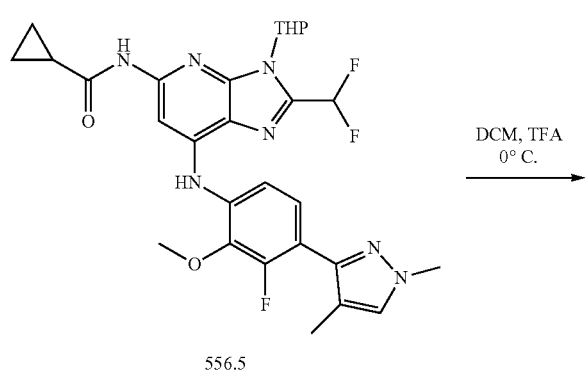

556.5

-continued

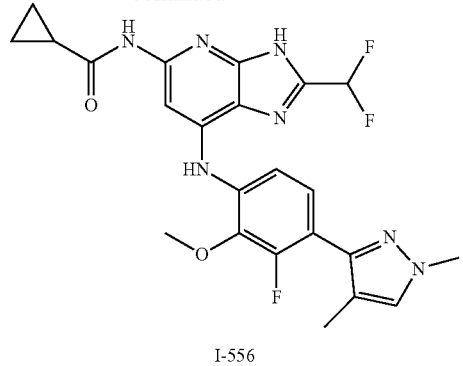

I-556

Synthesis of Compound 556.1.

To a solution of 3-fluoro-2-methoxyaniline (5 g, 35.42 mmol, 1.0 eq), in Acetic acid (40 mL) was added Bromine (4.5 g, 28.33 mmol, 0.8 eq) in Acetic acid (20 mL) dropwise. The reaction mixture was stirred for 30 min at r.t. After completion of reaction, precipitated solid filtered out and washed with Acetic acid. Crude material was suspended in water and basified with potassium hydroxide solution and extracted with ethyl acetate. Organic layers were combined, dried over Na₂SO₄ and concentrated in vacuo to obtain crude product. This was purified by column chromatography and compound was eluted in 15% ethyl acetate in hexane to obtain pure 556.1 (2.9 g, 37.20%). MS(ES): m/z 221.04 [M+H]⁺.

Synthesis of Compound 556.2.

To a solution of 556.1 (2.9 g, 13.18 mmol, 1.0 eq), in 1,4-dioxane (90 mL) was added 4,4,4',4',5,5,5',5'-octamethyl-2,2'-bi(1,3,2-dioxaborolane) 1.2 (3.65 g, 14.37 mmol, 1.09 eq) and potassium acetate (3.87 g, 39.54 mmol, 3.0 eq). The reaction mixture was degassed by argon for 30 min. [1,1'-Bis(diphenylphosphino)ferrocene]dichloropalladium (II)CH₂Cl₂ complex (0.537 g, 6.59 mmol, 0.05 eq) was added into the reaction mixture and again degassed by argon for 20 min. Further reaction mixture was stirred at 100° C. for 16 h. Upon completion, reaction mixture transferred into water and extracted with ethyl acetate. Organic layers were combined, dried over Na₂SO₄ and concentrated in vacuo to obtain crude product. This was purified by column chromatography and compound was eluted in 8% ethyl acetate in hexane to obtain pure 556.2 (0.600 g, 17.04%). MS(ES): m/z 268.11 [M+H]⁺.

Synthesis of Compound 556.3.

To a solution of 556.2 (0.600 g, 2.25 mmol, 1.0 eq), in 1,4-dioxane (12 mL) and water (1.2 mL) was added 3-bromo-1,4-dimethyl-1H-pyrazol (0.433 g, 2.47 mmol, 1.1 eq), Cs₂CO₃ (1.5 g, 4.50 mmol, 2.0 eq). The reaction mixture was degassed by argon for 30 min. [1,1'-Bis(diphenylphosphino)ferrocene]dichloropalladium(II) CH₂Cl₂ complex (0.275 g, 3.37 mmol, 0.15 eq) was added into the reaction mixture and again degassed by argon for 20 min. Further reaction mixture was stirred at 100° C. for 6 h. Upon completion, reaction mixture transferred into water and extracted with ethyl acetate. Organic layers were combined, dried over Na₂SO₄ and concentrated in vacuo to obtain crude product. This was purified by column chromatography and compound was eluted in 40% ethyl acetate in hexane to obtain pure 556.3 (0.250 g, 47.31%). MS(ES): m/z 236.26 [M+H]⁺.

1097

Synthesis of Compound 556.4.

Compound 556.4 was synthesized from 13.4 and 556.3 using general procedure A (Yield: 37.10%). MS(ES): m/z 521.94 [M+H]⁺.

Synthesis of Compound 556.5.

Compound 556.5 was synthesized from 556.4 and cyclopropanecarboxamide using general procedure B. (Yield: 51.83%). MS(ES): m/z 570.659 [M+H]⁺.

Synthesis of I-556.

Compound I-556 was synthesized from 556.5 using general procedure C (Yield: 55.21%). MS(ES): m/z: 486.62 [M+H]⁺, LCMS purity: 98.97%, HPLC purity: 95.08%, 1H NMR (DMSO-d6, 400 MHz): 13.48 (s, 1H), 10.58 (s, 1H), 8.44 (s, 1H), 7.70 (s, 1H), 7.58 (s, 1H), 7.25-7.23 (m, 1H), 7.17 (t, 1H), 3.85 (s, 6H), 2.01 (s, 4H), 1.23 (s, 1H), 0.77-0.74 (bs, 4H).

Example 557: Synthesis of N-(7-((4-(1,4-dimethyl-1H-pyrazol-3-yl)-3-fluoro-2-methoxyphenyl)amino)-2-methyl-3H-imidazo[4,5-b]pyridin-5-yl)cyclopropanecarboxamide, I-557

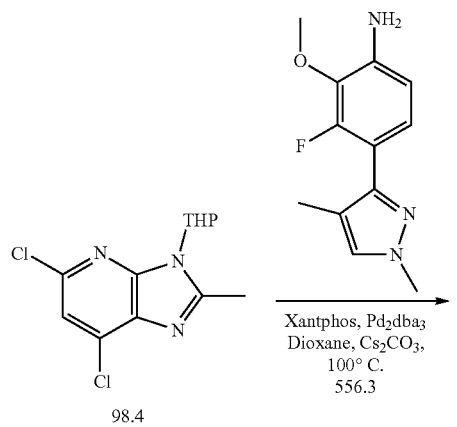

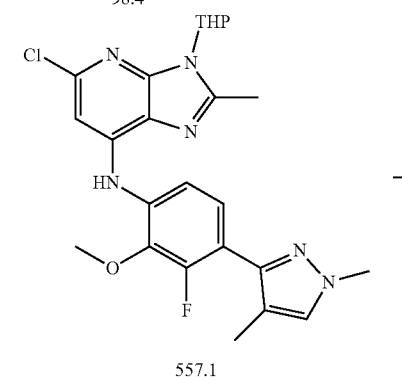

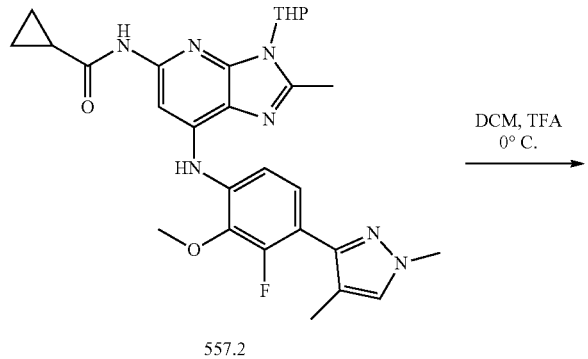

1098

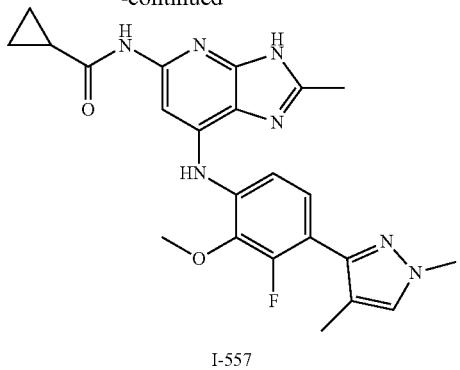

I-557

Synthesis of Compound 557.1.

Compound 557.1 was synthesized from 98.4 and 556.3 using general procedure A (Yield: 35.40%). MS(ES): m/z 485.96 [M+H]⁺.

Synthesis of Compound 557.2.

Compound 557.2 was synthesized from 557.1 and cyclopropanecarboxamide using general procedure B. (Yield: 51.50%). MS(ES): m/z 534.61 [M+H]⁺.

Synthesis of Compound I-557.

Compound I-557 was synthesized from 557.2 using general procedure C. (Yield: 62.85%). [M+H]⁺ MS(ES): m/z: 450.61 [M+H]⁺, LCMS purity: 96.91%, HPLC purity: 95.08%, 1H NMR (DMSO-d6, 400 MHz): 12.54 (s, 1H), 10.48 (s, 1H), 8.05 (s, 1H), 7.78 (s, 1H), 7.57 (s, 1H), 7.25-7.23 (d, J=8.4 Hz, 1H), 7.16-7.12 (s, 1H), 3.85 (s, 6H), 2.01 (s, 6H), 1.11-1.0 (m, 1H), 0.73 (m, 4H).

Example 558: Synthesis of 6-((2-(difluoromethyl)-7-((2-methoxy-3-(thiazol-2-yl)phenyl)amino)-3H-imidazo[4,5-b]pyridin-5-yl)amino)picolinonitrile, I-558

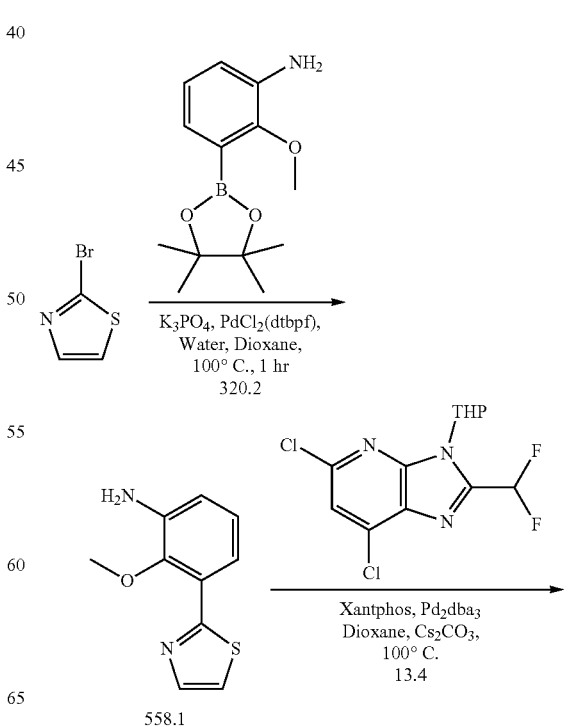

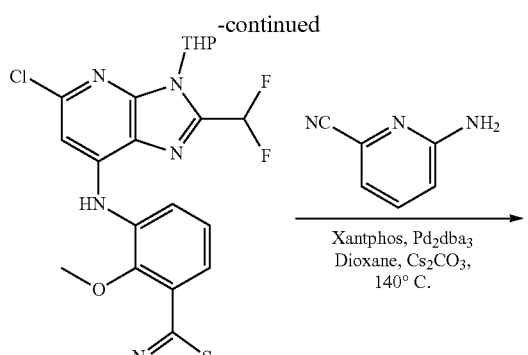
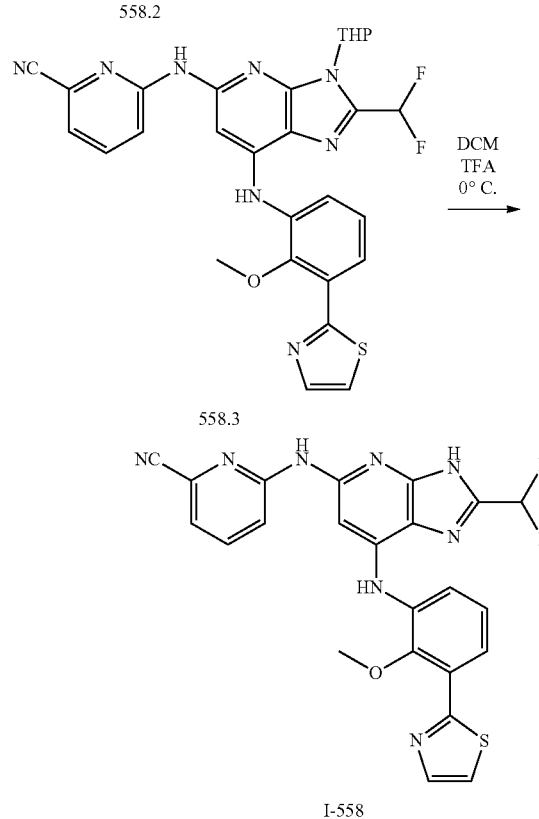

Synthesis of Compound 558.3.

Compound 558.3 was synthesized from 558.2 and 6-aminopicolinonitrile using general procedure B. (Yield: 35.67%). MS (ES): m/z 575.61 [M+H]$^+$.

Synthesis of Compound I-558.

Compound I-558 was synthesized from 558.3 using general procedure C. (Yield: 62.48%). MS(ES): m/z: 491.53 [M+H]$^+$, LCMS purity: 100%, HPLC purity: 98.73%, 1H NMR (DMSO, 400 MHz): 13.50 (s, 1H), 10.03 (s, 1H), 8.65 (s, 1H), 8.37-8.35 (d, J=8.4 Hz, 1H), 8.16-8.14 (d, J=7.2 Hz, 1H), 8.01-8.01 (d, J=2.8 Hz, 1H), 7.88-7.84 (m, 2H), 7.55-7.54 (d, J=6.8 Hz, 1H), 7.44-7.43 (d, J=7.2 Hz, 1H), 7.38-7.34 (t, J=8 Hz, 1H), 7.20 (t, 1H), 6.81 (s, 1H), 3.77 (s, 3H).

Example 559: Synthesis of N-(7-((4-(4,5-dimethyl-thiazol-2-yl)-2-methoxyphenyl)amino)-2-methyl-3H-imidazo[4,5-b]pyridin-5-yl)cyclopropanecarboxamide, I-559

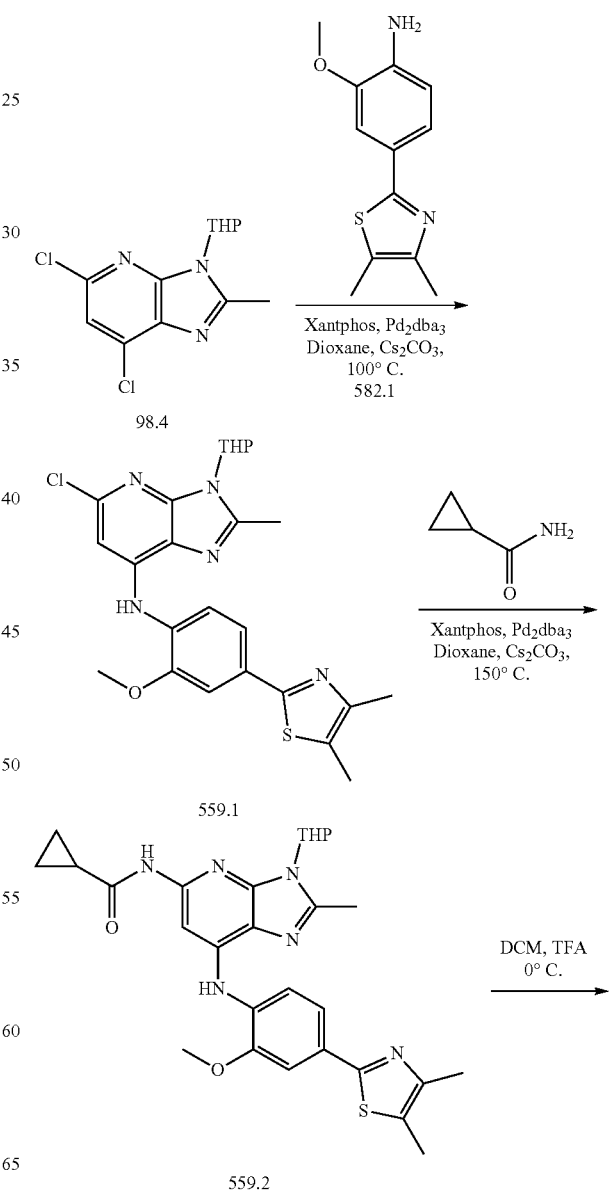

Synthesis of Compound 558.1.

To a solution of 2-bromo-thiazole (0.600 g, 3.66 mmol, 1 eq) in 1,4-dioxane (6 mL) and water (4 mL) was added 320.2 (1.8 g, 7.32 mmol, 2 eq), and potassium phosphate (2.32 g, 10.97 mmol, 3 eq). The reaction mixture was degassed by argon for 30 min. [1,1'-Bis(di-tert-butylphosphino)ferrocene]dichloropalladium(II) (0.071 g, 1.09 mmol, 0.03 eq), was added into reaction mixture and again reaction mixture was degassed by argon for 30 min. Further reaction mixture was stirred at 100° C. for 1 h. Upon completion, reaction mixture transferred into water and extracted with ethyl acetate. Organic layers were combined, dried over Na$_2$SO$_4$ and concentrated in vacuo to obtain crude product. This was purified by column chromatography and compound was eluted in 20% ethyl acetate in hexane to obtain pure 558.1 (0.400 g, 53.01%). MS(ES): m/z 207.26 [M+H]$^+$.

Synthesis of Compound 558.2.

Compound 558.2 was synthesized from 558.1 and 13.4 using general procedure A. (Yield: 58.93%). MS (ES): m/z 492.94 [M+H]$^+$.

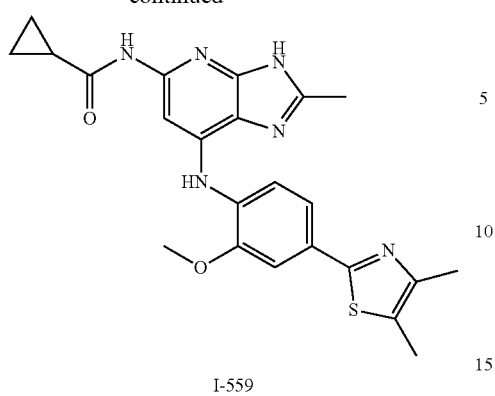

I-559

Synthesis of Compound 559.1.

Compound 559.1 was synthesized from 98.4 and 582.1 using general procedure A. (Yield: 34.66%). MS (ES): m/z 485.02 [M+H]+.

Synthesis of Compound 559.2.

Compound 559.2 was synthesized from 559.1 and cyclopropanecarboxamide using general procedure B. (Yield: 36.35%). MS (ES): m/z 533.66 [M+H]+.

Synthesis of Compound I-559.

Compound I-559 was synthesized from 559.2 using general procedure C. (Yield: 61.82%). MS(ES): m/z: 449.55 [M+H]+, LCMS purity: 100%, HPLC purity: 100%, 1H NMR (DMSO-d6, 400 MHz): 13.47 (s, 1H), 10.47 (s, 1H), 7.86 (s, 1H), 7.77 (s, 1H), 7.52 (s, 1H), 7.48-7.46 (s, 1H), 7.42-7.39 (s, 1H), 3.95 (s, 3H), 2.67 (s, 1H), 2.44 (s, 3H), 2.39 (s, 3H), 2.32 (s, 3H), 0.83-0.74 (bs, 4H).

Example 560: Synthesis of N-(2-methyl-7-((2-(methylsulfonyl)-4-(1,4,5-trimethyl-1H-pyrazol-3-yl)phenyl)amino)-3H-imidazo[4,5-b]pyridin-5-yl)cyclopropanecarboxamide, I-560

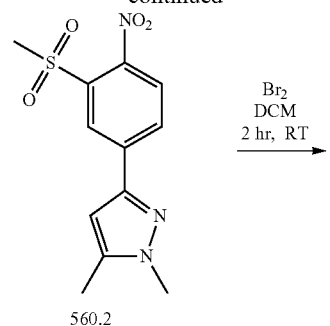

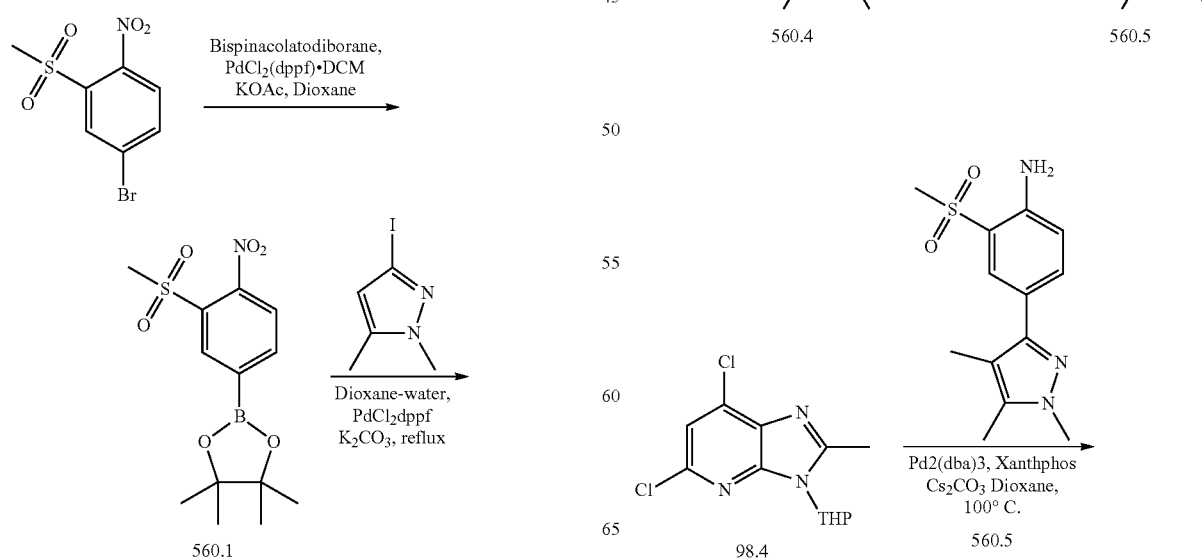

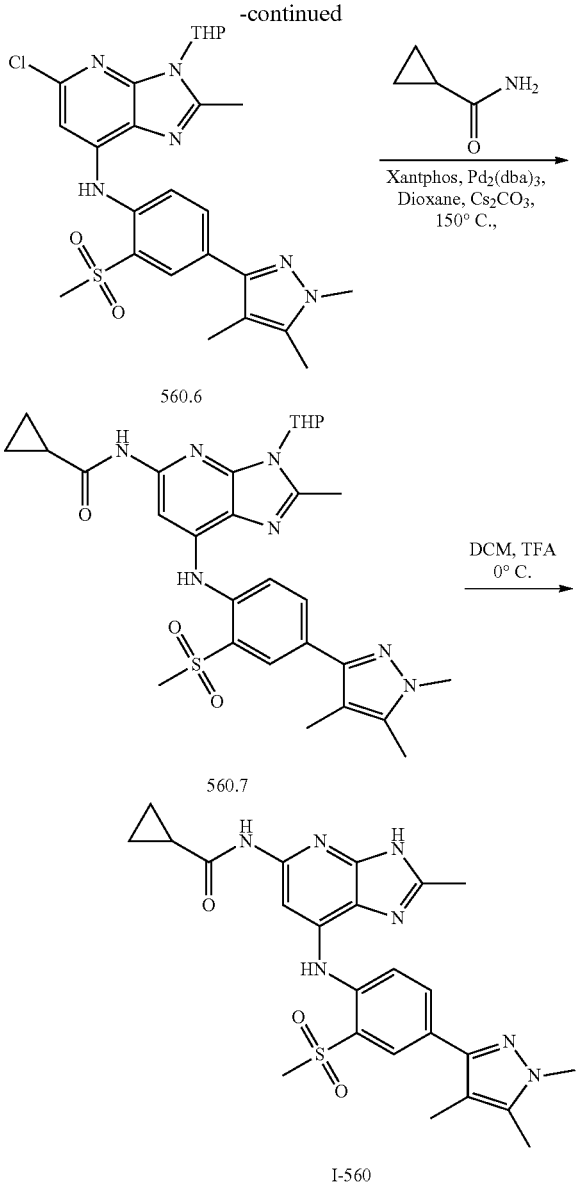

Synthesis of Compound 560.1.

To a solution of 4-bromo-2-(methylsulfonyl)-1-nitrobenzene (1 g, 3.57 mmol, 1 eq) in Dioxane (10 mL) was added Bispinacolatodiborane (0.997 g, 3.92 mmol, 1.1 eq), and potassium Acetate (1.05 g, 10.71 mmol, 3 eq). The reaction mixture was degassed by argon for 30 min. DCM [1,1'-Bis(diphenylphosphino)ferrocene]dichloropalladium(II) (0.116 g, 1.42 mmol, 0.04 eq), was added into reaction mixture and again reaction mixture was degassed by argon for 30 min. Further reaction mixture was stirred at 100° C. for 5 h. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 560.1 (0.520 g, 44.52%). MS(ES): m/z 328.16 $[M+H]^+$.

Synthesis of Compound 560.2.

To a solution of 3-iodo-1,5-dimethyl-1H-pyrazole (2 g, 9.01 mmol, 1 eq) in Dioxane (16 mL) and water (4 mL) was added 560.1 (2.95 g, 9.01 mmol, 1 eq), and potassium carbonate (3.73 g, 27.02 mmol, 3 eq). The reaction mixture was degassed by argon for 30 min. DCM [1,1'-Bis(diphenylphosphino)ferrocene]dichloropalladium(II) (0.367 g, 4.5 mmol, 0.05 eq), was added into reaction mixture and again reaction mixture was degassed by argon for 30 min. Further reaction mixture was stirred at 100° C. for 4 h. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 560.2 (1.3 g, 48.87%). MS(ES): m/z 296.31 $[M+H]^+$.

Synthesis of Compound 560.3.

To a solution of 560.2 (1.3 g, 4.40 mmol, 1.0 eq) in $CH_2Cl_2$ (20 mL) was added Bromine (0.846 g, 5.28 mmol, 1.2 eq) at 0° C. Reaction mixture was stirred for 2 h at r.t. Upon completion, reaction mixture transferred into water and basified with $NaHCO_3$ solution and extracted with ethyl acetate. Organic layers were combined, dried over $Na_2SO_4$ and concentrated in vacuo to obtain 560.3 (1.1 g, 66.78%). MS(ES): m/z 375.24 $[M+H]^+$.

Synthesis of Compound 560.4.

To a solution of 560.3 (1.1 g, 2.94 mmol, 1 eq) in Dimethylformamide (20 mL) was added Trimethylboroxine (0.735 g, 5.9 mmol, 2 eq), and potassium carbonate (2 g, 14.70 mmol, 5 eq). The reaction mixture was degassed by argon for 30 min. 1,1'-Bis(diphenylphosphino)ferrocene (0.107 g, 1.47 mmol, 0.05 eq), was added into reaction mixture and again reaction mixture was degassed by argon for 30 min. Further reaction mixture was stirred at 100° C. for 3 hr. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 560.4 (0.550 g, 60.49%). MS(ES): m/z 310.34 $[M+H]^+$.

Synthesis of Compound 560.5.

To a solution of 560.4 (5 g, 20.90 mmol, 1.0 eq) in MeOH (15 mL), 10% Pd/C (0.200 g) was added. Hydrogen was purged through reaction mixture for 2-3 hr at r.t. Upon completion, reaction mixture was filtered through celite-bed and washed with ethanol. Filtrate was concentrated in vacuo to obtain 560.5 (0.200 g, 40.27%). MS(ES): m/z 280.36 $[M+H]^+$.

Synthesis of Compound 560.6.

Compound 560.6 was synthesized from 560.5 and 98.4 using general procedure A. (Yield: 27.04%). MS (ES): m/z 530.06 $[M+H]^+$.

Synthesis of Compound 560.7.

Compound 560.7 was synthesized from 560.6 and cyclopropanecarboxamide using general procedure B. (Yield: 73.26%). MS (ES): m/z 578.70 $[M+H]^+$.

Synthesis of Compound I-560.

Compound I-560 was synthesized from 506.7 using general procedure C. (Yield: 73.15%). MS(ES): m/z: 494.61 $[M+H]^+$, LCMS purity: 98.56%, HPLC purity: 98.43%, 1H NMR (DMSO-d6, 400 MHz): 12.50 (s, 1H), 10.58 (s, 1H), 8.59 (s, 1H), 8.18 (s, 1H), 8.02-7.95 (m, 2H), 7.79 (s, 1H), 3.79 (s, 3H), 3.23 (s, 3H), 2.49 (s, 3H), 2.23 (s, 3H), 2.16 (s, 3H), 2.00 (s, 1H), 0.78-0.76 (m, 4H).

Example 561: Synthesis of N-(7-((4-(3,5-dimethyl-furan-2-yl)-2-(methylsulfonyl)phenyl)amino)-2-methyl-3H-imidazo[4,5-b]pyridin-5-yl)cyclopropan-ecarboxamide, I-561

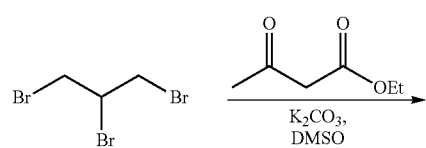

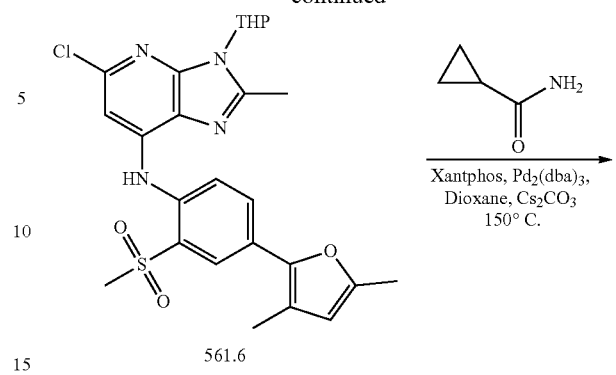

561.6

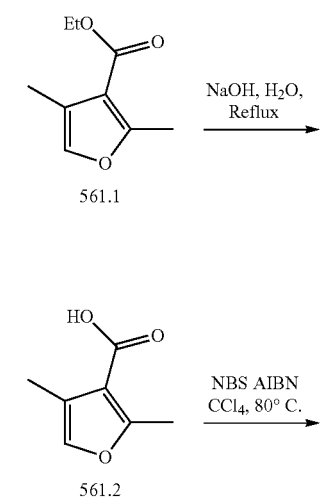

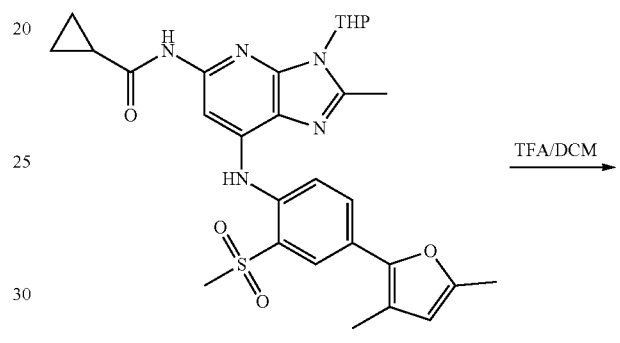

561.7

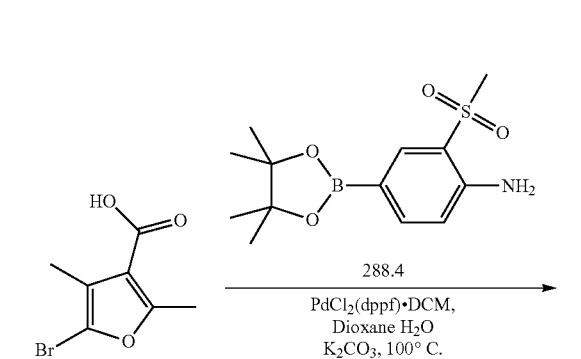

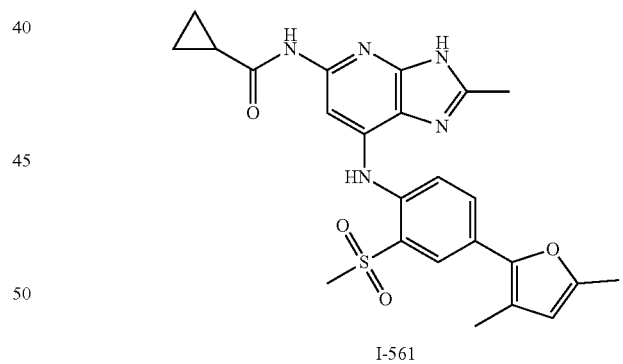

I-561

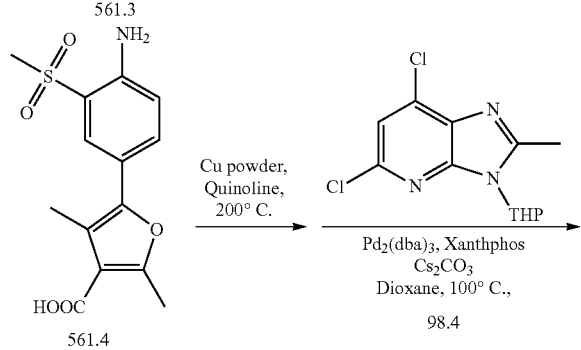

Synthesis of Compound 561.1.

To a solution of 1,2,3-tribromopropane (25 g, 89.04 mmol, 1.0 eq) in Dimethyl sulfoxide (120 mL) was added ethyl 3-oxobutanoate (46.56 g, 356.14 mmol, 4 eq), potassium carbonate (24.64 g, 178.5 mmol, 2 eq) at r.t. Reaction mixture heated at 80° C. for 16 h. Upon completion, reaction mixture was transferred into water and extracted with ethyl acetate. Combined Organic layer dried over $Na_2SO_4$ and concentrated in vacuo to obtain crude product. This was purified by column chromatography and compound was eluted in 10% ethyl acetate in hexane to obtain pure 561.1 (1 g, 73.45%). MS(ES): m/z 169.19 [M+H]$^+$.

Synthesis of Compound 561.2.

To a solution of 561.1 (1 g, 65.40 mmol, 1.0 eq) in ethanol (100 mL) and water (40 mL) was added sodium hydroxide (7.85 g, 196.4 mmol, 3 eq) at r.t. Reaction mixture heated at 80° C. for 2 h. Upon completion, reaction mixture was concentrated in vacuo, transferred into water. The pH of the solution was adjusted to neutral using 10% HCl to obtain precipitate which was filtered and dried well to obtain 561.2 (6.2 g, 67.65%). MS(ES): m/z 141.14 [M+H]⁺.

Synthesis of Compound 561.3.

To a solution of 561.2 (6.2 g, 44.24 mmol, 1.0 eq) in carbon tetrachloride (100 mL) was added N-Bromosuccinimide (11.75 g, 66.42 mmol, 1.5 eq), Azobisisobutyronitrile (0.363 g, 2.2 mmol, 0.05 eq) at r.t. Reaction mixture heated at 90° C. for 4 h. Upon completion, reaction mixture was transferred into water and extracted with ethyl acetate. Combined Organic layer dried over Na₂SO₄ and concentrated in vacuo to obtain crude product. This was purified by column chromatography and compound was eluted in 5% ethyl acetate in hexane to obtain pure 561.3 (2.2 g, 22.70%). MS(ES): m/z 220.03 [M+H]⁺.

Synthesis of Compound 561.4.

To a solution 561.3 (2.2 g, 10.04 mmol, 1 eq) in 1,4-dioxane (32 mL) and water(8 mL) was added 288 (4.48 g, 15.07 mmol, 1.5 eq), and potassium carbonate (3.97 g, 30.13 mmol, 3 eq). The reaction mixture was degassed by argon for 30 min. [1,1'-Bisdiphenylphosphinoferrocene]palladium (II) dichloride CH₂Cl₂ complex (0.246 g, 3.0 mmol, 0.03 eq), was added into reaction mixture and again reaction mixture was degassed by argon for 30 min. Further reaction mixture was stirred at 100° C. for 4 h. Upon completion, reaction mixture transferred into water and extracted with ethyl acetate. Organic layers were combined, dried over Na₂SO₄ and concentrated in vacuo to obtain crude product. This was purified by column chromatography and compound was eluted in 20% ethyl acetate in hexane to obtain pure 1.6 (1 g, 32.19%). MS(ES): m/z 310.34 [M+H]⁺.

Synthesis of Compound 561.5.

To a solution of 561.4 (0.700 g, 2.26 mmol, 1.0 eq) in Quinoline (2 mL) was added copper powder (0.140 g, 2.22 mmol, 1 eq) at r.t. Reaction mixture heated at 260° C. for 30 min. Upon completion, reaction mixture was concentrated in vacuo to obtain crude product. This was purified by column chromatography using neat CH₂Cl₂ as eluent to pure 561.5 (0.350 g, 58.29%). MS(ES): m/z 266.33 [M+H]⁺.

Synthesis of Compound 561.6.

Compound 561.6 was synthesized from 98.4 and using general procedure A (Yield: 22.08%). MS(ES): m/z 516.03 [M+H]⁺.

Synthesis of Compound 561.7.

Compound 561.7 was synthesized from 561.6 and cyclopropanecarboxamide using general procedure B. (Yield: 48.12%). MS(ES): m/z 564.67 [M+H]⁺.

Synthesis of I-561.

Compound I-561 was synthesized from 561.7 using general procedure C. (Yield: 73.46%). MS(ES): m/z: 480.55 [M+H]⁺, LCMS purity: 97.19%, HPLC purity: 98.32%, 1H NMR (DMSO, 400 MHz): 13.211 (s, 1H), 10.73 (s, 1H), 8.60 (s, 1H), 8.08 (s, 1H), 7.94-7.88 (m, 2H), 7.74-7.72 (d, J=0.8 Hz, 1H), 6.17 (s, 1H), 3.26 (s, 3H), 2.61 (s, 3H), 2.34 (s, 3H), 2.26 (s, 3H), 2.02-1.99 (m, 1H), 0.80-0.78 (m, 4H).

Example 562: Synthesis of N-(7-((4-(1-cyclopropyl-5-methyl-1H-pyrazol-4-yl)-2-(methylsulfonyl)phenyl)amino)-2-methyl-3H-imidazo[4,5-b]pyridin-5-yl)cyclopropanecarboxamide, I-562

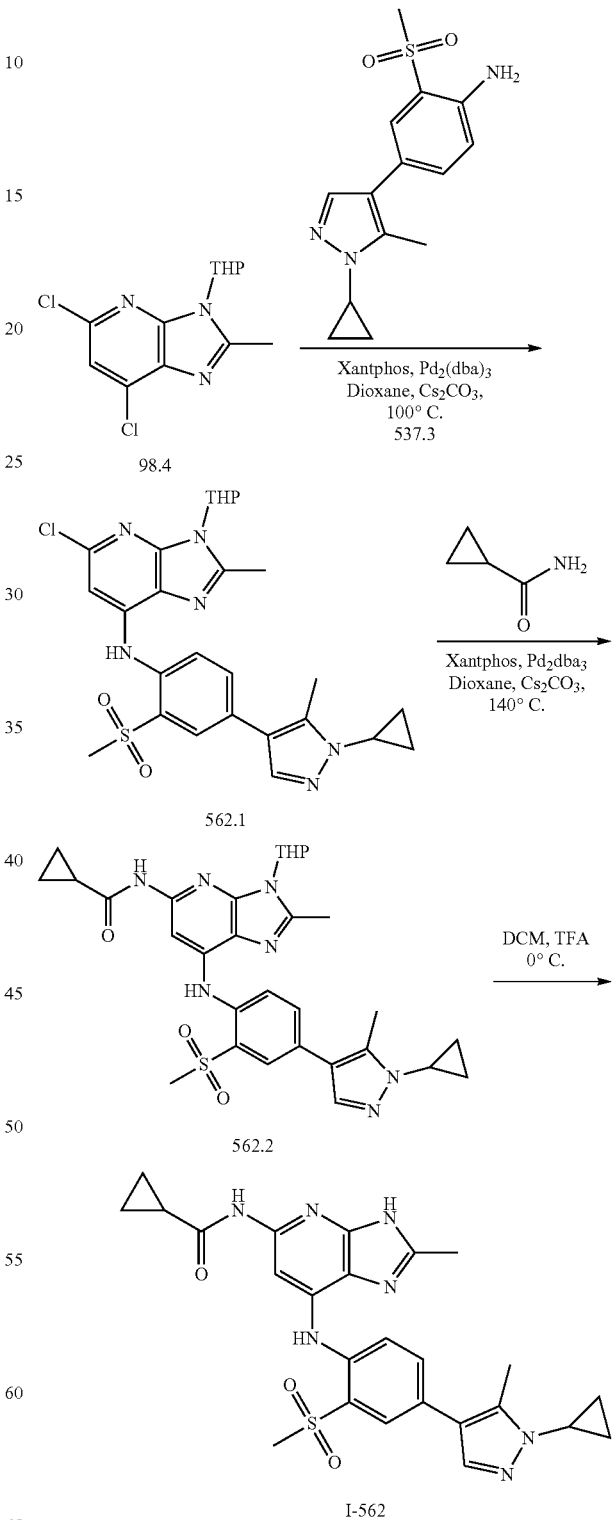

1109

Synthesis of Compound 562.1.

Compound 562.1 was synthesized from 537.3 and 98.4 using general procedure A (Yield: 29.90%). MS(ES): m/z 542.07 [M+H]$^+$.

Synthesis of Compound 562.2.

Compound 562.2 was synthesized from 562.1 and cyclopropanecarboxamide using general procedure B. (Yield: 54.22%). MS(ES): m/z 590.72 [M+H]$^+$.

Synthesis of I-562.

Compound I-562 was synthesized from 562.2 using general procedure C. (Yield: 62.80%). MS(ES): m/z: 506.73 [M+H]$^+$, LCMS purity: 99.44%, HPLC purity: 96.73%, 1H NMR (DMSO, 400 MHz): 12.49 (s, 1H), 10.58 (s, 1H), 8.60 (s, 1H), 8.01 (s, 1H), 7.87 (s, 1H), 7.79 (s, 2H), 7.67 (s, 1H), 3.59 (s, 1H), 3.34 (s, 3H), 2.52 (s, 6H), 2.02 (s, 1H), 1.09-1.07 (m, 4H), 0.79 (m, 4H).

Example 563: Synthesis of 2-(difluoromethyl)-N7-(4-(4,4-dimethyl-4,5-dihydrothiazol-2-yl)-2-(methylsulfonyl)phenyl)-N5-(2,6-dimethylpyrimidin-4-yl)-3H-imidazo[4,5-b]pyridine-5,7-diamine, I-563

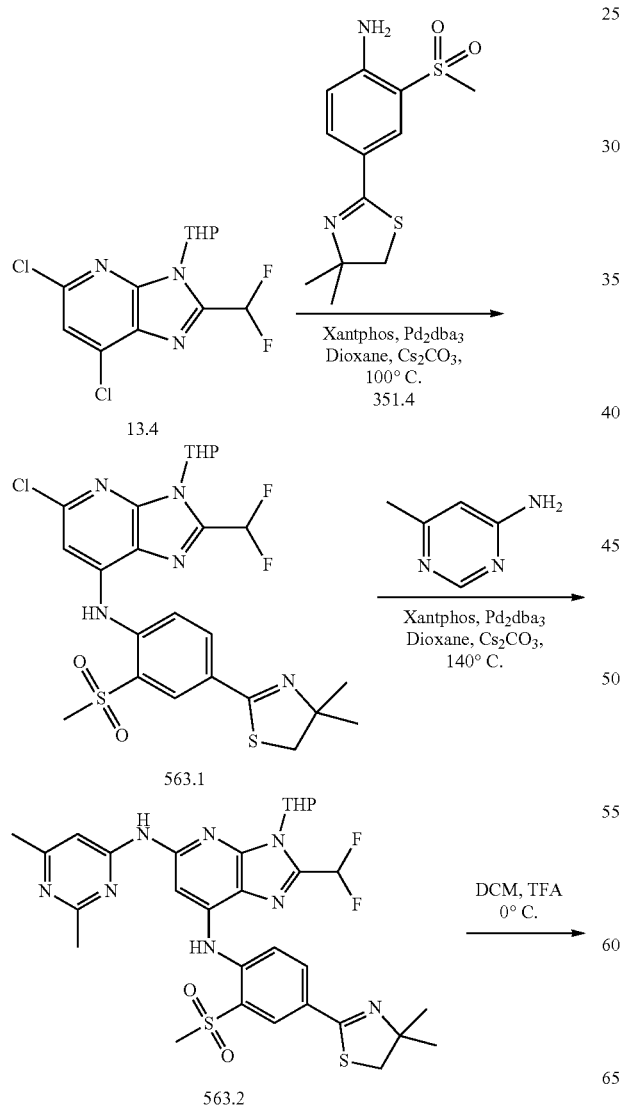

1110

-continued

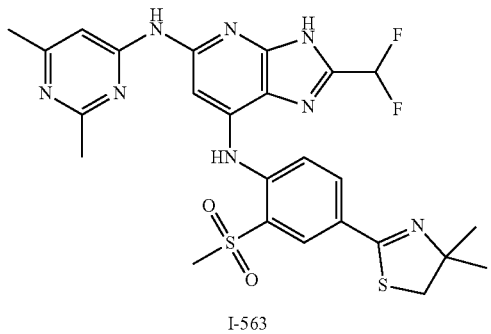

I-563

Synthesis of Compound 563.1.

Compound 563.1 was synthesized from 13.4 and 351.4 using general procedure A (Yield: 21.19%). MS(ES): m/z 571.07 [M+H]$^+$.

Synthesis of Compound 563.2.

Compound was synthesized from 563.1 and 2,6-dimethylpyrimidin-4-amine using general procedure B. (Yield: 52.08%). MS(ES): m/z 657.77 [M+H]$^+$.

Synthesis of Compound I-563.

Compound I-563 was synthesized from 563.2 using general procedure C. (Yield: 49.70%). [M+H]$^+$. MS(ES): m/z: 573.66 [M+H]$^+$, LCMS purity: 95.70%, HPLC purity: 95.00%, 1H NMR (DMSO-d6, 400 MHz): 13.75 (s, 1H), 10.02 (s, 1H), 9.04 (s, 1H), 8.29 (s, 1H), 8.03-7.97 (m, 2H), 7.66 (m, 2H), 7.19 (t, 1H), 3.34 (s, 2H), 3.32 (s, 3H), 2.43 (s, 3H), 2.34 (s, 3H), 1.42 (s, 6H).

Example 564: Synthesis of N7-(4-(4,4-dimethyl-4,5-dihydrothiazol-2-yl)-2-(methylsulfonyl)phenyl)-N5-(2,6-dimethylpyrimidin-4-yl)-2-methyl-3H-imidazo[4,5-b]pyridine-5,7-diamine, I-564

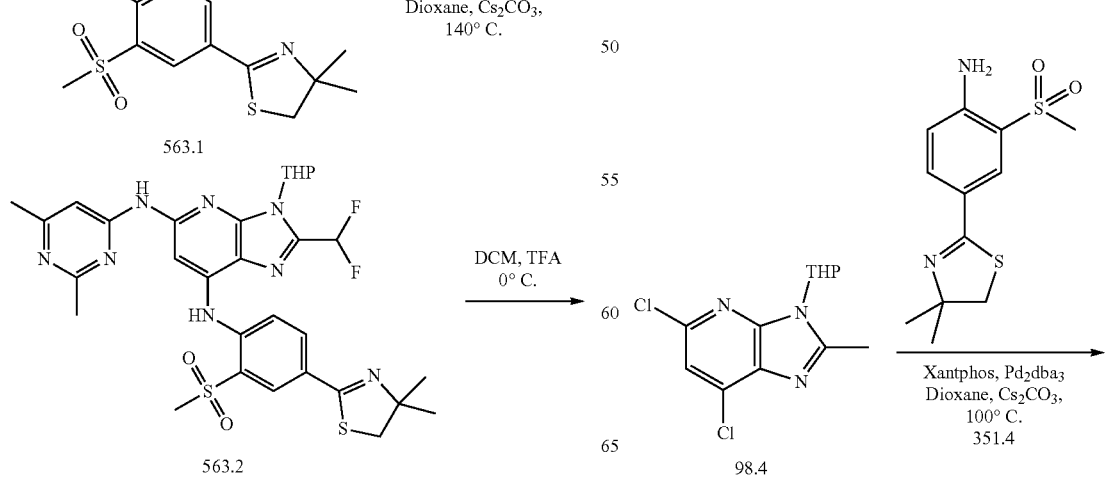

-continued

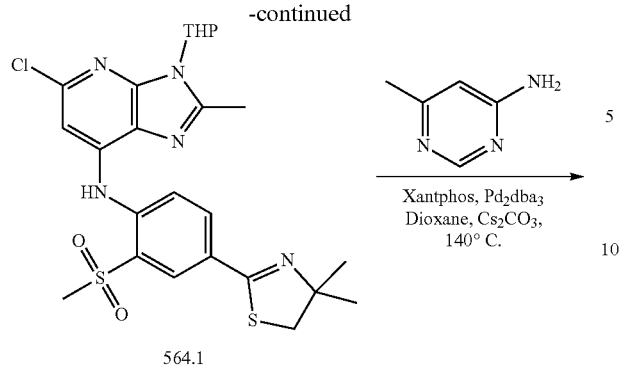

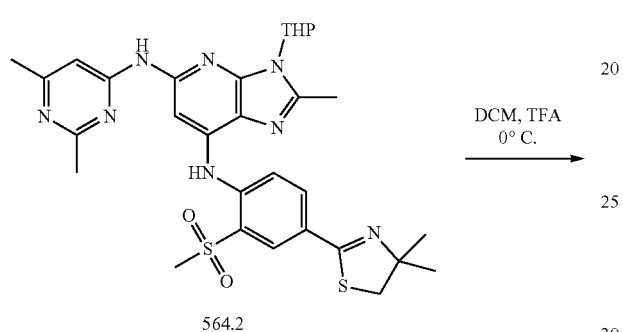

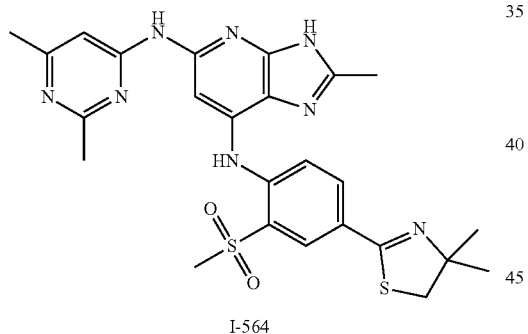

Synthesis of Compound 564.1.

Compound 564.1 was synthesized from 98.4 and 351.4 using general procedure A. (Yield: 25.45%). MS (ES): m/z 535.09 [M+H]⁺.

Synthesis of Compound 564.2.

Compound 564.2 was synthesized from 564.1 and 2,6-dimethylpyrimidin-4-amine using general procedure. (Yield: 44.45%). MS (ES): m/z 621.79 [M+H].

Synthesis of Compound I-564.

Compound I-564 was synthesized from 564.2 using general procedure C. (Yield: 70.90%). [M+H]⁺ MS(ES): m/z: 537.67 [M+H]⁺, LCMS purity: 100%, HPLC purity: 99.32%, 1H NMR (DMSO-d6, 400 MHz): 12.59 (s, 1H), 9.90 (s, 1H), 8.95 (s, 1H), 8.27 (s, 1H), 8.01-7.95 (m, 2H), 7.69 (s, 1H), 7.50 (s, 1H), 4.12 (s, 1H), 3.31 (s, 3H), 3.19 (s, 1H), 2.48 (s, 3H), 2.43 (s, 3H), 2.32 (s, 3H), 1.42 (s, 6H).

Example 565: Synthesis of 2-(difluoromethyl)-N7-(4-(4,4-dimethyl-4,5-dihydrothiazol-2-yl)-2-(methylsulfonyl)phenyl)-N5-(5,6-dimethylpyrazin-2-yl)-3H-imidazo[4,5-b]pyridine-5,7-diamine, I-565

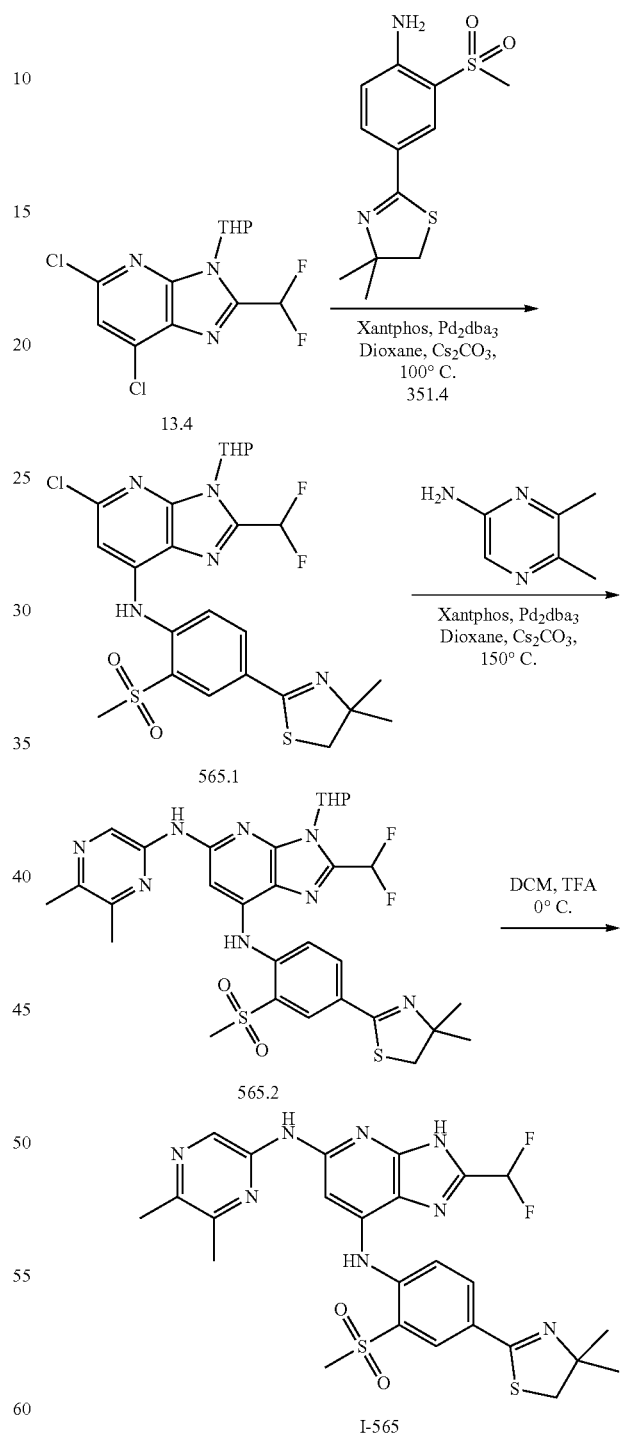

Synthesis of Compound 565.1.

Compound 565.1 was synthesized from 13.4 and 351.4 using general procedure A (Yield: 21.19%). MS(ES): m/z 571.07 [M+H]⁺.

Synthesis of Compound 565.2.

Compound 565.2 was synthesized from 565.1 and 5,6-dimethylpyrazin-2-amine using general procedure B. (Yield: 53.82%). MS(ES): m/z 657.77 [M+H]$^+$.

Synthesis of Compound I-565.

Compound I-565 was synthesized from 565.2 using general procedure C. (Yield: 51.80%). [M+H]$^+$. MS(ES): m/z: 573.56 [M+H]$^+$, LCMS purity: 99.33%, HPLC purity: 95.78%, 1H NMR (DMSO-d6, 400 MHz): 13.65 (s, 1H), 9.87 (s, 1H), 9.03 (s, 2H), 8.29 (s, 1H), 8.04-7.95 (d, J=5.6 Hz, 2H), 7.59 (s, 1H), 7.23 (t, 1H), 3.35 (s, 2H), 3.31 (s, 3H), 2.33 (s, 6H), 1.38 (s, 6H).

Example 566: Synthesis of N7-(4-(4,4-dimethyl-4,5-dihydrothiazol-2-yl)-2-(methylsulfonyl)phenyl)-N5-(5,6-dimethylpyrazin-2-yl)-2-methyl-3H-imidazo[4,5-b]pyridine-5,7-diamine, I-566

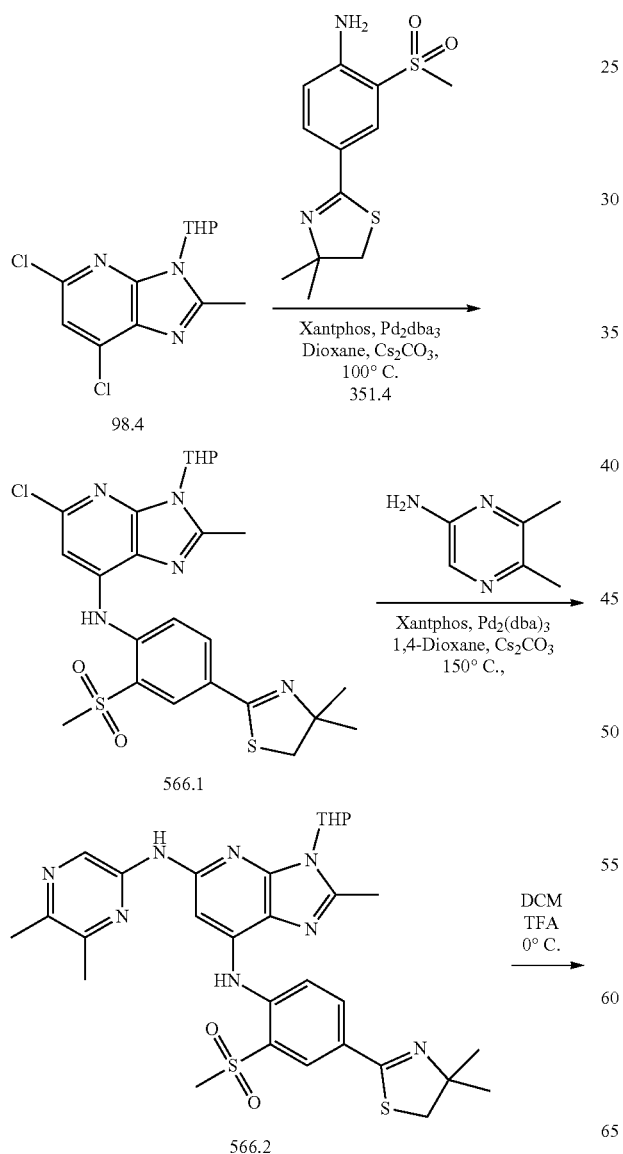

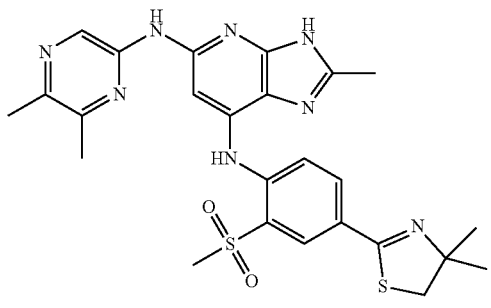

I-566

Synthesis of Compound 566.1.

Compound 566.1 was synthesized from 98.4 and 351.4 using general procedure A. (Yield: 25.45%). MS (ES): m/z 535.09 [M+H]$^+$.

Synthesis of Compound 566.2.

Compound 566.2 was synthesized from 566.1 and 5,6-dimethylpyrazin-2-amine using general procedure B. (Yield: 30.11%). MS (ES): m/z 621.79 [M+H]$^+$.

Synthesis of Compound I-566.

Compound I-566 was synthesized from 566.2 using general procedure C. (Yield: 66.10%). MS(ES): m/z: 537.60 [M+H]$^+$, LCMS purity: 99.82%, HPLC purity: 96.46%, 1H NMR (DMSO-d6, 400 MHz): 12.49 (s, 1H), 9.64 (s, 1H), 8.92-8.90 (d, J=8.4 Hz, 2H), 8.26 (s, 1H), 7.98 (s, 2H), 7.57 (s, 1H), 3.30 (s, 6H), 2.46 (s, 2H), 2.38 (s, 6H), 1.41 (s, 6H).

Example 567: Synthesis of N-(2-(difluoromethyl)-7-((4-(4,4-dimethyl-4,5-dihydrothiazol-2-yl)-2-(methylsulfonyl)phenyl)amino)-3H-imidazo[4,5-b]pyridin-5-yl)cyclopropanecarboxamide, I-567

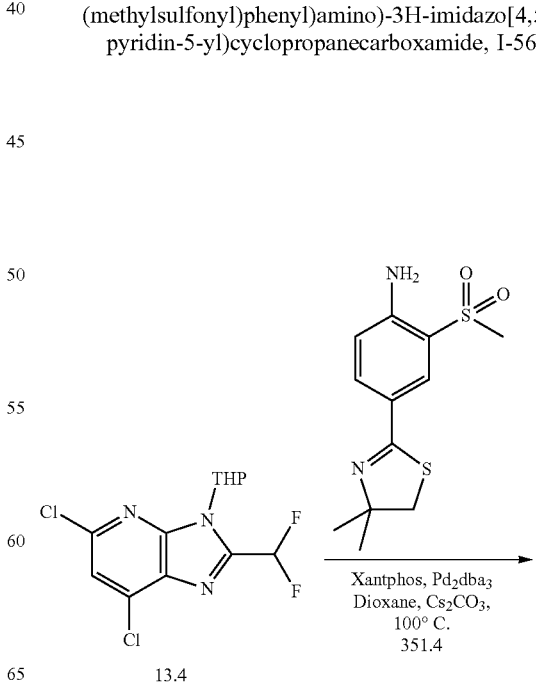

1115

-continued

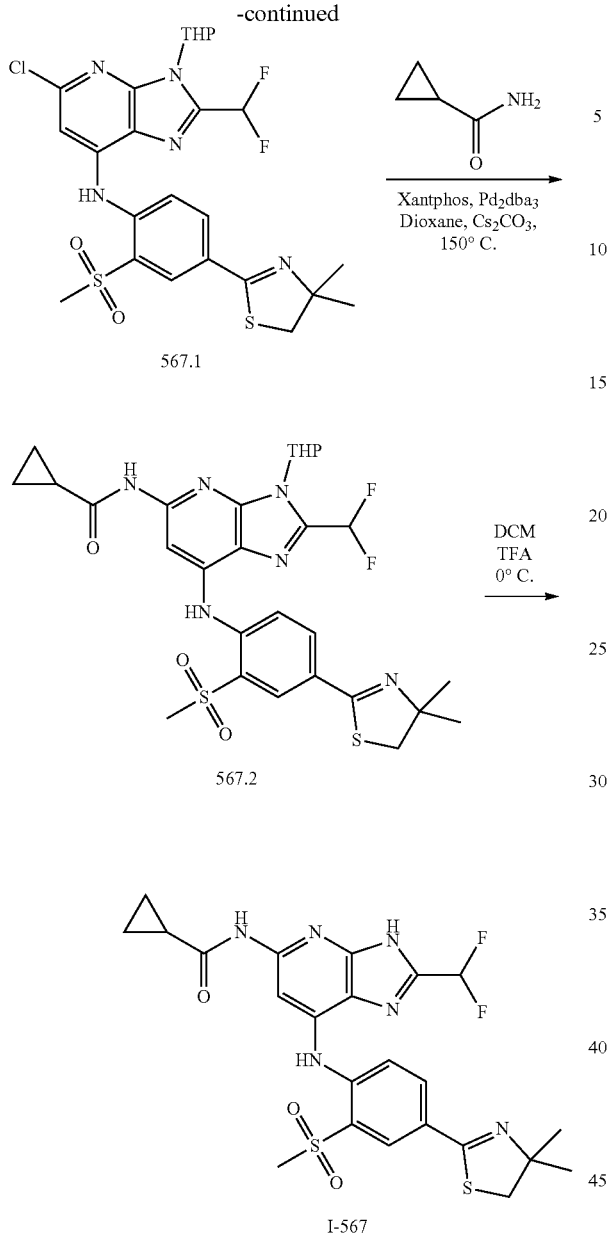

Synthesis of Compound 567.1.

Compound 567.1 was synthesized from 13.4 and 351.4 using general procedure A (Yield: 21.19%). MS(ES): m/z 571.07 [M+H]+.

Synthesis of Compound 567.2.

Compound 567.2 was synthesized from 567.1 and cyclopropanecarboxamide using general procedure B. (Yield: 64.50%). MS(ES): m/z 619.72 [M+H]+.

Synthesis of I-567.

Compound I-567 was synthesized from 567.2 using general procedure C (Yield: 53.05%). [M+H]+. MS(ES): m/z: 535.46 [M+H]+, LCMS purity: 95.77%, HPLC purity: 96.36%, 1H NMR (DMSO-d6, 400 MHz): 13.76 (s, 1H), 10.84 (s, 1H), 8.97 (s, 1H), 8.25 (s, 1H), 8.25-8.20 (m, 1H), 8.02-7.99 (m, 1H), 7.86-7.84 (m, 1H), 7.26 (t, 1H), 3.52 (s, 2H), 3.29 (s, 3H), 2.05 (s, 1H), 1.41 (s, 6H), 0.81 (bs, 4H).

1116

Example 568: Synthesis of N-(7-((4-(4,4-dimethyl-4,5-dihydrothiazol-2-yl)-2-(methylsulfonyl)phenyl)amino)-2-methyl-3H-imidazo[4,5-b]pyridin-5-yl)cyclopropanecarboxamide, I-568

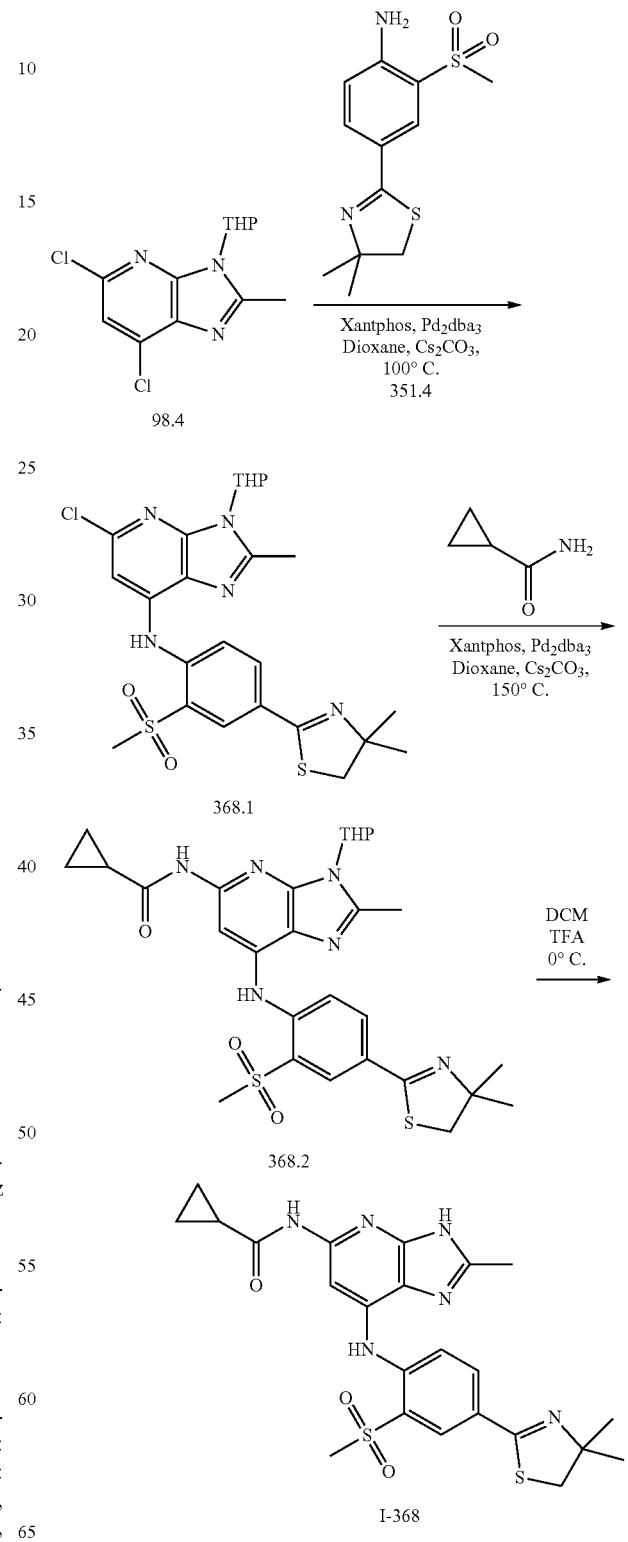

Synthesis of Compound 368.1.

Compound 368.1 was synthesized from 98.4 and 351.4 using general procedure A. (Yield: 25.45%). MS (ES): m/z 535.09 [M+H]⁺.

Synthesis of Compound 368.2

Compound 368.2 was synthesized from 368.1 and cyclopropanecarboxamide using general procedure B. (Yield: 45.83%). MS (ES): m/z 583.74 [M+H]⁺.

Synthesis of Compound I-368.

Compound I-368 was synthesized from 368.2 using general procedure C. (Yield: 74.02%). MS(ES): m/z: 499.56 [M+H]⁺, LCMS purity: 98.15%, HPLC purity: 98.32%, 1H NMR (DMSO-d6, 400 MHz): 12.57 (s, 1H), 10.66 (s, 1H), 8.82 (s, 1H), 8.22 (d, J=8.4 Hz, 1H), 8.09 (s, 1H), 7.98-7.96 (d, J=8.4 Hz, 1H), 7.82-7.80 (d, J=8.8 Hz, 1H), 3.28 (s, 3H), 3.17 (s, 2H), 2.48 (s, 3H), 2.00 (s, 1H), 1.40 (s, 6H), 0.78 (bs, 4H).

Example 569/570: Synthesis of (R)-6-((2-methyl-7-((2-(methylsulfonyl)-4-(tetrahydrofuran-2-yl)phenyl)amino)-3H-imidazo[4,5-b]pyridin-5-yl)amino)picolinonitrile, I-569 and (S)-6-((2-methyl-7-((2-(methylsulfonyl)-4-(tetrahydrofuran-2-yl)phenyl)amino)-3H-imidazo[4,5-b]pyridin-5-yl)amino)picolinonitrile, I-570

Synthesis of Compound I-569 and I-570.

Isomers of I-544 (0.095 g) were separated out using column CHIRALPAK AD-H (250 mm*4.6 mm, 5u) and 0.1% D EA_HEX_IPA-MEOH (50-50) flow rate of 4 mL/min. to get pure fraction-1 (FR-a) and fraction-2 (FR-b). FR-a was concentrated in vacuo at 30° C. to afford pure I-569 (0.025 g). MS(ES): m/z: 490.56 [M+H]⁺, LCMS purity: 100%, HPLC purity: 99.26%, Chiral HPLC Purity: 100%, 1H NMR (DMSO-d6, 400 MHz): 13.48 (s, 1H), 10.16 (s, 1H), 8.64 (m, 1H), 7.96-7.77 (m, 5H), 7.48-7.44 (m, 2H), 4.95-4.91 (t, J=15.8 Hz, 1H), 4.06-4.01 (m, 1H), 3.89-3.84 (m, 1H), 3.22 (s, 3H), 2.61 (s, 3H), 2.42-2.32 (m, 1H), 2.03-1.96 (m, 2H), 1.78-1.71 (m, 1H). FR-b was concentrated in vacuo at 30° C. to afford pure I-570 (0.027 g). MS(ES): m/z 490.56 [M+H]⁺, LCMS purity: 98.76%, HPLC Purity: 97.57%, Chiral HPLC: (95.96%), 1H NMR (MeOD, 400 MHz): 12.49 (s, 1H), 9.96 (s, 1H), 8.66 (s, 1H), 7.99-7.97 (d, J=8.8 Hz, 1H), 7.92-7.90 (d, J=8.8 Hz, 1H), 7.86-7.75 (m, 3H), 7.58 (s, 1H), 7.43-7.41 (d, J=7.2 Hz, 1H), 4.92-4.89 (t, J=7.2 Hz, 1H), 4.06-4.00 (m, 1H), 3.88-3.83 (m, 1H), 3.22 (s, 3H), 2.48 (s, 3H), 2.40-2.32 (m, 1H), 2.02-1.95 (m, 2H), 1.79-1.70 (m, 1H).

Example 571: Synthesis of N-(2-(difluoromethyl)-7-((4-(5,5-difluorotetrahydro-2H-pyran-2-yl)-2-(methylsulfonyl)phenyl)amino)-3H-imidazo[4,5-b]pyridin-5-yl)cyclopropanecarboxamide, I-571

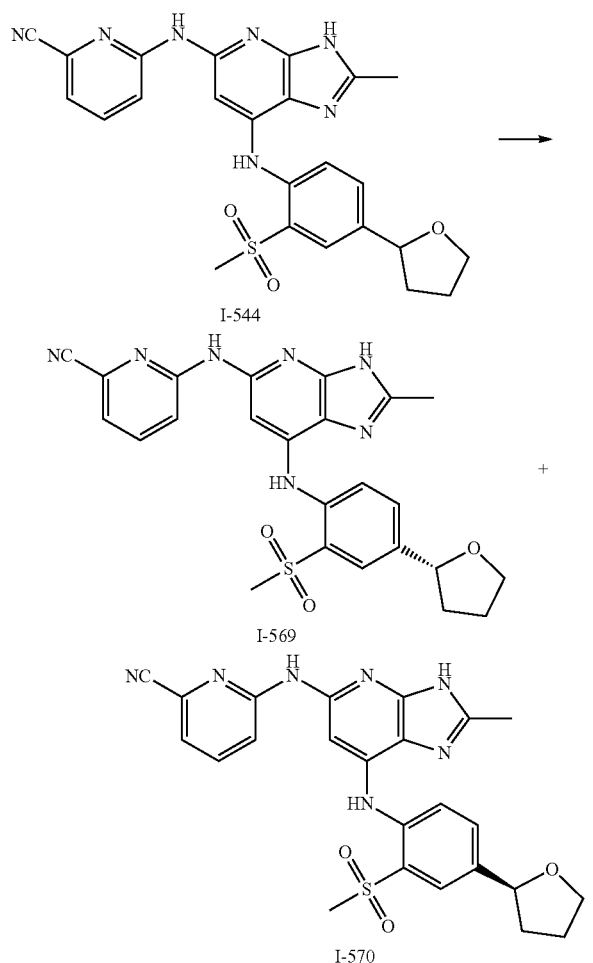

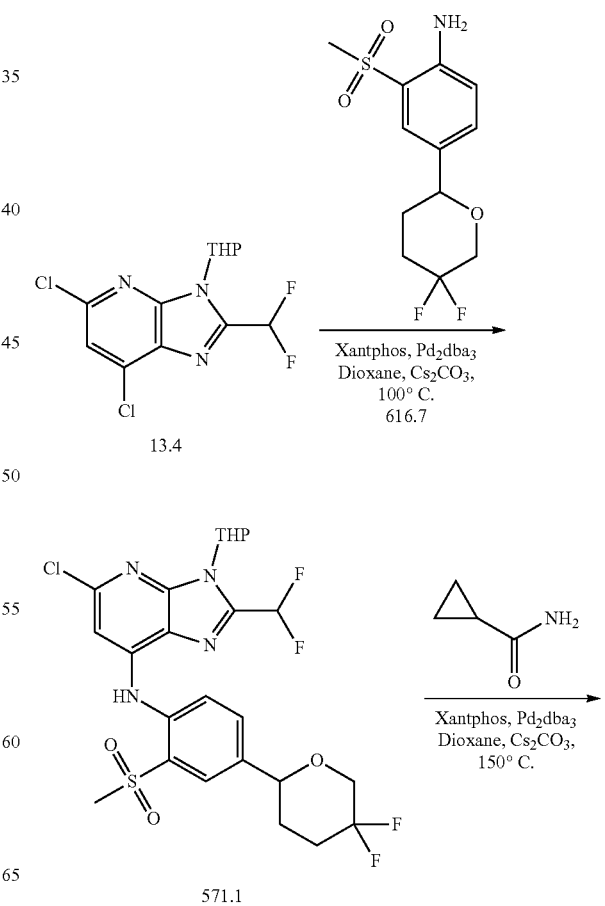

1119
-continued

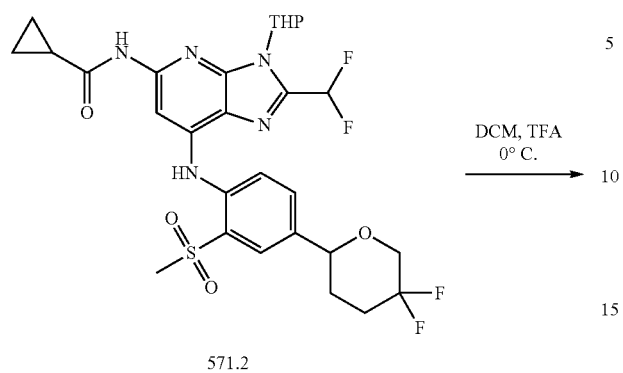

571.2

↓ DCM, TFA
0° C.

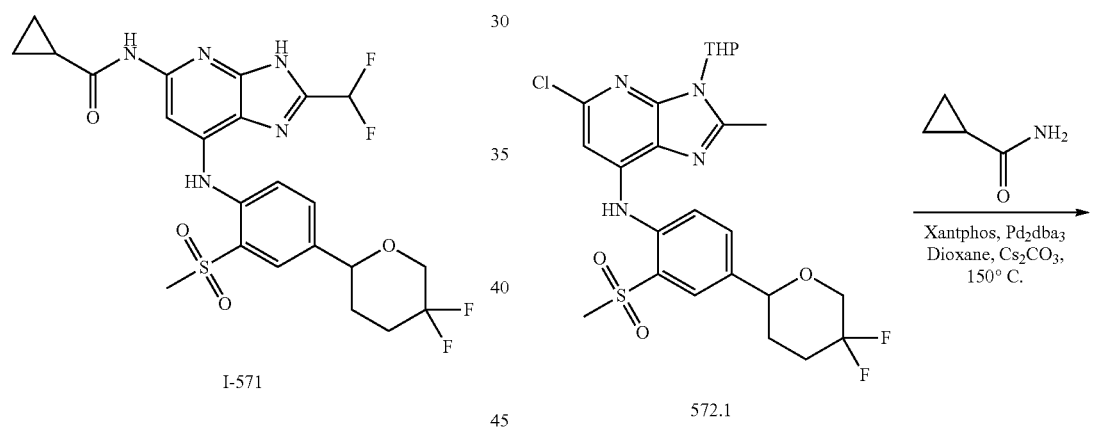

I-571

Synthesis of Compound 571.1.

Compound 571.1 was synthesized from 13.4 and 616.7 using general procedure A to obtain 2.0. (Yield: 30.49%). MS (ES): m/z 577.99 [M+H]+.

Synthesis of Compound 571.2.

Compound 571.2 was synthesized from 571.1 and cyclopropanecarboxamide using general procedure B. (Yield: 77.29%). MS (ES): m/z 626.64 [M+H]+.

Synthesis of Compound I-571.

Compound I-571 was synthesized from 571.2 using general procedure C. (Yield: 97.09%). MS(ES): m/z: 542.55 [M+H]+, LCMS purity: 97.91%, HPLC purity: 96.91%, Chiral HPLC Purity: 49.80% and 48.78%, 1H NMR (DMSO-d6, 400 MHz): 13.68 (s, 1H), 10.76 (s, 1H), 8.77 (s, 1H), 8.09 (s, 1H), 7.92 (s, 1H), 7.80-7.73 (m, 2H), 7.26 (t, 1H), 4.72-4.69 (d, J=8.0 Hz, 1H), 4.09 (s, 1H), 3.90-3.79 (m, 1H), 3.23 (s, 3H), 2.28 (s, 2H), 2.20-2.19 (d, 1H), 2.06-2.03 (t, 1H), 1.81-1.75 (m, 1H), 0.79 (bs, 4H).

1120

Example 572: Synthesis of N-(7-((4-(5,5-difluoro-tetrahydro-2H-pyran-2-yl)-2-(methylsulfonyl)phenyl)amino)-2-methyl-3H-imidazo[4,5-b]pyridin-5-yl)cyclopropanecarboxamide, I-572

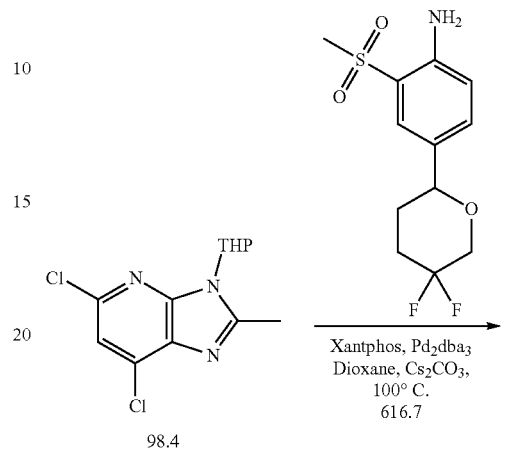

98.4    616.7

↓ Xantphos, Pd2dba3
Dioxane, Cs2CO3,
100° C.

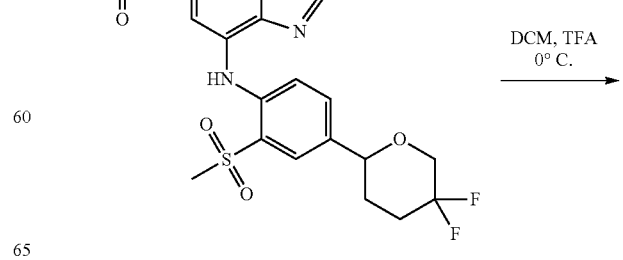

572.1

↓ Xantphos, Pd2dba3
Dioxane, Cs2CO3,
150° C.

572.2

↓ DCM, TFA
0° C.

-continued

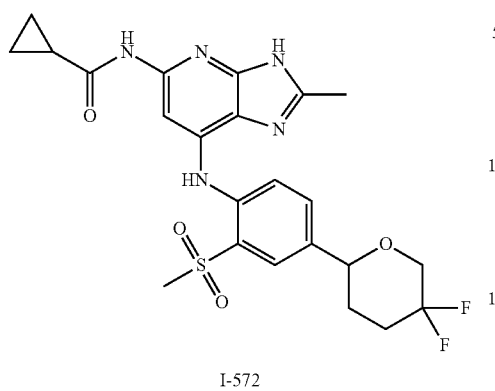

I-572

Synthesis of Compound 572.1.

Compound 572.1 was synthesized from 98.4 and 616.7 using general procedure A. (Yield: 30.63%). MS (ES): m/z 542.01 [M+H]$^+$.

Synthesis of Compound 572.2.

Compound 572.2 was synthesized from 572.1 and cyclopropanecarboxamide using general procedure B. (Yield: 73.13%). MS (ES): m/z 590.66 [M+H]$^+$.

Synthesis of Compound I-572.

Compound I-572 was synthesized from 572.2 using general procedure C. (Yield: 97.20%). MS(ES): m/z: 506.66 [M+H]$^+$, LCMS purity: 98.02%, HPLC purity: 96.81%, 1H NMR (DMSO-d6, 400 MHz): 12.49 (s, 1H), 10.58 (s, 1H), 8.58 (s, 1H), 8.00 (s, 1H), 7.88 (s, 1H), 7.77-7.69 (m, 2H), 4.69-4.67 (d, J=8.0 Hz, 1H), 4.12-4.06 (m, 1H), 3.20 (s, 3H), 3.17 (s, 2H), 2.49 (s, 3H), 2.30-2.14 (m, 4H), 0.76 (bs, 4H).

Example 573: Synthesis of 6-((7-((2-methoxy-3-(thiazol-2-yl)phenyl)amino)-2-methyl-3H-imidazo[4,5-b]pyridin-5-yl)amino)picolinonitrile, I-573

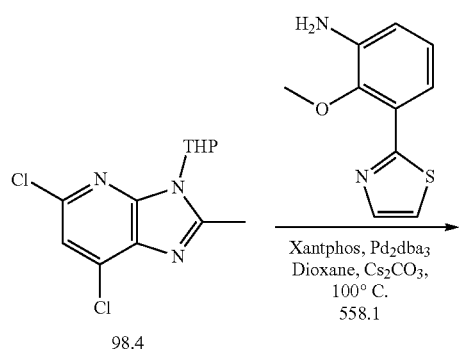

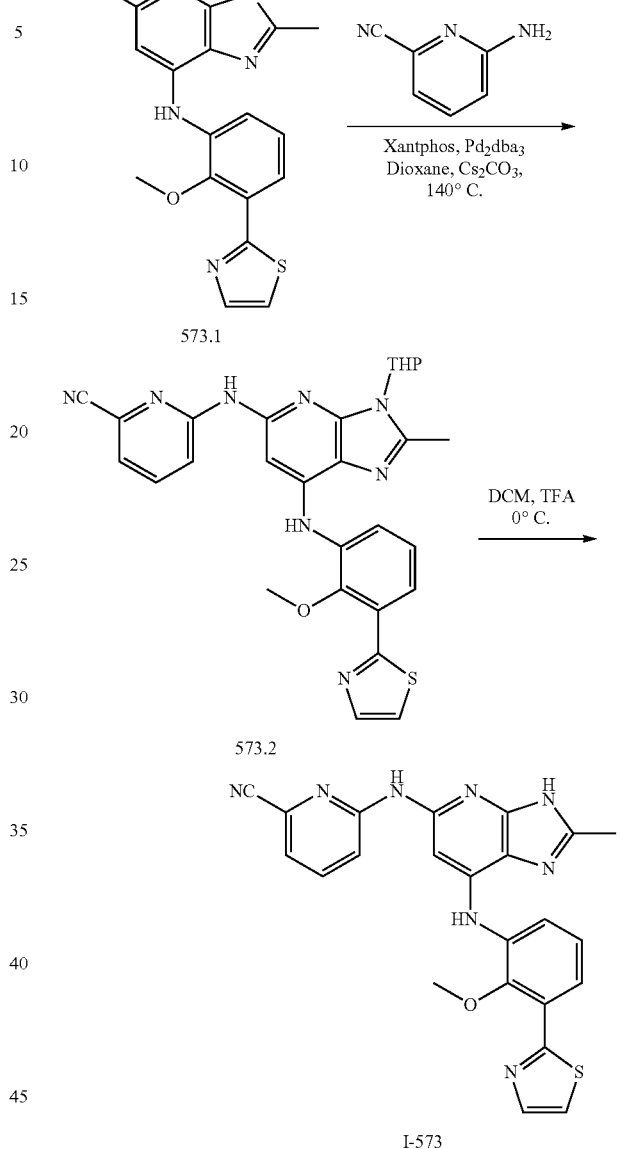

I-573

Synthesis of Compound 573.1.

Compound 573.1 was synthesized from 98.4 and 558.1 using general procedure A. (Yield: 31.38%). MS (ES): m/z 456.96 [M+H]$^+$.

Synthesis of Compound 573.2.

Compound 573.2 was synthesized from 573.1 and 6-aminopicolinonitrile using general procedure B. (Yield: 55.02%). MS (ES): m/z 539.63 [M+H]$^+$.

Synthesis of Compound I-573.

Compound I-573 was synthesized from 573.2 using general procedure (Yield: 63.81%). MS(ES): m/z: 455.57 [M+H]$^+$, LCMS purity: 100%, HPLC purity: 98.75%, 1H NMR (DMSO, 400 MHz): 12.50 (s, 1H), 9.88 (s, 1H), 8.21-8.19 (m, 2H), 8.06-8.00 (m, 2H), 7.87-7.80 (m, 2H), 7.61-7.59 (d, J=7.2 Hz, 1H), 7.40-7.33 (m, 2H), 7.02 (s, 1H), 3.78 (s, 3H), 2.47 (s, 3H).

Example 574: Synthesis of 6-((2-(difluoromethyl)-7-((2-methoxy-3-(2-methyl-2H-1,2,3-triazol-4-yl)phenyl)amino)-3H-imidazo[4,5-b]pyridin-5-yl)amino)picolinonitrile, I-574

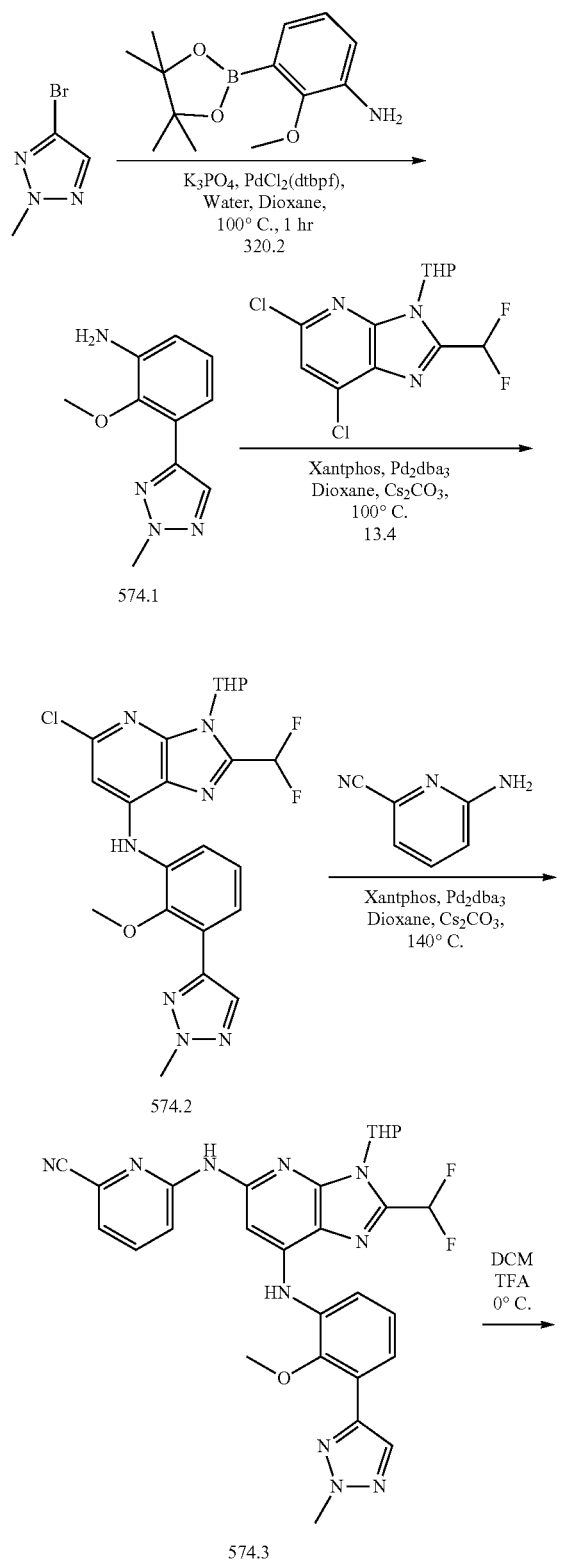

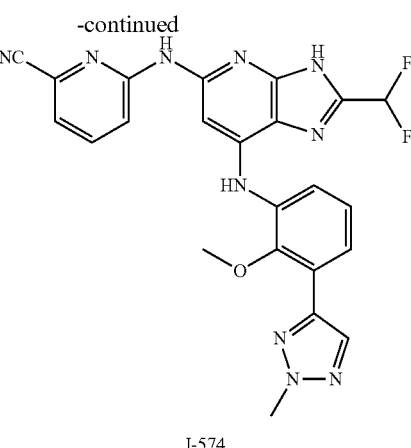

I-574

Synthesis of Compound 574.1.

To a solution of 4-bromo-2-methyl-2H-1,2,3-triazole (0.500 g, 3.09 mmol, 1 eq) in 1,4-dioxane (6 mL) and water (4 mL) was added 320.1 (0.845 g, 3.40 mmol, 1.5 eq), and potassium phosphate (1.97 g, 9.31 mmol, 3 eq). The reaction mixture was degassed by argon for 30 min. [1,1'-Pd$_2$(dba)$_3$ (0.085 g, 9.31 mmol, 0.03 eq), was added into reaction mixture and again reaction mixture was degassed by argon for 30 min. Further reaction mixture was stirred at 100° C. for 1 h. Upon completion, reaction mixture transferred into water and extracted with ethyl acetate. Organic layers were combined, dried over Na$_2$SO$_4$ and concentrated in vacuo to obtain crude product. This was purified by column chromatography and compound was eluted in 20% ethyl acetate in hexane to obtain pure 574.1 (0.300 g, 47.59%). MS(ES): m/z 205.23 [M+H]$^+$.

Synthesis of Compound 574.2.

Compound 574.2 was synthesized from 574.1 and 13.4 using general procedure A. (Yield: 35.07%). MS (ES): m/z 490.91 [M+H]$^+$.

Synthesis of Compound 574.3.

Compound 574.2 was synthesized from 574.2 and 6-aminopicolinonitrile using general procedure B. (Yield: 53.48%). MS (ES): m/z 573.58 [M+H]$^+$.

Synthesis of Compound I-574.

Compound I-574 was synthesized from 574.3 using general procedure C. (Yield: 70.33%). [M+H]$^+$ MS(ES): m/z: 489.45 [M+H]$^+$, LCMS purity: 99.59%, HPLC purity: 98.21%, 1H NMR (DMSO-d6, 400 MHz): 13.51 (s, 1H), 10.06 (s, 1H), 8.37 (s, 1H), 8.28-8.26 (d, J=8.8 Hz, 1H), 8.13 (s, 1H), 7.88-7.84 (t, J=12.4 Hz, 1H), 7.70-7.68 (d, J=, 1H), 7.55-7.53 (d, J=, 1H), 7.45-7.43 (d, J=, 1H), 7.34-7.30 (t, J=, 1H), 7.22 (s, 1H), 7.08 (s, 1H), 4.24 (s, 3H), 3.65 (s, 3H).

Example 575: Synthesis of 3-isopropyl-6-((2-methyl-7-((2-(methylsulfonyl)-4-(tetrahydrofuran-2-yl)phenyl)amino)-3H-imidazo[4,5-b]pyridin-5-yl)amino)picolinonitrile, I-575

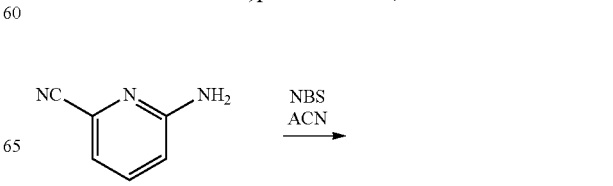

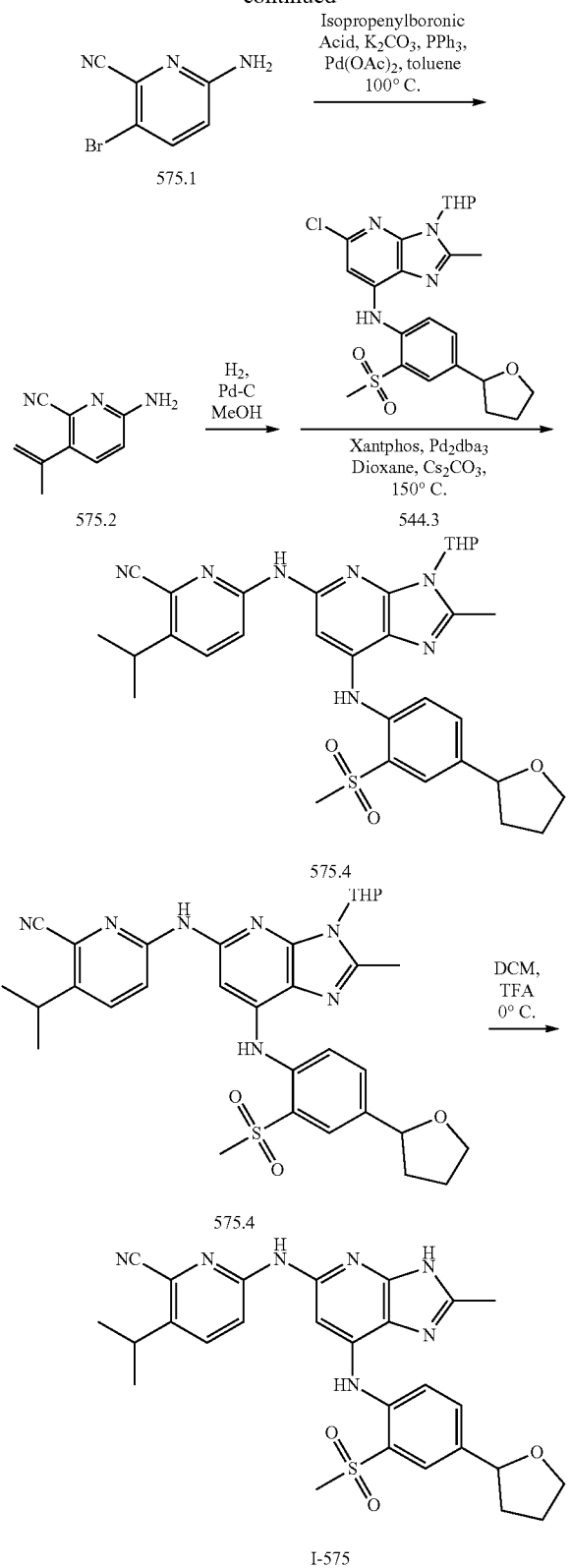

stirred for 2 h at r.t. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 15% ethyl acetate in hexane to obtain pure 575.1 (2.1 g, 42.11%). MS(ES): m/z 199.02 $[M+H]^+$.

Synthesis of Compound 575.2.

To a solution of 575.1 (2.1 g, 10.60 mmol, 1 eq) in Toluene (16 mL) and water (4 mL) was added Isopropenylboronic acid (1.12 g, 12.72 mmol, 1.2 eq), potassium carbonate (4.4 g, 31.81 mmol, 3 eq), Triphenylphosphine (0.214 g, 2.12 mmol, 0.2 eq). The reaction mixture was degassed by argon for 30 min. Palladium(II) acetate (0.237 g, 1.06 mmol, 0.1 eq), was added into reaction mixture and again degassed by argon for 30 min. Further reaction mixture was stirred at 100° C. for 5 h. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 575.2 (1.35 g, 79.97%). MS(ES): m/z 160.19 $[M+H]^+$.

Synthesis of Compound 575.3.

To a solution of 575.2 (1.35 g, 8.48 mmol, 1.0 eq) in MeOH (15 mL), 10% Pd/C (0.100 g) was added. Hydrogen was purged through reaction mixture for 2-3 hr at r.t. Upon completion, reaction mixture was filtered through celite-bed and washed with ethanol. Filtrate was concentrated in vacuo to obtain 575.3 (1.1 g, 80.46%). MS(ES): m/z 162.21 $[M+H]^+$.

Synthesis of Compound 575.4.

Compound 575.4 was synthesized from 575.3 and 544.3 using general procedure B to obtain 2.1. (Yield: 65.72%). MS (ES): m/z 616.75 $[M+H]^+$.

Synthesis of Compound I-575.

Compound I-575 was synthesized from 575.4 using general procedure C. (Yield: 92.66%). MS(ES): m/z: 532.60 $[M+H]^+$, LCMS purity: 98.17%, HPLC purity: 96.25%, Chiral HPLC Purity: 41.56% and 58.18%, 1H NMR (DMSO-d6, 400 MHz): 12.45 (s, 1H), 9.87 (s, 1H), 8.69 (s, 1H), 7.93-7.91 (d, J=8.3 Hz, 2H), 7.86-7.84 (d, J=12.8 Hz, 2H), 7.79-7.71 (m, 1H), 7.63 (s, 1H), 4.92-4.88 (m, 1H), 4.05-4.00 (m, 1H), 3.88-3.82 (m, 1H), 3.21 (s, 3H), 2.48 (s, 3H), 2.38-2.32 (m, 2H), 2.02-1.95 (m, 2H), 1.79-1.71 (m, 1H), 1.27-1.17 (m, 6H).

Example 576: Synthesis of N-(2-(difluoromethyl)-7-((4-(1,5-dimethyl-1H-pyrazol-3-yl)-3-fluoro-2-methoxyphenyl)amino)-3H-imidazo[4,5-b]pyridin-5-yl)cyclopropanecarboxamide, I-576

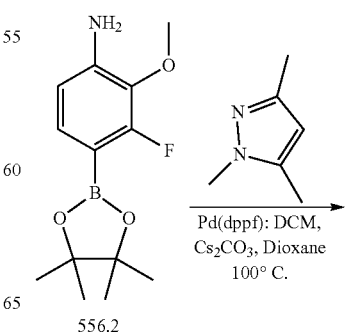

Synthesis of Compound 575.1.

To a solution of 6-aminopicolinonitrile (3 g, 25.18 mmol, 1.0 eq) in acetonitrile (30 mL) was added N-Bromosuccinimide (9 g, 50.42 mmol, 2.0 eq) at r.t. Reaction mixture was

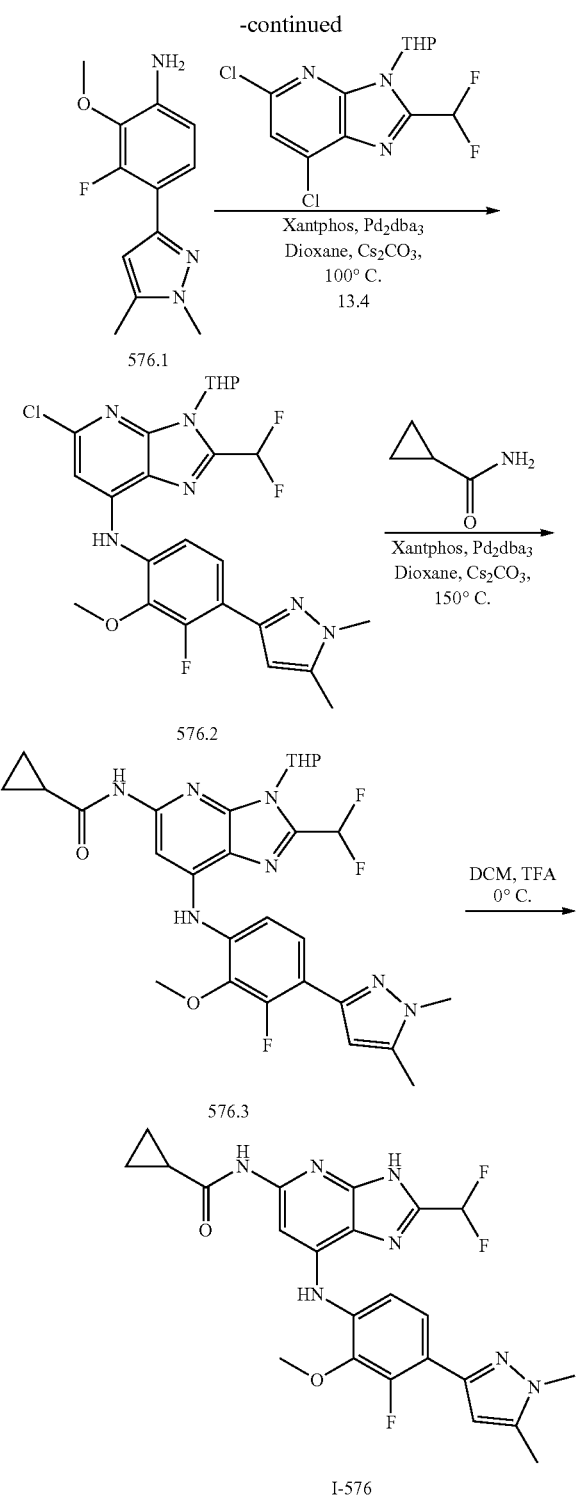

576.1

576.2

576.3

I-576

Synthesis of Compound 576.1.

To a solution of 556.2 (1 g, 3.74 mmol, 1.0 eq), in 1,4-dioxane (16 mL) and water (4 mL) was added 3-iodo-1,5-dimethyl-1H-pyrazole (0.914 g, 4.12 mmol, 1.1 eq), Cs₂CO₃ (2.43 g, 74.90 mmol, 2.0 eq). The reaction mixture was degassed by argon for 30 min. [1,1'-Bis(diphenylphosphino)ferrocene]dichloropalladium(II) CH₂Cl₂ complex (0.458 g, 0.561 mmol, 0.15 eq) was added into the reaction mixture and again degassed by argon for 20 min. Further reaction mixture was stirred at 100° C. for 5 h. Upon completion, reaction mixture transferred into water and extracted with ethyl acetate. Organic layers were combined, dried over Na₂SO₄ and concentrated in vacuo to obtain crude product. This was purified by column chromatography and compound was eluted in 40% ethyl acetate in hexane to obtain pure 576.1 (0.440 g, 49.96%). MS(ES): m/z 236.26 [M+H]⁺.

Synthesis of Compound 576.2.

Compound 576.2 was synthesized from 576.1 and 13.4 using general procedure A to obtain 1.4. (Yield: 37.73%). MS(ES): m/z 521.94 [M+H]⁺.

Synthesis of Compound 576.3.

Compound 576.3 was synthesized from 576.2 and cyclopropanecarboxamide using general procedure B. (Yield: 49.95%). MS(ES): m/z 574.62 [M+H]⁺.

Synthesis of Compound I-576.

Compound I-576 was synthesized from 576.3 using general procedure C (Yield: 71.61%). MS(ES): m/z: 486.57 [M+H]⁺, LCMS purity: 99.32%, HPLC purity: 98.84%, 1H NMR (DMSO-d6, 400 MHz): 10.25 (s, 1H), 7.78 (s, 1H), 7.56-7.50 (m, 2H), 7.39-7.37 (d, J=8.4 Hz, 1H), 7.21 (t, 1H), 6.80 (s, 1H), 6.40 (s, 1H), 3.93 (s, 3H), 3.79 (s, 3H), 2.31 (s, 3H), 1.98 (s, 1H), 0.79-0.72 (m, 4H).

Example 577: Synthesis of N-(7-((4-(1,5-dimethyl-1H-pyrazol-3-yl)-3-fluoro-2-methoxyphenyl)amino)-2-methyl-3H-imidazo[4,5-b]pyridin-5-yl)cyclopropanecarboxamide, I-577

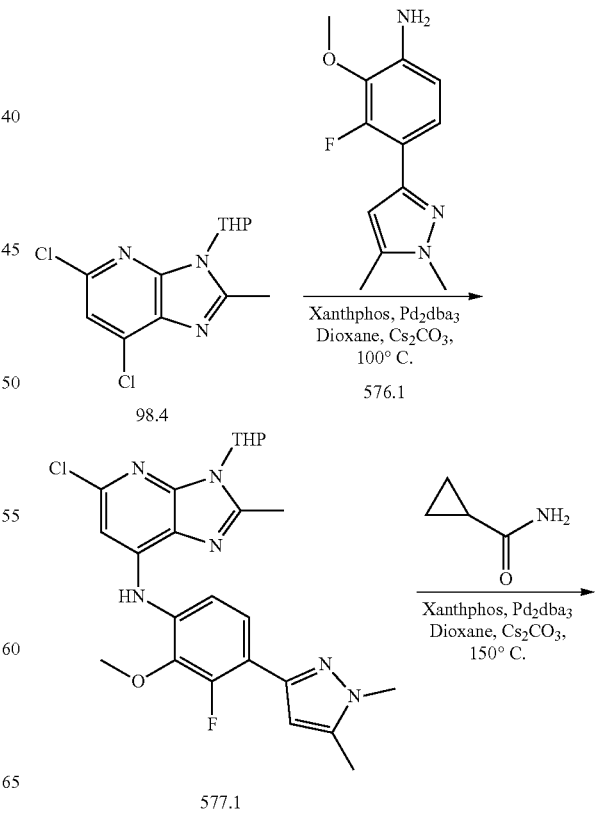

577.1

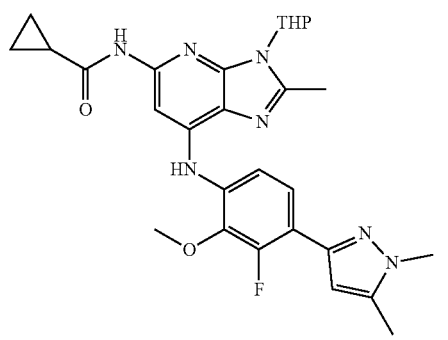

577.2

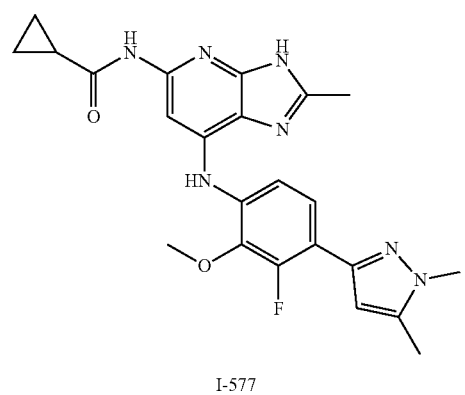

I-577

Synthesis of Compound 577.1.

Compound 577.1 was synthesized from 98.4 and 576.1 using general procedure A. (Yield: 26.82%). MS(ES): m/z 485.96 [M+H]+.

Synthesis of Compound 577.2.

Compound 577.2 was synthesized from 577.1 and cyclopropanecarboxamide using general procedure B. (Yield: 41.81%). MS(ES): m/z 534.61 [M+H]+.

Synthesis of Compound I-577.

Compound I-577 was synthesized from 577.2 using general procedure C. (Yield: 69.68%). MS(ES): m/z: 450.52 [M+H]+, LCMS purity: 100%, HPLC purity: 97.77%, 1H NMR (DMSO-d6, 400 MHz): 12.35 (s, 1H), 10.44 (s, 1H), 8.00 (s, 1H), 7.71 (s, 1H), 7.57-7.53 (t, J=11.8 Hz, 1H), 7.22-7.20 (d, J=6.8 Hz, 1H), 6.41-6.40 (d, J=4.0 Hz, 1H), 3.85-3.78 (d, 6H), 2.47 (s, 3H), 2.30 (s, 3H), 1.97 (s, 1H), 0.75 (bs, 4H).

Example 578: Synthesis of 2-(difluoromethyl)-N5-(2,6-dimethylpyrimidin-4-yl)-N7-(4-(2,5-dimethyl-thiazol-4-yl)-2-(methylsulfonyl)phenyl)-3H-imidazo[4,5-b]pyridine-5,7-diamine, I-578

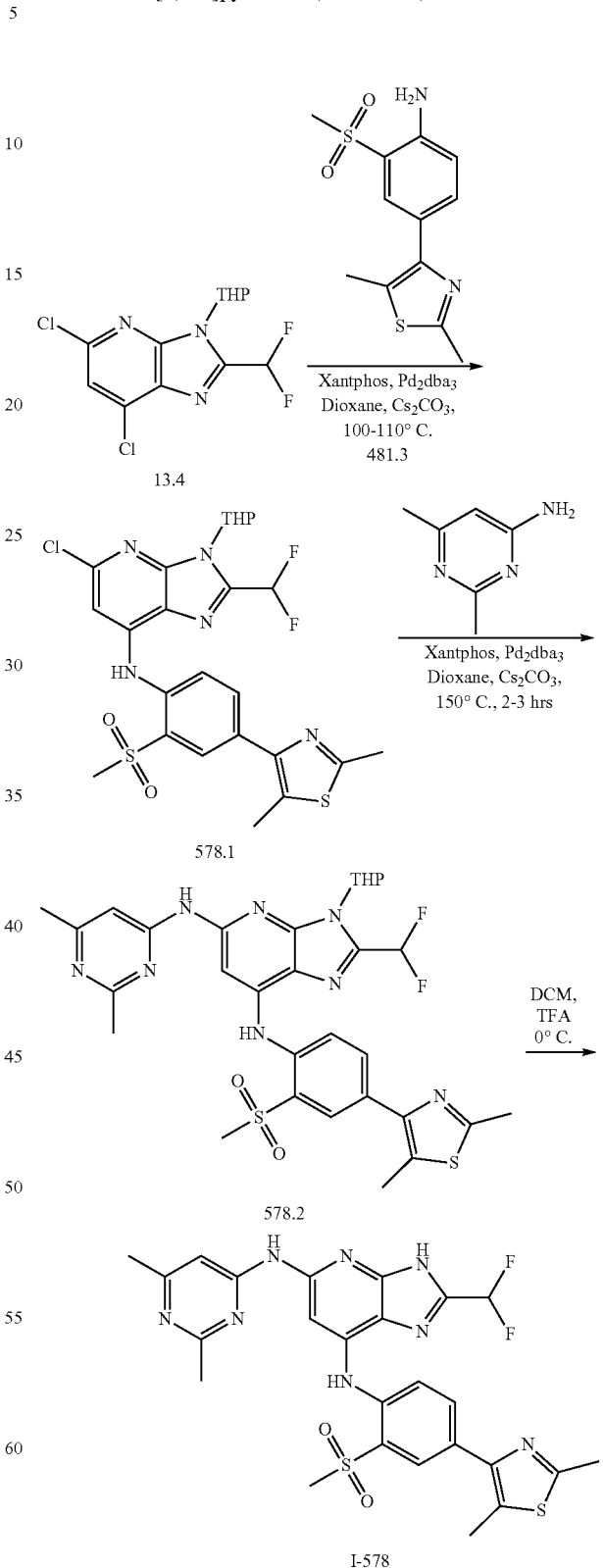

1131

Synthesis of Compound 578.1.

Compound 578.1 was synthesized from 13.4 and 481.3 using general procedure A. (Yield: 15.47%). MS(ES): m/z 569.05 [M+H]+.

Synthesis of Compound 578.2.

Compound 578.2 was synthesized from 578.1 and 2,6-dimethylpyrimidin-4-amine using general procedure (Yield: 52.05%). MS(ES): m/z 655.76 [M+H]+.

Synthesis of Compound I-578.

Compound I-578 was synthesized from 578.2 using general procedure C (Yield: 71.71%). MS(ES): m/z: 571.70 [M+H]+, LCMS purity: 98.32%, HPLC purity: 96.28%, 1H NMR (DMSO-d6, 400 MHz): 13.69 (s, 1H), 10.08 (s, 1H), 9.00 (s, 1H), 8.28 (s, 1H), 8.08-8.05 (m, 2H), 7.77 (s, 1H), 7.58 (s, 1H), 7.26 (s, 1H), 3.30 (s, 3H), 2.67 (s, 3H), 2.60 (s, 3H), 2.44 (s, 3H), 2.34 (s, 3H).

Example 579: Synthesis of N5-(2,6-dimethylpyrimidin-4-yl)-N7-(4-(2,5-dimethylthiazol-4-yl)-2-(methylsulfonyl)phenyl)-2-methyl-3H-imidazo[4,5-b]pyridine-5,7-diamine, I-579

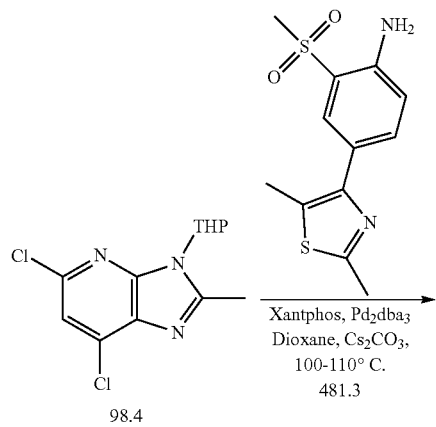

98.4

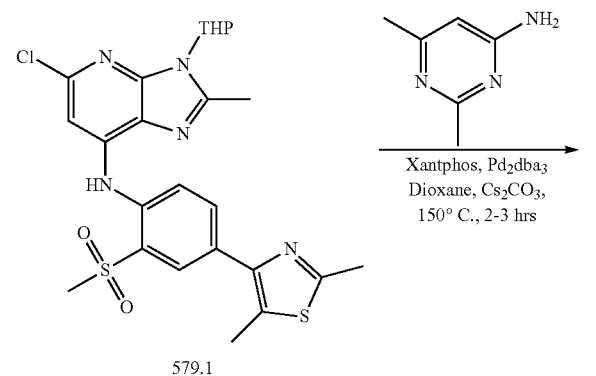

579.1

1132

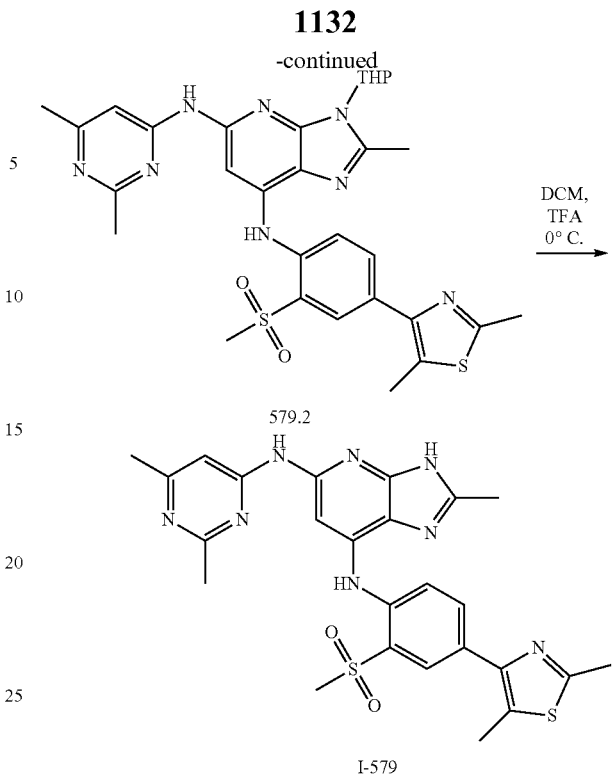

Synthesis of Compound 579.1.

Compound 579.1 was synthesized from 98.4 and 481.3 using general procedure A. (Yield: 13.45%). MS(ES): m/z 533.07 [M+H]+.

Synthesis of Compound 579.2.

Compound 579.2 was synthesized from 579.1 and 2,6-dimethylpyrimidin-4-amine using general procedure. (Yield: 42.99%). MS(ES): m/z 619.78 [M+H]+.

Synthesis of I-579.

Compound was synthesized using general procedure C. (Yield: 63.13%). MS(ES): m/z: 535.66 [M+H]+, LCMS purity: 99.42%, HPLC purity: 97.47%, 1H NMR (DMSO-d6, 400 MHz): 12.53 (s, 1H), 9.87 (s, 1H), 8.83 (s, 1H), 8.25 (s, 1H), 8.04-7.97 (m, 2H), 7.71 (s, 1H), 7.44 (s, 1H), 3.27 (s, 3H), 2.65 (s, 3H), 2.58 (s, 3H), 2.48 (s, 3H), 2.43 (s, 3H), 2.30 (s, 3H).

Example 580: Synthesis of 2-(difluoromethyl)-N5-(5,6-dimethylpyrazin-2-yl)-N7-(4-(2,5-dimethylthiazol-4-yl)-2-(methylsulfonyl)phenyl)-3H-imidazo[4,5-b]pyridine-5,7-diamine, I-580

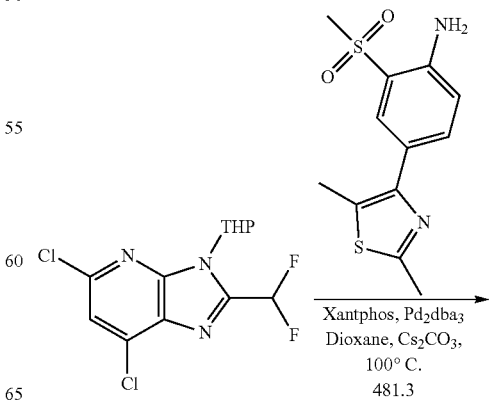

13.4

1133

-continued

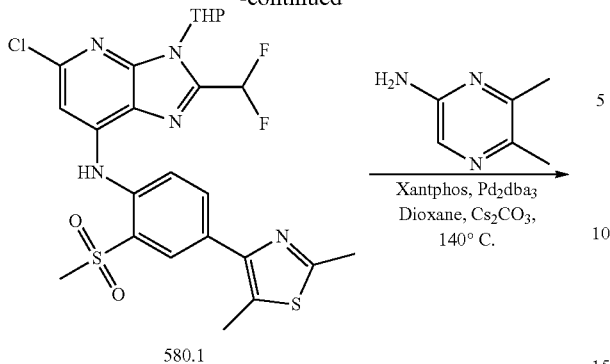

580.1

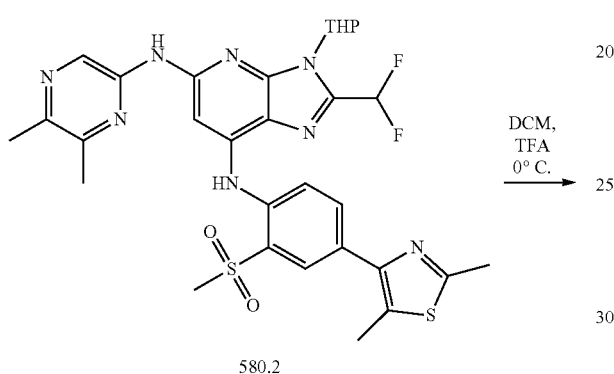

580.2

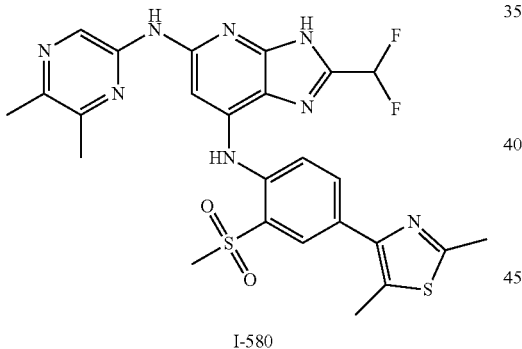

I-580

Synthesis of Compound 580.1.

Compound 580.1 was synthesized from 13.4 and 481.3 using general procedure A. (Yield: 15.47%). MS(ES): m/z 569.05 [M+H]$^+$.

Synthesis of Compound 580.2.

Compound 580.1 was synthesized from 580.1 and 5,6-dimethylpyrazin-2-amine using general procedure B. (Yield: 57.84%). MS(ES): m/z 655.76 [M+H]$^+$.

Synthesis of I-580.

Compound I-580 was synthesized from 580.2 using general procedure C. (Yield: 57.37%). MS(ES): m/z: 571.66 [M+H]$^+$, LCMS purity: 96.00%, HPLC purity: 95.99%, 1H NMR (DMSO, 400 MHz): 13.59 (s, 1H), 9.84 (s, 1H), 9.00 (s, 1H), 8.94 (s, 1H), 8.28 (s, 1H), 8.07-7.98 (m, 2H), 7.63 (s, 1H), 7.24 (t, 1H), 3.29 (s, 3H), 2.66 (s, 3H), 2.60 (s, 3H), 2.40 (s, 6H).

1134

Example 581: Synthesis of N5-(5,6-dimethylpyrazin-2-yl)-N7-(4-(2,5-dimethylthiazol-4-yl)-2-(methylsulfonyl)phenyl)-2-methyl-3H-imidazo[4,5-b]pyridine-5,7-diamine, I-581

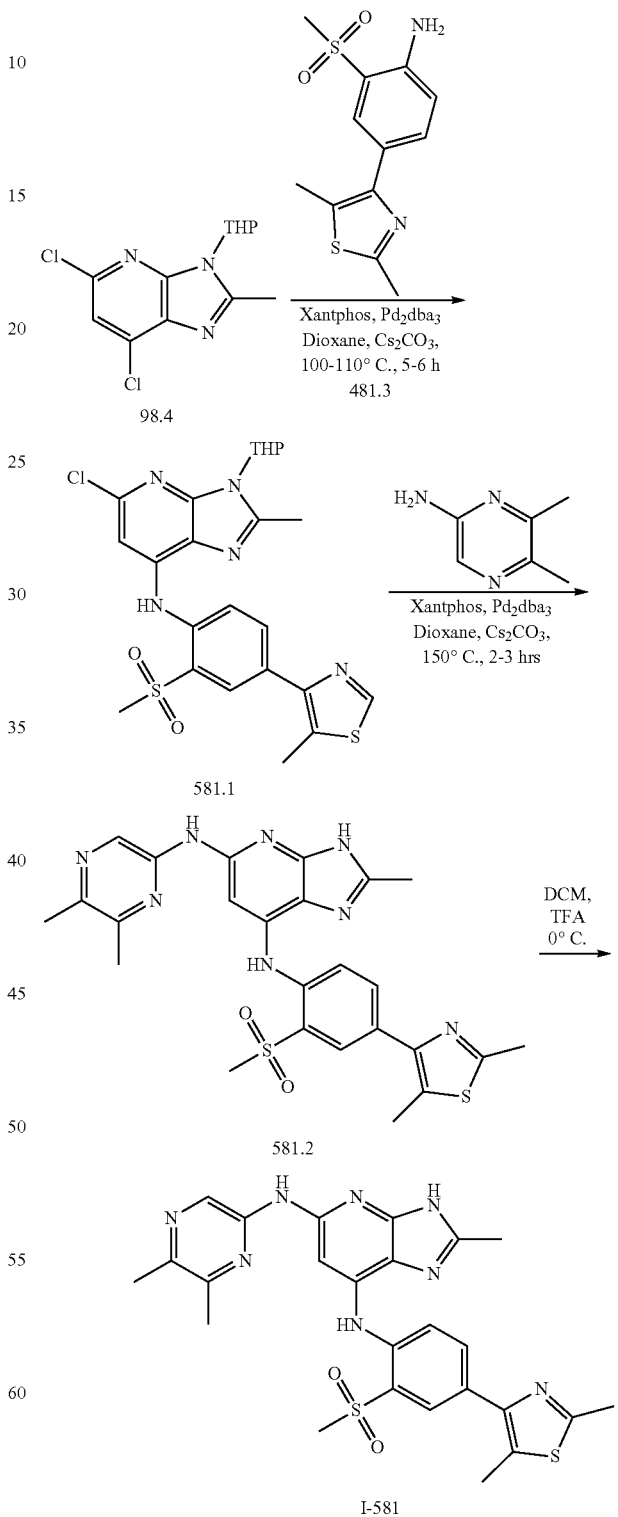

1135

Synthesis of Compound 581.1.

Compound 581.1 was synthesized from 481.3 and 98.4 using general procedure A. (Yield: 27.62%). MS(ES): m/z 519.43 [M+H]$^+$.

Synthesis of Compound 581.2.

Compound 581.2 was synthesized from 581.1 and 5,6-dimethylpyrazin-2-amine using general procedure B. (Yield: 54.80%). MS(ES): m/z 619.57 [M+H]$^+$.

Synthesis of I-581.

Compound I-581 was synthesized from 581.2 using general procedure C. (Yield: 61.08%). MS(ES): m/z: 535.65 [M+H]$^+$, LCMS purity, 98.28%, HPLC purity 98.05%, 1H NMR (DMSO, 400 MHz): 12.47 (s, 1H), 9.61 (s, 1H), 8.82 (s, 1H), 8.79 (s, 1H), 8.25 (s, 1H), 8.04-7.97 (m, 2H), 7.62 (t, 1H), 3.27 (s, 3H), 2.66 (s, 3H), 2.58 (s, 3H), 2.47 (m, 3H), 2.37 (s, 6H).

Example 582: Synthesis of N-(2-(difluoromethyl)-7-((4-(4,5-dimethylthiazol-2-yl)-2-methoxyphenyl)amino)-3H-imidazo[4,5-b]pyridin-5-yl)cyclopropanecarboxamide, I-582

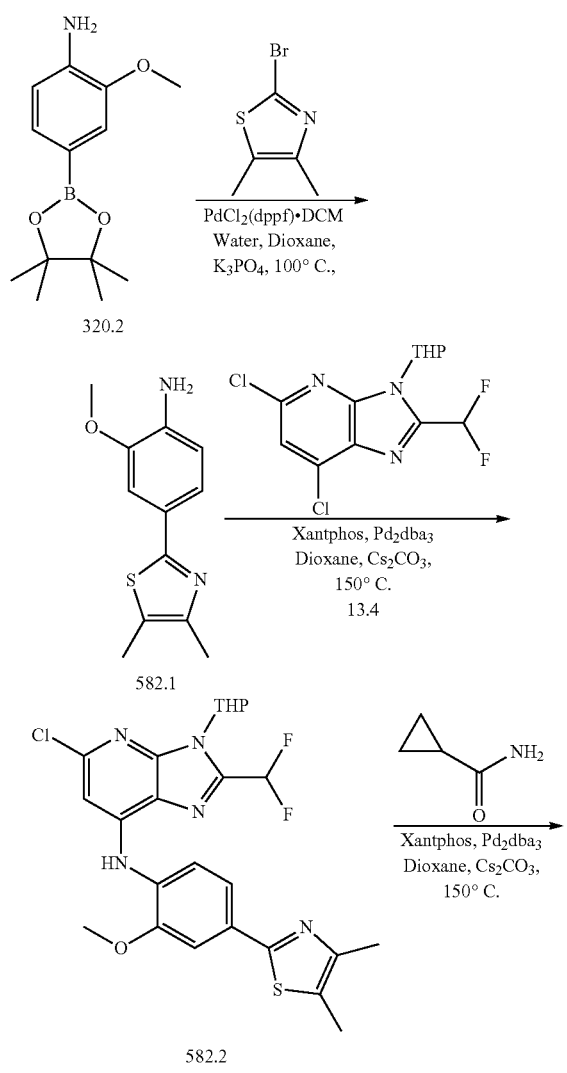

1136

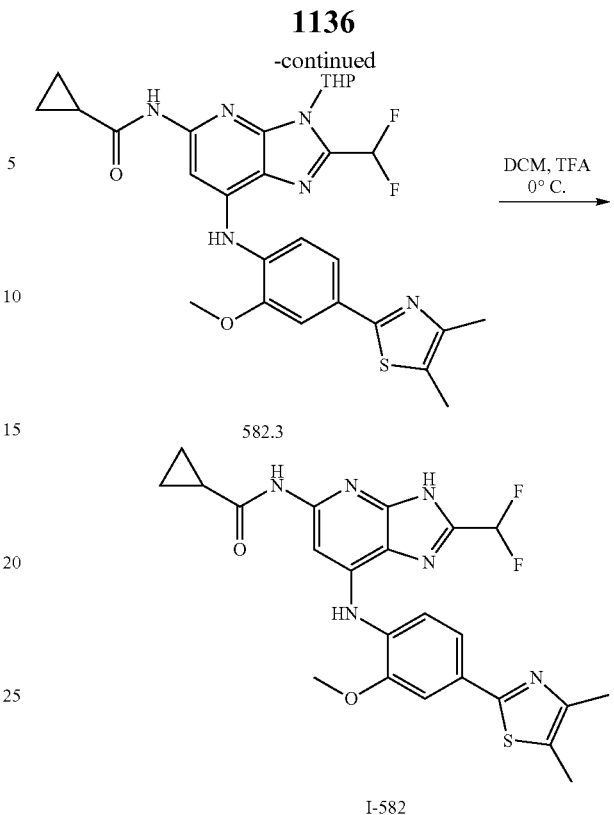

Synthesis of Compound 582.1.

To a solution of 320.2 (1 g, 4.21 mmol, 1 eq) in Dioxane (20 mL) and water (3 mL) was added 2-bromo-4,5-dimethylthiazole 1.1 (1.62 g, 8.43 mmol, 2 eq), and potassium carbonate (1.7 g, 12.04 mmol, 3 eq). The reaction mixture was degassed by argon for 30 min. DCM [1,1'-Bis(diphenylphosphino)ferrocene]dichloropalladium(II) (0.327 g, 4.01 mmol, 0.1 eq), was added into reaction mixture and again reaction mixture was degassed by argon for 30 min. Further reaction mixture was stirred at 100° C. for 12 h. Upon completion, reaction mixture transferred into water and extracted with ethyl acetate. Organic layers were combined, dried over Na$_2$SO$_4$ and concentrated in vacuo to obtain crude product. This was purified by column chromatography and compound was eluted in 20% ethyl acetate in hexane to obtain pure 582.1 (0.580 g, 58.73%). MS(ES): m/z 235.32 [M+H]$^+$.

Synthesis of Compound 582.2.

Compound 582.2 was synthesized from 582.1 and 13.4 using general procedure A. (Yield: 28.84%). MS (ES): m/z 521.00 [M+H].

Synthesis of Compound 582.3.

Compound 582.3 was synthesized from 582.2 and cyclopropanecarboxamide using general procedure B. (Yield: 47.42%). MS (ES): m/z 569.64 [M+H]$^+$.

Synthesis of Compound I-582.

Compound I-582 was synthesized from 582.3 using general procedure C (Yield: 67.06%). MS(ES): m/z: 485.50 [M+H]$^+$, LCMS purity: 100%, HPLC purity: 99.88%, 1H NMR (DMSO-d6, 400 MHz): 13.52 (s, 1H), 10.61 (s, 1H), 8.17 (s, 1H), 7.79 (s, 1H), 7.54 (s, 1H), 7.47-7.42 (m, 2H), 7.22 (t, 1H), 3.91 (s, 3H), 2.39 (s, 3H), 2.33 (s, 3H), 2.02 (s, 1H), 0.77 (bs, 4H).

Example 583: Synthesis of 6-((7-((4-(1,5-dimethyl-1H-pyrazol-3-yl)-2-(methylsulfonyl)phenyl)amino)-2-methyl-3H-imidazo[4,5-b]pyridin-5-yl)amino)picolinonitrile, I-583

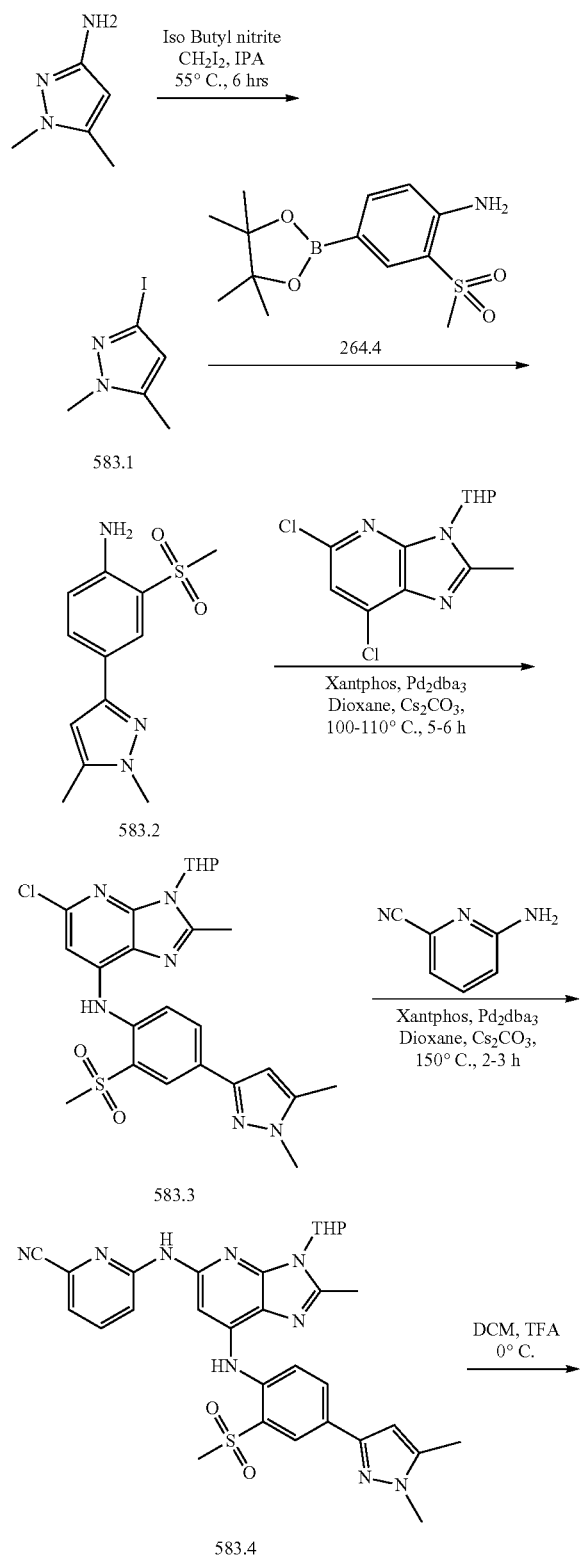

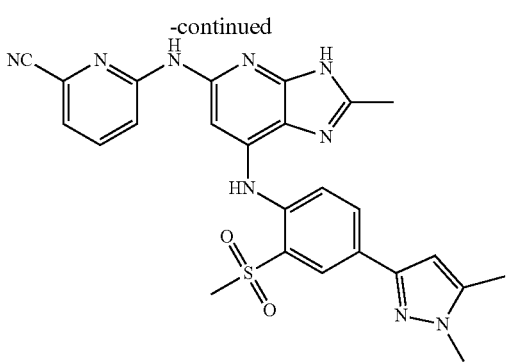

I-583

Synthesis of Compound 583.1.

To a solution of 1,5-dimethyl-1H-pyrazol-3-amine (5 g, 45.04 mmol, 1.0 eq) in isopropyl alcohol (50 mL), was added di-iodomethane (12.02 g, 45.04 mmol, 1.0 eq) and iso-butyl nitrite (1.55 g, 22.5 mmol, 0.5 eq). Reaction mixture was stirred at 55° C. for 6 h. After completion of the reaction, the reaction mixture was transferred into water and extracted with ethyl acetate. Organic layer combined, dried over anhydrous $Na_2SO_4$, filtered and concentrated in vacuo to obtain the crude material. This was purified by column chromatography using 25% ethyl acetate in hexane to obtain pure 1.1 (3.1 g, 31.04%). MS(ES): m/z 223.05 $[M+H]^+$.

Synthesis of Compound 583.2.

To compound 583.1 (0.5 g, 2.25 mmol, 1.0 eq) in a mixture of 1,4-dioxane (0.8 mL) and water (0.2 mL), compound 264.4 (0.73 g, 2.47 mmol, 1.1 eq) and potassium carbonate (0.93 g, 6.7 mmol, 3.0 eq) was added. Reaction mixture was degassed by argon for 15 min. Then, (1,1'-Bis(diphenylphosphino)ferrocene)palladium(II) dichloride (0.36 g, 0.4 mmol, 0.2 eq) was added and again degassed for 5 min. Reaction mixture was stirred at 110° C. for 4 h. After completion of the reaction, the reaction mixture was transferred to water and extracted with ethyl acetate. Organic layer combined, dried over anhydrous $Na_2SO_4$, filtered and concentrated in vacuo to obtain the crude material. This was purified by column chromatography using 12% ethyl acetate in hexane to obtain pure 583.2 (0.310 g, 51.88%). MS(ES): m/z 266.53 $[M+H]^+$.

Synthesis of Compound 583.3.

Compound 583.3 was synthesized from 582.2 and 98.4 using general procedure A. (Yield: 21.60%). MS(ES): m/z 516.23 $[M+H]^+$.

Synthesis of Compound 583.4.

Compound 583.4 was synthesized from 583.3 and 6-aminopicolinonitrile using general procedure B. (Yield: 46.40%). MS(ES): m/z 598.24 $[M+H]^+$.

Synthesis of I-583.

Compound I-583 was synthesized from 583.4 using general procedure C. (Yield: 59.85%). MS(ES): m/z: 514.64 $[M+H]^+$, LCMS purity: 100%, HPLC purity: 100%, 1H NMR (DMSO, 400 MHz): 12.58 (s, 1H), 10.02 (s, 1H), 8.72 (s, 1H), 8.38 (s, 1H), 8.12-8.10 (d, J=8.0 Hz, 1H), 8.01-7.99 (d, J=8.0 Hz, 1H), 7.93-7.91 (d, J=8.0 Hz, 1H), 7.85-7.81 (t, J=16.0 Hz, 1H), 7.57 (s, 1H), 7.43-7.42 (d, J=6.9 Hz, 1H), 6.49 (s, 1H), 2.30 (s, 3H), 2.48 (s, 3H), 3.24 (s, 3H), 3.79 (s, 3H).

Example 584: Synthesis of N-(2-(difluoromethyl)-7-((4-(5-(3-methoxypropyl)thiazol-2-yl)-2-(methylsulfonyl)phenyl)amino)-3H-imidazo[4,5-b]pyridin-5-yl)cyclopropanecarboxamide, I-584

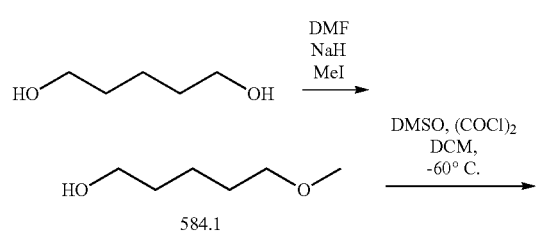
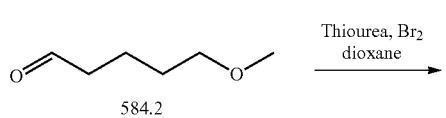
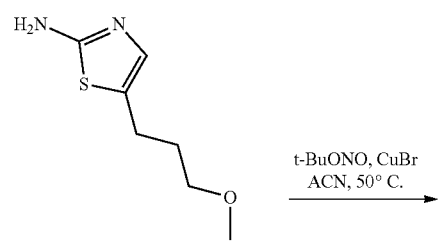
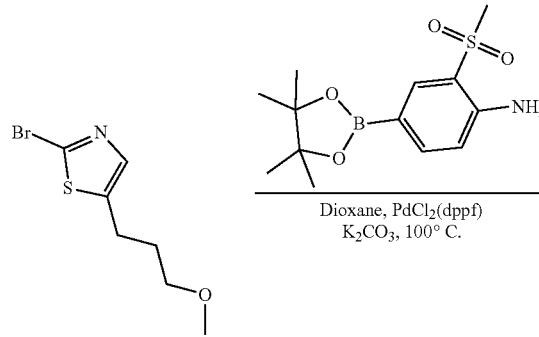
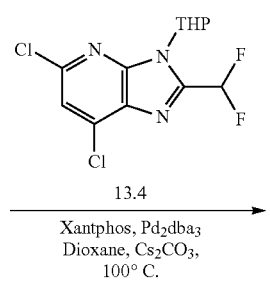

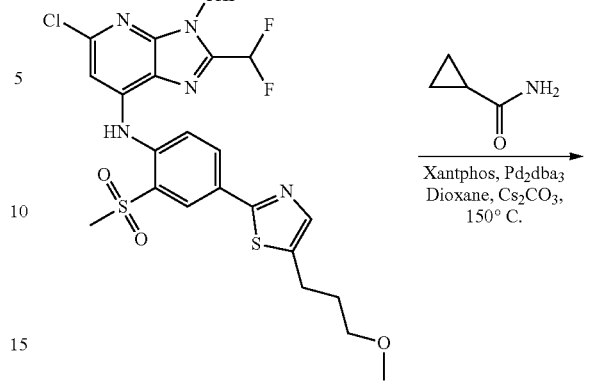
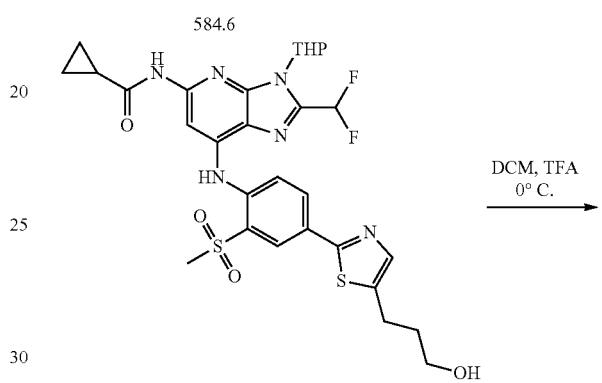
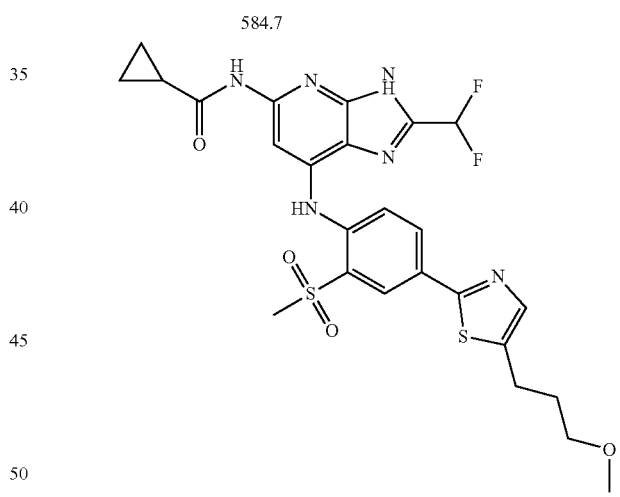

Synthesis of Compound 584.1.

To a solution of pentane-1,5-diol (20 g, 192.03 mmol, 1.0 eq), in Tetrahydrofuran (600 mL) was added sodium hydride (5.5 g, 230.6 mmol, 1.2 eq) at 0° C. The reaction mixture was stirred for 30 min at 0° C. Then Methyl Iodide (27.30 g, 192.03 mmol, 1.0 eq) was added into reaction mixture and stirred at r.t. for 2 h. Upon completion, reaction mixture transferred into ice cold water and extracted with ethyl acetate. Organic layers were combined, dried over Na$_2$SO$_4$ and concentrated in vacuo to obtain crude product 584.1 (6.2 g, 27.32%). MS(ES): m/z 119.18 [M+H]$^+$.

Synthesis of Compound 584.2.

To a solution of Oxalyl chloride (8 g, 63.05 mmol, 1.2 eq), in CH$_2$Cl$_2$ (60 mL) were added dropwise Dimethyl sulphoxide (12.3 gm, 157.62 mmol, 3.0 eq) at −60° C. Then a solution of 584.1 (6.2 g, 52.46 mmol, 1.0 eq) in $CH_2Cl_2$ (60 mL) was added into the reaction mixture. The reaction mixture was stirred at −60° C. for 30 min. Triethylamine (26.58 g, 262.71 mmol, 5.0 eq) was added at −60° C. and stirred for 2 hr at 0° C. Upon completion, reaction mixture transferred into water and extracted with $CH_2Cl_2$. Organic layer washed with 1M HCl solution and sodium bicabonate solution. Organic layers were combined, dried over $Na_2SO_4$ and concentrated in vacuo to obtain crude product 584.2 (3 g, 49.23%). MS(ES): m/z 117.16 [M+H]$^+$.

Synthesis of Compound 584.3.

To a solution of 584.2 (3 g, 25.83 mmol, 1.0 eq), in 1,4-dioxane (20 mL) was added Bromine (4.1 g, 25.83 mmol, 1.0 eq) in 1,4-dioxane (25 mL) dropwise at 0° C. The reaction mixture was stirred at r.t. for 2 h. Thiourea (3.7 g, 51.72 mmol, 2.0 eq), Ethanol (25 mL) was added into reaction mixture at r.t. and stirred the reaction mixture at r.t. for 18 h. Upon completion, reaction mixture concentrated in vacuo to obtained residue, which was taken in $CH_2Cl_2$ and extracted with 1M HCl solution. The aqueous layer was made basic by using 30% ammonium hydroxide solution and extracted again with $CH_2Cl_2$. Organic layers were combined, dried over $Na_2SO_4$ and concentrated in vacuo to obtain crude product. This was purified by column chromatography and compound was eluted in 25% ethyl acetate in hexane to obtain pure 584.3 (1.7 g, 38.22%). MS(ES): m/z 173.25 [M+H]$^+$.

Synthesis of Compound 584.4.

To a solution of cupper bromide (2.6 g, 11.8 mmol, 1.2 eq) in Acetonitrile (20 mL) was added tert-Butyl nitrite (1.5 g, 14.8 mmol, 1.5 eq) at 0° C. under nitrogen environment. To compound 584.3 (1.7 g, 9.87 mmol, 1.0 eq) in acetonitrile (20 mL) was added dropwise into the reaction mixture. Reaction mixture stirred at r.t. for 1 hr. Upon completion, reaction mixture was transferred into 1M HCl solution and extracted with ethyl acetate. Organic layers were combined, dried over $Na_2SO_4$ and concentrated in vacuo to obtain crude product. This was purified by column chromatography and compound was eluted in 25% ethyl acetate in hexane to obtain pure 584.4 (1.4 g, 60.07%). MS(ES): m/z 237.13 [M+H]$^+$.

Synthesis of Compound 584.5.

Compound 584.5 was synthesized from 584.4 and 288.4 using general procedure A.

Synthesis of Compound 584.6.

To a solution of 584.5 (1.4 g, 5.93 mmol, 1.0 eq), in 1,4-dioxane (20 mL) and water (1.8 mL) was added 288.4 (5.28 g, 17.79 mmol, 3.0 eq). The reaction mixture was degassed by argon for 30 min. (1,1'-Bis[diphenylphosphino]ferrocene)palladium(II)dichloride (0.433 g, 5.93 mmol, 0.1 eq), potassium carbonate (2.5 g, 17.79 mmol, 3.0 eq), were added into reaction mixture and again degassed by argon for 20 min. Further reaction mixture was stirred at 100° C. for 2 h. Upon completion, reaction mixture was transferred into water and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 584.6 (0.410 g, 21.18%). MS(ES): m/z 327.43 [M+H]$^+$.

Synthesis of Compound 584.7

Compound 584.7 was synthesized from 584.6 and cyclopropanecarboxamide using general procedure B. (Yield: 57.22%). MS(ES): m/z 661.76 [M+H]$^+$.

Synthesis of I-584.

Compound I-584 was synthesized from 584.7 using general procedure C. (Yield: 65.48%). MS(ES): m/z: 577.66 [M+H]$^+$, LCMS purity: 100%, HPLC purity: 99.17%, 1H NMR (DMSO, 400 MHz): 13.75 (s, 1H), 10.83 (s, 1H), 8.97 (s, 1H), 8.40 (s, 1H), 8.20 (s, 2H), 7.90-7.87 (d, J=8.4 Hz, 1H), 7.71 (s, 1H), 7.27 (t, 1H), 3.39 (s, 2H), 3.27 (s, 6H), 2.96-2.93 (t, J=6.8 Hz, 2H), 2.06 (s, 1H), 1.92-1.88 (t, J=6.8 Hz, 2H), 0.82 (s, 4H).

Example 585: Synthesis of N7-(4-(1,5-dimethyl-1H-pyrazol-4-yl)-2-(methylsulfonyl)phenyl)-2-methyl-N5-(6-(trifluoromethyl)pyridin-2-yl)-3H-imidazo[4,5-b]pyridine-5,7-diamine, I-585

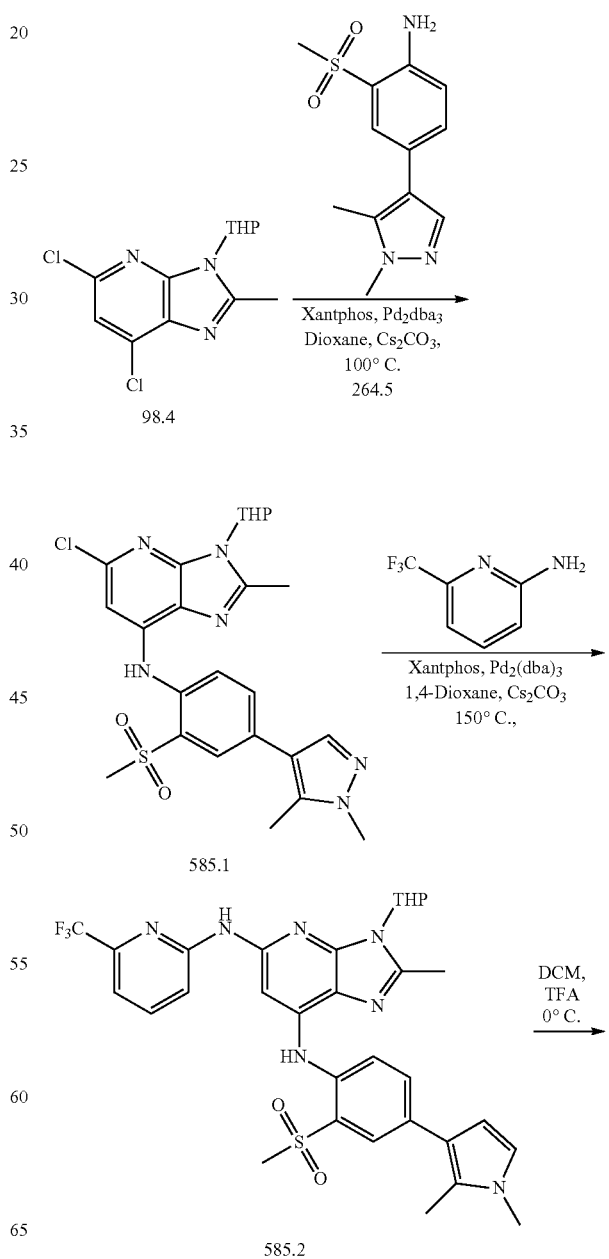

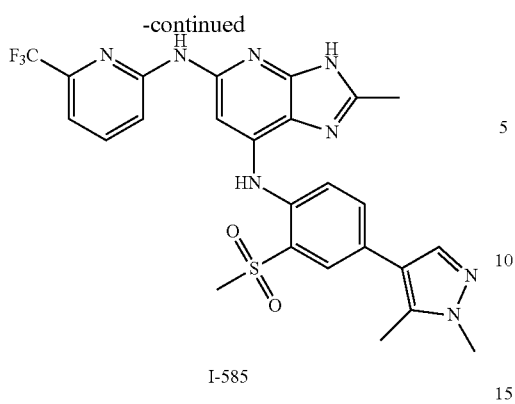

I-585

Synthesis of Compound 585.1.

Compound 585.1 was synthesized from 98.4 and 264.5 using general procedure A. (Yield: 19.84%). MS (ES): m/z 516.03 [M+H]$^+$.

Synthesis of compound 585.2 Compound 585.2 was synthesized from 585.1 and 6-(trifluoromethyl)pyridin-2-amine using general procedure. (Yield: 44.21%). MS (ES): m/z 641.69 [M+H]$^+$.

Synthesis of Compound I-585.

Compound I-585 was synthesized from 585.2 using general procedure C. (Yield: 69.07%). [M+H]$^+$ MS(ES): m/z: 557.67 [M+H]$^+$, LCMS purity: 97.28%, HPLC purity: 97.58%, 1H NMR (DMSO-d6, 400 MHz): 12.53 (s, 1H), 9.96 (s, 1H), 8.71 (s, 1H), 8.08-8.06 (d, J=8.4 Hz, 1H), 7.88 (s, 3H), 7.74-7.72 (t, J=8.0 Hz, 1H), 7.65 (s, 1H), 7.57 (s, 1H), 7.27-7.25 (d, J=8.4 Hz, 1H), 3.83 (s, 3H), 3.26 (s, 3H), 2.49 (s, 3H), 2.44 (s, 3H).

Example 586: Synthesis of (R)—N5-(6,7-dihydro-4H-pyrazolo[5,1-c][1,4]oxazin-2-yl)-2-methyl-N7-(2-(methylsulfonyl)-4-(tetrahydro-2H-pyran-2-yl) phenyl)-3H-imidazo[4,5-b]pyridine-5,7-diamine, I-586

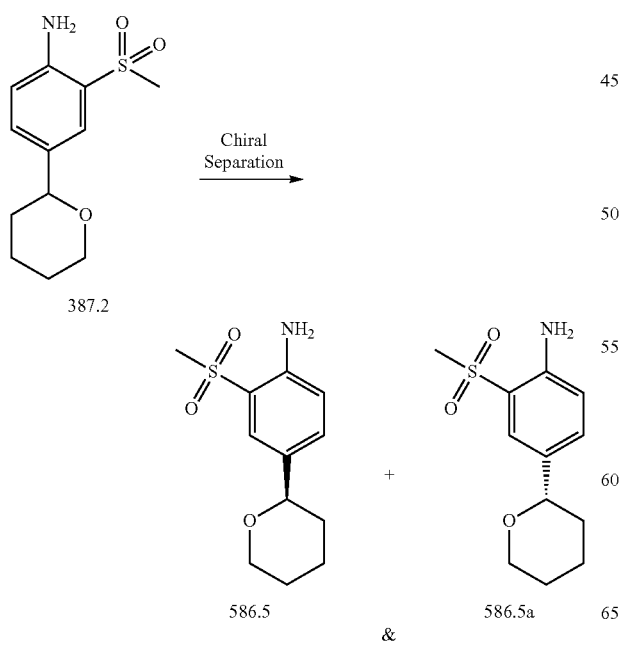

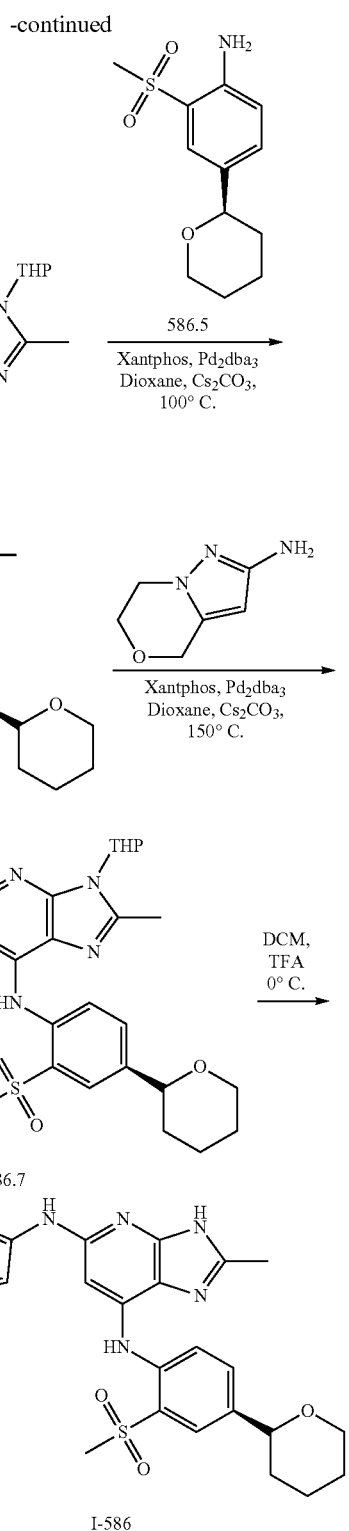

Synthesis of Compound 586.1.

To a solution of 4-bromo-2-fluoro-1-nitrobenzene (2.5 g, 13.64 mmol, 1 eq) in Dimethyl formamide (25 mL) was added dropwise Sodium thiomethoxide in water at 10° C. The reaction mixture was stirred at 20° C. for 4 h. Upon completion, reaction mixture transferred into ice water and stirred for 2 h. Then reaction mixture was filtered, and washed with water. Filtrate was concentrated in vacuo to obtain 586.1 (3 g, 88.68%). MS(ES): m/z 249.09 [M+H]⁺.

Synthesis of Compound 586.2.

To a solution of 586.1 (3 g, 13.75 mmol, 1.0 eq), 4,4,5,5-tetramethyl-2-(tetrahydro-2H-pyran-2-yl)-1,3,2-dioxaborolane (4.33 g, 20.63 mmol, 1.5 eq) in mixture of tetrahydrofuran (60 mL) and water (10 mL). The reaction mixture was degassed by argon for 30 min. 1,1'-bis(diphenylphosphanyl) ferrocene (1 g, 1.375 mmol, 0.1 eq), potassium carbonate (5 g, 36.29 mmol, 3 eq) was added into reaction mixture and again reaction mixture was degassed by argon for 30 min. Further reaction mixture was stirred at 60° C. for 3 h. After completion of reaction, water was added to reaction mixture and extracted with ethyl acetate. Organic layers were combined, dried over Na₂SO₄ and concentrated in vacuo to obtain crude product. This was purified by column chromatography and compound was eluted in 20% ethyl acetate in hexane to obtain pure 586.2 (1.4 g, 45.99%). MS(ES): m/z 224.33 [M+H]⁺.

Synthesis of Compound 586.3.

To a solution of 586.2 (1.4 g, 6.33 mmol, 1.0 eq) in ethanol (30 mL), 10% Pd/C (0.110 g) was added. Hydrogen was purged through reaction mixture for 24 h. Upon completion, reaction mixture was filtered through celite-bed and washed with ethanol. Filtrate was concentrated in vacuo to obtain 586.3 (0.600 g, 42.47%). MS(ES): m/z 224.33 [M+H]⁺.

Synthesis of Compound 586.4.

To a solution of 586.3 (0.600 g, 2.69 mmol, 1 eq) in acetic acid (130 mL) was added 30% hydrogen peroxide (0.663 g, 0.195 mmol, 7.26 eq) and sodium tungstate dihydrate (0.711 g, 0.003 mmol, 0.9 eq). Reaction mixture was stirred at r.t. for 2 h. Upon completion, reaction mixture was transferred in ice-water and precipitated product was filtered, washed with 25% ethyl acetate in hexane and dried well to obtain 586.4. (0.520 g, Yield: 75.81%). MS(ES): m/z 256.33 [M+H]⁺.

Synthesis of Compound 586.5 and 586.5a

Isomers of 586.4 (0.900 g) were separated out using column CHIRALPAK AD-H (250 mm*4.6 mm, 5u) and 0.1% DEA_HEX_IPA-MEOH (50-50) flow rate of 4 mL/min. to get pure fraction-1 (FR-a) and fraction-2 (FR-b). FR-a was concentrated in vacuo at 30° C. to afford pure 586.5 (0.240 g). MS(ES): m/z: 256.33 [M+H]⁺. FR-b was concentrated in vacuo at 30° C. to afford pure 586.5a (0.270 g). MS(ES): m/z: 256.43 [M+H]⁺.

Synthesis of Compound 586.6.

Compound 586.6 was synthesized from 586.5 and 98.4 using general procedure A (Yield: 25.18%). MS(ES): m/z 506.03 [M+H]⁺.

Synthesis of Compound 586.7.

Compound 586.7 was synthesized from 586.6 and 6,7-dihydro-4H-pyrazolo[5,1-c][1,4]oxazin-2-amine using general procedure B. (Yield: 45.01%). MS(ES): m/z 608.73 [M+H]⁺.

Synthesis of Compound I-586.

Compound I-586 was synthesized form 586.7 using general procedure C. (Yield: 71.42%). MS(ES): m/z: 524.66 [M+H]⁺, LCMS purity: 100%, HPLC purity: 99.58%, Chiral HPLC: (99.46%), 1H NMR (DMSO, 400 MHz): 12.27 (s, 1H), 9.02 (s, 1H), 8.51 (s, 1H), 7.88 (s, 1H), 7.81-7.79 (d, J=7.6 Hz, 1H), 7.70-7.68 (d, J=8 Hz, 1H), 7.08 (s, 1H), 6.24 (s, 1H), 4.76 (s, 1H), 4.45-4.42 (m, 1H), 4.07 (s, 2H), 3.95 (s, 2H), 3.84-3.77 (m, 1H), 3.62-3.52 (m, 1H), 3.20 (s, 3H), 2.43 (s, 3H), 1.92-1.89 (m, 2H), 1.69-1.59 (m, 3H), 1.49-1.42 (m, 2H).

Example 587: Synthesis of (R)—N5-(6,7-dihydro-4H-pyrazolo[5,1-c][1,4]oxazin-2-yl)-2-methyl-N7-(2-(methylsulfonyl)-4-(tetrahydro-2H-pyran-2-yl)phenyl)-3H-imidazo[4,5-b]pyridine-5,7-diamine, I-587

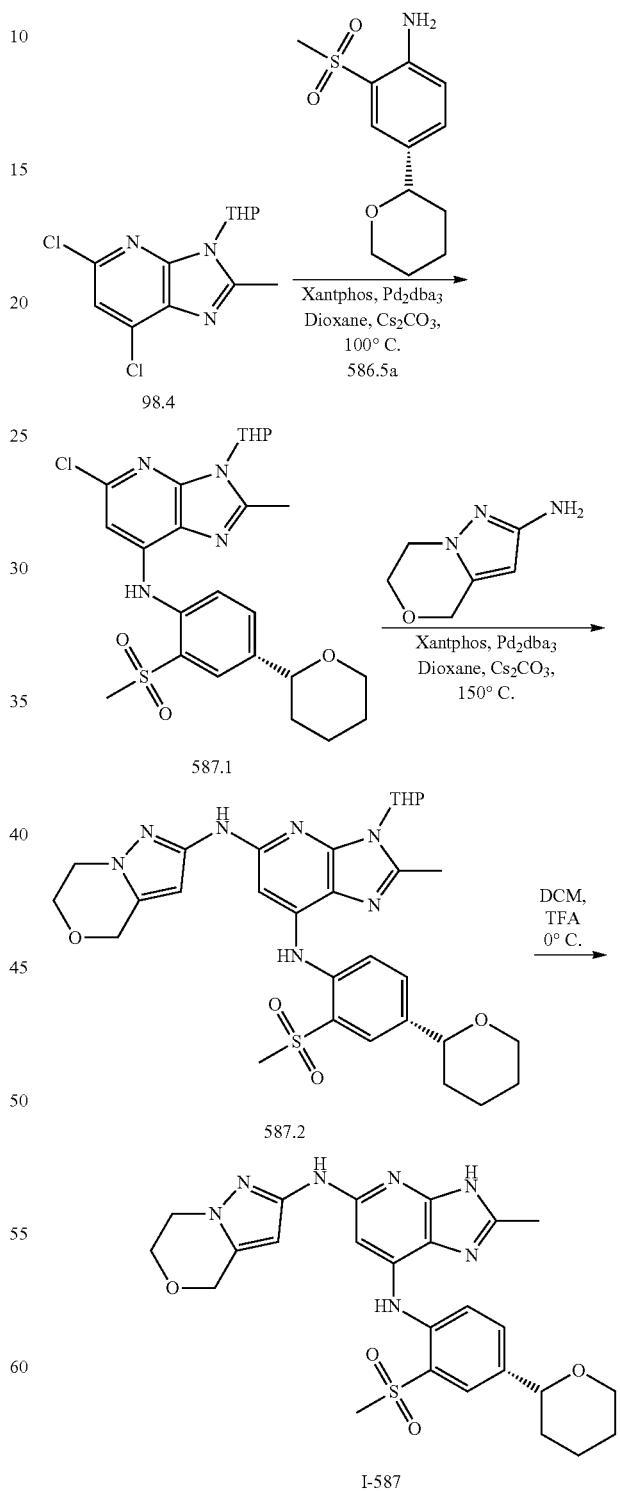

Synthesis of Compound 587.1.

Compound 587.1 was synthesized from 98.4 and 586.5a using general procedure A (Yield: 23.61%). MS(ES): m/z 506.03 [M+H]+.

Synthesis of Compound 587.2.

Compound 587.2 was synthesized from 587.1 and 6,7-dihydro-4H-pyrazolo[5,1-c][1,4]oxazin-2-amine using general procedure B. (Yield: 58.17%). MS(ES): m/z 608.73 [M+H]+.

Synthesis of Compound I-587.

Compound I-587 was synthesized from 587.2 using general procedure C. (Yield: 46.43%). MS(ES): m/z: 524.69 [M+H]+, LCMS purity: 100%, HPLC purity: 100%, Chiral HPLC: (99.54%), 1H NMR (DMSO, 400 MHz): 12.25 (s, 1H), 9.01 (s, 1H), 8.51 (s, 1H), 7.88 (s, 1H), 7.79 (s, 1H), 7.69 (s, 1H), 7.09 (s, 1H), 6.24 (s, 1H), 4.76 (s, 2H), 4.44-4.42 (m, 1H), 4.06 (s, 3H), 3.95 (s, 2H), 3.58 (s, 1H), 3.20 (s, 3H), 2.43 (s, 1H), 1.91-1.88 (m, 2H), 1.80 (s, 2H), 1.47-1.44 (m, 2H), 1.25 (s, 1H), 0.87 (s, 1H).

Example 588: Synthesis of N-(7-((4-(1,4-dioxan-2-yl)-2-(methylsulfonyl)phenyl)amino)-2-(difluoromethyl)-3H-imidazo[4,5-b]pyridin-5-yl)cyclopropanecarboxamide, I-588

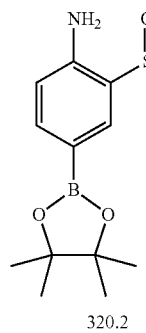

320.2

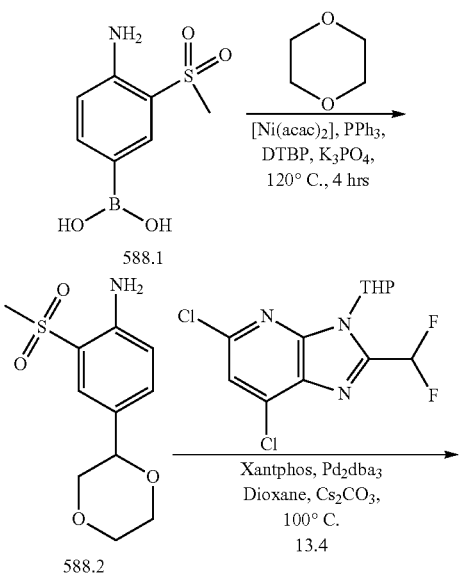

588.1

588.2

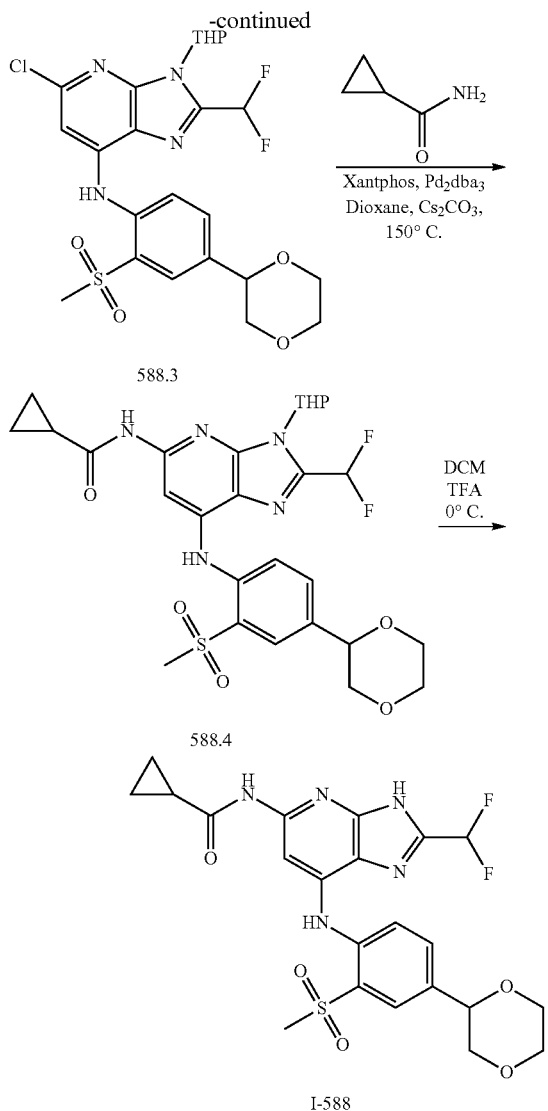

588.3

588.4

I-588

Synthesis of 588.1

To a solution of 320.2 (10 g, 33.65 mmol, 1.0 eq) in Acetone (100 mL) was added Sodium periodate (22.9 g, 67.34 mmol, 2 eq), ammonium acetate (5.18 g, 67.34 mmol, 2 eq) and water (50 mL) at r.t. The reaction mixture was stirred at r.t. for 16 h. Upon completion, reaction mixture was filtered through celite-bed and washed with acetone. Filtrate was concentrated in vacuo to obtain residue. Residue was dissolved in ethyl acetate and washed with water. Combined organic layer was washed with brine, dried over Na2SO4 and concentrated in vacuo to obtain 588.1 (4.2 g, 58.04%). MS(ES): m/z 216.03 [M+H]+.

Synthesis of Compound 588.2.

To a solution of 588.1 (0.750 g, 3.49 mmol, 1 eq) in 1,4-Dioxane(15 mL), was added potassium phosphate (0.756 g, 3.49 mmol, 1 eq), Triphenylphosphine (0.091 g, 3.49 mmol, 0.1 eq) at r.t. Nickel (II) acetylacetonate (0.089 g, 3.49 mmol, 0.1 eq), Di-tert-butyl peroxide (0.611 g, 4.18 mmol, 1.2 eq) was added to the reaction mixture under argon atmosphere. Reaction mixture was heated at 120° C. for 4 h. Upon completion, reaction mixture was transferred into water and extracted with ethyl acetate. Organic layers were combined, dried over Na2SO4 and concentrated in vacuo to obtain crude product. This was purified by column chromatography and compound was eluted in 20% ethyl acetate in hexane to obtain pure 588.2 (0.280 g, 31.20%). MS(ES): m/z 258.30 [M+H]⁺.

Synthesis of Compound 588.3.

Compound 588.3 was synthesized from 588.2 and 13.4 using general procedure A. (Yield: 23.73%). MS (ES): m/z 543.98 [M+H]⁺.

Synthesis of Compound 588.4.

Compound 588.4 was synthesized from 588.3 and cyclopropanecarboxamide using general procedure B. (Yield: 51.24%). MS (ES): m/z 592.63 [M+H]⁺.

Synthesis of Compound I-588.

Compound I-588 was synthesized from 588.4 using general procedure C. (Yield: 80.71%). MS(ES): m/z: 508.51 [M+H]⁺, LCMS purity: 97.29%, HPLC purity: 95.60%, Chiral HPLC: (50%, 50%), 1H NMR (DMSO, 400 MHz): 13.70 (s, 1H), 10.78 (s, 1H), 8.79 (s, 1H), 8.09 (s, 1H), 7.95 (s, 1H), 7.77 (s, 2H), 7.27 (t, 1H), 4.73-4.70 (m, 1H), 3.96-3.93 (d, J=11.2 Hz, 2H), 3.83-3.78 (m, 2H), 3.66-3.60 (m, 2H), 3.23 (s, 3H), 2.06-2.03 (m, 1H), 0.81-0.79 (m, 4H).

Example 589: Synthesis of N-(2-(difluoromethyl)-7-((4-(1,5-dimethyl-1H-pyrazol-3-yl)-2-methoxyphenyl)amino)-3H-imidazo[4,5-b]pyridin-5-yl)cyclopropanecarboxamide, I-589

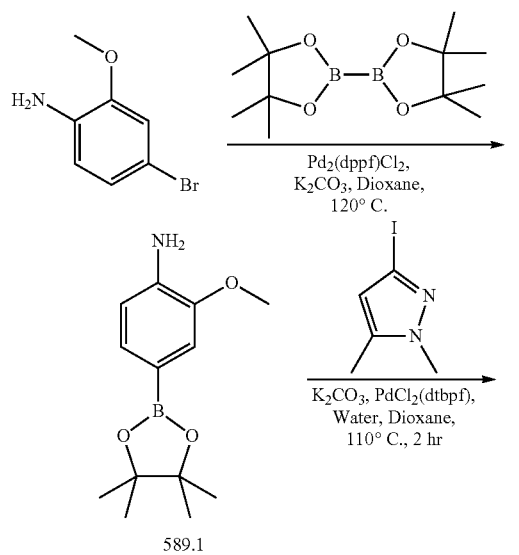

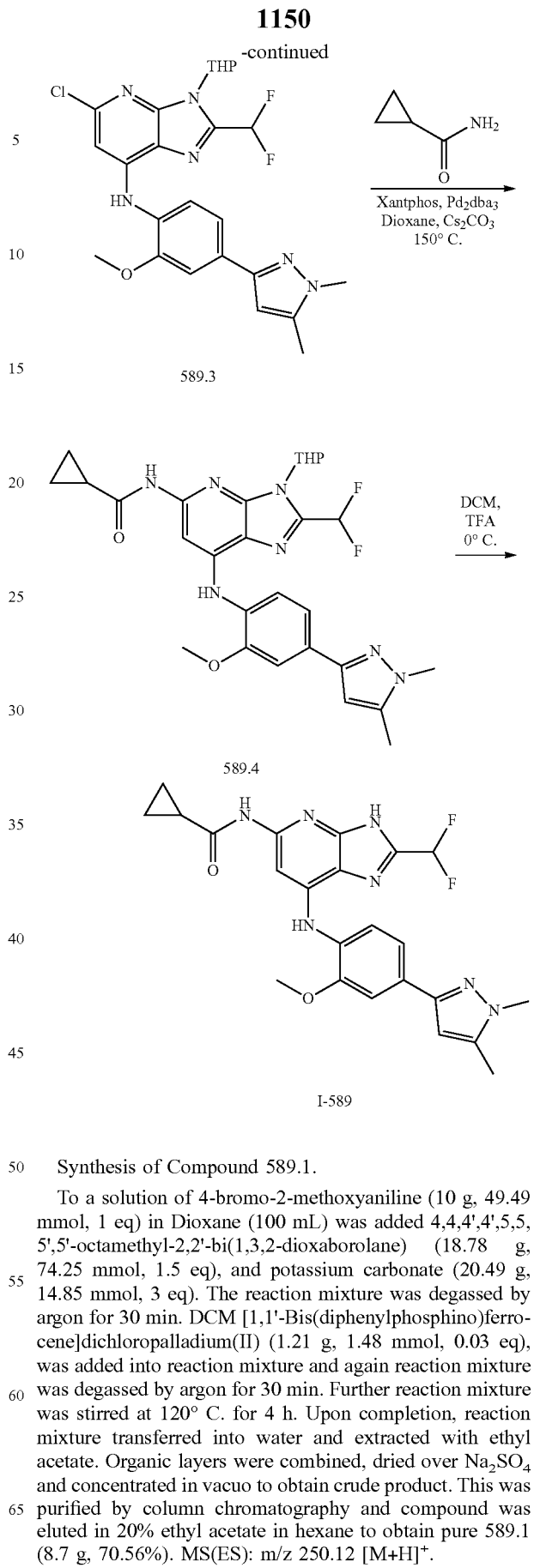

Synthesis of Compound 589.1.

To a solution of 4-bromo-2-methoxyaniline (10 g, 49.49 mmol, 1 eq) in Dioxane (100 mL) was added 4,4,4',4',5,5,5',5'-octamethyl-2,2'-bi(1,3,2-dioxaborolane) (18.78 g, 74.25 mmol, 1.5 eq), and potassium carbonate (20.49 g, 14.85 mmol, 3 eq). The reaction mixture was degassed by argon for 30 min. DCM [1,1'-Bis(diphenylphosphino)ferrocene]dichloropalladium(II) (1.21 g, 1.48 mmol, 0.03 eq), was added into reaction mixture and again reaction mixture was degassed by argon for 30 min. Further reaction mixture was stirred at 120° C. for 4 h. Upon completion, reaction mixture transferred into water and extracted with ethyl acetate. Organic layers were combined, dried over Na₂SO₄ and concentrated in vacuo to obtain crude product. This was purified by column chromatography and compound was eluted in 20% ethyl acetate in hexane to obtain pure 589.1 (8.7 g, 70.56%). MS(ES): m/z 250.12 [M+H]⁺.

Synthesis of Compound 589.2.

To a solution of 589.1 (2 g, 8.03 mmol, 1 eq) in Dioxane (40 mL) and water (6 mL) was added 3-iodo-1,5-dimethyl-1H-pyrazole (3.57 g, 16.06 mmol, 2 eq), and potassium carbonate (7.8 g, 24.09 mmol, 3 eq). The reaction mixture was degassed by argon for 30 min. DCM [1,1'-Bis(diphenylphosphino)ferrocene]dichloropalladium(II) (0.655 g, 0.803 mmol, 0.1 eq), was added into reaction mixture and again reaction mixture was degassed by argon for 30 min. Further reaction mixture was stirred at 110° C. for 2 h. Upon completion, reaction mixture transferred into water and extracted with ethyl acetate. Organic layers were combined, dried over Na$_2$SO$_4$ and concentrated in vacuo to obtain crude product. This was purified by column chromatography and compound was eluted in 20% ethyl acetate in hexane to obtain pure 589.2 (0.800 g, 45.86%). MS(ES): m/z 218.27 [M+H]$^+$.

Synthesis of Compound 589.3.

Compound 589.3 was synthesized from 589.2 and 13.4 using general procedure A. (Yield: 16.01%). MS (ES): m/z 503.95 [M+H]$^+$.

Synthesis of Compound 589.4.

Compound 589.4 was synthesized from 589.3 and cyclopropanecarboxamide using general procedure B. (Yield: 59.27%). MS (ES): m/z 552.60 [M+H]$^+$.

Synthesis of Compound I-589.

Compound I-589 was synthesized from 589.4 using general procedure C. (Yield: 72.61%). MS(ES): m/z: 468.62 [M+H]$^+$, LCMS purity: 100%, HPLC purity: 99.50%, 1H NMR (DMSO-d6, 400 MHz): 13.46 (s, 1H), 10.54 (s, 1H), 8.05 (s, 1H), 7.69 (s, 1H), 7.46 (s, 1H), 7.39-7.34 (m, 2H), 7.21 (s, 1H), 6.54 (s, 1H), 3.78 (s, 3H), 3.73 (s, 3H), 2.30 (s, 3H), 2.00 (s, 1H), 0.76 (bs, 4H).

Example 590: Synthesis of N-(7-((4-(1,5-dimethyl-1H-pyrazol-3-yl)-2-methoxyphenyl)amino)-2-methyl-3H-imidazo[4,5-b]pyridin-5-yl)cyclopropanecarboxamide, I-590

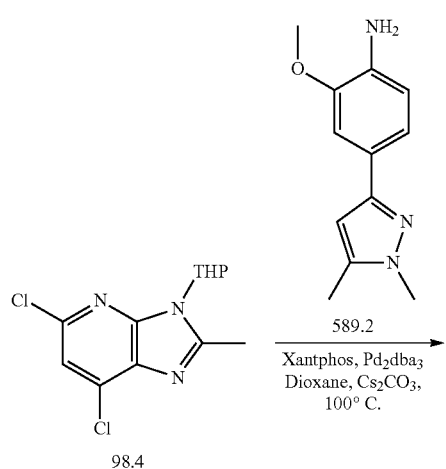

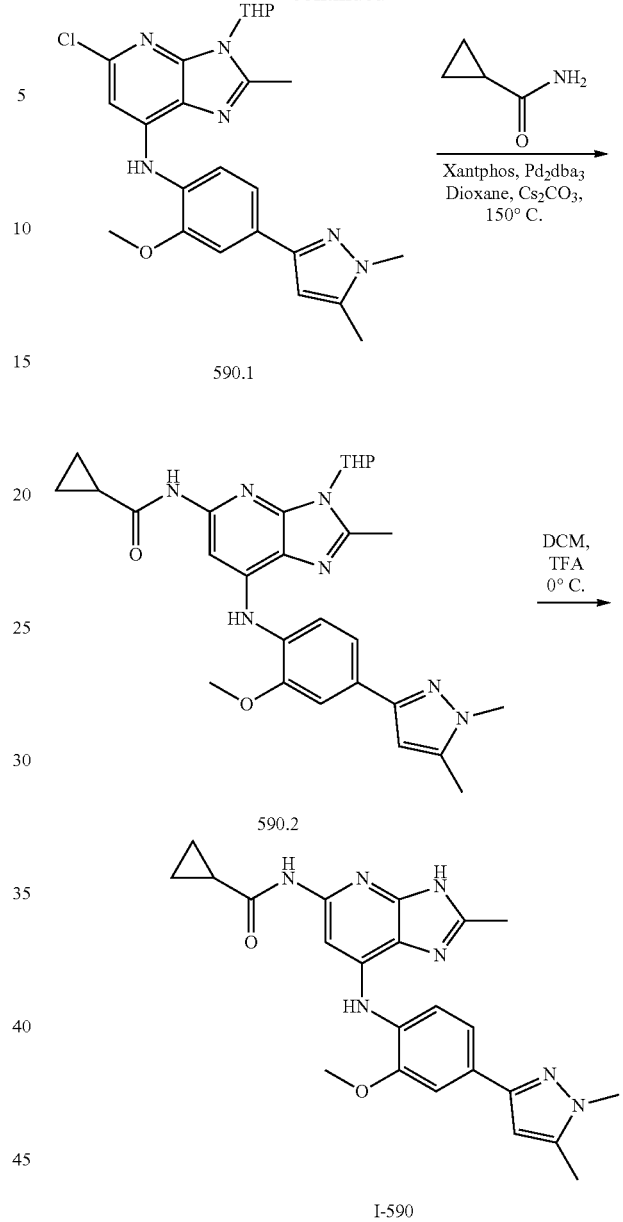

Synthesis of Compound 590.1.

Compound 590.1 was synthesized from 98.4 and 589.2 using general procedure A. (Yield: 18.38%). MS (ES): m/z 467.97 [M+H]$^+$.

Synthesis of Compound 590.2.

Compound 590.2 was synthesized from 590.1 and cyclopropanecarboxamide using general procedure B. (Yield: 67.92%). MS (ES): m/z 516.62 [M+H]$^+$.

Synthesis of Compound I-590.

Compound I-590 was synthesized from using general procedure C. (Yield: 69.04%). MS(ES): m/z: 432.62 [M+H]$^+$, LCMS purity: 97.71%, HPLC purity: 98.66%, 1H NMR (DMSO-d6, 400 MHz): 12.36 (s, 1H), 10.43 (s, 1H), 7.77 (s, 1H), 7.65 (s, 1H), 7.45-7.34 (m, 3H), 6.52 (s, 1H), 3.91 (s, 3H), 3.77 (s, 3H), 2.51 (s, 3H), 2.30 (s, 3H), 1.98 (s, 1H), 0.76 (bs, 4H).

Example 591: Synthesis of (R)—N-(7-((4-(5,5-dimethyltetrahydrofuran-2-yl)-2-(methylsulfonyl)phenyl)amino)-2-methyl-3H-imidazo[4,5-b]pyridine yl)cyclopropanecarboxamide, I-591

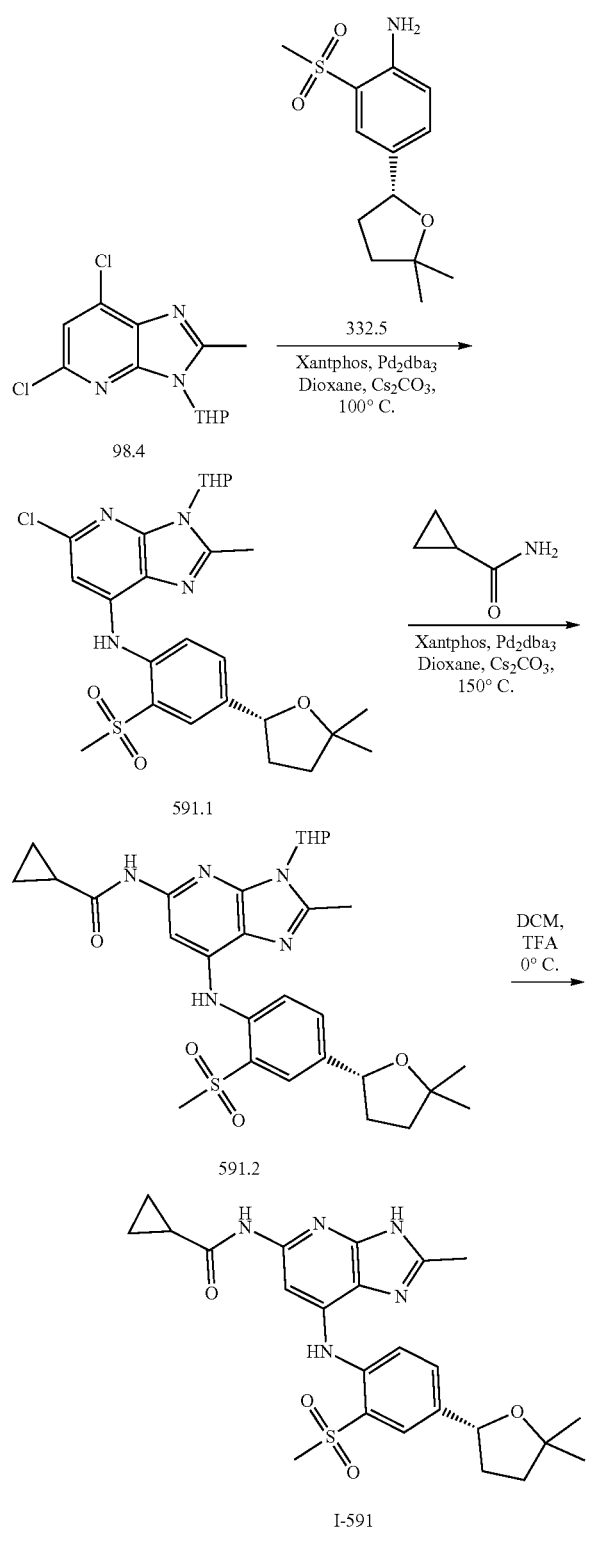

Synthesis of Compound 591.1.

Compound 591.1 was synthesized from 98.4 and 332.5 using general procedure A (Yield: 26.46%). MS(ES): m/z 520.06 [M+H]$^+$.

Synthesis of Compound 591.2.

Compound 591.2 was synthesized from 591.1 and cyclopropanecarboxamide using general procedure B. (Yield: 53.33%). MS(ES): m/z 568.71 [M+H]$^+$.

Synthesis of I-591.

Compound I-591 was synthesized from 591.2 using general procedure C. (Yield: 67.08%). MS(ES): m/z: 484.45 [M+H]$^+$, LCMS purity: 100%, HPLC purity: 96.24%, Chiral HPLC: (97.32%), 1H NMR (DMSO, 400 MHz): 13.41 (s, 1H), 10.73 (s, 1H), 8.53 (s, 1H), 7.91 (s, 1H), 7.86 (s, 1H), 7.70-7.68 (d, J=7.6 Hz, 1H), 7.65-63 (d, J=7.6 Hz, 1H), 5.02-4.99 (t, J=7.6 Hz, 1H), 3.19 (s, 3H), 2.60 (s, 3H), 2.41-2.39 (m, 2H), 1.99 (m, 1H), 1.87-1.84 (m, 2H), 1.33 (s, 3H), 1.30 (s, 3H), 0.78-0.76 (m, 4H).

Example 1-592: Synthesis of (S)—N-(7-((4-(5,5-dimethyltetrahydrofuran-2-yl)-2-(methylsulfonyl)phenyl)amino)-2-methyl-3H-imidazo[4,5-b]pyridin-5-yl)cyclopropanecarboxamide

1155

-continued

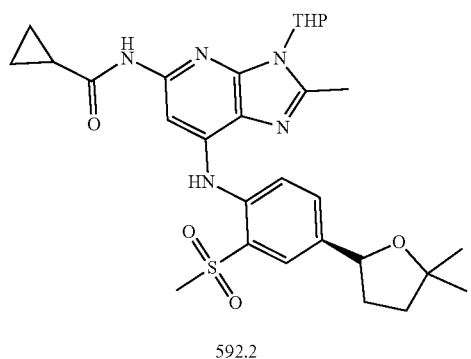

592.2

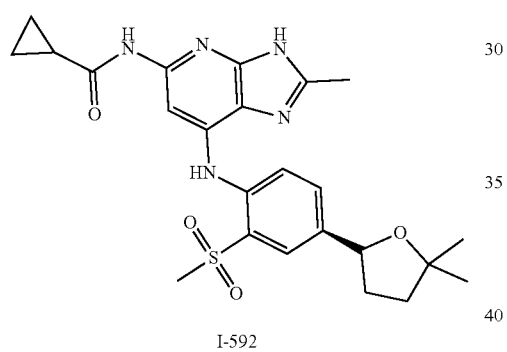

I-592

Synthesis of Compound 592.1.

Compound 592.1 was synthesized from 98.4 and 332.5 using general procedure A (Yield: 21.44%). MS(ES): m/z 520.06 [M+H]$^+$.

Synthesis of Compound 592.2.

Compound 592.2 was synthesized from 592.1 and cyclopropanecarboxamide using general procedure B. (Yield: 56.60%). MS(ES): m/z 568.71 [M+H]$^+$.

Synthesis of I-592.

Compound I-592 was synthesized from 592.2 using general procedure C. (Yield: 68.63%). MS(ES): m/z: 484.66 [M+H]$^+$, LCMS purity: 100%, HPLC purity: 99.73%, Chiral HPLC: (100%), 1H NMR (DMSO, 400 MHz): 12.52 (s, 1H), 10.58 (s, 1H), 8.50 (s, 1H), 7.96 (s, 1H), 7.86 (s, 1H), 7.72-7.65 (m, 2H), 5.00-4.97 (t, J=8 Hz, 1H), 3.18 (s, 3H), 2.49 (s, 3H), 2.41-2.36 (m, 2H), 1.99-1.98 (m, 1H), 1.87-1.78 (m, 2H), 1.33 (s, 3H), 1.29 (s, 3H), 0.77-0.75 (m, 4H).

1156

Example 593/594: Synthesis of (R)—N-(2-(difluoromethyl)-7-((4-(5,5-difluorotetrahydro-2H-pyran-2-yl)-2-(methylsulfonyl)phenyl)amino)-3H-imidazo[4,5-b]pyridin-5-yl)cyclopropanecarboxamide, I-593 and (S)—N-(2-(difluoromethyl)-7-((4-(5,5-difluorotetrahydro-2H-pyran-2-yl)-2-(methylsulfonyl)phenyl)amino)-3H-imidazo[4,5-b]pyridin-5-yl)cyclopropanecarboxamide, I-594

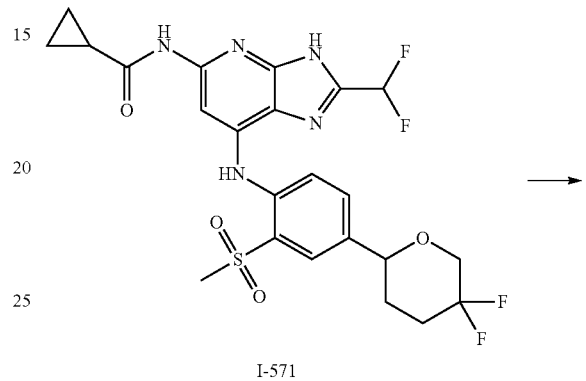

I-571

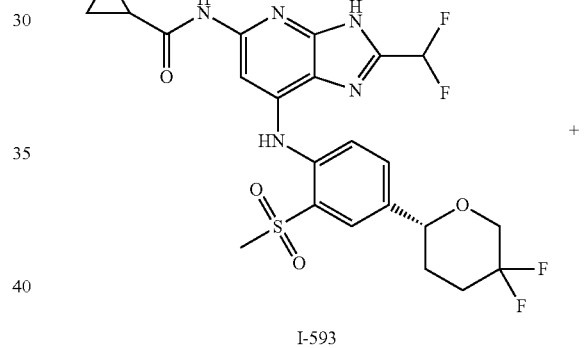

I-593

+

I-594

Synthesis of Compound I-593 and I-594.

Isomers of I-571 (0.090 g) were separated out using column CHIRALPAK AD-H (250 mm*4.6 mm, 5u) and 0.1% D EA_HEX_IPA-MEOH (50-50) flow rate of 4 mL/min. to get pure fraction-1 (FR-a) and fraction-2 (FR-b). FR-a was concentrated in vacuo at 30° C. to afford pure I-593 (0.035 g). MS(ES): m/z: 542.52 [M+H]$^+$, MS(ES): m/z: 542.65 [M+H]$^+$, LCMS purity: 100%, HPLC purity: 99.59%, Chiral HPLC Purity: 100%, 1H NMR (DMSO-d6, 400 MHz): 13.67 (s, 1H), 10.74 (s, 1H), 8.74 (s, 1H), 8.07 (s, 1H), 7.92 (s, 1H), 7.79-7.73 (m, 2H), 7.25 (t, 1H), 4.72-4.69 (d, J=10.4 Hz, 1H), 4.09 (s, 1H), 3.90-3.79 (m, 1H), 3.22 (s, 3H), 2.24 (s, 2H), 2.19 (s, 1H), 2.05-2.02 (t, 1H), 1.81-1.77 (s, 1H), 0.80 (bs, 4H). FR-b was concentrated in vacuo at 30° C. to afford pure I-594 (0.035 g). MS(ES): m/z: 542.52 [M+H]+ MS(ES): m/z: 542.65 [M+H]+, LCMS purity: 100%, HPLC purity: 100%, Chiral HPLC Purity: 100%, 1H NMR (DMSO-d6, 400 MHz): 13.65 (s, 1H), 10.74 (s, 1H), 8.73 (s, 1H), 8.06 (s, 1H), 7.91 (s, 1H), 7.79-7.73 (m, 2H), 7.24 (t, 1H), 4.09 (s, 1H), 3.90-3.79 (m, 1H), 3.19 (s, 3H), 2.24 (s, 2H), 2.16 (s, 2H), 2.05-2.02 (t, 1H), 1.81-1.77 (s, 1H), 0.79 (bs, 4H).

Example 595/596: Synthesis of (R)-3-isopropyl-6-((2-methyl-7-((2-(methylsulfonyl)-4-(tetrahydrofuran-2-yl)phenyl)amino)-3H-imidazo[4,5-b]pyridin-5-yl)amino)picolinonitrile, I-595 and (S)-3-isopropyl-6-((2-methyl-7-((2-(methylsulfonyl)-4-(tetrahydrofuran-2-yl)phenyl)amino)-3H-imidazo[4,5-b]pyridin-5-yl)amino)picolinonitrile, I-596

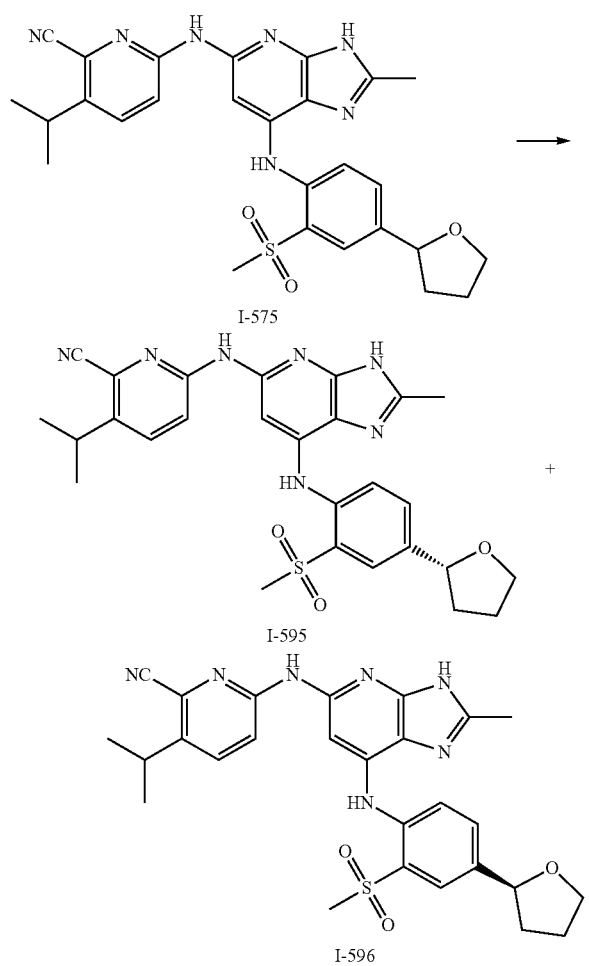

Synthesis of Compound I-595 and I-596.

Isomers of I-575 (0.100 g) were separated out using column CHIRALPAK AD-H (250 mm*4.6 mm, 5u) and 0.1% DEA_HEX_IPA-MEOH (50-50) flow rate of 4 mL/min. to get pure fraction-1 (FR-a) and fraction-2 (FR-b).

FR-a was concentrated in vacuo at 30° C. to afford pure I-595 (0.025 g). MS(ES): m/z 532.69 [M+H]+, LCMS purity: 99.53%, HPLC Purity: 98.96%, Chiral HPLC: (100%), 1H NMR (MeOD, 400 MHz): 12.46 (s, 1H), 9.89 (s, 1H), 8.70 (s, 1H), 7.94-7.91 (d, J=9.2 Hz, 2H), 7.87-7.85 (m, 2H), 7.79-7.77 (d, J=8.0 Hz, 1H), 7.64 (s, 1H), 4.92-4.89 (t, J=6.8 Hz, 1H), 4.06-4.00 (m, 1H), 3.88-3.82 (s, 1H), 3.215 (s, 3H), 2.481 (s, 3H), 2.39-2.32 (m, 2H), 2.02-1.95 (m, 2H), 1.77-1.73 (m, 1H), 1.27 (s, 3H), 1.25 (s, 3H). FR-b was concentrated in vacuo at 30° C. to afford pure I-596 (0.027 g). MS(ES): m/z 532.56 [M+H]+, LCMS purity: 100%, HPLC Purity: 99.94%, Chiral HPLC: (98.12%), 1H NMR (MeOD, 400 MHz): 12.46 (s, 1H), 9.89 (s, 1H), 8.70 (s, 1H), 7.94-7.91 (d, J=8.8 Hz, 2H), 7.87-7.85 (m, 2H), 7.79-7.77 (d, J=8.0 Hz, 1H), 7.64 (s, 1H), 4.92-4.89 (t, J=7.2 Hz, 1H), 4.06-4.00 (m, 1H), 3.88-3.85 (s, 1H), 3.21 (s, 3H), 2.48 (s, 3H), 2.38-2.34 (m, 2H), 2.02-1.95 (m, 2H), 1.78-1.73 (m, 1H), 1.27 (s, 3H), 1.25 (s, 3H).

Example 597: Synthesis of N5-(6,7-dihydro-5H-cyclopenta[c]pyridazin-3-yl)-2-methyl-N7-(2-(methylsulfonyl)phenyl)-3H-imidazo[4,5-b]pyridine-5,7-diamine, I-597

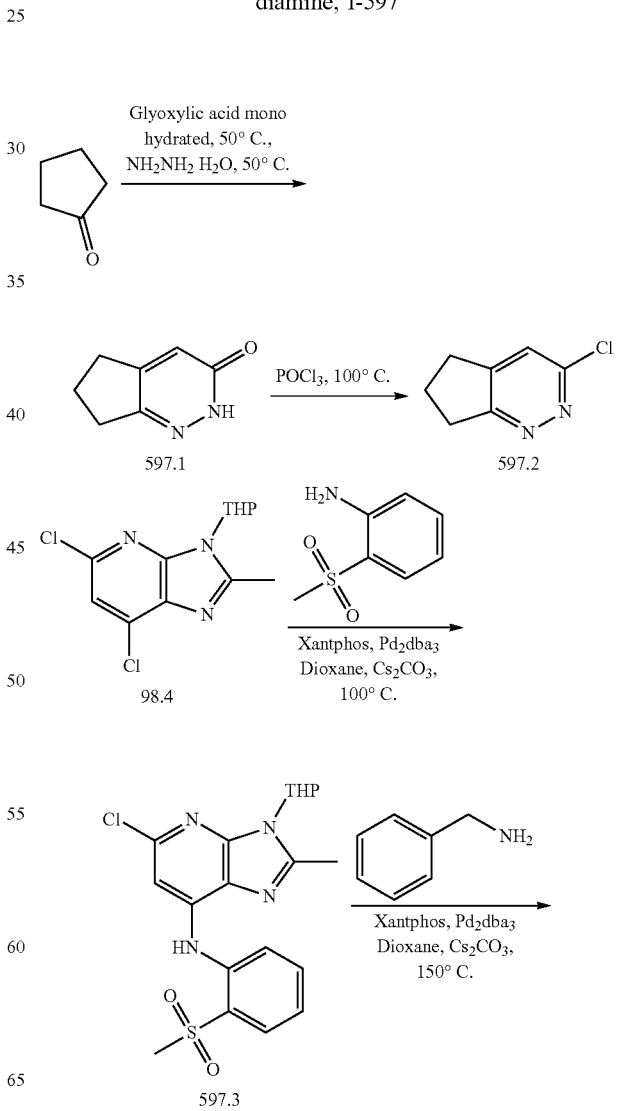

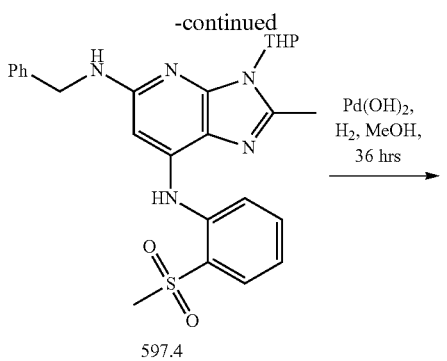

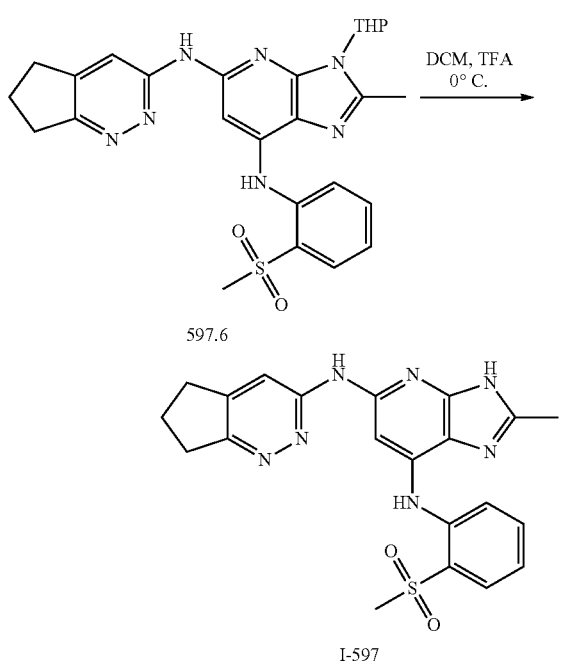

Synthesis of Compound 597.1.

A solution of cyclopentanone (1 g, 11.89 mmol, 1 eq) in glyoxylic acid mono hydrate (10 mL) was heated at 50° C. for 5 h. Then reaction mixture was cooled at 0° C. Hydrazine hydrate (0.893 g, 17.83 mmol, 1.5 eq) was added into the reaction mixture at 0° C. Reaction mixture was heated at 50° C. for 5 h. Upon completion, reaction mixture was filtered, and washed with ether. Filtrate was concentrated in vacuo to obtain crude product. The crude material was recrystallized with acetone to obtain pure 597.1. (Yield: 61.78%). MS (ES): m/z 137.15 [M+H]$^+$.

Synthesis of Compound 597.2.

A solution of 597.1 (1.5 g, 11.02 mmol, 1 eq) in Phosphoryl chloride (15 mL) was heated at 100° C. for 2 h. Upon completion, reaction mixture was concentrated under reduce pressure to obtain crude product. Crude material was transferred into saturated bicarbonate solution and extracted with $CH_2Cl_2$. Organic layers were combined, dried over $Na_2SO_4$ and concentrated in vacuo to obtain crude product. This was purified by column chromatography and compound was eluted in 20% ethyl acetate in hexane to obtain pure 597.2. (Yield: 52.84%). MS (ES): m/z 155.60 [M+H]$^+$.

Synthesis of Compound 597.3.

Compound 597.3 was synthesized from 98.4 and 2-(methylsulfonyl)aniline using general procedure A. (Yield: 44.65%). MS (ES): m/z 457.89 [M+H]$^+$.

Synthesis of Compound 597.4.

Compound 597.4 was synthesized from 597.3 and benzylamine using general procedure B. (Yield: 53.08%). MS (ES): m/z 492.61 [M+H].

Synthesis of Compound 597.5.

To a solution of 597.4 (0.310 g, 630.58 mmol, 1.0 eq) in MeOH (2 mL), 10% palladium hydroxide on charcoal (0.050 g) was added. Hydrogen was purged through reaction mixture for 36 h at r.t. Upon completion, reaction mixture was filtered through celite-bed and washed with MeOH. Filtrate was concentrated in vacuo to obtain 597.5 (0.150 g, 59.25%). MS(ES): m/z 402.49 [M+H]$^+$.

Synthesis of Compound 597.6.

Compound 597.6 was synthesized from 597.2 and 597.5 using general procedure B. (Yield: 24.72%). MS (ES): m/z 520.62 [M+H]$^+$.

Synthesis of Compound I-597.

Compound I-597 was synthesized from 597.6 using general procedure C. (Yield: 62.14%). MS(ES): m/z: 436.62 [M+H]$^+$, LCMS purity: 100%, HPLC purity: 98.39%, 1H NMR (DMSO-d6, 400 MHz): 12.47 (s, 1H), 9.80 (s, 1H), 8.66 (s, 1H), 8.14 (s, 1H), 7.93-7.85 (m, 2H), 7.73-7.70 (t, J=12.4 Hz, 1H), 7.37 (s, 1H), 7.32-7.29 (t, J=12.0 Hz, 1H), 3.23 (s, 3H), 2.99-2.90 (m, 4H), 2.46 (s, 3H), 2.09-2.05 (t, J=12.2 Hz, 2H).

Example 598: Synthesis of 6-((2-(difluoromethyl)-7-((2-methoxy-3-(5-methyl-1,2,4-oxadiazol-3-yl)phenyl)amino)-3H-imidazo[4,5-b]pyridin-5-yl)amino)picolinonitrile, I-598

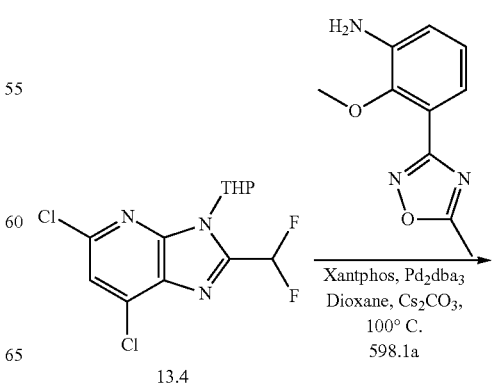

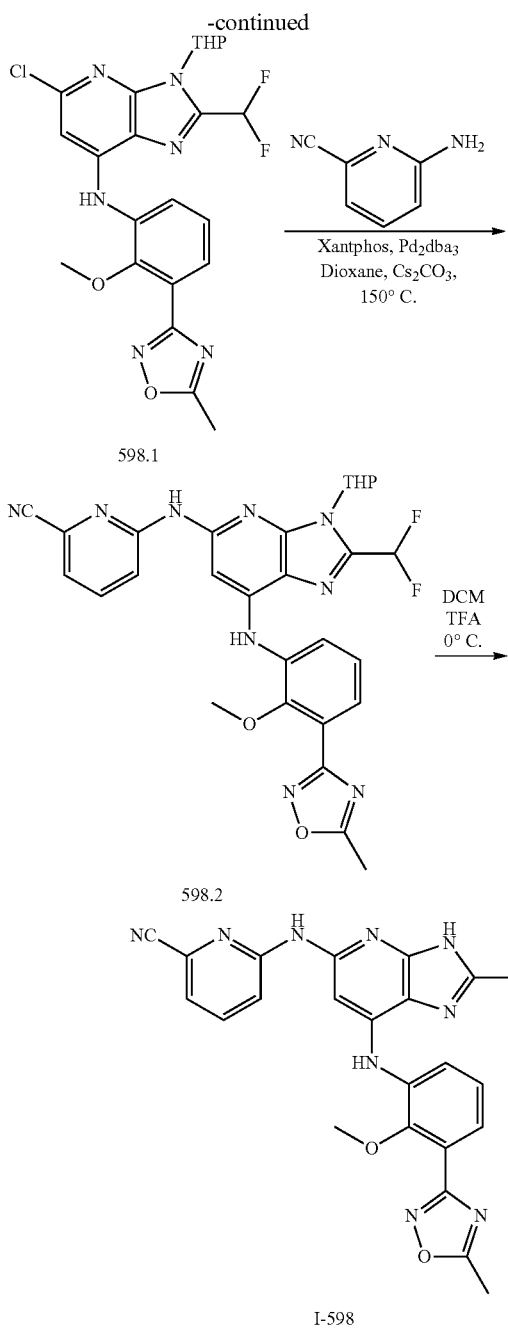

598.1

598.2

I-598

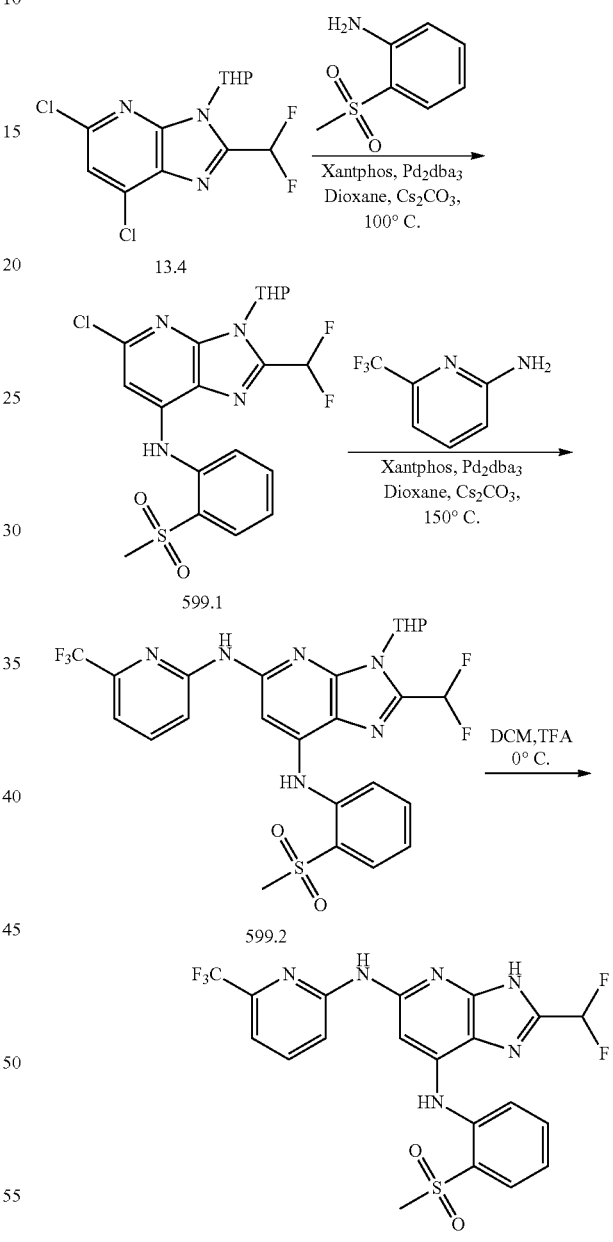

8.39 (s, 1H), 8.28-8.24 (m, 1H), 7.89-7.85 (m, 1H), 7.75-7.69 (m, 1H), 7.47-7.33 (m, 3H), 7.22 (s, 1H), 7.11 (t, 1H), 3.73 (s, 3H), 2.71 (s, 3H).

Example 599: Synthesis of 6-((2-methyl-7-((2-(methylsulfonyl)phenyl)amino)-3H-imidazo[4,5-b]pyridin-5-yl)amino)picolinonitrile, I-599

13.4

599.1

599.2

I-599

Synthesis of Compound 598.1.

Compound 598.1 was synthesized from 13.4 and 598.1a using general procedure A (Yield: 13.56%). MS(ES): m/z 491.90 [M+H]$^+$.

Synthesis of Compound 598.2.

Compound 598.2 was synthesized from 598.1 and 6-aminopicolinonitrile using general procedure B. (Yield: 52.46%). MS(ES): m/z 574.56 [M+H]$^+$.

Synthesis of I-598.

Compound I-598 was synthesized using from 598.2 general procedure C. (Yield: 67.84%). MS(ES): m/z: 490.45 [M+H]$^+$, LCMS purity: 100%, HPLC purity: 100%, 1H NMR (DMSO, 400 MHz): 13.540 (s, 1H), 10.08 (s, 1H), Synthesis of Compound 599.1.

Compound 599.1 was synthesized from 13.4 and 2-(methylsulfonyl)aniline using general procedure A. (Yield: 44.65%). MS (ES): m/z 457.89 [M+H]$^+$.

Synthesis of Compound 599.2.

Compound 599.2 was synthesized from 599.1 and 6-(trifluoromethyl)pyridin-2-amine using general procedure B. (Yield: 39.21%). MS (ES): m/z 583.55 [M+H]$^+$.

Synthesis of Compound I-599.

Compound I-599 was synthesized from 599.2 using general procedure C. (Yield: 74.80%). MS(ES): m/z: 499.58 [M+H]⁺, LCMS purity: 100%, HPLC purity: 100%, 1H NMR (DMSO-d6, 400 MHz): 13.66 (s, 1H), 10.17 (s, 1H), 8.90 (s, 1H), 8.23-8.21 (d, J=8.2 Hz, 1H), 7.96-7.88 (m, 3H), 7.78-7.74 (t, J=16.0 Hz, 1H), 7.57 (s, 1H), 7.40-7.31 (m, 2H), 7.24 (s, 1H), 3.23 (s, 3H).

Example 600: Synthesis of 2-methyl-N7-(2-(methylsulfonyl)phenyl)-N5-(6-(trifluoromethyl)pyridin-2-yl)-3H-imidazo[4,5-b]pyridine-5,7-diamine, I-600

Synthesis of Compound 600.1.

Compound 600.1 was synthesized from 98.4 and 2-(methylsulfonyl)aniline using general procedure A. (Yield: 46.65%). MS (ES): m/z 421.91 [M+H]⁺.

Synthesis of Compound 600.2.

Compound 600.2 was synthesized from 600.1 and 6-(trifluoromethyl)pyridin-2-amine using general procedure B. (Yield: 41.21%). MS (ES): m/z 547.57 [M+H]⁺.

Synthesis of Compound I-600.

Compound I-600 was synthesized from 600.2 using general procedure C. (Yield: 54.80%). MS(ES): m/z: 463.35 [M+H]⁺, LCMS purity: 100%, HPLC purity: 98.33%, 1H NMR (DMSO-d6, 400 MHz): 12.57 (s, 1H), 9.99 (s, 1H), 8.73 (s, 1H), 8.09-8.06 (d, J=8.2 Hz, 1H), 7.94-7.85 (m, 3H), 7.74-7.71 (t, 1H), 7.56 (s, 1H), 7.34-7.26 (m, 2H), 3.21 (s, 3H), 2.51 (s, 3H).

Example 601: Synthesis of N5-(5,6-dimethylpyrazin-2-yl)-N7-(4-(5,5-dimethyltetrahydro-2H-pyran-2-yl)-2-(methylsulfonyl)phenyl)-2-methyl-3H-imidazo[4,5-b]pyridine-5,7-diamine, I-601

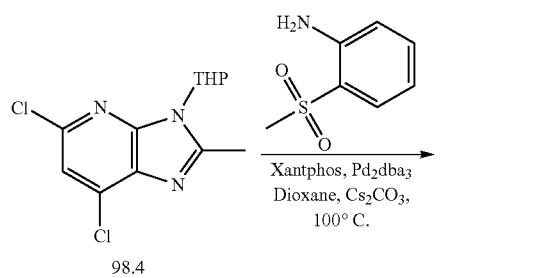

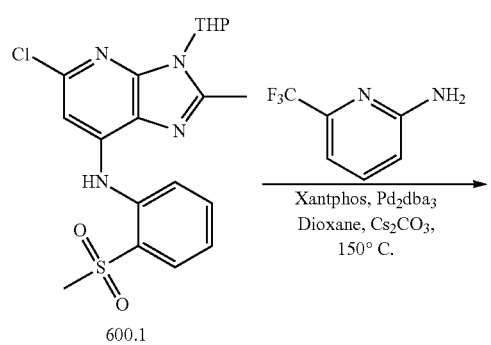

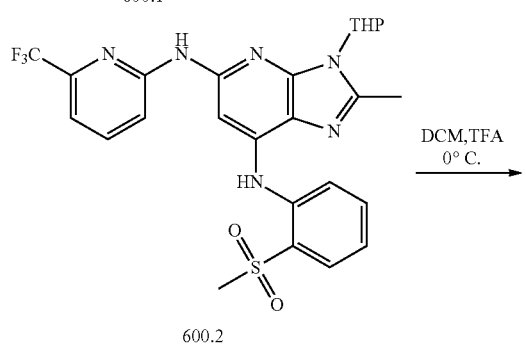

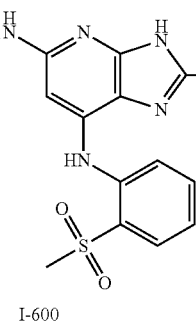

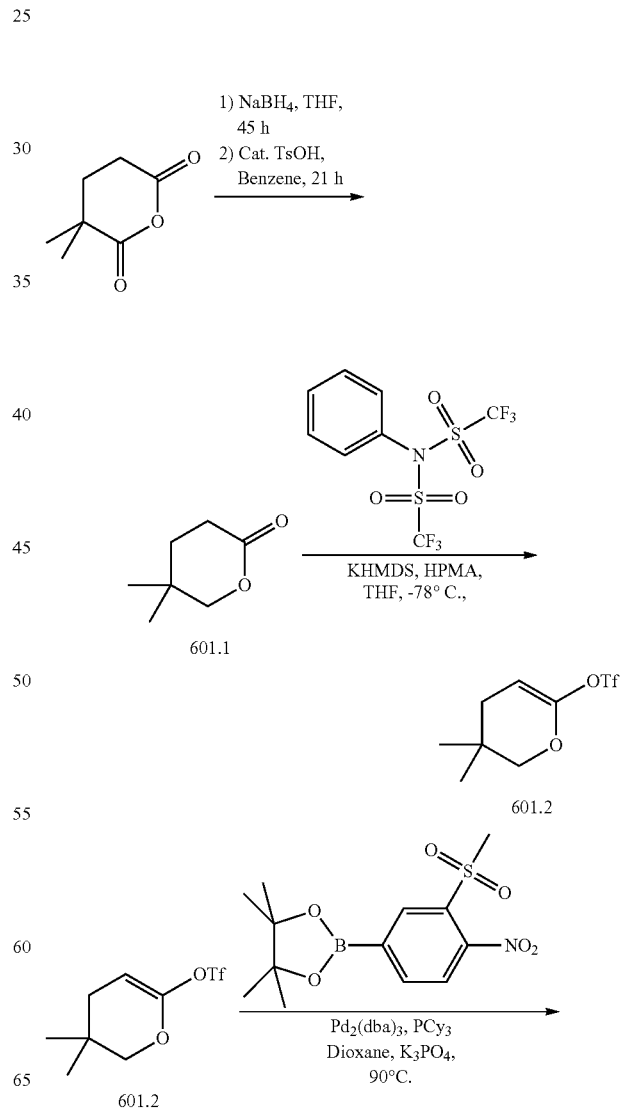

1165

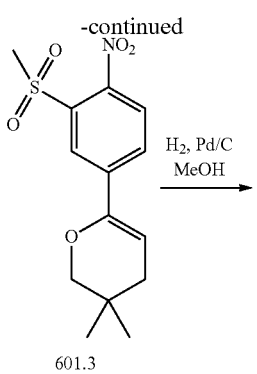

601.3

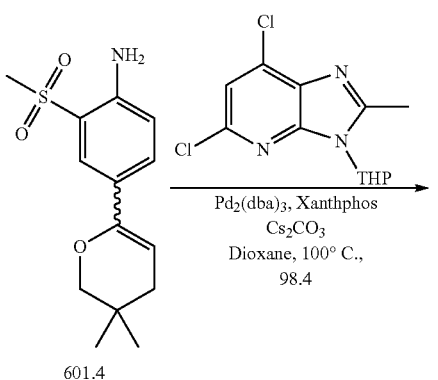

601.4

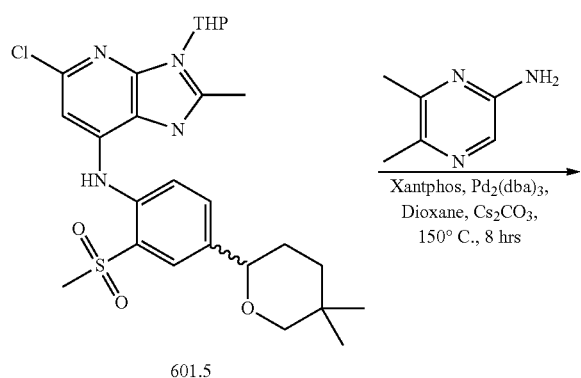

601.5

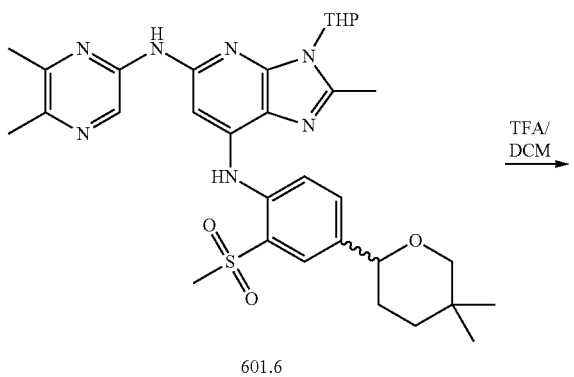

601.6

1166

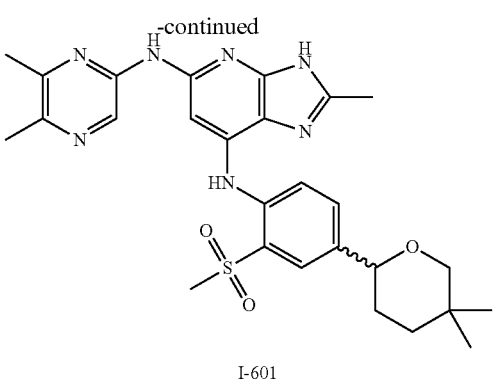

I-601

Synthesis of Compound 601.1.

To a solution of 3,3-dimethyldihydro-2H-pyran-2,6(3H)-dione 1 (15 g, 105.52 mmol, 1.0 eq), in Tetrahydrofuran (200 mL) was added sodium borohydrate (12 g, 316.9 mmol, 3.0 eq). The reaction mixture was stirred for 48 hr at r.t. Then Benzene (100 mL) and p-Toluenesulfonic acid (2 g, 10.56 mmol, 0.1 eq), was added into reaction mixture and stirred the reaction mixture at r.t. for 24 h. After completion of reaction, Ether was added to reaction mixture and washed with water. Organic layers were combined, dried over $Na_2SO_4$ and concentrated in vacuo to obtain crude product 601.1 (13 g, 96.12%). MS(ES): m/z 129.17 $[M+H]^+$.

Synthesis of Compound 601.2.

To a solution of 601.1 (5 g, 39.06 mmol, 1.0 eq), Hexamethylphosphoramide (8.75 g, 48.82 mmol, 1.25 eq), in Tetrahydrofuran (50 mL) was added Potassium bis(trimethylsilyl)amide at −78° C. Then a solution of 1,1,1-trifluoro-N-phenyl-N-((trifluoromethyl)sulfonyl)methanesulfonamide 1.2 (17.4 g, 48.82 mmol, 1.25 eq) in tetrahydrofuran (50 mL) was added into the reaction mixture. The reaction mixture was stirred at −78° C. for 2 hr and allowed to come at 0° C. and stirred for 1 hr at 0° C. Upon completion, reaction mixture transferred into the aqueous sodium hydroxide solution and diluted with water and extracted with diethyl ether. Organic layers were combined, dried over $Na_2SO_4$ and concentrated in vacuo to obtain crude product 601.2 (5 g, 49.25%). MS(ES): m/z 261.23 $[M+H]^+$.

Synthesis of Compound 601.3.

To a solution of 601.2 (4.35 g, 16.72 mmol, 1.0 eq), in 1,4-dioxane (50 mL) was added 4,4,5,5-tetramethyl-2-(3-(methylsulfonyl)-4-nitrophenyl)-1,3,2-dioxaborolane (6 g, 16.72 mmol, 1.0 eq). The reaction mixture was degassed by argon for 30 min. $Pd_2(dba)_3$ (3 g, 3.34 mmol, 0.2 eq), potassium carbonate (6.9 g, 50.19 mmol, 3.0 eq), Tricyclohexylphosphine(0.936 g, 3.34 mmol, 0.2 eq) were added into reaction mixture and again degassed by argon for 20 min. Further reaction mixture was stirred at 90° C. for 30 min. After completion of reaction, water was added to reaction mixture and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 601.3 (2.5 g, 48.03%). MS(ES): m/z 312.35 $[M+H]^+$.

Synthesis of Compound 601.4.

To a solution of 601.3 (2.5 g, 8.038 mmol, 1.0 eq) in MeOH (40 mL), 10% Pd/C (1.3 g) was added. Hydrogen was purged through reaction mixture for 2-3 h. Upon completion, reaction mixture was filtered through celite-bed and washed with MeOH. Filtrate was concentrated in vacuo to obtain 601.4 (0.600 g, 26.37%). MS(ES): m/z 384.39 [M+H]⁺.

Synthesis of Compound 601.5.

Compound 601.5 was synthesized from 98.4 and 601.4 using general procedure A (Yield: 31.31%). MS(ES): m/z 534.08 [M+H]⁺.

Synthesis of Compound 601.6.

Compound was synthesized from 601.5 and 5,6-dimethylpyrazin-2-amine using general procedure B. (Yield: 74.54%). MS(ES): m/z 620.79 [M+H]⁺.

Synthesis of Compound I-601.

Compound I-601 was synthesized from 601.6 using general procedure C. (Yield: 97.90%), MS(ES): m/z: 536.90 [M+H]⁺, LCMS purity: 95.30%, HPLC purity 92.74%, Chiral HPLC: (49%, 48%), 1H NMR (DMSO, 400 MHz): 12.51 (s, 1H), 9.57 (s, 1H), 8.86 (s, 1H), 8.57 (s, 1H), 7.90 (s, 1H), 7.84-7.82 (d, J=8.4 Hz, 1H), 7.73-7.71 (d, J=8.4 Hz, 1H), 7.45 (s, 1H), 4.37-4.34 (d, J=10.8 Hz, 1H), 3.58 (s, 1H), 3.20 (s, 3H), 2.47 (s, 3H), 2.37 (s, 3H), 2.36 (s, 3H), 2.35 (s, 2H), 1.79-1.77 (m, 1H), 1.62 (s, 2H), 1.08 (s, 3H), 0.86 (s, 3H).

Example 602: Synthesis of 6-((2-(difluoromethyl)-7-((2-(methylsulfonyl)phenyl)amino)-3H-imidazo[4,5-b]pyridin-5-yl)amino)picolinonitrile, I-602

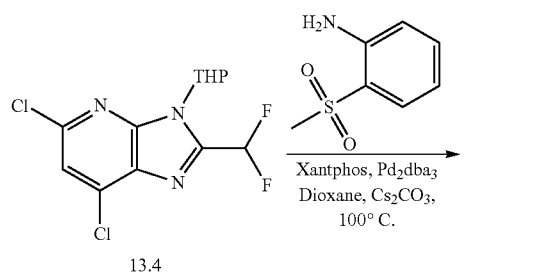

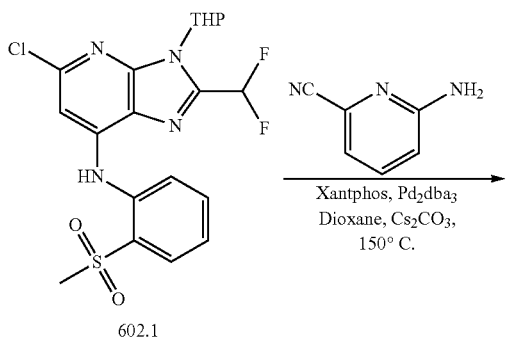

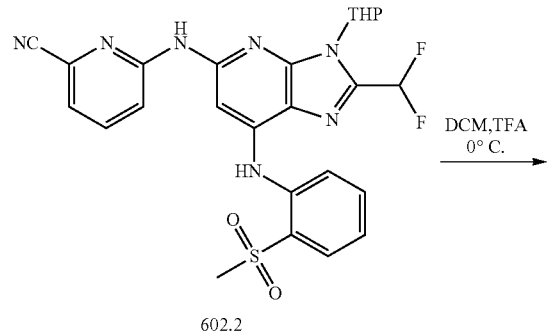

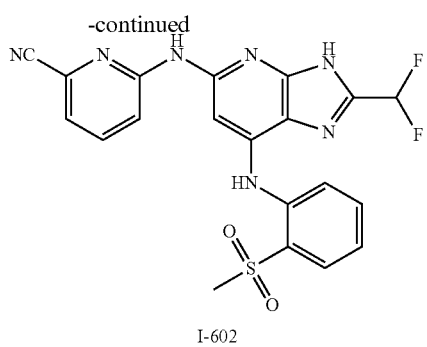

I-602

Synthesis of Compound 602.1.

Compound 602.1 was synthesized from 13.4 and 2-(methylsulfonyl)aniline using general procedure A. (Yield: 44.65%). MS (ES): m/z 457.89 [M+H]⁺.

Synthesis of Compound 602.2.

Compound 602.2 was synthesized from 602.1 and 6-aminopicolinonitrile using general procedure B. (Yield: 31.05%). MS (ES): m/z 540.56 [M+H]⁺.

Synthesis of Compound I-602.

Compound I-602 was synthesized from 602.2 using general procedure C. (Yield: 53.85%). MS(ES): m/z: 456.51 [M+H]⁺, LCMS purity: 99.07%, HPLC purity: 98.90%, 1H NMR (DMSO-d6, 400 MHz): 13.66 (s, 1H), 10.14 (s, 1H), 8.87 (s, 1H), 8.15-8.13 (d, J=8.4 Hz, 1H), 7.95-7.93 (d, J=8.3 Hz, 2H), 7.89-7.81 (m, 2H), 7.57 (s, 1H), 7.47-7.45 (d, J=8.2 Hz, 1H), 7.37-7.31 (m, 1H), 7.18 (s, 1H), 3.22 (s, 3H).

Example 603: Synthesis of 6-((2-methyl-7-((2-(methylsulfonyl)phenyl)amino)-3H-imidazo[4,5-b]pyridin-5-yl)amino)picolinonitrile, I-603

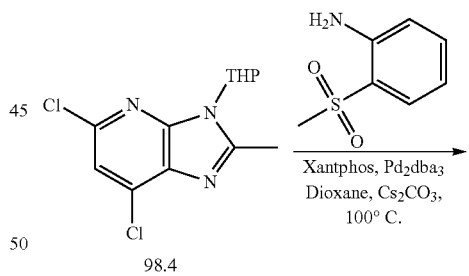

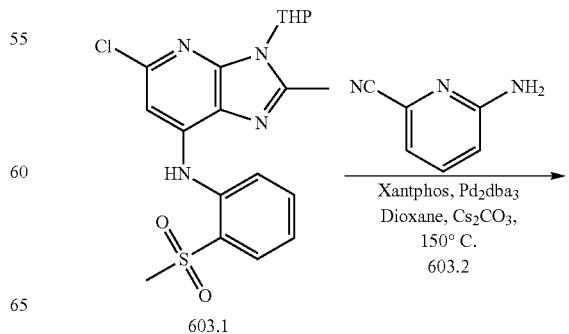

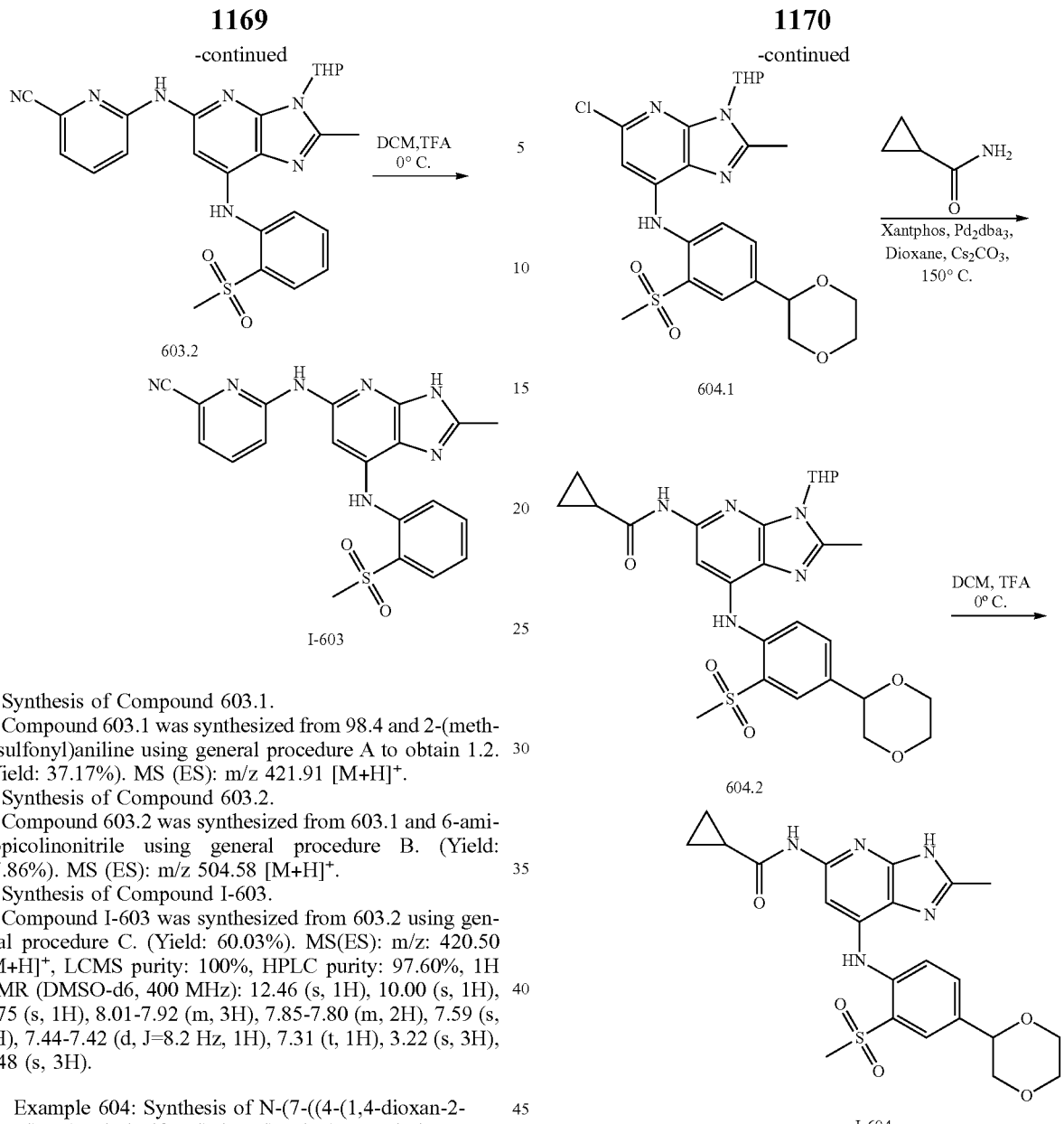

Synthesis of Compound 603.1.

Compound 603.1 was synthesized from 98.4 and 2-(methylsulfonyl)aniline using general procedure A to obtain 1.2. (Yield: 37.17%). MS (ES): m/z 421.91 [M+H]+.

Synthesis of Compound 603.2.

Compound 603.2 was synthesized from 603.1 and 6-aminopicolinonitrile using general procedure B. (Yield: 27.86%). MS (ES): m/z 504.58 [M+H]+.

Synthesis of Compound I-603.

Compound I-603 was synthesized from 603.2 using general procedure C. (Yield: 60.03%). MS(ES): m/z: 420.50 [M+H]+, LCMS purity: 100%, HPLC purity: 97.60%, 1H NMR (DMSO-d6, 400 MHz): 12.46 (s, 1H), 10.00 (s, 1H), 8.75 (s, 1H), 8.01-7.92 (m, 3H), 7.85-7.80 (m, 2H), 7.59 (s, 1H), 7.44-7.42 (d, J=8.2 Hz, 1H), 7.31 (t, 1H), 3.22 (s, 3H), 2.48 (s, 3H).

Example 604: Synthesis of N-(7-((4-(1,4-dioxan-2-yl)-2-(methylsulfonyl)phenyl)amino)-2-methyl-3H-imidazo[4,5-b]pyridin-5-yl)cyclopropanecarboxamide, I-604

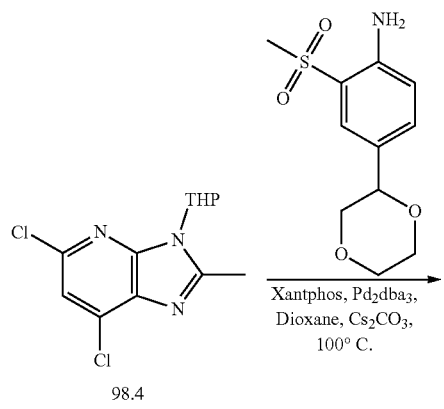

Synthesis of Compound 604.1.

Compound 604.1 was synthesized from 98.4 and 588.2 using general procedure A. (Yield: 26.20%). MS (ES): m/z 508.00 [M+H]+.

Synthesis of Compound 604.2.

Compound 604.2 was synthesized from 604.1 and cyclopropanecarboxamide using general procedure B. (Yield: 80.72%). MS (ES): m/z 556.65 [M+H]+.

Synthesis of Compound I-604.

Compound I-604 was synthesized from 604.2 using general procedure C. (Yield: 97.35%). MS(ES): m/z: 472.67 [M+H]+, LCMS purity: 98.23%, HPLC purity: 96.84%, Chiral HPLC: (50.77%, 49.23%), 1H NMR (DMSO, 400 MHz): 12.51 (s, 1H), 10.59 (s, 1H), 8.60 (s, 1H), 7.91 (s, 2H), 7.72 (s, 2H), 4.69-4.66 (m, 1H), 4.12 (s, 2H), 3.94-3.81 (m, 2H), 3.78-3.75 (m, 2H), 3.75 (s, 3H), 2.51 (s, 3H), 1.99 (s, 1H), 0.67-0.63 (bs, 4H).

Example 605: Synthesis of 2-(difluoromethyl)-N5-(5,6-dimethylpyrazin-2-yl)-N7-(4-(5,5-dimethyltetrahydro-2H-pyran-2-yl)-2-(methylsulfonyl)phenyl)-3H-imidazo[4,5-b]pyridine-5,7-diamine, I-605

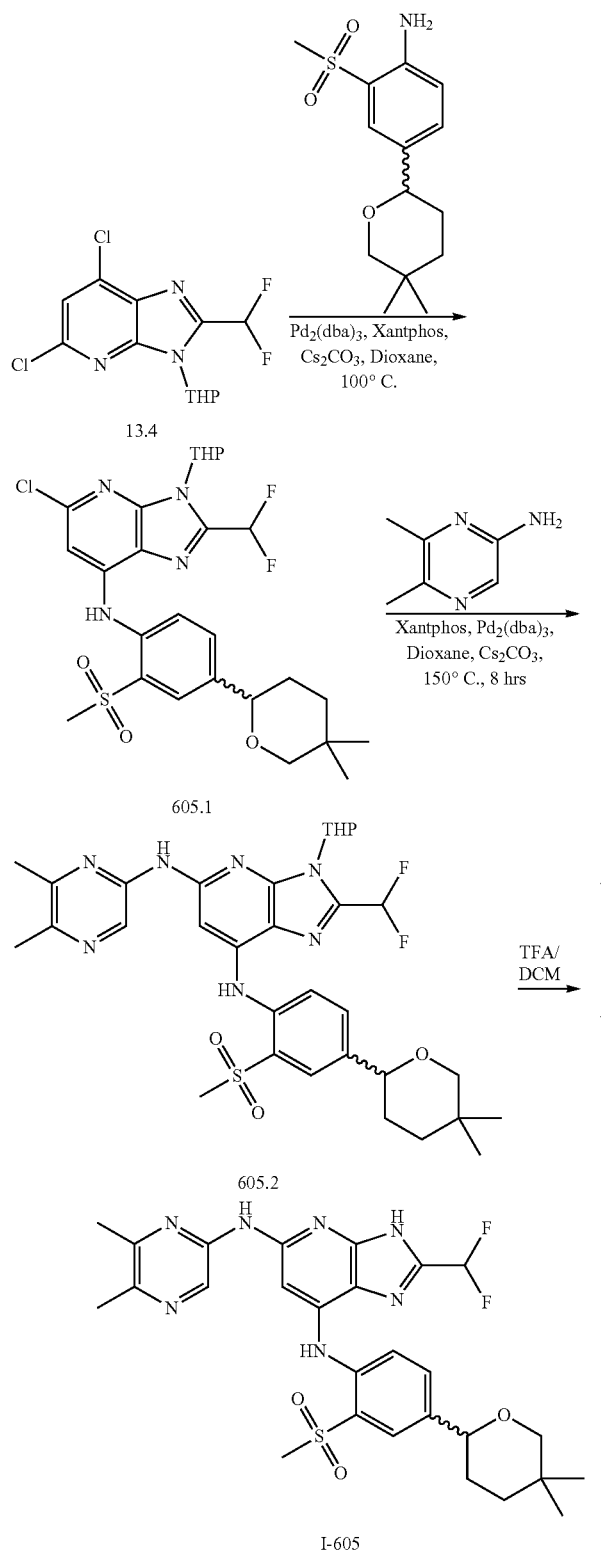

Synthesis of Compound 605.1.

Compound 605.1 was synthesized from 13.4 and 601.4 using general procedure A (Yield: 24.48%). MS(ES): m/z 570.06 [M+H]+.

Synthesis of Compound 605.2.

Compound 605.2 was synthesized from 605.1 and 5,6-dimethylpyrazin-2-amine using general procedure B. (Yield: 69.42%). MS(ES): m/z 656.77 [M+H]+.

Synthesis of I-605.

Compound I-605 was synthesized using general procedure C. (Yield: 90.82%). [M+H]+ MS(ES): m/z 572.71 [M+H]+, LCMS purity: 100%, HPLC Purity: 100%, Chiral HPLC: (45.56%, 54.44%), 1H NMR (DMSO, 400 MHz): 13.55 (s, 1H), 9.78 (s, 1H), 8.98 (s, 1H), 8.75 (s, 1H), 7.92-7.92 (d, J=1.6 Hz 1H), 7.87-7.85 (d, J=8.4 Hz, 1H), 7.76-7.74 (d, J=8.4 Hz, 1H), 7.49 (s, 1H), 7.22 (t, 1H), 4.39-4.36 (d, J=10.4 Hz, 1H), 3.59-3.56 (d, J=11.2 Hz, 2H), 3.22 (s, 3H), 2.37 (s, 3H), 2.33 (s, 3H), 1.81-1.81 (m, 2H), 1.67-1.63 (m, 2H), 1.08 (s, 3H), 0.87 (s, 3H).

Example 606: Synthesis of N7-(2-methoxy-3-(2-methyl-2H-1,2,3-triazol-4-yl)phenyl)-2-methyl-N5-(6-(trifluoromethyl)pyridin-2-yl)-3H-imidazo[4,5-b]pyridine-5,7-diamine, I-606

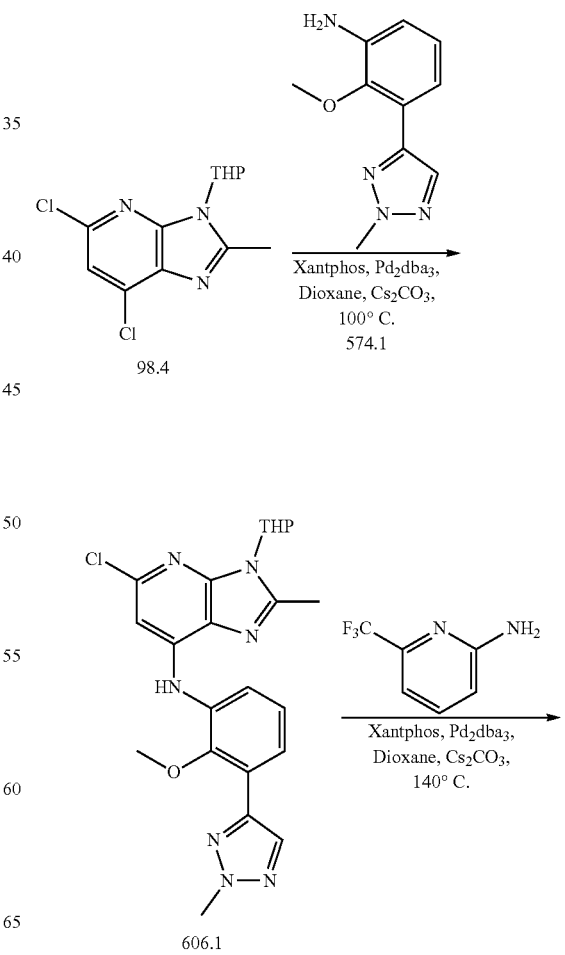

-continued

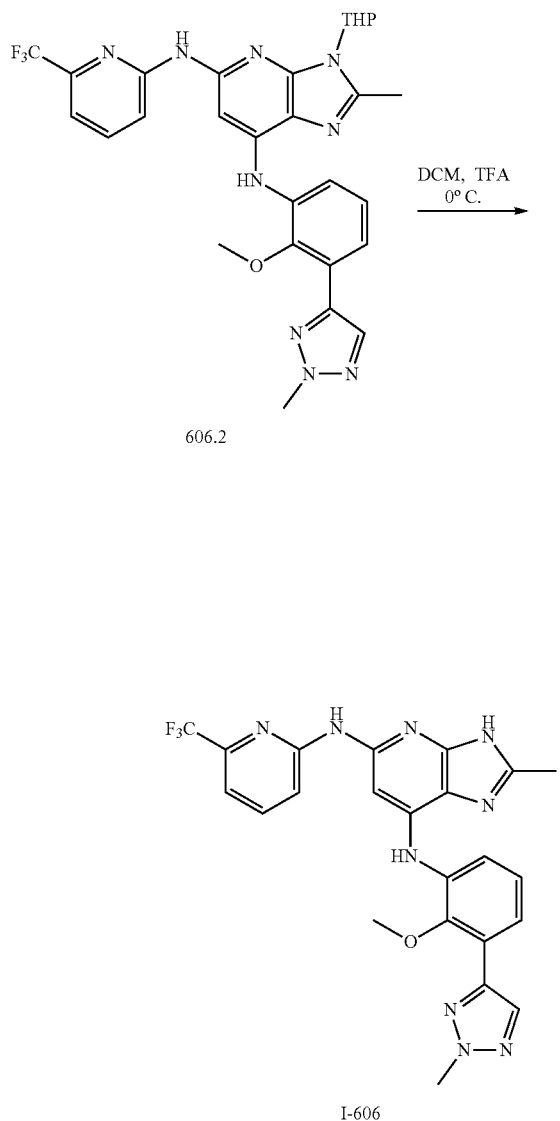

Synthesis of Compound 606.1

Compound 606.1 was synthesized from 98.4 and 574.1 synthesized using general procedure A. (Yield: 35.07%). MS (ES): m/z 454.91 [M+H]$^+$.

Synthesis of Compound 606.2.

Compound 606.2 was synthesized from 606.1 and 6-(trifluoromethyl)pyridin-2-amine using general procedure B. (Yield: 53.48%). MS (ES): m/z 580.5 [M+H]$^+$.

Synthesis of Compound I-606.

Compound I-606 was synthesized from 606.2 using general procedure C. (Yield: 70.33%). [M+H]$^+$ MS(ES): m/z: 496.58 [M+H]$^+$, LCMS purity: 100%, HPLC purity: 99.38%, 1H NMR (DMSO-d6, 400 MHz): 9.86 (s, 1H), 8.16 (s, 1H), 8.14 (s, 1H), 7.96 (s, 1H), 7.88-7.84 (t, J=12.4 Hz, 1H), 7.63-7.61 (d, 1H), 7.57-7.55 (d, 1H), 7.27-7.22 (m, 3H), 4.24 (s, 3H), 3.65 (s, 3H), 2.49 (s, 3H).

Example 607: Synthesis of 6-((2-(difluoromethyl)-7-((4-fluoro-2-(methylsulfonyl)phenyl)amino)-3H-imidazo[4,5-b]pyridin-5-yl)amino)-3-ethoxypicolinonitrile, I-607

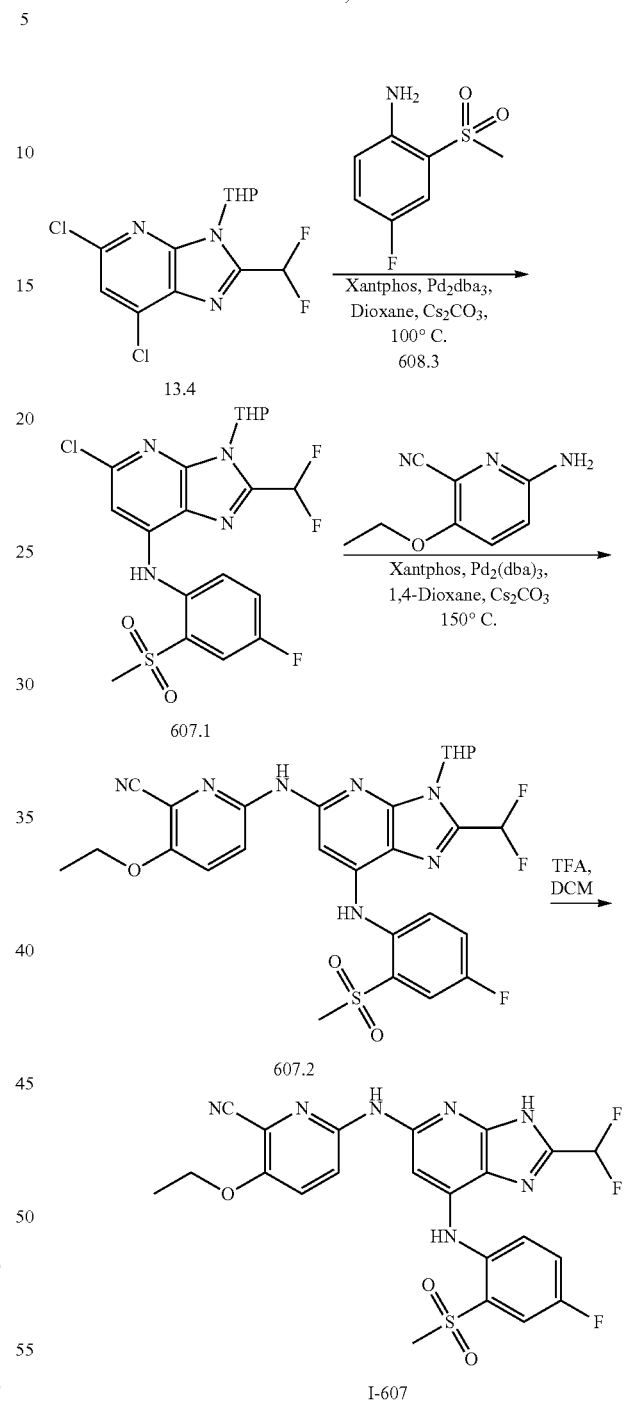

Synthesis of Compound 607.1.

Compound 607.1 was synthesized from 608.3 and 13.4 using general procedure A. (Yield: 54.27%). MS(ES): m/z 475.88 [M+H]$^+$.

Synthesis of Compound 607.2.

Compound 607.2 was synthesized from 607.1 and 6-amino-3-ethoxypicolinonitrile using general procedure B. (Yield: 28.94%). MS(ES): m/z 602.61 [M+H]$^+$.

Synthesis of Compound I-607.

Compound I-607 was synthesized from 607.2 using general procedure C. (Yield: 66.05%). MS(ES): m/z: 518.46 [M+H]+, LCMS purity: 99.04%, HPLC purity: 99.13%, 1H NMR (DMSO, 400 MHz): 13.57 (s, 1H), 9.90 (s, 1H), 8.70 (s, 1H), 8.14-8.12 (d, J=9.2 Hz, 1H), 7.93-7.89 (m, 1H), 7.80-7.69 (m, 3H), 7.35 (s, 1H), 7.22 (t, 1H), 4.25-4.20 (m, 2H), 3.29 (s, 3H), 1.39-1.19 (m, 3H).

Example 608: Synthesis of 3-ethoxy-6-((7-((4-fluoro-2-(methylsulfonyl)phenyl)amino)-2-methyl-3H-imidazo[4,5-b]pyridin-5-yl)amino)picolinonitrile, I-608

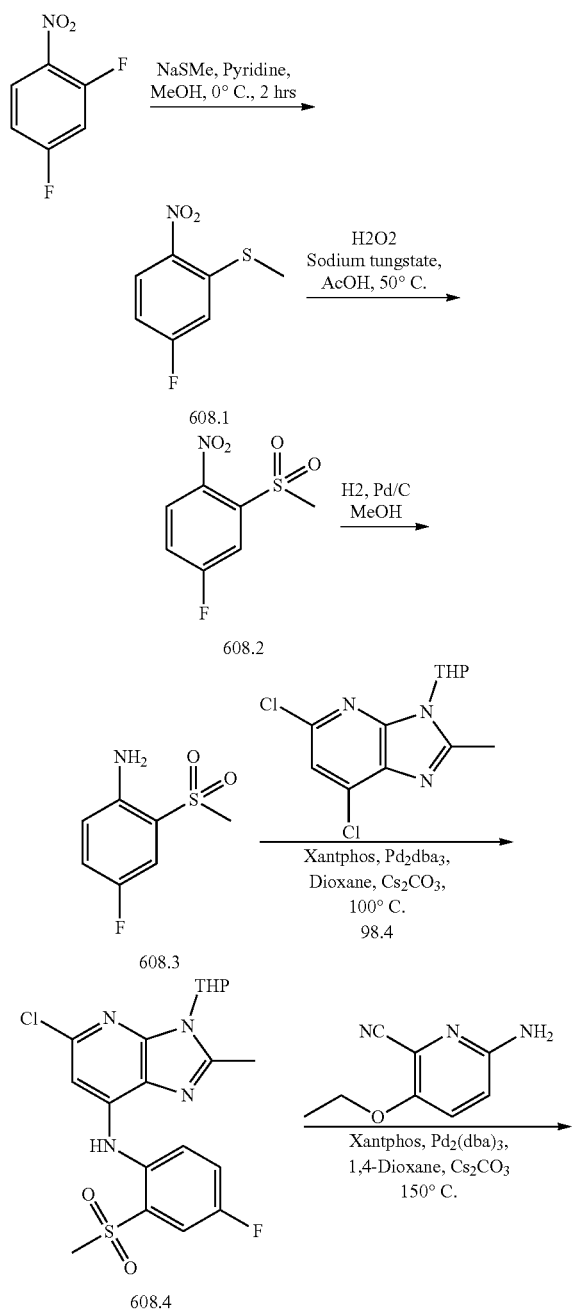

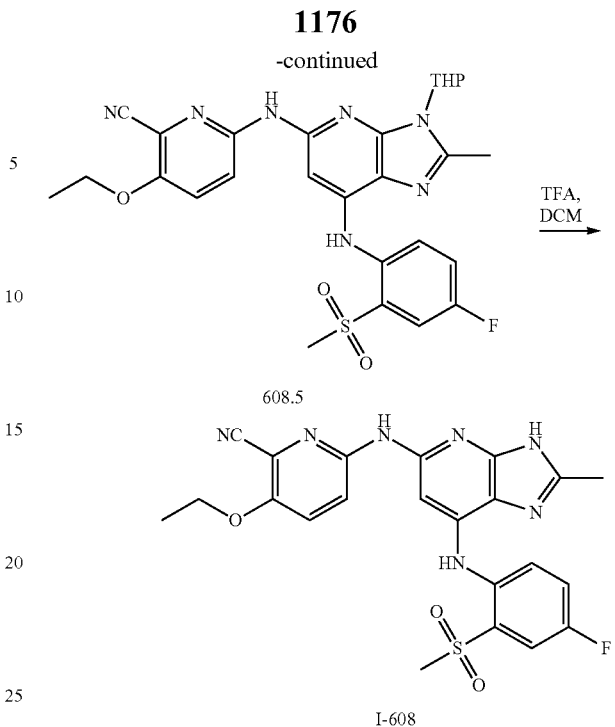

Synthesis of Compound 608.1.

To a solution of 2,4-difluoro-1-nitrobenzene 1 (10 g, 62.86 mmol, 1.0 eq) in MeOH (30 mL) was added Pyridine (12.4 g, 157.2 mmol, 2.5 eq) at r.t. Sodiumthiomethoxide (16.70 g, 69.18 mmol, 1.1 eq) in MeOH (10 mL) solution was added dropwise into the reaction mixture at 0° C. The reaction was stirred at 0° C. for 15 min. Upon completion, reaction mixture was transferred in ice cold water to obtain precipitate which was filtered, washed with water and dried well to obtained 608.1 (6 g, 50.99%). MS(ES): m/z 188.19 [M+H]+.

Synthesis of Compound 608.2.

To a solution of 608.1 (6 g, 32.05 mmol, 1 eq) in acetic acid (6 mL) was added 30% hydrogen peroxide (45 mL) and sodium tungstate dihydrate (7.4 g, 22.45 mmol, 0.7 eq) at 0° C. Reaction mixture was stirred at 65° C. for 4 hr. Upon completion, reaction mixture was transferred in ice-water and precipitate product was filtered, washed with water and dried well to obtain 1.2. (5 g, Yield: 71.17%). MS(ES): m/z 220.19 [M+H]+.

Synthesis of Compound 608.3.

To a solution of 608.2 (5 g, 22.81 mmol, 1.0 eq) in MeOH (200 mL), 10% Pd/C (3 g) was added. Hydrogen was purged through reaction mixture for 2-3 hr at r.t. Upon completion, reaction mixture was filtered through celite-bed and washed with ethanol. Filtrate was concentrated in vacuo to obtain 608.3 (3.8 g, 88.04%). MS(ES): m/z 190.20 [M+H]+.

Synthesis of Compound 608.4.

Compound 608.4 was synthesized from 608.3 and 98.4 using general procedure A. (Yield: 7.82%). MS(ES): m/z 439.90 [M+H]+.

Synthesis of Compound 608.5.

Compound 608.5 was synthesized from 608.4 and 6-amino-3-ethoxypicolinonitrile using general procedure B. (Yield: 45.26%). MS(ES): m/z 566.62 [M+H]+.

Synthesis of I-608.

Compound I-608 was synthesized from 608.5 using general procedure C. (Yield: 67.13%). MS(ES): m/z: 482.51 [M+H]+, LCMS purity: 100%, HPLC purity: 99.27%, 1H NMR (DMSO, 400 MHz): 12.43 (s, 1H), 9.71 (s, 1H), 8.53 (s, 1H), 8.03-8.00 (d, J=9.6 Hz, 1H), 7.91 (s, 1H), 7.77-7.69 (m, 3H), 7.40 (s, 1H), 4.24-4.19 (m, 2H), 3.27 (s, 3H), 2.47 (s, 3H), 1.38-1.35 (m, 3H).

Example 609/610: Synthesis of (R)—N5-(5,6-dimethylpyrazin-2-yl)-N7-(4-(5,5-dimethyltetrahydro-2H-pyran-2-yl)-2-(methylsulfonyl)phenyl)-2-methyl-3H-imidazo[4,5-b]pyridine-5,7-diamine, I-609 and (S)—N5-(5,6-dimethylpyrazin-2-yl)-N7-(4-(5,5-dimethyltetrahydro-2H-pyran-2-yl)-2-(methylsulfonyl)phenyl)-2-methyl-3H-imidazo[4,5-b]pyridine-5,7-diamine, I-610

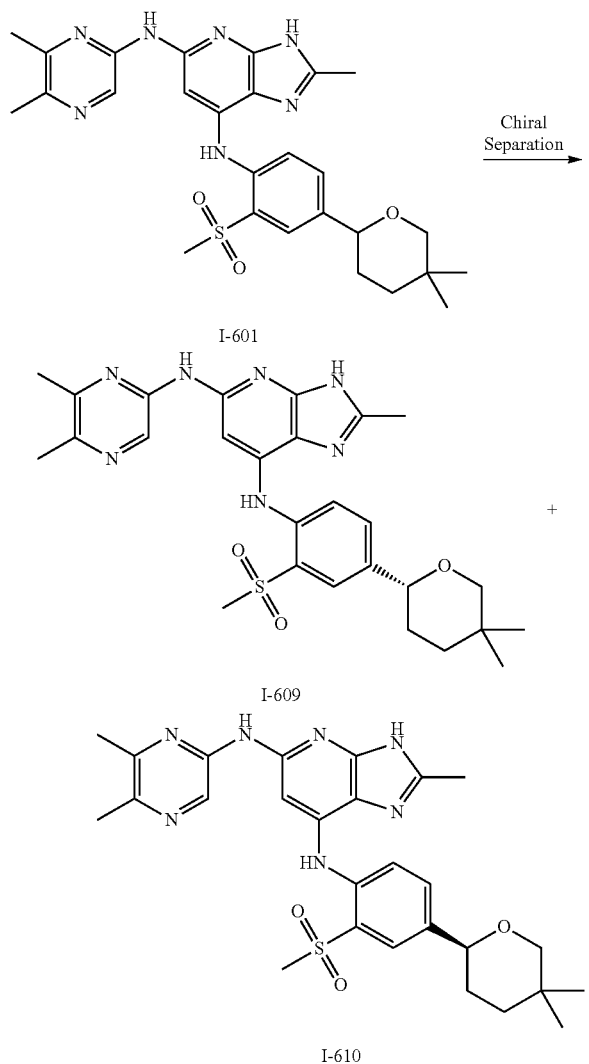

Synthesis of Compound I-609 and I-610.

Isomers of I-601 (0.095 g) were separated out using column (CHIRALCEL OX-H (250 mm*4.6 mm, 5u) and 0.1% DEA HEX:IPA (50:50) flow rate of 4 mL/min. to get pure fraction-1 (FR-a) and fraction-2 (FR-b). FR-a was concentrated in vacuo at 30° C. to afford pure I-609 (0.025 g). MS(ES): m/z 536.70 [M+H]$^+$, LCMS purity: 98.44%, HPLC Purity: 99.78%, Chiral HPLC: (99.26%), 1H NMR (DMSO, 400 MHz): 12.40 (s, 1H), 9.56 (s, 1H), 8.87 (s, 1H), 8.591 (s, 1H), 7.89-7.85 (m, 2H), 7.73-7.71 (d, J=8.8 Hz, 1H), 7.49 (s, 1H), 4.37-4.34 (d, J=10.8 Hz, 1H), 3.58-3.55 (d, J=11.2 Hz, 1H), 3.20 (s, 3H), 2.46 (s, 3H), 2.37 (s, 3H), 2.36 (s, 3H), 1.77 (s, 2H), 1.67-1.63 (m, 3H), 1.08 (s, 3H), 0.87 (s, 3H). FR-b was concentrated in vacuo at 30° C. to afford pure I-610 (0.050 g). MS(ES): m/z 536.70 [M+H]$^+$, LCMS purity: 98.07%, HPLC Purity: 99.25%, Chiral HPLC: (95.29%), 1H NMR (DMSO, 400 MHz): 12.45 (s, 1H), 9.57 (s, 1H), 8.87 (s, 1H), 8.58 (s, 1H), 7.89-7.84 (m, 2H), 7.73-7.71 (d, J=7.2 Hz, 1H), 7.47 (s, 1H), 4.37-4.35 (d, J=9.2 Hz, 1H), 3.58-3.51 (m, 1H), 3.20 (s, 3H), 2.46 (s, 3H), 2.36 (s, 6H), 1.80-1.77 (m, 2H), 1.65-1.58 (m, 3H), 1.08 (s, 3H), 0.87 (s, 3H).

Example 611/612 Synthesis of (R)—N-(7-((4-(1,4-dioxan-2-yl)-2-(methylsulfonyl)phenyl)amino)-2-methyl-3H-imidazo[4,5-b]pyridin-5-yl)cyclopropanecarboxamide, I-611 and (S)—N-(7-((4-(1,4-dioxan-2-yl)-2-(methylsulfonyl)phenyl)amino)-2-methyl-3H-imidazo[4,5-b]pyridin-5-yl)cyclopropanecarboxamide I-612

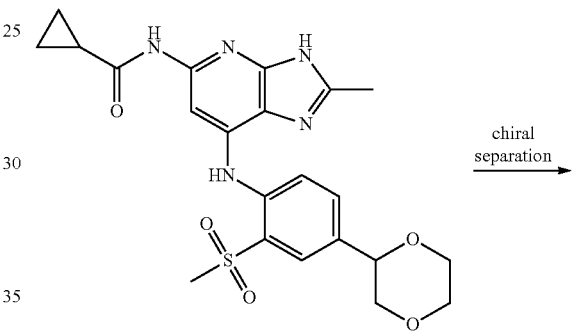

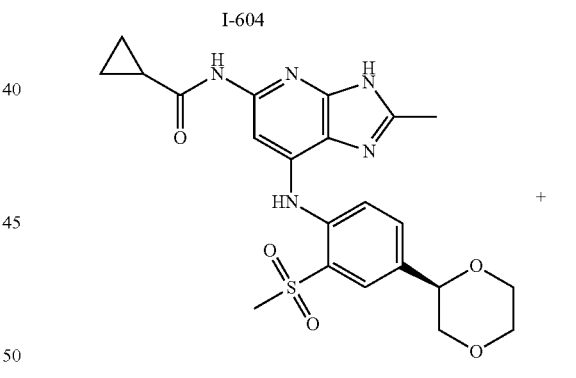

Synthesis of Compound I-611 and I-612.

Isomers of 1-604 (0.080 g) were separated out using column CHIRALPAK AD-H (250 mm*4.6 mm, 5u) and 0.1% D EA_HEX_IPA-MEOH (50-50) flow rate of 4 mL/min. to get pure fraction-1 (FR-a) and fraction-2 (FR-b). FR-a was concentrated in vacuo at 30° C. to afford pure I-611 (0.013 g). MS(ES): m/z: 472.57 [M+H]+, LCMS purity: 100%, HPLC purity: 99.02%, Chiral HPLC: (100%), 1H NMR (DMSO, 400 MHz): 12.49 (s, 1H), 10.59 (s, 1H), 8.61 (s, 1H), 8.00 (s, 1H), 7.74-7.70 (m, 3H), 4.70-4.68 (d, J=8.4 Hz, 1H), 3.92 (s, 2H), 3.82-3.76 (m, 2H), 3.65-3.63 (m, 2H), 3.20 (s, 3H), 2.49 (s, 3H), 2.06 (s, 1H), 0.91-0.88 (s, 4H). FR-b was concentrated in vacuo at 30° C. to afford pure I-612 (0.012 g). MS(ES): m/z: 472.57 [M+H]+, LCMS purity: 100%, HPLC purity: 98.61%, Chiral HPLC: (95.84%), 1H NMR (DMSO, 400 MHz): 10.59 (s, 1H), 8.61 (s, 1H), 8.00 (s, 1H), 7.91 (s, 1H), 7.76-7.68 (m, 3H), 4.70-4.68 (d, J=7.6 Hz, 1H), 4.16-4.14 (m, 2H), 3.92 (s, 2H), 3.82-3.76 (m, 2H), 3.20 (s, 3H), 2.49 (s, 3H), 2.06 (s, 1H), 0.91-0.87 (s, 4H).

Example 613/614: Synthesis of (R)—N-(7-((4-(1,4-dioxan-2-yl)-2-(methylsulfonyl)phenyl)amino)-2-(difluoromethyl)-3H-imidazo[4,5-b]pyridin-5-yl)cyclopropanecarboxamide, I-613 and (S)—N-(7-((4-(1,4-dioxan-2-yl)-2-(methylsulfonyl)phenyl)amino)-2-(difluoromethyl)-3H-imidazo[4,5-b]pyridin-5-yl)cyclopropanecarboxamide, I-614

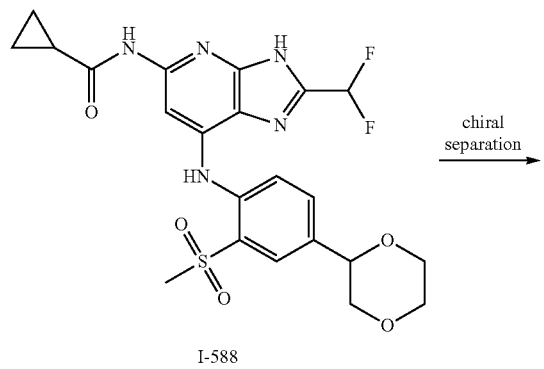

I-588 chiral separation →

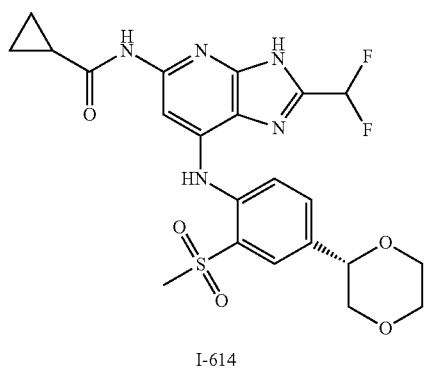

I-614

Synthesis of Compound I-613 and I-614.

Isomers of 1-588 (0.090 g) were separated out using column CHIRALPAK AD-H (250 mm*4.6 mm, 5u) and DEA_HEX_IPA-MEOH-DCM (40-40-20) flow rate of 4 mL/min. to get pure fraction-1 (FR-a) and fraction-2 (FR-b). FR-a was concentrated in vacuo at 30° C. to afford pure I-613 (0.025 g). MS(ES): m/z: 508.66 [M+H]+, LCMS purity: 100%, HPLC purity: 99.70%, Chiral HPLC: (100%), 1H NMR (DMSO, 400 MHz): 13.68 (s, 1H), 10.76 (s, 1H), 8.78 (s, 1H), 8.08 (s, 1H), 7.94 (s, 1H), 7.79-7.69 (m, 2H), 7.25 (t, 1H), 4.71-4.69 (m, 1H), 3.94 (s, 2H), 3.82-3.76 (m, 2H), 3.65-3.59 (m, 2H), 3.21 (s, 3H), 2.04-2.02 (m, 1H), 0.810-0.78 (m, 4H). FR-b was concentrated in vacuo at 30° C. to afford pure I-614 (0.027 g). MS(ES): m/z: 508.66 [M+H]+, LCMS purity: 99.45%, HPLC purity: 98.84%, Chiral HPLC: (98.32%), 1H NMR (DMSO, 400 MHz): 13.69 (s, 1H), 10.77 (s, 1H), 8.79 (s, 1H), 8.09 (s, 1H), 7.95 (s, 1H), 7.78 (s, 2H), 7.26 (t, 1H), 4.72-4.70 (m, 1H), 3.93 (s, 2H), 3.83-3.76 (m, 2H), 3.66-3.60 (m, 1H), 3.39 (s, 1H), 3.28 (s, 3H), 2.05-2.03 (m, 1H), 0.81-0.79 (m, 4H).

Example 615: Synthesis of (R)—N-(7-((4-(5,5-difluorotetrahydro-2H-pyran-2-yl)-2-(methylsulfonyl)phenyl)amino)-2-methyl-3H-imidazo[4,5-b]pyridin-5-yl)cyclopropanecarboxamide, I-615

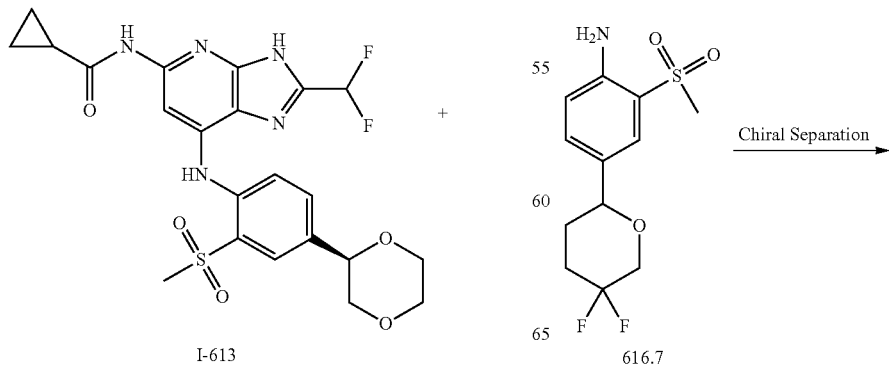

I-613 + 616.7 Chiral Separation →

-continued

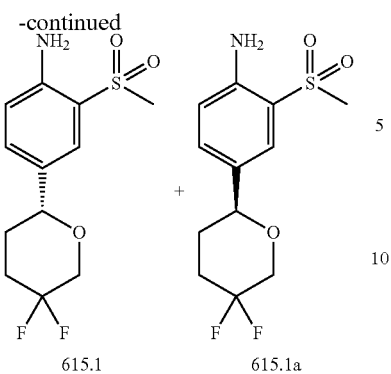

615.1     615.1a

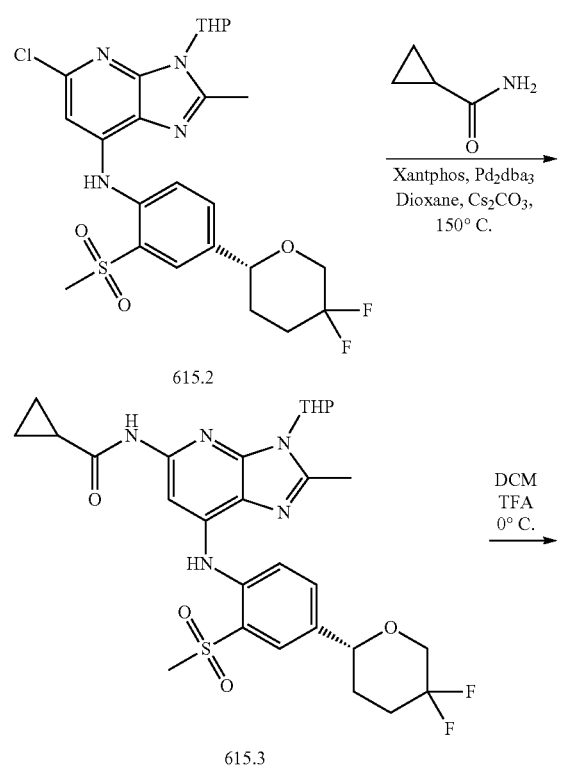

-continued

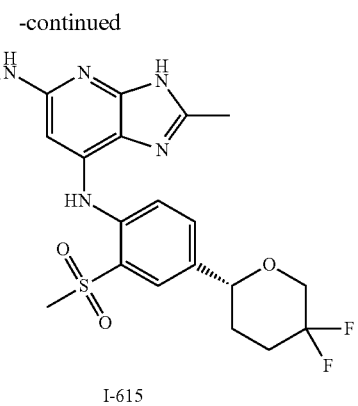

I-615

Synthesis of Compound 615.1 and 615.1a.

Isomers of 616.7 (0.293 g) were separated out using column CHIRALPAK AD-H (250 mm*4.6 mm, 5u) and 0.1% D EA_HEX_IPA-MEOH (50-50) flow rate of 4 mL/min. to get pure fraction-1 (FR-a) and fraction-2 (FR-b). FR-a was concentrated in vacuo at 30° C. to afford pure 615.1 (0.110 g). MS(ES): m/z: 292.31 [M+H]$^+$. FR-b was concentrated in vacuo at 30° C. to afford pure 615.1a (0.107 g). MS(ES): m/z: 292.31 [M+H]$^+$.

Synthesis of Compound 615.2.

Compound 615.2 was synthesized from 615.1 and 98.4 using general procedure A. (Yield: 37.51%). MS (ES): m/z 542.01 [M+H]$^+$.

Synthesis of Compound 615.3.

Compound 615.3 was synthesized from 615.2 and cyclopropanecarboxamide using general procedure B. (Yield: 79.99%). MS (ES): m/z 590.66 [M+H]$^+$.

Synthesis of Compound I-615.

Compound I-615 was synthesized from 615.3 using general procedure C. (Yield: 80.62%). MS(ES): m/z: 506.73 [M+H]$^+$, LCMS purity: 97.00%, HPLC purity: 96.34%, 1H NMR (DMSO-d6, 400 MHz): 12.49 (s, 1H), 10.58.

Example 616: Synthesis of (S)—N-(7-((4-(5,5-difluorotetrahydro-2H-pyran-2-yl)-2-(methylsulfonyl)phenyl)amino)-2-methyl-3H-imidazo[4,5-b]pyridin-5-yl)cyclopropanecarboxamide, I-616

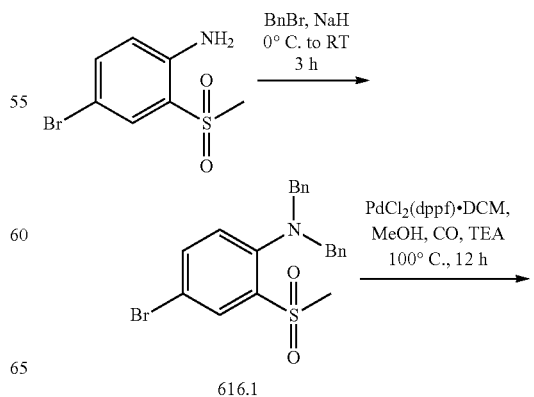

616.1

-continued
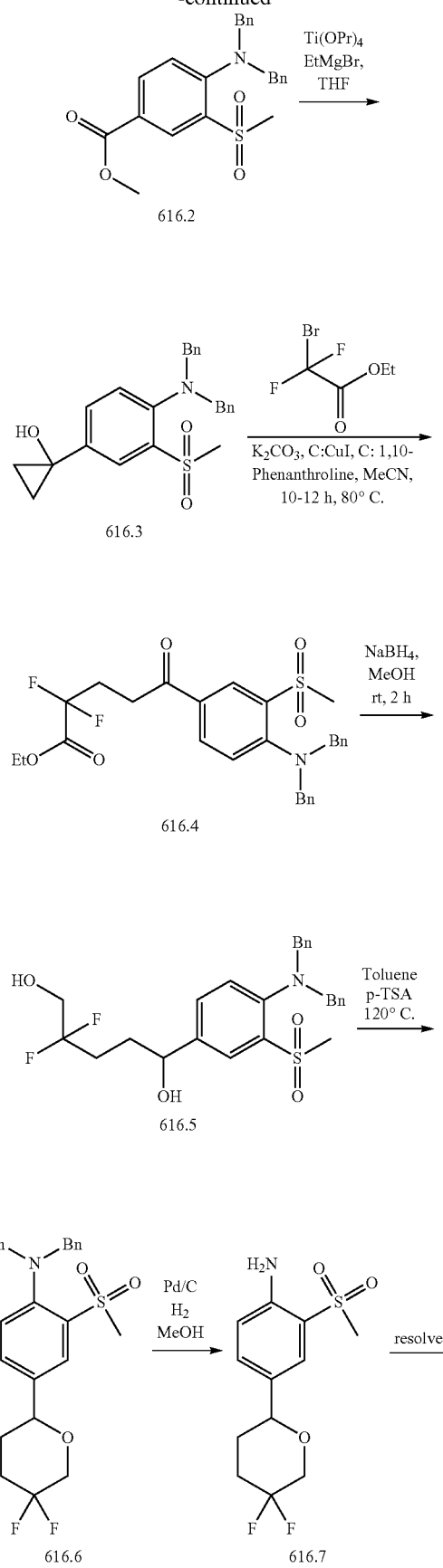
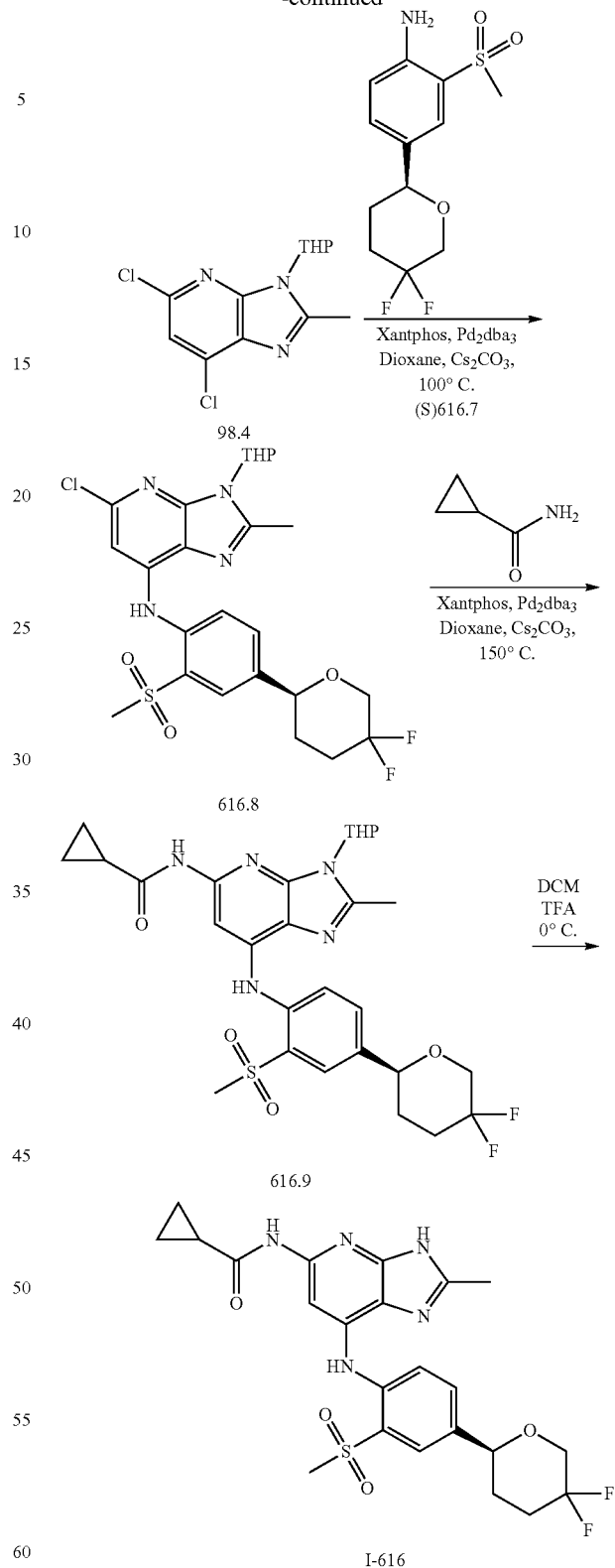
Synthesis of Compound 616.1.
To a solution of 4-bromo-2-(methylsulfonyl)aniline 1 (1 g, 4.00 mmol, 1 eq) in N, N-dimethylformamide (10 mL), was added sodium hydride (0.350 g, 14.0 mmol, 3.5 eq) at 0° C. Reaction mixture was stirred at 0° C. for 10 min.

Benzyl bromide (2 g, 12.4 mmol, 3 eq) was added dropwise into the reaction mixture at 0° C. for hr. Upon completion, reaction mixture was transferred into ice water and extracted with ethyl acetate. Organic layers were combined, dried over $Na_2SO_4$ and concentrated in vacuo to obtain crude product. This was purified by column chromatography and compound was eluted in 30% ethyl acetate in hexane to obtain pure 616.1. (0.500 g, 29.06%). MS(ES): m/z 431.36 $[M+H]^+$.

Synthesis of Compound 616.2.

To a solution of 616.1 (1 g, 2.23 mmol, 1 eq) in MeOH (10 mL) was added Triethyl amine (2.3 g, 23.25 mmol, 10 eq) and DCM [1,1'-Bis(diphenylphosphino)ferrocene]dichloropalladium(II) (3.79 g, 4.6 mmol, 2 eq). Reaction mixture was degassed by argon for 20 min. Further reaction mixture was stirred at 120° C. for 3 hr. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 616.2 (0.900 g, 94.58%). MS(ES): m/z 410.50 $[M+H]^+$.

Synthesis of Compound 616.3.

To a solution of 616.2 (4 g, 9.77 mmol, 1 eq) in Tetrahydrofuran (40 mL) was added dropwise Titanium isopropoxide (1.4 g, 4.9 mmol, 0.5 eq) at r.t. After 30 min, Ethyl magnesium bromide (2.67 g, 19.55 mmol, 2 eq) was added into the reaction mixture at r.t. Reaction mixture was stirred at r.t. for 12 h. Upon completion, reaction mixture transferred into water and extracted with ethyl acetate. Organic layers were combined, dried over $Na_2SO_4$ and concentrated in vacuo to 616.3 (3.5 g, 87.92%). MS(ES): m/z 408.53 $[M+H]^+$.

Synthesis of Compound 616.4.

To a solution of 616.3 (0.800 g, 1.96 mmol, 1.0 eq) in Acetonitrile (10 mL), was added potassium carbonate (0.541 g, 3.9 mmol, 2.0 eq), phenanthroline (0.070 g, 0.39 mmol, 0.2 eq), and copper iodide (0.037 g, 0.196 mmol, 0.1 eq). To a solution of ethyl 2-bromo-2,2-difluoroacetate (1.58 g, 7.84 mmol, 4 eq) in Acetonitrile (2 mL), was added into reaction mixture and heated the reaction mixture at 80° C. for 1 hr. Upon completion, reaction mixture transferred into water and extracted with ethyl acetate. Organic layers were combined, dried over $Na_2SO_4$ and concentrated in vacuo to crude material. This was purified by column chromatography and compound was eluted in 20% ethyl acetate in hexane to obtain pure 616.4 (0.540 g, 51.94%). MS(ES): m/z 530.60 $[M+H]^+$.

Synthesis of Compound 616.5

To a solution of 616.4 (0.540 g, 1.02 mmol, 1 eq) in MeOH (5 mL) was added Sodium Borohydride (0.076 g, 2.04 mmol, 2 eq) at r.t. Then reaction mixture was stirred at r.t. for 1 hr. Upon completion, reaction mixture transferred into water and extracted with ethyl acetate. Organic layers were combined, dried over $Na_2SO_4$ and concentrated in vacuo to obtain 616.5 (0.480 g, 96.16%). MS(ES): m/z 490.58 $[M+H]^+$.

Synthesis of Compound 616.6.

To a solution of 616.5 (0.510 g, 1.04 mmol, 1 eq) in Toluene (5 mL) was added p-Toluenesulfonic acid (0.020 g, 0.104 mmol, 0.1 eq) at r.t. Then reaction mixture was stirred at 120° C. for 2 h. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 616.6 (0.462 g, 94.05%). MS(ES): m/z 472.56 $[M+H]^+$.

Synthesis of Compound 616.7.

To a solution of 616.6 (0.462 g, 979.72 mmol, 1.0 eq) in MeOH (5 mL), 10% Pd/C (0.100 g) was added. Hydrogen was purged through reaction mixture for 2-3 h at r.t. Upon completion, reaction mixture was filtered through celite-bed and washed with MeOH. Filtrate was concentrated in vacuo to obtain 616.7 (0.250 g, 87.59%). MS(ES): m/z 292.31 $[M+H]^+$. 616.7 was resolved into its enantiomers by chiral HPLC.

Synthesis of Compound 616.8.

Compound 616.8 was synthesized from (S)-616.7 and 98.4 using general procedure A. (Yield: 35.10%). MS (ES): m/z 542.01 $[M+H]^+$.

Synthesis of Compound 616.9.

Compound 616.9 was synthesized from 616.8 and cyclopropanecarboxamide using general procedure B. (Yield: 77.54%). MS (ES): m/z 590.66 $[M+H]^+$.

Synthesis of Compound I-616.

Compound I-616 was synthesized from 616.9 using general procedure C. (Yield: 87.48%). MS(ES): m/z: 506.51 $[M+H]^+$, LCMS purity: 96.29%, HPLC purity: 96.21%, Chiral HPLC Purity: 98.21%, 1H NMR (DMSO-d6, 400 MHz): 12.54 (s, 1H), 10.60 (s, 1H), 8.57 (s, 1H), 7.99 (s, 1H), 7.89 (s, 1H), 7.69 (s, 2H), 4.70-4.67 (d, J=10.4 Hz, 1H), 3.94 (s, 3H), 3.94-3.78 (m, 2H), 3.21-3.18 (d, J=10.6 Hz, 4H), 2.28 (s, 1H), 2.10 (s, 1H), 1.25 (s, 2H), 0.76 (bs, 4H).

Example 617: Synthesis of N5-(7,7-difluoro-6,7-dihydro-5H-cyclopenta[b]pyridin-2-yl)-2-(difluoromethyl)-N7-(2-(methylsulfonyl)phenyl)-3H-imidazo[4,5-b]pyridine-5,7-diamine, I-617

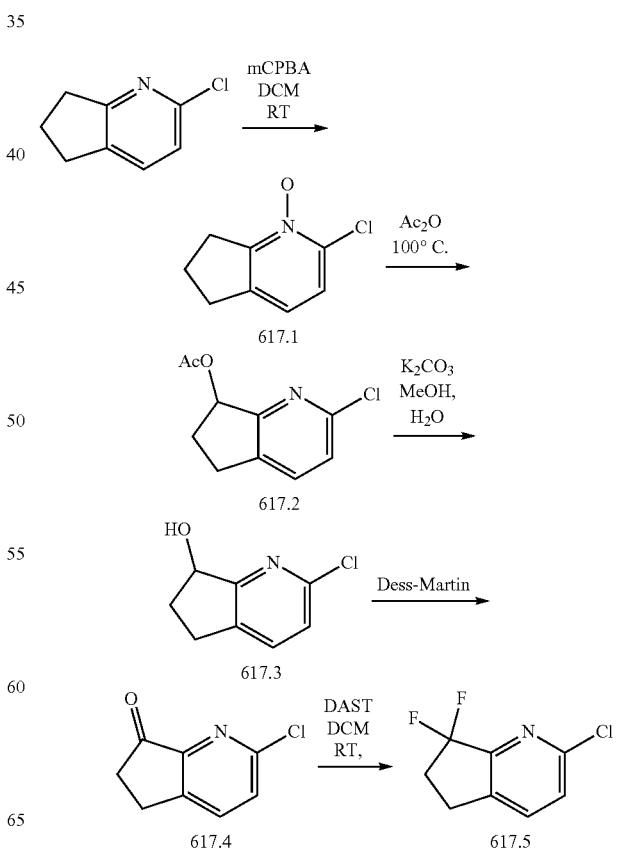

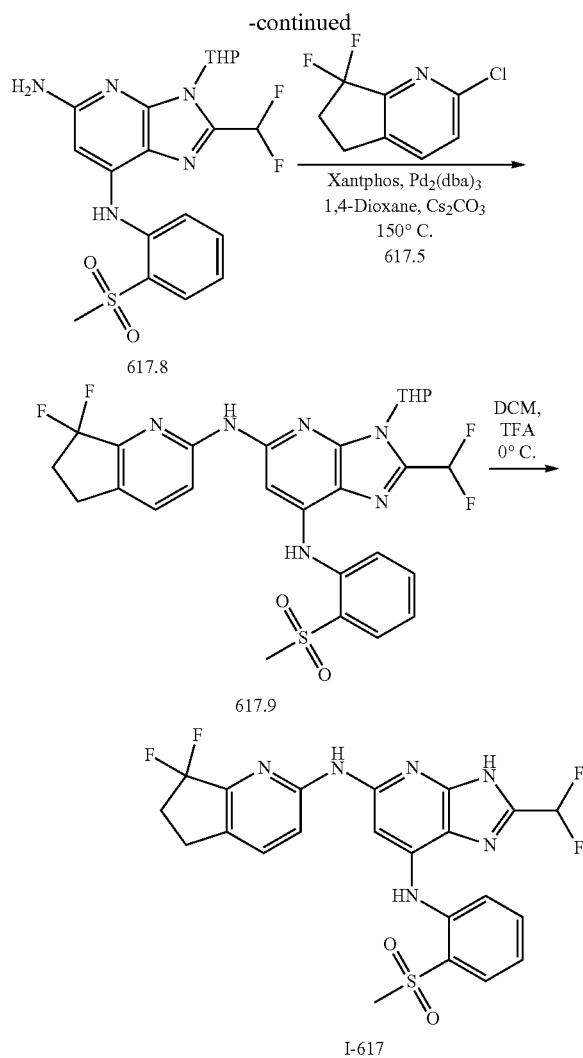

Synthesis of Compound 617.1.

To a solution 2-chloro-6,7-dihydro-5H-cyclopenta[b]pyridine 1 (3 g, 19.53 mmol, 1 eq) in CH$_2$Cl$_2$ (30 mL) was added meta-Chloroperbenzoic acid (11.75 g, 68.35 mmol, 3.5 eq) portion wise at 0° C. The reaction mixture was stirred at r.t. for 3 h. After completion of reaction, the reaction mixture was transferred into saturated NaHCO$_3$ solution and extracted with CH$_2$Cl$_2$. Combined Organic layer dried over Na$_2$SO$_4$ and concentrated in vacuo to obtain crude product. This was purified by column chromatography and compound was eluted in 30% ethyl acetate in hexane to obtain pure 617.1 (3 g, 90.57%). MS(ES): m/z 170.61 [M+H]$^+$.

Synthesis of Compound 617.2.

A solution 617.1 (3 g, 19.53 mmol, 1 eq) in Acetic anhydride (30 mL) was heated at 100° C. for 4 h. After completion of reaction, the reaction mixture was concentrated in vacuo to obtain crude product. The crude material was transferred into saturated NaHCO$_3$ solution and extracted with CH$_2$Cl$_2$. Combined Organic layer dried over Na$_2$SO$_4$ and concentrated in vacuo to obtain crude product. This was purified by column chromatography and compound was eluted in 20% ethyl acetate in hexane to obtain pure 617.2 (3 g, 80.14%). MS(ES): m/z 212.65 [M+H]$^+$.

Synthesis of Compound 617.3.

To a solution 617.2 (3 g, 14.17 mmol, 1 eq) in MeOH (24 mL) and water (6 mL) was added potassium carbonate (6.86 g, 49.76 mmol, 3.5 eq) at r.t. The reaction mixture was stirred at r.t. for 2 h. After completion of reaction, the reaction mixture was transferred into water and extracted with ethyl acetate. Combined Organic layer dried over Na$_2$SO$_4$ and concentrated in vacuo to obtain crude product. This was purified by column chromatography and compound was eluted in 40% ethyl acetate in hexane to obtain pure 617.3 (2.2 g, 91.51%). MS(ES): m/z 170.61 [M+H]$^+$.

Synthesis of Compound 617.4.

To a solution 617.3 (2.2 g, 12.97 mmol, 1 eq) in CH$_2$Cl$_2$ (30 mL) was added Dess martin periodinane (8.28 g, 19.52 mmol, 1.5 eq) at 0° C. The reaction mixture was stirred at r.t. for 2 h. After completion of reaction, the reaction mixture was transferred into saturated NaHCO$_3$ solution and extracted with CH$_2$Cl$_2$. Combined Organic layer dried over Na$_2$SO$_4$ and concentrated in vacuo to obtain crude product. This was purified by column chromatography and compound was eluted in 20% ethyl acetate in hexane to obtain pure 617.4 (1.8 g, 82.80%). MS(ES): m/z 168.59 [M+H]$^+$.

Synthesis of Compound 617.5.

To a solution 617.4 (0.850 g, 5.07 mmol, 1 eq) in CH$_2$Cl$_2$ (10 mL) was added Diethylaminosulfur trifluoride (4.1 g, 25.44 mmol, 5 eq) at 0° C. The reaction mixture was stirred at r.t. for 2 h. After completion of reaction, the reaction mixture was transferred into saturated NaHCO$_3$ solution and extracted with CH$_2$Cl$_2$. Combined Organic layer dried over Na$_2$SO$_4$ and concentrated in vacuo to obtain crude product. This was purified by column chromatography and compound was eluted in 10% ethyl acetate in hexane to obtain pure 617.5 (0.410 g, 42.64%). MS(ES): m/z 190.59 [M+H]$^+$.

Synthesis of Compound 617.9.

Compound 617.9 was synthesized from 617.5 and 617.8 using general procedure B. (Yield: 27.05%). MS(ES): m/z 591.60 [M+H]$^+$.

Synthesis of Compound I-617.

Compound I-617 was synthesized from 617.9 using general procedure C (Yield: 61.08%). MS(ES): m/z: 507.71 [M+H]$^+$, LCMS purity: 98.09%, HPLC purity: 96.08%, 1H NMR (DMSO-d6, 400 MHz): 12.57 (s, 1H), 9.49 (s, 1H), 8.61 (s, 1H), 8.22-8.20 (d, J=8.5 Hz, 1H), 7.99-7.97 (d, J=8.4 Hz, 1H), 7.87-7.86 (d, J=4.2 Hz, 1H), 7.67-7.65 (m, 2H), 7.32 (s, 1H), 7.20-7.16 (m, 1H), 6.79 (t, 1H), 3.21 (s, 3H), 2.90 (s, 2H), 2.58 (s, 2H).

Example 618: Synthesis of N5-(7,7-difluoro-6,7-dihydro-5H-cyclopenta[b]pyridin-2-yl)-2-methyl-N7-(2-(methylsulfonyl)phenyl)-3H-imidazo[4,5-b]pyridine-5,7-diamine, I-618

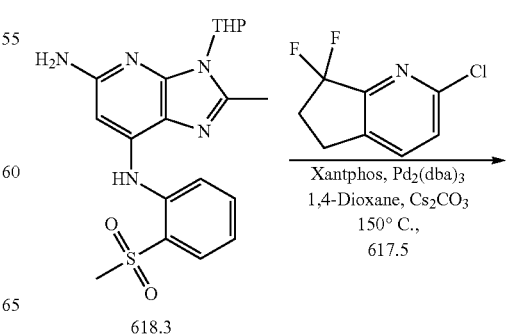

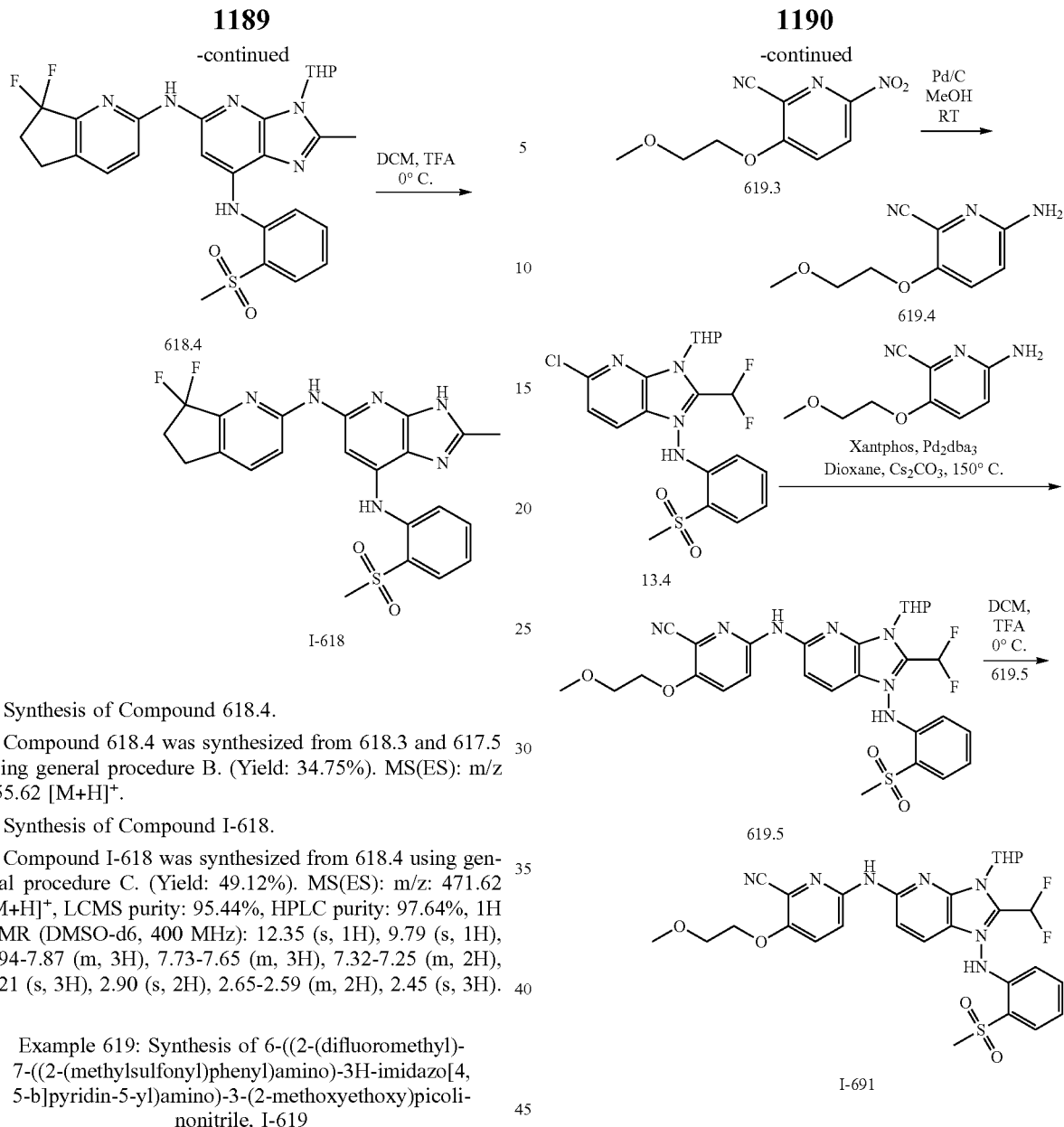

Synthesis of Compound 618.4.

Compound 618.4 was synthesized from 618.3 and 617.5 using general procedure B. (Yield: 34.75%). MS(ES): m/z 555.62 [M+H]⁺.

Synthesis of Compound I-618.

Compound I-618 was synthesized from 618.4 using general procedure C. (Yield: 49.12%). MS(ES): m/z: 471.62 [M+H]⁺, LCMS purity: 95.44%, HPLC purity: 97.64%, 1H NMR (DMSO-d6, 400 MHz): 12.35 (s, 1H), 9.79 (s, 1H), 7.94-7.87 (m, 3H), 7.73-7.65 (m, 3H), 7.32-7.25 (m, 2H), 3.21 (s, 3H), 2.90 (s, 2H), 2.65-2.59 (m, 2H), 2.45 (s, 3H).

Example 619: Synthesis of 6-((2-(difluoromethyl)-7-((2-(methylsulfonyl)phenyl)amino)-3H-imidazo[4,5-b]pyridin-5-yl)amino)-3-(2-methoxyethoxy)picolinonitrile, I-619

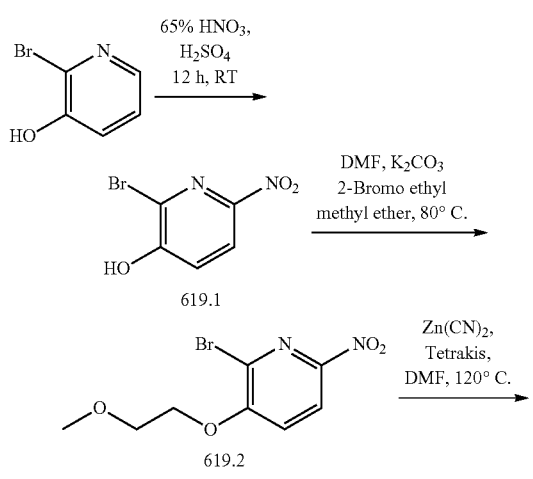

Synthesis of Compound 619.1.

To a solution of 2-bromopyridin-3-ol (20 g, 114.94 mmol, 1 eq) in concentrated H₂SO₄ (70 mL), concentrated nitric acid (12 mL) was added at 0° C. Reaction mixture was stirred at r.t. for 12 h. Upon completion, reaction mixture was transferred into ice water and extracted with ethyl acetate. Organic layers were combined, dried over Na₂SO₄ and concentrated in vacuo to obtain crude product. This was purified by column chromatography and compound was eluted in 30% ethyl acetate in hexane to obtain pure 619.1 (2.1 g, 8.34%). MS(ES): m/z 219.99 [M+H]⁺.

Synthesis of Compound 619.2.

To a solution of 619.1 (2.1 g, 9.59 mmol, 1 eq) in N,N-Dimethylformamide (25 mL) was added potassium carbonate (2.7 g, 19.26 mmol, 2 eq) at r.t. Then after 10 min, 2-Bromoethylmethyl ether (2 g, 14.44 mmol, 1.5 eq) was added into the reaction mixture at r.t. Then reaction mixture was heated at 80° C. for 2 hr. Upon completion, reaction mixture transferred into water and extracted with ethyl acetate. Organic layers were combined, dried over Na₂SO₄ and concentrated in vacuo to obtain 619.2 (0.630 g, 23.71%). MS(ES): m/z 278.07 [M+H]⁺.

Synthesis of Compound 619.3.

To a solution of 619.2 (0.630 g, 2.27 mmol, 1 eq) in N, N-Dimethylformamide (10 mL) was added Zinc cyanide (0.532 g, 4.54 mmol, 2 eq) Tetrakis (triphenylphosphine) palladium (0) (0.525 g, 0.454 mmol, 0.2 eq). Reaction mixture was degassed by argon for 20 min. Further reaction mixture was stirred at 120° C. for 3 h. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 619.3 (0.420 g, 82.76%). MS(ES): m/z 224.19 [M+H]+.

Synthesis of Compound 619.4.

To a solution of 619.3 (0.420 g, 1.88 mmol, 1.0 eq) in MeOH (10 mL), 10% Pd/C (0.120 g) was added. Hydrogen was purged through reaction mixture for 2-3 h at r.t. Upon completion, reaction mixture was filtered through celite-bed and washed with MeOH. Filtrate was concentrated in vacuo to obtain 619.4 (0.210 g, 57.76%). MS(ES): m/z 194.21 [M+H]+.

Synthesis of Compound 619.5.

Compound 619.5 was synthesized from 619.4 and 13.4 using general procedure B. (Yield: 40.95%). MS (ES): m/z 614.64 [M+H]+.

Synthesis of Compound I-619.

Compound I-619 was synthesized from 619.5 using general procedure C. (Yield: 63.21%). MS(ES): m/z: 530.69 [M+H]+, LCMS purity: 96.37%, HPLC purity: 91.51%, 1H NMR (DMSO-d6, 400 MHz): 13.60 (s, 1H), 9.96 (s, 1H), 8.90 (s, 1H), 8.17 (s, 1H), 8.15-7.96 (d, J=7.6 Hz, 2H), 7.92-7.81 (d, J=4.4 Hz, 2H), 7.50 (s, 1H), 7.39-7.37 (m, 1H), 7.23 (s, 1H), 4.32 (m, 2H), 3.70 (m, 2H), 3.29 (s, 3H), 3.23 (s, 3H).

Example 1-620: Synthesis of 3-(2-methoxyethoxy)-6-((2-methyl-7-((2-(methylsulfonyl)phenyl)amino)-3H-imidazo[4,5-b]pyridin-5-yl)amino)picolinonitrile, I-620

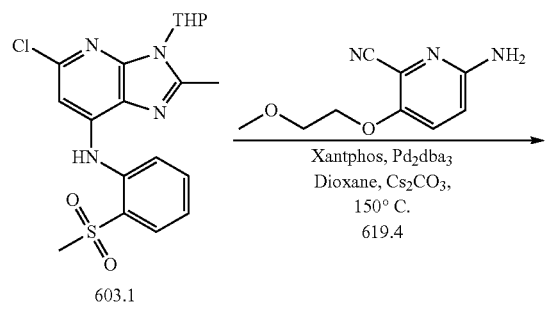

603.1

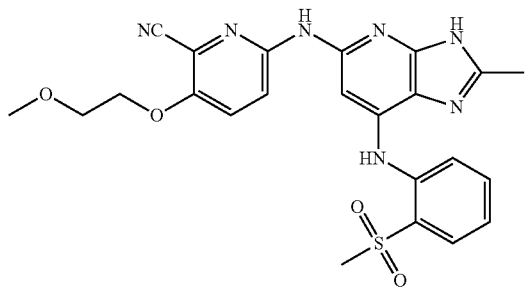

I-620

Synthesis of Compound 620.1.

Compound 620.1 was synthesized from 603.1 and 619.4 using general procedure B. (Yield: 47.36%). MS (ES): m/z 578.66 [M+H]+.

Synthesis of Compound I-620.

Compound I-620 was synthesized from 620.1 using general procedure C t. (Yield: 84.63%). MS(ES): m/z 494.54 [M+H]+, LCMS purity: 100%, HPLC purity: 98.85%, 1H NMR (DMSO-d6, 400 MHz): 12.43 (s, 1H), 9.70 (s, 1H), 8.73 (s, 1H), 8.07-8.05 (d, J=8.2 Hz, 1H), 7.92-7.90 (d, J=8.2 Hz, 2H), 7.82-7.76 (m, 2H), 7.44 (s, 1H), 7.29 (t, 1H), 4.29 (s, 2H), 3.69 (m, 2H), 3.21 (s, 3H), 2.51 (s, 3H), 2.46 (s, 3H).

Example 621: Synthesis if 6-((2-(difluoromethyl)-7-((4-fluoro-2-(methylsulfonyl)phenyl)amino)-3H-imidazo[4,5-b]pyridin-5-yl)amino)-3-(2-methoxyethoxy)picolinonitrile, I-621

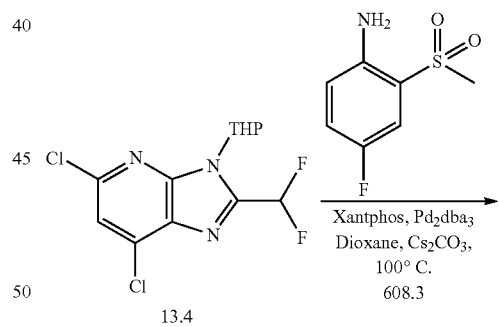

13.4

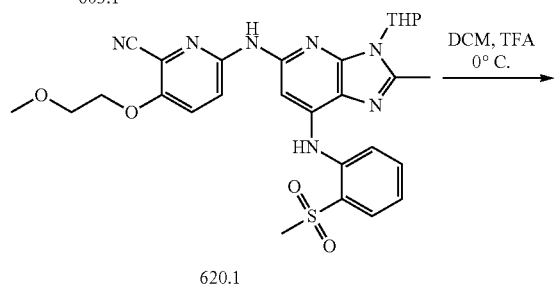

620.1

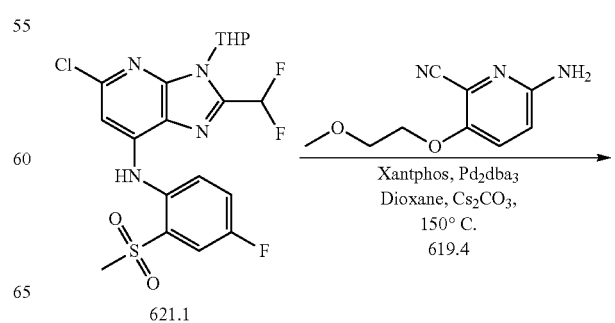

621.1

1193

-continued

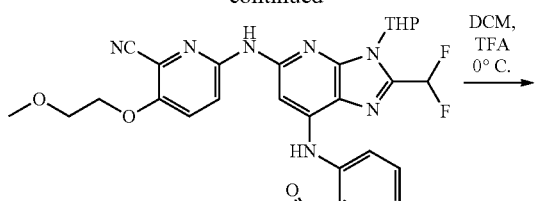
621.2

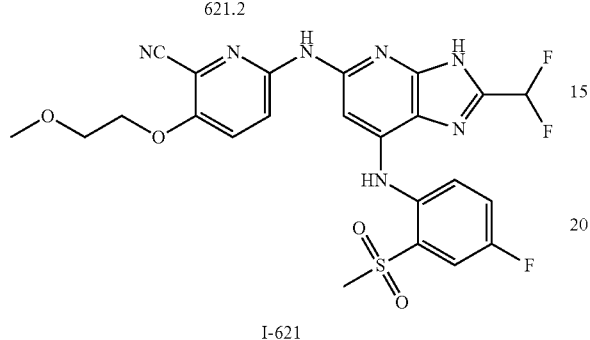
I-621

Synthesis of Compound 621.1.

Compound 621.1 was synthesized from 13.4 and 608.3 using general procedure A. (Yield: 54.27%). MS (ES): m/z 475.88 [M+H]$^+$.

Synthesis of Compound 621.2.

Compound 621.2 was synthesized from 621.1 and 619.4 using general procedure B. (Yield: 41.35%). MS (ES): m/z 632.63 [M+H]$^+$.

Synthesis of Compound I-621.

Compound I-621 was synthesized from 621.2 using general procedure C. (Yield: 73.41%). MS(ES): m/z: 548.52 [M+H]$^+$, LCMS purity: 100%, HPLC purity: 100%, 1H NMR (DMSO-d6, 400 MHz): 13.57 (s, 1H), 9.91 (s, 1H), 8.70 (s, 1H), 8.14-8.12 (d, J=10.0 Hz, 1H), 7.92-7.89 (m, 1H), 7.82-7.79 (d, J=11.4 Hz, 1H), 7.76-7.69 (m, 2H), 7.34 (s, 1H), 7.21 (t, 1H), 4.31-4.29 (t, J=12.0 Hz, 2H), 3.71-3.69 (t, J=10.2 Hz, 2H), 3.34 (s, 3H), 3.28 (s, 3H).

Example 622: Synthesis of 6-((7-((4-fluoro-2-(methylsulfonyl)phenyl)amino)-2-methyl-3H-imidazo[4,5-b]pyridin-5-yl)amino)-3-(2-methoxyethoxy)picolinonitrile, I-622

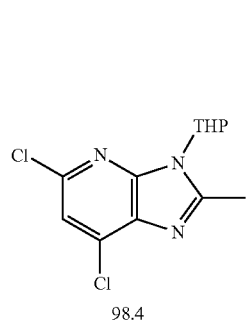
98.4

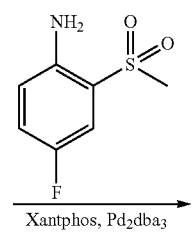
608.3

1194

-continued

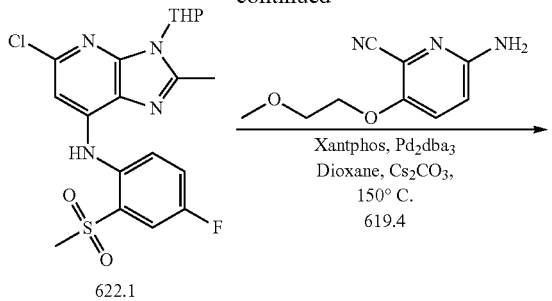
622.1

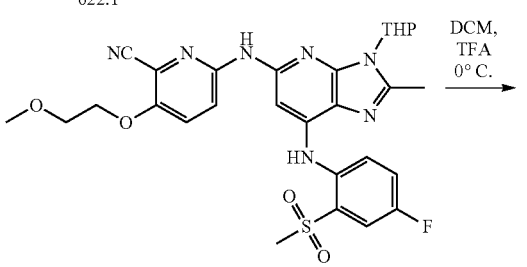
622.2

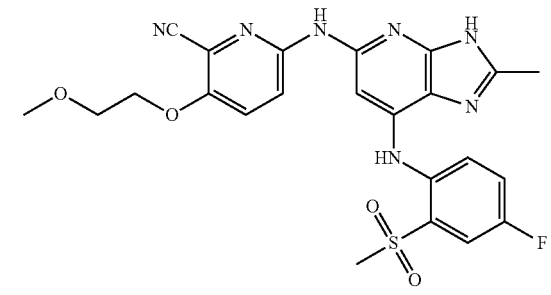
I-622

Synthesis of Compound 622.1.

Compound 622.1 was synthesized from 98.4 and 608.3 using general procedure A. (Yield: 54.27%). MS (ES): m/z 439.90 [M+H]$^+$ Synthesis of Compound 622.2.

Compound 622.2 was synthesized from 622.1 and 619.4 using general procedure B. (Yield: 51.58%). MS (ES): m/z 596.65 [M+H]$^+$.

Synthesis of Compound I-622.

Compound I-622 was synthesized from 622.2 using general procedure C. (Yield: 86.50%). MS(ES): m/z: 512.64 [M+H]$^+$, LCMS purity: 97.46%, HPLC purity: 99.26%, 1H NMR (DMSO-d6, 400 MHz): 12.43 (s, 1H), 9.71 (s, 1H), 8.52 (s, 1H), 8.02-8.00 (d, J=7.6 Hz, 1H), 7.91 (s, 1H), 7.79-7.76 (d, J=12.2 Hz, 1H), 7.72-7.66 (m, 2H), 7.39 (s, 1H), 4.30-4.27 (t, J=12.0 Hz, 2H), 3.70-3.68 (t, J=10.2 Hz, 2H), 3.26 (s, 3H), 2.51 (s, 3H), 2.46 (s, 3H).

Example 623: Synthesis of 6-((2-(difluoromethyl)-7-((2-(methylsulfonyl)phenyl)amino)-3H-imidazo[4,5-b]pyridin-5-yl)amino)-3-((tetrahydro-2H-pyran-4-yl)oxy)picolinonitrile, I-623

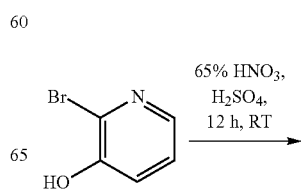

1195

-continued

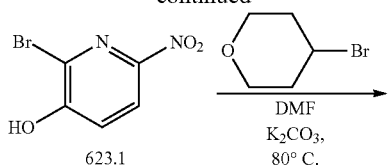

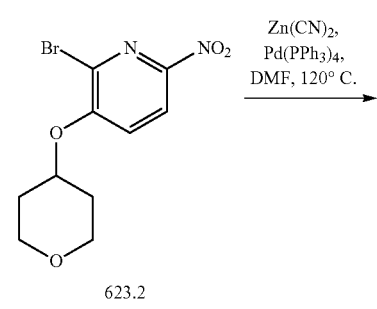

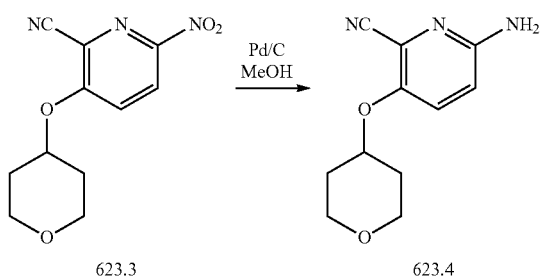

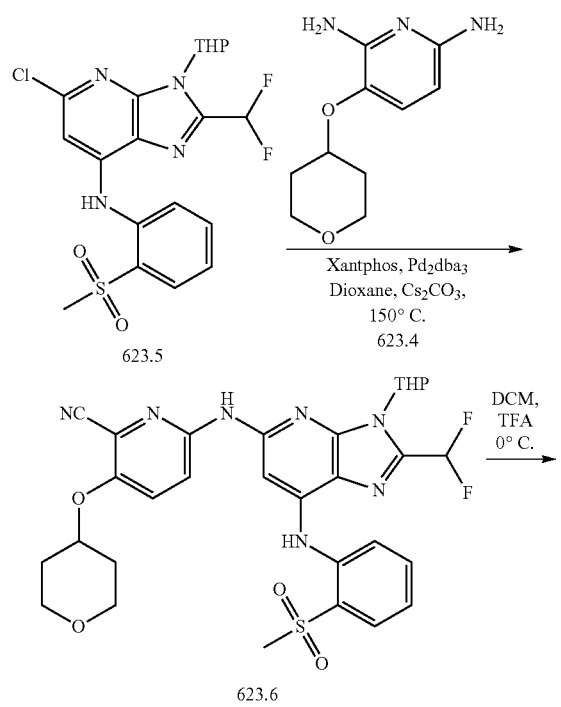

1196

-continued

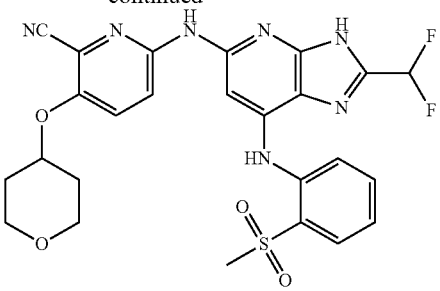

I-623

Synthesis of Compound 623.1.

To a solution of 2-bromopyridin-3-ol 1 (20 g, 114.94 mmol, 1 eq) in concentrated H₂SO₄ (70 mL), concentrated nitric acid (12 mL) was added at 0° C. Reaction mixture was stirred at r.t. for 12 h. Upon completion, reaction mixture was transferred into ice water and extracted with ethyl acetate. Organic layers were combined, dried over Na₂SO₄ and concentrated in vacuo to obtain crude product. This was purified by column chromatography and compound was eluted in 30% ethyl acetate in hexane to obtain pure 623.1. (2.1 g, 8.34%). MS(ES): m/z 219.99 [M+H]⁺.

Synthesis of Compound 623.2.

To a solution of 623.1 (2.7 g, 12.33 mmol, 1 eq) in Dimethylformamide (30 mL) was added 4-bromotetrahydro-2H-pyran 1.2 (4.07 g, 24.65 mmol, 2 eq), potassium carbonate (3.4 g, 24.65 mmol, 2 eq) at r.t. Then reaction mixture was heated at 12° C. for 12 h. Upon completion, reaction mixture transferred into water and extracted with ethyl acetate. Organic layers were combined, dried over Na₂SO₄ and concentrated in vacuo to obtain crude product. This was purified by column chromatography and compound was eluted in 20% ethyl acetate in hexane to obtain pure 623.2 (0.730 g, 19.53%). MS(ES): m/z 304.11 [M+H]⁺.

Synthesis of Compound 623.3.

To a solution of 623.2 (0.730 g, 2.41 mmol, 1 eq) in dimethylformamide (8 mL) was added Zinc cyanide (0.563 g, 4.8 mmol, 2 eq) at r.t. The reaction mixture was degassed by argon for 30 min. Tetrakis(triphenylphosphine)palladium (0) (0.278 g, 2.4 mmol, 0.1 eq), was added into reaction mixture and again reaction mixture was degassed by argon for 30 min. Further reaction mixture was stirred at 100° C. for 2 h. Upon completion, reaction mixture transferred into water and extracted with ethyl acetate. Organic layers were combined, dried over Na₂SO₄ and concentrated in vacuo to obtain crude product. This was purified by column chromatography and compound was eluted in 25% ethyl acetate in hexane to obtain pure 623.3 (0.330 g, 54.98%). MS(ES): m/z 250.23 [M+H]⁺.

Synthesis of Compound 623.4.

To a solution of 623.3 (0.330 g, 1.32 mmol, 1.0 eq) in MeOH (10 mL), 10% Pd/C (0.150 g) was added. Hydrogen was purged through reaction mixture for 2-3 hr at r.t. Upon completion, reaction mixture was filtered through celite-bed and washed with MeOH. Filtrate was concentrated in vacuo to obtain 623.4 (0.230 g, 79.23%). MS(ES): m/z 220.24 [M+H]⁺.

Synthesis of Compound 623.5.

Compound 623.5 was synthesized from 13.4 and 2-(methylsulfonyl)aniline using general procedure A. (Yield: 44.65%). MS (ES): m/z 457.89 [M+H]⁺.

Synthesis of Compound 623.6.

Compound 623.6 was synthesized from 623.4 and 623.5 using general procedure B. (Yield: 30.95%). MS (ES): m/z 640.68 [M+H]⁺.

Synthesis of Compound I-623.

Compound I-623 was synthesized from 623.6 using general procedure C. (Yield: 59.78%). MS(ES): m/z: 556.75 [M+H]⁺, LCMS purity: 100%, HPLC purity: 98.62%, 1H NMR (DMSO-d6, 400 MHz): 12.52 (s, 1H), 9.95 (s, 1H), 8.64 (s, 1H), 7.99-7.97 (d, J=8.2 Hz, 1H), 7.92-7.90 (d, J=8.4 Hz, 1H), 7.86-7.82 (m, 2H), 7.75-7.75 (m, 1H), 7.54 (s, 1H), 7.42-7.40 (d, J=8.8 Hz, 1H), 4.92-4.88 (t, 1H), 4.05-4.00 (m, 1H), 3.88-3.82 (m, 1H), 3.21 (s, 3H), 2.47 (s, 3H), 2.38 (m, 1H), 2.02-1.95 (m, 2H), 1.79-1.75 (m, 1H).

Example 624: Synthesis of 6-((2-methyl-7-((2-(methylsulfonyl)phenyl)amino)-3H-imidazo[4,5-b]pyridin-5-yl)amino)-3-((tetrahydro-2H-pyran-4-yl)oxy)picolinonitrile, I-624

Synthesis of Compound 624.2.

Compound was synthesized from 624.1 and 623.4 using general procedure B. (Yield: 49.39%). MS (ES): m/z 604.70 [M+H]⁺.

Synthesis of Compound I-624.

Compound I-624 was synthesized from 624.2 using general procedure C. (Yield: 82.02%). MS(ES): m/z: 520.64 [M+H]⁺, LCMS purity: 100%, HPLC purity: 100%, 1H NMR (DMSO-d6, 400 MHz): 12.45 (s, 1H), 9.78 (s, 1H), 8.75 (s, 1H), 8.01-7.80 (m, 5H), 7.54 (s, 1H), 7.33-7.29 (t, J=15.8 Hz, 1H), 4.73-4.69 (m, 1H), 3.90-3.85 (m, 2H), 3.54-3.48 (m, 2H), 3.21 (s, 3H), 2.47 (s, 3H), 1.99-1.97 (s, 2H), 1.69-1.61 (m, 2H).

Example 625: Synthesis of 6-((2-(difluoromethyl)-7-((4-fluoro-2-(methylsulfonyl)phenyl)amino)-3H-imidazo[4,5-b]pyridin-5-yl)amino)-3-((tetrahydro-2H-pyran-4-yl)oxy)picolinonitrile, I-625

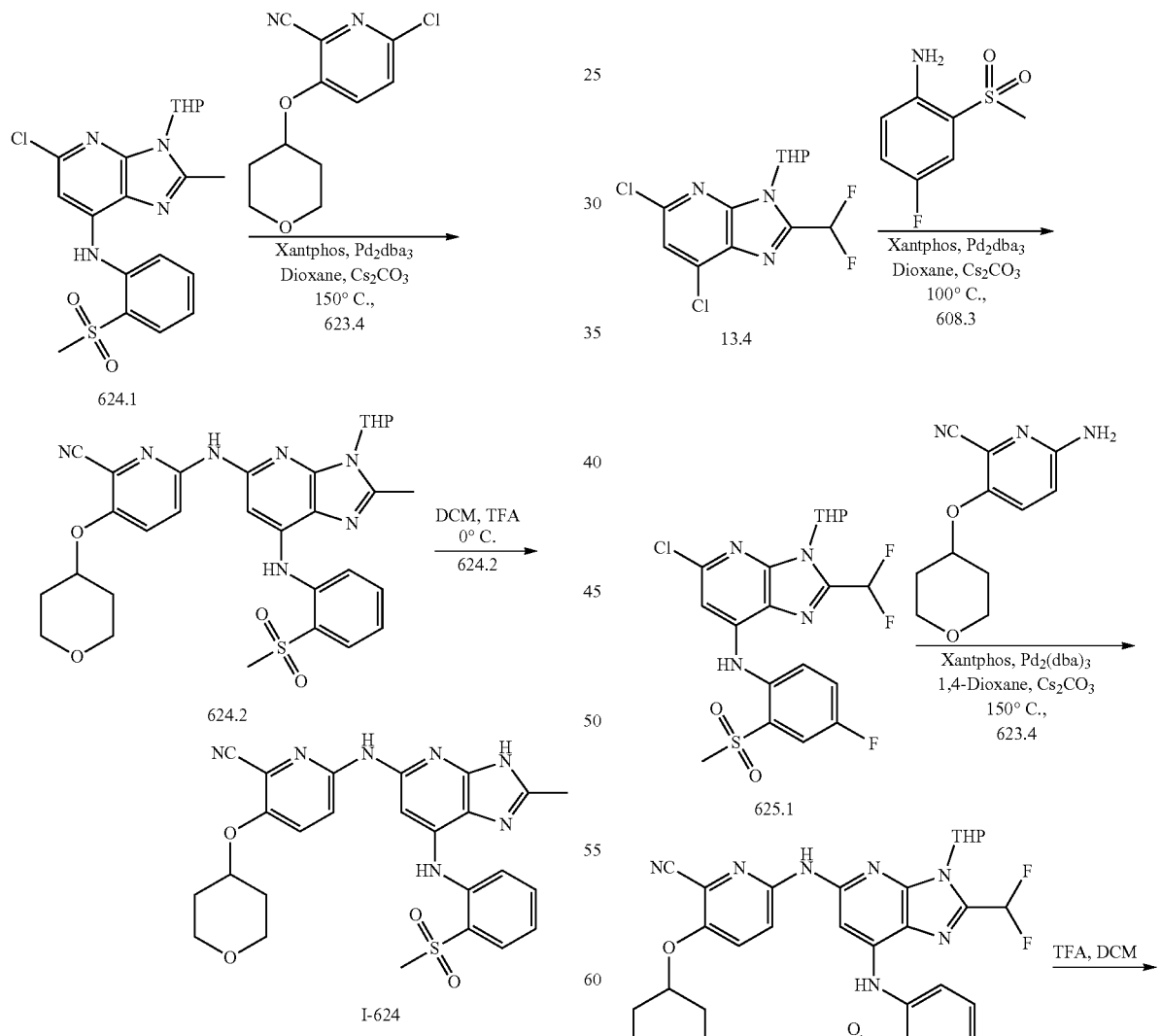

Synthesis of Compound 624.1.

Compound 624.1 was synthesized from 98.4 and 2-(methylsulfonyl)aniline using general procedure A. (Yield: 44.65%). MS (ES): m/z 421.91 [M+H]⁺.

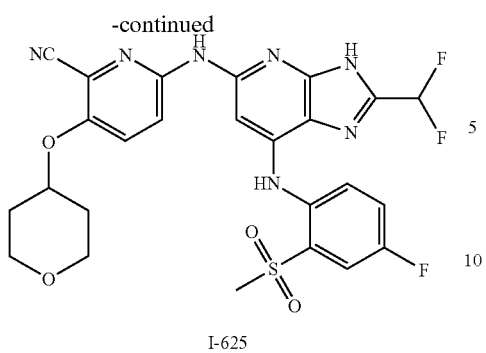

I-625

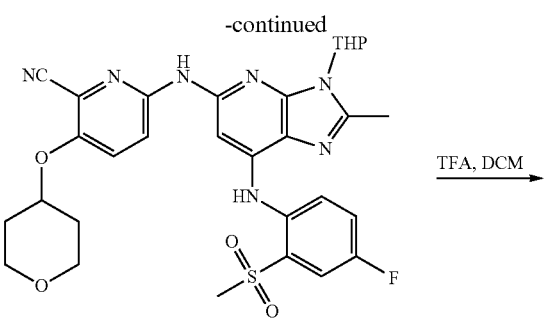

626.2

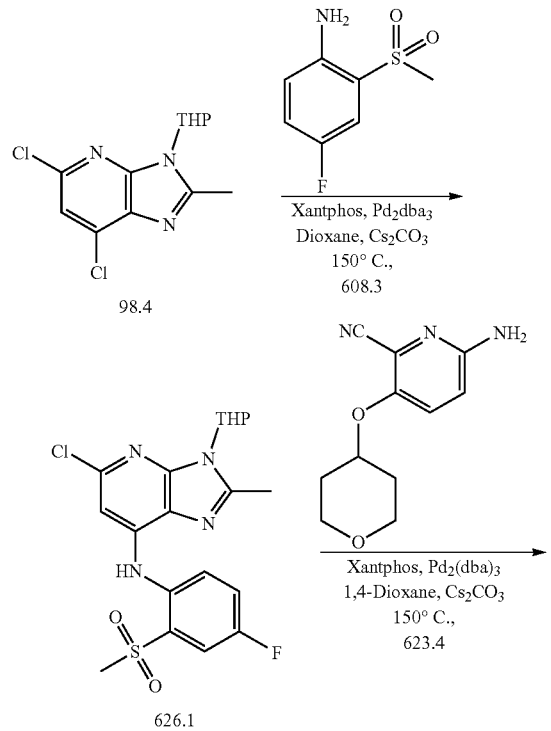

I-626

Synthesis of Compound 625.1.
Compound 625.1 was synthesized from 13.4 and 608.3 using general procedure A. (Yield: 54.27%). MS (ES): m/z 475.88 [M+H]$^+$.

Synthesis of Compound 625.2.
Compound 625.2 was synthesized from 625.1 and 623.4 using general procedure B. (Yield: 39.11%). MS (ES): m/z 658.67 [M+H]$^+$.

Synthesis of Compound I-625.
Compound I-625 was synthesized from 625.2 using general procedure C. (Yield: 70.56%). MS(ES): m/z: 574.42 [M+H]$^+$, LCMS purity: 98.92%, HPLC purity: 98.15%, 1H NMR (DMSO-d6, 400 MHz): 13.57 (s, 1H), 9.95 (s, 1H), 8.71 (s, 1H), 8.09-8.07 (d, J=8.0 Hz, 1H), 7.93-7.86 (m, 2H), 7.77-7.69 (m, 2H), 7.41 (s, 1H), 7.22 (t, 1H), 4.76-4.72 (m, 1H), 3.90-4.01 (m, 2H), 3.54-3.85 (m, 2H), 3.29 (s, 3H), 2.0-1.92 (m, 2H), 1.69-1.61 (m, 2H).

Example 626: Synthesis of 6-((7-((4-fluoro-2-(methylsulfonyl)phenyl)amino)-2-methyl-3H-imidazo[4,5-b]pyridin-5-yl)amino)-3-((tetrahydro-2H-pyran-4-yl)oxy)picolinonitrile, I-626

Synthesis of Compound 626.1.
Compound 626.1 was synthesized from 98.4 and 608.3 using general procedure A. (Yield: 54.27%). MS (ES): m/z 439.90 [M+H]$^+$.

Synthesis of Compound 626.2.
Compound 626.2 was synthesized from 626.1 and 623.4 using general procedure B. (Yield: 58.83%). MS (ES): m/z 622.69 [M+H]$^+$.

Synthesis of Compound I-626.
Compound I-626 was synthesized from 626.2 using general procedure C. (Yield: 82.11%). MS(ES): m/z: 538.75 [M+H]$^+$, LCMS purity: 100%, HPLC purity: 99.20%, 1H NMR (DMSO-d6, 400 MHz): 12.42 (s, 1H), 9.75 (s, 1H), 8.53 (s, 1H), 7.98-7.90 (m, 2H), 7.85-7.82 (d, J=12.4 Hz, 1H), 7.73-7.66 (m, 2H), 7.45 (s, 1H), 4.73-4.69 (m, 1H), 3.90-3.85 (m, 2H), 3.54-3.48 (m, 2H), 3.26 (s, 3H), 2.47 (s, 3H), 2.00-1.92 (m, 2H), 1.69-1.60 (m, 2H).

Example 627: Synthesis of N7-(2-methoxy-3-(1-methyl-1H-1,2,4-triazol-5-yl)phenyl)-2-methyl-N5-(6-(trifluoromethyl)pyridin-2-yl)-3H-imidazo[4,5-b]pyridine-5,7-diamine, I-627

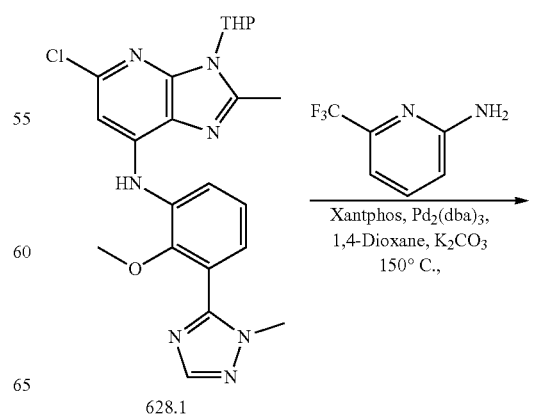

628.1

1201

-continued

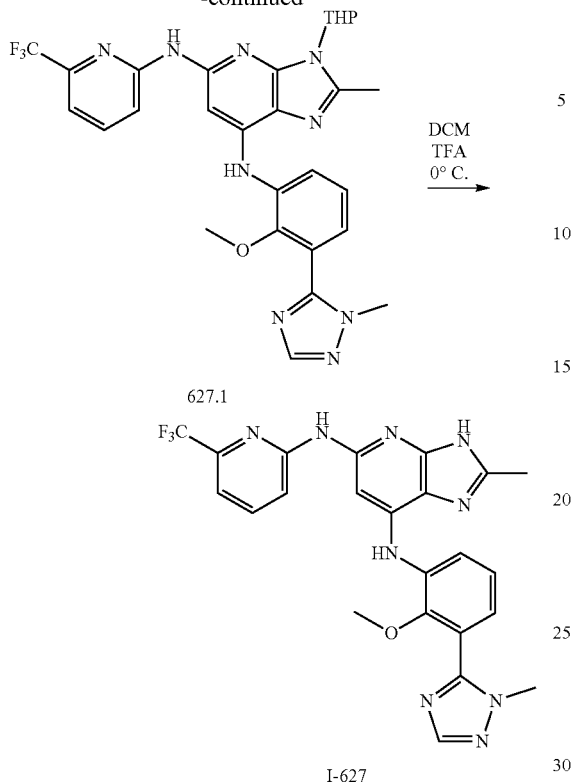

Synthesis of Compound 627.1.

Compound 627.1 was synthesized from 628.1 And 6-(trifluoromethyl)pyridin-2-amine using general procedure. (Yield: 39.16%). MS (ES): m/z 580.59 [M+H]+.

Synthesis of Compound I-627.

Compound I-627 was synthesized from 527.1 using general procedure C. (Yield: 64.34%). [M+H]+. MS(ES): m/z: 496.43 [M+H]+, LCMS purity: 98.67%, HPLC purity: 98.50%, 1H NMR (DMSO-d6, 400 MHz): 12.50 (s, 1H), 9.91 (s, 1H), 8.15-8.13 (d, J=8.0 Hz, 1H), 8.09-8.06 (m, 2H), 7.90-7.86 (t, J=12.0 Hz, 1H), 7.74-7.72 (d, J=6.5 Hz, 1H), 7.32-7.25 (m, 3H), 7.22-7.20 (d, J=8.4 Hz, 1H), 3.77 (s, 3H), 3.39 (s, 3H), 1.30-1.25 (m, 2H), 0.89-0.85 (m, 1H).

Example 628: Synthesis of N5-(7,7-difluoro-6,7-dihydro-5H-cyclopenta[b]pyridin-2-yl)-N7-(2-methoxy-3-(1-methyl-1H-1,2,4-triazol-5-yl)phenyl)-2-methyl-3H-imidazo[4,5-b]pyridine-5,7-diamine, I-628

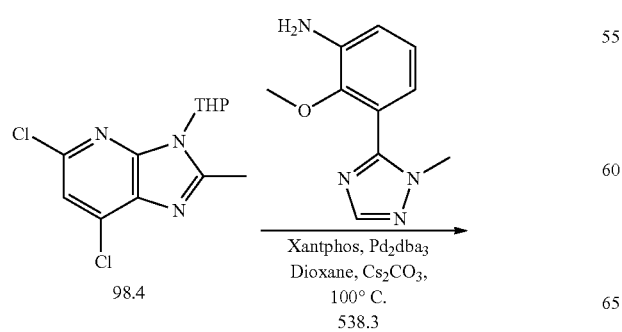

1202

-continued

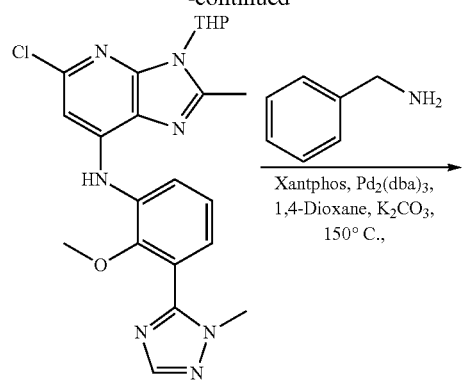

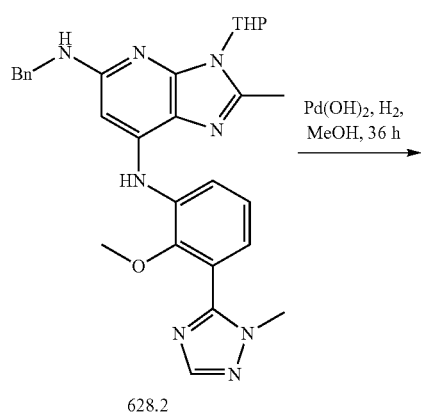

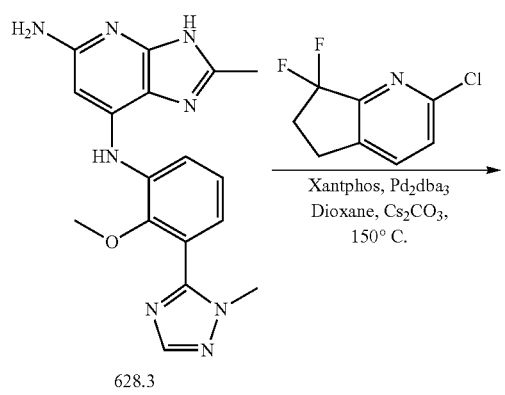

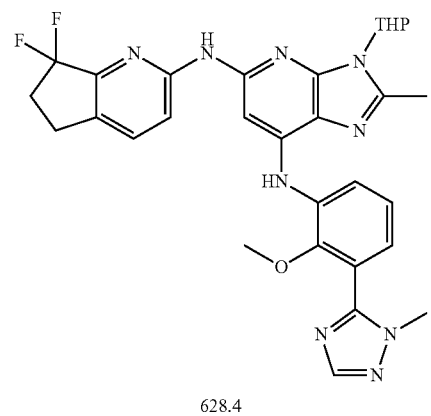

1H), 7.32-7.28 (t, J=15.8 Hz, 1H), 7.17-7.16 (m, 1H), 3.77 (s, 3H), 3.45 (s, 3H), 2.91 (s, 2H), 2.63-2.59 (m, 2H), 2.47 (s, 3H).

Example 629: Synthesis of N5-(7,7-difluoro-6,7-dihydro-5H-cyclopenta[b]pyridin-2-yl)-N7-(2-methoxy-3-(2-methyl-2H-1,2,3-triazol-4-yl)phenyl)-2-methyl-3H-imidazo[4,5-b]pyridine-5,7-diamine, I-629

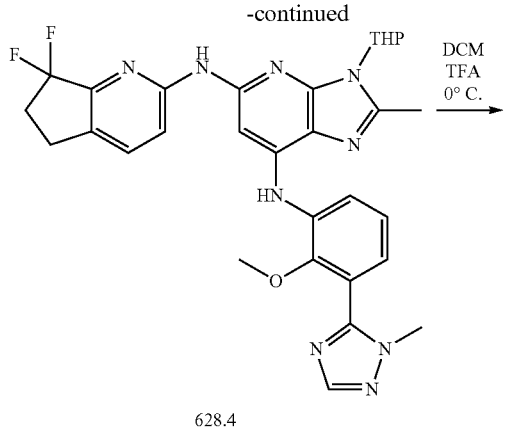

628.4

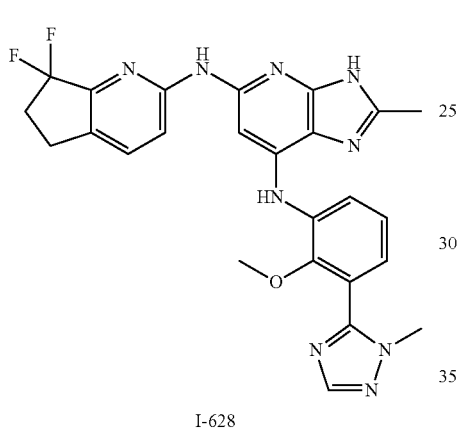

I-628

Synthesis of Compound 628.1.

Compound 628.1 was synthesized from 98.4 and 538.3 using general procedure A. (Yield: 35.12%). MS (ES): m/z 454.93 [M+H]$^+$.

Synthesis of Compound 628.2.

Compound 628.2 was synthesized from 628.1 and benzylamine using general procedure B. (Yield: 51.27%). MS (ES): m/z 525.63 [M+H]$^+$.

Synthesis of Compound 628.3.

To a solution of 628.2 (0.160 g, 304.98 mmol, 1.0 eq) in MeOH (1 mL), 10% palladium hydroxide on charcoal (0.020 g) was added. Hydrogen was purged through reaction mixture for 36 hr at r.t. Upon completion, reaction mixture was filtered through celite-bed and washed with MeOH. Filtrate was concentrated in vacuo to obtain 628.3 (0.075 g, 70.19%). MS(ES): m/z 351.39 [M+H]$^+$.

Synthesis of Compound 628.4.

Compound was synthesized from 628.3 and 2-chloro-7,7-difluoro-6,7-dihydro-5H-cyclopenta[b]pyridine using general procedure B. (Yield: 41.34%). MS (ES): m/z 588.64 [M+H]$^+$.

Synthesis of Compound I-628.

Compound I-628 was synthesized from 628.4 using general procedure C. (Yield: 56.11%). MS(ES): m/z: 504.63 [M+H]$^+$, LCMS purity: 96.96%, HPLC purity: 95.01%, 1H NMR (DMSO-d6, 400 MHz): 12.43 (s, 1H), 9.78 (s, 1H), 8.08 (s, 1H), 7.99-7.93 (m, 2H), 7.82-7.70 (m, 2H), 7.52 (s,

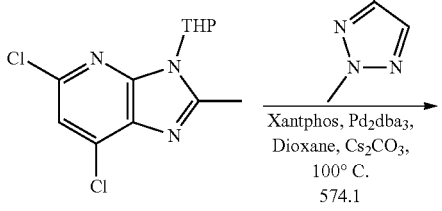

574.1

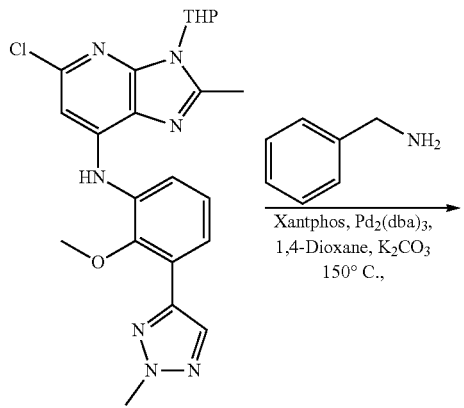

629.1

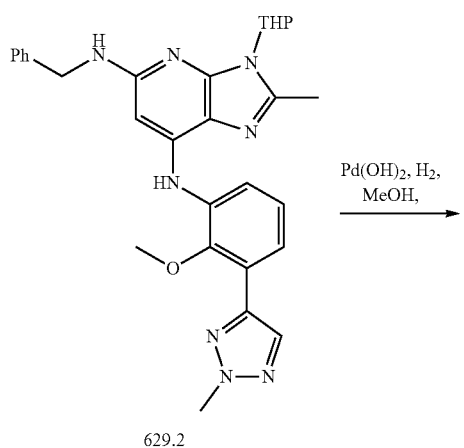

629.2

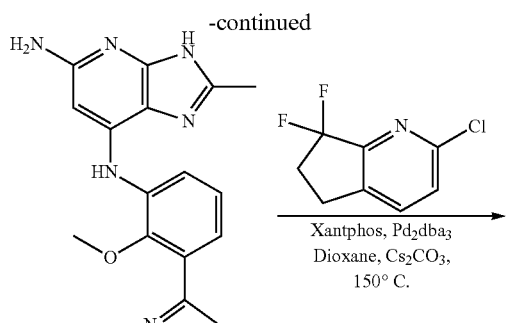

629.3

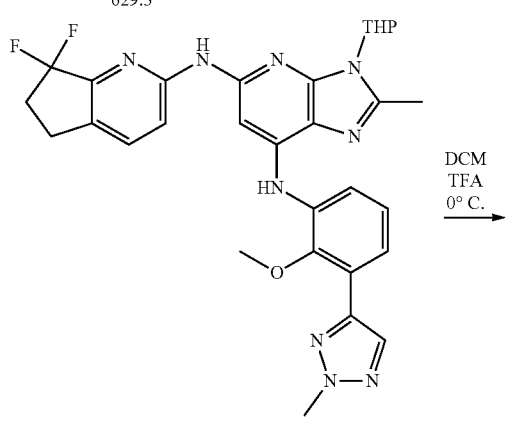

629.4

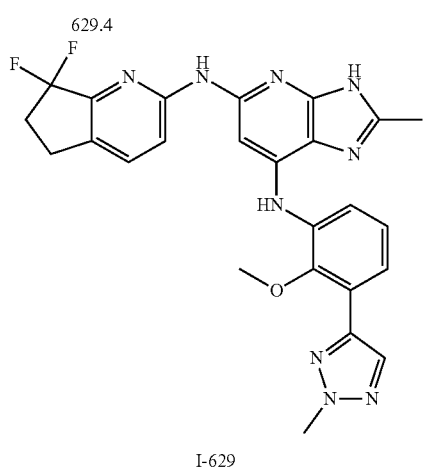

I-629

Synthesis of Compound 629.1.

Compound 629.1 was synthesized from 98.4 and 574.1 using general procedure A (Yield: 42.03%). MS(ES): m/z 454.93 [M+H]+.

Synthesis of Compound 629.2

Compound 629.2 was synthesized from 629.1 and benzylamine using general procedure B (Yield: 54.08%). MS(ES): m/z 525.63 [M+H]+.

Synthesis of Compound 629.3.

To a solution of 629.2 (0.200 g, 381.22 mmol, 1.0 eq) in MeOH (5 mL), 10% palladium hydroxide on charcoal (0.200) was added. Hydrogen was purged through reaction mixture for 24 hr. Upon completion, reaction mixture was filtered through celite-bed and washed with MeOH. Filtrate was concentrated in vacuo to obtain 629.3 (0.100 g, 60.37%). MS(ES): m/z 435.50 [M+H]+.

Synthesis of Compound 629.4.

Compound 629.4 was synthesized from 629.3 and 2-chloro-7,7-difluoro-6,7-dihydro-5H-cyclopenta[b]pyridine using general procedure B (Yield: 34.01%). MS(ES): m/z 588.64 [M+H]+.

Synthesis of Compound I-629.

Compound I-629 was synthesized using general procedure C. (Yield: 65.96%). MS(ES): m/z: 504.71 [M+H]+, LCMS purity: 95.28%, HPLC purity: 98.85%, 1H NMR (DMSO, 400 MHz): 12.37 (s, 1H), 9.75 (s, 1H), 8.14 (s, 1H), 7.91 (s, 2H), 7.70-7.55 (m, 4H), 7.24 (s, 1H), 4.25 (s, 3H), 3.68 (s, 3H), 2.91 (s, 2H), 2.61 (s, 2H), 2.51 (s, 3H).

Example 630: Synthesis of N5-(6-ethynylpyridin-2-yl)-N7-(4-fluoro-2-(methylsulfonyl)phenyl)-2-methyl-3H-imidazo[4,5-b]pyridine-5,7-diamine, I-630

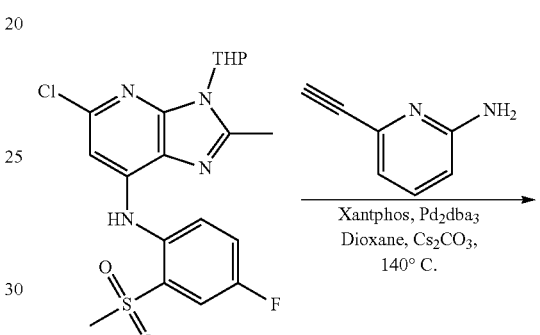

608.4

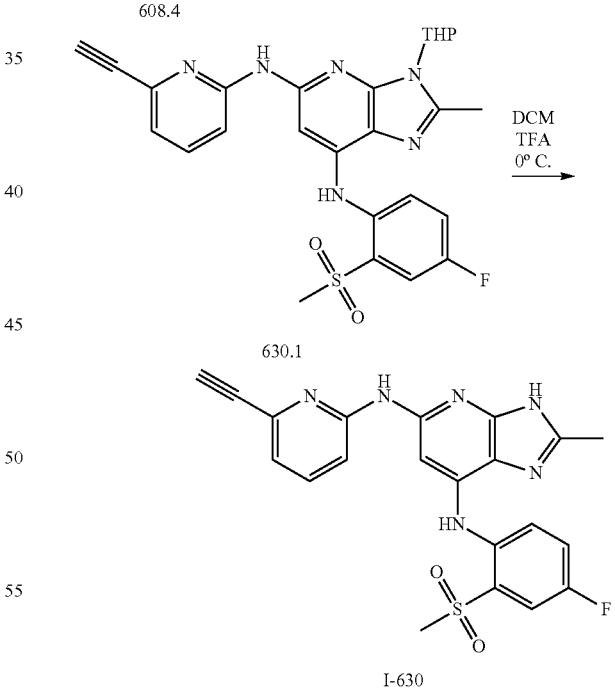

630.1

I-630

Synthesis of Compound 630.1.

Compound 630.1 was synthesized from 608.4 and 6-ethynylpyridin-2-amine using general procedure B. (Yield: 33.72%). MS (ES): m/z 521.58 [M+H]+.

Synthesis of Compound I-630.

Compound I-630 was synthesized using general procedure C. (Yield: 71.56%). MS(ES): m/z: 437.50 [M+H]+, LCMS purity: 100%, HPLC purity: 100%, 1H NMR (DMSO, 400 MHz): 9.67 (s, 1H), 8.53 (s, 1H), 7.93-7.90 (m, 1H), 7.82-7.80 (d, J=8.4 Hz, 1H), 7.73-7.63 (m, 4H), 7.43 (s, 1H), 7.02-7.00 (s, 1H), 4.28 (s, 1H), 3.27 (s, 3H), 2.47 (s, 3H).

Example 631: Synthesis of N-(2-(difluoromethyl)-7-((4-(1,5-dimethyl-1H-pyrazol-4-yl)-2-(N,S-dimethylsulfonimidoyl)phenyl)amino)-3H-imidazo[4,5-b]pyridin-5-yl)cyclopropanecarboxamide, I-631

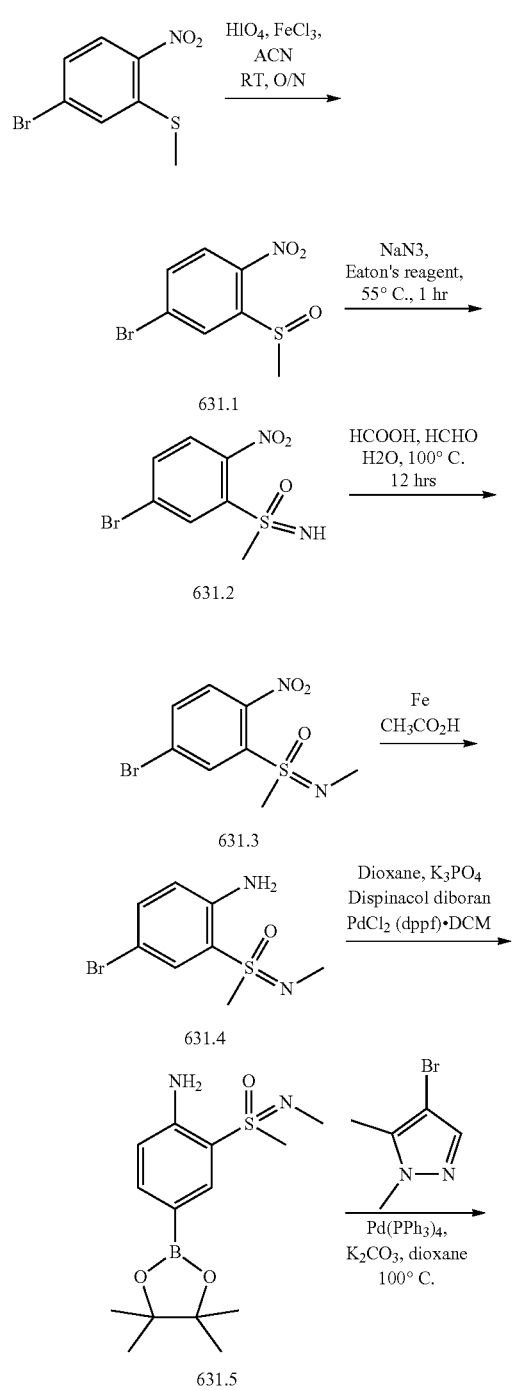

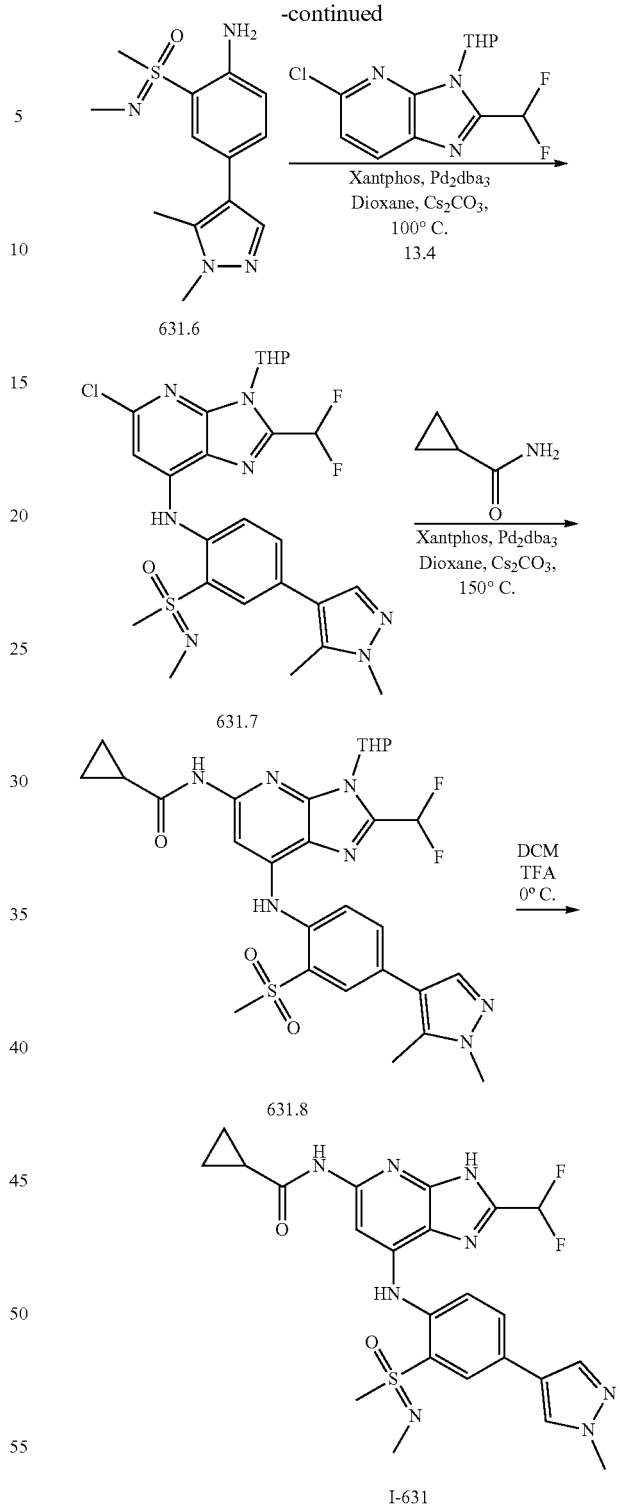

Synthesis of Compound 631.1.

To a solution of (5-bromo-2-nitrophenyl)(methyl)sulfane 1 (5 g, 20.15 mmol, 1.0 eq) in Acetonitrile (24 mL) was added Periodic acid (4.85 g, 21.27 mmol, 1.06 eq) and anhydrous Iron chloride (0.065 g, 4.03 mmol, 0.02 eq) at r.t. The reaction mixture was stirred at r.t. for 2 h. Upon completion, reaction mixture was transferred in sodium thiosulphate solution and extracted with $CH_2Cl_2$. Combined organic layer was washed with brine, dried over $Na_2SO_4$ and concentrated in vacuo to obtain 631.1 (4.8 g, 90.18%). MS(ES): m/z 265.09 [M+H]$^+$.

Synthesis of Compound 631.2.

To a solution of 631.1 (20 g, 75.73 mmol, 1 eq) in Eaton's reagent (300 mL), was added sodium azide (9.8 g, 151.5 mmol, 2 eq) at r.t. Reaction mixture was heated at 50° C. for 45 min. Upon completion, reaction mixture was transferred into water and the pH of the solution was adjusted to 7 using $NaHCO_3$ solution and then extracted with $CH_2Cl_2$. Organic layers were combined, dried over $Na_2SO_4$ and concentrated in vacuo to obtain 631.2. (15 g, 70.97%). MS(ES): m/z 280.11 [M+H]$^+$.

Synthesis of Compound 631.3.

To a solution of 631.2 (3.2 g, 11.47 mmol, 1 eq) in Formic acid (126 mL) was added Formaldehyde (25.6 mL). The reaction mixture was stirred at 100° C. for 12 h. Upon completion, reaction mixture was transferred to water and the pH of the solution was adjusted to 7 using $NaHCO_3$ solution and then extracted with $CH_2Cl_2$. Organic layers were combined, dried over $Na_2SO_4$ and concentrated in vacuo to obtain 631.3. (1.2 g, 35.71%). MS(ES): m/z 294.14 [M+H]$^+$.

Synthesis of Compound 631.4.

To a solution of 631.3 (1.2 g, 4.09 mmol, 1.0 eq) in ethanol (12.5 mL) and water (7.5 mL) was added Acetic acid (1.8 mL) dropwise at 0° C. and Iron powder (1.14 g, 20.47 mmol, 5 eq) was added into the reaction mixture at 0° C. Reaction mixture stirred for 1 hr at r.t. Upon completion, reaction mixture was transferred into water and the pH of the solution was adjusted to 7 using $NaHCO_3$ solution and filtered, washed with ethyl acetate. Organic layer was concentrated in vacuo to obtain crude the pH of the solution was adjusted to 7 using $NaHCO_3$ solution 631.4 (0.620 g, 57.55%). MS(ES): m/z 264.15 [M+H]$^+$.

Synthesis of Compound 631.5.

To a solution of 631.4 (0.620 g, 2.36 mmol, 1 eq) in 1,4-dioxane (12 mL) was added Bis(pinacolato)diboron (0.898 g, 3.53 mmol, 1.5 eq) and potassium acetate (0.693 g, 7.07 mmol, 3 eq). The reaction mixture was degassed with argon for 30 min. [1,1'-Bisdiphenylphosphinoferrocene]palladium(II) dichloride $CH_2Cl_2$ complex (0.058 g, 7.07 mmol, 0.03 eq), was added to reaction mixture and again reaction mixture was degassed by argon for 30 min. Further reaction mixture was stirred at 100° C. for 4 h. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 631.5 (0.300 g, 41.05%). MS(ES): m/z 311.22 [M+H]$^+$.

Synthesis of Compound 631.6.

To a solution of 1.5 (1 g, 3.22 mmol, 1 eq) in 1,4-dioxane (7.2 mL) and water (2.8 mL) was added 4-bromo-1,5-dimethyl-1H-pyrazole (0.780 g, 4.83 mmol, 1.5 eq), and potassium carbonate (1.27 g, 9.67 mmol, 3 eq). The reaction mixture was degassed by argon for 30 min. [1,1'-Bisdiphenylphosphinoferrocene]palladium(II) dichloride $CH_2Cl_2$ complex (0.080 g, 9.67 mmol, 0.03 eq), was added into reaction mixture and again reaction mixture was degassed by argon for 30 min. Further reaction mixture was stirred at 100° C. for 4 h. Upon completion, reaction mixture transferred into water and extracted with ethyl acetate. Organic layers were combined, dried over $Na_2SO_4$ and concentrated in vacuo to obtain crude product. This was purified by column chromatography and compound was eluted in 20% ethyl acetate in hexane to obtain pure 631.6 (0.530 g, 59.06%). MS(ES): m/z 279.37 [M+H]$^+$.

Synthesis of Compound 631.7.

Compound 631.7 was synthesized from 631.6 and 13.4 using general procedure A. (Yield: 16.16%). MS (ES): m/z 565.05 [M+H]$^+$.

Synthesis of Compound 631.8.

Compound 631.8 was synthesized from 631.7 and cyclopropanecarboxamide using general procedure B. (Yield: 78.56%). MS (ES): m/z 613.70 [M+H]$^+$.

Synthesis of Compound I-631.

Compound I-631 was synthesized from 631.8 using general procedure C. (Yield: 95.09%). MS(ES): m/z: 529.64 [M+H]$^+$, LCMS purity: 98.56%, HPLC purity: 97.14%, Chiral HPLC: (50%, 50%), 1H NMR (DMSO, 400 MHz): 13.68 (s, 1H), 10.78 (s, 1H), 9.86 (s, 1H), 8.17 (s, 1H), 7.86-7.86 (d, J=1.6 Hz, 1H), 7.83-7.77 (m, 2H), 7.69 (s, 1H), 7.26 (t, 1H), 3.82 (s, 3H), 3.23 (s, 3H), 2.75 (s, 3H), 2.47 (s, 3H), 2.10 (s, 1H), 0.81-0.79 (m, 4H).

Example 632. TYK2 JH2 Domain Binding Assay

Binding constants for compounds of the present invention against the JH2 domain were determined by the following protocol for a KINOMEscan® assay (DiscoveRx). A fusion protein of a partial length construct of human TYK2 (JH2domain-pseudokinase) (amino acids G556 to D888 based on reference sequence NP_003322.3) and the DNA binding domain of NFkB was expressed in transiently transfected HEK293 cells. From these HEK 293 cells, extracts were prepared in M-PER extraction buffer (Pierce) in the presence of Protease Inhibitor Cocktail Complete (Roche) and Phosphatase Inhibitor Cocktail Set II (Merck) per manufacturers' instructions. The TYK2 (JH2domain-pseudokinase) fusion protein was labeled with a chimeric double-stranded DNA tag containing the NFkB binding site (5'-GGGAATTCCC-3') fused to an amplicon for qPCR readout, which was added directly to the expression extract (the final concentration of DNA-tag in the binding reaction is 0.1 nM).

Streptavidin-coated magnetic beads (Dynal M280) were treated with a biotinylated small molecule ligand for 30 minutes at room temperature to generate affinity resins the binding assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding.

The binding reaction was assembled by combining 16 µl of DNA-tagged kinase extract, 3.8 µl liganded affinity beads, and 0.18 µl test compound (PBS/0.05% Tween 20/10 mM DTT/0.1% BSA/2 µg/ml sonicated salmon sperm DNA)]. Extracts were used directly in binding assays without any enzyme purification steps at a ≥10,000-fold overall stock dilution (final DNA-tagged enzyme concentration<0.1 nM). Extracts were loaded with DNA-tag and diluted into the binding reaction in a two step process. First extracts were diluted 1:100 in 1× binding buffer (PBS/0.05% Tween 20/10 mM DTT/0.1% BSA/2 µg/ml sonicated salmon sperm DNA) containing 10 nM DNA-tag. This dilution was allowed to equilibrate at room temperature for 15 minutes and then subsequently diluted 1:100 in 1× binding buffer. Test compounds were prepared as 111× stocks in 100% DMSO. $K_d$s were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. All reactions performed in polypropylene 384-well plates. Each was a final volume of 0.02 mL. Assays were incubated with shaking for 1 hour at room temperature. Then the beads were pelleted and washed with wash buffer (1×PBS, 0.05% Tween 20) to remove displaced kinase and test compound. The washed based were re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR. qPCR reactions were assembled by adding 2.5 µL of kinase eluate to 7.5 µL of qPCR master mix containing 0.15 µM amplicon primers and 0.15 µM amplicon probe. The qPCR protocol consisted of a 10 minute hot start at 95° C., followed by 35 cycles of 95° C. for 15 seconds, 60° C. for 1 minute.

Test compounds were prepared as 111× stocks in 100% DMSO. $K_d$s were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. The $K_d$s were determined using a compound top concentration of 30,000 nM. $K_d$ measurements were performed in duplicate.

Binding constants ($K_d$s) were calculated with a standard dose-response curve using the Hill equation:

$$\text{Response} = \text{Background} + \frac{(\text{Signal} - \text{Background})}{\left(1 + \left(\frac{Kd^{Hill\,Slope}}{\text{Dose}^{Hill\,Slope}}\right)\right)}$$

The Hill Slope was set to −1. Curves were fitted using a non-linear least square fit with the Levenberg-Marquardt algorithm (Levenberg, K., A method for the solution of certain non-linear problems in least squares, *Q. Appl. Math.* 2, 164-168 (1944)).

Results of the Tyk2 JH2 Domain Binding Assay are presented in Table 2. Compounds with activity denoted as "A" had a Kd<100 µM; compounds with activity denoted as "B" had a Kd greater than 100 µM but ≤500 µM; compounds with activity denoted as "C" had a Kd greater than 500 µM but <1 nM; compounds with activity denoted as "D" had a Kd greater than 1 nM but ≤10 nM; and compounds with activity denoted as "E" had a Kd greater than 10 nM.

TABLE 2

Results of the Tyk2 JH2 Domain Binding Assay

| Compound | JH2 Kd |
|---|---|
| I-1 | B |
| I-2 | C |
| I-3 | B |
| I-4 | B |
| I-5 | C |
| I-6 | C |
| I-7 | B |
| I-8 | D |
| I-9 | E |
| I-10 | D |
| I-11 | D |
| I-13 | B |
| I-14 | B |
| I-15 | D |
| I-16 | C |
| I-17 | B |
| I-18 | D |
| I-19 | E |
| I-20 | E |
| I-21 | C |
| I-22 | D |
| I-23 | D |
| I-24 | D |
| I-25 | B |
| I-26 | B |
| I-27 | D |
| I-28 | E |
| I-29 | E |
| I-30 | D |
| I-31 | D |
| I-32 | C |
| I-33 | C |
| I-34 | E |
| I-35 | D |
| I-36 | B |
| I-37 | B |
| I-38 | D |
| I-39 | B |
| I-40 | B |
| I-41 | E |
| I-42 | D |
| I-43 | B |
| I-44 | A |
| I-45 | B |
| I-46 | C |
| I-47 | D |
| I-48 | D |
| I-49 | E |
| I-50 | D |
| I-51 | E |
| I-53 | E |
| I-54 | E |
| I-55 | E |
| I-56 | D |
| I-58 | C |
| I-59 | B |
| I-60 | A |
| I-61 | B |
| I-62 | B |
| I-63 | C |
| I-64 | B |
| I-65 | B |
| I-80 | D |
| I-85 | C |
| I-87 | C |
| I-89 | C |
| I-93 | B |
| I-94 | C |
| I-95 | B |
| I-96 | B |
| I-97 | E |
| I-98 | C |
| I-100 | B |
| I-101 | D |
| I-103 | E |
| I-104 | E |
| I-105 | E |
| I-106 | E |
| I-107 | D |
| I-108 | B |
| I-109 | B |
| I-110 | D |
| I-111 | D |
| I-112 | B |
| I-113 | B |
| I-114 | D |
| I-115 | D |
| I-116 | D |
| I-117 | D |
| I-118 | B |
| I-120 | A |
| I-121 | E |
| I-122 | D |

TABLE 2-continued

Results of the Tyk2 JH2 Domain Binding Assay

| Compound | JH2 Kd |
|---|---|
| I-123 | B |
| I-124 | B |
| I-125 | B |
| I-126 | B |
| I-127 | B |
| I-128 | D |
| I-129 | D |
| I-130 | C |
| I-131 | C |
| I-132 | B |
| I-133 | D |
| I-134 | B |
| I-135 | B |
| I-136 | E |
| I-137 | E |
| I-138 | D |
| I-139 | C |
| I-140 | D |
| I-141 | E |
| I-142 | D |
| I-143 | D |
| I-144 | E |
| I-145 | C |
| I-146 | D |
| I-147 | A |
| I-148 | B |
| I-149 | E |
| I-150 | B |
| I-151 | D |
| I-152 | D |
| I-153 | B |
| I-154 | B |
| I-155 | D |
| I-156 | B |
| I-157 | D |
| I-158 | E |
| I-159 | B |
| I-160 | D |
| I-161 | D |
| I-162 | E |
| I-163 | C |
| I-164 | B |
| I-165 | E |
| I-166 | B |
| I-167 | E |
| I-168 | E |
| I-169 | B |
| I-170 | B |
| I-171 | B |
| I-172 | E |
| I-173 | E |
| I-174 | B |
| I-175 | C |
| I-176 | C |
| I-177 | B |
| I-178 | B |
| I-179 | B |
| I-180 | B |
| I-181 | B |
| I-182 | B |
| I-183 | B |
| I-184 | B |
| I-185 | B |
| I-186 | B |
| I-187 | B |
| I-188 | B |
| I-189 | B |
| I-190 | E |
| I-191 | C |
| I-192 | D |
| I-193 | E |
| I-194 | E |
| I-195 | B |
| I-196 | C |
| I-197 | B |
| I-198 | A |
| I-199 | A |
| I-200 | B |
| I-201 | B |
| I-202 | C |
| I-203 | B |
| I-204 | C |
| I-205 | C |
| I-206 | D |
| I-207 | B |
| I-208 | D |
| I-209 | B |
| I-210 | B |
| I-211 | B |
| I-212 | A |
| I-213 | B |
| I-214 | A |
| I-215 | A |
| I-216 | A |
| I-217 | A |
| I-218 | B |
| I-219 | B |
| I-220 | D |
| I-221 | C |
| I-222 | B |
| I-223 | B |
| I-224 | A |
| I-225 | B |
| I-226 | B |
| I-227 | B |
| I-228 | D |
| I-229 | D |
| I-230 | C |
| I-231 | D |
| I-232 | B |
| I-233 | B |
| I-234 | D |
| I-235 | A |
| I-236 | B |
| I-237 | C |
| I-238 | D |
| I-239 | B |
| I-240 | D |
| I-241 | A |
| I-242 | C |
| I-243 | E |
| I-244 | C |
| I-245 | D |
| I-246 | A |
| I-247 | B |
| I-248 | A |
| I-249 | D |
| I-250 | A |
| I-251 | B |
| I-252 | D |
| I-253 | B |
| I-254 | C |
| I-255 | B |
| I-256 | C |
| I-257 | D |
| I-258 | D |
| I-259 | D |
| I-260 | A |
| I-261 | B |
| I-262 | B |
| I-263 | A |
| I-264 | A |
| I-265 | A |
| I-266 | C |
| I-267 | D |
| I-268 | B |
| I-269 | B |
| I-270 | B |
| I-271 | D |
| I-272 | D |
| I-273 | C |
| I-274 | B |

TABLE 2-continued

Results of the Tyk2 JH2 Domain Binding Assay

| Compound | JH2 Kd |
|---|---|
| I-275 | D |
| I-276 | A |
| I-277 | B |
| I-278 | B |
| I-279 | D |
| I-280 | C |
| I-281 | D |
| I-282 | D |
| I-283 | D |
| I-284 | C |
| I-285 | B |
| I-286 | B |
| I-287 | B |
| I-288 | B |
| I-289 | B |
| I-290 | C |
| I-291 | C |
| I-292 | D |
| I-293 | D |
| I-294 | D |
| I-295 | B |
| I-296 | C |
| I-297 | C |
| I-298 | E |
| I-299 | C |
| I-300 | B |
| I-301 | B |
| I-302 | B |
| I-303 | C |
| I-304 | C |
| I-305 | B |
| I-306 | C |
| I-307 | D |
| I-308 | B |
| I-309 | B |
| I-310 | C |
| I-311 | D |
| I-312 | B |
| I-313 | C |
| I-314 | D |
| I-315 | B |
| I-316 | C |
| I-317 | B |
| I-318 | E |
| I-319 | E |
| I-320 | D |
| I-321 | D |
| I-322 | B |
| I-323 | B |
| I-324 | D |
| I-325 | C |
| I-326 | D |
| I-327 | B |
| I-328 | B |
| I-329 | D |
| I-330 | B |
| I-331 | B |
| I-332 | B |
| I-333 | D |
| I-334 | A |
| I-335 | E |
| I-336 | D |
| I-337 | D |
| I-338 | D |
| I-339 | D |
| I-340 | C |
| I-341 | B |
| I-342 | B |
| I-343 | B |
| I-344 | B |
| I-345 | B |
| I-346 | E |
| I-347 | B |
| I-348 | B |
| I-349 | D |
| I-350 | B |
| I-351 | E |
| I-352 | B |
| I-353 | B |
| I-354 | D |
| I-355 | B |
| I-356 | B |
| I-357 | D |
| I-358 | E |
| I-359 | D |
| I-360 | D |
| I-361 | D |
| I-362 | B |
| I-363 | D |
| I-364 | D |
| I-365 | C |
| I-366 | A |
| I-367 | A |
| I-368 | C |
| I-369 | B |
| I-370 | B |
| I-371 | B |
| I-372 | C |
| I-373 | D |
| I-374 | D |
| I-375 | B |
| I-376 | E |
| I-377 | C |
| I-378 | C |
| I-379 | B |
| I-380 | C |
| I-381 | D |
| I-382 | B |
| I-383 | E |
| I-384 | C |
| I-385 | C |
| I-386 | C |
| I-387 | A |
| I-388 | B |
| I-389 | C |
| I-390 | B |
| I-391 | B |
| I-392 | A |
| I-393 | C |
| I-394 | B |
| I-395 | B |
| I-396 | D |
| I-397 | B |
| I-398 | A |
| I-399 | E |
| I-400 | B |
| I-401 | A |
| I-402 | C |
| I-403 | C |
| I-404 | A |
| I-405 | B |
| I-406 | A |
| I-407 | B |
| I-408 | C |
| I-409 | B |
| I-410 | B |
| I-411 | D |
| I-412 | E |
| I-413 | C |
| I-414 | B |
| I-415 | D |
| I-416 | B |
| I-417 | D |
| I-418 | D |
| I-419 | B |
| I-420 | D |
| I-421 | B |
| I-422 | C |
| I-423 | D |
| I-424 | A |
| I-425 | B |
| I-426 | B |

TABLE 2-continued

Results of the Tyk2 JH2 Domain Binding Assay

| Compound | JH2 Kd |
|---|---|
| I-427 | B |
| I-428 | D |
| I-429 | A |
| I-430 | B |
| I-431 | C |
| I-432 | D |
| I-433 | B |
| I-434 | B |
| I-435 | B |
| I-436 | B |
| I-437 | A |
| I-438 | D |
| I-439 | D |
| I-440 | B |
| I-441 | D |
| I-442 | E |
| I-443 | B |
| I-444 | B |
| I-445 | B |
| I-446 | B |
| I-447 | B |
| I-448 | B |
| I-449 | B |
| I-450 | B |
| I-451 | B |
| I-452 | C |
| I-453 | B |
| I-454 | C |
| I-455 | D |
| I-456 | B |
| I-457 | B |
| I-458 | B |
| I-459 | D |
| I-460 | D |
| I-461 | B |
| I-462 | B |
| I-463 | D |
| I-464 | C |
| I-465 | D |
| I-466 | C |
| I-467 | B |
| I-468 | B |
| I-469 | C |
| I-470 | B |
| I-471 | D |
| I-472 | B |
| I-473 | A |
| I-474 | A |
| I-475 | B |
| I-476 | B |
| I-477 | B |
| I-478 | D |
| I-479 | D |
| I-480 | B |
| I-481 | B |
| I-482 | D |
| I-483 | E |
| I-484 | D |
| I-485 | E |
| I-486 | B |
| I-487 | C |
| I-488 | A |
| I-489 | B |
| I-490 | B |
| I-491 | A |
| I-492 | A |
| I-493 | B |
| I-494 | A |
| I-495 | B |
| I-496 | B |
| I-497 | A |
| I-498 | B |
| I-499 | D |
| I-500 | B |
| I-501 | B |
| I-502 | B |
| I-503 | B |
| I-504 | B |
| I-505 | B |
| I-506 | C |
| I-507 | D |
| I-508 | A |
| I-509 | A |
| I-510 | A |
| I-511 | A |
| I-512 | A |
| I-513 | C |
| I-514 | A |
| I-515 | A |
| I-516 | B |
| I-517 | C |
| I-518 | D |
| I-519 | B |
| I-520 | B |
| I-521 | A |
| I-522 | B |
| I-523 | A |
| I-524 | B |
| I-525 | A |
| I-526 | A |
| I-527 | B |
| I-528 | B |
| I-529 | A |
| I-530 | A |
| I-531 | A |
| I-532 | A |
| I-533 | B |
| I-534 | D |
| I-536 | A |
| I-537 | A |
| I-538 | C |
| I-539 | C |
| I-540 | B |
| I-541 | C |
| I-542 | C |
| I-543 | D |
| I-544 | B |
| I-545 | B |
| I-546 | D |
| I-547 | A |
| I-548 | B |
| I-549 | D |
| I-550 | A |
| I-551 | C |
| I-552 | B |
| I-553 | B |
| I-554 | D |
| I-555 | C |
| I-556 | E |
| I-557 | E |
| I-558 | D |
| I-559 | D |
| I-560 | A |
| I-561 | D |
| I-562 | A |
| I-563 | D |
| I-564 | B |
| I-565 | D |
| I-566 | D |
| I-567 | D |
| I-568 | C |
| I-569 | A |
| I-570 | B |
| I-571 | B |
| I-572 | B |
| I-573 | D |
| I-574 | B |
| I-575 | B |
| I-576 | E |
| I-577 | E |
| I-578 | B |
| I-579 | A |

TABLE 2-continued

Results of the Tyk2 JH2 Domain Binding Assay

| Compound | JH2 Kd |
|---|---|
| I-580 | B |
| I-581 | B |
| I-582 | E |
| I-583 | B |
| I-584 | B |
| I-585 | B |
| I-586 | B |
| I-587 | B |
| I-588 | B |
| I-589 | D |
| I-590 | D |
| I-591 | B |
| I-592 | C |
| I-593 | D |
| I-594 | B |
| I-595 | B |
| I-596 | C |
| I-597 | B |
| I-598 | C |
| I-599 | C |
| I-600 | B |
| I-601 | C |
| I-602 | A |
| I-603 | B |
| I-604 | B |
| I-605 | B |
| I-606 | D |
| I-607 | B |
| I-608 | B |
| I-609 | B |
| I-610 | D |
| I-611 | B |
| I-612 | B |
| I-613 | B |
| I-614 | B |
| I-615 | C |
| I-616 | B |
| I-617 | B |
| I-618 | A |
| I-619 | A |
| I-620 | A |
| I-621 | B |
| I-622 | A |
| I-623 | A |
| I-624 | A |
| I-625 | B |
| I-626 | A |
| I-627 | D |
| I-628 | C |
| I-629 | C |
| I-630 | A |
| I-631 | A |
| I-632 | B |
| I-633 | B |
| I-634 | B |
| I-635 | B |
| I-636 | B |
| I-637 | A |
| I-638 | B |
| I-639 | A |
| I-640 | B |
| I-641 | A |
| I-642 | A |
| I-643 | B |
| I-644 | B |
| I-645 | D |
| I-646 | C |
| I-647 | C |
| I-648 | B |
| I-649 | D |
| I-650 | B |

Example 633. Tyk2 & JAK2 Radioactive Kinase Assay

Peptide substrate, [KKSRGDYMTMQIG], (20 µM) is prepared in reaction buffer (20 mM Hepes pH 7.5, 10 mM $MgCl_2$, 1 mM EGTA, 0.02% Brij35, 0.02 mg/mL BSA, 0.1 mM $Na_3PO_4$, 2 mM DTT, 1% DMSO. TYK2 (Invitrogen) kinase is added, followed by compounds in DMSO. 33PATP is added to initiate the reaction in ATP at 10 µM. Kinase reaction is incubated for 120 min at room temp and reactions are spotted onto P81 ion exchange paper (Whatman #3698-915), and then washed extensively in 0.75% phosphoric acid, prior to reading the radioactivity counts. For JAK2 (Invitrogen) kinase assay the peptide substrate poly[Glu:Tyr](4:1), 0.2 mg/ml is used, in the reaction carried out the same as for TYK2.

Example 634. Tyk2 & JAK2 Caliper Assay

The caliper machine employs an off chip mobility shift assay to detect phosphorylated peptide substrates from kinase assays, using microfluidics technology. The assays are carried out at ATP concentration equivalent to the ATP Km, and at 1 mM ATP. Compounds are serially diluted in DMSO then further diluted in assay buffer (25 mM HEPES, pH 7.5, 0.01% Brij-35, 0.01% Triton, 0.5 mM EGTA). 5 ul of diluted compound was added into wells first, then 10 ul of enzyme mix was added into wells, followed by 10 uL of substrate mix (peptide and ATP in 10 mM $MgCl_2$) to start reaction. Reaction was incubated at 28° C. for 25 min and then added 25 ul stop buffer (100 mM HEPES, 0.015% Brij-35, 50 mM EDTA), followed by reading with Caliper. JAK2 at 1 nM final concentration and TYK2 at 9.75 nM are from Carna, and substrates used are ATP at 20 and 16 uM, respectively. JAK2 assay uses peptide 22 and TYK2 uses peptide 30 (Caliper), each at 3 uM.

Example 635. IL-12 Induced pSTAT4 in Human PBMC

Human PBMC are isolated from buffy coat and are stored frozen for assays as needed. Cells for assay are thawed and resuspended in complete media containing serum, then cells are diluted to 1.67 E6 cells/ml so that 120 µl per well is 200,000 cells. 15 µl of compound or DMSO is added to the well at the desired concentrations and incubated at 1 hr at 37 C. 15 µl of stimulus (final concentration of 1.7 ng/mL IL-12) is added for 30 minutes prior to pSTAT4 and total STAT4 analysis using cell lysates prepared and analyzed by MSD reagents as per manufacturer protocol. The final DMSO concentration of compound in the assay is 0.1%.

Example 636. GM-CSF Induced pSTAT5 in Human PBMC

Cells are prepared for analysis as in the above procedure and 15 µl of GM-CSF (final concentration 5 ng/mL) is added for 20 minutes prior to pSTAT5 and total STAT5 analysis using cell lysates prepared and analyzed by MSD reagents as per manufacturer protocol. The final DMSO concentration of compound in the assay is 0.1%.

Example 637. Ex Vivo Mouse IL-12 Induced IFNγ Studies

C57/BL6 mice are given a single oral dose of either vehicle or different doses of compound at a volume of 10 mL/kg. 30 minutes to 1 hour after dosing, animals are euthanized and blood was collected via vena cava into sodium heparin blood collection tubes and inverted several times. Blood is then plated on anti-CD3 coated plates and stimulated with 2 ng/ml of mouse IL-12 in RPMI media for 24 hours at 37° C. in humidified incubator with 5% $CO_2$. At the end of the incubation, blood is centrifuged at 260 g for 5 minutes to collect supernatant. IFNγ concentration in the supernatant is determined with mouse IFNγ MSD kit per manufacture's instruction (Meso Scale Discovery). At the time of the blood collection, plasma is collected for drug level analysis by LC-MS/MS.

Example 638. T-ALL Cell Proliferation Assay

T-ALL cell lines KOPT-K1, HPB-ALL, DND-41, PEER, and CCRF-CEM are cultured in RPMI-1640 medium with 10% fetal bovine serum and penicillin/streptomycin. Cells are plated in triplicate at $1\times10^4$ cells per well in 96-well plates. T-ALL cell lines DU.528, LOUCY, and SUP-T13 are cultured in the same medium and plated at a density of $1.5\times10^4$ cells per well. The cells are treated with DMSO or different concentrations of each compound of the invention. Cell viability at 72 hour exposure to the drug is assessed by CellTiter-Glo Luminescent Cell Viability Assay (Promega). CellTiter-Glo Reagent is added into the well and incubated for 10 minutes. Luminescence is measured subsequently using a 96-well plate luminescence reader. Cell viability is calculated by using the DMSO treated samples as 100%. $IC_{50}$ value is calculated by nonlinear regression using GraphPad Prism software.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A method of inhibiting TYK2 in a biological sample comprising contacting the sample with a compound of formula I':

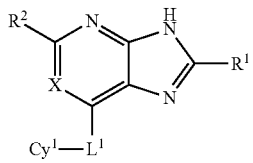

or a pharmaceutically acceptable salt thereof, wherein:
X is N or $C(R^3)$;
$R^1$ is $R^D$, —$NR_2$, —$NRR^D$, —$N(R^D)_2$, —$CH_2F$, —$CHF_2$, —$OR^D$, or an optionally substituted 3-7 membered saturated or partially unsaturated heterocyclic ring having 1-2 heteroatoms independently selected from nitrogen, oxygen, and sulfur;
$R^2$ is $R^C$, —$N(R)C(O)Cy^2$, —$N(R)S(O)_2Cy^2$, —$N(R)Cy^2$, —$OCy^2$, —$SCy^2$, or $Cy^2$;
$R^3$ is H, halogen, or $C_{1-6}$ aliphatic; or
$R^2$ and $R^3$ are taken together with their intervening atoms to form a 4-7 membered partially unsaturated or aromatic ring having 0-3 heteroatoms independently selected from nitrogen, oxygen, and sulfur; wherein said ring is substituted with m instances of $R^4$;
each of $Cy^1$ and $Cy^2$ is independently phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein $Cy^1$ is substituted with n instances of $R^5$; and; wherein $Cy^2$ is substituted with p instances of $R^6$;
$L^1$ is a covalent bond or a $C_{1-4}$ bivalent saturated or unsaturated, straight or branched hydrocarbon chain wherein one or two methylene units of the chain are optionally and independently replaced by $C(R^7)_2$—, $N(R)$—, —$N(R)C(O)$—, —$C(O)N(R)$—, —$N(R)S(O)_2$—, —$S(O)_2N(R)$—, —O—, —$C(O)$—, —OC(O)—, —$C(O)O$—, —S—, —$S(O)$— or —$S(O)_2$—;
each instance of $R^4$, $R^5$, $R^6$, and $R^7$ is independently $R^A$ or $R^B$, and is substituted by q instances of $R^C$;
each instance of $R^A$ is independently oxo, halogen, —CN, —$NO_2$, —OR, —$OR^D$, —SR, —$NR_2$, —$S(O)_2R$, —$S(O)(NR)R$, —$S(O)_2NR_2$, —$S(O)R$, —$S(O)NR_2$, —$C(O)R$, —$C(O)OR$, —$C(O)NR_2$, —$C(O)N(R)OR$, —$OC(O)R$, —$OC(O)NR_2$, —$N(R)C(O)OR$, —$N(R)C(O)R$, —$N(R)C(O)NR_2$, —$N(R)C(NR)NR_2$, —$N(R)S(O)_2NR_2$, —$N(R)S(O)_2R$, —$N(R^D)S(O)_2R$, —$N(R)S(O)_2R^D$, —$N(R^D)S(O)_2R^D$, or —$P(O)R_2$;
each instance of $R^B$ is independently $C_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;
each instance of $R^C$ is independently oxo, halogen, —CN, —$NO_2$, —OR, —SR, —$NR_2$, —$S(O)_2R$, —$S(O)_2NR_2$, —$S(O)R$, —$S(O)NR_2$, —$C(O)R$, —$C(O)OR$, —$C(O)NR_2$, —$C(O)N(R)OR$, —$OC(O)R$, —$OC(O)NR_2$, —$N(R)C(O)OR$, —$N(R)C(O)R$, —$N(R)C(O)NR_2$, —$N(R)C(NR)NR_2$, —$N(R)S(O)_2NR_2$, or —$N(R)S(O)_2R$ or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
$R^D$ is a C1-4 aliphatic group wherein one or more hydrogens are replaced by deuterium;
each R is independently hydrogen, or an optionally substituted group selected from $C_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and each of m, n, p, and q is independently 0, 1, 2, 3, or 4.

2. A method of treating a TYK2-mediated disorder, disease, or condition in a patient comprising administering to said patient a compound of formula I', or a pharmaceutical composition thereof:

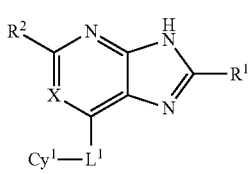

I' or a pharmaceutically acceptable salt thereof, wherein:

X is N or C(R$^3$);

R$^1$ is R$^D$, —NR$_2$, —NRR$^D$, —N(R$^D$)$_2$, —CH$_2$F, —CHF$_2$, —OR$^D$ or an optionally substituted 3-7 membered saturated or partially unsaturated heterocyclic ring having 1-2 heteroatoms independently selected from nitrogen, oxygen, and sulfur;

R$^2$ is R$^C$, —N(R)C(O)Cy$^2$, —N(R)S(O)$_2$Cy$^2$, —N(R)Cy$^2$, —OCy$^2$, —SCy$^2$, or Cy$^t$;

R$^3$ is H, halogen, or C$_{1-6}$ aliphatic; or

R$^2$ and R$^3$ are taken together with their intervening atoms to form a 4-7 membered partially unsaturated or aromatic ring having 0-3 heteroatoms independently selected from nitrogen, oxygen, and sulfur; wherein said ring is substituted with m instances of R$^4$;

each of Cy$^t$ and Cy$^2$ is independently phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated heterocyclic ring having 1-2 heteroatoms independently selected from nitrogen, oxygen, and sulfur; or a 3-7 membered saturated or partially unsaturated monocyclic carbocyclic ring; or a 7-12 membered saturated or partially unsaturated bicyclic heterocyclic ring having 1-4 heteroatoms independently selected from nitrogen, oxygen, and sulfur, wherein Cy$^t$ is substituted with n instances of R$^5$; and; wherein Cy$^2$ is substituted with p instances of R$^6$;

L$^1$ is a covalent bond or a C$_{1-4}$ bivalent saturated or unsaturated, straight or branched hydrocarbon chain wherein one or two methylene units of the chain are optionally and independently replaced by —C(R$^7$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

each instance of R$^4$, R$^5$, R$^6$, and R$^7$ is independently R$^A$ or R$^B$, and is substituted by q instances of R$^C$;

each instance of R$^A$ is independently oxo, halogen, —CN, —NO$_2$, —OR, —OR$^D$, —SR, —NR$_2$, —S(O)$_2$R, —S(O)(NR)R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, —N(R)S(O)$_2$R, —N(R$^D$)S(O)$_2$R, —N(R)S(O)$_2$R$^D$, —N(R$^D$)S(O)$_2$R$^D$, or —P(O)R$_2$;

each instance of R$^B$ is independently C$_{1-6}$ aliphatic; phenyl; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 3-7 membered saturated or partially unsaturated carbocyclic ring; a 3-7 membered saturated or partially unsaturated monocyclic heterocyclic ring having 1-2 heteroatoms independently selected from nitrogen, oxygen, and sulfur; or a 7-12 membered saturated or partially unsaturated bicyclic heterocyclic ring having 1-4 heteroatoms independently selected from nitrogen, oxygen, and sulfur;

each instance of R$^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)S(O)$_2$NR$_2$, or —N(R)S(O)$_2$R or an optionally substituted group selected from C$_{1-6}$ aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

R$^D$ is a C1-4 aliphatic group wherein one or more hydrogens are replaced by deuterium;

each R is independently hydrogen, or an optionally substituted group selected from C1.6 aliphatic, phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and each of m, n, p, and q is independently 0, 1, 2, 3, or 4.

3. The method of claim 2 wherein the disorder is selected from an autoimmune disorder, an inflammatory disorder, a proliferative disorder, an endocrine disorder, a neurological disorder, or a disorder associated with transplantation.

4. The method of claim 3 wherein the disorder is an autoimmune disorder.

5. The method of claim 4 wherein the autoimmune disorder is selected from type 1 diabetes, ankylosing spondylitis, systemic lupus erythematosus, multiple sclerosis, systemic sclerosis, psoriasis, Crohn's disease, ulcerative colitis, and inflammatory bowel disease.

6. The method of claim 3 wherein the disorder is an inflammatory disorder.

7. The method of claim 6 wherein the inflammatory disorder is selected from rheumatoid arthritis, asthma, chronic obstructive pulmonary disease, psoriasis, Crohn's disease, ulcerative colitis, and inflammatory bowel disease.

8. The method of claim 3 wherein the disorder is a proliferative disorder.

9. The method of claim 8 wherein the proliferative disorder is a hematological cancer.

10. The method of claim 8 wherein the proliferative disorder is a leukemia.

11. The method of claim 10 wherein the leukemia is a T-cell leukemia.

12. The method of claim 11 wherein the T-cell leukemia is T-cell acute lymphoblastic leukemia (T-ALL).

13. The method of claim 8 wherein the proliferative disorder is associated with one or more activating mutations in TYK2.

14. The method of claim 3 wherein the disorder is associated with transplantation.

15. The method of claim 14 wherein the disorder is transplant rejection or graft versus host disease.

16. The method of claim 3 wherein the disorder is an endocrine disorder.

17. The method of claim 16 wherein the endocrine disorder is polycystic ovary syndrome, Crouzon's syndrome, or type 1 diabetes.

18. The method of claim 3 wherein the disorder is a neurological disorder.

19. The method of claim 18 wherein the neurological disorder is Alzheimer's disease.

20. The method of claim 2 wherein the disorder is associated with type I interferon, IL-10, IL-12, or IL-23 signaling.

* * * * *